(12) United States Patent
Okuda et al.

(10) Patent No.: US 7,667,228 B2
(45) Date of Patent: Feb. 23, 2010

(54) METAL COMPLEX COMPOUND AND ORGANIC ELECTROLUMINESCENT DEVICE USING SAME

(75) Inventors: Fumio Okuda, Chiba (JP); Toshihiro Iwakuma, Chiba (JP); Keiko Yamamichi, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 154 days.

(21) Appl. No.: 10/565,274

(22) PCT Filed: Jul. 21, 2004

(86) PCT No.: PCT/JP2004/010687

§ 371 (c)(1), (2), (4) Date: Jan. 20, 2006

(87) PCT Pub. No.: WO2005/007767

PCT Pub. Date: Jan. 27, 2005

(65) Prior Publication Data

US 2006/0197077 A1    Sep. 7, 2006

(30) Foreign Application Priority Data

Jul. 22, 2003   (JP) .............................. 2003-199995

(51) Int. Cl.
H01L 35/24    (2006.01)
(52) U.S. Cl. ................. 257/40; 257/E51.022; 428/917; 313/504
(58) Field of Classification Search .................. 257/40, 257/57, 59, 79, E51.022; 428/690, 917; 313/504, 313/506
See application file for complete search history.

(56) References Cited

U.S. PATENT DOCUMENTS

| | | | | |
|---|---|---|---|---|
| 6,656,612 | B2 * | 12/2003 | Okada et al. ................. | 428/690 |
| 6,687,266 | B1 * | 2/2004 | Ma et al. ....................... | 372/7 |
| 6,933,673 | B2 * | 8/2005 | Yamazaki ................... | 313/506 |
| 2002/0094453 | A1 | 7/2002 | Takiguchi et al. | |
| 2002/0100906 | A1 * | 8/2002 | Takiguchi et al. ............. | 257/40 |
| 2004/0056244 | A1 * | 3/2004 | Marcus et al. ................. | 257/40 |
| 2004/0131881 | A1 * | 7/2004 | Zheng et al. ................. | 428/690 |
| 2006/0083947 | A1 * | 4/2006 | Ikeda et al. .................. | 428/690 |

FOREIGN PATENT DOCUMENTS

| | | |
|---|---|---|
| CN | 1726606 | 1/2006 |
| EP | 1 486 552 | 12/2004 |
| JP | 2003-109758 | 4/2003 |
| WO | WO 02/15645 | 2/2002 |
| WO | WO 02/45466 | 6/2002 |
| WO | WO 2004/045002 | 5/2004 |
| WO | WO 2006/098120 | 9/2006 |

OTHER PUBLICATIONS

Alonso, M.T., et al., "Palladium (II) coordination and cyclometallated complexes derived from 3- and 5-aryl-substituted pyrazoles," *Journal of Organometallic Chemistry* (1992), vol. 430, No. 3, pp. 335-347.

Huang, et al., "Highly Phosphorescent Bis-Cyclometalated Iridium Complexes Containing Benzoimidazole-Based Ligands," *Chem Mater*, No. 16, May 21, 2004, pp. 2480-2488.

Suarez, et al., "Cyclometallated Compounds of Pd(II) with 1-Methylphenylimidazoles," *Synth. React. Inorg. Met.-Org. Chem.*, 20(10), pp. 1425-1440 (1990).

Zamora, et al., "A Way to Obtain Cyclopalladation of Unsubstituted 2-Phenylimidazole Derivatives," *Journal of Organometallic Chemistry*, 522 (1996) pp. 97-103.

Navarro-Ranninger, et al., "Synthesis and NMR Structural Analysis of Several Orthopalladated Complexes of Substituted Benzo-Imidazole, -oxazole and—thiazole and Study of Two Polymorphic Crystals," *Journal of Organometallic Chemistry*, 518 (1996), pp. 29-36.

Database CA [Online] Chemical Abstracts Service, Columbus, Ohio, US; Yasukawa et al.: "Organic electroluminescent device, display, and lighting system," XP-002461421, Database Accession No. 2007:357133 (Abstract).

Database CA [Online] Chemical Abstracts Service, Columbus, Ohio, US; Yasukawa et al.: "Organic electroluminescent devices and displays, their materials, and illumination apparatuses therefor," XP-002461422, Database Accession No. 2007-30867 (Abstract).

XP-002461423, Database Accession No. 1987:478029, Suarez et al., "Synthesis, Properties, and Structure of [2-(1-methyl-4-imidazolyl)phenyl-1-C, 3'-N]palladium(II) acetylacetonate," *Zeitschrift fuer Anorganische und Allgemeine Chemie*, (1986), 535, 213-18 (Abstract).

XP-002461425, Database Accession No. 1998:43043, Vila et al., "Cyclometallated complexes of palladium(II) with 1-methyl-2-phenylimidazole and tertiary diphosphines. Crystal and molecular structure of [Pd[o-C6H4C:NC(H):C(H)Nme](Ph2PCH(Me)PPh2-P,P)][PF6]," *Journal of Organometallic Chemistry*, (1997), 547(2), 297-307.

XP-002461426, Database Accession No. 1997:548043, Zamora at al., "Pd(II) and Pt(II) complexes of 2-phenyl- and 2-benzylimidazoline: synthesis, structural characterization, DNA modification and in vitro antileukemic activity," *Applied Organometallic Chemistry*, (1997), 11(8), 659-666.

(Continued)

Primary Examiner—Khiem D Nguyen
(74) Attorney, Agent, or Firm—Steptoe & Johnson LLP

(57) ABSTRACT

A metal complex compound having a special structure containing metals such as iridium. An organic electroluminescence device which comprises at least one organic thin film layer sandwiched between a pair of electrode consisting of an anode and a cathode, wherein the organic thin film layer comprises the above metal complex compound, which emits light by applying an electric voltage between the pair of electrode. An organic EL device employing the novel metal complex compound emits various phosphorous lights including blue light having an enhanced current efficiency and prolonged lifetime.

8 Claims, No Drawings

OTHER PUBLICATIONS

XP-002461427, Database Accession No. 1996:58861, Navarro-Ranninger et al., "Cyclometalated complexes of Pd(II) and Pt(II) with 2-phenylimidazoline," *Journal of Organometallic Chemistry,* (1996), 506(1-2), 149-154.

XP-002461424, Database Accession No. 2000-665349, Lousame at al., "Synthesis and single-crystal X-ray diffraction studies of new cyclometallated phenylimidazole palladium (II) compounds," *European Journal of Inorganic Chemistry,* (2000), (9), 2055-2062.

Yersin, H., "Triplet Emitters for OLED Applications. Mechanisms of Exciton Trapping and Control of Emission Properties," Top Curr Chem (2004) 2431:1-26.

* cited by examiner

METAL COMPLEX COMPOUND AND ORGANIC ELECTROLUMINESCENT DEVICE USING SAME

CLAIM OF PRIORITY

This application claims priority under 35 USC 371 to International Application No. PCT/JP2004/010687, filed on Jul. 21, 2004, which claims priority to Japanese Patent Application No. 2003-199995, filed on Jul. 22, 2003, the entire contents of which are hereby incorporated by reference.

TECHNICAL FIELD

The present invention relates to a novel metal complex compound and an organic electroluminescence device using the compound. Particularly, the present invention relates to an organic electroluminescence device ("electroluminescence" will be referred to as "EL", hereinafter) having excellent efficiency of light emission and prolonged lifetime, and to a metal complex compound realizing it.

BACKGROUND ART

The organic EL devices have been expected to be applied to color wide screen image display devices replacing liquid crystal display devices, and have been intensively developed. Recently, although displays using the organic EL devices have now been used in practical applications, full-color image display devices using the same are still in the course of development because they lack in sufficient light emitting property. Very high efficiency green organic light emitting devices based on electrophosphorescence employing ortho metalized iridium complex (fac-tris(2-phenylpyridine)iridium) as a phosphorus light emitting material for improving properties of the organic EL device are proposed. (refer to, for example, D. F. O'Brien and M. A. Baldo et al "Improved energy transferring electrophosphorescent devices" Applied Physics letters Vol. 74 No. 3, pp 442-444, Jan. 18, 1999; and M. A. Baldo et al "Very high-efficiency green organic light emitting devices based on electrophosphorescence" Applied Physics letters Vol. 75 No. 1, pp 4-6, Jul. 5, 1999).

Because the current organic EL devices employing the phosphorus photoluminescence are limited to emitting only green light, coverage as the color display devices is narrow. Therefore, it has been demanded to develop organic EL devices which emit light of different colors from green with improved light emission property. Regarding particularly with EL devices which emit blue light, those having an external quantum yield exceeding 5% is not reported yet. Accordingly, an improvement in the EL devices which emit blue light, if possible, enables the display devices to display full colors or white light resultantly advancing toward practical use of phosphorus light EL device greatly.

Further, although International PCT Patent Publication No. WO 02/15645 discloses following structures of ligands (A) and (B):

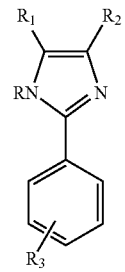

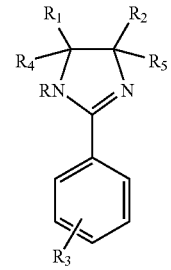

wherein $R_1$ to $R_5$ each independently represents a hydrogen atom, a halogen atom, an alkyl group, an aromatic group and an arylene group; and $R_1'$ and $R_2'$ an aromatic group, which may bond each other;

any practical synthesis example of real complex with the use of the ligands is not described.

DISCLOSURE OF THE INVENTION

The present invention has been made to overcome the above problems and has an object of providing an organic EL device having an enhanced efficiency of light emission and prolonged lifetime, and an object of providing a metal complex compound realizing it.

As a result of intensive researches and studies to achieve the above object by the present inventors, it was found that the iridium complex proposed in the former patent literature neither generates nor isolates stably in a case where R is H in the above ligands (A) and (B) and that it is important for stably isolating the iridium complex to replace an atom on a side of N without forming a coordinate bond with a metal to an atom except a hydrogen atom. Then, the inventors designed ligands having various kinds of substituent on N, and succeeded in synthesizing iridium complex for the first time. Further, it was found that an employment of a metal complex compound having a partial structure represented by a following general formula (I) provides the EL device achieving an external quantum yield of 8% and exhibits an enhanced efficiency of light emission not only in blue region but also about various phosphorus photoluminescence and prolonged lifetime, resultantly completing the present invention.

Namely, the present invention provides a metal complex compound having a partial structure represented by a following general formula (I):

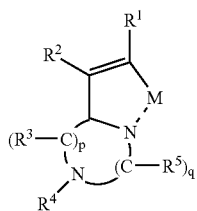

wherein $R^1$ to $R^5$ each independently represents a hydrogen atom, a cyano group, a nitro group, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, a substituted or unsubstituted acyl group having 1 to 20 carbon atoms or a substituted or unsubstituted aromatic group having 1 to 30 carbon atoms; and a couple of $R^1$ and $R^2$, a couple of $R^2$ and $R^3$, a couple of $R^3$ and $R^4$ and a couple of $R^4$ and $R^5$ may bond each other to form a ring structure;

p and q each independently represents an integer of 0 to 3; p+q being 2 or 3;

further, when p is an integer of 2 or greater, plural of $R^3$ may bond each other to form a ring structure; when q is an integer of 2 or greater, plural of $R^5$ may bond each other to form a ring structure; and M represents any one metal atom selected from iridium (Ir) atom, rhodium (Rh) atom, platinum (Pt) atom or palladium (Pd) atom.

Further, the present invention provides an organic EL device which comprises at least one organic thin film layer sandwiched between a pair of electrode consisting of an anode and a cathode, wherein the organic thin film layer comprises the above metal complex compound, which emits light by applying an electric voltage between the pair of electrode.

THE PREFERRED EMBODIMENT TO CARRY OUT THE INVENTION

The present invention provides a metal complex compound having a partial structure represented by a following general formula (I):

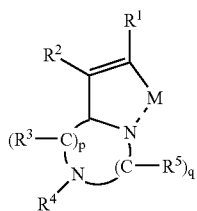

In the general formula (I), $R^1$ to $R^5$ each independently represents a hydrogen atom, a cyano group, a nitro group atom, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, a substituted or unsubstituted acyl group having 1 to 20 carbon atoms or a substituted or unsubstituted aromatic group having 1 to 30 carbon atoms; and a couple of $R^1$ and $R^2$, a couple of $R^2$ and $R^3$, a couple of $R^3$ and $R^4$ and a couple of $R^4$ and $R^5$ may bond each other to form a ring structure.

Examples of the halogen atom include fluorine atom, chlorine atom, bromine atom and iodine atom.

Examples of the alkyl group described above include methyl group, ethyl group, propyl group, isopropyl group, n-butyl group, s-butyl group, isobutyl group, t-butyl group, n-pentyl group, n-hexyl group, n-heptyl group, n-octyl group, etc.

The alkoxy group is expressed as —OY, wherein Y represents the same as the foregoing description about the alkyl group.

Examples of the alkylsilyl group include trimethylsilyl group, t-butyldimethylsilyl group, etc.

Examples of the acyl group include acetyl group, propionyl group, butyryl group, isobutyryl group, etc.

Examples of the above aromatic group include benzene, naphthalene, anthracene, phenanthrene, pyrene, coronene, biphenyl, terphenyl, pyrrole, furan, thiophene, benzothiophene, oxadiazoline, diphenylanthracene, indoline, carbazole, pyridine, benzoquinone, fluoranthene, acenaphtho fluoranthene, etc.

Further, examples of the substituent for those groups include cyano group, hydroxyl group, nitro group, halogen atom, substituted or unsubstituted alkyl group, substituted or unsubstituted amino group, substituted or unsubstituted alkoxyl group, substituted or unsubstituted alkylsilyl group, substituted or unsubstituted acyl group, substituted or unsubstituted aromatic group, substituted or unsubstituted alkenyl group, a substituted or unsubstituted cycloalkyl group, substituted or unsubstituted heterocyclic group, substituted or unsubstituted arylalkyl group, a substituted or unsubstituted aryloxy group, substituted or unsubstituted alkoxycarbonyl group, carboxyl group, etc.

Examples of the ring structure formed by bonding $R^1$ and $R^2$, $R^3$ and $R^4$, or $R^4$ and $R^5$ each independently include benzene, pyridine, naphthalene, benzothiazole, quinoline, etc.

It is preferable that $R^1$ to $R^5$ each independently represents a hydrogen atom, a cyano group, a nitro group, a fluorine atom, a trifluoromethyl group, a dimethylamino group, a methoxy group, a t-butyl group, a trimethylsilyl group and an acetyl group.

In the general formula (I), p and q each independently represents an integer of 0 to 3 (preferably 0 to 2); p+q being 2 or 3; further, when p is an integer of 2 or greater, plural of $R^3$ may bond each other to form a ring structure; when q is an integer of 2 or greater, plural of $R^5$ may bond each other to form a ring structure.

Examples of the ring structure formed by plural of $R^3$ and plural of $R^5$ each independently include benzene, pyridine, etc.

In the general formula (I), M represents any one metal atom selected from iridium (Ir) atom, rhodium (Rh) atom, platinum (Pt) atom or palladium (Pd) atom; while Ir and Pt are preferable and Ir is more preferable.

Further, it is preferable that the partial structure represented by general formula (I) is expressed by any one of (i) to (vii) or (i') to (vii') below, while (i) to (ii) being further preferable.

-continued
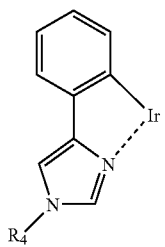
(i)
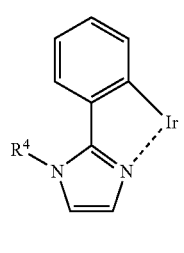
(ii)
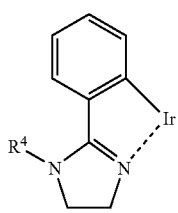
(iii)
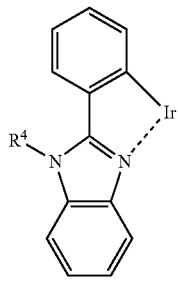
(iv)
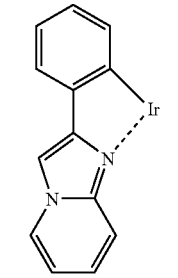
(v)
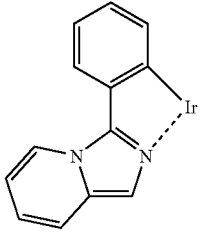
(vi)
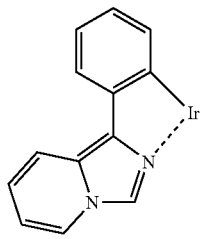
(vii)
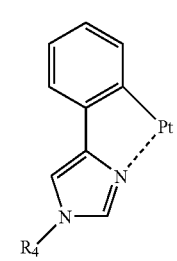
(i')
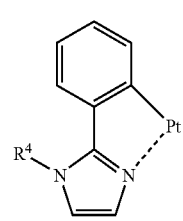
(ii')
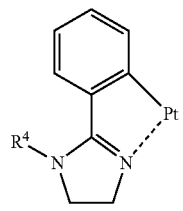
(iii')
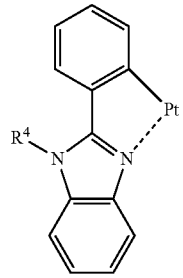
(iv')
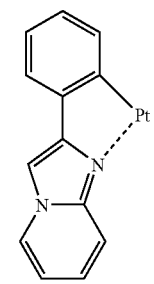
(v')

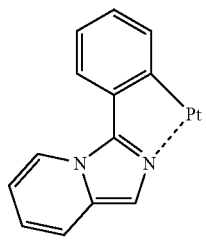
(vi')
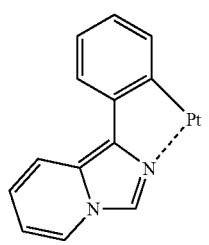
(vii')
Furthermore, it is preferable that the metal complex compound of the present invention has basic skeletal structure expressed by following general formulae 1 to 7 and 1' to 7'.
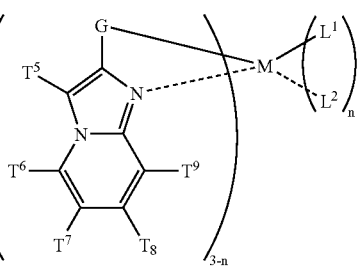
1
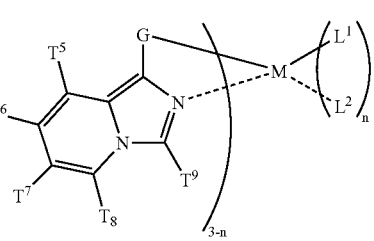
2
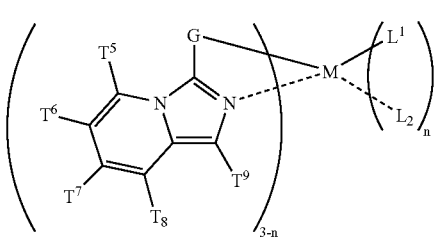
3
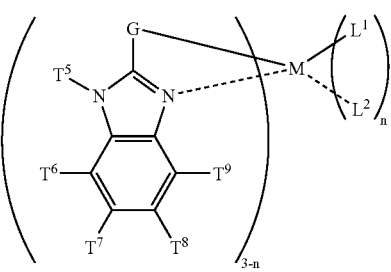
4
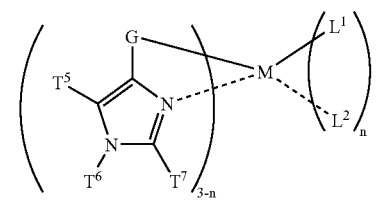
5
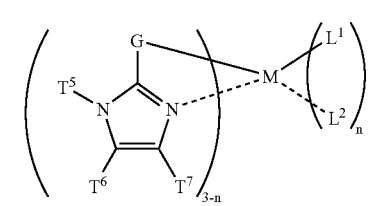
6
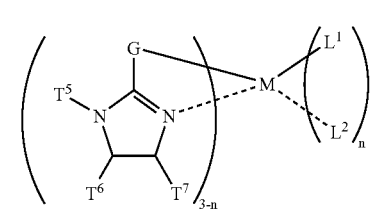
7
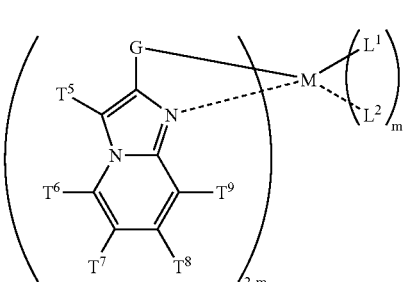
1'
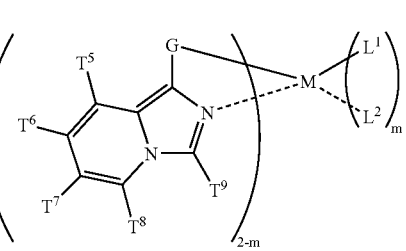
2'
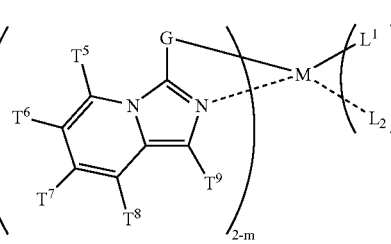
3'

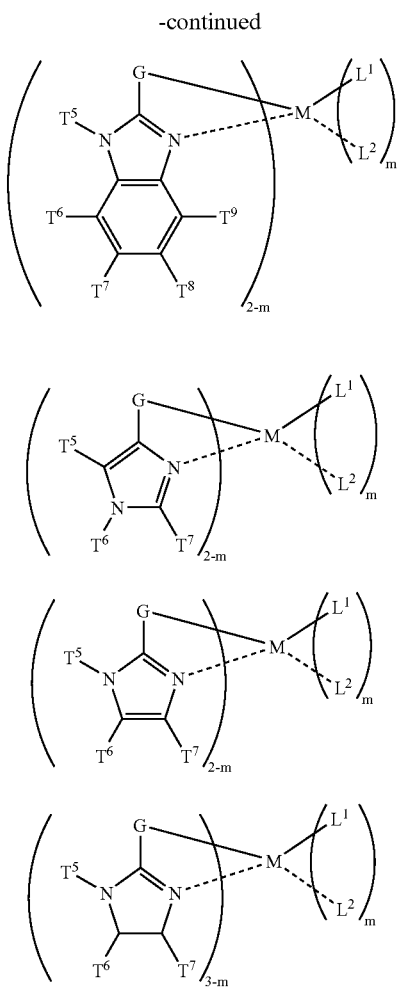

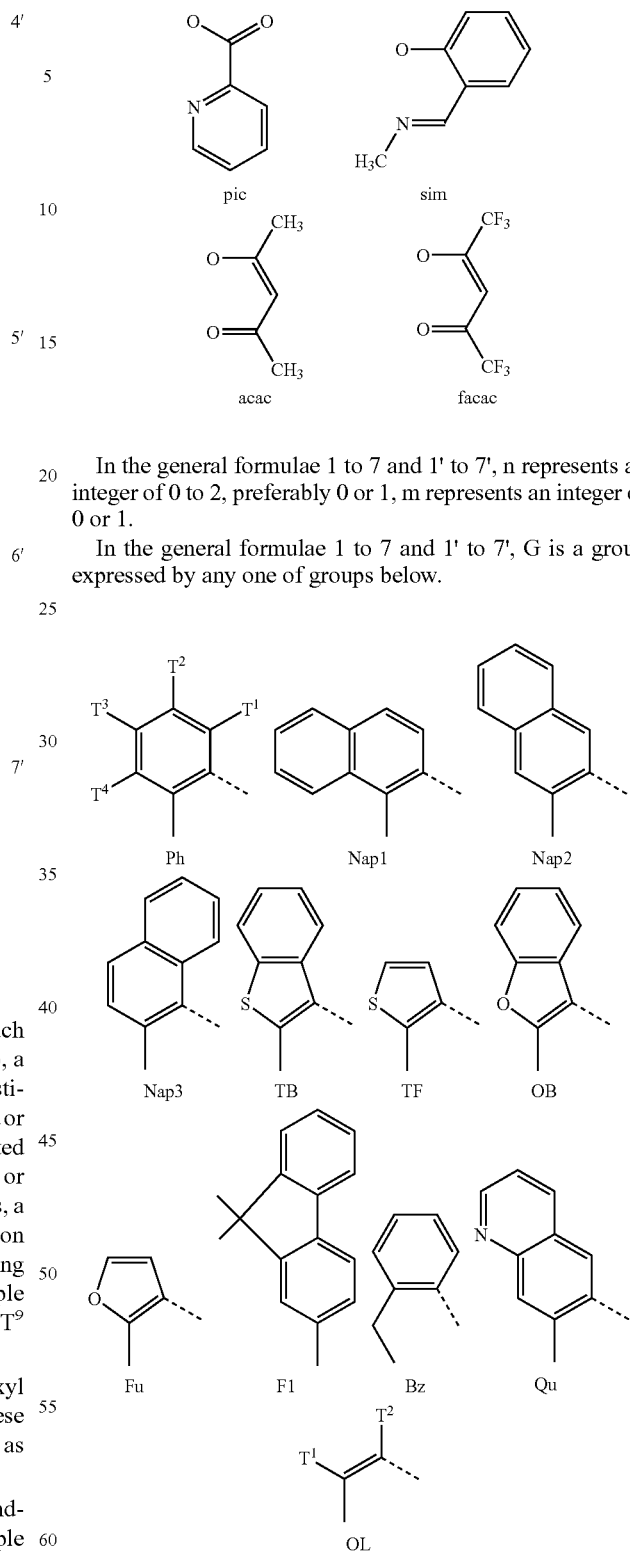

In the general formulae 1 to 7 and 1' to 7', n represents an integer of 0 to 2, preferably 0 or 1, m represents an integer of 0 or 1.

In the general formulae 1 to 7 and 1' to 7', G is a group expressed by any one of groups below.

In the general formulae 1 to 7 and 1' to 7', $T^5$ to $T^9$ each independently represents a hydrogen atom, a cyano group, a nitro group atom, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, a substituted or unsubstituted acyl group having 1 to 20 carbon atoms or a substituted or unsubstituted aromatic group having 1 to 30 carbon atom. Further, a couple of $T^5$ and $T^6$, a couple of $T^6$ and $T^7$, a couple of $T^7$ and $T^8$ and a couple of $T^8$ and $T^9$ may bond each other to form a ring structure.

Examples of the above halogen atom, alkyl group, alkoxyl group, alkylsilyl group, acyl group, aromatic group, these substituents, and these preferable examples are the same as explained about $R^1$ to $R^5$ in the general formula (I).

Moreover, examples of the ring structure formed by bonding the couple of $T^5$ and $T^6$, the couple of $T^6$ and $T^7$, the couple of $T^7$ and $T^8$ and the couple of $T^8$ and $T^9$ each independently include benzene, pyridine, etc.

In the general formulae 1 to 7 and 1' to 7', M is the same as the forgoing description.

In the general formulae 1 to 7 and 1' to 7', $L^1$ and $L^2$ are each expressed by any one of the following structures:

In the above groups, a dotted line ". . ." represents a covalent bond with M.

$T^1$ to $T^4$ in the above Ph and OL each may independently represents a hydrogen atom, a cyano group, a nitro group, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, a substituted or unsubstituted acyl group having 1 to 20 carbon atoms or a substituted or unsubstituted aromatic group having 1 to 30 carbon atom. Examples of those groups, their substituents and those preferable examples are the same as explained about $R^1$ to $R^5$ in the general formula (I).

Further, examples of the substituent forming the ring structure by bonding the couple of $T^1$ and $T^2$, the couple of $T^2$ and $T^3$ or the couple of $T^3$ and $T^4$ in the Ph include a divalent group expressed by any one of groups below, while BL, MES1, MES2, PS1 and PS2 being preferable.

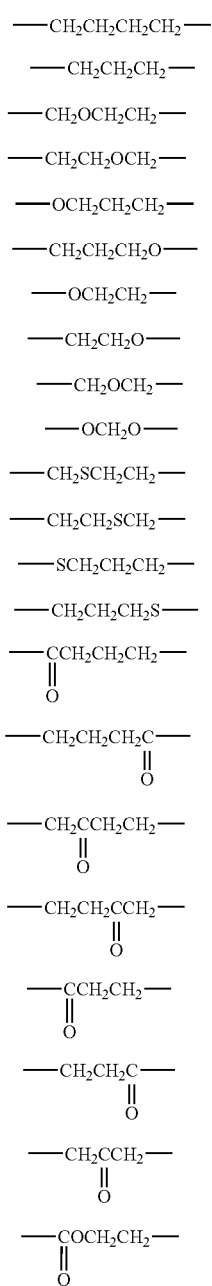

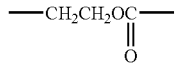 EES 2

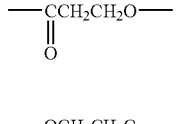 PAE 1

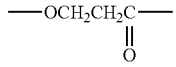 PAE 2

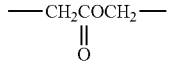 AME 1

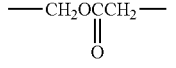 AME 2

 EAE 1

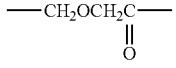 EAE 2

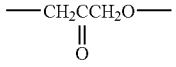 AAE 1

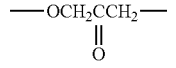 AAE 2

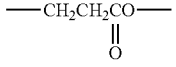 PME 1

 PME 2

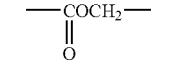 MES 1

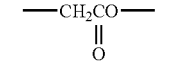 MES 2

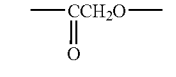 EE 1

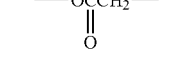 EE 2

 MS 1

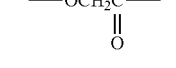 MS 2

However, the group with a smaller number of superscript among $T^1$ to $T^4$ bonds to the left of the divalent group and the group with a greater number superscript among $T^1$ to $T^4$ bonds to the right of the divalent group.

Specific examples of the metal complex compound having any one basic skeletal structure among the general formulae 1' to 7' will be shown in Tables below, though not limited thereto.

In the Tables below, $T^1$ to $T^9$, $L^1$ and $L^2$ (in the cases of the basic skeletal structures 1 to 4 and 1' to 4') or $T^1$ to $T^7$, $L^1$ and $L^2$ (in the cases of the basic skeletal structures 5 to 7 and 5' to 7') are described within the columns righter to the basic skeletal structures.

1

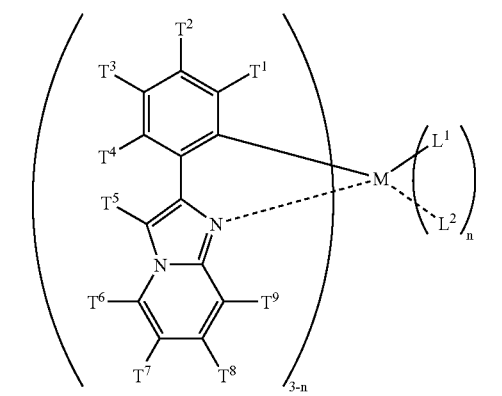

2

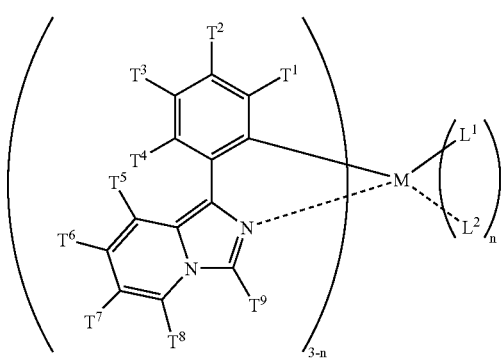

3

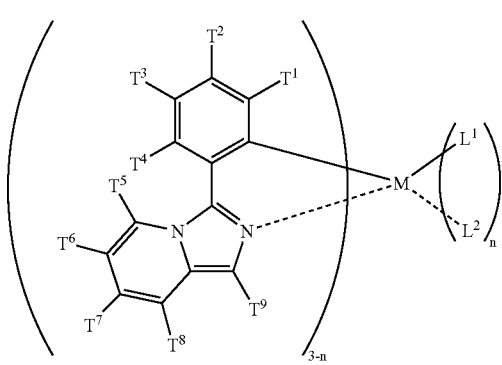

4

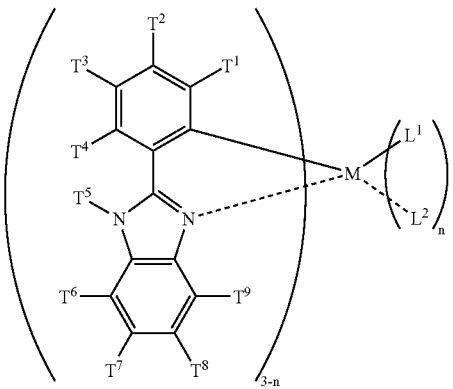

5

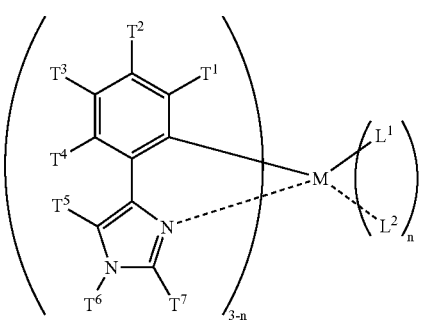

6

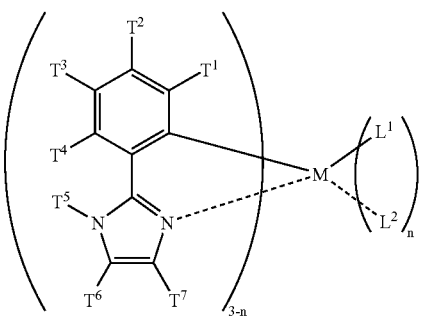

7

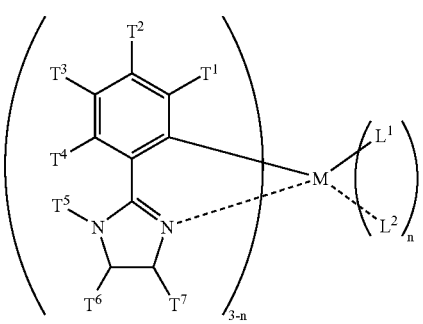

Further in the Tables below, "BBS" means Basic Skeletal Structure, and "BS" means Skeletal Structure.

TABLE 1

| No. | M | n | BSS | SS | G | T¹ | T² | T³ | T⁴ | T⁵ | T⁶ | T⁷ | T⁸ | T⁹ | L¹ L² |
|---|---|---|---|---|---|---|---|---|---|---|---|---|---|---|---|
| 1-1 | Ir | 1 | 1 | | Ph | H | H | H | H | H | H | H | H | H | pic |
| 1-1X | Ir | 1 | 1 | | Ph | H | H | H | H | H | H | H | H | H | acac |
| 1-1Y | Ir | 0 | 1 | | Ph | H | H | H | H | H | H | H | H | H | — — |
| 1-2 | Ir | 1 | 1 | | Ph | H | F | H | F | H | H | H | H | H | pic |
| 1-2X | Ir | 1 | 1 | | Ph | H | F | H | F | H | H | H | H | H | acac |
| 1-2Y | Ir | 0 | 1 | | Ph | H | F | H | F | H | H | H | H | H | — — |
| 1-3 | Ir | 1 | 1 | | Ph | F | H | H | F | H | H | H | H | H | pic |
| 1-3X | Ir | 1 | 1 | | Ph | F | H | H | F | H | H | H | H | H | acac |
| 1-3Y | Ir | 0 | 1 | | Ph | F | H | H | F | H | H | H | H | H | — — |
| 1-4 | Ir | 1 | 1 | | Ph | CF₃ | H | CF₃ | H | H | H | H | H | H | pic |
| 1-4X | Ir | 1 | 1 | | Ph | CF₃ | H | CF₃ | H | H | H | H | H | H | acac |
| 1-4Y | Ir | 0 | 1 | | Ph | CF₃ | H | CF₃ | H | H | H | H | H | H | — — |
| 1-5 | Ir | 1 | 1 | | Ph | H | F | CF₃ | H | H | H | H | H | H | pic |
| 1-5X | Ir | 1 | 1 | | Ph | H | F | CF₃ | H | H | H | H | H | H | acac |
| 1-5Y | Ir | 0 | 1 | | Ph | H | F | CF₃ | H | H | H | H | H | H | — — |
| 1-6 | Ir | 1 | 1 | | Ph | F | H | CF₃ | H | H | H | H | H | H | pic |
| 1-6X | Ir | 1 | 1 | | Ph | F | H | CF₃ | H | H | H | H | H | H | acac |
| 1-6Y | Ir | 0 | 1 | | Ph | F | H | CF₃ | H | H | H | H | H | H | — — |
| 1-7 | Ir | 1 | 1 | | Ph | F | F | F | F | H | H | H | H | H | pic |
| 1-7X | Ir | 1 | 1 | | Ph | F | F | F | F | H | H | H | H | H | acac |
| 1-7Y | Ir | 0 | 1 | | Ph | F | F | F | F | H | H | H | H | H | — — |
| 1-8 | Ir | 1 | 1 | | Ph | H | F | H | CH₃ | H | H | H | H | H | pic |
| 1-8X | Ir | 1 | 1 | | Ph | H | F | H | CH₃ | H | H | H | H | H | acac |
| 1-8Y | Ir | 0 | 1 | | Ph | H | F | H | CH₃ | H | H | H | H | H | — — |
| 1-9 | Ir | 1 | 1 | | Ph | H | F | H | ᵗC₄H₉ | H | H | H | H | H | pic |
| 1-9X | Ir | 1 | 1 | | Ph | H | F | H | ᵗC₄H₉ | H | H | H | H | H | acac |
| 1-9Y | Ir | 0 | 1 | | Ph | H | F | H | ᵗC₄H₉ | H | H | H | H | H | — — |
| 1-10 | Ir | 1 | 1 | | Ph | H | CF₃ | H | CF₃ | H | H | H | H | H | pic |
| 1-10X | Ir | 1 | 1 | | Ph | H | CF₃ | H | CF₃ | H | H | H | H | H | acac |
| 1-10Y | Ir | 0 | 1 | | Ph | H | CF₃ | H | CF₃ | H | H | H | H | H | — — |
| 1-11 | Ir | 1 | 1 | | Ph | CF₃ | H | H | ᵗC₄H₉ | H | H | H | H | H | pic |
| 1-11X | Ir | 1 | 1 | | Ph | CF₃ | H | H | ᵗC₄H₉ | H | H | H | H | H | acac |
| 1-11Y | Ir | 0 | 1 | | Ph | CF₃ | H | H | ᵗC₄H₉ | H | H | H | H | H | — — |
| 1-12 | Ir | 1 | 1 | | Ph | H | CF₃ | H | ᵗC₄H₉ | H | H | H | H | H | pic |
| 1-12X | Ir | 1 | 1 | | Ph | H | CF₃ | H | ᵗC₄H₉ | H | H | H | H | H | acac |
| 1-12Y | Ir | 0 | 1 | | Ph | H | CF₃ | H | ᵗC₄H₉ | H | H | H | H | H | — — |
| 1-13 | Ir | 1 | 1 | | Ph | H | CF₃ | H | CH₃ | H | H | H | H | H | pic |
| 1-13X | Ir | 1 | 1 | | Ph | H | CF₃ | H | CH₃ | H | H | H | H | H | acac |
| 1-13Y | Ir | 0 | 1 | | Ph | H | CF₃ | H | CH₃ | H | H | H | H | H | — — |
| 1-14 | Ir | 1 | 1 | | Ph | H | CF₃ | CF₃ | H | H | H | H | H | H | pic |
| 1-14X | Ir | 1 | 1 | | Ph | H | CF₃ | CF₃ | H | H | H | H | H | H | acac |
| 1-14Y | Ir | 0 | 1 | | Ph | H | CF₃ | CF₃ | H | H | H | H | H | H | — — |
| 1-15 | Ir | 1 | 1 | | Ph | H | H | NO₂ | H | H | H | H | H | H | pic |
| 1-15X | Ir | 1 | 1 | | Ph | H | H | NO₂ | H | H | H | H | H | H | acac |
| 1-15Y | Ir | 0 | 1 | | Ph | H | H | NO₂ | H | H | H | H | H | H | — — |
| 1-16 | Ir | 1 | 1 | | Ph | F | H | NO₂ | H | H | H | H | H | H | pic |
| 1-16X | Ir | 1 | 1 | | Ph | F | H | NO₂ | H | H | H | H | H | H | acac |
| 1-16Y | Ir | 0 | 1 | | Ph | F | H | NO₂ | H | H | H | H | H | H | — — |
| 1-17 | Ir | 1 | 1 | | Ph | F | H | NO₂ | F | H | H | H | H | H | pic |
| 1-17X | Ir | 1 | 1 | | Ph | F | H | NO₂ | F | H | H | H | H | H | acac |
| 1-17Y | Ir | 0 | 1 | | Ph | F | H | NO₂ | F | H | H | H | H | H | — — |
| 1-18 | Ir | 1 | 1 | | Ph | H | NO₂ | H | NO₂ | H | H | H | H | H | pic |
| 1-18X | Ir | 1 | 1 | | Ph | H | NO₂ | H | NO₂ | H | H | H | H | H | acac |
| 1-18Y | Ir | 0 | 1 | | Ph | H | NO₂ | H | NO₂ | H | H | H | H | H | — — |
| 1-19 | Ir | 1 | 1 | | Ph | NO₂ | H | H | NO₂ | H | H | H | H | H | pic |
| 1-19X | Ir | 1 | 1 | | Ph | NO₂ | H | H | NO₂ | H | H | H | H | H | acac |
| 1-19Y | Ir | 0 | 1 | | Ph | NO₂ | H | H | NO₂ | H | H | H | H | H | — — |
| 1-20 | Ir | 1 | 1 | | Ph | H | H | CF₃ | H | H | H | H | H | H | pic |
| 1-20X | Ir | 1 | 1 | | Ph | H | H | CF₃ | H | H | H | H | H | H | acac |
| 1-20Y | Ir | 0 | 1 | | Ph | H | H | CF₃ | H | H | H | H | H | H | — — |
| 1-21 | Ir | 1 | 1 | | Ph | H | Cl | CF₃ | H | H | H | H | H | H | pic |
| 1-21X | Ir | 1 | 1 | | Ph | H | Cl | CF₃ | H | H | H | H | H | H | acac |
| 1-21Y | Ir | 0 | 1 | | Ph | H | Cl | CF₃ | H | H | H | H | H | H | — — |
| 1-22 | Ir | 1 | 1 | | Ph | H | NO₂ | H | H | H | H | H | H | H | pic |
| 1-22X | Ir | 1 | 1 | | Ph | H | NO₂ | H | H | H | H | H | H | H | acac |
| 1-22Y | Ir | 0 | 1 | | Ph | H | NO₂ | H | H | H | H | H | H | H | — — |
| 1-23 | Ir | 1 | 1 | | Ph | H | CF₃ | H | H | H | H | H | H | H | pic |
| 1-23X | Ir | 1 | 1 | | Ph | H | CF₃ | H | H | H | H | H | H | H | acac |
| 1-23Y | Ir | 0 | 1 | | Ph | H | CF₃ | H | H | H | H | H | H | H | — — |
| 1-24 | Ir | 1 | 1 | | Ph | H | NO₂ | H | CH₃ | H | H | H | H | H | pic |
| 1-24X | Ir | 1 | 1 | | Ph | H | NO₂ | H | CH₃ | H | H | H | H | H | acac |
| 1-24Y | Ir | 0 | 1 | | Ph | H | NO₂ | H | CH₃ | H | H | H | H | H | — — |
| 1-25 | Ir | 1 | 1 | | Ph | H | NO₂ | H | ᵗC₄H₉ | H | H | H | H | H | pic |
| 1-25X | Ir | 1 | 1 | | Ph | H | NO₂ | H | ᵗC₄H₉ | H | H | H | H | H | acac |
| 1-25Y | Ir | 0 | 1 | | Ph | H | NO₂ | H | ᵗC₄H₉ | H | H | H | H | H | — — |
| 1-26 | Ir | 1 | 1 | | Ph | H | H | CH₃O | H | H | H | H | H | H | pic |
| 1-26X | Ir | 1 | 1 | | Ph | H | H | CH₃O | H | H | H | H | H | H | acac |

TABLE 1-continued

| No. | M | n | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 1-26Y | Ir | 0 | 1 | | Ph | H | H | CH$_3$O | H | H | H | H | H | H | — | — |
| 1-27 | Ir | 1 | 1 | | Ph | H | CH$_3$O | H | H | H | H | H | H | H | pic | |
| 1-27X | Ir | 1 | 1 | | Ph | H | CH$_3$O | H | H | H | H | H | H | H | acac | |
| 1-27Y | Ir | 0 | 1 | | Ph | H | CH$_3$O | H | H | H | H | H | H | H | — | — |
| 1-28 | Ir | 1 | 1 | | Ph | H | CH$_3$O | H | CH$_3$ | H | H | H | H | H | pic | |
| 1-28X | Ir | 1 | 1 | | Ph | H | CH$_3$O | H | CH$_3$ | H | H | H | H | H | acac | |
| 1-28Y | Ir | 0 | 1 | | Ph | H | CH$_3$O | H | CH$_3$ | H | H | H | H | H | — | — |
| 1-29 | Ir | 1 | 1 | | Ph | H | CH$_3$O | H | $^t$C$_4$H$_9$ | H | H | H | H | H | pic | |
| 1-29X | Ir | 1 | 1 | | Ph | H | CH$_3$O | H | $^t$C$_4$H$_9$ | H | H | H | H | H | acac | |
| 1-29Y | Ir | 0 | 1 | | Ph | H | CH$_3$O | H | $^t$C$_4$H$_9$ | H | H | H | H | H | — | — |
| 1-30 | Ir | 1 | 1 | | Ph | H | H | H | H | $^t$C$_4$H$_9$ | H | H | H | H | pic | |
| 1-30X | Ir | 1 | 1 | | Ph | H | H | H | H | $^t$C$_4$H$_9$ | H | H | H | H | acac | |
| 1-30Y | Ir | 0 | 1 | | Ph | H | H | H | H | $^t$C$_4$H$_9$ | H | H | H | H | — | — |
| 1-31 | Ir | 1 | 1 | | Ph | H | F | H | F | $^t$C$_4$H$_9$ | H | H | H | H | pic | |
| 1-31X | Ir | 1 | 1 | | Ph | H | F | H | F | $^t$C$_4$H$_9$ | H | H | H | H | acac | |
| 1-31Y | Ir | 0 | 1 | | Ph | H | F | H | F | $^t$C$_4$H$_9$ | H | H | H | H | — | — |
| 1-32 | Ir | 1 | 1 | | Ph | CF$_3$ | H | CF$_3$ | H | $^t$C$_4$H$_9$ | H | H | H | H | pic | |
| 1-32X | Ir | 1 | 1 | | Ph | CF$_3$ | H | CF$_3$ | H | $^t$C$_4$H$_9$ | H | H | H | H | acac | |
| 1-32Y | Ir | 0 | 1 | | Ph | CF$_3$ | H | CF$_3$ | H | $^t$C$_4$H$_9$ | H | H | H | H | — | — |
| 1-33 | Ir | 1 | 1 | | Ph | H | CF$_3$ | H | CH$_3$ | $^t$C$_4$H$_9$ | H | H | H | H | pic | |
| 1-33X | Ir | 1 | 1 | | Ph | H | CF$_3$ | H | CH$_3$ | $^t$C$_4$H$_9$ | H | H | H | H | acac | |
| 1-33Y | Ir | 0 | 1 | | Ph | H | CF$_3$ | H | CH$_3$ | $^t$C$_4$H$_9$ | H | H | H | H | — | — |
| 1-34 | Ir | 1 | 1 | | Ph | H | F | H | F | H | CH$_3$ | H | H | H | pic | |
| 1-34X | Ir | 1 | 1 | | Ph | H | F | H | F | H | CH$_3$ | H | H | H | acac | |
| 1-34Y | Ir | 0 | 1 | | Ph | H | F | H | F | H | CH$_3$ | H | H | H | — | — |
| 1-35 | Ir | 1 | 1 | | Ph | CF$_3$ | H | CF$_3$ | H | H | CH$_3$ | H | H | H | pic | |
| 1-35X | Ir | 1 | 1 | | Ph | CF$_3$ | H | CF$_3$ | H | H | CH$_3$ | H | H | H | acac | |
| 1-35Y | Ir | 0 | 1 | | Ph | CF$_3$ | H | CF$_3$ | H | H | CH$_3$ | H | H | H | — | — |
| 1-36 | Ir | 1 | 1 | | Ph | H | Si(CH$_3$)$_3$ | H | H | H | H | H | H | H | pic | |
| 1-36X | Ir | 1 | 1 | | Ph | H | Si(CH$_3$)$_3$ | H | H | H | H | H | H | H | acac | |
| 1-36Y | Ir | 0 | 1 | | Ph | H | Si(CH$_3$)$_3$ | H | H | H | H | H | H | H | — | — |
| 1-37 | Ir | 1 | 1 | | Ph | H | H | Si(CH$_3$)$_3$ | H | H | H | H | H | H | pic | |
| 1-37X | Ir | 1 | 1 | | Ph | H | H | Si(CH$_3$)$_3$ | H | H | H | H | H | H | acac | |
| 1-37Y | Ir | 0 | 1 | | Ph | H | H | Si(CH$_3$)$_3$ | H | H | H | H | H | H | — | — |
| 1-38 | Ir | 1 | 1 | | Ph | H | H | H | Si(CH$_3$)$_3$ | H | H | H | H | H | pic | |
| 1-38X | Ir | 1 | 1 | | Ph | H | H | H | Si(CH$_3$)$_3$ | H | H | H | H | H | acac | |
| 1-38Y | Ir | 0 | 1 | | Ph | H | H | H | Si(CH$_3$)$_3$ | H | H | H | H | H | — | — |
| 1-39 | Ir | 1 | 1 | | Ph | H | F | H | Si(CH$_3$)$_3$ | H | H | H | H | H | pic | |
| 1-39X | Ir | 1 | 1 | | Ph | H | F | H | Si(CH$_3$)$_3$ | H | H | H | H | H | acac | |
| 1-39Y | Ir | 0 | 1 | | Ph | H | F | H | Si(CH$_3$)$_3$ | H | H | H | H | H | — | — |
| 1-40 | Ir | 1 | 1 | | Ph | H | CF$_3$ | H | Si(CH$_3$)$_3$ | H | H | H | H | H | pic | |
| 1-40X | Ir | 1 | 1 | | Ph | H | CF$_3$ | H | Si(CH$_3$)$_3$ | H | H | H | H | H | acac | |
| 1-40Y | Ir | 0 | 1 | | Ph | H | CF$_3$ | H | Si(CH$_3$)$_3$ | H | H | H | H | H | — | — |
| 1-41 | Ir | 1 | 1 | | Ph | H | Si(CH$_3$)$_3$ | H | F | H | H | H | H | H | pic | |
| 1-41X | Ir | 1 | 1 | | Ph | H | Si(CH$_3$)$_3$ | H | F | H | H | H | H | H | acac | |
| 1-41Y | Ir | 0 | 1 | | Ph | H | Si(CH$_3$)$_3$ | H | F | H | H | H | H | H | — | — |
| 1-42 | Ir | 1 | 1 | | Ph | H | Si(CH$_3$)$_3$ | H | CF$_3$ | H | H | H | H | H | pic | |
| 1-42X | Ir | 1 | 1 | | Ph | H | Si(CH$_3$)$_3$ | H | CF$_3$ | H | H | H | H | H | acac | |
| 1-42Y | Ir | 0 | 1 | | Ph | H | Si(CH$_3$)$_3$ | H | CF$_3$ | H | H | H | H | H | — | — |
| 1-43 | Ir | 1 | 1 | | Ph | Si(CH$_3$)$_3$ | H | Si(CH$_3$)$_3$ | H | H | H | H | H | H | pic | |
| 1-43X | Ir | 1 | 1 | | Ph | Si(CH$_3$)$_3$ | H | Si(CH$_3$)$_3$ | H | H | H | H | H | H | acac | |
| 1-43Y | Ir | 0 | 1 | | Ph | Si(CH$_3$)$_3$ | H | Si(CH$_3$)$_3$ | H | H | H | H | H | H | — | — |
| 1-44 | Ir | 1 | 1 | | Ph | H | H | H | COCH$_3$ | H | H | H | H | H | pic | |
| 1-44X | Ir | 1 | 1 | | Ph | H | H | H | COCH$_3$ | H | H | H | H | H | acac | |
| 1-44Y | Ir | 0 | 1 | | Ph | H | H | H | COCH$_3$ | H | H | H | H | H | — | — |
| 1-45 | Ir | 1 | 1 | | Ph | H | H | COCH$_3$ | H | H | H | H | H | H | pic | |
| 1-45X | Ir | 1 | 1 | | Ph | H | H | COCH$_3$ | H | H | H | H | H | H | acac | |
| 1-45Y | Ir | 0 | 1 | | Ph | H | H | COCH$_3$ | H | H | H | H | H | H | — | — |
| 1-46 | Ir | 1 | 1 | | Ph | H | COCH$_3$ | H | H | H | H | H | H | H | pic | |
| 1-46X | Ir | 1 | 1 | | Ph | H | COCH$_3$ | H | H | H | H | H | H | H | acac | |
| 1-46Y | Ir | 0 | 1 | | Ph | H | COCH$_3$ | H | H | H | H | H | H | H | — | — |
| 1-47 | Ir | 1 | 1 | | Ph | H | H | BL | H | H | H | H | H | H | pic | |
| 1-47X | Ir | 1 | 1 | | Ph | H | H | BL | H | H | H | H | H | H | acac | |
| 1-47Y | Ir | 0 | 1 | | Ph | H | H | BL | H | H | H | H | H | H | — | — |
| 1-48 | Ir | 1 | 1 | | Ph | H | BL | H | H | H | H | H | H | H | pic | |
| 1-48X | Ir | 1 | 1 | | Ph | H | BL | H | H | H | H | H | H | H | acac | |
| 1-48Y | Ir | 0 | 1 | | Ph | H | BL | H | H | H | H | H | H | H | — | — |
| 1-49 | Ir | 1 | 1 | | Ph | H | H | PL | H | H | H | H | H | H | pic | |
| 1-49X | Ir | 1 | 1 | | Ph | H | H | PL | H | H | H | H | H | H | acac | |
| 1-49Y | Ir | 0 | 1 | | Ph | H | H | PL | H | H | H | H | H | H | — | — |
| 1-50 | Ir | 1 | 1 | | Ph | H | PL | H | H | H | H | H | H | H | pic | |
| 1-50X | Ir | 1 | 1 | | Ph | H | PL | H | H | H | H | H | H | H | acac | |
| 1-50Y | Ir | 0 | 1 | | Ph | H | PL | H | H | H | H | H | H | H | — | — |
| 1-51 | Ir | 1 | 1 | | Ph | H | H | MEE1 | H | H | H | H | H | H | pic | |
| 1-51X | Ir | 1 | 1 | | Ph | H | H | MEE1 | H | H | H | H | H | H | acac | |
| 1-51Y | Ir | 0 | 1 | | Ph | H | H | MEE1 | H | H | H | H | H | H | — | — |
| 1-52 | Ir | 1 | 1 | | Ph | H | MEE1 | H | H | H | H | H | H | H | pic | |

TABLE 1-continued

| No. | M | n | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 1-52X | Ir | 1 | 1 | | Ph | H | | MEE1 | | H | H | H | H | H | H | acac |
| 1-52Y | Ir | 0 | 1 | | Ph | H | | MEE1 | | H | H | H | H | H | H | — — |
| 1-53 | Ir | 1 | 1 | | Ph | H | H | | MEE2 | H | H | H | H | H | H | pic |
| 1-53X | Ir | 1 | 1 | | Ph | H | H | | MEE2 | H | H | H | H | H | H | acac |
| 1-53Y | Ir | 0 | 1 | | Ph | H | H | | MEE2 | H | H | H | H | H | H | — — |
| 1-54 | Ir | 1 | 1 | | Ph | H | | MEE2 | | H | H | H | H | H | H | pic |
| 1-54X | Ir | 1 | 1 | | Ph | H | | MEE2 | | H | H | H | H | H | H | acac |
| 1-54Y | Ir | 0 | 1 | | Ph | H | | MEE2 | | H | H | H | H | H | H | — — |
| 1-55 | Ir | 1 | 1 | | Ph | H | H | | PA1 | H | H | H | H | H | H | pic |
| 1-55X | Ir | 1 | 1 | | Ph | H | H | | PA1 | H | H | H | H | H | H | acac |
| 1-55Y | Ir | 0 | 1 | | Ph | H | H | | PA1 | H | H | H | H | H | H | — — |
| 1-56 | Ir | 1 | 1 | | Ph | H | | PA1 | | H | H | H | H | H | H | pic |
| 1-56X | Ir | 1 | 1 | | Ph | H | | PA1 | | H | H | H | H | H | H | acac |
| 1-56Y | Ir | 0 | 1 | | Ph | H | | PA1 | | H | H | H | H | H | H | — — |
| 1-57 | Ir | 1 | 1 | | Ph | H | H | | PA2 | H | H | H | H | H | H | pic |
| 1-57X | Ir | 1 | 1 | | Ph | H | H | | PA2 | H | H | H | H | H | H | acac |
| 1-57Y | Ir | 0 | 1 | | Ph | H | H | | PA2 | H | H | H | H | H | H | — — |
| 1-58 | Ir | 1 | 1 | | Ph | H | | PA2 | | H | H | H | H | H | H | pic |
| 1-58X | Ir | 1 | 1 | | Ph | H | | PA2 | | H | H | H | H | H | H | acac |
| 1-58Y | Ir | 0 | 1 | | Ph | H | | PA2 | | H | H | H | H | H | H | — — |
| 1-59 | Ir | 1 | 1 | | Ph | H | H | | EA1 | H | H | H | H | H | H | pic |
| 1-59X | Ir | 1 | 1 | | Ph | H | H | | EA1 | H | H | H | H | H | H | acac |
| 1-59Y | Ir | 0 | 1 | | Ph | H | H | | EA1 | H | H | H | H | H | H | — — |
| 1-60 | Ir | 1 | 1 | | Ph | H | | EA2 | | H | H | H | H | H | H | pic |
| 1-60X | Ir | 1 | 1 | | Ph | H | | EA2 | | H | H | H | H | H | H | acac |
| 1-60Y | Ir | 0 | 1 | | Ph | H | | EA2 | | H | H | H | H | H | H | — — |
| 1-61 | Ir | 1 | 1 | | Ph | H | H | | ME | H | H | H | H | H | H | pic |
| 1-61X | Ir | 1 | 1 | | Ph | H | H | | ME | H | H | H | H | H | H | acac |
| 1-61Y | Ir | 0 | 1 | | Ph | H | H | | ME | H | H | H | H | H | H | — — |
| 1-62 | Ir | 1 | 1 | | Ph | H | | ME | | H | H | H | H | H | H | pic |
| 1-62X | Ir | 1 | 1 | | Ph | H | | ME | | H | H | H | H | H | H | acac |
| 1-62Y | Ir | 0 | 1 | | Ph | H | | ME | | H | H | H | H | H | H | — — |
| 1-63 | Ir | 1 | 1 | | Ph | H | H | | AT | H | H | H | H | H | H | pic |
| 1-63X | Ir | 1 | 1 | | Ph | H | H | | AT | H | H | H | H | H | H | acac |
| 1-63Y | Ir | 0 | 1 | | Ph | H | H | | AT | H | H | H | H | H | H | — — |
| 1-64 | Ir | 1 | 1 | | Ph | H | | AT | | H | H | H | H | H | H | pic |
| 1-64X | Ir | 1 | 1 | | Ph | H | | AT | | H | H | H | H | H | H | acac |
| 1-64Y | Ir | 0 | 1 | | Ph | H | | AT | | H | H | H | H | H | H | — — |
| 1-65 | Ir | 1 | 1 | | Ph | H | H | | MES1 | H | H | H | H | H | H | pic |
| 1-65X | Ir | 1 | 1 | | Ph | H | H | | MES1 | H | H | H | H | H | H | acac |
| 1-65Y | Ir | 0 | 1 | | Ph | H | H | | MES1 | H | H | H | H | H | H | — — |
| 1-66 | Ir | 1 | 1 | | Ph | H | | MES1 | | H | H | H | H | H | H | pic |
| 1-66X | Ir | 1 | 1 | | Ph | H | | MES1 | | H | H | H | H | H | H | acac |
| 1-66Y | Ir | 0 | 1 | | Ph | H | | MES1 | | H | H | H | H | H | H | — — |
| 1-67 | Ir | 1 | 1 | | Ph | H | H | | MES2 | H | H | H | H | H | H | pic |
| 1-67X | Ir | 1 | 1 | | Ph | H | H | | MES2 | H | H | H | H | H | H | acac |
| 1-67Y | Ir | 0 | 1 | | Ph | H | H | | MES2 | H | H | H | H | H | H | — — |
| 1-68 | Ir | 1 | 1 | | Ph | H | | MES2 | | H | H | H | H | H | H | pic |
| 1-68X | Ir | 1 | 1 | | Ph | H | | MES2 | | H | H | H | H | H | H | acac |
| 1-68Y | Ir | 0 | 1 | | Ph | H | | MES2 | | H | H | H | H | H | H | — — |
| 1-69 | Ir | 1 | 1 | | Ph | H | H | | PS1 | H | H | H | H | H | H | pic |
| 1-69X | Ir | 1 | 1 | | Ph | H | H | | PS1 | H | H | H | H | H | H | acac |
| 1-69Y | Ir | 0 | 1 | | Ph | H | H | | PS1 | H | H | H | H | H | H | — — |
| 1-70 | Ir | 1 | 1 | | Ph | H | | PS1 | | H | H | H | H | H | H | pic |
| 1-70X | Ir | 1 | 1 | | Ph | H | | PS1 | | H | H | H | H | H | H | acac |
| 1-70Y | Ir | 0 | 1 | | Ph | H | | PS1 | | H | H | H | H | H | H | — — |
| 1-71 | Ir | 1 | 1 | | Ph | H | H | | PS2 | H | H | H | H | H | H | pic |
| 1-71X | Ir | 1 | 1 | | Ph | H | H | | PS2 | H | H | H | H | H | H | acac |
| 1-71Y | Ir | 0 | 1 | | Ph | H | H | | PS2 | H | H | H | H | H | H | — — |
| 1-72 | Ir | 1 | 1 | | Ph | H | | PS2 | | H | H | H | H | H | H | pic |
| 1-72X | Ir | 1 | 1 | | Ph | H | | PS2 | | H | H | H | H | H | H | acac |
| 1-72Y | Ir | 0 | 1 | | Ph | H | | PS2 | | H | H | H | H | H | H | — — |
| 1-73 | Ir | 1 | 1 | | Ph | H | H | | BAL1 | H | H | H | H | H | H | pic |
| 1-73X | Ir | 1 | 1 | | Ph | H | H | | BAL1 | H | H | H | H | H | H | acac |
| 1-73Y | Ir | 0 | 1 | | Ph | H | H | | BAL1 | H | H | H | H | H | H | — — |
| 1-74 | Ir | 1 | 1 | | Ph | H | | BAL1 | | H | H | H | H | H | H | pic |
| 1-74X | Ir | 1 | 1 | | Ph | H | | BAL1 | | H | H | H | H | H | H | acac |
| 1-74Y | Ir | 0 | 1 | | Ph | H | | BAL1 | | H | H | H | H | H | H | — — |
| 1-75 | Ir | 1 | 1 | | Ph | H | H | | BAL2 | H | H | H | H | H | H | pic |
| 1-75X | Ir | 1 | 1 | | Ph | H | H | | BAL2 | H | H | H | H | H | H | acac |
| 1-75Y | Ir | 0 | 1 | | Ph | H | H | | BAL2 | H | H | H | H | H | H | — — |
| 1-76 | Ir | 1 | 1 | | Ph | H | | BAL2 | | H | H | H | H | H | H | pic |
| 1-76X | Ir | 1 | 1 | | Ph | H | | BAL2 | | H | H | H | H | H | H | acac |
| 1-76Y | Ir | 0 | 1 | | Ph | H | | BAL2 | | H | H | H | H | H | H | — — |
| 1-77 | Ir | 1 | 1 | | Ph | H | H | | MEK1 | H | H | H | H | H | H | pic |
| 1-77X | Ir | 1 | 1 | | Ph | H | H | | MEK1 | H | H | H | H | H | H | acac |
| 1-77Y | Ir | 0 | 1 | | Ph | H | H | | MEK1 | H | H | H | H | H | H | — — |

TABLE 1-continued

| No. | M | n | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1-78  | Ir | 1 | 1 | Ph | H |      | MEK1 | H    | H | H | H | H | H | pic |
| 1-78X | Ir | 1 | 1 | Ph | H |      | MEK1 | H    | H | H | H | H | H | acac |
| 1-78Y | Ir | 0 | 1 | Ph | H |      | MEK1 | H    | H | H | H | H | H | — — |
| 1-79  | Ir | 1 | 1 | Ph | H | H    |      | MEK2 | H | H | H | H | H | pic |
| 1-79X | Ir | 1 | 1 | Ph | H | H    |      | MEK2 | H | H | H | H | H | acac |
| 1-79Y | Ir | 0 | 1 | Ph | H | H    |      | MEK2 | H | H | H | H | H | — — |
| 1-80  | Ir | 1 | 1 | Ph | H |      | MEK2 | H    | H | H | H | H | H | pic |
| 1-80X | Ir | 1 | 1 | Ph | H |      | MEK2 | H    | H | H | H | H | H | acac |
| 1-80Y | Ir | 0 | 1 | Ph | H |      | MEK2 | H    | H | H | H | H | H | — — |
| 1-81  | Ir | 1 | 1 | Ph | H | H    |      | PAL1 | H | H | H | H | H | pic |
| 1-81X | Ir | 1 | 1 | Ph | H | H    |      | PAL1 | H | H | H | H | H | acac |
| 1-81Y | Ir | 0 | 1 | Ph | H | H    |      | PAL1 | H | H | H | H | H | — — |
| 1-82  | Ir | 1 | 1 | Ph | H |      | PAL1 | H    | H | H | H | H | H | pic |
| 1-82X | Ir | 1 | 1 | Ph | H |      | PAL1 | H    | H | H | H | H | H | acac |
| 1-82Y | Ir | 0 | 1 | Ph | H |      | PAL1 | H    | H | H | H | H | H | — — |
| 1-83  | Ir | 1 | 1 | Ph | H | H    |      | PAL2 | H | H | H | H | H | pic |
| 1-83X | Ir | 1 | 1 | Ph | H | H    |      | PAL2 | H | H | H | H | H | acac |
| 1-83Y | Ir | 0 | 1 | Ph | H | H    |      | PAL2 | H | H | H | H | H | — — |
| 1-84  | Ir | 1 | 1 | Ph | H |      | PAL2 | H    | H | H | H | H | H | pic |
| 1-84X | Ir | 1 | 1 | Ph | H |      | PAL2 | H    | H | H | H | H | H | acac |
| 1-84Y | Ir | 0 | 1 | Ph | H |      | PAL2 | H    | H | H | H | H | H | — — |
| 1-85  | Ir | 1 | 1 | Ph | H | H    |      | MMK  | H | H | H | H | H | pic |
| 1-85X | Ir | 1 | 1 | Ph | H | H    |      | MMK  | H | H | H | H | H | acac |
| 1-85Y | Ir | 0 | 1 | Ph | H | H    |      | MMK  | H | H | H | H | H | — — |
| 1-86  | Ir | 1 | 1 | Ph | H |      | MMK  | H    | H | H | H | H | H | pic |
| 1-86X | Ir | 1 | 1 | Ph | H |      | MMK  | H    | H | H | H | H | H | acac |
| 1-86Y | Ir | 0 | 1 | Ph | H |      | MMK  | H    | H | H | H | H | H | — — |
| 1-87  | Ir | 1 | 1 | Ph | H | H    |      | EES1 | H | H | H | H | H | pic |
| 1-87X | Ir | 1 | 1 | Ph | H | H    |      | EES1 | H | H | H | H | H | acac |
| 1-87Y | Ir | 0 | 1 | Ph | H | H    |      | EES1 | H | H | H | H | H | — — |
| 1-88  | Ir | 1 | 1 | Ph | H |      | EES2 | H    | H | H | H | H | H | pic |
| 1-88X | Ir | 1 | 1 | Ph | H |      | EES2 | H    | H | H | H | H | H | acac |
| 1-88Y | Ir | 0 | 1 | Ph | H |      | EES2 | H    | H | H | H | H | H | — — |
| 1-89  | Ir | 1 | 1 | Ph | H | H    |      | PSE1 | H | H | H | H | H | pic |
| 1-89X | Ir | 1 | 1 | Ph | H | H    |      | PSE1 | H | H | H | H | H | acac |
| 1-89Y | Ir | 0 | 1 | Ph | H | H    |      | PSE1 | H | H | H | H | H | — — |
| 1-90  | Ir | 1 | 1 | Ph | H |      | PSE2 | H    | H | H | H | H | H | pic |
| 1-90X | Ir | 1 | 1 | Ph | H |      | PSE2 | H    | H | H | H | H | H | acac |
| 1-90Y | Ir | 0 | 1 | Ph | H |      | PSE2 | H    | H | H | H | H | H | — — |
| 1-91  | Ir | 1 | 1 | Ph | H | H    |      | AME1 | H | H | H | H | H | pic |
| 1-91X | Ir | 1 | 1 | Ph | H | H    |      | AME1 | H | H | H | H | H | acac |
| 1-91Y | Ir | 0 | 1 | Ph | H | H    |      | AME1 | H | H | H | H | H | — — |
| 1-92  | Ir | 1 | 1 | Ph | H |      | AME1 | H    | H | H | H | H | H | pic |
| 1-92X | Ir | 1 | 1 | Ph | H |      | AME1 | H    | H | H | H | H | H | acac |
| 1-92Y | Ir | 0 | 1 | Ph | H |      | AME1 | H    | H | H | H | H | H | — — |
| 1-93  | Ir | 1 | 1 | Ph | H | H    |      | AME2 | H | H | H | H | H | pic |
| 1-93X | Ir | 1 | 1 | Ph | H | H    |      | AME2 | H | H | H | H | H | acac |
| 1-93Y | Ir | 0 | 1 | Ph | H | H    |      | AME2 | H | H | H | H | H | — — |
| 1-94  | Ir | 1 | 1 | Ph | H |      | AME2 | H    | H | H | H | H | H | pic |
| 1-94X | Ir | 1 | 1 | Ph | H |      | AME2 | H    | H | H | H | H | H | acac |
| 1-94Y | Ir | 0 | 1 | Ph | H |      | AME2 | H    | H | H | H | H | H | — — |
| 1-95  | Ir | 1 | 1 | Ph | H | H    |      | EAE1 | H | H | H | H | H | pic |
| 1-95X | Ir | 1 | 1 | Ph | H | H    |      | EAE1 | H | H | H | H | H | acac |
| 1-95Y | Ir | 0 | 1 | Ph | H | H    |      | EAE1 | H | H | H | H | H | — — |
| 1-96  | Ir | 1 | 1 | Ph | H |      | EAE1 | H    | H | H | H | H | H | pic |
| 1-96X | Ir | 1 | 1 | Ph | H |      | EAE1 | H    | H | H | H | H | H | acac |
| 1-96Y | Ir | 0 | 1 | Ph | H |      | EAE1 | H    | H | H | H | H | H | — — |
| 1-97  | Ir | 1 | 1 | Ph | H | H    |      | EAE2 | H | H | H | H | H | pic |
| 1-97X | Ir | 1 | 1 | Ph | H | H    |      | EAE2 | H | H | H | H | H | acac |
| 1-97Y | Ir | 0 | 1 | Ph | H | H    |      | EAE2 | H | H | H | H | H | — — |
| 1-98  | Ir | 1 | 1 | Ph | H |      | EAE2 | H    | H | H | H | H | H | pic |
| 1-98X | Ir | 1 | 1 | Ph | H |      | EAE2 | H    | H | H | H | H | H | acac |
| 1-98Y | Ir | 0 | 1 | Ph | H |      | EAE2 | H    | H | H | H | H | H | — — |
| 1-99  | Ir | 1 | 1 | Ph | H | H    |      | AAE1 | H | H | H | H | H | pic |
| 1-99X | Ir | 1 | 1 | Ph | H | H    |      | AAE1 | H | H | H | H | H | acac |
| 1-99Y | Ir | 0 | 1 | Ph | H | H    |      | AAE1 | H | H | H | H | H | — — |
| 1-100  | Ir | 1 | 1 | Ph | H |      | AAE1 | H    | H | H | H | H | H | pic |
| 1-100X | Ir | 1 | 1 | Ph | H |      | AAE1 | H    | H | H | H | H | H | acac |
| 1-100Y | Ir | 0 | 1 | Ph | H |      | AAE1 | H    | H | H | H | H | H | — — |
| 1-101  | Ir | 1 | 1 | Ph | H | H    |      | AAE2 | H | H | H | H | H | pic |
| 1-101X | Ir | 1 | 1 | Ph | H | H    |      | AAE2 | H | H | H | H | H | acac |
| 1-101Y | Ir | 0 | 1 | Ph | H | H    |      | AAE2 | H | H | H | H | H | — — |
| 1-102  | Ir | 1 | 1 | Ph | H |      | AAE2 | H    | H | H | H | H | H | pic |
| 1-102X | Ir | 1 | 1 | Ph | H |      | AAE2 | H    | H | H | H | H | H | acac |
| 1-102Y | Ir | 0 | 1 | Ph | H |      | AAE2 | H    | H | H | H | H | H | — — |
| 1-103  | Ir | 1 | 1 | Ph | H | H    |      | PME1 | H | H | H | H | H | pic |
| 1-103X | Ir | 1 | 1 | Ph | H | H    |      | PME1 | H | H | H | H | H | acac |

TABLE 1-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 1-103Y | Ir | 0 | 1 | Ph | H | H | | PME1 | H | H | H | H | H | — | — |
| 1-104 | Ir | 1 | 1 | Ph | H | | PME1 | | H | H | H | H | H | pic | |
| 1-104X | Ir | 1 | 1 | Ph | H | | PME1 | | H | H | H | H | H | acac | |
| 1-104Y | Ir | 0 | 1 | Ph | H | | PME1 | | H | H | H | H | H | — | — |
| 1-105 | Ir | 1 | 1 | Ph | H | H | | PME2 | H | H | H | H | H | pic | |
| 1-105X | Ir | 1 | 1 | Ph | H | H | | PME2 | H | H | H | H | H | acac | |
| 1-105Y | Ir | 0 | 1 | Ph | H | H | | PME2 | H | H | H | H | H | — | — |
| 1-106 | Ir | 1 | 1 | Ph | H | | PME2 | | H | H | H | H | H | pic | |
| 1-106X | Ir | 1 | 1 | Ph | H | | PME2 | | H | H | H | H | H | acac | |
| 1-106Y | Ir | 0 | 1 | Ph | H | | PME2 | | H | H | H | H | H | — | — |
| 1-107 | Ir | 1 | 1 | Ph | H | H | | MET1 | H | H | H | H | H | pic | |
| 1-107X | Ir | 1 | 1 | Ph | H | H | | MET1 | H | H | H | H | H | acac | |
| 1-107Y | Ir | 0 | 1 | Ph | H | H | | MET1 | H | H | H | H | H | — | — |
| 1-108 | Ir | 1 | 1 | Ph | H | | MET1 | | H | H | H | H | H | pic | |
| 1-108X | Ir | 1 | 1 | Ph | H | | MET1 | | H | H | H | H | H | acac | |
| 1-108Y | Ir | 0 | 1 | Ph | H | | MET1 | | H | H | H | H | H | — | — |
| 1-109 | Ir | 1 | 1 | Ph | H | H | | MET2 | H | H | H | H | H | pic | |
| 1-109X | Ir | 1 | 1 | Ph | H | H | | MET2 | H | H | H | H | H | acac | |
| 1-109Y | Ir | 0 | 1 | Ph | H | H | | MET2 | H | H | H | H | H | — | — |
| 1-110 | Ir | 1 | 1 | Ph | H | | MET2 | | H | H | H | H | H | pic | |
| 1-110X | Ir | 1 | 1 | Ph | H | | MET2 | | H | H | H | H | H | acac | |
| 1-110Y | Ir | 0 | 1 | Ph | H | | MET2 | | H | H | H | H | H | — | — |
| 1-111 | Ir | 1 | 1 | Ph | H | H | | EE1 | H | H | H | H | H | pic | |
| 1-111X | Ir | 1 | 1 | Ph | H | H | | EE1 | H | H | H | H | H | acac | |
| 1-111Y | Ir | 0 | 1 | Ph | H | H | | EE1 | H | H | H | H | H | — | — |
| 1-112 | Ir | 1 | 1 | Ph | H | | EE1 | | H | H | H | H | H | pic | |
| 1-112X | Ir | 1 | 1 | Ph | H | | EE1 | | H | H | H | H | H | acac | |
| 1-112Y | Ir | 0 | 1 | Ph | H | | EE1 | | H | H | H | H | H | — | — |
| 1-113 | Ir | 1 | 1 | Ph | H | H | | EE2 | H | H | H | H | H | pic | |
| 1-113X | Ir | 1 | 1 | Ph | H | H | | EE2 | H | H | H | H | H | acac | |
| 1-113Y | Ir | 0 | 1 | Ph | H | H | | EE2 | H | H | H | H | H | — | — |
| 1-114 | Ir | 1 | 1 | Ph | H | | EE2 | | H | H | H | H | H | pic | |
| 1-114X | Ir | 1 | 1 | Ph | H | | EE2 | | H | H | H | H | H | acac | |
| 1-114Y | Ir | 0 | 1 | Ph | H | | EE2 | | H | H | H | H | H | — | — |
| 1-115 | Ir | 1 | 1 | Ph | H | H | | MS1 | H | H | H | H | H | pic | |
| 1-115X | Ir | 1 | 1 | Ph | H | H | | MS1 | H | H | H | H | H | acac | |
| 1-115Y | Ir | 0 | 1 | Ph | H | H | | MS1 | H | H | H | H | H | — | — |
| 1-116 | Ir | 1 | 1 | Ph | H | | MS1 | | H | H | H | H | H | pic | |
| 1-116X | Ir | 1 | 1 | Ph | H | | MS1 | | H | H | H | H | H | acac | |
| 1-116Y | Ir | 0 | 1 | Ph | H | | MS1 | | H | H | H | H | H | — | — |
| 1-117 | Ir | 1 | 1 | Ph | H | H | | MS2 | H | H | H | H | H | pic | |
| 1-117X | Ir | 1 | 1 | Ph | H | H | | MS2 | H | H | H | H | H | acac | |
| 1-117Y | Ir | 0 | 1 | Ph | H | H | | MS2 | H | H | H | H | H | — | — |
| 1-118 | Ir | 1 | 1 | Ph | H | | MS2 | | H | H | H | H | H | pic | |
| 1-118X | Ir | 1 | 1 | Ph | H | | MS2 | | H | H | H | H | H | acac | |
| 1-118Y | Ir | 0 | 1 | Ph | H | | MS2 | | H | H | H | H | H | — | — |

TABLE 2

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2-1 | Ir | 1 | 2 | Ph | H | H | H | H | H | H | H | H | H | pic | |
| 2-1X | Ir | 1 | 2 | Ph | H | H | H | H | H | H | H | H | H | acac | |
| 2-1Y | Ir | 0 | 2 | Ph | H | H | H | H | H | H | H | H | H | — | — |
| 2-2 | Ir | 1 | 2 | Ph | H | F | H | F | H | H | H | H | H | pic | |
| 2-2X | Ir | 1 | 2 | Ph | H | F | H | F | H | H | H | H | H | acac | |
| 2-2Y | Ir | 0 | 2 | Ph | H | F | H | F | H | H | H | H | H | — | — |
| 2-3 | Ir | 1 | 2 | Ph | F | H | H | F | H | H | H | H | H | pic | |
| 2-3X | Ir | 1 | 2 | Ph | F | H | H | F | H | H | H | H | H | acac | |
| 2-3Y | Ir | 0 | 2 | Ph | F | H | H | F | H | H | H | H | H | — | — |
| 2-4 | Ir | 1 | 2 | Ph | $CF_3$ | H | $CF_3$ | H | H | H | H | H | H | pic | |
| 2-4X | Ir | 1 | 2 | Ph | $CF_3$ | H | $CF_3$ | H | H | H | H | H | H | acac | |
| 2-4Y | Ir | 0 | 2 | Ph | $CF_3$ | H | $CF_3$ | H | H | H | H | H | H | — | — |
| 2-5 | Ir | 1 | 2 | Ph | H | F | $CF_3$ | H | H | H | H | H | H | pic | |
| 2-5X | Ir | 1 | 2 | Ph | H | F | $CF_3$ | H | H | H | H | H | H | acac | |
| 2-5Y | Ir | 0 | 2 | Ph | H | F | $CF_3$ | H | H | H | H | H | H | — | — |
| 2-6 | Ir | 1 | 2 | Ph | F | H | $CF_3$ | H | H | H | H | H | H | pic | |
| 2-6X | Ir | 1 | 2 | Ph | F | H | $CF_3$ | H | H | H | H | H | H | acac | |
| 2-6Y | Ir | 0 | 2 | Ph | F | H | $CF_3$ | H | H | H | H | H | H | — | — |
| 2-7 | Ir | 1 | 2 | Ph | F | F | F | F | H | H | H | H | H | pic | |
| 2-7X | Ir | 1 | 2 | Ph | F | F | F | F | H | H | H | H | H | acac | |
| 2-7Y | Ir | 0 | 2 | Ph | F | F | F | F | H | H | H | H | H | — | — |
| 2-8 | Ir | 1 | 2 | Ph | H | F | H | $CH_3$ | H | H | H | H | H | pic | |
| 2-8X | Ir | 1 | 2 | Ph | H | F | H | $CH_3$ | H | H | H | H | H | acac | |

TABLE 2-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2-8Y | Ir | 0 | 2 | Ph | H | F | H | CH₃ | H | H | H | H | H | — | — |
| 2-9 | Ir | 1 | 2 | Ph | H | F | H | ᵗC₄H₉ | H | H | H | H | H | pic | |
| 2-9X | Ir | 1 | 2 | Ph | H | F | H | ᵗC₄H₉ | H | H | H | H | H | acac | |
| 2-9Y | Ir | 0 | 2 | Ph | H | F | H | ᵗC₄H₉ | H | H | H | H | H | — | — |
| 2-10 | Ir | 1 | 2 | Ph | H | CF₃ | H | CF₃ | H | H | H | H | H | pic | |
| 2-10X | Ir | 1 | 2 | Ph | H | CF₃ | H | CF₃ | H | H | H | H | H | acac | |
| 2-10Y | Ir | 0 | 2 | Ph | H | CF₃ | H | CF₃ | H | H | H | H | H | — | — |
| 2-11 | Ir | 1 | 2 | Ph | CF₃ | H | H | ᵗC₄H₉ | H | H | H | H | H | pic | |
| 2-11X | Ir | 1 | 2 | Ph | CF₃ | H | H | ᵗC₄H₉ | H | H | H | H | H | acac | |
| 2-11Y | Ir | 0 | 2 | Ph | CF₃ | H | H | ᵗC₄H₉ | H | H | H | H | H | — | — |
| 2-12 | Ir | 1 | 2 | Ph | H | CF₃ | H | ᵗC₄H₉ | H | H | H | H | H | pic | |
| 2-12X | Ir | 1 | 2 | Ph | H | CF₃ | H | ᵗC₄H₉ | H | H | H | H | H | acac | |
| 2-12Y | Ir | 0 | 2 | Ph | H | CF₃ | H | ᵗC₄H₉ | H | H | H | H | H | — | — |
| 2-13 | Ir | 1 | 2 | Ph | H | CF₃ | H | CH₃ | H | H | H | H | H | pic | |
| 2-13X | Ir | 1 | 2 | Ph | H | CF₃ | H | CH₃ | H | H | H | H | H | acac | |
| 2-13Y | Ir | 0 | 2 | Ph | H | CF₃ | H | CH₃ | H | H | H | H | H | — | — |
| 2-14 | Ir | 1 | 2 | Ph | H | CF₃ | CF₃ | H | H | H | H | H | H | pic | |
| 2-14X | Ir | 1 | 2 | Ph | H | CF₃ | CF₃ | H | H | H | H | H | H | acac | |
| 2-14Y | Ir | 0 | 2 | Ph | H | CF₃ | CF₃ | H | H | H | H | H | H | — | — |
| 2-15 | Ir | 1 | 2 | Ph | H | H | NO₂ | H | H | H | H | H | H | pic | |
| 2-15X | Ir | 1 | 2 | Ph | H | H | NO₂ | H | H | H | H | H | H | acac | |
| 2-15Y | Ir | 0 | 2 | Ph | H | H | NO₂ | H | H | H | H | H | H | — | — |
| 2-16 | Ir | 1 | 2 | Ph | F | H | NO₂ | H | H | H | H | H | H | pic | |
| 2-16X | Ir | 1 | 2 | Ph | F | H | NO₂ | H | H | H | H | H | H | acac | |
| 2-16Y | Ir | 0 | 2 | Ph | F | H | NO₂ | H | H | H | H | H | H | — | — |
| 2-17 | Ir | 1 | 2 | Ph | F | H | NO₂ | F | H | H | H | H | H | pic | |
| 2-17X | Ir | 1 | 2 | Ph | F | H | NO₂ | F | H | H | H | H | H | acac | |
| 2-17Y | Ir | 0 | 2 | Ph | F | H | NO₂ | F | H | H | H | H | H | — | — |
| 2-18 | Ir | 1 | 2 | Ph | H | NO₂ | H | NO₂ | H | H | H | H | H | pic | |
| 2-18X | Ir | 1 | 2 | Ph | H | NO₂ | H | NO₂ | H | H | H | H | H | acac | |
| 2-18Y | Ir | 0 | 2 | Ph | H | NO₂ | H | NO₂ | H | H | H | H | H | — | — |
| 2-19 | Ir | 1 | 2 | Ph | NO₂ | H | H | NO₂ | H | H | H | H | H | pic | |
| 2-19X | Ir | 1 | 2 | Ph | NO₂ | H | H | NO₂ | H | H | H | H | H | acac | |
| 2-19Y | Ir | 0 | 2 | Ph | NO₂ | H | H | NO₂ | H | H | H | H | H | — | — |
| 2-20 | Ir | 1 | 2 | Ph | H | H | CF₃ | H | H | H | H | H | H | pic | |
| 2-20X | Ir | 1 | 2 | Ph | H | H | CF₃ | H | H | H | H | H | H | acac | |
| 2-20Y | Ir | 0 | 2 | Ph | H | H | CF₃ | H | H | H | H | H | H | — | — |
| 2-21 | Ir | 1 | 2 | Ph | H | Cl | CF₃ | H | H | H | H | H | H | pic | |
| 2-21X | Ir | 1 | 2 | Ph | H | Cl | CF₃ | H | H | H | H | H | H | acac | |
| 2-21Y | Ir | 0 | 2 | Ph | H | Cl | CF₃ | H | H | H | H | H | H | — | — |
| 2-22 | Ir | 1 | 2 | Ph | H | NO₂ | H | H | H | H | H | H | H | pic | |
| 2-22X | Ir | 1 | 2 | Ph | H | NO₂ | H | H | H | H | H | H | H | acac | |
| 2-22Y | Ir | 0 | 2 | Ph | H | NO₂ | H | H | H | H | H | H | H | — | — |
| 2-23 | Ir | 1 | 2 | Ph | H | CF₃ | H | H | H | H | H | H | H | pic | |
| 2-23X | Ir | 1 | 2 | Ph | H | CF₃ | H | H | H | H | H | H | H | acac | |
| 2-23Y | Ir | 0 | 2 | Ph | H | CF₃ | H | H | H | H | H | H | H | — | — |
| 2-24 | Ir | 1 | 2 | Ph | H | NO₂ | H | CH₃ | H | H | H | H | H | pic | |
| 2-24X | Ir | 1 | 2 | Ph | H | NO₂ | H | CH₃ | H | H | H | H | H | acac | |
| 2-24Y | Ir | 0 | 2 | Ph | H | NO₂ | H | CH₃ | H | H | H | H | H | — | — |
| 2-25 | Ir | 1 | 2 | Ph | H | NO₂ | H | ᵗC₄H₉ | H | H | H | H | H | pic | |
| 2-25X | Ir | 1 | 2 | Ph | H | NO₂ | H | ᵗC₄H₉ | H | H | H | H | H | acac | |
| 2-25Y | Ir | 0 | 2 | Ph | H | NO₂ | H | ᵗC₄H₉ | H | H | H | H | H | — | — |
| 2-26 | Ir | 1 | 2 | Ph | H | H | CH₃O | H | H | H | H | H | H | pic | |
| 2-26X | Ir | 1 | 2 | Ph | H | H | CH₃O | H | H | H | H | H | H | acac | |
| 2-26Y | Ir | 0 | 2 | Ph | H | H | CH₃O | H | H | H | H | H | H | — | — |
| 2-27 | Ir | 1 | 2 | Ph | H | CH₃O | H | H | H | H | H | H | H | pic | |
| 2-27X | Ir | 1 | 2 | Ph | H | CH₃O | H | H | H | H | H | H | H | acac | |
| 2-27Y | Ir | 0 | 2 | Ph | H | CH₃O | H | H | H | H | H | H | H | — | — |
| 2-28 | Ir | 1 | 2 | Ph | H | CH₃O | H | CH₃ | H | H | H | H | H | pic | |
| 2-28X | Ir | 1 | 2 | Ph | H | CH₃O | H | CH₃ | H | H | H | H | H | acac | |
| 2-28Y | Ir | 0 | 2 | Ph | H | CH₃O | H | CH₃ | H | H | H | H | H | — | — |
| 2-29 | Ir | 1 | 2 | Ph | H | CH₃O | H | ᵗC₄H₉ | H | H | H | H | H | pic | |
| 2-29X | Ir | 1 | 2 | Ph | H | CH₃O | H | ᵗC₄H₉ | H | H | H | H | H | acac | |
| 2-29Y | Ir | 0 | 2 | Ph | H | CH₃O | H | ᵗC₄H₉ | H | H | H | H | H | — | — |
| 2-30 | Ir | 1 | 2 | Ph | H | H | H | H | ᵗC₄H₉ | H | H | H | H | pic | |
| 2-30X | Ir | 1 | 2 | Ph | H | H | H | H | ᵗC₄H₉ | H | H | H | H | acac | |
| 2-30Y | Ir | 0 | 2 | Ph | H | H | H | H | ᵗC₄H₉ | H | H | H | H | — | — |
| 2-31 | Ir | 1 | 2 | Ph | H | F | H | F | ᵗC₄H₉ | H | H | H | H | pic | |
| 2-31X | Ir | 1 | 2 | Ph | H | F | H | F | ᵗC₄H₉ | H | H | H | H | acac | |
| 2-31Y | Ir | 0 | 2 | Ph | H | F | H | F | ᵗC₄H₉ | H | H | H | H | — | — |
| 2-32 | Ir | 1 | 2 | Ph | CF₃ | H | CF₃ | H | ᵗC₄H₉ | H | H | H | H | pic | |
| 2-32X | Ir | 1 | 2 | Ph | CF₃ | H | CF₃ | H | ᵗC₄H₉ | H | H | H | H | acac | |
| 2-32Y | Ir | 0 | 2 | Ph | CF₃ | H | CF₃ | H | ᵗC₄H₉ | H | H | H | H | — | — |
| 2-33 | Ir | 1 | 2 | Ph | H | CF₃ | H | CH₃ | ᵗC₄H₉ | H | H | H | H | pic | |
| 2-33X | Ir | 1 | 2 | Ph | H | CF₃ | H | CH₃ | ᵗC₄H₉ | H | H | H | H | acac | |
| 2-33Y | Ir | 0 | 2 | Ph | H | CF₃ | H | CH₃ | ᵗC₄H₉ | H | H | H | H | — | — |
| 2-34 | Ir | 1 | 2 | Ph | H | F | H | F | H | H | H | CH₃ | H | pic | |

TABLE 2-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2-34X | Ir | 1 | 2 | Ph | H | F | H | F | H | H | H | CH₃ | H | acac | |
| 2-34Y | Ir | 0 | 2 | Ph | H | F | H | F | H | H | H | CH₃ | H | — | — |
| 2-35 | Ir | 1 | 2 | Ph | CF₃ | H | CF₃ | H | H | H | H | CH₃ | H | pic | |
| 2-35X | Ir | 1 | 2 | Ph | CF₃ | H | CF₃ | H | H | H | H | CH₃ | H | acac | |
| 2-35Y | Ir | 0 | 2 | Ph | CF₃ | H | CF₃ | H | H | H | H | CH₃ | H | — | — |
| 2-36 | Ir | 1 | 2 | Ph | H | Si(CH₃)₃ | H | H | H | H | H | H | H | pic | |
| 2-36X | Ir | 1 | 2 | Ph | H | Si(CH₃)₃ | H | H | H | H | H | H | H | acac | |
| 2-36Y | Ir | 0 | 2 | Ph | H | Si(CH₃)₃ | H | H | H | H | H | H | H | — | — |
| 2-37 | Ir | 1 | 2 | Ph | H | H | Si(CH₃)₃ | H | H | H | H | H | H | pic | |
| 2-37X | Ir | 1 | 2 | Ph | H | H | Si(CH₃)₃ | H | H | H | H | H | H | acac | |
| 2-37Y | Ir | 0 | 2 | Ph | H | H | Si(CH₃)₃ | H | H | H | H | H | H | — | — |
| 2-38 | Ir | 1 | 2 | Ph | H | H | H | Si(CH₃)₃ | H | H | H | H | H | pic | |
| 2-38X | Ir | 1 | 2 | Ph | H | H | H | Si(CH₃)₃ | H | H | H | H | H | acac | |
| 2-38Y | Ir | 0 | 2 | Ph | H | H | H | Si(CH₃)₃ | H | H | H | H | H | — | — |
| 2-39 | Ir | 1 | 2 | Ph | H | F | H | Si(CH₃)₃ | H | H | H | H | H | pic | |
| 2-39X | Ir | 1 | 2 | Ph | H | F | H | Si(CH₃)₃ | H | H | H | H | H | acac | |
| 2-39Y | Ir | 0 | 2 | Ph | H | F | H | Si(CH₃)₃ | H | H | H | H | H | — | — |
| 2-40 | Ir | 1 | 2 | Ph | H | CF₃ | H | Si(CH₃)₃ | H | H | H | H | H | pic | |
| 2-40X | Ir | 1 | 2 | Ph | H | CF₃ | H | Si(CH₃)₃ | H | H | H | H | H | acac | |
| 2-40Y | Ir | 0 | 2 | Ph | H | CF₃ | H | Si(CH₃)₃ | H | H | H | H | H | — | — |
| 2-41 | Ir | 1 | 2 | Ph | H | Si(CH₃)₃ | H | F | H | H | H | H | H | pic | |
| 2-41X | Ir | 1 | 2 | Ph | H | Si(CH₃)₃ | H | F | H | H | H | H | H | acac | |
| 2-41Y | Ir | 0 | 2 | Ph | H | Si(CH₃)₃ | H | F | H | H | H | H | H | — | — |
| 2-42 | Ir | 1 | 2 | Ph | H | Si(CH₃)₃ | H | CF₃ | H | H | H | H | H | pic | |
| 2-42X | Ir | 1 | 2 | Ph | H | Si(CH₃)₃ | H | CF₃ | H | H | H | H | H | acac | |
| 2-42Y | Ir | 0 | 2 | Ph | H | Si(CH₃)₃ | H | CF₃ | H | H | H | H | H | — | — |
| 2-43 | Ir | 1 | 2 | Ph | Si(CH₃)₃ | H | Si(CH₃)₃ | H | H | H | H | H | H | pic | |
| 2-43X | Ir | 1 | 2 | Ph | Si(CH₃)₃ | H | Si(CH₃)₃ | H | H | H | H | H | H | acac | |
| 2-43Y | Ir | 0 | 2 | Ph | Si(CH₃)₃ | H | Si(CH₃)₃ | H | H | H | H | H | H | — | — |
| 2-44 | Ir | 1 | 2 | Ph | H | H | H | COCH₃ | H | H | H | H | H | pic | |
| 2-44X | Ir | 1 | 2 | Ph | H | H | H | COCH₃ | H | H | H | H | H | acac | |
| 2-44Y | Ir | 0 | 2 | Ph | H | H | H | COCH₃ | H | H | H | H | H | — | — |
| 2-45 | Ir | 1 | 2 | Ph | H | H | COCH₃ | H | H | H | H | H | H | pic | |
| 2-45X | Ir | 1 | 2 | Ph | H | H | COCH₃ | H | H | H | H | H | H | acac | |
| 2-45Y | Ir | 0 | 2 | Ph | H | H | COCH₃ | H | H | H | H | H | H | — | — |
| 2-46 | Ir | 1 | 2 | Ph | H | COCH₃ | H | H | H | H | H | H | H | pic | |
| 2-46X | Ir | 1 | 2 | Ph | H | COCH₃ | H | H | H | H | H | H | H | acac | |
| 2-46Y | Ir | 0 | 2 | Ph | H | COCH₃ | H | H | H | H | H | H | H | — | — |
| 2-47 | Ir | 1 | 2 | Ph | H | H | BL | | H | H | H | H | H | pic | |
| 2-47X | Ir | 1 | 2 | Ph | H | H | BL | | H | H | H | H | H | acac | |
| 2-47Y | Ir | 0 | 2 | Ph | H | H | BL | | H | H | H | H | H | — | — |
| 2-48 | Ir | 1 | 2 | Ph | H | BL | | H | H | H | H | H | H | pic | |
| 2-48X | Ir | 1 | 2 | Ph | H | BL | | H | H | H | H | H | H | acac | |
| 2-48Y | Ir | 0 | 2 | Ph | H | BL | | H | H | H | H | H | H | — | — |
| 2-49 | Ir | 1 | 2 | Ph | H | H | PL | H | H | H | H | H | H | pic | |
| 2-49X | Ir | 1 | 2 | Ph | H | H | PL | H | H | H | H | H | H | acac | |
| 2-49Y | Ir | 0 | 2 | Ph | H | H | PL | H | H | H | H | H | H | — | — |
| 2-50 | Ir | 1 | 2 | Ph | H | PL | H | H | H | H | H | H | H | pic | |
| 2-50X | Ir | 1 | 2 | Ph | H | PL | H | H | H | H | H | H | H | acac | |
| 2-50Y | Ir | 0 | 2 | Ph | H | PL | H | H | H | H | H | H | H | — | — |
| 2-51 | Ir | 1 | 2 | Ph | H | H | MEE1 | H | H | H | H | H | H | pic | |
| 2-51X | Ir | 1 | 2 | Ph | H | H | MEE1 | H | H | H | H | H | H | acac | |
| 2-51Y | Ir | 0 | 2 | Ph | H | H | MEE1 | H | H | H | H | H | H | — | — |
| 2-52 | Ir | 1 | 2 | Ph | H | MEE1 | H | H | H | H | H | H | H | pic | |
| 2-52X | Ir | 1 | 2 | Ph | H | MEE1 | H | H | H | H | H | H | H | acac | |
| 2-52Y | Ir | 0 | 2 | Ph | H | MEE1 | H | H | H | H | H | H | H | — | — |
| 2-53 | Ir | 1 | 2 | Ph | H | H | MEE2 | H | H | H | H | H | H | pic | |
| 2-53X | Ir | 1 | 2 | Ph | H | H | MEE2 | H | H | H | H | H | H | acac | |
| 2-53Y | Ir | 0 | 2 | Ph | H | H | MEE2 | H | H | H | H | H | H | — | — |
| 2-54 | Ir | 1 | 2 | Ph | H | MEE2 | H | H | H | H | H | H | H | pic | |
| 2-54X | Ir | 1 | 2 | Ph | H | MEE2 | H | H | H | H | H | H | H | acac | |
| 2-54Y | Ir | 0 | 2 | Ph | H | MEE2 | H | H | H | H | H | H | H | — | — |
| 2-55 | Ir | 1 | 2 | Ph | H | H | PA1 | H | H | H | H | H | H | pic | |
| 2-55X | Ir | 1 | 2 | Ph | H | H | PA1 | H | H | H | H | H | H | acac | |
| 2-55Y | Ir | 0 | 2 | Ph | H | H | PA1 | H | H | H | H | H | H | — | — |
| 2-56 | Ir | 1 | 2 | Ph | H | PA1 | H | H | H | H | H | H | H | pic | |
| 2-56X | Ir | 1 | 2 | Ph | H | PA1 | H | H | H | H | H | H | H | acac | |
| 2-56Y | Ir | 0 | 2 | Ph | H | PA1 | H | H | H | H | H | H | H | — | — |
| 2-57 | Ir | 1 | 2 | Ph | H | H | PA2 | H | H | H | H | H | H | pic | |
| 2-57X | Ir | 1 | 2 | Ph | H | H | PA2 | H | H | H | H | H | H | acac | |
| 2-57Y | Ir | 0 | 2 | Ph | H | H | PA2 | H | H | H | H | H | H | — | — |
| 2-58 | Ir | 1 | 2 | Ph | H | PA2 | H | H | H | H | H | H | H | pic | |
| 2-58X | Ir | 1 | 2 | Ph | H | PA2 | H | H | H | H | H | H | H | acac | |
| 2-58Y | Ir | 0 | 2 | Ph | H | PA2 | H | H | H | H | H | H | H | — | — |
| 2-59 | Ir | 1 | 2 | Ph | H | H | EA1 | H | H | H | H | H | H | pic | |
| 2-59X | Ir | 1 | 2 | Ph | H | H | EA1 | H | H | H | H | H | H | acac | |
| 2-59Y | Ir | 0 | 2 | Ph | H | H | EA1 | H | H | H | H | H | H | — | — |

TABLE 2-continued

| No. | M | n | BSS | SS G | $T^1$ | $T^2$ | $T^3$ | $T^4$ | $T^5$ | $T^6$ | $T^7$ | $T^8$ | $T^9$ | $L^1$ | $L^2$ |
|---|---|---|---|---|---|---|---|---|---|---|---|---|---|---|---|
| 2-60 | Ir | 1 | 2 | Ph | H | | EA2 | | H | H | H | H | H | H | pic |
| 2-60X | Ir | 1 | 2 | Ph | H | | EA2 | | H | H | H | H | H | H | acac |
| 2-60Y | Ir | 0 | 2 | Ph | H | | EA2 | | H | H | H | H | H | H | — — |
| 2-61 | Ir | 1 | 2 | Ph | H | H | | ME | H | H | H | H | H | H | pic |
| 2-61X | Ir | 1 | 2 | Ph | H | H | | ME | H | H | H | H | H | H | acac |
| 2-61Y | Ir | 0 | 2 | Ph | H | H | | ME | H | H | H | H | H | H | — — |
| 2-62 | Ir | 1 | 2 | Ph | H | | ME | | H | H | H | H | H | H | pic |
| 2-62X | Ir | 1 | 2 | Ph | H | | ME | | H | H | H | H | H | H | acac |
| 2-62Y | Ir | 0 | 2 | Ph | H | | ME | | H | H | H | H | H | H | — — |
| 2-63 | Ir | 1 | 2 | Ph | H | H | | AT | H | H | H | H | H | H | pic |
| 2-63X | Ir | 1 | 2 | Ph | H | H | | AT | H | H | H | H | H | H | acac |
| 2-63Y | Ir | 0 | 2 | Ph | H | H | | AT | H | H | H | H | H | H | — — |
| 2-64 | Ir | 1 | 2 | Ph | H | | AT | | H | H | H | H | H | H | pic |
| 2-64X | Ir | 1 | 2 | Ph | H | | AT | | H | H | H | H | H | H | acac |
| 2-64Y | Ir | 0 | 2 | Ph | H | | AT | | H | H | H | H | H | H | — — |
| 2-65 | Ir | 1 | 2 | Ph | H | H | | MES1 | H | H | H | H | H | H | pic |
| 2-65X | Ir | 1 | 2 | Ph | H | H | | MES1 | H | H | H | H | H | H | acac |
| 2-65Y | Ir | 0 | 2 | Ph | H | H | | MES1 | H | H | H | H | H | H | — — |
| 2-66 | Ir | 1 | 2 | Ph | H | | MES1 | | H | H | H | H | H | H | pic |
| 2-66X | Ir | 1 | 2 | Ph | H | | MES1 | | H | H | H | H | H | H | acac |
| 2-66Y | Ir | 0 | 2 | Ph | H | | MES1 | | H | H | H | H | H | H | — — |
| 2-67 | Ir | 1 | 2 | Ph | H | H | | MES2 | H | H | H | H | H | H | pic |
| 2-67X | Ir | 1 | 2 | Ph | H | H | | MES2 | H | H | H | H | H | H | acac |
| 2-67Y | Ir | 0 | 2 | Ph | H | H | | MES2 | H | H | H | H | H | H | — — |
| 2-68 | Ir | 1 | 2 | Ph | H | | MES2 | | H | H | H | H | H | H | pic |
| 2-68X | Ir | 1 | 2 | Ph | H | | MES2 | | H | H | H | H | H | H | acac |
| 2-68Y | Ir | 0 | 2 | Ph | H | | MES2 | | H | H | H | H | H | H | — — |
| 2-69 | Ir | 1 | 2 | Ph | H | H | | PS1 | H | H | H | H | H | H | pic |
| 2-69X | Ir | 1 | 2 | Ph | H | H | | PS1 | H | H | H | H | H | H | acac |
| 2-69Y | Ir | 0 | 2 | Ph | H | H | | PS1 | H | H | H | H | H | H | — — |
| 2-70 | Ir | 1 | 2 | Ph | H | | PS1 | | H | H | H | H | H | H | pic |
| 2-70X | Ir | 1 | 2 | Ph | H | | PS1 | | H | H | H | H | H | H | acac |
| 2-70Y | Ir | 0 | 2 | Ph | H | | PS1 | | H | H | H | H | H | H | — — |
| 2-71 | Ir | 1 | 2 | Ph | H | H | | PS2 | H | H | H | H | H | H | pic |
| 2-71X | Ir | 1 | 2 | Ph | H | H | | PS2 | H | H | H | H | H | H | acac |
| 2-71Y | Ir | 0 | 2 | Ph | H | H | | PS2 | H | H | H | H | H | H | — — |
| 2-72 | Ir | 1 | 2 | Ph | H | | PS2 | | H | H | H | H | H | H | pic |
| 2-72X | Ir | 1 | 2 | Ph | H | | PS2 | | H | H | H | H | H | H | acac |
| 2-72Y | Ir | 0 | 2 | Ph | H | | PS2 | | H | H | H | H | H | H | — — |
| 2-73 | Ir | 1 | 2 | Ph | H | H | | BAL1 | H | H | H | H | H | H | pic |
| 2-73X | Ir | 1 | 2 | Ph | H | H | | BAL1 | H | H | H | H | H | H | acac |
| 2-73Y | Ir | 0 | 2 | Ph | H | H | | BAL1 | H | H | H | H | H | H | — — |
| 2-74 | Ir | 1 | 2 | Ph | H | | BAL1 | | H | H | H | H | H | H | pic |
| 2-74X | Ir | 1 | 2 | Ph | H | | BAL1 | | H | H | H | H | H | H | acac |
| 2-74Y | Ir | 0 | 2 | Ph | H | | BAL1 | | H | H | H | H | H | H | — — |
| 2-75 | Ir | 1 | 2 | Ph | H | H | | BAL2 | H | H | H | H | H | H | pic |
| 2-75X | Ir | 1 | 2 | Ph | H | H | | BAL2 | H | H | H | H | H | H | acac |
| 2-75Y | Ir | 0 | 2 | Ph | H | H | | BAL2 | H | H | H | H | H | H | — — |
| 2-76 | Ir | 1 | 2 | Ph | H | | BAL2 | | H | H | H | H | H | H | pic |
| 2-76X | Ir | 1 | 2 | Ph | H | | BAL2 | | H | H | H | H | H | H | acac |
| 2-76Y | Ir | 0 | 2 | Ph | H | | BAL2 | | H | H | H | H | H | H | — — |
| 2-77 | Ir | 1 | 2 | Ph | H | H | | MEK1 | H | H | H | H | H | H | pic |
| 2-77X | Ir | 1 | 2 | Ph | H | H | | MEK1 | H | H | H | H | H | H | acac |
| 2-77Y | Ir | 0 | 2 | Ph | H | H | | MEK1 | H | H | H | H | H | H | — — |
| 2-78 | Ir | 1 | 2 | Ph | H | | MEK1 | | H | H | H | H | H | H | pic |
| 2-78X | Ir | 1 | 2 | Ph | H | | MEK1 | | H | H | H | H | H | H | acac |
| 2-78Y | Ir | 0 | 2 | Ph | H | | MEK1 | | H | H | H | H | H | H | — — |
| 2-79 | Ir | 1 | 2 | Ph | H | H | | MEK2 | H | H | H | H | H | H | pic |
| 2-79X | Ir | 1 | 2 | Ph | H | H | | MEK2 | H | H | H | H | H | H | acac |
| 2-79Y | Ir | 0 | 2 | Ph | H | H | | MEK2 | H | H | H | H | H | H | — — |
| 2-80 | Ir | 1 | 2 | Ph | H | | MEK2 | | H | H | H | H | H | H | pic |
| 2-80X | Ir | 1 | 2 | Ph | H | | MEK2 | | H | H | H | H | H | H | acac |
| 2-80Y | Ir | 0 | 2 | Ph | H | | MEK2 | | H | H | H | H | H | H | — — |
| 2-81 | Ir | 1 | 2 | Ph | H | H | | PAL1 | H | H | H | H | H | H | pic |
| 2-81X | Ir | 1 | 2 | Ph | H | H | | PAL1 | H | H | H | H | H | H | acac |
| 2-81Y | Ir | 0 | 2 | Ph | H | H | | PAL1 | H | H | H | H | H | H | — — |
| 2-82 | Ir | 1 | 2 | Ph | H | | PAL1 | | H | H | H | H | H | H | pic |
| 2-82X | Ir | 1 | 2 | Ph | H | | PAL1 | | H | H | H | H | H | H | acac |
| 2-82Y | Ir | 0 | 2 | Ph | H | | PAL1 | | H | H | H | H | H | H | — — |
| 2-83 | Ir | 1 | 2 | Ph | H | H | | PAL2 | H | H | H | H | H | H | pic |
| 2-83X | Ir | 1 | 2 | Ph | H | H | | PAL2 | H | H | H | H | H | H | acac |
| 2-83Y | Ir | 0 | 2 | Ph | H | H | | PAL2 | H | H | H | H | H | H | — — |
| 2-84 | Ir | 1 | 2 | Ph | H | | PAL2 | | H | H | H | H | H | H | pic |
| 2-84X | Ir | 1 | 2 | Ph | H | | PAL2 | | H | H | H | H | H | H | acac |
| 2-84Y | Ir | 0 | 2 | Ph | H | | PAL2 | | H | H | H | H | H | H | — — |
| 2-85 | Ir | 1 | 2 | Ph | H | H | | MMK | H | H | H | H | H | H | pic |
| 2-85X | Ir | 1 | 2 | Ph | H | H | | MMK | H | H | H | H | H | H | acac |

TABLE 2-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2-85Y | Ir | 0 | 2 | Ph | H | H | | MMK | H | H | H | H | H | — | — |
| 2-86 | Ir | 1 | 2 | Ph | H | | MMK | | H | H | H | H | H | pic | |
| 2-86X | Ir | 1 | 2 | Ph | H | | MMK | | H | H | H | H | H | acac | |
| 2-86Y | Ir | 0 | 2 | Ph | H | | MMK | | H | H | H | H | H | — | — |
| 2-87 | Ir | 1 | 2 | Ph | H | H | | EES1 | H | H | H | H | H | pic | |
| 2-87X | Ir | 1 | 2 | Ph | H | H | | EES1 | H | H | H | H | H | acac | |
| 2-87Y | Ir | 0 | 2 | Ph | H | H | | EES1 | H | H | H | H | H | — | — |
| 2-88 | Ir | 1 | 2 | Ph | H | | EES2 | | H | H | H | H | H | pic | |
| 2-88X | Ir | 1 | 2 | Ph | H | | EES2 | | H | H | H | H | H | acac | |
| 2-88Y | Ir | 0 | 2 | Ph | H | | EES2 | | H | H | H | H | H | — | — |
| 2-89 | Ir | 1 | 2 | Ph | H | H | | PAE1 | H | H | H | H | H | pic | |
| 2-89X | Ir | 1 | 2 | Ph | H | H | | PAE1 | H | H | H | H | H | acac | |
| 2-89Y | Ir | 0 | 2 | Ph | H | H | | PAE1 | H | H | H | H | H | — | — |
| 2-90 | Ir | 1 | 2 | Ph | H | | PAE2 | | H | H | H | H | H | pic | |
| 2-90X | Ir | 1 | 2 | Ph | H | | PAE2 | | H | H | H | H | H | acac | |
| 2-90Y | Ir | 0 | 2 | Ph | H | | PAE2 | | H | H | H | H | H | — | — |
| 2-91 | Ir | 1 | 2 | Ph | H | H | | AME1 | H | H | H | H | H | pic | |
| 2-91X | Ir | 1 | 2 | Ph | H | H | | AME1 | H | H | H | H | H | acac | |
| 2-91Y | Ir | 0 | 2 | Ph | H | H | | AME1 | H | H | H | H | H | — | — |
| 2-92 | Ir | 1 | 2 | Ph | H | | AME1 | | H | H | H | H | H | pic | |
| 2-92X | Ir | 1 | 2 | Ph | H | | AME1 | | H | H | H | H | H | acac | |
| 2-92Y | Ir | 0 | 2 | Ph | H | | AME1 | | H | H | H | H | H | — | — |
| 2-93 | Ir | 1 | 2 | Ph | H | H | | AME2 | H | H | H | H | H | pic | |
| 2-93X | Ir | 1 | 2 | Ph | H | H | | AME2 | H | H | H | H | H | acac | |
| 2-93Y | Ir | 0 | 2 | Ph | H | H | | AME2 | H | H | H | H | H | — | — |
| 2-94 | Ir | 1 | 2 | Ph | H | | AME2 | | H | H | H | H | H | pic | |
| 2-94X | Ir | 1 | 2 | Ph | H | | AME2 | | H | H | H | H | H | acac | |
| 2-94Y | Ir | 0 | 2 | Ph | H | | AME2 | | H | H | H | H | H | — | — |
| 2-95 | Ir | 1 | 2 | Ph | H | H | | EAE1 | H | H | H | H | H | pic | |
| 2-95X | Ir | 1 | 2 | Ph | H | H | | EAE1 | H | H | H | H | H | acac | |
| 2-95Y | Ir | 0 | 2 | Ph | H | H | | EAE1 | H | H | H | H | H | — | — |
| 2-96 | Ir | 1 | 2 | Ph | H | | EAE1 | | H | H | H | H | H | pic | |
| 2-96X | Ir | 1 | 2 | Ph | H | | EAE1 | | H | H | H | H | H | acac | |
| 2-96Y | Ir | 0 | 2 | Ph | H | | EAE1 | | H | H | H | H | H | — | — |
| 2-97 | Ir | 1 | 2 | Ph | H | H | | EAE2 | H | H | H | H | H | pic | |
| 2-97X | Ir | 1 | 2 | Ph | H | H | | EAE2 | H | H | H | H | H | acac | |
| 2-97Y | Ir | 0 | 2 | Ph | H | H | | EAE2 | H | H | H | H | H | — | — |
| 2-98 | Ir | 1 | 2 | Ph | H | | EAE2 | | H | H | H | H | H | pic | |
| 2-98X | Ir | 1 | 2 | Ph | H | | EAE2 | | H | H | H | H | H | acac | |
| 2-98Y | Ir | 0 | 2 | Ph | H | | EAE2 | | H | H | H | H | H | — | — |
| 2-99 | Ir | 1 | 2 | Ph | H | H | | AAE1 | H | H | H | H | H | pic | |
| 2-99X | Ir | 1 | 2 | Ph | H | H | | AAE1 | H | H | H | H | H | acac | |
| 2-99Y | Ir | 0 | 2 | Ph | H | H | | AAE1 | H | H | H | H | H | — | — |
| 2-100 | Ir | 1 | 2 | Ph | H | | AAE1 | | H | H | H | H | H | pic | |
| 2-100X | Ir | 1 | 2 | Ph | H | | AAE1 | | H | H | H | H | H | acac | |
| 2-100Y | Ir | 0 | 2 | Ph | H | | AAE1 | | H | H | H | H | H | — | — |
| 2-101 | Ir | 1 | 2 | Ph | H | H | | AAE2 | H | H | H | H | H | pic | |
| 2-101X | Ir | 1 | 2 | Ph | H | H | | AAE2 | H | H | H | H | H | acac | |
| 2-101Y | Ir | 0 | 2 | Ph | H | H | | AAE2 | H | H | H | H | H | — | — |
| 2-102 | Ir | 1 | 2 | Ph | H | | AAE2 | | H | H | H | H | H | pic | |
| 2-102X | Ir | 1 | 2 | Ph | H | | AAE2 | | H | H | H | H | H | acac | |
| 2-102Y | Ir | 0 | 2 | Ph | H | | AAE2 | | H | H | H | H | H | — | — |
| 2-103 | Ir | 1 | 2 | Ph | H | H | | PME1 | H | H | H | H | H | pic | |
| 2-103X | Ir | 1 | 2 | Ph | H | H | | PME1 | H | H | H | H | H | acac | |
| 2-103Y | Ir | 0 | 2 | Ph | H | H | | PME1 | H | H | H | H | H | — | — |
| 2-104 | Ir | 1 | 2 | Ph | H | | PME1 | | H | H | H | H | H | pic | |
| 2-104X | Ir | 1 | 2 | Ph | H | | PME1 | | H | H | H | H | H | acac | |
| 2-104Y | Ir | 0 | 2 | Ph | H | | PME1 | | H | H | H | H | H | — | — |
| 2-105 | Ir | 1 | 2 | Ph | H | H | | PME2 | H | H | H | H | H | pic | |
| 2-105X | Ir | 1 | 2 | Ph | H | H | | PME2 | H | H | H | H | H | acac | |
| 2-105Y | Ir | 0 | 2 | Ph | H | H | | PME2 | H | H | H | H | H | — | — |
| 2-106 | Ir | 1 | 2 | Ph | H | | PME2 | | H | H | H | H | H | pic | |
| 2-106X | Ir | 1 | 2 | Ph | H | | PME2 | | H | H | H | H | H | acac | |
| 2-106Y | Ir | 0 | 2 | Ph | H | | PME2 | | H | H | H | H | H | — | — |
| 2-107 | Ir | 1 | 2 | Ph | H | H | | MET1 | H | H | H | H | H | pic | |
| 2-107X | Ir | 1 | 2 | Ph | H | H | | MET1 | H | H | H | H | H | acac | |
| 2-107Y | Ir | 0 | 2 | Ph | H | H | | MET1 | H | H | H | H | H | — | — |
| 2-108 | Ir | 1 | 2 | Ph | H | | MET1 | | H | H | H | H | H | pic | |
| 2-108X | Ir | 1 | 2 | Ph | H | | MET1 | | H | H | H | H | H | acac | |
| 2-108Y | Ir | 0 | 2 | Ph | H | | MET1 | | H | H | H | H | H | — | — |
| 2-109 | Ir | 1 | 2 | Ph | H | H | | MET2 | H | H | H | H | H | pic | |
| 2-109X | Ir | 1 | 2 | Ph | H | H | | MET2 | H | H | H | H | H | acac | |
| 2-109Y | Ir | 0 | 2 | Ph | H | H | | MET2 | H | H | H | H | H | — | — |
| 2-110 | Ir | 1 | 2 | Ph | H | | MET2 | | H | H | H | H | H | pic | |
| 2-110X | Ir | 1 | 2 | Ph | H | | MET2 | | H | H | H | H | H | acac | |
| 2-110Y | Ir | 0 | 2 | Ph | H | | MET2 | | H | H | H | H | H | — | — |
| 2-111 | Ir | 1 | 2 | Ph | H | H | | EE1 | H | H | H | H | H | pic | |

TABLE 2-continued

| No. | M | n | BSS | SS | G | T$^1$ | T$^2$ | T$^3$ | T$^4$ | T$^5$ | T$^6$ | T$^7$ | T$^8$ | T$^9$ | L$^1$ L$^2$ |
|---|---|---|---|---|---|---|---|---|---|---|---|---|---|---|---|
| 2-111X | Ir | 1 | 2 | | Ph | H | H | | EE1 | H | H | H | H | H | acac |
| 2-111Y | Ir | 0 | 2 | | Ph | H | H | | EE1 | H | H | H | H | H | — — |
| 2-112 | Ir | 1 | 2 | | Ph | H | | EE1 | H | H | H | H | H | H | pic |
| 2-112X | Ir | 1 | 2 | | Ph | H | | EE1 | H | H | H | H | H | H | acac |
| 2-112Y | Ir | 0 | 2 | | Ph | H | | EE1 | H | H | H | H | H | H | — — |
| 2-113 | Ir | 1 | 2 | | Ph | H | H | | EE2 | H | H | H | H | H | pic |
| 2-113X | Ir | 1 | 2 | | Ph | H | H | | EE2 | H | H | H | H | H | acac |
| 2-113Y | Ir | 0 | 2 | | Ph | H | H | | EE2 | H | H | H | H | H | — — |
| 2-114 | Ir | 1 | 2 | | Ph | H | | EE2 | H | H | H | H | H | H | pic |
| 2-114X | Ir | 1 | 2 | | Ph | H | | EE2 | H | H | H | H | H | H | acac |
| 2-114Y | Ir | 0 | 2 | | Ph | H | | EE2 | H | H | H | H | H | H | — — |
| 2-115 | Ir | 1 | 2 | | Ph | H | H | | MS1 | H | H | H | H | H | pic |
| 2-115X | Ir | 1 | 2 | | Ph | H | H | | MS1 | H | H | H | H | H | acac |
| 2-115Y | Ir | 0 | 2 | | Ph | H | H | | MS1 | H | H | H | H | H | — — |
| 2-116 | Ir | 1 | 2 | | Ph | H | | MS1 | H | H | H | H | H | H | pic |
| 2-116X | Ir | 1 | 2 | | Ph | H | | MS1 | H | H | H | H | H | H | acac |
| 2-116Y | Ir | 0 | 2 | | Ph | H | | MS1 | H | H | H | H | H | H | — — |
| 2-117 | Ir | 1 | 2 | | Ph | H | H | | MS2 | H | H | H | H | H | pic |
| 2-117X | Ir | 1 | 2 | | Ph | H | H | | MS2 | H | H | H | H | H | acac |
| 2-117Y | Ir | 0 | 2 | | Ph | H | H | | MS2 | H | H | H | H | H | — — |
| 2-118 | Ir | 1 | 2 | | Ph | H | | MS2 | H | H | H | H | H | H | pic |
| 2-118X | Ir | 1 | 2 | | Ph | H | | MS2 | H | H | H | H | H | H | acac |
| 2-118Y | Ir | 0 | 2 | | Ph | H | | MS2 | H | H | H | H | H | H | — — |

TABLE 3

| No. | M | n | BBS | BS | G | T$^1$ | T$^2$ | T$^3$ | T$^4$ | T$^5$ | T$^6$ | T$^7$ | T$^8$ | T$^9$ | L$^1$ L$^2$ |
|---|---|---|---|---|---|---|---|---|---|---|---|---|---|---|---|
| 3-1 | Ir | 1 | 3 | | Ph | H | H | H | H | H | H | H | H | H | pic |
| 3-1X | Ir | 1 | 3 | | Ph | H | H | H | H | H | H | H | H | H | acac |
| 3-1Y | Ir | 0 | 3 | | Ph | H | H | H | H | H | H | H | H | H | — — |
| 3-2 | Ir | 1 | 3 | | Ph | H | F | H | F | H | H | H | H | H | pic |
| 3-2X | Ir | 1 | 3 | | Ph | H | F | H | F | H | H | H | H | H | acac |
| 3-2Y | Ir | 0 | 3 | | Ph | H | F | H | F | H | H | H | H | H | — — |
| 3-3 | Ir | 1 | 3 | | Ph | F | H | H | F | H | H | H | H | H | pic |
| 3-3X | Ir | 1 | 3 | | Ph | F | H | H | F | H | H | H | H | H | acac |
| 3-3Y | Ir | 0 | 3 | | Ph | F | H | H | F | H | H | H | H | H | — — |
| 3-4 | Ir | 1 | 3 | | Ph | CF$_3$ | H | CF$_3$ | H | H | H | H | H | H | pic |
| 3-4X | Ir | 1 | 3 | | Ph | CF$_3$ | H | CF$_3$ | H | H | H | H | H | H | acac |
| 3-4Y | Ir | 0 | 3 | | Ph | CF$_3$ | H | CF$_3$ | H | H | H | H | H | H | — — |
| 3-5 | Ir | 1 | 3 | | Ph | H | F | CF$_3$ | H | H | H | H | H | H | pic |
| 3-5X | Ir | 1 | 3 | | Ph | H | F | CF$_3$ | H | H | H | H | H | H | acac |
| 3-5Y | Ir | 0 | 3 | | Ph | H | F | CF$_3$ | H | H | H | H | H | H | — — |
| 3-6 | Ir | 1 | 3 | | Ph | F | H | CF$_3$ | H | H | H | H | H | H | pic |
| 3-6X | Ir | 1 | 3 | | Ph | F | H | CF$_3$ | H | H | H | H | H | H | acac |
| 3-6Y | Ir | 0 | 3 | | Ph | F | H | CF$_3$ | H | H | H | H | H | H | — — |
| 3-7 | Ir | 1 | 3 | | Ph | F | F | F | F | H | H | H | H | H | pic |
| 3-7X | Ir | 1 | 3 | | Ph | F | F | F | F | H | H | H | H | H | acac |
| 3-7Y | Ir | 0 | 3 | | Ph | F | F | F | F | H | H | H | H | H | — — |
| 3-8 | Ir | 1 | 3 | | Ph | H | F | H | CH$_3$ | H | H | H | H | H | pic |
| 3-8X | Ir | 1 | 3 | | Ph | H | F | H | CH$_3$ | H | H | H | H | H | acac |
| 3-8Y | Ir | 0 | 3 | | Ph | H | F | H | CH$_3$ | H | H | H | H | H | — — |
| 3-9 | Ir | 1 | 3 | | Ph | H | F | H | $^t$C$_4$H$_9$ | H | H | H | H | H | pic |
| 3-9X | Ir | 1 | 3 | | Ph | H | F | H | $^t$C$_4$H$_9$ | H | H | H | H | H | acac |
| 3-9Y | Ir | 0 | 3 | | Ph | H | F | H | $^t$C$_4$H$_9$ | H | H | H | H | H | — — |
| 3-10 | Ir | 1 | 3 | | Ph | H | CF$_3$ | H | CF$_3$ | H | H | H | H | H | pic |
| 3-10X | Ir | 1 | 3 | | Ph | H | CF$_3$ | H | CF$_3$ | H | H | H | H | H | acac |
| 3-10Y | Ir | 0 | 3 | | Ph | H | CF$_3$ | H | CF$_3$ | H | H | H | H | H | — — |
| 3-11 | Ir | 1 | 3 | | Ph | CF$_3$ | H | H | $^t$C$_4$H$_9$ | H | H | H | H | H | pic |
| 3-11X | Ir | 1 | 3 | | Ph | CF$_3$ | H | H | $^t$C$_4$H$_9$ | H | H | H | H | H | acac |
| 3-11Y | Ir | 0 | 3 | | Ph | CF$_3$ | H | H | $^t$C$_4$H$_9$ | H | H | H | H | H | — — |
| 3-12 | Ir | 1 | 3 | | Ph | H | CF$_3$ | H | $^t$C$_4$H$_9$ | H | H | H | H | H | pic |
| 3-12X | Ir | 1 | 3 | | Ph | H | CF$_3$ | H | $^t$C$_4$H$_9$ | H | H | H | H | H | acac |
| 3-12Y | Ir | 0 | 3 | | Ph | H | CF$_3$ | H | $^t$C$_4$H$_9$ | H | H | H | H | H | — — |
| 3-13 | Ir | 1 | 3 | | Ph | H | CF$_3$ | H | CH$_3$ | H | H | H | H | H | pic |
| 3-13X | Ir | 1 | 3 | | Ph | H | CF$_3$ | H | CH$_3$ | H | H | H | H | H | acac |
| 3-13Y | Ir | 0 | 3 | | Ph | H | CF$_3$ | H | CH$_3$ | H | H | H | H | H | — — |
| 3-14 | Ir | 1 | 3 | | Ph | H | CF$_3$ | CF$_3$ | H | H | H | H | H | H | pic |
| 3-14X | Ir | 1 | 3 | | Ph | H | CF$_3$ | CF$_3$ | H | H | H | H | H | H | acac |
| 3-14Y | Ir | 0 | 3 | | Ph | H | CF$_3$ | CF$_3$ | H | H | H | H | H | H | — — |
| 3-15 | Ir | 1 | 3 | | Ph | H | H | NO$_2$ | H | H | H | H | H | H | pic |
| 3-15X | Ir | 1 | 3 | | Ph | H | H | NO$_2$ | H | H | H | H | H | H | acac |
| 3-15Y | Ir | 0 | 3 | | Ph | H | H | NO$_2$ | H | H | H | H | H | H | — — |
| 3-16 | Ir | 1 | 3 | | Ph | F | H | NO$_2$ | H | H | H | H | H | H | pic |

TABLE 3-continued

| No. | M | n | BBS | BS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3-16X | Ir | 1 | 3 | Ph | F | H | NO$_2$ | H | H | H | H | H | H | acac | |
| 3-16Y | Ir | 0 | 3 | Ph | F | H | NO$_2$ | H | H | H | H | H | H | — | — |
| 3-17 | Ir | 1 | 3 | Ph | F | H | NO$_2$ | F | H | H | H | H | H | pic | |
| 3-17X | Ir | 1 | 3 | Ph | F | H | NO$_2$ | F | H | H | H | H | H | acac | |
| 3-17Y | Ir | 0 | 3 | Ph | F | H | NO$_2$ | F | H | H | H | H | H | — | — |
| 3-18 | Ir | 1 | 3 | Ph | H | NO$_2$ | H | NO$_2$ | H | H | H | H | H | pic | |
| 3-18X | Ir | 1 | 3 | Ph | H | NO$_2$ | H | NO$_2$ | H | H | H | H | H | acac | |
| 3-18Y | Ir | 0 | 3 | Ph | H | NO$_2$ | H | NO$_2$ | H | H | H | H | H | — | — |
| 3-19 | Ir | 1 | 3 | Ph | NO$_2$ | H | H | NO$_2$ | H | H | H | H | H | pic | |
| 3-19X | Ir | 1 | 3 | Ph | NO$_2$ | H | H | NO$_2$ | H | H | H | H | H | acac | |
| 3-19Y | Ir | 0 | 3 | Ph | NO$_2$ | H | H | NO$_2$ | H | H | H | H | H | — | — |
| 3-20 | Ir | 1 | 3 | Ph | H | H | CF$_3$ | H | H | H | H | H | H | pic | |
| 3-20X | Ir | 1 | 3 | Ph | H | H | CF$_3$ | H | H | H | H | H | H | acac | |
| 3-20Y | Ir | 0 | 3 | Ph | H | H | CF$_3$ | H | H | H | H | H | H | — | — |
| 3-21 | Ir | 1 | 3 | Ph | H | Cl | CF$_3$ | H | H | H | H | H | H | pic | |
| 3-21X | Ir | 1 | 3 | Ph | H | Cl | CF$_3$ | H | H | H | H | H | H | acac | |
| 3-21Y | Ir | 0 | 3 | Ph | H | Cl | CF$_3$ | H | H | H | H | H | H | — | — |
| 3-22 | Ir | 1 | 3 | Ph | H | NO$_2$ | H | H | H | H | H | H | H | pic | |
| 3-22X | Ir | 1 | 3 | Ph | H | NO$_2$ | H | H | H | H | H | H | H | acac | |
| 3-22Y | Ir | 0 | 3 | Ph | H | NO$_2$ | H | H | H | H | H | H | H | — | — |
| 3-23 | Ir | 1 | 3 | Ph | H | CF$_3$ | H | H | H | H | H | H | H | pic | |
| 3-23X | Ir | 1 | 3 | Ph | H | CF$_3$ | H | H | H | H | H | H | H | acac | |
| 3-23Y | Ir | 0 | 3 | Ph | H | CF$_3$ | H | H | H | H | H | H | H | — | — |
| 3-24 | Ir | 1 | 3 | Ph | H | NO$_2$ | H | CH$_3$ | H | H | H | H | H | pic | |
| 3-24X | Ir | 1 | 3 | Ph | H | NO$_2$ | H | CH$_3$ | H | H | H | H | H | acac | |
| 3-24Y | Ir | 0 | 3 | Ph | H | NO$_2$ | H | CH$_3$ | H | H | H | H | H | — | — |
| 3-25 | Ir | 1 | 3 | Ph | H | NO$_2$ | H | $^t$C$_4$H$_9$ | H | H | H | H | H | pic | |
| 3-25X | Ir | 1 | 3 | Ph | H | NO$_2$ | H | $^t$C$_4$H$_9$ | H | H | H | H | H | acac | |
| 3-25Y | Ir | 0 | 3 | Ph | H | NO$_2$ | H | $^t$C$_4$H$_9$ | H | H | H | H | H | — | — |
| 3-26 | Ir | 1 | 3 | Ph | H | H | CH$_3$O | H | H | H | H | H | H | pic | |
| 3-26X | Ir | 1 | 3 | Ph | H | H | CH$_3$O | H | H | H | H | H | H | acac | |
| 3-26Y | Ir | 0 | 3 | Ph | H | H | CH$_3$O | H | H | H | H | H | H | — | — |
| 3-27 | Ir | 1 | 3 | Ph | H | CH$_3$O | H | H | H | H | H | H | H | pic | |
| 3-27X | Ir | 1 | 3 | Ph | H | CH$_3$O | H | H | H | H | H | H | H | acac | |
| 3-27Y | Ir | 0 | 3 | Ph | H | CH$_3$O | H | H | H | H | H | H | H | — | — |
| 3-28 | Ir | 1 | 3 | Ph | H | CH$_3$O | H | CH$_3$ | H | H | H | H | H | pic | |
| 3-28X | Ir | 1 | 3 | Ph | H | CH$_3$O | H | CH$_3$ | H | H | H | H | H | acac | |
| 3-28Y | Ir | 0 | 3 | Ph | H | CH$_3$O | H | CH$_3$ | H | H | H | H | H | — | — |
| 3-29 | Ir | 1 | 3 | Ph | H | CH$_3$O | H | $^t$C$_4$H$_9$ | H | H | H | H | H | pic | |
| 3-29X | Ir | 1 | 3 | Ph | H | CH$_3$O | H | $^t$C$_4$H$_9$ | H | H | H | H | H | acac | |
| 3-29Y | Ir | 0 | 3 | Ph | H | CH$_3$O | H | $^t$C$_4$H$_9$ | H | H | H | H | H | — | — |
| 3-30 | Ir | 1 | 3 | Ph | H | H | H | H | $^t$C$_4$H$_9$ | H | H | H | H | pic | |
| 3-30X | Ir | 1 | 3 | Ph | H | H | H | H | $^t$C$_4$H$_9$ | H | H | H | H | acac | |
| 3-30Y | Ir | 0 | 3 | Ph | H | H | H | H | $^t$C$_4$H$_9$ | H | H | H | H | — | — |
| 3-31 | Ir | 1 | 3 | Ph | H | F | H | F | $^t$C$_4$H$_9$ | H | H | H | H | pic | |
| 3-31X | Ir | 1 | 3 | Ph | H | F | H | F | $^t$C$_4$H$_9$ | H | H | H | H | acac | |
| 3-31Y | Ir | 0 | 3 | Ph | H | F | H | F | $^t$C$_4$H$_9$ | H | H | H | H | — | — |
| 3-32 | Ir | 1 | 3 | Ph | CF$_3$ | H | CF$_3$ | H | $^t$C$_4$H$_9$ | H | H | H | H | pic | |
| 3-32X | Ir | 1 | 3 | Ph | CF$_3$ | H | CF$_3$ | H | $^t$C$_4$H$_9$ | H | H | H | H | acac | |
| 3-32Y | Ir | 0 | 3 | Ph | CF$_3$ | H | CF$_3$ | H | $^t$C$_4$H$_9$ | H | H | H | H | — | — |
| 3-33 | Ir | 1 | 3 | Ph | H | CF$_3$ | H | CH$_3$ | $^t$C$_4$H$_9$ | H | H | H | H | pic | |
| 3-33X | Ir | 1 | 3 | Ph | H | CF$_3$ | H | CH$_3$ | $^t$C$_4$H$_9$ | H | H | H | H | acac | |
| 3-33Y | Ir | 0 | 3 | Ph | H | CF$_3$ | H | CH$_3$ | $^t$C$_4$H$_9$ | H | H | H | H | — | — |
| 3-34 | Ir | 1 | 3 | Ph | H | Si(CH$_3$)$_3$ | H | H | H | H | H | H | H | pic | |
| 3-34X | Ir | 1 | 3 | Ph | H | Si(CH$_3$)$_3$ | H | H | H | H | H | H | H | acac | |
| 3-34Y | Ir | 0 | 3 | Ph | H | Si(CH$_3$)$_3$ | H | H | H | H | H | H | H | — | — |
| 3-35 | Ir | 1 | 3 | Ph | H | H | Si(CH$_3$)$_3$ | H | H | H | H | H | H | pic | |
| 3-35X | Ir | 1 | 3 | Ph | H | H | Si(CH$_3$)$_3$ | H | H | H | H | H | H | acac | |
| 3-35Y | Ir | 0 | 3 | Ph | H | H | Si(CH$_3$)$_3$ | H | H | H | H | H | H | — | — |
| 3-36 | Ir | 1 | 3 | Ph | H | H | H | Si(CH$_3$)$_3$ | H | H | H | H | H | pic | |
| 3-36X | Ir | 1 | 3 | Ph | H | H | H | Si(CH$_3$)$_3$ | H | H | H | H | H | acac | |
| 3-36Y | Ir | 0 | 3 | Ph | H | H | H | Si(CH$_3$)$_3$ | H | H | H | H | H | — | — |
| 3-37 | Ir | 1 | 3 | Ph | H | F | H | Si(CH$_3$)$_3$ | H | H | H | H | H | pic | |
| 3-37X | Ir | 1 | 3 | Ph | H | F | H | Si(CH$_3$)$_3$ | H | H | H | H | H | acac | |
| 3-37Y | Ir | 0 | 3 | Ph | H | F | H | Si(CH$_3$)$_3$ | H | H | H | H | H | — | — |
| 3-38 | Ir | 1 | 3 | Ph | H | CF$_3$ | H | Si(CH$_3$)$_3$ | H | H | H | H | H | pic | |
| 3-38X | Ir | 1 | 3 | Ph | H | CF$_3$ | H | Si(CH$_3$)$_3$ | H | H | H | H | H | acac | |
| 3-38Y | Ir | 0 | 3 | Ph | H | CF$_3$ | H | Si(CH$_3$)$_3$ | H | H | H | H | H | — | — |
| 3-39 | Ir | 1 | 3 | Ph | H | Si(CH$_3$)$_3$ | H | F | H | H | H | H | H | pic | |
| 3-39X | Ir | 1 | 3 | Ph | H | Si(CH$_3$)$_3$ | H | F | H | H | H | H | H | acac | |
| 3-39Y | Ir | 0 | 3 | Ph | H | Si(CH$_3$)$_3$ | H | F | H | H | H | H | H | — | — |
| 3-40 | Ir | 1 | 3 | Ph | H | Si(CH$_3$)$_3$ | H | CF$_3$ | H | H | H | H | H | pic | |
| 3-40X | Ir | 1 | 3 | Ph | H | Si(CH$_3$)$_3$ | H | CF$_3$ | H | H | H | H | H | acac | |
| 3-40Y | Ir | 0 | 3 | Ph | H | Si(CH$_3$)$_3$ | H | CF$_3$ | H | H | H | H | H | — | — |
| 3-41 | Ir | 1 | 3 | Ph | Si(CH$_3$)$_3$ | H | Si(CH$_3$)$_3$ | H | H | H | H | H | H | pic | |
| 3-41X | Ir | 1 | 3 | Ph | Si(CH$_3$)$_3$ | H | Si(CH$_3$)$_3$ | H | H | H | H | H | H | acac | |
| 3-41Y | Ir | 0 | 3 | Ph | Si(CH$_3$)$_3$ | H | Si(CH$_3$)$_3$ | H | H | H | H | H | H | — | — |

TABLE 3-continued

| No. | M | n | BBS | BS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3-42 | Ir | 1 | 3 | Ph | H | H | H | COCH₃ | H | H | H | H | H | pic | |
| 3-42X | Ir | 1 | 3 | Ph | H | H | H | COCH₃ | H | H | H | H | H | acac | |
| 3-42Y | Ir | 0 | 3 | Ph | H | H | H | COCH₃ | H | H | H | H | H | — | — |
| 3-43 | Ir | 1 | 3 | Ph | H | H | COCH₃ | H | H | H | H | H | H | pic | |
| 3-43X | Ir | 1 | 3 | Ph | H | H | COCH₃ | H | H | H | H | H | H | acac | |
| 3-43Y | Ir | 0 | 3 | Ph | H | H | COCH₃ | H | H | H | H | H | H | — | — |
| 3-44 | Ir | 1 | 3 | Ph | H | COCH₃ | H | H | H | H | H | H | H | pic | |
| 3-44X | Ir | 1 | 3 | Ph | H | COCH₃ | H | H | H | H | H | H | H | acac | |
| 3-44Y | Ir | 0 | 3 | Ph | H | COCH₃ | H | H | H | H | H | H | H | — | — |
| 3-45 | Ir | 1 | 3 | Ph | H | H | H | BL | H | H | H | H | H | pic | |
| 3-45X | Ir | 1 | 3 | Ph | H | H | H | BL | H | H | H | H | H | acac | |
| 3-45Y | Ir | 0 | 3 | Ph | H | H | H | BL | H | H | H | H | H | — | — |
| 3-46 | Ir | 1 | 3 | Ph | H | H | BL | H | H | H | H | H | H | pic | |
| 3-46X | Ir | 1 | 3 | Ph | H | H | BL | H | H | H | H | H | H | acac | |
| 3-46Y | Ir | 0 | 3 | Ph | H | H | BL | H | H | H | H | H | H | — | — |
| 3-47 | Ir | 1 | 3 | Ph | H | H | H | PL | H | H | H | H | H | pic | |
| 3-47X | Ir | 1 | 3 | Ph | H | H | H | PL | H | H | H | H | H | acac | |
| 3-47Y | Ir | 0 | 3 | Ph | H | H | H | PL | H | H | H | H | H | — | — |
| 3-48 | Ir | 1 | 3 | Ph | H | H | PL | H | H | H | H | H | H | pic | |
| 3-48X | Ir | 1 | 3 | Ph | H | H | PL | H | H | H | H | H | H | acac | |
| 3-48Y | Ir | 0 | 3 | Ph | H | H | PL | H | H | H | H | H | H | — | — |
| 3-49 | Ir | 1 | 3 | Ph | H | H | H | MEE1 | H | H | H | H | H | pic | |
| 3-49X | Ir | 1 | 3 | Ph | H | H | H | MEE1 | H | H | H | H | H | acac | |
| 3-49Y | Ir | 0 | 3 | Ph | H | H | H | MEE1 | H | H | H | H | H | — | — |
| 3-50 | Ir | 1 | 3 | Ph | H | H | MEE1 | H | H | H | H | H | H | pic | |
| 3-50X | Ir | 1 | 3 | Ph | H | H | MEE1 | H | H | H | H | H | H | acac | |
| 3-50Y | Ir | 0 | 3 | Ph | H | H | MEE1 | H | H | H | H | H | H | — | — |
| 3-51 | Ir | 1 | 3 | Ph | H | H | H | MEE2 | H | H | H | H | H | pic | |
| 3-51X | Ir | 1 | 3 | Ph | H | H | H | MEE2 | H | H | H | H | H | acac | |
| 3-51Y | Ir | 0 | 3 | Ph | H | H | H | MEE2 | H | H | H | H | H | — | — |
| 3-52 | Ir | 1 | 3 | Ph | H | H | MEE2 | H | H | H | H | H | H | pic | |
| 3-52X | Ir | 1 | 3 | Ph | H | H | MEE2 | H | H | H | H | H | H | acac | |
| 3-52Y | Ir | 0 | 3 | Ph | H | H | MEE2 | H | H | H | H | H | H | — | — |
| 3-53 | Ir | 1 | 3 | Ph | H | H | H | PA1 | H | H | H | H | H | pic | |
| 3-53X | Ir | 1 | 3 | Ph | H | H | H | PA1 | H | H | H | H | H | acac | |
| 3-53Y | Ir | 0 | 3 | Ph | H | H | H | PA1 | H | H | H | H | H | — | — |
| 3-54 | Ir | 1 | 3 | Ph | H | H | PA1 | H | H | H | H | H | H | pic | |
| 3-54X | Ir | 1 | 3 | Ph | H | H | PA1 | H | H | H | H | H | H | acac | |
| 3-54Y | Ir | 0 | 3 | Ph | H | H | PA1 | H | H | H | H | H | H | — | — |
| 3-55 | Ir | 1 | 3 | Ph | H | H | H | PA2 | H | H | H | H | H | pic | |
| 3-55X | Ir | 1 | 3 | Ph | H | H | H | PA2 | H | H | H | H | H | acac | |
| 3-55Y | Ir | 0 | 3 | Ph | H | H | H | PA2 | H | H | H | H | H | — | — |
| 3-56 | Ir | 1 | 3 | Ph | H | H | PA2 | H | H | H | H | H | H | pic | |
| 3-56X | Ir | 1 | 3 | Ph | H | H | PA2 | H | H | H | H | H | H | acac | |
| 3-56Y | Ir | 0 | 3 | Ph | H | H | PA2 | H | H | H | H | H | H | — | — |
| 3-57 | Ir | 1 | 3 | Ph | H | H | H | EA1 | H | H | H | H | H | pic | |
| 3-57X | Ir | 1 | 3 | Ph | H | H | H | EA1 | H | H | H | H | H | acac | |
| 3-57Y | Ir | 0 | 3 | Ph | H | H | H | EA1 | H | H | H | H | H | — | — |
| 3-58 | Ir | 1 | 3 | Ph | H | H | EA2 | H | H | H | H | H | H | pic | |
| 3-58X | Ir | 1 | 3 | Ph | H | H | EA2 | H | H | H | H | H | H | acac | |
| 3-58Y | Ir | 0 | 3 | Ph | H | H | EA2 | H | H | H | H | H | H | — | — |
| 3-59 | Ir | 1 | 3 | Ph | H | H | H | ME | H | H | H | H | H | pic | |
| 3-59X | Ir | 1 | 3 | Ph | H | H | H | ME | H | H | H | H | H | acac | |
| 3-59Y | Ir | 0 | 3 | Ph | H | H | H | ME | H | H | H | H | H | — | — |
| 3-60 | Ir | 1 | 3 | Ph | H | H | ME | H | H | H | H | H | H | pic | |
| 3-60X | Ir | 1 | 3 | Ph | H | H | ME | H | H | H | H | H | H | acac | |
| 3-60Y | Ir | 0 | 3 | Ph | H | H | ME | H | H | H | H | H | H | — | — |
| 3-61 | Ir | 1 | 3 | Ph | H | H | H | AT | H | H | H | H | H | pic | |
| 3-61X | Ir | 1 | 3 | Ph | H | H | H | AT | H | H | H | H | H | acac | |
| 3-61Y | Ir | 0 | 3 | Ph | H | H | H | AT | H | H | H | H | H | — | — |
| 3-62 | Ir | 1 | 3 | Ph | H | H | AT | H | H | H | H | H | H | pic | |
| 3-62X | Ir | 1 | 3 | Ph | H | H | AT | H | H | H | H | H | H | acac | |
| 3-62Y | Ir | 0 | 3 | Ph | H | H | AT | H | H | H | H | H | H | — | — |
| 3-63 | Ir | 1 | 3 | Ph | H | H | H | MES1 | H | H | H | H | H | pic | |
| 3-63X | Ir | 1 | 3 | Ph | H | H | H | MES1 | H | H | H | H | H | acac | |
| 3-63Y | Ir | 0 | 3 | Ph | H | H | H | MES1 | H | H | H | H | H | — | — |
| 3-64 | Ir | 1 | 3 | Ph | H | H | MES1 | H | H | H | H | H | H | pic | |
| 3-64X | Ir | 1 | 3 | Ph | H | H | MES1 | H | H | H | H | H | H | acac | |
| 3-64Y | Ir | 0 | 3 | Ph | H | H | MES1 | H | H | H | H | H | H | — | — |
| 3-65 | Ir | 1 | 3 | Ph | H | H | H | MES2 | H | H | H | H | H | pic | |
| 3-65X | Ir | 1 | 3 | Ph | H | H | H | MES2 | H | H | H | H | H | acac | |
| 3-65Y | Ir | 0 | 3 | Ph | H | H | H | MES2 | H | H | H | H | H | — | — |
| 3-66 | Ir | 1 | 3 | Ph | H | H | MES2 | H | H | H | H | H | H | pic | |
| 3-66X | Ir | 1 | 3 | Ph | H | H | MES2 | H | H | H | H | H | H | acac | |
| 3-66Y | Ir | 0 | 3 | Ph | H | H | MES2 | H | H | H | H | H | H | — | — |
| 3-67 | Ir | 1 | 3 | Ph | H | H | H | PS1 | H | H | H | H | H | pic | |
| 3-67X | Ir | 1 | 3 | Ph | H | H | H | PS1 | H | H | H | H | H | acac | |

TABLE 3-continued

| No. | M | n | BBS | BS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3-67Y | Ir | 0 | 3 | Ph | H | H | | PS1 | H | H | H | H | H | — | — |
| 3-68 | Ir | 1 | 3 | Ph | H | | PS1 | H | H | H | H | H | H | pic | |
| 3-68X | Ir | 1 | 3 | Ph | H | | PS1 | H | H | H | H | H | H | | acac |
| 3-68Y | Ir | 0 | 3 | Ph | H | | PS1 | H | H | H | H | H | H | — | — |
| 3-69 | Ir | 1 | 3 | Ph | H | H | | PS2 | H | H | H | H | H | pic | |
| 3-69X | Ir | 1 | 3 | Ph | H | H | | PS2 | H | H | H | H | H | | acac |
| 3-69Y | Ir | 0 | 3 | Ph | H | H | | PS2 | H | H | H | H | H | — | — |
| 3-70 | Ir | 1 | 3 | Ph | H | | PS2 | H | H | H | H | H | H | pic | |
| 3-70X | Ir | 1 | 3 | Ph | H | | PS2 | H | H | H | H | H | H | | acac |
| 3-70Y | Ir | 0 | 3 | Ph | H | | PS2 | H | H | H | H | H | H | — | — |
| 3-71 | Ir | 1 | 3 | Ph | H | H | | BAL1 | H | H | H | H | H | pic | |
| 3-71X | Ir | 1 | 3 | Ph | H | H | | BAL1 | H | H | H | H | H | | acac |
| 3-71Y | Ir | 0 | 3 | Ph | H | H | | BAL1 | H | H | H | H | H | — | — |
| 3-72 | Ir | 1 | 3 | Ph | H | | BAL1 | H | H | H | H | H | H | pic | |
| 3-72X | Ir | 1 | 3 | Ph | H | | BAL1 | H | H | H | H | H | H | | acac |
| 3-72Y | Ir | 0 | 3 | Ph | H | | BAL1 | H | H | H | H | H | H | — | — |
| 3-73 | Ir | 1 | 3 | Ph | H | H | | BAL2 | H | H | H | H | H | pic | |
| 3-73X | Ir | 1 | 3 | Ph | H | H | | BAL2 | H | H | H | H | H | | acac |
| 3-73Y | Ir | 0 | 3 | Ph | H | H | | BAL2 | H | H | H | H | H | — | — |
| 3-74 | Ir | 1 | 3 | Ph | H | | BAL2 | H | H | H | H | H | H | pic | |
| 3-74X | Ir | 1 | 3 | Ph | H | | BAL2 | H | H | H | H | H | H | | acac |
| 3-74Y | Ir | 0 | 3 | Ph | H | | BAL2 | H | H | H | H | H | H | — | — |
| 3-75 | Ir | 1 | 3 | Ph | H | H | | MEK1 | H | H | H | H | H | pic | |
| 3-75X | Ir | 1 | 3 | Ph | H | H | | MEK1 | H | H | H | H | H | | acac |
| 3-75Y | Ir | 0 | 3 | Ph | H | H | | MEK1 | H | H | H | H | H | — | — |
| 3-76 | Ir | 1 | 3 | Ph | H | | MEK1 | H | H | H | H | H | H | pic | |
| 3-76X | Ir | 1 | 3 | Ph | H | | MEK1 | H | H | H | H | H | H | | acac |
| 3-76Y | Ir | 0 | 3 | Ph | H | | MEK1 | H | H | H | H | H | H | — | — |
| 3-77 | Ir | 1 | 3 | Ph | H | H | | MEK2 | H | H | H | H | H | pic | |
| 3-77X | Ir | 1 | 3 | Ph | H | H | | MEK2 | H | H | H | H | H | | acac |
| 3-77Y | Ir | 0 | 3 | Ph | H | H | | MEK2 | H | H | H | H | H | — | — |
| 3-78 | Ir | 1 | 3 | Ph | H | | MEK2 | H | H | H | H | H | H | pic | |
| 3-78X | Ir | 1 | 3 | Ph | H | | MEK2 | H | H | H | H | H | H | | acac |
| 3-78Y | Ir | 0 | 3 | Ph | H | | MEK2 | H | H | H | H | H | H | — | — |
| 3-79 | Ir | 1 | 3 | Ph | H | H | | PAL1 | H | H | H | H | H | pic | |
| 3-79X | Ir | 1 | 3 | Ph | H | H | | PAL1 | H | H | H | H | H | | acac |
| 3-79Y | Ir | 0 | 3 | Ph | H | H | | PAL1 | H | H | H | H | H | — | — |
| 3-80 | Ir | 1 | 3 | Ph | H | | PAL1 | H | H | H | H | H | H | pic | |
| 3-80X | Ir | 1 | 3 | Ph | H | | PAL1 | H | H | H | H | H | H | | acac |
| 3-80Y | Ir | 0 | 3 | Ph | H | | PAL1 | H | H | H | H | H | H | — | — |
| 3-81 | Ir | 1 | 3 | Ph | H | H | | PAL2 | H | H | H | H | H | pic | |
| 3-81X | Ir | 1 | 3 | Ph | H | H | | PAL2 | H | H | H | H | H | | acac |
| 3-81Y | Ir | 0 | 3 | Ph | H | H | | PAL2 | H | H | H | H | H | — | — |
| 3-82 | Ir | 1 | 3 | Ph | H | | PAL2 | H | H | H | H | H | H | pic | |
| 3-82X | Ir | 1 | 3 | Ph | H | | PAL2 | H | H | H | H | H | H | | acac |
| 3-82Y | Ir | 0 | 3 | Ph | H | | PAL2 | H | H | H | H | H | H | — | — |
| 3-83 | Ir | 1 | 3 | Ph | H | H | | MMK | H | H | H | H | H | pic | |
| 3-83X | Ir | 1 | 3 | Ph | H | H | | MMK | H | H | H | H | H | | acac |
| 3-83Y | Ir | 0 | 3 | Ph | H | H | | MMK | H | H | H | H | H | — | — |
| 3-84 | Ir | 1 | 3 | Ph | H | | MMK | H | H | H | H | H | H | pic | |
| 3-84X | Ir | 1 | 3 | Ph | H | | MMK | H | H | H | H | H | H | | acac |
| 3-84Y | Ir | 0 | 3 | Ph | H | | MMK | H | H | H | H | H | H | — | — |
| 3-85 | Ir | 1 | 3 | Ph | H | H | | EES1 | H | H | H | H | H | pic | |
| 3-85X | Ir | 1 | 3 | Ph | H | H | | EES1 | H | H | H | H | H | | acac |
| 3-85Y | Ir | 0 | 3 | Ph | H | H | | EES1 | H | H | H | H | H | — | — |
| 3-86 | Ir | 1 | 3 | Ph | H | | EES2 | H | H | H | H | H | H | pic | |
| 3-86X | Ir | 1 | 3 | Ph | H | | EES2 | H | H | H | H | H | H | | acac |
| 3-86Y | Ir | 0 | 3 | Ph | H | | EES2 | H | H | H | H | H | H | — | — |
| 3-87 | Ir | 1 | 3 | Ph | H | H | | PAE1 | H | H | H | H | H | pic | |
| 3-87X | Ir | 1 | 3 | Ph | H | H | | PAE1 | H | H | H | H | H | | acac |
| 3-87Y | Ir | 0 | 3 | Ph | H | H | | PAE1 | H | H | H | H | H | — | — |
| 3-88 | Ir | 1 | 3 | Ph | H | | PAE2 | H | H | H | H | H | H | pic | |
| 3-88X | Ir | 1 | 3 | Ph | H | | PAE2 | H | H | H | H | H | H | | acac |
| 3-88Y | Ir | 0 | 3 | Ph | H | | PAE2 | H | H | H | H | H | H | — | — |
| 3-89 | Ir | 1 | 3 | Ph | H | H | | AME1 | H | H | H | H | H | pic | |
| 3-89X | Ir | 1 | 3 | Ph | H | H | | AME1 | H | H | H | H | H | | acac |
| 3-89Y | Ir | 0 | 3 | Ph | H | H | | AME1 | H | H | H | H | H | — | — |
| 3-90 | Ir | 1 | 3 | Ph | H | | AME1 | H | H | H | H | H | H | pic | |
| 3-90X | Ir | 1 | 3 | Ph | H | | AME1 | H | H | H | H | H | H | | acac |
| 3-90Y | Ir | 0 | 3 | Ph | H | | AME1 | H | H | H | H | H | H | — | — |
| 3-91 | Ir | 1 | 3 | Ph | H | H | | AME2 | H | H | H | H | H | pic | |
| 3-91X | Ir | 1 | 3 | Ph | H | H | | AME2 | H | H | H | H | H | | acac |
| 3-91Y | Ir | 0 | 3 | Ph | H | H | | AME2 | H | H | H | H | H | — | — |
| 3-92 | Ir | 1 | 3 | Ph | H | | AME2 | H | H | H | H | H | H | pic | |
| 3-92X | Ir | 1 | 3 | Ph | H | | AME2 | H | H | H | H | H | H | | acac |
| 3-92Y | Ir | 0 | 3 | Ph | H | | AME2 | H | H | H | H | H | H | — | — |
| 3-93 | Ir | 1 | 3 | Ph | H | H | | EAE1 | H | H | H | H | H | pic | |

TABLE 3-continued

| No. | M | n | BBS | BS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 3-93X | Ir | 1 | 3 | Ph | H | H | | EAE1 | H | H | H | H | H | acac |
| 3-93Y | Ir | 0 | 3 | Ph | H | H | | EAE1 | H | H | H | H | H | — — |
| 3-94 | Ir | 1 | 3 | Ph | H | | EAE1 | | H | H | H | H | H | pic |
| 3-94X | Ir | 1 | 3 | Ph | H | | EAE1 | | H | H | H | H | H | acac |
| 3-94Y | Ir | 0 | 3 | Ph | H | | EAE1 | | H | H | H | H | H | — — |
| 3-95 | Ir | 1 | 3 | Ph | H | H | | EAE2 | H | H | H | H | H | pic |
| 3-95X | Ir | 1 | 3 | Ph | H | H | | EAE2 | H | H | H | H | H | acac |
| 3-95Y | Ir | 0 | 3 | Ph | H | H | | EAE2 | H | H | H | H | H | — — |
| 3-96 | Ir | 1 | 3 | Ph | H | | EAE2 | | H | H | H | H | H | pic |
| 3-96X | Ir | 1 | 3 | Ph | H | | EAE2 | | H | H | H | H | H | acac |
| 3-96Y | Ir | 0 | 3 | Ph | H | | EAE2 | | H | H | H | H | H | — — |
| 3-97 | Ir | 1 | 3 | Ph | H | H | | AAE1 | H | H | H | H | H | pic |
| 3-97X | Ir | 1 | 3 | Ph | H | H | | AAE1 | H | H | H | H | H | acac |
| 3-97Y | Ir | 0 | 3 | Ph | H | H | | AAE1 | H | H | H | H | H | — — |
| 3-98 | Ir | 1 | 3 | Ph | H | | AAE1 | | H | H | H | H | H | pic |
| 3-98X | Ir | 1 | 3 | Ph | H | | AAE1 | | H | H | H | H | H | acac |
| 3-98Y | Ir | 0 | 3 | Ph | H | | AAE1 | | H | H | H | H | H | — — |
| 3-99 | Ir | 1 | 3 | Ph | H | H | | AAE2 | H | H | H | H | H | pic |
| 3-99X | Ir | 1 | 3 | Ph | H | H | | AAE2 | H | H | H | H | H | acac |
| 3-99Y | Ir | 0 | 3 | Ph | H | H | | AAE2 | H | H | H | H | H | — — |
| 3-100 | Ir | 1 | 3 | Ph | H | | AAE2 | | H | H | H | H | H | pic |
| 3-100X | Ir | 1 | 3 | Ph | H | | AAE2 | | H | H | H | H | H | acac |
| 3-100Y | Ir | 0 | 3 | Ph | H | | AAE2 | | H | H | H | H | H | — — |
| 3-101 | Ir | 1 | 3 | Ph | H | H | | PME1 | H | H | H | H | H | pic |
| 3-101X | Ir | 1 | 3 | Ph | H | H | | PME1 | H | H | H | H | H | acac |
| 3-101Y | Ir | 0 | 3 | Ph | H | H | | PME1 | H | H | H | H | H | — — |
| 3-102 | Ir | 1 | 3 | Ph | H | | PME1 | | H | H | H | H | H | pic |
| 3-102X | Ir | 1 | 3 | Ph | H | | PME1 | | H | H | H | H | H | acac |
| 3-102Y | Ir | 0 | 3 | Ph | H | | PME1 | | H | H | H | H | H | — — |
| 3-103 | Ir | 1 | 3 | Ph | H | H | | PME2 | H | H | H | H | H | pic |
| 3-103X | Ir | 1 | 3 | Ph | H | H | | PME2 | H | H | H | H | H | acac |
| 3-103Y | Ir | 0 | 3 | Ph | H | H | | PME2 | H | H | H | H | H | — — |
| 3-104 | Ir | 1 | 3 | Ph | H | | PME2 | | H | H | H | H | H | pic |
| 3-104X | Ir | 1 | 3 | Ph | H | | PME2 | | H | H | H | H | H | acac |
| 3-104Y | Ir | 0 | 3 | Ph | H | | PME2 | | H | H | H | H | H | — — |
| 3-105 | Ir | 1 | 3 | Ph | H | H | | MET1 | H | H | H | H | H | pic |
| 3-105X | Ir | 1 | 3 | Ph | H | H | | MET1 | H | H | H | H | H | acac |
| 3-105Y | Ir | 0 | 3 | Ph | H | H | | MET1 | H | H | H | H | H | — — |
| 3-106 | Ir | 1 | 3 | Ph | H | | MET1 | | H | H | H | H | H | pic |
| 3-106X | Ir | 1 | 3 | Ph | H | | MET1 | | H | H | H | H | H | acac |
| 3-106Y | Ir | 0 | 3 | Ph | H | | MET1 | | H | H | H | H | H | — — |
| 3-107 | Ir | 1 | 3 | Ph | H | H | | MET2 | H | H | H | H | H | pic |
| 3-107X | Ir | 1 | 3 | Ph | H | H | | MET2 | H | H | H | H | H | acac |
| 3-107Y | Ir | 0 | 3 | Ph | H | H | | MET2 | H | H | H | H | H | — — |
| 3-108 | Ir | 1 | 3 | Ph | H | | MET2 | | H | H | H | H | H | pic |
| 3-108X | Ir | 1 | 3 | Ph | H | | MET2 | | H | H | H | H | H | acac |
| 3-108Y | Ir | 0 | 3 | Ph | H | | MET2 | | H | H | H | H | H | — — |
| 3-109 | Ir | 1 | 3 | Ph | H | H | | EE1 | H | H | H | H | H | pic |
| 3-109X | Ir | 1 | 3 | Ph | H | H | | EE1 | H | H | H | H | H | acac |
| 3-109Y | Ir | 0 | 3 | Ph | H | H | | EE1 | H | H | H | H | H | — — |
| 3-110 | Ir | 1 | 3 | Ph | H | | EE1 | | H | H | H | H | H | pic |
| 3-110X | Ir | 1 | 3 | Ph | H | | EE1 | | H | H | H | H | H | acac |
| 3-110Y | Ir | 0 | 3 | Ph | H | | EE1 | | H | H | H | H | H | — — |
| 3-111 | Ir | 1 | 3 | Ph | H | H | | EE2 | H | H | H | H | H | pic |
| 3-111X | Ir | 1 | 3 | Ph | H | H | | EE2 | H | H | H | H | H | acac |
| 3-111Y | Ir | 0 | 3 | Ph | H | H | | EE2 | H | H | H | H | H | — — |
| 3-112 | Ir | 1 | 3 | Ph | H | | EE2 | | H | H | H | H | H | pic |
| 3-112X | Ir | 1 | 3 | Ph | H | | EE2 | | H | H | H | H | H | acac |
| 3-112Y | Ir | 0 | 3 | Ph | H | | EE2 | | H | H | H | H | H | — — |
| 3-113 | Ir | 1 | 3 | Ph | H | H | | MS1 | H | H | H | H | H | pic |
| 3-113X | Ir | 1 | 3 | Ph | H | H | | MS1 | H | H | H | H | H | acac |
| 3-113Y | Ir | 0 | 3 | Ph | H | H | | MS1 | H | H | H | H | H | — — |
| 3-114 | Ir | 1 | 3 | Ph | H | | MS1 | | H | H | H | H | H | pic |
| 3-114X | Ir | 1 | 3 | Ph | H | | MS1 | | H | H | H | H | H | acac |
| 3-114Y | Ir | 0 | 3 | Ph | H | | MS1 | | H | H | H | H | H | — — |
| 3-115 | Ir | 1 | 3 | Ph | H | H | | MS2 | H | H | H | H | H | pic |
| 3-115X | Ir | 1 | 3 | Ph | H | H | | MS2 | H | H | H | H | H | acac |
| 3-115Y | Ir | 0 | 3 | Ph | H | H | | MS2 | H | H | H | H | H | — — |
| 3-116 | Ir | 1 | 3 | Ph | H | | MS2 | | H | H | H | H | H | pic |
| 3-116X | Ir | 1 | 3 | Ph | H | | MS2 | | H | H | H | H | H | acac |
| 3-116Y | Ir | 0 | 3 | Ph | H | | MS2 | | H | H | H | H | H | — — |

TABLE 4

| No. | M | n | BSS | SS | G | T$^1$ | T$^2$ | T$^3$ | T$^4$ | T$^5$ | T$^6$ | T$^7$ | T$^8$ | T$^9$ | L$^1$ L$^2$ |
|---|---|---|---|---|---|---|---|---|---|---|---|---|---|---|---|
| 4-1 | Ir | 1 | 4 | | Ph | H | H | H | H | CH$_3$ | H | H | H | H | pic |
| 4-1X | Ir | 1 | 4 | | Ph | H | H | H | H | CH$_3$ | H | H | H | H | acac |
| 4-1Y | Ir | 0 | 4 | | Ph | H | H | H | H | CH$_3$ | H | H | H | H | — — |
| 4-2 | Ir | 1 | 4 | | Ph | H | H | H | H | $^t$C$_4$H$_9$ | H | H | H | H | pic |
| 4-2X | Ir | 1 | 4 | | Ph | H | H | H | H | $^t$C$_4$H$_9$ | H | H | H | H | acac |
| 4-2Y | Ir | 0 | 4 | | Ph | H | H | H | H | $^t$C$_4$H$_9$ | H | H | H | H | — — |
| 4-3 | Ir | 1 | 4 | | Ph | H | F | H | F | CH$_3$ | H | H | H | H | pic |
| 4-3X | Ir | 1 | 4 | | Ph | H | F | H | F | CH$_3$ | H | H | H | H | acac |
| 4-3Y | Ir | 0 | 4 | | Ph | H | F | H | F | CH$_3$ | H | H | H | H | — — |
| 4-4 | Ir | 1 | 4 | | Ph | H | F | H | F | $^t$C$_4$H$_9$ | H | H | H | H | pic |
| 4-4X | Ir | 1 | 4 | | Ph | H | F | H | F | $^t$C$_4$H$_9$ | H | H | H | H | acac |
| 4-4Y | Ir | 0 | 4 | | Ph | H | F | H | F | $^t$C$_4$H$_9$ | H | H | H | H | — — |
| 4-5 | Ir | 1 | 4 | | Ph | F | H | H | F | CH$_3$ | H | H | H | H | pic |
| 4-5X | Ir | 1 | 4 | | Ph | F | H | H | F | CH$_3$ | H | H | H | H | acac |
| 4-5Y | Ir | 0 | 4 | | Ph | F | H | H | F | CH$_3$ | H | H | H | H | — — |
| 4-6 | Ir | 1 | 4 | | Ph | F | H | H | F | $^t$C$_4$H$_9$ | H | H | H | H | pic |
| 4-6X | Ir | 1 | 4 | | Ph | F | H | H | F | $^t$C$_4$H$_9$ | H | H | H | H | acac |
| 4-6Y | Ir | 0 | 4 | | Ph | F | H | H | F | $^t$C$_4$H$_9$ | H | H | H | H | — — |
| 4-7 | Ir | 1 | 4 | | Ph | CF$_3$ | H | CF$_3$ | H | CH$_3$ | H | H | H | H | pic |
| 4-7X | Ir | 1 | 4 | | Ph | CF$_3$ | H | CF$_3$ | H | CH$_3$ | H | H | H | H | acac |
| 4-7Y | Ir | 0 | 4 | | Ph | CF$_3$ | H | CF$_3$ | H | CH$_3$ | H | H | H | H | — — |
| 4-8 | Ir | 1 | 4 | | Ph | CF$_3$ | H | CF$_3$ | H | $^t$C$_4$H$_9$ | H | H | H | H | pic |
| 4-8X | Ir | 1 | 4 | | Ph | CF$_3$ | H | CF$_3$ | H | $^t$C$_4$H$_9$ | H | H | H | H | acac |
| 4-8Y | Ir | 0 | 4 | | Ph | CF$_3$ | H | CF$_3$ | H | $^t$C$_4$H$_9$ | H | H | H | H | — — |
| 4-9 | Ir | 1 | 4 | | Ph | H | F | CF$_3$ | H | CH$_3$ | H | H | H | H | pic |
| 4-9X | Ir | 1 | 4 | | Ph | H | F | CF$_3$ | H | CH$_3$ | H | H | H | H | acac |
| 4-9Y | Ir | 0 | 4 | | Ph | H | F | CF$_3$ | H | CH$_3$ | H | H | H | H | — — |
| 4-10 | Ir | 1 | 4 | | Ph | F | H | CF$_3$ | H | CH$_3$ | H | H | H | H | pic |
| 4-10X | Ir | 1 | 4 | | Ph | F | H | CF$_3$ | H | CH$_3$ | H | H | H | H | acac |
| 4-10Y | Ir | 0 | 4 | | Ph | F | H | CF$_3$ | H | CH$_3$ | H | H | H | H | — — |
| 4-11 | Ir | 1 | 4 | | Ph | F | F | F | F | CH$_3$ | H | H | H | H | pic |
| 4-11X | Ir | 1 | 4 | | Ph | F | F | F | F | CH$_3$ | H | H | H | H | acac |
| 4-11Y | Ir | 0 | 4 | | Ph | F | F | F | F | CH$_3$ | H | H | H | H | — — |
| 4-12 | Ir | 1 | 4 | | Ph | H | F | H | CH$_3$ | CH$_3$ | H | H | H | H | pic |
| 4-12X | Ir | 1 | 4 | | Ph | H | F | H | CH$_3$ | CH$_3$ | H | H | H | H | acac |
| 4-12Y | Ir | 0 | 4 | | Ph | H | F | H | CH$_3$ | CH$_3$ | H | H | H | H | — — |
| 4-13 | Ir | 1 | 4 | | Ph | H | F | H | CH$_3$ | $^t$C$_4$H$_9$ | H | H | H | H | pic |
| 4-13X | Ir | 1 | 4 | | Ph | H | F | H | CH$_3$ | $^t$C$_4$H$_9$ | H | H | H | H | acac |
| 4-13Y | Ir | 0 | 4 | | Ph | H | F | H | CH$_3$ | $^t$C$_4$H$_9$ | H | H | H | H | — — |
| 4-14 | Ir | 1 | 4 | | Ph | H | F | H | $^t$C$_4$H$_9$ | CH$_3$ | H | H | H | H | pic |
| 4-14X | Ir | 1 | 4 | | Ph | H | F | H | $^t$C$_4$H$_9$ | CH$_3$ | H | H | H | H | acac |
| 4-14Y | Ir | 0 | 4 | | Ph | H | F | H | $^t$C$_4$H$_9$ | CH$_3$ | H | H | H | H | — — |
| 4-15 | Ir | 1 | 4 | | Ph | H | F | H | $^t$C$_4$H$_9$ | $^t$C$_4$H$_9$ | H | H | H | H | pic |
| 4-15X | Ir | 1 | 4 | | Ph | H | F | H | $^t$C$_4$H$_9$ | $^t$C$_4$H$_9$ | H | H | H | H | acac |
| 4-15Y | Ir | 0 | 4 | | Ph | H | F | H | $^t$C$_4$H$_9$ | $^t$C$_4$H$_9$ | H | H | H | H | — — |
| 4-16 | Ir | 1 | 4 | | Ph | H | CF$_3$ | H | CF$_3$ | CH$_3$ | H | H | H | H | pic |
| 4-16X | Ir | 1 | 4 | | Ph | H | CF$_3$ | H | CF$_3$ | CH$_3$ | H | H | H | H | acac |
| 4-16Y | Ir | 0 | 4 | | Ph | H | CF$_3$ | H | CF$_3$ | CH$_3$ | H | H | H | H | — — |
| 4-17 | Ir | 1 | 4 | | Ph | H | CF$_3$ | H | CF$_3$ | $^t$C$_4$H$_9$ | H | H | H | H | pic |
| 4-17X | Ir | 1 | 4 | | Ph | H | CF$_3$ | H | CF$_3$ | $^t$C$_4$H$_9$ | H | H | H | H | acac |
| 4-17Y | Ir | 0 | 4 | | Ph | H | CF$_3$ | H | CF$_3$ | $^t$C$_4$H$_9$ | H | H | H | H | — — |
| 4-18 | Ir | 1 | 4 | | Ph | CF$_3$ | H | H | $^t$C$_4$H$_9$ | CH$_3$ | H | H | H | H | pic |
| 4-18X | Ir | 1 | 4 | | Ph | CF$_3$ | H | H | $^t$C$_4$H$_9$ | CH$_3$ | H | H | H | H | acac |
| 4-18Y | Ir | 0 | 4 | | Ph | CF$_3$ | H | H | $^t$C$_4$H$_9$ | CH$_3$ | H | H | H | H | — — |
| 4-19 | Ir | 1 | 4 | | Ph | CF$_3$ | H | H | $^t$C$_4$H$_9$ | $^t$C$_4$H$_9$ | H | H | H | H | pic |
| 4-19X | Ir | 1 | 4 | | Ph | CF$_3$ | H | H | $^t$C$_4$H$_9$ | $^t$C$_4$H$_9$ | H | H | H | H | acac |
| 4-19Y | Ir | 0 | 4 | | Ph | CF$_3$ | H | H | $^t$C$_4$H$_9$ | $^t$C$_4$H$_9$ | H | H | H | H | — — |
| 4-20 | Ir | 1 | 4 | | Ph | H | CF$_3$ | H | $^t$C$_4$H$_9$ | CH$_3$ | H | H | H | H | pic |
| 4-20X | Ir | 1 | 4 | | Ph | H | CF$_3$ | H | $^t$C$_4$H$_9$ | CH$_3$ | H | H | H | H | acac |
| 4-20Y | Ir | 0 | 4 | | Ph | H | CF$_3$ | H | $^t$C$_4$H$_9$ | CH$_3$ | H | H | H | H | — — |
| 4-21 | Ir | 1 | 4 | | Ph | H | CF$_3$ | H | $^t$C$_4$H$_9$ | $^t$C$_4$H$_9$ | H | H | H | H | pic |
| 4-21X | Ir | 1 | 4 | | Ph | H | CF$_3$ | H | $^t$C$_4$H$_9$ | $^t$C$_4$H$_9$ | H | H | H | H | acac |
| 4-21Y | Ir | 0 | 4 | | Ph | H | CF$_3$ | H | $^t$C$_4$H$_9$ | $^t$C$_4$H$_9$ | H | H | H | H | — — |
| 4-22 | Ir | 1 | 4 | | Ph | H | CF$_3$ | H | CH$_3$ | CH$_3$ | H | H | H | H | pic |
| 4-22X | Ir | 1 | 4 | | Ph | H | CF$_3$ | H | CH$_3$ | CH$_3$ | H | H | H | H | acac |
| 4-22Y | Ir | 0 | 4 | | Ph | H | CF$_3$ | H | CH$_3$ | CH$_3$ | H | H | H | H | — — |
| 4-23 | Ir | 1 | 4 | | Ph | H | CF$_3$ | CF$_3$ | H | CH$_3$ | H | H | H | H | pic |
| 4-23X | Ir | 1 | 4 | | Ph | H | CF$_3$ | CF$_3$ | H | CH$_3$ | H | H | H | H | acac |
| 4-23Y | Ir | 0 | 4 | | Ph | H | CF$_3$ | CF$_3$ | H | CH$_3$ | H | H | H | H | — — |
| 4-24 | Ir | 1 | 4 | | Ph | H | H | NO$_2$ | H | CH$_3$ | H | H | H | H | pic |
| 4-24X | Ir | 1 | 4 | | Ph | H | H | NO$_2$ | H | CH$_3$ | H | H | H | H | acac |
| 4-24Y | Ir | 0 | 4 | | Ph | H | H | NO$_2$ | H | CH$_3$ | H | H | H | H | — — |
| 4-25 | Ir | 1 | 4 | | Ph | H | H | NO$_2$ | H | $^t$C$_4$H$_9$ | H | H | H | H | pic |
| 4-25X | Ir | 1 | 4 | | Ph | H | H | NO$_2$ | H | $^t$C$_4$H$_9$ | H | H | H | H | acac |
| 4-25Y | Ir | 0 | 4 | | Ph | H | H | NO$_2$ | H | $^t$C$_4$H$_9$ | H | H | H | H | — — |
| 4-26 | Ir | 1 | 4 | | Ph | F | H | NO$_2$ | H | CH$_3$ | H | H | H | H | pic |
| 4-26X | Ir | 1 | 4 | | Ph | F | H | NO$_2$ | H | CH$_3$ | H | H | H | H | acac |

TABLE 4-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4-26Y | Ir | 0 | 4 | Ph | F | H | NO₂ | H | CH₃ | H | H | H | H | — | — |
| 4-27 | Ir | 1 | 4 | Ph | F | H | NO₂ | F | CH₃ | H | H | H | H | pic | |
| 4-27X | Ir | 1 | 4 | Ph | F | H | NO₂ | F | CH₃ | H | H | H | H | acac | |
| 4-27Y | Ir | 0 | 4 | Ph | F | H | NO₂ | F | CH₃ | H | H | H | H | — | — |
| 4-28 | Ir | 1 | 4 | Ph | H | NO₂ | H | NO₂ | CH₃ | H | H | H | H | pic | |
| 4-28X | Ir | 1 | 4 | Ph | H | NO₂ | H | NO₂ | CH₃ | H | H | H | H | acac | |
| 4-28Y | Ir | 0 | 4 | Ph | H | NO₂ | H | NO₂ | CH₃ | H | H | H | H | — | — |
| 4-29 | Ir | 1 | 4 | Ph | H | NO₂ | H | NO₂ | ᵗC₄H₉ | H | H | H | H | pic | |
| 4-29X | Ir | 1 | 4 | Ph | H | NO₂ | H | NO₂ | ᵗC₄H₉ | H | H | H | H | acac | |
| 4-29Y | Ir | 0 | 4 | Ph | H | NO₂ | H | NO₂ | ᵗC₄H₉ | H | H | H | H | — | — |
| 4-30 | Ir | 1 | 4 | Ph | NO₂ | H | H | NO₂ | CH₃ | H | H | H | H | pic | |
| 4-30X | Ir | 1 | 4 | Ph | NO₂ | H | H | NO₂ | CH₃ | H | H | H | H | acac | |
| 4-30Y | Ir | 0 | 4 | Ph | NO₂ | H | H | NO₂ | CH₃ | H | H | H | H | — | — |
| 4-31 | Ir | 1 | 4 | Ph | NO₂ | H | H | NO₂ | ᵗC₄H₉ | H | H | H | H | pic | |
| 4-31X | Ir | 1 | 4 | Ph | NO₂ | H | H | NO₂ | ᵗC₄H₉ | H | H | H | H | acac | |
| 4-31Y | Ir | 0 | 4 | Ph | NO₂ | H | H | NO₂ | ᵗC₄H₉ | H | H | H | H | — | — |
| 4-32 | Ir | 1 | 4 | Ph | H | H | CF₃ | H | CH₃ | H | H | H | H | pic | |
| 4-32X | Ir | 1 | 4 | Ph | H | H | CF₃ | H | CH₃ | H | H | H | H | acac | |
| 4-32Y | Ir | 0 | 4 | Ph | H | H | CF₃ | H | CH₃ | H | H | H | H | — | — |
| 4-33 | Ir | 1 | 4 | Ph | H | H | CF₃ | H | ᵗC₄H₉ | H | H | H | H | pic | |
| 4-33X | Ir | 1 | 4 | Ph | H | H | CF₃ | H | ᵗC₄H₉ | H | H | H | H | acac | |
| 4-33Y | Ir | 0 | 4 | Ph | H | H | CF₃ | H | ᵗC₄H₉ | H | H | H | H | — | — |
| 4-34 | Ir | 1 | 4 | Ph | H | Cl | CF₃ | H | CH₃ | H | H | H | H | pic | |
| 4-34X | Ir | 1 | 4 | Ph | H | Cl | CF₃ | H | CH₃ | H | H | H | H | acac | |
| 4-34Y | Ir | 0 | 4 | Ph | H | Cl | CF₃ | H | CH₃ | H | H | H | H | — | — |
| 4-35 | Ir | 1 | 4 | Ph | H | Cl | CF₃ | H | ᵗC₄H₉ | H | H | H | H | pic | |
| 4-35X | Ir | 1 | 4 | Ph | H | Cl | CF₃ | H | ᵗC₄H₉ | H | H | H | H | acac | |
| 4-35Y | Ir | 0 | 4 | Ph | H | Cl | CF₃ | H | ᵗC₄H₉ | H | H | H | H | — | — |
| 4-36 | Ir | 1 | 4 | Ph | H | NO₂ | H | H | CH₃ | H | H | H | H | pic | |
| 4-36X | Ir | 1 | 4 | Ph | H | NO₂ | H | H | CH₃ | H | H | H | H | acac | |
| 4-36Y | Ir | 0 | 4 | Ph | H | NO₂ | H | H | CH₃ | H | H | H | H | — | — |
| 4-37 | Ir | 1 | 4 | Ph | H | CF₃ | H | H | CH₃ | H | H | H | H | pic | |
| 4-37X | Ir | 1 | 4 | Ph | H | CF₃ | H | H | CH₃ | H | H | H | H | acac | |
| 4-37Y | Ir | 0 | 4 | Ph | H | CF₃ | H | H | CH₃ | H | H | H | H | — | — |
| 4-38 | Ir | 1 | 4 | Ph | H | NO₂ | H | CH₃ | CH₃ | H | H | H | H | pic | |
| 4-38X | Ir | 1 | 4 | Ph | H | NO₂ | H | CH₃ | CH₃ | H | H | H | H | acac | |
| 4-38Y | Ir | 0 | 4 | Ph | H | NO₂ | H | CH₃ | CH₃ | H | H | H | H | — | — |
| 4-39 | Ir | 1 | 4 | Ph | H | NO₂ | H | CH₃ | ᵗC₄H₉ | H | H | H | H | pic | |
| 4-39X | Ir | 1 | 4 | Ph | H | NO₂ | H | CH₃ | ᵗC₄H₉ | H | H | H | H | acac | |
| 4-39Y | Ir | 0 | 4 | Ph | H | NO₂ | H | CH₃ | ᵗC₄H₉ | H | H | H | H | — | — |
| 4-40 | Ir | 1 | 4 | Ph | H | NO₂ | H | ᵗC₄H₉ | CH₃ | H | H | H | H | pic | |
| 4-40X | Ir | 1 | 4 | Ph | H | NO₂ | H | ᵗC₄H₉ | CH₃ | H | H | H | H | acac | |
| 4-40Y | Ir | 0 | 4 | Ph | H | NO₂ | H | ᵗC₄H₉ | CH₃ | H | H | H | H | — | — |
| 4-41 | Ir | 1 | 4 | Ph | H | NO₂ | H | ᵗC₄H₉ | ᵗC₄H₉ | H | H | H | H | pic | |
| 4-41X | Ir | 1 | 4 | Ph | H | NO₂ | H | ᵗC₄H₉ | ᵗC₄H₉ | H | H | H | H | acac | |
| 4-41Y | Ir | 0 | 4 | Ph | H | NO₂ | H | ᵗC₄H₉ | ᵗC₄H₉ | H | H | H | H | — | — |
| 4-42 | Ir | 1 | 4 | Ph | H | H | CH₃O | H | CH₃ | H | H | H | H | pic | |
| 4-42X | Ir | 1 | 4 | Ph | H | H | CH₃O | H | CH₃ | H | H | H | H | acac | |
| 4-42Y | Ir | 0 | 4 | Ph | H | H | CH₃O | H | CH₃ | H | H | H | H | — | — |
| 4-43 | Ir | 1 | 4 | Ph | H | CH₃O | H | H | CH₃ | H | H | H | H | pic | |
| 4-43X | Ir | 1 | 4 | Ph | H | CH₃O | H | H | CH₃ | H | H | H | H | acac | |
| 4-43Y | Ir | 0 | 4 | Ph | H | CH₃O | H | H | CH₃ | H | H | H | H | — | — |
| 4-44 | Ir | 1 | 4 | Ph | H | CH₃O | H | CH₃ | CH₃ | H | H | H | H | pic | |
| 4-44X | Ir | 1 | 4 | Ph | H | CH₃O | H | CH₃ | CH₃ | H | H | H | H | acac | |
| 4-44Y | Ir | 0 | 4 | Ph | H | CH₃O | H | CH₃ | CH₃ | H | H | H | H | — | — |
| 4-45 | Ir | 1 | 4 | Ph | H | CH₃O | H | ᵗC₄H₉ | CH₃ | H | H | H | H | pic | |
| 4-45X | Ir | 1 | 4 | Ph | H | CH₃O | H | ᵗC₄H₉ | CH₃ | H | H | H | H | acac | |
| 4-45Y | Ir | 0 | 4 | Ph | H | CH₃O | H | ᵗC₄H₉ | CH₃ | H | H | H | H | — | — |
| 4-46 | Ir | 1 | 4 | Ph | H | Si(CH₃)₃ | H | H | CH₃ | H | H | H | H | pic | |
| 4-46X | Ir | 1 | 4 | Ph | H | Si(CH₃)₃ | H | H | CH₃ | H | H | H | H | acac | |
| 4-46Y | Ir | 0 | 4 | Ph | H | Si(CH₃)₃ | H | H | CH₃ | H | H | H | H | — | — |
| 4-47 | Ir | 1 | 4 | Ph | H | Si(CH₃)₃ | H | H | ᵗC₄H₉ | H | H | H | H | pic | |
| 4-47X | Ir | 1 | 4 | Ph | H | Si(CH₃)₃ | H | H | ᵗC₄H₉ | H | H | H | H | acac | |
| 4-47Y | Ir | 0 | 4 | Ph | H | Si(CH₃)₃ | H | H | ᵗC₄H₉ | H | H | H | H | — | — |
| 4-48 | Ir | 1 | 4 | Ph | H | H | Si(CH₃)₃ | H | CH₃ | H | H | H | H | pic | |
| 4-48X | Ir | 1 | 4 | Ph | H | H | Si(CH₃)₃ | H | CH₃ | H | H | H | H | acac | |
| 4-48Y | Ir | 0 | 4 | Ph | H | H | Si(CH₃)₃ | H | CH₃ | H | H | H | H | — | — |
| 4-49 | Ir | 1 | 4 | Ph | H | H | H | Si(CH₃)₃ | CH₃ | H | H | H | H | pic | |
| 4-49X | Ir | 1 | 4 | Ph | H | H | H | Si(CH₃)₃ | CH₃ | H | H | H | H | acac | |
| 4-49Y | Ir | 0 | 4 | Ph | H | H | H | Si(CH₃)₃ | CH₃ | H | H | H | H | — | — |
| 4-50 | Ir | 1 | 4 | Ph | H | F | H | Si(CH₃)₃ | CH₃ | H | H | H | H | pic | |
| 4-50X | Ir | 1 | 4 | Ph | H | F | H | Si(CH₃)₃ | CH₃ | H | H | H | H | acac | |
| 4-50Y | Ir | 0 | 4 | Ph | H | F | H | Si(CH₃)₃ | CH₃ | H | H | H | H | — | — |
| 4-51 | Ir | 1 | 4 | Ph | H | CF₃ | H | Si(CH₃)₃ | CH₃ | H | H | H | H | pic | |
| 4-51X | Ir | 1 | 4 | Ph | H | CF₃ | H | Si(CH₃)₃ | CH₃ | H | H | H | H | acac | |
| 4-51Y | Ir | 0 | 4 | Ph | H | CF₃ | H | Si(CH₃)₃ | CH₃ | H | H | H | H | — | — |
| 4-52 | Ir | 1 | 4 | Ph | H | CF₃ | H | Si(CH₃)₃ | ᵗC₄H₉ | H | H | H | H | pic | |

TABLE 4-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4-52X | Ir | 1 | 4 | Ph | H | CF₃ | H | Si(CH₃)₃ | ᵗC₄H₉ | H | H | H | H | acac | |
| 4-52Y | Ir | 0 | 4 | Ph | H | CF₃ | H | Si(CH₃)₃ | ᵗC₄H₉ | H | H | H | H | — | — |
| 4-53 | Ir | 1 | 4 | Ph | H | Si(CH₃)₃ | H | F | CH₃ | H | H | H | H | pic | |
| 4-53X | Ir | 1 | 4 | Ph | H | Si(CH₃)₃ | H | F | CH₃ | H | H | H | H | acac | |
| 4-53Y | Ir | 0 | 4 | Ph | H | Si(CH₃)₃ | H | F | CH₃ | H | H | H | H | — | — |
| 4-54 | Ir | 1 | 4 | Ph | H | Si(CH₃)₃ | H | F | ᵗC₄H₉ | H | H | H | H | pic | |
| 4-54X | Ir | 1 | 4 | Ph | H | Si(CH₃)₃ | H | F | ᵗC₄H₉ | H | H | H | H | acac | |
| 4-54Y | Ir | 0 | 4 | Ph | H | Si(CH₃)₃ | H | F | ᵗC₄H₉ | H | H | H | H | — | — |
| 4-55 | Ir | 1 | 4 | Ph | H | Si(CH₃)₃ | H | CF₃ | CH₃ | H | H | H | H | pic | |
| 4-55X | Ir | 1 | 4 | Ph | H | Si(CH₃)₃ | H | CF₃ | CH₃ | H | H | H | H | acac | |
| 4-55Y | Ir | 0 | 4 | Ph | H | Si(CH₃)₃ | H | CF₃ | CH₃ | H | H | H | H | — | — |
| 4-56 | Ir | 1 | 4 | Ph | H | Si(CH₃)₃ | H | CF₃ | ᵗC₄H₉ | H | H | H | H | pic | |
| 4-56X | Ir | 1 | 4 | Ph | H | Si(CH₃)₃ | H | CF₃ | ᵗC₄H₉ | H | H | H | H | acac | |
| 4-56Y | Ir | 0 | 4 | Ph | H | Si(CH₃)₃ | H | CF₃ | ᵗC₄H₉ | H | H | H | H | — | — |
| 4-57 | Ir | 1 | 4 | Ph | Si(CH₃)₃ | H | Si(CH₃)₃ | H | CH₃ | H | H | H | H | pic | |
| 4-57X | Ir | 1 | 4 | Ph | Si(CH₃)₃ | H | Si(CH₃)₃ | H | CH₃ | H | H | H | H | acac | |
| 4-57Y | Ir | 0 | 4 | Ph | Si(CH₃)₃ | H | Si(CH₃)₃ | H | CH₃ | H | H | H | H | — | — |
| 4-58 | Ir | 1 | 4 | Ph | Si(CH₃)₃ | H | Si(CH₃)₃ | H | ᵗC₄H₉ | H | H | H | H | pic | |
| 4-58X | Ir | 1 | 4 | Ph | Si(CH₃)₃ | H | Si(CH₃)₃ | H | ᵗC₄H₉ | H | H | H | H | acac | |
| 4-58Y | Ir | 0 | 4 | Ph | Si(CH₃)₃ | H | Si(CH₃)₃ | H | ᵗC₄H₉ | H | H | H | H | — | — |
| 4-59 | Ir | 1 | 4 | Ph | H | H | H | COCH₃ | CH₃ | H | H | H | H | pic | |
| 4-59X | Ir | 1 | 4 | Ph | H | H | H | COCH₃ | CH₃ | H | H | H | H | acac | |
| 4-59Y | Ir | 0 | 4 | Ph | H | H | H | COCH₃ | CH₃ | H | H | H | H | — | — |
| 4-60 | Ir | 1 | 4 | Ph | H | H | COCH₃ | H | CH₃ | H | H | H | H | pic | |
| 4-60X | Ir | 1 | 4 | Ph | H | H | COCH₃ | H | CH₃ | H | H | H | H | acac | |
| 4-60Y | Ir | 0 | 4 | Ph | H | H | COCH₃ | H | CH₃ | H | H | H | H | — | — |
| 4-61 | Ir | 1 | 4 | Ph | H | COCH₃ | H | H | CH₃ | H | H | H | H | pic | |
| 4-61X | Ir | 1 | 4 | Ph | H | COCH₃ | H | H | CH₃ | H | H | H | H | acac | |
| 4-61Y | Ir | 0 | 4 | Ph | H | COCH₃ | H | H | CH₃ | H | H | H | H | — | — |
| 4-62 | Ir | 1 | 4 | Ph | H | H | BL | | CH₃ | H | H | H | H | pic | |
| 4-62X | Ir | 1 | 4 | Ph | H | H | BL | | CH₃ | H | H | H | H | acac | |
| 4-62Y | Ir | 0 | 4 | Ph | H | H | BL | | CH₃ | H | H | H | H | — | — |
| 4-63 | Ir | 1 | 4 | Ph | H | H | BL | | ᵗC₄H₉ | H | H | H | H | pic | |
| 4-63X | Ir | 1 | 4 | Ph | H | H | BL | | ᵗC₄H₉ | H | H | H | H | acac | |
| 4-63Y | Ir | 0 | 4 | Ph | H | H | BL | | ᵗC₄H₉ | H | H | H | H | — | — |
| 4-64 | Ir | 1 | 4 | Ph | H | BL | | H | CH₃ | H | H | H | H | pic | |
| 4-64X | Ir | 1 | 4 | Ph | H | BL | | H | CH₃ | H | H | H | H | acac | |
| 4-64Y | Ir | 0 | 4 | Ph | H | BL | | H | CH₃ | H | H | H | H | — | — |
| 4-65 | Ir | 1 | 4 | Ph | H | BL | | H | ᵗC₄H₉ | H | H | H | H | pic | |
| 4-65X | Ir | 1 | 4 | Ph | H | BL | | H | ᵗC₄H₉ | H | H | H | H | acac | |
| 4-65Y | Ir | 0 | 4 | Ph | H | BL | | H | ᵗC₄H₉ | H | H | H | H | — | — |
| 4-66 | Ir | 1 | 4 | Ph | H | H | PL | | CH₃ | H | H | H | H | pic | |
| 4-66X | Ir | 1 | 4 | Ph | H | H | PL | | CH₃ | H | H | H | H | acac | |
| 4-66Y | Ir | 0 | 4 | Ph | H | H | PL | | CH₃ | H | H | H | H | — | — |
| 4-67 | Ir | 1 | 4 | Ph | H | H | PL | | ᵗC₄H₉ | H | H | H | H | pic | |
| 4-67X | Ir | 1 | 4 | Ph | H | H | PL | | ᵗC₄H₉ | H | H | H | H | acac | |
| 4-67Y | Ir | 0 | 4 | Ph | H | H | PL | | ᵗC₄H₉ | H | H | H | H | — | — |
| 4-68 | Ir | 1 | 4 | Ph | H | PL | | H | CH₃ | H | H | H | H | pic | |
| 4-68X | Ir | 1 | 4 | Ph | H | PL | | H | CH₃ | H | H | H | H | acac | |
| 4-68Y | Ir | 0 | 4 | Ph | H | PL | | H | CH₃ | H | H | H | H | — | — |
| 4-69 | Ir | 1 | 4 | Ph | H | PL | | H | ᵗC₄H₉ | H | H | H | H | pic | |
| 4-69X | Ir | 1 | 4 | Ph | H | PL | | H | ᵗC₄H₉ | H | H | H | H | acac | |
| 4-69Y | Ir | 0 | 4 | Ph | H | PL | | H | ᵗC₄H₉ | H | H | H | H | — | — |
| 4-70 | Ir | 1 | 4 | Ph | H | H | | MEE1 | CH₃ | H | H | H | H | pic | |
| 4-70X | Ir | 1 | 4 | Ph | H | H | | MEE1 | CH₃ | H | H | H | H | acac | |
| 4-70Y | Ir | 0 | 4 | Ph | H | H | | MEE1 | CH₃ | H | H | H | H | — | — |
| 4-71 | Ir | 1 | 4 | Ph | H | | MEE1 | H | CH₃ | H | H | H | H | pic | |
| 4-71X | Ir | 1 | 4 | Ph | H | | MEE1 | H | CH₃ | H | H | H | H | acac | |
| 4-71Y | Ir | 0 | 4 | Ph | H | | MEE1 | H | CH₃ | H | H | H | H | — | — |
| 4-72 | Ir | 1 | 4 | Ph | H | H | | MEE2 | CH₃ | H | H | H | H | pic | |
| 4-72X | Ir | 1 | 4 | Ph | H | H | | MEE2 | CH₃ | H | H | H | H | acac | |
| 4-72Y | Ir | 0 | 4 | Ph | H | H | | MEE2 | CH₃ | H | H | H | H | — | — |
| 4-73 | Ir | 1 | 4 | Ph | H | | MEE2 | H | CH₃ | H | H | H | H | pic | |
| 4-73X | Ir | 1 | 4 | Ph | H | | MEE2 | H | CH₃ | H | H | H | H | acac | |
| 4-73Y | Ir | 0 | 4 | Ph | H | | MEE2 | H | CH₃ | H | H | H | H | — | — |
| 4-74 | Ir | 1 | 4 | Ph | H | H | | PA1 | CH₃ | H | H | H | H | pic | |
| 4-74X | Ir | 1 | 4 | Ph | H | H | | PA1 | CH₃ | H | H | H | H | acac | |
| 4-74Y | Ir | 0 | 4 | Ph | H | H | | PA1 | CH₃ | H | H | H | H | — | — |
| 4-75 | Ir | 1 | 4 | Ph | H | | PA1 | H | CH₃ | H | H | H | H | pic | |
| 4-75X | Ir | 1 | 4 | Ph | H | | PA1 | H | CH₃ | H | H | H | H | acac | |
| 4-75Y | Ir | 0 | 4 | Ph | H | | PA1 | H | CH₃ | H | H | H | H | — | — |
| 4-76 | Ir | 1 | 4 | Ph | H | H | | PA2 | CH₃ | H | H | H | H | pic | |
| 4-76X | Ir | 1 | 4 | Ph | H | H | | PA2 | CH₃ | H | H | H | H | acac | |
| 4-76Y | Ir | 0 | 4 | Ph | H | H | | PA2 | CH₃ | H | H | H | H | — | — |
| 4-77 | Ir | 1 | 4 | Ph | H | | PA2 | H | CH₃ | H | H | H | H | pic | |
| 4-77X | Ir | 1 | 4 | Ph | H | | PA2 | H | CH₃ | H | H | H | H | acac | |
| 4-77Y | Ir | 0 | 4 | Ph | H | | PA2 | H | CH₃ | H | H | H | H | — | — |

TABLE 4-continued

| No. | M | n | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 4-78 | Ir | 1 | 4 | | Ph | H | H | | EA1 | CH₃ | H | H | H | H | pic | |
| 4-78X | Ir | 1 | 4 | | Ph | H | H | | EA1 | CH₃ | H | H | H | H | acac | |
| 4-78Y | Ir | 0 | 4 | | Ph | H | H | | EA1 | CH₃ | H | H | H | H | — | — |
| 4-79 | Ir | 1 | 4 | | Ph | H | | EA2 | | H | CH₃ | H | H | H | H | pic |
| 4-79X | Ir | 1 | 4 | | Ph | H | | EA2 | | H | CH₃ | H | H | H | H | acac |
| 4-79Y | Ir | 0 | 4 | | Ph | H | | EA2 | | H | CH₃ | H | H | H | H | — — |
| 4-80 | Ir | 1 | 4 | | Ph | H | H | | ME | CH₃ | H | H | H | H | pic | |
| 4-80X | Ir | 1 | 4 | | Ph | H | H | | ME | CH₃ | H | H | H | H | acac | |
| 4-80Y | Ir | 0 | 4 | | Ph | H | H | | ME | CH₃ | H | H | H | H | — | — |
| 4-81 | Ir | 1 | 4 | | Ph | H | | ME | | H | CH₃ | H | H | H | H | pic |
| 4-81X | Ir | 1 | 4 | | Ph | H | | ME | | H | CH₃ | H | H | H | H | acac |
| 4-81Y | Ir | 0 | 4 | | Ph | H | | ME | | H | CH₃ | H | H | H | H | — — |
| 4-82 | Ir | 1 | 4 | | Ph | H | H | | AT | CH₃ | H | H | H | H | pic | |
| 4-82X | Ir | 1 | 4 | | Ph | H | H | | AT | CH₃ | H | H | H | H | acac | |
| 4-82Y | Ir | 0 | 4 | | Ph | H | H | | AT | CH₃ | H | H | H | H | — | — |
| 4-83 | Ir | 1 | 4 | | Ph | H | | AT | | H | CH₃ | H | H | H | H | pic |
| 4-83X | Ir | 1 | 4 | | Ph | H | | AT | | H | CH₃ | H | H | H | H | acac |
| 4-83Y | Ir | 0 | 4 | | Ph | H | | AT | | H | CH₃ | H | H | H | H | — — |
| 4-84 | Ir | 1 | 4 | | Ph | H | H | | MES1 | CH₃ | H | H | H | H | pic | |
| 4-84X | Ir | 1 | 4 | | Ph | H | H | | MES1 | CH₃ | H | H | H | H | acac | |
| 4-84Y | Ir | 0 | 4 | | Ph | H | H | | MES1 | CH₃ | H | H | H | H | — | — |
| 4-85 | Ir | 1 | 4 | | Ph | H | | MES1 | | H | CH₃ | H | H | H | H | pic |
| 4-85X | Ir | 1 | 4 | | Ph | H | | MES1 | | H | CH₃ | H | H | H | H | acac |
| 4-85Y | Ir | 0 | 4 | | Ph | H | | MES1 | | H | CH₃ | H | H | H | H | — — |
| 4-86 | Ir | 1 | 4 | | Ph | H | H | | MES2 | CH₃ | H | H | H | H | pic | |
| 4-86X | Ir | 1 | 4 | | Ph | H | H | | MES2 | CH₃ | H | H | H | H | acac | |
| 4-86Y | Ir | 0 | 4 | | Ph | H | H | | MES2 | CH₃ | H | H | H | H | — | — |
| 4-87 | Ir | 1 | 4 | | Ph | H | | MES2 | | H | CH₃ | H | H | H | H | pic |
| 4-87X | Ir | 1 | 4 | | Ph | H | | MES2 | | H | CH₃ | H | H | H | H | acac |
| 4-87Y | Ir | 0 | 4 | | Ph | H | | MES2 | | H | CH₃ | H | H | H | H | — — |
| 4-88 | Ir | 1 | 4 | | Ph | H | H | | PS1 | CH₃ | H | H | H | H | pic | |
| 4-88X | Ir | 1 | 4 | | Ph | H | H | | PS1 | CH₃ | H | H | H | H | acac | |
| 4-88Y | Ir | 0 | 4 | | Ph | H | H | | PS1 | CH₃ | H | H | H | H | — | — |
| 4-89 | Ir | 1 | 4 | | Ph | H | | PS1 | | H | CH₃ | H | H | H | H | pic |
| 4-89X | Ir | 1 | 4 | | Ph | H | | PS1 | | H | CH₃ | H | H | H | H | acac |
| 4-89Y | Ir | 0 | 4 | | Ph | H | | PS1 | | H | CH₃ | H | H | H | H | — — |
| 4-90 | Ir | 1 | 4 | | Ph | H | H | | PS2 | CH₃ | H | H | H | H | pic | |
| 4-90X | Ir | 1 | 4 | | Ph | H | H | | PS2 | CH₃ | H | H | H | H | acac | |
| 4-90Y | Ir | 0 | 4 | | Ph | H | H | | PS2 | CH₃ | H | H | H | H | — | — |
| 4-91 | Ir | 1 | 4 | | Ph | H | | PS2 | | H | CH₃ | H | H | H | H | pic |
| 4-91X | Ir | 1 | 4 | | Ph | H | | PS2 | | H | CH₃ | H | H | H | H | acac |
| 4-91Y | Ir | 0 | 4 | | Ph | H | | PS2 | | H | CH₃ | H | H | H | H | — — |
| 4-92 | Ir | 1 | 4 | | Ph | H | H | | BAL1 | CH₃ | H | H | H | H | pic | |
| 4-92X | Ir | 1 | 4 | | Ph | H | H | | BAL1 | CH₃ | H | H | H | H | acac | |
| 4-92Y | Ir | 0 | 4 | | Ph | H | H | | BAL1 | CH₃ | H | H | H | H | — | — |
| 4-93 | Ir | 1 | 4 | | Ph | H | | BAL1 | | H | CH₃ | H | H | H | H | pic |
| 4-93X | Ir | 1 | 4 | | Ph | H | | BAL1 | | H | CH₃ | H | H | H | H | acac |
| 4-93Y | Ir | 0 | 4 | | Ph | H | | BAL1 | | H | CH₃ | H | H | H | H | — — |
| 4-94 | Ir | 1 | 4 | | Ph | H | H | | BAL2 | CH₃ | H | H | H | H | pic | |
| 4-94X | Ir | 1 | 4 | | Ph | H | H | | BAL2 | CH₃ | H | H | H | H | acac | |
| 4-94Y | Ir | 0 | 4 | | Ph | H | H | | BAL2 | CH₃ | H | H | H | H | — | — |
| 4-95 | Ir | 1 | 4 | | Ph | H | | BAL2 | | H | CH₃ | H | H | H | H | pic |
| 4-95X | Ir | 1 | 4 | | Ph | H | | BAL2 | | H | CH₃ | H | H | H | H | acac |
| 4-95Y | Ir | 0 | 4 | | Ph | H | | BAL2 | | H | CH₃ | H | H | H | H | — — |
| 4-96 | Ir | 1 | 4 | | Ph | H | H | | MEK1 | CH₃ | H | H | H | H | pic | |
| 4-96X | Ir | 1 | 4 | | Ph | H | H | | MEK1 | CH₃ | H | H | H | H | acac | |
| 4-96Y | Ir | 0 | 4 | | Ph | H | H | | MEK1 | CH₃ | H | H | H | H | — | — |
| 4-97 | Ir | 1 | 4 | | Ph | H | | MEK1 | | H | CH₃ | H | H | H | H | pic |
| 4-97X | Ir | 1 | 4 | | Ph | H | | MEK1 | | H | CH₃ | H | H | H | H | acac |
| 4-97Y | Ir | 0 | 4 | | Ph | H | | MEK1 | | H | CH₃ | H | H | H | H | — — |
| 4-98 | Ir | 1 | 4 | | Ph | H | H | | MEK2 | CH₃ | H | H | H | H | pic | |
| 4-98X | Ir | 1 | 4 | | Ph | H | H | | MEK2 | CH₃ | H | H | H | H | acac | |
| 4-98Y | Ir | 0 | 4 | | Ph | H | H | | MEK2 | CH₃ | H | H | H | H | — | — |
| 4-99 | Ir | 1 | 4 | | Ph | H | | MEK2 | | H | CH₃ | H | H | H | H | pic |
| 4-99X | Ir | 1 | 4 | | Ph | H | | MEK2 | | H | CH₃ | H | H | H | H | acac |
| 4-99Y | Ir | 0 | 4 | | Ph | H | | MEK2 | | H | CH₃ | H | H | H | H | — — |
| 4-100 | Ir | 1 | 4 | | Ph | H | H | | PAL1 | CH₃ | H | H | H | H | pic | |
| 4-100X | Ir | 1 | 4 | | Ph | H | H | | PAL1 | CH₃ | H | H | H | H | acac | |
| 4-100Y | Ir | 0 | 4 | | Ph | H | H | | PAL1 | CH₃ | H | H | H | H | — | — |
| 4-101 | Ir | 1 | 4 | | Ph | H | | PAL1 | | H | CH₃ | H | H | H | H | pic |
| 4-101X | Ir | 1 | 4 | | Ph | H | | PAL1 | | H | CH₃ | H | H | H | H | acac |
| 4-101Y | Ir | 0 | 4 | | Ph | H | | PAL1 | | H | CH₃ | H | H | H | H | — — |
| 4-102 | Ir | 1 | 4 | | Ph | H | H | | PAL2 | CH₃ | H | H | H | H | pic | |
| 4-102X | Ir | 1 | 4 | | Ph | H | H | | PAL2 | CH₃ | H | H | H | H | acac | |
| 4-102Y | Ir | 0 | 4 | | Ph | H | H | | PAL2 | CH₃ | H | H | H | H | — | — |
| 4-103 | Ir | 1 | 4 | | Ph | H | | PAL2 | | H | CH₃ | H | H | H | H | pic |
| 4-103X | Ir | 1 | 4 | | Ph | H | | PAL2 | | H | CH₃ | H | H | H | H | acac |

TABLE 4-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4-103Y | Ir | 0 | 4 | Ph | H | | PAL2 | H | CH₃ | H | H | H | H | — | — |
| 4-104 | Ir | 1 | 4 | Ph | H | H | | MMK | CH₃ | H | H | H | H | | pic |
| 4-104X | Ir | 1 | 4 | Ph | H | H | | MMK | CH₃ | H | H | H | H | | acac |
| 4-104Y | Ir | 0 | 4 | Ph | H | H | | MMK | CH₃ | H | H | H | H | — | — |
| 4-105 | Ir | 1 | 4 | Ph | H | | MMK | H | CH₃ | H | H | H | H | | pic |
| 4-105X | Ir | 1 | 4 | Ph | H | | MMK | H | CH₃ | H | H | H | H | | acac |
| 4-105Y | Ir | 0 | 4 | Ph | H | | MMK | H | CH₃ | H | H | H | H | — | — |
| 4-106 | Ir | 1 | 4 | Ph | H | H | | EES1 | CH₃ | H | H | H | H | | pic |
| 4-106X | Ir | 1 | 4 | Ph | H | H | | EES1 | CH₃ | H | H | H | H | | acac |
| 4-106Y | Ir | 0 | 4 | Ph | H | H | | EES1 | CH₃ | H | H | H | H | — | — |
| 4-107 | Ir | 1 | 4 | Ph | H | | EES2 | H | CH₃ | H | H | H | H | | pic |
| 4-107X | Ir | 1 | 4 | Ph | H | | EES2 | H | CH₃ | H | H | H | H | | acac |
| 4-107Y | Ir | 0 | 4 | Ph | H | | EES2 | H | CH₃ | H | H | H | H | — | — |
| 4-108 | Ir | 1 | 4 | Ph | H | H | | PAE1 | CH₃ | H | H | H | H | | pic |
| 4-108X | Ir | 1 | 4 | Ph | H | H | | PAE1 | CH₃ | H | H | H | H | | acac |
| 4-108Y | Ir | 0 | 4 | Ph | H | H | | PAE1 | CH₃ | H | H | H | H | — | — |
| 4-109 | Ir | 1 | 4 | Ph | H | | PAE2 | H | CH₃ | H | H | H | H | | pic |
| 4-109X | Ir | 1 | 4 | Ph | H | | PAE2 | H | CH₃ | H | H | H | H | | acac |
| 4-109Y | Ir | 0 | 4 | Ph | H | | PAE2 | H | CH₃ | H | H | H | H | — | — |
| 4-110 | Ir | 1 | 4 | Ph | H | H | | AME1 | CH₃ | H | H | H | H | | pic |
| 4-110X | Ir | 1 | 4 | Ph | H | H | | AME1 | CH₃ | H | H | H | H | | acac |
| 4-110Y | Ir | 0 | 4 | Ph | H | H | | AME1 | CH₃ | H | H | H | H | — | — |
| 4-111 | Ir | 1 | 4 | Ph | H | | AME1 | H | CH₃ | H | H | H | H | | pic |
| 4-111X | Ir | 1 | 4 | Ph | H | | AME1 | H | CH₃ | H | H | H | H | | acac |
| 4-111Y | Ir | 0 | 4 | Ph | H | | AME1 | H | CH₃ | H | H | H | H | — | — |
| 4-112 | Ir | 1 | 4 | Ph | H | H | | AME2 | CH₃ | H | H | H | H | | pic |
| 4-112X | Ir | 1 | 4 | Ph | H | H | | AME2 | CH₃ | H | H | H | H | | acac |
| 4-112Y | Ir | 0 | 4 | Ph | H | H | | AME2 | CH₃ | H | H | H | H | — | — |
| 4-113 | Ir | 1 | 4 | Ph | H | | AME2 | H | CH₃ | H | H | H | H | | pic |
| 4-113X | Ir | 1 | 4 | Ph | H | | AME2 | H | CH₃ | H | H | H | H | | acac |
| 4-113Y | Ir | 0 | 4 | Ph | H | | AME2 | H | CH₃ | H | H | H | H | — | — |
| 4-114 | Ir | 1 | 4 | Ph | H | H | | EAE1 | CH₃ | H | H | H | H | | pic |
| 4-114X | Ir | 1 | 4 | Ph | H | H | | EAE1 | CH₃ | H | H | H | H | | acac |
| 4-114Y | Ir | 0 | 4 | Ph | H | H | | EAE1 | CH₃ | H | H | H | H | — | — |
| 4-115 | Ir | 1 | 4 | Ph | H | | EAE1 | H | CH₃ | H | H | H | H | | pic |
| 4-115X | Ir | 1 | 4 | Ph | H | | EAE1 | H | CH₃ | H | H | H | H | | acac |
| 4-115Y | Ir | 0 | 4 | Ph | H | | EAE1 | H | CH₃ | H | H | H | H | — | — |
| 4-116 | Ir | 1 | 4 | Ph | H | H | | EAE2 | CH₃ | H | H | H | H | | pic |
| 4-116X | Ir | 1 | 4 | Ph | H | H | | EAE2 | CH₃ | H | H | H | H | | acac |
| 4-116Y | Ir | 0 | 4 | Ph | H | H | | EAE2 | CH₃ | H | H | H | H | — | — |
| 4-117 | Ir | 1 | 4 | Ph | H | | EAE2 | H | CH₃ | H | H | H | H | | pic |
| 4-117X | Ir | 1 | 4 | Ph | H | | EAE2 | H | CH₃ | H | H | H | H | | acac |
| 4-117Y | Ir | 0 | 4 | Ph | H | | EAE2 | H | CH₃ | H | H | H | H | — | — |
| 4-118 | Ir | 1 | 4 | Ph | H | H | | AAE1 | CH₃ | H | H | H | H | | pic |
| 4-118X | Ir | 1 | 4 | Ph | H | H | | AAE1 | CH₃ | H | H | H | H | | acac |
| 4-118Y | Ir | 0 | 4 | Ph | H | H | | AAE1 | CH₃ | H | H | H | H | — | — |
| 4-119 | Ir | 1 | 4 | Ph | H | | AAE1 | H | CH₃ | H | H | H | H | | pic |
| 4-119X | Ir | 1 | 4 | Ph | H | | AAE1 | H | CH₃ | H | H | H | H | | acac |
| 4-119Y | Ir | 0 | 4 | Ph | H | | AAE1 | H | CH₃ | H | H | H | H | — | — |
| 4-120 | Ir | 1 | 4 | Ph | H | H | | AAE2 | CH₃ | H | H | H | H | | pic |
| 4-120X | Ir | 1 | 4 | Ph | H | H | | AAE2 | CH₃ | H | H | H | H | | acac |
| 4-120Y | Ir | 0 | 4 | Ph | H | H | | AAE2 | CH₃ | H | H | H | H | — | — |
| 4-121 | Ir | 1 | 4 | Ph | H | | AAE2 | H | CH₃ | H | H | H | H | | pic |
| 4-121X | Ir | 1 | 4 | Ph | H | | AAE2 | H | CH₃ | H | H | H | H | | acac |
| 4-121Y | Ir | 0 | 4 | Ph | H | | AAE2 | H | CH₃ | H | H | H | H | — | — |
| 4-122 | Ir | 1 | 4 | Ph | H | H | | PME1 | CH₃ | H | H | H | H | | pic |
| 4-122X | Ir | 1 | 4 | Ph | H | H | | PME1 | CH₃ | H | H | H | H | | acac |
| 4-122Y | Ir | 0 | 4 | Ph | H | H | | PME1 | CH₃ | H | H | H | H | — | — |
| 4-123 | Ir | 1 | 4 | Ph | H | | PME1 | H | CH₃ | H | H | H | H | | pic |
| 4-123X | Ir | 1 | 4 | Ph | H | | PME1 | H | CH₃ | H | H | H | H | | acac |
| 4-123Y | Ir | 0 | 4 | Ph | H | | PME1 | H | CH₃ | H | H | H | H | — | — |
| 4-124 | Ir | 1 | 4 | Ph | H | H | | PME2 | CH₃ | H | H | H | H | | pic |
| 4-124X | Ir | 1 | 4 | Ph | H | H | | PME2 | CH₃ | H | H | H | H | | acac |
| 4-124Y | Ir | 0 | 4 | Ph | H | H | | PME2 | CH₃ | H | H | H | H | — | — |
| 4-125 | Ir | 1 | 4 | Ph | H | | PME2 | H | CH₃ | H | H | H | H | | pic |
| 4-125X | Ir | 1 | 4 | Ph | H | | PME2 | H | CH₃ | H | H | H | H | | acac |
| 4-125Y | Ir | 0 | 4 | Ph | H | | PME2 | H | CH₃ | H | H | H | H | — | — |
| 4-126 | Ir | 1 | 4 | Ph | H | H | | MET1 | CH₃ | H | H | H | H | | pic |
| 4-126X | Ir | 1 | 4 | Ph | H | H | | MET1 | CH₃ | H | H | H | H | | acac |
| 4-126Y | Ir | 0 | 4 | Ph | H | H | | MET1 | CH₃ | H | H | H | H | — | — |
| 4-127 | Ir | 1 | 4 | Ph | H | | MET1 | H | CH₃ | H | H | H | H | | pic |
| 4-127X | Ir | 1 | 4 | Ph | H | | MET1 | H | CH₃ | H | H | H | H | | acac |
| 4-127Y | Ir | 0 | 4 | Ph | H | | MET1 | H | CH₃ | H | H | H | H | — | — |
| 4-128 | Ir | 1 | 4 | Ph | H | H | | MET2 | CH₃ | H | H | H | H | | pic |
| 4-128X | Ir | 1 | 4 | Ph | H | H | | MET2 | CH₃ | H | H | H | H | | acac |
| 4-128Y | Ir | 0 | 4 | Ph | H | H | | MET2 | CH₃ | H | H | H | H | — | — |
| 4-129 | Ir | 1 | 4 | Ph | H | | MET2 | H | CH₃ | H | H | H | H | | pic |

TABLE 4-continued

| No. | M | n | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 4-129X | Ir | 1 | 4 | Ph | H | | MET2 | | H | $CH_3$ | H | H | H | H acac |
| 4-129Y | Ir | 0 | 4 | Ph | H | | MET2 | | H | $CH_3$ | H | H | H | — — |
| 4-130 | Ir | 1 | 4 | Ph | H | H | | EE1 | | $CH_3$ | H | H | H | H pic |
| 4-130X | Ir | 1 | 4 | Ph | H | H | | EE1 | | $CH_3$ | H | H | H | H acac |
| 4-130Y | Ir | 0 | 4 | Ph | H | H | | EE1 | | $CH_3$ | H | H | H | H — — |
| 4-131 | Ir | 1 | 4 | Ph | H | | EE1 | | H | $CH_3$ | H | H | H | H pic |
| 4-131X | Ir | 1 | 4 | Ph | H | | EE1 | | H | $CH_3$ | H | H | H | H acac |
| 4-131Y | Ir | 0 | 4 | Ph | H | | EE1 | | H | $CH_3$ | H | H | H | H — — |
| 4-132 | Ir | 1 | 4 | Ph | H | H | | EE2 | | $CH_3$ | H | H | H | H pic |
| 4-132X | Ir | 1 | 4 | Ph | H | H | | EE2 | | $CH_3$ | H | H | H | H acac |
| 4-132Y | Ir | 0 | 4 | Ph | H | H | | EE2 | | $CH_3$ | H | H | H | H — — |
| 4-133 | Ir | 1 | 4 | Ph | H | | EE2 | | H | $CH_3$ | H | H | H | H pic |
| 4-133X | Ir | 1 | 4 | Ph | H | | EE2 | | H | $CH_3$ | H | H | H | H acac |
| 4-133Y | Ir | 0 | 4 | Ph | H | | EE2 | | H | $CH_3$ | H | H | H | H — — |
| 4-134 | Ir | 1 | 4 | Ph | H | H | | MS1 | | $CH_3$ | H | H | H | H pic |
| 4-134X | Ir | 1 | 4 | Ph | H | H | | MS1 | | $CH_3$ | H | H | H | H acac |
| 4-134Y | Ir | 0 | 4 | Ph | H | H | | MS1 | | $CH_3$ | H | H | H | H — — |
| 4-135 | Ir | 1 | 4 | Ph | H | | MS1 | | H | $CH_3$ | H | H | H | H pic |
| 4-135X | Ir | 1 | 4 | Ph | H | | MS1 | | H | $CH_3$ | H | H | H | H acac |
| 4-135Y | Ir | 0 | 4 | Ph | H | | MS1 | | H | $CH_3$ | H | H | H | H — — |
| 4-136 | Ir | 1 | 4 | Ph | H | H | | MS2 | | $CH_3$ | H | H | H | H pic |
| 4-136X | Ir | 1 | 4 | Ph | H | H | | MS2 | | $CH_3$ | H | H | H | H acac |
| 4-136Y | Ir | 0 | 4 | Ph | H | H | | MS2 | | $CH_3$ | H | H | H | H — — |
| 4-137 | Ir | 1 | 4 | Ph | H | | MS2 | | H | $CH_3$ | H | H | H | H pic |
| 4-137X | Ir | 1 | 4 | Ph | H | | MS2 | | H | $CH_3$ | H | H | H | H acac |
| 4-137Y | Ir | 0 | 4 | Ph | H | | MS2 | | H | $CH_3$ | H | H | H | H — — |

TABLE 5

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 5-1 | Ir | 1 | 5 | Ph | H | H | H | H | H | $CH_3$ | H | pic |
| 5-1X | Ir | 1 | 5 | Ph | H | H | H | H | H | $CH_3$ | H | acac |
| 5-1Y | Ir | 0 | 5 | Ph | H | H | H | H | H | $CH_3$ | H | — — |
| 5-2 | Ir | 1 | 5 | Ph | H | H | H | H | H | $^tC_4H_9$ | H | pic |
| 5-2X | Ir | 1 | 5 | Ph | H | H | H | H | H | $^tC_4H_9$ | H | acac |
| 5-2Y | Ir | 0 | 5 | Ph | H | H | H | H | H | $^tC_4H_9$ | H | — — |
| 5-3 | Ir | 1 | 5 | Ph | H | F | H | F | H | $CH_3$ | H | pic |
| 5-3X | Ir | 1 | 5 | Ph | H | F | H | F | H | $CH_3$ | H | acac |
| 5-3Y | Ir | 0 | 5 | Ph | H | F | H | F | H | $CH_3$ | H | — — |
| 5-4 | Ir | 1 | 5 | Ph | H | F | H | F | H | $^tC_4H_9$ | H | pic |
| 5-4X | Ir | 1 | 5 | Ph | H | F | H | F | H | $^tC_4H_9$ | H | acac |
| 5-4Y | Ir | 0 | 5 | Ph | H | F | H | F | H | $^tC_4H_9$ | H | — — |
| 5-5 | Ir | 1 | 5 | Ph | $CF_3$ | H | $CF_3$ | H | H | $CH_3$ | H | pic |
| 5-5X | Ir | 1 | 5 | Ph | $CF_3$ | H | $CF_3$ | H | H | $CH_3$ | H | acac |
| 5-5Y | Ir | 0 | 5 | Ph | $CF_3$ | H | $CF_3$ | H | H | $CH_3$ | H | — — |
| 5-6 | Ir | 1 | 5 | Ph | $CF_3$ | H | $CF_3$ | H | H | $^tC_4H_9$ | H | pic |
| 5-6X | Ir | 1 | 5 | Ph | $CF_3$ | H | $CF_3$ | H | H | $^tC_4H_9$ | H | acac |
| 5-6Y | Ir | 0 | 5 | Ph | $CF_3$ | H | $CF_3$ | H | H | $^tC_4H_9$ | H | — — |
| 5-7 | Ir | 1 | 5 | Ph | H | F | $CF_3$ | H | H | $CH_3$ | H | pic |
| 5-7X | Ir | 1 | 5 | Ph | H | F | $CF_3$ | H | H | $CH_3$ | H | acac |
| 5-7Y | Ir | 0 | 5 | Ph | H | F | $CF_3$ | H | H | $CH_3$ | H | — — |
| 5-8 | Ir | 1 | 5 | Ph | F | H | $CF_3$ | H | H | $CH_3$ | H | pic |
| 5-8X | Ir | 1 | 5 | Ph | F | H | $CF_3$ | H | H | $CH_3$ | H | acac |
| 5-8Y | Ir | 0 | 5 | Ph | F | H | $CF_3$ | H | H | $CH_3$ | H | — — |
| 5-9 | Ir | 1 | 5 | Ph | F | F | F | F | H | $CH_3$ | H | pic |
| 5-9X | Ir | 1 | 5 | Ph | F | F | F | F | H | $CH_3$ | H | acac |
| 5-9Y | Ir | 0 | 5 | Ph | F | F | F | F | H | $CH_3$ | H | — — |
| 5-10 | Ir | 1 | 5 | Ph | H | F | H | $CH_3$ | H | $CH_3$ | H | pic |
| 5-10X | Ir | 1 | 5 | Ph | H | F | H | $CH_3$ | H | $CH_3$ | H | acac |
| 5-10Y | Ir | 0 | 5 | Ph | H | F | H | $CH_3$ | H | $CH_3$ | H | — — |
| 5-11 | Ir | 1 | 5 | Ph | H | F | H | $CH_3$ | H | $^tC_4H_9$ | H | pic |
| 5-11X | Ir | 1 | 5 | Ph | H | F | H | $CH_3$ | H | $^tC_4H_9$ | H | acac |
| 5-11Y | Ir | 0 | 5 | Ph | H | F | H | $CH_3$ | H | $^tC_4H_9$ | H | — — |
| 5-12 | Ir | 1 | 5 | Ph | H | F | H | $^tC_4H_9$ | H | $CH_3$ | H | pic |
| 5-12X | Ir | 1 | 5 | Ph | H | F | H | $^tC_4H_9$ | H | $CH_3$ | H | acac |
| 5-12Y | Ir | 0 | 5 | Ph | H | F | H | $^tC_4H_9$ | H | $CH_3$ | H | — — |
| 5-13 | Ir | 1 | 5 | Ph | H | F | H | $^tC_4H_9$ | H | $^tC_4H_9$ | H | pic |
| 5-13X | Ir | 1 | 5 | Ph | H | F | H | $^tC_4H_9$ | H | $^tC_4H_9$ | H | acac |
| 5-13Y | Ir | 0 | 5 | Ph | H | F | H | $^tC_4H_9$ | H | $^tC_4H_9$ | H | — — |
| 5-14 | Ir | 1 | 5 | Ph | H | $CF_3$ | H | $CF_3$ | H | $CH_3$ | H | pic |
| 5-14X | Ir | 1 | 5 | Ph | H | $CF_3$ | H | $CF_3$ | H | $CH_3$ | H | acac |
| 5-14Y | Ir | 0 | 5 | Ph | H | $CF_3$ | H | $CF_3$ | H | $CH_3$ | H | — — |
| 5-15 | Ir | 1 | 5 | Ph | H | $CF_3$ | H | $CF_3$ | H | $^tC_4H_9$ | H | pic |

TABLE 5-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 5-15X | Ir | 1 | 5 | Ph | H | CF$_3$ | H | CF$_3$ | H | $^tC_4H_9$ | H | acac |
| 5-15Y | Ir | 0 | 5 | Ph | H | CF$_3$ | H | CF$_3$ | H | $^tC_4H_9$ | H | — — |
| 5-16 | Ir | 1 | 5 | Ph | CF$_3$ | H | H | $^tC_4H_9$ | H | CH$_3$ | H | pic |
| 5-16X | Ir | 1 | 5 | Ph | CF$_3$ | H | H | $^tC_4H_9$ | H | CH$_3$ | H | acac |
| 5-16Y | Ir | 0 | 5 | Ph | CF$_3$ | H | H | $^tC_4H_9$ | H | CH$_3$ | H | — — |
| 5-17 | Ir | 1 | 5 | Ph | CF$_3$ | H | H | $^tC_4H_9$ | H | $^tC_4H_9$ | H | pic |
| 5-17X | Ir | 1 | 5 | Ph | CF$_3$ | H | H | $^tC_4H_9$ | H | $^tC_4H_9$ | H | acac |
| 5-17Y | Ir | 0 | 5 | Ph | CF$_3$ | H | H | $^tC_4H_9$ | H | $^tC_4H_9$ | H | — — |
| 5-18 | Ir | 1 | 5 | Ph | H | CF$_3$ | H | $^tC_4H_9$ | H | CH$_3$ | H | pic |
| 5-18X | Ir | 1 | 5 | Ph | H | CF$_3$ | H | $^tC_4H_9$ | H | CH$_3$ | H | acac |
| 5-18Y | Ir | 0 | 5 | Ph | H | CF$_3$ | H | $^tC_4H_9$ | H | CH$_3$ | H | — — |
| 5-19 | Ir | 1 | 5 | Ph | H | CF$_3$ | H | $^tC_4H_9$ | H | $^tC_4H_9$ | H | pic |
| 5-19X | Ir | 1 | 5 | Ph | H | CF$_3$ | H | $^tC_4H_9$ | H | $^tC_4H_9$ | H | acac |
| 5-19Y | Ir | 0 | 5 | Ph | H | CF$_3$ | H | $^tC_4H_9$ | H | $^tC_4H_9$ | H | — — |
| 5-20 | Ir | 1 | 5 | Ph | H | CF$_3$ | H | CH$_3$ | H | CH$_3$ | H | pic |
| 5-20X | Ir | 1 | 5 | Ph | H | CF$_3$ | H | CH$_3$ | H | CH$_3$ | H | acac |
| 5-20Y | Ir | 0 | 5 | Ph | H | CF$_3$ | H | CH$_3$ | H | CH$_3$ | H | — — |
| 5-21 | Ir | 1 | 5 | Ph | H | CF$_3$ | CF$_3$ | H | H | CH$_3$ | H | pic |
| 5-21X | Ir | 1 | 5 | Ph | H | CF$_3$ | CF$_3$ | H | H | CH$_3$ | H | acac |
| 5-21Y | Ir | 0 | 5 | Ph | H | CF$_3$ | CF$_3$ | H | H | CH$_3$ | H | — — |
| 5-22 | Ir | 1 | 5 | Ph | H | H | NO$_2$ | H | H | CH$_3$ | H | pic |
| 5-22X | Ir | 1 | 5 | Ph | H | H | NO$_2$ | H | H | CH$_3$ | H | acac |
| 5-22Y | Ir | 0 | 5 | Ph | H | H | NO$_2$ | H | H | CH$_3$ | H | — — |
| 5-23 | Ir | 1 | 5 | Ph | H | H | NO$_2$ | H | H | $^tC_4H_9$ | H | pic |
| 5-23X | Ir | 1 | 5 | Ph | H | H | NO$_2$ | H | H | $^tC_4H_9$ | H | acac |
| 5-23Y | Ir | 0 | 5 | Ph | H | H | NO$_2$ | H | H | $^tC_4H_9$ | H | — — |
| 5-24 | Ir | 1 | 5 | Ph | F | H | NO$_2$ | H | H | CH$_3$ | H | pic |
| 5-24X | Ir | 1 | 5 | Ph | F | H | NO$_2$ | H | H | CH$_3$ | H | acac |
| 5-24Y | Ir | 0 | 5 | Ph | F | H | NO$_2$ | H | H | CH$_3$ | H | — — |
| 5-25 | Ir | 1 | 5 | Ph | F | H | NO$_2$ | H | H | $^tC_4H_9$ | H | pic |
| 5-25X | Ir | 1 | 5 | Ph | F | H | NO$_2$ | H | H | $^tC_4H_9$ | H | acac |
| 5-25Y | Ir | 0 | 5 | Ph | F | H | NO$_2$ | H | H | $^tC_4H_9$ | H | — — |
| 5-26 | Ir | 1 | 5 | Ph | F | H | NO$_2$ | F | H | CH$_3$ | H | pic |
| 5-26X | Ir | 1 | 5 | Ph | F | H | NO$_2$ | F | H | CH$_3$ | H | acac |
| 5-26Y | Ir | 0 | 5 | Ph | F | H | NO$_2$ | F | H | CH$_3$ | H | — — |
| 5-27 | Ir | 1 | 5 | Ph | F | H | NO$_2$ | F | H | $^tC_4H_9$ | H | pic |
| 5-27X | Ir | 1 | 5 | Ph | F | H | NO$_2$ | F | H | $^tC_4H_9$ | H | acac |
| 5-27Y | Ir | 0 | 5 | Ph | F | H | NO$_2$ | F | H | $^tC_4H_9$ | H | — — |
| 5-28 | Ir | 1 | 5 | Ph | H | NO$_2$ | H | NO$_2$ | H | CH$_3$ | H | pic |
| 5-28X | Ir | 1 | 5 | Ph | H | NO$_2$ | H | NO$_2$ | H | CH$_3$ | H | acac |
| 5-28Y | Ir | 0 | 5 | Ph | H | NO$_2$ | H | NO$_2$ | H | CH$_3$ | H | — — |
| 5-29 | Ir | 1 | 5 | Ph | H | NO$_2$ | H | NO$_2$ | H | $^tC_4H_9$ | H | pic |
| 5-29X | Ir | 1 | 5 | Ph | H | NO$_2$ | H | NO$_2$ | H | $^tC_4H_9$ | H | acac |
| 5-29Y | Ir | 0 | 5 | Ph | H | NO$_2$ | H | NO$_2$ | H | $^tC_4H_9$ | H | — — |
| 5-30 | Ir | 1 | 5 | Ph | NO$_2$ | H | H | NO$_2$ | H | CH$_3$ | H | pic |
| 5-30X | Ir | 1 | 5 | Ph | NO$_2$ | H | H | NO$_2$ | H | CH$_3$ | H | acac |
| 5-30Y | Ir | 0 | 5 | Ph | NO$_2$ | H | H | NO$_2$ | H | CH$_3$ | H | — — |
| 5-31 | Ir | 1 | 5 | Ph | H | H | CF$_3$ | H | H | CH$_3$ | H | pic |
| 5-31X | Ir | 1 | 5 | Ph | H | H | CF$_3$ | H | H | CH$_3$ | H | acac |
| 5-31Y | Ir | 0 | 5 | Ph | H | H | CF$_3$ | H | H | CH$_3$ | H | — — |
| 5-32 | Ir | 1 | 5 | Ph | H | Cl | CF$_3$ | H | H | CH$_3$ | H | pic |
| 5-32X | Ir | 1 | 5 | Ph | H | Cl | CF$_3$ | H | H | CH$_3$ | H | acac |
| 5-32Y | Ir | 0 | 5 | Ph | H | Cl | CF$_3$ | H | H | CH$_3$ | H | — — |
| 5-33 | Ir | 1 | 5 | Ph | H | Cl | CF$_3$ | H | H | $^tC_4H_9$ | H | pic |
| 5-33X | Ir | 1 | 5 | Ph | H | Cl | CF$_3$ | H | H | $^tC_4H_9$ | H | acac |
| 5-33Y | Ir | 0 | 5 | Ph | H | Cl | CF$_3$ | H | H | $^tC_4H_9$ | H | — — |
| 5-34 | Ir | 1 | 5 | Ph | H | NO$_2$ | H | H | H | CH$_3$ | H | pic |
| 5-34X | Ir | 1 | 5 | Ph | H | NO$_2$ | H | H | H | CH$_3$ | H | acac |
| 5-34Y | Ir | 0 | 5 | Ph | H | NO$_2$ | H | H | H | CH$_3$ | H | — — |
| 5-35 | Ir | 1 | 5 | Ph | H | CF$_3$ | H | H | H | CH$_3$ | H | pic |
| 5-35X | Ir | 1 | 5 | Ph | H | CF$_3$ | H | H | H | CH$_3$ | H | acac |
| 5-35Y | Ir | 0 | 5 | Ph | H | CF$_3$ | H | H | H | CH$_3$ | H | — — |
| 5-36 | Ir | 1 | 5 | Ph | H | NO$_2$ | H | CH$_3$ | H | CH$_3$ | H | pic |
| 5-36X | Ir | 1 | 5 | Ph | H | NO$_2$ | H | CH$_3$ | H | CH$_3$ | H | acac |
| 5-36Y | Ir | 0 | 5 | Ph | H | NO$_2$ | H | CH$_3$ | H | CH$_3$ | H | — — |
| 5-37 | Ir | 1 | 5 | Ph | H | NO$_2$ | H | CH$_3$ | H | $^tC_4H_9$ | H | pic |
| 5-37X | Ir | 1 | 5 | Ph | H | NO$_2$ | H | CH$_3$ | H | $^tC_4H_9$ | H | acac |
| 5-37Y | Ir | 0 | 5 | Ph | H | NO$_2$ | H | CH$_3$ | H | $^tC_4H_9$ | H | — — |
| 5-38 | Ir | 1 | 5 | Ph | H | NO$_2$ | H | $^tC_4H_9$ | H | CH$_3$ | H | pic |
| 5-38X | Ir | 1 | 5 | Ph | H | NO$_2$ | H | $^tC_4H_9$ | H | CH$_3$ | H | acac |
| 5-38Y | Ir | 0 | 5 | Ph | H | NO$_2$ | H | $^tC_4H_9$ | H | CH$_3$ | H | — — |
| 5-39 | Ir | 1 | 5 | Ph | H | H | CH$_3$O | H | H | CH$_3$ | H | pic |
| 5-39X | Ir | 1 | 5 | Ph | H | H | CH$_3$O | H | H | CH$_3$ | H | acac |
| 5-39Y | Ir | 0 | 5 | Ph | H | H | CH$_3$O | H | H | CH$_3$ | H | — — |
| 5-40 | Ir | 1 | 5 | Ph | H | CH$_3$O | H | H | H | CH$_3$ | H | pic |
| 5-40X | Ir | 1 | 5 | Ph | H | CH$_3$O | H | H | H | CH$_3$ | H | acac |
| 5-40Y | Ir | 0 | 5 | Ph | H | CH$_3$O | H | H | H | CH$_3$ | H | — — |

TABLE 5-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 5-41 | Ir | 1 | 5 | Ph | H | $CH_3O$ | H | $CH_3$ | H | $CH_3$ | H | pic |
| 5-41X | Ir | 1 | 5 | Ph | H | $CH_3O$ | H | $CH_3$ | H | $CH_3$ | H | acac |
| 5-41Y | Ir | 0 | 5 | Ph | H | $CH_3O$ | H | $CH_3$ | H | $CH_3$ | H | — — |
| 5-42 | Ir | 1 | 5 | Ph | H | $CH_3O$ | H | $^tC_4H_9$ | H | $CH_3$ | H | pic |
| 5-42X | Ir | 1 | 5 | Ph | H | $CH_3O$ | H | $^tC_4H_9$ | H | $CH_3$ | H | acac |
| 5-42Y | Ir | 0 | 5 | Ph | H | $CH_3O$ | H | $^tC_4H_9$ | H | $CH_3$ | H | — — |
| 5-43 | Ir | 1 | 5 | Ph | H | H | H | H | $^tC_4H_9$ | $CH_3$ | H | pic |
| 5-43X | Ir | 1 | 5 | Ph | H | H | H | H | $^tC_4H_9$ | $CH_3$ | H | acac |
| 5-43Y | Ir | 0 | 5 | Ph | H | H | H | H | $^tC_4H_9$ | $CH_3$ | H | — — |
| 5-44 | Ir | 1 | 5 | Ph | H | F | H | F | $^tC_4H_9$ | $CH_3$ | H | pic |
| 5-44X | Ir | 1 | 5 | Ph | H | F | H | F | $^tC_4H_9$ | $CH_3$ | H | acac |
| 5-44Y | Ir | 0 | 5 | Ph | H | F | H | F | $^tC_4H_9$ | $CH_3$ | H | — — |
| 5-45 | Ir | 1 | 5 | Ph | H | F | H | F | $^tC_4H_9$ | $^tC_4H_9$ | H | pic |
| 5-45X | Ir | 1 | 5 | Ph | H | F | H | F | $^tC_4H_9$ | $^tC_4H_9$ | H | acac |
| 5-45Y | Ir | 0 | 5 | Ph | H | F | H | F | $^tC_4H_9$ | $^tC_4H_9$ | H | — — |
| 5-46 | Ir | 1 | 5 | Ph | $CF_3$ | H | $CF_3$ | H | $^tC_4H_9$ | $CH_3$ | H | pic |
| 5-46X | Ir | 1 | 5 | Ph | $CF_3$ | H | $CF_3$ | H | $^tC_4H_9$ | $CH_3$ | H | acac |
| 5-46Y | Ir | 0 | 5 | Ph | $CF_3$ | H | $CF_3$ | H | $^tC_4H_9$ | $CH_3$ | H | — — |
| 5-47 | Ir | 1 | 5 | Ph | $CF_3$ | H | $CF_3$ | H | $^tC_4H_9$ | $^tC_4H_9$ | H | pic |
| 5-47X | Ir | 1 | 5 | Ph | $CF_3$ | H | $CF_3$ | H | $^tC_4H_9$ | $^tC_4H_9$ | H | acac |
| 5-47Y | Ir | 0 | 5 | Ph | $CF_3$ | H | $CF_3$ | H | $^tC_4H_9$ | $^tC_4H_9$ | H | — — |
| 5-48 | Ir | 1 | 5 | Ph | H | $CF_3$ | H | $CH_3$ | $^tC_4H_9$ | $CH_3$ | H | pic |
| 5-48X | Ir | 1 | 5 | Ph | H | $CF_3$ | H | $CH_3$ | $^tC_4H_9$ | $CH_3$ | H | acac |
| 5-48Y | Ir | 0 | 5 | Ph | H | $CF_3$ | H | $CH_3$ | $^tC_4H_9$ | $CH_3$ | H | — — |
| 5-49 | Ir | 1 | 5 | Ph | H | $Si(CH_3)_3$ | H | H | H | $CH_3$ | H | pic |
| 5-49X | Ir | 1 | 5 | Ph | H | $Si(CH_3)_3$ | H | H | H | $CH_3$ | H | acac |
| 5-49Y | Ir | 0 | 5 | Ph | H | $Si(CH_3)_3$ | H | H | H | $CH_3$ | H | — — |
| 5-50 | Ir | 1 | 5 | Ph | H | $Si(CH_3)_3$ | H | H | H | $^tC_4H_9$ | H | pic |
| 5-50X | Ir | 1 | 5 | Ph | H | $Si(CH_3)_3$ | H | H | H | $^tC_4H_9$ | H | acac |
| 5-50Y | Ir | 0 | 5 | Ph | H | $Si(CH_3)_3$ | H | H | H | $^tC_4H_9$ | H | — — |
| 5-51 | Ir | 1 | 5 | Ph | H | H | $Si(CH_3)_3$ | H | H | $CH_3$ | H | pic |
| 5-51X | Ir | 1 | 5 | Ph | H | H | $Si(CH_3)_3$ | H | H | $CH_3$ | H | acac |
| 5-51Y | Ir | 0 | 5 | Ph | H | H | $Si(CH_3)_3$ | H | H | $CH_3$ | H | — — |
| 5-52 | Ir | 1 | 5 | Ph | H | H | H | $Si(CH_3)_3$ | H | $CH_3$ | H | pic |
| 5-52X | Ir | 1 | 5 | Ph | H | H | H | $Si(CH_3)_3$ | H | $CH_3$ | H | acac |
| 5-52Y | Ir | 0 | 5 | Ph | H | H | H | $Si(CH_3)_3$ | H | $CH_3$ | H | — — |
| 5-53 | Ir | 1 | 5 | Ph | H | F | H | $Si(CH_3)_3$ | H | $CH_3$ | H | pic |
| 5-53X | Ir | 1 | 5 | Ph | H | F | H | $Si(CH_3)_3$ | H | $CH_3$ | H | acac |
| 5-53Y | Ir | 0 | 5 | Ph | H | F | H | $Si(CH_3)_3$ | H | $CH_3$ | H | — — |
| 5-54 | Ir | 1 | 5 | Ph | H | $CF_3$ | H | $Si(CH_3)_3$ | H | $CH_3$ | H | pic |
| 5-54X | Ir | 1 | 5 | Ph | H | $CF_3$ | H | $Si(CH_3)_3$ | H | $CH_3$ | H | acac |
| 5-54Y | Ir | 0 | 5 | Ph | H | $CF_3$ | H | $Si(CH_3)_3$ | H | $CH_3$ | H | — — |
| 5-55 | Ir | 1 | 5 | Ph | H | $Si(CH_3)_3$ | H | F | H | $CH_3$ | H | pic |
| 5-55X | Ir | 1 | 5 | Ph | H | $Si(CH_3)_3$ | H | F | H | $CH_3$ | H | acac |
| 5-55Y | Ir | 0 | 5 | Ph | H | $Si(CH_3)_3$ | H | F | H | $CH_3$ | H | — — |
| 5-56 | Ir | 1 | 5 | Ph | H | $Si(CH_3)_3$ | H | F | H | $^tC_4H_9$ | H | pic |
| 5-56X | Ir | 1 | 5 | Ph | H | $Si(CH_3)_3$ | H | F | H | $^tC_4H_9$ | H | acac |
| 5-56Y | Ir | 0 | 5 | Ph | H | $Si(CH_3)_3$ | H | F | H | $^tC_4H_9$ | H | — — |
| 5-57 | Ir | 1 | 5 | Ph | H | $Si(CH_3)_{33}$ | H | $CF_3$ | H | $CH_3$ | H | pic |
| 5-57X | Ir | 1 | 5 | Ph | H | $Si(CH_3)_3$ | H | $CF_3$ | H | $CH_3$ | H | acac |
| 5-57Y | Ir | 0 | 5 | Ph | H | $Si(CH_3)_3$ | H | $CF_3$ | H | $CH_3$ | H | — — |
| 5-58 | Ir | 1 | 5 | Ph | H | $Si(CH_3)_3$ | H | $CF_3$ | H | $^tC_4H_9$ | H | pic |
| 5-58X | Ir | 1 | 5 | Ph | H | $Si(CH_3)_3$ | H | $CF_3$ | H | $^tC_4H_9$ | H | acac |
| 5-58Y | Ir | 0 | 5 | Ph | H | $Si(CH_3)_3$ | H | $CF_3$ | H | $^tC_4H_9$ | H | — — |
| 5-59 | Ir | 1 | 5 | Ph | $Si(CH_3)_3$ | H | $Si(CH_3)_3$ | H | H | $CH_3$ | H | pic |
| 5-59X | Ir | 1 | 5 | Ph | $Si(CH_3)_3$ | H | $Si(CH_3)_3$ | H | H | $CH_3$ | H | acac |
| 5-59Y | Ir | 0 | 5 | Ph | $Si(CH_3)_3$ | H | $Si(CH_3)_3$ | H | H | $CH_3$ | H | — — |
| 5-60 | Ir | 1 | 5 | Ph | $Si(CH_3)_3$ | H | $Si(CH_3)_3$ | H | H | $^tC_4H_9$ | H | pic |
| 5-60X | Ir | 1 | 5 | Ph | $Si(CH_3)_3$ | H | $Si(CH_3)_3$ | H | H | $^tC_4H_9$ | H | acac |
| 5-60Y | Ir | 0 | 5 | Ph | $Si(CH_3)_3$ | H | $Si(CH_3)_3$ | H | H | $^tC_4H_9$ | H | — — |
| 5-61 | Ir | 1 | 5 | Ph | H | H | H | $COCH_3$ | H | $CH_3$ | H | pic |
| 5-61X | Ir | 1 | 5 | Ph | H | H | H | $COCH_3$ | H | $CH_3$ | H | acac |
| 5-61Y | Ir | 0 | 5 | Ph | H | H | H | $COCH_3$ | H | $CH_3$ | H | — — |
| 5-62 | Ir | 1 | 5 | Ph | H | H | $COCH_3$ | H | H | $CH_3$ | H | pic |
| 5-62X | Ir | 1 | 5 | Ph | H | H | $COCH_3$ | H | H | $CH_3$ | H | acac |
| 5-62Y | Ir | 0 | 5 | Ph | H | H | $COCH_3$ | H | H | $CH_3$ | H | — — |
| 5-63 | Ir | 1 | 5 | Ph | H | $COCH_3$ | H | H | H | $CH_3$ | H | pic |
| 5-63X | Ir | 1 | 5 | Ph | H | $COCH_3$ | H | H | H | $CH_3$ | H | acac |
| 5-63Y | Ir | 0 | 5 | Ph | H | $COCH_3$ | H | H | H | $CH_3$ | H | — — |
| 5-64 | Ir | 1 | 5 | Ph | H | H | BL | | H | $CH_3$ | H | pic |
| 5-64X | Ir | 1 | 5 | Ph | H | H | BL | | H | $CH_3$ | H | acac |
| 5-64Y | Ir | 0 | 5 | Ph | H | H | BL | | H | $CH_3$ | H | — — |
| 5-65 | Ir | 1 | 5 | Ph | H | H | BL | | H | $^tC_4H_9$ | H | pic |
| 5-65X | Ir | 1 | 5 | Ph | H | H | BL | | H | $^tC_4H_9$ | H | acac |
| 5-65Y | Ir | 0 | 5 | Ph | H | H | BL | | H | $^tC_4H_9$ | H | — — |
| 5-66 | Ir | 1 | 5 | Ph | H | BL | | H | H | $CH_3$ | H | pic |
| 5-66X | Ir | 1 | 5 | Ph | H | BL | | H | H | $CH_3$ | H | acac |

TABLE 5-continued

| No. | M | n | BSS | SS | G | T¹ | T² | T³ | T⁴ | T⁵ | T⁶ | T⁷ | L¹ | L² |
|---|---|---|---|---|---|---|---|---|---|---|---|---|---|---|
| 5-66Y | Ir | 0 | 5 | | Ph | H | | BL | | H | H | CH₃ | H | — — |
| 5-67 | Ir | 1 | 5 | | Ph | H | | BL | | H | H | ᵗC₄H₉ | H | pic |
| 5-67X | Ir | 1 | 5 | | Ph | H | | BL | | H | H | ᵗC₄H₉ | H | acac |
| 5-67Y | Ir | 0 | 5 | | Ph | H | | BL | | H | H | ᵗC₄H₉ | H | — — |
| 5-68 | Ir | 1 | 5 | | Ph | H | H | | PL | H | H | CH₃ | H | pic |
| 5-68X | Ir | 1 | 5 | | Ph | H | H | | PL | H | H | CH₃ | H | acac |
| 5-68Y | Ir | 0 | 5 | | Ph | H | H | | PL | H | H | CH₃ | H | — — |
| 5-69 | Ir | 1 | 5 | | Ph | H | H | | PL | H | H | ᵗC₄H₉ | H | pic |
| 5-69X | Ir | 1 | 5 | | Ph | H | H | | PL | H | H | ᵗC₄H₉ | H | acac |
| 5-69Y | Ir | 0 | 5 | | Ph | H | H | | PL | H | H | ᵗC₄H₉ | H | — — |
| 5-70 | Ir | 1 | 5 | | Ph | H | | PL | | H | H | CH₃ | H | pic |
| 5-70X | Ir | 1 | 5 | | Ph | H | | PL | | H | H | CH₃ | H | acac |
| 5-70Y | Ir | 0 | 5 | | Ph | H | | PL | | H | H | CH₃ | H | — — |
| 5-71 | Ir | 1 | 5 | | Ph | H | | PL | | H | H | ᵗC₄H₉ | H | pic |
| 5-71X | Ir | 1 | 5 | | Ph | H | | PL | | H | H | ᵗC₄H₉ | H | acac |
| 5-71Y | Ir | 0 | 5 | | Ph | H | | PL | | H | H | ᵗC₄H₉ | H | — — |
| 5-72 | Ir | 1 | 5 | | Ph | H | H | | MEE1 | H | H | CH₃ | H | pic |
| 5-72X | Ir | 1 | 5 | | Ph | H | H | | MEE1 | H | H | CH₃ | H | acac |
| 5-72Y | Ir | 0 | 5 | | Ph | H | H | | MEE1 | H | H | CH₃ | H | — — |
| 5-73 | Ir | 1 | 5 | | Ph | H | | MEE1 | | H | H | CH₃ | H | pic |
| 5-73X | Ir | 1 | 5 | | Ph | H | | MEE1 | | H | H | CH₃ | H | acac |
| 5-73Y | Ir | 0 | 5 | | Ph | H | | MEE1 | | H | H | CH₃ | H | — — |
| 5-74 | Ir | 1 | 5 | | Ph | H | H | | MEE2 | H | H | CH₃ | H | pic |
| 5-74X | Ir | 1 | 5 | | Ph | H | H | | MEE2 | H | H | CH₃ | H | acac |
| 5-74Y | Ir | 0 | 5 | | Ph | H | H | | MEE2 | H | H | CH₃ | H | — — |
| 5-75 | Ir | 1 | 5 | | Ph | H | | MEE2 | | H | H | CH₃ | H | pic |
| 5-75X | Ir | 1 | 5 | | Ph | H | | MEE2 | | H | H | CH₃ | H | acac |
| 5-75Y | Ir | 0 | 5 | | Ph | H | | MEE2 | | H | H | CH₃ | H | — — |
| 5-76 | Ir | 1 | 5 | | Ph | H | H | | PA1 | H | H | CH₃ | H | pic |
| 5-76X | Ir | 1 | 5 | | Ph | H | H | | PA1 | H | H | CH₃ | H | acac |
| 5-76Y | Ir | 0 | 5 | | Ph | H | H | | PA1 | H | H | CH₃ | H | — — |
| 5-77 | Ir | 1 | 5 | | Ph | H | | PA1 | | H | H | CH₃ | H | pic |
| 5-77X | Ir | 1 | 5 | | Ph | H | | PA1 | | H | H | CH₃ | H | acac |
| 5-77Y | Ir | 0 | 5 | | Ph | H | | PA1 | | H | H | CH₃ | H | — — |
| 5-78 | Ir | 1 | 5 | | Ph | H | H | | PA2 | H | H | CH₃ | H | pic |
| 5-78X | Ir | 1 | 5 | | Ph | H | H | | PA2 | H | H | CH₃ | H | acac |
| 5-78Y | Ir | 0 | 5 | | Ph | H | H | | PA2 | H | H | CH₃ | H | — — |
| 5-79 | Ir | 1 | 5 | | Ph | H | | PA2 | | H | H | CH₃ | H | pic |
| 5-79X | Ir | 1 | 5 | | Ph | H | | PA2 | | H | H | CH₃ | H | acac |
| 5-79Y | Ir | 0 | 5 | | Ph | H | | PA2 | | H | H | CH₃ | H | — — |
| 5-80 | Ir | 1 | 5 | | Ph | H | H | | EA1 | H | H | CH₃ | H | pic |
| 5-80X | Ir | 1 | 5 | | Ph | H | H | | EA1 | H | H | CH₃ | H | acac |
| 5-80Y | Ir | 0 | 5 | | Ph | H | H | | EA1 | H | H | CH₃ | H | — — |
| 5-81 | Ir | 1 | 5 | | Ph | H | | EA2 | | H | H | CH₃ | H | pic |
| 5-81X | Ir | 1 | 5 | | Ph | H | | EA2 | | H | H | CH₃ | H | acac |
| 5-81Y | Ir | 0 | 5 | | Ph | H | | EA2 | | H | H | CH₃ | H | — — |
| 5-82 | Ir | 1 | 5 | | Ph | H | H | | ME | H | H | CH₃ | H | pic |
| 5-82X | Ir | 1 | 5 | | Ph | H | H | | ME | H | H | CH₃ | H | acac |
| 5-82Y | Ir | 0 | 5 | | Ph | H | H | | ME | H | H | CH₃ | H | — — |
| 5-83 | Ir | 1 | 5 | | Ph | H | | ME | | H | H | CH₃ | H | pic |
| 5-83X | Ir | 1 | 5 | | Ph | H | | ME | | H | H | CH₃ | H | acac |
| 5-83Y | Ir | 0 | 5 | | Ph | H | | ME | | H | H | CH₃ | H | — — |
| 5-84 | Ir | 1 | 5 | | Ph | H | H | | AT | H | H | CH₃ | H | pic |
| 5-84X | Ir | 1 | 5 | | Ph | H | H | | AT | H | H | CH₃ | H | acac |
| 5-84Y | Ir | 0 | 5 | | Ph | H | H | | AT | H | H | CH₃ | H | — — |
| 5-85 | Ir | 1 | 5 | | Ph | H | | AT | | H | H | CH₃ | H | pic |
| 5-85X | Ir | 1 | 5 | | Ph | H | | AT | | H | H | CH₃ | H | acac |
| 5-85Y | Ir | 0 | 5 | | Ph | H | | AT | | H | H | CH₃ | H | — — |
| 5-86 | Ir | 1 | 5 | | Ph | H | H | | MES1 | H | H | CH₃ | H | pic |
| 5-86X | Ir | 1 | 5 | | Ph | H | H | | MES1 | H | H | CH₃ | H | acac |
| 5-86Y | Ir | 0 | 5 | | Ph | H | H | | MES1 | H | H | CH₃ | H | — — |
| 5-87 | Ir | 1 | 5 | | Ph | H | | MES1 | | H | H | CH₃ | H | pic |
| 5-87X | Ir | 1 | 5 | | Ph | H | | MES1 | | H | H | CH₃ | H | acac |
| 5-87Y | Ir | 0 | 5 | | Ph | H | | MES1 | | H | H | CH₃ | H | — — |
| 5-88 | Ir | 1 | 5 | | Ph | H | H | | MES2 | H | H | CH₃ | H | pic |
| 5-88X | Ir | 1 | 5 | | Ph | H | H | | MES2 | H | H | CH₃ | H | acac |
| 5-88Y | Ir | 0 | 5 | | Ph | H | H | | MES2 | H | H | CH₃ | H | — — |
| 5-89 | Ir | 1 | 5 | | Ph | H | | MES2 | | H | H | CH₃ | H | pic |
| 5-89X | Ir | 1 | 5 | | Ph | H | | MES2 | | H | H | CH₃ | H | acac |
| 5-89Y | Ir | 0 | 5 | | Ph | H | | MES2 | | H | H | CH₃ | H | — — |
| 5-90 | Ir | 1 | 5 | | Ph | H | H | | PS1 | H | H | CH₃ | H | pic |
| 5-90X | Ir | 1 | 5 | | Ph | H | H | | PS1 | H | H | CH₃ | H | acac |
| 5-90Y | Ir | 0 | 5 | | Ph | H | H | | PS1 | H | H | CH₃ | H | — — |
| 5-91 | Ir | 1 | 5 | | Ph | H | | PS1 | | H | H | CH₃ | H | pic |
| 5-91X | Ir | 1 | 5 | | Ph | H | | PS1 | | H | H | CH₃ | H | acac |
| 5-91Y | Ir | 0 | 5 | | Ph | H | | PS1 | | H | H | CH₃ | H | — — |
| 5-92 | Ir | 1 | 5 | | Ph | H | H | | PS2 | H | H | CH₃ | H | pic |

TABLE 5-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 5-92X | Ir | 1 | 5 | Ph | H | H | | PS2 | | H | CH₃ | H acac |
| 5-92Y | Ir | 0 | 5 | Ph | H | H | | PS2 | | H | CH₃ | H — |
| 5-93 | Ir | 1 | 5 | Ph | H | | PS2 | | H | H | CH₃ | H pic |
| 5-93X | Ir | 1 | 5 | Ph | H | | PS2 | | H | H | CH₃ | H acac |
| 5-93Y | Ir | 0 | 5 | Ph | H | | PS2 | | H | H | CH₃ | H — |
| 5-94 | Ir | 1 | 5 | Ph | H | H | | BAL1 | | H | CH₃ | H pic |
| 5-94X | Ir | 1 | 5 | Ph | H | H | | BAL1 | | H | CH₃ | H acac |
| 5-94Y | Ir | 0 | 5 | Ph | H | H | | BAL1 | | H | CH₃ | H — |
| 5-95 | Ir | 1 | 5 | Ph | H | | BAL1 | | H | H | CH₃ | H pic |
| 5-95X | Ir | 1 | 5 | Ph | H | | BAL1 | | H | H | CH₃ | H acac |
| 5-95Y | Ir | 0 | 5 | Ph | H | | BAL1 | | H | H | CH₃ | H — |
| 5-96 | Ir | 1 | 5 | Ph | H | H | | BAL2 | | H | CH₃ | H pic |
| 5-96X | Ir | 1 | 5 | Ph | H | H | | BAL2 | | H | CH₃ | H acac |
| 5-96Y | Ir | 0 | 5 | Ph | H | H | | BAL2 | | H | CH₃ | H — |
| 5-97 | Ir | 1 | 5 | Ph | H | | BAL2 | | H | H | CH₃ | H pic |
| 5-97X | Ir | 1 | 5 | Ph | H | | BAL2 | | H | H | CH₃ | H acac |
| 5-97Y | Ir | 0 | 5 | Ph | H | | BAL2 | | H | H | CH₃ | H — |
| 5-98 | Ir | 1 | 5 | Ph | H | H | | MEK1 | | H | CH₃ | H pic |
| 5-98X | Ir | 1 | 5 | Ph | H | H | | MEK1 | | H | CH₃ | H acac |
| 5-98Y | Ir | 0 | 5 | Ph | H | H | | MEK1 | | H | CH₃ | H — |
| 5-99 | Ir | 1 | 5 | Ph | H | | MEK1 | | H | H | CH₃ | H pic |
| 5-99X | Ir | 1 | 5 | Ph | H | | MEK1 | | H | H | CH₃ | H acac |
| 5-99Y | Ir | 0 | 5 | Ph | H | | MEK1 | | H | H | CH₃ | H — |
| 5-100 | Ir | 1 | 5 | Ph | H | H | | MEK2 | | H | CH₃ | H pic |
| 5-100X | Ir | 1 | 5 | Ph | H | H | | MEK2 | | H | CH₃ | H acac |
| 5-100Y | Ir | 0 | 5 | Ph | H | H | | MEK2 | | H | CH₃ | H — |
| 5-101 | Ir | 1 | 5 | Ph | H | | MEK2 | | H | H | CH₃ | H pic |
| 5-101X | Ir | 1 | 5 | Ph | H | | MEK2 | | H | H | CH₃ | H acac |
| 5-101Y | Ir | 0 | 5 | Ph | H | | MEK2 | | H | H | CH₃ | H — |
| 5-102 | Ir | 1 | 5 | Ph | H | H | | PAL1 | | H | CH₃ | H pic |
| 5-102X | Ir | 1 | 5 | Ph | H | H | | PAL1 | | H | CH₃ | H acac |
| 5-102Y | Ir | 0 | 5 | Ph | H | H | | PAL1 | | H | CH₃ | H — |
| 5-103 | Ir | 1 | 5 | Ph | H | | PAL1 | | H | H | CH₃ | H pic |
| 5-103X | Ir | 1 | 5 | Ph | H | | PAL1 | | H | H | CH₃ | H acac |
| 5-103Y | Ir | 0 | 5 | Ph | H | | PAL1 | | H | H | CH₃ | H — |
| 5-104 | Ir | 1 | 5 | Ph | H | H | | PAL2 | | H | CH₃ | H pic |
| 5-104X | Ir | 1 | 5 | Ph | H | H | | PAL2 | | H | CH₃ | H acac |
| 5-104Y | Ir | 0 | 5 | Ph | H | H | | PAL2 | | H | CH₃ | H — |
| 5-105 | Ir | 1 | 5 | Ph | H | | PAL2 | | H | H | CH₃ | H pic |
| 5-105X | Ir | 1 | 5 | Ph | H | | PAL2 | | H | H | CH₃ | H acac |
| 5-105Y | Ir | 0 | 5 | Ph | H | | PAL2 | | H | H | CH₃ | H — |
| 5-106 | Ir | 1 | 5 | Ph | H | H | | MMK | | H | CH₃ | H pic |
| 5-106X | Ir | 1 | 5 | Ph | H | H | | MMK | | H | CH₃ | H acac |
| 5-106Y | Ir | 0 | 5 | Ph | H | H | | MMK | | H | CH₃ | H — |
| 5-107 | Ir | 1 | 5 | Ph | H | | MMK | | H | H | CH₃ | H pic |
| 5-107X | Ir | 1 | 5 | Ph | H | | MMK | | H | H | CH₃ | H acac |
| 5-107Y | Ir | 0 | 5 | Ph | H | | MMK | | H | H | CH₃ | H — |
| 5-108 | Ir | 1 | 5 | Ph | H | H | | EES1 | | H | CH₃ | H pic |
| 5-108X | Ir | 1 | 5 | Ph | H | H | | EES1 | | H | CH₃ | H acac |
| 5-108Y | Ir | 0 | 5 | Ph | H | H | | EES1 | | H | CH₃ | H — |
| 5-109 | Ir | 1 | 5 | Ph | H | | EES2 | | H | H | CH₃ | H pic |
| 5-109X | Ir | 1 | 5 | Ph | H | | EES2 | | H | H | CH₃ | H acac |
| 5-109Y | Ir | 0 | 5 | Ph | H | | EES2 | | H | H | CH₃ | H — |
| 5-110 | Ir | 1 | 5 | Ph | H | H | | PAE1 | | H | CH₃ | H pic |
| 5-110X | Ir | 1 | 5 | Ph | H | H | | PAE1 | | H | CH₃ | H acac |
| 5-110Y | Ir | 0 | 5 | Ph | H | H | | PAE1 | | H | CH₃ | H — |
| 5-111 | Ir | 1 | 5 | Ph | H | | PAE2 | | H | H | CH₃ | H pic |
| 5-111X | Ir | 1 | 5 | Ph | H | | PAE2 | | H | H | CH₃ | H acac |
| 5-111Y | Ir | 0 | 5 | Ph | H | | PAE2 | | H | H | CH₃ | H — |
| 5-112 | Ir | 1 | 5 | Ph | H | H | | AME1 | | H | CH₃ | H pic |
| 5-112X | Ir | 1 | 5 | Ph | H | H | | AME1 | | H | CH₃ | H acac |
| 5-112Y | Ir | 0 | 5 | Ph | H | H | | AME1 | | H | CH₃ | H — |
| 5-113 | Ir | 1 | 5 | Ph | H | | AME1 | | H | H | CH₃ | H pic |
| 5-113X | Ir | 1 | 5 | Ph | H | | AME1 | | H | H | CH₃ | H acac |
| 5-113Y | Ir | 0 | 5 | Ph | H | | AME1 | | H | H | CH₃ | H — |
| 5-114 | Ir | 1 | 5 | Ph | H | H | | AME2 | | H | CH₃ | H pic |
| 5-114X | Ir | 1 | 5 | Ph | H | H | | AME2 | | H | CH₃ | H acac |
| 5-114Y | Ir | 0 | 5 | Ph | H | H | | AME2 | | H | CH₃ | H — |
| 5-115 | Ir | 1 | 5 | Ph | H | | AME2 | | H | H | CH₃ | H pic |
| 5-115X | Ir | 1 | 5 | Ph | H | | AME2 | | H | H | CH₃ | H acac |
| 5-115Y | Ir | 0 | 5 | Ph | H | | AME2 | | H | H | CH₃ | H — |
| 5-116 | Ir | 1 | 5 | Ph | H | H | | EAE1 | | H | CH₃ | H pic |
| 5-116X | Ir | 1 | 5 | Ph | H | H | | EAE1 | | H | CH₃ | H acac |
| 5-116Y | Ir | 0 | 5 | Ph | H | H | | EAE1 | | H | CH₃ | H — |
| 5-117 | Ir | 1 | 5 | Ph | H | | EAE1 | | H | H | CH₃ | H pic |
| 5-117X | Ir | 1 | 5 | Ph | H | | EAE1 | | H | H | CH₃ | H acac |
| 5-117Y | Ir | 0 | 5 | Ph | H | | EAE1 | | H | H | CH₃ | H — |

TABLE 5-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 5-118 | Ir | 1 | 5 | Ph | H | H | | EAE2 | H | CH₃ | H | pic | |
| 5-118X | Ir | 1 | 5 | Ph | H | H | | EAE2 | H | CH₃ | H | acac | |
| 5-118Y | Ir | 0 | 5 | Ph | H | H | | EAE2 | H | CH₃ | H | — | — |
| 5-119 | Ir | 1 | 5 | Ph | H | | EAE2 | | H | CH₃ | H | pic | |
| 5-119X | Ir | 1 | 5 | Ph | H | | EAE2 | | H | CH₃ | H | acac | |
| 5-119Y | Ir | 0 | 5 | Ph | H | | EAE2 | | H | CH₃ | H | — | — |
| 5-120 | Ir | 1 | 5 | Ph | H | H | | AAE1 | H | CH₃ | H | pic | |
| 5-120X | Ir | 1 | 5 | Ph | H | H | | AAE1 | H | CH₃ | H | acac | |
| 5-120Y | Ir | 0 | 5 | Ph | H | H | | AAE1 | H | CH₃ | H | — | — |
| 5-121 | Ir | 1 | 5 | Ph | H | | AAE1 | | H | CH₃ | H | pic | |
| 5-121X | Ir | 1 | 5 | Ph | H | | AAE1 | | H | CH₃ | H | acac | |
| 5-121Y | Ir | 0 | 5 | Ph | H | | AAE1 | | H | CH₃ | H | — | — |
| 5-122 | Ir | 1 | 5 | Ph | H | H | | AAE2 | H | CH₃ | H | pic | |
| 5-122X | Ir | 1 | 5 | Ph | H | H | | AAE2 | H | CH₃ | H | acac | |
| 5-122Y | Ir | 0 | 5 | Ph | H | H | | AAE2 | H | CH₃ | H | — | — |
| 5-123 | Ir | 1 | 5 | Ph | H | | AAE2 | | H | CH₃ | H | pic | |
| 5-123X | Ir | 1 | 5 | Ph | H | | AAE2 | | H | CH₃ | H | acac | |
| 5-123Y | Ir | 0 | 5 | Ph | H | | AAE2 | | H | CH₃ | H | — | — |
| 5-124 | Ir | 1 | 5 | Ph | H | H | | PME1 | H | CH₃ | H | pic | |
| 5-124X | Ir | 1 | 5 | Ph | H | H | | PME1 | H | CH₃ | H | acac | |
| 5-124Y | Ir | 0 | 5 | Ph | H | H | | PME1 | H | CH₃ | H | — | — |
| 5-125 | Ir | 1 | 5 | Ph | H | | PME1 | | H | CH₃ | H | pic | |
| 5-125X | Ir | 1 | 5 | Ph | H | | PME1 | | H | CH₃ | H | acac | |
| 5-125Y | Ir | 0 | 5 | Ph | H | | PME1 | | H | CH₃ | H | — | — |
| 5-126 | Ir | 1 | 5 | Ph | H | H | | PME2 | H | CH₃ | H | pic | |
| 5-126X | Ir | 1 | 5 | Ph | H | H | | PME2 | H | CH₃ | H | acac | |
| 5-126Y | Ir | 0 | 5 | Ph | H | H | | PME2 | H | CH₃ | H | — | — |
| 5-127 | Ir | 1 | 5 | Ph | H | | PME2 | | H | CH₃ | H | pic | |
| 5-127X | Ir | 1 | 5 | Ph | H | | PME2 | | H | CH₃ | H | acac | |
| 5-127Y | Ir | 0 | 5 | Ph | H | | PME2 | | H | CH₃ | H | — | — |
| 5-128 | Ir | 1 | 5 | Ph | H | H | | MET1 | H | CH₃ | H | pic | |
| 5-128X | Ir | 1 | 5 | Ph | H | H | | MET1 | H | CH₃ | H | acac | |
| 5-128Y | Ir | 0 | 5 | Ph | H | H | | MET1 | H | CH₃ | H | — | — |
| 5-129 | Ir | 1 | 5 | Ph | H | | MET1 | | H | CH₃ | H | pic | |
| 5-129X | Ir | 1 | 5 | Ph | H | | MET1 | | H | CH₃ | H | acac | |
| 5-129Y | Ir | 0 | 5 | Ph | H | | MET1 | | H | CH₃ | H | — | — |
| 5-130 | Ir | 1 | 5 | Ph | H | H | | MET2 | H | CH₃ | H | pic | |
| 5-130X | Ir | 1 | 5 | Ph | H | H | | MET2 | H | CH₃ | H | acac | |
| 5-130Y | Ir | 0 | 5 | Ph | H | H | | MET2 | H | CH₃ | H | — | — |
| 5-131 | Ir | 1 | 5 | Ph | H | | MET2 | | H | CH₃ | H | pic | |
| 5-131X | Ir | 1 | 5 | Ph | H | | MET2 | | H | CH₃ | H | acac | |
| 5-131Y | Ir | 0 | 5 | Ph | H | | MET2 | | H | CH₃ | H | — | — |
| 5-132 | Ir | 1 | 5 | Ph | H | H | | EE1 | H | CH₃ | H | pic | |
| 5-132X | Ir | 1 | 5 | Ph | H | H | | EE1 | H | CH₃ | H | acac | |
| 5-132Y | Ir | 0 | 5 | Ph | H | H | | EE1 | H | CH₃ | H | — | — |
| 5-133 | Ir | 1 | 5 | Ph | H | | EE1 | | H | CH₃ | H | pic | |
| 5-133X | Ir | 1 | 5 | Ph | H | | EE1 | | H | CH₃ | H | acac | |
| 5-133Y | Ir | 0 | 5 | Ph | H | | EE1 | | H | CH₃ | H | — | — |
| 5-134 | Ir | 1 | 5 | Ph | H | H | | EE2 | H | CH₃ | H | pic | |
| 5-134X | Ir | 1 | 5 | Ph | H | H | | EE2 | H | CH₃ | H | acac | |
| 5-134Y | Ir | 0 | 5 | Ph | H | H | | EE2 | H | CH₃ | H | — | — |
| 5-135 | Ir | 1 | 5 | Ph | H | | EE2 | | H | CH₃ | H | pic | |
| 5-135X | Ir | 1 | 5 | Ph | H | | EE2 | | H | CH₃ | H | acac | |
| 5-135Y | Ir | 0 | 5 | Ph | H | | EE2 | | H | CH₃ | H | — | — |
| 5-136 | Ir | 1 | 5 | Ph | H | H | | MS1 | H | CH₃ | H | pic | |
| 5-136X | Ir | 1 | 5 | Ph | H | H | | MS1 | H | CH₃ | H | acac | |
| 5-136Y | Ir | 0 | 5 | Ph | H | H | | MS1 | H | CH₃ | H | — | — |
| 5-137 | Ir | 1 | 5 | Ph | H | | MS1 | | H | CH₃ | H | pic | |
| 5-137X | Ir | 1 | 5 | Ph | H | | MS1 | | H | CH₃ | H | acac | |
| 5-137Y | Ir | 0 | 5 | Ph | H | | MS1 | | H | CH₃ | H | — | — |
| 5-138 | Ir | 1 | 5 | Ph | H | H | | MS2 | H | CH₃ | H | pic | |
| 5-138X | Ir | 1 | 5 | Ph | H | H | | MS2 | H | CH₃ | H | acac | |
| 5-138Y | Ir | 0 | 5 | Ph | H | H | | MS2 | H | CH₃ | H | — | — |
| 5-139 | Ir | 1 | 5 | Ph | H | | MS2 | | H | CH₃ | H | pic | |
| 5-139X | Ir | 1 | 5 | Ph | H | | MS2 | | H | CH₃ | H | acac | |
| 5-139Y | Ir | 0 | 5 | Ph | H | | MS2 | | H | CH₃ | H | — | — |

TABLE 6

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 6-1 | Ir | 1 | 6 | Ph | H | H | H | H | H | CH₃ | H | pic | |
| 6-1X | Ir | 1 | 6 | Ph | H | H | H | H | H | CH₃ | H | acac | |
| 6-1Y | Ir | 0 | 6 | Ph | H | H | H | H | H | CH₃ | H | — | — |

TABLE 6-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 6-2 | Ir | 1 | 6 | Ph | H | H | H | H | $^tC_4H_9$ | H | H | pic |
| 6-2X | Ir | 1 | 6 | Ph | H | H | H | H | $^tC_4H_9$ | H | H | acac |
| 6-2Y | Ir | 0 | 6 | Ph | H | H | H | H | $^tC_4H_9$ | H | H | — |
| 6-3 | Ir | 1 | 6 | Ph | H | F | H | F | $CH_3$ | H | H | pic |
| 6-3X | Ir | 1 | 6 | Ph | H | F | H | F | $CH_3$ | H | H | acac |
| 6-3Y | Ir | 0 | 6 | Ph | H | F | H | F | $CH_3$ | H | H | — |
| 6-4 | Ir | 1 | 6 | Ph | H | F | H | F | $^tC_4H_9$ | H | H | pic |
| 6-4X | Ir | 1 | 6 | Ph | H | F | H | F | $^tC_4H_9$ | H | H | acac |
| 6-4Y | Ir | 0 | 6 | Ph | H | F | H | F | $^tC_4H_9$ | H | H | — |
| 6-5 | Ir | 1 | 6 | Ph | F | H | H | F | $CH_3$ | H | H | pic |
| 6-5X | Ir | 1 | 6 | Ph | F | H | H | F | $CH_3$ | H | H | acac |
| 6-5Y | Ir | 0 | 6 | Ph | F | H | H | F | $CH_3$ | H | H | — |
| 6-6 | Ir | 1 | 6 | Ph | F | H | H | F | $^tC_4H_9$ | H | H | pic |
| 6-6X | Ir | 1 | 6 | Ph | F | H | H | F | $^tC_4H_9$ | H | H | acac |
| 6-6Y | Ir | 0 | 6 | Ph | F | H | H | F | $^tC_4H_9$ | H | H | — |
| 6-7 | Ir | 1 | 6 | Ph | $CF_3$ | H | $CF_3$ | H | $CH_3$ | H | H | pic |
| 6-7X | Ir | 1 | 6 | Ph | $CF_3$ | H | $CF_3$ | H | $CH_3$ | H | H | acac |
| 6-7Y | Ir | 0 | 6 | Ph | $CF_3$ | H | $CF_3$ | H | $CH_3$ | H | H | — |
| 6-8 | Ir | 1 | 6 | Ph | $CF_3$ | H | $CF_3$ | H | $^tC_4H_9$ | H | H | pic |
| 6-8X | Ir | 1 | 6 | Ph | $CF_3$ | H | $CF_3$ | H | $^tC_4H_9$ | H | H | acac |
| 6-8Y | Ir | 0 | 6 | Ph | $CF_3$ | H | $CF_3$ | H | $^tC_4H_9$ | H | H | — |
| 6-9 | Ir | 1 | 6 | Ph | H | F | $CF_3$ | H | $CH_3$ | H | H | pic |
| 6-9X | Ir | 1 | 6 | Ph | H | F | $CF_3$ | H | $CH_3$ | H | H | acac |
| 6-9Y | Ir | 0 | 6 | Ph | H | F | $CF_3$ | H | $CH_3$ | H | H | — |
| 6-10 | Ir | 1 | 6 | Ph | F | H | $CF_3$ | H | $CH_3$ | H | H | pic |
| 6-10X | Ir | 1 | 6 | Ph | F | H | $CF_3$ | H | $CH_3$ | H | H | acac |
| 6-10Y | Ir | 0 | 6 | Ph | F | H | $CF_3$ | H | $CH_3$ | H | H | — |
| 6-11 | Ir | 1 | 6 | Ph | F | F | F | F | $CH_3$ | H | H | pic |
| 6-11X | Ir | 1 | 6 | Ph | F | F | F | F | $CH_3$ | H | H | acac |
| 6-11Y | Ir | 0 | 6 | Ph | F | F | F | F | $CH_3$ | H | H | — |
| 6-12 | Ir | 1 | 6 | Ph | H | F | H | $CH_3$ | $CH_3$ | H | H | pic |
| 6-12X | Ir | 1 | 6 | Ph | H | F | H | $CH_3$ | $CH_3$ | H | H | acac |
| 6-12Y | Ir | 0 | 6 | Ph | H | F | H | $CH_3$ | $CH_3$ | H | H | — |
| 6-13 | Ir | 1 | 6 | Ph | H | F | H | $CH_3$ | $^tC_4H_9$ | H | H | pic |
| 6-13X | Ir | 1 | 6 | Ph | H | F | H | $CH_3$ | $^tC_4H_9$ | H | H | acac |
| 6-13Y | Ir | 0 | 6 | Ph | H | F | H | $CH_3$ | $^tC_4H_9$ | H | H | — |
| 6-14 | Ir | 1 | 6 | Ph | H | F | H | $^tC_4H_9$ | $CH_3$ | H | H | pic |
| 6-14X | Ir | 1 | 6 | Ph | H | F | H | $^tC_4H_9$ | $CH_3$ | H | H | acac |
| 6-14Y | Ir | 0 | 6 | Ph | H | F | H | $^tC_4H_9$ | $CH_3$ | H | H | — |
| 6-15 | Ir | 1 | 6 | Ph | H | F | H | $^tC_4H_9$ | $^tC_4H_9$ | H | H | pic |
| 6-15X | Ir | 1 | 6 | Ph | H | F | H | $^tC_4H_9$ | $^tC_4H_9$ | H | H | acac |
| 6-15Y | Ir | 0 | 6 | Ph | H | F | H | $^tC_4H_9$ | $^tC_4H_9$ | H | H | — |
| 6-16 | Ir | 1 | 6 | Ph | H | $CF_3$ | H | $CF_3$ | $CH_3$ | H | H | pic |
| 6-16X | Ir | 1 | 6 | Ph | H | $CF_3$ | H | $CF_3$ | $CH_3$ | H | H | acac |
| 6-16Y | Ir | 0 | 6 | Ph | H | $CF_3$ | H | $CF_3$ | $CH_3$ | H | H | — |
| 6-17 | Ir | 1 | 6 | Ph | H | $CF_3$ | H | $CF_3$ | $^tC_4H_9$ | H | H | pic |
| 6-17X | Ir | 1 | 6 | Ph | H | $CF_3$ | H | $CF_3$ | $^tC_4H_9$ | H | H | acac |
| 6-17Y | Ir | 0 | 6 | Ph | H | $CF_3$ | H | $CF_3$ | $^tC_4H_9$ | H | H | — |
| 6-18 | Ir | 1 | 6 | Ph | $CF_3$ | H | H | $^tC_4H_9$ | $CH_3$ | H | H | pic |
| 6-18X | Ir | 1 | 6 | Ph | $CF_3$ | H | H | $^tC_4H_9$ | $CH_3$ | H | H | acac |
| 6-18Y | Ir | 0 | 6 | Ph | $CF_3$ | H | H | $^tC_4H_9$ | $CH_3$ | H | H | — |
| 6-19 | Ir | 1 | 6 | Ph | $CF_3$ | H | H | $^tC_4H_9$ | $^tC_4H_9$ | H | H | pic |
| 6-19X | Ir | 1 | 6 | Ph | $CF_3$ | H | H | $^tC_4H_9$ | $^tC_4H_9$ | H | H | acac |
| 6-19Y | Ir | 0 | 6 | Ph | $CF_3$ | H | H | $^tC_4H_9$ | $^tC_4H_9$ | H | H | — |
| 6-20 | Ir | 1 | 6 | Ph | H | $CF_3$ | H | $^tC_4H_9$ | $CH_3$ | H | H | pic |
| 6-20X | Ir | 1 | 6 | Ph | H | $CF_3$ | H | $^tC_4H_9$ | $CH_3$ | H | H | acac |
| 6-20Y | Ir | 0 | 6 | Ph | H | $CF_3$ | H | $^tC_4H_9$ | $CH_3$ | H | H | — |
| 6-21 | Ir | 1 | 6 | Ph | H | $CF_3$ | H | $^tC_4H_9$ | $^tC_4H_9$ | H | H | pic |
| 6-21X | Ir | 1 | 6 | Ph | H | $CF_3$ | H | $^tC_4H_9$ | $^tC_4H_9$ | H | H | acac |
| 6-21Y | Ir | 0 | 6 | Ph | H | $CF_3$ | H | $^tC_4H_9$ | $^tC_4H_9$ | H | H | — |
| 6-22 | Ir | 1 | 6 | Ph | H | $CF_3$ | H | $CH_3$ | $CH_3$ | H | H | pic |
| 6-22X | Ir | 1 | 6 | Ph | H | $CF_3$ | H | $CH_3$ | $CH_3$ | H | H | acac |
| 6-22Y | Ir | 0 | 6 | Ph | H | $CF_3$ | H | $CH_3$ | $CH_3$ | H | H | — |
| 6-23 | Ir | 1 | 6 | Ph | H | $CF_3$ | $CF_3$ | H | $CH_3$ | H | H | pic |
| 6-23X | Ir | 1 | 6 | Ph | H | $CF_3$ | $CF_3$ | H | $CH_3$ | H | H | acac |
| 6-23Y | Ir | 0 | 6 | Ph | H | $CF_3$ | $CF_3$ | H | $CH_3$ | H | H | — |
| 6-24 | Ir | 1 | 6 | Ph | H | H | $NO_2$ | H | $CH_3$ | H | H | pic |
| 6-24X | Ir | 1 | 6 | Ph | H | H | $NO_2$ | H | $CH_3$ | H | H | acac |
| 6-24Y | Ir | 0 | 6 | Ph | H | H | $NO_2$ | H | $CH_3$ | H | H | — |
| 6-25 | Ir | 1 | 6 | Ph | H | H | $NO_2$ | H | $^tC_4H_9$ | H | H | pic |
| 6-25X | Ir | 1 | 6 | Ph | H | H | $NO_2$ | H | $^tC_4H_9$ | H | H | acac |
| 6-25Y | Ir | 0 | 6 | Ph | H | H | $NO_2$ | H | $^tC_4H_9$ | H | H | — |
| 6-26 | Ir | 1 | 6 | Ph | F | H | $NO_2$ | H | $CH_3$ | H | H | pic |
| 6-26X | Ir | 1 | 6 | Ph | F | H | $NO_2$ | H | $CH_3$ | H | H | acac |
| 6-26Y | Ir | 0 | 6 | Ph | F | H | $NO_2$ | H | $CH_3$ | H | H | — |
| 6-27 | Ir | 1 | 6 | Ph | F | H | $NO_2$ | F | $CH_3$ | H | H | pic |
| 6-27X | Ir | 1 | 6 | Ph | F | H | $NO_2$ | F | $CH_3$ | H | H | acac |

TABLE 6-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 6-27Y | Ir | 0 | 6 | Ph | F | H | $NO_2$ | F | $CH_3$ | H | H | — | — |
| 6-28 | Ir | 1 | 6 | Ph | H | $NO_2$ | H | $NO_2$ | $CH_3$ | H | H | pic | |
| 6-28X | Ir | 1 | 6 | Ph | H | $NO_2$ | H | $NO_2$ | $CH_3$ | H | H | acac | |
| 6-28Y | Ir | 0 | 6 | Ph | H | $NO_2$ | H | $NO_2$ | $CH_3$ | H | H | — | — |
| 6-29 | Ir | 1 | 6 | Ph | H | $NO_2$ | H | $NO_2$ | $^tC_4H_9$ | H | H | pic | |
| 6-29X | Ir | 1 | 6 | Ph | H | $NO_2$ | H | $NO_2$ | $^tC_4H_9$ | H | H | acac | |
| 6-29Y | Ir | 0 | 6 | Ph | H | $NO_2$ | H | $NO_2$ | $^tC_4H_9$ | H | H | — | — |
| 6-30 | Ir | 1 | 6 | Ph | $NO_2$ | H | H | $NO_2$ | $CH_3$ | H | H | pic | |
| 6-30X | Ir | 1 | 6 | Ph | $NO_2$ | H | H | $NO_2$ | $CH_3$ | H | H | acac | |
| 6-30Y | Ir | 0 | 6 | Ph | $NO_2$ | H | H | $NO_2$ | $CH_3$ | H | H | — | — |
| 6-31 | Ir | 1 | 6 | Ph | $NO_2$ | H | H | $NO_2$ | $^tC_4H_9$ | H | H | pic | |
| 6-31X | Ir | 1 | 6 | Ph | $NO_2$ | H | H | $NO_2$ | $^tC_4H_9$ | H | H | acac | |
| 6-31Y | Ir | 0 | 6 | Ph | $NO_2$ | H | H | $NO_2$ | $^tC_4H_9$ | H | H | — | — |
| 6-32 | Ir | 1 | 6 | Ph | H | H | $CF_3$ | H | $CH_3$ | H | H | pic | |
| 6-32X | Ir | 1 | 6 | Ph | H | H | $CF_3$ | H | $CH_3$ | H | H | acac | |
| 6-32Y | Ir | 0 | 6 | Ph | H | H | $CF_3$ | H | $CH_3$ | H | H | — | — |
| 6-33 | Ir | 1 | 6 | Ph | H | H | $CF_3$ | H | $^tC_4H_9$ | H | H | pic | |
| 6-33X | Ir | 1 | 6 | Ph | H | H | $CF_3$ | H | $^tC_4H_9$ | H | H | acac | |
| 6-33Y | Ir | 0 | 6 | Ph | H | H | $CF_3$ | H | $^tC_4H_9$ | H | H | — | — |
| 6-34 | Ir | 1 | 6 | Ph | H | Cl | $CF_3$ | H | $CH_3$ | H | H | pic | |
| 6-34X | Ir | 1 | 6 | Ph | H | Cl | $CF_3$ | H | $CH_3$ | H | H | acac | |
| 6-34Y | Ir | 0 | 6 | Ph | H | Cl | $CF_3$ | H | $CH_3$ | H | H | — | — |
| 6-35 | Ir | 1 | 6 | Ph | H | Cl | $CF_3$ | H | $^tC_4H_9$ | H | H | pic | |
| 6-35X | Ir | 1 | 6 | Ph | H | Cl | $CF_3$ | H | $^tC_4H_9$ | H | H | acac | |
| 6-35Y | Ir | 0 | 6 | Ph | H | Cl | $CF_3$ | H | $^tC_4H_9$ | H | H | — | — |
| 6-36 | Ir | 1 | 6 | Ph | H | $NO_2$ | H | H | $CH_3$ | H | H | pic | |
| 6-36X | Ir | 1 | 6 | Ph | H | $NO_2$ | H | H | $CH_3$ | H | H | acac | |
| 6-36Y | Ir | 0 | 6 | Ph | H | $NO_2$ | H | H | $CH_3$ | H | H | — | — |
| 6-37 | Ir | 1 | 6 | Ph | H | $CF_3$ | H | H | $CH_3$ | H | H | pic | |
| 6-37X | Ir | 1 | 6 | Ph | H | $CF_3$ | H | H | $CH_3$ | H | H | acac | |
| 6-37Y | Ir | 0 | 6 | Ph | H | $CF_3$ | H | H | $CH_3$ | H | H | — | — |
| 6-38 | Ir | 1 | 6 | Ph | H | $NO_2$ | H | $CH_3$ | $CH_3$ | H | H | pic | |
| 6-38X | Ir | 1 | 6 | Ph | H | $NO_2$ | H | $CH_3$ | $CH_3$ | H | H | acac | |
| 6-38Y | Ir | 0 | 6 | Ph | H | $NO_2$ | H | $CH_3$ | $CH_3$ | H | H | — | — |
| 6-39 | Ir | 1 | 6 | Ph | H | $NO_2$ | H | $CH_3$ | $^tC_4H_9$ | H | H | pic | |
| 6-39X | Ir | 1 | 6 | Ph | H | $NO_2$ | H | $CH_3$ | $^tC_4H_9$ | H | H | acac | |
| 6-39Y | Ir | 0 | 6 | Ph | H | $NO_2$ | H | $CH_3$ | $^tC_4H_9$ | H | H | — | — |
| 6-40 | Ir | 1 | 6 | Ph | H | $NO_2$ | H | $^tC_4H_9$ | $CH_3$ | H | H | pic | |
| 6-40X | Ir | 1 | 6 | Ph | H | $NO_2$ | H | $^tC_4H_9$ | $CH_3$ | H | H | acac | |
| 6-40Y | Ir | 0 | 6 | Ph | H | $NO_2$ | H | $^tC_4H_9$ | $CH_3$ | H | H | — | — |
| 6-41 | Ir | 1 | 6 | Ph | H | $NO_2$ | H | $^tC_4H_9$ | $^tC_4H_9$ | H | H | pic | |
| 6-41X | Ir | 1 | 6 | Ph | H | $NO_2$ | H | $^tC_4H_9$ | $^tC_4H_9$ | H | H | acac | |
| 6-41Y | Ir | 0 | 6 | Ph | H | $NO_2$ | H | $^tC_4H_9$ | $^tC_4H_9$ | H | H | — | — |
| 6-42 | Ir | 1 | 6 | Ph | H | H | $CH_3O$ | H | $CH_3$ | H | H | pic | |
| 6-42X | Ir | 1 | 6 | Ph | H | H | $CH_3O$ | H | $CH_3$ | H | H | acac | |
| 6-42Y | Ir | 0 | 6 | Ph | H | H | $CH_3O$ | H | $CH_3$ | H | H | — | — |
| 6-43 | Ir | 1 | 6 | Ph | H | $CH_3O$ | H | H | $CH_3$ | H | H | pic | |
| 6-43X | Ir | 1 | 6 | Ph | H | $CH_3O$ | H | H | $CH_3$ | H | H | acac | |
| 6-43Y | Ir | 0 | 6 | Ph | H | $CH_3O$ | H | H | $CH_3$ | H | H | — | — |
| 6-44 | Ir | 1 | 6 | Ph | H | $CH_3O$ | H | $CH_3$ | $CH_3$ | H | H | pic | |
| 6-44X | Ir | 1 | 6 | Ph | H | $CH_3O$ | H | $CH_3$ | $CH_3$ | H | H | acac | |
| 6-44Y | Ir | 0 | 6 | Ph | H | $CH_3O$ | H | $CH_3$ | $CH_3$ | H | H | — | — |
| 6-45 | Ir | 1 | 6 | Ph | H | $CH_3O$ | H | $^tC_4H_9$ | $CH_3$ | H | H | pic | |
| 6-45X | Ir | 1 | 6 | Ph | H | $CH_3O$ | H | $^tC_4H_9$ | $CH_3$ | H | H | acac | |
| 6-45Y | Ir | 0 | 6 | Ph | H | $CH_3O$ | H | $^tC_4H_9$ | $CH_3$ | H | H | — | — |
| 6-46 | Ir | 1 | 6 | Ph | H | $Si(CH_3)_3$ | H | H | $CH_3$ | H | H | pic | |
| 6-46X | Ir | 1 | 6 | Ph | H | $Si(CH_3)_3$ | H | H | $CH_3$ | H | H | acac | |
| 6-46Y | Ir | 0 | 6 | Ph | H | $Si(CH_3)_3$ | H | H | $CH_3$ | H | H | — | — |
| 6-47 | Ir | 1 | 6 | Ph | H | $Si(CH_3)_3$ | H | H | $^tC_4H_9$ | H | H | pic | |
| 6-47X | Ir | 1 | 6 | Ph | H | $Si(CH_3)_3$ | H | H | $^tC_4H_9$ | H | H | acac | |
| 6-47Y | Ir | 0 | 6 | Ph | H | $Si(CH_3)_3$ | H | H | $^tC_4H_9$ | H | H | — | — |
| 6-48 | Ir | 1 | 6 | Ph | H | H | $Si(CH_3)_3$ | H | $CH_3$ | H | H | pic | |
| 6-48X | Ir | 1 | 6 | Ph | H | H | $Si(CH_3)_3$ | H | $CH_3$ | H | H | acac | |
| 6-48Y | Ir | 0 | 6 | Ph | H | H | $Si(CH_3)_3$ | H | $CH_3$ | H | H | — | — |
| 6-49 | Ir | 1 | 6 | Ph | H | H | H | $Si(CH_3)_3$ | $CH_3$ | H | H | pic | |
| 6-49X | Ir | 1 | 6 | Ph | H | H | H | $Si(CH_3)_3$ | $CH_3$ | H | H | acac | |
| 6-49Y | Ir | 0 | 6 | Ph | H | H | H | $Si(CH_3)_3$ | $CH_3$ | H | H | — | — |
| 6-50 | Ir | 1 | 6 | Ph | H | F | H | $Si(CH_3)_3$ | $CH_3$ | H | H | pic | |
| 6-50X | Ir | 1 | 6 | Ph | H | F | H | $Si(CH_3)_3$ | $CH_3$ | H | H | acac | |
| 6-50Y | Ir | 0 | 6 | Ph | H | F | H | $Si(CH_3)_3$ | $CH_3$ | H | H | — | — |
| 6-51 | Ir | 1 | 6 | Ph | H | $CF_3$ | H | $Si(CH_3)_3$ | $CH_3$ | H | H | pic | |
| 6-51X | Ir | 1 | 6 | Ph | H | $CF_3$ | H | $Si(CH_3)_3$ | $CH_3$ | H | H | acac | |
| 6-51Y | Ir | 0 | 6 | Ph | H | $CF_3$ | H | $Si(CH_3)_3$ | $CH_3$ | H | H | — | — |
| 6-52 | Ir | 1 | 6 | Ph | H | $CF_3$ | H | $Si(CH_3)_3$ | $^tC_4H_9$ | H | H | pic | |
| 6-52X | Ir | 1 | 6 | Ph | H | $CF_3$ | H | $Si(CH_3)_3$ | $^tC_4H_9$ | H | H | acac | |
| 6-52Y | Ir | 0 | 6 | Ph | H | $CF_3$ | H | $Si(CH_3)_3$ | $^tC_4H_9$ | H | H | — | — |
| 6-53 | Ir | 1 | 6 | Ph | H | $Si(CH_3)_3$ | H | F | $CH_3$ | H | H | pic | |

TABLE 6-continued

| No. | M | n | BSS | SS | G | T¹ | T² | T³ | T⁴ | T⁵ | T⁶ | T⁷ | L¹ | L² |
|---|---|---|---|---|---|---|---|---|---|---|---|---|---|---|
| 6-53X | Ir | 1 | 6 | | Ph | H | Si(CH₃)₃ | H | F | CH₃ | H | H | acac | |
| 6-53Y | Ir | 0 | 6 | | Ph | H | Si(CH₃)₃ | H | F | CH₃ | H | H | — | — |
| 6-54 | Ir | 1 | 6 | | Ph | H | Si(CH₃)₃ | H | F | ᵗC₄H₉ | H | H | pic | |
| 6-54X | Ir | 1 | 6 | | Ph | H | Si(CH₃)₃ | H | F | ᵗC₄H₉ | H | H | acac | |
| 6-54Y | Ir | 0 | 6 | | Ph | H | Si(CH₃)₃ | H | F | ᵗC₄H₉ | H | H | — | — |
| 6-55 | Ir | 1 | 6 | | Ph | H | Si(CH₃)₃ | H | CF₃ | CH₃ | H | H | pic | |
| 6-55X | Ir | 1 | 6 | | Ph | H | Si(CH₃)₃ | H | CF₃ | CH₃ | H | H | acac | |
| 6-55Y | Ir | 0 | 6 | | Ph | H | Si(CH₃)₃ | H | CF₃ | CH₃ | H | H | — | — |
| 6-56 | Ir | 1 | 6 | | Ph | H | Si(CH₃)₃ | H | CF₃ | ᵗC₄H₉ | H | H | pic | |
| 6-56X | Ir | 1 | 6 | | Ph | H | Si(CH₃)₃ | H | CF₃ | ᵗC₄H₉ | H | H | acac | |
| 6-56Y | Ir | 0 | 6 | | Ph | H | Si(CH₃)₃ | H | CF₃ | ᵗC₄H₉ | H | H | — | — |
| 6-57 | Ir | 1 | 6 | | Ph | Si(CH₃)₃ | H | Si(CH₃)₃ | H | CH₃ | H | H | pic | |
| 6-57X | Ir | 1 | 6 | | Ph | Si(CH₃)₃ | H | Si(CH₃)₃ | H | CH₃ | H | H | acac | |
| 6-57Y | Ir | 0 | 6 | | Ph | Si(CH₃)₃ | H | Si(CH₃)₃ | H | CH₃ | H | H | — | — |
| 6-58 | Ir | 1 | 6 | | Ph | Si(CH₃)₃ | H | Si(CH₃)₃ | H | ᵗC₄H₉ | H | H | pic | |
| 6-58X | Ir | 1 | 6 | | Ph | Si(CH₃)₃ | H | Si(CH₃)₃ | H | ᵗC₄H₉ | H | H | acac | |
| 6-58Y | Ir | 0 | 6 | | Ph | Si(CH₃)₃ | H | Si(CH₃)₃ | H | ᵗC₄H₉ | H | H | — | — |
| 6-59 | Ir | 1 | 6 | | Ph | H | H | H | COCH₃ | CH₃ | H | H | pic | |
| 6-59X | Ir | 1 | 6 | | Ph | H | H | H | COCH₃ | CH₃ | H | H | acac | |
| 6-59Y | Ir | 0 | 6 | | Ph | H | H | H | COCH₃ | CH₃ | H | H | — | — |
| 6-60 | Ir | 1 | 6 | | Ph | H | H | COCH₃ | H | CH₃ | H | H | pic | |
| 6-60X | Ir | 1 | 6 | | Ph | H | H | COCH₃ | H | CH₃ | H | H | acac | |
| 6-60Y | Ir | 0 | 6 | | Ph | H | H | COCH₃ | H | CH₃ | H | H | — | — |
| 6-61 | Ir | 1 | 6 | | Ph | H | COCH₃ | H | H | CH₃ | H | H | pic | |
| 6-61X | Ir | 1 | 6 | | Ph | H | COCH₃ | H | H | CH₃ | H | H | acac | |
| 6-61Y | Ir | 0 | 6 | | Ph | H | COCH₃ | H | H | CH₃ | H | H | — | — |
| 6-62 | Ir | 1 | 6 | | Ph | H | H | H | BL | CH₃ | H | H | pic | |
| 6-62X | Ir | 1 | 6 | | Ph | H | H | H | BL | CH₃ | H | H | acac | |
| 6-62Y | Ir | 0 | 6 | | Ph | H | H | H | BL | CH₃ | H | H | — | — |
| 6-63 | Ir | 1 | 6 | | Ph | H | H | H | BL | ᵗC₄H₉ | H | H | pic | |
| 6-63X | Ir | 1 | 6 | | Ph | H | H | H | BL | ᵗC₄H₉ | H | H | acac | |
| 6-63Y | Ir | 0 | 6 | | Ph | H | H | H | BL | ᵗC₄H₉ | H | H | — | — |
| 6-64 | Ir | 1 | 6 | | Ph | H | BL | | H | CH₃ | H | H | pic | |
| 6-64X | Ir | 1 | 6 | | Ph | H | BL | | H | CH₃ | H | H | acac | |
| 6-64Y | Ir | 0 | 6 | | Ph | H | BL | | H | CH₃ | H | H | — | — |
| 6-65 | Ir | 1 | 6 | | Ph | H | BL | | H | ᵗC₄H₉ | H | H | pic | |
| 6-65X | Ir | 1 | 6 | | Ph | H | BL | | H | ᵗC₄H₉ | H | H | acac | |
| 6-65Y | Ir | 0 | 6 | | Ph | H | BL | | H | ᵗC₄H₉ | H | H | — | — |
| 6-66 | Ir | 1 | 6 | | Ph | H | H | | PL | CH₃ | H | H | pic | |
| 6-66X | Ir | 1 | 6 | | Ph | H | H | | PL | CH₃ | H | H | acac | |
| 6-66Y | Ir | 0 | 6 | | Ph | H | H | | PL | CH₃ | H | H | — | — |
| 6-67 | Ir | 1 | 6 | | Ph | H | H | | PL | ᵗC₄H₉ | H | H | pic | |
| 6-67X | Ir | 1 | 6 | | Ph | H | H | | PL | ᵗC₄H₉ | H | H | acac | |
| 6-67Y | Ir | 0 | 6 | | Ph | H | H | | PL | ᵗC₄H₉ | H | H | — | — |
| 6-68 | Ir | 1 | 6 | | Ph | H | PL | | H | CH₃ | H | H | pic | |
| 6-68X | Ir | 1 | 6 | | Ph | H | PL | | H | CH₃ | H | H | acac | |
| 6-68Y | Ir | 0 | 6 | | Ph | H | PL | | H | CH₃ | H | H | — | — |
| 6-69 | Ir | 1 | 6 | | Ph | H | PL | | H | ᵗC₄H₉ | H | H | pic | |
| 6-69X | Ir | 1 | 6 | | Ph | H | PL | | H | ᵗC₄H₉ | H | H | acac | |
| 6-69Y | Ir | 0 | 6 | | Ph | H | PL | | H | ᵗC₄H₉ | H | H | — | — |
| 6-70 | Ir | 1 | 6 | | Ph | H | H | | MEE1 | CH₃ | H | H | pic | |
| 6-70X | Ir | 1 | 6 | | Ph | H | H | | MEE1 | CH₃ | H | H | acac | |
| 6-70Y | Ir | 0 | 6 | | Ph | H | H | | MEE1 | CH₃ | H | H | — | — |
| 6-71 | Ir | 1 | 6 | | Ph | H | MEE1 | | H | CH₃ | H | H | pic | |
| 6-71X | Ir | 1 | 6 | | Ph | H | MEE1 | | H | CH₃ | H | H | acac | |
| 6-71Y | Ir | 0 | 6 | | Ph | H | MEE1 | | H | CH₃ | H | H | — | — |
| 6-72 | Ir | 1 | 6 | | Ph | H | H | | MEE2 | CH₃ | H | H | pic | |
| 6-72X | Ir | 1 | 6 | | Ph | H | H | | MEE2 | CH₃ | H | H | acac | |
| 6-72Y | Ir | 0 | 6 | | Ph | H | H | | MEE2 | CH₃ | H | H | — | — |
| 6-73 | Ir | 1 | 6 | | Ph | H | MEE2 | | H | CH₃ | H | H | pic | |
| 6-73X | Ir | 1 | 6 | | Ph | H | MEE2 | | H | CH₃ | H | H | acac | |
| 6-73Y | Ir | 0 | 6 | | Ph | H | MEE2 | | H | CH₃ | H | H | — | — |
| 6-74 | Ir | 1 | 6 | | Ph | H | H | | PA1 | CH₃ | H | H | pic | |
| 6-74X | Ir | 1 | 6 | | Ph | H | H | | PA1 | CH₃ | H | H | acac | |
| 6-74Y | Ir | 0 | 6 | | Ph | H | H | | PA1 | CH₃ | H | H | — | — |
| 6-75 | Ir | 1 | 6 | | Ph | H | PA1 | | H | CH₃ | H | H | pic | |
| 6-75X | Ir | 1 | 6 | | Ph | H | PA1 | | H | CH₃ | H | H | acac | |
| 6-75Y | Ir | 0 | 6 | | Ph | H | PA1 | | H | CH₃ | H | H | — | — |
| 6-76 | Ir | 1 | 6 | | Ph | H | H | | PA2 | CH₃ | H | H | pic | |
| 6-76X | Ir | 1 | 6 | | Ph | H | H | | PA2 | CH₃ | H | H | acac | |
| 6-76Y | Ir | 0 | 6 | | Ph | H | H | | PA2 | CH₃ | H | H | — | — |
| 6-77 | Ir | 1 | 6 | | Ph | H | PA2 | | H | CH₃ | H | H | pic | |
| 6-77X | Ir | 1 | 6 | | Ph | H | PA2 | | H | CH₃ | H | H | acac | |
| 6-77Y | Ir | 0 | 6 | | Ph | H | PA2 | | H | CH₃ | H | H | — | — |
| 6-78 | Ir | 1 | 6 | | Ph | H | H | | EA1 | CH₃ | H | H | pic | |
| 6-78X | Ir | 1 | 6 | | Ph | H | H | | EA1 | CH₃ | H | H | acac | |
| 6-78Y | Ir | 0 | 6 | | Ph | H | H | | EA1 | CH₃ | H | H | — | — |

TABLE 6-continued

| No. | M | n | BSS | SS G | T$^1$ | T$^2$ | T$^3$ | T$^4$ | T$^5$ | T$^6$ | T$^7$ | L$^1$ L$^2$ |
|---|---|---|---|---|---|---|---|---|---|---|---|---|
| 6-79 | Ir | 1 | 6 | Ph | H | | EA2 | H | CH$_3$ | H | H | pic |
| 6-79X | Ir | 1 | 6 | Ph | H | | EA2 | H | CH$_3$ | H | H | acac |
| 6-79Y | Ir | 0 | 6 | Ph | H | | EA2 | H | CH$_3$ | H | H | — |
| 6-80 | Ir | 1 | 6 | Ph | H | H | | ME | CH$_3$ | H | H | pic |
| 6-80X | Ir | 1 | 6 | Ph | H | H | | ME | CH$_3$ | H | H | acac |
| 6-80Y | Ir | 0 | 6 | Ph | H | H | | ME | CH$_3$ | H | H | — |
| 6-81 | Ir | 1 | 6 | Ph | H | | ME | H | CH$_3$ | H | H | pic |
| 6-81X | Ir | 1 | 6 | Ph | H | | ME | H | CH$_3$ | H | H | acac |
| 6-81Y | Ir | 0 | 6 | Ph | H | | ME | H | CH$_3$ | H | H | — |
| 6-82 | Ir | 1 | 6 | Ph | H | H | | AT | CH$_3$ | H | H | pic |
| 6-82X | Ir | 1 | 6 | Ph | H | H | | AT | CH$_3$ | H | H | acac |
| 6-82Y | Ir | 0 | 6 | Ph | H | H | | AT | CH$_3$ | H | H | — |
| 6-83 | Ir | 1 | 6 | Ph | H | | AT | H | CH$_3$ | H | H | pic |
| 6-83X | Ir | 1 | 6 | Ph | H | | AT | H | CH$_3$ | H | H | acac |
| 6-83Y | Ir | 0 | 6 | Ph | H | | AT | H | CH$_3$ | H | H | — |
| 6-84 | Ir | 1 | 6 | Ph | H | H | | MES1 | CH$_3$ | H | H | pic |
| 6-84X | Ir | 1 | 6 | Ph | H | H | | MES1 | CH$_3$ | H | H | acac |
| 6-84Y | Ir | 0 | 6 | Ph | H | H | | MES1 | CH$_3$ | H | H | — |
| 6-85 | Ir | 1 | 6 | Ph | H | | MES1 | H | CH$_3$ | H | H | pic |
| 6-85X | Ir | 1 | 6 | Ph | H | | MES1 | H | CH$_3$ | H | H | acac |
| 6-85Y | Ir | 0 | 6 | Ph | H | | MES1 | H | CH$_3$ | H | H | — |
| 6-86 | Ir | 1 | 6 | Ph | H | H | | MES2 | CH$_3$ | H | H | pic |
| 6-86X | Ir | 1 | 6 | Ph | H | H | | MES2 | CH$_3$ | H | H | acac |
| 6-86Y | Ir | 0 | 6 | Ph | H | H | | MES2 | CH$_3$ | H | H | — |
| 6-87 | Ir | 1 | 6 | Ph | H | | MES2 | H | CH$_3$ | H | H | pic |
| 6-87X | Ir | 1 | 6 | Ph | H | | MES2 | H | CH$_3$ | H | H | acac |
| 6-87Y | Ir | 0 | 6 | Ph | H | | MES2 | H | CH$_3$ | H | H | — |
| 6-88 | Ir | 1 | 6 | Ph | H | H | | PS1 | CH$_3$ | H | H | pic |
| 6-88X | Ir | 1 | 6 | Ph | H | H | | PS1 | CH$_3$ | H | H | acac |
| 6-88Y | Ir | 0 | 6 | Ph | H | H | | PS1 | CH$_3$ | H | H | — |
| 6-89 | Ir | 1 | 6 | Ph | H | | PS1 | H | CH$_3$ | H | H | pic |
| 6-89X | Ir | 1 | 6 | Ph | H | | PS1 | H | CH$_3$ | H | H | acac |
| 6-89Y | Ir | 0 | 6 | Ph | H | | PS1 | H | CH$_3$ | H | H | — |
| 6-90 | Ir | 1 | 6 | Ph | H | H | | PS2 | CH$_3$ | H | H | pic |
| 6-90X | Ir | 1 | 6 | Ph | H | H | | PS2 | CH$_3$ | H | H | acac |
| 6-90Y | Ir | 0 | 6 | Ph | H | H | | PS2 | CH$_3$ | H | H | — |
| 6-91 | Ir | 1 | 6 | Ph | H | | PS2 | H | CH$_3$ | H | H | pic |
| 6-91X | Ir | 1 | 6 | Ph | H | | PS2 | H | CH$_3$ | H | H | acac |
| 6-91Y | Ir | 0 | 6 | Ph | H | | PS2 | H | CH$_3$ | H | H | — |
| 6-92 | Ir | 1 | 6 | Ph | H | H | | BAL1 | CH$_3$ | H | H | pic |
| 6-92X | Ir | 1 | 6 | Ph | H | H | | BAL1 | CH$_3$ | H | H | acac |
| 6-92Y | Ir | 0 | 6 | Ph | H | H | | BAL1 | CH$_3$ | H | H | — |
| 6-93 | Ir | 1 | 6 | Ph | H | | BAL1 | H | CH$_3$ | H | H | pic |
| 6-93X | Ir | 1 | 6 | Ph | H | | BAL1 | H | CH$_3$ | H | H | acac |
| 6-93Y | Ir | 0 | 6 | Ph | H | | BAL1 | H | CH$_3$ | H | H | — |
| 6-94 | Ir | 1 | 6 | Ph | H | H | | BAL2 | CH$_3$ | H | H | pic |
| 6-94X | Ir | 1 | 6 | Ph | H | H | | BAL2 | CH$_3$ | H | H | acac |
| 6-94Y | Ir | 0 | 6 | Ph | H | H | | BAL2 | CH$_3$ | H | H | — |
| 6-95 | Ir | 1 | 6 | Ph | H | | BAL2 | H | CH$_3$ | H | H | pic |
| 6-95X | Ir | 1 | 6 | Ph | H | | BAL2 | H | CH$_3$ | H | H | acac |
| 6-95Y | Ir | 0 | 6 | Ph | H | | BAL2 | H | CH$_3$ | H | H | — |
| 6-96 | Ir | 1 | 6 | Ph | H | H | | MEK1 | CH$_3$ | H | H | pic |
| 6-96X | Ir | 1 | 6 | Ph | H | H | | MEK1 | CH$_3$ | H | H | acac |
| 6-96Y | Ir | 0 | 6 | Ph | H | H | | MEK1 | CH$_3$ | H | H | — |
| 6-97 | Ir | 1 | 6 | Ph | H | | MEK1 | H | CH$_3$ | H | H | pic |
| 6-97X | Ir | 1 | 6 | Ph | H | | MEK1 | H | CH$_3$ | H | H | acac |
| 6-97Y | Ir | 0 | 6 | Ph | H | | MEK1 | H | CH$_3$ | H | H | — |
| 6-98 | Ir | 1 | 6 | Ph | H | H | | MEK2 | CH$_3$ | H | H | pic |
| 6-98X | Ir | 1 | 6 | Ph | H | H | | MEK2 | CH$_3$ | H | H | acac |
| 6-98Y | Ir | 0 | 6 | Ph | H | H | | MEK2 | CH$_3$ | H | H | — |
| 6-99 | Ir | 1 | 6 | Ph | H | | MEK2 | H | CH$_3$ | H | H | pic |
| 6-99X | Ir | 1 | 6 | Ph | H | | MEK2 | H | CH$_3$ | H | H | acac |
| 6-99Y | Ir | 0 | 6 | Ph | H | | MEK2 | H | CH$_3$ | H | H | — |
| 6-100 | Ir | 1 | 6 | Ph | H | H | | PAL1 | CH$_3$ | H | H | pic |
| 6-100X | Ir | 1 | 6 | Ph | H | H | | PAL1 | CH$_3$ | H | H | acac |
| 6-100Y | Ir | 0 | 6 | Ph | H | H | | PAL1 | CH$_3$ | H | H | — |
| 6-101 | Ir | 1 | 6 | Ph | H | | PAL1 | H | CH$_3$ | H | H | pic |
| 6-101X | Ir | 1 | 6 | Ph | H | | PAL1 | H | CH$_3$ | H | H | acac |
| 6-101Y | Ir | 0 | 6 | Ph | H | | PAL1 | H | CH$_3$ | H | H | — |
| 6-102 | Ir | 1 | 6 | Ph | H | H | | PAL2 | CH$_3$ | H | H | pic |
| 6-102X | Ir | 1 | 6 | Ph | H | H | | PAL2 | CH$_3$ | H | H | acac |
| 6-102Y | Ir | 0 | 6 | Ph | H | H | | PAL2 | CH$_3$ | H | H | — |
| 6-103 | Ir | 1 | 6 | Ph | H | | PAL2 | H | CH$_3$ | H | H | pic |
| 6-103X | Ir | 1 | 6 | Ph | H | | PAL2 | H | CH$_3$ | H | H | acac |
| 6-103Y | Ir | 0 | 6 | Ph | H | | PAL2 | H | CH$_3$ | H | H | — |
| 6-104 | Ir | 1 | 6 | Ph | H | H | | MMK | CH$_3$ | H | H | pic |
| 6-104X | Ir | 1 | 6 | Ph | H | H | | MMK | CH$_3$ | H | H | acac |

TABLE 6-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 6-104Y | Ir | 0 | 6 | Ph | H | H |  | MMK | CH₃ | H | H | — | — |
| 6-105 | Ir | 1 | 6 | Ph | H |  | MMK |  | CH₃ | H | H | pic |  |
| 6-105X | Ir | 1 | 6 | Ph | H |  | MMK | H | CH₃ | H | H | acac |  |
| 6-105Y | Ir | 0 | 6 | Ph | H |  | MMK | H | CH₃ | H | H | — | — |
| 6-106 | Ir | 1 | 6 | Ph | H | H |  | EES1 | CH₃ | H | H | pic |  |
| 6-106X | Ir | 1 | 6 | Ph | H | H |  | EES1 | CH₃ | H | H | acac |  |
| 6-106Y | Ir | 0 | 6 | Ph | H | H |  | EES1 | CH₃ | H | H | — | — |
| 6-107 | Ir | 1 | 6 | Ph | H |  | EES2 |  | CH₃ | H | H | pic |  |
| 6-107X | Ir | 1 | 6 | Ph | H |  | EES2 | H | CH₃ | H | H | acac |  |
| 6-107Y | Ir | 0 | 6 | Ph | H |  | EES2 | H | CH₃ | H | H | — | — |
| 6-108 | Ir | 1 | 6 | Ph | H | H |  | PAE1 | CH₃ | H | H | pic |  |
| 6-108X | Ir | 1 | 6 | Ph | H | H |  | PAE1 | CH₃ | H | H | acac |  |
| 6-108Y | Ir | 0 | 6 | Ph | H | H |  | PAE1 | CH₃ | H | H | — | — |
| 6-109 | Ir | 1 | 6 | Ph | H |  | PAE2 | H | CH₃ | H | H | pic |  |
| 6-109X | Ir | 1 | 6 | Ph | H |  | PAE2 | H | CH₃ | H | H | acac |  |
| 6-109Y | Ir | 0 | 6 | Ph | H |  | PAE2 | H | CH₃ | H | H | — | — |
| 6-110 | Ir | 1 | 6 | Ph | H | H |  | AME1 | CH₃ | H | H | pic |  |
| 6-110X | Ir | 1 | 6 | Ph | H | H |  | AME1 | CH₃ | H | H | acac |  |
| 6-110Y | Ir | 0 | 6 | Ph | H | H |  | AME1 | CH₃ | H | H | — | — |
| 6-111 | Ir | 1 | 6 | Ph | H |  | AME1 | H | CH₃ | H | H | pic |  |
| 6-111X | Ir | 1 | 6 | Ph | H |  | AME1 | H | CH₃ | H | H | acac |  |
| 6-111Y | Ir | 0 | 6 | Ph | H |  | AME1 | H | CH₃ | H | H | — | — |
| 6-112 | Ir | 1 | 6 | Ph | H | H |  | AME2 | CH₃ | H | H | pic |  |
| 6-112X | Ir | 1 | 6 | Ph | H | H |  | AME2 | CH₃ | H | H | acac |  |
| 6-112Y | Ir | 0 | 6 | Ph | H | H |  | AME2 | CH₃ | H | H | — | — |
| 6-113 | Ir | 1 | 6 | Ph | H |  | AME2 | H | CH₃ | H | H | pic |  |
| 6-113X | Ir | 1 | 6 | Ph | H |  | AME2 | H | CH₃ | H | H | acac |  |
| 6-113Y | Ir | 0 | 6 | Ph | H |  | AME2 | H | CH₃ | H | H | — | — |
| 6-114 | Ir | 1 | 6 | Ph | H | H |  | EAE1 | CH₃ | H | H | pic |  |
| 6-114X | Ir | 1 | 6 | Ph | H | H |  | EAE1 | CH₃ | H | H | acac |  |
| 6-114Y | Ir | 0 | 6 | Ph | H | H |  | EAE1 | CH₃ | H | H | — | — |
| 6-115 | Ir | 1 | 6 | Ph | H |  | EAE1 | H | CH₃ | H | H | pic |  |
| 6-115X | Ir | 1 | 6 | Ph | H |  | EAE1 | H | CH₃ | H | H | acac |  |
| 6-115Y | Ir | 0 | 6 | Ph | H |  | EAE1 | H | CH₃ | H | H | — | — |
| 6-116 | Ir | 1 | 6 | Ph | H | H |  | EAE2 | CH₃ | H | H | pic |  |
| 6-116X | Ir | 1 | 6 | Ph | H | H |  | EAE2 | CH₃ | H | H | acac |  |
| 6-116Y | Ir | 0 | 6 | Ph | H | H |  | EAE2 | CH₃ | H | H | — | — |
| 6-117 | Ir | 1 | 6 | Ph | H |  | EAE2 | H | CH₃ | H | H | pic |  |
| 6-117X | Ir | 1 | 6 | Ph | H |  | EAE2 | H | CH₃ | H | H | acac |  |
| 6-117Y | Ir | 0 | 6 | Ph | H |  | EAE2 | H | CH₃ | H | H | — | — |
| 6-118 | Ir | 1 | 6 | Ph | H | H |  | AAE1 | CH₃ | H | H | pic |  |
| 6-118X | Ir | 1 | 6 | Ph | H | H |  | AAE1 | CH₃ | H | H | acac |  |
| 6-118Y | Ir | 0 | 6 | Ph | H | H |  | AAE1 | CH₃ | H | H | — | — |
| 6-119 | Ir | 1 | 6 | Ph | H |  | AAE1 | H | CH₃ | H | H | pic |  |
| 6-119X | Ir | 1 | 6 | Ph | H |  | AAE1 | H | CH₃ | H | H | acac |  |
| 6-119Y | Ir | 0 | 6 | Ph | H |  | AAE1 | H | CH₃ | H | H | — | — |
| 6-120 | Ir | 1 | 6 | Ph | H | H |  | AAE2 | CH₃ | H | H | pic |  |
| 6-120X | Ir | 1 | 6 | Ph | H | H |  | AAE2 | CH₃ | H | H | acac |  |
| 6-120Y | Ir | 0 | 6 | Ph | H | H |  | AAE2 | CH₃ | H | H | — | — |
| 6-121 | Ir | 1 | 6 | Ph | H |  | AAE2 | H | CH₃ | H | H | pic |  |
| 6-121X | Ir | 1 | 6 | Ph | H |  | AAE2 | H | CH₃ | H | H | acac |  |
| 6-121Y | Ir | 0 | 6 | Ph | H |  | AAE2 | H | CH₃ | H | H | — | — |
| 6-122 | Ir | 1 | 6 | Ph | H | H |  | PME1 | CH₃ | H | H | pic |  |
| 6-122X | Ir | 1 | 6 | Ph | H | H |  | PME1 | CH₃ | H | H | acac |  |
| 6-122Y | Ir | 0 | 6 | Ph | H | H |  | PME1 | CH₃ | H | H | — | — |
| 6-123 | Ir | 1 | 6 | Ph | H |  | PME1 | H | CH₃ | H | H | pic |  |
| 6-123X | Ir | 1 | 6 | Ph | H |  | PME1 | H | CH₃ | H | H | acac |  |
| 6-123Y | Ir | 0 | 6 | Ph | H |  | PME1 | H | CH₃ | H | H | — | — |
| 6-124 | Ir | 1 | 6 | Ph | H | H |  | PME2 | CH₃ | H | H | pic |  |
| 6-124X | Ir | 1 | 6 | Ph | H | H |  | PME2 | CH₃ | H | H | acac |  |
| 6-124Y | Ir | 0 | 6 | Ph | H | H |  | PME2 | CH₃ | H | H | — | — |
| 6-125 | Ir | 1 | 6 | Ph | H |  | PME2 | H | CH₃ | H | H | pic |  |
| 6-125X | Ir | 1 | 6 | Ph | H |  | PME2 | H | CH₃ | H | H | acac |  |
| 6-125Y | Ir | 0 | 6 | Ph | H |  | PME2 | H | CH₃ | H | H | — | — |
| 6-126 | Ir | 1 | 6 | Ph | H | H |  | MET1 | CH₃ | H | H | pic |  |
| 6-126X | Ir | 1 | 6 | Ph | H | H |  | MET1 | CH₃ | H | H | acac |  |
| 6-126Y | Ir | 0 | 6 | Ph | H | H |  | MET1 | CH₃ | H | H | — | — |
| 6-127 | Ir | 1 | 6 | Ph | H |  | MET1 | H | CH₃ | H | H | pic |  |
| 6-127X | Ir | 1 | 6 | Ph | H |  | MET1 | H | CH₃ | H | H | acac |  |
| 6-127Y | Ir | 0 | 6 | Ph | H |  | MET1 | H | CH₃ | H | H | — | — |
| 6-128 | Ir | 1 | 6 | Ph | H | H |  | MET2 | CH₃ | H | H | pic |  |
| 6-128X | Ir | 1 | 6 | Ph | H | H |  | MET2 | CH₃ | H | H | acac |  |
| 6-128Y | Ir | 0 | 6 | Ph | H | H |  | MET2 | CH₃ | H | H | — | — |
| 6-129 | Ir | 1 | 6 | Ph | H |  | MET2 | H | CH₃ | H | H | pic |  |
| 6-129X | Ir | 1 | 6 | Ph | H |  | MET2 | H | CH₃ | H | H | acac |  |
| 6-129Y | Ir | 0 | 6 | Ph | H |  | MET2 | H | CH₃ | H | H | — | — |
| 6-130 | Ir | 1 | 6 | Ph | H | H |  | EE1 | CH₃ | H | H | pic |  |

TABLE 6-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 6-130X | Ir | 1 | 6 | Ph | H | H | | EE1 | $CH_3$ | H | H | acac |
| 6-130Y | Ir | 0 | 6 | Ph | H | H | | EE1 | $CH_3$ | H | H | — — |
| 6-131 | Ir | 1 | 6 | Ph | H | | EE1 | H | $CH_3$ | H | H | pic |
| 6-131X | Ir | 1 | 6 | Ph | H | | EE1 | H | $CH_3$ | H | H | acac |
| 6-131Y | Ir | 0 | 6 | Ph | H | | EE1 | H | $CH_3$ | H | H | — — |
| 6-132 | Ir | 1 | 6 | Ph | H | H | | EE2 | $CH_3$ | H | H | pic |
| 6-132X | Ir | 1 | 6 | Ph | H | H | | EE2 | $CH_3$ | H | H | acac |
| 6-132Y | Ir | 0 | 6 | Ph | H | H | | EE2 | $CH_3$ | H | H | — — |
| 6-133 | Ir | 1 | 6 | Ph | H | | EE2 | H | $CH_3$ | H | H | pic |
| 6-133X | Ir | 1 | 6 | Ph | H | | EE2 | H | $CH_3$ | H | H | acac |
| 6-133Y | Ir | 0 | 6 | Ph | H | | EE2 | H | $CH_3$ | H | H | — — |
| 6-134 | Ir | 1 | 6 | Ph | H | H | | MS1 | $CH_3$ | H | H | pic |
| 6-134X | Ir | 1 | 6 | Ph | H | H | | MS1 | $CH_3$ | H | H | acac |
| 6-134Y | Ir | 0 | 6 | Ph | H | H | | MS1 | $CH_3$ | H | H | — — |
| 6-135 | Ir | 1 | 6 | Ph | H | | MS1 | H | $CH_3$ | H | H | pic |
| 6-135X | Ir | 1 | 6 | Ph | H | | MS1 | H | $CH_3$ | H | H | acac |
| 6-135Y | Ir | 0 | 6 | Ph | H | | MS1 | H | $CH_3$ | H | H | — — |
| 6-136 | Ir | 1 | 6 | Ph | H | H | | MS2 | $CH_3$ | H | H | pic |
| 6-136X | Ir | 1 | 6 | Ph | H | H | | MS2 | $CH_3$ | H | H | acac |
| 6-136Y | Ir | 0 | 6 | Ph | H | H | | MS2 | $CH_3$ | H | H | — — |
| 6-137 | Ir | 1 | 6 | Ph | H | | MS2 | H | $CH_3$ | H | H | pic |
| 6-137X | Ir | 1 | 6 | Ph | H | | MS2 | H | $CH_3$ | H | H | acac |
| 6-137Y | Ir | 0 | 6 | Ph | H | | MS2 | H | $CH_3$ | H | H | — — |

TABLE 7

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 7-1 | Ir | 1 | 7 | Ph | H | H | H | H | $CH_3$ | H | H | pic |
| 7-1X | Ir | 1 | 7 | Ph | H | H | H | H | $CH_3$ | H | H | acac |
| 7-1Y | Ir | 0 | 7 | Ph | H | H | H | H | $CH_3$ | H | H | — — |
| 7-2 | Ir | 1 | 7 | Ph | H | H | H | H | $^tC_4H_9$ | H | H | pic |
| 7-2X | Ir | 1 | 7 | Ph | H | H | H | H | $^tC_4H_9$ | H | H | acac |
| 7-2Y | Ir | 0 | 7 | Ph | H | H | H | H | $^tC_4H_9$ | H | H | — — |
| 7-3 | Ir | 1 | 7 | Ph | H | F | H | F | $CH_3$ | H | H | pic |
| 7-3X | Ir | 1 | 7 | Ph | H | F | H | F | $CH_3$ | H | H | acac |
| 7-3Y | Ir | 0 | 7 | Ph | H | F | H | F | $CH_3$ | H | H | — — |
| 7-4 | Ir | 1 | 7 | Ph | H | F | H | F | $^tC_4H_9$ | H | H | pic |
| 7-4X | Ir | 1 | 7 | Ph | H | F | H | F | $^tC_4H_9$ | H | H | acac |
| 7-4Y | Ir | 0 | 7 | Ph | H | F | H | F | $^tC_4H_9$ | H | H | — — |
| 7-5 | Ir | 1 | 7 | Ph | F | H | H | F | $CH_3$ | H | H | pic |
| 7-5X | Ir | 1 | 7 | Ph | F | H | H | F | $CH_3$ | H | H | acac |
| 7-5Y | Ir | 0 | 7 | Ph | F | H | H | F | $CH_3$ | H | H | — — |
| 7-6 | Ir | 1 | 7 | Ph | F | H | H | F | $^tC_4H_9$ | H | H | pic |
| 7-6X | Ir | 1 | 7 | Ph | F | H | H | F | $^tC_4H_9$ | H | H | acac |
| 7-6Y | Ir | 0 | 7 | Ph | F | H | H | F | $^tC_4H_9$ | H | H | — — |
| 7-7 | Ir | 1 | 7 | Ph | $CF_3$ | H | $CF_3$ | H | $CH_3$ | H | H | pic |
| 7-7X | Ir | 1 | 7 | Ph | $CF_3$ | H | $CF_3$ | H | $CH_3$ | H | H | acac |
| 7-7Y | Ir | 0 | 7 | Ph | $CF_3$ | H | $CF_3$ | H | $CH_3$ | H | H | — — |
| 7-8 | Ir | 1 | 7 | Ph | $CF_3$ | H | $CF_3$ | H | $^tC_4H_9$ | H | H | pic |
| 7-8X | Ir | 1 | 7 | Ph | $CF_3$ | H | $CF_3$ | H | $^tC_4H_9$ | H | H | acac |
| 7-8Y | Ir | 0 | 7 | Ph | $CF_3$ | H | $CF_3$ | H | $^tC_4H_9$ | H | H | — — |
| 7-9 | Ir | 1 | 7 | Ph | H | F | $CF_3$ | H | $CH_3$ | H | H | pic |
| 7-9X | Ir | 1 | 7 | Ph | H | F | $CF_3$ | H | $CH_3$ | H | H | acac |
| 7-9Y | Ir | 0 | 7 | Ph | H | F | $CF_3$ | H | $CH_3$ | H | H | — — |
| 7-10 | Ir | 1 | 7 | Ph | F | H | $CF_3$ | H | $CH_3$ | H | H | pic |
| 7-10X | Ir | 1 | 7 | Ph | F | H | $CF_3$ | H | $CH_3$ | H | H | acac |
| 7-10Y | Ir | 0 | 7 | Ph | F | H | $CF_3$ | H | $CH_3$ | H | H | — — |
| 7-11 | Ir | 1 | 7 | Ph | F | F | F | F | $CH_3$ | H | H | pic |
| 7-11X | Ir | 1 | 7 | Ph | F | F | F | F | $CH_3$ | H | H | acac |
| 7-11Y | Ir | 0 | 7 | Ph | F | F | F | F | $CH_3$ | H | H | — — |
| 7-12 | Ir | 1 | 7 | Ph | H | F | H | $CH_3$ | $CH_3$ | H | H | pic |
| 7-12X | Ir | 1 | 7 | Ph | H | F | H | $CH_3$ | $CH_3$ | H | H | acac |
| 7-12Y | Ir | 0 | 7 | Ph | H | F | H | $CH_3$ | $CH_3$ | H | H | — — |
| 7-13 | Ir | 1 | 7 | Ph | H | F | H | $CH_3$ | $^tC_4H_9$ | H | H | pic |
| 7-13X | Ir | 1 | 7 | Ph | H | F | H | $CH_3$ | $^tC_4H_9$ | H | H | acac |
| 7-13Y | Ir | 0 | 7 | Ph | H | F | H | $CH_3$ | $^tC_4H_9$ | H | H | — — |
| 7-14 | Ir | 1 | 7 | Ph | H | F | H | $^tC_4H_9$ | $CH_3$ | H | H | pic |
| 7-14X | Ir | 1 | 7 | Ph | H | F | H | $^tC_4H_9$ | $CH_3$ | H | H | acac |
| 7-14Y | Ir | 0 | 7 | Ph | H | F | H | $^tC_4H_9$ | $CH_3$ | H | H | — — |
| 7-15 | Ir | 1 | 7 | Ph | H | F | H | $^tC_4H_9$ | $^tC_4H_9$ | H | H | pic |
| 7-15X | Ir | 1 | 7 | Ph | H | F | H | $^tC_4H_9$ | $^tC_4H_9$ | H | H | acac |
| 7-15Y | Ir | 0 | 7 | Ph | H | F | H | $^tC_4H_9$ | $^tC_4H_9$ | H | H | — — |
| 7-16 | Ir | 1 | 7 | Ph | H | $CF_3$ | H | $CF_3$ | $CH_3$ | H | H | pic |

TABLE 7-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 7-16X | Ir | 1 | 7 | Ph | H | CF₃ | H | CF₃ | CH₃ | H | H | acac | |
| 7-16Y | Ir | 0 | 7 | Ph | H | CF₃ | H | CF₃ | CH₃ | H | H | — | — |
| 7-17 | Ir | 1 | 7 | Ph | H | CF₃ | H | CF₃ | ᵗC₄H₉ | H | H | pic | |
| 7-17X | Ir | 1 | 7 | Ph | H | CF₃ | H | CF₃ | ᵗC₄H₉ | H | H | acac | |
| 7-17Y | Ir | 0 | 7 | Ph | H | CF₃ | H | CF₃ | ᵗC₄H₉ | H | H | — | — |
| 7-18 | Ir | 1 | 7 | Ph | CF₃ | H | H | ᵗC₄H₉ | CH₃ | H | H | pic | |
| 7-18X | Ir | 1 | 7 | Ph | CF₃ | H | H | ᵗC₄H₉ | CH₃ | H | H | acac | |
| 7-18Y | Ir | 0 | 7 | Ph | CF₃ | H | H | ᵗC₄H₉ | CH₃ | H | H | — | — |
| 7-19 | Ir | 1 | 7 | Ph | CF₃ | H | H | ᵗC₄H₉ | ᵗC₄H₉ | H | H | pic | |
| 7-19X | Ir | 1 | 7 | Ph | CF₃ | H | H | ᵗC₄H₉ | ᵗC₄H₉ | H | H | acac | |
| 7-19Y | Ir | 0 | 7 | Ph | CF₃ | H | H | ᵗC₄H₉ | ᵗC₄H₉ | H | H | — | — |
| 7-20 | Ir | 1 | 7 | Ph | H | CF₃ | H | ᵗC₄H₉ | CH₃ | H | H | pic | |
| 7-20X | Ir | 1 | 7 | Ph | H | CF₃ | H | ᵗC₄H₉ | CH₃ | H | H | acac | |
| 7-20Y | Ir | 0 | 7 | Ph | H | CF₃ | H | ᵗC₄H₉ | CH₃ | H | H | — | — |
| 7-21 | Ir | 1 | 7 | Ph | H | CF₃ | H | ᵗC₄H₉ | ᵗC₄H₉ | H | H | pic | |
| 7-21X | Ir | 1 | 7 | Ph | H | CF₃ | H | ᵗC₄H₉ | ᵗC₄H₉ | H | H | acac | |
| 7-21Y | Ir | 0 | 7 | Ph | H | CF₃ | H | ᵗC₄H₉ | ᵗC₄H₉ | H | H | — | — |
| 7-22 | Ir | 1 | 7 | Ph | H | CF₃ | H | CH₃ | CH₃ | H | H | pic | |
| 7-22X | Ir | 1 | 7 | Ph | H | CF₃ | H | CH₃ | CH₃ | H | H | acac | |
| 7-22Y | Ir | 0 | 7 | Ph | H | CF₃ | H | CH₃ | CH₃ | H | H | — | — |
| 7-23 | Ir | 1 | 7 | Ph | H | CF₃ | CF₃ | H | CH₃ | H | H | pic | |
| 7-23X | Ir | 1 | 7 | Ph | H | CF₃ | CF₃ | H | CH₃ | H | H | acac | |
| 7-23Y | Ir | 0 | 7 | Ph | H | CF₃ | CF₃ | H | CH₃ | H | H | — | — |
| 7-24 | Ir | 1 | 7 | Ph | H | H | NO₂ | H | CH₃ | H | H | pic | |
| 7-24X | Ir | 1 | 7 | Ph | H | H | NO₂ | H | CH₃ | H | H | acac | |
| 7-24Y | Ir | 0 | 7 | Ph | H | H | NO₂ | H | CH₃ | H | H | — | — |
| 7-25 | Ir | 1 | 7 | Ph | H | H | NO₂ | H | ᵗC₄H₉ | H | H | pic | |
| 7-25X | Ir | 1 | 7 | Ph | H | H | NO₂ | H | ᵗC₄H₉ | H | H | acac | |
| 7-25Y | Ir | 0 | 7 | Ph | H | H | NO₂ | H | ᵗC₄H₉ | H | H | — | — |
| 7-26 | Ir | 1 | 7 | Ph | F | H | NO₂ | H | CH₃ | H | H | pic | |
| 7-26X | Ir | 1 | 7 | Ph | F | H | NO₂ | H | CH₃ | H | H | acac | |
| 7-26Y | Ir | 0 | 7 | Ph | F | H | NO₂ | H | CH₃ | H | H | — | — |
| 7-27 | Ir | 1 | 7 | Ph | F | H | NO₂ | F | CH₃ | H | H | pic | |
| 7-27X | Ir | 1 | 7 | Ph | F | H | NO₂ | F | CH₃ | H | H | acac | |
| 7-27Y | Ir | 0 | 7 | Ph | F | H | NO₂ | F | CH₃ | H | H | — | — |
| 7-28 | Ir | 1 | 7 | Ph | H | NO₂ | H | NO₂ | CH₃ | H | H | pic | |
| 7-28X | Ir | 1 | 7 | Ph | H | NO₂ | H | NO₂ | CH₃ | H | H | acac | |
| 7-28Y | Ir | 0 | 7 | Ph | H | NO₂ | H | NO₂ | CH₃ | H | H | — | — |
| 7-29 | Ir | 1 | 7 | Ph | H | NO₂ | H | NO₂ | ᵗC₄H₉ | H | H | pic | |
| 7-29X | Ir | 1 | 7 | Ph | H | NO₂ | H | NO₂ | ᵗC₄H₉ | H | H | acac | |
| 7-29Y | Ir | 0 | 7 | Ph | H | NO₂ | H | NO₂ | ᵗC₄H₉ | H | H | — | — |
| 7-30 | Ir | 1 | 7 | Ph | NO₂ | H | H | NO₂ | CH₃ | H | H | pic | |
| 7-30X | Ir | 1 | 7 | Ph | NO₂ | H | H | NO₂ | CH₃ | H | H | acac | |
| 7-30Y | Ir | 0 | 7 | Ph | NO₂ | H | H | NO₂ | CH₃ | H | H | — | — |
| 7-31 | Ir | 1 | 7 | Ph | NO₂ | H | H | NO₂ | ᵗC₄H₉ | H | H | pic | |
| 7-31X | Ir | 1 | 7 | Ph | NO₂ | H | H | NO₂ | ᵗC₄H₉ | H | H | acac | |
| 7-31Y | Ir | 0 | 7 | Ph | NO₂ | H | H | NO₂ | ᵗC₄H₉ | H | H | — | — |
| 7-32 | Ir | 1 | 7 | Ph | H | H | CF₃ | H | CH₃ | H | H | pic | |
| 7-32X | Ir | 1 | 7 | Ph | H | H | CF₃ | H | CH₃ | H | H | acac | |
| 7-32Y | Ir | 0 | 7 | Ph | H | H | CF₃ | H | CH₃ | H | H | — | — |
| 7-33 | Ir | 1 | 7 | Ph | H | H | CF₃ | H | ᵗC₄H₉ | H | H | pic | |
| 7-33X | Ir | 1 | 7 | Ph | H | H | CF₃ | H | ᵗC₄H₉ | H | H | acac | |
| 7-33Y | Ir | 0 | 7 | Ph | H | H | CF₃ | H | ᵗC₄H₉ | H | H | — | — |
| 7-34 | Ir | 1 | 7 | Ph | H | Cl | CF₃ | H | CH₃ | H | H | pic | |
| 7-34X | Ir | 1 | 7 | Ph | H | Cl | CF₃ | H | CH₃ | H | H | acac | |
| 7-34Y | Ir | 0 | 7 | Ph | H | Cl | CF₃ | H | CH₃ | H | H | — | — |
| 7-35 | Ir | 1 | 7 | Ph | H | Cl | CF₃ | H | ᵗC₄H₉ | H | H | pic | |
| 7-35X | Ir | 1 | 7 | Ph | H | Cl | CF₃ | H | ᵗC₄H₉ | H | H | acac | |
| 7-35Y | Ir | 0 | 7 | Ph | H | Cl | CF₃ | H | ᵗC₄H₉ | H | H | — | — |
| 7-36 | Ir | 1 | 7 | Ph | H | NO₂ | H | H | CH₃ | H | H | pic | |
| 7-36X | Ir | 1 | 7 | Ph | H | NO₂ | H | H | CH₃ | H | H | acac | |
| 7-36Y | Ir | 0 | 7 | Ph | H | NO₂ | H | H | CH₃ | H | H | — | — |
| 7-37 | Ir | 1 | 7 | Ph | H | CF₃ | H | H | CH₃ | H | H | pic | |
| 7-37X | Ir | 1 | 7 | Ph | H | CF₃ | H | H | CH₃ | H | H | acac | |
| 7-37Y | Ir | 0 | 7 | Ph | H | CF₃ | H | H | CH₃ | H | H | — | — |
| 7-38 | Ir | 1 | 7 | Ph | H | NO₂ | H | CH₃ | CH₃ | H | H | pic | |
| 7-38X | Ir | 1 | 7 | Ph | H | NO₂ | H | CH₃ | CH₃ | H | H | acac | |
| 7-38Y | Ir | 0 | 7 | Ph | H | NO₂ | H | CH₃ | CH₃ | H | H | — | — |
| 7-39 | Ir | 1 | 7 | Ph | H | NO₂ | H | CH₃ | ᵗC₄H₉ | H | H | pic | |
| 7-39X | Ir | 1 | 7 | Ph | H | NO₂ | H | CH₃ | ᵗC₄H₉ | H | H | acac | |
| 7-39Y | Ir | 0 | 7 | Ph | H | NO₂ | H | CH₃ | ᵗC₄H₉ | H | H | — | — |
| 7-40 | Ir | 1 | 7 | Ph | H | NO₂ | H | ᵗC₄H₉ | CH₃ | H | H | pic | |
| 7-40X | Ir | 1 | 7 | Ph | H | NO₂ | H | ᵗC₄H₉ | CH₃ | H | H | acac | |
| 7-40Y | Ir | 0 | 7 | Ph | H | NO₂ | H | ᵗC₄H₉ | CH₃ | H | H | — | — |
| 7-41 | Ir | 1 | 7 | Ph | H | NO₂ | H | ᵗC₄H₉ | ᵗC₄H₉ | H | H | pic | |
| 7-41X | Ir | 1 | 7 | Ph | H | NO₂ | H | ᵗC₄H₉ | ᵗC₄H₉ | H | H | acac | |
| 7-41Y | Ir | 0 | 7 | Ph | H | NO₂ | H | ᵗC₄H₉ | ᵗC₄H₉ | H | H | — | — |

TABLE 7-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 7-42 | Ir | 1 | 7 | Ph | H | H | CH$_3$O | H | CH$_3$ | H | H | pic | |
| 7-42X | Ir | 1 | 7 | Ph | H | H | CH$_3$O | H | CH$_3$ | H | H | acac | |
| 7-42Y | Ir | 0 | 7 | Ph | H | H | CH$_3$O | H | CH$_3$ | H | H | — | — |
| 7-43 | Ir | 1 | 7 | Ph | H | CH$_3$O | H | H | CH$_3$ | H | H | pic | |
| 7-43X | Ir | 1 | 7 | Ph | H | CH$_3$O | H | H | CH$_3$ | H | H | acac | |
| 7-43Y | Ir | 0 | 7 | Ph | H | CH$_3$O | H | H | CH$_3$ | H | H | — | — |
| 7-44 | Ir | 1 | 7 | Ph | H | CH$_3$O | H | CH$_3$ | CH$_3$ | H | H | pic | |
| 7-44X | Ir | 1 | 7 | Ph | H | CH$_3$O | H | CH$_3$ | CH$_3$ | H | H | acac | |
| 7-44Y | Ir | 0 | 7 | Ph | H | CH$_3$O | H | CH$_3$ | CH$_3$ | H | H | — | — |
| 7-45 | Ir | 1 | 7 | Ph | H | CH$_3$O | H | $^t$C$_4$H$_9$ | CH$_3$ | H | H | pic | |
| 7-45X | Ir | 1 | 7 | Ph | H | CH$_3$O | H | $^t$C$_4$H$_9$ | CH$_3$ | H | H | acac | |
| 7-45Y | Ir | 0 | 7 | Ph | H | CH$_3$O | H | $^t$C$_4$H$_9$ | CH$_3$ | H | H | — | — |
| 7-46 | Ir | 1 | 7 | Ph | H | Si(CH$_3$)$_3$ | H | H | CH$_3$ | H | H | pic | |
| 7-46X | Ir | 1 | 7 | Ph | H | Si(CH$_3$)$_3$ | H | H | CH$_3$ | H | H | acac | |
| 7-46Y | Ir | 0 | 7 | Ph | H | Si(CH$_3$)$_3$ | H | H | CH$_3$ | H | H | — | — |
| 7-47 | Ir | 1 | 7 | Ph | H | Si(CH$_3$)$_3$ | H | H | $^t$C$_4$H$_9$ | H | H | pic | |
| 7-47X | Ir | 1 | 7 | Ph | H | Si(CH$_3$)$_3$ | H | H | $^t$C$_4$H$_9$ | H | H | acac | |
| 7-47Y | Ir | 0 | 7 | Ph | H | Si(CH$_3$)$_3$ | H | H | $^t$C$_4$H$_9$ | H | H | — | — |
| 7-48 | Ir | 1 | 7 | Ph | H | H | Si(CH$_3$)$_3$ | H | CH$_3$ | H | H | pic | |
| 7-48X | Ir | 1 | 7 | Ph | H | H | Si(CH$_3$)$_3$ | H | CH$_3$ | H | H | acac | |
| 7-48Y | Ir | 0 | 7 | Ph | H | H | Si(CH$_3$)$_3$ | H | CH$_3$ | H | H | — | — |
| 7-49 | Ir | 1 | 7 | Ph | H | H | H | Si(CH$_3$)$_3$ | CH$_3$ | H | H | pic | |
| 7-49X | Ir | 1 | 7 | Ph | H | H | H | Si(CH$_3$)$_3$ | CH$_3$ | H | H | acac | |
| 7-49Y | Ir | 0 | 7 | Ph | H | H | H | Si(CH$_3$)$_3$ | CH$_3$ | H | H | — | — |
| 7-50 | Ir | 1 | 7 | Ph | H | F | H | Si(CH$_3$)$_3$ | CH$_3$ | H | H | pic | |
| 7-50X | Ir | 1 | 7 | Ph | H | F | H | Si(CH$_3$)$_3$ | CH$_3$ | H | H | acac | |
| 7-50Y | Ir | 0 | 7 | Ph | H | F | H | Si(CH$_3$)$_3$ | CH$_3$ | H | H | — | — |
| 7-51 | Ir | 1 | 7 | Ph | H | CF$_3$ | H | Si(CH$_3$)$_3$ | CH$_3$ | H | H | pic | |
| 7-51X | Ir | 1 | 7 | Ph | H | CF$_3$ | H | Si(CH$_3$)$_3$ | CH$_3$ | H | H | acac | |
| 7-51Y | Ir | 0 | 7 | Ph | H | CF$_3$ | H | Si(CH$_3$)$_3$ | CH$_3$ | H | H | — | — |
| 7-52 | Ir | 1 | 7 | Ph | H | CF$_3$ | H | Si(CH$_3$)$_3$ | $^t$C$_4$H$_9$ | H | H | pic | |
| 7-52X | Ir | 1 | 7 | Ph | H | CF$_3$ | H | Si(CH$_3$)$_3$ | $^t$C$_4$H$_9$ | H | H | acac | |
| 7-52Y | Ir | 0 | 7 | Ph | H | CF$_3$ | H | Si(CH$_3$)$_3$ | $^t$C$_4$H$_9$ | H | H | — | — |
| 7-53 | Ir | 1 | 7 | Ph | H | Si(CH$_3$)$_3$ | H | F | CH$_3$ | H | H | pic | |
| 7-53X | Ir | 1 | 7 | Ph | H | Si(CH$_3$)$_3$ | H | F | CH$_3$ | H | H | acac | |
| 7-53Y | Ir | 0 | 7 | Ph | H | Si(CH$_3$)$_3$ | H | F | CH$_3$ | H | H | — | — |
| 7-54 | Ir | 1 | 7 | Ph | H | Si(CH$_3$)$_3$ | H | F | $^t$C$_4$H$_9$ | H | H | pic | |
| 7-54X | Ir | 1 | 7 | Ph | H | Si(CH$_3$)$_3$ | H | F | $^t$C$_4$H$_9$ | H | H | acac | |
| 7-54Y | Ir | 0 | 7 | Ph | H | Si(CH$_3$)$_3$ | H | F | $^t$C$_4$H$_9$ | H | H | — | — |
| 7-55 | Ir | 1 | 7 | Ph | H | Si(CH$_3$)$_3$ | H | CF$_3$ | CH$_3$ | H | H | pic | |
| 7-55X | Ir | 1 | 7 | Ph | H | Si(CH$_3$)$_3$ | H | CF$_3$ | CH$_3$ | H | H | acac | |
| 7-55Y | Ir | 0 | 7 | Ph | H | Si(CH$_3$)$_3$ | H | CF$_3$ | CH$_3$ | H | H | — | — |
| 7-56 | Ir | 1 | 7 | Ph | H | Si(CH$_3$)$_3$ | H | CF$_3$ | $^t$C$_4$H$_9$ | H | H | pic | |
| 7-56X | Ir | 1 | 7 | Ph | H | Si(CH$_3$)$_3$ | H | CF$_3$ | $^t$C$_4$H$_9$ | H | H | acac | |
| 7-56Y | Ir | 0 | 7 | Ph | H | Si(CH$_3$)$_3$ | H | CF$_3$ | $^t$C$_4$H$_9$ | H | H | — | — |
| 7-57 | Ir | 1 | 7 | Ph | Si(CH$_3$)$_3$ | H | Si(CH$_3$)$_3$ | H | CH$_3$ | H | H | pic | |
| 7-57X | Ir | 1 | 7 | Ph | Si(CH$_3$)$_3$ | H | Si(CH$_3$)$_3$ | H | CH$_3$ | H | H | acac | |
| 7-57Y | Ir | 0 | 7 | Ph | Si(CH$_3$)$_3$ | H | Si(CH$_3$)$_3$ | H | CH$_3$ | H | H | — | — |
| 7-58 | Ir | 1 | 7 | Ph | Si(CH$_3$)$_3$ | H | Si(CH$_3$)$_3$ | H | $^t$C$_4$H$_9$ | H | H | pic | |
| 7-58X | Ir | 1 | 7 | Ph | Si(CH$_3$)$_3$ | H | Si(CH$_3$)$_3$ | H | $^t$C$_4$H$_9$ | H | H | acac | |
| 7-58Y | Ir | 0 | 7 | Ph | Si(CH$_3$)$_3$ | H | Si(CH$_3$)$_3$ | H | $^t$C$_4$H$_9$ | H | H | — | — |
| 7-59 | Ir | 1 | 7 | Ph | H | H | H | COCH$_3$ | CH$_3$ | H | H | pic | |
| 7-59X | Ir | 1 | 7 | Ph | H | H | H | COCH$_3$ | CH$_3$ | H | H | acac | |
| 7-59Y | Ir | 0 | 7 | Ph | H | H | H | COCH$_3$ | CH$_3$ | H | H | — | — |
| 7-60 | Ir | 1 | 7 | Ph | H | H | COCH$_3$ | H | CH$_3$ | H | H | pic | |
| 7-60X | Ir | 1 | 7 | Ph | H | H | COCH$_3$ | H | CH$_3$ | H | H | acac | |
| 7-60Y | Ir | 0 | 7 | Ph | H | H | COCH$_3$ | H | CH$_3$ | H | H | — | — |
| 7-61 | Ir | 1 | 7 | Ph | H | COCH$_3$ | H | H | CH$_3$ | H | H | pic | |
| 7-61X | Ir | 1 | 7 | Ph | H | COCH$_3$ | H | H | CH$_3$ | H | H | acac | |
| 7-61Y | Ir | 0 | 7 | Ph | H | COCH$_3$ | H | H | CH$_3$ | H | H | — | — |
| 7-62 | Ir | 1 | 7 | Ph | H | H | BL | | CH$_3$ | H | H | pic | |
| 7-62X | Ir | 1 | 7 | Ph | H | H | BL | | CH$_3$ | H | H | acac | |
| 7-62Y | Ir | 0 | 7 | Ph | H | H | BL | | CH$_3$ | H | H | — | — |
| 7-63 | Ir | 1 | 7 | Ph | H | H | BL | | $^t$C$_4$H$_9$ | H | H | pic | |
| 7-63X | Ir | 1 | 7 | Ph | H | H | BL | | $^t$C$_4$H$_9$ | H | H | acac | |
| 7-63Y | Ir | 0 | 7 | Ph | H | H | BL | | $^t$C$_4$H$_9$ | H | H | — | — |
| 7-64 | Ir | 1 | 7 | Ph | H | BL | | H | CH$_3$ | H | H | pic | |
| 7-64X | Ir | 1 | 7 | Ph | H | BL | | H | CH$_3$ | H | H | acac | |
| 7-64Y | Ir | 0 | 7 | Ph | H | BL | | H | CH$_3$ | H | H | — | — |
| 7-65 | Ir | 1 | 7 | Ph | H | BL | | H | $^t$C$_4$H$_9$ | H | H | pic | |
| 7-65X | Ir | 1 | 7 | Ph | H | BL | | H | $^t$C$_4$H$_9$ | H | H | acac | |
| 7-65Y | Ir | 0 | 7 | Ph | H | BL | | H | $^t$C$_4$H$_9$ | H | H | — | — |
| 7-66 | Ir | 1 | 7 | Ph | H | H | PL | | CH$_3$ | H | H | pic | |
| 7-66X | Ir | 1 | 7 | Ph | H | H | PL | | CH$_3$ | H | H | acac | |
| 7-66Y | Ir | 0 | 7 | Ph | H | H | PL | | CH$_3$ | H | H | — | — |
| 7-67 | Ir | 1 | 7 | Ph | H | H | PL | | $^t$C$_4$H$_9$ | H | H | pic | |
| 7-67X | Ir | 1 | 7 | Ph | H | H | PL | | $^t$C$_4$H$_9$ | H | H | acac | |

TABLE 7-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 7-67Y | Ir | 0 | 7 | Ph | H | H | | PL | $^tC_4H_9$ | H | H | — | — |
| 7-68 | Ir | 1 | 7 | Ph | H | | PL | | $CH_3$ | H | H | pic | |
| 7-68X | Ir | 1 | 7 | Ph | H | | PL | | $CH_3$ | H | H | acac | |
| 7-68Y | Ir | 0 | 7 | Ph | H | | PL | | $CH_3$ | H | H | — | — |
| 7-69 | Ir | 1 | 7 | Ph | H | | PL | | $^tC_4H_9$ | H | H | pic | |
| 7-69X | Ir | 1 | 7 | Ph | H | | PL | | $^tC_4H_9$ | H | H | acac | |
| 7-69Y | Ir | 0 | 7 | Ph | H | | PL | | $^tC_4H_9$ | H | H | — | — |
| 7-70 | Ir | 1 | 7 | Ph | H | H | | MEE1 | $CH_3$ | H | H | pic | |
| 7-70X | Ir | 1 | 7 | Ph | H | H | | MEE1 | $CH_3$ | H | H | acac | |
| 7-70Y | Ir | 0 | 7 | Ph | H | H | | MEE1 | $CH_3$ | H | H | — | — |
| 7-71 | Ir | 1 | 7 | Ph | H | | MEE1 | | $CH_3$ | H | H | pic | |
| 7-71X | Ir | 1 | 7 | Ph | H | | MEE1 | | $CH_3$ | H | H | acac | |
| 7-71Y | Ir | 0 | 7 | Ph | H | | MEE1 | | $CH_3$ | H | H | — | — |
| 7-72 | Ir | 1 | 7 | Ph | H | H | | MEE2 | $CH_3$ | H | H | pic | |
| 7-72X | Ir | 1 | 7 | Ph | H | H | | MEE2 | $CH_3$ | H | H | acac | |
| 7-72Y | Ir | 0 | 7 | Ph | H | H | | MEE2 | $CH_3$ | H | H | — | — |
| 7-73 | Ir | 1 | 7 | Ph | H | | MEE2 | | $CH_3$ | H | H | pic | |
| 7-73X | Ir | 1 | 7 | Ph | H | | MEE2 | | $CH_3$ | H | H | acac | |
| 7-73Y | Ir | 0 | 7 | Ph | H | | MEE2 | | $CH_3$ | H | H | — | — |
| 7-74 | Ir | 1 | 7 | Ph | H | H | | PA1 | $CH_3$ | H | H | pic | |
| 7-74X | Ir | 1 | 7 | Ph | H | H | | PA1 | $CH_3$ | H | H | acac | |
| 7-74Y | Ir | 0 | 7 | Ph | H | H | | PA1 | $CH_3$ | H | H | — | — |
| 7-75 | Ir | 1 | 7 | Ph | H | | PA1 | | $CH_3$ | H | H | pic | |
| 7-75X | Ir | 1 | 7 | Ph | H | | PA1 | | $CH_3$ | H | H | acac | |
| 7-75Y | Ir | 0 | 7 | Ph | H | | PA1 | | $CH_3$ | H | H | — | — |
| 7-76 | Ir | 1 | 7 | Ph | H | H | | PA2 | $CH_3$ | H | H | pic | |
| 7-76X | Ir | 1 | 7 | Ph | H | H | | PA2 | $CH_3$ | H | H | acac | |
| 7-76Y | Ir | 0 | 7 | Ph | H | H | | PA2 | $CH_3$ | H | H | — | — |
| 7-77 | Ir | 1 | 7 | Ph | H | | PA2 | | $CH_3$ | H | H | pic | |
| 7-77X | Ir | 1 | 7 | Ph | H | | PA2 | | $CH_3$ | H | H | acac | |
| 7-77Y | Ir | 0 | 7 | Ph | H | | PA2 | | $CH_3$ | H | H | — | — |
| 7-78 | Ir | 1 | 7 | Ph | H | H | | EA1 | $CH_3$ | H | H | pic | |
| 7-78X | Ir | 1 | 7 | Ph | H | H | | EA1 | $CH_3$ | H | H | acac | |
| 7-78Y | Ir | 0 | 7 | Ph | H | H | | EA1 | $CH_3$ | H | H | — | — |
| 7-79 | Ir | 1 | 7 | Ph | H | | EA2 | | $CH_3$ | H | H | pic | |
| 7-79X | Ir | 1 | 7 | Ph | H | | EA2 | | $CH_3$ | H | H | acac | |
| 7-79Y | Ir | 0 | 7 | Ph | H | | EA2 | | $CH_3$ | H | H | — | — |
| 7-80 | Ir | 1 | 7 | Ph | H | H | | ME | $CH_3$ | H | H | pic | |
| 7-80X | Ir | 1 | 7 | Ph | H | H | | ME | $CH_3$ | H | H | acac | |
| 7-80Y | Ir | 0 | 7 | Ph | H | H | | ME | $CH_3$ | H | H | — | — |
| 7-81 | Ir | 1 | 7 | Ph | H | | ME | | $CH_3$ | H | H | pic | |
| 7-81X | Ir | 1 | 7 | Ph | H | | ME | | $CH_3$ | H | H | acac | |
| 7-81Y | Ir | 0 | 7 | Ph | H | | ME | | $CH_3$ | H | H | — | — |
| 7-82 | Ir | 1 | 7 | Ph | H | H | | AT | $CH_3$ | H | H | pic | |
| 7-82X | Ir | 1 | 7 | Ph | H | H | | AT | $CH_3$ | H | H | acac | |
| 7-82Y | Ir | 0 | 7 | Ph | H | H | | AT | $CH_3$ | H | H | — | — |
| 7-83 | Ir | 1 | 7 | Ph | H | | AT | | $CH_3$ | H | H | pic | |
| 7-83X | Ir | 1 | 7 | Ph | H | | AT | | $CH_3$ | H | H | acac | |
| 7-83Y | Ir | 0 | 7 | Ph | H | | AT | | $CH_3$ | H | H | — | — |
| 7-84 | Ir | 1 | 7 | Ph | H | H | | MES1 | $CH_3$ | H | H | pic | |
| 7-84X | Ir | 1 | 7 | Ph | H | H | | MES1 | $CH_3$ | H | H | acac | |
| 7-84Y | Ir | 0 | 7 | Ph | H | H | | MES1 | $CH_3$ | H | H | — | — |
| 7-85 | Ir | 1 | 7 | Ph | H | | MES1 | | $CH_3$ | H | H | pic | |
| 7-85X | Ir | 1 | 7 | Ph | H | | MES1 | | $CH_3$ | H | H | acac | |
| 7-85Y | Ir | 0 | 7 | Ph | H | | MES1 | | $CH_3$ | H | H | — | — |
| 7-86 | Ir | 1 | 7 | Ph | H | H | | MES2 | $CH_3$ | H | H | pic | |
| 7-86X | Ir | 1 | 7 | Ph | H | H | | MES2 | $CH_3$ | H | H | acac | |
| 7-86Y | Ir | 0 | 7 | Ph | H | H | | MES2 | $CH_3$ | H | H | — | — |
| 7-87 | Ir | 1 | 7 | Ph | H | | MES2 | | $CH_3$ | H | H | pic | |
| 7-87X | Ir | 1 | 7 | Ph | H | | MES2 | | $CH_3$ | H | H | acac | |
| 7-87Y | Ir | 0 | 7 | Ph | H | | MES2 | | $CH_3$ | H | H | — | — |
| 7-88 | Ir | 1 | 7 | Ph | H | H | | PS1 | $CH_3$ | H | H | pic | |
| 7-88X | Ir | 1 | 7 | Ph | H | H | | PS1 | $CH_3$ | H | H | acac | |
| 7-88Y | Ir | 0 | 7 | Ph | H | H | | PS1 | $CH_3$ | H | H | — | — |
| 7-89 | Ir | 1 | 7 | Ph | H | | PS1 | | $CH_3$ | H | H | pic | |
| 7-89X | Ir | 1 | 7 | Ph | H | | PS1 | | $CH_3$ | H | H | acac | |
| 7-89Y | Ir | 0 | 7 | Ph | H | | PS1 | | $CH_3$ | H | H | — | — |
| 7-90 | Ir | 1 | 7 | Ph | H | H | | PS2 | $CH_3$ | H | H | pic | |
| 7-90X | Ir | 1 | 7 | Ph | H | H | | PS2 | $CH_3$ | H | H | acac | |
| 7-90Y | Ir | 0 | 7 | Ph | H | H | | PS2 | $CH_3$ | H | H | — | — |
| 7-91 | Ir | 1 | 7 | Ph | H | | PS2 | | $CH_3$ | H | H | pic | |
| 7-91X | Ir | 1 | 7 | Ph | H | | PS2 | | $CH_3$ | H | H | acac | |
| 7-91Y | Ir | 0 | 7 | Ph | H | | PS2 | | $CH_3$ | H | H | — | — |
| 7-92 | Ir | 1 | 7 | Ph | H | H | | BAL1 | $CH_3$ | H | H | pic | |
| 7-92X | Ir | 1 | 7 | Ph | H | H | | BAL1 | $CH_3$ | H | H | acac | |
| 7-92Y | Ir | 0 | 7 | Ph | H | H | | BAL1 | $CH_3$ | H | H | — | — |
| 7-93 | Ir | 1 | 7 | Ph | H | | BAL1 | | $CH_3$ | H | H | pic | |

TABLE 7-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 7-93X | Ir | 1 | 7 | Ph | H |  | BAL1 | H | CH₃ | H | H | acac |
| 7-93Y | Ir | 0 | 7 | Ph | H |  | BAL1 | H | CH₃ | H | H | — — |
| 7-94 | Ir | 1 | 7 | Ph | H | H |  | BAL2 | CH₃ | H | H | pic |
| 7-94X | Ir | 1 | 7 | Ph | H | H |  | BAL2 | CH₃ | H | H | acac |
| 7-94Y | Ir | 0 | 7 | Ph | H | H |  | BAL2 | CH₃ | H | H | — — |
| 7-95 | Ir | 1 | 7 | Ph | H |  | BAL2 | H | CH₃ | H | H | pic |
| 7-95X | Ir | 1 | 7 | Ph | H |  | BAL2 | H | CH₃ | H | H | acac |
| 7-95Y | Ir | 0 | 7 | Ph | H |  | BAL2 | H | CH₃ | H | H | — — |
| 7-96 | Ir | 1 | 7 | Ph | H | H |  | MEK1 | CH₃ | H | H | pic |
| 7-96X | Ir | 1 | 7 | Ph | H | H |  | MEK1 | CH₃ | H | H | acac |
| 7-96Y | Ir | 0 | 7 | Ph | H | H |  | MEK1 | CH₃ | H | H | — — |
| 7-97 | Ir | 1 | 7 | Ph | H |  | MEK1 | H | CH₃ | H | H | pic |
| 7-97X | Ir | 1 | 7 | Ph | H |  | MEK1 | H | CH₃ | H | H | acac |
| 7-97Y | Ir | 0 | 7 | Ph | H |  | MEK1 | H | CH₃ | H | H | — — |
| 7-98 | Ir | 1 | 7 | Ph | H | H |  | MEK2 | CH₃ | H | H | pic |
| 7-98X | Ir | 1 | 7 | Ph | H | H |  | MEK2 | CH₃ | H | H | acac |
| 7-98Y | Ir | 0 | 7 | Ph | H | H |  | MEK2 | CH₃ | H | H | — — |
| 7-99 | Ir | 1 | 7 | Ph | H |  | MEK2 | H | CH₃ | H | H | pic |
| 7-99X | Ir | 1 | 7 | Ph | H |  | MEK2 | H | CH₃ | H | H | acac |
| 7-99Y | Ir | 0 | 7 | Ph | H |  | MEK2 | H | CH₃ | H | H | — — |
| 7-100 | Ir | 1 | 7 | Ph | H | H |  | PAL1 | CH₃ | H | H | pic |
| 7-100X | Ir | 1 | 7 | Ph | H | H |  | PAL1 | CH₃ | H | H | acac |
| 7-100Y | Ir | 0 | 7 | Ph | H | H |  | PAL1 | CH₃ | H | H | — — |
| 7-101 | Ir | 1 | 7 | Ph | H |  | PAL1 | H | CH₃ | H | H | pic |
| 7-101X | Ir | 1 | 7 | Ph | H |  | PAL1 | H | CH₃ | H | H | acac |
| 7-101Y | Ir | 0 | 7 | Ph | H |  | PAL1 | H | CH₃ | H | H | — — |
| 7-102 | Ir | 1 | 7 | Ph | H | H |  | PAL2 | CH₃ | H | H | pic |
| 7-102X | Ir | 1 | 7 | Ph | H | H |  | PAL2 | CH₃ | H | H | acac |
| 7-102Y | Ir | 0 | 7 | Ph | H | H |  | PAL2 | CH₃ | H | H | — — |
| 7-103 | Ir | 1 | 7 | Ph | H |  | PAL2 | H | CH₃ | H | H | pic |
| 7-103X | Ir | 1 | 7 | Ph | H |  | PAL2 | H | CH₃ | H | H | acac |
| 7-103Y | Ir | 0 | 7 | Ph | H |  | PAL2 | H | CH₃ | H | H | — — |
| 7-104 | Ir | 1 | 7 | Ph | H | H |  | MMK | CH₃ | H | H | pic |
| 7-104X | Ir | 1 | 7 | Ph | H | H |  | MMK | CH₃ | H | H | acac |
| 7-104Y | Ir | 0 | 7 | Ph | H | H |  | MMK | CH₃ | H | H | — — |
| 7-105 | Ir | 1 | 7 | Ph | H |  | MMK | H | CH₃ | H | H | pic |
| 7-105X | Ir | 1 | 7 | Ph | H |  | MMK | H | CH₃ | H | H | acac |
| 7-105Y | Ir | 0 | 7 | Ph | H |  | MMK | H | CH₃ | H | H | — — |
| 7-106 | Ir | 1 | 7 | Ph | H | H |  | EES1 | CH₃ | H | H | pic |
| 7-106X | Ir | 1 | 7 | Ph | H | H |  | EES1 | CH₃ | H | H | acac |
| 7-106Y | Ir | 0 | 7 | Ph | H | H |  | EES1 | CH₃ | H | H | — — |
| 7-107 | Ir | 1 | 7 | Ph | H |  | EES2 | H | CH₃ | H | H | pic |
| 7-107X | Ir | 1 | 7 | Ph | H |  | EES2 | H | CH₃ | H | H | acac |
| 7-107Y | Ir | 0 | 7 | Ph | H |  | EES2 | H | CH₃ | H | H | — — |
| 7-108 | Ir | 1 | 7 | Ph | H | H |  | PAE1 | CH₃ | H | H | pic |
| 7-108X | Ir | 1 | 7 | Ph | H | H |  | PAE1 | CH₃ | H | H | acac |
| 7-108Y | Ir | 0 | 7 | Ph | H | H |  | PAE1 | CH₃ | H | H | — — |
| 7-109 | Ir | 1 | 7 | Ph | H |  | PAE2 | H | CH₃ | H | H | pic |
| 7-109X | Ir | 1 | 7 | Ph | H |  | PAE2 | H | CH₃ | H | H | acac |
| 7-109Y | Ir | 0 | 7 | Ph | H |  | PAE2 | H | CH₃ | H | H | — — |
| 7-110 | Ir | 1 | 7 | Ph | H | H |  | AME1 | CH₃ | H | H | pic |
| 7-110X | Ir | 1 | 7 | Ph | H | H |  | AME1 | CH₃ | H | H | acac |
| 7-110Y | Ir | 0 | 7 | Ph | H | H |  | AME1 | CH₃ | H | H | — — |
| 7-111 | Ir | 1 | 7 | Ph | H |  | AME1 | H | CH₃ | H | H | pic |
| 7-111X | Ir | 1 | 7 | Ph | H |  | AME1 | H | CH₃ | H | H | acac |
| 7-111Y | Ir | 0 | 7 | Ph | H |  | AME1 | H | CH₃ | H | H | — — |
| 7-112 | Ir | 1 | 7 | Ph | H | H |  | AME2 | CH₃ | H | H | pic |
| 7-112X | Ir | 1 | 7 | Ph | H | H |  | AME2 | CH₃ | H | H | acac |
| 7-112Y | Ir | 0 | 7 | Ph | H | H |  | AME2 | CH₃ | H | H | — — |
| 7-113 | Ir | 1 | 7 | Ph | H |  | AME2 | H | CH₃ | H | H | pic |
| 7-113X | Ir | 1 | 7 | Ph | H |  | AME2 | H | CH₃ | H | H | acac |
| 7-113Y | Ir | 0 | 7 | Ph | H |  | AME2 | H | CH₃ | H | H | — — |
| 7-114 | Ir | 1 | 7 | Ph | H | H |  | EAE1 | CH₃ | H | H | pic |
| 7-114X | Ir | 1 | 7 | Ph | H | H |  | EAE1 | CH₃ | H | H | acac |
| 7-114Y | Ir | 0 | 7 | Ph | H | H |  | EAE1 | CH₃ | H | H | — — |
| 7-115 | Ir | 1 | 7 | Ph | H |  | EAE1 | H | CH₃ | H | H | pic |
| 7-115X | Ir | 1 | 7 | Ph | H |  | EAE1 | H | CH₃ | H | H | acac |
| 7-115Y | Ir | 0 | 7 | Ph | H |  | EAE1 | H | CH₃ | H | H | — — |
| 7-116 | Ir | 1 | 7 | Ph | H | H |  | EAE2 | CH₃ | H | H | pic |
| 7-116X | Ir | 1 | 7 | Ph | H | H |  | EAE2 | CH₃ | H | H | acac |
| 7-116Y | Ir | 0 | 7 | Ph | H | H |  | EAE2 | CH₃ | H | H | — — |
| 7-117 | Ir | 1 | 7 | Ph | H |  | EAE2 | H | CH₃ | H | H | pic |
| 7-117X | Ir | 1 | 7 | Ph | H |  | EAE2 | H | CH₃ | H | H | acac |
| 7-117Y | Ir | 0 | 7 | Ph | H |  | EAE2 | H | CH₃ | H | H | — — |
| 7-118 | Ir | 1 | 7 | Ph | H | H |  | AAE1 | CH₃ | H | H | pic |
| 7-118X | Ir | 1 | 7 | Ph | H | H |  | AAE1 | CH₃ | H | H | acac |
| 7-118Y | Ir | 0 | 7 | Ph | H | H |  | AAE1 | CH₃ | H | H | — — |

TABLE 7-continued

| No. | M | n | BSS | SS | G | T¹ | T² | T³ | T⁴ | T⁵ | T⁶ | T⁷ | L¹ | L² |
|---|---|---|---|---|---|---|---|---|---|---|---|---|---|---|
| 7-119 | Ir | 1 | 7 | | Ph | H | | AAE1 | H | CH₃ | H | H | pic | |
| 7-119X | Ir | 1 | 7 | | Ph | H | | AAE1 | H | CH₃ | H | H | acac | |
| 7-119Y | Ir | 0 | 7 | | Ph | H | | AAE1 | H | CH₃ | H | H | — | — |
| 7-120 | Ir | 1 | 7 | | Ph | H | H | | AAE2 | CH₃ | H | H | pic | |
| 7-120X | Ir | 1 | 7 | | Ph | H | H | | AAE2 | CH₃ | H | H | acac | |
| 7-120Y | Ir | 0 | 7 | | Ph | H | H | | AAE2 | CH₃ | H | H | — | — |
| 7-121 | Ir | 1 | 7 | | Ph | H | | AAE2 | H | CH₃ | H | H | pic | |
| 7-121X | Ir | 1 | 7 | | Ph | H | | AAE2 | H | CH₃ | H | H | acac | |
| 7-121Y | Ir | 0 | 7 | | Ph | H | | AAE2 | H | CH₃ | H | H | — | — |
| 7-122 | Ir | 1 | 7 | | Ph | H | H | | PME1 | CH₃ | H | H | pic | |
| 7-122X | Ir | 1 | 7 | | Ph | H | H | | PME1 | CH₃ | H | H | acac | |
| 7-122Y | Ir | 0 | 7 | | Ph | H | H | | PME1 | CH₃ | H | H | — | — |
| 7-123 | Ir | 1 | 7 | | Ph | H | | PME1 | H | CH₃ | H | H | pic | |
| 7-123X | Ir | 1 | 7 | | Ph | H | | PME1 | H | CH₃ | H | H | acac | |
| 7-123Y | Ir | 0 | 7 | | Ph | H | | PME1 | H | CH₃ | H | H | — | — |
| 7-124 | Ir | 1 | 7 | | Ph | H | H | | PME2 | CH₃ | H | H | pic | |
| 7-124X | Ir | 1 | 7 | | Ph | H | H | | PME2 | CH₃ | H | H | acac | |
| 7-124Y | Ir | 0 | 7 | | Ph | H | H | | PME2 | CH₃ | H | H | — | — |
| 7-125 | Ir | 1 | 7 | | Ph | H | | PME2 | H | CH₃ | H | H | pic | |
| 7-125X | Ir | 1 | 7 | | Ph | H | | PME2 | H | CH₃ | H | H | acac | |
| 7-125Y | Ir | 0 | 7 | | Ph | H | | PME2 | H | CH₃ | H | H | — | — |
| 7-126 | Ir | 1 | 7 | | Ph | H | H | | MET1 | CH₃ | H | H | pic | |
| 7-126X | Ir | 1 | 7 | | Ph | H | H | | MET1 | CH₃ | H | H | acac | |
| 7-126Y | Ir | 0 | 7 | | Ph | H | H | | MET1 | CH₃ | H | H | — | — |
| 7-127 | Ir | 1 | 7 | | Ph | H | | MET1 | H | CH₃ | H | H | pic | |
| 7-127X | Ir | 1 | 7 | | Ph | H | | MET1 | H | CH₃ | H | H | acac | |
| 7-127Y | Ir | 0 | 7 | | Ph | H | | MET1 | H | CH₃ | H | H | — | — |
| 7-128 | Ir | 1 | 7 | | Ph | H | H | | MET2 | CH₃ | H | H | pic | |
| 7-128X | Ir | 1 | 7 | | Ph | H | H | | MET2 | CH₃ | H | H | acac | |
| 7-128Y | Ir | 0 | 7 | | Ph | H | H | | MET2 | CH₃ | H | H | — | — |
| 7-129 | Ir | 1 | 7 | | Ph | H | | MET2 | H | CH₃ | H | H | pic | |
| 7-129X | Ir | 1 | 7 | | Ph | H | | MET2 | H | CH₃ | H | H | acac | |
| 7-129Y | Ir | 0 | 7 | | Ph | H | | MET2 | H | CH₃ | H | H | — | — |
| 7-130 | Ir | 1 | 7 | | Ph | H | H | | EE1 | CH₃ | H | H | pic | |
| 7-130X | Ir | 1 | 7 | | Ph | H | H | | EE1 | CH₃ | H | H | acac | |
| 7-130Y | Ir | 0 | 7 | | Ph | H | H | | EE1 | CH₃ | H | H | — | — |
| 7-131 | Ir | 1 | 7 | | Ph | H | | EE1 | H | CH₃ | H | H | pic | |
| 7-131X | Ir | 1 | 7 | | Ph | H | | EE1 | H | CH₃ | H | H | acac | |
| 7-131Y | Ir | 0 | 7 | | Ph | H | | EE1 | H | CH₃ | H | H | — | — |
| 7-132 | Ir | 1 | 7 | | Ph | H | H | | EE2 | CH₃ | H | H | pic | |
| 7-132X | Ir | 1 | 7 | | Ph | H | H | | EE2 | CH₃ | H | H | acac | |
| 7-132Y | Ir | 0 | 7 | | Ph | H | H | | EE2 | CH₃ | H | H | — | — |
| 7-133 | Ir | 1 | 7 | | Ph | H | | EE2 | H | CH₃ | H | H | pic | |
| 7-133X | Ir | 1 | 7 | | Ph | H | | EE2 | H | CH₃ | H | H | acac | |
| 7-133Y | Ir | 0 | 7 | | Ph | H | | EE2 | H | CH₃ | H | H | — | — |
| 7-134 | Ir | 1 | 7 | | Ph | H | H | | MS1 | CH₃ | H | H | pic | |
| 7-134X | Ir | 1 | 7 | | Ph | H | H | | MS1 | CH₃ | H | H | acac | |
| 7-134Y | Ir | 0 | 7 | | Ph | H | H | | MS1 | CH₃ | H | H | — | — |
| 7-135 | Ir | 1 | 7 | | Ph | H | | MS1 | H | CH₃ | H | H | pic | |
| 7-135X | Ir | 1 | 7 | | Ph | H | | MS1 | H | CH₃ | H | H | acac | |
| 7-135Y | Ir | 0 | 7 | | Ph | H | | MS1 | H | CH₃ | H | H | — | — |
| 7-136 | Ir | 1 | 7 | | Ph | H | H | | MS2 | CH₃ | H | H | pic | |
| 7-136X | Ir | 1 | 7 | | Ph | H | H | | MS2 | CH₃ | H | H | acac | |
| 7-136Y | Ir | 0 | 7 | | Ph | H | H | | MS2 | CH₃ | H | H | — | — |
| 7-137 | Ir | 1 | 7 | | Ph | H | | MS2 | H | CH₃ | H | H | pic | |
| 7-137X | Ir | 1 | 7 | | Ph | H | | MS2 | H | CH₃ | H | H | acac | |
| 7-137Y | Ir | 0 | 7 | | Ph | H | | MS2 | H | CH₃ | H | H | — | — |

-continued
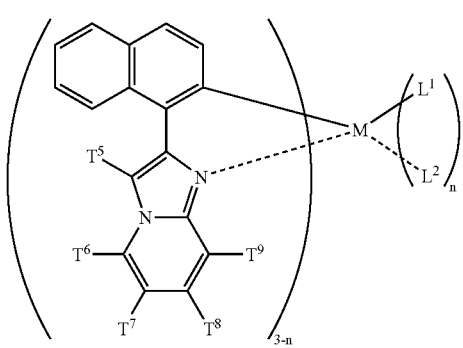
BBS 1, G:NAP1
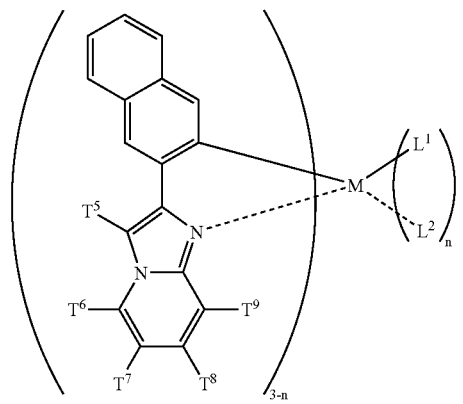
BBS 1, G:NAP2
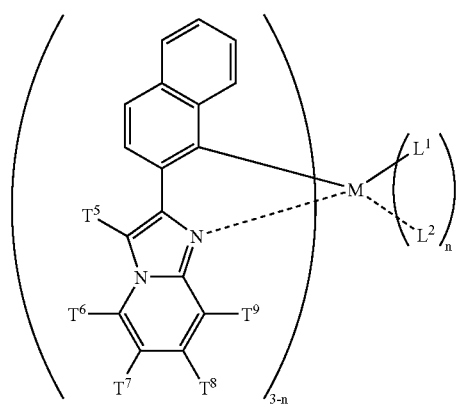
BBS 1, G:NAP3
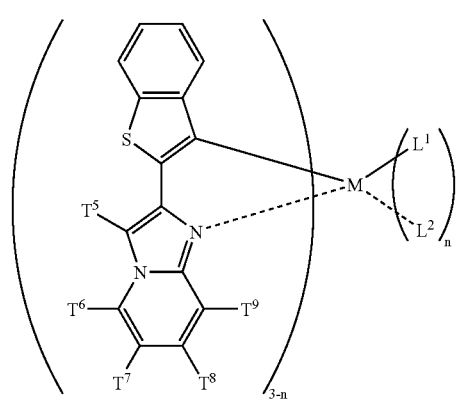
BBS 1, G:TB
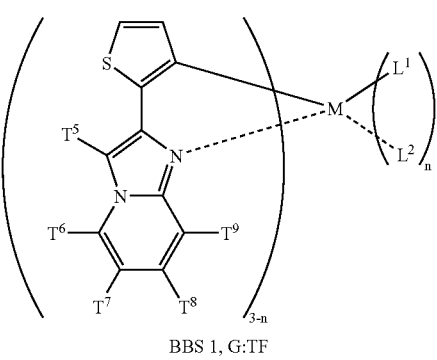
BBS 1, G:TF
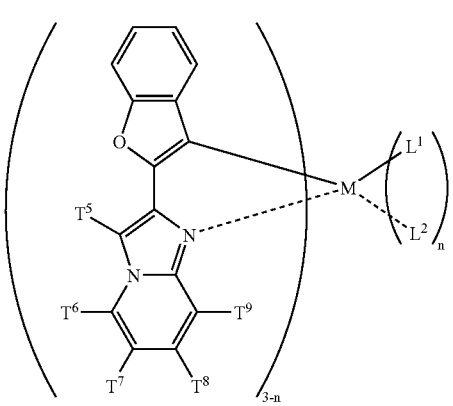
BBS 1, G:OB
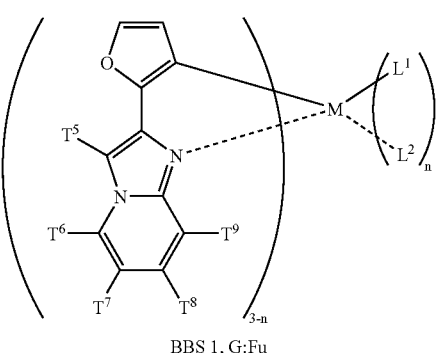
BBS 1, G:Fu
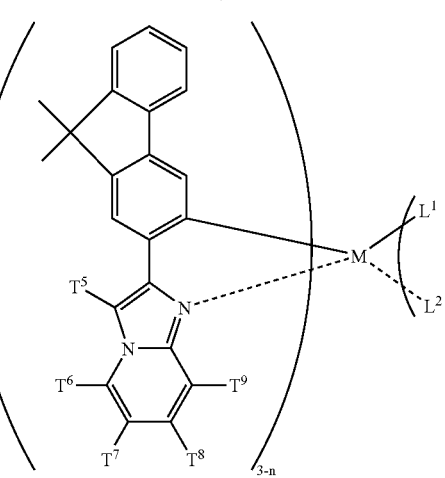
BBS 1, G:Fl

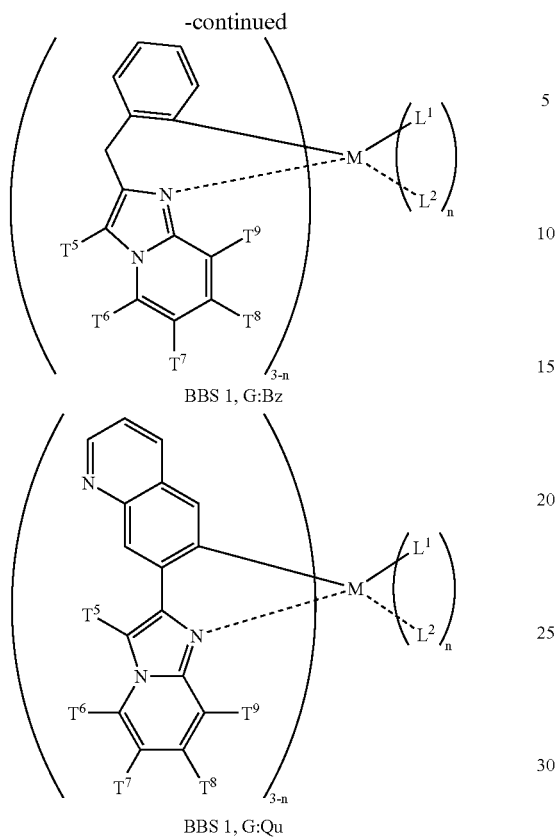

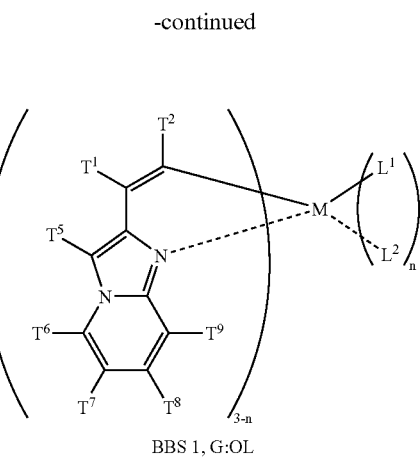

TABLE 8

| No. | M | n | BSS | SS | G | $T^1$ | $T^2$ | $T^5$ | $T^6$ | $T^7$ | $T^8$ | $T^9$ | $L^1$ $L^2$ |
|---|---|---|---|---|---|---|---|---|---|---|---|---|---|
| 1-119 | Ir | 1 | 1 | Nap1 | — | — | H | H | H | H | H | pic |
| 1-119X | Ir | 1 | 1 | Nap1 | — | — | H | H | H | H | H | acac |
| 1-119Y | Ir | 0 | 1 | Nap1 | — | — | H | H | H | H | H | — — |
| 1-120 | Ir | 1 | 1 | Nap1 | — | — | $^tC_4H_9$ | H | H | H | H | pic |
| 1-120X | Ir | 1 | 1 | Nap1 | — | — | $^tC_4H_9$ | H | H | H | H | acac |
| 1-120Y | Ir | 0 | 1 | Nap1 | — | — | $^tC_4H_9$ | H | H | H | H | — — |
| 1-121 | Ir | 1 | 1 | Nap1 | — | — | $CH_3$ | H | H | H | H | pic |
| 1-121X | Ir | 1 | 1 | Nap1 | — | — | $CH_3$ | H | H | H | H | acac |
| 1-121Y | Ir | 0 | 1 | Nap1 | — | — | $CH_3$ | H | H | H | H | — — |
| 1-122 | Ir | 1 | 1 | Nap1 | — | — | $^tC_4H_9$ | $CH_3$ | H | H | H | pic |
| 1-122X | Ir | 1 | 1 | Nap1 | — | — | $^tC_4H_9$ | $CH_3$ | H | H | H | acac |
| 1-122Y | Ir | 0 | 1 | Nap1 | — | — | $^tC_4H_9$ | $CH_3$ | H | H | H | — — |
| 1-123 | Ir | 1 | 1 | Nap1 | — | — | $CH_3$ | $CH_3$ | H | H | H | pic |
| 1-123X | Ir | 1 | 1 | Nap1 | — | — | $CH_3$ | $CH_3$ | H | H | H | acac |
| 1-123Y | Ir | 0 | 1 | Nap1 | — | — | $CH_3$ | $CH_3$ | H | H | H | — — |
| 1-124 | Ir | 1 | 1 | Nap1 | — | — | H | $CH_3$ | H | H | H | pic |
| 1-124X | Ir | 1 | 1 | Nap1 | — | — | H | $CH_3$ | H | H | H | acac |
| 1-124Y | Ir | 0 | 1 | Nap1 | — | — | H | $CH_3$ | H | H | H | — — |
| 1-125 | Ir | 1 | 1 | Nap2 | — | — | H | H | H | H | H | pic |
| 1-125X | Ir | 1 | 1 | Nap2 | — | — | H | H | H | H | H | acac |
| 1-125Y | Ir | 0 | 1 | Nap2 | — | — | H | H | H | H | H | — — |
| 1-126 | Ir | 1 | 1 | Nap2 | — | — | $^tC_4H_9$ | H | H | H | H | pic |
| 1-126X | Ir | 1 | 1 | Nap2 | — | — | $^tC_4H_9$ | H | H | H | H | acac |
| 1-126Y | Ir | 0 | 1 | Nap2 | — | — | $^tC_4H_9$ | H | H | H | H | — — |
| 1-127 | Ir | 1 | 1 | Nap2 | — | — | $CH_3$ | H | H | H | H | pic |
| 1-127X | Ir | 1 | 1 | Nap2 | — | — | $CH_3$ | H | H | H | H | acac |
| 1-127Y | Ir | 0 | 1 | Nap2 | — | — | $CH_3$ | H | H | H | H | — — |
| 1-128 | Ir | 1 | 1 | Nap2 | — | — | $^tC_4H_9$ | $CH_3$ | H | H | H | pic |
| 1-128X | Ir | 1 | 1 | Nap2 | — | — | $^tC_4H_9$ | $CH_3$ | H | H | H | acac |
| 1-128Y | Ir | 0 | 1 | Nap2 | — | — | $^tC_4H_9$ | $CH_3$ | H | H | H | — — |
| 1-129 | Ir | 1 | 1 | Nap2 | — | — | $CH_3$ | $CH_3$ | H | H | H | pic |
| 1-129X | Ir | 1 | 1 | Nap2 | — | — | $CH_3$ | $CH_3$ | H | H | H | acac |
| 1-129Y | Ir | 0 | 1 | Nap2 | — | — | $CH_3$ | $CH_3$ | H | H | H | — — |
| 1-130 | Ir | 1 | 1 | Nap2 | — | — | H | $CH_3$ | H | H | H | pic |

TABLE 8-continued

| No. | M | n | BSS | SS G | T¹ | T² | T⁵ | T⁶ | T⁷ | T⁸ | T⁹ | L¹ | L² |
|---|---|---|---|---|---|---|---|---|---|---|---|---|---|
| 1-130X | Ir | 1 | 1 | Nap2 | — | — | H | CH$_3$ | H | H | H | acac | |
| 1-130Y | Ir | 0 | 1 | Nap2 | — | — | H | CH$_3$ | H | H | H | — | — |
| 1-131 | Ir | 1 | 1 | Nap3 | — | — | H | H | H | H | H | pic | |
| 1-131X | Ir | 1 | 1 | Nap3 | — | — | H | H | H | H | H | acac | |
| 1-131Y | Ir | 0 | 1 | Nap3 | — | — | H | H | H | H | H | — | — |
| 1-132 | Ir | 1 | 1 | Nap3 | — | — | $^t$C$_4$H$_9$ | H | H | H | H | pic | |
| 1-132X | Ir | 1 | 1 | Nap3 | — | — | $^t$C$_4$H$_9$ | H | H | H | H | acac | |
| 1-132Y | Ir | 0 | 1 | Nap3 | — | — | $^t$C$_4$H$_9$ | H | H | H | H | — | — |
| 1-133 | Ir | 1 | 1 | Nap3 | — | — | CH$_3$ | H | H | H | H | pic | |
| 1-133X | Ir | 1 | 1 | Nap3 | — | — | CH$_3$ | H | H | H | H | acac | |
| 1-133Y | Ir | 0 | 1 | Nap3 | — | — | CH$_3$ | H | H | H | H | — | — |
| 1-134 | Ir | 1 | 1 | Nap3 | — | — | $^t$C$_4$H$_9$ | CH$_3$ | H | H | H | pic | |
| 1-134X | Ir | 1 | 1 | Nap3 | — | — | $^t$C$_4$H$_9$ | CH$_3$ | H | H | H | acac | |
| 1-134Y | Ir | 0 | 1 | Nap3 | — | — | $^t$C$_4$H$_9$ | CH$_3$ | H | H | H | — | — |
| 1-135 | Ir | 1 | 1 | Nap3 | — | — | CH$_3$ | CH$_3$ | H | H | H | pic | |
| 1-135X | Ir | 1 | 1 | Nap3 | — | — | CH$_3$ | CH$_3$ | H | H | H | acac | |
| 1-135Y | Ir | 0 | 1 | Nap3 | — | — | CH$_3$ | CH$_3$ | H | H | H | — | — |
| 1-136 | Ir | 1 | 1 | Nap3 | — | — | H | CH$_3$ | H | H | H | pic | |
| 1-136X | Ir | 1 | 1 | Nap3 | — | — | H | CH$_3$ | H | H | H | acac | |
| 1-136Y | Ir | 0 | 1 | Nap3 | — | — | H | CH$_3$ | H | H | H | — | — |
| 1-137 | Ir | 1 | 1 | TB | — | — | H | H | H | H | H | pic | |
| 1-137X | Ir | 1 | 1 | TB | — | — | H | H | H | H | H | acac | |
| 1-137Y | Ir | 0 | 1 | TB | — | — | H | H | H | H | H | — | — |
| 1-138 | Ir | 1 | 1 | TB | — | — | $^t$C$_4$H$_9$ | H | H | H | H | pic | |
| 1-138X | Ir | 1 | 1 | TB | — | — | $^t$C$_4$H$_9$ | H | H | H | H | acac | |
| 1-138Y | Ir | 0 | 1 | TB | — | — | $^t$C$_4$H$_9$ | H | H | H | H | — | — |
| 1-139 | Ir | 1 | 1 | TB | — | — | CH$_3$ | H | H | H | H | pic | |
| 1-139X | Ir | 1 | 1 | TB | — | — | CH$_3$ | H | H | H | H | acac | |
| 1-139Y | Ir | 0 | 1 | TB | — | — | CH$_3$ | H | H | H | H | — | — |
| 1-140 | Ir | 1 | 1 | TB | — | — | $^t$C$_4$H$_9$ | CH$_3$ | H | H | H | pic | |
| 1-140X | Ir | 1 | 1 | TB | — | — | $^t$C$_4$H$_9$ | CH$_3$ | H | H | H | acac | |
| 1-140Y | Ir | 0 | 1 | TB | — | — | $^t$C$_4$H$_9$ | CH$_3$ | H | H | H | — | — |
| 1-141 | Ir | 1 | 1 | TB | — | — | CH$_3$ | CH$_3$ | H | H | H | pic | |
| 1-141X | Ir | 1 | 1 | TB | — | — | CH$_3$ | CH$_3$ | H | H | H | acac | |
| 1-141Y | Ir | 0 | 1 | TB | — | — | CH$_3$ | CH$_3$ | H | H | H | — | — |
| 1-142 | Ir | 1 | 1 | TB | — | — | H | CH$_3$ | H | H | H | pic | |
| 1-142X | Ir | 1 | 1 | TB | — | — | H | CH$_3$ | H | H | H | acac | |
| 1-142Y | Ir | 0 | 1 | TB | — | — | H | CH$_3$ | H | H | H | — | — |
| 1-143 | Ir | 1 | 1 | TF | — | — | H | H | H | H | H | pic | |
| 1-143X | Ir | 1 | 1 | TF | — | — | H | H | H | H | H | acac | |
| 1-143Y | Ir | 0 | 1 | TF | — | — | H | H | H | H | H | — | — |
| 1-144 | Ir | 1 | 1 | TF | — | — | $^t$C$_4$H$_9$ | H | H | H | H | pic | |
| 1-144X | Ir | 1 | 1 | TF | — | — | $^t$C$_4$H$_9$ | H | H | H | H | acac | |
| 1-144Y | Ir | 0 | 1 | TF | — | — | $^t$C$_4$H$_9$ | H | H | H | H | — | — |
| 1-145 | Ir | 1 | 1 | TF | — | — | CH$_3$ | H | H | H | H | pic | |
| 1-145X | Ir | 1 | 1 | TF | — | — | CH$_3$ | H | H | H | H | acac | |
| 1-145Y | Ir | 0 | 1 | TF | — | — | CH$_3$ | H | H | H | H | — | — |
| 1-146 | Ir | 1 | 1 | TF | — | — | $^t$C$_4$H$_9$ | CH$_3$ | H | H | H | pic | |
| 1-146X | Ir | 1 | 1 | TF | — | — | $^t$C$_4$H$_9$ | CH$_3$ | H | H | H | acac | |
| 1-146Y | Ir | 0 | 1 | TF | — | — | $^t$C$_4$H$_9$ | CH$_3$ | H | H | H | — | — |
| 1-147 | Ir | 1 | 1 | TF | — | — | CH$_3$ | CH$_3$ | H | H | H | pic | |
| 1-147X | Ir | 1 | 1 | TF | — | — | CH$_3$ | CH$_3$ | H | H | H | acac | |
| 1-147Y | Ir | 0 | 1 | TF | — | — | CH$_3$ | CH$_3$ | H | H | H | — | — |
| 1-148 | Ir | 1 | 1 | TF | — | — | H | CH$_3$ | H | H | H | pic | |
| 1-148X | Ir | 1 | 1 | TF | — | — | H | CH$_3$ | H | H | H | acac | |
| 1-148Y | Ir | 0 | 1 | TF | — | — | H | CH$_3$ | H | H | H | — | — |
| 1-149 | Ir | 1 | 1 | OB | — | — | H | H | H | H | H | pic | |
| 1-149X | Ir | 1 | 1 | OB | — | — | H | H | H | H | H | acac | |
| 1-149Y | Ir | 0 | 1 | OB | — | — | H | H | H | H | H | — | — |
| 1-150 | Ir | 1 | 1 | OB | — | — | $^t$C$_4$H$_9$ | H | H | H | H | pic | |
| 1-150X | Ir | 1 | 1 | OB | — | — | $^t$C$_4$H$_9$ | H | H | H | H | acac | |
| 1-150Y | Ir | 0 | 1 | OB | — | — | $^t$C$_4$H$_9$ | H | H | H | H | — | — |
| 1-151 | Ir | 1 | 1 | OB | — | — | CH$_3$ | H | H | H | H | pic | |
| 1-151X | Ir | 1 | 1 | OB | — | — | CH$_3$ | H | H | H | H | acac | |
| 1-151Y | Ir | 0 | 1 | OB | — | — | CH$_3$ | H | H | H | H | — | — |
| 1-152 | Ir | 1 | 1 | OB | — | — | $^t$C$_4$H$_9$ | CH$_3$ | H | H | H | pic | |
| 1-152X | Ir | 1 | 1 | OB | — | — | $^t$C$_4$H$_9$ | CH$_3$ | H | H | H | acac | |
| 1-152Y | Ir | 0 | 1 | OB | — | — | $^t$C$_4$H$_9$ | CH$_3$ | H | H | H | — | — |
| 1-153 | Ir | 1 | 1 | OB | — | — | CH$_3$ | CH$_3$ | H | H | H | pic | |
| 1-153X | Ir | 1 | 1 | OB | — | — | CH$_3$ | CH$_3$ | H | H | H | acac | |
| 1-153Y | Ir | 0 | 1 | OB | — | — | CH$_3$ | CH$_3$ | H | H | H | — | — |
| 1-154 | Ir | 1 | 1 | OB | — | — | H | CH$_3$ | H | H | H | pic | |
| 1-154X | Ir | 1 | 1 | OB | — | — | H | CH$_3$ | H | H | H | acac | |
| 1-154Y | Ir | 0 | 1 | OB | — | — | H | CH$_3$ | H | H | H | — | — |
| 1-155 | Ir | 1 | 1 | Fu | — | — | H | H | H | H | H | pic | |
| 1-155X | Ir | 1 | 1 | Fu | — | — | H | H | H | H | H | acac | |
| 1-155Y | Ir | 0 | 1 | Fu | — | — | H | H | H | H | H | — | — |

TABLE 8-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 1-156 | Ir | 1 | 1 | | Fu | — | — | $^tC_4H_9$ | H | H | H | H | pic | |
| 1-156X | Ir | 1 | 1 | | Fu | — | — | $^tC_4H_9$ | H | H | H | H | acac | |
| 1-156Y | Ir | 0 | 1 | | Fu | — | — | $^tC_4H_9$ | H | H | H | H | — | |
| 1-157 | Ir | 1 | 1 | | Fu | — | — | $CH_3$ | H | H | H | H | pic | |
| 1-157X | Ir | 1 | 1 | | Fu | — | — | $CH_3$ | H | H | H | H | acac | |
| 1-157Y | Ir | 0 | 1 | | Fu | — | — | $CH_3$ | H | H | H | H | — | |
| 1-158 | Ir | 1 | 1 | | Fu | — | — | $^tC_4H_9$ | $CH_3$ | H | H | H | pic | |
| 1-158X | Ir | 1 | 1 | | Fu | — | — | $^tC_4H_9$ | $CH_3$ | H | H | H | acac | |
| 1-158Y | Ir | 0 | 1 | | Fu | — | — | $^tC_4H_9$ | $CH_3$ | H | H | H | — | |
| 1-159 | Ir | 1 | 1 | | Fu | — | — | $CH_3$ | $CH_3$ | H | H | H | pic | |
| 1-159X | Ir | 1 | 1 | | Fu | — | — | $CH_3$ | $CH_3$ | H | H | H | acac | |
| 1-159Y | Ir | 0 | 1 | | Fu | — | — | $CH_3$ | $CH_3$ | H | H | H | — | |
| 1-160 | Ir | 1 | 1 | | Fu | — | — | H | $CH_3$ | H | H | H | pic | |
| 1-160X | Ir | 1 | 1 | | Fu | — | — | H | $CH_3$ | H | H | H | acac | |
| 1-160Y | Ir | 0 | 1 | | Fu | — | — | H | $CH_3$ | H | H | H | — | |
| 1-161 | Ir | 1 | 1 | | Fl | — | — | H | H | H | H | H | pic | |
| 1-161X | Ir | 1 | 1 | | Fl | — | — | H | H | H | H | H | acac | |
| 1-161Y | Ir | 0 | 1 | | Fl | — | — | H | H | H | H | H | — | |
| 1-162 | Ir | 1 | 1 | | Fl | — | — | $^tC_4H_9$ | H | H | H | H | pic | |
| 1-162X | Ir | 1 | 1 | | Fl | — | — | $^tC_4H_9$ | H | H | H | H | acac | |
| 1-162Y | Ir | 0 | 1 | | Fl | — | — | $^tC_4H_9$ | H | H | H | H | — | |
| 1-163 | Ir | 1 | 1 | | Fl | — | — | $CH_3$ | H | H | H | H | pic | |
| 1-163X | Ir | 1 | 1 | | Fl | — | — | $CH_3$ | H | H | H | H | acac | |
| 1-163Y | Ir | 0 | 1 | | Fl | — | — | $CH_3$ | H | H | H | H | — | |
| 1-164 | Ir | 1 | 1 | | Fl | — | — | $^tC_4H_9$ | $CH_3$ | H | H | H | pic | |
| 1-164X | Ir | 1 | 1 | | Fl | — | — | $^tC_4H_9$ | $CH_3$ | H | H | H | acac | |
| 1-164Y | Ir | 0 | 1 | | Fl | — | — | $^tC_4H_9$ | $CH_3$ | H | H | H | — | |
| 1-165 | Ir | 1 | 1 | | Fl | — | — | $CH_3$ | $CH_3$ | H | H | H | pic | |
| 1-165X | Ir | 1 | 1 | | Fl | — | — | $CH_3$ | $CH_3$ | H | H | H | acac | |
| 1-165Y | Ir | 0 | 1 | | Fl | — | — | $CH_3$ | $CH_3$ | H | H | H | — | |
| 1-166 | Ir | 1 | 1 | | Fl | — | — | H | $CH_3$ | H | H | H | pic | |
| 1-166X | Ir | 1 | 1 | | Fl | — | — | H | $CH_3$ | H | H | H | acac | |
| 1-166Y | Ir | 0 | 1 | | Fl | — | — | H | $CH_3$ | H | H | H | — | |
| 1-167 | Ir | 1 | 1 | | Bz | — | — | H | H | H | H | H | pic | |
| 1-167X | Ir | 1 | 1 | | Bz | — | — | H | H | H | H | H | acac | |
| 1-167Y | Ir | 0 | 1 | | Bz | — | — | H | H | H | H | H | — | |
| 1-168 | Ir | 1 | 1 | | Bz | — | — | $^tC_4H_9$ | H | H | H | H | pic | |
| 1-168X | Ir | 1 | 1 | | Bz | — | — | $^tC_4H_9$ | H | H | H | H | acac | |
| 1-168Y | Ir | 0 | 1 | | Bz | — | — | $^tC_4H_9$ | H | H | H | H | — | |
| 1-169 | Ir | 1 | 1 | | Bz | — | — | $CH_3$ | H | H | H | H | pic | |
| 1-169X | Ir | 1 | 1 | | Bz | — | — | $CH_3$ | H | H | H | H | acac | |
| 1-169Y | Ir | 0 | 1 | | Bz | — | — | $CH_3$ | H | H | H | H | — | |
| 1-170 | Ir | 1 | 1 | | Bz | — | — | $^tC_4H_9$ | $CH_3$ | H | H | H | pic | |
| 1-170X | Ir | 1 | 1 | | Bz | — | — | $^tC_4H_9$ | $CH_3$ | H | H | H | acac | |
| 1-170Y | Ir | 0 | 1 | | Bz | — | — | $^tC_4H_9$ | $CH_3$ | H | H | H | — | |
| 1-171 | Ir | 1 | 1 | | Bz | — | — | $CH_3$ | $CH_3$ | H | H | H | pic | |
| 1-171X | Ir | 1 | 1 | | Bz | — | — | $CH_3$ | $CH_3$ | H | H | H | acac | |
| 1-171Y | Ir | 0 | 1 | | Bz | — | — | $CH_3$ | $CH_3$ | H | H | H | — | |
| 1-172 | Ir | 1 | 1 | | Bz | — | — | H | $CH_3$ | H | H | H | pic | |
| 1-172X | Ir | 1 | 1 | | Bz | — | — | H | $CH_3$ | H | H | H | acac | |
| 1-172Y | Ir | 0 | 1 | | Bz | — | — | H | $CH_3$ | H | H | H | — | |
| 1-173 | Ir | 1 | 1 | | Qu | — | — | H | H | H | H | H | pic | |
| 1-173X | Ir | 1 | 1 | | Qu | — | — | H | H | H | H | H | acac | |
| 1-173Y | Ir | 0 | 1 | | Qu | — | — | H | H | H | H | H | — | |
| 1-174 | Ir | 1 | 1 | | Qu | — | — | $^tC_4H_9$ | H | H | H | H | pic | |
| 1-174X | Ir | 1 | 1 | | Qu | — | — | $^tC_4H_9$ | H | H | H | H | acac | |
| 1-174Y | Ir | 0 | 1 | | Qu | — | — | $^tC_4H_9$ | H | H | H | H | — | |
| 1-175 | Ir | 1 | 1 | | Qu | — | — | $CH_3$ | H | H | H | H | pic | |
| 1-175X | Ir | 1 | 1 | | Qu | — | — | $CH_3$ | H | H | H | H | acac | |
| 1-175Y | Ir | 0 | 1 | | Qu | — | — | $CH_3$ | H | H | H | H | — | |
| 1-176 | Ir | 1 | 1 | | Qu | — | — | $^tC_4H_9$ | $CH_3$ | H | H | H | pic | |
| 1-176X | Ir | 1 | 1 | | Qu | — | — | $^tC_4H_9$ | $CH_3$ | H | H | H | acac | |
| 1-176Y | Ir | 0 | 1 | | Qu | — | — | $^tC_4H_9$ | $CH_3$ | H | H | H | — | |
| 1-177 | Ir | 1 | 1 | | Qu | — | — | $CH_3$ | $CH_3$ | H | H | H | pic | |
| 1-177X | Ir | 1 | 1 | | Qu | — | — | $CH_3$ | $CH_3$ | H | H | H | acac | |
| 1-177Y | Ir | 0 | 1 | | Qu | — | — | $CH_3$ | $CH_3$ | H | H | H | — | |
| 1-178 | Ir | 1 | 1 | | Qu | — | — | H | $CH_3$ | H | H | H | pic | |
| 1-178X | Ir | 1 | 1 | | Qu | — | — | H | $CH_3$ | H | H | H | acac | |
| 1-178Y | Ir | 0 | 1 | | Qu | — | — | H | $CH_3$ | H | H | H | — | |
| 1-179 | Ir | 1 | 1 | | OL | H | $^nC_4H_9$ | H | H | H | H | H | pic | |
| 1-179X | Ir | 1 | 1 | | OL | H | $^nC_4H_9$ | H | H | H | H | H | acac | |
| 1-179Y | Ir | 0 | 1 | | OL | H | $^nC_4H_9$ | H | H | H | H | H | — | |
| 1-180 | Ir | 1 | 1 | | OL | H | $^tC_4H_9$ | H | H | H | H | H | pic | |
| 1-180X | Ir | 1 | 1 | | OL | H | $^tC_4H_9$ | H | H | H | H | H | acac | |
| 1-180Y | Ir | 0 | 1 | | OL | H | $^tC_4H_9$ | H | H | H | H | H | — | |
| 1-181 | Ir | 1 | 1 | | OL | $CH_3$ | $^nC_4H_9$ | H | H | H | H | H | pic | |
| 1-181X | Ir | 1 | 1 | | OL | $CH_3$ | $^nC_4H_9$ | H | H | H | H | H | acac | |

TABLE 8-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 1-181Y | Ir | 0 | 1 | | OL | $CH_3$ | $^nC_4H_9$ | H | H | H | H | H | — | — |
| 1-182 | Ir | 1 | 1 | | OL | $CH_3$ | $^tC_4H_9$ | H | H | H | H | H | pic | |
| 1-182X | Ir | 1 | 1 | | OL | $CH_3$ | $^tC_4H_9$ | H | H | H | H | H | acac | |
| 1-182Y | Ir | 0 | 1 | | OL | $CH_3$ | $^tC_4H_9$ | H | H | H | H | H | — | — |
| 1-183 | Ir | 1 | 1 | | OL | H | H | H | H | H | H | H | pic | |
| 1-183X | Ir | 1 | 1 | | OL | H | H | H | H | H | H | H | acac | |
| 1-183Y | Ir | 0 | 1 | | OL | H | H | H | H | H | H | H | — | — |
| 1-184 | Ir | 1 | 1 | | OL | H | $^nC_4H_9$ | $CH_3$ | H | H | H | H | pic | |
| 1-184X | Ir | 1 | 1 | | OL | H | $^nC_4H_9$ | $CH_3$ | H | H | H | H | acac | |
| 1-184Y | Ir | 0 | 1 | | OL | H | $^nC_4H_9$ | $CH_3$ | H | H | H | H | — | — |
| 1-185 | Ir | 1 | 1 | | OL | H | $^tC_4H_9$ | $CH_3$ | H | H | H | H | pic | |
| 1-185X | Ir | 1 | 1 | | OL | H | $^tC_4H_9$ | $CH_3$ | H | H | H | H | acac | |
| 1-185Y | Ir | 0 | 1 | | OL | H | $^tC_4H_9$ | $CH_3$ | H | H | H | H | — | — |
| 1-186 | Ir | 1 | 1 | | OL | —$CH_2CH_2CH_2$— | | H | H | H | H | H | pic | |
| 1-186X | Ir | 1 | 1 | | OL | —$CH_2CH_2CH_2$— | | H | H | H | H | H | acac | |
| 1-186Y | Ir | 0 | 1 | | OL | —$CH_2CH_2CH_2$— | | H | H | H | H | H | — | — |

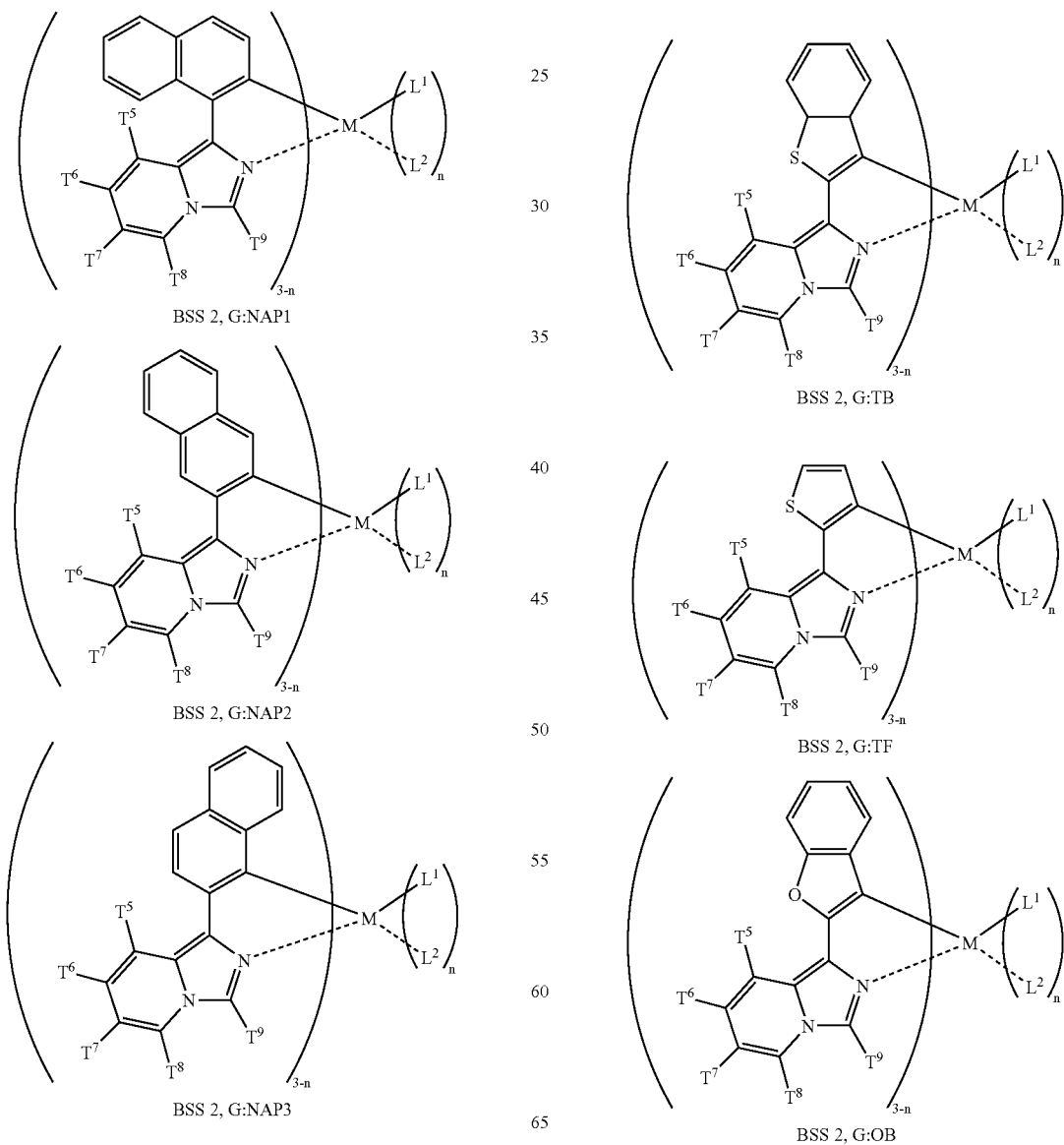

-continued

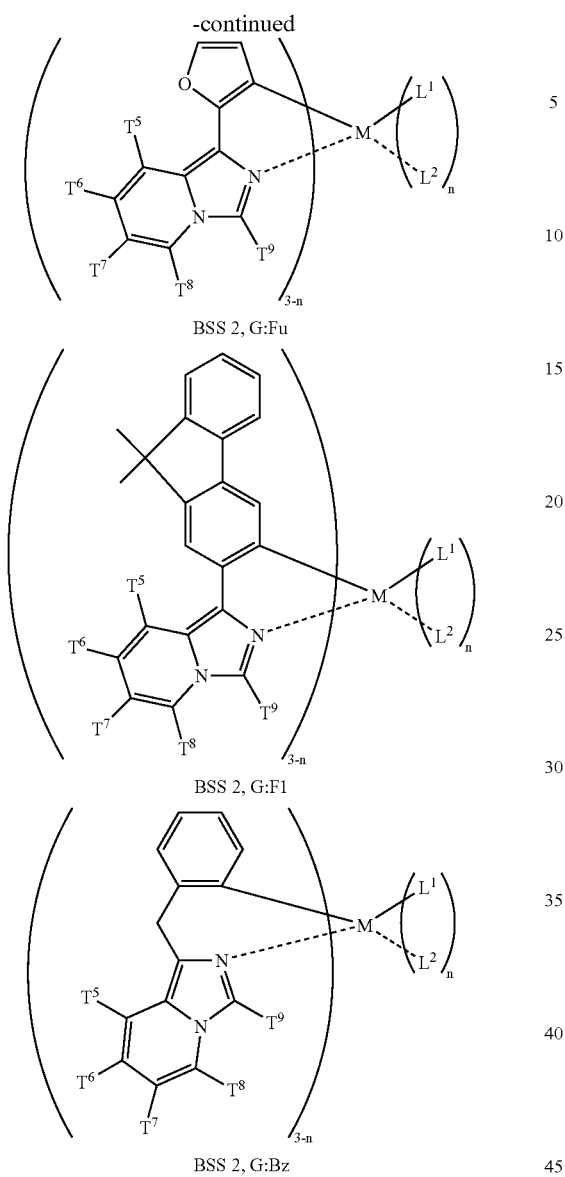

BSS 2, G:Fu

BSS 2, G:Fl

BSS 2, G:Bz

-continued

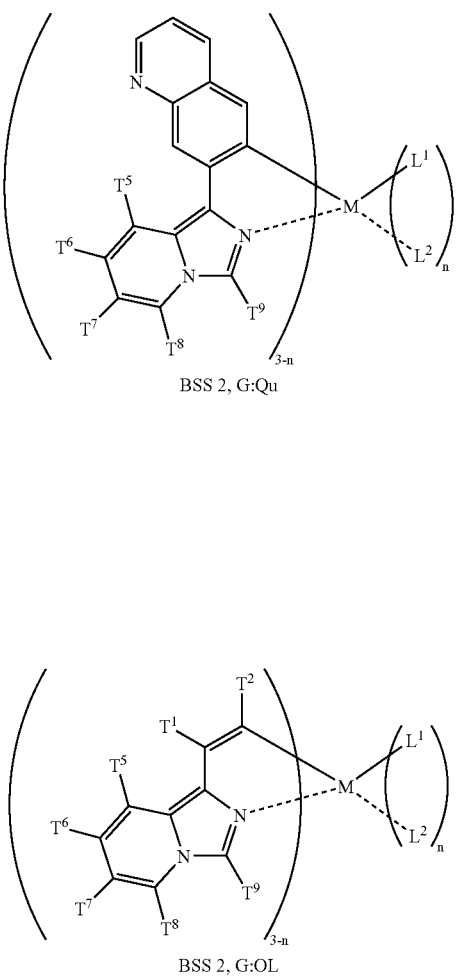

BSS 2, G:Qu

BSS 2, G:OL

TABLE 9

| No. | M | n | BSS | SS | G | T$^1$ | T$^2$ | T$^5$ | T$^6$ | T$^7$ | T$^8$ | T$^9$ | L$^1$ | L$^2$ |
|---|---|---|---|---|---|---|---|---|---|---|---|---|---|---|
| 2-119 | Ir | 1 | 2 | | Nap1 | — | — | H | H | H | H | H | pic | |
| 2-119X | Ir | 1 | 2 | | Nap1 | — | — | H | H | H | H | H | acac | |
| 2-119Y | Ir | 0 | 2 | | Nap1 | — | — | H | H | H | H | H | — | — |
| 2-120 | Ir | 1 | 2 | | Nap1 | — | — | $^tC_4H_9$ | H | H | H | H | pic | |
| 2-120X | Ir | 1 | 2 | | Nap1 | — | — | $^tC_4H_9$ | H | H | H | H | acac | |
| 2-120Y | Ir | 0 | 2 | | Nap1 | — | — | $^tC_4H_9$ | H | H | H | H | — | — |
| 2-121 | Ir | 1 | 2 | | Nap1 | — | — | $CH_3$ | H | H | H | H | pic | |
| 2-121X | Ir | 1 | 2 | | Nap1 | — | — | $CH_3$ | H | H | H | H | acac | |
| 2-121Y | Ir | 0 | 2 | | Nap1 | — | — | $CH_3$ | H | H | H | H | — | — |
| 2-122 | Ir | 1 | 2 | | Nap1 | — | — | $^tC_4H_9$ | H | H | $CH_3$ | H | pic | |
| 2-122X | Ir | 1 | 2 | | Nap1 | — | — | $^tC_4H_9$ | H | H | $CH_3$ | H | acac | |
| 2-122Y | Ir | 0 | 2 | | Nap1 | — | — | $^tC_4H_9$ | H | H | $CH_3$ | H | — | — |
| 2-123 | Ir | 1 | 2 | | Nap1 | — | — | $CH_3$ | H | H | $CH_3$ | H | pic | |
| 2-123X | Ir | 1 | 2 | | Nap1 | — | — | $CH_3$ | H | H | $CH_3$ | H | acac | |
| 2-123Y | Ir | 0 | 2 | | Nap1 | — | — | $CH_3$ | H | H | $CH_3$ | H | — | — |
| 2-124 | Ir | 1 | 2 | | Nap1 | — | — | H | H | H | $CH_3$ | H | pic | |
| 2-124X | Ir | 1 | 2 | | Nap1 | — | — | H | H | H | $CH_3$ | H | acac | |
| 2-124Y | Ir | 0 | 2 | | Nap1 | — | — | H | H | H | $CH_3$ | H | — | — |

TABLE 9-continued

| No. | M | n | BSS | SS G | T¹ | T² | T⁵ | T⁶ | T⁷ | T⁸ | T⁹ | L¹ L² |
|---|---|---|---|---|---|---|---|---|---|---|---|---|
| 2-125 | Ir | 1 | 2 | Nap2 | — | — | H | H | H | H | H | pic |
| 2-125X | Ir | 1 | 2 | Nap2 | — | — | H | H | H | H | H | acac |
| 2-125Y | Ir | 0 | 2 | Nap2 | — | — | H | H | H | H | H | — — |
| 2-126 | Ir | 1 | 2 | Nap2 | — | — | $^tC_4H_9$ | H | H | H | H | pic |
| 2-126X | Ir | 1 | 2 | Nap2 | — | — | $^tC_4H_9$ | H | H | H | H | acac |
| 2-126Y | Ir | 0 | 2 | Nap2 | — | — | $^tC_4H_9$ | H | H | H | H | — — |
| 2-127 | Ir | 1 | 2 | Nap2 | — | — | $CH_3$ | H | H | H | H | pic |
| 2-127X | Ir | 1 | 2 | Nap2 | — | — | $CH_3$ | H | H | H | H | acac |
| 2-127Y | Ir | 0 | 2 | Nap2 | — | — | $CH_3$ | H | H | H | H | — — |
| 2-128 | Ir | 1 | 2 | Nap2 | — | — | $^tC_4H_9$ | H | H | $CH_3$ | H | pic |
| 2-128X | Ir | 1 | 2 | Nap2 | — | — | $^tC_4H_9$ | H | H | $CH_3$ | H | acac |
| 2-128Y | Ir | 0 | 2 | Nap2 | — | — | $^tC_4H_9$ | H | H | $CH_3$ | H | — — |
| 2-129 | Ir | 1 | 2 | Nap2 | — | — | $CH_3$ | H | H | $CH_3$ | H | pic |
| 2-129X | Ir | 1 | 2 | Nap2 | — | — | $CH_3$ | H | H | $CH_3$ | H | acac |
| 2-129Y | Ir | 0 | 2 | Nap2 | — | — | $CH_3$ | H | H | $CH_3$ | H | — — |
| 2-130 | Ir | 1 | 2 | Nap2 | — | — | H | H | H | $CH_3$ | H | pic |
| 2-130X | Ir | 1 | 2 | Nap2 | — | — | H | H | H | $CH_3$ | H | acac |
| 2-130Y | Ir | 0 | 2 | Nap2 | — | — | H | H | H | $CH_3$ | H | — — |
| 2-131 | Ir | 1 | 2 | Nap3 | — | — | H | H | H | H | H | pic |
| 2-131X | Ir | 1 | 2 | Nap3 | — | — | H | H | H | H | H | acac |
| 2-131Y | Ir | 0 | 2 | Nap3 | — | — | H | H | H | H | H | — — |
| 2-132 | Ir | 1 | 2 | Nap3 | — | — | $^tC_4H_9$ | H | H | H | H | pic |
| 2-132X | Ir | 1 | 2 | Nap3 | — | — | $^tC_4H_9$ | H | H | H | H | acac |
| 2-132Y | Ir | 0 | 2 | Nap3 | — | — | $^tC_4H_9$ | H | H | H | H | — — |
| 2-133 | Ir | 1 | 2 | Nap3 | — | — | $CH_3$ | H | H | H | H | pic |
| 2-133X | Ir | 1 | 2 | Nap3 | — | — | $CH_3$ | H | H | H | H | acac |
| 2-133Y | Ir | 0 | 2 | Nap3 | — | — | $CH_3$ | H | H | H | H | — — |
| 2-134 | Ir | 1 | 2 | Nap3 | — | — | $^tC_4H_9$ | H | H | $CH_3$ | H | pic |
| 2-134X | Ir | 1 | 2 | Nap3 | — | — | $^tC_4H_9$ | H | H | $CH_3$ | H | acac |
| 2-134Y | Ir | 0 | 2 | Nap3 | — | — | $^tC_4H_9$ | H | H | $CH_3$ | H | — — |
| 2-135 | Ir | 1 | 2 | Nap3 | — | — | $CH_3$ | H | H | $CH_3$ | H | pic |
| 2-135X | Ir | 1 | 2 | Nap3 | — | — | $CH_3$ | H | H | $CH_3$ | H | acac |
| 2-135Y | Ir | 0 | 2 | Nap3 | — | — | $CH_3$ | H | H | $CH_3$ | H | — — |
| 2-136 | Ir | 1 | 2 | Nap3 | — | — | H | H | H | $CH_3$ | H | pic |
| 2-136X | Ir | 1 | 2 | Nap3 | — | — | H | H | H | $CH_3$ | H | acac |
| 2-136Y | Ir | 0 | 2 | Nap3 | — | — | H | H | H | $CH_3$ | H | — — |
| 2-137 | Ir | 1 | 2 | TB | — | — | H | H | H | H | H | pic |
| 2-137X | Ir | 1 | 2 | TB | — | — | H | H | H | H | H | acac |
| 2-137Y | Ir | 0 | 2 | TB | — | — | H | H | H | H | H | — — |
| 2-138 | Ir | 1 | 2 | TB | — | — | $^tC_4H_9$ | H | H | H | H | pic |
| 2-138X | Ir | 1 | 2 | TB | — | — | $^tC_4H_9$ | H | H | H | H | acac |
| 2-138Y | Ir | 0 | 2 | TB | — | — | $^tC_4H_9$ | H | H | H | H | — — |
| 2-139 | Ir | 1 | 2 | TB | — | — | $CH_3$ | H | H | H | H | pic |
| 2-139X | Ir | 1 | 2 | TB | — | — | $CH_3$ | H | H | H | H | acac |
| 2-139Y | Ir | 0 | 2 | TB | — | — | $CH_3$ | H | H | H | H | — — |
| 2-140 | Ir | 1 | 2 | TB | — | — | $^tC_4H_9$ | H | H | $CH_3$ | H | pic |
| 2-140X | Ir | 1 | 2 | TB | — | — | $^tC_4H_9$ | H | H | $CH_3$ | H | acac |
| 2-140Y | Ir | 0 | 2 | TB | — | — | $^tC_4H_9$ | H | H | $CH_3$ | H | — — |
| 2-141 | Ir | 1 | 2 | TB | — | — | $CH_3$ | H | H | $CH_3$ | H | pic |
| 2-141X | Ir | 1 | 2 | TB | — | — | $CH_3$ | H | H | $CH_3$ | H | acac |
| 2-141Y | Ir | 0 | 2 | TB | — | — | $CH_3$ | H | H | $CH_3$ | H | — — |
| 2-142 | Ir | 1 | 2 | TB | — | — | H | H | H | $CH_3$ | H | pic |
| 2-142X | Ir | 1 | 2 | TB | — | — | H | H | H | $CH_3$ | H | acac |
| 2-142Y | Ir | 0 | 2 | TB | — | — | H | H | H | $CH_3$ | H | — — |
| 2-143 | Ir | 1 | 2 | TF | — | — | H | H | H | H | H | pic |
| 2-143X | Ir | 1 | 2 | TF | — | — | H | H | H | H | H | acac |
| 2-143Y | Ir | 0 | 2 | TF | — | — | H | H | H | H | H | — — |
| 2-144 | Ir | 1 | 2 | TF | — | — | $^tC_4H_9$ | H | H | H | H | pic |
| 2-144X | Ir | 1 | 2 | TF | — | — | $^tC_4H_9$ | H | H | H | H | acac |
| 2-144Y | Ir | 0 | 2 | TF | — | — | $^tC_4H_9$ | H | H | H | H | — — |
| 2-145 | Ir | 1 | 2 | TF | — | — | $CH_3$ | H | H | H | H | pic |
| 2-145X | Ir | 1 | 2 | TF | — | — | $CH_3$ | H | H | H | H | acac |
| 2-145Y | Ir | 0 | 2 | TF | — | — | $CH_3$ | H | H | H | H | — — |
| 2-146 | Ir | 1 | 2 | TF | — | — | $^tC_4H_9$ | H | H | $CH_3$ | H | pic |
| 2-146X | Ir | 1 | 2 | TF | — | — | $^tC_4H_9$ | H | H | $CH_3$ | H | acac |
| 2-146Y | Ir | 0 | 2 | TF | — | — | $^tC_4H_9$ | H | H | $CH_3$ | H | — — |
| 2-147 | Ir | 1 | 2 | TF | — | — | $CH_3$ | H | H | $CH_3$ | H | pic |
| 2-147X | Ir | 1 | 2 | TF | — | — | $CH_3$ | H | H | $CH_3$ | H | acac |
| 2-147Y | Ir | 0 | 2 | TF | — | — | $CH_3$ | H | H | $CH_3$ | H | — — |
| 2-148 | Ir | 1 | 2 | TF | — | — | H | H | H | $CH_3$ | H | pic |
| 2-148X | Ir | 1 | 2 | TF | — | — | H | H | H | $CH_3$ | H | acac |
| 2-148Y | Ir | 0 | 2 | TF | — | — | H | H | H | $CH_3$ | H | — — |
| 2-149 | Ir | 1 | 2 | OB | — | — | H | H | H | H | H | pic |
| 2-149X | Ir | 1 | 2 | OB | — | — | H | H | H | H | H | acac |
| 2-149Y | Ir | 0 | 2 | OB | — | — | H | H | H | H | H | — — |
| 2-150 | Ir | 1 | 2 | OB | — | — | $^tC_4H_9$ | H | H | H | H | pic |
| 2-150X | Ir | 1 | 2 | OB | — | — | $^tC_4H_9$ | H | H | H | H | acac |

TABLE 9-continued

| No. | M | n | BSS | SS G | T¹ | T² | T⁵ | T⁶ | T⁷ | T⁸ | T⁹ | L¹ | L² |
|---|---|---|---|---|---|---|---|---|---|---|---|---|---|
| 2-150Y | Ir | 0 | 2 | OB | — | — | $^tC_4H_9$ | H | H | H | H | — | — |
| 2-151 | Ir | 1 | 2 | OB | — | — | $CH_3$ | H | H | H | H | pic | |
| 2-151X | Ir | 1 | 2 | OB | — | — | $CH_3$ | H | H | H | H | acac | |
| 2-151Y | Ir | 0 | 2 | OB | — | — | $CH_3$ | H | H | H | H | — | — |
| 2-152 | Ir | 1 | 2 | OB | — | — | $^tC_4H_9$ | H | H | $CH_3$ | H | pic | |
| 2-152X | Ir | 1 | 2 | OB | — | — | $^tC_4H_9$ | H | H | $CH_3$ | H | acac | |
| 2-152Y | Ir | 0 | 2 | OB | — | — | $^tC_4H_9$ | H | H | $CH_3$ | H | — | — |
| 2-153 | Ir | 1 | 2 | OB | — | — | $CH_3$ | H | H | $CH_3$ | H | pic | |
| 2-153X | Ir | 1 | 2 | OB | — | — | $CH_3$ | H | H | $CH_3$ | H | acac | |
| 2-153Y | Ir | 0 | 2 | OB | — | — | $CH_3$ | H | H | $CH_3$ | H | — | — |
| 2-154 | Ir | 1 | 2 | OB | — | — | H | H | H | $CH_3$ | H | pic | |
| 2-154X | Ir | 1 | 2 | OB | — | — | H | H | H | $CH_3$ | H | acac | |
| 2-154Y | Ir | 0 | 2 | OB | — | — | H | H | H | $CH_3$ | H | — | — |
| 2-155 | Ir | 1 | 2 | Fu | — | — | H | H | H | H | H | pic | |
| 2-155X | Ir | 1 | 2 | Fu | — | — | H | H | H | H | H | acac | |
| 2-155Y | Ir | 0 | 2 | Fu | — | — | H | H | H | H | H | — | — |
| 2-156 | Ir | 1 | 2 | Fu | — | — | $^tC_4H_9$ | H | H | H | H | pic | |
| 2-156X | Ir | 1 | 2 | Fu | — | — | $^tC_4H_9$ | H | H | H | H | acac | |
| 2-156Y | Ir | 0 | 2 | Fu | — | — | $^tC_4H_9$ | H | H | H | H | — | — |
| 2-157 | Ir | 1 | 2 | Fu | — | — | $CH_3$ | H | H | H | H | pic | |
| 2-157X | Ir | 1 | 2 | Fu | — | — | $CH_3$ | H | H | H | H | acac | |
| 2-157Y | Ir | 0 | 2 | Fu | — | — | $CH_3$ | H | H | H | H | — | — |
| 2-158 | Ir | 1 | 2 | Fu | — | — | $^tC_4H_9$ | H | H | $CH_3$ | H | pic | |
| 2-158X | Ir | 1 | 2 | Fu | — | — | $^tC_4H_9$ | H | H | $CH_3$ | H | acac | |
| 2-158Y | Ir | 0 | 2 | Fu | — | — | $^tC_4H_9$ | H | H | $CH_3$ | H | — | — |
| 2-159 | Ir | 1 | 2 | Fu | — | — | $CH_3$ | H | H | $CH_3$ | H | pic | |
| 2-159X | Ir | 1 | 2 | Fu | — | — | $CH_3$ | H | H | $CH_3$ | H | acac | |
| 2-159Y | Ir | 0 | 2 | Fu | — | — | $CH_3$ | H | H | $CH_3$ | H | — | — |
| 2-160 | Ir | 1 | 2 | Fu | — | — | H | H | H | $CH_3$ | H | pic | |
| 2-160X | Ir | 1 | 2 | Fu | — | — | H | H | H | $CH_3$ | H | acac | |
| 2-160Y | Ir | 0 | 2 | Fu | — | — | H | H | H | $CH_3$ | H | — | — |
| 2-161 | Ir | 1 | 2 | Fl | — | — | H | H | H | H | H | pic | |
| 2-161X | Ir | 1 | 2 | Fl | — | — | H | H | H | H | H | acac | |
| 2-161Y | Ir | 0 | 2 | Fl | — | — | H | H | H | H | H | — | — |
| 2-162 | Ir | 1 | 2 | Fl | — | — | $^tC_4H_9$ | H | H | H | H | pic | |
| 2-162X | Ir | 1 | 2 | Fl | — | — | $^tC_4H_9$ | H | H | H | H | acac | |
| 2-162Y | Ir | 0 | 2 | Fl | — | — | $^tC_4H_9$ | H | H | H | H | — | — |
| 2-163 | Ir | 1 | 2 | Fl | — | — | $CH_3$ | H | H | H | H | pic | |
| 2-163X | Ir | 1 | 2 | Fl | — | — | $CH_3$ | H | H | H | H | acac | |
| 2-163Y | Ir | 0 | 2 | Fl | — | — | $CH_3$ | H | H | H | H | — | — |
| 2-164 | Ir | 1 | 2 | Fl | — | — | $^tC_4H_9$ | H | H | $CH_3$ | H | pic | |
| 2-164X | Ir | 1 | 2 | Fl | — | — | $^tC_4H_9$ | H | H | $CH_3$ | H | acac | |
| 2-164Y | Ir | 0 | 2 | Fl | — | — | $^tC_4H_9$ | H | H | $CH_3$ | H | — | — |
| 2-165 | Ir | 1 | 2 | Fl | — | — | $CH_3$ | H | H | $CH_3$ | H | pic | |
| 2-165X | Ir | 1 | 2 | Fl | — | — | $CH_3$ | H | H | $CH_3$ | H | acac | |
| 2-165Y | Ir | 0 | 2 | Fl | — | — | $CH_3$ | H | H | $CH_3$ | H | — | — |
| 2-166 | Ir | 1 | 2 | Fl | — | — | H | H | H | $CH_3$ | H | pic | |
| 2-166X | Ir | 1 | 2 | Fl | — | — | H | H | H | $CH_3$ | H | acac | |
| 2-166Y | Ir | 0 | 2 | Fl | — | — | H | H | H | $CH_3$ | H | — | — |
| 2-167 | Ir | 1 | 2 | Bz | — | — | H | H | H | H | H | pic | |
| 2-167X | Ir | 1 | 2 | Bz | — | — | H | H | H | H | H | acac | |
| 2-167Y | Ir | 0 | 2 | Bz | — | — | H | H | H | H | H | — | — |
| 2-168 | Ir | 1 | 2 | Bz | — | — | $^tC_4H_9$ | H | H | H | H | pic | |
| 2-168X | Ir | 1 | 2 | Bz | — | — | $^tC_4H_9$ | H | H | H | H | acac | |
| 2-168Y | Ir | 0 | 2 | Bz | — | — | $^tC_4H_9$ | H | H | H | H | — | — |
| 2-169 | Ir | 1 | 2 | Bz | — | — | $CH_3$ | H | H | H | H | pic | |
| 2-169X | Ir | 1 | 2 | Bz | — | — | $CH_3$ | H | H | H | H | acac | |
| 2-169Y | Ir | 0 | 2 | Bz | — | — | $CH_3$ | H | H | H | H | — | — |
| 2-170 | Ir | 1 | 2 | Bz | — | — | $^tC_4H_9$ | H | H | $CH_3$ | H | pic | |
| 2-170X | Ir | 1 | 2 | Bz | — | — | $^tC_4H_9$ | H | H | $CH_3$ | H | acac | |
| 2-170Y | Ir | 0 | 2 | Bz | — | — | $^tC_4H_9$ | H | H | $CH_3$ | H | — | — |
| 2-171 | Ir | 1 | 2 | Bz | — | — | $CH_3$ | H | H | $CH_3$ | H | pic | |
| 2-171X | Ir | 1 | 2 | Bz | — | — | $CH_3$ | H | H | $CH_3$ | H | acac | |
| 2-171Y | Ir | 0 | 2 | Bz | — | — | $CH_3$ | H | H | $CH_3$ | H | — | — |
| 2-172 | Ir | 1 | 2 | Bz | — | — | H | H | H | $CH_3$ | H | pic | |
| 2-172X | Ir | 1 | 2 | Bz | — | — | H | H | H | $CH_3$ | H | acac | |
| 2-172Y | Ir | 0 | 2 | Bz | — | — | H | H | H | $CH_3$ | H | — | — |
| 2-173 | Ir | 1 | 2 | Qu | — | — | H | H | H | H | H | pic | |
| 2-173X | Ir | 1 | 2 | Qu | — | — | H | H | H | H | H | acac | |
| 2-173Y | Ir | 0 | 2 | Qu | — | — | H | H | H | H | H | — | — |
| 2-174 | Ir | 1 | 2 | Qu | — | — | $^tC_4H_9$ | H | H | H | H | pic | |
| 2-174X | Ir | 1 | 2 | Qu | — | — | $^tC_4H_9$ | H | H | H | H | acac | |
| 2-174Y | Ir | 0 | 2 | Qu | — | — | $^tC_4H_9$ | H | H | H | H | — | — |
| 2-175 | Ir | 1 | 2 | Qu | — | — | $CH_3$ | H | H | H | H | pic | |
| 2-175X | Ir | 1 | 2 | Qu | — | — | $CH_3$ | H | H | H | H | acac | |
| 2-175Y | Ir | 0 | 2 | Qu | — | — | $CH_3$ | H | H | H | H | — | — |
| 2-176 | Ir | 1 | 2 | Qu | — | — | $^tC_4H_9$ | H | H | $CH_3$ | H | pic | |

TABLE 9-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 2-176X | Ir | 1 | 2 | | Qu | — | — | $^tC_4H_9$ | H | H | $CH_3$ | H | acac | |
| 2-176Y | Ir | 0 | 2 | | Qu | — | — | $^tC_4H_9$ | H | H | $CH_3$ | H | — | — |
| 2-177 | Ir | 1 | 2 | | Qu | — | — | $CH_3$ | H | H | $CH_3$ | H | pic | |
| 2-177X | Ir | 1 | 2 | | Qu | — | — | $CH_3$ | H | H | $CH_3$ | H | acac | |
| 2-177Y | Ir | 0 | 2 | | Qu | — | — | $CH_3$ | H | H | $CH_3$ | H | — | — |
| 2-178 | Ir | 1 | 2 | | Qu | — | — | H | H | H | $CH_3$ | H | pic | |
| 2-178X | Ir | 1 | 2 | | Qu | — | — | H | H | H | $CH_3$ | H | acac | |
| 2-178Y | Ir | 0 | 2 | | Qu | — | — | H | H | H | $CH_3$ | H | — | — |
| 2-179 | Ir | 1 | 2 | | OL | H | $^nC_4H_9$ | H | H | H | H | H | pic | |
| 2-179X | Ir | 1 | 2 | | OL | H | $^nC_4H_9$ | H | H | H | H | H | acac | |
| 2-179Y | Ir | 0 | 2 | | OL | H | $^nC_4H_9$ | H | H | H | H | H | — | — |
| 2-180 | Ir | 1 | 2 | | OL | H | $^tC_4H_9$ | H | H | H | H | H | pic | |
| 2-180X | Ir | 1 | 2 | | OL | H | $^tC_4H_9$ | H | H | H | H | H | acac | |
| 2-180Y | Ir | 0 | 2 | | OL | H | $^tC_4H_9$ | H | H | H | H | H | — | — |
| 2-181 | Ir | 1 | 2 | | OL | $CH_3$ | $^nC_4H_9$ | H | H | H | H | H | pic | |
| 2-181X | Ir | 1 | 2 | | OL | $CH_3$ | $^nC_4H_9$ | H | H | H | H | H | acac | |
| 2-181Y | Ir | 0 | 2 | | OL | $CH_3$ | $^nC_4H_9$ | H | H | H | H | H | — | — |
| 2-182 | Ir | 1 | 2 | | OL | $CH_3$ | $^tC_4H_9$ | H | H | H | H | H | pic | |
| 2-182X | Ir | 1 | 2 | | OL | $CH_3$ | $^tC_4H_9$ | H | H | H | H | H | acac | |
| 2-182Y | Ir | 0 | 2 | | OL | $CH_3$ | $^tC_4H_9$ | H | H | H | H | H | — | — |
| 2-183 | Ir | 1 | 2 | | OL | H | H | H | H | H | H | H | pic | |
| 2-183X | Ir | 1 | 2 | | OL | H | H | H | H | H | H | H | acac | |
| 2-183Y | Ir | 0 | 2 | | OL | H | H | H | H | H | H | H | — | — |
| 2-184 | Ir | 1 | 2 | | OL | H | $^nC_4H_9$ | $CH_3$ | H | H | H | H | pic | |
| 2-184X | Ir | 1 | 2 | | OL | H | $^nC_4H_9$ | $CH_3$ | H | H | H | H | acac | |
| 2-184Y | Ir | 0 | 2 | | OL | H | $^nC_4H_9$ | $CH_3$ | H | H | H | H | — | — |
| 2-185 | Ir | 1 | 2 | | OL | H | $^tC_4H_9$ | $CH_3$ | H | H | H | H | pic | |
| 2-185X | Ir | 1 | 2 | | OL | H | $^tC_4H_9$ | $CH_3$ | H | H | H | H | acac | |
| 2-185Y | Ir | 0 | 2 | | OL | H | $^tC_4H_9$ | $CH_3$ | H | H | H | H | — | — |
| 2-186 | Ir | 1 | 2 | | OL | —$CH_2CH_2CH_2$— | | H | H | H | H | H | pic | |
| 2-186X | Ir | 1 | 2 | | OL | —$CH_2CH_2CH_2$— | | H | H | H | H | H | acac | |
| 2-186Y | Ir | 0 | 2 | | OL | —$CH_2CH_2CH_2$— | | H | H | H | H | H | — | — |

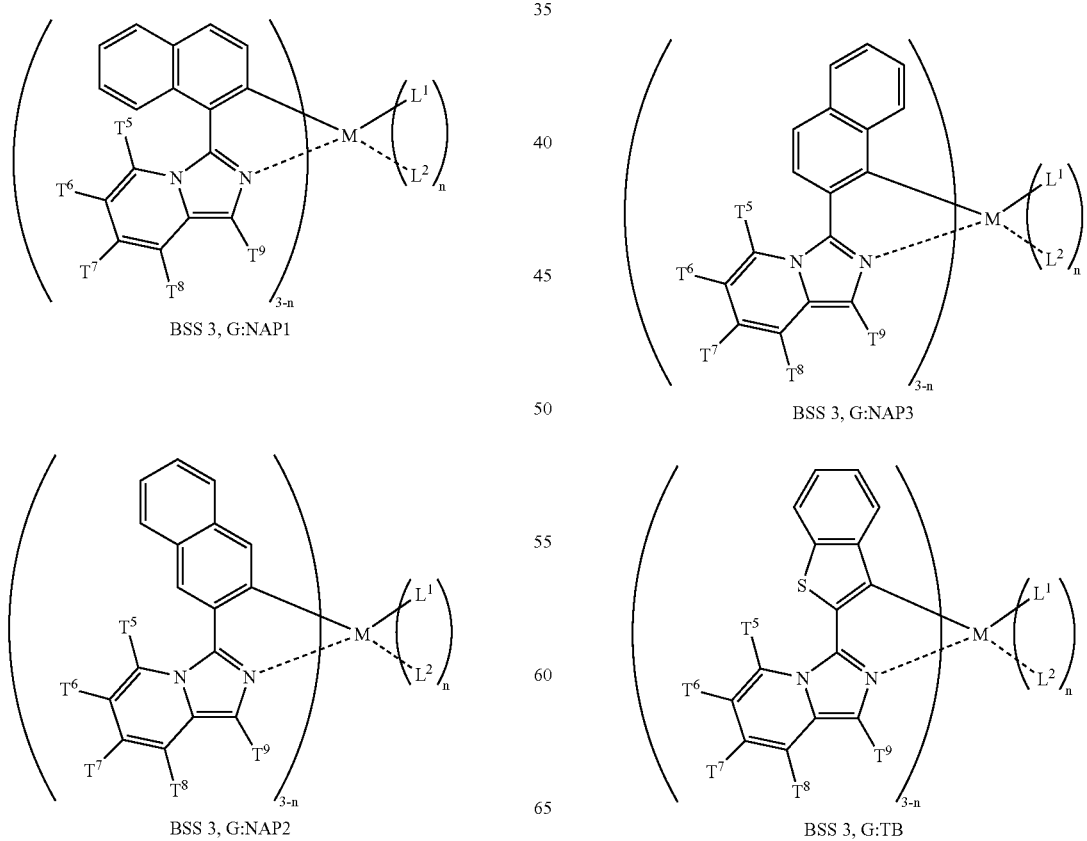

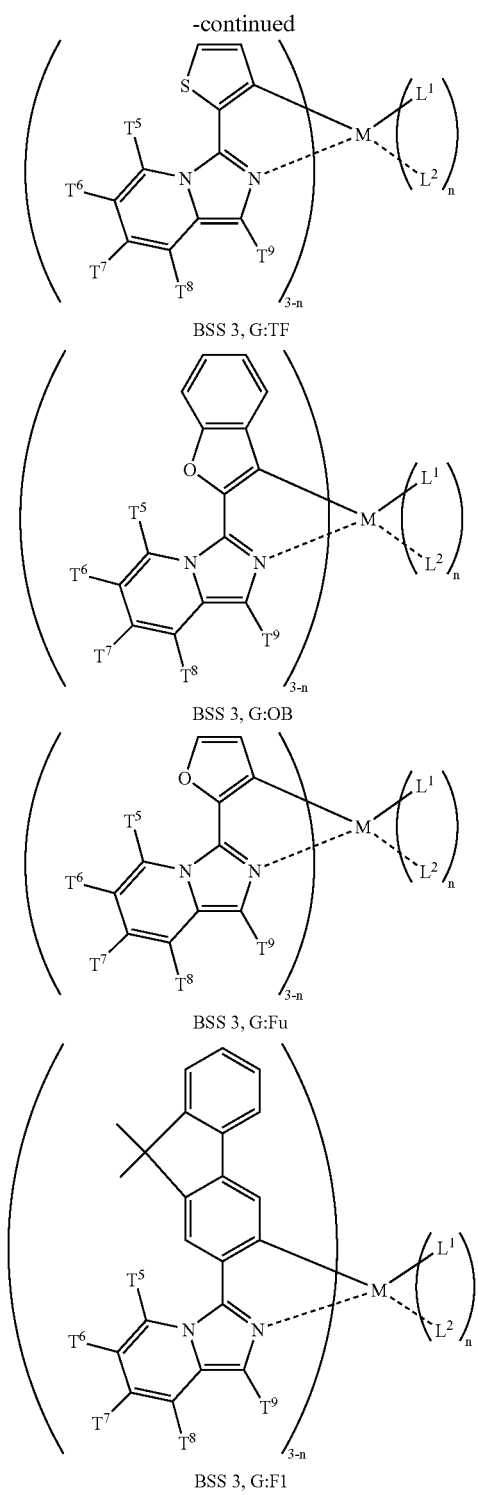
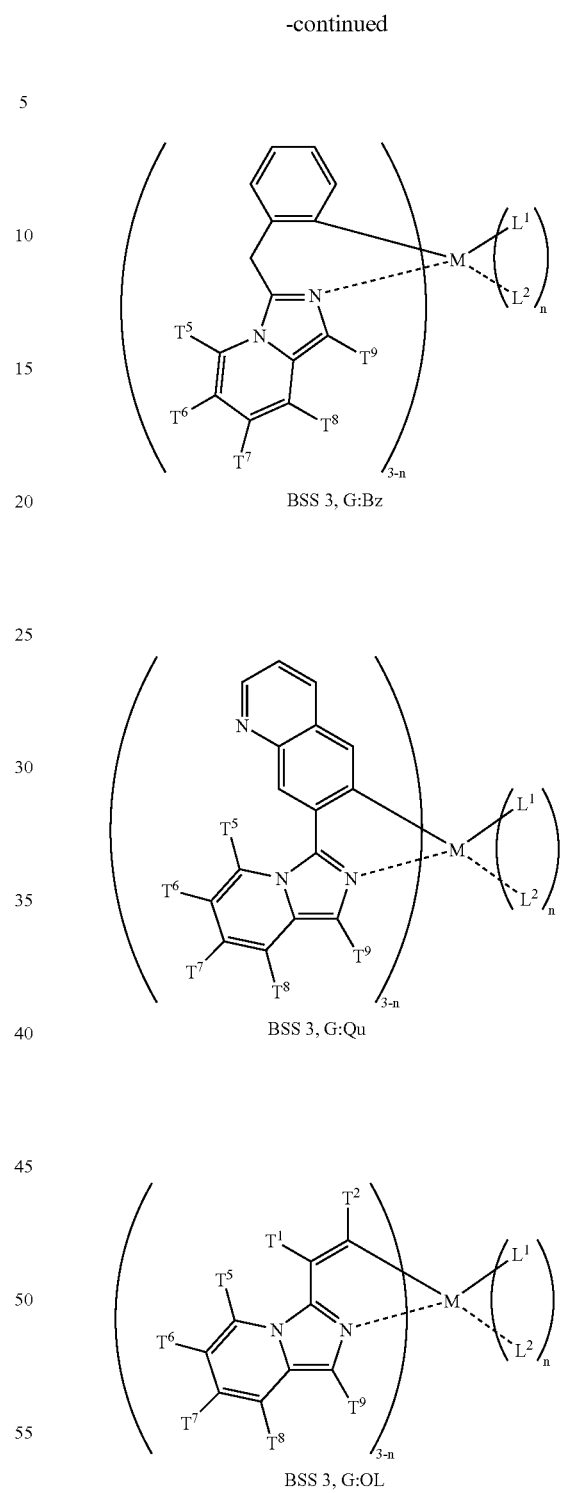
TABLE 10
| No. | M | n | BSS | SS | G | T¹ | T² | T⁵ | T⁶ | T⁷ | T⁸ | T⁹ | L¹ L² |
|---|---|---|---|---|---|---|---|---|---|---|---|---|---|
| 3-117 | Ir | 1 | 3 | | Nap1 | — | — | H | H | H | H | H | pic |
| 3-117X | Ir | 1 | 3 | | Nap1 | — | — | H | H | H | H | H | acac |
| 3-117Y | Ir | 0 | 3 | | Nap1 | — | — | H | H | H | H | H | — — |

TABLE 10-continued

| No. | M | n | BSS | SS G | T¹ | T² | T⁵ | T⁶ | T⁷ | T⁸ | T⁹ | L¹ L² |
|---|---|---|---|---|---|---|---|---|---|---|---|---|
| 3-118 | Ir | 1 | 3 | Nap1 | — | — | $^tC_4H_9$ | H | H | H | H | pic |
| 3-118X | Ir | 1 | 3 | Nap1 | — | — | $^tC_4H_9$ | H | H | H | H | acac |
| 3-118Y | Ir | 0 | 3 | Nap1 | — | — | $^tC_4H_9$ | H | H | H | H | — — |
| 3-119 | Ir | 1 | 3 | Nap1 | — | — | $CH_3$ | H | H | H | H | pic |
| 3-119X | Ir | 1 | 3 | Nap1 | — | — | $CH_3$ | H | H | H | H | acac |
| 3-119Y | Ir | 0 | 3 | Nap1 | — | — | $CH_3$ | H | H | H | H | — — |
| 3-120 | Ir | 1 | 3 | Nap2 | — | — | H | H | H | H | H | pic |
| 3-120X | Ir | 1 | 3 | Nap2 | — | — | H | H | H | H | H | acac |
| 3-120Y | Ir | 0 | 3 | Nap2 | — | — | H | H | H | H | H | — — |
| 3-121 | Ir | 1 | 3 | Nap2 | — | — | $^tC_4H_9$ | H | H | H | H | pic |
| 3-121X | Ir | 1 | 3 | Nap2 | — | — | $^tC_4H_9$ | H | H | H | H | acac |
| 3-121Y | Ir | 0 | 3 | Nap2 | — | — | $^tC_4H_9$ | H | H | H | H | — — |
| 3-122 | Ir | 1 | 3 | Nap2 | — | — | $CH_3$ | H | H | H | H | pic |
| 3-122X | Ir | 1 | 3 | Nap2 | — | — | $CH_3$ | H | H | H | H | acac |
| 3-122Y | Ir | 0 | 3 | Nap2 | — | — | $CH_3$ | H | H | H | H | — — |
| 3-123 | Ir | 1 | 3 | Nap3 | — | — | H | H | H | H | H | pic |
| 3-123X | Ir | 1 | 3 | Nap3 | — | — | H | H | H | H | H | acac |
| 3-123Y | Ir | 0 | 3 | Nap3 | — | — | H | H | H | H | H | — — |
| 3-124 | Ir | 1 | 3 | Nap3 | — | — | $^tC_4H_9$ | H | H | H | H | pic |
| 3-124X | Ir | 1 | 3 | Nap3 | — | — | $^tC_4H_9$ | H | H | H | H | acac |
| 3-124Y | Ir | 0 | 3 | Nap3 | — | — | $^tC_4H_9$ | H | H | H | H | — — |
| 3-125 | Ir | 1 | 3 | Nap3 | — | — | $CH_3$ | H | H | H | H | pic |
| 3-125X | Ir | 1 | 3 | Nap3 | — | — | $CH_3$ | H | H | H | H | acac |
| 3-125Y | Ir | 0 | 3 | Nap3 | — | — | $CH_3$ | H | H | H | H | — — |
| 3-126 | Ir | 1 | 3 | TB | — | — | H | H | H | H | H | pic |
| 3-126X | Ir | 1 | 3 | TB | — | — | H | H | H | H | H | acac |
| 3-126Y | Ir | 0 | 3 | TB | — | — | H | H | H | H | H | — — |
| 3-127 | Ir | 1 | 3 | TB | — | — | $^tC_4H_9$ | H | H | H | H | pic |
| 3-127X | Ir | 1 | 3 | TB | — | — | $^tC_4H_9$ | H | H | H | H | acac |
| 3-127Y | Ir | 0 | 3 | TB | — | — | $^tC_4H_9$ | H | H | H | H | — — |
| 3-128 | Ir | 1 | 3 | TB | — | — | $CH_3$ | H | H | H | H | pic |
| 3-128X | Ir | 1 | 3 | TB | — | — | $CH_3$ | H | H | H | H | acac |
| 3-128Y | Ir | 0 | 3 | TB | — | — | $CH_3$ | H | H | H | H | — — |
| 3-129 | Ir | 1 | 3 | TF | — | — | H | H | H | H | H | pic |
| 3-129X | Ir | 1 | 3 | TF | — | — | H | H | H | H | H | acac |
| 3-129Y | Ir | 0 | 3 | TF | — | — | H | H | H | H | H | — — |
| 3-130 | Ir | 1 | 3 | TF | — | — | $^tC_4H_9$ | H | H | H | H | pic |
| 3-130X | Ir | 1 | 3 | TF | — | — | $^tC_4H_9$ | H | H | H | H | acac |
| 3-130Y | Ir | 0 | 3 | TF | — | — | $^tC_4H_9$ | H | H | H | H | — — |
| 3-131 | Ir | 1 | 3 | TF | — | — | $CH_3$ | H | H | H | H | pic |
| 3-131X | Ir | 1 | 3 | TF | — | — | $CH_3$ | H | H | H | H | acac |
| 3-131Y | Ir | 0 | 3 | TF | — | — | $CH_3$ | H | H | H | H | — — |
| 3-132 | Ir | 1 | 3 | OB | — | — | H | H | H | H | H | pic |
| 3-132X | Ir | 1 | 3 | OB | — | — | H | H | H | H | H | acac |
| 3-132Y | Ir | 0 | 3 | OB | — | — | H | H | H | H | H | — — |
| 3-133 | Ir | 1 | 3 | OB | — | — | $^tC_4H_9$ | H | H | H | H | pic |
| 3-133X | Ir | 1 | 3 | OB | — | — | $^tC_4H_9$ | H | H | H | H | acac |
| 3-133Y | Ir | 0 | 3 | OB | — | — | $^tC_4H_9$ | H | H | H | H | — — |
| 3-134 | Ir | 1 | 3 | OB | — | — | $CH_3$ | H | H | H | H | pic |
| 3-134X | Ir | 1 | 3 | OB | — | — | $CH_3$ | H | H | H | H | acac |
| 3-134Y | Ir | 0 | 3 | OB | — | — | $CH_3$ | H | H | H | H | — — |
| 3-135 | Ir | 1 | 3 | Fu | — | — | H | H | H | H | H | pic |
| 3-135X | Ir | 1 | 3 | Fu | — | — | H | H | H | H | H | acac |
| 3-135Y | Ir | 0 | 3 | Fu | — | — | H | H | H | H | H | — — |
| 3-136 | Ir | 1 | 3 | Fu | — | — | $^tC_4H_9$ | H | H | H | H | pic |
| 3-136X | Ir | 1 | 3 | Fu | — | — | $^tC_4H_9$ | H | H | H | H | acac |
| 3-136Y | Ir | 0 | 3 | Fu | — | — | $^tC_4H_9$ | H | H | H | H | — — |
| 3-137 | Ir | 1 | 3 | Fu | — | — | $CH_3$ | H | H | H | H | pic |
| 3-137X | Ir | 1 | 3 | Fu | — | — | $CH_3$ | H | H | H | H | acac |
| 3-137Y | Ir | 0 | 3 | Fu | — | — | $CH_3$ | H | H | H | H | — — |
| 3-138 | Ir | 1 | 3 | Fl | — | — | H | H | H | H | H | pic |
| 3-138X | Ir | 1 | 3 | Fl | — | — | H | H | H | H | H | acac |
| 3-138Y | Ir | 0 | 3 | Fl | — | — | H | H | H | H | H | — — |
| 3-139 | Ir | 1 | 3 | Fl | — | — | $^tC_4H_9$ | H | H | H | H | pic |
| 3-139X | Ir | 1 | 3 | Fl | — | — | $^tC_4H_9$ | H | H | H | H | acac |
| 3-139Y | Ir | 0 | 3 | Fl | — | — | $^tC_4H_9$ | H | H | H | H | — — |
| 3-140 | Ir | 1 | 3 | Fl | — | — | $CH_3$ | H | H | H | H | pic |
| 3-140X | Ir | 1 | 3 | Fl | — | — | $CH_3$ | H | H | H | H | acac |
| 3-140Y | Ir | 0 | 3 | Fl | — | — | $CH_3$ | H | H | H | H | — — |
| 3-141 | Ir | 1 | 3 | Bz | — | — | H | H | H | H | H | pic |
| 3-141X | Ir | 1 | 3 | Bz | — | — | H | H | H | H | H | acac |
| 3-141Y | Ir | 0 | 3 | Bz | — | — | H | H | H | H | H | — — |
| 3-142 | Ir | 1 | 3 | Bz | — | — | $^tC_4H_9$ | H | H | H | H | pic |
| 3-142X | Ir | 1 | 3 | Bz | — | — | $^tC_4H_9$ | H | H | H | H | acac |

TABLE 10-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 3-142Y | Ir | 0 | 3 | | Bz | — | — | $^tC_4H_9$ | H | H | H | H | — | — |
| 3-143 | Ir | 1 | 3 | | Bz | — | — | $CH_3$ | H | H | H | H | pic | |
| 3-143X | Ir | 1 | 3 | | Bz | — | — | $CH_3$ | H | H | H | H | acac | |
| 3-143Y | Ir | 0 | 3 | | Bz | — | — | $CH_3$ | H | H | H | H | — | — |
| 3-144 | Ir | 1 | 3 | | Qu | — | — | H | H | H | H | H | pic | |
| 3-144X | Ir | 1 | 3 | | Qu | — | — | H | H | H | H | H | acac | |
| 3-144Y | Ir | 0 | 3 | | Qu | — | — | H | H | H | H | H | — | — |
| 3-145 | Ir | 1 | 3 | | Qu | — | — | $^tC_4H_9$ | H | H | H | H | pic | |
| 3-145X | Ir | 1 | 3 | | Qu | — | — | $^tC_4H_9$ | H | H | H | H | acac | |
| 3-145Y | Ir | 0 | 3 | | Qu | — | — | $^tC_4H_9$ | H | H | H | H | — | — |
| 3-146 | Ir | 1 | 3 | | Qu | — | — | $CH_3$ | H | H | H | H | pic | |
| 3-146X | Ir | 1 | 3 | | Qu | — | — | $CH_3$ | H | H | H | H | acac | |
| 3-146Y | Ir | 0 | 3 | | Qu | — | — | $CH_3$ | H | H | H | H | — | — |
| 3-147 | Ir | 1 | 3 | | OL | H | $^nC_4H_9$ | H | H | H | H | H | pic | |
| 3-147X | Ir | 1 | 3 | | OL | H | $^nC_4H_9$ | H | H | H | H | H | acac | |
| 3-147Y | Ir | 0 | 3 | | OL | H | $^nC_4H_9$ | H | H | H | H | H | — | — |
| 3-148 | Ir | 1 | 3 | | OL | H | $^tC_4H_9$ | H | H | H | H | H | pic | |
| 3-148X | Ir | 1 | 3 | | OL | H | $^tC_4H_9$ | H | H | H | H | H | acac | |
| 3-148Y | Ir | 0 | 3 | | OL | H | $^tC_4H_9$ | H | H | H | H | H | — | — |
| 3-149 | Ir | 1 | 3 | | OL | $CH_3$ | $^nC_4H_9$ | H | H | H | H | H | pic | |
| 3-149X | Ir | 1 | 3 | | OL | $CH_3$ | $^nC_4H_9$ | H | H | H | H | H | acac | |
| 3-149Y | Ir | 0 | 3 | | OL | $CH_3$ | $^nC_4H_9$ | H | H | H | H | H | — | — |
| 3-150 | Ir | 1 | 3 | | OL | $CH_3$ | $^tC_4H_9$ | H | H | H | H | H | pic | |
| 3-150X | Ir | 1 | 3 | | OL | $CH_3$ | $^tC_4H_9$ | H | H | H | H | H | acac | |
| 3-150Y | Ir | 0 | 3 | | OL | $CH_3$ | $^tC_4H_9$ | H | H | H | H | H | — | — |
| 3-151 | Ir | 1 | 3 | | OL | H | H | H | H | H | H | H | pic | |
| 3-151X | Ir | 1 | 3 | | OL | H | H | H | H | H | H | H | acac | |
| 3-151Y | Ir | 0 | 3 | | OL | H | H | H | H | H | H | H | — | — |
| 3-152 | Ir | 1 | 3 | | OL | H | $^nC_4H_9$ | $CH_3$ | H | H | H | H | pic | |
| 3-152X | Ir | 1 | 3 | | OL | H | $^nC_4H_9$ | $CH_3$ | H | H | H | H | acac | |
| 3-152Y | Ir | 0 | 3 | | OL | H | $^nC_4H_9$ | $CH_3$ | H | H | H | H | — | — |
| 3-153 | Ir | 1 | 3 | | OL | H | $^tC_4H_9$ | $CH_3$ | H | H | H | H | pic | |
| 3-153X | Ir | 1 | 3 | | OL | H | $^tC_4H_9$ | $CH_3$ | H | H | H | H | acac | |
| 3-153Y | Ir | 0 | 3 | | OL | H | $^tC_4H_9$ | $CH_3$ | H | H | H | H | — | — |
| 3-154 | Ir | 1 | 3 | | OL | —$CH_2CH_2CH_2$— | | H | H | H | H | H | pic | |
| 3-154X | Ir | 1 | 3 | | OL | —$CH_2CH_2CH_2$— | | H | H | H | H | H | acac | |
| 3-154Y | Ir | 0 | 3 | | OL | —$CH_2CH_2CH_2$— | | H | H | H | H | H | — | — |

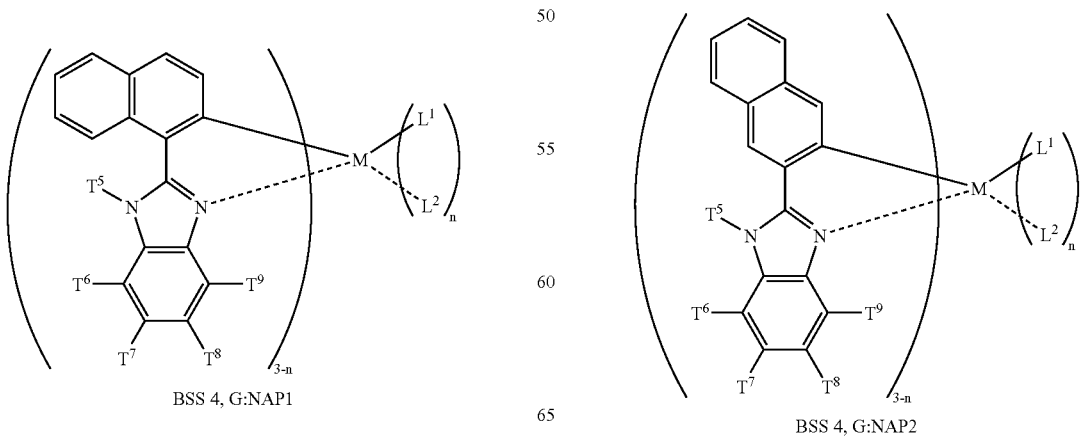

BSS 4, G:NAP1

BSS 4, G:NAP2

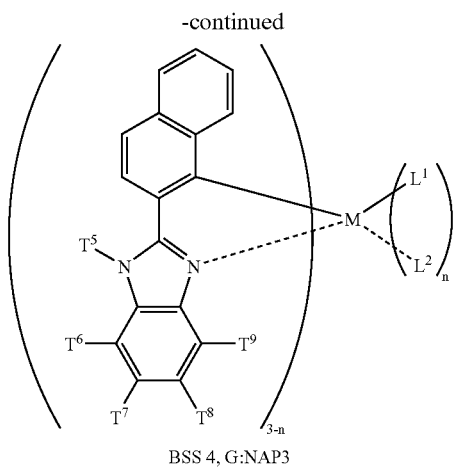
BSS 4, G:NAP3
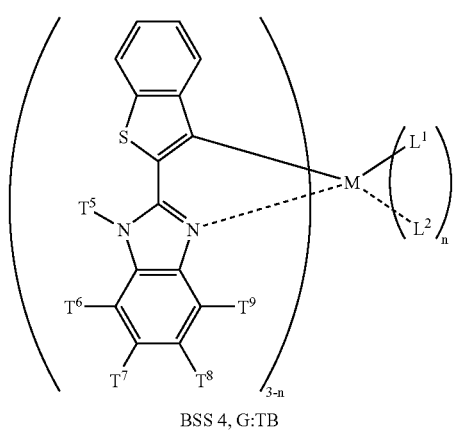
BSS 4, G:TB
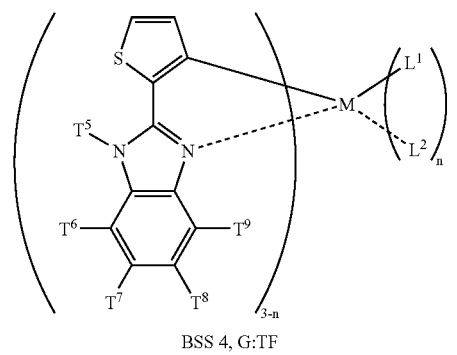
BSS 4, G:TF
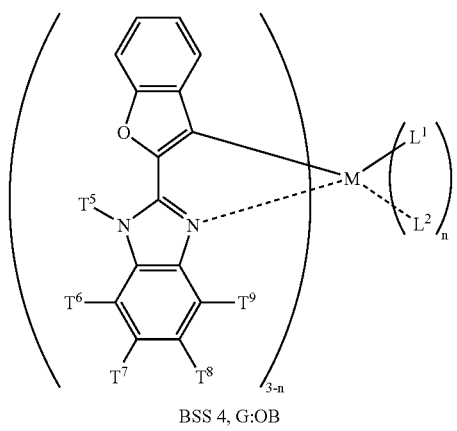
BSS 4, G:OB
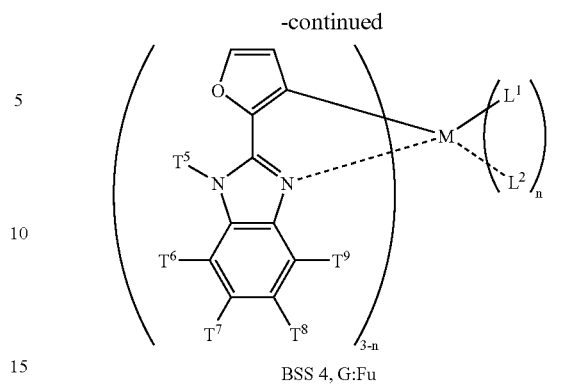
BSS 4, G:Fu
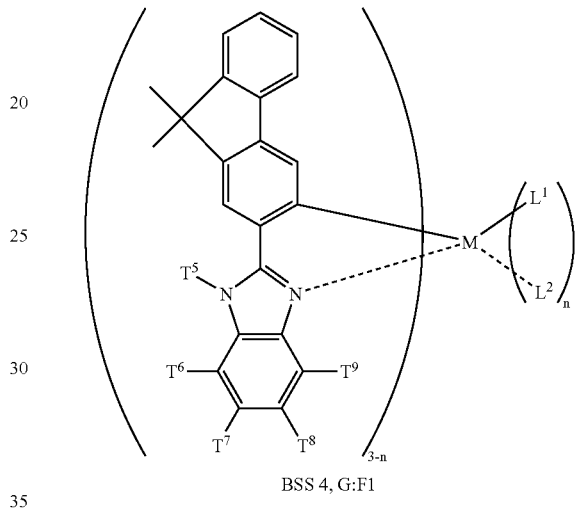
BSS 4, G:Fl
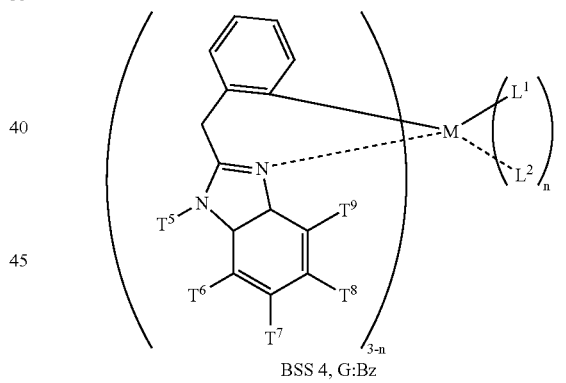
BSS 4, G:Bz
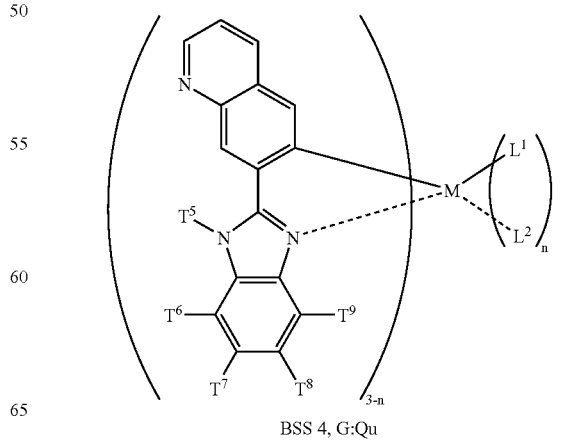
BSS 4, G:Qu -continued

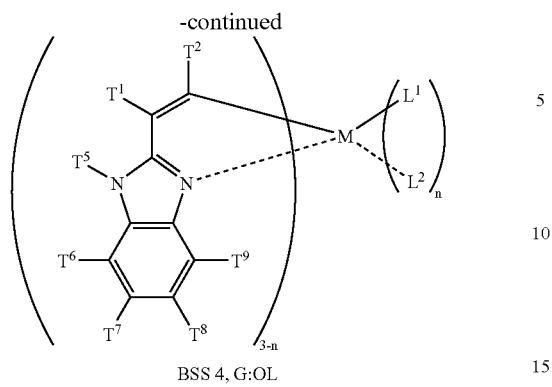

BSS 4, G:OL

TABLE 11

| No. | M | n | BSS | SS G | T¹ | T² | T⁵ | T⁶ | T⁷ | T⁸ | T⁹ | L¹ | L² |
|---|---|---|---|---|---|---|---|---|---|---|---|---|---|
| 4-138 | Ir | 1 | 4 | Nap1 | — | — | $CH_3$ | H | H | H | H | pic | |
| 4-138X | Ir | 1 | 4 | Nap1 | — | — | $CH_3$ | H | H | H | H | acac | |
| 4-138Y | Ir | 0 | 4 | Nap1 | — | — | $CH_3$ | H | H | H | H | — | — |
| 4-139 | Ir | 1 | 4 | Nap1 | — | — | $^tC_4H_9$ | H | H | H | H | pic | |
| 4-139X | Ir | 1 | 4 | Nap1 | — | — | $^tC_4H_9$ | H | H | H | H | acac | |
| 4-139Y | Ir | 0 | 4 | Nap1 | — | — | $^tC_4H_9$ | H | H | H | H | — | — |
| 4-140 | Ir | 1 | 4 | Nap2 | — | — | $CH_3$ | H | H | H | H | pic | |
| 4-140X | Ir | 1 | 4 | Nap2 | — | — | $CH_3$ | H | H | H | H | acac | |
| 4-140Y | Ir | 0 | 4 | Nap2 | — | — | $CH_3$ | H | H | H | H | — | — |
| 4-141 | Ir | 1 | 4 | Nap2 | — | — | $^tC_4H_9$ | H | H | H | H | pic | |
| 4-141X | Ir | 1 | 4 | Nap2 | — | — | $^tC_4H_9$ | H | H | H | H | acac | |
| 4-141Y | Ir | 0 | 4 | Nap2 | — | — | $^tC_4H_9$ | H | H | H | H | — | — |
| 4-142 | Ir | 1 | 4 | Nap3 | — | — | $CH_3$ | H | H | H | H | pic | |
| 4-142X | Ir | 1 | 4 | Nap3 | — | — | $CH_3$ | H | H | H | H | acac | |
| 4-142Y | Ir | 0 | 4 | Nap3 | — | — | $CH_3$ | H | H | H | H | — | — |
| 4-143 | Ir | 1 | 4 | Nap3 | — | — | $^tC_4H_9$ | H | H | H | H | pic | |
| 4-143X | Ir | 1 | 4 | Nap3 | — | — | $^tC_4H_9$ | H | H | H | H | acac | |
| 4-143Y | Ir | 0 | 4 | Nap3 | — | — | $^tC_4H_9$ | H | H | H | H | — | — |
| 4-144 | Ir | 1 | 4 | TB | — | — | $CH_3$ | H | H | H | H | pic | |
| 4-144X | Ir | 1 | 4 | TB | — | — | $CH_3$ | H | H | H | H | acac | |
| 4-144Y | Ir | 0 | 4 | TB | — | — | $CH_3$ | H | H | H | H | — | — |
| 4-145 | Ir | 1 | 4 | TB | — | — | $^tC_4H_9$ | H | H | H | H | pic | |
| 4-145X | Ir | 1 | 4 | TB | — | — | $^tC_4H_9$ | H | H | H | H | acac | |
| 4-145Y | Ir | 0 | 4 | TB | — | — | $^tC_4H_9$ | H | H | H | H | — | — |
| 4-146 | Ir | 1 | 4 | TF | — | — | $CH_3$ | H | H | H | H | pic | |
| 4-146X | Ir | 1 | 4 | TF | — | — | $CH_3$ | H | H | H | H | acac | |
| 4-146Y | Ir | 0 | 4 | TF | — | — | $CH_3$ | H | H | H | H | — | — |
| 4-147 | Ir | 1 | 4 | TF | — | — | $^tC_4H_9$ | H | H | H | H | pic | |
| 4-147X | Ir | 1 | 4 | TF | — | — | $^tC_4H_9$ | H | H | H | H | acac | |
| 4-147Y | Ir | 0 | 4 | TF | — | — | $^tC_4H_9$ | H | H | H | H | — | — |
| 4-148 | Ir | 1 | 4 | OB | — | — | $CH_3$ | H | H | H | H | pic | |
| 4-148X | Ir | 1 | 4 | OB | — | — | $CH_3$ | H | H | H | H | acac | |
| 4-148Y | Ir | 0 | 4 | OB | — | — | $CH_3$ | H | H | H | H | — | — |
| 4-149 | Ir | 1 | 4 | OB | — | — | $^tC_4H_9$ | H | H | H | H | pic | |
| 4-149X | Ir | 1 | 4 | OB | — | — | $^tC_4H_9$ | H | H | H | H | acac | |
| 4-149Y | Ir | 0 | 4 | OB | — | — | $^tC_4H_9$ | H | H | H | H | — | — |
| 4-150 | Ir | 1 | 4 | Fu | — | — | $CH_3$ | H | H | H | H | pic | |
| 4-150X | Ir | 1 | 4 | Fu | — | — | $CH_3$ | H | H | H | H | acac | |
| 4-150Y | Ir | 0 | 4 | Fu | — | — | $CH_3$ | H | H | H | H | — | — |
| 4-151 | Ir | 1 | 4 | Fu | — | — | $^tC_4H_9$ | H | H | H | H | pic | |
| 4-151X | Ir | 1 | 4 | Fu | — | — | $^tC_4H_9$ | H | H | H | H | acac | |
| 4-151Y | Ir | 0 | 4 | Fu | — | — | $^tC_4H_9$ | H | H | H | H | — | — |
| 4-152 | Ir | 1 | 4 | Fl | — | — | $CH_3$ | H | H | H | H | pic | |
| 4-152X | Ir | 1 | 4 | Fl | — | — | $CH_3$ | H | H | H | H | acac | |
| 4-152Y | Ir | 0 | 4 | Fl | — | — | $CH_3$ | H | H | H | H | — | — |
| 4-153 | Ir | 1 | 4 | Fl | — | — | $^tC_4H_9$ | H | H | H | H | pic | |
| 4-153X | Ir | 1 | 4 | Fl | — | — | $^tC_4H_9$ | H | H | H | H | acac | |
| 4-153Y | Ir | 0 | 4 | Fl | — | — | $^tC_4H_9$ | H | H | H | H | — | — |
| 4-154 | Ir | 1 | 4 | Bz | — | — | $CH_3$ | H | H | H | H | pic | |
| 4-154X | Ir | 1 | 4 | Bz | — | — | $CH_3$ | H | H | H | H | acac | |
| 4-154Y | Ir | 0 | 4 | Bz | — | — | $CH_3$ | H | H | H | H | — | — |
| 4-155 | Ir | 1 | 4 | Bz | — | — | $^tC_4H_9$ | H | H | H | H | pic | |
| 4-155X | Ir | 1 | 4 | Bz | — | — | $^tC_4H_9$ | H | H | H | H | acac | |
| 4-155Y | Ir | 0 | 4 | Bz | — | — | $^tC_4H_9$ | H | H | H | H | — | — |

TABLE 11-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 4-156 | Ir | 1 | 4 | | Qu | — | — | CH₃ | H | H | H | H | pic | |
| 4-156X | Ir | 1 | 4 | | Qu | — | — | CH₃ | H | H | H | H | acac | |
| 4-156Y | Ir | 0 | 4 | | Qu | — | — | CH₃ | H | H | H | H | — | — |
| 4-157 | Ir | 1 | 4 | | Qu | — | — | ᵗC₄H₉ | H | H | H | H | pic | |
| 4-157X | Ir | 1 | 4 | | Qu | — | — | ᵗC₄H₉ | H | H | H | H | acac | |
| 4-157Y | Ir | 0 | 4 | | Qu | — | — | ᵗC₄H₉ | H | H | H | H | — | — |
| 4-158 | Ir | 1 | 4 | | OL | H | ⁿC₄H₉ | CH₃ | H | H | H | H | pic | |
| 4-158X | Ir | 1 | 4 | | OL | H | ⁿC₄H₉ | CH₃ | H | H | H | H | acac | |
| 4-158Y | Ir | 0 | 4 | | OL | H | ⁿC₄H₉ | CH₃ | H | H | H | H | — | — |
| 4-159 | Ir | 1 | 4 | | OL | H | ⁿC₄H₉ | ᵗC₄H₉ | H | H | H | H | pic | |
| 4-159X | Ir | 1 | 4 | | OL | H | ⁿC₄H₉ | ᵗC₄H₉ | H | H | H | H | acac | |
| 4-159Y | Ir | 0 | 4 | | OL | H | ⁿC₄H₉ | ᵗC₄H₉ | H | H | H | H | — | — |
| 4-160 | Ir | 1 | 4 | | OL | H | ᵗC₄H₉ | CH₃ | H | H | H | H | pic | |
| 4-160X | Ir | 1 | 4 | | OL | H | ᵗC₄H₉ | CH₃ | H | H | H | H | acac | |
| 4-160Y | Ir | 0 | 4 | | OL | H | ᵗC₄H₉ | CH₃ | H | H | H | H | — | — |
| 4-161 | Ir | 1 | 4 | | OL | H | ᵗC₄H₉ | ᵗC₄H₉ | H | H | H | H | pic | |
| 4-161X | Ir | 1 | 4 | | OL | H | ᵗC₄H₉ | ᵗC₄H₉ | H | H | H | H | acac | |
| 4-161Y | Ir | 0 | 4 | | OL | H | ᵗC₄H₉ | ᵗC₄H₉ | H | H | H | H | — | — |
| 4-162 | Ir | 1 | 4 | | OL | CH₃ | ⁿC₄H₉ | CH₃ | H | H | H | H | pic | |
| 4-162X | Ir | 1 | 4 | | OL | CH₃ | ⁿC₄H₉ | CH₃ | H | H | H | H | acac | |
| 4-162Y | Ir | 0 | 4 | | OL | CH₃ | ⁿC₄H₉ | CH₃ | H | H | H | H | — | — |
| 4-163 | Ir | 1 | 4 | | OL | CH₃ | ᵗC₄H₉ | CH₃ | H | H | H | H | pic | |
| 4-163X | Ir | 1 | 4 | | OL | CH₃ | ᵗC₄H₉ | CH₃ | H | H | H | H | acac | |
| 4-163Y | Ir | 0 | 4 | | OL | CH₃ | ᵗC₄H₉ | CH₃ | H | H | H | H | — | — |
| 4-164 | Ir | 1 | 4 | | OL | H | H | CH₃ | H | H | H | H | pic | |
| 4-164X | Ir | 1 | 4 | | OL | H | H | CH₃ | H | H | H | H | acac | |
| 4-164Y | Ir | 0 | 4 | | OL | H | H | CH₃ | H | H | H | H | — | — |
| 4-165 | Ir | 1 | 4 | | OL | —CH₂CH₂CH₂— | | CH₃ | H | H | H | H | pic | |
| 4-165X | Ir | 1 | 4 | | OL | —CH₂CH₂CH₂— | | CH₃ | H | H | H | H | acac | |
| 4-165Y | Ir | 0 | 4 | | OL | —CH₂CH₂CH₂— | | CH₃ | H | H | H | H | — | — |
| 4-166 | Ir | 1 | 4 | | OL | —CH₂CH₂CH₂— | | ᵗC₄H₉ | H | H | H | H | pic | |
| 4-166X | Ir | 1 | 4 | | OL | —CH₂CH₂CH₂— | | ᵗC₄H₉ | H | H | H | H | acac | |
| 4-166Y | Ir | 0 | 4 | | OL | —CH₂CH₂CH₂— | | ᵗC₄H₉ | H | H | H | H | — | — |

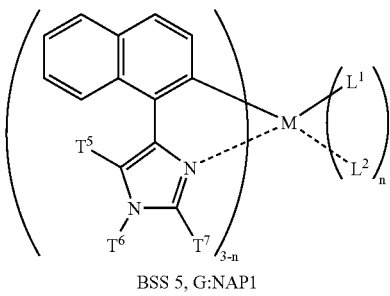

BSS 5, G:NAP1

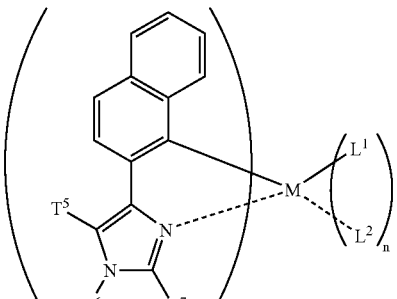

-continued

BSS 5, G:NAP3

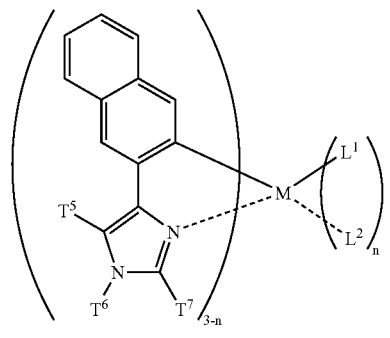

BSS 5, G:NAP2

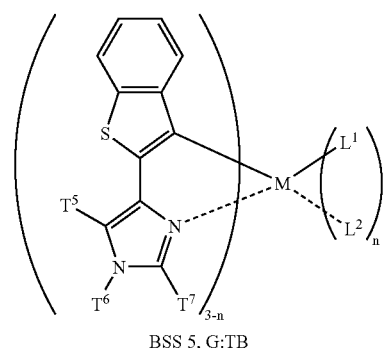

BSS 5, G:TB

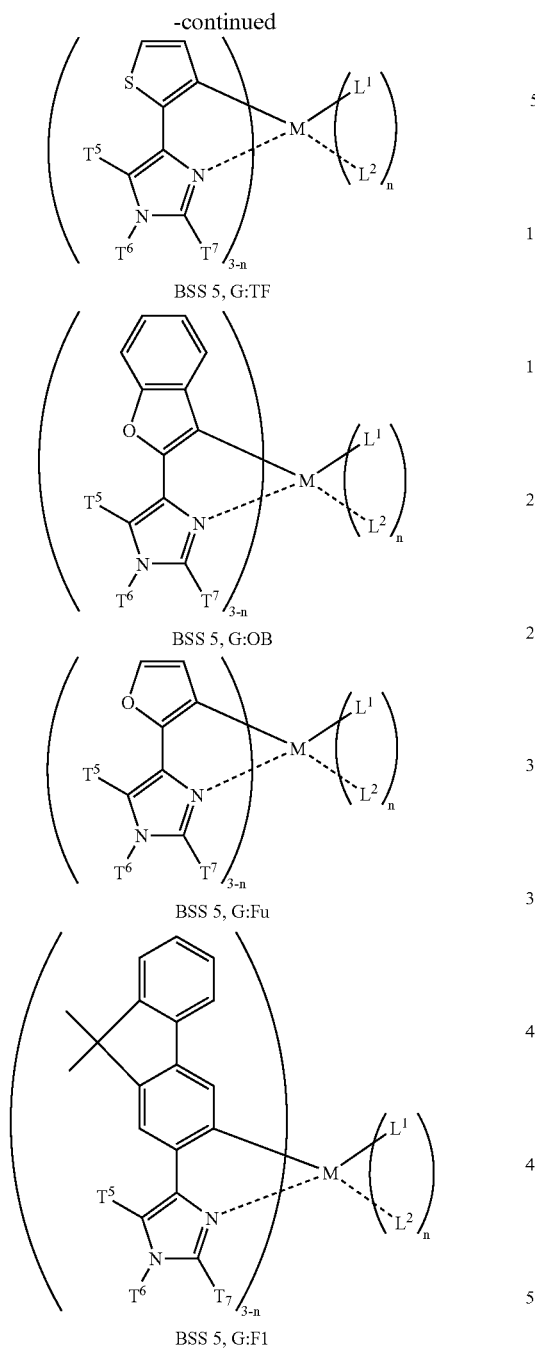
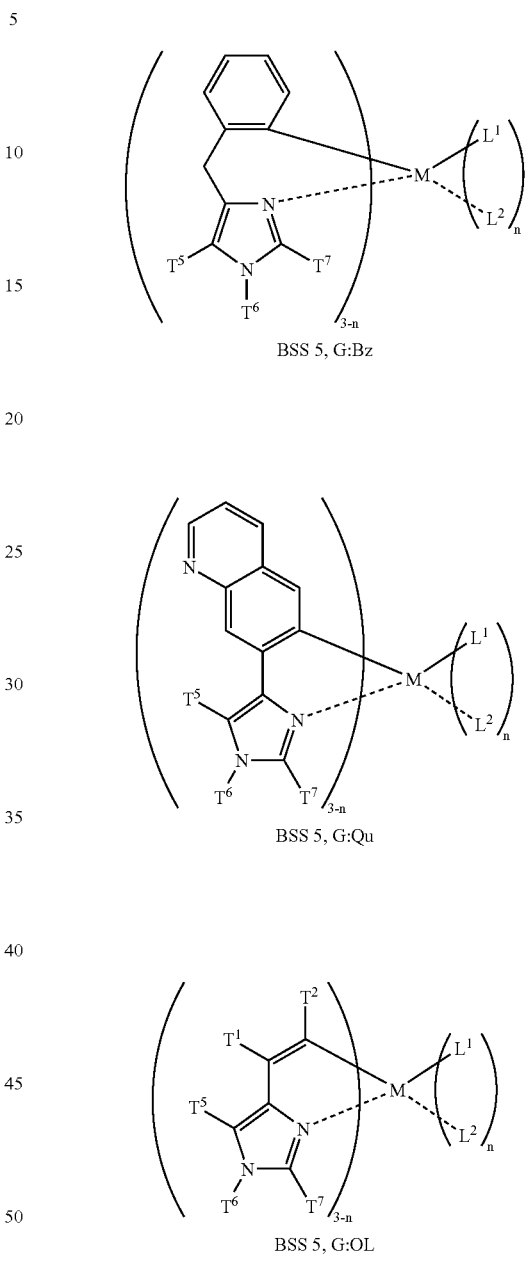
TABLE 12
| No. | M | n | BSS | SS | G | T$^1$ | T$^2$ | T$^5$ | T$^6$ | T$^7$ | L$^1$ | L$^2$ |
|---|---|---|---|---|---|---|---|---|---|---|---|---|
| 5-140 | Ir | 1 | 5 | | Nap1 | — | — | H | CH$_3$ | H | pic | |
| 5-140X | Ir | 1 | 5 | | Nap1 | — | — | H | CH$_3$ | H | acac | |
| 5-140Y | Ir | 0 | 5 | | Nap1 | — | — | H | CH$_3$ | H | — | — |
| 5-141 | Ir | 1 | 5 | | Nap1 | — | — | H | $^tC_4H_9$ | H | pic | |
| 5-141X | Ir | 1 | 5 | | Nap1 | — | — | H | $^tC_4H_9$ | H | acac | |
| 5-141Y | Ir | 0 | 5 | | Nap1 | — | — | H | $^tC_4H_9$ | H | — | — |
| 5-142 | Ir | 1 | 5 | | Nap1 | — | — | $^tC_4H_9$ | CH$_3$ | H | pic | |
| 5-142X | Ir | 1 | 5 | | Nap1 | — | — | $^tC_4H_9$ | CH$_3$ | H | acac | |
| 5-142Y | Ir | 0 | 5 | | Nap1 | — | — | $^tC_4H_9$ | CH$_3$ | H | — | — |
| 5-143 | Ir | 1 | 5 | | Nap1 | — | — | $^tC_4H_9$ | $^tC_4H_9$ | H | pic | |

TABLE 12-continued

| No. | M | n | BSS | SS G | T$^1$ | T$^2$ | T$^5$ | T$^6$ | T$^7$ | L$^1$ | L$^2$ |
|---|---|---|---|---|---|---|---|---|---|---|---|
| 5-143X | Ir | 1 | 5 | Nap1 | — | — | $^tC_4H_9$ | $^tC_4H_9$ | H | acac | |
| 5-143Y | Ir | 0 | 5 | Nap1 | — | — | $^tC_4H_9$ | $^tC_4H_9$ | H | — | — |
| 5-144 | Ir | 1 | 5 | Nap1 | — | — | CH$_3$ | CH$_3$ | H | pic | |
| 5-144X | Ir | 1 | 5 | Nap1 | — | — | CH$_3$ | CH$_3$ | H | acac | |
| 5-144Y | Ir | 0 | 5 | Nap1 | — | — | CH$_3$ | CH$_3$ | H | — | — |
| 5-145 | Ir | 1 | 5 | Nap1 | — | — | CH$_3$ | $^tC_4H_9$ | H | pic | |
| 5-145X | Ir | 1 | 5 | Nap1 | — | — | CH$_3$ | $^tC_4H_9$ | H | acac | |
| 5-145Y | Ir | 0 | 5 | Nap1 | — | — | CH$_3$ | $^tC_4H_9$ | H | — | — |
| 5-146 | Ir | 1 | 5 | Nap2 | — | — | H | CH$_3$ | H | pic | |
| 5-146X | Ir | 1 | 5 | Nap2 | — | — | H | CH$_3$ | H | acac | |
| 5-146Y | Ir | 0 | 5 | Nap2 | — | — | H | CH$_3$ | H | — | — |
| 5-147 | Ir | 1 | 5 | Nap2 | — | — | H | $^tC_4H_9$ | H | pic | |
| 5-147X | Ir | 1 | 5 | Nap2 | — | — | H | $^tC_4H_9$ | H | acac | |
| 5-147Y | Ir | 0 | 5 | Nap2 | — | — | H | $^tC_4H_9$ | H | — | — |
| 5-148 | Ir | 1 | 5 | Nap2 | — | — | $^tC_4H_9$ | CH$_3$ | H | pic | |
| 5-148X | Ir | 1 | 5 | Nap2 | — | — | $^tC_4H_9$ | CH$_3$ | H | acac | |
| 5-148Y | Ir | 0 | 5 | Nap2 | — | — | $^tC_4H_9$ | CH$_3$ | H | — | — |
| 5-149 | Ir | 1 | 5 | Nap2 | — | — | $^tC_4H_9$ | $^tC_4H_9$ | H | pic | |
| 5-149X | Ir | 1 | 5 | Nap2 | — | — | $^tC_4H_9$ | $^tC_4H_9$ | H | acac | |
| 5-149Y | Ir | 0 | 5 | Nap2 | — | — | $^tC_4H_9$ | $^tC_4H_9$ | H | — | — |
| 5-150 | Ir | 1 | 5 | Nap2 | — | — | CH$_3$ | CH$_3$ | H | pic | |
| 5-150X | Ir | 1 | 5 | Nap2 | — | — | CH$_3$ | CH$_3$ | H | acac | |
| 5-150Y | Ir | 0 | 5 | Nap2 | — | — | CH$_3$ | CH$_3$ | H | — | — |
| 5-151 | Ir | 1 | 5 | Nap2 | — | — | CH$_3$ | $^tC_4H_9$ | H | pic | |
| 5-151X | Ir | 1 | 5 | Nap2 | — | — | CH$_3$ | $^tC_4H_9$ | H | acac | |
| 5-151Y | Ir | 0 | 5 | Nap2 | — | — | CH$_3$ | $^tC_4H_9$ | H | — | — |
| 5-152 | Ir | 1 | 5 | Nap3 | — | — | H | CH$_3$ | H | pic | |
| 5-152X | Ir | 1 | 5 | Nap3 | — | — | H | CH$_3$ | H | acac | |
| 5-152Y | Ir | 0 | 5 | Nap3 | — | — | H | CH$_3$ | H | — | — |
| 5-153 | Ir | 1 | 5 | Nap3 | — | — | H | $^tC_4H_9$ | H | pic | |
| 5-153X | Ir | 1 | 5 | Nap3 | — | — | H | $^tC_4H_9$ | H | acac | |
| 5-153Y | Ir | 0 | 5 | Nap3 | — | — | H | $^tC_4H_9$ | H | — | — |
| 5-154 | Ir | 1 | 5 | Nap3 | — | — | $^tC_4H_9$ | CH$_3$ | H | pic | |
| 5-154X | Ir | 1 | 5 | Nap3 | — | — | $^tC_4H_9$ | CH$_3$ | H | acac | |
| 5-154Y | Ir | 0 | 5 | Nap3 | — | — | $^tC_4H_9$ | CH$_3$ | H | — | — |
| 5-155 | Ir | 1 | 5 | Nap3 | — | — | $^tC_4H_9$ | $^tC_4H_9$ | H | pic | |
| 5-155X | Ir | 1 | 5 | Nap3 | — | — | $^tC_4H_9$ | $^tC_4H_9$ | H | acac | |
| 5-155Y | Ir | 0 | 5 | Nap3 | — | — | $^tC_4H_9$ | $^tC_4H_9$ | H | — | — |
| 5-156 | Ir | 1 | 5 | Nap3 | — | — | CH$_3$ | CH$_3$ | H | pic | |
| 5-156X | Ir | 1 | 5 | Nap3 | — | — | CH$_3$ | CH$_3$ | H | acac | |
| 5-156Y | Ir | 0 | 5 | Nap3 | — | — | CH$_3$ | CH$_3$ | H | — | — |
| 5-157 | Ir | 1 | 5 | Nap3 | — | — | CH$_3$ | $^tC_4H_9$ | H | pic | |
| 5-157X | Ir | 1 | 5 | Nap3 | — | — | CH$_3$ | $^tC_4H_9$ | H | acac | |
| 5-157Y | Ir | 0 | 5 | Nap3 | — | — | CH$_3$ | $^tC_4H_9$ | H | — | — |
| 5-158 | Ir | 1 | 5 | TB | — | — | H | CH$_3$ | H | pic | |
| 5-158X | Ir | 1 | 5 | TB | — | — | H | CH$_3$ | H | acac | |
| 5-158Y | Ir | 0 | 5 | TB | — | — | H | CH$_3$ | H | — | — |
| 5-159 | Ir | 1 | 5 | TB | — | — | H | $^tC_4H_9$ | H | pic | |
| 5-159X | Ir | 1 | 5 | TB | — | — | H | $^tC_4H_9$ | H | acac | |
| 5-159Y | Ir | 0 | 5 | TB | — | — | H | $^tC_4H_9$ | H | — | — |
| 5-160 | Ir | 1 | 5 | TB | — | — | $^tC_4H_9$ | CH$_3$ | H | pic | |
| 5-160X | Ir | 1 | 5 | TB | — | — | $^tC_4H_9$ | CH$_3$ | H | acac | |
| 5-160Y | Ir | 0 | 5 | TB | — | — | $^tC_4H_9$ | CH$_3$ | H | — | — |
| 5-161 | Ir | 1 | 5 | TB | — | — | $^tC_4H_9$ | $^tC_4H_9$ | H | pic | |
| 5-161X | Ir | 1 | 5 | TB | — | — | $^tC_4H_9$ | $^tC_4H_9$ | H | acac | |
| 5-161Y | Ir | 0 | 5 | TB | — | — | $^tC_4H_9$ | $^tC_4H_9$ | H | — | — |
| 5-162 | Ir | 1 | 5 | TB | — | — | CH$_3$ | CH$_3$ | H | pic | |
| 5-162X | Ir | 1 | 5 | TB | — | — | CH$_3$ | CH$_3$ | H | acac | |
| 5-162Y | Ir | 0 | 5 | TB | — | — | CH$_3$ | CH$_3$ | H | — | — |
| 5-163 | Ir | 1 | 5 | TB | — | — | CH$_3$ | $^tC_4H_9$ | H | pic | |
| 5-163X | Ir | 1 | 5 | TB | — | — | CH$_3$ | $^tC_4H_9$ | H | acac | |
| 5-163Y | Ir | 0 | 5 | TB | — | — | CH$_3$ | $^tC_4H_9$ | H | — | — |
| 5-164 | Ir | 1 | 5 | TF | — | — | H | CH$_3$ | H | pic | |
| 5-164X | Ir | 1 | 5 | TF | — | — | H | CH$_3$ | H | acac | |
| 5-164Y | Ir | 0 | 5 | TF | — | — | H | CH$_3$ | H | — | — |
| 5-165 | Ir | 1 | 5 | TF | — | — | H | $^tC_4H_9$ | H | pic | |
| 5-165X | Ir | 1 | 5 | TF | — | — | H | $^tC_4H_9$ | H | acac | |
| 5-165Y | Ir | 0 | 5 | TF | — | — | H | $^tC_4H_9$ | H | — | — |
| 5-166 | Ir | 1 | 5 | TF | — | — | $^tC_4H_9$ | CH$_3$ | H | pic | |
| 5-166X | Ir | 1 | 5 | TF | — | — | $^tC_4H_9$ | CH$_3$ | H | acac | |
| 5-166Y | Ir | 0 | 5 | TF | — | — | $^tC_4H_9$ | CH$_3$ | H | — | — |
| 5-167 | Ir | 1 | 5 | TF | — | — | $^tC_4H_9$ | $^tC_4H_9$ | H | pic | |
| 5-167X | Ir | 1 | 5 | TF | — | — | $^tC_4H_9$ | $^tC_4H_9$ | H | acac | |
| 5-167Y | Ir | 0 | 5 | TF | — | — | $^tC_4H_9$ | $^tC_4H_9$ | H | — | — |
| 5-168 | Ir | 1 | 5 | TF | — | — | CH$_3$ | CH$_3$ | H | pic | |
| 5-168X | Ir | 1 | 5 | TF | — | — | CH$_3$ | CH$_3$ | H | acac | |
| 5-168Y | Ir | 0 | 5 | TF | — | — | CH$_3$ | CH$_3$ | H | — | — |

TABLE 12-continued

| No. | M | n | BSS | SS G | T¹ | T² | T⁵ | T⁶ | T⁷ | L¹ | L² |
|---|---|---|---|---|---|---|---|---|---|---|---|
| 5-169 | Ir | 1 | 5 | TF | — | — | CH$_3$ | $^t$C$_4$H$_9$ | H | pic | |
| 5-169X | Ir | 1 | 5 | TF | — | — | CH$_3$ | $^t$C$_4$H$_9$ | H | acac | |
| 5-169Y | Ir | 0 | 5 | TF | — | — | CH$_3$ | $^t$C$_4$H$_9$ | H | — | |
| 5-170 | Ir | 1 | 5 | OB | — | — | H | CH$_3$ | H | pic | |
| 5-170X | Ir | 1 | 5 | OB | — | — | H | CH$_3$ | H | acac | |
| 5-170Y | Ir | 0 | 5 | OB | — | — | H | CH$_3$ | H | — | |
| 5-171 | Ir | 1 | 5 | OB | — | — | H | $^t$C$_4$H$_9$ | H | pic | |
| 5-171X | Ir | 1 | 5 | OB | — | — | H | $^t$C$_4$H$_9$ | H | acac | |
| 5-171Y | Ir | 0 | 5 | OB | — | — | H | $^t$C$_4$H$_9$ | H | — | |
| 5-172 | Ir | 1 | 5 | OB | — | — | $^t$C$_4$H$_9$ | CH$_3$ | H | pic | |
| 5-172X | Ir | 1 | 5 | OB | — | — | $^t$C$_4$H$_9$ | CH$_3$ | H | acac | |
| 5-172Y | Ir | 0 | 5 | OB | — | — | $^t$C$_4$H$_9$ | CH$_3$ | H | — | |
| 5-173 | Ir | 1 | 5 | OB | — | — | $^t$C$_4$H$_9$ | $^t$C$_4$H$_9$ | H | pic | |
| 5-173X | Ir | 1 | 5 | OB | — | — | $^t$C$_4$H$_9$ | $^t$C$_4$H$_9$ | H | acac | |
| 5-173Y | Ir | 0 | 5 | OB | — | — | $^t$C$_4$H$_9$ | $^t$C$_4$H$_9$ | H | — | |
| 5-174 | Ir | 1 | 5 | OB | — | — | CH$_3$ | CH$_3$ | H | pic | |
| 5-174X | Ir | 1 | 5 | OB | — | — | CH$_3$ | CH$_3$ | H | acac | |
| 5-174Y | Ir | 0 | 5 | OB | — | — | CH$_3$ | CH$_3$ | H | — | |
| 5-175 | Ir | 1 | 5 | OB | — | — | CH$_3$ | $^t$C$_4$H$_9$ | H | pic | |
| 5-175X | Ir | 1 | 5 | OB | — | — | CH$_3$ | $^t$C$_4$H$_9$ | H | acac | |
| 5-175Y | Ir | 0 | 5 | OB | — | — | CH$_3$ | $^t$C$_4$H$_9$ | H | — | |
| 5-176 | Ir | 1 | 5 | Fu | — | — | H | CH$_3$ | H | pic | |
| 5-176X | Ir | 1 | 5 | Fu | — | — | H | CH$_3$ | H | acac | |
| 5-176Y | Ir | 0 | 5 | Fu | — | — | H | CH$_3$ | H | — | |
| 5-177 | Ir | 1 | 5 | Fu | — | — | H | $^t$C$_4$H$_9$ | H | pic | |
| 5-177X | Ir | 1 | 5 | Fu | — | — | H | $^t$C$_4$H$_9$ | H | acac | |
| 5-177Y | Ir | 0 | 5 | Fu | — | — | H | $^t$C$_4$H$_9$ | H | — | |
| 5-178 | Ir | 1 | 5 | Fu | — | — | $^t$C$_4$H$_9$ | CH$_3$ | H | pic | |
| 5-178X | Ir | 1 | 5 | Fu | — | — | $^t$C$_4$H$_9$ | CH$_3$ | H | acac | |
| 5-178Y | Ir | 0 | 5 | Fu | — | — | $^t$C$_4$H$_9$ | CH$_3$ | H | — | |
| 5-179 | Ir | 1 | 5 | Fu | — | — | $^t$C$_4$H$_9$ | $^t$C$_4$H$_9$ | H | pic | |
| 5-179X | Ir | 1 | 5 | Fu | — | — | $^t$C$_4$H$_9$ | $^t$C$_4$H$_9$ | H | acac | |
| 5-179Y | Ir | 0 | 5 | Fu | — | — | $^t$C$_4$H$_9$ | $^t$C$_4$H$_9$ | H | — | |
| 5-180 | Ir | 1 | 5 | Fu | — | — | CH$_3$ | CH$_3$ | H | pic | |
| 5-180X | Ir | 1 | 5 | Fu | — | — | CH$_3$ | CH$_3$ | H | acac | |
| 5-180Y | Ir | 0 | 5 | Fu | — | — | CH$_3$ | CH$_3$ | H | — | |
| 5-181 | Ir | 1 | 5 | Fu | — | — | CH$_3$ | $^t$C$_4$H$_9$ | H | pic | |
| 5-181X | Ir | 1 | 5 | Fu | — | — | CH$_3$ | $^t$C$_4$H$_9$ | H | acac | |
| 5-181Y | Ir | 0 | 5 | Fu | — | — | CH$_3$ | $^t$C$_4$H$_9$ | H | — | |
| 5-182 | Ir | 1 | 5 | Fl | — | — | H | CH$_3$ | H | pic | |
| 5-182X | Ir | 1 | 5 | Fl | — | — | H | CH$_3$ | H | acac | |
| 5-182Y | Ir | 0 | 5 | Fl | — | — | H | CH$_3$ | H | — | |
| 5-183 | Ir | 1 | 5 | Fl | — | — | H | $^t$C$_4$H$_9$ | H | pic | |
| 5-183X | Ir | 1 | 5 | Fl | — | — | H | $^t$C$_4$H$_9$ | H | acac | |
| 5-183Y | Ir | 0 | 5 | Fl | — | — | H | $^t$C$_4$H$_9$ | H | — | |
| 5-184 | Ir | 1 | 5 | Fl | — | — | $^t$C$_4$H$_9$ | CH$_3$ | H | pic | |
| 5-184X | Ir | 1 | 5 | Fl | — | — | $^t$C$_4$H$_9$ | CH$_3$ | H | acac | |
| 5-184Y | Ir | 0 | 5 | Fl | — | — | $^t$C$_4$H$_9$ | CH$_3$ | H | — | |
| 5-185 | Ir | 1 | 5 | Fl | — | — | $^t$C$_4$H$_9$ | $^t$C$_4$H$_9$ | H | pic | |
| 5-185X | Ir | 1 | 5 | Fl | — | — | $^t$C$_4$H$_9$ | $^t$C$_4$H$_9$ | H | acac | |
| 5-185Y | Ir | 0 | 5 | Fl | — | — | $^t$C$_4$H$_9$ | $^t$C$_4$H$_9$ | H | — | |
| 5-186 | Ir | 1 | 5 | Fl | — | — | CH$_3$ | CH$_3$ | H | pic | |
| 5-186X | Ir | 1 | 5 | Fl | — | — | CH$_3$ | CH$_3$ | H | acac | |
| 5-186Y | Ir | 0 | 5 | Fl | — | — | CH$_3$ | CH$_3$ | H | — | |
| 5-187 | Ir | 1 | 5 | Fl | — | — | CH$_3$ | $^t$C$_4$H$_9$ | H | pic | |
| 5-187X | Ir | 1 | 5 | Fl | — | — | CH$_3$ | $^t$C$_4$H$_9$ | H | acac | |
| 5-187Y | Ir | 0 | 5 | Fl | — | — | CH$_3$ | $^t$C$_4$H$_9$ | H | — | |
| 5-188 | Ir | 1 | 5 | Bz | — | — | H | CH$_3$ | H | pic | |
| 5-188X | Ir | 1 | 5 | Bz | — | — | H | CH$_3$ | H | acac | |
| 5-188Y | Ir | 0 | 5 | Bz | — | — | H | CH$_3$ | H | — | |
| 5-189 | Ir | 1 | 5 | Bz | — | — | H | $^t$C$_4$H$_9$ | H | pic | |
| 5-189X | Ir | 1 | 5 | Bz | — | — | H | $^t$C$_4$H$_9$ | H | acac | |
| 5-189Y | Ir | 0 | 5 | Bz | — | — | H | $^t$C$_4$H$_9$ | H | — | |
| 5-190 | Ir | 1 | 5 | Bz | — | — | $^t$C$_4$H$_9$ | CH$_3$ | H | pic | |
| 5-190X | Ir | 1 | 5 | Bz | — | — | $^t$C$_4$H$_9$ | CH$_3$ | H | acac | |
| 5-190Y | Ir | 0 | 5 | Bz | — | — | $^t$C$_4$H$_9$ | CH$_3$ | H | — | |
| 5-191 | Ir | 1 | 5 | Bz | — | — | $^t$C$_4$H$_9$ | $^t$C$_4$H$_9$ | H | pic | |
| 5-191X | Ir | 1 | 5 | Bz | — | — | $^t$C$_4$H$_9$ | $^t$C$_4$H$_9$ | H | acac | |
| 5-191Y | Ir | 0 | 5 | Bz | — | — | $^t$C$_4$H$_9$ | $^t$C$_4$H$_9$ | H | — | |
| 5-192 | Ir | 1 | 5 | Bz | — | — | CH$_3$ | CH$_3$ | H | pic | |
| 5-192X | Ir | 1 | 5 | Bz | — | — | CH$_3$ | CH$_3$ | H | acac | |
| 5-192Y | Ir | 0 | 5 | Bz | — | — | CH$_3$ | CH$_3$ | H | — | |
| 5-193 | Ir | 1 | 5 | Bz | — | — | CH$_3$ | $^t$C$_4$H$_9$ | H | pic | |
| 5-193X | Ir | 1 | 5 | Bz | — | — | CH$_3$ | $^t$C$_4$H$_9$ | H | acac | |
| 5-193Y | Ir | 0 | 5 | Bz | — | — | CH$_3$ | $^t$C$_4$H$_9$ | H | — | |
| 5-194 | Ir | 1 | 5 | Qu | — | — | H | CH$_3$ | H | pic | |
| 5-194X | Ir | 1 | 5 | Bz | — | — | H | CH$_3$ | H | acac | |

TABLE 12-continued

| No. | M | n | BSS | SS | G | T¹ | T² | T⁵ | T⁶ | T⁷ | L¹ | L² |
|---|---|---|---|---|---|---|---|---|---|---|---|---|
| 5-194Y | Ir | 0 | 5 | | Bz | — | — | H | CH$_3$ | H | — | — |
| 5-195 | Ir | 1 | 5 | | Bz | — | — | H | $^tC_4H_9$ | H | pic | |
| 5-195X | Ir | 1 | 5 | | Bz | — | — | H | $^tC_4H_9$ | H | acac | |
| 5-195Y | Ir | 0 | 5 | | Bz | — | — | H | $^tC_4H_9$ | H | — | — |
| 5-196 | Ir | 1 | 5 | | Bz | — | — | $^tC_4H_9$ | CH$_3$ | H | pic | |
| 5-196X | Ir | 1 | 5 | | Bz | — | — | $^tC_4H_9$ | CH$_3$ | H | acac | |
| 5-196Y | Ir | 0 | 5 | | Bz | — | — | $^tC_4H_9$ | CH$_3$ | H | — | — |
| 5-197 | Ir | 1 | 5 | | Bz | — | — | $^tC_4H_9$ | $^tC_4H_9$ | H | pic | |
| 5-197X | Ir | 1 | 5 | | Bz | — | — | $^tC_4H_9$ | $^tC_4H_9$ | H | acac | |
| 5-197Y | Ir | 0 | 5 | | Bz | — | — | $^tC_4H_9$ | $^tC_4H_9$ | H | — | — |
| 5-198 | Ir | 1 | 5 | | Bz | — | — | CH$_3$ | CH$_3$ | H | pic | |
| 5-198X | Ir | 1 | 5 | | Bz | — | — | CH$_3$ | CH$_3$ | H | acac | |
| 5-198Y | Ir | 0 | 5 | | Bz | — | — | CH$_3$ | CH$_3$ | H | — | — |
| 5-199 | Ir | 1 | 5 | | Bz | — | — | CH$_3$ | $^tC_4H_9$ | H | pic | |
| 5-199X | Ir | 1 | 5 | | Bz | — | — | CH$_3$ | $^tC_4H_9$ | H | acac | |
| 5-199Y | Ir | 0 | 5 | | Bz | — | — | CH$_3$ | $^tC_4H_9$ | H | — | — |
| 5-200 | Ir | 1 | 5 | | OL | H | $^nC_4H_9$ | H | CH$_3$ | H | pic | |
| 5-200X | Ir | 1 | 5 | | OL | H | $^nC_4H_9$ | H | CH$_3$ | H | acac | |
| 5-200Y | Ir | 0 | 5 | | OL | H | $^nC_4H_9$ | H | CH$_3$ | H | — | — |
| 5-201 | Ir | 1 | 5 | | OL | H | $^nC_4H_9$ | H | $^tC_4H_9$ | H | pic | |
| 5-201X | Ir | 1 | 5 | | OL | H | $^nC_4H_9$ | H | $^tC_4H_9$ | H | acac | |
| 5-201Y | Ir | 0 | 5 | | OL | H | $^nC_4H_9$ | H | $^tC_4H_9$ | H | — | — |
| 5-202 | Ir | 1 | 5 | | OL | H | $^tC_4H_9$ | H | CH$_3$ | H | pic | |
| 5-202X | Ir | 1 | 5 | | OL | H | $^tC_4H_9$ | H | CH$_3$ | H | acac | |
| 5-202Y | Ir | 0 | 5 | | OL | H | $^tC_4H_9$ | H | CH$_3$ | H | — | — |
| 5-203 | Ir | 1 | 5 | | OL | H | $^tC_4H_9$ | H | $^tC_4H_9$ | H | pic | |
| 5-203X | Ir | 1 | 5 | | OL | H | $^tC_4H_9$ | H | $^tC_4H_9$ | H | acac | |
| 5-203Y | Ir | 0 | 5 | | OL | H | $^tC_4H_9$ | H | $^tC_4H_9$ | H | — | — |
| 5-204 | Ir | 1 | 5 | | OL | CH$_3$ | $^nC_4H_9$ | H | CH$_3$ | H | pic | |
| 5-204X | Ir | 1 | 5 | | OL | CH$_3$ | $^nC_4H_9$ | H | CH$_3$ | H | acac | |
| 5-204Y | Ir | 0 | 5 | | OL | CH$_3$ | $^nC_4H_9$ | H | CH$_3$ | H | — | — |
| 5-205 | Ir | 1 | 5 | | OL | CH$_3$ | $^tC_4H_9$ | H | CH$_3$ | H | pic | |
| 5-205X | Ir | 1 | 5 | | OL | CH$_3$ | $^tC_4H_9$ | H | CH$_3$ | H | acac | |
| 5-205Y | Ir | 0 | 5 | | OL | CH$_3$ | $^tC_4H_9$ | H | CH$_3$ | H | — | — |
| 5-206 | Ir | 1 | 5 | | OL | H | H | H | CH$_3$ | H | pic | |
| 5-206X | Ir | 1 | 5 | | OL | H | H | H | CH$_3$ | H | acac | |
| 5-206Y | Ir | 0 | 5 | | OL | H | H | H | CH$_3$ | H | — | — |
| 5-207 | Ir | 1 | 5 | | OL | H | $^nC_4H_9$ | CH$_3$ | $^tC_4H_9$ | H | pic | |
| 5-207X | Ir | 1 | 5 | | OL | H | $^nC_4H_9$ | CH$_3$ | $^tC_4H_9$ | H | acac | |
| 5-207Y | Ir | 0 | 5 | | OL | H | $^nC_4H_9$ | CH$_3$ | $^tC_4H_9$ | H | — | — |
| 5-208 | Ir | 1 | 5 | | OL | H | $^tC_4H_9$ | CH$_3$ | $^tC_4H_9$ | H | pic | |
| 5-208X | Ir | 1 | 5 | | OL | H | $^tC_4H_9$ | CH$_3$ | $^tC_4H_9$ | H | acac | |
| 5-208Y | Ir | 0 | 5 | | OL | H | $^tC_4H_9$ | CH$_3$ | $^tC_4H_9$ | H | — | — |
| 5-209 | Ir | 1 | 5 | | OL | —CH$_2$CH$_2$CH$_2$— | | H | CH$_3$ | H | pic | |
| 5-209X | Ir | 1 | 5 | | OL | —CH$_2$CH$_2$CH$_2$— | | H | CH$_3$ | H | acac | |
| 5-209Y | Ir | 0 | 5 | | OL | —CH$_2$CH$_2$CH$_2$— | | H | CH$_3$ | H | — | — |
| 5-210 | Ir | 1 | 5 | | OL | —CH$_2$CH$_2$CH$_2$— | | H | $^tC_4H_9$ | H | pic | |
| 5-210X | Ir | 1 | 5 | | OL | —CH$_2$CH$_2$CH$_2$— | | H | $^tC_4H_9$ | H | acac | |
| 5-210Y | Ir | 0 | 5 | | OL | —CH$_2$CH$_2$CH$_2$— | | H | $^tC_4H_9$ | H | — | — |

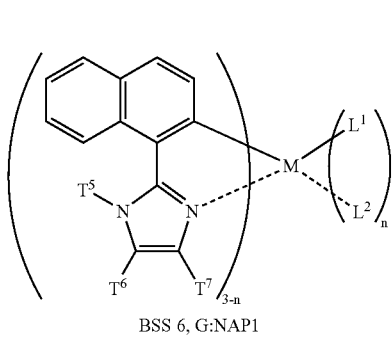

BSS 6, G:NAP1

-continued

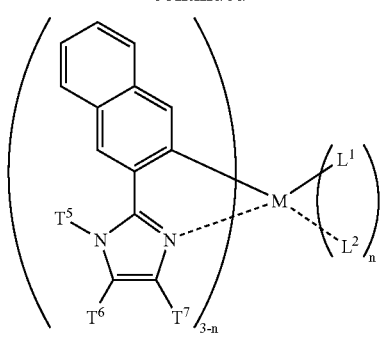

BSS 6, G:NAP2

-continued
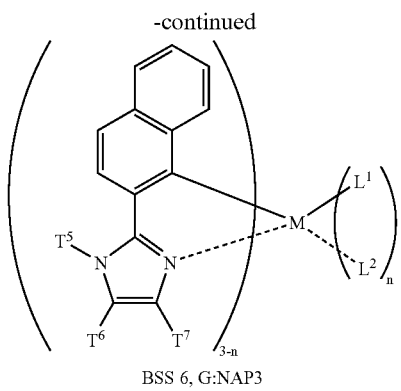
BSS 6, G:NAP3
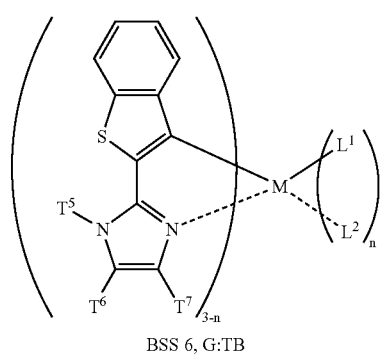
BSS 6, G:TB
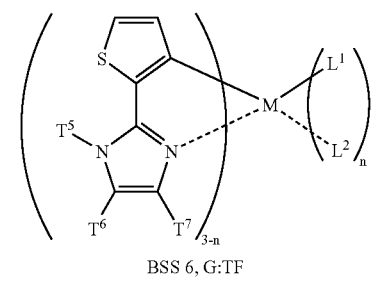
BSS 6, G:TF
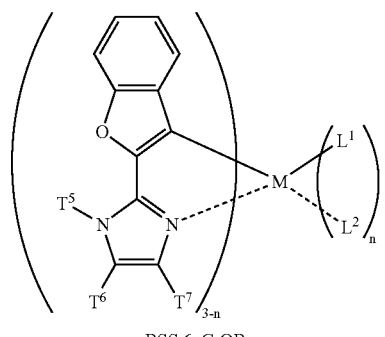
BSS 6, G:OB
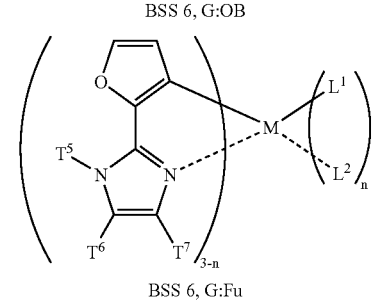
BSS 6, G:Fu
-continued
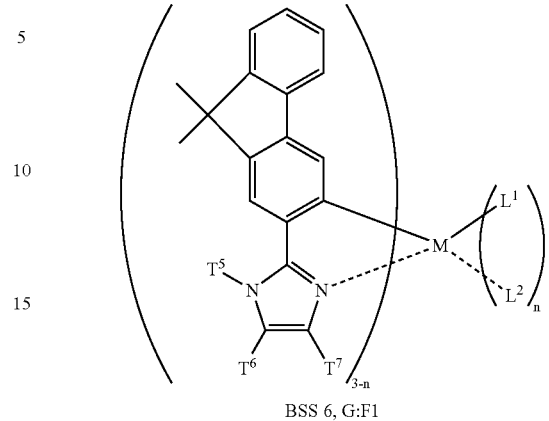
BSS 6, G:F1
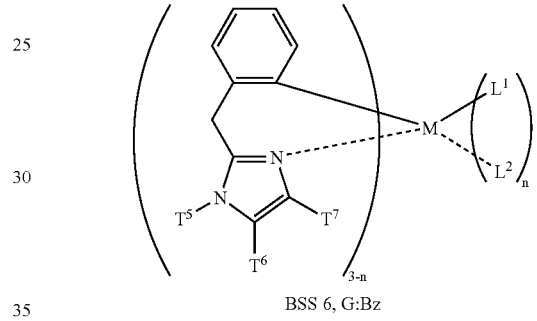
BSS 6, G:Bz
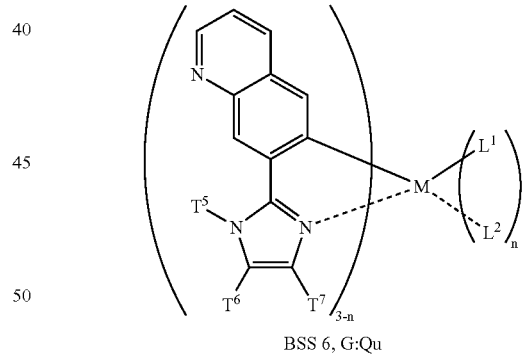
BSS 6, G:Qu
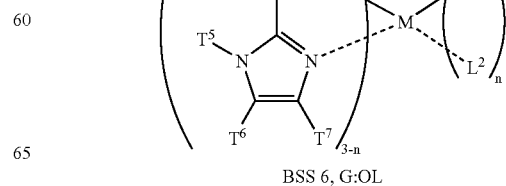
BSS 6, G:OL

TABLE 13

| No. | M | n | BSS | SS G | T$^1$ | T$^2$ | T$^5$ | T$^6$ | T$^7$ | L$^1$ | L$^2$ |
|---|---|---|---|---|---|---|---|---|---|---|---|
| 6-138 | Ir | 1 | 6 | Nap1 | — | — | CH$_3$ | H | H | pic | |
| 6-138X | Ir | 1 | 6 | Nap1 | — | — | CH$_3$ | H | H | acac | |
| 6-138Y | Ir | 0 | 6 | Nap1 | — | — | CH$_3$ | H | H | — | |
| 6-139 | Ir | 1 | 6 | Nap1 | — | — | $^t$C$_4$H$_9$ | H | H | pic | |
| 6-139X | Ir | 1 | 6 | Nap1 | — | — | $^t$C$_4$H$_9$ | H | H | acac | |
| 6-139Y | Ir | 0 | 6 | Nap1 | — | — | $^t$C$_4$H$_9$ | H | H | — | |
| 6-140 | Ir | 1 | 6 | Nap2 | — | — | CH$_3$ | H | H | pic | |
| 6-140X | Ir | 1 | 6 | Nap2 | — | — | CH$_3$ | H | H | acac | |
| 6-140Y | Ir | 0 | 6 | Nap2 | — | — | CH$_3$ | H | H | — | |
| 6-141 | Ir | 1 | 6 | Nap2 | — | — | $^t$C$_4$H$_9$ | H | H | pic | |
| 6-141X | Ir | 1 | 6 | Nap2 | — | — | $^t$C$_4$H$_9$ | H | H | acac | |
| 6-141Y | Ir | 0 | 6 | Nap2 | — | — | $^t$C$_4$H$_9$ | H | H | — | |
| 6-142 | Ir | 1 | 6 | Nap3 | — | — | CH$_3$ | H | H | pic | |
| 6-142X | Ir | 1 | 6 | Nap3 | — | — | CH$_3$ | H | H | acac | |
| 6-142Y | Ir | 0 | 6 | Nap3 | — | — | CH$_3$ | H | H | — | |
| 6-143 | Ir | 1 | 6 | Nap3 | — | — | $^t$C$_4$H$_9$ | H | H | pic | |
| 6-143X | Ir | 1 | 6 | Nap3 | — | — | $^t$C$_4$H$_9$ | H | H | acac | |
| 6-143Y | Ir | 0 | 6 | Nap3 | — | — | $^t$C$_4$H$_9$ | H | H | — | |
| 6-144 | Ir | 1 | 6 | TB | — | — | CH$_3$ | H | H | pic | |
| 6-144X | Ir | 1 | 6 | TB | — | — | CH$_3$ | H | H | acac | |
| 6-144Y | Ir | 0 | 6 | TB | — | — | CH$_3$ | H | H | — | |
| 6-145 | Ir | 1 | 6 | TB | — | — | $^t$C$_4$H$_9$ | H | H | pic | |
| 6-145X | Ir | 1 | 6 | TB | — | — | $^t$C$_4$H$_9$ | H | H | acac | |
| 6-145Y | Ir | 0 | 6 | TB | — | — | $^t$C$_4$H$_9$ | H | H | — | |
| 6-146 | Ir | 1 | 6 | TF | — | — | CH$_3$ | H | H | pic | |
| 6-146X | Ir | 1 | 6 | TF | — | — | CH$_3$ | H | H | acac | |
| 6-146Y | Ir | 0 | 6 | TF | — | — | CH$_3$ | H | H | — | |
| 6-147 | Ir | 1 | 6 | TF | — | — | $^t$C$_4$H$_9$ | H | H | pic | |
| 6-147X | Ir | 1 | 6 | TF | — | — | $^t$C$_4$H$_9$ | H | H | acac | |
| 6-147Y | Ir | 0 | 6 | TF | — | — | $^t$C$_4$H$_9$ | H | H | — | |
| 6-148 | Ir | 1 | 6 | OB | — | — | CH$_3$ | H | H | pic | |
| 6-148X | Ir | 1 | 6 | OB | — | — | CH$_3$ | H | H | acac | |
| 6-148Y | Ir | 0 | 6 | OB | — | — | CH$_3$ | H | H | — | |
| 6-149 | Ir | 1 | 6 | OB | — | — | $^t$C$_4$H$_9$ | H | H | pic | |
| 6-149X | Ir | 1 | 6 | OB | — | — | $^t$C$_4$H$_9$ | H | H | acac | |
| 6-149Y | Ir | 0 | 6 | OB | — | — | $^t$C$_4$H$_9$ | H | H | — | |
| 6-150 | Ir | 1 | 6 | Fu | — | — | CH$_3$ | H | H | pic | |
| 6-150X | Ir | 1 | 6 | Fu | — | — | CH$_3$ | H | H | acac | |
| 6-150Y | Ir | 0 | 6 | Fu | — | — | CH$_3$ | H | H | — | |
| 6-151 | Ir | 1 | 6 | Fu | — | — | $^t$C$_4$H$_9$ | H | H | pic | |
| 6-151X | Ir | 1 | 6 | Fu | — | — | $^t$C$_4$H$_9$ | H | H | acac | |
| 6-151Y | Ir | 0 | 6 | Fu | — | — | $^t$C$_4$H$_9$ | H | H | — | |
| 6-152 | Ir | 1 | 6 | Fl | — | — | CH$_3$ | H | H | pic | |
| 6-152X | Ir | 1 | 6 | Fl | — | — | CH$_3$ | H | H | acac | |
| 6-152Y | Ir | 0 | 6 | Fl | — | — | CH$_3$ | H | H | — | |
| 6-153 | Ir | 1 | 6 | Fl | — | — | $^t$C$_4$H$_9$ | H | H | pic | |
| 6-153X | Ir | 1 | 6 | Fl | — | — | $^t$C$_4$H$_9$ | H | H | acac | |
| 6-153Y | Ir | 0 | 6 | Fl | — | — | $^t$C$_4$H$_9$ | H | H | — | |
| 6-154 | Ir | 1 | 6 | Bz | — | — | CH$_3$ | H | H | pic | |
| 6-154X | Ir | 1 | 6 | Bz | — | — | CH$_3$ | H | H | acac | |
| 6-154Y | Ir | 0 | 6 | Bz | — | — | CH$_3$ | H | H | — | |
| 6-155 | Ir | 1 | 6 | Bz | — | — | $^t$C$_4$H$_9$ | H | H | pic | |
| 6-155X | Ir | 1 | 6 | Bz | — | — | $^t$C$_4$H$_9$ | H | H | acac | |
| 6-155Y | Ir | 0 | 6 | Bz | — | — | $^t$C$_4$H$_9$ | H | H | — | |
| 6-156 | Ir | 1 | 6 | Qu | — | — | CH$_3$ | H | H | pic | |
| 6-156X | Ir | 1 | 6 | Qu | — | — | CH$_3$ | H | H | acac | |
| 6-156Y | Ir | 0 | 6 | Qu | — | — | CH$_3$ | H | H | — | |
| 6-157 | Ir | 1 | 6 | Qu | — | — | $^t$C$_4$H$_9$ | H | H | pic | |
| 6-157X | Ir | 1 | 6 | Qu | — | — | $^t$C$_4$H$_9$ | H | H | acac | |
| 6-157Y | Ir | 0 | 6 | Qu | — | — | $^t$C$_4$H$_9$ | H | H | — | |
| 6-158 | Ir | 1 | 6 | OL | H | $^n$C$_4$H$_9$ | CH$_3$ | H | H | pic | |
| 6-158X | Ir | 1 | 6 | OL | H | $^n$C$_4$H$_9$ | CH$_3$ | H | H | acac | |
| 6-158Y | Ir | 0 | 6 | OL | H | $^n$C$_4$H$_9$ | CH$_3$ | H | H | — | |
| 6-159 | Ir | 1 | 6 | OL | H | $^n$C$_4$H$_9$ | $^t$C$_4$H$_9$ | H | H | pic | |
| 6-159X | Ir | 1 | 6 | OL | H | $^n$C$_4$H$_9$ | $^t$C$_4$H$_9$ | H | H | acac | |
| 6-159Y | Ir | 0 | 6 | OL | H | $^n$C$_4$H$_9$ | $^t$C$_4$H$_9$ | H | H | — | |
| 6-160 | Ir | 1 | 6 | OL | H | $^t$C$_4$H$_9$ | CH$_3$ | H | H | pic | |
| 6-160X | Ir | 1 | 6 | OL | H | $^t$C$_4$H$_9$ | CH$_3$ | H | H | acac | |
| 6-160Y | Ir | 0 | 6 | OL | H | $^t$C$_4$H$_9$ | CH$_3$ | H | H | — | |
| 6-161 | Ir | 1 | 6 | OL | H | $^t$C$_4$H$_9$ | $^t$C$_4$H$_9$ | H | H | pic | |
| 6-161X | Ir | 1 | 6 | OL | H | $^t$C$_4$H$_9$ | $^t$C$_4$H$_9$ | H | H | acac | |
| 6-161Y | Ir | 0 | 6 | OL | H | $^t$C$_4$H$_9$ | $^t$C$_4$H$_9$ | H | H | — | |
| 6-162 | Ir | 1 | 6 | OL | CH$_3$ | $^n$C$_4$H$_9$ | CH$_3$ | H | H | pic | |
| 6-162X | Ir | 1 | 6 | OL | CH$_3$ | $^n$C$_4$H$_9$ | CH$_3$ | H | H | acac | |
| 6-162Y | Ir | 0 | 6 | OL | CH$_3$ | $^n$C$_4$H$_9$ | CH$_3$ | H | H | — | |
| 6-163 | Ir | 1 | 6 | OL | CH$_3$ | $^t$C$_4$H$_9$ | CH$_3$ | H | H | pic | |
| 6-163X | Ir | 1 | 6 | OL | CH$_3$ | $^t$C$_4$H$_9$ | CH$_3$ | H | H | acac | |

TABLE 13-continued
| No. | M | n | BSS | SS G | T¹ | T² | T⁵ | T⁶ | T⁷ | L¹ | L² |
|---|---|---|---|---|---|---|---|---|---|---|---|
| 6-163Y | Ir | 0 | 6 | OL | CH₃ | ᵗC₄H₉ | CH₃ | H | H | — | — |
| 6-164 | Ir | 1 | 6 | OL | H | H | CH₃ | H | H | | pic |
| 6-164X | Ir | 1 | 6 | OL | H | H | CH₃ | H | H | | acac |
| 6-164Y | Ir | 0 | 6 | OL | H | H | CH₃ | H | H | — | — |
| 6-165 | Ir | 1 | 6 | OL | —CH₂CH₂CH₂— | | CH₃ | H | H | | pic |
| 6-165X | Ir | 1 | 6 | OL | —CH₂CH₂CH₂— | | CH₃ | H | H | | acac |
| 6-165Y | Ir | 0 | 6 | OL | —CH₂CH₂CH₂— | | CH₃ | H | H | — | — |
| 6-166 | Ir | 1 | 6 | OL | —CH₂CH₂CH₂— | | ᵗC₄H₉ | H | H | | pic |
| 6-166X | Ir | 1 | 6 | OL | —CH₂CH₂CH₂— | | ᵗC₄H₉ | H | H | | acac |
| 6-166Y | Ir | 0 | 6 | OL | —CH₂CH₂CH₂— | | ᵗC₄H₉ | H | H | — | — |
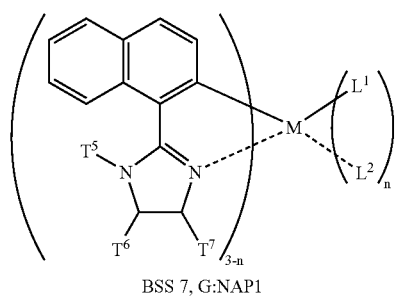
BSS 7, G:NAP1
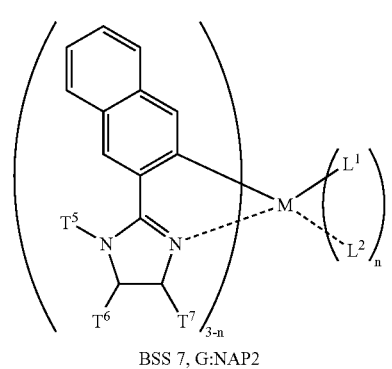
BSS 7, G:NAP2
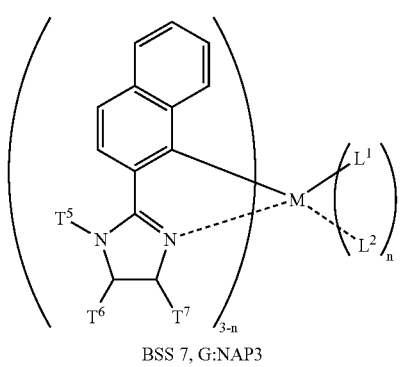
BSS 7, G:NAP3
-continued
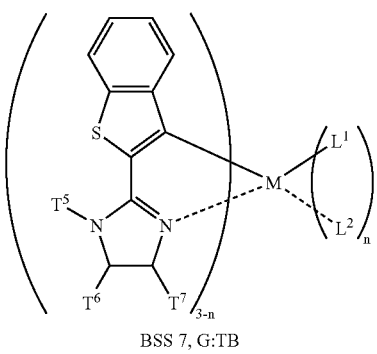
BSS 7, G:TB
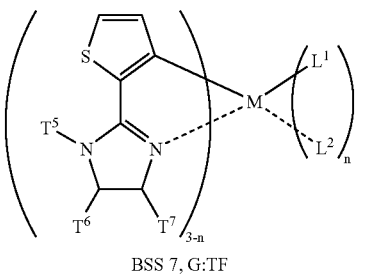
BSS 7, G:TF
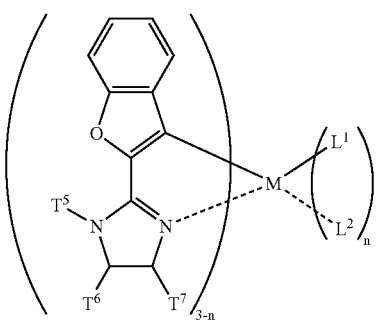
BSS 7, G:OB
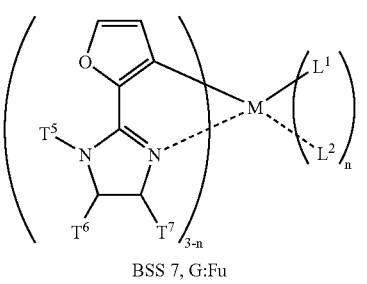
BSS 7, G:Fu

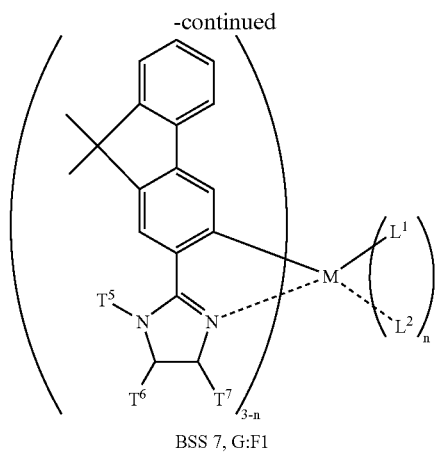

BSS 7, G:Fl

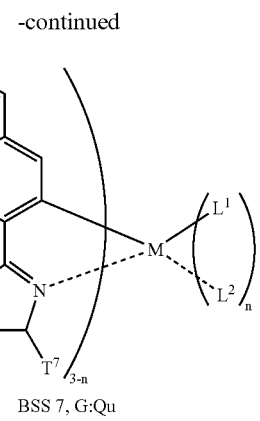

BSS 7, G:Qu

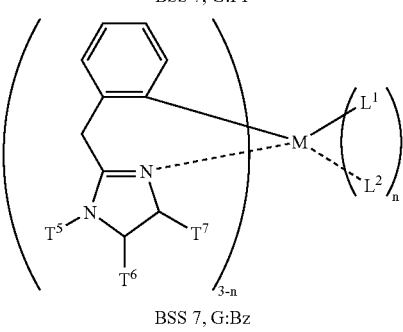

BSS 7, G:Bz

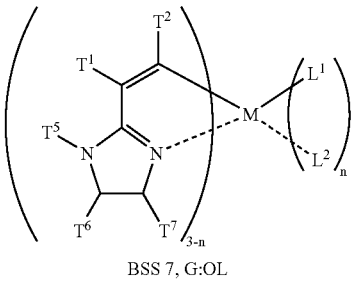

BSS 7, G:OL

TABLE 14

| No. | M | n | BSS | SS G | T¹ | T² | T⁵ | T⁶ | T⁷ | L¹ | L² |
|---|---|---|---|---|---|---|---|---|---|---|---|
| 7-138 | Ir | 1 | 7 | Nap1 | — | — | $CH_3$ | H | H | pic | |
| 7-138X | Ir | 1 | 7 | Nap1 | — | — | $CH_3$ | H | H | acac | |
| 7-138Y | Ir | 0 | 7 | Nap1 | — | — | $CH_3$ | H | H | — | — |
| 7-139 | Ir | 1 | 7 | Nap1 | — | — | $^tC_4H_9$ | H | H | pic | |
| 7-139X | Ir | 1 | 7 | Nap1 | — | — | $^tC_4H_9$ | H | H | acac | |
| 7-139Y | Ir | 0 | 7 | Nap1 | — | — | $^tC_4H_9$ | H | H | — | — |
| 7-140 | Ir | 1 | 7 | Nap2 | — | — | $CH_3$ | H | H | pic | |
| 7-140X | Ir | 1 | 7 | Nap2 | — | — | $CH_3$ | H | H | acac | |
| 7-140Y | Ir | 0 | 7 | Nap2 | — | — | $CH_3$ | H | H | — | — |
| 7-141 | Ir | 1 | 7 | Nap2 | — | — | $^tC_4H_9$ | H | H | pic | |
| 7-141X | Ir | 1 | 7 | Nap2 | — | — | $^tC_4H_9$ | H | H | acac | |
| 7-141Y | Ir | 0 | 7 | Nap2 | — | — | $^tC_4H_9$ | H | H | — | — |
| 7-142 | Ir | 1 | 7 | Nap3 | — | — | $CH_3$ | H | H | pic | |
| 7-142X | Ir | 1 | 7 | Nap3 | — | — | $CH_3$ | H | H | acac | |
| 7-142Y | Ir | 0 | 7 | Nap3 | — | — | $CH_3$ | H | H | — | — |
| 7-143 | Ir | 1 | 7 | Nap3 | — | — | $^tC_4H_9$ | H | H | pic | |
| 7-143X | Ir | 1 | 7 | Nap3 | — | — | $^tC_4H_9$ | H | H | acac | |
| 7-143Y | Ir | 0 | 7 | Nap3 | — | — | $^tC_4H_9$ | H | H | — | — |
| 7-144 | Ir | 1 | 7 | TB | — | — | $CH_3$ | H | H | pic | |
| 7-144X | Ir | 1 | 7 | TB | — | — | $CH_3$ | H | H | acac | |
| 7-144Y | Ir | 0 | 7 | TB | — | — | $CH_3$ | H | H | — | — |
| 7-145 | Ir | 1 | 7 | TB | — | — | $^tC_4H_9$ | H | H | pic | |
| 7-145X | Ir | 1 | 7 | TB | — | — | $^tC_4H_9$ | H | H | acac | |
| 7-145Y | Ir | 0 | 7 | TB | — | — | $^tC_4H_9$ | H | H | — | — |
| 7-146 | Ir | 1 | 7 | TF | — | — | $CH_3$ | H | H | pic | |
| 7-146X | Ir | 1 | 7 | TF | — | — | $CH_3$ | H | H | acac | |
| 7-146Y | Ir | 0 | 7 | TF | — | — | $CH_3$ | H | H | — | — |
| 7-147 | Ir | 1 | 7 | TF | — | — | $^tC_4H_9$ | H | H | pic | |
| 7-147X | Ir | 1 | 7 | TF | — | — | $^tC_4H_9$ | H | H | acac | |
| 7-147Y | Ir | 0 | 7 | TF | — | — | $^tC_4H_9$ | H | H | — | — |
| 7-148 | Ir | 1 | 7 | OB | — | — | $CH_3$ | H | H | pic | |
| 7-148X | Ir | 1 | 7 | OB | — | — | $CH_3$ | H | H | acac | |
| 7-148Y | Ir | 0 | 7 | OB | — | — | $CH_3$ | H | H | — | — |
| 7-149 | Ir | 1 | 7 | OB | — | — | $^tC_4H_9$ | H | H | pic | |
| 7-149X | Ir | 1 | 7 | OB | — | — | $^tC_4H_9$ | H | H | acac | |
| 7-149Y | Ir | 0 | 7 | OB | — | — | $^tC_4H_9$ | H | H | — | — |
| 7-150 | Ir | 1 | 7 | Fu | — | — | $CH_3$ | H | H | pic | |

TABLE 14-continued

| No. | M | n | BSS | SS G | T¹ | T² | T⁵ | T⁶ | T⁷ | L¹ | L² |
|---|---|---|---|---|---|---|---|---|---|---|---|
| 7-150X | Ir | 1 | 7 | Fu | — | — | $CH_3$ | H | H | acac | |
| 7-150Y | Ir | 0 | 7 | Fu | — | — | $CH_3$ | H | H | — | — |
| 7-151 | Ir | 1 | 7 | Fu | — | — | $^tC_4H_9$ | H | H | pic | |
| 7-151X | Ir | 1 | 7 | Fu | — | — | $^tC_4H_9$ | H | H | acac | |
| 7-151Y | Ir | 0 | 7 | Fu | — | — | $^tC_4H_9$ | H | H | — | — |
| 7-152 | Ir | 1 | 7 | Fl | — | — | $CH_3$ | H | H | pic | |
| 7-152X | Ir | 1 | 7 | Fl | — | — | $CH_3$ | H | H | acac | |
| 7-152Y | Ir | 0 | 7 | Fl | — | — | $CH_3$ | H | H | — | — |
| 7-153 | Ir | 1 | 7 | Fl | — | — | $^tC_4H_9$ | H | H | pic | |
| 7-153X | Ir | 1 | 7 | Fl | — | — | $^tC_4H_9$ | H | H | acac | |
| 7-153Y | Ir | 0 | 7 | Fl | — | — | $^tC_4H_9$ | H | H | — | — |
| 7-154 | Ir | 1 | 7 | Bz | — | — | $CH_3$ | H | H | pic | |
| 7-154X | Ir | 1 | 7 | Bz | — | — | $CH_3$ | H | H | acac | |
| 7-154Y | Ir | 0 | 7 | Bz | — | — | $CH_3$ | H | H | — | — |
| 7-155 | Ir | 1 | 7 | Bz | — | — | $^tC_4H_9$ | H | H | pic | |
| 7-155X | Ir | 1 | 7 | Bz | — | — | $^tC_4H_9$ | H | H | acac | |
| 7-155Y | Ir | 0 | 7 | Bz | — | — | $^tC_4H_9$ | H | H | — | — |
| 7-156 | Ir | 1 | 7 | Qu | — | — | $CH_3$ | H | H | pic | |
| 7-156X | Ir | 1 | 7 | Qu | — | — | $CH_3$ | H | H | acac | |
| 7-156Y | Ir | 0 | 7 | Qu | — | — | $CH_3$ | H | H | — | — |
| 7-157 | Ir | 1 | 7 | Qu | — | — | $^tC_4H_9$ | H | H | pic | |
| 7-157X | Ir | 1 | 7 | Qu | — | — | $^tC_4H_9$ | H | H | acac | |
| 7-157Y | Ir | 0 | 7 | Qu | — | — | $^tC_4H_9$ | H | H | — | — |
| 7-158 | Ir | 1 | 7 | OL | H | $^nC_4H_9$ | $CH_3$ | H | H | pic | |
| 7-158X | Ir | 1 | 7 | OL | H | $^nC_4H_9$ | $CH_3$ | H | H | acac | |
| 7-158Y | Ir | 0 | 7 | OL | H | $^nC_4H_9$ | $CH_3$ | H | H | — | — |
| 7-159 | Ir | 1 | 7 | OL | H | $^nC_4H_9$ | $^tC_4H_9$ | H | H | pic | |
| 7-159X | Ir | 1 | 7 | OL | H | $^nC_4H_9$ | $^tC_4H_9$ | H | H | acac | |
| 7-159Y | Ir | 0 | 7 | OL | H | $^nC_4H_9$ | $^tC_4H_9$ | H | H | — | — |
| 7-160 | Ir | 1 | 7 | OL | H | $^tC_4H_9$ | $CH_3$ | H | H | pic | |
| 7-160X | Ir | 1 | 7 | OL | H | $^tC_4H_9$ | $CH_3$ | H | H | acac | |
| 7-160Y | Ir | 0 | 7 | OL | H | $^tC_4H_9$ | $CH_3$ | H | H | — | — |
| 7-161 | Ir | 1 | 7 | OL | H | $^tC_4H_9$ | $^tC_4H_9$ | H | H | pic | |
| 7-161X | Ir | 1 | 7 | OL | H | $^tC_4H_9$ | $^tC_4H_9$ | H | H | acac | |
| 7-161Y | Ir | 0 | 7 | OL | H | $^tC_4H_9$ | $^tC_4H_9$ | H | H | — | — |
| 7-162 | Ir | 1 | 7 | OL | $CH_3$ | $^nC_4H_9$ | $CH_3$ | H | H | pic | |
| 7-162X | Ir | 1 | 7 | OL | $CH_3$ | $^nC_4H_9$ | $CH_3$ | H | H | acac | |
| 7-162Y | Ir | 0 | 7 | OL | $CH_3$ | $^nC_4H_9$ | $CH_3$ | H | H | — | — |
| 7-163 | Ir | 1 | 7 | OL | $CH_3$ | $^tC_4H_9$ | $CH_3$ | H | H | pic | |
| 7-163X | Ir | 1 | 7 | OL | $CH_3$ | $^tC_4H_9$ | $CH_3$ | H | H | acac | |
| 7-163Y | Ir | 0 | 7 | OL | $CH_3$ | $^tC_4H_9$ | $CH_3$ | H | H | — | — |
| 7-164 | Ir | 1 | 7 | OL | H | H | $CH_3$ | H | H | pic | |
| 7-164X | Ir | 1 | 7 | OL | H | H | $CH_3$ | H | H | acac | |
| 7-164Y | Ir | 0 | 7 | OL | H | H | $CH_3$ | H | H | — | — |
| 7-165 | Ir | 1 | 7 | OL | —$CH_2CH_2CH_2$— | | $CH_3$ | H | H | pic | |
| 7-165X | Ir | 1 | 7 | OL | —$CH_2CH_2CH_2$— | | $CH_3$ | H | H | acac | |
| 7-165Y | Ir | 0 | 7 | OL | —$CH_2CH_2CH_2$— | | $CH_3$ | H | H | — | — |
| 7-166 | Ir | 1 | 7 | OL | —$CH_2CH_2CH_2$— | | $^tC_4H_9$ | H | H | pic | |
| 7-166X | Ir | 1 | 7 | OL | —$CH_2CH_2CH_2$— | | $^tC_4H_9$ | H | H | acac | |
| 7-166Y | Ir | 0 | 7 | OL | —$CH_2CH_2CH_2$— | | $^tC_4H_9$ | H | H | — | — |

-continued

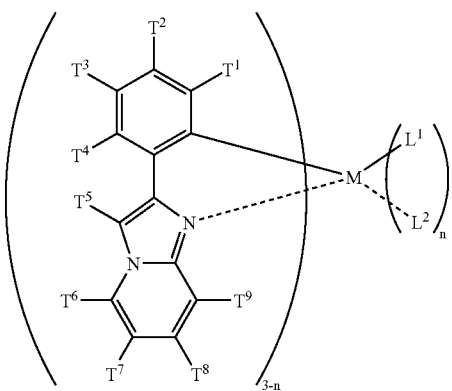

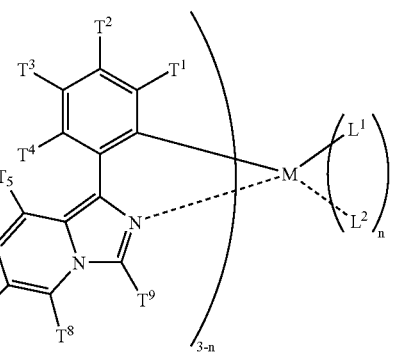

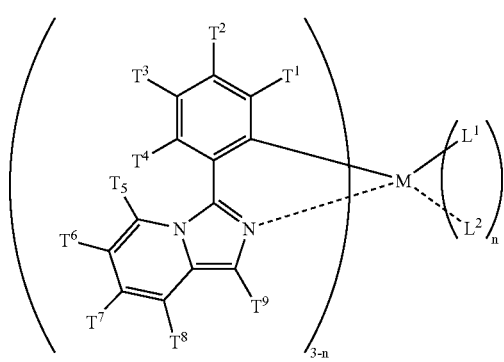

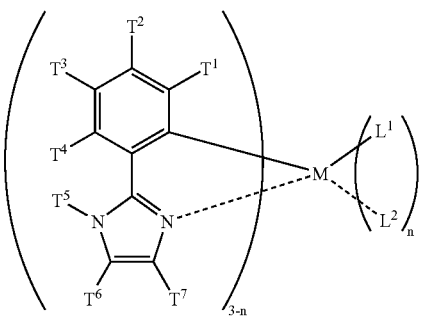

TABLE 15

| No. | M | n | BSS | SS | G | T¹ | T² | T³ | T⁴ | T⁵ | T⁶ | T⁷ | T⁸ | T⁹ | L¹ L² |
|---|---|---|---|---|---|---|---|---|---|---|---|---|---|---|---|
| 1-187 | Rh | 1 | 1 | | Ph | H | H | H | H | H | H | H | H | H | pic |
| 1-187X | Rh | 1 | 1 | | Ph | H | H | H | H | H | H | H | H | H | acac |
| 1-187Y | Rh | 0 | 1 | | Ph | H | H | H | H | H | H | H | H | H | — — |
| 1-188 | Rh | 1 | 1 | | Ph | H | F | H | F | H | H | H | H | H | pic |
| 1-188X | Rh | 1 | 1 | | Ph | H | F | H | F | H | H | H | H | H | acac |
| 1-188Y | Rh | 0 | 1 | | Ph | H | F | H | F | H | H | H | H | H | — — |
| 1-189 | Rh | 1 | 1 | | Ph | F | H | H | F | H | H | H | H | H | pic |
| 1-189X | Rh | 1 | 1 | | Ph | F | H | H | F | H | H | H | H | H | acac |
| 1-189Y | Rh | 0 | 1 | | Ph | F | H | H | F | H | H | H | H | H | — — |
| 1-190 | Rh | 1 | 1 | | Ph | $CF_3$ | H | $CF_3$ | H | H | H | H | H | H | pic |
| 1-190X | Rh | 1 | 1 | | Ph | $CF_3$ | H | $CF_3$ | H | H | H | H | H | H | acac |
| 1-190Y | Rh | 0 | 1 | | Ph | $CF_3$ | H | $CF_3$ | H | H | H | H | H | H | — — |
| 1-191 | Rh | 1 | 1 | | Ph | H | F | $CF_3$ | H | H | H | H | H | H | pic |
| 1-191X | Rh | 1 | 1 | | Ph | H | F | $CF_3$ | H | H | H | H | H | H | acac |
| 1-191Y | Rh | 0 | 1 | | Ph | H | F | $CF_3$ | H | H | H | H | H | H | — — |
| 1-192 | Rh | 1 | 1 | | Ph | F | H | $CF_3$ | H | H | H | H | H | H | pic |
| 1-192X | Rh | 1 | 1 | | Ph | F | H | $CF_3$ | H | H | H | H | H | H | acac |
| 1-192Y | Rh | 0 | 1 | | Ph | F | H | $CF_3$ | H | H | H | H | H | H | — — |
| 1-193 | Rh | 1 | 1 | | Ph | F | F | F | F | H | H | H | H | H | pic |
| 1-193X | Rh | 1 | 1 | | Ph | F | F | F | F | H | H | H | H | H | acac |

TABLE 15-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 1-193Y | Rh | 0 | 1 | Ph | F | F | F | F | H | H | H | H | H | — | — |
| 1-194 | Rh | 1 | 1 | Ph | H | F | H | CH₃ | H | H | H | H | H | pic | |
| 1-194X | Rh | 1 | 1 | Ph | H | F | H | CH₃ | H | H | H | H | H | acac | |
| 1-194Y | Rh | 0 | 1 | Ph | H | F | H | CH₃ | H | H | H | H | H | — | — |
| 1-195 | Rh | 1 | 1 | Ph | H | F | H | $^tC_4H_9$ | H | H | H | H | H | pic | |
| 1-195X | Rh | 1 | 1 | Ph | H | F | H | $^tC_4H_9$ | H | H | H | H | H | acac | |
| 1-195Y | Rh | 0 | 1 | Ph | H | F | H | $^tC_4H_9$ | H | H | H | H | H | — | — |
| 1-196 | Rh | 1 | 1 | Ph | H | CF₃ | H | CF₃ | H | H | H | H | H | pic | |
| 1-196X | Rh | 1 | 1 | Ph | H | CF₃ | H | CF₃ | H | H | H | H | H | acac | |
| 1-196Y | Rh | 0 | 1 | Ph | H | CF₃ | H | CF₃ | H | H | H | H | H | — | — |
| 1-197 | Rh | 1 | 1 | Ph | CF₃ | H | H | $^tC_4H_9$ | H | H | H | H | H | pic | |
| 1-197X | Rh | 1 | 1 | Ph | CF₃ | H | H | $^tC_4H_9$ | H | H | H | H | H | acac | |
| 1-197Y | Rh | 0 | 1 | Ph | CF₃ | H | H | $^tC_4H_9$ | H | H | H | H | H | — | — |
| 1-198 | Rh | 1 | 1 | Ph | H | CF₃ | H | $^tC_4H_9$ | H | H | H | H | H | pic | |
| 1-198X | Rh | 1 | 1 | Ph | H | CF₃ | H | $^tC_4H_9$ | H | H | H | H | H | acac | |
| 1-198Y | Rh | 0 | 1 | Ph | H | CF₃ | H | $^tC_4H_9$ | H | H | H | H | H | — | — |
| 1-199 | Rh | 1 | 1 | Ph | H | CF₃ | H | CH₃ | H | H | H | H | H | pic | |
| 1-199X | Rh | 1 | 1 | Ph | H | CF₃ | H | CH₃ | H | H | H | H | H | acac | |
| 1-199Y | Rh | 0 | 1 | Ph | H | CF₃ | H | CH₃ | H | H | H | H | H | — | — |
| 1-200 | Rh | 1 | 1 | Ph | H | CF₃ | CF₃ | H | H | H | H | H | H | pic | |
| 1-200X | Rh | 1 | 1 | Ph | H | CF₃ | CF₃ | H | H | H | H | H | H | acac | |
| 1-200Y | Rh | 0 | 1 | Ph | H | CF₃ | CF₃ | H | H | H | H | H | H | — | — |
| 1-201 | Rh | 1 | 1 | Ph | H | H | NO₂ | H | H | H | H | H | H | pic | |
| 1-201X | Rh | 1 | 1 | Ph | H | H | NO₂ | H | H | H | H | H | H | acac | |
| 1-201Y | Rh | 0 | 1 | Ph | H | H | NO₂ | H | H | H | H | H | H | — | — |
| 1-202 | Rh | 1 | 1 | Ph | F | H | NO₂ | H | H | H | H | H | H | pic | |
| 1-202X | Rh | 1 | 1 | Ph | F | H | NO₂ | H | H | H | H | H | H | acac | |
| 1-202Y | Rh | 0 | 1 | Ph | F | H | NO₂ | H | H | H | H | H | H | — | — |
| 1-203 | Rh | 1 | 1 | Ph | F | H | NO₂ | F | H | H | H | H | H | pic | |
| 1-203X | Rh | 1 | 1 | Ph | F | H | NO₂ | F | H | H | H | H | H | acac | |
| 1-203Y | Rh | 0 | 1 | Ph | F | H | NO₂ | F | H | H | H | H | H | — | — |
| 1-204 | Rh | 1 | 1 | Ph | H | NO₂ | H | NO₂ | H | H | H | H | H | pic | |
| 1-204X | Rh | 1 | 1 | Ph | H | NO₂ | H | NO₂ | H | H | H | H | H | acac | |
| 1-204Y | Rh | 0 | 1 | Ph | H | NO₂ | H | NO₂ | H | H | H | H | H | — | — |
| 1-205 | Rh | 1 | 1 | Ph | NO₂ | H | H | NO₂ | H | H | H | H | H | pic | |
| 1-205X | Rh | 1 | 1 | Ph | NO₂ | H | H | NO₂ | H | H | H | H | H | acac | |
| 1-205Y | Rh | 0 | 1 | Ph | NO₂ | H | H | NO₂ | H | H | H | H | H | — | — |
| 1-206 | Rh | 1 | 1 | Ph | H | H | CF₃ | H | H | H | H | H | H | pic | |
| 1-206X | Rh | 1 | 1 | Ph | H | H | CF₃ | H | H | H | H | H | H | acac | |
| 1-206Y | Rh | 0 | 1 | Ph | H | H | CF₃ | H | H | H | H | H | H | — | — |
| 1-207 | Rh | 1 | 1 | Ph | H | Cl | CF₃ | H | H | H | H | H | H | pic | |
| 1-207X | Rh | 1 | 1 | Ph | H | Cl | CF₃ | H | H | H | H | H | H | acac | |
| 1-207Y | Rh | 0 | 1 | Ph | H | Cl | CF₃ | H | H | H | H | H | H | — | — |
| 1-208 | Rh | 1 | 1 | Ph | H | NO₂ | H | H | H | H | H | H | H | pic | |
| 1-208X | Rh | 1 | 1 | Ph | H | NO₂ | H | H | H | H | H | H | H | acac | |
| 1-208Y | Rh | 0 | 1 | Ph | H | NO₂ | H | H | H | H | H | H | H | — | — |
| 1-209 | Rh | 1 | 1 | Ph | H | CF₃ | H | H | H | H | H | H | H | pic | |
| 1-209X | Rh | 1 | 1 | Ph | H | CF₃ | H | H | H | H | H | H | H | acac | |
| 1-209Y | Rh | 0 | 1 | Ph | H | CF₃ | H | H | H | H | H | H | H | — | — |
| 1-210 | Rh | 1 | 1 | Ph | H | NO₂ | H | CH₃ | H | H | H | H | H | pic | |
| 1-210X | Rh | 1 | 1 | Ph | H | NO₂ | H | CH₃ | H | H | H | H | H | acac | |
| 1-210Y | Rh | 0 | 1 | Ph | H | NO₂ | H | CH₃ | H | H | H | H | H | — | — |
| 1-211 | Rh | 1 | 1 | Ph | H | NO₂ | H | $^tC_4H_9$ | H | H | H | H | H | pic | |
| 1-211X | Rh | 1 | 1 | Ph | H | NO₂ | H | $^tC_4H_9$ | H | H | H | H | H | acac | |
| 1-211Y | Rh | 0 | 1 | Ph | H | NO₂ | H | $^tC_4H_9$ | H | H | H | H | H | — | — |
| 1-212 | Rh | 1 | 1 | Ph | H | H | CH₃O | H | H | H | H | H | H | pic | |
| 1-212X | Rh | 1 | 1 | Ph | H | H | CH₃O | H | H | H | H | H | H | acac | |
| 1-212Y | Rh | 0 | 1 | Ph | H | H | CH₃O | H | H | H | H | H | H | — | — |
| 1-213 | Rh | 1 | 1 | Ph | H | CH₃O | H | H | H | H | H | H | H | pic | |
| 1-213X | Rh | 1 | 1 | Ph | H | CH₃O | H | H | H | H | H | H | H | acac | |
| 1-213Y | Rh | 0 | 1 | Ph | H | CH₃O | H | H | H | H | H | H | H | — | — |
| 1-214 | Rh | 1 | 1 | Ph | H | CH₃O | H | CH₃ | H | H | H | H | H | pic | |
| 1-214X | Rh | 1 | 1 | Ph | H | CH₃O | H | CH₃ | H | H | H | H | H | acac | |
| 1-214Y | Rh | 0 | 1 | Ph | H | CH₃O | H | CH₃ | H | H | H | H | H | — | — |
| 1-215 | Rh | 1 | 1 | Ph | H | CH₃O | H | $^tC_4H_9$ | H | H | H | H | H | pic | |
| 1-215X | Rh | 1 | 1 | Ph | H | CH₃O | H | $^tC_4H_9$ | H | H | H | H | H | acac | |
| 1-215Y | Rh | 0 | 1 | Ph | H | CH₃O | H | $^tC_4H_9$ | H | H | H | H | H | — | — |
| 1-216 | Rh | 1 | 1 | Ph | H | H | H | H | $^tC_4H_9$ | H | H | H | H | pic | |
| 1-216X | Rh | 1 | 1 | Ph | H | H | H | H | $^tC_4H_9$ | H | H | H | H | acac | |
| 1-216Y | Rh | 0 | 1 | Ph | H | H | H | H | $^tC_4H_9$ | H | H | H | H | — | — |
| 1-217 | Rh | 1 | 1 | Ph | H | F | H | F | $^tC_4H_9$ | H | H | H | H | pic | |
| 1-217X | Rh | 1 | 1 | Ph | H | F | H | F | $^tC_4H_9$ | H | H | H | H | acac | |
| 1-217Y | Rh | 0 | 1 | Ph | H | F | H | F | $^tC_4H_9$ | H | H | H | H | — | — |
| 1-218 | Rh | 1 | 1 | Ph | CF₃ | H | CF₃ | H | $^tC_4H_9$ | H | H | H | H | pic | |
| 1-218X | Rh | 1 | 1 | Ph | CF₃ | H | CF₃ | H | $^tC_4H_9$ | H | H | H | H | acac | |
| 1-218Y | Rh | 0 | 1 | Ph | CF₃ | H | CF₃ | H | $^tC_4H_9$ | H | H | H | H | — | — |
| 1-219 | Rh | 1 | 1 | Ph | H | CF₃ | H | CH₃ | $^tC_4H_9$ | H | H | H | H | pic | |

TABLE 15-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 1-219X | Rh | 1 | 1 | Ph | H | CF₃ | H | CH₃ | ᵗC₄H₉ | H | H | H | H | acac | |
| 1-219Y | Rh | 0 | 1 | Ph | H | CF₃ | H | CH₃ | ᵗC₄H₉ | H | H | H | H | — | — |
| 1-220 | Rh | 1 | 1 | Ph | H | F | H | F | H | CH₃ | H | H | H | pic | |
| 1-220X | Rh | 1 | 1 | Ph | H | F | H | F | H | CH₃ | H | H | H | acac | |
| 1-220Y | Rh | 0 | 1 | Ph | H | F | H | F | H | CH₃ | H | H | H | — | — |
| 1-221 | Rh | 1 | 1 | Ph | CF₃ | H | CF₃ | H | H | CH₃ | H | H | H | pic | |
| 1-221X | Rh | 1 | 1 | Ph | CF₃ | H | CF₃ | H | H | CH₃ | H | H | H | acac | |
| 1-221Y | Rh | 0 | 1 | Ph | CF₃ | H | CF₃ | H | H | CH₃ | H | H | H | — | — |
| 1-222 | Rh | 1 | 1 | Ph | H | Si(CH₃)₃ | H | H | H | H | H | H | H | pic | |
| 1-222X | Rh | 1 | 1 | Ph | H | Si(CH₃)₃ | H | H | H | H | H | H | H | acac | |
| 1-222Y | Rh | 0 | 1 | Ph | H | Si(CH₃)₃ | H | H | H | H | H | H | H | — | — |
| 1-223 | Rh | 1 | 1 | Ph | H | H | Si(CH₃)₃ | H | H | H | H | H | H | pic | |
| 1-223X | Rh | 1 | 1 | Ph | H | H | Si(CH₃)₃ | H | H | H | H | H | H | acac | |
| 1-223Y | Rh | 0 | 1 | Ph | H | H | Si(CH₃)₃ | H | H | H | H | H | H | — | — |
| 1-224 | Rh | 1 | 1 | Ph | H | H | H | Si(CH₃)₃ | H | H | H | H | H | pic | |
| 1-224X | Rh | 1 | 1 | Ph | H | H | H | Si(CH₃)₃ | H | H | H | H | H | acac | |
| 1-224Y | Rh | 0 | 1 | Ph | H | H | H | Si(CH₃)₃ | H | H | H | H | H | — | — |
| 1-225 | Rh | 1 | 1 | Ph | H | F | H | Si(CH₃)₃ | H | H | H | H | H | pic | |
| 1-225X | Rh | 1 | 1 | Ph | H | F | H | Si(CH₃)₃ | H | H | H | H | H | acac | |
| 1-225Y | Rh | 0 | 1 | Ph | H | F | H | Si(CH₃)₃ | H | H | H | H | H | — | — |
| 1-226 | Rh | 1 | 1 | Ph | H | CF₃ | H | Si(CH₃)₃ | H | H | H | H | H | pic | |
| 1-226X | Rh | 1 | 1 | Ph | H | CF₃ | H | Si(CH₃)₃ | H | H | H | H | H | acac | |
| 1-226Y | Rh | 0 | 1 | Ph | H | CF₃ | H | Si(CH₃)₃ | H | H | H | H | H | — | — |
| 1-227 | Rh | 1 | 1 | Ph | H | Si(CH₃)₃ | H | F | H | H | H | H | H | pic | |
| 1-227X | Rh | 1 | 1 | Ph | H | Si(CH₃)₃ | H | F | H | H | H | H | H | acac | |
| 1-227Y | Rh | 0 | 1 | Ph | H | Si(CH₃)₃ | H | F | H | H | H | H | H | — | — |
| 1-228 | Rh | 1 | 1 | Ph | H | Si(CH₃)₃ | H | CF₃ | H | H | H | H | H | pic | |
| 1-228X | Rh | 1 | 1 | Ph | H | Si(CH₃)₃ | H | CF₃ | H | H | H | H | H | acac | |
| 1-228Y | Rh | 0 | 1 | Ph | H | Si(CH₃)₃ | H | CF₃ | H | H | H | H | H | — | — |
| 1-229 | Rh | 1 | 1 | Ph | Si(CH₃)₃ | H | Si(CH₃)₃ | H | H | H | H | H | H | pic | |
| 1-229X | Rh | 1 | 1 | Ph | Si(CH₃)₃ | H | Si(CH₃)₃ | H | H | H | H | H | H | acac | |
| 1-229Y | Rh | 0 | 1 | Ph | Si(CH₃)₃ | H | Si(CH₃)₃ | H | H | H | H | H | H | — | — |
| 1-230 | Rh | 1 | 1 | Ph | H | H | H | COCH₃ | H | H | H | H | H | pic | |
| 1-230X | Rh | 1 | 1 | Ph | H | H | H | COCH₃ | H | H | H | H | H | acac | |
| 1-230Y | Rh | 0 | 1 | Ph | H | H | H | COCH₃ | H | H | H | H | H | — | — |
| 1-231 | Rh | 1 | 1 | Ph | H | H | COCH₃ | H | H | H | H | H | H | pic | |
| 1-231X | Rh | 1 | 1 | Ph | H | H | COCH₃ | H | H | H | H | H | H | acac | |
| 1-231Y | Rh | 0 | 1 | Ph | H | H | COCH₃ | H | H | H | H | H | H | — | — |
| 1-232 | Rh | 1 | 1 | Ph | H | COCH₃ | H | H | H | H | H | H | H | pic | |
| 1-232X | Rh | 1 | 1 | Ph | H | COCH₃ | H | H | H | H | H | H | H | acac | |
| 1-232Y | Rh | 0 | 1 | Ph | H | COCH₃ | H | H | H | H | H | H | H | — | — |
| 1-233 | Rh | 1 | 1 | Ph | H | H | BL | H | H | H | H | H | H | pic | |
| 1-233X | Rh | 1 | 1 | Ph | H | H | BL | H | H | H | H | H | H | acac | |
| 1-233Y | Rh | 0 | 1 | Ph | H | H | BL | H | H | H | H | H | H | — | — |
| 1-234 | Rh | 1 | 1 | Ph | H | BL | H | H | H | H | H | H | H | pic | |
| 1-234X | Rh | 1 | 1 | Ph | H | BL | H | H | H | H | H | H | H | acac | |
| 1-234Y | Rh | 0 | 1 | Ph | H | BL | H | H | H | H | H | H | H | — | — |
| 1-235 | Rh | 1 | 1 | Ph | H | H | PL | H | H | H | H | H | H | pic | |
| 1-235X | Rh | 1 | 1 | Ph | H | H | PL | H | H | H | H | H | H | acac | |
| 1-235Y | Rh | 0 | 1 | Ph | H | H | PL | H | H | H | H | H | H | — | — |
| 1-236 | Rh | 1 | 1 | Ph | H | PL | H | H | H | H | H | H | H | pic | |
| 1-236X | Rh | 1 | 1 | Ph | H | PL | H | H | H | H | H | H | H | acac | |
| 1-236Y | Rh | 0 | 1 | Ph | H | PL | H | H | H | H | H | H | H | — | — |
| 1-237 | Rh | 1 | 1 | Ph | H | H | MEE1 | H | H | H | H | H | H | pic | |
| 1-237X | Rh | 1 | 1 | Ph | H | H | MEE1 | H | H | H | H | H | H | acac | |
| 1-237Y | Rh | 0 | 1 | Ph | H | H | MEE1 | H | H | H | H | H | H | — | — |
| 1-238 | Rh | 1 | 1 | Ph | H | MEE1 | H | H | H | H | H | H | H | pic | |
| 1-238X | Rh | 1 | 1 | Ph | H | MEE1 | H | H | H | H | H | H | H | acac | |
| 1-238Y | Rh | 0 | 1 | Ph | H | MEE1 | H | H | H | H | H | H | H | — | — |
| 1-239 | Rh | 1 | 1 | Ph | H | H | MEE2 | H | H | H | H | H | H | pic | |
| 1-239X | Rh | 1 | 1 | Ph | H | H | MEE2 | H | H | H | H | H | H | acac | |
| 1-239Y | Rh | 0 | 1 | Ph | H | H | MEE2 | H | H | H | H | H | H | — | — |
| 1-240 | Rh | 1 | 1 | Ph | H | MEE2 | H | H | H | H | H | H | H | pic | |
| 1-240X | Rh | 1 | 1 | Ph | H | MEE2 | H | H | H | H | H | H | H | acac | |
| 1-240Y | Rh | 0 | 1 | Ph | H | MEE2 | H | H | H | H | H | H | H | — | — |
| 1-241 | Rh | 1 | 1 | Ph | H | H | PA1 | H | H | H | H | H | H | pic | |
| 1-241X | Rh | 1 | 1 | Ph | H | H | PA1 | H | H | H | H | H | H | acac | |
| 1-241Y | Rh | 0 | 1 | Ph | H | H | PA1 | H | H | H | H | H | H | — | — |
| 1-242 | Rh | 1 | 1 | Ph | H | PA1 | H | H | H | H | H | H | H | pic | |
| 1-242X | Rh | 1 | 1 | Ph | H | PA1 | H | H | H | H | H | H | H | acac | |
| 1-242Y | Rh | 0 | 1 | Ph | H | PA1 | H | H | H | H | H | H | H | — | — |
| 1-243 | Rh | 1 | 1 | Ph | H | H | PA2 | H | H | H | H | H | H | pic | |
| 1-243X | Rh | 1 | 1 | Ph | H | H | PA2 | H | H | H | H | H | H | acac | |
| 1-243Y | Rh | 0 | 1 | Ph | H | H | PA2 | H | H | H | H | H | H | — | — |
| 1-244 | Rh | 1 | 1 | Ph | H | PA2 | H | H | H | H | H | H | H | pic | |
| 1-244X | Rh | 1 | 1 | Ph | H | PA2 | H | H | H | H | H | H | H | acac | |
| 1-244Y | Rh | 0 | 1 | Ph | H | PA2 | H | H | H | H | H | H | H | — | — |

TABLE 15-continued

| No. | M | n | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 1-245 | Rh | 1 | 1 | | Ph | H | H | | EA1 | H | H | H | H | H | pic | |
| 1-245X | Rh | 1 | 1 | | Ph | H | H | | EA1 | H | H | H | H | H | acac | |
| 1-245Y | Rh | 0 | 1 | | Ph | H | H | | EA1 | H | H | H | H | H | — | — |
| 1-246 | Rh | 1 | 1 | | Ph | H | | EA2 | | H | H | H | H | H | pic | |
| 1-246X | Rh | 1 | 1 | | Ph | H | | EA2 | | H | H | H | H | H | acac | |
| 1-246Y | Rh | 0 | 1 | | Ph | H | | EA2 | | H | H | H | H | H | — | — |
| 1-247 | Rh | 1 | 1 | | Ph | H | H | | ME | H | H | H | H | H | pic | |
| 1-247X | Rh | 1 | 1 | | Ph | H | H | | ME | H | H | H | H | H | acac | |
| 1-247Y | Rh | 0 | 1 | | Ph | H | H | | ME | H | H | H | H | H | — | — |
| 1-248 | Rh | 1 | 1 | | Ph | H | | ME | | H | H | H | H | H | pic | |
| 1-248X | Rh | 1 | 1 | | Ph | H | | ME | | H | H | H | H | H | acac | |
| 1-248Y | Rh | 0 | 1 | | Ph | H | | ME | | H | H | H | H | H | — | — |
| 1-249 | Rh | 1 | 1 | | Ph | H | H | | AT | H | H | H | H | H | pic | |
| 1-249X | Rh | 1 | 1 | | Ph | H | H | | AT | H | H | H | H | H | acac | |
| 1-249Y | Rh | 0 | 1 | | Ph | H | H | | AT | H | H | H | H | H | — | — |
| 1-250 | Rh | 1 | 1 | | Ph | H | | AT | | H | H | H | H | H | pic | |
| 1-250X | Rh | 1 | 1 | | Ph | H | | AT | | H | H | H | H | H | acac | |
| 1-250Y | Rh | 0 | 1 | | Ph | H | | AT | | H | H | H | H | H | — | — |
| 1-251 | Rh | 1 | 1 | | Ph | H | H | | MES1 | H | H | H | H | H | pic | |
| 1-251X | Rh | 1 | 1 | | Ph | H | H | | MES1 | H | H | H | H | H | acac | |
| 1-251Y | Rh | 0 | 1 | | Ph | H | H | | MES1 | H | H | H | H | H | — | — |
| 1-252 | Rh | 1 | 1 | | Ph | H | | MES1 | | H | H | H | H | H | pic | |
| 1-252X | Rh | 1 | 1 | | Ph | H | | MES1 | | H | H | H | H | H | acac | |
| 1-252Y | Rh | 0 | 1 | | Ph | H | | MES1 | | H | H | H | H | H | — | — |
| 1-253 | Rh | 1 | 1 | | Ph | H | H | | MES2 | H | H | H | H | H | pic | |
| 1-253X | Rh | 1 | 1 | | Ph | H | H | | MES2 | H | H | H | H | H | acac | |
| 1-253Y | Rh | 0 | 1 | | Ph | H | H | | MES2 | H | H | H | H | H | — | — |
| 1-254 | Rh | 1 | 1 | | Ph | H | | MES2 | | H | H | H | H | H | pic | |
| 1-254X | Rh | 1 | 1 | | Ph | H | | MES2 | | H | H | H | H | H | acac | |
| 1-254Y | Rh | 0 | 1 | | Ph | H | | MES2 | | H | H | H | H | H | — | — |
| 1-255 | Rh | 1 | 1 | | Ph | H | H | | PS1 | H | H | H | H | H | pic | |
| 1-255X | Rh | 1 | 1 | | Ph | H | H | | PS1 | H | H | H | H | H | acac | |
| 1-255Y | Rh | 0 | 1 | | Ph | H | H | | PS1 | H | H | H | H | H | — | — |
| 1-256 | Rh | 1 | 1 | | Ph | H | | PS1 | | H | H | H | H | H | pic | |
| 1-256X | Rh | 1 | 1 | | Ph | H | | PS1 | | H | H | H | H | H | acac | |
| 1-256Y | Rh | 0 | 1 | | Ph | H | | PS1 | | H | H | H | H | H | — | — |
| 1-257 | Rh | 1 | 1 | | Ph | H | H | | PS2 | H | H | H | H | H | pic | |
| 1-257X | Rh | 1 | 1 | | Ph | H | H | | PS2 | H | H | H | H | H | acac | |
| 1-257Y | Rh | 0 | 1 | | Ph | H | H | | PS2 | H | H | H | H | H | — | — |
| 1-258 | Rh | 1 | 1 | | Ph | H | | PS2 | | H | H | H | H | H | pic | |
| 1-258X | Rh | 1 | 1 | | Ph | H | | PS2 | | H | H | H | H | H | acac | |
| 1-258Y | Rh | 0 | 1 | | Ph | H | | PS2 | | H | H | H | H | H | — | — |
| 1-259 | Rh | 1 | 1 | | Ph | H | H | | BAL1 | H | H | H | H | H | pic | |
| 1-259X | Rh | 1 | 1 | | Ph | H | H | | BAL1 | H | H | H | H | H | acac | |
| 1-259Y | Rh | 0 | 1 | | Ph | H | H | | BAL1 | H | H | H | H | H | — | — |
| 1-260 | Rh | 1 | 1 | | Ph | H | | BAL1 | | H | H | H | H | H | pic | |
| 1-260X | Rh | 1 | 1 | | Ph | H | | BAL1 | | H | H | H | H | H | acac | |
| 1-260Y | Rh | 0 | 1 | | Ph | H | | BAL1 | | H | H | H | H | H | — | — |
| 1-261 | Rh | 1 | 1 | | Ph | H | H | | BAL2 | H | H | H | H | H | pic | |
| 1-261X | Rh | 1 | 1 | | Ph | H | H | | BAL2 | H | H | H | H | H | acac | |
| 1-261Y | Rh | 0 | 1 | | Ph | H | H | | BAL2 | H | H | H | H | H | — | — |
| 1-262 | Rh | 1 | 1 | | Ph | H | | BAL2 | | H | H | H | H | H | pic | |
| 1-262X | Rh | 1 | 1 | | Ph | H | | BAL2 | | H | H | H | H | H | acac | |
| 1-262Y | Rh | 0 | 1 | | Ph | H | | BAL2 | | H | H | H | H | H | — | — |
| 1-263 | Rh | 1 | 1 | | Ph | H | H | | MEK1 | H | H | H | H | H | pic | |
| 1-263X | Rh | 1 | 1 | | Ph | H | H | | MEK1 | H | H | H | H | H | acac | |
| 1-263Y | Rh | 0 | 1 | | Ph | H | H | | MEK1 | H | H | H | H | H | — | — |
| 1-264 | Rh | 1 | 1 | | Ph | H | | MEK1 | | H | H | H | H | H | pic | |
| 1-264X | Rh | 1 | 1 | | Ph | H | | MEK1 | | H | H | H | H | H | acac | |
| 1-264Y | Rh | 0 | 1 | | Ph | H | | MEK1 | | H | H | H | H | H | — | — |
| 1-265 | Rh | 1 | 1 | | Ph | H | H | | MEK2 | H | H | H | H | H | pic | |
| 1-265X | Rh | 1 | 1 | | Ph | H | H | | MEK2 | H | H | H | H | H | acac | |
| 1-265Y | Rh | 0 | 1 | | Ph | H | H | | MEK2 | H | H | H | H | H | — | — |
| 1-266 | Rh | 1 | 1 | | Ph | H | | MEK2 | | H | H | H | H | H | pic | |
| 1-266X | Rh | 1 | 1 | | Ph | H | | MEK2 | | H | H | H | H | H | acac | |
| 1-266Y | Rh | 0 | 1 | | Ph | H | | MEK2 | | H | H | H | H | H | — | — |
| 1-267 | Rh | 1 | 1 | | Ph | H | H | | PAL1 | H | H | H | H | H | pic | |
| 1-267X | Rh | 1 | 1 | | Ph | H | H | | PAL1 | H | H | H | H | H | acac | |
| 1-267Y | Rh | 0 | 1 | | Ph | H | H | | PAL1 | H | H | H | H | H | — | — |
| 1-268 | Rh | 1 | 1 | | Ph | H | | PAL1 | | H | H | H | H | H | pic | |
| 1-268X | Rh | 1 | 1 | | Ph | H | | PAL1 | | H | H | H | H | H | acac | |
| 1-268Y | Rh | 0 | 1 | | Ph | H | | PAL1 | | H | H | H | H | H | — | — |
| 1-269 | Rh | 1 | 1 | | Ph | H | H | | PAL2 | H | H | H | H | H | pic | |
| 1-269X | Rh | 1 | 1 | | Ph | H | H | | PAL2 | H | H | H | H | H | acac | |
| 1-269Y | Rh | 0 | 1 | | Ph | H | H | | PAL2 | H | H | H | H | H | — | — |
| 1-270 | Rh | 1 | 1 | | Ph | H | | PAL2 | | H | H | H | H | H | pic | |
| 1-270X | Rh | 1 | 1 | | Ph | H | | PAL2 | | H | H | H | H | H | acac | |

TABLE 15-continued

| No. | M | n | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 1-270Y | Rh | 0 | 1 | | Ph | H | | PAL2 | H | H | H | H | H | H | — | — |
| 1-271 | Rh | 1 | 1 | | Ph | H | H | | MMK | H | H | H | H | H | pic | |
| 1-271X | Rh | 1 | 1 | | Ph | H | H | | MMK | H | H | H | H | H | acac | |
| 1-271Y | Rh | 0 | 1 | | Ph | H | H | | MMK | H | H | H | H | H | — | — |
| 1-272 | Rh | 1 | 1 | | Ph | H | | MMK | H | H | H | H | H | H | pic | |
| 1-272X | Rh | 1 | 1 | | Ph | H | | MMK | H | H | H | H | H | H | acac | |
| 1-272Y | Rh | 0 | 1 | | Ph | H | | MMK | H | H | H | H | H | H | — | — |
| 1-273 | Rh | 1 | 1 | | Ph | H | H | | EES1 | H | H | H | H | H | pic | |
| 1-273X | Rh | 1 | 1 | | Ph | H | H | | EES1 | H | H | H | H | H | acac | |
| 1-273Y | Rh | 0 | 1 | | Ph | H | H | | EES1 | H | H | H | H | H | — | — |
| 1-274 | Rh | 1 | 1 | | Ph | H | | EES2 | H | H | H | H | H | H | pic | |
| 1-274X | Rh | 1 | 1 | | Ph | H | | EES2 | H | H | H | H | H | H | acac | |
| 1-274Y | Rh | 0 | 1 | | Ph | H | | EES2 | H | H | H | H | H | H | — | — |
| 1-275 | Rh | 1 | 1 | | Ph | H | H | | PAE1 | H | H | H | H | H | pic | |
| 1-275X | Rh | 1 | 1 | | Ph | H | H | | PAE1 | H | H | H | H | H | acac | |
| 1-275Y | Rh | 0 | 1 | | Ph | H | H | | PAE1 | H | H | H | H | H | — | — |
| 1-276 | Rh | 1 | 1 | | Ph | H | | PAE2 | H | H | H | H | H | H | pic | |
| 1-276X | Rh | 1 | 1 | | Ph | H | | PAE2 | H | H | H | H | H | H | acac | |
| 1-276Y | Rh | 0 | 1 | | Ph | H | | PAE2 | H | H | H | H | H | H | — | — |
| 1-277 | Rh | 1 | 1 | | Ph | H | H | | AME1 | H | H | H | H | H | pic | |
| 1-277X | Rh | 1 | 1 | | Ph | H | H | | AME1 | H | H | H | H | H | acac | |
| 1-277Y | Rh | 0 | 1 | | Ph | H | H | | AME1 | H | H | H | H | H | — | — |
| 1-278 | Rh | 1 | 1 | | Ph | H | | AME1 | H | H | H | H | H | H | pic | |
| 1-278X | Rh | 1 | 1 | | Ph | H | | AME1 | H | H | H | H | H | H | acac | |
| 1-278Y | Rh | 0 | 1 | | Ph | H | | AME1 | H | H | H | H | H | H | — | — |
| 1-279 | Rh | 1 | 1 | | Ph | H | H | | AME2 | H | H | H | H | H | pic | |
| 1-279X | Rh | 1 | 1 | | Ph | H | H | | AME2 | H | H | H | H | H | acac | |
| 1-279Y | Rh | 0 | 1 | | Ph | H | H | | AME2 | H | H | H | H | H | — | — |
| 1-280 | Rh | 1 | 1 | | Ph | H | | AME2 | H | H | H | H | H | H | pic | |
| 1-280X | Rh | 1 | 1 | | Ph | H | | AME2 | H | H | H | H | H | H | acac | |
| 1-280Y | Rh | 0 | 1 | | Ph | H | | AME2 | H | H | H | H | H | H | — | — |
| 1-281 | Rh | 1 | 1 | | Ph | H | H | | EAE1 | H | H | H | H | H | pic | |
| 1-281X | Rh | 1 | 1 | | Ph | H | H | | EAE1 | H | H | H | H | H | acac | |
| 1-281Y | Rh | 0 | 1 | | Ph | H | H | | EAE1 | H | H | H | H | H | — | — |
| 1-282 | Rh | 1 | 1 | | Ph | H | | EAE1 | H | H | H | H | H | H | pic | |
| 1-282X | Rh | 1 | 1 | | Ph | H | | EAE1 | H | H | H | H | H | H | acac | |
| 1-282Y | Rh | 0 | 1 | | Ph | H | | EAE1 | H | H | H | H | H | H | — | — |
| 1-283 | Rh | 1 | 1 | | Ph | H | H | | EAE2 | H | H | H | H | H | pic | |
| 1-283X | Rh | 1 | 1 | | Ph | H | H | | EAE2 | H | H | H | H | H | acac | |
| 1-283Y | Rh | 0 | 1 | | Ph | H | H | | EAE2 | H | H | H | H | H | — | — |
| 1-284 | Rh | 1 | 1 | | Ph | H | | EAE2 | H | H | H | H | H | H | pic | |
| 1-284X | Rh | 1 | 1 | | Ph | H | | EAE2 | H | H | H | H | H | H | acac | |
| 1-284Y | Rh | 0 | 1 | | Ph | H | | EAE2 | H | H | H | H | H | H | — | — |
| 1-285 | Rh | 1 | 1 | | Ph | H | H | | AAE1 | H | H | H | H | H | pic | |
| 1-285X | Rh | 1 | 1 | | Ph | H | H | | AAE1 | H | H | H | H | H | acac | |
| 1-285Y | Rh | 0 | 1 | | Ph | H | H | | AAE1 | H | H | H | H | H | — | — |
| 1-286 | Rh | 1 | 1 | | Ph | H | | AAE1 | H | H | H | H | H | H | pic | |
| 1-286X | Rh | 1 | 1 | | Ph | H | | AAE1 | H | H | H | H | H | H | acac | |
| 1-286Y | Rh | 0 | 1 | | Ph | H | | AAE1 | H | H | H | H | H | H | — | — |
| 1-287 | Rh | 1 | 1 | | Ph | H | H | | AAE2 | H | H | H | H | H | pic | |
| 1-287X | Rh | 1 | 1 | | Ph | H | H | | AAE2 | H | H | H | H | H | acac | |
| 1-287Y | Rh | 0 | 1 | | Ph | H | H | | AAE2 | H | H | H | H | H | — | — |
| 1-288 | Rh | 1 | 1 | | Ph | H | | AAE2 | H | H | H | H | H | H | pic | |
| 1-288X | Rh | 1 | 1 | | Ph | H | | AAE2 | H | H | H | H | H | H | acac | |
| 1-288Y | Rh | 0 | 1 | | Ph | H | | AAE2 | H | H | H | H | H | H | — | — |
| 1-289 | Rh | 1 | 1 | | Ph | H | H | | PME1 | H | H | H | H | H | pic | |
| 1-289X | Rh | 1 | 1 | | Ph | H | H | | PME1 | H | H | H | H | H | acac | |
| 1-289Y | Rh | 0 | 1 | | Ph | H | H | | PME1 | H | H | H | H | H | — | — |
| 1-290 | Rh | 1 | 1 | | Ph | H | | PME1 | H | H | H | H | H | H | pic | |
| 1-290X | Rh | 1 | 1 | | Ph | H | | PME1 | H | H | H | H | H | H | acac | |
| 1-290Y | Rh | 0 | 1 | | Ph | H | | PME1 | H | H | H | H | H | H | — | — |
| 1-291 | Rh | 1 | 1 | | Ph | H | H | | PME2 | H | H | H | H | H | pic | |
| 1-291X | Rh | 1 | 1 | | Ph | H | H | | PME2 | H | H | H | H | H | acac | |
| 1-291Y | Rh | 0 | 1 | | Ph | H | H | | PME2 | H | H | H | H | H | — | — |
| 1-292 | Rh | 1 | 1 | | Ph | H | | PME2 | H | H | H | H | H | H | pic | |
| 1-292X | Rh | 1 | 1 | | Ph | H | | PME2 | H | H | H | H | H | H | acac | |
| 1-292Y | Rh | 0 | 1 | | Ph | H | | PME2 | H | H | H | H | H | H | — | — |
| 1-293 | Rh | 1 | 1 | | Ph | H | H | | MET1 | H | H | H | H | H | pic | |
| 1-293X | Rh | 1 | 1 | | Ph | H | H | | MET1 | H | H | H | H | H | acac | |
| 1-293Y | Rh | 0 | 1 | | Ph | H | H | | MET1 | H | H | H | H | H | — | — |
| 1-294 | Rh | 1 | 1 | | Ph | H | | MET1 | H | H | H | H | H | H | pic | |
| 1-294X | Rh | 1 | 1 | | Ph | H | | MET1 | H | H | H | H | H | H | acac | |
| 1-294Y | Rh | 0 | 1 | | Ph | H | | MET1 | H | H | H | H | H | H | — | — |
| 1-295 | Rh | 1 | 1 | | Ph | H | H | | MET2 | H | H | H | H | H | pic | |
| 1-295X | Rh | 1 | 1 | | Ph | H | H | | MET2 | H | H | H | H | H | acac | |
| 1-295Y | Rh | 0 | 1 | | Ph | H | H | | MET2 | H | H | H | H | H | — | — |
| 1-296 | Rh | 1 | 1 | | Ph | H | | MET2 | H | H | H | H | H | H | pic | |

TABLE 15-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 1-296X | Rh | 1 | 1 | Ph | H | | MET2 | H | H | H | H | H | H | acac | |
| 1-296Y | Rh | 0 | 1 | Ph | H | | MET2 | H | H | H | H | H | H | — | — |
| 1-297 | Rh | 1 | 1 | Ph | H | H | | EE1 | H | H | H | H | H | pic | |
| 1-297X | Rh | 1 | 1 | Ph | H | H | | EE1 | H | H | H | H | H | acac | |
| 1-297Y | Rh | 0 | 1 | Ph | H | H | | EE1 | H | H | H | H | H | — | — |
| 1-298 | Rh | 1 | 1 | Ph | H | | EE1 | H | H | H | H | H | H | pic | |
| 1-298X | Rh | 1 | 1 | Ph | H | | EE1 | H | H | H | H | H | H | acac | |
| 1-298Y | Rh | 0 | 1 | Ph | H | | EE1 | H | H | H | H | H | H | — | — |
| 1-299 | Rh | 1 | 1 | Ph | H | H | | EE2 | H | H | H | H | H | pic | |
| 1-299X | Rh | 1 | 1 | Ph | H | H | | EE2 | H | H | H | H | H | acac | |
| 1-299Y | Rh | 0 | 1 | Ph | H | H | | EE2 | H | H | H | H | H | — | — |
| 1-300 | Rh | 1 | 1 | Ph | H | | EE2 | H | H | H | H | H | H | pic | |
| 1-300X | Rh | 1 | 1 | Ph | H | | EE2 | H | H | H | H | H | H | acac | |
| 1-300Y | Rh | 0 | 1 | Ph | H | | EE2 | H | H | H | H | H | H | — | — |
| 1-301 | Rh | 1 | 1 | Ph | H | H | | MS1 | H | H | H | H | H | pic | |
| 1-301X | Rh | 1 | 1 | Ph | H | H | | MS1 | H | H | H | H | H | acac | |
| 1-301Y | Rh | 0 | 1 | Ph | H | H | | MS1 | H | H | H | H | H | — | — |
| 1-302 | Rh | 1 | 1 | Ph | H | | MS1 | H | H | H | H | H | H | pic | |
| 1-302X | Rh | 1 | 1 | Ph | H | | MS1 | H | H | H | H | H | H | acac | |
| 1-302Y | Rh | 0 | 1 | Ph | H | | MS1 | H | H | H | H | H | H | — | — |
| 1-303 | Rh | 1 | 1 | Ph | H | H | | MS2 | H | H | H | H | H | pic | |
| 1-303X | Rh | 1 | 1 | Ph | H | H | | MS2 | H | H | H | H | H | acac | |
| 1-303Y | Rh | 0 | 1 | Ph | H | H | | MS2 | H | H | H | H | H | — | — |
| 1-304 | Rh | 1 | 1 | Ph | H | | MS2 | H | H | H | H | H | H | pic | |
| 1-304X | Rh | 1 | 1 | Ph | H | | MS2 | H | H | H | H | H | H | acac | |
| 1-304Y | Rh | 0 | 1 | Ph | H | | MS2 | H | H | H | H | H | H | — | — |

TABLE 16

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2-187 | Rh | 1 | 2 | Ph | H | H | H | H | H | H | H | H | H | pic | |
| 2-187X | Rh | 1 | 2 | Ph | H | H | H | H | H | H | H | H | H | acac | |
| 2-187Y | Rh | 0 | 2 | Ph | H | H | H | H | H | H | H | H | H | — | — |
| 2-188 | Rh | 1 | 2 | Ph | H | F | H | F | H | H | H | H | H | pic | |
| 2-188X | Rh | 1 | 2 | Ph | H | F | H | F | H | H | H | H | H | acac | |
| 2-188Y | Rh | 0 | 2 | Ph | H | F | H | F | H | H | H | H | H | — | — |
| 2-189 | Rh | 1 | 2 | Ph | F | H | H | F | H | H | H | H | H | pic | |
| 2-189X | Rh | 1 | 2 | Ph | F | H | H | F | H | H | H | H | H | acac | |
| 2-189Y | Rh | 0 | 2 | Ph | F | H | H | F | H | H | H | H | H | — | — |
| 2-190 | Rh | 1 | 2 | Ph | $CF_3$ | H | $CF_3$ | H | H | H | H | H | H | pic | |
| 2-190X | Rh | 1 | 2 | Ph | $CF_3$ | H | $CF_3$ | H | H | H | H | H | H | acac | |
| 2-190Y | Rh | 0 | 2 | Ph | $CF_3$ | H | $CF_3$ | H | H | H | H | H | H | — | — |
| 2-191 | Rh | 1 | 2 | Ph | H | F | $CF_3$ | H | H | H | H | H | H | pic | |
| 2-191X | Rh | 1 | 2 | Ph | H | F | $CF_3$ | H | H | H | H | H | H | acac | |
| 2-191Y | Rh | 0 | 2 | Ph | H | F | $CF_3$ | H | H | H | H | H | H | — | — |
| 2-192 | Rh | 1 | 2 | Ph | F | H | $CF_3$ | H | H | H | H | H | H | pic | |
| 2-192X | Rh | 1 | 2 | Ph | F | H | $CF_3$ | H | H | H | H | H | H | acac | |
| 2-192Y | Rh | 0 | 2 | Ph | F | H | $CF_3$ | H | H | H | H | H | H | — | — |
| 2-193 | Rh | 1 | 2 | Ph | F | F | F | F | H | H | H | H | H | pic | |
| 2-193X | Rh | 1 | 2 | Ph | F | F | F | F | H | H | H | H | H | acac | |
| 2-193Y | Rh | 0 | 2 | Ph | F | F | F | F | H | H | H | H | H | — | — |
| 2-194 | Rh | 1 | 2 | Ph | H | F | H | $CH_3$ | H | H | H | H | H | pic | |
| 2-194X | Rh | 1 | 2 | Ph | H | F | H | $CH_3$ | H | H | H | H | H | acac | |
| 2-194Y | Rh | 0 | 2 | Ph | H | F | H | $CH_3$ | H | H | H | H | H | — | — |
| 2-195 | Rh | 1 | 2 | Ph | H | F | H | $^tC_4H_9$ | H | H | H | H | H | pic | |
| 2-195X | Rh | 1 | 2 | Ph | H | F | H | $^tC_4H_9$ | H | H | H | H | H | acac | |
| 2-195Y | Rh | 0 | 2 | Ph | H | F | H | $^tC_4H_9$ | H | H | H | H | H | — | — |
| 2-196 | Rh | 1 | 2 | Ph | H | $CF_3$ | H | $CF_3$ | H | H | H | H | H | pic | |
| 2-196X | Rh | 1 | 2 | Ph | H | $CF_3$ | H | $CF_3$ | H | H | H | H | H | acac | |
| 2-196Y | Rh | 0 | 2 | Ph | H | $CF_3$ | H | $CF_3$ | H | H | H | H | H | — | — |
| 2-197 | Rh | 1 | 2 | Ph | $CF_3$ | H | H | $^tC_4H_9$ | H | H | H | H | H | pic | |
| 2-197X | Rh | 1 | 2 | Ph | $CF_3$ | H | H | $^tC_4H_9$ | H | H | H | H | H | acac | |
| 2-197Y | Rh | 0 | 2 | Ph | $CF_3$ | H | H | $^tC_4H_9$ | H | H | H | H | H | — | — |
| 2-198 | Rh | 1 | 2 | Ph | H | $CF_3$ | H | $^tC_4H_9$ | H | H | H | H | H | pic | |
| 2-198X | Rh | 1 | 2 | Ph | H | $CF_3$ | H | $^tC_4H_9$ | H | H | H | H | H | acac | |
| 2-198Y | Rh | 0 | 2 | Ph | H | $CF_3$ | H | $^tC_4H_9$ | H | H | H | H | H | — | — |
| 2-199 | Rh | 1 | 2 | Ph | H | $CF_3$ | H | $CH_3$ | H | H | H | H | H | pic | |
| 2-199X | Rh | 1 | 2 | Ph | H | $CF_3$ | H | $CH_3$ | H | H | H | H | H | acac | |
| 2-199Y | Rh | 0 | 2 | Ph | H | $CF_3$ | H | $CH_3$ | H | H | H | H | H | — | — |
| 2-200 | Rh | 1 | 2 | Ph | H | $CF_3$ | $CF_3$ | H | H | H | H | H | H | pic | |
| 2-200X | Rh | 1 | 2 | Ph | H | $CF_3$ | $CF_3$ | H | H | H | H | H | H | acac | |
| 2-200Y | Rh | 0 | 2 | Ph | H | $CF_3$ | $CF_3$ | H | H | H | H | H | H | — | — |
| 2-201 | Rh | 1 | 2 | Ph | H | H | $NO_2$ | H | H | H | H | H | H | pic | |

TABLE 16-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2-201X | Rh | 1 | 2 | Ph | H | H | NO$_2$ | H | H | H | H | H | H | acac | |
| 2-201Y | Rh | 0 | 2 | Ph | H | H | NO$_2$ | H | H | H | H | H | H | — | — |
| 2-202 | Rh | 1 | 2 | Ph | F | H | NO$_2$ | H | H | H | H | H | H | pic | |
| 2-202X | Rh | 1 | 2 | Ph | F | H | NO$_2$ | H | H | H | H | H | H | acac | |
| 2-202Y | Rh | 0 | 2 | Ph | F | H | NO$_2$ | H | H | H | H | H | H | — | — |
| 2-203 | Rh | 1 | 2 | Ph | F | H | NO$_2$ | F | H | H | H | H | H | pic | |
| 2-203X | Rh | 1 | 2 | Ph | F | H | NO$_2$ | F | H | H | H | H | H | acac | |
| 2-203Y | Rh | 0 | 2 | Ph | F | H | NO$_2$ | F | H | H | H | H | H | — | — |
| 2-204 | Rh | 1 | 2 | Ph | H | NO$_2$ | H | NO$_2$ | H | H | H | H | H | pic | |
| 2-204X | Rh | 1 | 2 | Ph | H | NO$_2$ | H | NO$_2$ | H | H | H | H | H | acac | |
| 2-204Y | Rh | 0 | 2 | Ph | H | NO$_2$ | H | NO$_2$ | H | H | H | H | H | — | — |
| 2-205 | Rh | 1 | 2 | Ph | NO$_2$ | H | H | NO$_2$ | H | H | H | H | H | pic | |
| 2-205X | Rh | 1 | 2 | Ph | NO$_2$ | H | H | NO$_2$ | H | H | H | H | H | acac | |
| 2-205Y | Rh | 0 | 2 | Ph | NO$_2$ | H | H | NO$_2$ | H | H | H | H | H | — | — |
| 2-206 | Rh | 1 | 2 | Ph | H | H | CF$_3$ | H | H | H | H | H | H | pic | |
| 2-206X | Rh | 1 | 2 | Ph | H | H | CF$_3$ | H | H | H | H | H | H | acac | |
| 2-206Y | Rh | 0 | 2 | Ph | H | H | CF$_3$ | H | H | H | H | H | H | — | — |
| 2-207 | Rh | 1 | 2 | Ph | H | Cl | CF$_3$ | H | H | H | H | H | H | pic | |
| 2-207X | Rh | 1 | 2 | Ph | H | Cl | CF$_3$ | H | H | H | H | H | H | acac | |
| 2-207Y | Rh | 0 | 2 | Ph | H | Cl | CF$_3$ | H | H | H | H | H | H | — | — |
| 2-208 | Rh | 1 | 2 | Ph | H | NO$_2$ | H | H | H | H | H | H | H | pic | |
| 2-208X | Rh | 1 | 2 | Ph | H | NO$_2$ | H | H | H | H | H | H | H | acac | |
| 2-208Y | Rh | 0 | 2 | Ph | H | NO$_2$ | H | H | H | H | H | H | H | — | — |
| 2-209 | Rh | 1 | 2 | Ph | H | CF$_3$ | H | H | H | H | H | H | H | pic | |
| 2-209X | Rh | 1 | 2 | Ph | H | CF$_3$ | H | H | H | H | H | H | H | acac | |
| 2-209Y | Rh | 0 | 2 | Ph | H | CF$_3$ | H | H | H | H | H | H | H | — | — |
| 2-210 | Rh | 1 | 2 | Ph | H | NO$_2$ | H | CH$_3$ | H | H | H | H | H | pic | |
| 2-210X | Rh | 1 | 2 | Ph | H | NO$_2$ | H | CH$_3$ | H | H | H | H | H | acac | |
| 2-210Y | Rh | 0 | 2 | Ph | H | NO$_2$ | H | CH$_3$ | H | H | H | H | H | — | — |
| 2-211 | Rh | 1 | 2 | Ph | H | NO$_2$ | H | $^tC_4H_9$ | H | H | H | H | H | pic | |
| 2-211X | Rh | 1 | 2 | Ph | H | NO$_2$ | H | $^tC_4H_9$ | H | H | H | H | H | acac | |
| 2-211Y | Rh | 0 | 2 | Ph | H | NO$_2$ | H | $^tC_4H_9$ | H | H | H | H | H | — | — |
| 2-212 | Rh | 1 | 2 | Ph | H | H | CH$_3$O | H | H | H | H | H | H | pic | |
| 2-212X | Rh | 1 | 2 | Ph | H | H | CH$_3$O | H | H | H | H | H | H | acac | |
| 2-212Y | Rh | 0 | 2 | Ph | H | H | CH$_3$O | H | H | H | H | H | H | — | — |
| 2-213 | Rh | 1 | 2 | Ph | H | CH$_3$O | H | H | H | H | H | H | H | pic | |
| 2-213X | Rh | 1 | 2 | Ph | H | CH$_3$O | H | H | H | H | H | H | H | acac | |
| 2-213Y | Rh | 0 | 2 | Ph | H | CH$_3$O | H | H | H | H | H | H | H | — | — |
| 2-214 | Rh | 1 | 2 | Ph | H | CH$_3$O | H | CH$_3$ | H | H | H | H | H | pic | |
| 2-214X | Rh | 1 | 2 | Ph | H | CH$_3$O | H | CH$_3$ | H | H | H | H | H | acac | |
| 2-214Y | Rh | 0 | 2 | Ph | H | CH$_3$O | H | CH$_3$ | H | H | H | H | H | — | — |
| 2-215 | Rh | 1 | 2 | Ph | H | CH$_3$O | H | $^tC_4H_9$ | H | H | H | H | H | pic | |
| 2-215X | Rh | 1 | 2 | Ph | H | CH$_3$O | H | $^tC_4H_9$ | H | H | H | H | H | acac | |
| 2-215Y | Rh | 0 | 2 | Ph | H | CH$_3$O | H | $^tC_4H_9$ | H | H | H | H | H | — | — |
| 2-216 | Rh | 1 | 2 | Ph | H | H | H | H | $^tC_4H_9$ | H | H | H | H | pic | |
| 2-216X | Rh | 1 | 2 | Ph | H | H | H | H | $^tC_4H_9$ | H | H | H | H | acac | |
| 2-216Y | Rh | 0 | 2 | Ph | H | H | H | H | $^tC_4H_9$ | H | H | H | H | — | — |
| 2-217 | Rh | 1 | 2 | Ph | H | F | H | F | $^tC_4H_9$ | H | H | H | H | pic | |
| 2-217X | Rh | 1 | 2 | Ph | H | F | H | F | $^tC_4H_9$ | H | H | H | H | acac | |
| 2-217Y | Rh | 0 | 2 | Ph | H | F | H | F | $^tC_4H_9$ | H | H | H | H | — | — |
| 2-218 | Rh | 1 | 2 | Ph | CF$_3$ | H | CF$_3$ | H | $^tC_4H_9$ | H | H | H | H | pic | |
| 2-218X | Rh | 1 | 2 | Ph | CF$_3$ | H | CF$_3$ | H | $^tC_4H_9$ | H | H | H | H | acac | |
| 2-218Y | Rh | 0 | 2 | Ph | CF$_3$ | H | CF$_3$ | H | $^tC_4H_9$ | H | H | H | H | — | — |
| 2-219 | Rh | 1 | 2 | Ph | H | CF$_3$ | H | CH$_3$ | $^tC_4H_9$ | H | H | H | H | pic | |
| 2-219X | Rh | 1 | 2 | Ph | H | CF$_3$ | H | CH$_3$ | $^tC_4H_9$ | H | H | H | H | acac | |
| 2-219Y | Rh | 0 | 2 | Ph | H | CF$_3$ | H | CH$_3$ | $^tC_4H_9$ | H | H | H | H | — | — |
| 2-220 | Rh | 1 | 2 | Ph | H | F | H | F | H | H | H | CH$_3$ | H | pic | |
| 2-220X | Rh | 1 | 2 | Ph | H | F | H | F | H | H | H | CH$_3$ | H | acac | |
| 2-220Y | Rh | 0 | 2 | Ph | H | F | H | F | H | H | H | CH$_3$ | H | — | — |
| 2-221 | Rh | 1 | 2 | Ph | CF$_3$ | H | CF$_3$ | H | H | H | H | CH$_3$ | H | pic | |
| 2-221X | Rh | 1 | 2 | Ph | CF$_3$ | H | CF$_3$ | H | H | H | H | CH$_3$ | H | acac | |
| 2-221Y | Rh | 0 | 2 | Ph | CF$_3$ | H | CF$_3$ | H | H | H | H | CH$_3$ | H | — | — |
| 2-222 | Rh | 1 | 2 | Ph | H | Si(CH$_3$)$_3$ | H | H | H | H | H | H | H | pic | |
| 2-222X | Rh | 1 | 2 | Ph | H | Si(CH$_3$)$_3$ | H | H | H | H | H | H | H | acac | |
| 2-222Y | Rh | 0 | 2 | Ph | H | Si(CH$_3$)$_3$ | H | H | H | H | H | H | H | — | — |
| 2-223 | Rh | 1 | 2 | Ph | H | H | Si(CH$_3$)$_3$ | H | H | H | H | H | H | pic | |
| 2-223X | Rh | 1 | 2 | Ph | H | H | Si(CH$_3$)$_3$ | H | H | H | H | H | H | acac | |
| 2-223Y | Rh | 0 | 2 | Ph | H | H | Si(CH$_3$)$_3$ | H | H | H | H | H | H | — | — |
| 2-224 | Rh | 1 | 2 | Ph | H | H | H | Si(CH$_3$)$_3$ | H | H | H | H | H | pic | |
| 2-224X | Rh | 1 | 2 | Ph | H | H | H | Si(CH$_3$)$_3$ | H | H | H | H | H | acac | |
| 2-224Y | Rh | 0 | 2 | Ph | H | H | H | Si(CH$_3$)$_3$ | H | H | H | H | H | — | — |
| 2-225 | Rh | 1 | 2 | Ph | H | F | H | Si(CH$_3$)$_3$ | H | H | H | H | H | pic | |
| 2-225X | Rh | 1 | 2 | Ph | H | F | H | Si(CH$_3$)$_3$ | H | H | H | H | H | acac | |
| 2-225Y | Rh | 0 | 2 | Ph | H | F | H | Si(CH$_3$)$_3$ | H | H | H | H | H | — | — |
| 2-226 | Rh | 1 | 2 | Ph | H | CF$_3$ | H | Si(CH$_3$)$_3$ | H | H | H | H | H | pic | |
| 2-226X | Rh | 1 | 2 | Ph | H | CF$_3$ | H | Si(CH$_3$)$_3$ | H | H | H | H | H | acac | |
| 2-226Y | Rh | 0 | 2 | Ph | H | CF$_3$ | H | Si(CH$_3$)$_3$ | H | H | H | H | H | — | — |

TABLE 16-continued

| No. | M | n | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 2-227 | Rh | 1 | 2 | | Ph | H | Si(CH$_3$)$_3$ | H | F | H | H | H | H | H | pic | |
| 2-227X | Rh | 1 | 2 | | Ph | H | Si(CH$_3$)$_3$ | H | F | H | H | H | H | H | acac | |
| 2-227Y | Rh | 0 | 2 | | Ph | H | Si(CH$_3$)$_3$ | H | F | H | H | H | H | H | — | — |
| 2-228 | Rh | 1 | 2 | | Ph | H | Si(CH$_3$)$_3$ | H | CF$_3$ | H | H | H | H | H | pic | |
| 2-228X | Rh | 1 | 2 | | Ph | H | Si(CH$_3$)$_3$ | H | CF$_3$ | H | H | H | H | H | acac | |
| 2-228Y | Rh | 0 | 2 | | Ph | H | Si(CH$_3$)$_3$ | H | CF$_3$ | H | H | H | H | H | — | — |
| 2-229 | Rh | 1 | 2 | | Ph | Si(CH$_3$)$_3$ | H | Si(CH$_3$)$_3$ | H | H | H | H | H | H | pic | |
| 2-229X | Rh | 1 | 2 | | Ph | Si(CH$_3$)$_3$ | H | Si(CH$_3$)$_3$ | H | H | H | H | H | H | acac | |
| 2-229Y | Rh | 0 | 2 | | Ph | Si(CH$_3$)$_3$ | H | Si(CH$_3$)$_3$ | H | H | H | H | H | H | — | — |
| 2-230 | Rh | 1 | 2 | | Ph | H | H | H | COCH$_3$ | H | H | H | H | H | pic | |
| 2-230X | Rh | 1 | 2 | | Ph | H | H | H | COCH$_3$ | H | H | H | H | H | acac | |
| 2-230Y | Rh | 0 | 2 | | Ph | H | H | H | COCH$_3$ | H | H | H | H | H | — | — |
| 2-231 | Rh | 1 | 2 | | Ph | H | H | COCH$_3$ | H | H | H | H | H | H | pic | |
| 2-231X | Rh | 1 | 2 | | Ph | H | H | COCH$_3$ | H | H | H | H | H | H | acac | |
| 2-231Y | Rh | 0 | 2 | | Ph | H | H | COCH$_3$ | H | H | H | H | H | H | — | — |
| 2-232 | Rh | 1 | 2 | | Ph | H | COCH$_3$ | H | H | H | H | H | H | H | pic | |
| 2-232X | Rh | 1 | 2 | | Ph | H | COCH$_3$ | H | H | H | H | H | H | H | acac | |
| 2-232Y | Rh | 0 | 2 | | Ph | H | COCH$_3$ | H | H | H | H | H | H | H | — | — |
| 2-233 | Rh | 1 | 2 | | Ph | H | H | BL | | H | H | H | H | H | pic | |
| 2-233X | Rh | 1 | 2 | | Ph | H | H | BL | | H | H | H | H | H | acac | |
| 2-233Y | Rh | 0 | 2 | | Ph | H | H | BL | | H | H | H | H | H | — | — |
| 2-234 | Rh | 1 | 2 | | Ph | H | BL | | H | H | H | H | H | H | pic | |
| 2-234X | Rh | 1 | 2 | | Ph | H | BL | | H | H | H | H | H | H | acac | |
| 2-234Y | Rh | 0 | 2 | | Ph | H | BL | | H | H | H | H | H | H | — | — |
| 2-235 | Rh | 1 | 2 | | Ph | H | H | PL | H | H | H | H | H | H | pic | |
| 2-235X | Rh | 1 | 2 | | Ph | H | H | PL | H | H | H | H | H | H | acac | |
| 2-235Y | Rh | 0 | 2 | | Ph | H | H | PL | H | H | H | H | H | H | — | — |
| 2-236 | Rh | 1 | 2 | | Ph | H | PL | | H | H | H | H | H | H | pic | |
| 2-236X | Rh | 1 | 2 | | Ph | H | PL | | H | H | H | H | H | H | acac | |
| 2-236Y | Rh | 0 | 2 | | Ph | H | PL | | H | H | H | H | H | H | — | — |
| 2-237 | Rh | 1 | 2 | | Ph | H | H | MEE1 | H | H | H | H | H | H | pic | |
| 2-237X | Rh | 1 | 2 | | Ph | H | H | MEE1 | H | H | H | H | H | H | acac | |
| 2-237Y | Rh | 0 | 2 | | Ph | H | H | MEE1 | H | H | H | H | H | H | — | — |
| 2-238 | Rh | 1 | 2 | | Ph | H | MEE1 | H | | H | H | H | H | H | pic | |
| 2-238X | Rh | 1 | 2 | | Ph | H | MEE1 | H | | H | H | H | H | H | acac | |
| 2-238Y | Rh | 0 | 2 | | Ph | H | MEE1 | H | | H | H | H | H | H | — | — |
| 2-239 | Rh | 1 | 2 | | Ph | H | H | MEE2 | H | H | H | H | H | H | pic | |
| 2-239X | Rh | 1 | 2 | | Ph | H | H | MEE2 | H | H | H | H | H | H | acac | |
| 2-239Y | Rh | 0 | 2 | | Ph | H | H | MEE2 | H | H | H | H | H | H | — | — |
| 2-240 | Rh | 1 | 2 | | Ph | H | MEE2 | H | | H | H | H | H | H | pic | |
| 2-240X | Rh | 1 | 2 | | Ph | H | MEE2 | H | | H | H | H | H | H | acac | |
| 2-240Y | Rh | 0 | 2 | | Ph | H | MEE2 | H | | H | H | H | H | H | — | — |
| 2-241 | Rh | 1 | 2 | | Ph | H | H | PA1 | H | H | H | H | H | H | pic | |
| 2-241X | Rh | 1 | 2 | | Ph | H | H | PA1 | H | H | H | H | H | H | acac | |
| 2-241Y | Rh | 0 | 2 | | Ph | H | H | PA1 | H | H | H | H | H | H | — | — |
| 2-242 | Rh | 1 | 2 | | Ph | H | PA1 | | H | H | H | H | H | H | pic | |
| 2-242X | Rh | 1 | 2 | | Ph | H | PA1 | | H | H | H | H | H | H | acac | |
| 2-242Y | Rh | 0 | 2 | | Ph | H | PA1 | | H | H | H | H | H | H | — | — |
| 2-243 | Rh | 1 | 2 | | Ph | H | H | PA2 | H | H | H | H | H | H | pic | |
| 2-243X | Rh | 1 | 2 | | Ph | H | H | PA2 | H | H | H | H | H | H | acac | |
| 2-243Y | Rh | 0 | 2 | | Ph | H | H | PA2 | H | H | H | H | H | H | — | — |
| 2-244 | Rh | 1 | 2 | | Ph | H | PA2 | | H | H | H | H | H | H | pic | |
| 2-244X | Rh | 1 | 2 | | Ph | H | PA2 | | H | H | H | H | H | H | acac | |
| 2-244Y | Rh | 0 | 2 | | Ph | H | PA2 | | H | H | H | H | H | H | — | — |
| 2-245 | Rh | 1 | 2 | | Ph | H | H | EA1 | H | H | H | H | H | H | pic | |
| 2-245X | Rh | 1 | 2 | | Ph | H | H | EA1 | H | H | H | H | H | H | acac | |
| 2-245Y | Rh | 0 | 2 | | Ph | H | H | EA1 | H | H | H | H | H | H | — | — |
| 2-246 | Rh | 1 | 2 | | Ph | H | EA2 | | H | H | H | H | H | H | pic | |
| 2-246X | Rh | 1 | 2 | | Ph | H | EA2 | | H | H | H | H | H | H | acac | |
| 2-246Y | Rh | 0 | 2 | | Ph | H | EA2 | | H | H | H | H | H | H | — | — |
| 2-247 | Rh | 1 | 2 | | Ph | H | H | ME | H | H | H | H | H | H | pic | |
| 2-247X | Rh | 1 | 2 | | Ph | H | H | ME | H | H | H | H | H | H | acac | |
| 2-247Y | Rh | 0 | 2 | | Ph | H | H | ME | H | H | H | H | H | H | — | — |
| 2-248 | Rh | 1 | 2 | | Ph | H | ME | | H | H | H | H | H | H | pic | |
| 2-248X | Rh | 1 | 2 | | Ph | H | ME | | H | H | H | H | H | H | acac | |
| 2-248Y | Rh | 0 | 2 | | Ph | H | ME | | H | H | H | H | H | H | — | — |
| 2-249 | Rh | 1 | 2 | | Ph | H | H | AT | H | H | H | H | H | H | pic | |
| 2-249X | Rh | 1 | 2 | | Ph | H | H | AT | H | H | H | H | H | H | acac | |
| 2-249Y | Rh | 0 | 2 | | Ph | H | H | AT | H | H | H | H | H | H | — | — |
| 2-250 | Rh | 1 | 2 | | Ph | H | AT | | H | H | H | H | H | H | pic | |
| 2-250X | Rh | 1 | 2 | | Ph | H | AT | | H | H | H | H | H | H | acac | |
| 2-250Y | Rh | 0 | 2 | | Ph | H | AT | | H | H | H | H | H | H | — | — |
| 2-251 | Rh | 1 | 2 | | Ph | H | H | MES1 | H | H | H | H | H | H | pic | |
| 2-251X | Rh | 1 | 2 | | Ph | H | H | MES1 | H | H | H | H | H | H | acac | |
| 2-251Y | Rh | 0 | 2 | | Ph | H | H | MES1 | H | H | H | H | H | H | — | — |
| 2-252 | Rh | 1 | 2 | | Ph | H | MES1 | | H | H | H | H | H | H | pic | |
| 2-252X | Rh | 1 | 2 | | Ph | H | MES1 | | H | H | H | H | H | H | acac | |

TABLE 16-continued

| No. | M | n | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 2-252Y | Rh | 0 | 2 | | Ph | H | | MES1 | H | H | H | H | H | H | — | — |
| 2-253 | Rh | 1 | 2 | | Ph | H | H | | MES2 | H | H | H | H | H | pic | |
| 2-253X | Rh | 1 | 2 | | Ph | H | H | | MES2 | H | H | H | H | H | acac | |
| 2-253Y | Rh | 0 | 2 | | Ph | H | H | | MES2 | H | H | H | H | H | — | — |
| 2-254 | Rh | 1 | 2 | | Ph | H | | MES2 | H | H | H | H | H | H | pic | |
| 2-254X | Rh | 1 | 2 | | Ph | H | | MES2 | H | H | H | H | H | H | acac | |
| 2-254Y | Rh | 0 | 2 | | Ph | H | | MES2 | H | H | H | H | H | H | — | — |
| 2-255 | Rh | 1 | 2 | | Ph | H | H | | PS1 | H | H | H | H | H | pic | |
| 2-255X | Rh | 1 | 2 | | Ph | H | H | | PS1 | H | H | H | H | H | acac | |
| 2-255Y | Rh | 0 | 2 | | Ph | H | H | | PS1 | H | H | H | H | H | — | — |
| 2-256 | Rh | 1 | 2 | | Ph | H | | PS1 | H | H | H | H | H | H | pic | |
| 2-256X | Rh | 1 | 2 | | Ph | H | | PS1 | H | H | H | H | H | H | acac | |
| 2-256Y | Rh | 0 | 2 | | Ph | H | | PS1 | H | H | H | H | H | H | — | — |
| 2-257 | Rh | 1 | 2 | | Ph | H | H | | PS2 | H | H | H | H | H | pic | |
| 2-257X | Rh | 1 | 2 | | Ph | H | H | | PS2 | H | H | H | H | H | acac | |
| 2-257Y | Rh | 0 | 2 | | Ph | H | H | | PS2 | H | H | H | H | H | — | — |
| 2-258 | Rh | 1 | 2 | | Ph | H | | PS2 | H | H | H | H | H | H | pic | |
| 2-258X | Rh | 1 | 2 | | Ph | H | | PS2 | H | H | H | H | H | H | acac | |
| 2-258Y | Rh | 0 | 2 | | Ph | H | | PS2 | H | H | H | H | H | H | — | — |
| 2-259 | Rh | 1 | 2 | | Ph | H | H | | BAL1 | H | H | H | H | H | pic | |
| 2-259X | Rh | 1 | 2 | | Ph | H | H | | BAL1 | H | H | H | H | H | acac | |
| 2-259Y | Rh | 0 | 2 | | Ph | H | H | | BAL1 | H | H | H | H | H | — | — |
| 2-260 | Rh | 1 | 2 | | Ph | H | | BAL1 | H | H | H | H | H | H | pic | |
| 2-260X | Rh | 1 | 2 | | Ph | H | | BAL1 | H | H | H | H | H | H | acac | |
| 2-260Y | Rh | 0 | 2 | | Ph | H | | BAL1 | H | H | H | H | H | H | — | — |
| 2-261 | Rh | 1 | 2 | | Ph | H | H | | BAL2 | H | H | H | H | H | pic | |
| 2-261X | Rh | 1 | 2 | | Ph | H | H | | BAL2 | H | H | H | H | H | acac | |
| 2-261Y | Rh | 0 | 2 | | Ph | H | H | | BAL2 | H | H | H | H | H | — | — |
| 2-262 | Rh | 1 | 2 | | Ph | H | | BAL2 | H | H | H | H | H | H | pic | |
| 2-262X | Rh | 1 | 2 | | Ph | H | | BAL2 | H | H | H | H | H | H | acac | |
| 2-262Y | Rh | 0 | 2 | | Ph | H | | BAL2 | H | H | H | H | H | H | — | — |
| 2-263 | Rh | 1 | 2 | | Ph | H | H | | MEK1 | H | H | H | H | H | pic | |
| 2-263X | Rh | 1 | 2 | | Ph | H | H | | MEK1 | H | H | H | H | H | acac | |
| 2-263Y | Rh | 0 | 2 | | Ph | H | H | | MEK1 | H | H | H | H | H | — | — |
| 2-264 | Rh | 1 | 2 | | Ph | H | | MEK1 | H | H | H | H | H | H | pic | |
| 2-264X | Rh | 1 | 2 | | Ph | H | | MEK1 | H | H | H | H | H | H | acac | |
| 2-264Y | Rh | 0 | 2 | | Ph | H | | MEK1 | H | H | H | H | H | H | — | — |
| 2-265 | Rh | 1 | 2 | | Ph | H | H | | MEK2 | H | H | H | H | H | pic | |
| 2-265X | Rh | 1 | 2 | | Ph | H | H | | MEK2 | H | H | H | H | H | acac | |
| 2-265Y | Rh | 0 | 2 | | Ph | H | H | | MEK2 | H | H | H | H | H | — | — |
| 2-266 | Rh | 1 | 2 | | Ph | H | | MEK2 | H | H | H | H | H | H | pic | |
| 2-266X | Rh | 1 | 2 | | Ph | H | | MEK2 | H | H | H | H | H | H | acac | |
| 2-266Y | Rh | 0 | 2 | | Ph | H | | MEK2 | H | H | H | H | H | H | — | — |
| 2-267 | Rh | 1 | 2 | | Ph | H | H | | PAL1 | H | H | H | H | H | pic | |
| 2-267X | Rh | 1 | 2 | | Ph | H | H | | PAL1 | H | H | H | H | H | acac | |
| 2-267Y | Rh | 0 | 2 | | Ph | H | H | | PAL1 | H | H | H | H | H | — | — |
| 2-268 | Rh | 1 | 2 | | Ph | H | | PAL1 | H | H | H | H | H | H | pic | |
| 2-268X | Rh | 1 | 2 | | Ph | H | | PAL1 | H | H | H | H | H | H | acac | |
| 2-268Y | Rh | 0 | 2 | | Ph | H | | PAL1 | H | H | H | H | H | H | — | — |
| 2-269 | Rh | 1 | 2 | | Ph | H | H | | PAL2 | H | H | H | H | H | pic | |
| 2-269X | Rh | 1 | 2 | | Ph | H | H | | PAL2 | H | H | H | H | H | acac | |
| 2-269Y | Rh | 0 | 2 | | Ph | H | H | | PAL2 | H | H | H | H | H | — | — |
| 2-270 | Rh | 1 | 2 | | Ph | H | | PAL2 | H | H | H | H | H | H | pic | |
| 2-270X | Rh | 1 | 2 | | Ph | H | | PAL2 | H | H | H | H | H | H | acac | |
| 2-270Y | Rh | 0 | 2 | | Ph | H | | PAL2 | H | H | H | H | H | H | — | — |
| 2-271 | Rh | 1 | 2 | | Ph | H | H | | MMK | H | H | H | H | H | pic | |
| 2-271X | Rh | 1 | 2 | | Ph | H | H | | MMK | H | H | H | H | H | acac | |
| 2-271Y | Rh | 0 | 2 | | Ph | H | H | | MMK | H | H | H | H | H | — | — |
| 2-272 | Rh | 1 | 2 | | Ph | H | | MMK | H | H | H | H | H | H | pic | |
| 2-272X | Rh | 1 | 2 | | Ph | H | | MMK | H | H | H | H | H | H | acac | |
| 2-272Y | Rh | 0 | 2 | | Ph | H | | MMK | H | H | H | H | H | H | — | — |
| 2-273 | Rh | 1 | 2 | | Ph | H | H | | EES1 | H | H | H | H | H | pic | |
| 2-273X | Rh | 1 | 2 | | Ph | H | H | | EES1 | H | H | H | H | H | acac | |
| 2-273Y | Rh | 0 | 2 | | Ph | H | H | | EES1 | H | H | H | H | H | — | — |
| 2-274 | Rh | 1 | 2 | | Ph | H | | EES2 | H | H | H | H | H | H | pic | |
| 2-274X | Rh | 1 | 2 | | Ph | H | | EES2 | H | H | H | H | H | H | acac | |
| 2-274Y | Rh | 0 | 2 | | Ph | H | | EES2 | H | H | H | H | H | H | — | — |
| 2-275 | Rh | 1 | 2 | | Ph | H | H | | PAE1 | H | H | H | H | H | pic | |
| 2-275X | Rh | 1 | 2 | | Ph | H | H | | PAE1 | H | H | H | H | H | acac | |
| 2-275Y | Rh | 0 | 2 | | Ph | H | H | | PAE1 | H | H | H | H | H | — | — |
| 2-276 | Rh | 1 | 2 | | Ph | H | | PAE2 | H | H | H | H | H | H | pic | |
| 2-276X | Rh | 1 | 2 | | Ph | H | | PAE2 | H | H | H | H | H | H | acac | |
| 2-276Y | Rh | 0 | 2 | | Ph | H | | PAE2 | H | H | H | H | H | H | — | — |
| 2-277 | Rh | 1 | 2 | | Ph | H | H | | AME1 | H | H | H | H | H | pic | |
| 2-277X | Rh | 1 | 2 | | Ph | H | H | | AME1 | H | H | H | H | H | acac | |
| 2-277Y | Rh | 0 | 2 | | Ph | H | H | | AME1 | H | H | H | H | H | — | — |
| 2-278 | Rh | 1 | 2 | | Ph | H | | AME1 | H | H | H | H | H | H | pic | |

TABLE 16-continued

| No. | M | n | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 2-278X | Rh | 1 | 2 | Ph | H | | AME1 | H | H | H | H | H | H | acac |
| 2-278Y | Rh | 0 | 2 | Ph | H | | AME1 | H | H | H | H | H | H | — — |
| 2-279 | Rh | 1 | 2 | Ph | H | H | | AME2 | H | H | H | H | H | pic |
| 2-279X | Rh | 1 | 2 | Ph | H | H | | AME2 | H | H | H | H | H | acac |
| 2-279Y | Rh | 0 | 2 | Ph | H | H | | AME2 | H | H | H | H | H | — — |
| 2-280 | Rh | 1 | 2 | Ph | H | | AME2 | H | H | H | H | H | H | pic |
| 2-280X | Rh | 1 | 2 | Ph | H | | AME2 | H | H | H | H | H | H | acac |
| 2-280Y | Rh | 0 | 2 | Ph | H | | AME2 | H | H | H | H | H | H | — — |
| 2-281 | Rh | 1 | 2 | Ph | H | H | | EAE1 | H | H | H | H | H | pic |
| 2-281X | Rh | 1 | 2 | Ph | H | H | | EAE1 | H | H | H | H | H | acac |
| 2-281Y | Rh | 0 | 2 | Ph | H | H | | EAE1 | H | H | H | H | H | — — |
| 2-282 | Rh | 1 | 2 | Ph | H | | EAE1 | H | H | H | H | H | H | pic |
| 2-282X | Rh | 1 | 2 | Ph | H | | EAE1 | H | H | H | H | H | H | acac |
| 2-282Y | Rh | 0 | 2 | Ph | H | | EAE1 | H | H | H | H | H | H | — — |
| 2-283 | Rh | 1 | 2 | Ph | H | H | | EAE2 | H | H | H | H | H | pic |
| 2-283X | Rh | 1 | 2 | Ph | H | H | | EAE2 | H | H | H | H | H | acac |
| 2-283Y | Rh | 0 | 2 | Ph | H | H | | EAE2 | H | H | H | H | H | — — |
| 2-284 | Rh | 1 | 2 | Ph | H | | EAE2 | H | H | H | H | H | H | pic |
| 2-284X | Rh | 1 | 2 | Ph | H | | EAE2 | H | H | H | H | H | H | acac |
| 2-284Y | Rh | 0 | 2 | Ph | H | | EAE2 | H | H | H | H | H | H | — — |
| 2-285 | Rh | 1 | 2 | Ph | H | H | | AAE1 | H | H | H | H | H | pic |
| 2-285X | Rh | 1 | 2 | Ph | H | H | | AAE1 | H | H | H | H | H | acac |
| 2-285Y | Rh | 0 | 2 | Ph | H | H | | AAE1 | H | H | H | H | H | — — |
| 2-286 | Rh | 1 | 2 | Ph | H | | AAE1 | H | H | H | H | H | H | pic |
| 2-286X | Rh | 1 | 2 | Ph | H | | AAE1 | H | H | H | H | H | H | acac |
| 2-286Y | Rh | 0 | 2 | Ph | H | | AAE1 | H | H | H | H | H | H | — — |
| 2-287 | Rh | 1 | 2 | Ph | H | H | | AAE2 | H | H | H | H | H | pic |
| 2-287X | Rh | 1 | 2 | Ph | H | H | | AAE2 | H | H | H | H | H | acac |
| 2-287Y | Rh | 0 | 2 | Ph | H | H | | AAE2 | H | H | H | H | H | — — |
| 2-288 | Rh | 1 | 2 | Ph | H | | AAE2 | H | H | H | H | H | H | pic |
| 2-288X | Rh | 1 | 2 | Ph | H | | AAE2 | H | H | H | H | H | H | acac |
| 2-288Y | Rh | 0 | 2 | Ph | H | | AAE2 | H | H | H | H | H | H | — — |
| 2-289 | Rh | 1 | 2 | Ph | H | H | | PME1 | H | H | H | H | H | pic |
| 2-289X | Rh | 1 | 2 | Ph | H | H | | PME1 | H | H | H | H | H | acac |
| 2-289Y | Rh | 0 | 2 | Ph | H | H | | PME1 | H | H | H | H | H | — — |
| 2-290 | Rh | 1 | 2 | Ph | H | | PME1 | H | H | H | H | H | H | pic |
| 2-290X | Rh | 1 | 2 | Ph | H | | PME1 | H | H | H | H | H | H | acac |
| 2-290Y | Rh | 0 | 2 | Ph | H | | PME1 | H | H | H | H | H | H | — — |
| 2-291 | Rh | 1 | 2 | Ph | H | H | | PME2 | H | H | H | H | H | pic |
| 2-291X | Rh | 1 | 2 | Ph | H | H | | PME2 | H | H | H | H | H | acac |
| 2-291Y | Rh | 0 | 2 | Ph | H | H | | PME2 | H | H | H | H | H | — — |
| 2-292 | Rh | 1 | 2 | Ph | H | | PME2 | H | H | H | H | H | H | pic |
| 2-292X | Rh | 1 | 2 | Ph | H | | PME2 | H | H | H | H | H | H | acac |
| 2-292Y | Rh | 0 | 2 | Ph | H | | PME2 | H | H | H | H | H | H | — — |
| 2-293 | Rh | 1 | 2 | Ph | H | H | | MET1 | H | H | H | H | H | pic |
| 2-293X | Rh | 1 | 2 | Ph | H | H | | MET1 | H | H | H | H | H | acac |
| 2-293Y | Rh | 0 | 2 | Ph | H | H | | MET1 | H | H | H | H | H | — — |
| 2-294 | Rh | 1 | 2 | Ph | H | | MET1 | H | H | H | H | H | H | pic |
| 2-294X | Rh | 1 | 2 | Ph | H | | MET1 | H | H | H | H | H | H | acac |
| 2-294Y | Rh | 0 | 2 | Ph | H | | MET1 | H | H | H | H | H | H | — — |
| 2-295 | Rh | 1 | 2 | Ph | H | H | | MET2 | H | H | H | H | H | pic |
| 2-295X | Rh | 1 | 2 | Ph | H | H | | MET2 | H | H | H | H | H | acac |
| 2-295Y | Rh | 0 | 2 | Ph | H | H | | MET2 | H | H | H | H | H | — — |
| 2-296 | Rh | 1 | 2 | Ph | H | | MET2 | H | H | H | H | H | H | pic |
| 2-296X | Rh | 1 | 2 | Ph | H | | MET2 | H | H | H | H | H | H | acac |
| 2-296Y | Rh | 0 | 2 | Ph | H | | MET2 | H | H | H | H | H | H | — — |
| 2-297 | Rh | 1 | 2 | Ph | H | H | | EE1 | H | H | H | H | H | pic |
| 2-297X | Rh | 1 | 2 | Ph | H | H | | EE1 | H | H | H | H | H | acac |
| 2-297Y | Rh | 0 | 2 | Ph | H | H | | EE1 | H | H | H | H | H | — — |
| 2-298 | Rh | 1 | 2 | Ph | H | | EE1 | H | H | H | H | H | H | pic |
| 2-298X | Rh | 1 | 2 | Ph | H | | EE1 | H | H | H | H | H | H | acac |
| 2-298Y | Rh | 0 | 2 | Ph | H | | EE1 | H | H | H | H | H | H | — — |
| 2-299 | Rh | 1 | 2 | Ph | H | H | | EE2 | H | H | H | H | H | pic |
| 2-299X | Rh | 1 | 2 | Ph | H | H | | EE2 | H | H | H | H | H | acac |
| 2-299Y | Rh | 0 | 2 | Ph | H | H | | EE2 | H | H | H | H | H | — — |
| 2-300 | Rh | 1 | 2 | Ph | H | | EE2 | H | H | H | H | H | H | pic |
| 2-300X | Rh | 1 | 2 | Ph | H | | EE2 | H | H | H | H | H | H | acac |
| 2-300Y | Rh | 0 | 2 | Ph | H | | EE2 | H | H | H | H | H | H | — — |
| 2-301 | Rh | 1 | 2 | Ph | H | H | | MS1 | H | H | H | H | H | pic |
| 2-301X | Rh | 1 | 2 | Ph | H | H | | MS1 | H | H | H | H | H | acac |
| 2-301Y | Rh | 0 | 2 | Ph | H | H | | MS1 | H | H | H | H | H | — — |
| 2-302 | Rh | 1 | 2 | Ph | H | | MS1 | H | H | H | H | H | H | pic |
| 2-302X | Rh | 1 | 2 | Ph | H | | MS1 | H | H | H | H | H | H | acac |
| 2-302Y | Rh | 0 | 2 | Ph | H | | MS1 | H | H | H | H | H | H | — — |
| 2-303 | Rh | 1 | 2 | Ph | H | H | | MS2 | H | H | H | H | H | pic |
| 2-303X | Rh | 1 | 2 | Ph | H | H | | MS2 | H | H | H | H | H | acac |
| 2-303Y | Rh | 0 | 2 | Ph | H | H | | MS2 | H | H | H | H | H | — — |

TABLE 16-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2-304 | Rh | 1 | 2 | Ph | H | | MS2 | H | H | H | H | H | H | pic | |
| 2-304X | Rh | 1 | 2 | Ph | H | | MS2 | H | H | H | H | H | H | acac | |
| 2-304Y | Rh | 0 | 2 | Ph | H | | MS2 | H | H | H | H | H | H | — | — |

TABLE 17

| No. | M | n | BBS | BS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3-155 | Rh | 1 | 3 | Ph | H | H | H | H | H | H | H | H | H | pic | |
| 3-155X | Rh | 1 | 3 | Ph | H | H | H | H | H | H | H | H | H | acac | |
| 3-155Y | Rh | 0 | 3 | Ph | H | H | H | H | H | H | H | H | H | — | — |
| 3-156 | Rh | 1 | 3 | Ph | H | F | H | F | H | H | H | H | H | pic | |
| 3-156X | Rh | 1 | 3 | Ph | H | F | H | F | H | H | H | H | H | acac | |
| 3-156Y | Rh | 0 | 3 | Ph | H | F | H | F | H | H | H | H | H | — | — |
| 3-157 | Rh | 1 | 3 | Ph | F | H | H | F | H | H | H | H | H | pic | |
| 3-157X | Rh | 1 | 3 | Ph | F | H | H | F | H | H | H | H | H | acac | |
| 3-157Y | Rh | 0 | 3 | Ph | F | H | H | F | H | H | H | H | H | — | — |
| 3-158 | Rh | 1 | 3 | Ph | CF₃ | H | CF₃ | H | H | H | H | H | H | pic | |
| 3-158X | Rh | 1 | 3 | Ph | CF₃ | H | CF₃ | H | H | H | H | H | H | acac | |
| 3-158Y | Rh | 0 | 3 | Ph | CF₃ | H | CF₃ | H | H | H | H | H | H | — | — |
| 3-159 | Rh | 1 | 3 | Ph | H | F | CF₃ | H | H | H | H | H | H | pic | |
| 3-159X | Rh | 1 | 3 | Ph | H | F | CF₃ | H | H | H | H | H | H | acac | |
| 3-159Y | Rh | 0 | 3 | Ph | H | F | CF₃ | H | H | H | H | H | H | — | — |
| 3-160 | Rh | 1 | 3 | Ph | F | H | CF₃ | H | H | H | H | H | H | pic | |
| 3-160X | Rh | 1 | 3 | Ph | F | H | CF₃ | H | H | H | H | H | H | acac | |
| 3-160Y | Rh | 0 | 3 | Ph | F | H | CF₃ | H | H | H | H | H | H | — | — |
| 3-161 | Rh | 1 | 3 | Ph | F | F | F | F | H | H | H | H | H | pic | |
| 3-161X | Rh | 1 | 3 | Ph | F | F | F | F | H | H | H | H | H | acac | |
| 3-161Y | Rh | 0 | 3 | Ph | F | F | F | F | H | H | H | H | H | — | — |
| 3-162 | Rh | 1 | 3 | Ph | H | F | H | CH₃ | H | H | H | H | H | pic | |
| 3-162X | Rh | 1 | 3 | Ph | H | F | H | CH₃ | H | H | H | H | H | acac | |
| 3-162Y | Rh | 0 | 3 | Ph | H | F | H | CH₃ | H | H | H | H | H | — | — |
| 3-163 | Rh | 1 | 3 | Ph | H | F | H | ᵗC₄H₉ | H | H | H | H | H | pic | |
| 3-163X | Rh | 1 | 3 | Ph | H | F | H | ᵗC₄H₉ | H | H | H | H | H | acac | |
| 3-163Y | Rh | 0 | 3 | Ph | H | F | H | ᵗC₄H₉ | H | H | H | H | H | — | — |
| 3-164 | Rh | 1 | 3 | Ph | H | CF₃ | H | CF₃ | H | H | H | H | H | pic | |
| 3-164X | Rh | 1 | 3 | Ph | H | CF₃ | H | CF₃ | H | H | H | H | H | acac | |
| 3-164Y | Rh | 0 | 3 | Ph | H | CF₃ | H | CF₃ | H | H | H | H | H | — | — |
| 3-165 | Rh | 1 | 3 | Ph | CF₃ | H | H | ᵗC₄H₉ | H | H | H | H | H | pic | |
| 3-165X | Rh | 1 | 3 | Ph | CF₃ | H | H | ᵗC₄H₉ | H | H | H | H | H | acac | |
| 3-165Y | Rh | 0 | 3 | Ph | CF₃ | H | H | ᵗC₄H₉ | H | H | H | H | H | — | — |
| 3-166 | Rh | 1 | 3 | Ph | H | CF₃ | H | ᵗC₄H₉ | H | H | H | H | H | pic | |
| 3-166X | Rh | 1 | 3 | Ph | H | CF₃ | H | ᵗC₄H₉ | H | H | H | H | H | acac | |
| 3-166Y | Rh | 0 | 3 | Ph | H | CF₃ | H | ᵗC₄H₉ | H | H | H | H | H | — | — |
| 3-167 | Rh | 1 | 3 | Ph | H | CF₃ | H | CH₃ | H | H | H | H | H | pic | |
| 3-167X | Rh | 1 | 3 | Ph | H | CF₃ | H | CH₃ | H | H | H | H | H | acac | |
| 3-167Y | Rh | 0 | 3 | Ph | H | CF₃ | H | CH₃ | H | H | H | H | H | — | — |
| 3-168 | Rh | 1 | 3 | Ph | H | CF₃ | CF₃ | H | H | H | H | H | H | pic | |
| 3-168X | Rh | 1 | 3 | Ph | H | CF₃ | CF₃ | H | H | H | H | H | H | acac | |
| 3-168Y | Rh | 0 | 3 | Ph | H | CF₃ | CF₃ | H | H | H | H | H | H | — | — |
| 3-169 | Rh | 1 | 3 | Ph | H | H | NO₂ | H | H | H | H | H | H | pic | |
| 3-169X | Rh | 1 | 3 | Ph | H | H | NO₂ | H | H | H | H | H | H | acac | |
| 3-169Y | Rh | 0 | 3 | Ph | H | H | NO₂ | H | H | H | H | H | H | — | — |
| 3-170 | Rh | 1 | 3 | Ph | F | H | NO₂ | H | H | H | H | H | H | pic | |
| 3-170X | Rh | 1 | 3 | Ph | F | H | NO₂ | H | H | H | H | H | H | acac | |
| 3-170Y | Rh | 0 | 3 | Ph | F | H | NO₂ | H | H | H | H | H | H | — | — |
| 3-171 | Rh | 1 | 3 | Ph | F | H | NO₂ | F | H | H | H | H | H | pic | |
| 3-171X | Rh | 1 | 3 | Ph | F | H | NO₂ | F | H | H | H | H | H | acac | |
| 3-171Y | Rh | 0 | 3 | Ph | F | H | NO₂ | F | H | H | H | H | H | — | — |
| 3-172 | Rh | 1 | 3 | Ph | H | NO₂ | H | NO₂ | H | H | H | H | H | pic | |
| 3-172X | Rh | 1 | 3 | Ph | H | NO₂ | H | NO₂ | H | H | H | H | H | acac | |
| 3-172Y | Rh | 0 | 3 | Ph | H | NO₂ | H | NO₂ | H | H | H | H | H | — | — |
| 3-173 | Rh | 1 | 3 | Ph | NO₂ | H | H | NO₂ | H | H | H | H | H | pic | |
| 3-173X | Rh | 1 | 3 | Ph | NO₂ | H | H | NO₂ | H | H | H | H | H | acac | |
| 3-173Y | Rh | 0 | 3 | Ph | NO₂ | H | H | NO₂ | H | H | H | H | H | — | — |
| 3-174 | Rh | 1 | 3 | Ph | H | H | CF₃ | H | H | H | H | H | H | pic | |
| 3-174X | Rh | 1 | 3 | Ph | H | H | CF₃ | H | H | H | H | H | H | acac | |
| 3-174Y | Rh | 0 | 3 | Ph | H | H | CF₃ | H | H | H | H | H | H | — | — |
| 3-175 | Rh | 1 | 3 | Ph | H | Cl | CF₃ | H | H | H | H | H | H | pic | |
| 3-175X | Rh | 1 | 3 | Ph | H | Cl | CF₃ | H | H | H | H | H | H | acac | |
| 3-175Y | Rh | 0 | 3 | Ph | H | Cl | CF₃ | H | H | H | H | H | H | — | — |
| 3-176 | Rh | 1 | 3 | Ph | H | NO₂ | H | H | H | H | H | H | H | pic | |
| 3-176X | Rh | 1 | 3 | Ph | H | NO₂ | H | H | H | H | H | H | H | acac | |
| 3-176Y | Rh | 0 | 3 | Ph | H | NO₂ | H | H | H | H | H | H | H | — | — |

TABLE 17-continued

| No. | M | n | BBS | BS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3-177 | Rh | 1 | 3 | Ph | H | CF₃ | H | H | H | H | H | H | H | pic | |
| 3-177X | Rh | 1 | 3 | Ph | H | CF₃ | H | H | H | H | H | H | H | acac | |
| 3-177Y | Rh | 0 | 3 | Ph | H | CF₃ | H | H | H | H | H | H | H | — | — |
| 3-178 | Rh | 1 | 3 | Ph | H | NO₂ | H | CH₃ | H | H | H | H | H | pic | |
| 3-178X | Rh | 1 | 3 | Ph | H | NO₂ | H | CH₃ | H | H | H | H | H | acac | |
| 3-178Y | Rh | 0 | 3 | Ph | H | NO₂ | H | CH₃ | H | H | H | H | H | — | — |
| 3-179 | Rh | 1 | 3 | Ph | H | NO₂ | H | ᵗC₄H₉ | H | H | H | H | H | pic | |
| 3-179X | Rh | 1 | 3 | Ph | H | NO₂ | H | ᵗC₄H₉ | H | H | H | H | H | acac | |
| 3-179Y | Rh | 0 | 3 | Ph | H | NO₂ | H | ᵗC₄H₉ | H | H | H | H | H | — | — |
| 3-180 | Rh | 1 | 3 | Ph | H | H | CH₃O | H | H | H | H | H | H | pic | |
| 3-180X | Rh | 1 | 3 | Ph | H | H | CH₃O | H | H | H | H | H | H | acac | |
| 3-180Y | Rh | 0 | 3 | Ph | H | H | CH₃O | H | H | H | H | H | H | — | — |
| 3-181 | Rh | 1 | 3 | Ph | H | CH₃O | H | H | H | H | H | H | H | pic | |
| 3-181X | Rh | 1 | 3 | Ph | H | CH₃O | H | H | H | H | H | H | H | acac | |
| 3-181Y | Rh | 0 | 3 | Ph | H | CH₃O | H | H | H | H | H | H | H | — | — |
| 3-182 | Rh | 1 | 3 | Ph | H | CH₃O | H | CH₃ | H | H | H | H | H | pic | |
| 3-182X | Rh | 1 | 3 | Ph | H | CH₃O | H | CH₃ | H | H | H | H | H | acac | |
| 3-182Y | Rh | 0 | 3 | Ph | H | CH₃O | H | CH₃ | H | H | H | H | H | — | — |
| 3-183 | Rh | 1 | 3 | Ph | H | CH₃O | H | ᵗC₄H₉ | H | H | H | H | H | pic | |
| 3-183X | Rh | 1 | 3 | Ph | H | CH₃O | H | ᵗC₄H₉ | H | H | H | H | H | acac | |
| 3-183Y | Rh | 0 | 3 | Ph | H | CH₃O | H | ᵗC₄H₉ | H | H | H | H | H | — | — |
| 3-184 | Rh | 1 | 3 | Ph | H | H | H | H | ᵗC₄H₉ | H | H | H | H | pic | |
| 3-184X | Rh | 1 | 3 | Ph | H | H | H | H | ᵗC₄H₉ | H | H | H | H | acac | |
| 3-184Y | Rh | 0 | 3 | Ph | H | H | H | H | ᵗC₄H₉ | H | H | H | H | — | — |
| 3-185 | Rh | 1 | 3 | Ph | H | F | H | F | ᵗC₄H₉ | H | H | H | H | pic | |
| 3-185X | Rh | 1 | 3 | Ph | H | F | H | F | ᵗC₄H₉ | H | H | H | H | acac | |
| 3-185Y | Rh | 0 | 3 | Ph | H | F | H | F | ᵗC₄H₉ | H | H | H | H | — | — |
| 3-186 | Rh | 1 | 3 | Ph | CF₃ | H | CF₃ | H | ᵗC₄H₉ | H | H | H | H | pic | |
| 3-186X | Rh | 1 | 3 | Ph | CF₃ | H | CF₃ | H | ᵗC₄H₉ | H | H | H | H | acac | |
| 3-186Y | Rh | 0 | 3 | Ph | CF₃ | H | CF₃ | H | ᵗC₄H₉ | H | H | H | H | — | — |
| 3-187 | Rh | 1 | 3 | Ph | H | CF₃ | H | CH₃ | ᵗC₄H₉ | H | H | H | H | pic | |
| 3-187X | Rh | 1 | 3 | Ph | H | CF₃ | H | CH₃ | ᵗC₄H₉ | H | H | H | H | acac | |
| 3-187Y | Rh | 0 | 3 | Ph | H | CF₃ | H | CH₃ | ᵗC₄H₉ | H | H | H | H | — | — |
| 3-188 | Rh | 1 | 3 | Ph | H | Si(CH₃)₃ | H | H | H | H | H | H | H | pic | |
| 3-188X | Rh | 1 | 3 | Ph | H | Si(CH₃)₃ | H | H | H | H | H | H | H | acac | |
| 3-188Y | Rh | 0 | 3 | Ph | H | Si(CH₃)₃ | H | H | H | H | H | H | H | — | — |
| 3-189 | Rh | 1 | 3 | Ph | H | H | Si(CH₃)₃ | H | H | H | H | H | H | pic | |
| 3-189X | Rh | 1 | 3 | Ph | H | H | Si(CH₃)₃ | H | H | H | H | H | H | acac | |
| 3-189Y | Rh | 0 | 3 | Ph | H | H | Si(CH₃)₃ | H | H | H | H | H | H | — | — |
| 3-190 | Rh | 1 | 3 | Ph | H | H | H | Si(CH₃)₃ | H | H | H | H | H | pic | |
| 3-190X | Rh | 1 | 3 | Ph | H | H | H | Si(CH₃)₃ | H | H | H | H | H | acac | |
| 3-190Y | Rh | 0 | 3 | Ph | H | H | H | Si(CH₃)₃ | H | H | H | H | H | — | — |
| 3-191 | Rh | 1 | 3 | Ph | H | F | H | Si(CH₃)₃ | H | H | H | H | H | pic | |
| 3-191X | Rh | 1 | 3 | Ph | H | F | H | Si(CH₃)₃ | H | H | H | H | H | acac | |
| 3-191Y | Rh | 0 | 3 | Ph | H | F | H | Si(CH₃)₃ | H | H | H | H | H | — | — |
| 3-192 | Rh | 1 | 3 | Ph | H | CF₃ | H | Si(CH₃)₃ | H | H | H | H | H | pic | |
| 3-192X | Rh | 1 | 3 | Ph | H | CF₃ | H | Si(CH₃)₃ | H | H | H | H | H | acac | |
| 3-192Y | Rh | 0 | 3 | Ph | H | CF₃ | H | Si(CH₃)₃ | H | H | H | H | H | — | — |
| 3-193 | Rh | 1 | 3 | Ph | H | Si(CH₃)₃ | H | F | H | H | H | H | H | pic | |
| 3-193X | Rh | 1 | 3 | Ph | H | Si(CH₃)₃ | H | F | H | H | H | H | H | acac | |
| 3-193Y | Rh | 0 | 3 | Ph | H | Si(CH₃)₃ | H | F | H | H | H | H | H | — | — |
| 3-194 | Rh | 1 | 3 | Ph | H | Si(CH₃)₃ | H | CF₃ | H | H | H | H | H | pic | |
| 3-194X | Rh | 1 | 3 | Ph | H | Si(CH₃)₃ | H | CF₃ | H | H | H | H | H | acac | |
| 3-194Y | Rh | 0 | 3 | Ph | H | Si(CH₃)₃ | H | CF₃ | H | H | H | H | H | — | — |
| 3-195 | Rh | 1 | 3 | Ph | Si(CH₃)₃ | H | Si(CH₃)₃ | H | H | H | H | H | H | pic | |
| 3-195X | Rh | 1 | 3 | Ph | Si(CH₃)₃ | H | Si(CH₃)₃3 | H | H | H | H | H | H | acac | |
| 3-195Y | Rh | 0 | 3 | Ph | Si(CH₃)₃ | H | Si(CH₃)₃ | H | H | H | H | H | H | — | — |
| 3-196 | Rh | 1 | 3 | Ph | H | H | H | COCH₃ | H | H | H | H | H | pic | |
| 3-196X | Rh | 1 | 3 | Ph | H | H | H | COCH₃ | H | H | H | H | H | acac | |
| 3-196Y | Rh | 0 | 3 | Ph | H | H | H | COCH₃ | H | H | H | H | H | — | — |
| 3-197 | Rh | 1 | 3 | Ph | H | H | COCH₃ | H | H | H | H | H | H | pic | |
| 3-197X | Rh | 1 | 3 | Ph | H | H | COCH₃ | H | H | H | H | H | H | acac | |
| 3-197Y | Rh | 0 | 3 | Ph | H | H | COCH₃ | H | H | H | H | H | H | — | — |
| 3-198 | Rh | 1 | 3 | Ph | H | COCH₃ | H | H | H | H | H | H | H | pic | |
| 3-198X | Rh | 1 | 3 | Ph | H | COCH₃ | H | H | H | H | H | H | H | acac | |
| 3-198Y | Rh | 0 | 3 | Ph | H | COCH₃ | H | H | H | H | H | H | H | — | — |
| 3-199 | Rh | 1 | 3 | Ph | H | H | BL | H | H | H | H | H | H | pic | |
| 3-199X | Rh | 1 | 3 | Ph | H | H | BL | H | H | H | H | H | H | acac | |
| 3-199Y | Rh | 0 | 3 | Ph | H | H | BL | H | H | H | H | H | H | — | — |
| 3-200 | Rh | 1 | 3 | Ph | H | BL | H | H | H | H | H | H | H | pic | |
| 3-200X | Rh | 1 | 3 | Ph | H | BL | H | H | H | H | H | H | H | acac | |
| 3-200Y | Rh | 0 | 3 | Ph | H | BL | H | H | H | H | H | H | H | — | — |
| 3-201 | Rh | 1 | 3 | Ph | H | H | PL | H | H | H | H | H | H | pic | |
| 3-201X | Rh | 1 | 3 | Ph | H | H | PL | H | H | H | H | H | H | acac | |
| 3-201Y | Rh | 0 | 3 | Ph | H | H | PL | H | H | H | H | H | H | — | — |
| 3-202 | Rh | 1 | 3 | Ph | H | PL | H | H | H | H | H | H | H | pic | |
| 3-202X | Rh | 1 | 3 | Ph | H | PL | H | H | H | H | H | H | H | acac | |

TABLE 17-continued

| No. | M | n | BBS | BS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3-202Y | Rh | 0 | 3 | Ph | H | | PL | H | H | H | H | H | H | — | — |
| 3-203 | Rh | 1 | 3 | Ph | H | H | | MEE1 | H | H | H | H | H | pic | |
| 3-203X | Rh | 1 | 3 | Ph | H | | H | MEE1 | H | H | H | H | H | acac | |
| 3-203Y | Rh | 0 | 3 | Ph | H | | H | MEE1 | H | H | H | H | H | — | — |
| 3-204 | Rh | 1 | 3 | Ph | H | | MEE1 | | H | H | H | H | H | H | pic |
| 3-204X | Rh | 1 | 3 | Ph | H | | MEE1 | | H | H | H | H | H | H | acac |
| 3-204Y | Rh | 0 | 3 | Ph | H | | MEE1 | | H | H | H | H | H | H | — — |
| 3-205 | Rh | 1 | 3 | Ph | H | H | | MEE2 | H | H | H | H | H | pic | |
| 3-205X | Rh | 1 | 3 | Ph | H | | H | MEE2 | H | H | H | H | H | acac | |
| 3-205Y | Rh | 0 | 3 | Ph | H | | H | MEE2 | H | H | H | H | H | — | — |
| 3-206 | Rh | 1 | 3 | Ph | H | | MEE2 | | H | H | H | H | H | H | pic |
| 3-206X | Rh | 1 | 3 | Ph | H | | MEE2 | | H | H | H | H | H | H | acac |
| 3-206Y | Rh | 0 | 3 | Ph | H | | MEE2 | | H | H | H | H | H | H | — — |
| 3-207 | Rh | 1 | 3 | Ph | H | H | | PA1 | H | H | H | H | H | pic | |
| 3-207X | Rh | 1 | 3 | Ph | H | | H | PA1 | H | H | H | H | H | acac | |
| 3-207Y | Rh | 0 | 3 | Ph | H | | H | PA1 | H | H | H | H | H | — | — |
| 3-208 | Rh | 1 | 3 | Ph | H | | PA1 | | H | H | H | H | H | H | pic |
| 3-208X | Rh | 1 | 3 | Ph | H | | PA1 | | H | H | H | H | H | H | acac |
| 3-208Y | Rh | 0 | 3 | Ph | H | | PA1 | | H | H | H | H | H | H | — — |
| 3-209 | Rh | 1 | 3 | Ph | H | H | | PA2 | H | H | H | H | H | pic | |
| 3-209X | Rh | 1 | 3 | Ph | H | | H | PA2 | H | H | H | H | H | acac | |
| 3-209Y | Rh | 0 | 3 | Ph | H | | H | PA2 | H | H | H | H | H | — | — |
| 3-210 | Rh | 1 | 3 | Ph | H | | PA2 | | H | H | H | H | H | H | pic |
| 3-210X | Rh | 1 | 3 | Ph | H | | PA2 | | H | H | H | H | H | H | acac |
| 3-210Y | Rh | 0 | 3 | Ph | H | | PA2 | | H | H | H | H | H | H | — — |
| 3-211 | Rh | 1 | 3 | Ph | H | H | | EA1 | H | H | H | H | H | pic | |
| 3-211X | Rh | 1 | 3 | Ph | H | | H | EA1 | H | H | H | H | H | acac | |
| 3-211Y | Rh | 0 | 3 | Ph | H | | H | EA1 | H | H | H | H | H | — | — |
| 3-212 | Rh | 1 | 3 | Ph | H | | EA2 | | H | H | H | H | H | H | pic |
| 3-212X | Rh | 1 | 3 | Ph | H | | EA2 | | H | H | H | H | H | H | acac |
| 3-212Y | Rh | 0 | 3 | Ph | H | | EA2 | | H | H | H | H | H | H | — — |
| 3-213 | Rh | 1 | 3 | Ph | H | H | | ME | H | H | H | H | H | pic | |
| 3-213X | Rh | 1 | 3 | Ph | H | | H | ME | H | H | H | H | H | acac | |
| 3-213Y | Rh | 0 | 3 | Ph | H | | H | ME | H | H | H | H | H | — | — |
| 3-214 | Rh | 1 | 3 | Ph | H | | ME | | H | H | H | H | H | H | pic |
| 3-214X | Rh | 1 | 3 | Ph | H | | ME | | H | H | H | H | H | H | acac |
| 3-214Y | Rh | 0 | 3 | Ph | H | | ME | | H | H | H | H | H | H | — — |
| 3-215 | Rh | 1 | 3 | Ph | H | H | | AT | H | H | H | H | H | pic | |
| 3-215X | Rh | 1 | 3 | Ph | H | | H | AT | H | H | H | H | H | acac | |
| 3-215Y | Rh | 0 | 3 | Ph | H | | H | AT | H | H | H | H | H | — | — |
| 3-216 | Rh | 1 | 3 | Ph | H | | AT | | H | H | H | H | H | H | pic |
| 3-216X | Rh | 1 | 3 | Ph | H | | AT | | H | H | H | H | H | H | acac |
| 3-216Y | Rh | 0 | 3 | Ph | H | | AT | | H | H | H | H | H | H | — — |
| 3-217 | Rh | 1 | 3 | Ph | H | H | | MES1 | H | H | H | H | H | pic | |
| 3-217X | Rh | 1 | 3 | Ph | H | | H | MES1 | H | H | H | H | H | acac | |
| 3-217Y | Rh | 0 | 3 | Ph | H | | H | MES1 | H | H | H | H | H | — | — |
| 3-218 | Rh | 1 | 3 | Ph | H | | MES1 | | H | H | H | H | H | H | pic |
| 3-218X | Rh | 1 | 3 | Ph | H | | MES1 | | H | H | H | H | H | H | acac |
| 3-218Y | Rh | 0 | 3 | Ph | H | | MES1 | | H | H | H | H | H | H | — — |
| 3-219 | Rh | 1 | 3 | Ph | H | H | | MES2 | H | H | H | H | H | pic | |
| 3-219X | Rh | 1 | 3 | Ph | H | | H | MES2 | H | H | H | H | H | acac | |
| 3-219Y | Rh | 0 | 3 | Ph | H | | H | MES2 | H | H | H | H | H | — | — |
| 3-220 | Rh | 1 | 3 | Ph | H | | MES2 | | H | H | H | H | H | H | pic |
| 3-220X | Rh | 1 | 3 | Ph | H | | MES2 | | H | H | H | H | H | H | acac |
| 3-220Y | Rh | 0 | 3 | Ph | H | | MES2 | | H | H | H | H | H | H | — — |
| 3-221 | Rh | 1 | 3 | Ph | H | H | | PS1 | H | H | H | H | H | pic | |
| 3-221X | Rh | 1 | 3 | Ph | H | | H | PS1 | H | H | H | H | H | acac | |
| 3-221Y | Rh | 0 | 3 | Ph | H | | H | PS1 | H | H | H | H | H | — | — |
| 3-222 | Rh | 1 | 3 | Ph | H | | PS1 | | H | H | H | H | H | H | pic |
| 3-222X | Rh | 1 | 3 | Ph | H | | PS1 | | H | H | H | H | H | H | acac |
| 3-222Y | Rh | 0 | 3 | Ph | H | | PS1 | | H | H | H | H | H | H | — — |
| 3-223 | Rh | 1 | 3 | Ph | H | H | | PS2 | H | H | H | H | H | pic | |
| 3-223X | Rh | 1 | 3 | Ph | H | | H | PS2 | H | H | H | H | H | acac | |
| 3-223Y | Rh | 0 | 3 | Ph | H | | H | PS2 | H | H | H | H | H | — | — |
| 3-224 | Rh | 1 | 3 | Ph | H | | PS2 | | H | H | H | H | H | H | pic |
| 3-224X | Rh | 1 | 3 | Ph | H | | PS2 | | H | H | H | H | H | H | acac |
| 3-224Y | Rh | 0 | 3 | Ph | H | | PS2 | | H | H | H | H | H | H | — — |
| 3-225 | Rh | 1 | 3 | Ph | H | H | | BAL1 | H | H | H | H | H | pic | |
| 3-225X | Rh | 1 | 3 | Ph | H | | H | BAL1 | H | H | H | H | H | acac | |
| 3-225Y | Rh | 0 | 3 | Ph | H | | H | BAL1 | H | H | H | H | H | — | — |
| 3-226 | Rh | 1 | 3 | Ph | H | | BAL1 | | H | H | H | H | H | H | pic |
| 3-226X | Rh | 1 | 3 | Ph | H | | BAL1 | | H | H | H | H | H | H | acac |
| 3-226Y | Rh | 0 | 3 | Ph | H | | BAL1 | | H | H | H | H | H | H | — — |
| 3-227 | Rh | 1 | 3 | Ph | H | H | | BAL2 | H | H | H | H | H | pic | |
| 3-227X | Rh | 1 | 3 | Ph | H | | H | BAL2 | H | H | H | H | H | acac | |
| 3-227Y | Rh | 0 | 3 | Ph | H | | H | BAL2 | H | H | H | H | H | — | — |
| 3-228 | Rh | 1 | 3 | Ph | H | | BAL2 | | H | H | H | H | H | H | pic |

TABLE 17-continued

| No. | M | n | BBS | BS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3-228X | Rh | 1 | 3 | Ph | H | | BAL2 | | H | H | H | H | H | H | acac |
| 3-228Y | Rh | 0 | 3 | Ph | H | | BAL2 | | H | H | H | H | H | — | — |
| 3-229 | Rh | 1 | 3 | Ph | H | H | | MEK1 | H | H | H | H | H | H | pic |
| 3-229X | Rh | 1 | 3 | Ph | H | H | | MEK1 | H | H | H | H | H | H | acac |
| 3-229Y | Rh | 0 | 3 | Ph | H | H | | MEK1 | H | H | H | H | H | — | — |
| 3-230 | Rh | 1 | 3 | Ph | H | | MEK1 | | H | H | H | H | H | H | pic |
| 3-230X | Rh | 1 | 3 | Ph | H | | MEK1 | | H | H | H | H | H | H | acac |
| 3-230Y | Rh | 0 | 3 | Ph | H | | MEK1 | | H | H | H | H | H | — | — |
| 3-231 | Rh | 1 | 3 | Ph | H | H | | MEK2 | H | H | H | H | H | H | pic |
| 3-231X | Rh | 1 | 3 | Ph | H | H | | MEK2 | H | H | H | H | H | H | acac |
| 3-231Y | Rh | 0 | 3 | Ph | H | H | | MEK2 | H | H | H | H | H | — | — |
| 3-232 | Rh | 1 | 3 | Ph | H | | MEK2 | | H | H | H | H | H | H | pic |
| 3-232X | Rh | 1 | 3 | Ph | H | | MEK2 | | H | H | H | H | H | H | acac |
| 3-232Y | Rh | 0 | 3 | Ph | H | | MEK2 | | H | H | H | H | H | — | — |
| 3-233 | Rh | 1 | 3 | Ph | H | H | | PAL1 | H | H | H | H | H | H | pic |
| 3-233X | Rh | 1 | 3 | Ph | H | H | | PAL1 | H | H | H | H | H | H | acac |
| 3-233Y | Rh | 0 | 3 | Ph | H | H | | PAL1 | H | H | H | H | H | — | — |
| 3-234 | Rh | 1 | 3 | Ph | H | | PAL1 | | H | H | H | H | H | H | pic |
| 3-234X | Rh | 1 | 3 | Ph | H | | PAL1 | | H | H | H | H | H | H | acac |
| 3-234Y | Rh | 0 | 3 | Ph | H | | PAL1 | | H | H | H | H | H | — | — |
| 3-235 | Rh | 1 | 3 | Ph | H | H | | PAL2 | H | H | H | H | H | H | pic |
| 3-235X | Rh | 1 | 3 | Ph | H | H | | PAL2 | H | H | H | H | H | H | acac |
| 3-235Y | Rh | 0 | 3 | Ph | H | H | | PAL2 | H | H | H | H | H | — | — |
| 3-236 | Rh | 1 | 3 | Ph | H | | PAL2 | | H | H | H | H | H | H | pic |
| 3-236X | Rh | 1 | 3 | Ph | H | | PAL2 | | H | H | H | H | H | H | acac |
| 3-236Y | Rh | 0 | 3 | Ph | H | | PAL2 | | H | H | H | H | H | — | — |
| 3-237 | Rh | 1 | 3 | Ph | H | H | | MMK | H | H | H | H | H | H | pic |
| 3-237X | Rh | 1 | 3 | Ph | H | H | | MMK | H | H | H | H | H | H | acac |
| 3-237Y | Rh | 0 | 3 | Ph | H | H | | MMK | H | H | H | H | H | — | — |
| 3-238 | Rh | 1 | 3 | Ph | H | | MMK | | H | H | H | H | H | H | pic |
| 3-238X | Rh | 1 | 3 | Ph | H | | MMK | | H | H | H | H | H | H | acac |
| 3-238Y | Rh | 0 | 3 | Ph | H | | MMK | | H | H | H | H | H | — | — |
| 3-239 | Rh | 1 | 3 | Ph | H | H | | EES1 | H | H | H | H | H | H | pic |
| 3-239X | Rh | 1 | 3 | Ph | H | H | | EES1 | H | H | H | H | H | H | acac |
| 3-239Y | Rh | 0 | 3 | Ph | H | H | | EES1 | H | H | H | H | H | — | — |
| 3-240 | Rh | 1 | 3 | Ph | H | | EES2 | | H | H | H | H | H | H | pic |
| 3-240X | Rh | 1 | 3 | Ph | H | | EES2 | | H | H | H | H | H | H | acac |
| 3-240Y | Rh | 0 | 3 | Ph | H | | EES2 | | H | H | H | H | H | — | — |
| 3-241 | Rh | 1 | 3 | Ph | H | H | | PAE1 | H | H | H | H | H | H | pic |
| 3-241X | Rh | 1 | 3 | Ph | H | H | | PAE1 | H | H | H | H | H | H | acac |
| 3-241Y | Rh | 0 | 3 | Ph | H | H | | PAE1 | H | H | H | H | H | — | — |
| 3-242 | Rh | 1 | 3 | Ph | H | | PAE2 | | H | H | H | H | H | H | pic |
| 3-242X | Rh | 1 | 3 | Ph | H | | PAE2 | | H | H | H | H | H | H | acac |
| 3-242Y | Rh | 0 | 3 | Ph | H | | PAE2 | | H | H | H | H | H | — | — |
| 3-243 | Rh | 1 | 3 | Ph | H | H | | AME1 | H | H | H | H | H | H | pic |
| 3-243X | Rh | 1 | 3 | Ph | H | H | | AME1 | H | H | H | H | H | H | acac |
| 3-243Y | Rh | 0 | 3 | Ph | H | H | | AME1 | H | H | H | H | H | — | — |
| 3-244 | Rh | 1 | 3 | Ph | H | | AME1 | | H | H | H | H | H | H | pic |
| 3-244X | Rh | 1 | 3 | Ph | H | | AME1 | | H | H | H | H | H | H | acac |
| 3-244Y | Rh | 0 | 3 | Ph | H | | AME1 | | H | H | H | H | H | — | — |
| 3-245 | Rh | 1 | 3 | Ph | H | H | | AME2 | H | H | H | H | H | H | pic |
| 3-245X | Rh | 1 | 3 | Ph | H | H | | AME2 | H | H | H | H | H | H | acac |
| 3-245Y | Rh | 0 | 3 | Ph | H | H | | AME2 | H | H | H | H | H | — | — |
| 3-246 | Rh | 1 | 3 | Ph | H | | AME2 | | H | H | H | H | H | H | pic |
| 3-246X | Rh | 1 | 3 | Ph | H | | AME2 | | H | H | H | H | H | H | acac |
| 3-246Y | Rh | 0 | 3 | Ph | H | | AME2 | | H | H | H | H | H | — | — |
| 3-247 | Rh | 1 | 3 | Ph | H | H | | EAE1 | H | H | H | H | H | H | pic |
| 3-247X | Rh | 1 | 3 | Ph | H | H | | EAE1 | H | H | H | H | H | H | acac |
| 3-247Y | Rh | 0 | 3 | Ph | H | H | | EAE1 | H | H | H | H | H | — | — |
| 3-248 | Rh | 1 | 3 | Ph | H | | EAE1 | | H | H | H | H | H | H | pic |
| 3-248X | Rh | 1 | 3 | Ph | H | | EAE1 | | H | H | H | H | H | H | acac |
| 3-248Y | Rh | 0 | 3 | Ph | H | | EAE1 | | H | H | H | H | H | — | — |
| 3-249 | Rh | 1 | 3 | Ph | H | H | | EAE2 | H | H | H | H | H | H | pic |
| 3-249X | Rh | 1 | 3 | Ph | H | H | | EAE2 | H | H | H | H | H | H | acac |
| 3-249Y | Rh | 0 | 3 | Ph | H | H | | EAE2 | H | H | H | H | H | — | — |
| 3-250 | Rh | 1 | 3 | Ph | H | | EAE2 | | H | H | H | H | H | H | pic |
| 3-250X | Rh | 1 | 3 | Ph | H | | EAE2 | | H | H | H | H | H | H | acac |
| 3-250Y | Rh | 0 | 3 | Ph | H | | EAE2 | | H | H | H | H | H | — | — |
| 3-251 | Rh | 1 | 3 | Ph | H | H | | AAE1 | H | H | H | H | H | H | pic |
| 3-251X | Rh | 1 | 3 | Ph | H | H | | AAE1 | H | H | H | H | H | H | acac |
| 3-251Y | Rh | 0 | 3 | Ph | H | H | | AAE1 | H | H | H | H | H | — | — |
| 3-252 | Rh | 1 | 3 | Ph | H | | AAE1 | | H | H | H | H | H | H | pic |
| 3-252X | Rh | 1 | 3 | Ph | H | | AAE1 | | H | H | H | H | H | H | acac |
| 3-252Y | Rh | 0 | 3 | Ph | H | | AAE1 | | H | H | H | H | H | — | — |
| 3-253 | Rh | 1 | 3 | Ph | H | H | | AAE2 | H | H | H | H | H | H | pic |
| 3-253X | Rh | 1 | 3 | Ph | H | H | | AAE2 | H | H | H | H | H | H | acac |
| 3-253Y | Rh | 0 | 3 | Ph | H | H | | AAE2 | H | H | H | H | H | — | — |

TABLE 17-continued

| No. | M | n | BBS | BS G | T$^1$ | T$^2$ | T$^3$ | T$^4$ | T$^5$ | T$^6$ | T$^7$ | T$^8$ | T$^9$ | L$^1$ | L$^2$ |
|---|---|---|---|---|---|---|---|---|---|---|---|---|---|---|---|
| 3-254 | Rh | 1 | 3 | Ph | H | | AAE2 | H | H | H | H | H | H | pic | |
| 3-254X | Rh | 1 | 3 | Ph | H | | AAE2 | H | H | H | H | H | H | acac | |
| 3-254Y | Rh | 0 | 3 | Ph | H | | AAE2 | H | H | H | H | H | H | — | — |
| 3-255 | Rh | 1 | 3 | Ph | H | H | | PME1 | H | H | H | H | H | pic | |
| 3-255X | Rh | 1 | 3 | Ph | H | H | | PME1 | H | H | H | H | H | acac | |
| 3-255Y | Rh | 0 | 3 | Ph | H | H | | PME1 | H | H | H | H | H | — | — |
| 3-256 | Rh | 1 | 3 | Ph | H | | PME1 | H | H | H | H | H | H | pic | |
| 3-256X | Rh | 1 | 3 | Ph | H | | PME1 | H | H | H | H | H | H | acac | |
| 3-256Y | Rh | 0 | 3 | Ph | H | | PME1 | H | H | H | H | H | H | — | — |
| 3-257 | Rh | 1 | 3 | Ph | H | H | | PME2 | H | H | H | H | H | pic | |
| 3-257X | Rh | 1 | 3 | Ph | H | H | | PME2 | H | H | H | H | H | acac | |
| 3-257Y | Rh | 0 | 3 | Ph | H | H | | PME2 | H | H | H | H | H | — | — |
| 3-258 | Rh | 1 | 3 | Ph | H | | PME2 | H | H | H | H | H | H | pic | |
| 3-258X | Rh | 1 | 3 | Ph | H | | PME2 | H | H | H | H | H | H | acac | |
| 3-258Y | Rh | 0 | 3 | Ph | H | | PME2 | H | H | H | H | H | H | — | — |
| 3-259 | Rh | 1 | 3 | Ph | H | H | | MET1 | H | H | H | H | H | pic | |
| 3-259X | Rh | 1 | 3 | Ph | H | H | | MET1 | H | H | H | H | H | acac | |
| 3-259Y | Rh | 0 | 3 | Ph | H | H | | MET1 | H | H | H | H | H | — | — |
| 3-260 | Rh | 1 | 3 | Ph | H | | MET1 | H | H | H | H | H | H | pic | |
| 3-260X | Rh | 1 | 3 | Ph | H | | MET1 | H | H | H | H | H | H | acac | |
| 3-260Y | Rh | 0 | 3 | Ph | H | | MET1 | H | H | H | H | H | H | — | — |
| 3-261 | Rh | 1 | 3 | Ph | H | H | | MET2 | H | H | H | H | H | pic | |
| 3-261X | Rh | 1 | 3 | Ph | H | H | | MET2 | H | H | H | H | H | acac | |
| 3-261Y | Rh | 0 | 3 | Ph | H | H | | MET2 | H | H | H | H | H | — | — |
| 3-262 | Rh | 1 | 3 | Ph | H | | MET2 | H | H | H | H | H | H | pic | |
| 3-262X | Rh | 1 | 3 | Ph | H | | MET2 | H | H | H | H | H | H | acac | |
| 3-262Y | Rh | 0 | 3 | Ph | H | | MET2 | H | H | H | H | H | H | — | — |
| 3-263 | Rh | 1 | 3 | Ph | H | H | | EE1 | H | H | H | H | H | pic | |
| 3-263X | Rh | 1 | 3 | Ph | H | H | | EE1 | H | H | H | H | H | acac | |
| 3-263Y | Rh | 0 | 3 | Ph | H | H | | EE1 | H | H | H | H | H | — | — |
| 3-264 | Rh | 1 | 3 | Ph | H | | EE1 | H | H | H | H | H | H | pic | |
| 3-264X | Rh | 1 | 3 | Ph | H | | EE1 | H | H | H | H | H | H | acac | |
| 3-264Y | Rh | 0 | 3 | Ph | H | | EE1 | H | H | H | H | H | H | — | — |
| 3-265 | Rh | 1 | 3 | Ph | H | H | | EE2 | H | H | H | H | H | pic | |
| 3-265X | Rh | 1 | 3 | Ph | H | H | | EE2 | H | H | H | H | H | acac | |
| 3-265Y | Rh | 0 | 3 | Ph | H | H | | EE2 | H | H | H | H | H | — | — |
| 3-266 | Rh | 1 | 3 | Ph | H | | EE2 | H | H | H | H | H | H | pic | |
| 3-266X | Rh | 1 | 3 | Ph | H | | EE2 | H | H | H | H | H | H | acac | |
| 3-266Y | Rh | 0 | 3 | Ph | H | | EE2 | H | H | H | H | H | H | — | — |
| 3-267 | Rh | 1 | 3 | Ph | H | H | | MS1 | H | H | H | H | H | pic | |
| 3-267X | Rh | 1 | 3 | Ph | H | H | | MS1 | H | H | H | H | H | acac | |
| 3-267Y | Rh | 0 | 3 | Ph | H | H | | MS1 | H | H | H | H | H | — | — |
| 3-268 | Rh | 1 | 3 | Ph | H | | MS1 | H | H | H | H | H | H | pic | |
| 3-268X | Rh | 1 | 3 | Ph | H | | MS1 | H | H | H | H | H | H | acac | |
| 3-268Y | Rh | 0 | 3 | Ph | H | | MS1 | H | H | H | H | H | H | — | — |
| 3-269 | Rh | 1 | 3 | Ph | H | H | | MS2 | H | H | H | H | H | pic | |
| 3-269X | Rh | 1 | 3 | Ph | H | H | | MS2 | H | H | H | H | H | acac | |
| 3-269Y | Rh | 0 | 3 | Ph | H | H | | MS2 | H | H | H | H | H | — | — |
| 3-270 | Rh | 1 | 3 | Ph | H | | MS2 | H | H | H | H | H | H | pic | |
| 3-270X | Rh | 1 | 3 | Ph | H | | MS2 | H | H | H | H | H | H | acac | |
| 3-270Y | Rh | 0 | 3 | Ph | H | | MS2 | H | H | H | H | H | H | — | — |

TABLE 18

| No. | M | n | BSS | SS G | T$^1$ | T$^2$ | T$^3$ | T$^4$ | T$^5$ | T$^6$ | T$^7$ | T$^8$ | T$^9$ | L$^1$ | L$^2$ |
|---|---|---|---|---|---|---|---|---|---|---|---|---|---|---|---|
| 4-167 | Rh | 1 | 4 | Ph | H | H | H | H | CH$_3$ | H | H | H | H | pic | |
| 4-167X | Rh | 1 | 4 | Ph | H | H | H | H | CH$_3$ | H | H | H | H | acac | |
| 4-167Y | Rh | 0 | 4 | Ph | H | H | H | H | CH$_3$ | H | H | H | H | — | — |
| 4-168 | Rh | 1 | 4 | Ph | H | H | H | H | $^tC_4H_9$ | H | H | H | H | pic | |
| 4-168X | Rh | 1 | 4 | Ph | H | H | H | H | $^tC_4H_9$ | H | H | H | H | acac | |
| 4-168Y | Rh | 0 | 4 | Ph | H | H | H | H | $^tC_4H_9$ | H | H | H | H | — | — |
| 4-169 | Rh | 1 | 4 | Ph | H | F | H | F | CH$_3$ | H | H | H | H | pic | |
| 4-169X | Rh | 1 | 4 | Ph | H | F | H | F | CH$_3$ | H | H | H | H | acac | |
| 4-169Y | Rh | 0 | 4 | Ph | H | F | H | F | CH$_3$ | H | H | H | H | — | — |
| 4-170 | Rh | 1 | 4 | Ph | H | F | H | F | $^tC_4H_9$ | H | H | H | H | pic | |
| 4-170X | Rh | 1 | 4 | Ph | H | F | H | F | $^tC_4H_9$ | H | H | H | H | acac | |
| 4-170Y | Rh | 0 | 4 | Ph | H | F | H | F | $^tC_4H_9$ | H | H | H | H | — | — |
| 4-171 | Rh | 1 | 4 | Ph | F | H | H | F | CH$_3$ | H | H | H | H | pic | |
| 4-171X | Rh | 1 | 4 | Ph | F | H | H | F | CH$_3$ | H | H | H | H | acac | |
| 4-171Y | Rh | 0 | 4 | Ph | F | H | H | F | CH$_3$ | H | H | H | H | — | — |
| 4-172 | Rh | 1 | 4 | Ph | F | H | H | F | $^tC_4H_9$ | H | H | H | H | pic | |
| 4-172X | Rh | 1 | 4 | Ph | F | H | H | F | $^tC_4H_9$ | H | H | H | H | acac | |
| 4-172Y | Rh | 0 | 4 | Ph | F | H | H | F | $^tC_4H_9$ | H | H | H | H | — | — |

TABLE 18-continued

| No. | M | n | BSS | SS G | T$^1$ | T$^2$ | T$^3$ | T$^4$ | T$^5$ | T$^6$ | T$^7$ | T$^8$ | T$^9$ | L$^1$ | L$^2$ |
|---|---|---|---|---|---|---|---|---|---|---|---|---|---|---|---|
| 4-173 | Rh | 1 | 4 | Ph | CF$_3$ | H | CF$_3$ | H | CH$_3$ | H | H | H | H | pic | |
| 4-173X | Rh | 1 | 4 | Ph | CF$_3$ | H | CF$_3$ | H | CH$_3$ | H | H | H | H | acac | |
| 4-173Y | Rh | 0 | 4 | Ph | CF$_3$ | H | CF$_3$ | H | CH$_3$ | H | H | H | H | — | — |
| 4-174 | Rh | 1 | 4 | Ph | CF$_3$ | H | CF$_3$ | H | $^t$C$_4$H$_9$ | H | H | H | H | pic | |
| 4-174X | Rh | 1 | 4 | Ph | CF$_3$ | H | CF$_3$ | H | $^t$C$_4$H$_9$ | H | H | H | H | acac | |
| 4-174Y | Rh | 0 | 4 | Ph | CF$_3$ | H | CF$_3$ | H | $^t$C$_4$H$_9$ | H | H | H | H | — | — |
| 4-175 | Rh | 1 | 4 | Ph | H | F | CF$_3$ | H | CH$_3$ | H | H | H | H | pic | |
| 4-175X | Rh | 1 | 4 | Ph | H | F | CF$_3$ | H | CH$_3$ | H | H | H | H | acac | |
| 4-175Y | Rh | 0 | 4 | Ph | H | F | CF$_3$ | H | CH$_3$ | H | H | H | H | — | — |
| 4-176 | Rh | 1 | 4 | Ph | F | H | CF$_3$ | H | CH$_3$ | H | H | H | H | pic | |
| 4-176X | Rh | 1 | 4 | Ph | F | H | CF$_3$ | H | CH$_3$ | H | H | H | H | acac | |
| 4-176Y | Rh | 0 | 4 | Ph | F | H | CF$_3$ | H | CH$_3$ | H | H | H | H | — | — |
| 4-177 | Rh | 1 | 4 | Ph | F | F | F | F | CH$_3$ | H | H | H | H | pic | |
| 4-177X | Rh | 1 | 4 | Ph | F | F | F | F | CH$_3$ | H | H | H | H | acac | |
| 4-177Y | Rh | 0 | 4 | Ph | F | F | F | F | CH$_3$ | H | H | H | H | — | — |
| 4-178 | Rh | 1 | 4 | Ph | H | F | H | CH$_3$ | CH$_3$ | H | H | H | H | pic | |
| 4-178X | Rh | 1 | 4 | Ph | H | F | H | CH$_3$ | CH$_3$ | H | H | H | H | acac | |
| 4-178Y | Rh | 0 | 4 | Ph | H | F | H | CH$_3$ | CH$_3$ | H | H | H | H | — | — |
| 4-179 | Rh | 1 | 4 | Ph | H | F | H | CH$_3$ | $^t$C$_4$H$_9$ | H | H | H | H | pic | |
| 4-179X | Rh | 1 | 4 | Ph | H | F | H | CH$_3$ | $^t$C$_4$H$_9$ | H | H | H | H | acac | |
| 4-179Y | Rh | 0 | 4 | Ph | H | F | H | CH$_3$ | $^t$C$_4$H$_9$ | H | H | H | H | — | — |
| 4-180 | Rh | 1 | 4 | Ph | H | F | H | $^t$C$_4$H$_9$ | CH$_3$ | H | H | H | H | pic | |
| 4-180X | Rh | 1 | 4 | Ph | H | F | H | $^t$C$_4$H$_9$ | CH$_3$ | H | H | H | H | acac | |
| 4-180Y | Rh | 0 | 4 | Ph | H | F | H | $^t$C$_4$H$_9$ | CH$_3$ | H | H | H | H | — | — |
| 4-181 | Rh | 1 | 4 | Ph | H | F | H | $^t$C$_4$H$_9$ | $^t$C$_4$H$_9$ | H | H | H | H | pic | |
| 4-181X | Rh | 1 | 4 | Ph | H | F | H | $^t$C$_4$H$_9$ | $^t$C$_4$H$_9$ | H | H | H | H | acac | |
| 4-181Y | Rh | 0 | 4 | Ph | H | F | H | $^t$C$_4$H$_9$ | $^t$C$_4$H$_9$ | H | H | H | H | — | — |
| 4-182 | Rh | 1 | 4 | Ph | H | CF$_3$ | H | CF$_3$ | CH$_3$ | H | H | H | H | pic | |
| 4-182X | Rh | 1 | 4 | Ph | H | CF$_3$ | H | CF$_3$ | CH$_3$ | H | H | H | H | acac | |
| 4-182Y | Rh | 0 | 4 | Ph | H | CF$_3$ | H | CF$_3$ | CH$_3$ | H | H | H | H | — | — |
| 4-183 | Rh | 1 | 4 | Ph | H | CF$_3$ | H | CF$_3$ | $^t$C$_4$H$_9$ | H | H | H | H | pic | |
| 4-183X | Rh | 1 | 4 | Ph | H | CF$_3$ | H | CF$_3$ | $^t$C$_4$H$_9$ | H | H | H | H | acac | |
| 4-183Y | Rh | 0 | 4 | Ph | H | CF$_3$ | H | CF$_3$ | $^t$C$_4$H$_9$ | H | H | H | H | — | — |
| 4-184 | Rh | 1 | 4 | Ph | CF$_3$ | H | H | $^t$C$_4$H$_9$ | CH$_3$ | H | H | H | H | pic | |
| 4-184X | Rh | 1 | 4 | Ph | CF$_3$ | H | H | $^t$C$_4$H$_9$ | CH$_3$ | H | H | H | H | acac | |
| 4-184Y | Rh | 0 | 4 | Ph | CF$_3$ | H | H | $^t$C$_4$H$_9$ | CH$_3$ | H | H | H | H | — | — |
| 4-185 | Rh | 1 | 4 | Ph | CF$_3$ | H | H | $^t$C$_4$H$_9$ | $^t$C$_4$H$_9$ | H | H | H | H | pic | |
| 4-185X | Rh | 1 | 4 | Ph | CF$_3$ | H | H | $^t$C$_4$H$_9$ | $^t$C$_4$H$_9$ | H | H | H | H | acac | |
| 4-185Y | Rh | 0 | 4 | Ph | CF$_3$ | H | H | $^t$C$_4$H$_9$ | $^t$C$_4$H$_9$ | H | H | H | H | — | — |
| 4-186 | Rh | 1 | 4 | Ph | H | CF$_3$ | H | $^t$C$_4$H$_9$ | CH$_3$ | H | H | H | H | pic | |
| 4-186X | Rh | 1 | 4 | Ph | H | CF$_3$ | H | $^t$C$_4$H$_9$ | CH$_3$ | H | H | H | H | acac | |
| 4-186Y | Rh | 0 | 4 | Ph | H | CF$_3$ | H | $^t$C$_4$H$_9$ | CH$_3$ | H | H | H | H | — | — |
| 4-187 | Rh | 1 | 4 | Ph | H | CF$_3$ | H | $^t$C$_4$H$_9$ | $^t$C$_4$H$_9$ | H | H | H | H | pic | |
| 4-187X | Rh | 1 | 4 | Ph | H | CF$_3$ | H | $^t$C$_4$H$_9$ | $^t$C$_4$H$_9$ | H | H | H | H | acac | |
| 4-187Y | Rh | 0 | 4 | Ph | H | CF$_3$ | H | $^t$C$_4$H$_9$ | $^t$C$_4$H$_9$ | H | H | H | H | — | — |
| 4-188 | Rh | 1 | 4 | Ph | H | CF$_3$ | H | CH$_3$ | CH$_3$ | H | H | H | H | pic | |
| 4-188X | Rh | 1 | 4 | Ph | H | CF$_3$ | H | CH$_3$ | CH$_3$ | H | H | H | H | acac | |
| 4-188Y | Rh | 0 | 4 | Ph | H | CF$_3$ | H | CH$_3$ | CH$_3$ | H | H | H | H | — | — |
| 4-189 | Rh | 1 | 4 | Ph | H | CF$_3$ | CF$_3$ | H | CH$_3$ | H | H | H | H | pic | |
| 4-189X | Rh | 1 | 4 | Ph | H | CF$_3$ | CF$_3$ | H | CH$_3$ | H | H | H | H | acac | |
| 4-189Y | Rh | 0 | 4 | Ph | H | CF$_3$ | CF$_3$ | H | CH$_3$ | H | H | H | H | — | — |
| 4-190 | Rh | 1 | 4 | Ph | H | H | NO$_2$ | H | CH$_3$ | H | H | H | H | pic | |
| 4-190X | Rh | 1 | 4 | Ph | H | H | NO$_2$ | H | CH$_3$ | H | H | H | H | acac | |
| 4-190Y | Rh | 0 | 4 | Ph | H | H | NO$_2$ | H | CH$_3$ | H | H | H | H | — | — |
| 4-191 | Rh | 1 | 4 | Ph | H | H | NO$_2$ | H | $^t$C$_4$H$_9$ | H | H | H | H | pic | |
| 4-191X | Rh | 1 | 4 | Ph | H | H | NO$_2$ | H | $^t$C$_4$H$_9$ | H | H | H | H | acac | |
| 4-191Y | Rh | 0 | 4 | Ph | H | H | NO$_2$ | H | $^t$C$_4$H$_9$ | H | H | H | H | — | — |
| 4-192 | Rh | 1 | 4 | Ph | F | H | NO$_2$ | H | CH$_3$ | H | H | H | H | pic | |
| 4-192X | Rh | 1 | 4 | Ph | F | H | NO$_2$ | H | CH$_3$ | H | H | H | H | acac | |
| 4-192Y | Rh | 0 | 4 | Ph | F | H | NO$_2$ | H | CH$_3$ | H | H | H | H | — | — |
| 4-193 | Rh | 1 | 4 | Ph | F | H | NO$_2$ | F | CH$_3$ | H | H | H | H | pic | |
| 4-193X | Rh | 1 | 4 | Ph | F | H | NO$_2$ | F | CH$_3$ | H | H | H | H | acac | |
| 4-193Y | Rh | 0 | 4 | Ph | F | H | NO$_2$ | F | CH$_3$ | H | H | H | H | — | — |
| 4-194 | Rh | 1 | 4 | Ph | H | NO$_2$ | H | NO$_2$ | CH$_3$ | H | H | H | H | pic | |
| 4-194X | Rh | 1 | 4 | Ph | H | NO$_2$ | H | NO$_2$ | CH$_3$ | H | H | H | H | acac | |
| 4-194Y | Rh | 0 | 4 | Ph | H | NO$_2$ | H | NO$_2$ | CH$_3$ | H | H | H | H | — | — |
| 4-195 | Rh | 1 | 4 | Ph | H | NO$_2$ | H | NO$_2$ | $^t$C$_4$H$_9$ | H | H | H | H | pic | |
| 4-195X | Rh | 1 | 4 | Ph | H | NO$_2$ | H | NO$_2$ | $^t$C$_4$H$_9$ | H | H | H | H | acac | |
| 4-195Y | Rh | 0 | 4 | Ph | H | NO$_2$ | H | NO$_2$ | $^t$C$_4$H$_9$ | H | H | H | H | — | — |
| 4-196 | Rh | 1 | 4 | Ph | NO$_2$ | H | H | NO$_2$ | CH$_3$ | H | H | H | H | pic | |
| 4-196X | Rh | 1 | 4 | Ph | NO$_2$ | H | H | NO$_2$ | CH$_3$ | H | H | H | H | acac | |
| 4-196Y | Rh | 0 | 4 | Ph | NO$_2$ | H | H | NO$_2$ | CH$_3$ | H | H | H | H | — | — |
| 4-197 | Rh | 1 | 4 | Ph | NO$_2$ | H | H | NO$_2$ | $^t$C$_4$H$_9$ | H | H | H | H | pic | |
| 4-197X | Rh | 1 | 4 | Ph | NO$_2$ | H | H | NO$_2$ | $^t$C$_4$H$_9$ | H | H | H | H | acac | |
| 4-197Y | Rh | 0 | 4 | Ph | NO$_2$ | H | H | NO$_2$ | $^t$C$_4$H$_9$ | H | H | H | H | — | — |
| 4-198 | Rh | 1 | 4 | Ph | H | H | CF$_3$ | H | CH$_3$ | H | H | H | H | pic | |
| 4-198X | Rh | 1 | 4 | Ph | H | H | CF$_3$ | H | CH$_3$ | H | H | H | H | acac | |

TABLE 18-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4-198Y | Rh | 0 | 4 | Ph | H | H | CF₃ | H | CH₃ | H | H | H | H | — | — |
| 4-199 | Rh | 1 | 4 | Ph | H | H | CF₃ | H | ᵗC₄H₉ | H | H | H | H | pic | |
| 4-199X | Rh | 1 | 4 | Ph | H | H | CF₃ | H | ᵗC₄H₉ | H | H | H | H | acac | |
| 4-199Y | Rh | 0 | 4 | Ph | H | H | CF₃ | H | ᵗC₄H₉ | H | H | H | H | — | — |
| 4-200 | Rh | 1 | 4 | Ph | H | Cl | CF₃ | H | CH₃ | H | H | H | H | pic | |
| 4-200X | Rh | 1 | 4 | Ph | H | Cl | CF₃ | H | CH₃ | H | H | H | H | acac | |
| 4-200Y | Rh | 0 | 4 | Ph | H | Cl | CF₃ | H | CH₃ | H | H | H | H | — | — |
| 4-201 | Rh | 1 | 4 | Ph | H | Cl | CF₃ | H | ᵗC₄H₉ | H | H | H | H | pic | |
| 4-201X | Rh | 1 | 4 | Ph | H | Cl | CF₃ | H | ᵗC₄H₉ | H | H | H | H | acac | |
| 4-201Y | Rh | 0 | 4 | Ph | H | Cl | CF₃ | H | ᵗC₄H₉ | H | H | H | H | — | — |
| 4-202 | Rh | 1 | 4 | Ph | H | NO₂ | H | H | CH₃ | H | H | H | H | pic | |
| 4-202X | Rh | 1 | 4 | Ph | H | NO₂ | H | H | CH₃ | H | H | H | H | acac | |
| 4-202Y | Rh | 0 | 4 | Ph | H | NO₂ | H | H | CH₃ | H | H | H | H | — | — |
| 4-203 | Rh | 1 | 4 | Ph | H | CF₃ | H | H | CH₃ | H | H | H | H | pic | |
| 4-203X | Rh | 1 | 4 | Ph | H | CF₃ | H | H | CH₃ | H | H | H | H | acac | |
| 4-203Y | Rh | 0 | 4 | Ph | H | CF₃ | H | H | CH₃ | H | H | H | H | — | — |
| 4-204 | Rh | 1 | 4 | Ph | H | NO₂ | H | CH₃ | CH₃ | H | H | H | H | pic | |
| 4-204X | Rh | 1 | 4 | Ph | H | NO₂ | H | CH₃ | CH₃ | H | H | H | H | acac | |
| 4-204Y | Rh | 0 | 4 | Ph | H | NO₂ | H | CH₃ | CH₃ | H | H | H | H | — | — |
| 4-205 | Rh | 1 | 4 | Ph | H | NO₂ | H | CH₃ | ᵗC₄H₉ | H | H | H | H | pic | |
| 4-205X | Rh | 1 | 4 | Ph | H | NO₂ | H | CH₃ | ᵗC₄H₉ | H | H | H | H | acac | |
| 4-205Y | Rh | 0 | 4 | Ph | H | NO₂ | H | CH₃ | ᵗC₄H₉ | H | H | H | H | — | — |
| 4-206 | Rh | 1 | 4 | Ph | H | NO₂ | H | ᵗC₄H₉ | CH₃ | H | H | H | H | pic | |
| 4-206X | Rh | 1 | 4 | Ph | H | NO₂ | H | ᵗC₄H₉ | CH₃ | H | H | H | H | acac | |
| 4-206Y | Rh | 0 | 4 | Ph | H | NO₂ | H | ᵗC₄H₉ | CH₃ | H | H | H | H | — | — |
| 4-207 | Rh | 1 | 4 | Ph | H | NO₂ | H | ᵗC₄H₉ | ᵗC₄H₉ | H | H | H | H | pic | |
| 4-207X | Rh | 1 | 4 | Ph | H | NO₂ | H | ᵗC₄H₉ | ᵗC₄H₉ | H | H | H | H | acac | |
| 4-207Y | Rh | 0 | 4 | Ph | H | NO₂ | H | ᵗC₄H₉ | ᵗC₄H₉ | H | H | H | H | — | — |
| 4-208 | Rh | 1 | 4 | Ph | H | H | CH₃O | H | CH₃ | H | H | H | H | pic | |
| 4-208X | Rh | 1 | 4 | Ph | H | H | CH₃O | H | CH₃ | H | H | H | H | acac | |
| 4-208Y | Rh | 0 | 4 | Ph | H | H | CH₃O | H | CH₃ | H | H | H | H | — | — |
| 4-209 | Rh | 1 | 4 | Ph | H | CH₃O | H | H | CH₃ | H | H | H | H | pic | |
| 4-209X | Rh | 1 | 4 | Ph | H | CH₃O | H | H | CH₃ | H | H | H | H | acac | |
| 4-209Y | Rh | 0 | 4 | Ph | H | CH₃O | H | H | CH₃ | H | H | H | H | — | — |
| 4-210 | Rh | 1 | 4 | Ph | H | CH₃O | H | CH₃ | CH₃ | H | H | H | H | pic | |
| 4-210X | Rh | 1 | 4 | Ph | H | CH₃O | H | CH₃ | CH₃ | H | H | H | H | acac | |
| 4-210Y | Rh | 0 | 4 | Ph | H | CH₃O | H | CH₃ | CH₃ | H | H | H | H | — | — |
| 4-211 | Rh | 1 | 4 | Ph | H | CH₃O | H | ᵗC₄H₉ | CH₃ | H | H | H | H | pic | |
| 4-211X | Rh | 1 | 4 | Ph | H | CH₃O | H | ᵗC₄H₉ | CH₃ | H | H | H | H | acac | |
| 4-211Y | Rh | 0 | 4 | Ph | H | CH₃O | H | ᵗC₄H₉ | CH₃ | H | H | H | H | — | — |
| 4-212 | Rh | 1 | 4 | Ph | H | Si(CH₃)₃ | H | H | CH₃ | H | H | H | H | pic | |
| 4-212X | Rh | 1 | 4 | Ph | H | Si(CH₃)₃ | H | H | CH₃ | H | H | H | H | acac | |
| 4-212Y | Rh | 0 | 4 | Ph | H | Si(CH₃)₃ | H | H | CH₃ | H | H | H | H | — | — |
| 4-213 | Rh | 1 | 4 | Ph | H | Si(CH₃)₃ | H | H | ᵗC₄H₉ | H | H | H | H | pic | |
| 4-213X | Rh | 1 | 4 | Ph | H | Si(CH₃)₃ | H | H | ᵗC₄H₉ | H | H | H | H | acac | |
| 4-213Y | Rh | 0 | 4 | Ph | H | Si(CH₃)₃ | H | H | ᵗC₄H₉ | H | H | H | H | — | — |
| 4-214 | Rh | 1 | 4 | Ph | H | H | Si(CH₃)₃ | H | CH₃ | H | H | H | H | pic | |
| 4-214X | Rh | 1 | 4 | Ph | H | H | Si(CH₃)₃ | H | CH₃ | H | H | H | H | acac | |
| 4-214Y | Rh | 0 | 4 | Ph | H | H | Si(CH₃)₃ | H | CH₃ | H | H | H | H | — | — |
| 4-215 | Rh | 1 | 4 | Ph | H | H | H | Si(CH₃)₃ | CH₃ | H | H | H | H | pic | |
| 4-215X | Rh | 1 | 4 | Ph | H | H | H | Si(CH₃)₃ | CH₃ | H | H | H | H | acac | |
| 4-215Y | Rh | 0 | 4 | Ph | H | H | H | Si(CH₃)₃ | CH₃ | H | H | H | H | — | — |
| 4-216 | Rh | 1 | 4 | Ph | H | F | H | Si(CH₃)₃ | CH₃ | H | H | H | H | pic | |
| 4-216X | Rh | 1 | 4 | Ph | H | F | H | Si(CH₃)₃ | CH₃ | H | H | H | H | acac | |
| 4-216Y | Rh | 0 | 4 | Ph | H | F | H | Si(CH₃)₃ | CH₃ | H | H | H | H | — | — |
| 4-217 | Rh | 1 | 4 | Ph | H | CF₃ | H | Si(CH₃)₃ | CH₃ | H | H | H | H | pic | |
| 4-217X | Rh | 1 | 4 | Ph | H | CF₃ | H | Si(CH₃)₃ | CH₃ | H | H | H | H | acac | |
| 4-217Y | Rh | 0 | 4 | Ph | H | CF₃ | H | Si(CH₃)₃ | CH₃ | H | H | H | H | — | — |
| 4-218 | Rh | 1 | 4 | Ph | H | CF₃ | H | Si(CH₃)₃ | ᵗC₄H₉ | H | H | H | H | pic | |
| 4-218X | Rh | 1 | 4 | Ph | H | CF₃ | H | Si(CH₃)₃ | ᵗC₄H₉ | H | H | H | H | acac | |
| 4-218Y | Rh | 0 | 4 | Ph | H | CF₃ | H | Si(CH₃)₃ | ᵗC₄H₉ | H | H | H | H | — | — |
| 4-219 | Rh | 1 | 4 | Ph | H | Si(CH₃)₃ | H | F | CH₃ | H | H | H | H | pic | |
| 4-219X | Rh | 1 | 4 | Ph | H | Si(CH₃)₃ | H | F | CH₃ | H | H | H | H | acac | |
| 4-219Y | Rh | 0 | 4 | Ph | H | Si(CH₃)₃ | H | F | CH₃ | H | H | H | H | — | — |
| 4-220 | Rh | 1 | 4 | Ph | H | Si(CH₃)₃ | H | F | ᵗC₄H₉ | H | H | H | H | pic | |
| 4-220X | Rh | 1 | 4 | Ph | H | Si(CH₃)₃ | H | F | ᵗC₄H₉ | H | H | H | H | acac | |
| 4-220Y | Rh | 0 | 4 | Ph | H | Si(CH₃)₃ | H | F | ᵗC₄H₉ | H | H | H | H | — | — |
| 4-221 | Rh | 1 | 4 | Ph | H | Si(CH₃)₃ | H | CF₃ | CH₃ | H | H | H | H | pic | |
| 4-221X | Rh | 1 | 4 | Ph | H | Si(CH₃)₃ | H | CF₃ | CH₃ | H | H | H | H | acac | |
| 4-221Y | Rh | 0 | 4 | Ph | H | Si(CH₃)₃ | H | CF₃ | CH₃ | H | H | H | H | — | — |
| 4-222 | Rh | 1 | 4 | Ph | H | Si(CH₃)₃ | H | CF₃ | ᵗC₄H₉ | H | H | H | H | pic | |
| 4-222X | Rh | 1 | 4 | Ph | H | Si(CH₃)₃ | H | CF₃ | ᵗC₄H₉ | H | H | H | H | acac | |
| 4-222Y | Rh | 0 | 4 | Ph | H | Si(CH₃)₃ | H | CF₃ | ᵗC₄H₉ | H | H | H | H | — | — |
| 4-223 | Rh | 1 | 4 | Ph | Si(CH₃)₃ | H | Si(CH₃)₃ | H | CH₃ | H | H | H | H | pic | |
| 4-223X | Rh | 1 | 4 | Ph | Si(CH₃)₃ | H | Si(CH₃)₃ | H | CH₃ | H | H | H | H | acac | |
| 4-223Y | Rh | 0 | 4 | Ph | Si(CH₃)₃ | H | Si(CH₃)₃ | H | CH₃ | H | H | H | H | — | — |
| 4-224 | Rh | 1 | 4 | Ph | Si(CH₃)₃ | H | Si(CH₃)₃ | H | ᵗC₄H₉ | H | H | H | H | pic | |

TABLE 18-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4-224X | Rh | 1 | 4 | Ph | Si(CH₃)₃ | H | Si(CH₃)₃ | H | ᵗC₄H₉ | H | H | H | H | acac | |
| 4-224Y | Rh | 0 | 4 | Ph | Si(CH₃)₃ | H | Si(CH₃)₃ | H | ᵗC₄H₉ | H | H | H | H | — | — |
| 4-225 | Rh | 1 | 4 | Ph | H | H | H | COCH₃ | CH₃ | H | H | H | H | pic | |
| 4-225X | Rh | 1 | 4 | Ph | H | H | H | COCH₃ | CH₃ | H | H | H | H | acac | |
| 4-225Y | Rh | 0 | 4 | Ph | H | H | H | COCH₃ | CH₃ | H | H | H | H | — | — |
| 4-226 | Rh | 1 | 4 | Ph | H | H | COCH₃ | H | CH₃ | H | H | H | H | pic | |
| 4-226X | Rh | 1 | 4 | Ph | H | H | COCH₃ | H | CH₃ | H | H | H | H | acac | |
| 4-226Y | Rh | 0 | 4 | Ph | H | H | COCH₃ | H | CH₃ | H | H | H | H | — | — |
| 4-227 | Rh | 1 | 4 | Ph | H | COCH₃ | H | H | CH₃ | H | H | H | H | pic | |
| 4-227X | Rh | 1 | 4 | Ph | H | COCH₃ | H | H | CH₃ | H | H | H | H | acac | |
| 4-227Y | Rh | 0 | 4 | Ph | H | COCH₃ | H | H | CH₃ | H | H | H | H | — | — |
| 4-228 | Rh | 1 | 4 | Ph | H | H | BL | | CH₃ | H | H | H | H | pic | |
| 4-228X | Rh | 1 | 4 | Ph | H | H | BL | | CH₃ | H | H | H | H | acac | |
| 4-228Y | Rh | 0 | 4 | Ph | H | H | BL | | CH₃ | H | H | H | H | — | — |
| 4-229 | Rh | 1 | 4 | Ph | H | H | BL | | ᵗC₄H₉ | H | H | H | H | pic | |
| 4-229X | Rh | 1 | 4 | Ph | H | H | BL | | ᵗC₄H₉ | H | H | H | H | acac | |
| 4-229Y | Rh | 0 | 4 | Ph | H | H | BL | | ᵗC₄H₉ | H | H | H | H | — | — |
| 4-230 | Rh | 1 | 4 | Ph | H | BL | | H | CH₃ | H | H | H | H | pic | |
| 4-230X | Rh | 1 | 4 | Ph | H | BL | | H | CH₃ | H | H | H | H | acac | |
| 4-230Y | Rh | 0 | 4 | Ph | H | BL | | H | CH₃ | H | H | H | H | — | — |
| 4-231 | Rh | 1 | 4 | Ph | H | BL | | H | ᵗC₄H₉ | H | H | H | H | pic | |
| 4-231X | Rh | 1 | 4 | Ph | H | BL | | H | ᵗC₄H₉ | H | H | H | H | acac | |
| 4-231Y | Rh | 0 | 4 | Ph | H | BL | | H | ᵗC₄H₉ | H | H | H | H | — | — |
| 4-232 | Rh | 1 | 4 | Ph | H | H | PL | | CH₃ | H | H | H | H | pic | |
| 4-232X | Rh | 1 | 4 | Ph | H | H | PL | | CH₃ | H | H | H | H | acac | |
| 4-232Y | Rh | 0 | 4 | Ph | H | H | PL | | CH₃ | H | H | H | H | — | — |
| 4-233 | Rh | 1 | 4 | Ph | H | H | PL | | ᵗC₄H₉ | H | H | H | H | pic | |
| 4-233X | Rh | 1 | 4 | Ph | H | H | PL | | ᵗC₄H₉ | H | H | H | H | acac | |
| 4-233Y | Rh | 0 | 4 | Ph | H | H | PL | | ᵗC₄H₉ | H | H | H | H | — | — |
| 4-234 | Rh | 1 | 4 | Ph | H | PL | | H | CH₃ | H | H | H | H | pic | |
| 4-234X | Rh | 1 | 4 | Ph | H | PL | | H | CH₃ | H | H | H | H | acac | |
| 4-234Y | Rh | 0 | 4 | Ph | H | PL | | H | CH₃ | H | H | H | H | — | — |
| 4-235 | Rh | 1 | 4 | Ph | H | PL | | H | ᵗC₄H₉ | H | H | H | H | pic | |
| 4-235X | Rh | 1 | 4 | Ph | H | PL | | H | ᵗC₄H₉ | H | H | H | H | acac | |
| 4-235Y | Rh | 0 | 4 | Ph | H | PL | | H | ᵗC₄H₉ | H | H | H | H | — | — |
| 4-236 | Rh | 1 | 4 | Ph | H | H | MEE1 | | CH₃ | H | H | H | H | pic | |
| 4-236X | Rh | 1 | 4 | Ph | H | H | MEE1 | | CH₃ | H | H | H | H | acac | |
| 4-236Y | Rh | 0 | 4 | Ph | H | H | MEE1 | | CH₃ | H | H | H | H | — | — |
| 4-237 | Rh | 1 | 4 | Ph | H | MEE1 | | H | CH₃ | H | H | H | H | pic | |
| 4-237X | Rh | 1 | 4 | Ph | H | MEE1 | | H | CH₃ | H | H | H | H | acac | |
| 4-237Y | Rh | 0 | 4 | Ph | H | MEE1 | | H | CH₃ | H | H | H | H | — | — |
| 4-238 | Rh | 1 | 4 | Ph | H | H | MEE2 | | CH₃ | H | H | H | H | pic | |
| 4-238X | Rh | 1 | 4 | Ph | H | H | MEE2 | | CH₃ | H | H | H | H | acac | |
| 4-238Y | Rh | 0 | 4 | Ph | H | H | MEE2 | | CH₃ | H | H | H | H | — | — |
| 4-239 | Rh | 1 | 4 | Ph | H | MEE2 | | H | CH₃ | H | H | H | H | pic | |
| 4-239X | Rh | 1 | 4 | Ph | H | MEE2 | | H | CH₃ | H | H | H | H | acac | |
| 4-239Y | Rh | 0 | 4 | Ph | H | MEE2 | | H | CH₃ | H | H | H | H | — | — |
| 4-240 | Rh | 1 | 4 | Ph | H | H | PA1 | | CH₃ | H | H | H | H | pic | |
| 4-240X | Rh | 1 | 4 | Ph | H | H | PA1 | | CH₃ | H | H | H | H | acac | |
| 4-240Y | Rh | 0 | 4 | Ph | H | H | PA1 | | CH₃ | H | H | H | H | — | — |
| 4-241 | Rh | 1 | 4 | Ph | H | PA1 | | H | CH₃ | H | H | H | H | pic | |
| 4-241X | Rh | 1 | 4 | Ph | H | PA1 | | H | CH₃ | H | H | H | H | acac | |
| 4-241Y | Rh | 0 | 4 | Ph | H | PA1 | | H | CH₃ | H | H | H | H | — | — |
| 4-242 | Rh | 1 | 4 | Ph | H | H | PA2 | | CH₃ | H | H | H | H | pic | |
| 4-242X | Rh | 1 | 4 | Ph | H | H | PA2 | | CH₃ | H | H | H | H | acac | |
| 4-242Y | Rh | 0 | 4 | Ph | H | H | PA2 | | CH₃ | H | H | H | H | — | — |
| 4-243 | Rh | 1 | 4 | Ph | H | PA2 | | H | CH₃ | H | H | H | H | pic | |
| 4-243X | Rh | 1 | 4 | Ph | H | PA2 | | H | CH₃ | H | H | H | H | acac | |
| 4-243Y | Rh | 0 | 4 | Ph | H | PA2 | | H | CH₃ | H | H | H | H | — | — |
| 4-244 | Rh | 1 | 4 | Ph | H | H | EA1 | | CH₃ | H | H | H | H | pic | |
| 4-244X | Rh | 1 | 4 | Ph | H | H | EA1 | | CH₃ | H | H | H | H | acac | |
| 4-244Y | Rh | 0 | 4 | Ph | H | H | EA1 | | CH₃ | H | H | H | H | — | — |
| 4-245 | Rh | 1 | 4 | Ph | H | EA2 | | H | CH₃ | H | H | H | H | pic | |
| 4-245X | Rh | 1 | 4 | Ph | H | EA2 | | H | CH₃ | H | H | H | H | acac | |
| 4-245Y | Rh | 0 | 4 | Ph | H | EA2 | | H | CH₃ | H | H | H | H | — | — |
| 4-246 | Rh | 1 | 4 | Ph | H | H | ME | | CH₃ | H | H | H | H | pic | |
| 4-246X | Rh | 1 | 4 | Ph | H | H | ME | | CH₃ | H | H | H | H | acac | |
| 4-246Y | Rh | 0 | 4 | Ph | H | H | ME | | CH₃ | H | H | H | H | — | — |
| 4-247 | Rh | 1 | 4 | Ph | H | ME | | H | CH₃ | H | H | H | H | pic | |
| 4-247X | Rh | 1 | 4 | Ph | H | ME | | H | CH₃ | H | H | H | H | acac | |
| 4-247Y | Rh | 0 | 4 | Ph | H | ME | | H | CH₃ | H | H | H | H | — | — |
| 4-248 | Rh | 1 | 4 | Ph | H | H | AT | | CH₃ | H | H | H | H | pic | |
| 4-248X | Rh | 1 | 4 | Ph | H | H | AT | | CH₃ | H | H | H | H | acac | |
| 4-248Y | Rh | 0 | 4 | Ph | H | H | AT | | CH₃ | H | H | H | H | — | — |
| 4-249 | Rh | 1 | 4 | Ph | H | AT | | H | CH₃ | H | H | H | H | pic | |
| 4-249X | Rh | 1 | 4 | Ph | H | AT | | H | CH₃ | H | H | H | H | acac | |
| 4-249Y | Rh | 0 | 4 | Ph | H | AT | | H | CH₃ | H | H | H | H | — | — |

TABLE 18-continued

| No. | M | n | BSS | SS G | $T^1$ | $T^2$ | $T^3$ | $T^4$ | $T^5$ | $T^6$ | $T^7$ | $T^8$ | $T^9$ | $L^1$ | $L^2$ |
|---|---|---|---|---|---|---|---|---|---|---|---|---|---|---|---|
| 4-250 | Rh | 1 | 4 | Ph | H | H | | MES1 | $CH_3$ | H | H | H | H | pic | |
| 4-250X | Rh | 1 | 4 | Ph | H | H | | MES1 | $CH_3$ | H | H | H | H | acac | |
| 4-250Y | Rh | 0 | 4 | Ph | H | H | | MES1 | $CH_3$ | H | H | H | H | — | — |
| 4-251 | Rh | 1 | 4 | Ph | H | | MES1 | | H | $CH_3$ | H | H | H | H | pic |
| 4-251X | Rh | 1 | 4 | Ph | H | | MES1 | | H | $CH_3$ | H | H | H | H | acac |
| 4-251Y | Rh | 0 | 4 | Ph | H | | MES1 | | H | $CH_3$ | H | H | H | H | — — |
| 4-252 | Rh | 1 | 4 | Ph | H | H | | MES2 | $CH_3$ | H | H | H | H | pic | |
| 4-252X | Rh | 1 | 4 | Ph | H | H | | MES2 | $CH_3$ | H | H | H | H | acac | |
| 4-252Y | Rh | 0 | 4 | Ph | H | H | | MES2 | $CH_3$ | H | H | H | H | — | — |
| 4-253 | Rh | 1 | 4 | Ph | H | | MES2 | | H | $CH_3$ | H | H | H | H | pic |
| 4-253X | Rh | 1 | 4 | Ph | H | | MES2 | | H | $CH_3$ | H | H | H | H | acac |
| 4-253Y | Rh | 0 | 4 | Ph | H | | MES2 | | H | $CH_3$ | H | H | H | H | — — |
| 4-254 | Rh | 1 | 4 | Ph | H | H | | PS1 | $CH_3$ | H | H | H | H | pic | |
| 4-254X | Rh | 1 | 4 | Ph | H | H | | PS1 | $CH_3$ | H | H | H | H | acac | |
| 4-254Y | Rh | 0 | 4 | Ph | H | H | | PS1 | $CH_3$ | H | H | H | H | — | — |
| 4-255 | Rh | 1 | 4 | Ph | H | | PS1 | | H | $CH_3$ | H | H | H | H | pic |
| 4-255X | Rh | 1 | 4 | Ph | H | | PS1 | | H | $CH_3$ | H | H | H | H | acac |
| 4-255Y | Rh | 0 | 4 | Ph | H | | PS1 | | H | $CH_3$ | H | H | H | H | — — |
| 4-256 | Rh | 1 | 4 | Ph | H | H | | PS2 | $CH_3$ | H | H | H | H | pic | |
| 4-256X | Rh | 1 | 4 | Ph | H | H | | PS2 | $CH_3$ | H | H | H | H | acac | |
| 4-256Y | Rh | 0 | 4 | Ph | H | H | | PS2 | $CH_3$ | H | H | H | H | — | — |
| 4-257 | Rh | 1 | 4 | Ph | H | | PS2 | | H | $CH_3$ | H | H | H | H | pic |
| 4-257X | Rh | 1 | 4 | Ph | H | | PS2 | | H | $CH_3$ | H | H | H | H | acac |
| 4-257Y | Rh | 0 | 4 | Ph | H | | PS2 | | H | $CH_3$ | H | H | H | H | — — |
| 4-258 | Rh | 1 | 4 | Ph | H | H | | BAL1 | $CH_3$ | H | H | H | H | pic | |
| 4-258X | Rh | 1 | 4 | Ph | H | H | | BAL1 | $CH_3$ | H | H | H | H | acac | |
| 4-258Y | Rh | 0 | 4 | Ph | H | H | | BAL1 | $CH_3$ | H | H | H | H | — | — |
| 4-259 | Rh | 1 | 4 | Ph | H | | BAL1 | | H | $CH_3$ | H | H | H | H | pic |
| 4-259X | Rh | 1 | 4 | Ph | H | | BAL1 | | H | $CH_3$ | H | H | H | H | acac |
| 4-259Y | Rh | 0 | 4 | Ph | H | | BAL1 | | H | $CH_3$ | H | H | H | H | — — |
| 4-260 | Rh | 1 | 4 | Ph | H | H | | BAL2 | $CH_3$ | H | H | H | H | pic | |
| 4-260X | Rh | 1 | 4 | Ph | H | H | | BAL2 | $CH_3$ | H | H | H | H | acac | |
| 4-260Y | Rh | 0 | 4 | Ph | H | H | | BAL2 | $CH_3$ | H | H | H | H | — | — |
| 4-261 | Rh | 1 | 4 | Ph | H | | BAL2 | | H | $CH_3$ | H | H | H | H | pic |
| 4-261X | Rh | 1 | 4 | Ph | H | | BAL2 | | H | $CH_3$ | H | H | H | H | acac |
| 4-261Y | Rh | 0 | 4 | Ph | H | | BAL2 | | H | $CH_3$ | H | H | H | H | — — |
| 4-262 | Rh | 1 | 4 | Ph | H | H | | MEK1 | $CH_3$ | H | H | H | H | pic | |
| 4-262X | Rh | 1 | 4 | Ph | H | H | | MEK1 | $CH_3$ | H | H | H | H | acac | |
| 4-262Y | Rh | 0 | 4 | Ph | H | H | | MEK1 | $CH_3$ | H | H | H | H | — | — |
| 4-263 | Rh | 1 | 4 | Ph | H | | MEK1 | | H | $CH_3$ | H | H | H | H | pic |
| 4-263X | Rh | 1 | 4 | Ph | H | | MEK1 | | H | $CH_3$ | H | H | H | H | acac |
| 4-263Y | Rh | 0 | 4 | Ph | H | | MEK1 | | H | $CH_3$ | H | H | H | H | — — |
| 4-264 | Rh | 1 | 4 | Ph | H | H | | MEK2 | $CH_3$ | H | H | H | H | pic | |
| 4-264X | Rh | 1 | 4 | Ph | H | H | | MEK2 | $CH_3$ | H | H | H | H | acac | |
| 4-264Y | Rh | 0 | 4 | Ph | H | H | | MEK2 | $CH_3$ | H | H | H | H | — | — |
| 4-265 | Rh | 1 | 4 | Ph | H | | MEK2 | | H | $CH_3$ | H | H | H | H | pic |
| 4-265X | Rh | 1 | 4 | Ph | H | | MEK2 | | H | $CH_3$ | H | H | H | H | acac |
| 4-265Y | Rh | 0 | 4 | Ph | H | | MEK2 | | H | $CH_3$ | H | H | H | H | — — |
| 4-266 | Rh | 1 | 4 | Ph | H | H | | PAL1 | $CH_3$ | H | H | H | H | pic | |
| 4-266X | Rh | 1 | 4 | Ph | H | H | | PAL1 | $CH_3$ | H | H | H | H | acac | |
| 4-266Y | Rh | 0 | 4 | Ph | H | H | | PAL1 | $CH_3$ | H | H | H | H | — | — |
| 4-267 | Rh | 1 | 4 | Ph | H | | PAL1 | | H | $CH_3$ | H | H | H | H | pic |
| 4-267X | Rh | 1 | 4 | Ph | H | | PAL1 | | H | $CH_3$ | H | H | H | H | acac |
| 4-267Y | Rh | 0 | 4 | Ph | H | | PAL1 | | H | $CH_3$ | H | H | H | H | — — |
| 4-268 | Rh | 1 | 4 | Ph | H | H | | PAL2 | $CH_3$ | H | H | H | H | pic | |
| 4-268X | Rh | 1 | 4 | Ph | H | H | | PAL2 | $CH_3$ | H | H | H | H | acac | |
| 4-268Y | Rh | 0 | 4 | Ph | H | H | | PAL2 | $CH_3$ | H | H | H | H | — | — |
| 4-269 | Rh | 1 | 4 | Ph | H | | PAL2 | | H | $CH_3$ | H | H | H | H | pic |
| 4-269X | Rh | 1 | 4 | Ph | H | | PAL2 | | H | $CH_3$ | H | H | H | H | acac |
| 4-269Y | Rh | 0 | 4 | Ph | H | | PAL2 | | H | $CH_3$ | H | H | H | H | — — |
| 4-270 | Rh | 1 | 4 | Ph | H | H | | MMK | $CH_3$ | H | H | H | H | pic | |
| 4-270X | Rh | 1 | 4 | Ph | H | H | | MMK | $CH_3$ | H | H | H | H | acac | |
| 4-270Y | Rh | 0 | 4 | Ph | H | H | | MMK | $CH_3$ | H | H | H | H | — | — |
| 4-271 | Rh | 1 | 4 | Ph | H | | MMK | | H | $CH_3$ | H | H | H | H | pic |
| 4-271X | Rh | 1 | 4 | Ph | H | | MMK | | H | $CH_3$ | H | H | H | H | acac |
| 4-271Y | Rh | 0 | 4 | Ph | H | | MMK | | H | $CH_3$ | H | H | H | H | — — |
| 4-272 | Rh | 1 | 4 | Ph | H | H | | EES1 | $CH_3$ | H | H | H | H | pic | |
| 4-272X | Rh | 1 | 4 | Ph | H | H | | EES1 | $CH_3$ | H | H | H | H | acac | |
| 4-272Y | Rh | 0 | 4 | Ph | H | H | | EES1 | $CH_3$ | H | H | H | H | — | — |
| 4-273 | Rh | 1 | 4 | Ph | H | | EES2 | | H | $CH_3$ | H | H | H | H | pic |
| 4-273X | Rh | 1 | 4 | Ph | H | | EES2 | | H | $CH_3$ | H | H | H | H | acac |
| 4-273Y | Rh | 0 | 4 | Ph | H | | EES2 | | H | $CH_3$ | H | H | H | H | — — |
| 4-274 | Rh | 1 | 4 | Ph | H | H | | PAE1 | $CH_3$ | H | H | H | H | pic | |
| 4-274X | Rh | 1 | 4 | Ph | H | H | | PAE1 | $CH_3$ | H | H | H | H | acac | |
| 4-274Y | Rh | 0 | 4 | Ph | H | H | | PAE1 | $CH_3$ | H | H | H | H | — | — |
| 4-275 | Rh | 1 | 4 | Ph | H | | PAE2 | | H | $CH_3$ | H | H | H | H | pic |
| 4-275X | Rh | 1 | 4 | Ph | H | | PAE2 | | H | $CH_3$ | H | H | H | H | acac |

TABLE 18-continued

| No. | M | n | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4-275Y | Rh | 0 | 4 | Ph | H | | PAE2 | H | CH₃ | H | H | H | H | — | — |
| 4-276 | Rh | 1 | 4 | Ph | H | H | | AME1 | CH₃ | H | H | H | H | pic | |
| 4-276X | Rh | 1 | 4 | Ph | H | H | | AME1 | CH₃ | H | H | H | H | acac | |
| 4-276Y | Rh | 0 | 4 | Ph | H | H | | AME1 | CH₃ | H | H | H | H | — | — |
| 4-277 | Rh | 1 | 4 | Ph | H | | AME1 | H | CH₃ | H | H | H | H | pic | |
| 4-277X | Rh | 1 | 4 | Ph | H | | AME1 | H | CH₃ | H | H | H | H | acac | |
| 4-277Y | Rh | 0 | 4 | Ph | H | | AME1 | H | CH₃ | H | H | H | H | — | — |
| 4-278 | Rh | 1 | 4 | Ph | H | H | | AME2 | CH₃ | H | H | H | H | pic | |
| 4-278X | Rh | 1 | 4 | Ph | H | H | | AME2 | CH₃ | H | H | H | H | acac | |
| 4-278Y | Rh | 0 | 4 | Ph | H | H | | AME2 | CH₃ | H | H | H | H | — | — |
| 4-279 | Rh | 1 | 4 | Ph | H | | AME2 | H | CH₃ | H | H | H | H | pic | |
| 4-279X | Rh | 1 | 4 | Ph | H | | AME2 | H | CH₃ | H | H | H | H | acac | |
| 4-279Y | Rh | 0 | 4 | Ph | H | | AME2 | H | CH₃ | H | H | H | H | — | — |
| 4-280 | Rh | 1 | 4 | Ph | H | H | | EAE1 | CH₃ | H | H | H | H | pic | |
| 4-280X | Rh | 1 | 4 | Ph | H | H | | EAE1 | CH₃ | H | H | H | H | acac | |
| 4-280Y | Rh | 0 | 4 | Ph | H | H | | EAE1 | CH₃ | H | H | H | H | — | — |
| 4-281 | Rh | 1 | 4 | Ph | H | | EAE1 | H | CH₃ | H | H | H | H | pic | |
| 4-281X | Rh | 1 | 4 | Ph | H | | EAE1 | H | CH₃ | H | H | H | H | acac | |
| 4-281Y | Rh | 0 | 4 | Ph | H | | EAE1 | H | CH₃ | H | H | H | H | — | — |
| 4-282 | Rh | 1 | 4 | Ph | H | H | | EAE2 | CH₃ | H | H | H | H | pic | |
| 4-282X | Rh | 1 | 4 | Ph | H | H | | EAE2 | CH₃ | H | H | H | H | acac | |
| 4-282Y | Rh | 0 | 4 | Ph | H | H | | EAE2 | CH₃ | H | H | H | H | — | — |
| 4-283 | Rh | 1 | 4 | Ph | H | | EAE2 | H | CH₃ | H | H | H | H | pic | |
| 4-283X | Rh | 1 | 4 | Ph | H | | EAE2 | H | CH₃ | H | H | H | H | acac | |
| 4-283Y | Rh | 0 | 4 | Ph | H | | EAE2 | H | CH₃ | H | H | H | H | — | — |
| 4-284 | Rh | 1 | 4 | Ph | H | H | | AAE1 | CH₃ | H | H | H | H | pic | |
| 4-284X | Rh | 1 | 4 | Ph | H | H | | AAE1 | CH₃ | H | H | H | H | acac | |
| 4-284Y | Rh | 0 | 4 | Ph | H | H | | AAE1 | CH₃ | H | H | H | H | — | — |
| 4-285 | Rh | 1 | 4 | Ph | H | | AAE1 | H | CH₃ | H | H | H | H | pic | |
| 4-285X | Rh | 1 | 4 | Ph | H | | AAE1 | H | CH₃ | H | H | H | H | acac | |
| 4-285Y | Rh | 0 | 4 | Ph | H | | AAE1 | H | CH₃ | H | H | H | H | — | — |
| 4-286 | Rh | 1 | 4 | Ph | H | H | | AAE2 | CH₃ | H | H | H | H | pic | |
| 4-286X | Rh | 1 | 4 | Ph | H | H | | AAE2 | CH₃ | H | H | H | H | acac | |
| 4-286Y | Rh | 0 | 4 | Ph | H | H | | AAE2 | CH₃ | H | H | H | H | — | — |
| 4-287 | Rh | 1 | 4 | Ph | H | | AAE2 | H | CH₃ | H | H | H | H | pic | |
| 4-287X | Rh | 1 | 4 | Ph | H | | AAE2 | H | CH₃ | H | H | H | H | acac | |
| 4-287Y | Rh | 0 | 4 | Ph | H | | AAE2 | H | CH₃ | H | H | H | H | — | — |
| 4-288 | Rh | 1 | 4 | Ph | H | H | | PME1 | CH₃ | H | H | H | H | pic | |
| 4-288X | Rh | 1 | 4 | Ph | H | H | | PME1 | CH₃ | H | H | H | H | acac | |
| 4-288Y | Rh | 0 | 4 | Ph | H | H | | PME1 | CH₃ | H | H | H | H | — | — |
| 4-289 | Rh | 1 | 4 | Ph | H | | PME1 | H | CH₃ | H | H | H | H | pic | |
| 4-289X | Rh | 1 | 4 | Ph | H | | PME1 | H | CH₃ | H | H | H | H | acac | |
| 4-289Y | Rh | 0 | 4 | Ph | H | | PME1 | H | CH₃ | H | H | H | H | — | — |
| 4-290 | Rh | 1 | 4 | Ph | H | H | | PME2 | CH₃ | H | H | H | H | pic | |
| 4-290X | Rh | 1 | 4 | Ph | H | H | | PME2 | CH₃ | H | H | H | H | acac | |
| 4-290Y | Rh | 0 | 4 | Ph | H | H | | PME2 | CH₃ | H | H | H | H | — | — |
| 4-291 | Rh | 1 | 4 | Ph | H | | PME2 | H | CH₃ | H | H | H | H | pic | |
| 4-291X | Rh | 1 | 4 | Ph | H | | PME2 | H | CH₃ | H | H | H | H | acac | |
| 4-291Y | Rh | 0 | 4 | Ph | H | | PME2 | H | CH₃ | H | H | H | H | — | — |
| 4-292 | Rh | 1 | 4 | Ph | H | H | | MET1 | CH₃ | H | H | H | H | pic | |
| 4-292X | Rh | 1 | 4 | Ph | H | H | | MET1 | CH₃ | H | H | H | H | acac | |
| 4-292Y | Rh | 0 | 4 | Ph | H | H | | MET1 | CH₃ | H | H | H | H | — | — |
| 4-293 | Rh | 1 | 4 | Ph | H | | MET1 | H | CH₃ | H | H | H | H | pic | |
| 4-293X | Rh | 1 | 4 | Ph | H | | MET1 | H | CH₃ | H | H | H | H | acac | |
| 4-293Y | Rh | 0 | 4 | Ph | H | | MET1 | H | CH₃ | H | H | H | H | — | — |
| 4-294 | Rh | 1 | 4 | Ph | H | H | | MET2 | CH₃ | H | H | H | H | pic | |
| 4-294X | Rh | 1 | 4 | Ph | H | H | | MET2 | CH₃ | H | H | H | H | acac | |
| 4-294Y | Rh | 0 | 4 | Ph | H | H | | MET2 | CH₃ | H | H | H | H | — | — |
| 4-295 | Rh | 1 | 4 | Ph | H | | MET2 | H | CH₃ | H | H | H | H | pic | |
| 4-295X | Rh | 1 | 4 | Ph | H | | MET2 | H | CH₃ | H | H | H | H | acac | |
| 4-295Y | Rh | 0 | 4 | Ph | H | | MET2 | H | CH₃ | H | H | H | H | — | — |
| 4-296 | Rh | 1 | 4 | Ph | H | H | | EE1 | CH₃ | H | H | H | H | pic | |
| 4-296X | Rh | 1 | 4 | Ph | H | H | | EE1 | CH₃ | H | H | H | H | acac | |
| 4-296Y | Rh | 0 | 4 | Ph | H | H | | EE1 | CH₃ | H | H | H | H | — | — |
| 4-297 | Rh | 1 | 4 | Ph | H | | EE1 | H | CH₃ | H | H | H | H | pic | |
| 4-297X | Rh | 1 | 4 | Ph | H | | EE1 | H | CH₃ | H | H | H | H | acac | |
| 4-297Y | Rh | 0 | 4 | Ph | H | | EE1 | H | CH₃ | H | H | H | H | — | — |
| 4-298 | Rh | 1 | 4 | Ph | H | H | | EE2 | CH₃ | H | H | H | H | pic | |
| 4-298X | Rh | 1 | 4 | Ph | H | H | | EE2 | CH₃ | H | H | H | H | acac | |
| 4-298Y | Rh | 0 | 4 | Ph | H | H | | EE2 | CH₃ | H | H | H | H | — | — |
| 4-299 | Rh | 1 | 4 | Ph | H | | EE2 | H | CH₃ | H | H | H | H | pic | |
| 4-299X | Rh | 1 | 4 | Ph | H | | EE2 | H | CH₃ | H | H | H | H | acac | |
| 4-299Y | Rh | 0 | 4 | Ph | H | | EE2 | H | CH₃ | H | H | H | H | — | — |
| 4-300 | Rh | 1 | 4 | Ph | H | H | | MS1 | CH₃ | H | H | H | H | pic | |
| 4-300X | Rh | 1 | 4 | Ph | H | H | | MS1 | CH₃ | H | H | H | H | acac | |
| 4-300Y | Rh | 0 | 4 | Ph | H | H | | MS1 | CH₃ | H | H | H | H | — | — |
| 4-301 | Rh | 1 | 4 | Ph | H | | MS1 | H | CH₃ | H | H | H | H | pic | |

TABLE 18-continued

| No. | M | n | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 4-301X | Rh | 1 | 4 | Ph | H | | MS1 | | H | $CH_3$ | H | H | H | H | acac |
| 4-301Y | Rh | 0 | 4 | Ph | H | | MS1 | | H | $CH_3$ | H | H | H | H | — — |
| 4-302 | Rh | 1 | 4 | Ph | H | H | | MS2 | | $CH_3$ | H | H | H | H | pic |
| 4-302X | Rh | 1 | 4 | Ph | H | H | | MS2 | | $CH_3$ | H | H | H | H | acac |
| 4-302Y | Rh | 0 | 4 | Ph | H | H | | MS2 | | $CH_3$ | H | H | H | H | — — |
| 4-303 | Rh | 1 | 4 | Ph | H | | MS2 | | H | $CH_3$ | H | H | H | H | pic |
| 4-303X | Rh | 1 | 4 | Ph | H | | MS2 | | H | $CH_3$ | H | H | H | H | acac |
| 4-303Y | Rh | 0 | 4 | Ph | H | | MS2 | | H | $CH_3$ | H | H | H | H | — — |

TABLE 19

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 5-211 | Rh | 1 | 5 | Ph | H | H | H | H | H | $CH_3$ | H | pic |
| 5-211X | Rh | 1 | 5 | Ph | H | H | H | H | H | $CH_3$ | H | acac |
| 5-211Y | Rh | 0 | 5 | Ph | H | H | H | H | H | $CH_3$ | H | — — |
| 5-212 | Rh | 1 | 5 | Ph | H | H | H | H | H | $^tC_4H_9$ | H | pic |
| 5-212X | Rh | 1 | 5 | Ph | H | H | H | H | H | $^tC_4H_9$ | H | acac |
| 5-212Y | Rh | 0 | 5 | Ph | H | H | H | H | H | $^tC_4H_9$ | H | — — |
| 5-213 | Rh | 1 | 5 | Ph | H | F | H | F | H | $CH_3$ | H | pic |
| 5-213X | Rh | 1 | 5 | Ph | H | F | H | F | H | $CH_3$ | H | acac |
| 5-213Y | Rh | 0 | 5 | Ph | H | F | H | F | H | $CH_3$ | H | — — |
| 5-214 | Rh | 1 | 5 | Ph | H | F | H | F | H | $^tC_4H_9$ | H | pic |
| 5-214X | Rh | 1 | 5 | Ph | H | F | H | F | H | $^tC_4H_9$ | H | acac |
| 5-214Y | Rh | 0 | 5 | Ph | H | F | H | F | H | $^tC_4H_9$ | H | — — |
| 5-215 | Rh | 1 | 5 | Ph | $CF_3$ | H | $CF_3$ | H | H | $CH_3$ | H | pic |
| 5-215X | Rh | 1 | 5 | Ph | $CF_3$ | H | $CF_3$ | H | H | $CH_3$ | H | acac |
| 5-215Y | Rh | 0 | 5 | Ph | $CF_3$ | H | $CF_3$ | H | H | $CH_3$ | H | — — |
| 5-216 | Rh | 1 | 5 | Ph | $CF_3$ | H | $CF_3$ | H | H | $^tC_4H_9$ | H | pic |
| 5-216X | Rh | 1 | 5 | Ph | $CF_3$ | H | $CF_3$ | H | H | $^tC_4H_9$ | H | acac |
| 5-216Y | Rh | 0 | 5 | Ph | $CF_3$ | H | $CF_3$ | H | H | $^tC_4H_9$ | H | — — |
| 5-217 | Rh | 1 | 5 | Ph | H | F | $CF_3$ | H | H | $CH_3$ | H | pic |
| 5-217X | Rh | 1 | 5 | Ph | H | F | $CF_3$ | H | H | $CH_3$ | H | acac |
| 5-217Y | Rh | 0 | 5 | Ph | H | F | $CF_3$ | H | H | $CH_3$ | H | — — |
| 5-218 | Rh | 1 | 5 | Ph | F | H | $CF_3$ | H | H | $CH_3$ | H | pic |
| 5-218X | Rh | 1 | 5 | Ph | F | H | $CF_3$ | H | H | $CH_3$ | H | acac |
| 5-218Y | Rh | 0 | 5 | Ph | F | H | $CF_3$ | H | H | $CH_3$ | H | — — |
| 5-219 | Rh | 1 | 5 | Ph | F | F | F | F | H | $CH_3$ | H | pic |
| 5-219X | Rh | 1 | 5 | Ph | F | F | F | F | H | $CH_3$ | H | acac |
| 5-219Y | Rh | 0 | 5 | Ph | F | F | F | F | H | $CH_3$ | H | — — |
| 5-220 | Rh | 1 | 5 | Ph | H | F | H | $CH_3$ | H | $CH_3$ | H | pic |
| 5-220X | Rh | 1 | 5 | Ph | H | F | H | $CH_3$ | H | $CH_3$ | H | acac |
| 5-220Y | Rh | 0 | 5 | Ph | H | F | H | $CH_3$ | H | $CH_3$ | H | — — |
| 5-221 | Rh | 1 | 5 | Ph | H | F | H | $CH_3$ | H | $^tC_4H_9$ | H | pic |
| 5-221X | Rh | 1 | 5 | Ph | H | F | H | $CH_3$ | H | $^tC_4H_9$ | H | acac |
| 5-221Y | Rh | 0 | 5 | Ph | H | F | H | $CH_3$ | H | $^tC_4H_9$ | H | — — |
| 5-222 | Rh | 1 | 5 | Ph | H | F | H | $^tC_4H_9$ | H | $CH_3$ | H | pic |
| 5-222X | Rh | 1 | 5 | Ph | H | F | H | $^tC_4H_9$ | H | $CH_3$ | H | acac |
| 5-222Y | Rh | 0 | 5 | Ph | H | F | H | $^tC_4H_9$ | H | $CH_3$ | H | — — |
| 5-223 | Rh | 1 | 5 | Ph | H | F | H | $^tC_4H_9$ | H | $^tC_4H_9$ | H | pic |
| 5-223X | Rh | 1 | 5 | Ph | H | F | H | $^tC_4H_9$ | H | $^tC_4H_9$ | H | acac |
| 5-223Y | Rh | 0 | 5 | Ph | H | F | H | $^tC_4H_9$ | H | $^tC_4H_9$ | H | — — |
| 5-224 | Rh | 1 | 5 | Ph | H | $CF_3$ | H | $CF_3$ | H | $CH_3$ | H | pic |
| 5-224X | Rh | 1 | 5 | Ph | H | $CF_3$ | H | $CF_3$ | H | $CH_3$ | H | acac |
| 5-224Y | Rh | 0 | 5 | Ph | H | $CF_3$ | H | $CF_3$ | H | $CH_3$ | H | — — |
| 5-225 | Rh | 1 | 5 | Ph | H | $CF_3$ | H | $CF_3$ | H | $^tC_4H_9$ | H | pic |
| 5-225X | Rh | 1 | 5 | Ph | H | $CF_3$ | H | $CF_3$ | H | $^tC_4H_9$ | H | acac |
| 5-225Y | Rh | 0 | 5 | Ph | H | $CF_3$ | H | $CF_3$ | H | $^tC_4H_9$ | H | — — |
| 5-226 | Rh | 1 | 5 | Ph | $CF_3$ | H | H | $^tC_4H_9$ | H | $CH_3$ | H | pic |
| 5-226X | Rh | 1 | 5 | Ph | $CF_3$ | H | H | $^tC_4H_9$ | H | $CH_3$ | H | acac |
| 5-226Y | Rh | 0 | 5 | Ph | $CF_3$ | H | H | $^tC_4H_9$ | H | $CH_3$ | H | — — |
| 5-227 | Rh | 1 | 5 | Ph | $CF_3$ | H | H | $^tC_4H_9$ | H | $^tC_4H_9$ | H | pic |
| 5-227X | Rh | 1 | 5 | Ph | $CF_3$ | H | H | $^tC_4H_9$ | H | $^tC_4H_9$ | H | acac |
| 5-227Y | Rh | 0 | 5 | Ph | $CF_3$ | H | H | $^tC_4H_9$ | H | $^tC_4H_9$ | H | — — |
| 5-228 | Rh | 1 | 5 | Ph | H | $CF_3$ | H | $^tC_4H_9$ | H | $CH_3$ | H | pic |
| 5-228X | Rh | 1 | 5 | Ph | H | $CF_3$ | H | $^tC_4H_9$ | H | $CH_3$ | H | acac |
| 5-228Y | Rh | 0 | 5 | Ph | H | $CF_3$ | H | $^tC_4H_9$ | H | $CH_3$ | H | — — |
| 5-229 | Rh | 1 | 5 | Ph | H | $CF_3$ | H | $^tC_4H_9$ | H | $^tC_4H_9$ | H | pic |
| 5-229X | Rh | 1 | 5 | Ph | H | $CF_3$ | H | $^tC_4H_9$ | H | $^tC_4H_9$ | H | acac |
| 5-229Y | Rh | 0 | 5 | Ph | H | $CF_3$ | H | $^tC_4H_9$ | H | $^tC_4H_9$ | H | — — |
| 5-230 | Rh | 1 | 5 | Ph | H | $CF_3$ | H | $CH_3$ | H | $CH_3$ | H | pic |
| 5-230X | Rh | 1 | 5 | Ph | H | $CF_3$ | H | $CH_3$ | H | $CH_3$ | H | acac |
| 5-230Y | Rh | 0 | 5 | Ph | H | $CF_3$ | H | $CH_3$ | H | $CH_3$ | H | — — |
| 5-231 | Rh | 1 | 5 | Ph | H | $CF_3$ | $CF_3$ | H | H | $CH_3$ | H | pic |

TABLE 19-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 5-231X | Rh | 1 | 5 | Ph | H | $CF_3$ | $CF_3$ | H | H | $CH_3$ | H | acac | |
| 5-231Y | Rh | 0 | 5 | Ph | H | $CF_3$ | $CF_3$ | H | H | $CH_3$ | H | — | — |
| 5-232 | Rh | 1 | 5 | Ph | H | H | $NO_2$ | H | H | $CH_3$ | H | pic | |
| 5-232X | Rh | 1 | 5 | Ph | H | H | $NO_2$ | H | H | $CH_3$ | H | acac | |
| 5-232Y | Rh | 0 | 5 | Ph | H | H | $NO_2$ | H | H | $CH_3$ | H | — | — |
| 5-233 | Rh | 1 | 5 | Ph | H | H | $NO_2$ | H | H | $^tC_4H_9$ | H | pic | |
| 5-233X | Rh | 1 | 5 | Ph | H | H | $NO_2$ | H | H | $^tC_4H_9$ | H | acac | |
| 5-233Y | Rh | 0 | 5 | Ph | H | H | $NO_2$ | H | H | $^tC_4H_9$ | H | — | — |
| 5-234 | Rh | 1 | 5 | Ph | F | H | $NO_2$ | H | H | $CH_3$ | H | pic | |
| 5-234X | Rh | 1 | 5 | Ph | F | H | $NO_2$ | H | H | $CH_3$ | H | acac | |
| 5-234Y | Rh | 0 | 5 | Ph | F | H | $NO_2$ | H | H | $CH_3$ | H | — | — |
| 5-235 | Rh | 1 | 5 | Ph | F | H | $NO_2$ | H | H | $^tC_4H_9$ | H | pic | |
| 5-235X | Rh | 1 | 5 | Ph | F | H | $NO_2$ | H | H | $^tC_4H_9$ | H | acac | |
| 5-235Y | Rh | 0 | 5 | Ph | F | H | $NO_2$ | H | H | $^tC_4H_9$ | H | — | — |
| 5-236 | Rh | 1 | 5 | Ph | F | H | $NO_2$ | F | H | $CH_3$ | H | pic | |
| 5-236X | Rh | 1 | 5 | Ph | F | H | $NO_2$ | F | H | $CH_3$ | H | acac | |
| 5-236Y | Rh | 0 | 5 | Ph | F | H | $NO_2$ | F | H | $CH_3$ | H | — | — |
| 5-237 | Rh | 1 | 5 | Ph | F | H | $NO_2$ | F | H | $^tC_4H_9$ | H | pic | |
| 5-237X | Rh | 1 | 5 | Ph | F | H | $NO_2$ | F | H | $^tC_4H_9$ | H | acac | |
| 5-237Y | Rh | 0 | 5 | Ph | F | H | $NO_2$ | F | H | $^tC_4H_9$ | H | — | — |
| 5-238 | Rh | 1 | 5 | Ph | H | $NO_2$ | H | $NO_2$ | H | $CH_3$ | H | pic | |
| 5-238X | Rh | 1 | 5 | Ph | H | $NO_2$ | H | $NO_2$ | H | $CH_3$ | H | acac | |
| 5-238Y | Rh | 0 | 5 | Ph | H | $NO_2$ | H | $NO_2$ | H | $CH_3$ | H | — | — |
| 5-239 | Rh | 1 | 5 | Ph | H | $NO_2$ | H | $NO_2$ | H | $^tC_4H_9$ | H | pic | |
| 5-239X | Rh | 1 | 5 | Ph | H | $NO_2$ | H | $NO_2$ | H | $^tC_4H_9$ | H | acac | |
| 5-239Y | Rh | 0 | 5 | Ph | H | $NO_2$ | H | $NO_2$ | H | $^tC_4H_9$ | H | — | — |
| 5-240 | Rh | 1 | 5 | Ph | $NO_2$ | H | H | $NO_2$ | H | $CH_3$ | H | pic | |
| 5-240X | Rh | 1 | 5 | Ph | $NO_2$ | H | H | $NO_2$ | H | $CH_3$ | H | acac | |
| 5-240Y | Rh | 0 | 5 | Ph | $NO_2$ | H | H | $NO_2$ | H | $CH_3$ | H | — | — |
| 5-241 | Rh | 1 | 5 | Ph | H | H | $CF_3$ | H | H | $CH_3$ | H | pic | |
| 5-241X | Rh | 1 | 5 | Ph | H | H | $CF_3$ | H | H | $CH_3$ | H | acac | |
| 5-241Y | Rh | 0 | 5 | Ph | H | H | $CF_3$ | H | H | $CH_3$ | H | — | — |
| 5-242 | Rh | 1 | 5 | Ph | H | Cl | $CF_3$ | H | H | $CH_3$ | H | pic | |
| 5-242X | Rh | 1 | 5 | Ph | H | Cl | $CF_3$ | H | H | $CH_3$ | H | acac | |
| 5-242Y | Rh | 0 | 5 | Ph | H | Cl | $CF_3$ | H | H | $CH_3$ | H | — | — |
| 5-243 | Rh | 1 | 5 | Ph | H | Cl | $CF_3$ | H | H | $^tC_4H_9$ | H | pic | |
| 5-243X | Rh | 1 | 5 | Ph | H | Cl | $CF_3$ | H | H | $^tC_4H_9$ | H | acac | |
| 5-243Y | Rh | 0 | 5 | Ph | H | Cl | $CF_3$ | H | H | $^tC_4H_9$ | H | — | — |
| 5-244 | Rh | 1 | 5 | Ph | H | $NO_2$ | H | H | H | $CH_3$ | H | pic | |
| 5-244X | Rh | 1 | 5 | Ph | H | $NO_2$ | H | H | H | $CH_3$ | H | acac | |
| 5-244Y | Rh | 0 | 5 | Ph | H | $NO_2$ | H | H | H | $CH_3$ | H | — | — |
| 5-245 | Rh | 1 | 5 | Ph | H | $CF_3$ | H | H | H | $CH_3$ | H | pic | |
| 5-245X | Rh | 1 | 5 | Ph | H | $CF_3$ | H | H | H | $CH_3$ | H | acac | |
| 5-245Y | Rh | 0 | 5 | Ph | H | $CF_3$ | H | H | H | $CH_3$ | H | — | — |
| 5-246 | Rh | 1 | 5 | Ph | H | $NO_2$ | H | $CH_3$ | H | $CH_3$ | H | pic | |
| 5-246X | Rh | 1 | 5 | Ph | H | $NO_2$ | H | $CH_3$ | H | $CH_3$ | H | acac | |
| 5-246Y | Rh | 0 | 5 | Ph | H | $NO_2$ | H | $CH_3$ | H | $CH_3$ | H | — | — |
| 5-247 | Rh | 1 | 5 | Ph | H | $NO_2$ | H | $CH_3$ | H | $^tC_4H_9$ | H | pic | |
| 5-247X | Rh | 1 | 5 | Ph | H | $NO_2$ | H | $CH_3$ | H | $^tC_4H_9$ | H | acac | |
| 5-247Y | Rh | 0 | 5 | Ph | H | $NO_2$ | H | $CH_3$ | H | $^tC_4H_9$ | H | — | — |
| 5-248 | Rh | 1 | 5 | Ph | H | $NO_2$ | H | $^tC_4H_9$ | H | $CH_3$ | H | pic | |
| 5-248X | Rh | 1 | 5 | Ph | H | $NO_2$ | H | $^tC_4H_9$ | H | $CH_3$ | H | acac | |
| 5-248Y | Rh | 0 | 5 | Ph | H | $NO_2$ | H | $^tC_4H_9$ | H | $CH_3$ | H | — | — |
| 5-249 | Rh | 1 | 5 | Ph | H | H | $CH_3O$ | H | H | $CH_3$ | H | pic | |
| 5-249X | Rh | 1 | 5 | Ph | H | H | $CH_3O$ | H | H | $CH_3$ | H | acac | |
| 5-249Y | Rh | 0 | 5 | Ph | H | H | $CH_3O$ | H | H | $CH_3$ | H | — | — |
| 5-250 | Rh | 1 | 5 | Ph | H | $CH_3O$ | H | H | H | $CH_3$ | H | pic | |
| 5-250X | Rh | 1 | 5 | Ph | H | $CH_3O$ | H | H | H | $CH_3$ | H | acac | |
| 5-250Y | Rh | 0 | 5 | Ph | H | $CH_3O$ | H | H | H | $CH_3$ | H | — | — |
| 5-251 | Rh | 1 | 5 | Ph | H | $CH_3O$ | H | $CH_3$ | H | $CH_3$ | H | pic | |
| 5-251X | Rh | 1 | 5 | Ph | H | $CH_3O$ | H | $CH_3$ | H | $CH_3$ | H | acac | |
| 5-251Y | Rh | 0 | 5 | Ph | H | $CH_3O$ | H | $CH_3$ | H | $CH_3$ | H | — | — |
| 5-252 | Rh | 1 | 5 | Ph | H | $CH_3O$ | H | $^tC_4H_9$ | H | $CH_3$ | H | pic | |
| 5-252X | Rh | 1 | 5 | Ph | H | $CH_3O$ | H | $^tC_4H_9$ | H | $CH_3$ | H | acac | |
| 5-252Y | Rh | 0 | 5 | Ph | H | $CH_3O$ | H | $^tC_4H_9$ | H | $CH_3$ | H | — | — |
| 5-253 | Rh | 1 | 5 | Ph | H | H | H | H | $^tC_4H_9$ | $CH_3$ | H | pic | |
| 5-253X | Rh | 1 | 5 | Ph | H | H | H | H | $^tC_4H_9$ | $CH_3$ | H | acac | |
| 5-253Y | Rh | 0 | 5 | Ph | H | H | H | H | $^tC_4H_9$ | $CH_3$ | H | — | — |
| 5-254 | Rh | 1 | 5 | Ph | H | F | H | F | $^tC_4H_9$ | $CH_3$ | H | pic | |
| 5-254X | Rh | 1 | 5 | Ph | H | F | H | F | $^tC_4H_9$ | $CH_3$ | H | acac | |
| 5-254Y | Rh | 0 | 5 | Ph | H | F | H | F | $^tC_4H_9$ | $CH_3$ | H | — | — |
| 5-255 | Rh | 1 | 5 | Ph | H | F | H | F | $^tC_4H_9$ | $^tC_4H_9$ | H | pic | |
| 5-255X | Rh | 1 | 5 | Ph | H | F | H | F | $^tC_4H_9$ | $^tC_4H_9$ | H | acac | |
| 5-255Y | Rh | 0 | 5 | Ph | H | F | H | F | $^tC_4H_9$ | $^tC_4H_9$ | H | — | — |
| 5-256 | Rh | 1 | 5 | Ph | $CF_3$ | H | $CF_3$ | H | $^tC_4H_9$ | $CH_3$ | H | pic | |
| 5-256X | Rh | 1 | 5 | Ph | $CF_3$ | H | $CF_3$ | H | $^tC_4H_9$ | $CH_3$ | H | acac | |
| 5-256Y | Rh | 0 | 5 | Ph | $CF_3$ | H | $CF_3$ | H | $^tC_4H_9$ | $CH_3$ | H | — | — |

TABLE 19-continued

| No. | M | n | BSS | SS | G | T¹ | T² | T³ | T⁴ | T⁵ | T⁶ | T⁷ | L¹ | L² |
|---|---|---|---|---|---|---|---|---|---|---|---|---|---|---|
| 5-257 | Rh | 1 | 5 | | Ph | CF₃ | H | CF₃ | H | ᵗC₄H₉ | ᵗC₄H₉ | H | pic | |
| 5-257X | Rh | 1 | 5 | | Ph | CF₃ | H | CF₃ | H | ᵗC₄H₉ | ᵗC₄H₉ | H | acac | |
| 5-257Y | Rh | 0 | 5 | | Ph | CF₃ | H | CF₃ | H | ᵗC₄H₉ | ᵗC₄H₉ | H | — | — |
| 5-258 | Rh | 1 | 5 | | Ph | H | CF₃ | H | CH₃ | ᵗC₄H₉ | CH₃ | H | pic | |
| 5-258X | Rh | 1 | 5 | | Ph | H | CF₃ | H | CH₃ | ᵗC₄H₉ | CH₃ | H | acac | |
| 5-258Y | Rh | 0 | 5 | | Ph | H | CF₃ | H | CH₃ | ᵗC₄H₉ | CH₃ | H | — | — |
| 5-259 | Rh | 1 | 5 | | Ph | H | Si(CH₃)₃ | H | H | H | CH₃ | H | pic | |
| 5-259X | Rh | 1 | 5 | | Ph | H | Si(CH₃)₃ | H | H | H | CH₃ | H | acac | |
| 5-259Y | Rh | 0 | 5 | | Ph | H | Si(CH₃)₃ | H | H | H | CH₃ | H | — | — |
| 5-260 | Rh | 1 | 5 | | Ph | H | Si(CH₃)₃ | H | H | H | ᵗC₄H₉ | H | pic | |
| 5-260X | Rh | 1 | 5 | | Ph | H | Si(CH₃)₃ | H | H | H | ᵗC₄H₉ | H | acac | |
| 5-260Y | Rh | 0 | 5 | | Ph | H | Si(CH₃)₃ | H | H | H | ᵗC₄H₉ | H | — | — |
| 5-261 | Rh | 1 | 5 | | Ph | H | H | Si(CH₃)₃ | H | H | CH₃ | H | pic | |
| 5-261X | Rh | 1 | 5 | | Ph | H | H | Si(CH₃)₃ | H | H | CH₃ | H | acac | |
| 5-261Y | Rh | 0 | 5 | | Ph | H | H | Si(CH₃)₃ | H | H | CH₃ | H | — | — |
| 5-262 | Rh | 1 | 5 | | Ph | H | H | H | Si(CH₃)₃ | H | CH₃ | H | pic | |
| 5-262X | Rh | 1 | 5 | | Ph | H | H | H | Si(CH₃)₃ | H | CH₃ | H | acac | |
| 5-262Y | Rh | 0 | 5 | | Ph | H | H | H | Si(CH₃)₃ | H | CH₃ | H | — | — |
| 5-263 | Rh | 1 | 5 | | Ph | H | F | H | Si(CH₃)₃ | H | CH₃ | H | pic | |
| 5-263X | Rh | 1 | 5 | | Ph | H | F | H | Si(CH₃)₃ | H | CH₃ | H | acac | |
| 5-263Y | Rh | 0 | 5 | | Ph | H | F | H | Si(CH₃)₃ | H | CH₃ | H | — | — |
| 5-264 | Rh | 1 | 5 | | Ph | H | CF₃ | H | Si(CH₃)₃ | H | CH₃ | H | pic | |
| 5-264X | Rh | 1 | 5 | | Ph | H | CF₃ | H | Si(CH₃)₃ | H | CH₃ | H | acac | |
| 5-264Y | Rh | 0 | 5 | | Ph | H | CF₃ | H | Si(CH₃)₃ | H | CH₃ | H | — | — |
| 5-265 | Rh | 1 | 5 | | Ph | H | Si(CH₃)₃ | H | F | H | CH₃ | H | pic | |
| 5-265X | Rh | 1 | 5 | | Ph | H | Si(CH₃)₃ | H | F | H | CH₃ | H | acac | |
| 5-265Y | Rh | 0 | 5 | | Ph | H | Si(CH₃)₃ | H | F | H | CH₃ | H | — | — |
| 5-266 | Rh | 1 | 5 | | Ph | H | Si(CH₃)₃ | H | F | H | ᵗC₄H₉ | H | pic | |
| 5-266X | Rh | 1 | 5 | | Ph | H | Si(CH₃)₃ | H | F | H | ᵗC₄H₉ | H | acac | |
| 5-266Y | Rh | 0 | 5 | | Ph | H | Si(CH₃)₃ | H | F | H | ᵗC₄H₉ | H | — | — |
| 5-267 | Rh | 1 | 5 | | Ph | H | Si(CH₃)₃ | H | CF₃ | H | CH₃ | H | pic | |
| 5-267X | Rh | 1 | 5 | | Ph | H | Si(CH₃)₃ | H | CF₃ | H | CH₃ | H | acac | |
| 5-267Y | Rh | 0 | 5 | | Ph | H | Si(CH₃)₃ | H | CF₃ | H | CH₃ | H | — | — |
| 5-268 | Rh | 1 | 5 | | Ph | H | Si(CH₃)₃ | H | CF₃ | H | ᵗC₄H₉ | H | pic | |
| 5-268X | Rh | 1 | 5 | | Ph | H | Si(CH₃)₃ | H | CF₃ | H | ᵗC₄H₉ | H | acac | |
| 5-268Y | Rh | 0 | 5 | | Ph | H | Si(CH₃)₃ | H | CF₃ | H | ᵗC₄H₉ | H | — | — |
| 5-269 | Rh | 1 | 5 | | Ph | Si(CH₃)₃ | H | Si(CH₃)₃ | H | H | CH₃ | H | pic | |
| 5-269X | Rh | 1 | 5 | | Ph | Si(CH₃)₃ | H | Si(CH₃)₃ | H | H | CH₃ | H | acac | |
| 5-269Y | Rh | 0 | 5 | | Ph | Si(CH₃)₃ | H | Si(CH₃)₃ | H | H | CH₃ | H | — | — |
| 5-270 | Rh | 1 | 5 | | Ph | Si(CH₃)₃ | H | Si(CH₃)₃ | H | H | ᵗC₄H₉ | H | pic | |
| 5-270X | Rh | 1 | 5 | | Ph | Si(CH₃)₃ | H | Si(CH₃)₃ | H | H | ᵗC₄H₉ | H | acac | |
| 5-270Y | Rh | 0 | 5 | | Ph | Si(CH₃)₃ | H | Si(CH₃)₃ | H | H | ᵗC₄H₉ | H | — | — |
| 5-271 | Rh | 1 | 5 | | Ph | H | H | H | COCH₃ | H | CH₃ | H | pic | |
| 5-271X | Rh | 1 | 5 | | Ph | H | H | H | COCH₃ | H | CH₃ | H | acac | |
| 5-271Y | Rh | 0 | 5 | | Ph | H | H | H | COCH₃ | H | CH₃ | H | — | — |
| 5-272 | Rh | 1 | 5 | | Ph | H | H | COCH₃ | H | H | CH₃ | H | pic | |
| 5-272X | Rh | 1 | 5 | | Ph | H | H | COCH₃ | H | H | CH₃ | H | acac | |
| 5-272Y | Rh | 0 | 5 | | Ph | H | H | COCH₃ | H | H | CH₃ | H | — | — |
| 5-273 | Rh | 1 | 5 | | Ph | H | COCH₃ | H | H | H | CH₃ | H | pic | |
| 5-273X | Rh | 1 | 5 | | Ph | H | COCH₃ | H | H | H | CH₃ | H | acac | |
| 5-273Y | Rh | 0 | 5 | | Ph | H | COCH₃ | H | H | H | CH₃ | H | — | — |
| 5-274 | Rh | 1 | 5 | | Ph | H | H | BL | | H | CH₃ | H | pic | |
| 5-274X | Rh | 1 | 5 | | Ph | H | H | BL | | H | CH₃ | H | acac | |
| 5-274Y | Rh | 0 | 5 | | Ph | H | H | BL | | H | CH₃ | H | — | — |
| 5-275 | Rh | 1 | 5 | | Ph | H | H | BL | | H | ᵗC₄H₉ | H | pic | |
| 5-275X | Rh | 1 | 5 | | Ph | H | H | BL | | H | ᵗC₄H₉ | H | acac | |
| 5-275Y | Rh | 0 | 5 | | Ph | H | H | BL | | H | ᵗC₄H₉ | H | — | — |
| 5-276 | Rh | 1 | 5 | | Ph | H | BL | | H | H | CH₃ | H | pic | |
| 5-276X | Rh | 1 | 5 | | Ph | H | BL | | H | H | CH₃ | H | acac | |
| 5-276Y | Rh | 0 | 5 | | Ph | H | BL | | H | H | CH₃ | H | — | — |
| 5-277 | Rh | 1 | 5 | | Ph | H | BL | | H | H | ᵗC₄H₉ | H | pic | |
| 5-277X | Rh | 1 | 5 | | Ph | H | BL | | H | H | ᵗC₄H₉ | H | acac | |
| 5-277Y | Rh | 0 | 5 | | Ph | H | BL | | H | H | ᵗC₄H₉ | H | — | — |
| 5-278 | Rh | 1 | 5 | | Ph | H | H | PL | | H | CH₃ | H | pic | |
| 5-278X | Rh | 1 | 5 | | Ph | H | H | PL | | H | CH₃ | H | acac | |
| 5-278Y | Rh | 0 | 5 | | Ph | H | H | PL | | H | CH₃ | H | — | — |
| 5-279 | Rh | 1 | 5 | | Ph | H | H | PL | | H | ᵗC₄H₉ | H | pic | |
| 5-279X | Rh | 1 | 5 | | Ph | H | H | PL | | H | ᵗC₄H₉ | H | acac | |
| 5-279Y | Rh | 0 | 5 | | Ph | H | H | PL | | H | ᵗC₄H₉ | H | — | — |
| 5-280 | Rh | 1 | 5 | | Ph | H | PL | | H | H | CH₃ | H | pic | |
| 5-280X | Rh | 1 | 5 | | Ph | H | PL | | H | H | CH₃ | H | acac | |
| 5-280Y | Rh | 0 | 5 | | Ph | H | PL | | H | H | CH₃ | H | — | — |
| 5-281 | Rh | 1 | 5 | | Ph | H | PL | | H | H | ᵗC₄H₉ | H | pic | |
| 5-281X | Rh | 1 | 5 | | Ph | H | PL | | H | H | ᵗC₄H₉ | H | acac | |
| 5-281Y | Rh | 0 | 5 | | Ph | H | PL | | H | H | ᵗC₄H₉ | H | — | — |
| 5-282 | Rh | 1 | 5 | | Ph | H | H | MEE1 | | H | CH₃ | H | pic | |
| 5-282X | Rh | 1 | 5 | | Ph | H | H | MEE1 | | H | CH₃ | H | acac | |

TABLE 19-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 5-282Y | Rh | 0 | 5 | Ph | H | H | | MEE1 | H | CH₃ | H | — | — |
| 5-283 | Rh | 1 | 5 | Ph | H | | MEE1 | | H | CH₃ | H | pic | |
| 5-283X | Rh | 1 | 5 | Ph | H | | MEE1 | | H | CH₃ | H | acac | |
| 5-283Y | Rh | 0 | 5 | Ph | H | | MEE1 | | H | CH₃ | H | — | — |
| 5-284 | Rh | 1 | 5 | Ph | H | H | | MEE2 | H | CH₃ | H | pic | |
| 5-284X | Rh | 1 | 5 | Ph | H | H | | MEE2 | H | CH₃ | H | acac | |
| 5-284Y | Rh | 0 | 5 | Ph | H | H | | MEE2 | H | CH₃ | H | — | — |
| 5-285 | Rh | 1 | 5 | Ph | H | | MEE2 | | H | CH₃ | H | pic | |
| 5-285X | Rh | 1 | 5 | Ph | H | | MEE2 | | H | CH₃ | H | acac | |
| 5-285Y | Rh | 0 | 5 | Ph | H | | MEE2 | | H | CH₃ | H | — | — |
| 5-286 | Rh | 1 | 5 | Ph | H | H | | PA1 | H | CH₃ | H | pic | |
| 5-286X | Rh | 1 | 5 | Ph | H | H | | PA1 | H | CH₃ | H | acac | |
| 5-286Y | Rh | 0 | 5 | Ph | H | H | | PA1 | H | CH₃ | H | — | — |
| 5-287 | Rh | 1 | 5 | Ph | H | | PA1 | | H | CH₃ | H | pic | |
| 5-287X | Rh | 1 | 5 | Ph | H | | PA1 | | H | CH₃ | H | acac | |
| 5-287Y | Rh | 0 | 5 | Ph | H | | PA1 | | H | CH₃ | H | — | — |
| 5-288 | Rh | 1 | 5 | Ph | H | H | | PA2 | H | CH₃ | H | pic | |
| 5-288X | Rh | 1 | 5 | Ph | H | H | | PA2 | H | CH₃ | H | acac | |
| 5-288Y | Rh | 0 | 5 | Ph | H | H | | PA2 | H | CH₃ | H | — | — |
| 5-289 | Rh | 1 | 5 | Ph | H | | PA2 | | H | CH₃ | H | pic | |
| 5-289X | Rh | 1 | 5 | Ph | H | | PA2 | | H | CH₃ | H | acac | |
| 5-289Y | Rh | 0 | 5 | Ph | H | | PA2 | | H | CH₃ | H | — | — |
| 5-290 | Rh | 1 | 5 | Ph | H | H | | EA1 | H | CH₃ | H | pic | |
| 5-290X | Rh | 1 | 5 | Ph | H | H | | EA1 | H | CH₃ | H | acac | |
| 5-290Y | Rh | 0 | 5 | Ph | H | H | | EA1 | H | CH₃ | H | — | — |
| 5-291 | Rh | 1 | 5 | Ph | H | | EA2 | | H | CH₃ | H | pic | |
| 5-291X | Rh | 1 | 5 | Ph | H | | EA2 | | H | CH₃ | H | acac | |
| 5-291Y | Rh | 0 | 5 | Ph | H | | EA2 | | H | CH₃ | H | — | — |
| 5-292 | Rh | 1 | 5 | Ph | H | H | | ME | H | CH₃ | H | pic | |
| 5-292X | Rh | 1 | 5 | Ph | H | H | | ME | H | CH₃ | H | acac | |
| 5-292Y | Rh | 0 | 5 | Ph | H | H | | ME | H | CH₃ | H | — | — |
| 5-293 | Rh | 1 | 5 | Ph | H | | ME | | H | CH₃ | H | pic | |
| 5-293X | Rh | 1 | 5 | Ph | H | | ME | | H | CH₃ | H | acac | |
| 5-293Y | Rh | 0 | 5 | Ph | H | | ME | | H | CH₃ | H | — | — |
| 5-294 | Rh | 1 | 5 | Ph | H | H | | AT | H | CH₃ | H | pic | |
| 5-294X | Rh | 1 | 5 | Ph | H | H | | AT | H | CH₃ | H | acac | |
| 5-294Y | Rh | 0 | 5 | Ph | H | H | | AT | H | CH₃ | H | — | — |
| 5-295 | Rh | 1 | 5 | Ph | H | | AT | | H | CH₃ | H | pic | |
| 5-295X | Rh | 1 | 5 | Ph | H | | AT | | H | CH₃ | H | acac | |
| 5-295Y | Rh | 0 | 5 | Ph | H | | AT | | H | CH₃ | H | — | — |
| 5-296 | Rh | 1 | 5 | Ph | H | H | | MES1 | H | CH₃ | H | pic | |
| 5-296X | Rh | 1 | 5 | Ph | H | H | | MES1 | H | CH₃ | H | acac | |
| 5-296Y | Rh | 0 | 5 | Ph | H | H | | MES1 | H | CH₃ | H | — | — |
| 5-297 | Rh | 1 | 5 | Ph | H | | MES1 | | H | CH₃ | H | pic | |
| 5-297X | Rh | 1 | 5 | Ph | H | | MES1 | | H | CH₃ | H | acac | |
| 5-297Y | Rh | 0 | 5 | Ph | H | | MES1 | | H | CH₃ | H | — | — |
| 5-298 | Rh | 1 | 5 | Ph | H | H | | MES2 | H | CH₃ | H | pic | |
| 5-298X | Rh | 1 | 5 | Ph | H | H | | MES2 | H | CH₃ | H | acac | |
| 5-298Y | Rh | 0 | 5 | Ph | H | H | | MES2 | H | CH₃ | H | — | — |
| 5-299 | Rh | 1 | 5 | Ph | H | | MES2 | | H | CH₃ | H | pic | |
| 5-299X | Rh | 1 | 5 | Ph | H | | MES2 | | H | CH₃ | H | acac | |
| 5-299Y | Rh | 0 | 5 | Ph | H | | MES2 | | H | CH₃ | H | — | — |
| 5-300 | Rh | 1 | 5 | Ph | H | H | | PS1 | H | CH₃ | H | pic | |
| 5-300X | Rh | 1 | 5 | Ph | H | H | | PS1 | H | CH₃ | H | acac | |
| 5-300Y | Rh | 0 | 5 | Ph | H | H | | PS1 | H | CH₃ | H | — | — |
| 5-301 | Rh | 1 | 5 | Ph | H | | PS1 | | H | CH₃ | H | pic | |
| 5-301X | Rh | 1 | 5 | Ph | H | | PS1 | | H | CH₃ | H | acac | |
| 5-301Y | Rh | 0 | 5 | Ph | H | | PS1 | | H | CH₃ | H | — | — |
| 5-302 | Rh | 1 | 5 | Ph | H | H | | PS2 | H | CH₃ | H | pic | |
| 5-302X | Rh | 1 | 5 | Ph | H | H | | PS2 | H | CH₃ | H | acac | |
| 5-302Y | Rh | 0 | 5 | Ph | H | H | | PS2 | H | CH₃ | H | — | — |
| 5-303 | Rh | 1 | 5 | Ph | H | | PS2 | | H | CH₃ | H | pic | |
| 5-303X | Rh | 1 | 5 | Ph | H | | PS2 | | H | CH₃ | H | acac | |
| 5-303Y | Rh | 0 | 5 | Ph | H | | PS2 | | H | CH₃ | H | — | — |
| 5-304 | Rh | 1 | 5 | Ph | H | H | | BAL1 | H | CH₃ | H | pic | |
| 5-304X | Rh | 1 | 5 | Ph | H | H | | BAL1 | H | CH₃ | H | acac | |
| 5-304Y | Rh | 0 | 5 | Ph | H | H | | BAL1 | H | CH₃ | H | — | — |
| 5-305 | Rh | 1 | 5 | Ph | H | | BAL1 | | H | CH₃ | H | pic | |
| 5-305X | Rh | 1 | 5 | Ph | H | | BAL1 | | H | CH₃ | H | acac | |
| 5-305Y | Rh | 0 | 5 | Ph | H | | BAL1 | | H | CH₃ | H | — | — |
| 5-306 | Rh | 1 | 5 | Ph | H | H | | BAL2 | H | CH₃ | H | pic | |
| 5-306X | Rh | 1 | 5 | Ph | H | H | | BAL2 | H | CH₃ | H | acac | |
| 5-306Y | Rh | 0 | 5 | Ph | H | H | | BAL2 | H | CH₃ | H | — | — |
| 5-307 | Rh | 1 | 5 | Ph | H | | BAL2 | | H | CH₃ | H | pic | |
| 5-307X | Rh | 1 | 5 | Ph | H | | BAL2 | | H | CH₃ | H | acac | |
| 5-307Y | Rh | 0 | 5 | Ph | H | | BAL2 | | H | CH₃ | H | — | — |
| 5-308 | Rh | 1 | 5 | Ph | H | H | | MEK1 | H | CH₃ | H | pic | |

TABLE 19-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 5-308X | Rh | 1 | 5 | Ph | H | H | | MEK1 | H | $CH_3$ | H | acac |
| 5-308Y | Rh | 0 | 5 | Ph | H | H | | MEK1 | H | $CH_3$ | H | — — |
| 5-309 | Rh | 1 | 5 | Ph | H | | MEK1 | | H | $CH_3$ | H | pic |
| 5-309X | Rh | 1 | 5 | Ph | H | | MEK1 | | H | $CH_3$ | H | acac |
| 5-309Y | Rh | 0 | 5 | Ph | H | | MEK1 | | H | $CH_3$ | H | — — |
| 5-310 | Rh | 1 | 5 | Ph | H | H | | MEK2 | H | $CH_3$ | H | pic |
| 5-310X | Rh | 1 | 5 | Ph | H | H | | MEK2 | H | $CH_3$ | H | acac |
| 5-310Y | Rh | 0 | 5 | Ph | H | H | | MEK2 | H | $CH_3$ | H | — — |
| 5-311 | Rh | 1 | 5 | Ph | H | | MEK2 | | H | $CH_3$ | H | pic |
| 5-311X | Rh | 1 | 5 | Ph | H | | MEK2 | | H | $CH_3$ | H | acac |
| 5-311Y | Rh | 0 | 5 | Ph | H | | MEK2 | | H | $CH_3$ | H | — — |
| 5-312 | Rh | 1 | 5 | Ph | H | H | | PAL1 | H | $CH_3$ | H | pic |
| 5-312X | Rh | 1 | 5 | Ph | H | H | | PAL1 | H | $CH_3$ | H | acac |
| 5-312Y | Rh | 0 | 5 | Ph | H | H | | PAL1 | H | $CH_3$ | H | — — |
| 5-313 | Rh | 1 | 5 | Ph | H | | PAL1 | | H | $CH_3$ | H | pic |
| 5-313X | Rh | 1 | 5 | Ph | H | | PAL1 | | H | $CH_3$ | H | acac |
| 5-313Y | Rh | 0 | 5 | Ph | H | | PAL1 | | H | $CH_3$ | H | — — |
| 5-314 | Rh | 1 | 5 | Ph | H | H | | PAL2 | H | $CH_3$ | H | pic |
| 5-314X | Rh | 1 | 5 | Ph | H | H | | PAL2 | H | $CH_3$ | H | acac |
| 5-314Y | Rh | 0 | 5 | Ph | H | H | | PAL2 | H | $CH_3$ | H | — — |
| 5-315 | Rh | 1 | 5 | Ph | H | | PAL2 | | H | $CH_3$ | H | pic |
| 5-315X | Rh | 1 | 5 | Ph | H | | PAL2 | | H | $CH_3$ | H | acac |
| 5-315Y | Rh | 0 | 5 | Ph | H | | PAL2 | | H | $CH_3$ | H | — — |
| 5-316 | Rh | 1 | 5 | Ph | H | H | | MMK | H | $CH_3$ | H | pic |
| 5-316X | Rh | 1 | 5 | Ph | H | H | | MMK | H | $CH_3$ | H | acac |
| 5-316Y | Rh | 0 | 5 | Ph | H | H | | MMK | H | $CH_3$ | H | — — |
| 5-317 | Rh | 1 | 5 | Ph | H | | MMK | | H | $CH_3$ | H | pic |
| 5-317X | Rh | 1 | 5 | Ph | H | | MMK | | H | $CH_3$ | H | acac |
| 5-317Y | Rh | 0 | 5 | Ph | H | | MMK | | H | $CH_3$ | H | — — |
| 5-318 | Rh | 1 | 5 | Ph | H | H | | EES1 | H | $CH_3$ | H | pic |
| 5-318X | Rh | 1 | 5 | Ph | H | H | | EES1 | H | $CH_3$ | H | acac |
| 5-318Y | Rh | 0 | 5 | Ph | H | H | | EES1 | H | $CH_3$ | H | — — |
| 5-319 | Rh | 1 | 5 | Ph | H | | EES2 | | H | $CH_3$ | H | pic |
| 5-319X | Rh | 1 | 5 | Ph | H | | EES2 | | H | $CH_3$ | H | acac |
| 5-319Y | Rh | 0 | 5 | Ph | H | | EES2 | | H | $CH_3$ | H | — — |
| 5-320 | Rh | 1 | 5 | Ph | H | H | | PAE1 | H | $CH_3$ | H | pic |
| 5-320X | Rh | 1 | 5 | Ph | H | H | | PAE1 | H | $CH_3$ | H | acac |
| 5-320Y | Rh | 0 | 5 | Ph | H | H | | PAE1 | H | $CH_3$ | H | — — |
| 5-321 | Rh | 1 | 5 | Ph | H | | PAE2 | | H | $CH_3$ | H | pic |
| 5-321X | Rh | 1 | 5 | Ph | H | | PAE2 | | H | $CH_3$ | H | acac |
| 5-321Y | Rh | 0 | 5 | Ph | H | | PAE2 | | H | $CH_3$ | H | — — |
| 5-322 | Rh | 1 | 5 | Ph | H | H | | AME1 | H | $CH_3$ | H | pic |
| 5-322X | Rh | 1 | 5 | Ph | H | H | | AME1 | H | $CH_3$ | H | acac |
| 5-322Y | Rh | 0 | 5 | Ph | H | H | | AME1 | H | $CH_3$ | H | — — |
| 5-323 | Rh | 1 | 5 | Ph | H | | AME1 | | H | $CH_3$ | H | pic |
| 5-323X | Rh | 1 | 5 | Ph | H | | AME1 | | H | $CH_3$ | H | acac |
| 5-323Y | Rh | 0 | 5 | Ph | H | | AME1 | | H | $CH_3$ | H | — — |
| 5-324 | Rh | 1 | 5 | Ph | H | H | | AME2 | H | $CH_3$ | H | pic |
| 5-324X | Rh | 1 | 5 | Ph | H | H | | AME2 | H | $CH_3$ | H | acac |
| 5-324Y | Rh | 0 | 5 | Ph | H | H | | AME2 | H | $CH_3$ | H | — — |
| 5-325 | Rh | 1 | 5 | Ph | H | | AME2 | | H | $CH_3$ | H | pic |
| 5-325X | Rh | 1 | 5 | Ph | H | | AME2 | | H | $CH_3$ | H | acac |
| 5-325Y | Rh | 0 | 5 | Ph | H | | AME2 | | H | $CH_3$ | H | — — |
| 5-326 | Rh | 1 | 5 | Ph | H | H | | EAE1 | H | $CH_3$ | H | pic |
| 5-326X | Rh | 1 | 5 | Ph | H | H | | EAE1 | H | $CH_3$ | H | acac |
| 5-326Y | Rh | 0 | 5 | Ph | H | H | | EAE1 | H | $CH_3$ | H | — — |
| 5-327 | Rh | 1 | 5 | Ph | H | | EAE1 | | H | $CH_3$ | H | pic |
| 5-327X | Rh | 1 | 5 | Ph | H | | EAE1 | | H | $CH_3$ | H | acac |
| 5-327Y | Rh | 0 | 5 | Ph | H | | EAE1 | | H | $CH_3$ | H | — — |
| 5-328 | Rh | 1 | 5 | Ph | H | H | | EAE2 | H | $CH_3$ | H | pic |
| 5-328X | Rh | 1 | 5 | Ph | H | H | | EAE2 | H | $CH_3$ | H | acac |
| 5-328Y | Rh | 0 | 5 | Ph | H | H | | EAE2 | H | $CH_3$ | H | — — |
| 5-329 | Rh | 1 | 5 | Ph | H | | EAE2 | | H | $CH_3$ | H | pic |
| 5-329X | Rh | 1 | 5 | Ph | H | | EAE2 | | H | $CH_3$ | H | acac |
| 5-329Y | Rh | 0 | 5 | Ph | H | | EAE2 | | H | $CH_3$ | H | — — |
| 5-330 | Rh | 1 | 5 | Ph | H | H | | AAE1 | H | $CH_3$ | H | pic |
| 5-330X | Rh | 1 | 5 | Ph | H | H | | AAE1 | H | $CH_3$ | H | acac |
| 5-330Y | Rh | 0 | 5 | Ph | H | H | | AAE1 | H | $CH_3$ | H | — — |
| 5-331 | Rh | 1 | 5 | Ph | H | | AAE1 | | H | $CH_3$ | H | pic |
| 5-331X | Rh | 1 | 5 | Ph | H | | AAE1 | | H | $CH_3$ | H | acac |
| 5-331Y | Rh | 0 | 5 | Ph | H | | AAE1 | | H | $CH_3$ | H | — — |
| 5-332 | Rh | 1 | 5 | Ph | H | H | | AAE2 | H | $CH_3$ | H | pic |
| 5-332X | Rh | 1 | 5 | Ph | H | H | | AAE2 | H | $CH_3$ | H | acac |
| 5-332Y | Rh | 0 | 5 | Ph | H | H | | AAE2 | H | $CH_3$ | H | — — |
| 5-333 | Rh | 1 | 5 | Ph | H | | AAE2 | | H | $CH_3$ | H | pic |
| 5-333X | Rh | 1 | 5 | Ph | H | | AAE2 | | H | $CH_3$ | H | acac |
| 5-333Y | Rh | 0 | 5 | Ph | H | | AAE2 | | H | $CH_3$ | H | — — |

TABLE 19-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 5-334 | Rh | 1 | 5 | Ph | H | H | | PME1 | H | CH₃ | H | pic |
| 5-334X | Rh | 1 | 5 | Ph | H | H | | PME1 | H | CH₃ | H | acac |
| 5-334Y | Rh | 0 | 5 | Ph | H | H | | PME1 | H | CH₃ | H | — — |
| 5-335 | Rh | 1 | 5 | Ph | H | | PME1 | H | H | CH₃ | H | pic |
| 5-335X | Rh | 1 | 5 | Ph | H | | PME1 | H | H | CH₃ | H | acac |
| 5-335Y | Rh | 0 | 5 | Ph | H | | PME1 | H | H | CH₃ | H | — — |
| 5-336 | Rh | 1 | 5 | Ph | H | H | | PME2 | H | CH₃ | H | pic |
| 5-336X | Rh | 1 | 5 | Ph | H | H | | PME2 | H | CH₃ | H | acac |
| 5-336Y | Rh | 0 | 5 | Ph | H | H | | PME2 | H | CH₃ | H | — — |
| 5-337 | Rh | 1 | 5 | Ph | H | | PME2 | H | H | CH₃ | H | pic |
| 5-337X | Rh | 1 | 5 | Ph | H | | PME2 | H | H | CH₃ | H | acac |
| 5-337Y | Rh | 0 | 5 | Ph | H | | PME2 | H | H | CH₃ | H | — — |
| 5-338 | Rh | 1 | 5 | Ph | H | H | | MET1 | H | CH₃ | H | pic |
| 5-338X | Rh | 1 | 5 | Ph | H | H | | MET1 | H | CH₃ | H | acac |
| 5-338Y | Rh | 0 | 5 | Ph | H | H | | MET1 | H | CH₃ | H | — — |
| 5-339 | Rh | 1 | 5 | Ph | H | | MET1 | H | H | CH₃ | H | pic |
| 5-339X | Rh | 1 | 5 | Ph | H | | MET1 | H | H | CH₃ | H | acac |
| 5-339Y | Rh | 0 | 5 | Ph | H | | MET1 | H | H | CH₃ | H | — — |
| 5-340 | Rh | 1 | 5 | Ph | H | H | | MET2 | H | CH₃ | H | pic |
| 5-340X | Rh | 1 | 5 | Ph | H | H | | MET2 | H | CH₃ | H | acac |
| 5-340Y | Rh | 0 | 5 | Ph | H | H | | MET2 | H | CH₃ | H | — — |
| 5-341 | Rh | 1 | 5 | Ph | H | | MET2 | H | H | CH₃ | H | pic |
| 5-341X | Rh | 1 | 5 | Ph | H | | MET2 | H | H | CH₃ | H | acac |
| 5-341Y | Rh | 0 | 5 | Ph | H | | MET2 | H | H | CH₃ | H | — — |
| 5-342 | Rh | 1 | 5 | Ph | H | H | | EE1 | H | CH₃ | H | pic |
| 5-342X | Rh | 1 | 5 | Ph | H | H | | EE1 | H | CH₃ | H | acac |
| 5-342Y | Rh | 0 | 5 | Ph | H | H | | EE1 | H | CH₃ | H | — — |
| 5-343 | Rh | 1 | 5 | Ph | H | | EE1 | H | H | CH₃ | H | pic |
| 5-343X | Rh | 1 | 5 | Ph | H | | EE1 | H | H | CH₃ | H | acac |
| 5-343Y | Rh | 0 | 5 | Ph | H | | EE1 | H | H | CH₃ | H | — — |
| 5-344 | Rh | 1 | 5 | Ph | H | H | | EE2 | H | CH₃ | H | pic |
| 5-344X | Rh | 1 | 5 | Ph | H | H | | EE2 | H | CH₃ | H | acac |
| 5-344Y | Rh | 0 | 5 | Ph | H | H | | EE2 | H | CH₃ | H | — — |
| 5-345 | Rh | 1 | 5 | Ph | H | | EE2 | H | H | CH₃ | H | pic |
| 5-345X | Rh | 1 | 5 | Ph | H | | EE2 | H | H | CH₃ | H | acac |
| 5-345Y | Rh | 0 | 5 | Ph | H | | EE2 | H | H | CH₃ | H | — — |
| 5-346 | Rh | 1 | 5 | Ph | H | H | | MS1 | H | CH₃ | H | pic |
| 5-346X | Rh | 1 | 5 | Ph | H | H | | MS1 | H | CH₃ | H | acac |
| 5-346Y | Rh | 0 | 5 | Ph | H | H | | MS1 | H | CH₃ | H | — — |
| 5-347 | Rh | 1 | 5 | Ph | H | | MS1 | H | H | CH₃ | H | pic |
| 5-347X | Rh | 1 | 5 | Ph | H | | MS1 | H | H | CH₃ | H | acac |
| 5-347Y | Rh | 0 | 5 | Ph | H | | MS1 | H | H | CH₃ | H | — — |
| 5-348 | Rh | 1 | 5 | Ph | H | H | | MS2 | H | CH₃ | H | pic |
| 5-348X | Rh | 1 | 5 | Ph | H | H | | MS2 | H | CH₃ | H | acac |
| 5-348Y | Rh | 0 | 5 | Ph | H | H | | MS2 | H | CH₃ | H | — — |
| 5-349 | Rh | 1 | 5 | Ph | H | | MS2 | H | H | CH₃ | H | pic |
| 5-349X | Rh | 1 | 5 | Ph | H | | MS2 | H | H | CH₃ | H | acac |
| 5-349Y | Rh | 0 | 5 | Ph | H | | MS2 | H | H | CH₃ | H | — — |

TABLE 20

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 6-167 | Rh | 1 | 6 | Ph | H | H | H | H | CH₃ | H | H | pic |
| 6-167X | Rh | 1 | 6 | Ph | H | H | H | H | CH₃ | H | H | acac |
| 6-167Y | Rh | 0 | 6 | Ph | H | H | H | H | CH₃ | H | H | — — |
| 6-168 | Rh | 1 | 6 | Ph | H | H | H | H | $^tC_4H_9$ | H | H | pic |
| 6-168X | Rh | 1 | 6 | Ph | H | H | H | H | $^tC_4H_9$ | H | H | acac |
| 6-168Y | Rh | 0 | 6 | Ph | H | H | H | H | $^tC_4H_9$ | H | H | — — |
| 6-169 | Rh | 1 | 6 | Ph | H | F | H | F | CH₃ | H | H | pic |
| 6-169X | Rh | 1 | 6 | Ph | H | F | H | F | CH₃ | H | H | acac |
| 6-169Y | Rh | 0 | 6 | Ph | H | F | H | F | CH₃ | H | H | — — |
| 6-170 | Rh | 1 | 6 | Ph | H | F | H | F | $^tC_4H_9$ | H | H | pic |
| 6-170X | Rh | 1 | 6 | Ph | H | F | H | F | $^tC_4H_9$ | H | H | acac |
| 6-170Y | Rh | 0 | 6 | Ph | H | F | H | F | $^tC_4H_9$ | H | H | — — |
| 6-171 | Rh | 1 | 6 | Ph | F | H | H | F | CH₃ | H | H | pic |
| 6-171X | Rh | 1 | 6 | Ph | F | H | H | F | CH₃ | H | H | acac |
| 6-171Y | Rh | 0 | 6 | Ph | F | H | H | F | CH₃ | H | H | — — |
| 6-172 | Rh | 1 | 6 | Ph | F | H | H | F | $^tC_4H_9$ | H | H | pic |
| 6-172X | Rh | 1 | 6 | Ph | F | H | H | F | $^tC_4H_9$ | H | H | acac |
| 6-172Y | Rh | 0 | 6 | Ph | F | H | H | F | $^tC_4H_9$ | H | H | — — |
| 6-173 | Rh | 1 | 6 | Ph | CF₃ | H | CF₃ | H | CH₃ | H | H | pic |
| 6-173X | Rh | 1 | 6 | Ph | CF₃ | H | CF₃ | H | CH₃ | H | H | acac |
| 6-173Y | Rh | 0 | 6 | Ph | CF₃ | H | CF₃ | H | CH₃ | H | H | — — |

TABLE 20-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 6-174 | Rh | 1 | 6 | Ph | CF₃ | H | CF₃ | H | $^tC_4H_9$ | H | H | pic | |
| 6-174X | Rh | 1 | 6 | Ph | CF₃ | H | CF₃ | H | $^tC_4H_9$ | H | H | acac | |
| 6-174Y | Rh | 0 | 6 | Ph | CF₃ | H | CF₃ | H | $^tC_4H_9$ | H | H | — | — |
| 6-175 | Rh | 1 | 6 | Ph | H | F | CF₃ | H | CH₃ | H | H | pic | |
| 6-175X | Rh | 1 | 6 | Ph | H | F | CF₃ | H | CH₃ | H | H | acac | |
| 6-175Y | Rh | 0 | 6 | Ph | H | F | CF₃ | H | CH₃ | H | H | — | — |
| 6-176 | Rh | 1 | 6 | Ph | F | H | CF₃ | H | CH₃ | H | H | pic | |
| 6-176X | Rh | 1 | 6 | Ph | F | H | CF₃ | H | CH₃ | H | H | acac | |
| 6-176Y | Rh | 0 | 6 | Ph | F | H | CF₃ | H | CH₃ | H | H | — | — |
| 6-177 | Rh | 1 | 6 | Ph | F | F | F | F | CH₃ | H | H | pic | |
| 6-177X | Rh | 1 | 6 | Ph | F | F | F | F | CH₃ | H | H | acac | |
| 6-177Y | Rh | 0 | 6 | Ph | F | F | F | F | CH₃ | H | H | — | — |
| 6-178 | Rh | 1 | 6 | Ph | H | F | H | CH₃ | CH₃ | H | H | pic | |
| 6-178X | Rh | 1 | 6 | Ph | H | F | H | CH₃ | CH₃ | H | H | acac | |
| 6-178Y | Rh | 0 | 6 | Ph | H | F | H | CH₃ | CH₃ | H | H | — | — |
| 6-179 | Rh | 1 | 6 | Ph | H | F | H | CH₃ | $^tC_4H_9$ | H | H | pic | |
| 6-179X | Rh | 1 | 6 | Ph | H | F | H | CH₃ | $^tC_4H_9$ | H | H | acac | |
| 6-179Y | Rh | 0 | 6 | Ph | H | F | H | CH₃ | $^tC_4H_9$ | H | H | — | — |
| 6-180 | Rh | 1 | 6 | Ph | H | F | H | $^tC_4H_9$ | CH₃ | H | H | pic | |
| 6-180X | Rh | 1 | 6 | Ph | H | F | H | $^tC_4H_9$ | CH₃ | H | H | acac | |
| 6-180Y | Rh | 0 | 6 | Ph | H | F | H | $^tC_4H_9$ | CH₃ | H | H | — | — |
| 6-181 | Rh | 1 | 6 | Ph | H | F | H | $^tC_4H_9$ | $^tC_4H_9$ | H | H | pic | |
| 6-181X | Rh | 1 | 6 | Ph | H | F | H | $^tC_4H_9$ | $^tC_4H_9$ | H | H | acac | |
| 6-181Y | Rh | 0 | 6 | Ph | H | F | H | $^tC_4H_9$ | $^tC_4H_9$ | H | H | — | — |
| 6-182 | Rh | 1 | 6 | Ph | H | CF₃ | H | CF₃ | CH₃ | H | H | pic | |
| 6-182X | Rh | 1 | 6 | Ph | H | CF₃ | H | CF₃ | CH₃ | H | H | acac | |
| 6-182Y | Rh | 0 | 6 | Ph | H | CF₃ | H | CF₃ | CH₃ | H | H | — | — |
| 6-183 | Rh | 1 | 6 | Ph | H | CF₃ | H | CF₃ | $^tC_4H_9$ | H | H | pic | |
| 6-183X | Rh | 1 | 6 | Ph | H | CF₃ | H | CF₃ | $^tC_4H_9$ | H | H | acac | |
| 6-183Y | Rh | 0 | 6 | Ph | H | CF₃ | H | CF₃ | $^tC_4H_9$ | H | H | — | — |
| 6-184 | Rh | 1 | 6 | Ph | CF₃ | H | H | $^tC_4H_9$ | CH₃ | H | H | pic | |
| 6-184X | Rh | 1 | 6 | Ph | CF₃ | H | H | $^tC_4H_9$ | CH₃ | H | H | acac | |
| 6-184Y | Rh | 0 | 6 | Ph | CF₃ | H | H | $^tC_4H_9$ | CH₃ | H | H | — | — |
| 6-185 | Rh | 1 | 6 | Ph | CF₃ | H | H | $^tC_4H_9$ | $^tC_4H_9$ | H | H | pic | |
| 6-185X | Rh | 1 | 6 | Ph | CF₃ | H | H | $^tC_4H_9$ | $^tC_4H_9$ | H | H | acac | |
| 6-185Y | Rh | 0 | 6 | Ph | CF₃ | H | H | $^tC_4H_9$ | $^tC_4H_9$ | H | H | — | — |
| 6-186 | Rh | 1 | 6 | Ph | H | CF₃ | H | $^tC_4H_9$ | CH₃ | H | H | pic | |
| 6-186X | Rh | 1 | 6 | Ph | H | CF₃ | H | $^tC_4H_9$ | CH₃ | H | H | acac | |
| 6-186Y | Rh | 0 | 6 | Ph | H | CF₃ | H | $^tC_4H_9$ | CH₃ | H | H | — | — |
| 6-187 | Rh | 1 | 6 | Ph | H | CF₃ | H | $^tC_4H_9$ | $^tC_4H_9$ | H | H | pic | |
| 6-187X | Rh | 1 | 6 | Ph | H | CF₃ | H | $^tC_4H_9$ | $^tC_4H_9$ | H | H | acac | |
| 6-187Y | Rh | 0 | 6 | Ph | H | CF₃ | H | $^tC_4H_9$ | $^tC_4H_9$ | H | H | — | — |
| 6-188 | Rh | 1 | 6 | Ph | H | CF₃ | H | CH₃ | CH₃ | H | H | pic | |
| 6-188X | Rh | 1 | 6 | Ph | H | CF₃ | H | CH₃ | CH₃ | H | H | acac | |
| 6-188Y | Rh | 0 | 6 | Ph | H | CF₃ | H | CH₃ | CH₃ | H | H | — | — |
| 6-189 | Rh | 1 | 6 | Ph | H | CF₃ | CF₃ | H | CH₃ | H | H | pic | |
| 6-189X | Rh | 1 | 6 | Ph | H | CF₃ | CF₃ | H | CH₃ | H | H | acac | |
| 6-189Y | Rh | 0 | 6 | Ph | H | CF₃ | CF₃ | H | CH₃ | H | H | — | — |
| 6-190 | Rh | 1 | 6 | Ph | H | H | NO₂ | H | CH₃ | H | H | pic | |
| 6-190X | Rh | 1 | 6 | Ph | H | H | NO₂ | H | CH₃ | H | H | acac | |
| 6-190Y | Rh | 0 | 6 | Ph | H | H | NO₂ | H | CH₃ | H | H | — | — |
| 6-191 | Rh | 1 | 6 | Ph | H | H | NO₂ | H | $^tC_4H_9$ | H | H | pic | |
| 6-191X | Rh | 1 | 6 | Ph | H | H | NO₂ | H | $^tC_4H_9$ | H | H | acac | |
| 6-191Y | Rh | 0 | 6 | Ph | H | H | NO₂ | H | $^tC_4H_9$ | H | H | — | — |
| 6-192 | Rh | 1 | 6 | Ph | F | H | NO₂ | H | CH₃ | H | H | pic | |
| 6-192X | Rh | 1 | 6 | Ph | F | H | NO₂ | H | CH₃ | H | H | acac | |
| 6-192Y | Rh | 0 | 6 | Ph | F | H | NO₂ | H | CH₃ | H | H | — | — |
| 6-193 | Rh | 1 | 6 | Ph | F | H | NO₂ | F | CH₃ | H | H | pic | |
| 6-193X | Rh | 1 | 6 | Ph | F | H | NO₂ | F | CH₃ | H | H | acac | |
| 6-193Y | Rh | 0 | 6 | Ph | F | H | NO₂ | F | CH₃ | H | H | — | — |
| 6-194 | Rh | 1 | 6 | Ph | H | NO₂ | H | NO₂ | CH₃ | H | H | pic | |
| 6-194X | Rh | 1 | 6 | Ph | H | NO₂ | H | NO₂ | CH₃ | H | H | acac | |
| 6-194Y | Rh | 0 | 6 | Ph | H | NO₂ | H | NO₂ | CH₃ | H | H | — | — |
| 6-195 | Rh | 1 | 6 | Ph | H | NO₂ | H | NO₂ | $^tC_4H_9$ | H | H | pic | |
| 6-195X | Rh | 1 | 6 | Ph | H | NO₂ | H | NO₂ | $^tC_4H_9$ | H | H | acac | |
| 6-195Y | Rh | 0 | 6 | Ph | H | NO₂ | H | NO₂ | $^tC_4H_9$ | H | H | — | — |
| 6-196 | Rh | 1 | 6 | Ph | NO₂ | H | H | NO₂ | CH₃ | H | H | pic | |
| 6-196X | Rh | 1 | 6 | Ph | NO₂ | H | H | NO₂ | CH₃ | H | H | acac | |
| 6-196Y | Rh | 0 | 6 | Ph | NO₂ | H | H | NO₂ | CH₃ | H | H | — | — |
| 6-197 | Rh | 1 | 6 | Ph | NO₂ | H | H | NO₂ | $^tC_4H_9$ | H | H | pic | |
| 6-197X | Rh | 1 | 6 | Ph | NO₂ | H | H | NO₂ | $^tC_4H_9$ | H | H | acac | |
| 6-197Y | Rh | 0 | 6 | Ph | NO₂ | H | H | NO₂ | $^tC_4H_9$ | H | H | — | — |
| 6-198 | Rh | 1 | 6 | Ph | H | H | CF₃ | H | CH₃ | H | H | pic | |
| 6-198X | Rh | 1 | 6 | Ph | H | H | CF₃ | H | CH₃ | H | H | acac | |
| 6-198Y | Rh | 0 | 6 | Ph | H | H | CF₃ | H | CH₃ | H | H | — | — |
| 6-199 | Rh | 1 | 6 | Ph | H | H | CF₃ | H | $^tC_4H_9$ | H | H | pic | |
| 6-199X | Rh | 1 | 6 | Ph | H | H | CF₃ | H | $^tC_4H_9$ | H | H | acac | |

TABLE 20-continued

| No. | M | n | BSS | SS | G | T¹ | T² | T³ | T⁴ | T⁵ | T⁶ | T⁷ | L¹ | L² |
|---|---|---|---|---|---|---|---|---|---|---|---|---|---|---|
| 6-199Y | Rh | 0 | 6 | | Ph | H | H | CF₃ | H | ᵗC₄H₉ | H | H | — | — |
| 6-200 | Rh | 1 | 6 | | Ph | H | Cl | CF₃ | H | CH₃ | H | H | pic | |
| 6-200X | Rh | 1 | 6 | | Ph | H | Cl | CF₃ | H | CH₃ | H | H | acac | |
| 6-200Y | Rh | 0 | 6 | | Ph | H | Cl | CF₃ | H | CH₃ | H | H | — | — |
| 6-201 | Rh | 1 | 6 | | Ph | H | Cl | CF₃ | H | ᵗC₄H₉ | H | H | pic | |
| 6-201X | Rh | 1 | 6 | | Ph | H | Cl | CF₃ | H | ᵗC₄H₉ | H | H | acac | |
| 6-201Y | Rh | 0 | 6 | | Ph | H | Cl | CF₃ | H | ᵗC₄H₉ | H | H | — | — |
| 6-202 | Rh | 1 | 6 | | Ph | H | NO₂ | H | H | CH₃ | H | H | pic | |
| 6-202X | Rh | 1 | 6 | | Ph | H | NO₂ | H | H | CH₃ | H | H | acac | |
| 6-202Y | Rh | 0 | 6 | | Ph | H | NO₂ | H | H | CH₃ | H | H | — | — |
| 6-203 | Rh | 1 | 6 | | Ph | H | CF₃ | H | H | CH₃ | H | H | pic | |
| 6-203X | Rh | 1 | 6 | | Ph | H | CF₃ | H | H | CH₃ | H | H | acac | |
| 6-203Y | Rh | 0 | 6 | | Ph | H | CF₃ | H | H | CH₃ | H | H | — | — |
| 6-204 | Rh | 1 | 6 | | Ph | H | NO₂ | H | CH₃ | CH₃ | H | H | pic | |
| 6-204X | Rh | 1 | 6 | | Ph | H | NO₂ | H | CH₃ | CH₃ | H | H | acac | |
| 6-204Y | Rh | 0 | 6 | | Ph | H | NO₂ | H | CH₃ | CH₃ | H | H | — | — |
| 6-205 | Rh | 1 | 6 | | Ph | H | NO₂ | H | CH₃ | ᵗC₄H₉ | H | H | pic | |
| 6-205X | Rh | 1 | 6 | | Ph | H | NO₂ | H | CH₃ | ᵗC₄H₉ | H | H | acac | |
| 6-205Y | Rh | 0 | 6 | | Ph | H | NO₂ | H | CH₃ | ᵗC₄H₉ | H | H | — | — |
| 6-206 | Rh | 1 | 6 | | Ph | H | NO₂ | H | ᵗC₄H₉ | CH₃ | H | H | pic | |
| 6-206X | Rh | 1 | 6 | | Ph | H | NO₂ | H | ᵗC₄H₉ | CH₃ | H | H | acac | |
| 6-206Y | Rh | 0 | 6 | | Ph | H | NO₂ | H | ᵗC₄H₉ | CH₃ | H | H | — | — |
| 6-207 | Rh | 1 | 6 | | Ph | H | NO₂ | H | ᵗC₄H₉ | ᵗC₄H₉ | H | H | pic | |
| 6-207X | Rh | 1 | 6 | | Ph | H | NO₂ | H | ᵗC₄H₉ | ᵗC₄H₉ | H | H | acac | |
| 6-207Y | Rh | 0 | 6 | | Ph | H | NO₂ | H | ᵗC₄H₉ | ᵗC₄H₉ | H | H | — | — |
| 6-208 | Rh | 1 | 6 | | Ph | H | H | CH₃O | H | CH₃ | H | H | pic | |
| 6-208X | Rh | 1 | 6 | | Ph | H | H | CH₃O | H | CH₃ | H | H | acac | |
| 6-208Y | Rh | 0 | 6 | | Ph | H | H | CH₃O | H | CH₃ | H | H | — | — |
| 6-209 | Rh | 1 | 6 | | Ph | H | CH₃O | H | H | CH₃ | H | H | pic | |
| 6-209X | Rh | 1 | 6 | | Ph | H | CH₃O | H | H | CH₃ | H | H | acac | |
| 6-209Y | Rh | 0 | 6 | | Ph | H | CH₃O | H | H | CH₃ | H | H | — | — |
| 6-210 | Rh | 1 | 6 | | Ph | H | CH₃O | H | CH₃ | CH₃ | H | H | pic | |
| 6-210X | Rh | 1 | 6 | | Ph | H | CH₃O | H | CH₃ | CH₃ | H | H | acac | |
| 6-210Y | Rh | 0 | 6 | | Ph | H | CH₃O | H | CH₃ | CH₃ | H | H | — | — |
| 6-211 | Rh | 1 | 6 | | Ph | H | CH₃O | H | ᵗC₄H₉ | CH₃ | H | H | pic | |
| 6-211X | Rh | 1 | 6 | | Ph | H | CH₃O | H | ᵗC₄H₉ | CH₃ | H | H | acac | |
| 6-211Y | Rh | 0 | 6 | | Ph | H | CH₃O | H | ᵗC₄H₉ | CH₃ | H | H | — | — |
| 6-212 | Rh | 1 | 6 | | Ph | H | Si(CH₃)₃ | H | H | CH₃ | H | H | pic | |
| 6-212X | Rh | 1 | 6 | | Ph | H | Si(CH₃)₃ | H | H | CH₃ | H | H | acac | |
| 6-212Y | Rh | 0 | 6 | | Ph | H | Si(CH₃)₃ | H | H | CH₃ | H | H | — | — |
| 6-213 | Rh | 1 | 6 | | Ph | H | Si(CH₃)₃ | H | H | ᵗC₄H₉ | H | H | pic | |
| 6-213X | Rh | 1 | 6 | | Ph | H | Si(CH₃)₃ | H | H | ᵗC₄H₉ | H | H | acac | |
| 6-213Y | Rh | 0 | 6 | | Ph | H | Si(CH₃)₃ | H | H | ᵗC₄H₉ | H | H | — | — |
| 6-214 | Rh | 1 | 6 | | Ph | H | H | Si(CH₃)₃ | H | CH₃ | H | H | pic | |
| 6-214X | Rh | 1 | 6 | | Ph | H | H | Si(CH₃)₃ | H | CH₃ | H | H | acac | |
| 6-214Y | Rh | 0 | 6 | | Ph | H | H | Si(CH₃)₃ | H | CH₃ | H | H | — | — |
| 6-215 | Rh | 1 | 6 | | Ph | H | H | H | Si(CH₃)₃ | CH₃ | H | H | pic | |
| 6-215X | Rh | 1 | 6 | | Ph | H | H | H | Si(CH₃)₃ | CH₃ | H | H | acac | |
| 6-215Y | Rh | 0 | 6 | | Ph | H | H | H | Si(CH₃)₃ | CH₃ | H | H | — | — |
| 6-216 | Rh | 1 | 6 | | Ph | H | F | H | Si(CH₃)₃ | CH₃ | H | H | pic | |
| 6-216X | Rh | 1 | 6 | | Ph | H | F | H | Si(CH₃)₃ | CH₃ | H | H | acac | |
| 6-216Y | Rh | 0 | 6 | | Ph | H | F | H | Si(CH₃)₃ | CH₃ | H | H | — | — |
| 6-217 | Rh | 1 | 6 | | Ph | H | CF₃ | H | Si(CH₃)₃ | CH₃ | H | H | pic | |
| 6-217X | Rh | 1 | 6 | | Ph | H | CF₃ | H | Si(CH₃)₃ | CH₃ | H | H | acac | |
| 6-217Y | Rh | 0 | 6 | | Ph | H | CF₃ | H | Si(CH₃)₃ | CH₃ | H | H | — | — |
| 6-218 | Rh | 1 | 6 | | Ph | H | CF₃ | H | Si(CH₃)₃ | ᵗC₄H₉ | H | H | pic | |
| 6-218X | Rh | 1 | 6 | | Ph | H | CF₃ | H | Si(CH₃)₃ | ᵗC₄H₉ | H | H | acac | |
| 6-218Y | Rh | 0 | 6 | | Ph | H | CF₃ | H | Si(CH₃)₃ | ᵗC₄H₉ | H | H | — | — |
| 6-219 | Rh | 1 | 6 | | Ph | H | Si(CH₃)₃ | H | F | CH₃ | H | H | pic | |
| 6-219X | Rh | 1 | 6 | | Ph | H | Si(CH₃)₃ | H | F | CH₃ | H | H | acac | |
| 6-219Y | Rh | 0 | 6 | | Ph | H | Si(CH₃)₃ | H | F | CH₃ | H | H | — | — |
| 6-220 | Rh | 1 | 6 | | Ph | H | Si(CH₃)₃ | H | F | ᵗC₄H₉ | H | H | pic | |
| 6-220X | Rh | 1 | 6 | | Ph | H | Si(CH₃)₃ | H | F | ᵗC₄H₉ | H | H | acac | |
| 6-220Y | Rh | 0 | 6 | | Ph | H | Si(CH₃)₃ | H | F | ᵗC₄H₉ | H | H | — | — |
| 6-221 | Rh | 1 | 6 | | Ph | H | Si(CH₃)₃ | H | CF₃ | CH₃ | H | H | pic | |
| 6-221X | Rh | 1 | 6 | | Ph | H | Si(CH₃)₃ | H | CF₃ | CH₃ | H | H | acac | |
| 6-221Y | Rh | 0 | 6 | | Ph | H | Si(CH₃)₃ | H | CF₃ | CH₃ | H | H | — | — |
| 6-222 | Rh | 1 | 6 | | Ph | H | Si(CH₃)₃ | H | CF₃ | ᵗC₄H₉ | H | H | pic | |
| 6-222X | Rh | 1 | 6 | | Ph | H | Si(CH₃)₃ | H | CF₃ | ᵗC₄H₉ | H | H | acac | |
| 6-222Y | Rh | 0 | 6 | | Ph | H | Si(CH₃)₃ | H | CF₃ | ᵗC₄H₉ | H | H | — | — |
| 6-223 | Rh | 1 | 6 | | Ph | Si(CH₃)₃ | H | Si(CH₃)₃ | H | CH₃ | H | H | pic | |
| 6-223X | Rh | 1 | 6 | | Ph | Si(CH₃)₃ | H | Si(CH₃)₃ | H | CH₃ | H | H | acac | |
| 6-223Y | Rh | 0 | 6 | | Ph | Si(CH₃)₃ | H | Si(CH₃)₃ | H | CH₃ | H | H | — | — |
| 6-224 | Rh | 1 | 6 | | Ph | Si(CH₃)₃ | H | Si(CH₃)₃ | H | ᵗC₄H₉ | H | H | pic | |
| 6-224X | Rh | 1 | 6 | | Ph | Si(CH₃)₃ | H | Si(CH₃)₃ | H | ᵗC₄H₉ | H | H | acac | |
| 6-224Y | Rh | 0 | 6 | | Ph | Si(CH₃)₃ | H | Si(CH₃)₃ | H | ᵗC₄H₉ | H | H | — | — |
| 6-225 | Rh | 1 | 6 | | Ph | H | H | H | COCH₃ | CH₃ | H | H | pic | |

TABLE 20-continued

| No. | M | n | BSS | SS G | T$^1$ | T$^2$ | T$^3$ | T$^4$ | T$^5$ | T$^6$ | T$^7$ | L$^1$ L$^2$ |
|---|---|---|---|---|---|---|---|---|---|---|---|---|
| 6-225X | Rh | 1 | 6 | Ph | H | H | H | COCH$_3$ | CH$_3$ | H | H | acac |
| 6-225Y | Rh | 0 | 6 | Ph | H | H | H | COCH$_3$ | CH$_3$ | H | H | — — |
| 6-226 | Rh | 1 | 6 | Ph | H | H | COCH$_3$ | H | CH$_3$ | H | H | pic |
| 6-226X | Rh | 1 | 6 | Ph | H | H | COCH$_3$ | H | CH$_3$ | H | H | acac |
| 6-226Y | Rh | 0 | 6 | Ph | H | H | COCH$_3$ | H | CH$_3$ | H | H | — — |
| 6-227 | Rh | 1 | 6 | Ph | H | COCH$_3$ | H | H | CH$_3$ | H | H | pic |
| 6-227X | Rh | 1 | 6 | Ph | H | COCH$_3$ | H | H | CH$_3$ | H | H | acac |
| 6-227Y | Rh | 0 | 6 | Ph | H | COCH$_3$ | H | H | CH$_3$ | H | H | — — |
| 6-228 | Rh | 1 | 6 | Ph | H | H | | BL | CH$_3$ | H | H | pic |
| 6-228X | Rh | 1 | 6 | Ph | H | H | | BL | CH$_3$ | H | H | acac |
| 6-228Y | Rh | 0 | 6 | Ph | H | H | | BL | CH$_3$ | H | H | — — |
| 6-229 | Rh | 1 | 6 | Ph | H | H | | BL | $^tC_4H_9$ | H | H | pic |
| 6-229X | Rh | 1 | 6 | Ph | H | H | | BL | $^tC_4H_9$ | H | H | acac |
| 6-229Y | Rh | 0 | 6 | Ph | H | H | | BL | $^tC_4H_9$ | H | H | — — |
| 6-230 | Rh | 1 | 6 | Ph | H | | BL | | H | CH$_3$ | H | H | pic |
| 6-230X | Rh | 1 | 6 | Ph | H | | BL | | H | CH$_3$ | H | H | acac |
| 6-230Y | Rh | 0 | 6 | Ph | H | | BL | | H | CH$_3$ | H | H | — — |
| 6-231 | Rh | 1 | 6 | Ph | H | | BL | | H | $^tC_4H_9$ | H | H | pic |
| 6-231X | Rh | 1 | 6 | Ph | H | | BL | | H | $^tC_4H_9$ | H | H | acac |
| 6-231Y | Rh | 0 | 6 | Ph | H | | BL | | H | $^tC_4H_9$ | H | H | — — |
| 6-232 | Rh | 1 | 6 | Ph | H | H | | PL | CH$_3$ | H | H | pic |
| 6-232X | Rh | 1 | 6 | Ph | H | H | | PL | CH$_3$ | H | H | acac |
| 6-232Y | Rh | 0 | 6 | Ph | H | H | | PL | CH$_3$ | H | H | — — |
| 6-233 | Rh | 1 | 6 | Ph | H | H | | PL | $^tC_4H_9$ | H | H | pic |
| 6-233X | Rh | 1 | 6 | Ph | H | H | | PL | $^tC_4H_9$ | H | H | acac |
| 6-233Y | Rh | 0 | 6 | Ph | H | H | | PL | $^tC_4H_9$ | H | H | — — |
| 6-234 | Rh | 1 | 6 | Ph | H | | PL | | H | CH$_3$ | H | H | pic |
| 6-234X | Rh | 1 | 6 | Ph | H | | PL | | H | CH$_3$ | H | H | acac |
| 6-234Y | Rh | 0 | 6 | Ph | H | | PL | | H | CH$_3$ | H | H | — — |
| 6-235 | Rh | 1 | 6 | Ph | H | | PL | | H | $^tC_4H_9$ | H | H | pic |
| 6-235X | Rh | 1 | 6 | Ph | H | | PL | | H | $^tC_4H_9$ | H | H | acac |
| 6-235Y | Rh | 0 | 6 | Ph | H | | PL | | H | $^tC_4H_9$ | H | H | — — |
| 6-236 | Rh | 1 | 6 | Ph | H | H | | MEE1 | CH$_3$ | H | H | pic |
| 6-236X | Rh | 1 | 6 | Ph | H | H | | MEE1 | CH$_3$ | H | H | acac |
| 6-236Y | Rh | 0 | 6 | Ph | H | H | | MEE1 | CH$_3$ | H | H | — — |
| 6-237 | Rh | 1 | 6 | Ph | H | | MEE1 | | H | CH$_3$ | H | H | pic |
| 6-237X | Rh | 1 | 6 | Ph | H | | MEE1 | | H | CH$_3$ | H | H | acac |
| 6-237Y | Rh | 0 | 6 | Ph | H | | MEE1 | | H | CH$_3$ | H | H | — — |
| 6-238 | Rh | 1 | 6 | Ph | H | H | | MEE2 | CH$_3$ | H | H | pic |
| 6-238X | Rh | 1 | 6 | Ph | H | H | | MEE2 | CH$_3$ | H | H | acac |
| 6-238Y | Rh | 0 | 6 | Ph | H | H | | MEE2 | CH$_3$ | H | H | — — |
| 6-239 | Rh | 1 | 6 | Ph | H | | MEE2 | | H | CH$_3$ | H | H | pic |
| 6-239X | Rh | 1 | 6 | Ph | H | | MEE2 | | H | CH$_3$ | H | H | acac |
| 6-239Y | Rh | 0 | 6 | Ph | H | | MEE2 | | H | CH$_3$ | H | H | — — |
| 6-240 | Rh | 1 | 6 | Ph | H | H | | PA1 | CH$_3$ | H | H | pic |
| 6-240X | Rh | 1 | 6 | Ph | H | H | | PA1 | CH$_3$ | H | H | acac |
| 6-240Y | Rh | 0 | 6 | Ph | H | H | | PA1 | CH$_3$ | H | H | — — |
| 6-241 | Rh | 1 | 6 | Ph | H | | PA1 | | H | CH$_3$ | H | H | pic |
| 6-241X | Rh | 1 | 6 | Ph | H | | PA1 | | H | CH$_3$ | H | H | acac |
| 6-241Y | Rh | 0 | 6 | Ph | H | | PA1 | | H | CH$_3$ | H | H | — — |
| 6-242 | Rh | 1 | 6 | Ph | H | H | | PA2 | CH$_3$ | H | H | pic |
| 6-242X | Rh | 1 | 6 | Ph | H | H | | PA2 | CH$_3$ | H | H | acac |
| 6-242Y | Rh | 0 | 6 | Ph | H | H | | PA2 | CH$_3$ | H | H | — — |
| 6-243 | Rh | 1 | 6 | Ph | H | | PA2 | | H | CH$_3$ | H | H | pic |
| 6-243X | Rh | 1 | 6 | Ph | H | | PA2 | | H | CH$_3$ | H | H | acac |
| 6-243Y | Rh | 0 | 6 | Ph | H | | PA2 | | H | CH$_3$ | H | H | — — |
| 6-244 | Rh | 1 | 6 | Ph | H | H | | EA1 | CH$_3$ | H | H | pic |
| 6-244X | Rh | 1 | 6 | Ph | H | H | | EA1 | CH$_3$ | H | H | acac |
| 6-244Y | Rh | 0 | 6 | Ph | H | H | | EA1 | CH$_3$ | H | H | — — |
| 6-245 | Rh | 1 | 6 | Ph | H | | EA2 | | H | CH$_3$ | H | H | pic |
| 6-245X | Rh | 1 | 6 | Ph | H | | EA2 | | H | CH$_3$ | H | H | acac |
| 6-245Y | Rh | 0 | 6 | Ph | H | | EA2 | | H | CH$_3$ | H | H | — — |
| 6-246 | Rh | 1 | 6 | Ph | H | H | | ME | CH$_3$ | H | H | pic |
| 6-246X | Rh | 1 | 6 | Ph | H | H | | ME | CH$_3$ | H | H | acac |
| 6-246Y | Rh | 0 | 6 | Ph | H | H | | ME | CH$_3$ | H | H | — — |
| 6-247 | Rh | 1 | 6 | Ph | H | | ME | | H | CH$_3$ | H | H | pic |
| 6-247X | Rh | 1 | 6 | Ph | H | | ME | | H | CH$_3$ | H | H | acac |
| 6-247Y | Rh | 0 | 6 | Ph | H | | ME | | H | CH$_3$ | H | H | — — |
| 6-248 | Rh | 1 | 6 | Ph | H | H | | AT | CH$_3$ | H | H | pic |
| 6-248X | Rh | 1 | 6 | Ph | H | H | | AT | CH$_3$ | H | H | acac |
| 6-248Y | Rh | 0 | 6 | Ph | H | H | | AT | CH$_3$ | H | H | — — |
| 6-249 | Rh | 1 | 6 | Ph | H | | AT | | H | CH$_3$ | H | H | pic |
| 6-249X | Rh | 1 | 6 | Ph | H | | AT | | H | CH$_3$ | H | H | acac |
| 6-249Y | Rh | 0 | 6 | Ph | H | | AT | | H | CH$_3$ | H | H | — — |
| 6-250 | Rh | 1 | 6 | Ph | H | H | | MES1 | CH$_3$ | H | H | pic |
| 6-250X | Rh | 1 | 6 | Ph | H | H | | MES1 | CH$_3$ | H | H | acac |
| 6-250Y | Rh | 0 | 6 | Ph | H | H | | MES1 | CH$_3$ | H | H | — — |

TABLE 20-continued

| No. | M | n | BSS | SS G | T$^1$ | T$^2$ | T$^3$ | T$^4$ | T$^5$ | T$^6$ | T$^7$ | L$^1$ L$^2$ |
|---|---|---|---|---|---|---|---|---|---|---|---|---|
| 6-251 | Rh | 1 | 6 | Ph | H | | MES1 | | H | CH$_3$ | H | H pic |
| 6-251X | Rh | 1 | 6 | Ph | H | | MES1 | | H | CH$_3$ | H | H acac |
| 6-251Y | Rh | 0 | 6 | Ph | H | | MES1 | | H | CH$_3$ | H | H — |
| 6-252 | Rh | 1 | 6 | Ph | H | H | | MES2 | | CH$_3$ | H | H pic |
| 6-252X | Rh | 1 | 6 | Ph | H | H | | MES2 | | CH$_3$ | H | H acac |
| 6-252Y | Rh | 0 | 6 | Ph | H | H | | MES2 | | CH$_3$ | H | H — |
| 6-253 | Rh | 1 | 6 | Ph | H | | MES2 | | H | CH$_3$ | H | H pic |
| 6-253X | Rh | 1 | 6 | Ph | H | | MES2 | | H | CH$_3$ | H | H acac |
| 6-253Y | Rh | 0 | 6 | Ph | H | | MES2 | | H | CH$_3$ | H | H — |
| 6-254 | Rh | 1 | 6 | Ph | H | H | | PS1 | | CH$_3$ | H | H pic |
| 6-254X | Rh | 1 | 6 | Ph | H | H | | PS1 | | CH$_3$ | H | H acac |
| 6-254Y | Rh | 0 | 6 | Ph | H | H | | PS1 | | CH$_3$ | H | H — |
| 6-255 | Rh | 1 | 6 | Ph | H | | PS1 | | H | CH$_3$ | H | H pic |
| 6-255X | Rh | 1 | 6 | Ph | H | | PS1 | | H | CH$_3$ | H | H acac |
| 6-255Y | Rh | 0 | 6 | Ph | H | | PS1 | | H | CH$_3$ | H | H — |
| 6-256 | Rh | 1 | 6 | Ph | H | H | | PS2 | | CH$_3$ | H | H pic |
| 6-256X | Rh | 1 | 6 | Ph | H | H | | PS2 | | CH$_3$ | H | H acac |
| 6-256Y | Rh | 0 | 6 | Ph | H | H | | PS2 | | CH$_3$ | H | H — |
| 6-257 | Rh | 1 | 6 | Ph | H | | PS2 | | H | CH$_3$ | H | H pic |
| 6-257X | Rh | 1 | 6 | Ph | H | | PS2 | | H | CH$_3$ | H | H acac |
| 6-257Y | Rh | 0 | 6 | Ph | H | | PS2 | | H | CH$_3$ | H | H — |
| 6-258 | Rh | 1 | 6 | Ph | H | H | | BAL1 | | CH$_3$ | H | H pic |
| 6-258X | Rh | 1 | 6 | Ph | H | H | | BAL1 | | CH$_3$ | H | H acac |
| 6-258Y | Rh | 0 | 6 | Ph | H | H | | BAL1 | | CH$_3$ | H | H — |
| 6-259 | Rh | 1 | 6 | Ph | H | | BAL1 | | H | CH$_3$ | H | H pic |
| 6-259X | Rh | 1 | 6 | Ph | H | | BAL1 | | H | CH$_3$ | H | H acac |
| 6-259Y | Rh | 0 | 6 | Ph | H | | BAL1 | | H | CH$_3$ | H | H — |
| 6-260 | Rh | 1 | 6 | Ph | H | H | | BAL2 | | CH$_3$ | H | H pic |
| 6-260X | Rh | 1 | 6 | Ph | H | H | | BAL2 | | CH$_3$ | H | H acac |
| 6-260Y | Rh | 0 | 6 | Ph | H | H | | BAL2 | | CH$_3$ | H | H — |
| 6-261 | Rh | 1 | 6 | Ph | H | | BAL2 | | H | CH$_3$ | H | H pic |
| 6-261X | Rh | 1 | 6 | Ph | H | | BAL2 | | H | CH$_3$ | H | H acac |
| 6-261Y | Rh | 0 | 6 | Ph | H | | BAL2 | | H | CH$_3$ | H | H — |
| 6-262 | Rh | 1 | 6 | Ph | H | H | | MEK1 | | CH$_3$ | H | H pic |
| 6-262X | Rh | 1 | 6 | Ph | H | H | | MEK1 | | CH$_3$ | H | H acac |
| 6-262Y | Rh | 0 | 6 | Ph | H | H | | MEK1 | | CH$_3$ | H | H — |
| 6-263 | Rh | 1 | 6 | Ph | H | | MEK1 | | H | CH$_3$ | H | H pic |
| 6-263X | Rh | 1 | 6 | Ph | H | | MEK1 | | H | CH$_3$ | H | H acac |
| 6-263Y | Rh | 0 | 6 | Ph | H | | MEK1 | | H | CH$_3$ | H | H — |
| 6-264 | Rh | 1 | 6 | Ph | H | H | | MEK2 | | CH$_3$ | H | H pic |
| 6-264X | Rh | 1 | 6 | Ph | H | H | | MEK2 | | CH$_3$ | H | H acac |
| 6-264Y | Rh | 0 | 6 | Ph | H | H | | MEK2 | | CH$_3$ | H | H — |
| 6-265 | Rh | 1 | 6 | Ph | H | | MEK2 | | H | CH$_3$ | H | H pic |
| 6-265X | Rh | 1 | 6 | Ph | H | | MEK2 | | H | CH$_3$ | H | H acac |
| 6-265Y | Rh | 0 | 6 | Ph | H | | MEK2 | | H | CH$_3$ | H | H — |
| 6-266 | Rh | 1 | 6 | Ph | H | H | | PAL1 | | CH$_3$ | H | H pic |
| 6-266X | Rh | 1 | 6 | Ph | H | H | | PAL1 | | CH$_3$ | H | H acac |
| 6-266Y | Rh | 0 | 6 | Ph | H | H | | PAL1 | | CH$_3$ | H | H — |
| 6-267 | Rh | 1 | 6 | Ph | H | | PAL1 | | H | CH$_3$ | H | H pic |
| 6-267X | Rh | 1 | 6 | Ph | H | | PAL1 | | H | CH$_3$ | H | H acac |
| 6-267Y | Rh | 0 | 6 | Ph | H | | PAL1 | | H | CH$_3$ | H | H — |
| 6-268 | Rh | 1 | 6 | Ph | H | H | | PAL2 | | CH$_3$ | H | H pic |
| 6-268X | Rh | 1 | 6 | Ph | H | H | | PAL2 | | CH$_3$ | H | H acac |
| 6-268Y | Rh | 0 | 6 | Ph | H | H | | PAL2 | | CH$_3$ | H | H — |
| 6-269 | Rh | 1 | 6 | Ph | H | | PAL2 | | H | CH$_3$ | H | H pic |
| 6-269X | Rh | 1 | 6 | Ph | H | | PAL2 | | H | CH$_3$ | H | H acac |
| 6-269Y | Rh | 0 | 6 | Ph | H | | PAL2 | | H | CH$_3$ | H | H — |
| 6-270 | Rh | 1 | 6 | Ph | H | H | | MMK | | CH$_3$ | H | H pic |
| 6-270X | Rh | 1 | 6 | Ph | H | H | | MMK | | CH$_3$ | H | H acac |
| 6-270Y | Rh | 0 | 6 | Ph | H | H | | MMK | | CH$_3$ | H | H — |
| 6-271 | Rh | 1 | 6 | Ph | H | | MMK | | H | CH$_3$ | H | H pic |
| 6-271X | Rh | 1 | 6 | Ph | H | | MMK | | H | CH$_3$ | H | H acac |
| 6-271Y | Rh | 0 | 6 | Ph | H | | MMK | | H | CH$_3$ | H | H — |
| 6-272 | Rh | 1 | 6 | Ph | H | H | | EES1 | | CH$_3$ | H | H pic |
| 6-272X | Rh | 1 | 6 | Ph | H | H | | EES1 | | CH$_3$ | H | H acac |
| 6-272Y | Rh | 0 | 6 | Ph | H | H | | EES1 | | CH$_3$ | H | H — |
| 6-273 | Rh | 1 | 6 | Ph | H | | EES2 | | H | CH$_3$ | H | H pic |
| 6-273X | Rh | 1 | 6 | Ph | H | | EES2 | | H | CH$_3$ | H | H acac |
| 6-273Y | Rh | 0 | 6 | Ph | H | | EES2 | | H | CH$_3$ | H | H — |
| 6-274 | Rh | 1 | 6 | Ph | H | H | | PAE1 | | CH$_3$ | H | H pic |
| 6-274X | Rh | 1 | 6 | Ph | H | H | | PAE1 | | CH$_3$ | H | H acac |
| 6-274Y | Rh | 0 | 6 | Ph | H | H | | PAE1 | | CH$_3$ | H | H — |
| 6-275 | Rh | 1 | 6 | Ph | H | | PAE2 | | H | CH$_3$ | H | H pic |
| 6-275X | Rh | 1 | 6 | Ph | H | | PAE2 | | H | CH$_3$ | H | H acac |
| 6-275Y | Rh | 0 | 6 | Ph | H | | PAE2 | | H | CH$_3$ | H | H — |
| 6-276 | Rh | 1 | 6 | Ph | H | H | | AME1 | | CH$_3$ | H | H pic |
| 6-276X | Rh | 1 | 6 | Ph | H | H | | AME1 | | CH$_3$ | H | H acac |

TABLE 20-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 6-276Y | Rh | 0 | 6 | Ph | H | H | | AME1 | CH₃ | H | H | — | — |
| 6-277 | Rh | 1 | 6 | Ph | H | | AME1 | H | CH₃ | H | H | pic | |
| 6-277X | Rh | 1 | 6 | Ph | H | | AME1 | H | CH₃ | H | H | acac | |
| 6-277Y | Rh | 0 | 6 | Ph | H | | AME1 | H | CH₃ | H | H | — | — |
| 6-278 | Rh | 1 | 6 | Ph | H | H | | AME2 | CH₃ | H | H | pic | |
| 6-278X | Rh | 1 | 6 | Ph | H | H | | AME2 | CH₃ | H | H | acac | |
| 6-278Y | Rh | 0 | 6 | Ph | H | H | | AME2 | CH₃ | H | H | — | — |
| 6-279 | Rh | 1 | 6 | Ph | H | | AME2 | H | CH₃ | H | H | pic | |
| 6-279X | Rh | 1 | 6 | Ph | H | | AME2 | H | CH₃ | H | H | acac | |
| 6-279Y | Rh | 0 | 6 | Ph | H | | AME2 | H | CH₃ | H | H | — | — |
| 6-280 | Rh | 1 | 6 | Ph | H | H | | EAE1 | CH₃ | H | H | pic | |
| 6-280X | Rh | 1 | 6 | Ph | H | H | | EAE1 | CH₃ | H | H | acac | |
| 6-280Y | Rh | 0 | 6 | Ph | H | H | | EAE1 | CH₃ | H | H | — | — |
| 6-281 | Rh | 1 | 6 | Ph | H | | EAE1 | H | CH₃ | H | H | pic | |
| 6-281X | Rh | 1 | 6 | Ph | H | | EAE1 | H | CH₃ | H | H | acac | |
| 6-281Y | Rh | 0 | 6 | Ph | H | | EAE1 | H | CH₃ | H | H | — | — |
| 6-282 | Rh | 1 | 6 | Ph | H | H | | EAE2 | CH₃ | H | H | pic | |
| 6-282X | Rh | 1 | 6 | Ph | H | H | | EAE2 | CH₃ | H | H | acac | |
| 6-282Y | Rh | 0 | 6 | Ph | H | H | | EAE2 | CH₃ | H | H | — | — |
| 6-283 | Rh | 1 | 6 | Ph | H | | EAE2 | H | CH₃ | H | H | pic | |
| 6-283X | Rh | 1 | 6 | Ph | H | | EAE2 | H | CH₃ | H | H | acac | |
| 6-283Y | Rh | 0 | 6 | Ph | H | | EAE2 | H | CH₃ | H | H | — | — |
| 6-284 | Rh | 1 | 6 | Ph | H | H | | AAE1 | CH₃ | H | H | pic | |
| 6-284X | Rh | 1 | 6 | Ph | H | H | | AAE1 | CH₃ | H | H | acac | |
| 6-284Y | Rh | 0 | 6 | Ph | H | H | | AAE1 | CH₃ | H | H | — | — |
| 6-285 | Rh | 1 | 6 | Ph | H | | AAE1 | H | CH₃ | H | H | pic | |
| 6-285X | Rh | 1 | 6 | Ph | H | | AAE1 | H | CH₃ | H | H | acac | |
| 6-285Y | Rh | 0 | 6 | Ph | H | | AAE1 | H | CH₃ | H | H | — | — |
| 6-286 | Rh | 1 | 6 | Ph | H | H | | AAE2 | CH₃ | H | H | pic | |
| 6-286X | Rh | 1 | 6 | Ph | H | H | | AAE2 | CH₃ | H | H | acac | |
| 6-286Y | Rh | 0 | 6 | Ph | H | H | | AAE2 | CH₃ | H | H | — | — |
| 6-287 | Rh | 1 | 6 | Ph | H | | AAE2 | H | CH₃ | H | H | pic | |
| 6-287X | Rh | 1 | 6 | Ph | H | | AAE2 | H | CH₃ | H | H | acac | |
| 6-287Y | Rh | 0 | 6 | Ph | H | | AAE2 | H | CH₃ | H | H | — | — |
| 6-288 | Rh | 1 | 6 | Ph | H | H | | PME1 | CH₃ | H | H | pic | |
| 6-288X | Rh | 1 | 6 | Ph | H | H | | PME1 | CH₃ | H | H | acac | |
| 6-288Y | Rh | 0 | 6 | Ph | H | H | | PME1 | CH₃ | H | H | — | — |
| 6-289 | Rh | 1 | 6 | Ph | H | | PME1 | H | CH₃ | H | H | pic | |
| 6-289X | Rh | 1 | 6 | Ph | H | | PME1 | H | CH₃ | H | H | acac | |
| 6-289Y | Rh | 0 | 6 | Ph | H | | PME1 | H | CH₃ | H | H | — | — |
| 6-290 | Rh | 1 | 6 | Ph | H | H | | PME2 | CH₃ | H | H | pic | |
| 6-290X | Rh | 1 | 6 | Ph | H | H | | PME2 | CH₃ | H | H | acac | |
| 6-290Y | Rh | 0 | 6 | Ph | H | H | | PME2 | CH₃ | H | H | — | — |
| 6-291 | Rh | 1 | 6 | Ph | H | | PME2 | H | CH₃ | H | H | pic | |
| 6-291X | Rh | 1 | 6 | Ph | H | | PME2 | H | CH₃ | H | H | acac | |
| 6-291Y | Rh | 0 | 6 | Ph | H | | PME2 | H | CH₃ | H | H | — | — |
| 6-292 | Rh | 1 | 6 | Ph | H | H | | MET1 | CH₃ | H | H | pic | |
| 6-292X | Rh | 1 | 6 | Ph | H | H | | MET1 | CH₃ | H | H | acac | |
| 6-292Y | Rh | 0 | 6 | Ph | H | H | | MET1 | CH₃ | H | H | — | — |
| 6-293 | Rh | 1 | 6 | Ph | H | | MET1 | H | CH₃ | H | H | pic | |
| 6-293X | Rh | 1 | 6 | Ph | H | | MET1 | H | CH₃ | H | H | acac | |
| 6-293Y | Rh | 0 | 6 | Ph | H | | MET1 | H | CH₃ | H | H | — | — |
| 6-294 | Rh | 1 | 6 | Ph | H | H | | MET2 | CH₃ | H | H | pic | |
| 6-294X | Rh | 1 | 6 | Ph | H | H | | MET2 | CH₃ | H | H | acac | |
| 6-294Y | Rh | 0 | 6 | Ph | H | H | | MET2 | CH₃ | H | H | — | — |
| 6-295 | Rh | 1 | 6 | Ph | H | | MET2 | H | CH₃ | H | H | pic | |
| 6-295X | Rh | 1 | 6 | Ph | H | | MET2 | H | CH₃ | H | H | acac | |
| 6-295Y | Rh | 0 | 6 | Ph | H | | MET2 | H | CH₃ | H | H | — | — |
| 6-296 | Rh | 1 | 6 | Ph | H | H | | EE1 | CH₃ | H | H | pic | |
| 6-296X | Rh | 1 | 6 | Ph | H | H | | EE1 | CH₃ | H | H | acac | |
| 6-296Y | Rh | 0 | 6 | Ph | H | H | | EE1 | CH₃ | H | H | — | — |
| 6-297 | Rh | 1 | 6 | Ph | H | | EE1 | H | CH₃ | H | H | pic | |
| 6-297X | Rh | 1 | 6 | Ph | H | | EE1 | H | CH₃ | H | H | acac | |
| 6-297Y | Rh | 0 | 6 | Ph | H | | EE1 | H | CH₃ | H | H | — | — |
| 6-298 | Rh | 1 | 6 | Ph | H | H | | EE2 | CH₃ | H | H | pic | |
| 6-298X | Rh | 1 | 6 | Ph | H | H | | EE2 | CH₃ | H | H | acac | |
| 6-298Y | Rh | 0 | 6 | Ph | H | H | | EE2 | CH₃ | H | H | — | — |
| 6-299 | Rh | 1 | 6 | Ph | H | | EE2 | H | CH₃ | H | H | pic | |
| 6-299X | Rh | 1 | 6 | Ph | H | | EE2 | H | CH₃ | H | H | acac | |
| 6-299Y | Rh | 0 | 6 | Ph | H | | EE2 | H | CH₃ | H | H | — | — |
| 6-300 | Rh | 1 | 6 | Ph | H | H | | MS1 | CH₃ | H | H | pic | |
| 6-300X | Rh | 1 | 6 | Ph | H | H | | MS1 | CH₃ | H | H | acac | |
| 6-300Y | Rh | 0 | 6 | Ph | H | H | | MS1 | CH₃ | H | H | — | — |
| 6-301 | Rh | 1 | 6 | Ph | H | | MS1 | H | CH₃ | H | H | pic | |
| 6-301X | Rh | 1 | 6 | Ph | H | | MS1 | H | CH₃ | H | H | acac | |
| 6-301Y | Rh | 0 | 6 | Ph | H | | MS1 | H | CH₃ | H | H | — | — |
| 6-302 | Rh | 1 | 6 | Ph | H | H | | MS2 | CH₃ | H | H | pic | |

TABLE 20-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 6-302X | Rh | 1 | 6 | Ph | H | H |  | MS2 | $CH_3$ | H | H | acac |  |
| 6-302Y | Rh | 0 | 6 | Ph | H | H |  | MS2 | $CH_3$ | H | H | — | — |
| 6-303 | Rh | 1 | 6 | Ph | H |  | MS2 | H | $CH_3$ | H | H | pic |  |
| 6-303X | Rh | 1 | 6 | Ph | H |  | MS2 | H | $CH_3$ | H | H | acac |  |
| 6-303Y | Rh | 0 | 6 | Ph | H |  | MS2 | H | $CH_3$ | H | H | — | — |

TABLE 21

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 7-167 | Ir | 1 | 7 | Ph | H | H | H | H | $CH_3$ | H | H | pic |  |
| 7-167X | Ir | 1 | 7 | Ph | H | H | H | H | $CH_3$ | H | H | acac |  |
| 7-167Y | Ir | 0 | 7 | Ph | H | H | H | H | $CH_3$ | H | H | — | — |
| 7-168 | Ir | 1 | 7 | Ph | H | H | H | H | $^tC_4H_9$ | H | H | pic |  |
| 7-168X | Ir | 1 | 7 | Ph | H | H | H | H | $^tC_4H_9$ | H | H | acac |  |
| 7-168Y | Ir | 0 | 7 | Ph | H | H | H | H | $^tC_4H_9$ | H | H | — | — |
| 7-169 | Ir | 1 | 7 | Ph | H | F | H | F | $CH_3$ | H | H | pic |  |
| 7-169X | Ir | 1 | 7 | Ph | H | F | H | F | $CH_3$ | H | H | acac |  |
| 7-169Y | Ir | 0 | 7 | Ph | H | F | H | F | $CH_3$ | H | H | — | — |
| 7-170 | Ir | 1 | 7 | Ph | H | F | H | F | $^tC_4H_9$ | H | H | pic |  |
| 7-170X | Ir | 1 | 7 | Ph | H | F | H | F | $^tC_4H_9$ | H | H | acac |  |
| 7-170Y | Ir | 0 | 7 | Ph | H | F | H | F | $^tC_4H_9$ | H | H | — | — |
| 7-171 | Ir | 1 | 7 | Ph | F | H | H | F | $CH_3$ | H | H | pic |  |
| 7-171X | Ir | 1 | 7 | Ph | F | H | H | F | $CH_3$ | H | H | acac |  |
| 7-171Y | Ir | 0 | 7 | Ph | F | H | H | F | $CH_3$ | H | H | — | — |
| 7-172 | Ir | 1 | 7 | Ph | F | H | H | F | $^tC_4H_9$ | H | H | pic |  |
| 7-172X | Ir | 1 | 7 | Ph | F | H | H | F | $^tC_4H_9$ | H | H | acac |  |
| 7-172Y | Ir | 0 | 7 | Ph | F | H | H | F | $^tC_4H_9$ | H | H | — | — |
| 7-173 | Ir | 1 | 7 | Ph | $CF_3$ | H | $CF_3$ | H | $CH_3$ | H | H | pic |  |
| 7-173X | Ir | 1 | 7 | Ph | $CF_3$ | H | $CF_3$ | H | $CH_3$ | H | H | acac |  |
| 7-173Y | Ir | 0 | 7 | Ph | $CF_3$ | H | $CF_3$ | H | $CH_3$ | H | H | — | — |
| 7-174 | Ir | 1 | 7 | Ph | $CF_3$ | H | $CF_3$ | H | $^tC_4H_9$ | H | H | pic |  |
| 7-174X | Ir | 1 | 7 | Ph | $CF_3$ | H | $CF_3$ | H | $^tC_4H_9$ | H | H | acac |  |
| 7-174Y | Ir | 0 | 7 | Ph | $CF_3$ | H | $CF_3$ | H | $^tC_4H_9$ | H | H | — | — |
| 7-175 | Ir | 1 | 7 | Ph | H | F | $CF_3$ | H | $CH_3$ | H | H | pic |  |
| 7-175X | Ir | 1 | 7 | Ph | H | F | $CF_3$ | H | $CH_3$ | H | H | acac |  |
| 7-175Y | Ir | 0 | 7 | Ph | H | F | $CF_3$ | H | $CH_3$ | H | H | — | — |
| 7-176 | Ir | 1 | 7 | Ph | F | H | $CF_3$ | H | $CH_3$ | H | H | pic |  |
| 7-176X | Ir | 1 | 7 | Ph | F | H | $CF_3$ | H | $CH_3$ | H | H | acac |  |
| 7-176Y | Ir | 0 | 7 | Ph | F | H | $CF_3$ | H | $CH_3$ | H | H | — | — |
| 7-177 | Ir | 1 | 7 | Ph | F | F | F | F | $CH_3$ | H | H | pic |  |
| 7-177X | Ir | 1 | 7 | Ph | F | F | F | F | $CH_3$ | H | H | acac |  |
| 7-177Y | Ir | 0 | 7 | Ph | F | F | F | F | $CH_3$ | H | H | — | — |
| 7-178 | Ir | 1 | 7 | Ph | H | F | H | $CH_3$ | $CH_3$ | H | H | pic |  |
| 7-178X | Ir | 1 | 7 | Ph | H | F | H | $CH_3$ | $CH_3$ | H | H | acac |  |
| 7-178Y | Ir | 0 | 7 | Ph | H | F | H | $CH_3$ | $CH_3$ | H | H | — | — |
| 7-179 | Ir | 1 | 7 | Ph | H | F | H | $CH_3$ | $^tC_4H_9$ | H | H | pic |  |
| 7-179X | Ir | 1 | 7 | Ph | H | F | H | $CH_3$ | $^tC_4H_9$ | H | H | acac |  |
| 7-179Y | Ir | 0 | 7 | Ph | H | F | H | $CH_3$ | $^tC_4H_9$ | H | H | — | — |
| 7-180 | Ir | 1 | 7 | Ph | H | F | H | $^tC_4H_9$ | $CH_3$ | H | H | pic |  |
| 7-180X | Ir | 1 | 7 | Ph | H | F | H | $^tC_4H_9$ | $CH_3$ | H | H | acac |  |
| 7-180Y | Ir | 0 | 7 | Ph | H | F | H | $^tC_4H_9$ | $CH_3$ | H | H | — | — |
| 7-181 | Ir | 1 | 7 | Ph | H | F | H | $^tC_4H_9$ | $^tC_4H_9$ | H | H | pic |  |
| 7-181X | Ir | 1 | 7 | Ph | H | F | H | $^tC_4H_9$ | $^tC_4H_9$ | H | H | acac |  |
| 7-181Y | Ir | 0 | 7 | Ph | H | F | H | $^tC_4H_9$ | $^tC_4H_9$ | H | H | — | — |
| 7-182 | Ir | 1 | 7 | Ph | H | $CF_3$ | H | $CF_3$ | $CH_3$ | H | H | pic |  |
| 7-182X | Ir | 1 | 7 | Ph | H | $CF_3$ | H | $CF_3$ | $CH_3$ | H | H | acac |  |
| 7-182Y | Ir | 0 | 7 | Ph | H | $CF_3$ | H | $CF_3$ | $CH_3$ | H | H | — | — |
| 7-183 | Ir | 1 | 7 | Ph | H | $CF_3$ | H | $CF_3$ | $^tC_4H_9$ | H | H | pic |  |
| 7-183X | Ir | 1 | 7 | Ph | H | $CF_3$ | H | $CF_3$ | $^tC_4H_9$ | H | H | acac |  |
| 7-183Y | Ir | 0 | 7 | Ph | H | $CF_3$ | H | $CF_3$ | $^tC_4H_9$ | H | H | — | — |
| 7-184 | Ir | 1 | 7 | Ph | $CF_3$ | H | H | $^tC_4H_9$ | $CH_3$ | H | H | pic |  |
| 7-184X | Ir | 1 | 7 | Ph | $CF_3$ | H | H | $^tC_4H_9$ | $CH_3$ | H | H | acac |  |
| 7-184Y | Ir | 0 | 7 | Ph | $CF_3$ | H | H | $^tC_4H_9$ | $CH_3$ | H | H | — | — |
| 7-185 | Ir | 1 | 7 | Ph | $CF_3$ | H | H | $^tC_4H_9$ | $^tC_4H_9$ | H | H | pic |  |
| 7-185X | Ir | 1 | 7 | Ph | $CF_3$ | H | H | $^tC_4H_9$ | $^tC_4H_9$ | H | H | acac |  |
| 7-185Y | Ir | 0 | 7 | Ph | $CF_3$ | H | H | $^tC_4H_9$ | $^tC_4H_9$ | H | H | — | — |
| 7-186 | Ir | 1 | 7 | Ph | H | $CF_3$ | H | $^tC_4H_9$ | $CH_3$ | H | H | pic |  |
| 7-186X | Ir | 1 | 7 | Ph | H | $CF_3$ | H | $^tC_4H_9$ | $CH_3$ | H | H | acac |  |
| 7-186Y | Ir | 0 | 7 | Ph | H | $CF_3$ | H | $^tC_4H_9$ | $CH_3$ | H | H | — | — |
| 7-187 | Ir | 1 | 7 | Ph | H | $CF_3$ | H | $^tC_4H_9$ | $^tC_4H_9$ | H | H | pic |  |
| 7-187X | Ir | 1 | 7 | Ph | H | $CF_3$ | H | $^tC_4H_9$ | $^tC_4H_9$ | H | H | acac |  |
| 7-187Y | Ir | 0 | 7 | Ph | H | $CF_3$ | H | $^tC_4H_9$ | $^tC_4H_9$ | H | H | — | — |
| 7-188 | Ir | 1 | 7 | Ph | H | $CF_3$ | H | $CH_3$ | $CH_3$ | H | H | pic |  |

TABLE 21-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 7-188X | Ir | 1 | 7 | Ph | H | CF$_3$ | H | CH$_3$ | CH$_3$ | H | H | acac |
| 7-188Y | Ir | 0 | 7 | Ph | H | CF$_3$ | H | CH$_3$ | CH$_3$ | H | H | — — |
| 7-189 | Ir | 1 | 7 | Ph | H | CF$_3$ | CF$_3$ | H | CH$_3$ | H | H | pic |
| 7-189X | Ir | 1 | 7 | Ph | H | CF$_3$ | CF$_3$ | H | CH$_3$ | H | H | acac |
| 7-189Y | Ir | 0 | 7 | Ph | H | CF$_3$ | CF$_3$ | H | CH$_3$ | H | H | — — |
| 7-190 | Ir | 1 | 7 | Ph | H | H | NO$_2$ | H | CH$_3$ | H | H | pic |
| 7-190X | Ir | 1 | 7 | Ph | H | H | NO$_2$ | H | CH$_3$ | H | H | acac |
| 7-190Y | Ir | 0 | 7 | Ph | H | H | NO$_2$ | H | CH$_3$ | H | H | — — |
| 7-191 | Ir | 1 | 7 | Ph | H | H | NO$_2$ | H | $^tC_4H_9$ | H | H | pic |
| 7-191X | Ir | 1 | 7 | Ph | H | H | NO$_2$ | H | $^tC_4H_9$ | H | H | acac |
| 7-191Y | Ir | 0 | 7 | Ph | H | H | NO$_2$ | H | $^tC_4H_9$ | H | H | — — |
| 7-192 | Ir | 1 | 7 | Ph | F | H | NO$_2$ | H | CH$_3$ | H | H | pic |
| 7-192X | Ir | 1 | 7 | Ph | F | H | NO$_2$ | H | CH$_3$ | H | H | acac |
| 7-192Y | Ir | 0 | 7 | Ph | F | H | NO$_2$ | H | CH$_3$ | H | H | — — |
| 7-193 | Ir | 1 | 7 | Ph | F | H | NO$_2$ | F | CH$_3$ | H | H | pic |
| 7-193X | Ir | 1 | 7 | Ph | F | H | NO$_2$ | F | CH$_3$ | H | H | acac |
| 7-193Y | Ir | 0 | 7 | Ph | F | H | NO$_2$ | F | CH$_3$ | H | H | — — |
| 7-194 | Ir | 1 | 7 | Ph | H | NO$_2$ | H | NO$_2$ | CH$_3$ | H | H | pic |
| 7-194X | Ir | 1 | 7 | Ph | H | NO$_2$ | H | NO$_2$ | CH$_3$ | H | H | acac |
| 7-194Y | Ir | 0 | 7 | Ph | H | NO$_2$ | H | NO$_2$ | CH$_3$ | H | H | — — |
| 7-195 | Ir | 1 | 7 | Ph | H | NO$_2$ | H | NO$_2$ | $^tC_4H_9$ | H | H | pic |
| 7-195X | Ir | 1 | 7 | Ph | H | NO$_2$ | H | NO$_2$ | $^tC_4H_9$ | H | H | acac |
| 7-195Y | Ir | 0 | 7 | Ph | H | NO$_2$ | H | NO$_2$ | $^tC_4H_9$ | H | H | — — |
| 7-196 | Ir | 1 | 7 | Ph | NO$_2$ | H | H | NO$_2$ | CH$_3$ | H | H | pic |
| 7-196X | Ir | 1 | 7 | Ph | NO$_2$ | H | H | NO$_2$ | CH$_3$ | H | H | acac |
| 7-196Y | Ir | 0 | 7 | Ph | NO$_2$ | H | H | NO$_2$ | CH$_3$ | H | H | — — |
| 7-197 | Ir | 1 | 7 | Ph | NO$_2$ | H | H | NO$_2$ | $^tC_4H_9$ | H | H | pic |
| 7-197X | Ir | 1 | 7 | Ph | NO$_2$ | H | H | NO$_2$ | $^tC_4H_9$ | H | H | acac |
| 7-197Y | Ir | 0 | 7 | Ph | NO$_2$ | H | H | NO$_2$ | $^tC_4H_9$ | H | H | — — |
| 7-198 | Ir | 1 | 7 | Ph | H | H | CF$_3$ | H | CH$_3$ | H | H | pic |
| 7-198X | Ir | 1 | 7 | Ph | H | H | CF$_3$ | H | CH$_3$ | H | H | acac |
| 7-198Y | Ir | 0 | 7 | Ph | H | H | CF$_3$ | H | CH$_3$ | H | H | — — |
| 7-199 | Ir | 1 | 7 | Ph | H | H | CF$_3$ | H | $^tC_4H_9$ | H | H | pic |
| 7-199X | Ir | 1 | 7 | Ph | H | H | CF$_3$ | H | $^tC_4H_9$ | H | H | acac |
| 7-199Y | Ir | 0 | 7 | Ph | H | H | CF$_3$ | H | $^tC_4H_9$ | H | H | — — |
| 7-200 | Ir | 1 | 7 | Ph | H | Cl | CF$_3$ | H | CH$_3$ | H | H | pic |
| 7-200X | Ir | 1 | 7 | Ph | H | Cl | CF$_3$ | H | CH$_3$ | H | H | acac |
| 7-200Y | Ir | 0 | 7 | Ph | H | Cl | CF$_3$ | H | CH$_3$ | H | H | — — |
| 7-201 | Ir | 1 | 7 | Ph | H | Cl | CF$_3$ | H | $^tC_4H_9$ | H | H | pic |
| 7-201X | Ir | 1 | 7 | Ph | H | Cl | CF$_3$ | H | $^tC_4H_9$ | H | H | acac |
| 7-201Y | Ir | 0 | 7 | Ph | H | Cl | CF$_3$ | H | $^tC_4H_9$ | H | H | — — |
| 7-202 | Ir | 1 | 7 | Ph | H | NO$_2$ | H | H | CH$_3$ | H | H | pic |
| 7-202X | Ir | 1 | 7 | Ph | H | NO$_2$ | H | H | CH$_3$ | H | H | acac |
| 7-202Y | Ir | 0 | 7 | Ph | H | NO$_2$ | H | H | CH$_3$ | H | H | — — |
| 7-203 | Ir | 1 | 7 | Ph | H | CF$_3$ | H | H | CH$_3$ | H | H | pic |
| 7-203X | Ir | 1 | 7 | Ph | H | CF$_3$ | H | H | CH$_3$ | H | H | acac |
| 7-203Y | Ir | 0 | 7 | Ph | H | CF$_3$ | H | H | CH$_3$ | H | H | — — |
| 7-204 | Ir | 1 | 7 | Ph | H | NO$_2$ | H | CH$_3$ | CH$_3$ | H | H | pic |
| 7-204X | Ir | 1 | 7 | Ph | H | NO$_2$ | H | CH$_3$ | CH$_3$ | H | H | acac |
| 7-204Y | Ir | 0 | 7 | Ph | H | NO$_2$ | H | CH$_3$ | CH$_3$ | H | H | — — |
| 7-205 | Ir | 1 | 7 | Ph | H | NO$_2$ | H | CH$_3$ | $^tC_4H_9$ | H | H | pic |
| 7-205X | Ir | 1 | 7 | Ph | H | NO$_2$ | H | CH$_3$ | $^tC_4H_9$ | H | H | acac |
| 7-205Y | Ir | 0 | 7 | Ph | H | NO$_2$ | H | CH$_3$ | $^tC_4H_9$ | H | H | — — |
| 7-206 | Ir | 1 | 7 | Ph | H | NO$_2$ | H | $^tC_4H_9$ | CH$_3$ | H | H | pic |
| 7-206X | Ir | 1 | 7 | Ph | H | NO$_2$ | H | $^tC_4H_9$ | CH$_3$ | H | H | acac |
| 7-206Y | Ir | 0 | 7 | Ph | H | NO$_2$ | H | $^tC_4H_9$ | CH$_3$ | H | H | — — |
| 7-207 | Ir | 1 | 7 | Ph | H | NO$_2$ | H | $^tC_4H_9$ | $^tC_4H_9$ | H | H | pic |
| 7-207X | Ir | 1 | 7 | Ph | H | NO$_2$ | H | $^tC_4H_9$ | $^tC_4H_9$ | H | H | acac |
| 7-207Y | Ir | 0 | 7 | Ph | H | NO$_2$ | H | $^tC_4H_9$ | $^tC_4H_9$ | H | H | — — |
| 7-208 | Ir | 1 | 7 | Ph | H | H | CH$_3$O | H | CH$_3$ | H | H | pic |
| 7-208X | Ir | 1 | 7 | Ph | H | H | CH$_3$O | H | CH$_3$ | H | H | acac |
| 7-208Y | Ir | 0 | 7 | Ph | H | H | CH$_3$O | H | CH$_3$ | H | H | — — |
| 7-209 | Ir | 1 | 7 | Ph | H | CH$_3$O | H | H | CH$_3$ | H | H | pic |
| 7-209X | Ir | 1 | 7 | Ph | H | CH$_3$O | H | H | CH$_3$ | H | H | acac |
| 7-209Y | Ir | 0 | 7 | Ph | H | CH$_3$O | H | H | CH$_3$ | H | H | — — |
| 7-210 | Ir | 1 | 7 | Ph | H | CH$_3$O | H | CH$_3$ | CH$_3$ | H | H | pic |
| 7-210X | Ir | 1 | 7 | Ph | H | CH$_3$O | H | CH$_3$ | CH$_3$ | H | H | acac |
| 7-210Y | Ir | 0 | 7 | Ph | H | CH$_3$O | H | CH$_3$ | CH$_3$ | H | H | — — |
| 7-211 | Ir | 1 | 7 | Ph | H | CH$_3$O | H | $^tC_4H_9$ | CH$_3$ | H | H | pic |
| 7-211X | Ir | 1 | 7 | Ph | H | CH$_3$O | H | $^tC_4H_9$ | CH$_3$ | H | H | acac |
| 7-211Y | Ir | 0 | 7 | Ph | H | CH$_3$O | H | $^tC_4H_9$ | CH$_3$ | H | H | — — |
| 7-212 | Ir | 1 | 7 | Ph | H | Si(CH$_3$)$_3$ | H | H | CH$_3$ | H | H | pic |
| 7-212X | Ir | 1 | 7 | Ph | H | Si(CH$_3$)$_3$ | H | H | CH$_3$ | H | H | acac |
| 7-212Y | Ir | 0 | 7 | Ph | H | Si(CH$_3$)$_3$ | H | H | CH$_3$ | H | H | — — |
| 7-213 | Ir | 1 | 7 | Ph | H | Si(CH$_3$)$_3$ | H | H | $^tC_4H_9$ | H | H | pic |
| 7-213X | Ir | 1 | 7 | Ph | H | Si(CH$_3$)$_3$ | H | H | $^tC_4H_9$ | H | H | acac |
| 7-213Y | Ir | 0 | 7 | Ph | H | Si(CH$_3$)$_3$ | H | H | $^tC_4H_9$ | H | H | — — |

TABLE 21-continued

| No. | M | n | BSS | SS G | T¹ | T² | T³ | T⁴ | T⁵ | T⁶ | T⁷ | L¹ L² |
|---|---|---|---|---|---|---|---|---|---|---|---|---|
| 7-214 | Ir | 1 | 7 | Ph | H | H | Si(CH$_3$)$_3$ | H | CH$_3$ | H | H | pic |
| 7-214X | Ir | 1 | 7 | Ph | H | H | Si(CH$_3$)$_3$ | H | CH$_3$ | H | H | acac |
| 7-214Y | Ir | 0 | 7 | Ph | H | H | Si(CH$_3$)$_3$ | H | CH$_3$ | H | H | — — |
| 7-215 | Ir | 1 | 7 | Ph | H | H | H | Si(CH$_3$)$_3$ | CH$_3$ | H | H | pic |
| 7-215X | Ir | 1 | 7 | Ph | H | H | H | Si(CH$_3$)$_3$ | CH$_3$ | H | H | acac |
| 7-215Y | Ir | 0 | 7 | Ph | H | H | H | Si(CH$_3$)$_3$ | CH$_3$ | H | H | — — |
| 7-216 | Ir | 1 | 7 | Ph | H | F | H | Si(CH$_3$)$_3$ | CH$_3$ | H | H | pic |
| 7-216X | Ir | 1 | 7 | Ph | H | F | H | Si(CH$_3$)$_3$ | CH$_3$ | H | H | acac |
| 7-216Y | Ir | 0 | 7 | Ph | H | F | H | Si(CH$_3$)$_3$ | CH$_3$ | H | H | — — |
| 7-217 | Ir | 1 | 7 | Ph | H | CF$_3$ | H | Si(CH$_3$)$_3$ | CH$_3$ | H | H | pic |
| 7-217X | Ir | 1 | 7 | Ph | H | CF$_3$ | H | Si(CH$_3$)$_3$ | CH$_3$ | H | H | acac |
| 7-217Y | Ir | 0 | 7 | Ph | H | CF$_3$ | H | Si(CH$_3$)$_3$ | CH$_3$ | H | H | — — |
| 7-218 | Ir | 1 | 7 | Ph | H | CF$_3$ | H | Si(CH$_3$)$_3$ | $^t$C$_4$H$_9$ | H | H | pic |
| 7-218X | Ir | 1 | 7 | Ph | H | CF$_3$ | H | Si(CH$_3$)$_3$ | $^t$C$_4$H$_9$ | H | H | acac |
| 7-218Y | Ir | 0 | 7 | Ph | H | CF$_3$ | H | Si(CH$_3$)$_3$ | $^t$C$_4$H$_9$ | H | H | — — |
| 7-219 | Ir | 1 | 7 | Ph | H | Si(CH$_3$)$_3$ | H | F | CH$_3$ | H | H | pic |
| 7-219X | Ir | 1 | 7 | Ph | H | Si(CH$_3$)$_3$ | H | F | CH$_3$ | H | H | acac |
| 7-219Y | Ir | 0 | 7 | Ph | H | Si(CH$_3$)$_3$ | H | F | CH$_3$ | H | H | — — |
| 7-220 | Ir | 1 | 7 | Ph | H | Si(CH$_3$)$_3$ | H | F | $^t$C$_4$H$_9$ | H | H | pic |
| 7-220X | Ir | 1 | 7 | Ph | H | Si(CH$_3$)$_3$ | H | F | $^t$C$_4$H$_9$ | H | H | acac |
| 7-220Y | Ir | 0 | 7 | Ph | H | Si(CH$_3$)$_3$ | H | F | $^t$C$_4$H$_9$ | H | H | — — |
| 7-221 | Ir | 1 | 7 | Ph | H | Si(CH$_3$)$_3$ | H | CF$_3$ | CH$_3$ | H | H | pic |
| 7-221X | Ir | 1 | 7 | Ph | H | Si(CH$_3$)$_3$ | H | CF$_3$ | CH$_3$ | H | H | acac |
| 7-221Y | Ir | 0 | 7 | Ph | H | Si(CH$_3$)$_3$ | H | CF$_3$ | CH$_3$ | H | H | — — |
| 7-222 | Ir | 1 | 7 | Ph | H | Si(CH$_3$)$_3$ | H | CF$_3$ | $^t$C$_4$H$_9$ | H | H | pic |
| 7-222X | Ir | 1 | 7 | Ph | H | Si(CH$_3$)$_3$ | H | CF$_3$ | $^t$C$_4$H$_9$ | H | H | acac |
| 7-222Y | Ir | 0 | 7 | Ph | H | Si(CH$_3$)$_3$ | H | CF$_3$ | $^t$C$_4$H$_9$ | H | H | — — |
| 7-223 | Ir | 1 | 7 | Ph | Si(CH$_3$)$_3$ | H | Si(CH$_3$)$_3$ | H | CH$_3$ | H | H | pic |
| 7-223X | Ir | 1 | 7 | Ph | Si(CH$_3$)$_3$ | H | Si(CH$_3$)$_3$ | H | CH$_3$ | H | H | acac |
| 7-223Y | Ir | 0 | 7 | Ph | Si(CH$_3$)$_3$ | H | Si(CH$_3$)$_3$ | H | CH$_3$ | H | H | — — |
| 7-224 | Ir | 1 | 7 | Ph | Si(CH$_3$)$_3$ | H | Si(CH$_3$)$_3$ | H | $^t$C$_4$H$_9$ | H | H | pic |
| 7-224X | Ir | 1 | 7 | Ph | Si(CH$_3$)$_3$ | H | Si(CH$_3$)$_3$ | H | $^t$C$_4$H$_9$ | H | H | acac |
| 7-224Y | Ir | 0 | 7 | Ph | Si(CH$_3$)$_3$ | H | Si(CH$_3$)$_3$ | H | $^t$C$_4$H$_9$ | H | H | — — |
| 7-225 | Ir | 1 | 7 | Ph | H | H | H | COCH$_3$ | CH$_3$ | H | H | pic |
| 7-225X | Ir | 1 | 7 | Ph | H | H | H | COCH$_3$ | CH$_3$ | H | H | acac |
| 7-225Y | Ir | 0 | 7 | Ph | H | H | H | COCH$_3$ | CH$_3$ | H | H | — — |
| 7-226 | Ir | 1 | 7 | Ph | H | H | COCH$_3$ | H | CH$_3$ | H | H | pic |
| 7-226X | Ir | 1 | 7 | Ph | H | H | COCH$_3$ | H | CH$_3$ | H | H | acac |
| 7-226Y | Ir | 0 | 7 | Ph | H | H | COCH$_3$ | H | CH$_3$ | H | H | — — |
| 7-227 | Ir | 1 | 7 | Ph | H | COCH$_3$ | H | H | CH$_3$ | H | H | pic |
| 7-227X | Ir | 1 | 7 | Ph | H | COCH$_3$ | H | H | CH$_3$ | H | H | acac |
| 7-227Y | Ir | 0 | 7 | Ph | H | COCH$_3$ | H | H | CH$_3$ | H | H | — — |
| 7-228 | Ir | 1 | 7 | Ph | H | H | BL | | CH$_3$ | H | H | pic |
| 7-228X | Ir | 1 | 7 | Ph | H | H | BL | | CH$_3$ | H | H | acac |
| 7-228Y | Ir | 0 | 7 | Ph | H | H | BL | | CH$_3$ | H | H | — — |
| 7-229 | Ir | 1 | 7 | Ph | H | H | BL | | $^t$C$_4$H$_9$ | H | H | pic |
| 7-229X | Ir | 1 | 7 | Ph | H | H | BL | | $^t$C$_4$H$_9$ | H | H | acac |
| 7-229Y | Ir | 0 | 7 | Ph | H | H | BL | | $^t$C$_4$H$_9$ | H | H | — — |
| 7-230 | Ir | 1 | 7 | Ph | H | BL | | H | CH$_3$ | H | H | pic |
| 7-230X | Ir | 1 | 7 | Ph | H | BL | | H | CH$_3$ | H | H | acac |
| 7-230Y | Ir | 0 | 7 | Ph | H | BL | | H | CH$_3$ | H | H | — — |
| 7-231 | Ir | 1 | 7 | Ph | H | BL | | H | $^t$C$_4$H$_9$ | H | H | pic |
| 7-231X | Ir | 1 | 7 | Ph | H | BL | | H | $^t$C$_4$H$_9$ | H | H | acac |
| 7-231Y | Ir | 0 | 7 | Ph | H | BL | | H | $^t$C$_4$H$_9$ | H | H | — — |
| 7-232 | Ir | 1 | 7 | Ph | H | H | PL | | CH$_3$ | H | H | pic |
| 7-232X | Ir | 1 | 7 | Ph | H | H | PL | | CH$_3$ | H | H | acac |
| 7-232Y | Ir | 0 | 7 | Ph | H | H | PL | | CH$_3$ | H | H | — — |
| 7-233 | Ir | 1 | 7 | Ph | H | H | PL | | $^t$C$_4$H$_9$ | H | H | pic |
| 7-233X | Ir | 1 | 7 | Ph | H | H | PL | | $^t$C$_4$H$_9$ | H | H | acac |
| 7-233Y | Ir | 0 | 7 | Ph | H | H | PL | | $^t$C$_4$H$_9$ | H | H | — — |
| 7-234 | Ir | 1 | 7 | Ph | H | PL | | H | CH$_3$ | H | H | pic |
| 7-234X | Ir | 1 | 7 | Ph | H | PL | | H | CH$_3$ | H | H | acac |
| 7-234Y | Ir | 0 | 7 | Ph | H | PL | | H | CH$_3$ | H | H | — — |
| 7-235 | Ir | 1 | 7 | Ph | H | PL | | H | $^t$C$_4$H$_9$ | H | H | pic |
| 7-235X | Ir | 1 | 7 | Ph | H | PL | | H | $^t$C$_4$H$_9$ | H | H | acac |
| 7-235Y | Ir | 0 | 7 | Ph | H | PL | | H | $^t$C$_4$H$_9$ | H | H | — — |
| 7-236 | Ir | 1 | 7 | Ph | H | H | MEE1 | | CH$_3$ | H | H | pic |
| 7-236X | Ir | 1 | 7 | Ph | H | H | MEE1 | | CH$_3$ | H | H | acac |
| 7-236Y | Ir | 0 | 7 | Ph | H | H | MEE1 | | CH$_3$ | H | H | — — |
| 7-237 | Ir | 1 | 7 | Ph | H | MEE1 | | H | CH$_3$ | H | H | pic |
| 7-237X | Ir | 1 | 7 | Ph | H | MEE1 | | H | CH$_3$ | H | H | acac |
| 7-237Y | Ir | 0 | 7 | Ph | H | MEE1 | | H | CH$_3$ | H | H | — — |
| 7-238 | Ir | 1 | 7 | Ph | H | H | MEE2 | | CH$_3$ | H | H | pic |
| 7-238X | Ir | 1 | 7 | Ph | H | H | MEE2 | | CH$_3$ | H | H | acac |
| 7-238Y | Ir | 0 | 7 | Ph | H | H | MEE2 | | CH$_3$ | H | H | — — |
| 7-239 | Ir | 1 | 7 | Ph | H | MEE2 | | H | CH$_3$ | H | H | pic |
| 7-239X | Ir | 1 | 7 | Ph | H | MEE2 | | H | CH$_3$ | H | H | acac |

TABLE 21-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 7-239Y | Ir | 0 | 7 | Ph | H | | MEE2 | H | CH₃ | H | H | — | — |
| 7-240 | Ir | 1 | 7 | Ph | H | H | | PA1 | CH₃ | H | H | pic | |
| 7-240X | Ir | 1 | 7 | Ph | H | H | | PA1 | CH₃ | H | H | acac | |
| 7-240Y | Ir | 0 | 7 | Ph | H | H | | PA1 | CH₃ | H | H | — | — |
| 7-241 | Ir | 1 | 7 | Ph | H | | PA1 | H | CH₃ | H | H | pic | |
| 7-241X | Ir | 1 | 7 | Ph | H | | PA1 | H | CH₃ | H | H | acac | |
| 7-241Y | Ir | 0 | 7 | Ph | H | | PA1 | H | CH₃ | H | H | — | — |
| 7-242 | Ir | 1 | 7 | Ph | H | H | | PA2 | CH₃ | H | H | pic | |
| 7-242X | Ir | 1 | 7 | Ph | H | H | | PA2 | CH₃ | H | H | acac | |
| 7-242Y | Ir | 0 | 7 | Ph | H | H | | PA2 | CH₃ | H | H | — | — |
| 7-243 | Ir | 1 | 7 | Ph | H | | PA2 | H | CH₃ | H | H | pic | |
| 7-243X | Ir | 1 | 7 | Ph | H | | PA2 | H | CH₃ | H | H | acac | |
| 7-243Y | Ir | 0 | 7 | Ph | H | | PA2 | H | CH₃ | H | H | — | — |
| 7-244 | Ir | 1 | 7 | Ph | H | H | | EA1 | CH₃ | H | H | pic | |
| 7-244X | Ir | 1 | 7 | Ph | H | H | | EA1 | CH₃ | H | H | acac | |
| 7-244Y | Ir | 0 | 7 | Ph | H | H | | EA1 | CH₃ | H | H | — | — |
| 7-245 | Ir | 1 | 7 | Ph | H | | EA2 | H | CH₃ | H | H | pic | |
| 7-245X | Ir | 1 | 7 | Ph | H | | EA2 | H | CH₃ | H | H | acac | |
| 7-245Y | Ir | 0 | 7 | Ph | H | | EA2 | H | CH₃ | H | H | — | — |
| 7-246 | Ir | 1 | 7 | Ph | H | H | | ME | CH₃ | H | H | pic | |
| 7-246X | Ir | 1 | 7 | Ph | H | H | | ME | CH₃ | H | H | acac | |
| 7-246Y | Ir | 0 | 7 | Ph | H | H | | ME | CH₃ | H | H | — | — |
| 7-247 | Ir | 1 | 7 | Ph | H | | ME | H | CH₃ | H | H | pic | |
| 7-247X | Ir | 1 | 7 | Ph | H | | ME | H | CH₃ | H | H | acac | |
| 7-247Y | Ir | 0 | 7 | Ph | H | | ME | H | CH₃ | H | H | — | — |
| 7-248 | Ir | 1 | 7 | Ph | H | H | | AT | CH₃ | H | H | pic | |
| 7-248X | Ir | 1 | 7 | Ph | H | H | | AT | CH₃ | H | H | acac | |
| 7-248Y | Ir | 0 | 7 | Ph | H | H | | AT | CH₃ | H | H | — | — |
| 7-249 | Ir | 1 | 7 | Ph | H | | AT | H | CH₃ | H | H | pic | |
| 7-249X | Ir | 1 | 7 | Ph | H | | AT | H | CH₃ | H | H | acac | |
| 7-249Y | Ir | 0 | 7 | Ph | H | | AT | H | CH₃ | H | H | — | — |
| 7-250 | Ir | 1 | 7 | Ph | H | H | | MES1 | CH₃ | H | H | pic | |
| 7-250X | Ir | 1 | 7 | Ph | H | H | | MES1 | CH₃ | H | H | acac | |
| 7-250Y | Ir | 0 | 7 | Ph | H | H | | MES1 | CH₃ | H | H | — | — |
| 7-251 | Ir | 1 | 7 | Ph | H | | MES1 | H | CH₃ | H | H | pic | |
| 7-251X | Ir | 1 | 7 | Ph | H | | MES1 | H | CH₃ | H | H | acac | |
| 7-251Y | Ir | 0 | 7 | Ph | H | | MES1 | H | CH₃ | H | H | — | — |
| 7-252 | Ir | 1 | 7 | Ph | H | H | | MES2 | CH₃ | H | H | pic | |
| 7-252X | Ir | 1 | 7 | Ph | H | H | | MES2 | CH₃ | H | H | acac | |
| 7-252Y | Ir | 0 | 7 | Ph | H | H | | MES2 | CH₃ | H | H | — | — |
| 7-253 | Ir | 1 | 7 | Ph | H | | MES2 | H | CH₃ | H | H | pic | |
| 7-253X | Ir | 1 | 7 | Ph | H | | MES2 | H | CH₃ | H | H | acac | |
| 7-253Y | Ir | 0 | 7 | Ph | H | | MES2 | H | CH₃ | H | H | — | — |
| 7-254 | Ir | 1 | 7 | Ph | H | H | | PS1 | CH₃ | H | H | pic | |
| 7-254X | Ir | 1 | 7 | Ph | H | H | | PS1 | CH₃ | H | H | acac | |
| 7-254Y | Ir | 0 | 7 | Ph | H | H | | PS1 | CH₃ | H | H | — | — |
| 7-255 | Ir | 1 | 7 | Ph | H | | PS1 | H | CH₃ | H | H | pic | |
| 7-255X | Ir | 1 | 7 | Ph | H | | PS1 | H | CH₃ | H | H | acac | |
| 7-255Y | Ir | 0 | 7 | Ph | H | | PS1 | H | CH₃ | H | H | — | — |
| 7-256 | Ir | 1 | 7 | Ph | H | H | | PS2 | CH₃ | H | H | pic | |
| 7-256X | Ir | 1 | 7 | Ph | H | H | | PS2 | CH₃ | H | H | acac | |
| 7-256Y | Ir | 0 | 7 | Ph | H | H | | PS2 | CH₃ | H | H | — | — |
| 7-257 | Ir | 1 | 7 | Ph | H | | PS2 | H | CH₃ | H | H | pic | |
| 7-257X | Ir | 1 | 7 | Ph | H | | PS2 | H | CH₃ | H | H | acac | |
| 7-257Y | Ir | 0 | 7 | Ph | H | | PS2 | H | CH₃ | H | H | — | — |
| 7-258 | Ir | 1 | 7 | Ph | H | H | | BAL1 | CH₃ | H | H | pic | |
| 7-258X | Ir | 1 | 7 | Ph | H | H | | BAL1 | CH₃ | H | H | acac | |
| 7-258Y | Ir | 0 | 7 | Ph | H | H | | BAL1 | CH₃ | H | H | — | — |
| 7-259 | Ir | 1 | 7 | Ph | H | | BAL1 | H | CH₃ | H | H | pic | |
| 7-259X | Ir | 1 | 7 | Ph | H | | BAL1 | H | CH₃ | H | H | acac | |
| 7-259Y | Ir | 0 | 7 | Ph | H | | BAL1 | H | CH₃ | H | H | — | — |
| 7-260 | Ir | 1 | 7 | Ph | H | H | | BAL2 | CH₃ | H | H | pic | |
| 7-260X | Ir | 1 | 7 | Ph | H | H | | BAL2 | CH₃ | H | H | acac | |
| 7-260Y | Ir | 0 | 7 | Ph | H | H | | BAL2 | CH₃ | H | H | — | — |
| 7-261 | Ir | 1 | 7 | Ph | H | | BAL2 | H | CH₃ | H | H | pic | |
| 7-261X | Ir | 1 | 7 | Ph | H | | BAL2 | H | CH₃ | H | H | acac | |
| 7-261Y | Ir | 0 | 7 | Ph | H | | BAL2 | H | CH₃ | H | H | — | — |
| 7-262 | Ir | 1 | 7 | Ph | H | H | | MEK1 | CH₃ | H | H | pic | |
| 7-262X | Ir | 1 | 7 | Ph | H | H | | MEK1 | CH₃ | H | H | acac | |
| 7-262Y | Ir | 0 | 7 | Ph | H | H | | MEK1 | CH₃ | H | H | — | — |
| 7-263 | Ir | 1 | 7 | Ph | H | | MEK1 | H | CH₃ | H | H | pic | |
| 7-263X | Ir | 1 | 7 | Ph | H | | MEK1 | H | CH₃ | H | H | acac | |
| 7-263Y | Ir | 0 | 7 | Ph | H | | MEK1 | H | CH₃ | H | H | — | — |
| 7-264 | Ir | 1 | 7 | Ph | H | H | | MEK2 | CH₃ | H | H | pic | |
| 7-264X | Ir | 1 | 7 | Ph | H | H | | MEK2 | CH₃ | H | H | acac | |
| 7-264Y | Ir | 0 | 7 | Ph | H | H | | MEK2 | CH₃ | H | H | — | — |
| 7-265 | Ir | 1 | 7 | Ph | H | | MEK2 | H | CH₃ | H | H | pic | |

TABLE 21-continued

| No. | M | n | BSS | SS G | T¹ | T² | T³ | T⁴ | T⁵ | T⁶ | T⁷ | L¹ | L² |
|---|---|---|---|---|---|---|---|---|---|---|---|---|---|
| 7-265X | Ir | 1 | 7 | Ph | H | | MEK2 | H | $CH_3$ | H | H | acac | |
| 7-265Y | Ir | 0 | 7 | Ph | H | | MEK2 | H | $CH_3$ | H | H | — | — |
| 7-266 | Ir | 1 | 7 | Ph | H | H | | PAL1 | $CH_3$ | H | H | pic | |
| 7-266X | Ir | 1 | 7 | Ph | H | H | | PAL1 | $CH_3$ | H | H | acac | |
| 7-266Y | Ir | 0 | 7 | Ph | H | H | | PAL1 | $CH_3$ | H | H | — | — |
| 7-267 | Ir | 1 | 7 | Ph | H | | PAL1 | H | $CH_3$ | H | H | pic | |
| 7-267X | Ir | 1 | 7 | Ph | H | | PAL1 | H | $CH_3$ | H | H | acac | |
| 7-267Y | Ir | 0 | 7 | Ph | H | | PAL1 | H | $CH_3$ | H | H | — | — |
| 7-268 | Ir | 1 | 7 | Ph | H | H | | PAL2 | $CH_3$ | H | H | pic | |
| 7-268X | Ir | 1 | 7 | Ph | H | H | | PAL2 | $CH_3$ | H | H | acac | |
| 7-268Y | Ir | 0 | 7 | Ph | H | H | | PAL2 | $CH_3$ | H | H | — | — |
| 7-269 | Ir | 1 | 7 | Ph | H | | PAL2 | H | $CH_3$ | H | H | pic | |
| 7-269X | Ir | 1 | 7 | Ph | H | | PAL2 | H | $CH_3$ | H | H | acac | |
| 7-269Y | Ir | 0 | 7 | Ph | H | | PAL2 | H | $CH_3$ | H | H | — | — |
| 7-270 | Ir | 1 | 7 | Ph | H | H | | MMK | $CH_3$ | H | H | pic | |
| 7-270X | Ir | 1 | 7 | Ph | H | H | | MMK | $CH_3$ | H | H | acac | |
| 7-270Y | Ir | 0 | 7 | Ph | H | H | | MMK | $CH_3$ | H | H | — | — |
| 7-271 | Ir | 1 | 7 | Ph | H | | MMK | H | $CH_3$ | H | H | pic | |
| 7-271X | Ir | 1 | 7 | Ph | H | | MMK | H | $CH_3$ | H | H | acac | |
| 7-271Y | Ir | 0 | 7 | Ph | H | | MMK | H | $CH_3$ | H | H | — | — |
| 7-272 | Ir | 1 | 7 | Ph | H | H | | EES1 | $CH_3$ | H | H | pic | |
| 7-272X | Ir | 1 | 7 | Ph | H | H | | EES1 | $CH_3$ | H | H | acac | |
| 7-272Y | Ir | 0 | 7 | Ph | H | H | | EES1 | $CH_3$ | H | H | — | — |
| 7-273 | Ir | 1 | 7 | Ph | H | | EES2 | H | $CH_3$ | H | H | pic | |
| 7-273X | Ir | 1 | 7 | Ph | H | | EES2 | H | $CH_3$ | H | H | acac | |
| 7-273Y | Ir | 0 | 7 | Ph | H | | EES2 | H | $CH_3$ | H | H | — | — |
| 7-274 | Ir | 1 | 7 | Ph | H | H | | PAE1 | $CH_3$ | H | H | pic | |
| 7-274X | Ir | 1 | 7 | Ph | H | H | | PAE1 | $CH_3$ | H | H | acac | |
| 7-274Y | Ir | 0 | 7 | Ph | H | H | | PAE1 | $CH_3$ | H | H | — | — |
| 7-275 | Ir | 1 | 7 | Ph | H | | PAE2 | H | $CH_3$ | H | H | pic | |
| 7-275X | Ir | 1 | 7 | Ph | H | | PAE2 | H | $CH_3$ | H | H | acac | |
| 7-275Y | Ir | 0 | 7 | Ph | H | | PAE2 | H | $CH_3$ | H | H | — | — |
| 7-276 | Ir | 1 | 7 | Ph | H | H | | AME1 | $CH_3$ | H | H | pic | |
| 7-276X | Ir | 1 | 7 | Ph | H | H | | AME1 | $CH_3$ | H | H | acac | |
| 7-276Y | Ir | 0 | 7 | Ph | H | H | | AME1 | $CH_3$ | H | H | — | — |
| 7-277 | Ir | 1 | 7 | Ph | H | | AME1 | H | $CH_3$ | H | H | pic | |
| 7-277X | Ir | 1 | 7 | Ph | H | | AME1 | H | $CH_3$ | H | H | acac | |
| 7-277Y | Ir | 0 | 7 | Ph | H | | AME1 | H | $CH_3$ | H | H | — | — |
| 7-278 | Ir | 1 | 7 | Ph | H | H | | AME2 | $CH_3$ | H | H | pic | |
| 7-278X | Ir | 1 | 7 | Ph | H | H | | AME2 | $CH_3$ | H | H | acac | |
| 7-278Y | Ir | 0 | 7 | Ph | H | H | | AME2 | $CH_3$ | H | H | — | — |
| 7-279 | Ir | 1 | 7 | Ph | H | | AME2 | H | $CH_3$ | H | H | pic | |
| 7-279X | Ir | 1 | 7 | Ph | H | | AME2 | H | $CH_3$ | H | H | acac | |
| 7-279Y | Ir | 0 | 7 | Ph | H | | AME2 | H | $CH_3$ | H | H | — | — |
| 7-280 | Ir | 1 | 7 | Ph | H | H | | EAE1 | $CH_3$ | H | H | pic | |
| 7-280X | Ir | 1 | 7 | Ph | H | H | | EAE1 | $CH_3$ | H | H | acac | |
| 7-280Y | Ir | 0 | 7 | Ph | H | H | | EAE1 | $CH_3$ | H | H | — | — |
| 7-281 | Ir | 1 | 7 | Ph | H | | EAE1 | H | $CH_3$ | H | H | pic | |
| 7-281X | Ir | 1 | 7 | Ph | H | | EAE1 | H | $CH_3$ | H | H | acac | |
| 7-281Y | Ir | 0 | 7 | Ph | H | | EAE1 | H | $CH_3$ | H | H | — | — |
| 7-282 | Ir | 1 | 7 | Ph | H | H | | EAE2 | $CH_3$ | H | H | pic | |
| 7-282X | Ir | 1 | 7 | Ph | H | H | | EAE2 | $CH_3$ | H | H | acac | |
| 7-282Y | Ir | 0 | 7 | Ph | H | H | | EAE2 | $CH_3$ | H | H | — | — |
| 7-283 | Ir | 1 | 7 | Ph | H | | EAE2 | H | $CH_3$ | H | H | pic | |
| 7-283X | Ir | 1 | 7 | Ph | H | | EAE2 | H | $CH_3$ | H | H | acac | |
| 7-283Y | Ir | 0 | 7 | Ph | H | | EAE2 | H | $CH_3$ | H | H | — | — |
| 7-284 | Ir | 1 | 7 | Ph | H | H | | AAE1 | $CH_3$ | H | H | pic | |
| 7-284X | Ir | 1 | 7 | Ph | H | H | | AAE1 | $CH_3$ | H | H | acac | |
| 7-284Y | Ir | 0 | 7 | Ph | H | H | | AAE1 | $CH_3$ | H | H | — | — |
| 7-285 | Ir | 1 | 7 | Ph | H | | AAE1 | H | $CH_3$ | H | H | pic | |
| 7-285X | Ir | 1 | 7 | Ph | H | | AAE1 | H | $CH_3$ | H | H | acac | |
| 7-285Y | Ir | 0 | 7 | Ph | H | | AAE1 | H | $CH_3$ | H | H | — | — |
| 7-286 | Ir | 1 | 7 | Ph | H | H | | AAE2 | $CH_3$ | H | H | pic | |
| 7-286X | Ir | 1 | 7 | Ph | H | H | | AAE2 | $CH_3$ | H | H | acac | |
| 7-286Y | Ir | 0 | 7 | Ph | H | H | | AAE2 | $CH_3$ | H | H | — | — |
| 7-287 | Ir | 1 | 7 | Ph | H | | AAE2 | H | $CH_3$ | H | H | pic | |
| 7-287X | Ir | 1 | 7 | Ph | H | | AAE2 | H | $CH_3$ | H | H | acac | |
| 7-287Y | Ir | 0 | 7 | Ph | H | | AAE2 | H | $CH_3$ | H | H | — | — |
| 7-288 | Ir | 1 | 7 | Ph | H | H | | PME1 | $CH_3$ | H | H | pic | |
| 7-288X | Ir | 1 | 7 | Ph | H | H | | PME1 | $CH_3$ | H | H | acac | |
| 7-288Y | Ir | 0 | 7 | Ph | H | H | | PME1 | $CH_3$ | H | H | — | — |
| 7-289 | Ir | 1 | 7 | Ph | H | | PME1 | H | $CH_3$ | H | H | pic | |
| 7-289X | Ir | 1 | 7 | Ph | H | | PME1 | H | $CH_3$ | H | H | acac | |
| 7-289Y | Ir | 0 | 7 | Ph | H | | PME1 | H | $CH_3$ | H | H | — | — |

TABLE 21-continued

| No. | M | n | BSS | SS | G | T¹ | T² | T³ | T⁴ | T⁵ | T⁶ | T⁷ | L¹ | L² |
|---|---|---|---|---|---|---|---|---|---|---|---|---|---|---|
| 7-290 | Ir | 1 | 7 | | Ph | H | H | | PME2 | CH₃ | H | H | pic | |
| 7-290X | Ir | 1 | 7 | | Ph | H | H | | PME2 | CH₃ | H | H | acac | |
| 7-290Y | Ir | 0 | 7 | | Ph | H | H | | PME2 | CH₃ | H | H | — | — |
| 7-291 | Ir | 1 | 7 | | Ph | H | | PME2 | H | CH₃ | H | H | pic | |
| 7-291X | Ir | 1 | 7 | | Ph | H | | PME2 | H | CH₃ | H | H | acac | |
| 7-291Y | Ir | 0 | 7 | | Ph | H | | PME2 | H | CH₃ | H | H | — | — |
| 7-292 | Ir | 1 | 7 | | Ph | H | H | | MET1 | CH₃ | H | H | pic | |
| 7-292X | Ir | 1 | 7 | | Ph | H | H | | MET1 | CH₃ | H | H | acac | |
| 7-292Y | Ir | 0 | 7 | | Ph | H | H | | MET1 | CH₃ | H | H | — | — |
| 7-293 | Ir | 1 | 7 | | Ph | H | | MET1 | H | CH₃ | H | H | pic | |
| 7-293X | Ir | 1 | 7 | | Ph | H | | MET1 | H | CH₃ | H | H | acac | |
| 7-293Y | Ir | 0 | 7 | | Ph | H | | MET1 | H | CH₃ | H | H | — | — |
| 7-294 | Ir | 1 | 7 | | Ph | H | H | | MET2 | CH₃ | H | H | pic | |
| 7-294X | Ir | 1 | 7 | | Ph | H | H | | MET2 | CH₃ | H | H | acac | |
| 7-294Y | Ir | 0 | 7 | | Ph | H | H | | MET2 | CH₃ | H | H | — | — |
| 7-295 | Ir | 1 | 7 | | Ph | H | | MET2 | H | CH₃ | H | H | pic | |
| 7-295X | Ir | 1 | 7 | | Ph | H | | MET2 | H | CH₃ | H | H | acac | |
| 7-295Y | Ir | 0 | 7 | | Ph | H | | MET2 | H | CH₃ | H | H | — | — |
| 7-296 | Ir | 1 | 7 | | Ph | H | H | | EE1 | CH₃ | H | H | pic | |
| 7-296X | Ir | 1 | 7 | | Ph | H | H | | EE1 | CH₃ | H | H | acac | |
| 7-296Y | Rh | 0 | 7 | | Ph | H | H | | EE1 | CH₃ | H | H | — | — |
| 7-297 | Rh | 1 | 7 | | Ph | H | | EE1 | H | CH₃ | H | H | pic | |
| 7-297X | Rh | 1 | 7 | | Ph | H | | EE1 | H | CH₃ | H | H | acac | |
| 7-297Y | Rh | 0 | 7 | | Ph | H | | EE1 | H | CH₃ | H | H | — | — |
| 7-298 | Rh | 1 | 7 | | Ph | H | H | | EE2 | CH₃ | H | H | pic | |
| 7-298X | Rh | 1 | 7 | | Ph | H | H | | EE2 | CH₃ | H | H | acac | |
| 7-298Y | Rh | 0 | 7 | | Ph | H | H | | EE2 | CH₃ | H | H | — | — |
| 7-299 | Rh | 1 | 7 | | Ph | H | | EE2 | H | CH₃ | H | H | pic | |
| 7-299X | Rh | 1 | 7 | | Ph | H | | EE2 | H | CH₃ | H | H | acac | |
| 7-299Y | Rh | 0 | 7 | | Ph | H | | EE2 | H | CH₃ | H | H | — | — |
| 7-300 | Rh | 1 | 7 | | Ph | H | H | | MS1 | CH₃ | H | H | pic | |
| 7-300X | Rh | 1 | 7 | | Ph | H | H | | MS1 | CH₃ | H | H | acac | |
| 7-300Y | Rh | 0 | 7 | | Ph | H | H | | MS1 | CH₃ | H | H | — | — |
| 7-301 | Rh | 1 | 7 | | Ph | H | | MS1 | H | CH₃ | H | H | pic | |
| 7-301X | Rh | 1 | 7 | | Ph | H | | MS1 | H | CH₃ | H | H | acac | |
| 7-301Y | Rh | 0 | 7 | | Ph | H | | MS1 | H | CH₃ | H | H | — | — |
| 7-302 | Rh | 1 | 7 | | Ph | H | H | | MS2 | CH₃ | H | H | pic | |
| 7-302X | Rh | 1 | 7 | | Ph | H | H | | MS2 | CH₃ | H | H | acac | |
| 7-302Y | Rh | 0 | 7 | | Ph | H | H | | MS2 | CH₃ | H | H | — | — |
| 7-303 | Rh | 1 | 7 | | Ph | H | | MS2 | H | CH₃ | H | H | pic | |
| 7-303X | Rh | 1 | 7 | | Ph | H | | MS2 | H | CH₃ | H | H | acac | |
| 7-303Y | Rh | 0 | 7 | | Ph | H | | MS2 | H | CH₃ | H | H | — | — |

-continued

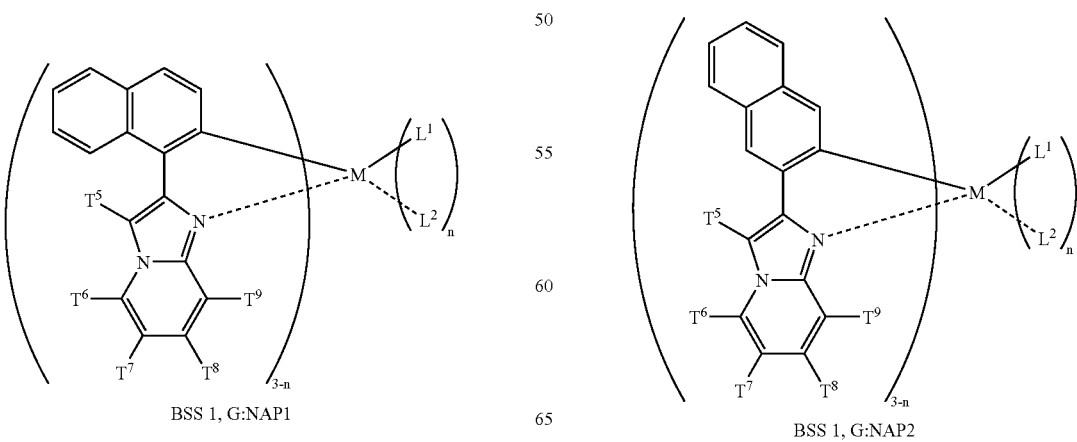

BSS 1, G:NAP1

BSS 1, G:NAP2

-continued
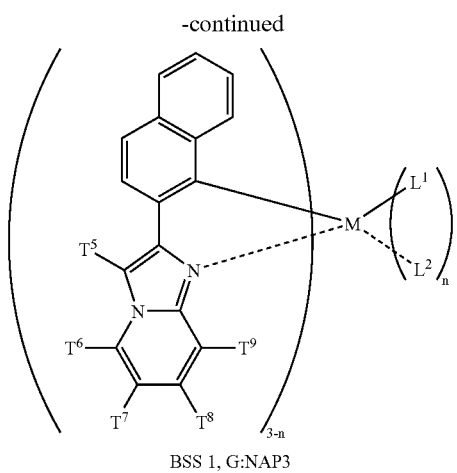
BSS 1, G:NAP3
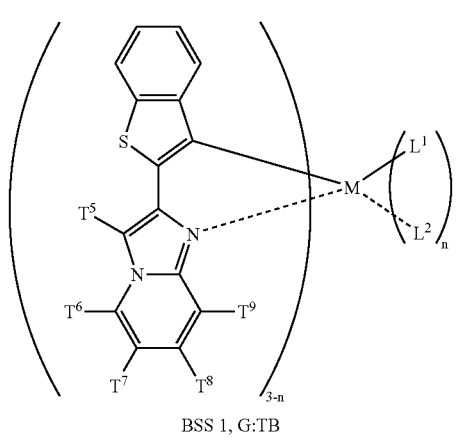
BSS 1, G:TB
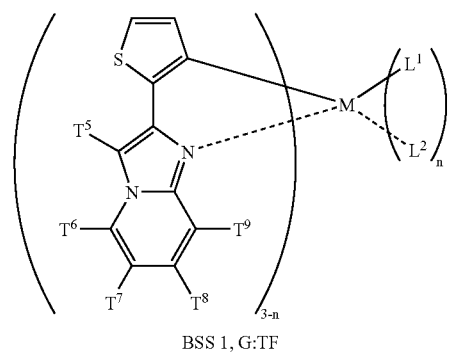
BSS 1, G:TF
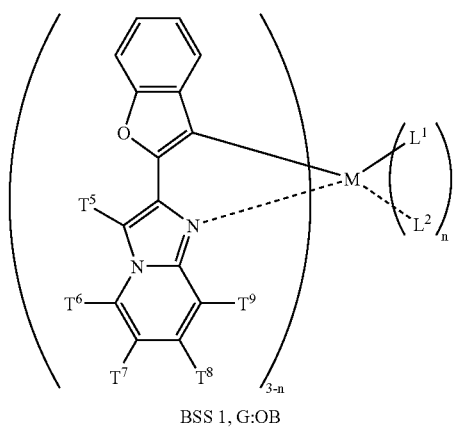
BSS 1, G:OB
-continued
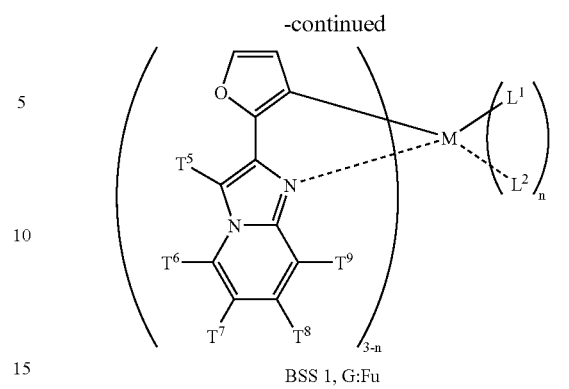
BSS 1, G:Fu
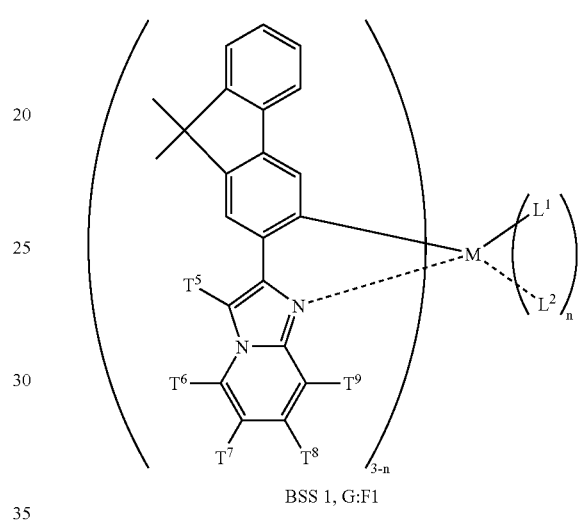
BSS 1, G:Fl
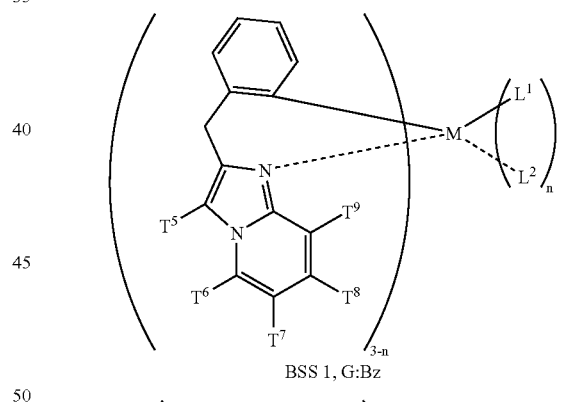
BSS 1, G:Bz
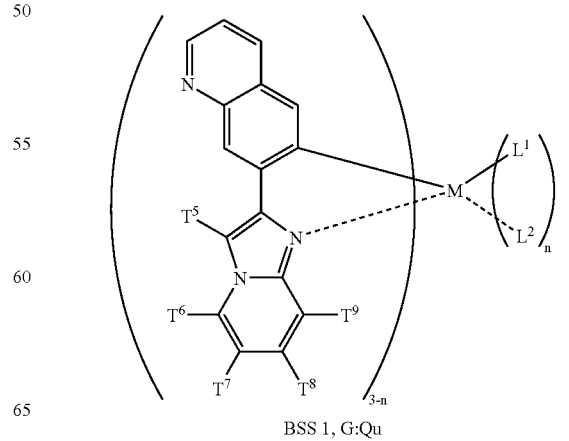
BSS 1, G:Qu -continued

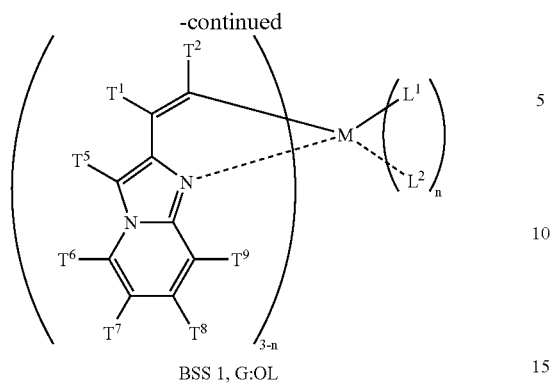

BSS 1, G:OL

TABLE 22

| No. | M | n | BSS | SS | G | T¹ | T² | T⁵ | T⁶ | T⁷ | T⁸ | T⁹ | L¹ L² |
|---|---|---|---|---|---|---|---|---|---|---|---|---|---|
| 1-305 | Rh | 1 | 1 | Nap1 | — | — | — | H | H | H | H | H | pic |
| 1-305X | Rh | 1 | 1 | Nap1 | — | — | — | H | H | H | H | H | acac |
| 1-305Y | Rh | 0 | 1 | Nap1 | — | — | — | H | H | H | H | H | — — |
| 1-306 | Rh | 1 | 1 | Nap1 | — | — | — | $^tC_4H_9$ | H | H | H | H | pic |
| 1-306X | Rh | 1 | 1 | Nap1 | — | — | — | $^tC_4H_9$ | H | H | H | H | acac |
| 1-306Y | Rh | 0 | 1 | Nap1 | — | — | — | $^tC_4H_9$ | H | H | H | H | — — |
| 1-307 | Rh | 1 | 1 | Nap1 | — | — | — | $CH_3$ | H | H | H | H | pic |
| 1-307X | Rh | 1 | 1 | Nap1 | — | — | — | $CH_3$ | H | H | H | H | acac |
| 1-307Y | Rh | 0 | 1 | Nap1 | — | — | — | $CH_3$ | H | H | H | H | — — |
| 1-308 | Rh | 1 | 1 | Nap1 | — | — | — | $^tC_4H_9$ | $CH_3$ | H | H | H | pic |
| 1-308X | Rh | 1 | 1 | Nap1 | — | — | — | $^tC_4H_9$ | $CH_3$ | H | H | H | acac |
| 1-308Y | Rh | 0 | 1 | Nap1 | — | — | — | $^tC_4H_9$ | $CH_3$ | H | H | H | — — |
| 1-309 | Rh | 1 | 1 | Nap1 | — | — | — | $CH_3$ | $CH_3$ | H | H | H | pic |
| 1-309X | Rh | 1 | 1 | Nap1 | — | — | — | $CH_3$ | $CH_3$ | H | H | H | acac |
| 1-309Y | Rh | 0 | 1 | Nap1 | — | — | — | $CH_3$ | $CH_3$ | H | H | H | — — |
| 1-310 | Rh | 1 | 1 | Nap1 | — | — | — | H | $CH_3$ | H | H | H | pic |
| 1-310X | Rh | 1 | 1 | Nap1 | — | — | — | H | $CH_3$ | H | H | H | acac |
| 1-310Y | Rh | 0 | 1 | Nap1 | — | — | — | H | $CH_3$ | H | H | H | — — |
| 1-311 | Rh | 1 | 1 | Nap2 | — | — | — | H | H | H | H | H | pic |
| 1-311X | Rh | 1 | 1 | Nap2 | — | — | — | H | H | H | H | H | acac |
| 1-311Y | Rh | 0 | 1 | Nap2 | — | — | — | H | H | H | H | H | — — |
| 1-312 | Rh | 1 | 1 | Nap2 | — | — | — | $^tC_4H_9$ | H | H | H | H | pic |
| 1-312X | Rh | 1 | 1 | Nap2 | — | — | — | $^tC_4H_9$ | H | H | H | H | acac |
| 1-312Y | Rh | 0 | 1 | Nap2 | — | — | — | $^tC_4H_9$ | H | H | H | H | — — |
| 1-313 | Rh | 1 | 1 | Nap2 | — | — | — | $CH_3$ | H | H | H | H | pic |
| 1-313X | Rh | 1 | 1 | Nap2 | — | — | — | $CH_3$ | H | H | H | H | acac |
| 1-313Y | Rh | 0 | 1 | Nap2 | — | — | — | $CH_3$ | H | H | H | H | — — |
| 1-314 | Rh | 1 | 1 | Nap2 | — | — | — | $^tC_4H_9$ | $CH_3$ | H | H | H | pic |
| 1-314X | Rh | 1 | 1 | Nap2 | — | — | — | $^tC_4H_9$ | $CH_3$ | H | H | H | acac |
| 1-314Y | Rh | 0 | 1 | Nap2 | — | — | — | $^tC_4H_9$ | $CH_3$ | H | H | H | — — |
| 1-315 | Rh | 1 | 1 | Nap2 | — | — | — | $CH_3$ | $CH_3$ | H | H | H | pic |
| 1-315X | Rh | 1 | 1 | Nap2 | — | — | — | $CH_3$ | $CH_3$ | H | H | H | acac |
| 1-315Y | Rh | 0 | 1 | Nap2 | — | — | — | $CH_3$ | $CH_3$ | H | H | H | — — |
| 1-316 | Rh | 1 | 1 | Nap2 | — | — | — | H | $CH_3$ | H | H | H | pic |
| 1-316X | Rh | 1 | 1 | Nap2 | — | — | — | H | $CH_3$ | H | H | H | acac |
| 1-316Y | Rh | 0 | 1 | Nap2 | — | — | — | H | $CH_3$ | H | H | H | — — |
| 1-317 | Rh | 1 | 1 | Nap3 | — | — | — | H | H | H | H | H | pic |
| 1-317X | Rh | 1 | 1 | Nap3 | — | — | — | H | H | H | H | H | acac |
| 1-317Y | Rh | 0 | 1 | Nap3 | — | — | — | H | H | H | H | H | — — |
| 1-318 | Rh | 1 | 1 | Nap3 | — | — | — | $^tC_4H_9$ | H | H | H | H | pic |
| 1-318X | Rh | 1 | 1 | Nap3 | — | — | — | $^tC_4H_9$ | H | H | H | H | acac |
| 1-318Y | Rh | 0 | 1 | Nap3 | — | — | — | $^tC_4H_9$ | H | H | H | H | — — |
| 1-319 | Rh | 1 | 1 | Nap3 | — | — | — | $CH_3$ | H | H | H | H | pic |
| 1-319X | Rh | 1 | 1 | Nap3 | — | — | — | $CH_3$ | H | H | H | H | acac |
| 1-319Y | Rh | 0 | 1 | Nap3 | — | — | — | $CH_3$ | H | H | H | H | — — |
| 1-320 | Rh | 1 | 1 | Nap3 | — | — | — | $^tC_4H_9$ | $CH_3$ | H | H | H | pic |
| 1-320X | Rh | 1 | 1 | Nap3 | — | — | — | $^tC_4H_9$ | $CH_3$ | H | H | H | acac |
| 1-320Y | Rh | 0 | 1 | Nap3 | — | — | — | $^tC_4H_9$ | $CH_3$ | H | H | H | — — |
| 1-321 | Rh | 1 | 1 | Nap3 | — | — | — | $CH_3$ | $CH_3$ | H | H | H | pic |
| 1-321X | Rh | 1 | 1 | Nap3 | — | — | — | $CH_3$ | $CH_3$ | H | H | H | acac |
| 1-321Y | Rh | 0 | 1 | Nap3 | — | — | — | $CH_3$ | $CH_3$ | H | H | H | — — |
| 1-322 | Rh | 1 | 1 | Nap3 | — | — | — | H | $CH_3$ | H | H | H | pic |
| 1-322X | Rh | 1 | 1 | Nap3 | — | — | — | H | $CH_3$ | H | H | H | acac |
| 1-322Y | Rh | 0 | 1 | Nap3 | — | — | — | H | $CH_3$ | H | H | H | — — |

TABLE 22-continued

| No. | M | n | BSS | SS G | T¹ | T² | T⁵ | T⁶ | T⁷ | T⁸ | T⁹ | L¹ L² |
|---|---|---|---|---|---|---|---|---|---|---|---|---|
| 1-323 | Rh | 1 | 1 | TB | — | — | H | H | H | H | H | pic |
| 1-323X | Rh | 1 | 1 | TB | — | — | H | H | H | H | H | acac |
| 1-323Y | Rh | 0 | 1 | TB | — | — | H | H | H | H | H | — — |
| 1-324 | Rh | 1 | 1 | TB | — | — | $^tC_4H_9$ | H | H | H | H | pic |
| 1-324X | Rh | 1 | 1 | TB | — | — | $^tC_4H_9$ | H | H | H | H | acac |
| 1-324Y | Rh | 0 | 1 | TB | — | — | $^tC_4H_9$ | H | H | H | H | — — |
| 1-325 | Rh | 1 | 1 | TB | — | — | $CH_3$ | H | H | H | H | pic |
| 1-325X | Rh | 1 | 1 | TB | — | — | $CH_3$ | H | H | H | H | acac |
| 1-325Y | Rh | 0 | 1 | TB | — | — | $CH_3$ | H | H | H | H | — — |
| 1-326 | Rh | 1 | 1 | TB | — | — | $^tC_4H_9$ | $CH_3$ | H | H | H | pic |
| 1-326X | Rh | 1 | 1 | TB | — | — | $^tC_4H_9$ | $CH_3$ | H | H | H | acac |
| 1-326Y | Rh | 0 | 1 | TB | — | — | $^tC_4H_9$ | $CH_3$ | H | H | H | — — |
| 1-327 | Rh | 1 | 1 | TB | — | — | $CH_3$ | $CH_3$ | H | H | H | pic |
| 1-327X | Rh | 1 | 1 | TB | — | — | $CH_3$ | $CH_3$ | H | H | H | acac |
| 1-327Y | Rh | 0 | 1 | TB | — | — | $CH_3$ | $CH_3$ | H | H | H | — — |
| 1-328 | Rh | 1 | 1 | TB | — | — | H | $CH_3$ | H | H | H | pic |
| 1-328X | Rh | 1 | 1 | TB | — | — | H | $CH_3$ | H | H | H | acac |
| 1-328Y | Rh | 0 | 1 | TB | — | — | H | $CH_3$ | H | H | H | — — |
| 1-329 | Rh | 1 | 1 | TF | — | — | H | H | H | H | H | pic |
| 1-329X | Rh | 1 | 1 | TF | — | — | H | H | H | H | H | acac |
| 1-329Y | Rh | 0 | 1 | TF | — | — | H | H | H | H | H | — — |
| 1-330 | Rh | 1 | 1 | TF | — | — | $^tC_4H_9$ | H | H | H | H | pic |
| 1-330X | Rh | 1 | 1 | TF | — | — | $^tC_4H_9$ | H | H | H | H | acac |
| 1-330Y | Rh | 0 | 1 | TF | — | — | $^tC_4H_9$ | H | H | H | H | — — |
| 1-331 | Rh | 1 | 1 | TF | — | — | $CH_3$ | H | H | H | H | pic |
| 1-331X | Rh | 1 | 1 | TF | — | — | $CH_3$ | H | H | H | H | acac |
| 1-331Y | Rh | 0 | 1 | TF | — | — | $CH_3$ | H | H | H | H | — — |
| 1-332 | Rh | 1 | 1 | TF | — | — | $^tC_4H_9$ | $CH_3$ | H | H | H | pic |
| 1-332X | Rh | 1 | 1 | TF | — | — | $^tC_4H_9$ | $CH_3$ | H | H | H | acac |
| 1-332Y | Rh | 0 | 1 | TF | — | — | $^tC_4H_9$ | $CH_3$ | H | H | H | — — |
| 1-333 | Rh | 1 | 1 | TF | — | — | $CH_3$ | $CH_3$ | H | H | H | pic |
| 1-333X | Rh | 1 | 1 | TF | — | — | $CH_3$ | $CH_3$ | H | H | H | acac |
| 1-333Y | Rh | 0 | 1 | TF | — | — | $CH_3$ | $CH_3$ | H | H | H | — — |
| 1-334 | Rh | 1 | 1 | TF | — | — | H | $CH_3$ | H | H | H | pic |
| 1-334X | Rh | 1 | 1 | TF | — | — | H | $CH_3$ | H | H | H | acac |
| 1-334Y | Rh | 0 | 1 | TF | — | — | H | $CH_3$ | H | H | H | — — |
| 1-335 | Rh | 1 | 1 | OB | — | — | H | H | H | H | H | pic |
| 1-335X | Rh | 1 | 1 | OB | — | — | H | H | H | H | H | acac |
| 1-335Y | Rh | 0 | 1 | OB | — | — | H | H | H | H | H | — — |
| 1-336 | Rh | 1 | 1 | OB | — | — | $^tC_4H_9$ | H | H | H | H | pic |
| 1-336X | Rh | 1 | 1 | OB | — | — | $^tC_4H_9$ | H | H | H | H | acac |
| 1-336Y | Rh | 0 | 1 | OB | — | — | $^tC_4H_9$ | H | H | H | H | — — |
| 1-337 | Rh | 1 | 1 | OB | — | — | $CH_3$ | H | H | H | H | pic |
| 1-337X | Rh | 1 | 1 | OB | — | — | $CH_3$ | H | H | H | H | acac |
| 1-337Y | Rh | 0 | 1 | OB | — | — | $CH_3$ | H | H | H | H | — — |
| 1-338 | Rh | 1 | 1 | OB | — | — | $^tC_4H_9$ | $CH_3$ | H | H | H | pic |
| 1-338X | Rh | 1 | 1 | OB | — | — | $^tC_4H_9$ | $CH_3$ | H | H | H | acac |
| 1-338Y | Rh | 0 | 1 | OB | — | — | $^tC_4H_9$ | $CH_3$ | H | H | H | — — |
| 1-339 | Rh | 1 | 1 | OB | — | — | $CH_3$ | $CH_3$ | H | H | H | pic |
| 1-339X | Rh | 1 | 1 | OB | — | — | $CH_3$ | $CH_3$ | H | H | H | acac |
| 1-339Y | Rh | 0 | 1 | OB | — | — | $CH_3$ | $CH_3$ | H | H | H | — — |
| 1-340 | Rh | 1 | 1 | OB | — | — | H | $CH_3$ | H | H | H | pic |
| 1-340X | Rh | 1 | 1 | OB | — | — | H | $CH_3$ | H | H | H | acac |
| 1-340Y | Rh | 0 | 1 | OB | — | — | H | $CH_3$ | H | H | H | — — |
| 1-341 | Rh | 1 | 1 | Fu | — | — | H | H | H | H | H | pic |
| 1-341X | Rh | 1 | 1 | Fu | — | — | H | H | H | H | H | acac |
| 1-341Y | Rh | 0 | 1 | Fu | — | — | H | H | H | H | H | — — |
| 1-342 | Rh | 1 | 1 | Fu | — | — | $^tC_4H_9$ | H | H | H | H | pic |
| 1-342X | Rh | 1 | 1 | Fu | — | — | $^tC_4H_9$ | H | H | H | H | acac |
| 1-342Y | Rh | 0 | 1 | Fu | — | — | $^tC_4H_9$ | H | H | H | H | — — |
| 1-343 | Rh | 1 | 1 | Fu | — | — | $CH_3$ | H | H | H | H | pic |
| 1-343X | Rh | 1 | 1 | Fu | — | — | $CH_3$ | H | H | H | H | acac |
| 1-343Y | Rh | 0 | 1 | Fu | — | — | $CH_3$ | H | H | H | H | — — |
| 1-344 | Rh | 1 | 1 | Fu | — | — | $^tC_4H_9$ | $CH_3$ | H | H | H | pic |
| 1-344X | Rh | 1 | 1 | Fu | — | — | $^tC_4H_9$ | $CH_3$ | H | H | H | acac |
| 1-344Y | Rh | 0 | 1 | Fu | — | — | $^tC_4H_9$ | $CH_3$ | H | H | H | — — |
| 1-345 | Rh | 1 | 1 | Fu | — | — | $CH_3$ | $CH_3$ | H | H | H | pic |
| 1-345X | Rh | 1 | 1 | Fu | — | — | $CH_3$ | $CH_3$ | H | H | H | acac |
| 1-345Y | Rh | 0 | 1 | Fu | — | — | $CH_3$ | $CH_3$ | H | H | H | — — |
| 1-346 | Rh | 1 | 1 | Fu | — | — | H | $CH_3$ | H | H | H | pic |
| 1-346X | Rh | 1 | 1 | Fu | — | — | H | $CH_3$ | H | H | H | acac |
| 1-346Y | Rh | 0 | 1 | Fu | — | — | H | $CH_3$ | H | H | H | — — |
| 1-347 | Rh | 1 | 1 | Fl | — | — | H | H | H | H | H | pic |
| 1-347X | Rh | 1 | 1 | Fl | — | — | H | H | H | H | H | acac |
| 1-347Y | Rh | 0 | 1 | Fl | — | — | H | H | H | H | H | — — |
| 1-348 | Rh | 1 | 1 | Fl | — | — | $^tC_4H_9$ | H | H | H | H | pic |
| 1-348X | Rh | 1 | 1 | Fl | — | — | $^tC_4H_9$ | H | H | H | H | acac |

TABLE 22-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 1-348Y | Rh | 0 | 1 | | Fl | — | — | $^tC_4H_9$ | H | H | H | H | — | — |
| 1-349 | Rh | 1 | 1 | | Fl | — | — | $CH_3$ | H | H | H | H | pic | |
| 1-349X | Rh | 1 | 1 | | Fl | — | — | $CH_3$ | H | H | H | H | acac | |
| 1-349Y | Rh | 0 | 1 | | Fl | — | — | $CH_3$ | H | H | H | H | — | — |
| 1-350 | Rh | 1 | 1 | | Fl | — | — | $^tC_4H_9$ | $CH_3$ | H | H | H | pic | |
| 1-350X | Rh | 1 | 1 | | Fl | — | — | $^tC_4H_9$ | $CH_3$ | H | H | H | acac | |
| 1-350Y | Rh | 0 | 1 | | Fl | — | — | $^tC_4H_9$ | $CH_3$ | H | H | H | — | — |
| 1-351 | Rh | 1 | 1 | | Fl | — | — | $CH_3$ | $CH_3$ | H | H | H | pic | |
| 1-351X | Rh | 1 | 1 | | Fl | — | — | $CH_3$ | $CH_3$ | H | H | H | acac | |
| 1-351Y | Rh | 0 | 1 | | Fl | — | — | $CH_3$ | $CH_3$ | H | H | H | — | — |
| 1-352 | Rh | 1 | 1 | | Fl | — | — | H | $CH_3$ | H | H | H | pic | |
| 1-352X | Rh | 1 | 1 | | Fl | — | — | H | $CH_3$ | H | H | H | acac | |
| 1-352Y | Rh | 0 | 1 | | Fl | — | — | H | $CH_3$ | H | H | H | — | — |
| 1-353 | Rh | 1 | 1 | | Bz | — | — | H | H | H | H | H | pic | |
| 1-353X | Rh | 1 | 1 | | Bz | — | — | H | H | H | H | H | acac | |
| 1-353Y | Rh | 0 | 1 | | Bz | — | — | H | H | H | H | H | — | — |
| 1-354 | Rh | 1 | 1 | | Bz | — | — | $^tC_4H_9$ | H | H | H | H | pic | |
| 1-354X | Rh | 1 | 1 | | Bz | — | — | $^tC_4H_9$ | H | H | H | H | acac | |
| 1-354Y | Rh | 0 | 1 | | Bz | — | — | $^tC_4H_9$ | H | H | H | H | — | — |
| 1-355 | Rh | 1 | 1 | | Bz | — | — | $CH_3$ | H | H | H | H | pic | |
| 1-355X | Rh | 1 | 1 | | Bz | — | — | $CH_3$ | H | H | H | H | acac | |
| 1-355Y | Rh | 0 | 1 | | Bz | — | — | $CH_3$ | H | H | H | H | — | — |
| 1-356 | Rh | 1 | 1 | | Bz | — | — | $^tC_4H_9$ | $CH_3$ | H | H | H | pic | |
| 1-356X | Rh | 1 | 1 | | Bz | — | — | $^tC_4H_9$ | $CH_3$ | H | H | H | acac | |
| 1-356Y | Rh | 0 | 1 | | Bz | — | — | $^tC_4H_9$ | $CH_3$ | H | H | H | — | — |
| 1-357 | Rh | 1 | 1 | | Bz | — | — | $CH_3$ | $CH_3$ | H | H | H | pic | |
| 1-357X | Rh | 1 | 1 | | Bz | — | — | $CH_3$ | $CH_3$ | H | H | H | acac | |
| 1-357Y | Rh | 0 | 1 | | Bz | — | — | $CH_3$ | $CH_3$ | H | H | H | — | — |
| 1-358 | Rh | 1 | 1 | | Bz | — | — | H | $CH_3$ | H | H | H | pic | |
| 1-358X | Rh | 1 | 1 | | Bz | — | — | H | $CH_3$ | H | H | H | acac | |
| 1-358Y | Rh | 0 | 1 | | Bz | — | — | H | $CH_3$ | H | H | H | — | — |
| 1-359 | Rh | 1 | 1 | | Qu | — | — | H | H | H | H | H | pic | |
| 1-359X | Rh | 1 | 1 | | Qu | — | — | H | H | H | H | H | acac | |
| 1-359Y | Rh | 0 | 1 | | Qu | — | — | H | H | H | H | H | — | — |
| 1-360 | Rh | 1 | 1 | | Qu | — | — | $^tC_4H_9$ | H | H | H | H | pic | |
| 1-360X | Rh | 1 | 1 | | Qu | — | — | $^tC_4H_9$ | H | H | H | H | acac | |
| 1-360Y | Rh | 0 | 1 | | Qu | — | — | $^tC_4H_9$ | H | H | H | H | — | — |
| 1-361 | Rh | 1 | 1 | | Qu | — | — | $CH_3$ | H | H | H | H | pic | |
| 1-361X | Rh | 1 | 1 | | Qu | — | — | $CH_3$ | H | H | H | H | acac | |
| 1-361Y | Rh | 0 | 1 | | Qu | — | — | $CH_3$ | H | H | H | H | — | — |
| 1-362 | Rh | 1 | 1 | | Qu | — | — | $^tC_4H_9$ | $CH_3$ | H | H | H | pic | |
| 1-362X | Rh | 1 | 1 | | Qu | — | — | $^tC_4H_9$ | $CH_3$ | H | H | H | acac | |
| 1-362Y | Rh | 0 | 1 | | Qu | — | — | $^tC_4H_9$ | $CH_3$ | H | H | H | — | — |
| 1-363 | Rh | 1 | 1 | | Qu | — | — | $CH_3$ | $CH_3$ | H | H | H | pic | |
| 1-363X | Rh | 1 | 1 | | Qu | — | — | $CH_3$ | $CH_3$ | H | H | H | acac | |
| 1-363Y | Rh | 0 | 1 | | Qu | — | — | $CH_3$ | $CH_3$ | H | H | H | — | — |
| 1-364 | Rh | 1 | 1 | | Qu | — | — | H | $CH_3$ | H | H | H | pic | |
| 1-364X | Rh | 1 | 1 | | Qu | — | — | H | $CH_3$ | H | H | H | acac | |
| 1-364Y | Rh | 0 | 1 | | Qu | — | — | H | $CH_3$ | H | H | H | — | — |
| 1-365 | Rh | 1 | 1 | | OL | H | $^nC_4H_9$ | H | H | H | H | H | pic | |
| 1-365X | Rh | 1 | 1 | | OL | H | $^nC_4H_9$ | H | H | H | H | H | acac | |
| 1-365Y | Rh | 0 | 1 | | OL | H | $^nC_4H_9$ | H | H | H | H | H | — | — |
| 1-366 | Rh | 1 | 1 | | OL | H | $^tC_4H_9$ | H | H | H | H | H | pic | |
| 1-366X | Rh | 1 | 1 | | OL | H | $^tC_4H_9$ | H | H | H | H | H | acac | |
| 1-366Y | Rh | 0 | 1 | | OL | H | $^tC_4H_9$ | H | H | H | H | H | — | — |
| 1-367 | Rh | 1 | 1 | | OL | $CH_3$ | $^nC_4H_9$ | H | H | H | H | H | pic | |
| 1-367X | Rh | 1 | 1 | | OL | $CH_3$ | $^nC_4H_9$ | H | H | H | H | H | acac | |
| 1-367Y | Rh | 0 | 1 | | OL | $CH_3$ | $^nC_4H_9$ | H | H | H | H | H | — | — |
| 1-368 | Rh | 1 | 1 | | OL | $CH_3$ | $^tC_4H_9$ | H | H | H | H | H | pic | |
| 1-368X | Rh | 1 | 1 | | OL | $CH_3$ | $^tC_4H_9$ | H | H | H | H | H | acac | |
| 1-368Y | Rh | 0 | 1 | | OL | $CH_3$ | $^tC_4H_9$ | H | H | H | H | H | — | — |
| 1-369 | Rh | 1 | 1 | | OL | H | H | H | H | H | H | H | pic | |
| 1-369X | Rh | 1 | 1 | | OL | H | H | H | H | H | H | H | acac | |
| 1-369Y | Rh | 0 | 1 | | OL | H | H | H | H | H | H | H | — | — |
| 1-370 | Rh | 1 | 1 | | OL | H | $^nC_4H_9$ | $CH_3$ | H | H | H | H | pic | |
| 1-370X | Rh | 1 | 1 | | OL | H | $^nC_4H_9$ | $CH_3$ | H | H | H | H | acac | |
| 1-370Y | Rh | 0 | 1 | | OL | H | $^nC_4H_9$ | $CH_3$ | H | H | H | H | — | — |
| 1-371 | Rh | 1 | 1 | | OL | H | $^tC_4H_9$ | $CH_3$ | H | H | H | H | pic | |
| 1-371X | Rh | 1 | 1 | | OL | H | $^tC_4H_9$ | $CH_3$ | H | H | H | H | acac | |
| 1-371Y | Rh | 0 | 1 | | OL | H | $^tC_4H_9$ | $CH_3$ | H | H | H | H | — | — |
| 1-372 | Rh | 1 | 1 | | OL | —$CH_2CH_2CH_2$— | | H | H | H | H | H | pic | |
| 1-372X | Rh | 1 | 1 | | OL | —$CH_2CH_2CH_2$— | | H | H | H | H | H | acac | |
| 1-372Y | Rh | 0 | 1 | | OL | —$CH_2CH_2CH_2$— | | H | H | H | H | H | — | — |

-continued
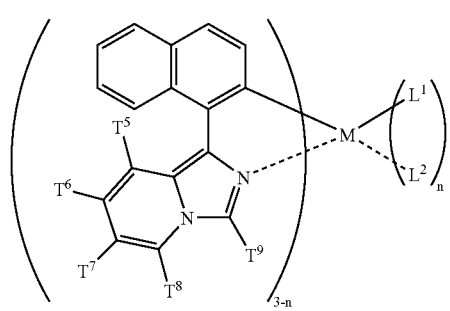
BSS 2, G:NAP1
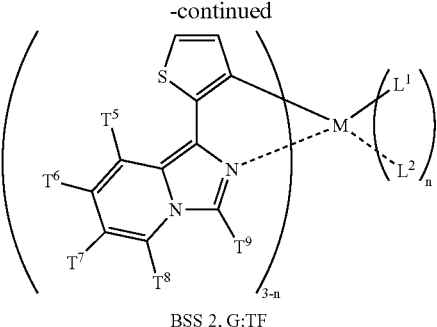
BSS 2, G:TF
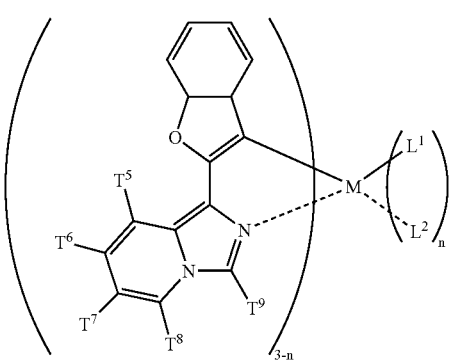
BSS 2, G:OB
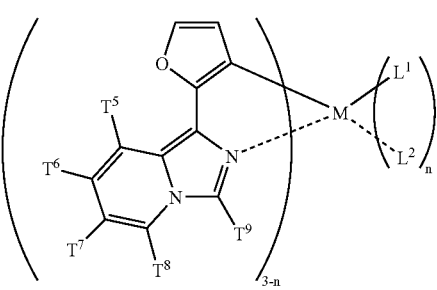
BSS 2, G:NAP2
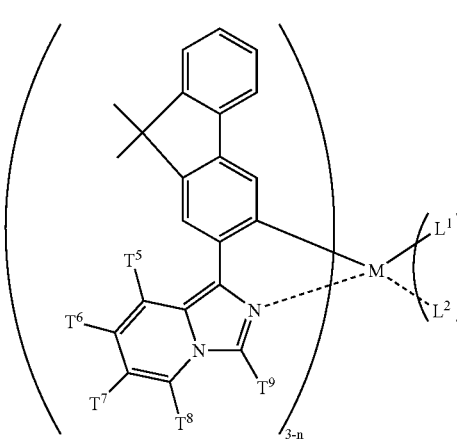
BSS 2, G:Fu
BSS 2, G:NAP3
BSS 2, G:TB
BSS 2, G:Fl

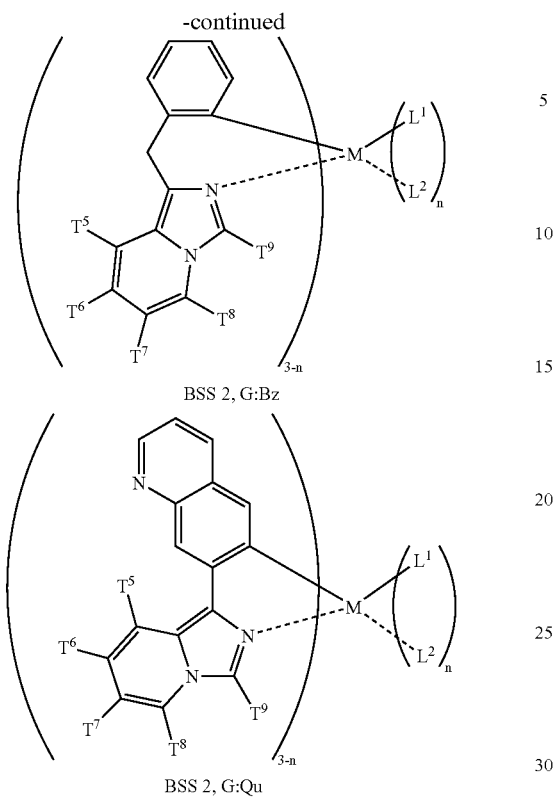
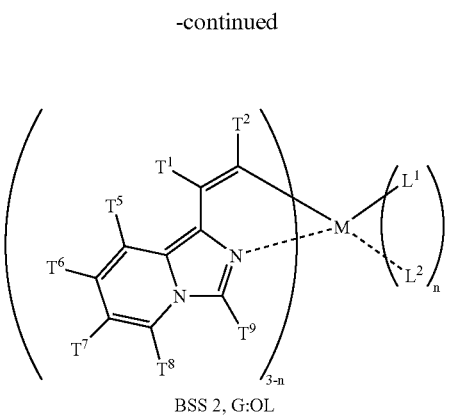

TABLE 23

| No. | M | n | BSS | SS | G | T¹ | T² | T⁵ | T⁶ | T⁷ | T⁸ | T⁹ | L¹ L² |
|---|---|---|---|---|---|---|---|---|---|---|---|---|---|
| 2-305 | Rh | 1 | 2 | | Nap1 | — | — | H | H | H | H | H | pic |
| 2-305X | Rh | 1 | 2 | | Nap1 | — | — | H | H | H | H | H | acac |
| 2-305Y | Rh | 0 | 2 | | Nap1 | — | — | H | H | H | H | H | — — |
| 2-306 | Rh | 1 | 2 | | Nap1 | — | — | $^tC_4H_9$ | H | H | H | H | pic |
| 2-306X | Rh | 1 | 2 | | Nap1 | — | — | $^tC_4H_9$ | H | H | H | H | acac |
| 2-306Y | Rh | 0 | 2 | | Nap1 | — | — | $^tC_4H_9$ | H | H | H | H | — — |
| 2-307 | Rh | 1 | 2 | | Nap1 | — | — | $CH_3$ | H | H | H | H | pic |
| 2-307X | Rh | 1 | 2 | | Nap1 | — | — | $CH_3$ | H | H | H | H | acac |
| 2-307Y | Rh | 0 | 2 | | Nap1 | — | — | $CH_3$ | H | H | H | H | — — |
| 2-308 | Rh | 1 | 2 | | Nap1 | — | — | $^tC_4H_9$ | H | H | $CH_3$ | H | pic |
| 2-308X | Rh | 1 | 2 | | Nap1 | — | — | $^tC_4H_9$ | H | H | $CH_3$ | H | acac |
| 2-308Y | Rh | 0 | 2 | | Nap1 | — | — | $^tC_4H_9$ | H | H | $CH_3$ | H | — — |
| 2-309 | Rh | 1 | 2 | | Nap1 | — | — | $CH_3$ | H | H | $CH_3$ | H | pic |
| 2-309X | Rh | 1 | 2 | | Nap1 | — | — | $CH_3$ | H | H | $CH_3$ | H | acac |
| 2-309Y | Rh | 0 | 2 | | Nap1 | — | — | $CH_3$ | H | H | $CH_3$ | H | — — |
| 2-310 | Rh | 1 | 2 | | Nap1 | — | — | H | H | H | $CH_3$ | H | pic |
| 2-310X | Rh | 1 | 2 | | Nap1 | — | — | H | H | H | $CH_3$ | H | acac |
| 2-310Y | Rh | 0 | 2 | | Nap1 | — | — | H | H | H | $CH_3$ | H | — — |
| 2-311 | Rh | 1 | 2 | | Nap2 | — | — | H | H | H | H | H | pic |
| 2-311X | Rh | 1 | 2 | | Nap2 | — | — | H | H | H | H | H | acac |
| 2-311Y | Rh | 0 | 2 | | Nap2 | — | — | H | H | H | H | H | — — |
| 2-312 | Rh | 1 | 2 | | Nap2 | — | — | $^tC_4H_9$ | H | H | H | H | pic |
| 2-312X | Rh | 1 | 2 | | Nap2 | — | — | $^tC_4H_9$ | H | H | H | H | acac |
| 2-312Y | Rh | 0 | 2 | | Nap2 | — | — | $^tC_4H_9$ | H | H | H | H | — — |
| 2-313 | Rh | 1 | 2 | | Nap2 | — | — | $CH_3$ | H | H | H | H | pic |
| 2-313X | Rh | 1 | 2 | | Nap2 | — | — | $CH_3$ | H | H | H | H | acac |
| 2-313Y | Rh | 0 | 2 | | Nap2 | — | — | $CH_3$ | H | H | H | H | — — |
| 2-314 | Rh | 1 | 2 | | Nap2 | — | — | $^tC_4H_9$ | H | H | $CH_3$ | H | pic |
| 2-314X | Rh | 1 | 2 | | Nap2 | — | — | $^tC_4H_9$ | H | H | $CH_3$ | H | acac |
| 2-314Y | Rh | 0 | 2 | | Nap2 | — | — | $^tC_4H_9$ | H | H | $CH_3$ | H | — — |
| 2-315 | Rh | 1 | 2 | | Nap2 | — | — | $CH_3$ | H | H | $CH_3$ | H | pic |
| 2-315X | Rh | 1 | 2 | | Nap2 | — | — | $CH_3$ | H | H | $CH_3$ | H | acac |
| 2-315Y | Rh | 0 | 2 | | Nap2 | — | — | $CH_3$ | H | H | $CH_3$ | H | — — |
| 2-316 | Rh | 1 | 2 | | Nap2 | — | — | H | H | H | $CH_3$ | H | pic |
| 2-316X | Rh | 1 | 2 | | Nap2 | — | — | H | H | H | $CH_3$ | H | acac |
| 2-316Y | Rh | 0 | 2 | | Nap2 | — | — | H | H | H | $CH_3$ | H | — — |

TABLE 23-continued

| No. | M | n | BSS | SS G | T¹ | T² | T⁵ | T⁶ | T⁷ | T⁸ | T⁹ | L¹ | L² |
|---|---|---|---|---|---|---|---|---|---|---|---|---|---|
| 2-317 | Rh | 1 | 2 | Nap3 | — | — | H | H | H | H | H | pic | |
| 2-317X | Rh | 1 | 2 | Nap3 | — | — | H | H | H | H | H | acac | |
| 2-317Y | Rh | 0 | 2 | Nap3 | — | — | H | H | H | H | H | — | |
| 2-318 | Rh | 1 | 2 | Nap3 | — | — | $^tC_4H_9$ | H | H | H | H | pic | |
| 2-318X | Rh | 1 | 2 | Nap3 | — | — | $^tC_4H_9$ | H | H | H | H | acac | |
| 2-318Y | Rh | 0 | 2 | Nap3 | — | — | $^tC_4H_9$ | H | H | H | H | — | |
| 2-319 | Rh | 1 | 2 | Nap3 | — | — | $CH_3$ | H | H | H | H | pic | |
| 2-319X | Rh | 1 | 2 | Nap3 | — | — | $CH_3$ | H | H | H | H | acac | |
| 2-319Y | Rh | 0 | 2 | Nap3 | — | — | $CH_3$ | H | H | H | H | — | |
| 2-320 | Rh | 1 | 2 | Nap3 | — | — | $^tC_4H_9$ | H | H | $CH_3$ | H | pic | |
| 2-320X | Rh | 1 | 2 | Nap3 | — | — | $^tC_4H_9$ | H | H | $CH_3$ | H | acac | |
| 2-320Y | Rh | 0 | 2 | Nap3 | — | — | $^tC_4H_9$ | H | H | $CH_3$ | H | — | |
| 2-321 | Rh | 1 | 2 | Nap3 | — | — | $CH_3$ | H | H | $CH_3$ | H | pic | |
| 2-321X | Rh | 1 | 2 | Nap3 | — | — | $CH_3$ | H | H | $CH_3$ | H | acac | |
| 2-321Y | Rh | 0 | 2 | Nap3 | — | — | $CH_3$ | H | H | $CH_3$ | H | — | |
| 2-322 | Rh | 1 | 2 | Nap3 | — | — | H | H | H | $CH_3$ | H | pic | |
| 2-322X | Rh | 1 | 2 | Nap3 | — | — | H | H | H | $CH_3$ | H | acac | |
| 2-322Y | Rh | 0 | 2 | Nap3 | — | — | H | H | H | $CH_3$ | H | — | |
| 2-323 | Rh | 1 | 2 | TB | — | — | H | H | H | H | H | pic | |
| 2-323X | Rh | 1 | 2 | TB | — | — | H | H | H | H | H | acac | |
| 2-323Y | Rh | 0 | 2 | TB | — | — | H | H | H | H | H | — | |
| 2-324 | Rh | 1 | 2 | TB | — | — | $^tC_4H_9$ | H | H | H | H | pic | |
| 2-324X | Rh | 1 | 2 | TB | — | — | $^tC_4H_9$ | H | H | H | H | acac | |
| 2-324Y | Rh | 0 | 2 | TB | — | — | $^tC_4H_9$ | H | H | H | H | — | |
| 2-325 | Rh | 1 | 2 | TB | — | — | $CH_3$ | H | H | H | H | pic | |
| 2-325X | Rh | 1 | 2 | TB | — | — | $CH_3$ | H | H | H | H | acac | |
| 2-325Y | Rh | 0 | 2 | TB | — | — | $CH_3$ | H | H | H | H | — | |
| 2-326 | Rh | 1 | 2 | TB | — | — | $^tC_4H_9$ | H | H | $CH_3$ | H | pic | |
| 2-326X | Rh | 1 | 2 | TB | — | — | $^tC_4H_9$ | H | H | $CH_3$ | H | acac | |
| 2-326Y | Rh | 0 | 2 | TB | — | — | $^tC_4H_9$ | H | H | $CH_3$ | H | — | |
| 2-327 | Rh | 1 | 2 | TB | — | — | $CH_3$ | H | H | $CH_3$ | H | pic | |
| 2-327X | Rh | 1 | 2 | TB | — | — | $CH_3$ | H | H | $CH_3$ | H | acac | |
| 2-327Y | Rh | 0 | 2 | TB | — | — | $CH_3$ | H | H | $CH_3$ | H | — | |
| 2-328 | Rh | 1 | 2 | TB | — | — | H | H | H | $CH_3$ | H | pic | |
| 2-328X | Rh | 1 | 2 | TB | — | — | H | H | H | $CH_3$ | H | acac | |
| 2-328Y | Rh | 0 | 2 | TB | — | — | H | H | H | $CH_3$ | H | — | |
| 2-329 | Rh | 1 | 2 | TF | — | — | H | H | H | H | H | pic | |
| 2-329X | Rh | 1 | 2 | TF | — | — | H | H | H | H | H | acac | |
| 2-329Y | Rh | 0 | 2 | TF | — | — | H | H | H | H | H | — | |
| 2-330 | Rh | 1 | 2 | TF | — | — | $^tC_4H_9$ | H | H | H | H | pic | |
| 2-330X | Rh | 1 | 2 | TF | — | — | $^tC_4H_9$ | H | H | H | H | acac | |
| 2-330Y | Rh | 0 | 2 | TF | — | — | $^tC_4H_9$ | H | H | H | H | — | |
| 2-331 | Rh | 1 | 2 | TF | — | — | $CH_3$ | H | H | H | H | pic | |
| 2-331X | Rh | 1 | 2 | TF | — | — | $CH_3$ | H | H | H | H | acac | |
| 2-331Y | Rh | 0 | 2 | TF | — | — | $CH_3$ | H | H | H | H | — | |
| 2-332 | Rh | 1 | 2 | TF | — | — | $^tC_4H_9$ | H | H | $CH_3$ | H | pic | |
| 2-332X | Rh | 1 | 2 | TF | — | — | $^tC_4H_9$ | H | H | $CH_3$ | H | acac | |
| 2-332Y | Rh | 0 | 2 | TF | — | — | $^tC_4H_9$ | H | H | $CH_3$ | H | — | |
| 2-333 | Rh | 1 | 2 | TF | — | — | $CH_3$ | H | H | $CH_3$ | H | pic | |
| 2-333X | Rh | 1 | 2 | TF | — | — | $CH_3$ | H | H | $CH_3$ | H | acac | |
| 2-333Y | Rh | 0 | 2 | TF | — | — | $CH_3$ | H | H | $CH_3$ | H | — | |
| 2-334 | Rh | 1 | 2 | TF | — | — | H | H | H | $CH_3$ | H | pic | |
| 2-334X | Rh | 1 | 2 | TF | — | — | H | H | H | $CH_3$ | H | acac | |
| 2-334Y | Rh | 0 | 2 | TF | — | — | H | H | H | $CH_3$ | H | — | |
| 2-335 | Rh | 1 | 2 | OB | — | — | H | H | H | H | H | pic | |
| 2-335X | Rh | 1 | 2 | OB | — | — | H | H | H | H | H | acac | |
| 2-335Y | Rh | 0 | 2 | OB | — | — | H | H | H | H | H | — | |
| 2-336 | Rh | 1 | 2 | OB | — | — | $^tC_4H_9$ | H | H | H | H | pic | |
| 2-336X | Rh | 1 | 2 | OB | — | — | $^tC_4H_9$ | H | H | H | H | acac | |
| 2-336Y | Rh | 0 | 2 | OB | — | — | $^tC_4H_9$ | H | H | H | H | — | |
| 2-337 | Rh | 1 | 2 | OB | — | — | $CH_3$ | H | H | H | H | pic | |
| 2-337X | Rh | 1 | 2 | OB | — | — | $CH_3$ | H | H | H | H | acac | |
| 2-337Y | Rh | 0 | 2 | OB | — | — | $CH_3$ | H | H | H | H | — | |
| 2-338 | Rh | 1 | 2 | OB | — | — | $^tC_4H_9$ | H | H | $CH_3$ | H | pic | |
| 2-338X | Rh | 1 | 2 | OB | — | — | $^tC_4H_9$ | H | H | $CH_3$ | H | acac | |
| 2-338Y | Rh | 0 | 2 | OB | — | — | $^tC_4H_9$ | H | H | $CH_3$ | H | — | |
| 2-339 | Rh | 1 | 2 | OB | — | — | $CH_3$ | H | H | $CH_3$ | H | pic | |
| 2-339X | Rh | 1 | 2 | OB | — | — | $CH_3$ | H | H | $CH_3$ | H | acac | |
| 2-339Y | Rh | 0 | 2 | OB | — | — | $CH_3$ | H | H | $CH_3$ | H | — | |
| 2-340 | Rh | 1 | 2 | OB | — | — | H | H | H | $CH_3$ | H | pic | |
| 2-340X | Rh | 1 | 2 | OB | — | — | H | H | H | $CH_3$ | H | acac | |
| 2-340Y | Rh | 0 | 2 | OB | — | — | H | H | H | $CH_3$ | H | — | |
| 2-341 | Rh | 1 | 2 | Fu | — | — | H | H | H | H | H | pic | |
| 2-341X | Rh | 1 | 2 | Fu | — | — | H | H | H | H | H | acac | |
| 2-341Y | Rh | 0 | 2 | Fu | — | — | H | H | H | H | H | — | |
| 2-342 | Rh | 1 | 2 | Fu | — | — | $^tC_4H_9$ | H | H | H | H | pic | |
| 2-342X | Rh | 1 | 2 | Fu | — | — | $^tC_4H_9$ | H | H | H | H | acac | |

TABLE 23-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 2-342Y | Rh | 0 | 2 | Fu | | — | — | $^tC_4H_9$ | H | H | H | H | — | — |
| 2-343 | Rh | 1 | 2 | Fu | | — | — | $CH_3$ | H | H | H | H | pic | |
| 2-343X | Rh | 1 | 2 | Fu | | — | — | $CH_3$ | H | H | H | H | acac | |
| 2-343Y | Rh | 0 | 2 | Fu | | — | — | $CH_3$ | H | H | H | H | — | — |
| 2-344 | Rh | 1 | 2 | Fu | | — | — | $^tC_4H_9$ | H | H | $CH_3$ | H | pic | |
| 2-344X | Rh | 1 | 2 | Fu | | — | — | $^tC_4H_9$ | H | H | $CH_3$ | H | acac | |
| 2-344Y | Rh | 0 | 2 | Fu | | — | — | $^tC_4H_9$ | H | H | $CH_3$ | H | — | — |
| 2-345 | Rh | 1 | 2 | Fu | | — | — | $CH_3$ | H | H | $CH_3$ | H | pic | |
| 2-345X | Rh | 1 | 2 | Fu | | — | — | $CH_3$ | H | H | $CH_3$ | H | acac | |
| 2-345Y | Rh | 0 | 2 | Fu | | — | — | $CH_3$ | H | H | $CH_3$ | H | — | — |
| 2-346 | Rh | 1 | 2 | Fu | | — | — | H | H | H | $CH_3$ | H | pic | |
| 2-346X | Rh | 1 | 2 | Fu | | — | — | H | H | H | $CH_3$ | H | acac | |
| 2-346Y | Rh | 0 | 2 | Fu | | — | — | H | H | H | $CH_3$ | H | — | — |
| 2-347 | Rh | 1 | 2 | Fl | | — | — | H | H | H | H | H | pic | |
| 2-347X | Rh | 1 | 2 | Fl | | — | — | H | H | H | H | H | acac | |
| 2-347Y | Rh | 0 | 2 | Fl | | — | — | H | H | H | H | H | — | — |
| 2-348 | Rh | 1 | 2 | Fl | | — | — | $^tC_4H_9$ | H | H | H | H | pic | |
| 2-348X | Rh | 1 | 2 | Fl | | — | — | $^tC_4H_9$ | H | H | H | H | acac | |
| 2-348Y | Rh | 0 | 2 | Fl | | — | — | $^tC_4H_9$ | H | H | H | H | — | — |
| 2-349 | Rh | 1 | 2 | Fl | | — | — | $CH_3$ | H | H | H | H | pic | |
| 2-349X | Rh | 1 | 2 | Fl | | — | — | $CH_3$ | H | H | H | H | acac | |
| 2-349Y | Rh | 0 | 2 | Fl | | — | — | $CH_3$ | H | H | H | H | — | — |
| 2-350 | Rh | 1 | 2 | Fl | | — | — | $^tC_4H_9$ | H | H | $CH_3$ | H | pic | |
| 2-350X | Rh | 1 | 2 | Fl | | — | — | $^tC_4H_9$ | H | H | $CH_3$ | H | acac | |
| 2-350Y | Rh | 0 | 2 | Fl | | — | — | $^tC_4H_9$ | H | H | $CH_3$ | H | — | — |
| 2-351 | Rh | 1 | 2 | Fl | | — | — | $CH_3$ | H | H | $CH_3$ | H | pic | |
| 2-351X | Rh | 1 | 2 | Fl | | — | — | $CH_3$ | H | H | $CH_3$ | H | acac | |
| 2-351Y | Rh | 0 | 2 | Fl | | — | — | $CH_3$ | H | H | $CH_3$ | H | — | — |
| 2-352 | Rh | 1 | 2 | Fl | | — | — | H | H | H | $CH_3$ | H | pic | |
| 2-352X | Rh | 1 | 2 | Fl | | — | — | H | H | H | $CH_3$ | H | acac | |
| 2-352Y | Rh | 0 | 2 | Fl | | — | — | H | H | H | $CH_3$ | H | — | — |
| 2-353 | Rh | 1 | 2 | Bz | | — | — | H | H | H | H | H | pic | |
| 2-353X | Rh | 1 | 2 | Bz | | — | — | H | H | H | H | H | acac | |
| 2-353Y | Rh | 0 | 2 | Bz | | — | — | H | H | H | H | H | — | — |
| 2-354 | Rh | 1 | 2 | Bz | | — | — | $^tC_4H_9$ | H | H | H | H | pic | |
| 2-354X | Rh | 1 | 2 | Bz | | — | — | $^tC_4H_9$ | H | H | H | H | acac | |
| 2-354Y | Rh | 0 | 2 | Bz | | — | — | $^tC_4H_9$ | H | H | H | H | — | — |
| 2-355 | Rh | 1 | 2 | Bz | | — | — | $CH_3$ | H | H | H | H | pic | |
| 2-355X | Rh | 1 | 2 | Bz | | — | — | $CH_3$ | H | H | H | H | acac | |
| 2-355Y | Rh | 0 | 2 | Bz | | — | — | $CH_3$ | H | H | H | H | — | — |
| 2-356 | Rh | 1 | 2 | Bz | | — | — | $^tC_4H_9$ | H | H | $CH_3$ | H | pic | |
| 2-356X | Rh | 1 | 2 | Bz | | — | — | $^tC_4H_9$ | H | H | $CH_3$ | H | acac | |
| 2-356Y | Rh | 0 | 2 | Bz | | — | — | $^tC_4H_9$ | H | H | $CH_3$ | H | — | — |
| 2-357 | Rh | 1 | 2 | Bz | | — | — | $CH_3$ | H | H | $CH_3$ | H | pic | |
| 2-357X | Rh | 1 | 2 | Bz | | — | — | $CH_3$ | H | H | $CH_3$ | H | acac | |
| 2-357Y | Rh | 0 | 2 | Bz | | — | — | $CH_3$ | H | H | $CH_3$ | H | — | — |
| 2-358 | Rh | 1 | 2 | Bz | | — | — | H | H | H | $CH_3$ | H | pic | |
| 2-358X | Rh | 1 | 2 | Bz | | — | — | H | H | H | $CH_3$ | H | acac | |
| 2-358Y | Rh | 0 | 2 | Bz | | — | — | H | H | H | $CH_3$ | H | — | — |
| 2-359 | Rh | 1 | 2 | Qu | | — | — | H | H | H | H | H | pic | |
| 2-359X | Rh | 1 | 2 | Qu | | — | — | H | H | H | H | H | acac | |
| 2-359Y | Rh | 0 | 2 | Qu | | — | — | H | H | H | H | H | — | — |
| 2-360 | Rh | 1 | 2 | Qu | | — | — | $^tC_4H_9$ | H | H | H | H | pic | |
| 2-360X | Rh | 1 | 2 | Qu | | — | — | $^tC_4H_9$ | H | H | H | H | acac | |
| 2-360Y | Rh | 0 | 2 | Qu | | — | — | $^tC_4H_9$ | H | H | H | H | — | — |
| 2-361 | Rh | 1 | 2 | Qu | | — | — | $CH_3$ | H | H | H | H | pic | |
| 2-361X | Rh | 1 | 2 | Qu | | — | — | $CH_3$ | H | H | H | H | acac | |
| 2-361Y | Rh | 0 | 2 | Qu | | — | — | $CH_3$ | H | H | H | H | — | — |
| 2-362 | Rh | 1 | 2 | Qu | | — | — | $^tC_4H_9$ | H | H | $CH_3$ | H | pic | |
| 2-362X | Rh | 1 | 2 | Qu | | — | — | $^tC_4H_9$ | H | H | $CH_3$ | H | acac | |
| 2-362Y | Rh | 0 | 2 | Qu | | — | — | $^tC_4H_9$ | H | H | $CH_3$ | H | — | — |
| 2-363 | Rh | 1 | 2 | Qu | | — | — | $CH_3$ | H | H | $CH_3$ | H | pic | |
| 2-363X | Rh | 1 | 2 | Qu | | — | — | $CH_3$ | H | H | $CH_3$ | H | acac | |
| 2-363Y | Rh | 0 | 2 | Qu | | — | — | $CH_3$ | H | H | $CH_3$ | H | — | — |
| 2-364 | Rh | 1 | 2 | Qu | | — | — | H | H | H | $CH_3$ | H | pic | |
| 2-364X | Rh | 1 | 2 | Qu | | — | — | H | H | H | $CH_3$ | H | acac | |
| 2-364Y | Rh | 0 | 2 | Qu | | — | — | H | H | H | $CH_3$ | H | — | — |
| 2-365 | Rh | 1 | 2 | OL | | H | $^nC_4H_9$ | H | H | H | H | H | pic | |
| 2-365X | Rh | 1 | 2 | OL | | H | $^nC_4H_9$ | H | H | H | H | H | acac | |
| 2-365Y | Rh | 0 | 2 | OL | | H | $^nC_4H_9$ | H | H | H | H | H | — | — |
| 2-366 | Rh | 1 | 2 | OL | | H | $^tC_4H_9$ | H | H | H | H | H | pic | |
| 2-366X | Rh | 1 | 2 | OL | | H | $^tC_4H_9$ | H | H | H | H | H | acac | |
| 2-366Y | Rh | 0 | 2 | OL | | H | $^tC_4H_9$ | H | H | H | H | H | — | — |
| 2-367 | Rh | 1 | 2 | OL | | $CH_3$ | $^nC_4H_9$ | H | H | H | H | H | pic | |
| 2-367X | Rh | 1 | 2 | OL | | $CH_3$ | $^nC_4H_9$ | H | H | H | H | H | acac | |
| 2-367Y | Rh | 0 | 2 | OL | | $CH_3$ | $^nC_4H_9$ | H | H | H | H | H | — | — |
| 2-368 | Rh | 1 | 2 | OL | | $CH_3$ | $^tC_4H_9$ | H | H | H | H | H | pic | |

TABLE 23-continued

| No. | M | n | BSS | SS | G | T¹ | T² | T⁵ | T⁶ | T⁷ | T⁸ | T⁹ | L¹ L² |
|---|---|---|---|---|---|---|---|---|---|---|---|---|---|
| 2-368X | Rh | 1 | 2 | | OL | CH₃ | $^tC_4H_9$ | H | H | H | H | H | acac |
| 2-368Y | Rh | 0 | 2 | | OL | CH₃ | $^tC_4H_9$ | H | H | H | H | H | — — |
| 2-369 | Rh | 1 | 2 | | OL | H | H | H | H | H | H | H | pic |
| 2-369X | Rh | 1 | 2 | | OL | H | H | H | H | H | H | H | acac |
| 2-369Y | Rh | 0 | 2 | | OL | H | H | H | H | H | H | H | — — |
| 2-370 | Rh | 1 | 2 | | OL | H | $^nC_4H_9$ | CH₃ | H | H | H | H | pic |
| 2-370X | Rh | 1 | 2 | | OL | H | $^nC_4H_9$ | CH₃ | H | H | H | H | acac |
| 2-370Y | Rh | 0 | 2 | | OL | H | $^nC_4H_9$ | CH₃ | H | H | H | H | — — |
| 2-371 | Rh | 1 | 2 | | OL | H | $^tC_4H_9$ | CH₃ | H | H | H | H | pic |
| 2-371X | Rh | 1 | 2 | | OL | H | $^tC_4H_9$ | CH₃ | H | H | H | H | acac |
| 2-371Y | Rh | 0 | 2 | | OL | H | $^tC_4H_9$ | CH₃ | H | H | H | H | — — |
| 2-372 | Rh | 1 | 2 | | OL | —CH₂CH₂CH₂— | | H | H | H | H | H | pic |
| 2-372X | Rh | 1 | 2 | | OL | —CH₂CH₂CH₂— | | H | H | H | H | H | acac |
| 2-372Y | Rh | 0 | 2 | | OL | —CH₂CH₂CH₂— | | H | H | H | H | H | — — |

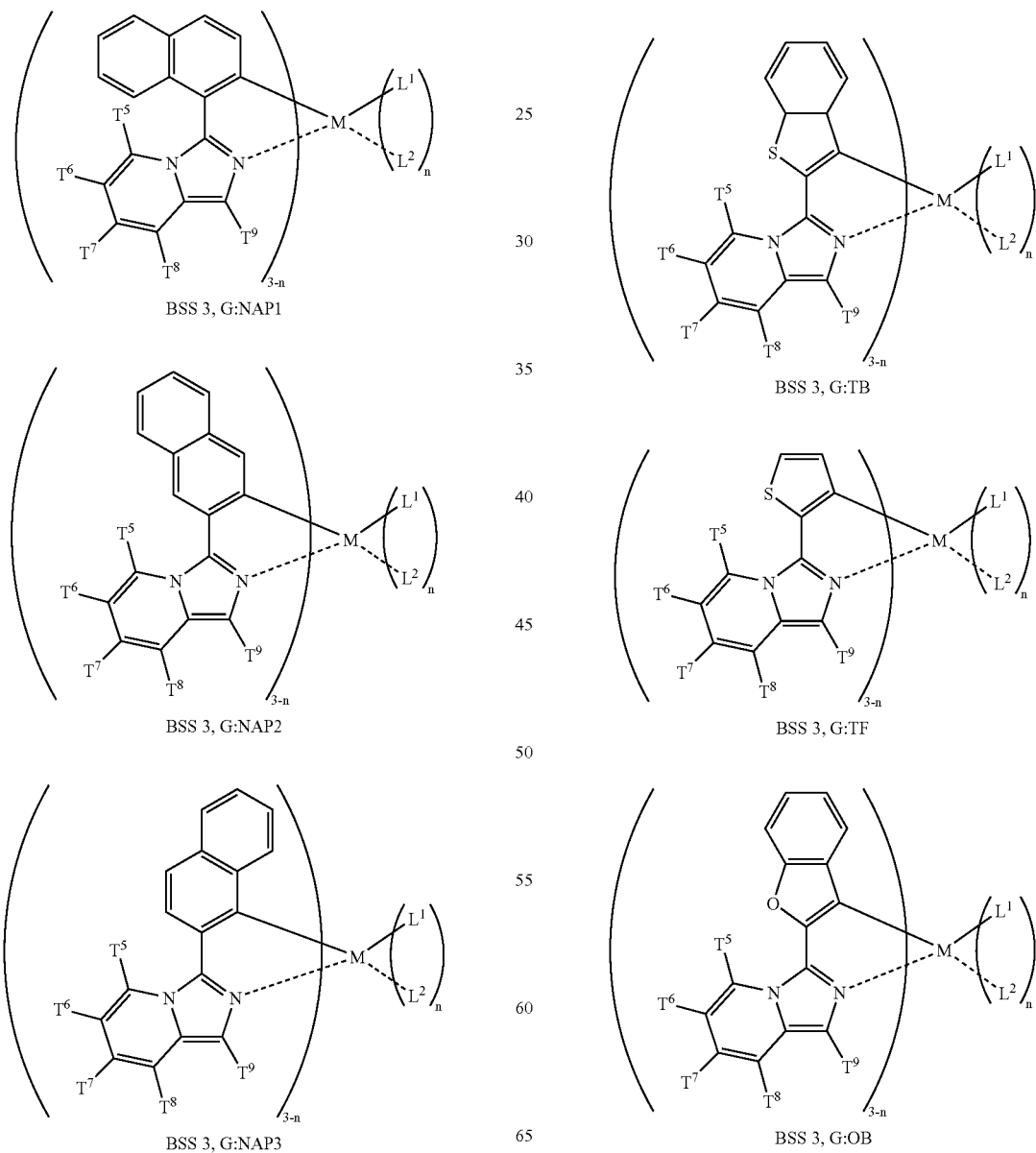

-continued

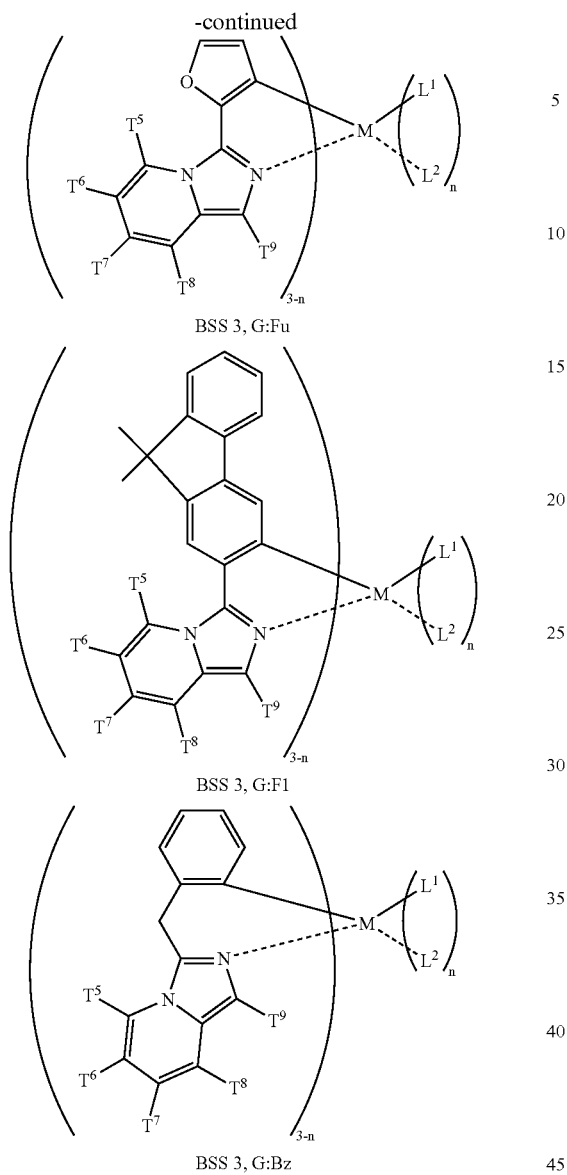

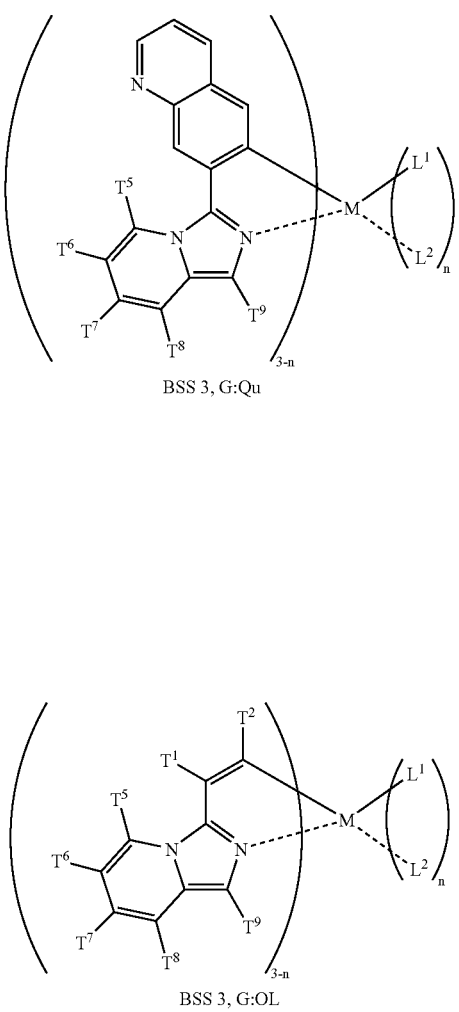

TABLE 24

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 3-271 | Rh | 1 | 3 | | Nap1 | — | — | H | H | H | H | H | pic | |
| 3-271X | Rh | 1 | 3 | | Nap1 | — | — | H | H | H | H | H | acac | |
| 3-271Y | Rh | 0 | 3 | | Nap1 | — | — | H | H | H | H | H | — | — |
| 3-272 | Rh | 1 | 3 | | Nap1 | — | — | $^tC_4H_9$ | H | H | H | H | pic | |
| 3-272X | Rh | 1 | 3 | | Nap1 | — | — | $^tC_4H_9$ | H | H | H | H | acac | |
| 3-272Y | Rh | 0 | 3 | | Nap1 | — | — | $^tC_4H_9$ | H | H | H | H | — | — |
| 3-273 | Rh | 1 | 3 | | Nap1 | — | — | $CH_3$ | H | H | H | H | pic | |
| 3-273X | Rh | 1 | 3 | | Nap1 | — | — | $CH_3$ | H | H | H | H | acac | |
| 3-273Y | Rh | 0 | 3 | | Nap1 | — | — | $CH_3$ | H | H | H | H | — | — |
| 3-274 | Rh | 1 | 3 | | Nap2 | — | — | H | H | H | H | H | pic | |
| 3-274X | Rh | 1 | 3 | | Nap2 | — | — | H | H | H | H | H | acac | |
| 3-274Y | Rh | 0 | 3 | | Nap2 | — | — | H | H | H | H | H | — | — |
| 3-275 | Rh | 1 | 3 | | Nap2 | — | — | $^tC_4H_9$ | H | H | H | H | pic | |
| 3-275X | Rh | 1 | 3 | | Nap2 | — | — | $^tC_4H_9$ | H | H | H | H | acac | |
| 3-275Y | Rh | 0 | 3 | | Nap2 | — | — | $^tC_4H_9$ | H | H | H | H | — | — |
| 3-276 | Rh | 1 | 3 | | Nap2 | — | — | $CH_3$ | H | H | H | H | pic | |
| 3-276X | Rh | 1 | 3 | | Nap2 | — | — | $CH_3$ | H | H | H | H | acac | |
| 3-276Y | Rh | 0 | 3 | | Nap2 | — | — | $CH_3$ | H | H | H | H | — | — |

TABLE 24-continued

| No. | M | n | BSS | SS G | T¹ | T² | T⁵ | T⁶ | T⁷ | T⁸ | T⁹ | L¹ | L² |
|---|---|---|---|---|---|---|---|---|---|---|---|---|---|
| 3-277 | Rh | 1 | 3 | Nap3 | — | — | H | H | H | H | H | pic | |
| 3-277X | Rh | 1 | 3 | Nap3 | — | — | H | H | H | H | H | acac | |
| 3-277Y | Rh | 0 | 3 | Nap3 | — | — | H | H | H | H | H | — | — |
| 3-278 | Rh | 1 | 3 | Nap3 | — | — | $^tC_4H_9$ | H | H | H | H | pic | |
| 3-278X | Rh | 1 | 3 | Nap3 | — | — | $^tC_4H_9$ | H | H | H | H | acac | |
| 3-278Y | Rh | 0 | 3 | Nap3 | — | — | $^tC_4H_9$ | H | H | H | H | — | — |
| 3-279 | Rh | 1 | 3 | Nap3 | — | — | $CH_3$ | H | H | H | H | pic | |
| 3-279X | Rh | 1 | 3 | Nap3 | — | — | $CH_3$ | H | H | H | H | acac | |
| 3-279Y | Rh | 0 | 3 | Nap3 | — | — | $CH_3$ | H | H | H | H | — | — |
| 3-280 | Rh | 1 | 3 | TB | — | — | H | H | H | H | H | pic | |
| 3-280X | Rh | 1 | 3 | TB | — | — | H | H | H | H | H | acac | |
| 3-280Y | Rh | 0 | 3 | TB | — | — | H | H | H | H | H | — | — |
| 3-281 | Rh | 1 | 3 | TB | — | — | $^tC_4H_9$ | H | H | H | H | pic | |
| 3-281X | Rh | 1 | 3 | TB | — | — | $^tC_4H_9$ | H | H | H | H | acac | |
| 3-281Y | Rh | 0 | 3 | TB | — | — | $^tC_4H_9$ | H | H | H | H | — | — |
| 3-282 | Rh | 1 | 3 | TB | — | — | $CH_3$ | H | H | H | H | pic | |
| 3-282X | Rh | 1 | 3 | TB | — | — | $CH_3$ | H | H | H | H | acac | |
| 3-282Y | Rh | 0 | 3 | TB | — | — | $CH_3$ | H | H | H | H | — | — |
| 3-283 | Rh | 1 | 3 | TF | — | — | H | H | H | H | H | pic | |
| 3-283X | Rh | 1 | 3 | TF | — | — | H | H | H | H | H | acac | |
| 3-283Y | Rh | 0 | 3 | TF | — | — | H | H | H | H | H | — | — |
| 3-284 | Rh | 1 | 3 | TF | — | — | $^tC_4H_9$ | H | H | H | H | pic | |
| 3-284X | Rh | 1 | 3 | TF | — | — | $^tC_4H_9$ | H | H | H | H | acac | |
| 3-284Y | Rh | 0 | 3 | TF | — | — | $^tC_4H_9$ | H | H | H | H | — | — |
| 3-285 | Rh | 1 | 3 | TF | — | — | $CH_3$ | H | H | H | H | pic | |
| 3-285X | Rh | 1 | 3 | TF | — | — | $CH_3$ | H | H | H | H | acac | |
| 3-285Y | Rh | 0 | 3 | TF | — | — | $CH_3$ | H | H | H | H | — | — |
| 3-286 | Rh | 1 | 3 | OB | — | — | H | H | H | H | H | pic | |
| 3-286X | Rh | 1 | 3 | OB | — | — | H | H | H | H | H | acac | |
| 3-286Y | Rh | 0 | 3 | OB | — | — | H | H | H | H | H | — | — |
| 3-287 | Rh | 1 | 3 | OB | — | — | $^tC_4H_9$ | H | H | H | H | pic | |
| 3-287X | Rh | 1 | 3 | OB | — | — | $^tC_4H_9$ | H | H | H | H | acac | |
| 3-287Y | Rh | 0 | 3 | OB | — | — | $^tC_4H_9$ | H | H | H | H | — | — |
| 3-288 | Rh | 1 | 3 | OB | — | — | $CH_3$ | H | H | H | H | pic | |
| 3-288X | Rh | 1 | 3 | OB | — | — | $CH_3$ | H | H | H | H | acac | |
| 3-288Y | Rh | 0 | 3 | OB | — | — | $CH_3$ | H | H | H | H | — | — |
| 3-289 | Rh | 1 | 3 | Fu | — | — | H | H | H | H | H | pic | |
| 3-289X | Rh | 1 | 3 | Fu | — | — | H | H | H | H | H | acac | |
| 3-289Y | Rh | 0 | 3 | Fu | — | — | H | H | H | H | H | — | — |
| 3-290 | Rh | 1 | 3 | Fu | — | — | $^tC_4H_9$ | H | H | H | H | pic | |
| 3-290X | Rh | 1 | 3 | Fu | — | — | $^tC_4H_9$ | H | H | H | H | acac | |
| 3-290Y | Rh | 0 | 3 | Fu | — | — | $^tC_4H_9$ | H | H | H | H | — | — |
| 3-291 | Rh | 1 | 3 | Fu | — | — | $CH_3$ | H | H | H | H | pic | |
| 3-291X | Rh | 1 | 3 | Fu | — | — | $CH_3$ | H | H | H | H | acac | |
| 3-291Y | Rh | 0 | 3 | Fu | — | — | $CH_3$ | H | H | H | H | — | — |
| 3-292 | Rh | 1 | 3 | Fl | — | — | H | H | H | H | H | pic | |
| 3-292X | Rh | 1 | 3 | Fl | — | — | H | H | H | H | H | acac | |
| 3-292Y | Rh | 0 | 3 | Fl | — | — | H | H | H | H | H | — | — |
| 3-293 | Rh | 1 | 3 | Fl | — | — | $^tC_4H_9$ | H | H | H | H | pic | |
| 3-293X | Rh | 1 | 3 | Fl | — | — | $^tC_4H_9$ | H | H | H | H | acac | |
| 3-293Y | Rh | 0 | 3 | Fl | — | — | $^tC_4H_9$ | H | H | H | H | — | — |
| 3-294 | Rh | 1 | 3 | Fl | — | — | $CH_3$ | H | H | H | H | pic | |
| 3-294X | Rh | 1 | 3 | Fl | — | — | $CH_3$ | H | H | H | H | acac | |
| 3-294Y | Rh | 0 | 3 | Fl | — | — | $CH_3$ | H | H | H | H | — | — |
| 3-295 | Rh | 1 | 3 | Bz | — | — | H | H | H | H | H | pic | |
| 3-295X | Rh | 1 | 3 | Bz | — | — | H | H | H | H | H | acac | |
| 3-295Y | Rh | 0 | 3 | Bz | — | — | H | H | H | H | H | — | — |
| 3-296 | Rh | 1 | 3 | Bz | — | — | $^tC_4H_9$ | H | H | H | H | pic | |
| 3-296X | Rh | 1 | 3 | Bz | — | — | $^tC_4H_9$ | H | H | H | H | acac | |
| 3-296Y | Rh | 0 | 3 | Bz | — | — | $^tC_4H_9$ | H | H | H | H | — | — |
| 3-297 | Rh | 1 | 3 | Bz | — | — | $CH_3$ | H | H | H | H | pic | |
| 3-297X | Rh | 1 | 3 | Bz | — | — | $CH_3$ | H | H | H | H | acac | |
| 3-297Y | Rh | 0 | 3 | Bz | — | — | $CH_3$ | H | H | H | H | — | — |
| 3-298 | Rh | 1 | 3 | Qu | — | — | H | H | H | H | H | pic | |
| 3-298X | Rh | 1 | 3 | Qu | — | — | H | H | H | H | H | acac | |
| 3-298Y | Rh | 0 | 3 | Qu | — | — | H | H | H | H | H | — | — |
| 3-299 | Rh | 1 | 3 | Qu | — | — | $^tC_4H_9$ | H | H | H | H | pic | |
| 3-299X | Rh | 1 | 3 | Qu | — | — | $^tC_4H_9$ | H | H | H | H | acac | |
| 3-299Y | Rh | 0 | 3 | Qu | — | — | $^tC_4H_9$ | H | H | H | H | — | — |
| 3-300 | Rh | 1 | 3 | Qu | — | — | $CH_3$ | H | H | H | H | pic | |
| 3-300X | Rh | 1 | 3 | Qu | — | — | $CH_3$ | H | H | H | H | acac | |
| 3-300Y | Rh | 0 | 3 | Qu | — | — | $CH_3$ | H | H | H | H | — | — |
| 3-301 | Rh | 1 | 3 | OL | H | $^nC_4H_9$ | H | H | H | H | H | pic | |
| 3-301X | Rh | 1 | 3 | OL | H | $^nC_4H_9$ | H | H | H | H | H | acac | |

TABLE 24-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 3-301Y | Rh | 0 | 3 | OL | | H | $^nC_4H_9$ | H | H | H | H | H | — | — |
| 3-302 | Rh | 1 | 3 | OL | | H | $^tC_4H_9$ | H | H | H | H | H | pic | |
| 3-302X | Rh | 1 | 3 | OL | | H | $^tC_4H_9$ | H | H | H | H | H | acac | |
| 3-302Y | Rh | 0 | 3 | OL | | H | $^tC_4H_9$ | H | H | H | H | H | — | — |
| 3-303 | Rh | 1 | 3 | OL | | $CH_3$ | $^nC_4H_9$ | H | H | H | H | H | pic | |
| 3-303X | Rh | 1 | 3 | OL | | $CH_3$ | $^nC_4H_9$ | H | H | H | H | H | acac | |
| 3-303Y | Rh | 0 | 3 | OL | | $CH_3$ | $^nC_4H_9$ | H | H | H | H | H | — | — |
| 3-304 | Rh | 1 | 3 | OL | | $CH_3$ | $^tC_4H_9$ | H | H | H | H | H | pic | |
| 3-304X | Rh | 1 | 3 | OL | | $CH_3$ | $^tC_4H_9$ | H | H | H | H | H | acac | |
| 3-304Y | Rh | 0 | 3 | OL | | $CH_3$ | $^tC_4H_9$ | H | H | H | H | H | — | — |
| 3-305 | Rh | 1 | 3 | OL | | H | H | H | H | H | H | H | pic | |
| 3-305X | Rh | 1 | 3 | OL | | H | H | H | H | H | H | H | acac | |
| 3-305Y | Rh | 0 | 3 | OL | | H | H | H | H | H | H | H | — | — |
| 3-306 | Rh | 1 | 3 | OL | | H | $^nC_4H_9$ | $CH_3$ | H | H | H | H | pic | |
| 3-306X | Rh | 1 | 3 | OL | | H | $^nC_4H_9$ | $CH_3$ | H | H | H | H | acac | |
| 3-306Y | Rh | 0 | 3 | OL | | H | $^nC_4H_9$ | $CH_3$ | H | H | H | H | — | — |
| 3-307 | Rh | 1 | 3 | OL | | H | $^tC_4H_9$ | $CH_3$ | H | H | H | H | pic | |
| 3-307X | Rh | 1 | 3 | OL | | H | $^tC_4H_9$ | $CH_3$ | H | H | H | H | acac | |
| 3-307Y | Rh | 0 | 3 | OL | | H | $^tC_4H_9$ | $CH_3$ | H | H | H | H | — | — |
| 3-308 | Rh | 1 | 3 | OL | | —$CH_2CH_2CH_2$— | | H | H | H | H | H | pic | |
| 3-308X | Rh | 1 | 3 | OL | | —$CH_2CH_2CH_2$— | | H | H | H | H | H | acac | |
| 3-308Y | Rh | 0 | 3 | OL | | —$CH_2CH_2CH_2$— | | H | H | H | H | H | — | — |

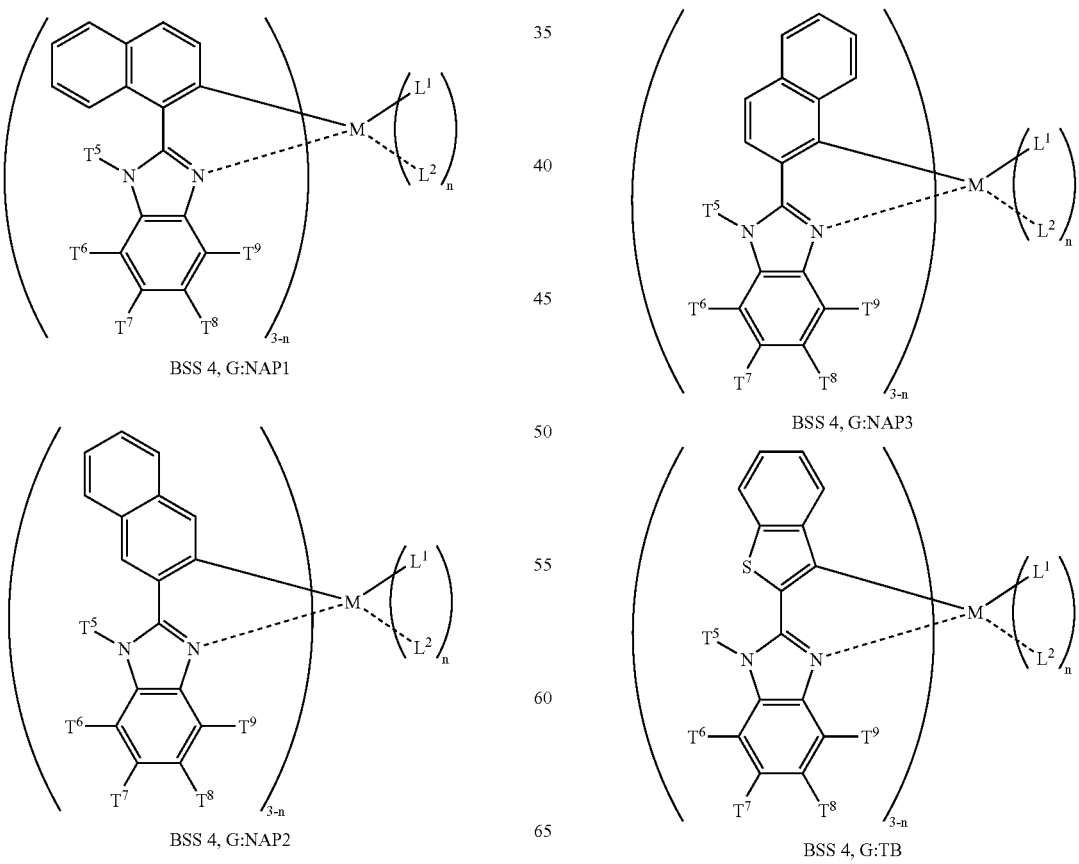

BSS 4, G:NAP1

BSS 4, G:NAP3

BSS 4, G:NAP2

BSS 4, G:TB

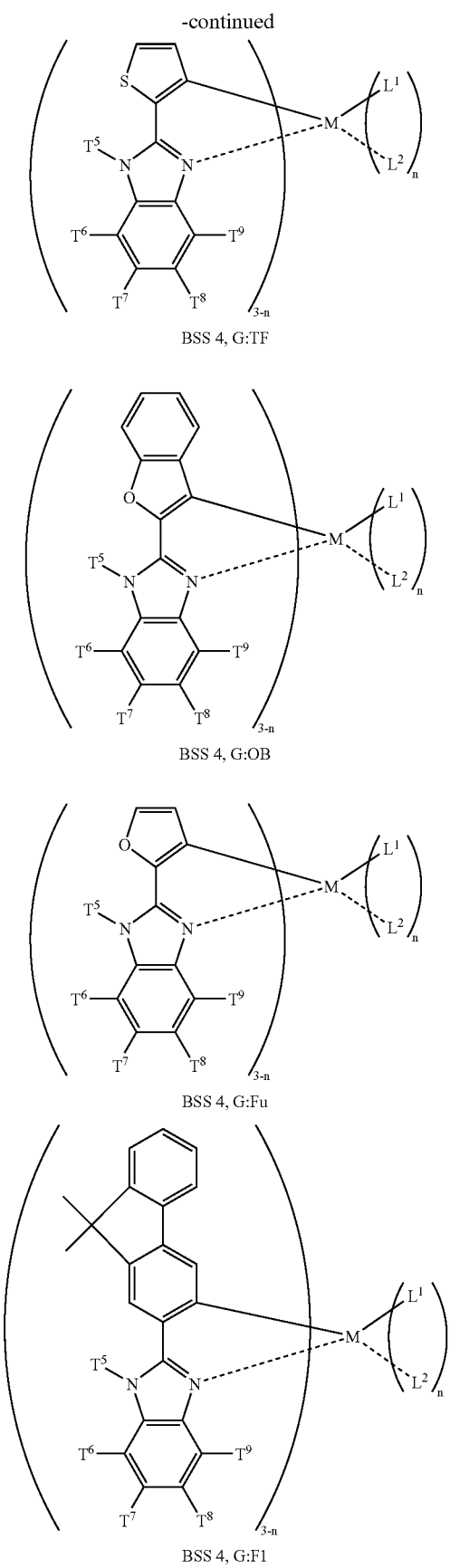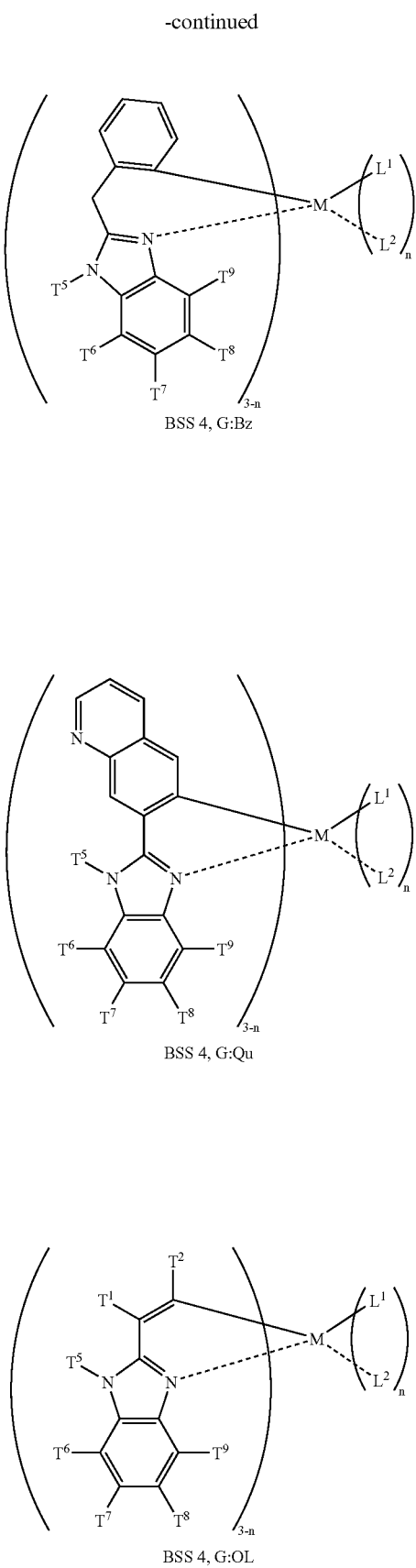

TABLE 25

| No. | M | n | BSS | SS G | T¹ | T² | T⁵ | T⁶ | T⁷ | T⁸ | T⁹ | L¹ L² |
|---|---|---|---|---|---|---|---|---|---|---|---|---|
| 4-304 | Rh | 1 | 4 | Nap1 | — | — | $CH_3$ | H | H | H | H | pic |
| 4-304X | Rh | 1 | 4 | Nap1 | — | — | $CH_3$ | H | H | H | H | acac |
| 4-304Y | Rh | 0 | 4 | Nap1 | — | — | $CH_3$ | H | H | H | H | — — |
| 4-305 | Rh | 1 | 4 | Nap1 | — | — | $^tC_4H_9$ | H | H | H | H | pic |
| 4-305X | Rh | 1 | 4 | Nap1 | — | — | $^tC_4H_9$ | H | H | H | H | acac |
| 4-305Y | Rh | 0 | 4 | Nap1 | — | — | $^tC_4H_9$ | H | H | H | H | — — |
| 4-306 | Rh | 1 | 4 | Nap2 | — | — | $CH_3$ | H | H | H | H | pic |
| 4-306X | Rh | 1 | 4 | Nap2 | — | — | $CH_3$ | H | H | H | H | acac |
| 4-306Y | Rh | 0 | 4 | Nap2 | — | — | $CH_3$ | H | H | H | H | — — |
| 4-307 | Rh | 1 | 4 | Nap2 | — | — | $^tC_4H_9$ | H | H | H | H | pic |
| 4-307X | Rh | 1 | 4 | Nap2 | — | — | $^tC_4H_9$ | H | H | H | H | acac |
| 4-307Y | Rh | 0 | 4 | Nap2 | — | — | $^tC_4H_9$ | H | H | H | H | — — |
| 4-308 | Rh | 1 | 4 | Nap3 | — | — | $CH_3$ | H | H | H | H | pic |
| 4-308X | Rh | 1 | 4 | Nap3 | — | — | $CH_3$ | H | H | H | H | acac |
| 4-308Y | Rh | 0 | 4 | Nap3 | — | — | $CH_3$ | H | H | H | H | — — |
| 4-309 | Rh | 1 | 4 | Nap3 | — | — | $^tC_4H_9$ | H | H | H | H | pic |
| 4-309X | Rh | 1 | 4 | Nap3 | — | — | $^tC_4H_9$ | H | H | H | H | acac |
| 4-309Y | Rh | 0 | 4 | Nap3 | — | — | $^tC_4H_9$ | H | H | H | H | — — |
| 4-310 | Rh | 1 | 4 | TB | — | — | $CH_3$ | H | H | H | H | pic |
| 4-310X | Rh | 1 | 4 | TB | — | — | $CH_3$ | H | H | H | H | acac |
| 4-310Y | Rh | 0 | 4 | TB | — | — | $CH_3$ | H | H | H | H | — — |
| 4-311 | Rh | 1 | 4 | TB | — | — | $^tC_4H_9$ | H | H | H | H | pic |
| 4-311X | Rh | 1 | 4 | TB | — | — | $^tC_4H_9$ | H | H | H | H | acac |
| 4-311Y | Rh | 0 | 4 | TB | — | — | $^tC_4H_9$ | H | H | H | H | — — |
| 4-312 | Rh | 1 | 4 | TF | — | — | $CH_3$ | H | H | H | H | pic |
| 4-312X | Rh | 1 | 4 | TF | — | — | $CH_3$ | H | H | H | H | acac |
| 4-312Y | Rh | 0 | 4 | TF | — | — | $CH_3$ | H | H | H | H | — — |
| 4-313 | Rh | 1 | 4 | TF | — | — | $^tC_4H_9$ | H | H | H | H | pic |
| 4-313X | Rh | 1 | 4 | TF | — | — | $^tC_4H_9$ | H | H | H | H | acac |
| 4-313Y | Rh | 0 | 4 | TF | — | — | $^tC_4H_9$ | H | H | H | H | — — |
| 4-314 | Rh | 1 | 4 | OB | — | — | $CH_3$ | H | H | H | H | pic |
| 4-314X | Rh | 1 | 4 | OB | — | — | $CH_3$ | H | H | H | H | acac |
| 4-314Y | Rh | 0 | 4 | OB | — | — | $CH_3$ | H | H | H | H | — — |
| 4-315 | Rh | 1 | 4 | OB | — | — | $^tC_4H_9$ | H | H | H | H | pic |
| 4-315X | Rh | 1 | 4 | OB | — | — | $^tC_4H_9$ | H | H | H | H | acac |
| 4-315Y | Rh | 0 | 4 | OB | — | — | $^tC_4H_9$ | H | H | H | H | — — |
| 4-316 | Rh | 1 | 4 | Fu | — | — | $CH_3$ | H | H | H | H | pic |
| 4-316X | Rh | 1 | 4 | Fu | — | — | $CH_3$ | H | H | H | H | acac |
| 4-316Y | Rh | 0 | 4 | Fu | — | — | $CH_3$ | H | H | H | H | — — |
| 4-317 | Rh | 1 | 4 | Fu | — | — | $^tC_4H_9$ | H | H | H | H | pic |
| 4-317X | Rh | 1 | 4 | Fu | — | — | $^tC_4H_9$ | H | H | H | H | acac |
| 4-317Y | Rh | 0 | 4 | Fu | — | — | $^tC_4H_9$ | H | H | H | H | — — |
| 4-318 | Rh | 1 | 4 | Fl | — | — | $CH_3$ | H | H | H | H | pic |
| 4-318X | Rh | 1 | 4 | Fl | — | — | $CH_3$ | H | H | H | H | acac |
| 4-318Y | Rh | 0 | 4 | Fl | — | — | $CH_3$ | H | H | H | H | — — |
| 4-319 | Rh | 1 | 4 | Fl | — | — | $^tC_4H_9$ | H | H | H | H | pic |
| 4-319X | Rh | 1 | 4 | Fl | — | — | $^tC_4H_9$ | H | H | H | H | acac |
| 4-319Y | Rh | 0 | 4 | Fl | — | — | $^tC_4H_9$ | H | H | H | H | — — |
| 4-320 | Rh | 1 | 4 | Bz | — | — | $CH_3$ | H | H | H | H | pic |
| 4-320X | Rh | 1 | 4 | Bz | — | — | $CH_3$ | H | H | H | H | acac |
| 4-320Y | Rh | 0 | 4 | Bz | — | — | $CH_3$ | H | H | H | H | — — |
| 4-321 | Rh | 1 | 4 | Bz | — | — | $^tC_4H_9$ | H | H | H | H | pic |
| 4-321X | Rh | 1 | 4 | Bz | — | — | $^tC_4H_9$ | H | H | H | H | acac |
| 4-321Y | Rh | 0 | 4 | Bz | — | — | $^tC_4H_9$ | H | H | H | H | — — |
| 4-322 | Rh | 1 | 4 | Qu | — | — | $CH_3$ | H | H | H | H | pic |
| 4-322X | Rh | 1 | 4 | Qu | — | — | $CH_3$ | H | H | H | H | acac |
| 4-322Y | Rh | 0 | 4 | Qu | — | — | $CH_3$ | H | H | H | H | — — |
| 4-323 | Rh | 1 | 4 | Qu | — | — | $^tC_4H_9$ | H | H | H | H | pic |
| 4-323X | Rh | 1 | 4 | Qu | — | — | $^tC_4H_9$ | H | H | H | H | acac |
| 4-323Y | Rh | 0 | 4 | Qu | — | — | $^tC_4H_9$ | H | H | H | H | — — |
| 4-324 | Rh | 1 | 4 | OL | H | $^nC_4H_9$ | $CH_3$ | H | H | H | H | pic |
| 4-324X | Rh | 1 | 4 | OL | H | $^nC_4H_9$ | $CH_3$ | H | H | H | H | acac |
| 4-324Y | Rh | 0 | 4 | OL | H | $^nC_4H_9$ | $CH_3$ | H | H | H | H | — — |
| 4-325 | Rh | 1 | 4 | OL | H | $^nC_4H_9$ | $^tC_4H_9$ | H | H | H | H | pic |
| 4-325X | Rh | 1 | 4 | OL | H | $^nC_4H_9$ | $^tC_4H_9$ | H | H | H | H | acac |
| 4-325Y | Rh | 0 | 4 | OL | H | $^nC_4H_9$ | $^tC_4H_9$ | H | H | H | H | — — |
| 4-326 | Rh | 1 | 4 | OL | H | $^tC_4H_9$ | $CH_3$ | H | H | H | H | pic |
| 4-326X | Rh | 1 | 4 | OL | H | $^tC_4H_9$ | $CH_3$ | H | H | H | H | acac |
| 4-326Y | Rh | 0 | 4 | OL | H | $^tC_4H_9$ | $CH_3$ | H | H | H | H | — — |
| 4-327 | Rh | 1 | 4 | OL | H | $^tC_4H_9$ | $^tC_4H_9$ | H | H | H | H | pic |
| 4-327X | Rh | 1 | 4 | OL | H | $^tC_4H_9$ | $^tC_4H_9$ | H | H | H | H | acac |
| 4-327Y | Rh | 0 | 4 | OL | H | $^tC_4H_9$ | $^tC_4H_9$ | H | H | H | H | — — |
| 4-328 | Rh | 1 | 4 | OL | $CH_3$ | $^nC_4H_9$ | $CH_3$ | H | H | H | H | pic |
| 4-328X | Rh | 1 | 4 | OL | $CH_3$ | $^nC_4H_9$ | $CH_3$ | H | H | H | H | acac |
| 4-328Y | Rh | 0 | 4 | OL | $CH_3$ | $^nC_4H_9$ | $CH_3$ | H | H | H | H | — — |
| 4-329 | Rh | 1 | 4 | OL | $CH_3$ | $^tC_4H_9$ | $CH_3$ | H | H | H | H | pic |
| 4-329X | Rh | 1 | 4 | OL | $CH_3$ | $^tC_4H_9$ | $CH_3$ | H | H | H | H | acac |

TABLE 25-continued

| No. | M | n | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 4-329Y | Rh | 0 | 4 | | OL | CH₃ | ᵗC₄H₉ | CH₃ | H | H | H | H | — | — |
| 4-330 | Rh | 1 | 4 | | OL | H | H | CH₃ | H | H | H | H | pic | |
| 4-330X | Rh | 1 | 4 | | OL | H | H | CH₃ | H | H | H | H | acac | |
| 4-330Y | Rh | 0 | 4 | | OL | H | H | CH₃ | H | H | H | H | — | — |
| 4-331 | Rh | 1 | 4 | | OL | —CH₂CH₂CH₂— | | CH₃ | H | H | H | H | pic | |
| 4-331X | Rh | 1 | 4 | | OL | —CH₂CH₂CH₂— | | CH₃ | H | H | H | H | acac | |
| 4-331Y | Rh | 0 | 4 | | OL | —CH₂CH₂CH₂— | | CH₃ | H | H | H | H | — | — |
| 4-332 | Rh | 1 | 4 | | OL | —CH₂CH₂CH₂— | | ᵗC₄H₉ | H | H | H | H | pic | |
| 4-332X | Rh | 1 | 4 | | OL | —CH₂CH₂CH₂— | | ᵗC₄H₉ | H | H | H | H | acac | |
| 4-332Y | Rh | 0 | 4 | | OL | —CH₂CH₂CH₂— | | ᵗC₄H₉ | H | H | H | H | — | — |

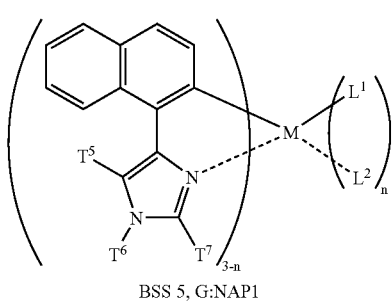

BSS 5, G:NAP1

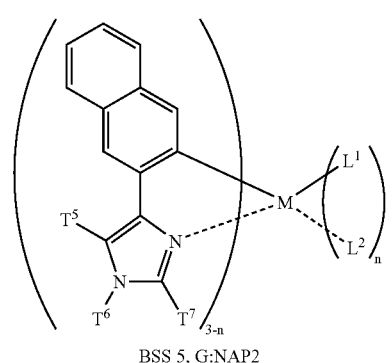

BSS 5, G:NAP2

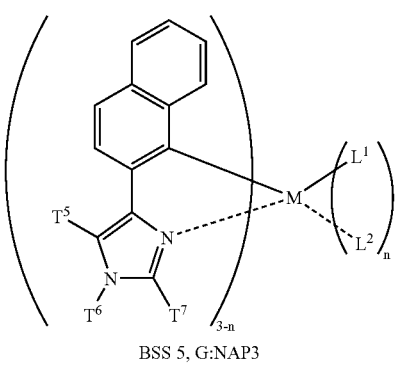

BSS 5, G:NAP3

-continued

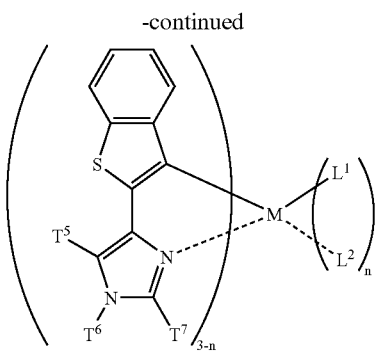

BSS 5, G:TB

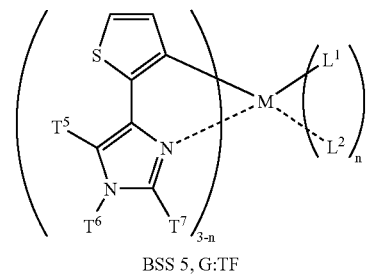

BSS 5, G:TF

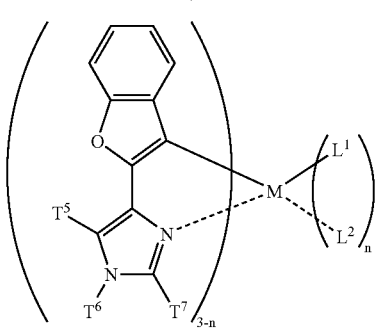

BSS 5, G:OB

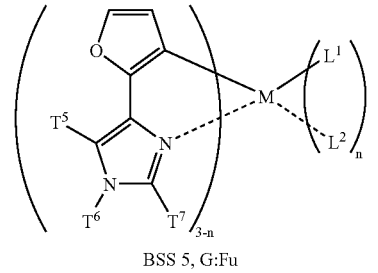

BSS 5, G:Fu

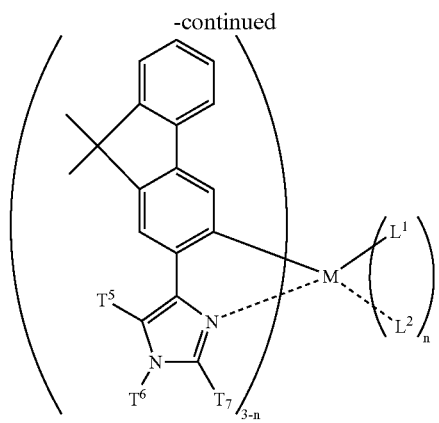

BSS 5, G:Fl

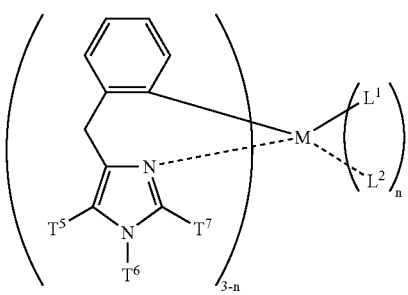

BSS 5, G:Bz

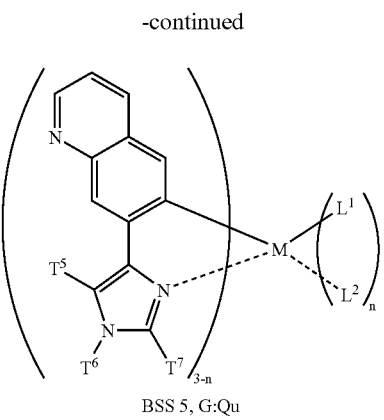

BSS 5, G:Qu

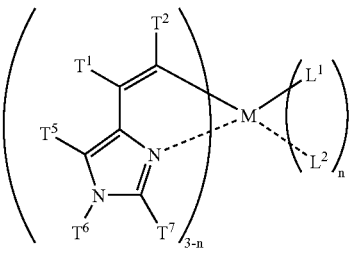

BSS 5, G:OL

TABLE 26

| No. | M | n | BSS | SS G | T¹ | T² | T⁵ | T⁶ | T⁷ | L¹ L² |
|---|---|---|---|---|---|---|---|---|---|---|
| 5-350 | Rh | 1 | 5 | Nap1 | — | — | H | CH$_3$ | H | pic |
| 5-351X | Rh | 1 | 5 | Nap1 | — | — | H | CH$_3$ | H | acac |
| 5-351Y | Rh | 0 | 5 | Nap1 | — | — | H | CH$_3$ | H | — — |
| 5-351 | Rh | 1 | 5 | Nap1 | — | — | H | $^tC_4H_9$ | H | pic |
| 5-352X | Rh | 1 | 5 | Nap1 | — | — | H | $^tC_4H_9$ | H | acac |
| 5-352Y | Rh | 0 | 5 | Nap1 | — | — | H | $^tC_4H_9$ | H | — — |
| 5-352 | Rh | 1 | 5 | Nap1 | — | — | $^tC_4H_9$ | CH$_3$ | H | pic |
| 5-353X | Rh | 1 | 5 | Nap1 | — | — | $^tC_4H_9$ | CH$_3$ | H | acac |
| 5-353Y | Rh | 0 | 5 | Nap1 | — | — | $^tC_4H_9$ | CH$_3$ | H | — — |
| 5-353 | Rh | 1 | 5 | Nap1 | — | — | $^tC_4H_9$ | $^tC_4H_9$ | H | pic |
| 5-354X | Rh | 1 | 5 | Nap1 | — | — | $^tC_4H_9$ | $^tC_4H_9$ | H | acac |
| 5-354Y | Rh | 0 | 5 | Nap1 | — | — | $^tC_4H_9$ | $^tC_4H_9$ | H | — — |
| 5-354 | Rh | 1 | 5 | Nap1 | — | — | CH$_3$ | CH$_3$ | H | pic |
| 5-355X | Rh | 1 | 5 | Nap1 | — | — | CH$_3$ | CH$_3$ | H | acac |
| 5-355Y | Rh | 0 | 5 | Nap1 | — | — | CH$_3$ | CH$_3$ | H | — — |
| 5-355 | Rh | 1 | 5 | Nap1 | — | — | CH$_3$ | $^tC_4H_9$ | H | pic |
| 5-356X | Rh | 1 | 5 | Nap1 | — | — | CH$_3$ | $^tC_4H_9$ | H | acac |
| 5-356Y | Rh | 0 | 5 | Nap1 | — | — | CH$_3$ | $^tC_4H_9$ | H | — — |
| 5-356 | Rh | 1 | 5 | Nap2 | — | — | H | CH$_3$ | H | pic |
| 5-357X | Rh | 1 | 5 | Nap2 | — | — | H | CH$_3$ | H | acac |
| 5-357Y | Rh | 0 | 5 | Nap2 | — | — | H | CH$_3$ | H | — — |
| 5-357 | Rh | 1 | 5 | Nap2 | — | — | H | $^tC_4H_9$ | H | pic |
| 5-358X | Rh | 1 | 5 | Nap2 | — | — | H | $^tC_4H_9$ | H | acac |
| 5-358Y | Rh | 0 | 5 | Nap2 | — | — | H | $^tC_4H_9$ | H | — — |
| 5-358 | Rh | 1 | 5 | Nap2 | — | — | $^tC_4H_9$ | CH$_3$ | H | pic |
| 5-359X | Rh | 1 | 5 | Nap2 | — | — | $^tC_4H_9$ | CH$_3$ | H | acac |
| 5-359Y | Rh | 0 | 5 | Nap2 | — | — | $^tC_4H_9$ | CH$_3$ | H | — — |
| 5-359 | Rh | 1 | 5 | Nap2 | — | — | $^tC_4H_9$ | $^tC_4H_9$ | H | pic |
| 5-360X | Rh | 1 | 5 | Nap2 | — | — | $^tC_4H_9$ | $^tC_4H_9$ | H | acac |
| 5-360Y | Rh | 0 | 5 | Nap2 | — | — | $^tC_4H_9$ | $^tC_4H_9$ | H | — — |
| 5-360 | Rh | 1 | 5 | Nap2 | — | — | CH$_3$ | CH$_3$ | H | pic |
| 5-361X | Rh | 1 | 5 | Nap2 | — | — | CH$_3$ | CH$_3$ | H | acac |
| 5-361Y | Rh | 0 | 5 | Nap2 | — | — | CH$_3$ | CH$_3$ | H | — — |
| 5-361 | Rh | 1 | 5 | Nap2 | — | — | CH$_3$ | $^tC_4H_9$ | H | pic |
| 5-362X | Rh | 1 | 5 | Nap2 | — | — | CH$_3$ | $^tC_4H_9$ | H | acac |
| 5-362Y | Rh | 0 | 5 | Nap2 | — | — | CH$_3$ | $^tC_4H_9$ | H | — — |
| 5-362 | Rh | 1 | 5 | Nap3 | — | — | H | CH$_3$ | H | pic |

TABLE 26-continued

| No. | M | n | BSS | SS G | T¹ | T² | T⁵ | T⁶ | T⁷ | L¹ | L² |
|---|---|---|---|---|---|---|---|---|---|---|---|
| 5-363X | Rh | 1 | 5 | Nap3 | — | — | H | $CH_3$ | H | acac | |
| 5-363Y | Rh | 0 | 5 | Nap3 | — | — | H | $CH_3$ | H | — | |
| 5-363 | Rh | 1 | 5 | Nap3 | — | — | H | $^tC_4H_9$ | H | pic | |
| 5-364X | Rh | 1 | 5 | Nap3 | — | — | H | $^tC_4H_9$ | H | acac | |
| 5-364Y | Rh | 0 | 5 | Nap3 | — | — | H | $^tC_4H_9$ | H | — | |
| 5-364 | Rh | 1 | 5 | Nap3 | — | — | $^tC_4H_9$ | $CH_3$ | H | pic | |
| 5-365X | Rh | 1 | 5 | Nap3 | — | — | $^tC_4H_9$ | $CH_3$ | H | acac | |
| 5-365Y | Rh | 0 | 5 | Nap3 | — | — | $^tC_4H_9$ | $CH_3$ | H | — | |
| 5-365 | Rh | 1 | 5 | Nap3 | — | — | $^tC_4H_9$ | $^tC_4H_9$ | H | pic | |
| 5-366X | Rh | 1 | 5 | Nap3 | — | — | $^tC_4H_9$ | $^tC_4H_9$ | H | acac | |
| 5-366Y | Rh | 0 | 5 | Nap3 | — | — | $^tC_4H_9$ | $^tC_4H_9$ | H | — | |
| 5-366 | Rh | 1 | 5 | Nap3 | — | — | $CH_3$ | $CH_3$ | H | pic | |
| 5-367X | Rh | 1 | 5 | Nap3 | — | — | $CH_3$ | $CH_3$ | H | acac | |
| 5-367Y | Rh | 0 | 5 | Nap3 | — | — | $CH_3$ | $CH_3$ | H | — | |
| 5-367 | Rh | 1 | 5 | Nap3 | — | — | $CH_3$ | $^tC_4H_9$ | H | pic | |
| 5-368X | Rh | 1 | 5 | Nap3 | — | — | $CH_3$ | $^tC_4H_9$ | H | acac | |
| 5-368Y | Rh | 0 | 5 | Nap3 | — | — | $CH_3$ | $^tC_4H_9$ | H | — | |
| 5-368 | Rh | 1 | 5 | TB | — | — | H | $CH_3$ | H | pic | |
| 5-369X | Rh | 1 | 5 | TB | — | — | H | $CH_3$ | H | acac | |
| 5-369Y | Rh | 0 | 5 | TB | — | — | H | $CH_3$ | H | — | |
| 5-369 | Rh | 1 | 5 | TB | — | — | H | $^tC_4H_9$ | H | pic | |
| 5-370X | Rh | 1 | 5 | TB | — | — | H | $^tC_4H_9$ | H | acac | |
| 5-370Y | Rh | 0 | 5 | TB | — | — | H | $^tC_4H_9$ | H | — | |
| 5-370 | Rh | 1 | 5 | TB | — | — | $^tC_4H_9$ | $CH_3$ | H | pic | |
| 5-371X | Rh | 1 | 5 | TB | — | — | $^tC_4H_9$ | $CH_3$ | H | acac | |
| 5-371Y | Rh | 0 | 5 | TB | — | — | $^tC_4H_9$ | $CH_3$ | H | — | |
| 5-371 | Rh | 1 | 5 | TB | — | — | $^tC_4H_9$ | $^tC_4H_9$ | H | pic | |
| 5-372X | Rh | 1 | 5 | TB | — | — | $^tC_4H_9$ | $^tC_4H_9$ | H | acac | |
| 5-372Y | Rh | 0 | 5 | TB | — | — | $^tC_4H_9$ | $^tC_4H_9$ | H | — | |
| 5-372 | Rh | 1 | 5 | TB | — | — | $CH_3$ | $CH_3$ | H | pic | |
| 5-373X | Rh | 1 | 5 | TB | — | — | $CH_3$ | $CH_3$ | H | acac | |
| 5-373Y | Rh | 0 | 5 | TB | — | — | $CH_3$ | $CH_3$ | H | — | |
| 5-373 | Rh | 1 | 5 | TB | — | — | $CH_3$ | $^tC_4H_9$ | H | pic | |
| 5-374X | Rh | 1 | 5 | TB | — | — | $CH_3$ | $^tC_4H_9$ | H | acac | |
| 5-374Y | Rh | 0 | 5 | TB | — | — | $CH_3$ | $^tC_4H_9$ | H | — | |
| 5-374 | Rh | 1 | 5 | TF | — | — | H | $CH_3$ | H | pic | |
| 5-375X | Rh | 1 | 5 | TF | — | — | H | $CH_3$ | H | acac | |
| 5-375Y | Rh | 0 | 5 | TF | — | — | H | $CH_3$ | H | — | |
| 5-375 | Rh | 1 | 5 | TF | — | — | H | $^tC_4H_9$ | H | pic | |
| 5-376X | Rh | 1 | 5 | TF | — | — | H | $^tC_4H_9$ | H | acac | |
| 5-376Y | Rh | 0 | 5 | TF | — | — | H | $^tC_4H_9$ | H | — | |
| 5-376 | Rh | 1 | 5 | TF | — | — | $^tC_4H_9$ | $CH_3$ | H | pic | |
| 5-377X | Rh | 1 | 5 | TF | — | — | $^tC_4H_9$ | $CH_3$ | H | acac | |
| 5-377Y | Rh | 0 | 5 | TF | — | — | $^tC_4H_9$ | $CH_3$ | H | — | |
| 5-377 | Rh | 1 | 5 | TF | — | — | $^tC_4H_9$ | $^tC_4H_9$ | H | pic | |
| 5-378X | Rh | 1 | 5 | TF | — | — | $^tC_4H_9$ | $^tC_4H_9$ | H | acac | |
| 5-378Y | Rh | 0 | 5 | TF | — | — | $^tC_4H_9$ | $^tC_4H_9$ | H | — | |
| 5-378 | Rh | 1 | 5 | TF | — | — | $CH_3$ | $CH_3$ | H | pic | |
| 5-379X | Rh | 1 | 5 | TF | — | — | $CH_3$ | $CH_3$ | H | acac | |
| 5-379Y | Rh | 0 | 5 | TF | — | — | $CH_3$ | $CH_3$ | H | — | |
| 5-379 | Rh | 1 | 5 | TF | — | — | $CH_3$ | $^tC_4H_9$ | H | pic | |
| 5-380X | Rh | 1 | 5 | TF | — | — | $CH_3$ | $^tC_4H_9$ | H | acac | |
| 5-380Y | Rh | 0 | 5 | TF | — | — | $CH_3$ | $^tC_4H_9$ | H | — | |
| 5-380 | Rh | 1 | 5 | OB | — | — | H | $CH_3$ | H | pic | |
| 5-381X | Rh | 1 | 5 | OB | — | — | H | $CH_3$ | H | acac | |
| 5-381Y | Rh | 0 | 5 | OB | — | — | H | $CH_3$ | H | — | |
| 5-381 | Rh | 1 | 5 | OB | — | — | H | $^tC_4H_9$ | H | pic | |
| 5-382X | Rh | 1 | 5 | OB | — | — | H | $^tC_4H_9$ | H | acac | |
| 5-382Y | Rh | 0 | 5 | OB | — | — | H | $^tC_4H_9$ | H | — | |
| 5-382 | Rh | 1 | 5 | OB | — | — | $^tC_4H_9$ | $CH_3$ | H | pic | |
| 5-383X | Rh | 1 | 5 | OB | — | — | $^tC_4H_9$ | $CH_3$ | H | acac | |
| 5-383Y | Rh | 0 | 5 | OB | — | — | $^tC_4H_9$ | $CH_3$ | H | — | |
| 5-383 | Rh | 1 | 5 | OB | — | — | $^tC_4H_9$ | $^tC_4H_9$ | H | pic | |
| 5-384X | Rh | 1 | 5 | OB | — | — | $^tC_4H_9$ | $^tC_4H_9$ | H | acac | |
| 5-384Y | Rh | 0 | 5 | OB | — | — | $^tC_4H_9$ | $^tC_4H_9$ | H | — | |
| 5-384 | Rh | 1 | 5 | OB | — | — | $CH_3$ | $CH_3$ | H | pic | |
| 5-385X | Rh | 1 | 5 | OB | — | — | $CH_3$ | $CH_3$ | H | acac | |
| 5-385Y | Rh | 0 | 5 | OB | — | — | $CH_3$ | $CH_3$ | H | — | |
| 5-385 | Rh | 1 | 5 | OB | — | — | $CH_3$ | $^tC_4H_9$ | H | pic | |
| 5-386X | Rh | 1 | 5 | OB | — | — | $CH_3$ | $^tC_4H_9$ | H | acac | |
| 5-386Y | Rh | 0 | 5 | OB | — | — | $CH_3$ | $^tC_4H_9$ | H | — | |
| 5-386 | Rh | 1 | 5 | Fu | — | — | H | $CH_3$ | H | pic | |
| 5-387X | Rh | 1 | 5 | Fu | — | — | H | $CH_3$ | H | acac | |
| 5-387Y | Rh | 0 | 5 | Fu | — | — | H | $CH_3$ | H | — | |
| 5-387 | Rh | 1 | 5 | Fu | — | — | H | $^tC_4H_9$ | H | pic | |
| 5-388X | Rh | 1 | 5 | Fu | — | — | H | $^tC_4H_9$ | H | acac | |
| 5-388Y | Rh | 0 | 5 | Fu | — | — | H | $^tC_4H_9$ | H | — | |

TABLE 26-continued

| No. | M | n | BSS | SS G | T¹ | T² | T⁵ | T⁶ | T⁷ | L¹ | L² |
|---|---|---|---|---|---|---|---|---|---|---|---|
| 5-388 | Rh | 1 | 5 | Fu | — | — | $^tC_4H_9$ | $CH_3$ | H | pic | |
| 5-389X | Rh | 1 | 5 | Fu | — | — | $^tC_4H_9$ | $CH_3$ | H | acac | |
| 5-389Y | Rh | 0 | 5 | Fu | — | — | $^tC_4H_9$ | $CH_3$ | H | — | |
| 5-389 | Rh | 1 | 5 | Fu | — | — | $^tC_4H_9$ | $^tC_4H_9$ | H | pic | |
| 5-390X | Rh | 1 | 5 | Fu | — | — | $^tC_4H_9$ | $^tC_4H_9$ | H | acac | |
| 5-390Y | Rh | 0 | 5 | Fu | — | — | $^tC_4H_9$ | $^tC_4H_9$ | H | — | |
| 5-390 | Rh | 1 | 5 | Fu | — | — | $CH_3$ | $CH_3$ | H | pic | |
| 5-391X | Rh | 1 | 5 | Fu | — | — | $CH_3$ | $CH_3$ | H | acac | |
| 5-391Y | Rh | 0 | 5 | Fu | — | — | $CH_3$ | $CH_3$ | H | — | |
| 5-391 | Rh | 1 | 5 | Fu | — | — | $CH_3$ | $^tC_4H_9$ | H | pic | |
| 5-392X | Rh | 1 | 5 | Fu | — | — | $CH_3$ | $^tC_4H_9$ | H | acac | |
| 5-392Y | Rh | 0 | 5 | Fu | — | — | $CH_3$ | $^tC_4H_9$ | H | — | |
| 5-392 | Rh | 1 | 5 | Fl | — | — | H | $CH_3$ | H | pic | |
| 5-393X | Rh | 1 | 5 | Fl | — | — | H | $CH_3$ | H | acac | |
| 5-393Y | Rh | 0 | 5 | Fl | — | — | H | $CH_3$ | H | — | |
| 5-393 | Rh | 1 | 5 | Fl | — | — | H | $^tC_4H_9$ | H | pic | |
| 5-394X | Rh | 1 | 5 | Fl | — | — | H | $^tC_4H_9$ | H | acac | |
| 5-394Y | Rh | 0 | 5 | Fl | — | — | H | $^tC_4H_9$ | H | — | |
| 5-394 | Rh | 1 | 5 | Fl | — | — | $^tC_4H_9$ | $CH_3$ | H | pic | |
| 5-395X | Rh | 1 | 5 | Fl | — | — | $^tC_4H_9$ | $CH_3$ | H | acac | |
| 5-395Y | Rh | 0 | 5 | Fl | — | — | $^tC_4H_9$ | $CH_3$ | H | — | |
| 5-395 | Rh | 1 | 5 | Fl | — | — | $^tC_4H_9$ | $^tC_4H_9$ | H | pic | |
| 5-396X | Rh | 1 | 5 | Fl | — | — | $^tC_4H_9$ | $^tC_4H_9$ | H | acac | |
| 5-396Y | Rh | 0 | 5 | Fl | — | — | $^tC_4H_9$ | $^tC_4H_9$ | H | — | |
| 5-396 | Rh | 1 | 5 | Fl | — | — | $CH_3$ | $CH_3$ | H | pic | |
| 5-397X | Rh | 1 | 5 | Fl | — | — | $CH_3$ | $CH_3$ | H | acac | |
| 5-397Y | Rh | 0 | 5 | Fl | — | — | $CH_3$ | $CH_3$ | H | — | |
| 5-397 | Rh | 1 | 5 | Fl | — | — | $CH_3$ | $^tC_4H_9$ | H | pic | |
| 5-398X | Rh | 1 | 5 | Fl | — | — | $CH_3$ | $^tC_4H_9$ | H | acac | |
| 5-398Y | Rh | 0 | 5 | Fl | — | — | $CH_3$ | $^tC_4H_9$ | H | — | |
| 5-398 | Rh | 1 | 5 | Bz | — | — | H | $CH_3$ | H | pic | |
| 5-399X | Rh | 1 | 5 | Bz | — | — | H | $CH_3$ | H | acac | |
| 5-399Y | Rh | 0 | 5 | Bz | — | — | H | $CH_3$ | H | — | |
| 5-399 | Rh | 1 | 5 | Bz | — | — | H | $^tC_4H_9$ | H | pic | |
| 5-400X | Rh | 1 | 5 | Bz | — | — | H | $^tC_4H_9$ | H | acac | |
| 5-400Y | Rh | 0 | 5 | Bz | — | — | H | $^tC_4H_9$ | H | — | |
| 5-400 | Rh | 1 | 5 | Bz | — | — | $^tC_4H_9$ | $CH_3$ | H | pic | |
| 5-401X | Rh | 1 | 5 | Bz | — | — | $^tC_4H_9$ | $CH_3$ | H | acac | |
| 5-401Y | Rh | 0 | 5 | Bz | — | — | $^tC_4H_9$ | $CH_3$ | H | — | |
| 5-401 | Rh | 1 | 5 | Bz | — | — | $^tC_4H_9$ | $^tC_4H_9$ | H | pic | |
| 5-402X | Rh | 1 | 5 | Bz | — | — | $^tC_4H_9$ | $^tC_4H_9$ | H | acac | |
| 5-402Y | Rh | 0 | 5 | Bz | — | — | $^tC_4H_9$ | $^tC_4H_9$ | H | — | |
| 5-402 | Rh | 1 | 5 | Bz | — | — | $CH_3$ | $CH_3$ | H | pic | |
| 5-403X | Rh | 1 | 5 | Bz | — | — | $CH_3$ | $CH_3$ | H | acac | |
| 5-403Y | Rh | 0 | 5 | Bz | — | — | $CH_3$ | $CH_3$ | H | — | |
| 5-403 | Rh | 1 | 5 | Bz | — | — | $CH_3$ | $^tC_4H_9$ | H | pic | |
| 5-404X | Rh | 1 | 5 | Bz | — | — | $CH_3$ | $^tC_4H_9$ | H | acac | |
| 5-404Y | Rh | 0 | 5 | Bz | — | — | $CH_3$ | $^tC_4H_9$ | H | — | |
| 5-404 | Rh | 1 | 5 | Qu | — | — | H | $CH_3$ | H | pic | |
| 5-405X | Rh | 1 | 5 | Bz | — | — | H | $CH_3$ | H | acac | |
| 5-405Y | Rh | 0 | 5 | Bz | — | — | H | $CH_3$ | H | — | |
| 5-405 | Rh | 1 | 5 | Bz | — | — | H | $^tC_4H_9$ | H | pic | |
| 5-406X | Rh | 1 | 5 | Bz | — | — | H | $^tC_4H_9$ | H | acac | |
| 5-406Y | Rh | 0 | 5 | Bz | — | — | H | $^tC_4H_9$ | H | — | |
| 5-406 | Rh | 1 | 5 | Bz | — | — | $^tC_4H_9$ | $CH_3$ | H | pic | |
| 5-407X | Rh | 1 | 5 | Bz | — | — | $^tC_4H_9$ | $CH_3$ | H | acac | |
| 5-407Y | Rh | 0 | 5 | Bz | — | — | $^tC_4H_9$ | $CH_3$ | H | — | |
| 5-407 | Rh | 1 | 5 | Bz | — | — | $^tC_4H_9$ | $^tC_4H_9$ | H | pic | |
| 5-408X | Rh | 1 | 5 | Bz | — | — | $^tC_4H_9$ | $^tC_4H_9$ | H | acac | |
| 5-408Y | Rh | 0 | 5 | Bz | — | — | $^tC_4H_9$ | $^tC_4H_9$ | H | — | |
| 5-408 | Rh | 1 | 5 | Bz | — | — | $CH_3$ | $CH_3$ | H | pic | |
| 5-409X | Rh | 1 | 5 | Bz | — | — | $CH_3$ | $CH_3$ | H | acac | |
| 5-409Y | Rh | 0 | 5 | Bz | — | — | $CH_3$ | $CH_3$ | H | — | |
| 5-409 | Rh | 1 | 5 | Bz | — | — | $CH_3$ | $^tC_4H_9$ | H | pic | |
| 5-410X | Rh | 1 | 5 | Bz | — | — | $CH_3$ | $^tC_4H_9$ | H | acac | |
| 5-410Y | Rh | 0 | 5 | Bz | — | — | $CH_3$ | $^tC_4H_9$ | H | — | |
| 5-410 | Rh | 1 | 5 | OL | H | $^nC_4H_9$ | H | $CH_3$ | H | pic | |
| 5-411X | Rh | 1 | 5 | OL | H | $^nC_4H_9$ | H | $CH_3$ | H | acac | |
| 5-411Y | Rh | 0 | 5 | OL | H | $^nC_4H_9$ | H | $CH_3$ | H | — | |
| 5-411 | Rh | 1 | 5 | OL | H | $^nC_4H_9$ | H | $^tC_4H_9$ | H | pic | |
| 5-412X | Rh | 1 | 5 | OL | H | $^nC_4H_9$ | H | $^tC_4H_9$ | H | acac | |
| 5-412Y | Rh | 0 | 5 | OL | H | $^nC_4H_9$ | H | $^tC_4H_9$ | H | — | |
| 5-412 | Rh | 1 | 5 | OL | H | $^tC_4H_9$ | H | $CH_3$ | H | pic | |
| 5-413X | Rh | 1 | 5 | OL | H | $^tC_4H_9$ | H | $CH_3$ | H | acac | |
| 5-413Y | Rh | 0 | 5 | OL | H | $^tC_4H_9$ | H | $CH_3$ | H | — | |
| 5-413 | Rh | 1 | 5 | OL | H | $^tC_4H_9$ | H | $^tC_4H_9$ | H | pic | |
| 5-414X | Rh | 1 | 5 | OL | H | $^tC_4H_9$ | H | $^tC_4H_9$ | H | acac | |

TABLE 26-continued

| No. | M | n | BSS | SS G | T$^1$ | T$^2$ | T$^5$ | T$^6$ | T$^7$ | L$^1$ | L$^2$ |
|---|---|---|---|---|---|---|---|---|---|---|---|
| 5-414Y | Rh | 0 | 5 | OL | H | $^t$C$_4$H$_9$ | H | $^t$C$_4$H$_9$ | H | — | — |
| 5-414 | Rh | 1 | 5 | OL | CH$_3$ | $^n$C$_4$H$_9$ | H | CH$_3$ | H | pic | |
| 5-415X | Rh | 1 | 5 | OL | CH$_3$ | $^n$C$_4$H$_9$ | H | CH$_3$ | H | acac | |
| 5-415Y | Rh | 0 | 5 | OL | CH$_3$ | $^n$C$_4$H$_9$ | H | CH$_3$ | H | — | — |
| 5-415 | Rh | 1 | 5 | OL | CH$_3$ | $^t$C$_4$H$_9$ | H | CH$_3$ | H | pic | |
| 5-416X | Rh | 1 | 5 | OL | CH$_3$ | $^t$C$_4$H$_9$ | H | CH$_3$ | H | acac | |
| 5-416Y | Rh | 0 | 5 | OL | CH$_3$ | $^t$C$_4$H$_9$ | H | CH$_3$ | H | — | — |
| 5-416 | Rh | 1 | 5 | OL | H | H | H | CH$_3$ | H | pic | |
| 5-417X | Rh | 1 | 5 | OL | H | H | H | CH$_3$ | H | acac | |
| 5-417Y | Rh | 0 | 5 | OL | H | H | H | CH$_3$ | H | — | — |
| 5-417 | Rh | 1 | 5 | OL | H | $^n$C$_4$H$_9$ | CH$_3$ | $^t$C$_4$H$_9$ | H | pic | |
| 5-418X | Rh | 1 | 5 | OL | H | $^n$C$_4$H$_9$ | CH$_3$ | $^t$C$_4$H$_9$ | H | acac | |
| 5-418Y | Rh | 0 | 5 | OL | H | $^n$C$_4$H$_9$ | CH$_3$ | $^t$C$_4$H$_9$ | H | — | — |
| 5-418 | Rh | 1 | 5 | OL | H | $^t$C$_4$H$_9$ | CH$_3$ | $^t$C$_4$H$_9$ | H | pic | |
| 5-419X | Rh | 1 | 5 | OL | H | $^t$C$_4$H$_9$ | CH$_3$ | $^t$C$_4$H$_9$ | H | acac | |
| 5-419Y | Rh | 0 | 5 | OL | H | $^t$C$_4$H$_9$ | CH$_3$ | $^t$C$_4$H$_9$ | H | — | — |
| 5-419 | Rh | 1 | 5 | OL | —CH$_2$CH$_2$CH$_2$— | | H | CH$_3$ | H | pic | |
| 5-420X | Rh | 1 | 5 | OL | —CH$_2$CH$_2$CH$_2$— | | H | CH$_3$ | H | acac | |
| 5-420Y | Rh | 0 | 5 | OL | —CH$_2$CH$_2$CH$_2$— | | H | CH$_3$ | H | — | — |
| 5-420 | Rh | 1 | 5 | OL | —CH$_2$CH$_2$CH$_2$— | | H | $^t$C$_4$H$_9$ | H | pic | |
| 5-421X | Rh | 1 | 5 | OL | —CH$_2$CH$_2$CH$_2$— | | H | $^t$C$_4$H$_9$ | H | acac | |
| 5-421Y | Rh | 0 | 5 | OL | —CH$_2$CH$_2$CH$_2$— | | H | $^t$C$_4$H$_9$ | H | — | — |

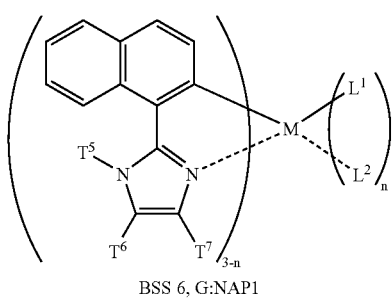

BSS 6, G:NAP1

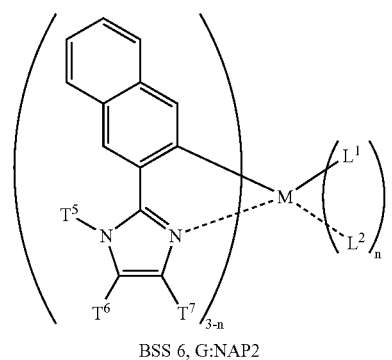

BSS 6, G:NAP2

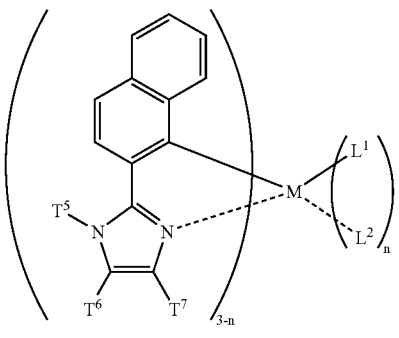

BSS 6, G:NAP3

-continued

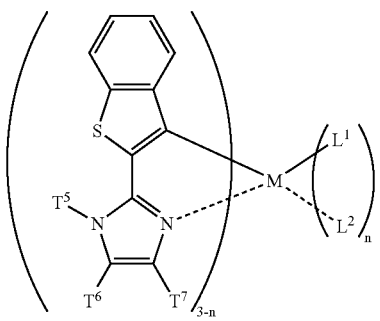

BSS 6, G:TB

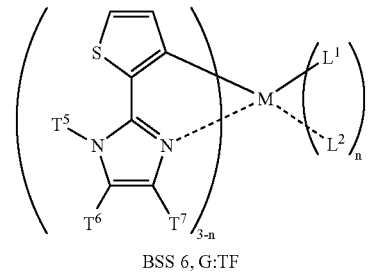

BSS 6, G:TF

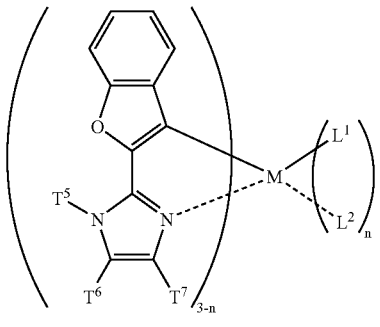

BSS 6, G:OB

-continued

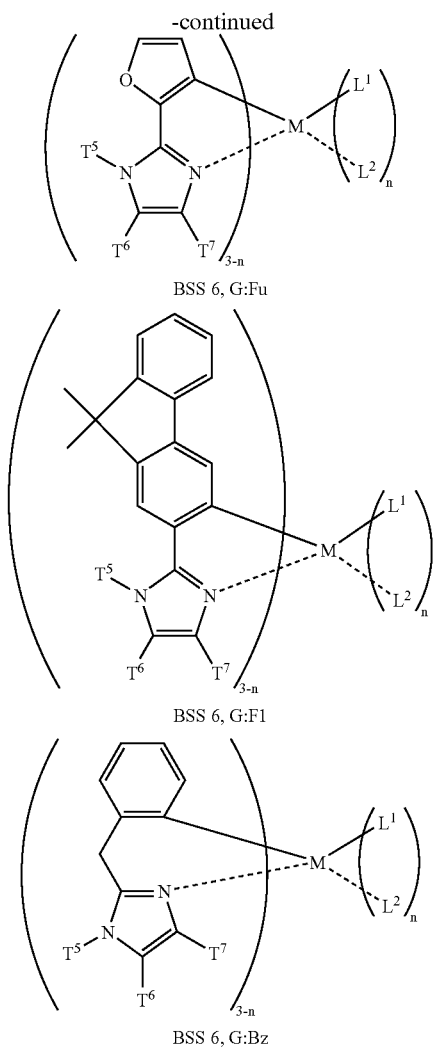

BSS 6, G:Fu

BSS 6, G:Fl

BSS 6, G:Bz

-continued

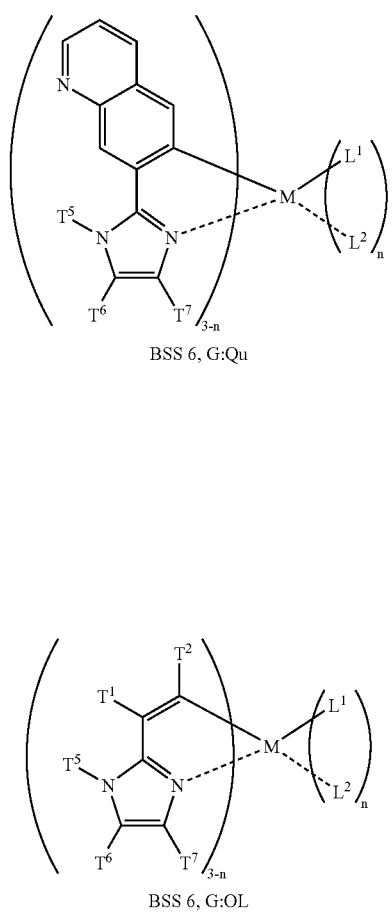

BSS 6, G:Qu

BSS 6, G:OL

TABLE 27

| No. | M | n | BSS | SS | G | $T^1$ | $T^2$ | $T^5$ | $T^6$ | $T^7$ | $L^1$ | $L^2$ |
|---|---|---|---|---|---|---|---|---|---|---|---|---|
| 6-304  | Rh | 1 | 6 |   | Nap1 | — | — | $CH_3$    | H | H | pic  |      |
| 6-304X | Rh | 1 | 6 |   | Nap1 | — | — | $CH_3$    | H | H | acac |      |
| 6-304Y | Rh | 0 | 6 |   | Nap1 | — | — | $CH_3$    | H | H | —    | —    |
| 6-305  | Rh | 1 | 6 |   | Nap1 | — | — | $^tC_4H_9$ | H | H | pic  |      |
| 6-305X | Rh | 1 | 6 |   | Nap1 | — | — | $^tC_4H_9$ | H | H | acac |      |
| 6-305Y | Rh | 0 | 6 |   | Nap1 | — | — | $^tC_4H_9$ | H | H | —    | —    |
| 6-306  | Rh | 1 | 6 |   | Nap2 | — | — | $CH_3$    | H | H | pic  |      |
| 6-306X | Rh | 1 | 6 |   | Nap2 | — | — | $CH_3$    | H | H | acac |      |
| 6-306Y | Rh | 0 | 6 |   | Nap2 | — | — | $CH_3$    | H | H | —    | —    |
| 6-307  | Rh | 1 | 6 |   | Nap2 | — | — | $^tC_4H_9$ | H | H | pic  |      |
| 6-307X | Rh | 1 | 6 |   | Nap2 | — | — | $^tC_4H_9$ | H | H | acac |      |
| 6-307Y | Rh | 0 | 6 |   | Nap2 | — | — | $^tC_4H_9$ | H | H | —    | —    |
| 6-308  | Rh | 1 | 6 |   | Nap3 | — | — | $CH_3$    | H | H | pic  |      |
| 6-308X | Rh | 1 | 6 |   | Nap3 | — | — | $CH_3$    | H | H | acac |      |
| 6-308Y | Rh | 0 | 6 |   | Nap3 | — | — | $CH_3$    | H | H | —    | —    |
| 6-309  | Rh | 1 | 6 |   | Nap3 | — | — | $^tC_4H_9$ | H | H | pic  |      |
| 6-309X | Rh | 1 | 6 |   | Nap3 | — | — | $^tC_4H_9$ | H | H | acac |      |
| 6-309Y | Rh | 0 | 6 |   | Nap3 | — | — | $^tC_4H_9$ | H | H | —    | —    |
| 6-310  | Rh | 1 | 6 |   | TB   | — | — | $CH_3$    | H | H | pic  |      |
| 6-310X | Rh | 1 | 6 |   | TB   | — | — | $CH_3$    | H | H | acac |      |
| 6-310Y | Rh | 0 | 6 |   | TB   | — | — | $CH_3$    | H | H | —    | —    |
| 6-311  | Rh | 1 | 6 |   | TB   | — | — | $^tC_4H_9$ | H | H | pic  |      |
| 6-311X | Rh | 1 | 6 |   | TB   | — | — | $^tC_4H_9$ | H | H | acac |      |
| 6-311Y | Rh | 0 | 6 |   | TB   | — | — | $^tC_4H_9$ | H | H | —    | —    |

TABLE 27-continued

| No. | M | n | BSS | SS G | T¹ | T² | T⁵ | T⁶ | T⁷ | L¹ | L² |
|---|---|---|---|---|---|---|---|---|---|---|---|
| 6-312 | Rh | 1 | 6 | TF | — | — | CH$_3$ | H | H | pic | |
| 6-312X | Rh | 1 | 6 | TF | — | — | CH$_3$ | H | H | acac | |
| 6-312Y | Rh | 0 | 6 | TF | — | — | CH$_3$ | H | H | — | — |
| 6-313 | Rh | 1 | 6 | TF | — | — | $^tC_4H_9$ | H | H | pic | |
| 6-313X | Rh | 1 | 6 | TF | — | — | $^tC_4H_9$ | H | H | acac | |
| 6-313Y | Rh | 0 | 6 | TF | — | — | $^tC_4H_9$ | H | H | — | — |
| 6-314 | Rh | 1 | 6 | OB | — | — | CH$_3$ | H | H | pic | |
| 6-314X | Rh | 1 | 6 | OB | — | — | CH$_3$ | H | H | acac | |
| 6-314Y | Rh | 0 | 6 | OB | — | — | CH$_3$ | H | H | — | — |
| 6-315 | Rh | 1 | 6 | OB | — | — | $^tC_4H_9$ | H | H | pic | |
| 6-315X | Rh | 1 | 6 | OB | — | — | $^tC_4H_9$ | H | H | acac | |
| 6-315Y | Rh | 0 | 6 | OB | — | — | $^tC_4H_9$ | H | H | — | — |
| 6-316 | Rh | 1 | 6 | Fu | — | — | CH$_3$ | H | H | pic | |
| 6-316X | Rh | 1 | 6 | Fu | — | — | CH$_3$ | H | H | acac | |
| 6-316Y | Rh | 0 | 6 | Fu | — | — | CH$_3$ | H | H | — | — |
| 6-317 | Rh | 1 | 6 | Fu | — | — | $^tC_4H_9$ | H | H | pic | |
| 6-317X | Rh | 1 | 6 | Fu | — | — | $^tC_4H_9$ | H | H | acac | |
| 6-317Y | Rh | 0 | 6 | Fu | — | — | $^tC_4H_9$ | H | H | — | — |
| 6-318 | Rh | 1 | 6 | Fl | — | — | CH$_3$ | H | H | pic | |
| 6-318X | Rh | 1 | 6 | Fl | — | — | CH$_3$ | H | H | acac | |
| 6-318Y | Rh | 0 | 6 | Fl | — | — | CH$_3$ | H | H | — | — |
| 6-319 | Rh | 1 | 6 | Fl | — | — | $^tC_4H_9$ | H | H | pic | |
| 6-319X | Rh | 1 | 6 | Fl | — | — | $^tC_4H_9$ | H | H | acac | |
| 6-319Y | Rh | 0 | 6 | Fl | — | — | $^tC_4H_9$ | H | H | — | — |
| 6-320 | Rh | 1 | 6 | Bz | — | — | CH$_3$ | H | H | pic | |
| 6-320X | Rh | 1 | 6 | Bz | — | — | CH$_3$ | H | H | acac | |
| 6-320Y | Rh | 0 | 6 | Bz | — | — | CH$_3$ | H | H | — | — |
| 6-321 | Rh | 1 | 6 | Bz | — | — | $^tC_4H_9$ | H | H | pic | |
| 6-321X | Rh | 1 | 6 | Bz | — | — | $^tC_4H_9$ | H | H | acac | |
| 6-321Y | Rh | 0 | 6 | Bz | — | — | $^tC_4H_9$ | H | H | — | — |
| 6-322 | Rh | 1 | 6 | Qu | — | — | CH$_3$ | H | H | pic | |
| 6-322X | Rh | 1 | 6 | Qu | — | — | CH$_3$ | H | H | acac | |
| 6-322Y | Rh | 0 | 6 | Qu | — | — | CH$_3$ | H | H | — | — |
| 6-323 | Rh | 1 | 6 | Qu | — | — | $^tC_4H_9$ | H | H | pic | |
| 6-323X | Rh | 1 | 6 | Qu | — | — | $^tC_4H_9$ | H | H | acac | |
| 6-323Y | Rh | 0 | 6 | Qu | — | — | $^tC_4H_9$ | H | H | — | — |
| 6-324 | Rh | 1 | 6 | OL | H | $^nC_4H_9$ | CH$_3$ | H | H | pic | |
| 6-324X | Rh | 1 | 6 | OL | H | $^nC_4H_9$ | CH$_3$ | H | H | acac | |
| 6-324Y | Rh | 0 | 6 | OL | H | $^nC_4H_9$ | CH$_3$ | H | H | — | — |
| 6-325 | Rh | 1 | 6 | OL | H | $^nC_4H_9$ | $^tC_4H_9$ | H | H | pic | |
| 6-325X | Rh | 1 | 6 | OL | H | $^nC_4H_9$ | $^tC_4H_9$ | H | H | acac | |
| 6-325Y | Rh | 0 | 6 | OL | H | $^nC_4H_9$ | $^tC_4H_9$ | H | H | — | — |
| 6-326 | Rh | 1 | 6 | OL | H | $^tC_4H_9$ | CH$_3$ | H | H | pic | |
| 6-326X | Rh | 1 | 6 | OL | H | $^tC_4H_9$ | CH$_3$ | H | H | acac | |
| 6-326Y | Rh | 0 | 6 | OL | H | $^tC_4H_9$ | CH$_3$ | H | H | — | — |
| 6-327 | Rh | 1 | 6 | OL | H | $^tC_4H_9$ | $^tC_4H_9$ | H | H | pic | |
| 6-327X | Rh | 1 | 6 | OL | H | $^tC_4H_9$ | $^tC_4H_9$ | H | H | acac | |
| 6-327Y | Rh | 0 | 6 | OL | H | $^tC_4H_9$ | $^tC_4H_9$ | H | H | — | — |
| 6-328 | Rh | 1 | 6 | OL | CH$_3$ | $^nC_4H_9$ | CH$_3$ | H | H | pic | |
| 6-328X | Rh | 1 | 6 | OL | CH$_3$ | $^nC_4H_9$ | CH$_3$ | H | H | acac | |
| 6-328Y | Rh | 0 | 6 | OL | CH$_3$ | $^nC_4H_9$ | CH$_3$ | H | H | — | — |
| 6-329 | Rh | 1 | 6 | OL | CH$_3$ | $^tC_4H_9$ | CH$_3$ | H | H | pic | |
| 6-329X | Rh | 1 | 6 | OL | CH$_3$ | $^tC_4H_9$ | CH$_3$ | H | H | acac | |
| 6-329Y | Rh | 0 | 6 | OL | CH$_3$ | $^tC_4H_9$ | CH$_3$ | H | H | — | — |
| 6-330 | Rh | 1 | 6 | OL | H | H | CH$_3$ | H | H | pic | |
| 6-330X | Rh | 1 | 6 | OL | H | H | CH$_3$ | H | H | acac | |
| 6-330Y | Rh | 0 | 6 | OL | H | H | CH$_3$ | H | H | — | — |
| 6-331 | Rh | 1 | 6 | OL | —CH$_2$CH$_2$CH$_2$— | | CH$_3$ | H | H | pic | |
| 6-331X | Rh | 1 | 6 | OL | —CH$_2$CH$_2$CH$_2$— | | CH$_3$ | H | H | acac | |
| 6-331Y | Rh | 0 | 6 | OL | —CH$_2$CH$_2$CH$_2$— | | CH$_3$ | H | H | — | — |
| 6-332 | Rh | 1 | 6 | OL | —CH$_2$CH$_2$CH$_2$— | | $^tC_4H_9$ | H | H | pic | |
| 6-332X | Rh | 1 | 6 | OL | —CH$_2$CH$_2$CH$_2$— | | $^tC_4H_9$ | H | H | acac | |
| 6-332Y | Rh | 0 | 6 | OL | —CH$_2$CH$_2$CH$_2$— | | $^tC_4H_9$ | H | H | — | — |

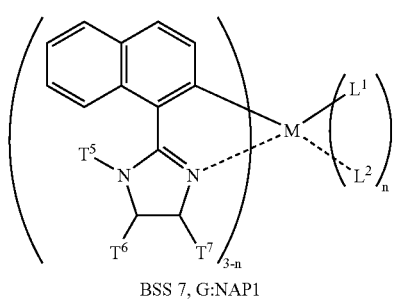
BSS 7, G:NAP1
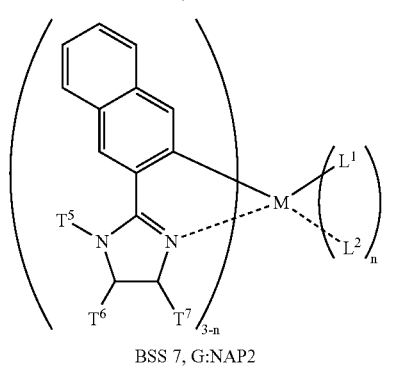
BSS 7, G:NAP2
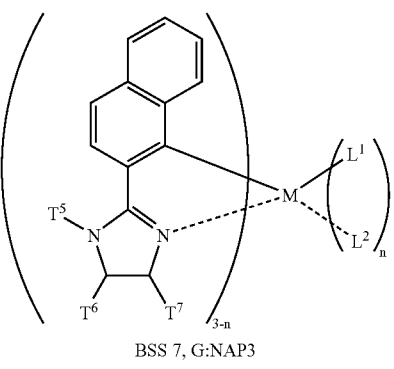
BSS 7, G:NAP3
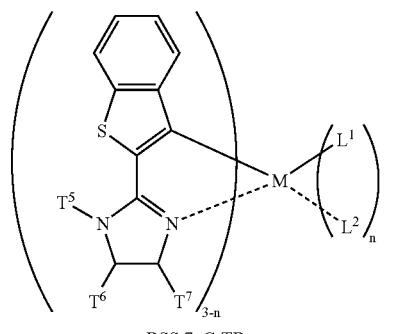
BSS 7, G:TB
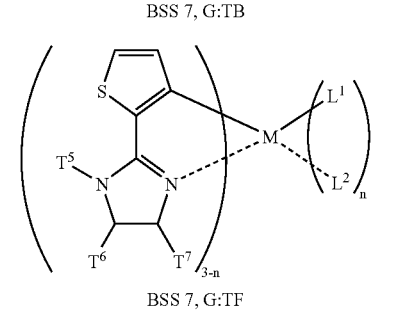
BSS 7, G:TF
-continued
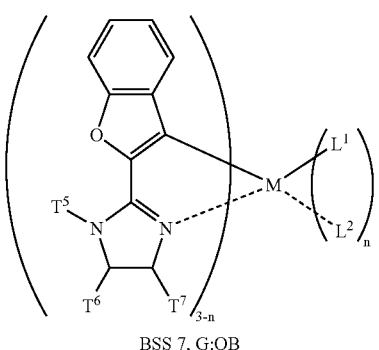
BSS 7, G:OB
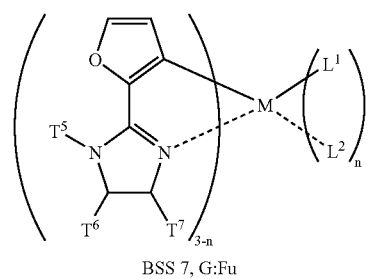
BSS 7, G:Fu
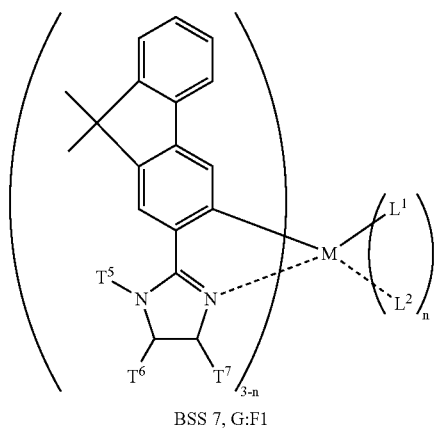
BSS 7, G:Fl
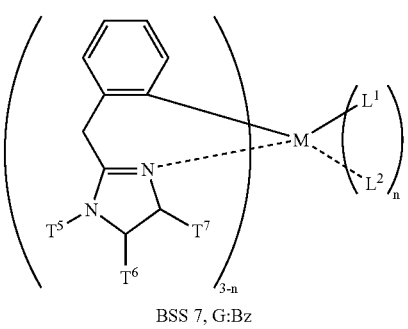
BSS 7, G:Bz

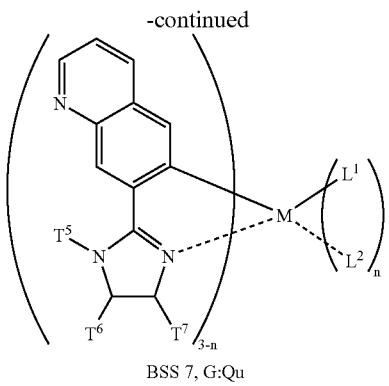

BSS 7, G:Qu

-continued

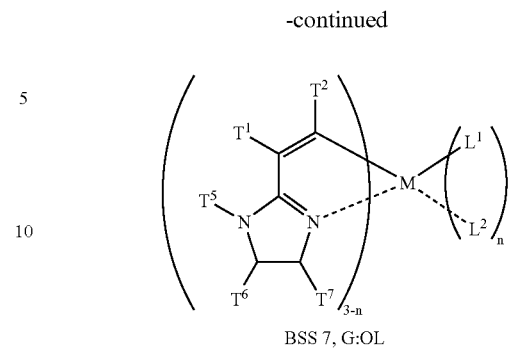

BSS 7, G:OL

TABLE 28

| No. | M | n | BSS | SS G | T¹ | T² | T⁵ | T⁶ | T⁷ | L¹ | L² |
|---|---|---|---|---|---|---|---|---|---|---|---|
| 7-304 | Rh | 1 | 7 | Nap1 | — | — | $CH_3$ | H | H | pic | |
| 7-304X | Rh | 1 | 7 | Nap1 | — | — | $CH_3$ | H | H | acac | |
| 7-304Y | Rh | 0 | 7 | Nap1 | — | — | $CH_3$ | H | H | — | — |
| 7-305 | Rh | 1 | 7 | Nap1 | — | — | $^tC_4H_9$ | H | H | pic | |
| 7-305X | Rh | 1 | 7 | Nap1 | — | — | $^tC_4H_9$ | H | H | acac | |
| 7-305Y | Rh | 0 | 7 | Nap1 | — | — | $^tC_4H_9$ | H | H | — | — |
| 7-306 | Rh | 1 | 7 | Nap2 | — | — | $CH_3$ | H | H | pic | |
| 7-306X | Rh | 1 | 7 | Nap2 | — | — | $CH_3$ | H | H | acac | |
| 7-306Y | Rh | 0 | 7 | Nap2 | — | — | $CH_3$ | H | H | — | — |
| 7-307 | Rh | 1 | 7 | Nap2 | — | — | $^tC_4H_9$ | H | H | pic | |
| 7-307X | Rh | 1 | 7 | Nap2 | — | — | $^tC_4H_9$ | H | H | acac | |
| 7-307Y | Rh | 0 | 7 | Nap2 | — | — | $^tC_4H_9$ | H | H | — | — |
| 7-308 | Rh | 1 | 7 | Nap3 | — | — | $CH_3$ | H | H | pic | |
| 7-308X | Rh | 1 | 7 | Nap3 | — | — | $CH_3$ | H | H | acac | |
| 7-308Y | Rh | 0 | 7 | Nap3 | — | — | $CH_3$ | H | H | — | — |
| 7-309 | Rh | 1 | 7 | Nap3 | — | — | $^tC_4H_9$ | H | H | pic | |
| 7-309X | Rh | 1 | 7 | Nap3 | — | — | $^tC_4H_9$ | H | H | acac | |
| 7-309Y | Rh | 0 | 7 | Nap3 | — | — | $^tC_4H_9$ | H | H | — | — |
| 7-310 | Rh | 1 | 7 | TB | — | — | $CH_3$ | H | H | pic | |
| 7-310X | Rh | 1 | 7 | TB | — | — | $CH_3$ | H | H | acac | |
| 7-310Y | Rh | 0 | 7 | TB | — | — | $CH_3$ | H | H | — | — |
| 7-311 | Rh | 1 | 7 | TB | — | — | $^tC_4H_9$ | H | H | pic | |
| 7-311X | Rh | 1 | 7 | TB | — | — | $^tC_4H_9$ | H | H | acac | |
| 7-311Y | Rh | 0 | 7 | TB | — | — | $^tC_4H_9$ | H | H | — | — |
| 7-312 | Rh | 1 | 7 | TF | — | — | $CH_3$ | H | H | pic | |
| 7-312X | Rh | 1 | 7 | TF | — | — | $CH_3$ | H | H | acac | |
| 7-312Y | Rh | 0 | 7 | TF | — | — | $CH_3$ | H | H | — | — |
| 7-313 | Rh | 1 | 7 | TF | — | — | $^tC_4H_9$ | H | H | pic | |
| 7-313X | Rh | 1 | 7 | TF | — | — | $^tC_4H_9$ | H | H | acac | |
| 7-313Y | Rh | 0 | 7 | TF | — | — | $^tC_4H_9$ | H | H | — | — |
| 7-314 | Rh | 1 | 7 | OB | — | — | $CH_3$ | H | H | pic | |
| 7-314X | Rh | 1 | 7 | OB | — | — | $CH_3$ | H | H | acac | |
| 7-314Y | Rh | 0 | 7 | OB | — | — | $CH_3$ | H | H | — | — |
| 7-315 | Rh | 1 | 7 | OB | — | — | $^tC_4H_9$ | H | H | pic | |
| 7-315X | Rh | 1 | 7 | OB | — | — | $^tC_4H_9$ | H | H | acac | |
| 7-315Y | Rh | 0 | 7 | OB | — | — | $^tC_4H_9$ | H | H | — | — |
| 7-316 | Rh | 1 | 7 | Fu | — | — | $CH_3$ | H | H | pic | |
| 7-316X | Rh | 1 | 7 | Fu | — | — | $CH_3$ | H | H | acac | |
| 7-316Y | Rh | 0 | 7 | Fu | — | — | $CH_3$ | H | H | — | — |
| 7-317 | Rh | 1 | 7 | Fu | — | — | $^tC_4H_9$ | H | H | pic | |
| 7-317X | Rh | 1 | 7 | Fu | — | — | $^tC_4H_9$ | H | H | acac | |
| 7-317Y | Rh | 0 | 7 | Fu | — | — | $^tC_4H_9$ | H | H | — | — |
| 7-318 | Rh | 1 | 7 | Fl | — | — | $CH_3$ | H | H | pic | |
| 7-318X | Rh | 1 | 7 | Fl | — | — | $CH_3$ | H | H | acac | |
| 7-318Y | Rh | 0 | 7 | Fl | — | — | $CH_3$ | H | H | — | — |
| 7-319 | Rh | 1 | 7 | Fl | — | — | $^tC_4H_9$ | H | H | pic | |
| 7-319X | Rh | 1 | 7 | Fl | — | — | $^tC_4H_9$ | H | H | acac | |
| 7-319Y | Rh | 0 | 7 | Fl | — | — | $^tC_4H_9$ | H | H | — | — |
| 7-320 | Rh | 1 | 7 | Bz | — | — | $CH_3$ | H | H | pic | |
| 7-320X | Rh | 1 | 7 | Bz | — | — | $CH_3$ | H | H | acac | |
| 7-320Y | Rh | 0 | 7 | Bz | — | — | $CH_3$ | H | H | — | — |
| 7-321 | Rh | 1 | 7 | Bz | — | — | $^tC_4H_9$ | H | H | pic | |
| 7-321X | Rh | 1 | 7 | Bz | — | — | $^tC_4H_9$ | H | H | acac | |
| 7-321Y | Rh | 0 | 7 | Bz | — | — | $^tC_4H_9$ | H | H | — | — |
| 7-322 | Rh | 1 | 7 | Qu | — | — | $CH_3$ | H | H | pic | |

TABLE 28-continued

| No. | M | n | BSS | SS G | T¹ | T² | T⁵ | T⁸ | T⁷ | L¹ | L² |
|---|---|---|---|---|---|---|---|---|---|---|---|
| 7-322X | Rh | 1 | 7 | Qu | — | — | $CH_3$ | H | H | acac | |
| 7-322Y | Rh | 0 | 7 | Qu | — | — | $CH_3$ | H | H | — | — |
| 7-323 | Rh | 1 | 7 | Qu | — | — | $^tC_4H_9$ | H | H | pic | |
| 7-323X | Rh | 1 | 7 | Qu | — | — | $^tC_4H_9$ | H | H | acac | |
| 7-323Y | Rh | 0 | 7 | Qu | — | — | $^tC_4H_9$ | H | H | — | — |
| 7-324 | Rh | 1 | 7 | OL | H | $^nC_4H_9$ | $CH_3$ | H | H | pic | |
| 7-324X | Rh | 1 | 7 | OL | H | $^nC_4H_9$ | $CH_3$ | H | H | acac | |
| 7-324Y | Rh | 0 | 7 | OL | H | $^nC_4H_9$ | $CH_3$ | H | H | — | — |
| 7-325 | Rh | 1 | 7 | OL | H | $^nC_4H_9$ | $^tC_4H_9$ | H | H | pic | |
| 7-325X | Rh | 1 | 7 | OL | H | $^nC_4H_9$ | $^tC_4H_9$ | H | H | acac | |
| 7-325Y | Rh | 0 | 7 | OL | H | $^nC_4H_9$ | $^tC_4H_9$ | H | H | — | — |
| 7-326 | Rh | 1 | 7 | OL | H | $^tC_4H_9$ | $CH_3$ | H | H | pic | |
| 7-326X | Rh | 1 | 7 | OL | H | $^tC_4H_9$ | $CH_3$ | H | H | acac | |
| 7-326Y | Rh | 0 | 7 | OL | H | $^tC_4H_9$ | $CH_3$ | H | H | — | — |
| 7-327 | Rh | 1 | 7 | OL | H | $^tC_4H_9$ | $^tC_4H_9$ | H | H | pic | |
| 7-327X | Rh | 1 | 7 | OL | H | $^tC_4H_9$ | $^tC_4H_9$ | H | H | acac | |
| 7-327Y | Rh | 0 | 7 | OL | H | $^tC_4H_9$ | $^tC_4H_9$ | H | H | — | — |
| 7-328 | Rh | 1 | 7 | OL | $CH_3$ | $^nC_4H_9$ | $CH_3$ | H | H | pic | |
| 7-328X | Rh | 1 | 7 | OL | $CH_3$ | $^nC_4H_9$ | $CH_3$ | H | H | acac | |
| 7-328Y | Rh | 0 | 7 | OL | $CH_3$ | $^nC_4H_9$ | $CH_3$ | H | H | — | — |
| 7-329 | Rh | 1 | 7 | OL | $CH_3$ | $^tC_4H_9$ | $CH_3$ | H | H | pic | |
| 7-329X | Rh | 1 | 7 | OL | $CH_3$ | $^tC_4H_9$ | $CH_3$ | H | H | acac | |
| 7-329Y | Rh | 0 | 7 | OL | $CH_3$ | $^tC_4H_9$ | $CH_3$ | H | H | — | — |
| 7-330 | Rh | 1 | 7 | OL | H | H | $CH_3$ | H | H | pic | |
| 7-330X | Rh | 1 | 7 | OL | H | H | $CH_3$ | H | H | acac | |
| 7-330Y | Rh | 0 | 7 | OL | H | H | $CH_3$ | H | H | — | — |
| 7-331 | Rh | 1 | 7 | OL | —$CH_2CH_2CH_2$— | | $CH_3$ | H | H | pic | |
| 7-331X | Rh | 1 | 7 | OL | —$CH_2CH_2CH_2$— | | $CH_3$ | H | H | acac | |
| 7-331Y | Rh | 0 | 7 | OL | —$CH_2CH_2CH_2$— | | $CH_3$ | H | H | — | — |
| 7-332 | Rh | 1 | 7 | OL | —$CH_2CH_2CH_2$— | | $^tC_4H_9$ | H | H | pic | |
| 7-332X | Rh | 1 | 7 | OL | —$CH_2CH_2CH_2$— | | $^tC_4H_9$ | H | H | acac | |
| 7-332Y | Rh | 0 | 7 | OL | —$CH_2CH_2CH_2$— | | $^tC_4H_9$ | H | H | — | — |

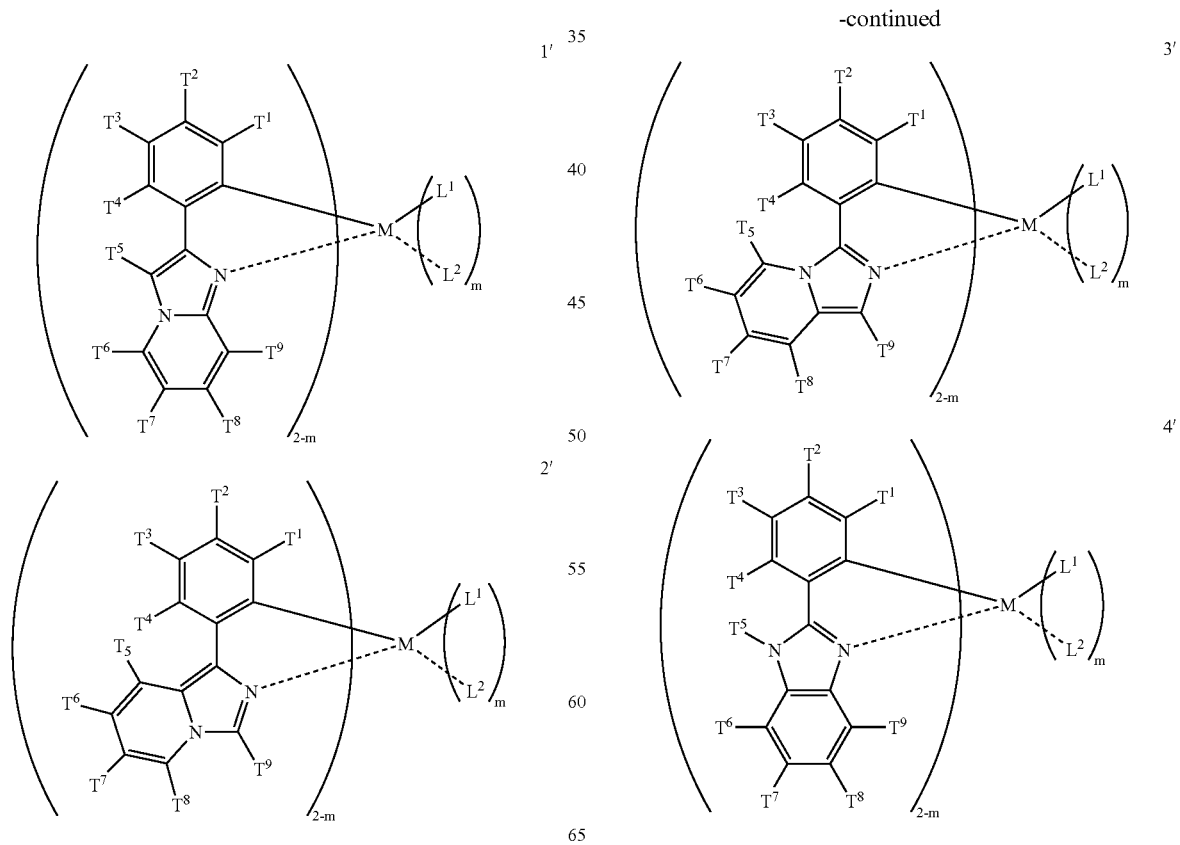

-continued

-continued

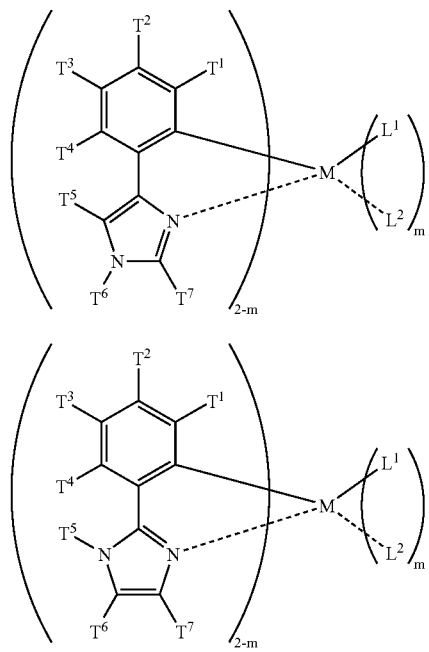

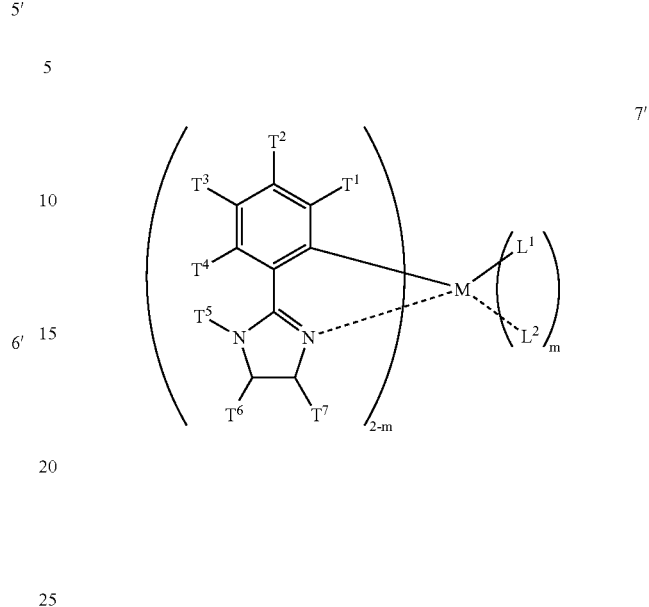

TABLE 29

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1'-1 | Pt | 1 | 1' | Ph | H | H | H | H | H | H | H | H | H | pic |
| 1'-1X | Pt | 1 | 1' | Ph | H | H | H | H | H | H | H | H | H | acac |
| 1'-1Y | Pt | 0 | 1' | Ph | H | H | H | H | H | H | H | H | H | — — |
| 1'-2 | Pt | 1 | 1' | Ph | H | F | H | F | H | H | H | H | H | pic |
| 1'-2X | Pt | 1 | 1' | Ph | H | F | H | F | H | H | H | H | H | acac |
| 1'-2Y | Pt | 0 | 1' | Ph | H | F | H | F | H | H | H | H | H | — — |
| 1'-3 | Pt | 1 | 1' | Ph | F | H | H | F | H | H | H | H | H | pic |
| 1'-3X | Pt | 1 | 1' | Ph | F | H | H | F | H | H | H | H | H | acac |
| 1'-3Y | Pt | 0 | 1' | Ph | F | H | H | F | H | H | H | H | H | — — |
| 1'-4 | Pt | 1 | 1' | Ph | $CF_3$ | H | $CF_3$ | H | H | H | H | H | H | pic |
| 1'-4X | Pt | 1 | 1' | Ph | $CF_3$ | H | $CF_3$ | H | H | H | H | H | H | acac |
| 1'-4Y | Pt | 0 | 1' | Ph | $CF_3$ | H | $CF_3$ | H | H | H | H | H | H | — — |
| 1'-5 | Pt | 1 | 1' | Ph | H | F | $CF_3$ | H | H | H | H | H | H | pic |
| 1'-5X | Pt | 1 | 1' | Ph | H | F | $CF_3$ | H | H | H | H | H | H | acac |
| 1'-5Y | Pt | 0 | 1' | Ph | H | F | $CF_3$ | H | H | H | H | H | H | — — |
| 1'-6 | Pt | 1 | 1' | Ph | F | H | $CF_3$ | H | H | H | H | H | H | pic |
| 1'-6X | Pt | 1 | 1' | Ph | F | H | $CF_3$ | H | H | H | H | H | H | acac |
| 1'-6Y | Pt | 0 | 1' | Ph | F | H | $CF_3$ | H | H | H | H | H | H | — — |
| 1'-7 | Pt | 1 | 1' | Ph | F | F | F | F | H | H | H | H | H | pic |
| 1'-7X | Pt | 1 | 1' | Ph | F | F | F | F | H | H | H | H | H | acac |
| 1'-7Y | Pt | 0 | 1' | Ph | F | F | F | F | H | H | H | H | H | — — |
| 1'-8 | Pt | 1 | 1' | Ph | H | F | H | $CH_3$ | H | H | H | H | H | pic |
| 1'-8X | Pt | 1 | 1' | Ph | H | F | H | $CH_3$ | H | H | H | H | H | acac |
| 1'-8Y | Pt | 0 | 1' | Ph | H | F | H | $CH_3$ | H | H | H | H | H | — — |
| 1'-9 | Pt | 1 | 1' | Ph | H | F | H | $^tC_4H_9$ | H | H | H | H | H | pic |
| 1'-9X | Pt | 1 | 1' | Ph | H | F | H | $^tC_4H_9$ | H | H | H | H | H | acac |
| 1'-9Y | Pt | 0 | 1' | Ph | H | F | H | $^tC_4H_9$ | H | H | H | H | H | — — |
| 1'-10 | Pt | 1 | 1' | Ph | H | $CF_3$ | H | $CF_3$ | H | H | H | H | H | pic |
| 1'-10X | Pt | 1 | 1' | Ph | H | $CF_3$ | H | $CF_3$ | H | H | H | H | H | acac |
| 1'-10Y | Pt | 0 | 1' | Ph | H | $CF_3$ | H | $CF_3$ | H | H | H | H | H | — — |
| 1'-11 | Pt | 1 | 1' | Ph | $CF_3$ | H | H | $^tC_4H_9$ | H | H | H | H | H | pic |
| 1'-11X | Pt | 1 | 1' | Ph | $CF_3$ | H | H | $^tC_4H_9$ | H | H | H | H | H | acac |
| 1'-11Y | Pt | 0 | 1' | Ph | $CF_3$ | H | H | $^tC_4H_9$ | H | H | H | H | H | — — |
| 1'-12 | Pt | 1 | 1' | Ph | H | $CF_3$ | H | $^tC_4H_9$ | H | H | H | H | H | pic |
| 1'-12X | Pt | 1 | 1' | Ph | H | $CF_3$ | H | $^tC_4H_9$ | H | H | H | H | H | acac |
| 1'-12Y | Pt | 0 | 1' | Ph | H | $CF_3$ | H | $^tC_4H_9$ | H | H | H | H | H | — — |
| 1'-13 | Pt | 1 | 1' | Ph | H | $CF_3$ | H | $CH_3$ | H | H | H | H | H | pic |
| 1'-13X | Pt | 1 | 1' | Ph | H | $CF_3$ | H | $CH_3$ | H | H | H | H | H | acac |
| 1'-13Y | Pt | 0 | 1' | Ph | H | $CF_3$ | H | $CH_3$ | H | H | H | H | H | — — |
| 1'-14 | Pt | 1 | 1' | Ph | H | $CF_3$ | $CF_3$ | H | H | H | H | H | H | pic |
| 1'-14X | Pt | 1 | 1' | Ph | H | $CF_3$ | $CF_3$ | H | H | H | H | H | H | acac |

TABLE 29-continued

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1'-14Y | Pt | 0 | 1' | Ph | H | CF₃ | CF₃ | H | H | H | H | H | H | — — |
| 1'-15 | Pt | 1 | 1' | Ph | H | H | NO₂ | H | H | H | H | H | H | pic |
| 1'-15X | Pt | 1 | 1' | Ph | H | H | NO₂ | H | H | H | H | H | H | acac |
| 1'-15Y | Pt | 0 | 1' | Ph | H | H | NO₂ | H | H | H | H | H | H | — — |
| 1'-16 | Pt | 1 | 1' | Ph | F | H | NO₂ | H | H | H | H | H | H | pic |
| 1'-16X | Pt | 1 | 1' | Ph | F | H | NO₂ | H | H | H | H | H | H | acac |
| 1'-16Y | Pt | 0 | 1' | Ph | F | H | NO₂ | H | H | H | H | H | H | — — |
| 1'-17 | Pt | 1 | 1' | Ph | F | H | NO₂ | F | H | H | H | H | H | pic |
| 1'-17X | Pt | 1 | 1' | Ph | F | H | NO₂ | F | H | H | H | H | H | acac |
| 1'-17Y | Pt | 0 | 1' | Ph | F | H | NO₂ | F | H | H | H | H | H | — — |
| 1'-18 | Pt | 1 | 1' | Ph | H | NO₂ | H | NO₂ | H | H | H | H | H | pic |
| 1'-18X | Pt | 1 | 1' | Ph | H | NO₂ | H | NO₂ | H | H | H | H | H | acac |
| 1'-18Y | Pt | 0 | 1' | Ph | H | NO₂ | H | NO₂ | H | H | H | H | H | — — |
| 1'-19 | Pt | 1 | 1' | Ph | NO₂ | H | H | NO₂ | H | H | H | H | H | pic |
| 1'-19X | Pt | 1 | 1' | Ph | NO₂ | H | H | NO₂ | H | H | H | H | H | acac |
| 1'-19Y | Pt | 0 | 1' | Ph | NO₂ | H | H | NO₂ | H | H | H | H | H | — — |
| 1'-20 | Pt | 1 | 1' | Ph | H | H | CF₃ | H | H | H | H | H | H | pic |
| 1'-20X | Pt | 1 | 1' | Ph | H | H | CF₃ | H | H | H | H | H | H | acac |
| 1'-20Y | Pt | 0 | 1' | Ph | H | H | CF₃ | H | H | H | H | H | H | — — |
| 1'-21 | Pt | 1 | 1' | Ph | H | Cl | CF₃ | H | H | H | H | H | H | pic |
| 1'-21X | Pt | 1 | 1' | Ph | H | Cl | CF₃ | H | H | H | H | H | H | acac |
| 1'-21Y | Pt | 0 | 1' | Ph | H | Cl | CF₃ | H | H | H | H | H | H | — — |
| 1'-22 | Pt | 1 | 1' | Ph | H | NO₂ | H | H | H | H | H | H | H | pic |
| 1'-22X | Pt | 1 | 1' | Ph | H | NO₂ | H | H | H | H | H | H | H | acac |
| 1'-22Y | Pt | 0 | 1' | Ph | H | NO₂ | H | H | H | H | H | H | H | — — |
| 1'-23 | Pt | 1 | 1' | Ph | H | CF₃ | H | H | H | H | H | H | H | pic |
| 1'-23X | Pt | 1 | 1 | Ph | H | CF₃ | H | H | H | H | H | H | H | acac |
| 1'-23Y | Pt | 0 | 1' | Ph | H | CF₃ | H | H | H | H | H | H | H | — — |
| 1'-24 | Pt | 1 | 1' | Ph | H | NO₂ | H | CH₃ | H | H | H | H | H | pic |
| 1'-24X | Pt | 1 | 1' | Ph | H | NO₂ | H | CH₃ | H | H | H | H | H | acac |
| 1'-24Y | Pt | 0 | 1' | Ph | H | NO₂ | H | CH₃ | H | H | H | H | H | — — |
| 1'-25 | Pt | 1 | 1' | Ph | H | NO₂ | H | $^tC_4H_9$ | H | H | H | H | H | pic |
| 1'-25X | Pt | 1 | 1' | Ph | H | NO₂ | H | $^tC_4H_9$ | H | H | H | H | H | acac |
| 1'-25Y | Pt | 0 | 1' | Ph | H | NO₂ | H | $^tC_4H_9$ | H | H | H | H | H | — — |
| 1'-26 | Pt | 1 | 1' | Ph | H | H | CH₃O | H | H | H | H | H | H | pic |
| 1'-26X | Pt | 1 | 1' | Ph | H | H | CH₃O | H | H | H | H | H | H | acac |
| 1'-26Y | Pt | 0 | 1' | Ph | H | H | CH₃O | H | H | H | H | H | H | — — |
| 1'-27 | Pt | 1 | 1' | Ph | H | CH₃O | H | H | H | H | H | H | H | pic |
| 1'-27X | Pt | 1 | 1' | Ph | H | CH₃O | H | H | H | H | H | H | H | acac |
| 1'-27Y | Pt | 0 | 1' | Ph | H | CH₃O | H | H | H | H | H | H | H | — — |
| 1'-28 | Pt | 1 | 1' | Ph | H | CH₃O | H | CH₃ | H | H | H | H | H | pic |
| 1'-28X | Pt | 1 | 1' | Ph | H | CH₃O | H | CH₃ | H | H | H | H | H | acac |
| 1'-28Y | Pt | 0 | 1' | Ph | H | CH₃O | H | CH₃ | H | H | H | H | H | — — |
| 1'-29 | Pt | 1 | 1' | Ph | H | CH₃O | H | $^tC_4H_9$ | H | H | H | H | H | pic |
| 1'-29X | Pt | 1 | 1' | Ph | H | CH₃O | H | $^tC_4H_9$ | H | H | H | H | H | acac |
| 1'-29Y | Pt | 0 | 1' | Ph | H | CH₃O | H | $^tC_4H_9$ | H | H | H | H | H | — — |
| 1'-30 | Pt | 1 | 1' | Ph | H | H | H | H | $^tC_4H_9$ | H | H | H | H | pic |
| 1'-30X | Pt | 1 | 1' | Ph | H | H | H | H | $^tC_4H_9$ | H | H | H | H | acac |
| 1'-30Y | Pt | 0 | 1' | Ph | H | H | H | H | $^tC_4H_9$ | H | H | H | H | — — |
| 1'-31 | Pt | 1 | 1' | Ph | H | F | H | F | $^tC_4H_9$ | H | H | H | H | pic |
| 1'-31X | Pt | 1 | 1' | Ph | H | F | H | F | $^tC_4H_9$ | H | H | H | H | acac |
| 1'-31Y | Pt | 0 | 1' | Ph | H | F | H | F | $^tC_4H_9$ | H | H | H | H | — — |
| 1'-32 | Pt | 1 | 1' | Ph | CF₃ | H | CF₃ | H | $^tC_4H_9$ | H | H | H | H | pic |
| 1'-32X | Pt | 1 | 1' | Ph | CF₃ | H | CF₃ | H | $^tC_4H_9$ | H | H | H | H | acac |
| 1'-32Y | Pt | 0 | 1' | Ph | CF₃ | H | CF₃ | H | $^tC_4H_9$ | H | H | H | H | — — |
| 1'-33 | Pt | 1 | 1' | Ph | H | CF₃ | H | CH₃ | $^tC_4H_9$ | H | H | H | H | pic |
| 1'-33X | Pt | 1 | 1' | Ph | H | CF₃ | H | CH₃ | $^tC_4H_9$ | H | H | H | H | acac |
| 1'-33Y | Pt | 0 | 1' | Ph | H | CF₃ | H | CH₃ | $^tC_4H_9$ | H | H | H | H | — — |
| 1'-34 | Pt | 1 | 1' | Ph | H | F | H | F | H | CH₃ | H | H | H | pic |
| 1'-34X | Pt | 1 | 1' | Ph | H | F | H | F | H | CH₃ | H | H | H | acac |
| 1'-34Y | Pt | 0 | 1' | Ph | H | F | H | F | H | CH₃ | H | H | H | — — |
| 1'-35 | Pt | 1 | 1' | Ph | CF₃ | H | CF₃ | H | H | CH₃ | H | H | H | pic |
| 1'-35X | Pt | 1 | 1' | Ph | CF₃ | H | CF₃ | H | H | CH₃ | H | H | H | acac |
| 1'-35Y | Pt | 0 | 1' | Ph | CF₃ | H | CF₃ | H | H | CH₃ | H | H | H | — — |
| 1'-36 | Pt | 1 | 1' | Ph | H | Si(CH₃)₃ | H | H | H | H | H | H | H | pic |
| 1'-36X | Pt | 1 | 1' | Ph | H | Si(CH₃)₃ | H | H | H | H | H | H | H | acac |
| 1'-36Y | Pt | 0 | 1' | Ph | H | Si(CH₃)₃ | H | H | H | H | H | H | H | — — |
| 1'-37 | Pt | 1 | 1' | Ph | H | H | Si(CH₃)₃ | H | H | H | H | H | H | pic |
| 1'-37X | Pt | 1 | 1' | Ph | H | H | Si(CH₃)₃ | H | H | H | H | H | H | acac |
| 1'-37Y | Pt | 0 | 1' | Ph | H | H | Si(CH₃)₃ | H | H | H | H | H | H | — — |
| 1'-38 | Pt | 1 | 1' | Ph | H | H | H | Si(CH₃)₃ | H | H | H | H | H | pic |
| 1'-38X | Pt | 1 | 1' | Ph | H | H | H | Si(CH₃)₃ | H | H | H | H | H | acac |
| 1'-38Y | Pt | 0 | 1' | Ph | H | H | H | Si(CH₃)₃ | H | H | H | H | H | — — |
| 1'-39 | Pt | 1 | 1' | Ph | H | F | H | Si(CH₃)₃ | H | H | H | H | H | pic |
| 1'-39X | Pt | 1 | 1' | Ph | H | F | H | Si(CH₃)₃ | H | H | H | H | H | acac |
| 1'-39Y | Pt | 0 | 1' | Ph | H | F | H | Si(CH₃)₃ | H | H | H | H | H | — — |
| 1'-40 | Pt | 1 | 1' | Ph | H | CF₃ | H | Si(CH₃)₃ | H | H | H | H | H | pic |

TABLE 29-continued

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1'-40X | Pt | 1 | 1' | Ph | H | CF₃ | H | Si(CH₃)₃ | H | H | H | H | H | acac |
| 1'-40Y | Pt | 0 | 1' | Ph | H | CF₃ | H | Si(CH₃)₃ | H | H | H | H | H | — — |
| 1'-41 | Pt | 1 | 1' | Ph | H | Si(CH₃)₃ | H | F | H | H | H | H | H | pic |
| 1'-41X | Pt | 1 | 1' | Ph | H | Si(CH₃)₃ | H | F | H | H | H | H | H | acac |
| 1'-41Y | Pt | 0 | 1' | Ph | H | Si(CH₃)₃ | H | F | H | H | H | H | H | — — |
| 1'-42 | Pt | 1 | 1' | Ph | H | Si(CH₃)₃ | H | CF₃ | H | H | H | H | H | pic |
| 1'-42X | Pt | 1 | 1' | Ph | H | Si(CH₃)₃ | H | CF₃ | H | H | H | H | H | acac |
| 1'-42Y | Pt | 0 | 1' | Ph | H | Si(CH₃)₃ | H | CF₃ | H | H | H | H | H | — — |
| 1'-43 | Pt | 1 | 1' | Ph | Si(CH₃)₃ | H | Si(CH₃)₃ | H | H | H | H | H | H | pic |
| 1'-43X | Pt | 1 | 1' | Ph | Si(CH₃)₃ | H | Si(CH₃)₃ | H | H | H | H | H | H | acac |
| 1'-43Y | Pt | 0 | 1' | Ph | Si(CH₃)₃ | H | Si(CH₃)₃ | H | H | H | H | H | H | — — |
| 1'-44 | Pt | 1 | 1' | Ph | H | H | H | COCH₃ | H | H | H | H | H | pic |
| 1'-44X | Pt | 1 | 1' | Ph | H | H | H | COCH₃ | H | H | H | H | H | acac |
| 1'-44Y | Pt | 0 | 1' | Ph | H | H | H | COCH₃ | H | H | H | H | H | — — |
| 1'-45 | Pt | 1 | 1' | Ph | H | H | COCH₃ | H | H | H | H | H | H | pic |
| 1'-45X | Pt | 1 | 1' | Ph | H | H | COCH₃ | H | H | H | H | H | H | acac |
| 1'-45Y | Pt | 0 | 1' | Ph | H | H | COCH₃ | H | H | H | H | H | H | — — |
| 1'-46 | Pt | 1 | 1' | Ph | H | COCH₃ | H | H | H | H | H | H | H | pic |
| 1'-46X | Pt | 1 | 1' | Ph | H | COCH₃ | H | H | H | H | H | H | H | acac |
| 1'-46Y | Pt | 0 | 1' | Ph | H | COCH₃ | H | H | H | H | H | H | H | — — |
| 1'-47 | Pt | 1 | 1' | Ph | H | H | BL | H | H | H | H | H | H | pic |
| 1'-47X | Pt | 1 | 1' | Ph | H | H | BL | H | H | H | H | H | H | acac |
| 1'-47Y | Pt | 0 | 1' | Ph | H | H | BL | H | H | H | H | H | H | — — |
| 1'-48 | Pt | 1 | 1' | Ph | H | BL | H | H | H | H | H | H | H | pic |
| 1'-48X | Pt | 1 | 1' | Ph | H | BL | H | H | H | H | H | H | H | acac |
| 1'-48Y | Pt | 0 | 1' | Ph | H | BL | H | H | H | H | H | H | H | — — |
| 1'-49 | Pt | 1 | 1' | Ph | H | H | PL | H | H | H | H | H | H | pic |
| 1'-49X | Pt | 1 | 1' | Ph | H | H | PL | H | H | H | H | H | H | acac |
| 1'-49Y | Pt | 0 | 1' | Ph | H | H | PL | H | H | H | H | H | H | — — |
| 1'-50 | Pt | 1 | 1' | Ph | H | PL | H | H | H | H | H | H | H | pic |
| 1'-50X | Pt | 1 | 1' | Ph | H | PL | H | H | H | H | H | H | H | acac |
| 1'-50Y | Pt | 0 | 1' | Ph | H | PL | H | H | H | H | H | H | H | — — |
| 1'-51 | Pt | 1 | 1' | Ph | H | H | MEE1 | H | H | H | H | H | H | pic |
| 1'-51X | Pt | 1 | 1' | Ph | H | H | MEE1 | H | H | H | H | H | H | acac |
| 1'-51Y | Pt | 0 | 1' | Ph | H | H | MEE1 | H | H | H | H | H | H | — — |
| 1'-52 | Pt | 1 | 1' | Ph | H | MEE1 | H | H | H | H | H | H | H | pic |
| 1'-52X | Pt | 1 | 1' | Ph | H | MEE1 | H | H | H | H | H | H | H | acac |
| 1'-52Y | Pt | 0 | 1' | Ph | H | MEE1 | H | H | H | H | H | H | H | — — |
| 1'-53 | Pt | 1 | 1' | Ph | H | H | MEE2 | H | H | H | H | H | H | pic |
| 1'-53X | Pt | 1 | 1' | Ph | H | H | MEE2 | H | H | H | H | H | H | acac |
| 1'-53Y | Pt | 0 | 1' | Ph | H | H | MEE2 | H | H | H | H | H | H | — — |
| 1'-54 | Pt | 1 | 1' | Ph | H | MEE2 | H | H | H | H | H | H | H | pic |
| 1'-54X | Pt | 1 | 1' | Ph | H | MEE2 | H | H | H | H | H | H | H | acac |
| 1'-54Y | Pt | 0 | 1' | Ph | H | MEE2 | H | H | H | H | H | H | H | — — |
| 1'-55 | Pt | 1 | 1' | Ph | H | H | PA1 | H | H | H | H | H | H | pic |
| 1'-55X | Pt | 1 | 1' | Ph | H | H | PA1 | H | H | H | H | H | H | acac |
| 1'-55Y | Pt | 0 | 1' | Ph | H | H | PA1 | H | H | H | H | H | H | — — |
| 1'-56 | Pt | 1 | 1' | Ph | H | PA1 | H | H | H | H | H | H | H | pic |
| 1'-56X | Pt | 1 | 1' | Ph | H | PA1 | H | H | H | H | H | H | H | acac |
| 1'-56Y | Pt | 0 | 1' | Ph | H | PA1 | H | H | H | H | H | H | H | — — |
| 1'-57 | Pt | 1 | 1' | Ph | H | H | PA2 | H | H | H | H | H | H | pic |
| 1'-57X | Pt | 1 | 1' | Ph | H | H | PA2 | H | H | H | H | H | H | acac |
| 1'-57Y | Pt | 0 | 1' | Ph | H | H | PA2 | H | H | H | H | H | H | — — |
| 1'-58 | Pt | 1 | 1' | Ph | H | PA2 | H | H | H | H | H | H | H | pic |
| 1'-58X | Pt | 1 | 1' | Ph | H | PA2 | H | H | H | H | H | H | H | acac |
| 1'-58Y | Pt | 0 | 1' | Ph | H | PA2 | H | H | H | H | H | H | H | — — |
| 1'-59 | Pt | 1 | 1 | Ph | H | H | EA1 | H | H | H | H | H | H | pic |
| 1'-59X | Pt | 1 | 1' | Ph | H | H | EA1 | H | H | H | H | H | H | acac |
| 1'-59Y | Pt | 0 | 1' | Ph | H | H | EA1 | H | H | H | H | H | H | — — |
| 1'-60 | Pt | 1 | 1' | Ph | H | EA2 | H | H | H | H | H | H | H | pic |
| 1'-60X | Pt | 1 | 1' | Ph | H | EA2 | H | H | H | H | H | H | H | acac |
| 1'-60Y | Pt | 0 | 1' | Ph | H | EA2 | H | H | H | H | H | H | H | — — |
| 1'-61 | Pt | 1 | 1' | Ph | H | H | ME | H | H | H | H | H | H | pic |
| 1'-61X | Pt | 1 | 1' | Ph | H | H | ME | H | H | H | H | H | H | acac |
| 1'-61Y | Pt | 0 | 1' | Ph | H | H | ME | H | H | H | H | H | H | — — |
| 1'-62 | Pt | 1 | 1' | Ph | H | ME | H | H | H | H | H | H | H | pic |
| 1'-62X | Pt | 1 | 1' | Ph | H | ME | H | H | H | H | H | H | H | acac |
| 1'-62Y | Pt | 0 | 1' | Ph | H | ME | H | H | H | H | H | H | H | — — |
| 1'-63 | Pt | 1 | 1' | Ph | H | H | AT | H | H | H | H | H | H | pic |
| 1'-63X | Pt | 1 | 1' | Ph | H | H | AT | H | H | H | H | H | H | acac |
| 1'-63Y | Pt | 0 | 1' | Ph | H | H | AT | H | H | H | H | H | H | — — |
| 1'-64 | Pt | 1 | 1' | Ph | H | AT | H | H | H | H | H | H | H | pic |
| 1'-64X | Pt | 1 | 1' | Ph | H | AT | H | H | H | H | H | H | H | acac |
| 1'-64Y | Pt | 0 | 1' | Ph | H | AT | H | H | H | H | H | H | H | — — |
| 1'-65 | Pt | 1 | 1' | Ph | H | H | MES1 | H | H | H | H | H | H | pic |
| 1'-65X | Pt | 1 | 1' | Ph | H | H | MES1 | H | H | H | H | H | H | acac |
| 1'-65Y | Pt | 0 | 1' | Ph | H | H | MES1 | H | H | H | H | H | H | — — |

TABLE 29-continued

| No. | M | m | BSS | SS | G | T¹ | T² | T³ | T⁴ | T⁵ | T⁶ | T⁷ | T⁸ | T⁹ | L¹ L² |
|---|---|---|---|---|---|---|---|---|---|---|---|---|---|---|---|
| 1'-66 | Pt | 1 | 1' | | Ph | H | | MES1 | | H | H | H | H | H | H | pic |
| 1'-66X | Pt | 1 | 1' | | Ph | H | | MES1 | | H | H | H | H | H | H | acac |
| 1'-66Y | Pt | 0 | 1' | | Ph | H | | MES1 | | H | H | H | H | H | H | — — |
| 1'-67 | Pt | 1 | 1' | | Ph | H | H | | MES2 | | H | H | H | H | H | pic |
| 1'-67X | Pt | 1 | 1' | | Ph | H | H | | MES2 | | H | H | H | H | H | acac |
| 1'-67Y | Pt | 0 | 1' | | Ph | H | H | | MES2 | | H | H | H | H | H | — — |
| 1'-68 | Pt | 1 | 1' | | Ph | H | | MES2 | | H | H | H | H | H | H | pic |
| 1'-68X | Pt | 1 | 1' | | Ph | H | | MES2 | | H | H | H | H | H | H | acac |
| 1'-68Y | Pt | 0 | 1' | | Ph | H | | MES2 | | H | H | H | H | H | H | — — |
| 1'-69 | Pt | 1 | 1' | | Ph | H | H | | PS1 | | H | H | H | H | H | pic |
| 1'-69X | Pt | 1 | 1' | | Ph | H | H | | PS1 | | H | H | H | H | H | acac |
| 1'-69Y | Pt | 0 | 1' | | Ph | H | H | | PS1 | | H | H | H | H | H | — — |
| 1'-70 | Pt | 1 | 1' | | Ph | H | | PS1 | | H | H | H | H | H | H | pic |
| 1'-70X | Pt | 1 | 1' | | Ph | H | | PS1 | | H | H | H | H | H | H | acac |
| 1'-70Y | Pt | 0 | 1' | | Ph | H | | PS1 | | H | H | H | H | H | H | — — |
| 1'-71 | Pt | 1 | 1' | | Ph | H | H | | PS2 | | H | H | H | H | H | pic |
| 1'-71X | Pt | 1 | 1' | | Ph | H | H | | PS2 | | H | H | H | H | H | acac |
| 1'-71Y | Pt | 0 | 1' | | Ph | H | H | | PS2 | | H | H | H | H | H | — — |
| 1'-72 | Pt | 1 | 1' | | Ph | H | | PS2 | | H | H | H | H | H | H | pic |
| 1'-72X | Pt | 1 | 1' | | Ph | H | | PS2 | | H | H | H | H | H | H | acac |
| 1'-72Y | Pt | 0 | 1' | | Ph | H | | PS2 | | H | H | H | H | H | H | — — |
| 1'-73 | Pt | 1 | 1' | | Ph | H | H | | BAL1 | | H | H | H | H | H | pic |
| 1'-73X | Pt | 1 | 1' | | Ph | H | H | | BAL1 | | H | H | H | H | H | acac |
| 1'-73Y | Pt | 0 | 1' | | Ph | H | H | | BAL1 | | H | H | H | H | H | — — |
| 1'-74 | Pt | 1 | 1' | | Ph | H | | BAL1 | | H | H | H | H | H | H | pic |
| 1'-74X | Pt | 1 | 1' | | Ph | H | | BAL1 | | H | H | H | H | H | H | acac |
| 1'-74Y | Pt | 0 | 1' | | Ph | H | | BAL1 | | H | H | H | H | H | H | — — |
| 1'-75 | Pt | 1 | 1' | | Ph | H | H | | BAL2 | | H | H | H | H | H | pic |
| 1'-75X | Pt | 1 | 1' | | Ph | H | H | | BAL2 | | H | H | H | H | H | acac |
| 1'-75Y | Pt | 0 | 1' | | Ph | H | H | | BAL2 | | H | H | H | H | H | — — |
| 1'-76 | Pt | 1 | 1' | | Ph | H | | BAL2 | | H | H | H | H | H | H | pic |
| 1'-76X | Pt | 1 | 1' | | Ph | H | | BAL2 | | H | H | H | H | H | H | acac |
| 1'-76Y | Pt | 0 | 1' | | Ph | H | | BAL2 | | H | H | H | H | H | H | — — |
| 1'-77 | Pt | 1 | 1' | | Ph | H | H | | MEK1 | | H | H | H | H | H | pic |
| 1'-77X | Pt | 1 | 1' | | Ph | H | H | | MEK1 | | H | H | H | H | H | acac |
| 1'-77Y | Pt | 0 | 1' | | Ph | H | H | | MEK1 | | H | H | H | H | H | — — |
| 1'-78 | Pt | 1 | 1' | | Ph | H | | MEK1 | | H | H | H | H | H | H | pic |
| 1'-78X | Pt | 1 | 1' | | Ph | H | | MEK1 | | H | H | H | H | H | H | acac |
| 1'-78Y | Pt | 0 | 1' | | Ph | H | | MEK1 | | H | H | H | H | H | H | — — |
| 1'-79 | Pt | 1 | 1' | | Ph | H | H | | MEK2 | | H | H | H | H | H | pic |
| 1'-79X | Pt | 1 | 1' | | Ph | H | H | | MEK2 | | H | H | H | H | H | acac |
| 1'-79Y | Pt | 0 | 1' | | Ph | H | H | | MEK2 | | H | H | H | H | H | — — |
| 1'-80 | Pt | 1 | 1' | | Ph | H | | MEK2 | | H | H | H | H | H | H | pic |
| 1'-80X | Pt | 1 | 1' | | Ph | H | | MEK2 | | H | H | H | H | H | H | acac |
| 1'-80Y | Pt | 0 | 1' | | Ph | H | | MEK2 | | H | H | H | H | H | H | — — |
| 1'-81 | Pt | 1 | 1' | | Ph | H | H | | PAL1 | | H | H | H | H | H | pic |
| 1'-81X | Pt | 1 | 1' | | Ph | H | H | | PAL1 | | H | H | H | H | H | acac |
| 1'-81Y | Pt | 0 | 1' | | Ph | H | H | | PAL1 | | H | H | H | H | H | — — |
| 1'-82 | Pt | 1 | 1' | | Ph | H | | PAL1 | | H | H | H | H | H | H | pic |
| 1'-82X | Pt | 1 | 1' | | Ph | H | | PAL1 | | H | H | H | H | H | H | acac |
| 1'-82Y | Pt | 0 | 1' | | Ph | H | | PAL1 | | H | H | H | H | H | H | — — |
| 1'-83 | Pt | 1 | 1' | | Ph | H | H | | PAL2 | | H | H | H | H | H | pic |
| 1'-83X | Pt | 1 | 1' | | Ph | H | H | | PAL2 | | H | H | H | H | H | acac |
| 1'-83Y | Pt | 0 | 1' | | Ph | H | H | | PAL2 | | H | H | H | H | H | — — |
| 1'-84 | Pt | 1 | 1' | | Ph | H | | PAL2 | | H | H | H | H | H | H | pic |
| 1'-84X | Pt | 1 | 1' | | Ph | H | | PAL2 | | H | H | H | H | H | H | acac |
| 1'-84Y | Pt | 0 | 1' | | Ph | H | | PAL2 | | H | H | H | H | H | H | — — |
| 1'-85 | Pt | 1 | 1' | | Ph | H | H | | MMK | | H | H | H | H | H | pic |
| 1'-85X | Pt | 1 | 1' | | Ph | H | H | | MMK | | H | H | H | H | H | acac |
| 1'-85Y | Pt | 0 | 1' | | Ph | H | H | | MMK | | H | H | H | H | H | — — |
| 1'-86 | Pt | 1 | 1' | | Ph | H | | MMK | | H | H | H | H | H | H | pic |
| 1'-86X | Pt | 1 | 1' | | Ph | H | | MMK | | H | H | H | H | H | H | acac |
| 1'-86Y | Pt | 0 | 1' | | Ph | H | | MMK | | H | H | H | H | H | H | — — |
| 1'-87 | Pt | 1 | 1' | | Ph | H | H | | EES1 | | H | H | H | H | H | pic |
| 1'-87X | Pt | 1 | 1' | | Ph | H | H | | EES1 | | H | H | H | H | H | acac |
| 1'-87Y | Pt | 0 | 1' | | Ph | H | H | | EES1 | | H | H | H | H | H | — — |
| 1'-88 | Pt | 1 | 1' | | Ph | H | | EES2 | | H | H | H | H | H | H | pic |
| 1'-88X | Pt | 1 | 1' | | Ph | H | | EES2 | | H | H | H | H | H | H | acac |
| 1'-88Y | Pt | 0 | 1' | | Ph | H | | EES2 | | H | H | H | H | H | H | — — |
| 1'-89 | Pt | 1 | 1' | | Ph | H | H | | PAE1 | | H | H | H | H | H | pic |
| 1'-89X | Pt | 1 | 1' | | Ph | H | H | | PAE1 | | H | H | H | H | H | acac |
| 1'-89Y | Pt | 0 | 1' | | Ph | H | H | | PAE1 | | H | H | H | H | H | — — |
| 1'-90 | Pt | 1 | 1' | | Ph | H | | PAE2 | | H | H | H | H | H | H | pic |
| 1'-90X | Pt | 1 | 1' | | Ph | H | | PAE2 | | H | H | H | H | H | H | acac |
| 1'-90Y | Pt | 0 | 1' | | Ph | H | | PAE2 | | H | H | H | H | H | H | — — |
| 1'-91 | Pt | 1 | 1' | | Ph | H | H | | AME1 | | H | H | H | H | H | pic |
| 1'-91X | Pt | 1 | 1' | | Ph | H | H | | AME1 | | H | H | H | H | H | acac |

TABLE 29-continued

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1'-91Y | Pt | 0 | 1' | Ph | H | H | | AME1 | H | H | H | H | H | — — |
| 1'-92 | Pt | 1 | 1' | Ph | H | | AME1 | H | H | H | H | H | H | pic |
| 1'-92X | Pt | 1 | 1' | Ph | H | | AME1 | H | H | H | H | H | H | acac |
| 1'-92Y | Pt | 0 | 1' | Ph | H | | AME1 | H | H | H | H | H | H | — — |
| 1'-93 | Pt | 1 | 1' | Ph | H | H | | AME2 | H | H | H | H | H | pic |
| 1'-93X | Pt | 1 | 1' | Ph | H | H | | AME2 | H | H | H | H | H | acac |
| 1'-93Y | Pt | 0 | 1' | Ph | H | H | | AME2 | H | H | H | H | H | — — |
| 1'-94 | Pt | 1 | 1' | Ph | H | | AME2 | H | H | H | H | H | H | pic |
| 1'-94X | Pt | 1 | 1' | Ph | H | | AME2 | H | H | H | H | H | H | acac |
| 1'-94Y | Pt | 0 | 1' | Ph | H | | AME2 | H | H | H | H | H | H | — — |
| 1'-95 | Pt | 1 | 1' | Ph | H | H | | EAE1 | H | H | H | H | H | pic |
| 1'-95X | Pt | 1 | 1' | Ph | H | H | | EAE1 | H | H | H | H | H | acac |
| 1'-95Y | Pt | 0 | 1' | Ph | H | H | | EAE1 | H | H | H | H | H | — — |
| 1'-96 | Pt | 1 | 1' | Ph | H | | EAE1 | H | H | H | H | H | H | pic |
| 1'-96X | Pt | 1 | 1' | Ph | H | | EAE1 | H | H | H | H | H | H | acac |
| 1'-96Y | Pt | 0 | 1' | Ph | H | | EAE1 | H | H | H | H | H | H | — — |
| 1'-97 | Pt | 1 | 1' | Ph | H | H | | EAE2 | H | H | H | H | H | pic |
| 1'-97X | Pt | 1 | 1' | Ph | H | H | | EAE2 | H | H | H | H | H | acac |
| 1'-97Y | Pt | 0 | 1' | Ph | H | H | | EAE2 | H | H | H | H | H | — — |
| 1'-98 | Pt | 1 | 1' | Ph | H | | EAE2 | H | H | H | H | H | H | pic |
| 1'-98X | Pt | 1 | 1' | Ph | H | | EAE2 | H | H | H | H | H | H | acac |
| 1'-98Y | Pt | 0 | 1' | Ph | H | | EAE2 | H | H | H | H | H | H | — — |
| 1'-99 | Pt | 1 | 1' | Ph | H | H | | AAE1 | H | H | H | H | H | pic |
| 1'-99X | Pt | 1 | 1' | Ph | H | H | | AAE1 | H | H | H | H | H | acac |
| 1'-99Y | Pt | 0 | 1' | Ph | H | H | | AAE1 | H | H | H | H | H | — — |
| 1'-100 | Pt | 1 | 1' | Ph | H | | AAE1 | H | H | H | H | H | H | pic |
| 1'-100X | Pt | 1 | 1' | Ph | H | | AAE1 | H | H | H | H | H | H | acac |
| 1'-100Y | Pt | 0 | 1' | Ph | H | | AAE1 | H | H | H | H | H | H | — — |
| 1'-101 | Pt | 1 | 1' | Ph | H | H | | AAE2 | H | H | H | H | H | pic |
| 1'-101X | Pt | 1 | 1' | Ph | H | H | | AAE2 | H | H | H | H | H | acac |
| 1'-101Y | Pt | 0 | 1' | Ph | H | H | | AAE2 | H | H | H | H | H | — — |
| 1'-102 | Pt | 1 | 1' | Ph | H | | AAE2 | H | H | H | H | H | H | pic |
| 1'-102X | Pt | 1 | 1' | Ph | H | | AAE2 | H | H | H | H | H | H | acac |
| 1'-102Y | Pt | 0 | 1' | Ph | H | | AAE2 | H | H | H | H | H | H | — — |
| 1'-103 | Pt | 1 | 1' | Ph | H | H | | PME1 | H | H | H | H | H | pic |
| 1'-103X | Pt | 1 | 1' | Ph | H | H | | PME1 | H | H | H | H | H | acac |
| 1'-103Y | Pt | 0 | 1' | Ph | H | H | | PME1 | H | H | H | H | H | — — |
| 1'-104 | Pt | 1 | 1' | Ph | H | | PME1 | H | H | H | H | H | H | pic |
| 1'-104X | Pt | 1 | 1' | Ph | H | | PME1 | H | H | H | H | H | H | acac |
| 1'-104Y | Pt | 0 | 1' | Ph | H | | PME1 | H | H | H | H | H | H | — — |
| 1'-105 | Pt | 1 | 1' | Ph | H | H | | PME2 | H | H | H | H | H | pic |
| 1'-105X | Pt | 1 | 1' | Ph | H | H | | PME2 | H | H | H | H | H | acac |
| 1'-105Y | Pt | 0 | 1' | Ph | H | H | | PME2 | H | H | H | H | H | — — |
| 1'-106 | Pt | 1 | 1' | Ph | H | | PME2 | H | H | H | H | H | H | pic |
| 1'-106X | Pt | 1 | 1' | Ph | H | | PME2 | H | H | H | H | H | H | acac |
| 1'-106Y | Pt | 0 | 1' | Ph | H | | PME2 | H | H | H | H | H | H | — — |
| 1'-107 | Pt | 1 | 1' | Ph | H | H | | MET1 | H | H | H | H | H | pic |
| 1'-107X | Pt | 1 | 1' | Ph | H | H | | MET1 | H | H | H | H | H | acac |
| 1'-107Y | Pt | 0 | 1' | Ph | H | H | | MET1 | H | H | H | H | H | — — |
| 1'-108 | Pt | 1 | 1' | Ph | H | | MET1 | H | H | H | H | H | H | pic |
| 1'-108X | Pt | 1 | 1' | Ph | H | | MET1 | H | H | H | H | H | H | acac |
| 1'-108Y | Pt | 0 | 1' | Ph | H | | MET1 | H | H | H | H | H | H | — — |
| 1'-109 | Pt | 1 | 1' | Ph | H | H | | MET2 | H | H | H | H | H | pic |
| 1'-109X | Pt | 1 | 1' | Ph | H | H | | MET2 | H | H | H | H | H | acac |
| 1'-109Y | Pt | 0 | 1' | Ph | H | H | | MET2 | H | H | H | H | H | — — |
| 1'-110 | Pt | 1 | 1' | Ph | H | | MET2 | H | H | H | H | H | H | pic |
| 1'-110X | Pt | 1 | 1' | Ph | H | | MET2 | H | H | H | H | H | H | acac |
| 1'-110Y | Pt | 0 | 1' | Ph | H | | MET2 | H | H | H | H | H | H | — — |
| 1'-111 | Pt | 1 | 1' | Ph | H | H | | EE1 | H | H | H | H | H | pic |
| 1'-111X | Pt | 1 | 1' | Ph | H | H | | EE1 | H | H | H | H | H | acac |
| 1'-111Y | Pt | 0 | 1' | Ph | H | H | | EE1 | H | H | H | H | H | — — |
| 1'-112 | Pt | 1 | 1' | Ph | H | | EE1 | H | H | H | H | H | H | pic |
| 1'-112X | Pt | 1 | 1' | Ph | H | | EE1 | H | H | H | H | H | H | acac |
| 1'-112Y | Pt | 0 | 1' | Ph | H | | EE1 | H | H | H | H | H | H | — — |
| 1'-113 | Pt | 1 | 1' | Ph | H | H | | EE2 | H | H | H | H | H | pic |
| 1'-113X | Pt | 1 | 1' | Ph | H | H | | EE2 | H | H | H | H | H | acac |
| 1'-113Y | Pt | 0 | 1' | Ph | H | H | | EE2 | H | H | H | H | H | — — |
| 1'-114 | Pt | 1 | 1' | Ph | H | | EE2 | H | H | H | H | H | H | pic |
| 1'-114X | Pt | 1 | 1' | Ph | H | | EE2 | H | H | H | H | H | H | acac |
| 1'-114Y | Pt | 0 | 1' | Ph | H | | EE2 | H | H | H | H | H | H | — — |
| 1'-115 | Pt | 1 | 1' | Ph | H | H | | MS1 | H | H | H | H | H | pic |
| 1'-115X | Pt | 1 | 1' | Ph | H | H | | MS1 | H | H | H | H | H | acac |
| 1'-115Y | Pt | 0 | 1' | Ph | H | H | | MS1 | H | H | H | H | H | — — |
| 1'-116 | Pt | 1 | 1' | Ph | H | | MS1 | H | H | H | H | H | H | pic |
| 1'-116X | Pt | 1 | 1' | Ph | H | | MS1 | H | H | H | H | H | H | acac |
| 1'-116Y | Pt | 0 | 1' | Ph | H | | MS1 | H | H | H | H | H | H | — — |
| 1'-117 | Pt | 1 | 1' | Ph | H | H | | MS2 | H | H | H | H | H | pic |

TABLE 29-continued

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1'-117X | Pt | 1 | 1' | Ph | H | H | | MS2 | H | H | H | H | H | acac |
| 1'-117Y | Pt | 0 | 1' | Ph | H | H | | MS2 | H | H | H | H | H | — — |
| 1'-118 | Pt | 1 | 1' | Ph | H | MS2 | | H | H | H | H | H | H | pic |
| 1'-118X | Pt | 1 | 1' | Ph | H | MS2 | | H | H | H | H | H | H | acac |
| 1'-118Y | Pt | 0 | 1' | Ph | H | MS2 | | H | H | H | H | H | H | — — |

TABLE 30

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 2'-1 | Pt | 1 | 2' | Ph | H | H | H | H | H | H | H | H | H | pic |
| 2'-1X | Pt | 1 | 2' | Ph | H | H | H | H | H | H | H | H | H | acac |
| 2'-1Y | Pt | 0 | 2' | Ph | H | H | H | H | H | H | H | H | H | — — |
| 2'-2 | Pt | 1 | 2' | Ph | H | F | H | F | H | H | H | H | H | pic |
| 2'-2X | Pt | 1 | 2' | Ph | H | F | H | F | H | H | H | H | H | acac |
| 2'-2Y | Pt | 0 | 2' | Ph | H | F | H | F | H | H | H | H | H | — — |
| 2'-3 | Pt | 1 | 2' | Ph | F | H | H | F | H | H | H | H | H | pic |
| 2'-3X | Pt | 1 | 2' | Ph | F | H | H | F | H | H | H | H | H | acac |
| 2'-3Y | Pt | 0 | 2' | Ph | F | H | H | F | H | H | H | H | H | — — |
| 2'-4 | Pt | 1 | 2' | Ph | CF₃ | H | CF₃ | H | H | H | H | H | H | pic |
| 2'-4X | Pt | 1 | 2' | Ph | CF₃ | H | CF₃ | H | H | H | H | H | H | acac |
| 2'-4Y | Pt | 0 | 2' | Ph | CF₃ | H | CF₃ | H | H | H | H | H | H | — — |
| 2'-5 | Pt | 1 | 2' | Ph | H | F | CF₃ | H | H | H | H | H | H | pic |
| 2'-5X | Pt | 1 | 2' | Ph | H | F | CF₃ | H | H | H | H | H | H | acac |
| 2'-5Y | Pt | 0 | 2' | Ph | H | F | CF₃ | H | H | H | H | H | H | — — |
| 2'-6 | Pt | 1 | 2' | Ph | F | H | CF₃ | H | H | H | H | H | H | pic |
| 2'-6X | Pt | 1 | 2' | Ph | F | H | CF₃ | H | H | H | H | H | H | acac |
| 2'-6Y | Pt | 0 | 2' | Ph | F | H | CF₃ | H | H | H | H | H | H | — — |
| 2'-7 | Pt | 1 | 2' | Ph | F | F | F | F | H | H | H | H | H | pic |
| 2'-7X | Pt | 1 | 2' | Ph | F | F | F | F | H | H | H | H | H | acac |
| 2'-7Y | Pt | 0 | 2' | Ph | F | F | F | F | H | H | H | H | H | — — |
| 2'-8 | Pt | 1 | 2' | Ph | H | F | H | CH₃ | H | H | H | H | H | pic |
| 2'-8X | Pt | 1 | 2' | Ph | H | F | H | CH₃ | H | H | H | H | H | acac |
| 2'-8Y | Pt | 0 | 2' | Ph | H | F | H | CH₃ | H | H | H | H | H | — — |
| 2'-9 | Pt | 1 | 2' | Ph | H | F | H | ᵗC₄H₉ | H | H | H | H | H | pic |
| 2'-9X | Pt | 1 | 2' | Ph | H | F | H | ᵗC₄H₉ | H | H | H | H | H | acac |
| 2'-9Y | Pt | 0 | 2' | Ph | H | F | H | ᵗC₄H₉ | H | H | H | H | H | — — |
| 2'-10 | Pt | 1 | 2' | Ph | H | CF₃ | H | CF₃ | H | H | H | H | H | pic |
| 2'-10X | Pt | 1 | 2' | Ph | H | CF₃ | H | CF₃ | H | H | H | H | H | acac |
| 2'-10Y | Pt | 0 | 2' | Ph | H | CF₃ | H | CF₃ | H | H | H | H | H | — — |
| 2'-11 | Pt | 1 | 2' | Ph | CF₃ | H | H | ᵗC₄H₉ | H | H | H | H | H | pic |
| 2'-11X | Pt | 1 | 2' | Ph | CF₃ | H | H | ᵗC₄H₉ | H | H | H | H | H | acac |
| 2'-11Y | Pt | 0 | 2' | Ph | CF₃ | H | H | ᵗC₄H₉ | H | H | H | H | H | — — |
| 2'-12 | Pt | 1 | 2' | Ph | H | CF₃ | H | ᵗC₄H₉ | H | H | H | H | H | pic |
| 2'-12X | Pt | 1 | 2' | Ph | H | CF₃ | H | ᵗC₄H₉ | H | H | H | H | H | acac |
| 2'-12Y | Pt | 0 | 2' | Ph | H | CF₃ | H | ᵗC₄H₉ | H | H | H | H | H | — — |
| 2'-13 | Pt | 1 | 2' | Ph | H | CF₃ | H | CH₃ | H | H | H | H | H | pic |
| 2'-13X | Pt | 1 | 2' | Ph | H | CF₃ | H | CH₃ | H | H | H | H | H | acac |
| 2'-13Y | Pt | 0 | 2' | Ph | H | CF₃ | H | CH₃ | H | H | H | H | H | — — |
| 2'-14 | Pt | 1 | 2' | Ph | H | CF₃ | CF₃ | H | H | H | H | H | H | pic |
| 2'-14X | Pt | 1 | 2' | Ph | H | CF₃ | CF₃ | H | H | H | H | H | H | acac |
| 2'-14Y | Pt | 0 | 2' | Ph | H | CF₃ | CF₃ | H | H | H | H | H | H | — — |
| 2'-15 | Pt | 1 | 2' | Ph | H | H | NO₂ | H | H | H | H | H | H | pic |
| 2'-15X | Pt | 1 | 2' | Ph | H | H | NO₂ | H | H | H | H | H | H | acac |
| 2'-15Y | Pt | 0 | 2' | Ph | H | H | NO₂ | H | H | H | H | H | H | — — |
| 2'-16 | Pt | 1 | 2' | Ph | F | H | NO₂ | H | H | H | H | H | H | pic |
| 2'-16X | Pt | 1 | 2' | Ph | F | H | NO₂ | H | H | H | H | H | H | acac |
| 2'-16Y | Pt | 0 | 2' | Ph | F | H | NO₂ | H | H | H | H | H | H | — — |
| 2'-17 | Pt | 1 | 2' | Ph | F | H | NO₂ | F | H | H | H | H | H | pic |
| 2'-17X | Pt | 1 | 2' | Ph | F | H | NO₂ | F | H | H | H | H | H | acac |
| 2'-17Y | Pt | 0 | 2' | Ph | F | H | NO₂ | F | H | H | H | H | H | — — |
| 2'-18 | Pt | 1 | 2' | Ph | H | NO₂ | H | NO₂ | H | H | H | H | H | pic |
| 2'-18X | Pt | 1 | 2' | Ph | H | NO₂ | H | NO₂ | H | H | H | H | H | acac |
| 2'-18Y | Pt | 0 | 2' | Ph | H | NO₂ | H | NO₂ | H | H | H | H | H | — — |
| 2'-19 | Pt | 1 | 2' | Ph | NO₂ | H | H | NO₂ | H | H | H | H | H | pic |
| 2'-19X | Pt | 1 | 2' | Ph | NO₂ | H | H | NO₂ | H | H | H | H | H | acac |
| 2'-19Y | Pt | 0 | 2' | Ph | NO₂ | H | H | NO₂ | H | H | H | H | H | — — |
| 2'-20 | Pt | 1 | 2' | Ph | H | H | CF₃ | H | H | H | H | H | H | pic |
| 2'-20X | Pt | 1 | 2' | Ph | H | H | CF₃ | H | H | H | H | H | H | acac |
| 2'-20Y | Pt | 0 | 2' | Ph | H | H | CF₃ | H | H | H | H | H | H | — — |
| 2'-21 | Pt | 1 | 2' | Ph | H | Cl | CF₃ | H | H | H | H | H | H | pic |
| 2'-21X | Pt | 1 | 2' | Ph | H | Cl | CF₃ | H | H | H | H | H | H | acac |
| 2'-21Y | Pt | 0 | 2' | Ph | H | Cl | CF₃ | H | H | H | H | H | H | — — |
| 2'-22 | Pt | 1 | 2' | Ph | H | NO₂ | H | H | H | H | H | H | H | pic |

TABLE 30-continued

| No. | M | m | BSS | SS G | T$^1$ | T$^2$ | T$^3$ | T$^4$ | T$^5$ | T$^6$ | T$^7$ | T$^8$ | T$^9$ | L$^1$ L$^2$ |
|---|---|---|---|---|---|---|---|---|---|---|---|---|---|---|
| 2'-22X | Pt | 1 | 2' | Ph | H | NO$_2$ | H | H | H | H | H | H | H | acac |
| 2'-22Y | Pt | 0 | 2' | Ph | H | NO$_2$ | H | H | H | H | H | H | H | — — |
| 2'-23 | Pt | 1 | 2' | Ph | H | CF$_3$ | H | H | H | H | H | H | H | pic |
| 2'-23X | Pt | 1 | 2' | Ph | H | CF$_3$ | H | H | H | H | H | H | H | acac |
| 2'-23Y | Pt | 0 | 2' | Ph | H | CF$_3$ | H | H | H | H | H | H | H | — — |
| 2'-24 | Pt | 1 | 2' | Ph | H | NO$_2$ | H | CH$_3$ | H | H | H | H | H | pic |
| 2'-24X | Pt | 1 | 2' | Ph | H | NO$_2$ | H | CH$_3$ | H | H | H | H | H | acac |
| 2'-24Y | Pt | 0 | 2' | Ph | H | NO$_2$ | H | CH$_3$ | H | H | H | H | H | — — |
| 2'-25 | Pt | 1 | 2' | Ph | H | NO$_2$ | H | $^t$C$_4$H$_9$ | H | H | H | H | H | pic |
| 2'-25X | Pt | 1 | 2' | Ph | H | NO$_2$ | H | $^t$C$_4$H$_9$ | H | H | H | H | H | acac |
| 2'-25Y | Pt | 0 | 2' | Ph | H | NO$_2$ | H | $^t$C$_4$H$_9$ | H | H | H | H | H | — — |
| 2'-26 | Pt | 1 | 2' | Ph | H | H | CH$_3$O | H | H | H | H | H | H | pic |
| 2'-26X | Pt | 1 | 2' | Ph | H | H | CH$_3$O | H | H | H | H | H | H | acac |
| 2'-26Y | Pt | 0 | 2' | Ph | H | H | CH$_3$O | H | H | H | H | H | H | — — |
| 2'-27 | Pt | 1 | 2' | Ph | H | CH$_3$O | H | H | H | H | H | H | H | pic |
| 2'-27X | Pt | 1 | 2' | Ph | H | CH$_3$O | H | H | H | H | H | H | H | acac |
| 2'-27Y | Pt | 0 | 2' | Ph | H | CH$_3$O | H | H | H | H | H | H | H | — — |
| 2'-28 | Pt | 1 | 2' | Ph | H | CH$_3$O | H | CH$_3$ | H | H | H | H | H | pic |
| 2'-28X | Pt | 1 | 2' | Ph | H | CH$_3$O | H | CH$_3$ | H | H | H | H | H | acac |
| 2'-28Y | Pt | 0 | 2' | Ph | H | CH$_3$O | H | CH$_3$ | H | H | H | H | H | — — |
| 2'-29 | Pt | 1 | 2' | Ph | H | CH$_3$O | H | $^t$C$_4$H$_9$ | H | H | H | H | H | pic |
| 2'-29X | Pt | 1 | 2' | Ph | H | CH$_3$O | H | $^t$C$_4$H$_9$ | H | H | H | H | H | acac |
| 2'-29Y | Pt | 0 | 2' | Ph | H | CH$_3$O | H | $^t$C$_4$H$_9$ | H | H | H | H | H | — — |
| 2'-30 | Pt | 1 | 2' | Ph | H | H | H | H | $^t$C$_4$H$_9$ | H | H | H | H | pic |
| 2'-30X | Pt | 1 | 2' | Ph | H | H | H | H | $^t$C$_4$H$_9$ | H | H | H | H | acac |
| 2'-30Y | Pt | 0 | 2' | Ph | H | H | H | H | $^t$C$_4$H$_9$ | H | H | H | H | — — |
| 2'-31 | Pt | 1 | 2' | Ph | H | F | H | F | $^t$C$_4$H$_9$ | H | H | H | H | pic |
| 2'-31X | Pt | 1 | 2' | Ph | H | F | H | F | $^t$C$_4$H$_9$ | H | H | H | H | acac |
| 2'-31Y | Pt | 0 | 2' | Ph | H | F | H | F | $^t$C$_4$H$_9$ | H | H | H | H | — — |
| 2'-32 | Pt | 1 | 2' | Ph | CF$_3$ | H | CF$_3$ | H | $^t$C$_4$H$_9$ | H | H | H | H | pic |
| 2'-32X | Pt | 1 | 2' | Ph | CF$_3$ | H | CF$_3$ | H | $^t$C$_4$H$_9$ | H | H | H | H | acac |
| 2'-32Y | Pt | 0 | 2' | Ph | CF$_3$ | H | CF$_3$ | H | $^t$C$_4$H$_9$ | H | H | H | H | — — |
| 2'-33 | Pt | 1 | 2' | Ph | H | CF$_3$ | H | CH$_3$ | $^t$C$_4$H$_9$ | H | H | H | H | pic |
| 2'-33X | Pt | 1 | 2' | Ph | H | CF$_3$ | H | CH$_3$ | $^t$C$_4$H$_9$ | H | H | H | H | acac |
| 2'-33Y | Pt | 0 | 2' | Ph | H | CF$_3$ | H | CH$_3$ | $^t$C$_4$H$_9$ | H | H | H | H | — — |
| 2'-34 | Pt | 1 | 2' | Ph | H | F | H | F | H | H | H | CH$_3$ | H | pic |
| 2'-34X | Pt | 1 | 2' | Ph | H | F | H | F | H | H | H | CH$_3$ | H | acac |
| 2'-34Y | Pt | 0 | 2' | Ph | H | F | H | F | H | H | H | CH$_3$ | H | — — |
| 2'-35 | Pt | 1 | 2' | Ph | CF$_3$ | H | CF$_3$ | H | H | H | H | CH$_3$ | H | pic |
| 2'-35X | Pt | 1 | 2' | Ph | CF$_3$ | H | CF$_3$ | H | H | H | H | CH$_3$ | H | acac |
| 2'-35Y | Pt | 0 | 2' | Ph | CF$_3$ | H | CF$_3$ | H | H | H | H | CH$_3$ | H | — — |
| 2'-36 | Pt | 1 | 2' | Ph | H | Si(CH$_3$)$_3$ | H | H | H | H | H | H | H | pic |
| 2'-36X | Pt | 1 | 2' | Ph | H | Si(CH$_3$)$_3$ | H | H | H | H | H | H | H | acac |
| 2'-36Y | Pt | 0 | 2' | Ph | H | Si(CH$_3$)$_3$ | H | H | H | H | H | H | H | — — |
| 2'-37 | Pt | 1 | 2' | Ph | H | H | Si(CH$_3$)$_3$ | H | H | H | H | H | H | pic |
| 2'-37X | Pt | 1 | 2' | Ph | H | H | Si(CH$_3$)$_3$ | H | H | H | H | H | H | acac |
| 2'-37Y | Pt | 0 | 2' | Ph | H | H | Si(CH$_3$)$_3$ | H | H | H | H | H | H | — — |
| 2'-38 | Pt | 1 | 2' | Ph | H | H | H | Si(CH$_3$)$_3$ | H | H | H | H | H | pic |
| 2'-38X | Pt | 1 | 2' | Ph | H | H | H | Si(CH$_3$)$_3$ | H | H | H | H | H | acac |
| 2'-38Y | Pt | 0 | 2' | Ph | H | H | H | Si(CH$_3$)$_3$ | H | H | H | H | H | — — |
| 2'-39 | Pt | 1 | 2' | Ph | H | F | H | Si(CH$_3$)$_3$ | H | H | H | H | H | pic |
| 2'-39X | Pt | 1 | 2' | Ph | H | F | H | Si(CH$_3$)$_3$ | H | H | H | H | H | acac |
| 2'-39Y | Pt | 0 | 2' | Ph | H | F | H | Si(CH$_3$)$_3$ | H | H | H | H | H | — — |
| 2'-40 | Pt | 1 | 2' | Ph | H | CF$_3$ | H | Si(CH$_3$)$_3$ | H | H | H | H | H | pic |
| 2'-40X | Pt | 1 | 2' | Ph | H | CF$_3$ | H | Si(CH$_3$)$_3$ | H | H | H | H | H | acac |
| 2'-40Y | Pt | 0 | 2' | Ph | H | CF$_3$ | H | Si(CH$_3$)$_3$ | H | H | H | H | H | — — |
| 2'-41 | Pt | 1 | 2' | Ph | H | Si(CH$_3$)$_3$ | H | F | H | H | H | H | H | pic |
| 2'-41X | Pt | 1 | 2' | Ph | H | Si(CH$_3$)$_3$ | H | F | H | H | H | H | H | acac |
| 2'-41Y | Pt | 0 | 2' | Ph | H | Si(CH$_3$)$_3$ | H | F | H | H | H | H | H | — — |
| 2'-42 | Pt | 1 | 2' | Ph | H | Si(CH$_3$)$_3$ | H | CF$_3$ | H | H | H | H | H | pic |
| 2'-42X | Pt | 1 | 2' | Ph | H | Si(CH$_3$)$_3$ | H | CF$_3$ | H | H | H | H | H | acac |
| 2'-42Y | Pt | 0 | 2' | Ph | H | Si(CH$_3$)$_3$ | H | CF$_3$ | H | H | H | H | H | — — |
| 2'-43 | Pt | 1 | 2' | Ph | Si(CH$_3$)$_3$ | H | Si(CH$_3$)$_3$ | H | H | H | H | H | H | pic |
| 2'-43X | Pt | 1 | 2' | Ph | Si(CH$_3$)$_4$ | H | Si(CH$_3$)$_4$ | H | H | H | H | H | H | acac |
| 2'-43Y | Pt | 0 | 2' | Ph | Si(CH$_3$)$_5$ | H | Si(CH$_3$)$_5$ | H | H | H | H | H | H | — — |
| 2'-44 | Pt | 1 | 2' | Ph | H | H | H | COCH$_3$ | H | H | H | H | H | pic |
| 2'-44X | Pt | 1 | 2' | Ph | H | H | H | COCH$_3$ | H | H | H | H | H | acac |
| 2'-44Y | Pt | 0 | 2' | Ph | H | H | H | COCH$_3$ | H | H | H | H | H | — — |
| 2'-45 | Pt | 1 | 2' | Ph | H | H | COCH$_3$ | H | H | H | H | H | H | pic |
| 2'-45X | Pt | 1 | 2' | Ph | H | H | COCH$_3$ | H | H | H | H | H | H | acac |
| 2'-45Y | Pt | 0 | 2' | Ph | H | H | COCH$_3$ | H | H | H | H | H | H | — — |
| 2'-46 | Pt | 1 | 2' | Ph | H | COCH$_3$ | H | H | H | H | H | H | H | pic |
| 2'-46X | Pt | 1 | 2' | Ph | H | COCH$_3$ | H | H | H | H | H | H | H | acac |
| 2'-46Y | Pt | 0 | 2' | Ph | H | COCH$_3$ | H | H | H | H | H | H | H | — — |
| 2'-47 | Pt | 1 | 2' | Ph | H | H | BL | | H | H | H | H | H | pic |
| 2'47X | Pt | 1 | 2' | Ph | H | H | BL | | H | H | H | H | H | acac |
| 2'-47Y | Pt | 0 | 2' | Ph | H | H | BL | | H | H | H | H | H | — — |

TABLE 30-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2'-48 | Pt | 1 | 2' | Ph | H | | BL | | H | H | H | H | H | H | pic |
| 2'-48X | Pt | 1 | 2' | Ph | H | | BL | | H | H | H | H | H | H | acac |
| 2'-48Y | Pt | 0 | 2' | Ph | H | | BL | | H | H | H | H | H | H | — | — |
| 2'-49 | Pt | 1 | 2' | Ph | H | H | | PL | H | H | H | H | H | H | pic |
| 2'-49X | Pt | 1 | 2' | Ph | H | H | | PL | H | H | H | H | H | H | acac |
| 2'-49Y | Pt | 0 | 2' | Ph | H | H | | PL | H | H | H | H | H | H | — | — |
| 2'-50 | Pt | 1 | 2' | Ph | H | | PL | | H | H | H | H | H | H | pic |
| 2'-50X | Pt | 1 | 2' | Ph | H | | PL | | H | H | H | H | H | H | acac |
| 2'-50Y | Pt | 0 | 2' | Ph | H | | PL | | H | H | H | H | H | H | — | — |
| 2'-51 | Pt | 1 | 2' | Ph | H | H | | MEE1 | H | H | H | H | H | H | pic |
| 2'-51X | Pt | 1 | 2' | Ph | H | H | | MEE1 | H | H | H | H | H | H | acac |
| 2'-51Y | Pt | 0 | 2' | Ph | H | H | | MEE1 | H | H | H | H | H | H | — | — |
| 2'-52 | Pt | 1 | 2' | Ph | H | | MEE1 | | H | H | H | H | H | H | pic |
| 2'-52X | Pt | 1 | 2' | Ph | H | | MEE1 | | H | H | H | H | H | H | acac |
| 2'-52Y | Pt | 0 | 2' | Ph | H | | MEE1 | | H | H | H | H | H | H | — | — |
| 2'-53 | Pt | 1 | 2' | Ph | H | H | | MEE2 | H | H | H | H | H | H | pic |
| 2'-53X | Pt | 1 | 2' | Ph | H | H | | MEE2 | H | H | H | H | H | H | acac |
| 2'-53Y | Pt | 0 | 2' | Ph | H | H | | MEE2 | H | H | H | H | H | H | — | — |
| 2'-54 | Pt | 1 | 2' | Ph | H | | MEE2 | | H | H | H | H | H | H | pic |
| 2'-54X | Pt | 1 | 2' | Ph | H | | MEE2 | | H | H | H | H | H | H | acac |
| 2'-54Y | Pt | 0 | 2' | Ph | H | | MEE2 | | H | H | H | H | H | H | — | — |
| 2'-55 | Pt | 1 | 2' | Ph | H | H | | PA1 | H | H | H | H | H | H | pic |
| 2'-55X | Pt | 1 | 2' | Ph | H | H | | PA1 | H | H | H | H | H | H | acac |
| 2'-55Y | Pt | 0 | 2' | Ph | H | H | | PA1 | H | H | H | H | H | H | — | — |
| 2'-56 | Pt | 1 | 2' | Ph | H | | PA1 | | H | H | H | H | H | H | pic |
| 2'-56X | Pt | 1 | 2' | Ph | H | | PA1 | | H | H | H | H | H | H | acac |
| 2'-56Y | Pt | 0 | 2' | Ph | H | | PA1 | | H | H | H | H | H | H | — | — |
| 2'-57 | Pt | 1 | 2' | Ph | H | H | | PA2 | H | H | H | H | H | H | pic |
| 2'-57X | Pt | 1 | 2' | Ph | H | H | | PA2 | H | H | H | H | H | H | acac |
| 2'-57Y | Pt | 0 | 2' | Ph | H | H | | PA2 | H | H | H | H | H | H | — | — |
| 2'-58 | Pt | 1 | 2' | Ph | H | | PA2 | | H | H | H | H | H | H | pic |
| 2'-58X | Pt | 1 | 2' | Ph | H | | PA2 | | H | H | H | H | H | H | acac |
| 2'-58Y | Pt | 0 | 2' | Ph | H | | PA2 | | H | H | H | H | H | H | — | — |
| 2'-59 | Pt | 1 | 2' | Ph | H | H | EA1 | | H | H | H | H | H | H | pic |
| 2'-59X | Pt | 1 | 2' | Ph | H | H | EA1 | | H | H | H | H | H | H | acac |
| 2'-59Y | Pt | 0 | 2' | Ph | H | H | | EA1 | H | H | H | H | H | H | — | — |
| 2'-60 | Pt | 1 | 2' | Ph | H | | EA2 | | H | H | H | H | H | H | pic |
| 2'-60X | Pt | 1 | 2' | Ph | H | | EA2 | | H | H | H | H | H | H | acac |
| 2'-60Y | Pt | 0 | 2' | Ph | H | | EA2 | | H | H | H | H | H | H | — | — |
| 2'-61 | Pt | 1 | 2' | Ph | H | H | | ME | H | H | H | H | H | H | pic |
| 2'-61X | Pt | 1 | 2' | Ph | H | H | | ME | H | H | H | H | H | H | acac |
| 2'-61Y | Pt | 0 | 2' | Ph | H | H | | ME | H | H | H | H | H | H | — | — |
| 2'-62 | Pt | 1 | 2' | Ph | H | | ME | | H | H | H | H | H | H | pic |
| 2'-62X | Pt | 1 | 2' | Ph | H | | ME | | H | H | H | H | H | H | acac |
| 2'-62Y | Pt | 0 | 2' | Ph | H | | ME | | H | H | H | H | H | H | — | — |
| 2'-63 | Pt | 1 | 2' | Ph | H | H | | AT | H | H | H | H | H | H | pic |
| 2'-63X | Pt | 1 | 2' | Ph | H | H | | AT | H | H | H | H | H | H | acac |
| 2'-63Y | Pt | 0 | 2' | Ph | H | H | | AT | H | H | H | H | H | H | — | — |
| 2'-64 | Pt | 1 | 2' | Ph | H | | AT | | H | H | H | H | H | H | pic |
| 2'-64X | Pt | 1 | 2' | Ph | H | | AT | | H | H | H | H | H | H | acac |
| 2'-64Y | Pt | 0 | 2' | Ph | H | | AT | | H | H | H | H | H | H | — | — |
| 2'-65 | Pt | 1 | 2' | Ph | H | H | | MES1 | H | H | H | H | H | H | pic |
| 2'-65X | Pt | 1 | 2' | Ph | H | H | | MES1 | H | H | H | H | H | H | acac |
| 2'-65Y | Pt | 0 | 2' | Ph | H | H | | MES1 | H | H | H | H | H | H | — | — |
| 2'-66 | Pt | 1 | 2' | Ph | H | | MES1 | | H | H | H | H | H | H | pic |
| 2'-66X | Pt | 1 | 2' | Ph | H | | MES1 | | H | H | H | H | H | H | acac |
| 2'-66Y | Pt | 0 | 2' | Ph | H | | MES1 | | H | H | H | H | H | H | — | — |
| 2'-67 | Pt | 1 | 2' | Ph | H | H | | MES2 | H | H | H | H | H | H | pic |
| 2'-67X | Pt | 1 | 2' | Ph | H | H | | MES2 | H | H | H | H | H | H | acac |
| 2'-67Y | Pt | 0 | 2' | Ph | H | H | | MES2 | H | H | H | H | H | H | — | — |
| 2'-68 | Pt | 1 | 2' | Ph | H | | MES2 | | H | H | H | H | H | H | pic |
| 2'-68X | Pt | 1 | 2' | Ph | H | | MES2 | | H | H | H | H | H | H | acac |
| 2'-68Y | Pt | 0 | 2' | Ph | H | | MES2 | | H | H | H | H | H | H | — | — |
| 2'-69 | Pt | 1 | 2' | Ph | H | H | | PS1 | H | H | H | H | H | H | pic |
| 2'-69X | Pt | 1 | 2' | Ph | H | H | | PS1 | H | H | H | H | H | H | acac |
| 2'-69Y | Pt | 0 | 2' | Ph | H | H | | PS1 | H | H | H | H | H | H | — | — |
| 2'-70 | Pt | 1 | 2' | Ph | H | | PS1 | | H | H | H | H | H | H | pic |
| 2'-70X | Pt | 1 | 2' | Ph | H | | PS1 | | H | H | H | H | H | H | acac |
| 2'-70Y | Pt | 0 | 2' | Ph | H | | PS1 | | H | H | H | H | H | H | — | — |
| 2'-71 | Pt | 1 | 2' | Ph | H | H | | PS2 | H | H | H | H | H | H | pic |
| 2'-71X | Pt | 1 | 2' | Ph | H | H | | PS2 | H | H | H | H | H | H | acac |
| 2'-71Y | Pt | 0 | 2' | Ph | H | H | | PS2 | H | H | H | H | H | H | — | — |
| 2'-72 | Pt | 1 | 2' | Ph | H | | PS2 | | H | H | H | H | H | H | pic |
| 2'-72X | Pt | 1 | 2' | Ph | H | | PS2 | | H | H | H | H | H | H | acac |
| 2'-72Y | Pt | 0 | 2' | Ph | H | | PS2 | | H | H | H | H | H | H | — | — |
| 2'-73 | Pt | 1 | 2' | Ph | H | H | | BAL1 | H | H | H | H | H | H | pic |
| 2'-73X | Pt | 1 | 2' | Ph | H | H | | BAL1 | H | H | H | H | H | H | acac |

TABLE 30-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2'-73Y | Pt | 0 | 2' | Ph | H | H | | BAL1 | H | H | H | H | H | — | — |
| 2'-74 | Pt | 1 | 2' | Ph | H | | BAL1 | | H | H | H | H | H | pic | |
| 2'-74X | Pt | 1 | 2' | Ph | H | | BAL1 | | H | H | H | H | H | acac | |
| 2'-74Y | Pt | 0 | 2' | Ph | H | | BAL1 | | H | H | H | H | H | — | — |
| 2'-75 | Pt | 1 | 2' | Ph | H | H | | BAL2 | H | H | H | H | H | pic | |
| 2'-75X | Pt | 1 | 2' | Ph | H | H | | BAL2 | H | H | H | H | H | acac | |
| 2'-75Y | Pt | 0 | 2' | Ph | H | H | | BAL2 | H | H | H | H | H | — | — |
| 2'-76 | Pt | 1 | 2' | Ph | H | | BAL2 | | H | H | H | H | H | pic | |
| 2'-76X | Pt | 1 | 2' | Ph | H | | BAL2 | | H | H | H | H | H | acac | |
| 2'-76Y | Pt | 0 | 2' | Ph | H | | BAL2 | | H | H | H | H | H | — | — |
| 2'-77 | Pt | 1 | 2' | Ph | H | H | | MEK1 | H | H | H | H | H | pic | |
| 2'-77X | Pt | 1 | 2' | Ph | H | H | | MEK1 | H | H | H | H | H | acac | |
| 2'-77Y | Pt | 0 | 2' | Ph | H | H | | MEK1 | H | H | H | H | H | — | — |
| 2'-78 | Pt | 1 | 2' | Ph | H | | MEK1 | | H | H | H | H | H | pic | |
| 2'-78X | Pt | 1 | 2' | Ph | H | | MEK1 | | H | H | H | H | H | acac | |
| 2'-78Y | Pt | 0 | 2' | Ph | H | | MEK1 | | H | H | H | H | H | — | — |
| 2'-79 | Pt | 1 | 2' | Ph | H | H | | MEK2 | H | H | H | H | H | pic | |
| 2'-79X | Pt | 1 | 2' | Ph | H | H | | MEK2 | H | H | H | H | H | acac | |
| 2'-79Y | Pt | 0 | 2' | Ph | H | H | | MEK2 | H | H | H | H | H | — | — |
| 2'-80 | Pt | 1 | 2' | Ph | H | | MEK2 | | H | H | H | H | H | pic | |
| 2'-80X | Pt | 1 | 2' | Ph | H | | MEK2 | | H | H | H | H | H | acac | |
| 2'-80Y | Pt | 0 | 2' | Ph | H | | MEK2 | | H | H | H | H | H | — | — |
| 2'-81 | Pt | 1 | 2' | Ph | H | H | | PAL1 | H | H | H | H | H | pic | |
| 2'-81X | Pt | 1 | 2' | Ph | H | H | | PAL1 | H | H | H | H | H | acac | |
| 2'-81Y | Pt | 0 | 2' | Ph | H | H | | PAL1 | H | H | H | H | H | — | — |
| 2'-82 | Pt | 1 | 2' | Ph | H | | PAL1 | | H | H | H | H | H | pic | |
| 2'-82X | Pt | 1 | 2' | Ph | H | | PAL1 | | H | H | H | H | H | acac | |
| 2'-82Y | Pt | 0 | 2' | Ph | H | | PAL1 | | H | H | H | H | H | — | — |
| 2'-83 | Pt | 1 | 2' | Ph | H | H | | PAL2 | H | H | H | H | H | pic | |
| 2'-83X | Pt | 1 | 2' | Ph | H | H | | PAL2 | H | H | H | H | H | acac | |
| 2'-83Y | Pt | 0 | 2' | Ph | H | H | | PAL2 | H | H | H | H | H | — | — |
| 2'-84 | Pt | 1 | 2' | Ph | H | | PAL2 | | H | H | H | H | H | pic | |
| 2'-84X | Pt | 1 | 2' | Ph | H | | PAL2 | | H | H | H | H | H | acac | |
| 2'-84Y | Pt | 0 | 2' | Ph | H | | PAL2 | | H | H | H | H | H | — | — |
| 2'-85 | Pt | 1 | 2' | Ph | H | H | | MMK | H | H | H | H | H | pic | |
| 2'-85X | Pt | 1 | 2' | Ph | H | H | | MMK | H | H | H | H | H | acac | |
| 2'-85Y | Pt | 0 | 2' | Ph | H | H | | MMK | H | H | H | H | H | — | — |
| 2'-86 | Pt | 1 | 2' | Ph | H | | MMK | | H | H | H | H | H | pic | |
| 2'-86X | Pt | 1 | 2' | Ph | H | | MMK | | H | H | H | H | H | acac | |
| 2'-86Y | Pt | 0 | 2' | Ph | H | | MMK | | H | H | H | H | H | — | — |
| 2'-87 | Pt | 1 | 2' | Ph | H | H | | EES1 | H | H | H | H | H | pic | |
| 2'-87X | Pt | 1 | 2' | Ph | H | H | | EES1 | H | H | H | H | H | acac | |
| 2'-87Y | Pt | 0 | 2' | Ph | H | H | | EES1 | H | H | H | H | H | — | — |
| 2'-88 | Pt | 1 | 2' | Ph | H | | EES2 | | H | H | H | H | H | pic | |
| 2'-88X | Pt | 1 | 2' | Ph | H | | EES2 | | H | H | H | H | H | acac | |
| 2'-88Y | Pt | 0 | 2' | Ph | H | | EES2 | | H | H | H | H | H | — | — |
| 2'-89 | Pt | 1 | 2' | Ph | H | H | | PAE1 | H | H | H | H | H | pic | |
| 2'-89X | Pt | 1 | 2' | Ph | H | H | | PAE1 | H | H | H | H | H | acac | |
| 2'-89Y | Pt | 0 | 2' | Ph | H | H | | PAE1 | H | H | H | H | H | — | — |
| 2'-90 | Pt | 1 | 2' | Ph | H | | PAE2 | | H | H | H | H | H | pic | |
| 2'-90X | Pt | 1 | 2' | Ph | H | | PAE2 | | H | H | H | H | H | acac | |
| 2'-90Y | Pt | 0 | 2' | Ph | H | | PAE2 | | H | H | H | H | H | — | — |
| 2'-91 | Pt | 1 | 2' | Ph | H | H | | AME1 | H | H | H | H | H | pic | |
| 2'-91X | Pt | 1 | 2' | Ph | H | H | | AME1 | H | H | H | H | H | acac | |
| 2'-91Y | Pt | 0 | 2' | Ph | H | H | | AME1 | H | H | H | H | H | — | — |
| 2'-92 | Pt | 1 | 2' | Ph | H | | AME1 | | H | H | H | H | H | pic | |
| 2'-92X | Pt | 1 | 2' | Ph | H | | AME1 | | H | H | H | H | H | acac | |
| 2'-92Y | Pt | 0 | 2' | Ph | H | | AME1 | | H | H | H | H | H | — | — |
| 2'-93 | Pt | 1 | 2' | Ph | H | H | | AME2 | H | H | H | H | H | pic | |
| 2'-93X | Pt | 1 | 2' | Ph | H | H | | AME2 | H | H | H | H | H | acac | |
| 2'-93Y | Pt | 0 | 2' | Ph | H | H | | AME2 | H | H | H | H | H | — | — |
| 2'-94 | Pt | 1 | 2' | Ph | H | | AME2 | | H | H | H | H | H | pic | |
| 2'-94X | Pt | 1 | 2' | Ph | H | | AME2 | | H | H | H | H | H | acac | |
| 2'-94Y | Pt | 0 | 2' | Ph | H | | AME2 | | H | H | H | H | H | — | — |
| 2'-95 | Pt | 1 | 2' | Ph | H | H | | EAE1 | H | H | H | H | H | pic | |
| 2'-95X | Pt | 1 | 2' | Ph | H | H | | EAE1 | H | H | H | H | H | acac | |
| 2'-95Y | Pt | 0 | 2' | Ph | H | H | | EAE1 | H | H | H | H | H | — | — |
| 2'-96 | Pt | 1 | 2' | Ph | H | | EAE1 | | H | H | H | H | H | pic | |
| 2'-96X | Pt | 1 | 2' | Ph | H | | EAE1 | | H | H | H | H | H | acac | |
| 2'-96Y | Pt | 0 | 2' | Ph | H | | EAE1 | | H | H | H | H | H | — | — |
| 2'-97 | Pt | 1 | 2' | Ph | H | H | | EAE2 | H | H | H | H | H | pic | |
| 2'-97X | Pt | 1 | 2' | Ph | H | H | | EAE2 | H | H | H | H | H | acac | |
| 2'-97Y | Pt | 0 | 2' | Ph | H | H | | EAE2 | H | H | H | H | H | — | — |
| 2'-98 | Pt | 1 | 2' | Ph | H | | EAE2 | | H | H | H | H | H | pic | |
| 2'-98X | Pt | 1 | 2' | Ph | H | | EAE2 | | H | H | H | H | H | acac | |
| 2'-98Y | Pt | 0 | 2' | Ph | H | | EAE2 | | H | H | H | H | H | — | — |
| 2'-99 | Pt | 1 | 2' | Ph | H | H | | AAE1 | H | H | H | H | H | pic | |

TABLE 30-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2'-99X | Pt | 1 | 2' | Ph | H | H |  | AAE1 | H | H | H | H | H | acac |  |
| 2'-99Y | Pt | 0 | 2' | Ph | H | H |  | AAE1 | H | H | H | H | H | — | — |
| 2'-100 | Pt | 1 | 2' | Ph | H |  | AAE1 |  | H | H | H | H | H | pic |  |
| 2'-100X | Pt | 1 | 2' | Ph | H |  | AAE1 |  | H | H | H | H | H | acac |  |
| 2'-100Y | Pt | 0 | 2' | Ph | H |  | AAE1 |  | H | H | H | H | H | — | — |
| 2'-101 | Pt | 1 | 2' | Ph | H | H |  | AAE2 | H | H | H | H | H | pic |  |
| 2'-101X | Pt | 1 | 2' | Ph | H | H |  | AAE2 | H | H | H | H | H | acac |  |
| 2'-101Y | Pt | 0 | 2' | Ph | H | H |  | AAE2 | H | H | H | H | H | — | — |
| 2'-102 | Pt | 1 | 2' | Ph | H |  | AAE2 |  | H | H | H | H | H | pic |  |
| 2'-102X | Pt | 1 | 2' | Ph | H |  | AAE2 |  | H | H | H | H | H | acac |  |
| 2'-102Y | Pt | 0 | 2' | Ph | H |  | AAE2 |  | H | H | H | H | H | — | — |
| 2'-103 | Pt | 1 | 2' | Ph | H | H |  | PME1 | H | H | H | H | H | pic |  |
| 2'-103X | Pt | 1 | 2' | Ph | H | H |  | PME1 | H | H | H | H | H | acac |  |
| 2'-103Y | Pt | 0 | 2' | Ph | H | H |  | PME1 | H | H | H | H | H | — | — |
| 2'-104 | Pt | 1 | 2' | Ph | H |  | PME1 |  | H | H | H | H | H | pic |  |
| 2'-104X | Pt | 1 | 2' | Ph | H |  | PME1 |  | H | H | H | H | H | acac |  |
| 2'-104Y | Pt | 0 | 2' | Ph | H |  | PME1 |  | H | H | H | H | H | — | — |
| 2'-105 | Pt | 1 | 2' | Ph | H | H |  | PME2 | H | H | H | H | H | pic |  |
| 2'-105X | Pt | 1 | 2' | Ph | H | H |  | PME2 | H | H | H | H | H | acac |  |
| 2'-105Y | Pt | 0 | 2' | Ph | H | H |  | PME2 | H | H | H | H | H | — | — |
| 2'-106 | Pt | 1 | 2' | Ph | H |  | PME2 |  | H | H | H | H | H | pic |  |
| 2'-106X | Pt | 1 | 2' | Ph | H |  | PME2 |  | H | H | H | H | H | acac |  |
| 2'-106Y | Pt | 0 | 2' | Ph | H |  | PME2 |  | H | H | H | H | H | — | — |
| 2'-107 | Pt | 1 | 2' | Ph | H | H |  | MET1 | H | H | H | H | H | pic |  |
| 2'-107X | Pt | 1 | 2' | Ph | H | H |  | MET1 | H | H | H | H | H | acac |  |
| 2'-107Y | Pt | 0 | 2' | Ph | H | H |  | MET1 | H | H | H | H | H | — | — |
| 2'-108 | Pt | 1 | 2' | Ph | H |  | MET1 |  | H | H | H | H | H | pic |  |
| 2'-108X | Pt | 1 | 2' | Ph | H |  | MET1 |  | H | H | H | H | H | acac |  |
| 2'-108Y | Pt | 0 | 2' | Ph | H |  | MET1 |  | H | H | H | H | H | — | — |
| 2'-109 | Pt | 1 | 2' | Ph | H | H |  | MET2 | H | H | H | H | H | pic |  |
| 2'-109X | Pt | 1 | 2' | Ph | H | H |  | MET2 | H | H | H | H | H | acac |  |
| 2'-109Y | Pt | 0 | 2' | Ph | H | H |  | MET2 | H | H | H | H | H | — | — |
| 2'-110 | Pt | 1 | 2' | Ph | H |  | MET2 |  | H | H | H | H | H | pic |  |
| 2'-110X | Pt | 1 | 2' | Ph | H |  | MET2 |  | H | H | H | H | H | acac |  |
| 2'-110Y | Pt | 0 | 2' | Ph | H |  | MET2 |  | H | H | H | H | H | — | — |
| 2'-111 | Pt | 1 | 2 | Ph | H | H |  | EE1 | H | H | H | H | H | pic |  |
| 2'-111X | Pt | 1 | 2' | Ph | H | H |  | EE1 | H | H | H | H | H | acac |  |
| 2'-111Y | Pt | 0 | 2' | Ph | H | H |  | EE1 | H | H | H | H | H | — | — |
| 2'-112 | Pt | 1 | 2' | Ph | H |  | EE1 |  | H | H | H | H | H | pic |  |
| 2'-112X | Pt | 1 | 2' | Ph | H |  | EE1 |  | H | H | H | H | H | acac |  |
| 2'-112Y | Pt | 0 | 2' | Ph | H |  | EE1 |  | H | H | H | H | H | — | — |
| 2'-113 | Pt | 1 | 2' | Ph | H | H |  | EE2 | H | H | H | H | H | pic |  |
| 2'-113X | Pt | 1 | 2' | Ph | H | H |  | EE2 | H | H | H | H | H | acac |  |
| 2'-113Y | Pt | 0 | 2' | Ph | H | H |  | EE2 | H | H | H | H | H | — | — |
| 2'-114 | Pt | 1 | 2' | Ph | H |  | EE2 |  | H | H | H | H | H | pic |  |
| 2'-114X | Pt | 1 | 2' | Ph | H |  | EE2 |  | H | H | H | H | H | acac |  |
| 2'-114Y | Pt | 0 | 2' | Ph | H |  | EE2 |  | H | H | H | H | H | — | — |
| 2'-115 | Pt | 1 | 2' | Ph | H | H |  | MS1 | H | H | H | H | H | pic |  |
| 2'-115X | Pt | 1 | 2' | Ph | H | H |  | MS1 | H | H | H | H | H | acac |  |
| 2'-115Y | Pt | 0 | 2' | Ph | H | H |  | MS1 | H | H | H | H | H | — | — |
| 2'-116 | Pt | 1 | 2' | Ph | H |  | MS1 |  | H | H | H | H | H | pic |  |
| 2'-116X | Pt | 1 | 2' | Ph | H |  | MS1 |  | H | H | H | H | H | acac |  |
| 2'-116Y | Pt | 0 | 2' | Ph | H |  | MS1 |  | H | H | H | H | H | — | — |
| 2'-117 | Pt | 1 | 2' | Ph | H | H |  | MS2 | H | H | H | H | H | pic |  |
| 2'-117X | Pt | 1 | 2' | Ph | H | H |  | MS2 | H | H | H | H | H | acac |  |
| 2'-117Y | Pt | 0 | 2' | Ph | H | H |  | MS2 | H | H | H | H | H | — | — |
| 2'-118 | Pt | 1 | 2' | Ph | H |  | MS2 |  | H | H | H | H | H | pic |  |
| 2'-118X | Pt | 1 | 2' | Ph | H |  | MS2 |  | H | H | H | H | H | acac |  |
| 2'-118Y | Pt | 0 | 2' | Ph | H |  | MS2 |  | H | H | H | H | H | — | — |

TABLE 31

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-1 | Pt | 1 | 3' | Ph | H | H | H | H | H | H | H | H | H | pic |  |
| 3'-1X | Pt | 1 | 3' | Ph | H | H | H | H | H | H | H | H | H | acac |  |
| 3'-1Y | Pt | 0 | 3' | Ph | H | H | H | H | H | H | H | H | H | — | — |
| 3'-2 | Pt | 1 | 3' | Ph | H | F | H | F | H | H | H | H | H | pic |  |
| 3'-2X | Pt | 1 | 3' | Ph | H | F | H | F | H | H | H | H | H | acac |  |
| 3'-2Y | Pt | 0 | 3' | Ph | H | F | H | F | H | H | H | H | H | — | — |
| 3'-3 | Pt | 1 | 3' | Ph | F | H | H | F | H | H | H | H | H | pic |  |
| 3'-3X | Pt | 1 | 3' | Ph | F | H | H | F | H | H | H | H | H | acac |  |
| 3'-3Y | Pt | 0 | 3' | Ph | F | H | H | F | H | H | H | H | H | — | — |
| 3'-4 | Pt | 1 | 3' | Ph | CF₃ | H | CF₃ | H | H | H | H | H | H | pic |  |

TABLE 31-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-4X | Pt | 1 | 3' | Ph | CF₃ | H | CF₃ | H | H | H | H | H | H | acac | |
| 3'-4Y | Pt | 0 | 3' | Ph | CF₃ | H | CF₃ | H | H | H | H | H | H | — | — |
| 3'-5 | Pt | 1 | 3' | Ph | H | F | CF₃ | H | H | H | H | H | H | | pic |
| 3'-5X | Pt | 1 | 3' | Ph | H | F | CF₃ | H | H | H | H | H | H | acac | |
| 3'-5Y | Pt | 0 | 3' | Ph | H | F | CF₃ | H | H | H | H | H | H | — | — |
| 3'-6 | Pt | 1 | 3' | Ph | F | H | CF₃ | H | H | H | H | H | H | | pic |
| 3'-6X | Pt | 1 | 3' | Ph | F | H | CF₃ | H | H | H | H | H | H | acac | |
| 3'-6Y | Pt | 0 | 3' | Ph | F | H | CF₃ | H | H | H | H | H | H | — | — |
| 3'-7 | Pt | 1 | 3' | Ph | F | F | F | F | H | H | H | H | H | | pic |
| 3'-7X | Pt | 1 | 3' | Ph | F | F | F | F | H | H | H | H | H | acac | |
| 3'-7Y | Pt | 0 | 3' | Ph | F | F | F | F | H | H | H | H | H | — | — |
| 3'-8 | Pt | 1 | 3' | Ph | H | F | H | CH₃ | H | H | H | H | H | | pic |
| 3'-8X | Pt | 1 | 3' | Ph | H | F | H | CH₃ | H | H | H | H | H | acac | |
| 3'-8Y | Pt | 0 | 3' | Ph | H | F | H | CH₃ | H | H | H | H | H | — | — |
| 3'-9 | Pt | 1 | 3' | Ph | H | F | H | ᵗC₄H₉ | H | H | H | H | H | | pic |
| 3'-9X | Pt | 1 | 3' | Ph | H | F | H | ᵗC₄H₉ | H | H | H | H | H | acac | |
| 3'-9Y | Pt | 0 | 3' | Ph | H | F | H | ᵗC₄H₉ | H | H | H | H | H | — | — |
| 3'-10 | Pt | 1 | 3' | Ph | H | CF₃ | H | CF₃ | H | H | H | H | H | | pic |
| 3'-10X | Pt | 1 | 3' | Ph | H | CF₃ | H | CF₃ | H | H | H | H | H | acac | |
| 3'-10Y | Pt | 0 | 3' | Ph | H | CF₃ | H | CF₃ | H | H | H | H | H | — | — |
| 3'-11 | Pt | 1 | 3' | Ph | CF₃ | H | H | ᵗC₄H₉ | H | H | H | H | H | | pic |
| 3'-11X | Pt | 1 | 3' | Ph | CF₃ | H | H | ᵗC₄H₉ | H | H | H | H | H | acac | |
| 3'-11Y | Pt | 0 | 3' | Ph | CF₃ | H | H | ᵗC₄H₉ | H | H | H | H | H | — | — |
| 3'-12 | Pt | 1 | 3' | Ph | H | CF₃ | H | ᵗC₄H₉ | H | H | H | H | H | | pic |
| 3'-12X | Pt | 1 | 3' | Ph | H | CF₃ | H | ᵗC₄H₉ | H | H | H | H | H | acac | |
| 3'-12Y | Pt | 0 | 3' | Ph | H | CF₃ | H | ᵗC₄H₉ | H | H | H | H | H | — | — |
| 3'-13 | Pt | 1 | 3' | Ph | H | CF₃ | H | CH₃ | H | H | H | H | H | | pic |
| 3'-13X | Pt | 1 | 3' | Ph | H | CF₃ | H | CH₃ | H | H | H | H | H | acac | |
| 3'-13Y | Pt | 0 | 3' | Ph | H | CF₃ | H | CH₃ | H | H | H | H | H | — | — |
| 3'-14 | Pt | 1 | 3' | Ph | H | CF₃ | CF₃ | H | H | H | H | H | H | | pic |
| 3'-14X | Pt | 1 | 3' | Ph | H | CF₃ | CF₃ | H | H | H | H | H | H | acac | |
| 3'-14Y | Pt | 0 | 3' | Ph | H | CF₃ | CF₃ | H | H | H | H | H | H | — | — |
| 3'-15 | Pt | 1 | 3' | Ph | H | H | NO₂ | H | H | H | H | H | H | | pic |
| 3'-15X | Pt | 1 | 3' | Ph | H | H | NO₂ | H | H | H | H | H | H | acac | |
| 3'-15Y | Pt | 0 | 3' | Ph | H | H | NO₂ | H | H | H | H | H | H | — | — |
| 3'-16 | Pt | 1 | 3' | Ph | F | H | NO₂ | H | H | H | H | H | H | | pic |
| 3'-16X | Pt | 1 | 3' | Ph | F | H | NO₂ | H | H | H | H | H | H | acac | |
| 3'-16Y | Pt | 0 | 3' | Ph | F | H | NO₂ | H | H | H | H | H | H | — | — |
| 3'-17 | Pt | 1 | 3' | Ph | F | H | NO₂ | F | H | H | H | H | H | | pic |
| 3'-17X | Pt | 1 | 3' | Ph | F | H | NO₂ | F | H | H | H | H | H | acac | |
| 3'-17Y | Pt | 0 | 3' | Ph | F | H | NO₂ | F | H | H | H | H | H | — | — |
| 3'-18 | Pt | 1 | 3' | Ph | H | NO₂ | H | NO₂ | H | H | H | H | H | | pic |
| 3'-18X | Pt | 1 | 3' | Ph | H | NO₂ | H | NO₂ | H | H | H | H | H | acac | |
| 3'-18Y | Pt | 0 | 3' | Ph | H | NO₂ | H | NO₂ | H | H | H | H | H | — | — |
| 3'-19 | Pt | 1 | 3' | Ph | NO₂ | H | H | NO₂ | H | H | H | H | H | | pic |
| 3'-19X | Pt | 1 | 3' | Ph | NO₂ | H | H | NO₂ | H | H | H | H | H | acac | |
| 3'-19Y | Pt | 0 | 3' | Ph | NO₂ | H | H | NO₂ | H | H | H | H | H | — | — |
| 3'-20 | Pt | 1 | 3' | Ph | H | H | CF₃ | H | H | H | H | H | H | | pic |
| 3'-20X | Pt | 1 | 3' | Ph | H | H | CF₃ | H | H | H | H | H | H | acac | |
| 3'-20Y | Pt | 0 | 3' | Ph | H | H | CF₃ | H | H | H | H | H | H | — | — |
| 3'-21 | Pt | 1 | 3' | Ph | H | Cl | CF₃ | H | H | H | H | H | H | | pic |
| 3'-21X | Pt | 1 | 3' | Ph | H | Cl | CF₃ | H | H | H | H | H | H | acac | |
| 3'-21Y | Pt | 0 | 3' | Ph | H | Cl | CF₃ | H | H | H | H | H | H | — | — |
| 3'-22 | Pt | 1 | 3' | Ph | H | NO₂ | H | H | H | H | H | H | H | | pic |
| 3'-22X | Pt | 1 | 3' | Ph | H | NO₂ | H | H | H | H | H | H | H | acac | |
| 3'-22Y | Pt | 0 | 3' | Ph | H | NO₂ | H | H | H | H | H | H | H | — | — |
| 3'-23 | Pt | 1 | 3' | Ph | H | CF₃ | H | H | H | H | H | H | H | | pic |
| 3'-23X | Pt | 1 | 3' | Ph | H | CF₃ | H | H | H | H | H | H | H | acac | |
| 3'-23Y | Pt | 0 | 3' | Ph | H | CF₃ | H | H | H | H | H | H | H | — | — |
| 3'-24 | Pt | 1 | 3' | Ph | H | NO₂ | H | CH₃ | H | H | H | H | H | | pic |
| 3'-24X | Pt | 1 | 3' | Ph | H | NO₂ | H | CH₃ | H | H | H | H | H | acac | |
| 3'-24Y | Pt | 0 | 3' | Ph | H | NO₂ | H | CH₃ | H | H | H | H | H | — | — |
| 3'-25 | Pt | 1 | 3' | Ph | H | NO₂ | H | ᵗC₄H₉ | H | H | H | H | H | | pic |
| 3'-25X | Pt | 1 | 3' | Ph | H | NO₂ | H | ᵗC₄H₉ | H | H | H | H | H | acac | |
| 3'-25Y | Pt | 0 | 3' | Ph | H | NO₂ | H | ᵗC₄H₉ | H | H | H | H | H | — | — |
| 3'-26 | Pt | 1 | 3' | Ph | H | H | CH₃O | H | H | H | H | H | H | | pic |
| 3'-26X | Pt | 1 | 3' | Ph | H | H | CH₃O | H | H | H | H | H | H | acac | |
| 3'-26Y | Pt | 0 | 3' | Ph | H | H | CH₃O | H | H | H | H | H | H | — | — |
| 3'-27 | Pt | 1 | 3' | Ph | H | CH₃O | H | H | H | H | H | H | H | | pic |
| 3'-27X | Pt | 1 | 3' | Ph | H | CH₃O | H | H | H | H | H | H | H | acac | |
| 3'-27Y | Pt | 0 | 3' | Ph | H | CH₃O | H | H | H | H | H | H | H | — | — |
| 3'-28 | Pt | 1 | 3' | Ph | H | CH₃O | H | CH₃ | H | H | H | H | H | | pic |
| 3'-28X | Pt | 1 | 3' | Ph | H | CH₃O | H | CH₃ | H | H | H | H | H | acac | |
| 3'-28Y | Pt | 0 | 3' | Ph | H | CH₃O | H | CH₃ | H | H | H | H | H | — | — |
| 3'-29 | Pt | 1 | 3' | Ph | H | CH₃O | H | ᵗC₄H₉ | H | H | H | H | H | | pic |
| 3'-29X | Pt | 1 | 3' | Ph | H | CH₃O | H | ᵗC₄H₉ | H | H | H | H | H | acac | |
| 3'-29Y | Pt | 0 | 3' | Ph | H | CH₃O | H | ᵗC₄H₉ | H | H | H | H | H | — | — |

TABLE 31-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-30 | Pt | 1 | 3' | Ph | H | H | H | H | $^tC_4H_9$ | H | H | H | H | pic | |
| 3'-30X | Pt | 1 | 3' | Ph | H | H | H | H | $^tC_4H_9$ | H | H | H | H | acac | |
| 3'-30Y | Pt | 0 | 3' | Ph | H | H | H | H | $^tC_4H_9$ | H | H | H | H | — | — |
| 3'-31 | Pt | 1 | 3' | Ph | H | F | H | F | $^tC_4H_9$ | H | H | H | H | pic | |
| 3'-31X | Pt | 1 | 3' | Ph | H | F | H | F | $^tC_4H_9$ | H | H | H | H | acac | |
| 3'-31Y | Pt | 0 | 3' | Ph | H | F | H | F | $^tC_4H_9$ | H | H | H | H | — | — |
| 3'-32 | Pt | 1 | 3' | Ph | $CF_3$ | H | $CF_3$ | H | $^tC_4H_9$ | H | H | H | H | pic | |
| 3'-32X | Pt | 1 | 3' | Ph | $CF_3$ | H | $CF_3$ | H | $^tC_4H_9$ | H | H | H | H | acac | |
| 3'-32Y | Pt | 0 | 3' | Ph | $CF_3$ | H | $CF_3$ | H | $^tC_4H_9$ | H | H | H | H | — | — |
| 3'-33 | Pt | 1 | 3' | Ph | H | $CF_3$ | H | $CH_3$ | $^tC_4H_9$ | H | H | H | H | pic | |
| 3'-33X | Pt | 1 | 3' | Ph | H | $CF_3$ | H | $CH_3$ | $^tC_4H_9$ | H | H | H | H | acac | |
| 3'-33Y | Pt | 0 | 3' | Ph | H | $CF_3$ | H | $CH_3$ | $^tC_4H_9$ | H | H | H | H | — | — |
| 3'-34 | Pt | 1 | 3' | Ph | H | $Si(CH_3)_3$ | H | H | H | H | H | H | H | pic | |
| 3'-34X | Pt | 1 | 3' | Ph | H | $Si(CH_3)_3$ | H | H | H | H | H | H | H | acac | |
| 3'-34Y | Pt | 0 | 3' | Ph | H | $Si(CH_3)_3$ | H | H | H | H | H | H | H | — | — |
| 3'-35 | Pt | 1 | 3' | Ph | H | H | $Si(CH_3)_3$ | H | H | H | H | H | H | pic | |
| 3'-35X | Pt | 1 | 3' | Ph | H | H | $Si(CH_3)_3$ | H | H | H | H | H | H | acac | |
| 3'-35Y | Pt | 0 | 3' | Ph | H | H | $Si(CH_3)_3$ | H | H | H | H | H | H | — | — |
| 3'-36 | Pt | 1 | 3' | Ph | H | H | H | $Si(CH_3)_3$ | H | H | H | H | H | pic | |
| 3'-36X | Pt | 1 | 3' | Ph | H | H | H | $Si(CH_3)_3$ | H | H | H | H | H | acac | |
| 3'-36Y | Pt | 0 | 3' | Ph | H | H | H | $Si(CH_3)_3$ | H | H | H | H | H | — | — |
| 3'-37 | Pt | 1 | 3' | Ph | H | F | H | $Si(CH_3)_3$ | H | H | H | H | H | pic | |
| 3'-37X | Pt | 1 | 3' | Ph | H | F | H | $Si(CH_3)_3$ | H | H | H | H | H | acac | |
| 3'-37Y | Pt | 0 | 3' | Ph | H | F | H | $Si(CH_3)_3$ | H | H | H | H | H | — | — |
| 3'-38 | Pt | 1 | 3' | Ph | H | $CF_3$ | H | $Si(CH_3)_3$ | H | H | H | H | H | pic | |
| 3'-38X | Pt | 1 | 3' | Ph | H | $CF_3$ | H | $Si(CH_3)_3$ | H | H | H | H | H | acac | |
| 3'-38Y | Pt | 0 | 3' | Ph | H | $CF_3$ | H | $Si(CH_3)_3$ | H | H | H | H | H | — | — |
| 3'-39 | Pt | 1 | 3' | Ph | H | $Si(CH_3)_3$ | H | F | H | H | H | H | H | pic | |
| 3'-39X | Pt | 1 | 3' | Ph | H | $Si(CH_3)_3$ | H | F | H | H | H | H | H | acac | |
| 3'-39Y | Pt | 0 | 3' | Ph | H | $Si(CH_3)_3$ | H | F | H | H | H | H | H | — | — |
| 3'-40 | Pt | 1 | 3' | Ph | H | $Si(CH_3)_3$ | H | $CF_3$ | H | H | H | H | H | pic | |
| 3'-40X | Pt | 1 | 3' | Ph | H | $Si(CH_3)_3$ | H | $CF_3$ | H | H | H | H | H | acac | |
| 3'-40Y | Pt | 0 | 3' | Ph | H | $Si(CH_3)_3$ | H | $CF_3$ | H | H | H | H | H | — | — |
| 3'-41 | Pt | 1 | 3' | Ph | $Si(CH_3)_3$ | H | $Si(CH_3)_3$ | H | H | H | H | H | H | pic | |
| 3'-41X | Pt | 1 | 3' | Ph | $Si(CH_3)_3$ | H | $Si(CH_3)_3$ | H | H | H | H | H | H | acac | |
| 3'-41Y | Pt | 0 | 3' | Ph | $Si(CH_3)_3$ | H | $Si(CH_3)_3$ | H | H | H | H | H | H | — | — |
| 3'-42 | Pt | 1 | 3' | Ph | H | H | H | $COCH_3$ | H | H | H | H | H | pic | |
| 3'-42X | Pt | 1 | 3' | Ph | H | H | H | $COCH_3$ | H | H | H | H | H | acac | |
| 3'-42Y | Pt | 0 | 3' | Ph | H | H | H | $COCH_3$ | H | H | H | H | H | — | — |
| 3'-43 | Pt | 1 | 3' | Ph | H | H | $COCH_3$ | H | H | H | H | H | H | pic | |
| 3'-43X | Pt | 1 | 3' | Ph | H | H | $COCH_3$ | H | H | H | H | H | H | acac | |
| 3'-43Y | Pt | 0 | 3' | Ph | H | H | $COCH_3$ | H | H | H | H | H | H | — | — |
| 3'-44 | Pt | 1 | 3' | Ph | H | $COCH_3$ | H | H | H | H | H | H | H | pic | |
| 3'-44X | Pt | 1 | 3' | Ph | H | $COCH_3$ | H | H | H | H | H | H | H | acac | |
| 3'-44Y | Pt | 0 | 3' | Ph | H | $COCH_3$ | H | H | H | H | H | H | H | — | — |
| 3'-45 | Pt | 1 | 3' | Ph | H | H | BL | H | H | H | H | H | H | pic | |
| 3'-45X | Pt | 1 | 3' | Ph | H | H | BL | H | H | H | H | H | H | acac | |
| 3'-45Y | Pt | 0 | 3' | Ph | H | H | BL | H | H | H | H | H | H | — | — |
| 3'-46 | Pt | 1 | 3' | Ph | H | BL | H | H | H | H | H | H | H | pic | |
| 3'-46X | Pt | 1 | 3' | Ph | H | BL | H | H | H | H | H | H | H | acac | |
| 3'-46Y | Pt | 0 | 3' | Ph | H | BL | H | H | H | H | H | H | H | — | — |
| 3'-47 | Pt | 1 | 3' | Ph | H | H | PL | H | H | H | H | H | H | pic | |
| 3'-47X | Pt | 1 | 3' | Ph | H | H | PL | H | H | H | H | H | H | acac | |
| 3'-47Y | Pt | 0 | 3' | Ph | H | H | PL | H | H | H | H | H | H | — | — |
| 3'-48 | Pt | 1 | 3' | Ph | H | PL | H | H | H | H | H | H | H | pic | |
| 3'-48X | Pt | 1 | 3' | Ph | H | PL | H | H | H | H | H | H | H | acac | |
| 3'-48Y | Pt | 0 | 3' | Ph | H | PL | H | H | H | H | H | H | H | — | — |
| 3'-49 | Pt | 1 | 3' | Ph | H | H | MEE1 | H | H | H | H | H | H | pic | |
| 3'-49X | Pt | 1 | 3' | Ph | H | H | MEE1 | H | H | H | H | H | H | acac | |
| 3'-49Y | Pt | 0 | 3' | Ph | H | H | MEE1 | H | H | H | H | H | H | — | — |
| 3'-50 | Pt | 1 | 3' | Ph | H | MEE1 | H | H | H | H | H | H | H | pic | |
| 3'-50X | Pt | 1 | 3' | Ph | H | MEE1 | H | H | H | H | H | H | H | acac | |
| 3'-50Y | Pt | 0 | 3' | Ph | H | MEE1 | H | H | H | H | H | H | H | — | — |
| 3'-51 | Pt | 1 | 3' | Ph | H | H | MEE2 | H | H | H | H | H | H | pic | |
| 3'-51X | Pt | 1 | 3' | Ph | H | H | MEE2 | H | H | H | H | H | H | acac | |
| 3'-51Y | Pt | 0 | 3' | Ph | H | H | MEE2 | H | H | H | H | H | H | — | — |
| 3'-52 | Pt | 1 | 3' | Ph | H | MEE2 | H | H | H | H | H | H | H | pic | |
| 3'-52X | Pt | 1 | 3' | Ph | H | MEE2 | H | H | H | H | H | H | H | acac | |
| 3'-52Y | Pt | 0 | 3' | Ph | H | MEE2 | H | H | H | H | H | H | H | — | — |
| 3'-53 | Pt | 1 | 3' | Ph | H | H | PA1 | H | H | H | H | H | H | pic | |
| 3'-53X | Pt | 1 | 3' | Ph | H | H | PA1 | H | H | H | H | H | H | acac | |
| 3'-53Y | Pt | 0 | 3' | Ph | H | H | PA1 | H | H | H | H | H | H | — | — |
| 3'-54 | Pt | 1 | 3' | Ph | H | PA1 | H | H | H | H | H | H | H | pic | |
| 3'-54X | Pt | 1 | 3' | Ph | H | PA1 | H | H | H | H | H | H | H | acac | |
| 3'-54Y | Pt | 0 | 3' | Ph | H | PA1 | H | H | H | H | H | H | H | — | — |
| 3'-55 | Pt | 1 | 3' | Ph | H | H | PA2 | H | H | H | H | H | H | pic | |
| 3'-55X | Pt | 1 | 3' | Ph | H | H | PA2 | H | H | H | H | H | H | acac | |

TABLE 31-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-55Y | Pt | 0 | 3' | Ph | H | H | | PA2 | H | H | H | H | H | — | — |
| 3'-56 | Pt | 1 | 3' | Ph | H | | PA2 | H | H | H | H | H | H | pic | |
| 3'-56X | Pt | 1 | 3' | Ph | H | | PA2 | H | H | H | H | H | H | acac | |
| 3'-56Y | Pt | 0 | 3' | Ph | H | | PA2 | H | H | H | H | H | H | — | — |
| 3'-57 | Pt | 1 | 3' | Ph | H | H | | EA1 | H | H | H | H | H | pic | |
| 3'-57X | Pt | 1 | 3' | Ph | H | H | | EA1 | H | H | H | H | H | acac | |
| 3'-57Y | Pt | 0 | 3' | Ph | H | H | | EA1 | H | H | H | H | H | — | — |
| 3'-58 | Pt | 1 | 3' | Ph | H | | EA2 | H | H | H | H | H | H | pic | |
| 3'-58X | Pt | 1 | 3' | Ph | H | | EA2 | H | H | H | H | H | H | acac | |
| 3'-58Y | Pt | 0 | 3' | Ph | H | | EA2 | H | H | H | H | H | H | — | — |
| 3'-59 | Pt | 1 | 3' | Ph | H | H | | ME | H | H | H | H | H | pic | |
| 3'-59X | Pt | 1 | 3' | Ph | H | H | | ME | H | H | H | H | H | acac | |
| 3'-59Y | Pt | 0 | 3' | Ph | H | H | | ME | H | H | H | H | H | — | — |
| 3'-60 | Pt | 1 | 3' | Ph | H | | ME | H | H | H | H | H | H | pic | |
| 3'-60X | Pt | 1 | 3' | Ph | H | | ME | H | H | H | H | H | H | acac | |
| 3'-60Y | Pt | 0 | 3' | Ph | H | | ME | H | H | H | H | H | H | — | — |
| 3'-61 | Pt | 1 | 3' | Ph | H | H | | AT | H | H | H | H | H | pic | |
| 3'-61X | Pt | 1 | 3' | Ph | H | H | | AT | H | H | H | H | H | acac | |
| 3'-61Y | Pt | 0 | 3' | Ph | H | H | | AT | H | H | H | H | H | — | — |
| 3'-62 | Pt | 1 | 3' | Ph | H | | AT | H | H | H | H | H | H | pic | |
| 3'-62X | Pt | 1 | 3' | Ph | H | | AT | H | H | H | H | H | H | acac | |
| 3'-62Y | Pt | 0 | 3' | Ph | H | | AT | H | H | H | H | H | H | — | — |
| 3'-63 | Pt | 1 | 3' | Ph | H | H | | MES1 | H | H | H | H | H | pic | |
| 3'-63X | Pt | 1 | 3' | Ph | H | H | | MES1 | H | H | H | H | H | acac | |
| 3'-63Y | Pt | 0 | 3' | Ph | H | H | | MES1 | H | H | H | H | H | — | — |
| 3'-64 | Pt | 1 | 3' | Ph | H | | MES1 | H | H | H | H | H | H | pic | |
| 3'-64X | Pt | 1 | 3' | Ph | H | | MES1 | H | H | H | H | H | H | acac | |
| 3'-64Y | Pt | 0 | 3' | Ph | H | | MES1 | H | H | H | H | H | H | — | — |
| 3'-65 | Pt | 1 | 3' | Ph | H | H | | MES2 | H | H | H | H | H | pic | |
| 3'-65X | Pt | 1 | 3' | Ph | H | H | | MES2 | H | H | H | H | H | acac | |
| 3'-65Y | Pt | 0 | 3' | Ph | H | H | | MES2 | H | H | H | H | H | — | — |
| 3'-66 | Pt | 1 | 3' | Ph | H | | MES2 | H | H | H | H | H | H | pic | |
| 3'-66X | Pt | 1 | 3' | Ph | H | | MES2 | H | H | H | H | H | H | acac | |
| 3'-66Y | Pt | 0 | 3' | Ph | H | | MES2 | H | H | H | H | H | H | — | — |
| 3'-67 | Pt | 1 | 3' | Ph | H | H | | PS1 | H | H | H | H | H | pic | |
| 3'-67X | Pt | 1 | 3' | Ph | H | H | | PS1 | H | H | H | H | H | acac | |
| 3'-67Y | Pt | 0 | 3' | Ph | H | H | | PS1 | H | H | H | H | H | — | — |
| 3'-68 | Pt | 1 | 3' | Ph | H | | PS1 | H | H | H | H | H | H | pic | |
| 3'-68X | Pt | 1 | 3' | Ph | H | | PS1 | H | H | H | H | H | H | acac | |
| 3'-68Y | Pt | 0 | 3' | Ph | H | | PS1 | H | H | H | H | H | H | — | — |
| 3'-69 | Pt | 1 | 3' | Ph | H | H | | PS2 | H | H | H | H | H | pic | |
| 3'-69X | Pt | 1 | 3' | Ph | H | H | | PS2 | H | H | H | H | H | acac | |
| 3'-69Y | Pt | 0 | 3' | Ph | H | H | | PS2 | H | H | H | H | H | — | — |
| 3'-70 | Pt | 1 | 3' | Ph | H | | PS2 | H | H | H | H | H | H | pic | |
| 3'-70X | Pt | 1 | 3' | Ph | H | | PS2 | H | H | H | H | H | H | acac | |
| 3'-70Y | Pt | 0 | 3' | Ph | H | | PS2 | H | H | H | H | H | H | — | — |
| 3'-71 | Pt | 1 | 3' | Ph | H | H | | BAL1 | H | H | H | H | H | pic | |
| 3'-71X | Pt | 1 | 3' | Ph | H | H | | BAL1 | H | H | H | H | H | acac | |
| 3'-71Y | Pt | 0 | 3' | Ph | H | H | | BAL1 | H | H | H | H | H | — | — |
| 3'-72 | Pt | 1 | 3' | Ph | H | | BAL1 | H | H | H | H | H | H | pic | |
| 3'-72X | Pt | 1 | 3' | Ph | H | | BAL1 | H | H | H | H | H | H | acac | |
| 3'-72Y | Pt | 0 | 3' | Ph | H | | BAL1 | H | H | H | H | H | H | — | — |
| 3'-73 | Pt | 1 | 3' | Ph | H | H | | BAL2 | H | H | H | H | H | pic | |
| 3'-73X | Pt | 1 | 3' | Ph | H | H | | BAL2 | H | H | H | H | H | acac | |
| 3'-73Y | Pt | 0 | 3' | Ph | H | H | | BAL2 | H | H | H | H | H | — | — |
| 3'-74 | Pt | 1 | 3' | Ph | H | | BAL2 | H | H | H | H | H | H | pic | |
| 3'-74X | Pt | 1 | 3' | Ph | H | | BAL2 | H | H | H | H | H | H | acac | |
| 3'-74Y | Pt | 0 | 3' | Ph | H | | BAL2 | H | H | H | H | H | H | — | — |
| 3'-75 | Pt | 1 | 3' | Ph | H | H | | MEK1 | H | H | H | H | H | pic | |
| 3'-75X | Pt | 1 | 3' | Ph | H | H | | MEK1 | H | H | H | H | H | acac | |
| 3'-75Y | Pt | 0 | 3' | Ph | H | H | | MEK1 | H | H | H | H | H | — | — |
| 3'-76 | Pt | 1 | 3' | Ph | H | | MEK1 | H | H | H | H | H | H | pic | |
| 3'-76X | Pt | 1 | 3' | Ph | H | | MEK1 | H | H | H | H | H | H | acac | |
| 3'-76Y | Pt | 0 | 3' | Ph | H | | MEK1 | H | H | H | H | H | H | — | — |
| 3'-77 | Pt | 1 | 3' | Ph | H | H | | MEK2 | H | H | H | H | H | pic | |
| 3'-77X | Pt | 1 | 3' | Ph | H | H | | MEK2 | H | H | H | H | H | acac | |
| 3'-77Y | Pt | 0 | 3' | Ph | H | H | | MEK2 | H | H | H | H | H | — | — |
| 3'-78 | Pt | 1 | 3' | Ph | H | | MEK2 | H | H | H | H | H | H | pic | |
| 3'-78X | Pt | 1 | 3' | Ph | H | | MEK2 | H | H | H | H | H | H | acac | |
| 3'-78Y | Pt | 0 | 3' | Ph | H | | MEK2 | H | H | H | H | H | H | — | — |
| 3'-79 | Pt | 1 | 3' | Ph | H | H | | PAL1 | H | H | H | H | H | pic | |
| 3'-79X | Pt | 1 | 3' | Ph | H | H | | PAL1 | H | H | H | H | H | acac | |
| 3'-79Y | Pt | 0 | 3' | Ph | H | H | | PAL1 | H | H | H | H | H | — | — |
| 3'-80 | Pt | 1 | 3' | Ph | H | | PAL1 | H | H | H | H | H | H | pic | |
| 3'-80X | Pt | 1 | 3' | Ph | H | | PAL1 | H | H | H | H | H | H | acac | |
| 3'-80Y | Pt | 0 | 3' | Ph | H | | PAL1 | H | H | H | H | H | H | — | — |
| 3'-81 | Pt | 1 | 3' | Ph | H | H | | PAL2 | H | H | H | H | H | pic | |

TABLE 31-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-81X | Pt | 1 | 3' | Ph | H | H | | PAL2 | H | H | H | H | H | acac | |
| 3'-81Y | Pt | 0 | 3' | Ph | H | H | | PAL2 | H | H | H | H | H | — | — |
| 3'-82 | Pt | 1 | 3' | Ph | H | | PAL2 | H | H | H | H | H | H | pic | |
| 3'-82X | Pt | 1 | 3' | Ph | H | | PAL2 | H | H | H | H | H | H | acac | |
| 3'-82Y | Pt | 0 | 3' | Ph | H | | PAL2 | H | H | H | H | H | H | — | — |
| 3'-83 | Pt | 1 | 3' | Ph | H | H | | MMK | H | H | H | H | H | pic | |
| 3'-83X | Pt | 1 | 3' | Ph | H | H | | MMK | H | H | H | H | H | acac | |
| 3'-83Y | Pt | 0 | 3' | Ph | H | H | | MMK | H | H | H | H | H | — | — |
| 3'-84 | Pt | 1 | 3' | Ph | H | | MMK | H | H | H | H | H | H | pic | |
| 3'-84X | Pt | 1 | 3' | Ph | H | | MMK | H | H | H | H | H | H | acac | |
| 3'-84Y | Pt | 0 | 3' | Ph | H | | MMK | H | H | H | H | H | H | — | — |
| 3'-85 | Pt | 1 | 3' | Ph | H | H | | EES1 | H | H | H | H | H | pic | |
| 3'-85X | Pt | 1 | 3' | Ph | H | H | | EES1 | H | H | H | H | H | acac | |
| 3'-85Y | Pt | 0 | 3' | Ph | H | H | | EES1 | H | H | H | H | H | — | — |
| 3'-86 | Pt | 1 | 3' | Ph | H | | EES2 | H | H | H | H | H | H | pic | |
| 3'-86X | Pt | 1 | 3' | Ph | H | | EES2 | H | H | H | H | H | H | acac | |
| 3'-86Y | Pt | 0 | 3' | Ph | H | | EES2 | H | H | H | H | H | H | — | — |
| 3'-87 | Pt | 1 | 3' | Ph | H | H | | PAE1 | H | H | H | H | H | pic | |
| 3'-87X | Pt | 1 | 3' | Ph | H | H | | PAE1 | H | H | H | H | H | acac | |
| 3'-87Y | Pt | 0 | 3' | Ph | H | H | | PAE1 | H | H | H | H | H | — | — |
| 3'-88 | Pt | 1 | 3' | Ph | H | | PAE2 | H | H | H | H | H | H | pic | |
| 3'-88X | Pt | 1 | 3' | Ph | H | | PAE2 | H | H | H | H | H | H | acac | |
| 3'-88Y | Pt | 0 | 3' | Ph | H | | PAE2 | H | H | H | H | H | H | — | — |
| 3'-89 | Pt | 1 | 3' | Ph | H | H | | AME1 | H | H | H | H | H | pic | |
| 3'-89X | Pt | 1 | 3' | Ph | H | H | | AME1 | H | H | H | H | H | acac | |
| 3'-89Y | Pt | 0 | 3' | Ph | H | H | | AME1 | H | H | H | H | H | — | — |
| 3'-90 | Pt | 1 | 3' | Ph | H | | AME1 | H | H | H | H | H | H | pic | |
| 3'-90X | Pt | 1 | 3' | Ph | H | | AME1 | H | H | H | H | H | H | acac | |
| 3'-90Y | Pt | 0 | 3' | Ph | H | | AME1 | H | H | H | H | H | H | — | — |
| 3'-91 | Pt | 1 | 3' | Ph | H | H | | AME2 | H | H | H | H | H | pic | |
| 3'-91X | Pt | 1 | 3' | Ph | H | H | | AME2 | H | H | H | H | H | acac | |
| 3'-91Y | Pt | 0 | 3' | Ph | H | H | | AME2 | H | H | H | H | H | — | — |
| 3'-92 | Pt | 1 | 3' | Ph | H | | AME2 | H | H | H | H | H | H | pic | |
| 3'-92X | Pt | 1 | 3' | Ph | H | | AME2 | H | H | H | H | H | H | acac | |
| 3'-92Y | Pt | 0 | 3' | Ph | H | | AME2 | H | H | H | H | H | H | — | — |
| 3'-93 | Pt | 1 | 3' | Ph | H | H | | EAE1 | H | H | H | H | H | pic | |
| 3'-93X | Pt | 1 | 3' | Ph | H | H | | EAE1 | H | H | H | H | H | acac | |
| 3'-93Y | Pt | 0 | 3' | Ph | H | H | | EAE1 | H | H | H | H | H | — | — |
| 3'-94 | Pt | 1 | 3' | Ph | H | | EAE1 | H | H | H | H | H | H | pic | |
| 3'-94X | Pt | 1 | 3' | Ph | H | | EAE1 | H | H | H | H | H | H | acac | |
| 3'-94Y | Pt | 0 | 3' | Ph | H | | EAE1 | H | H | H | H | H | H | — | — |
| 3'-95 | Pt | 1 | 3' | Ph | H | H | | EAE2 | H | H | H | H | H | pic | |
| 3'-95X | Pt | 1 | 3' | Ph | H | H | | EAE2 | H | H | H | H | H | acac | |
| 3'-95Y | Pt | 0 | 3' | Ph | H | H | | EAE2 | H | H | H | H | H | — | — |
| 3'-96 | Pt | 1 | 3' | Ph | H | | EAE2 | H | H | H | H | H | H | pic | |
| 3'-96X | Pt | 1 | 3' | Ph | H | | EAE2 | H | H | H | H | H | H | acac | |
| 3'-96Y | Pt | 0 | 3' | Ph | H | | EAE2 | H | H | H | H | H | H | — | — |
| 3'-97 | Pt | 1 | 3' | Ph | H | H | | AAE1 | H | H | H | H | H | pic | |
| 3'-97X | Pt | 1 | 3' | Ph | H | H | | AAE1 | H | H | H | H | H | acac | |
| 3'-97Y | Pt | 0 | 3' | Ph | H | H | | AAE1 | H | H | H | H | H | — | — |
| 3'-98 | Pt | 1 | 3' | Ph | H | | AAE1 | H | H | H | H | H | H | pic | |
| 3'-98X | Pt | 1 | 3' | Ph | H | | AAE1 | H | H | H | H | H | H | acac | |
| 3'-98Y | Pt | 0 | 3' | Ph | H | | AAE1 | H | H | H | H | H | H | — | — |
| 3'-99 | Pt | 1 | 3' | Ph | H | H | | AAE2 | H | H | H | H | H | pic | |
| 3'-99X | Pt | 1 | 3' | Ph | H | H | | AAE2 | H | H | H | H | H | acac | |
| 3'-99Y | Pt | 0 | 3' | Ph | H | H | | AAE2 | H | H | H | H | H | — | — |
| 3'-100 | Pt | 1 | 3' | Ph | H | | AAE2 | H | H | H | H | H | H | pic | |
| 3'-100X | Pt | 1 | 3' | Ph | H | | AAE2 | H | H | H | H | H | H | acac | |
| 3'-100Y | Pt | 0 | 3' | Ph | H | | AAE2 | H | H | H | H | H | H | — | — |
| 3'-101 | Pt | 1 | 3' | Ph | H | H | | PME1 | H | H | H | H | H | pic | |
| 3'-101X | Pt | 1 | 3' | Ph | H | H | | PME1 | H | H | H | H | H | acac | |
| 3'-101Y | Pt | 0 | 3' | Ph | H | H | | PME1 | H | H | H | H | H | — | — |
| 3'-102 | Pt | 1 | 3' | Ph | H | | PME1 | H | H | H | H | H | H | pic | |
| 3'-102X | Pt | 1 | 3' | Ph | H | | PME1 | H | H | H | H | H | H | acac | |
| 3'-102Y | Pt | 0 | 3' | Ph | H | | PME1 | H | H | H | H | H | H | — | — |
| 3'-103 | Pt | 1 | 3' | Ph | H | H | | PME2 | H | H | H | H | H | pic | |
| 3'-103X | Pt | 1 | 3' | Ph | H | H | | PME2 | H | H | H | H | H | acac | |
| 3'-103Y | Pt | 0 | 3' | Ph | H | H | | PME2 | H | H | H | H | H | — | — |
| 3'-104 | Pt | 1 | 3' | Ph | H | | PME2 | H | H | H | H | H | H | pic | |
| 3'-104X | Pt | 1 | 3' | Ph | H | | PME2 | H | H | H | H | H | H | acac | |
| 3'-104Y | Pt | 0 | 3' | Ph | H | | PME2 | H | H | H | H | H | H | — | — |
| 3'-105 | Pt | 1 | 3' | Ph | H | H | | MET1 | H | H | H | H | H | pic | |
| 3'-105X | Pt | 1 | 3' | Ph | H | H | | MET1 | H | H | H | H | H | acac | |
| 3'-105Y | Pt | 0 | 3' | Ph | H | H | | MET1 | H | H | H | H | H | — | — |
| 3'-106 | Pt | 1 | 3' | Ph | H | | MET1 | H | H | H | H | H | H | pic | |
| 3'-106X | Pt | 1 | 3' | Ph | H | | MET1 | H | H | H | H | H | H | acac | |
| 3'-106Y | Pt | 0 | 3' | Ph | H | | MET1 | H | H | H | H | H | H | — | — |

TABLE 31-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-107 | Pt | 1 | 3' | Ph | H | H | | MET2 | H | H | H | H | H | pic | |
| 3'-107X | Pt | 1 | 3' | Ph | H | H | | MET2 | H | H | H | H | H | acac | |
| 3'-107Y | Pt | 0 | 3' | Ph | H | H | | MET2 | H | H | H | H | H | — | — |
| 3'-108 | Pt | 1 | 3' | Ph | H | | MET2 | H | H | H | H | H | H | pic | |
| 3'-108X | Pt | 1 | 3' | Ph | H | | MET2 | H | H | H | H | H | H | acac | |
| 3'-108Y | Pt | 0 | 3' | Ph | H | | MET2 | H | H | H | H | H | H | — | — |
| 3'-109 | Pt | 1 | 3' | Ph | H | H | | EE1 | H | H | H | H | H | pic | |
| 3'-109X | Pt | 1 | 3' | Ph | H | H | | EE1 | H | H | H | H | H | acac | |
| 3'-109Y | Pt | 0 | 3' | Ph | H | H | | EE1 | H | H | H | H | H | — | — |
| 3'-110 | Pt | 1 | 3' | Ph | H | | EE1 | H | H | H | H | H | H | pic | |
| 3'-110X | Pt | 1 | 3' | Ph | H | | EE1 | H | H | H | H | H | H | acac | |
| 3'-110Y | Pt | 0 | 3' | Ph | H | | EE1 | H | H | H | H | H | H | — | — |
| 3'-111 | Pt | 1 | 3' | Ph | H | H | | EE2 | H | H | H | H | H | pic | |
| 3'-111X | Pt | 1 | 3' | Ph | H | H | | EE2 | H | H | H | H | H | acac | |
| 3'-111Y | Pt | 0 | 3' | Ph | H | H | | EE2 | H | H | H | H | H | — | — |
| 3'-112 | Pt | 1 | 3' | Ph | H | | EE2 | H | H | H | H | H | H | pic | |
| 3'-112X | Pt | 1 | 3' | Ph | H | | EE2 | H | H | H | H | H | H | acac | |
| 3'-112Y | Pt | 0 | 3' | Ph | H | | EE2 | H | H | H | H | H | H | — | — |
| 3'-113 | Pt | 1 | 3' | Ph | H | H | | MS1 | H | H | H | H | H | pic | |
| 3'-113X | Pt | 1 | 3' | Ph | H | H | | MS1 | H | H | H | H | H | acac | |
| 3'-113Y | Pt | 0 | 3' | Ph | H | H | | MS1 | H | H | H | H | H | — | — |
| 3'-114 | Pt | 1 | 3' | Ph | H | | MS1 | H | H | H | H | H | H | pic | |
| 3'-114X | Pt | 1 | 3' | Ph | H | | MS1 | H | H | H | H | H | H | acac | |
| 3'-114Y | Pt | 0 | 3' | Ph | H | | MS1 | H | H | H | H | H | H | — | — |
| 3'-115 | Pt | 1 | 3' | Ph | H | H | | MS2 | H | H | H | H | H | pic | |
| 3'-115X | Pt | 1 | 3' | Ph | H | H | | MS2 | H | H | H | H | H | acac | |
| 3'-115Y | Pt | 0 | 3' | Ph | H | H | | MS2 | H | H | H | H | H | — | — |
| 3'-116 | Pt | 1 | 3' | Ph | H | | MS2 | H | H | H | H | H | H | pic | |
| 3'-116X | Pt | 1 | 3' | Ph | H | | MS2 | H | H | H | H | H | H | acac | |
| 3'-116Y | Pt | 0 | 3' | Ph | H | | MS2 | H | H | H | H | H | H | — | — |

TABLE 32

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-1 | Pt | 1 | 4' | Ph | H | H | H | H | $CH_3$ | H | H | H | H | pic | |
| 4'-1X | Pt | 1 | 4' | Ph | H | H | H | H | $CH_3$ | H | H | H | H | acac | |
| 4'-1Y | Pt | 0 | 4' | Ph | H | H | H | H | $CH_3$ | H | H | H | H | — | — |
| 4'-2 | Pt | 1 | 4' | Ph | H | H | H | H | $^tC_4H_9$ | H | H | H | H | pic | |
| 4'-2X | Pt | 1 | 4' | Ph | H | H | H | H | $^tC_4H_9$ | H | H | H | H | acac | |
| 4'-2Y | Pt | 0 | 4' | Ph | H | H | H | H | $^tC_4H_9$ | H | H | H | H | — | — |
| 4'-3 | Pt | 1 | 4' | Ph | H | F | H | F | $CH_3$ | H | H | H | H | pic | |
| 4'-3X | Pt | 1 | 4' | Ph | H | F | H | F | $CH_3$ | H | H | H | H | acac | |
| 4'-3Y | Pt | 0 | 4' | Ph | H | F | H | F | $CH_3$ | H | H | H | H | — | — |
| 4'-4 | Pt | 1 | 4' | Ph | H | F | H | F | $^tC_4H_9$ | H | H | H | H | pic | |
| 4'-4X | Pt | 1 | 4' | Ph | H | F | H | F | $^tC_4H_9$ | H | H | H | H | acac | |
| 4'-4Y | Pt | 0 | 4' | Ph | H | F | H | F | $^tC_4H_9$ | H | H | H | H | — | — |
| 4'-5 | Pt | 1 | 4' | Ph | F | H | H | F | $CH_3$ | H | H | H | H | pic | |
| 4'-5X | Pt | 1 | 4' | Ph | F | H | H | F | $CH_3$ | H | H | H | H | acac | |
| 4'-5Y | Pt | 0 | 4' | Ph | F | H | H | F | $CH_3$ | H | H | H | H | — | — |
| 4'-6 | Pt | 1 | 4' | Ph | F | H | H | F | $^tC_4H_9$ | H | H | H | H | pic | |
| 4'-6X | Pt | 1 | 4' | Ph | F | H | H | F | $^tC_4H_9$ | H | H | H | H | acac | |
| 4'-6Y | Pt | 0 | 4' | Ph | F | H | H | F | $^tC_4H_9$ | H | H | H | H | — | — |
| 4'-7 | Pt | 1 | 4' | Ph | $CF_3$ | H | $CF_3$ | H | $CH_3$ | H | H | H | H | pic | |
| 4'-7X | Pt | 1 | 4' | Ph | $CF_3$ | H | $CF_3$ | H | $CH_3$ | H | H | H | H | acac | |
| 4'-7Y | Pt | 0 | 4' | Ph | $CF_3$ | H | $CF_3$ | H | $CH_3$ | H | H | H | H | — | — |
| 4'-8 | Pt | 1 | 4' | Ph | $CF_3$ | H | $CF_3$ | H | $^tC_4H_9$ | H | H | H | H | pic | |
| 4'-8X | Pt | 1 | 4' | Ph | $CF_3$ | H | $CF_3$ | H | $^tC_4H_9$ | H | H | H | H | acac | |
| 4'-8Y | Pt | 0 | 4' | Ph | $CF_3$ | H | $CF_3$ | H | $^tC_4H_9$ | H | H | H | H | — | — |
| 4'-9 | Pt | 1 | 4' | Ph | H | F | $CF_3$ | H | $CH_3$ | H | H | H | H | pic | |
| 4'-9X | Pt | 1 | 4' | Ph | H | F | $CF_3$ | H | $CH_3$ | H | H | H | H | acac | |
| 4'-9Y | Pt | 0 | 4' | Ph | H | F | $CF_3$ | H | $CH_3$ | H | H | H | H | — | — |
| 4'-10 | Pt | 1 | 4' | Ph | F | H | $CF_3$ | H | $CH_3$ | H | H | H | H | pic | |
| 4'-10X | Pt | 1 | 4' | Ph | F | H | $CF_3$ | H | $CH_3$ | H | H | H | H | acac | |
| 4'-10Y | Pt | 0 | 4' | Ph | F | H | $CF_3$ | H | $CH_3$ | H | H | H | H | — | — |
| 4'-11 | Pt | 1 | 4' | Ph | F | F | F | F | $CH_3$ | H | H | H | H | pic | |
| 4'-11X | Pt | 1 | 4' | Ph | F | F | F | F | $CH_3$ | H | H | H | H | acac | |
| 4'-11Y | Pt | 0 | 4' | Ph | F | F | F | F | $CH_3$ | H | H | H | H | — | — |
| 4'-12 | Pt | 1 | 4' | Ph | H | F | H | $CH_3$ | $CH_3$ | H | H | H | H | pic | |
| 4'-12X | Pt | 1 | 4' | Ph | H | F | H | $CH_3$ | $CH_3$ | H | H | H | H | acac | |
| 4'-12Y | Pt | 0 | 4' | Ph | H | F | H | $CH_3$ | $CH_3$ | H | H | H | H | — | — |
| 4'-13 | Pt | 1 | 4' | Ph | H | F | H | $CH_3$ | $^tC_4H_9$ | H | H | H | H | pic | |
| 4'-13X | Pt | 1 | 4' | Ph | H | F | H | $CH_3$ | $^tC_4H_9$ | H | H | H | H | acac | |
| 4'-13Y | Pt | 0 | 4' | Ph | H | F | H | $CH_3$ | $^tC_4H_9$ | H | H | H | H | — | — |

TABLE 32-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-14 | Pt | 1 | 4' | Ph | H | F | H | $^tC_4H_9$ | $CH_3$ | H | H | H | H | pic | |
| 4'-14X | Pt | 1 | 4' | Ph | H | F | H | $^tC_4H_9$ | $CH_3$ | H | H | H | H | acac | |
| 4'-14Y | Pt | 0 | 4' | Ph | H | F | H | $^tC_4H_9$ | $CH_3$ | H | H | H | H | — | — |
| 4'-15 | Pt | 1 | 4' | Ph | H | F | H | $^tC_4H_9$ | $^tC_4H_9$ | H | H | H | H | pic | |
| 4'-15X | Pt | 1 | 4' | Ph | H | F | H | $^tC_4H_9$ | $^tC_4H_9$ | H | H | H | H | acac | |
| 4'-15Y | Pt | 0 | 4' | Ph | H | F | H | $^tC_4H_9$ | $^tC_4H_9$ | H | H | H | H | — | — |
| 4'-16 | Pt | 1 | 4' | Ph | H | $CF_3$ | H | $CF_3$ | $CH_3$ | H | H | H | H | pic | |
| 4'-16X | Pt | 1 | 4' | Ph | H | $CF_3$ | H | $CF_3$ | $CH_3$ | H | H | H | H | acac | |
| 4'-16Y | Pt | 0 | 4' | Ph | H | $CF_3$ | H | $CF_3$ | $CH_3$ | H | H | H | H | — | — |
| 4'-17 | Pt | 1 | 4' | Ph | H | $CF_3$ | H | $CF_3$ | $^tC_4H_9$ | H | H | H | H | pic | |
| 4'-17X | Pt | 1 | 4' | Ph | H | $CF_3$ | H | $CF_3$ | $^tC_4H_9$ | H | H | H | H | acac | |
| 4'-17Y | Pt | 0 | 4' | Ph | H | $CF_3$ | H | $CF_3$ | $^tC_4H_9$ | H | H | H | H | — | — |
| 4'-18 | Pt | 1 | 4' | Ph | $CF_3$ | H | H | $^tC_4H_9$ | $CH_3$ | H | H | H | H | pic | |
| 4'-18X | Pt | 1 | 4' | Ph | $CF_3$ | H | H | $^tC_4H_9$ | $CH_3$ | H | H | H | H | acac | |
| 4'-18Y | Pt | 0 | 4' | Ph | $CF_3$ | H | H | $^tC_4H_9$ | $CH_3$ | H | H | H | H | — | — |
| 4'-19 | Pt | 1 | 4' | Ph | $CF_3$ | H | H | $^tC_4H_9$ | $^tC_4H_9$ | H | H | H | H | pic | |
| 4'-19X | Pt | 1 | 4' | Ph | $CF_3$ | H | H | $^tC_4H_9$ | $^tC_4H_9$ | H | H | H | H | acac | |
| 4'-19Y | Pt | 0 | 4' | Ph | $CF_3$ | H | H | $^tC_4H_9$ | $^tC_4H_9$ | H | H | H | H | — | — |
| 4'-20 | Pt | 1 | 4' | Ph | H | $CF_3$ | H | $^tC_4H_9$ | $CH_3$ | H | H | H | H | pic | |
| 4'-20X | Pt | 1 | 4' | Ph | H | $CF_3$ | H | $^tC_4H_9$ | $CH_3$ | H | H | H | H | acac | |
| 4'-20Y | Pt | 0 | 4' | Ph | H | $CF_3$ | H | $^tC_4H_9$ | $CH_3$ | H | H | H | H | — | — |
| 4'-21 | Pt | 1 | 4' | Ph | H | $CF_3$ | H | $^tC_4H_9$ | $^tC_4H_9$ | H | H | H | H | pic | |
| 4'-21X | Pt | 1 | 4' | Ph | H | $CF_3$ | H | $^tC_4H_9$ | $^tC_4H_9$ | H | H | H | H | acac | |
| 4'-21Y | Pt | 0 | 4' | Ph | H | $CF_3$ | H | $^tC_4H_9$ | $^tC_4H_9$ | H | H | H | H | — | — |
| 4'-22 | Pt | 1 | 4' | Ph | H | $CF_3$ | H | $CH_3$ | $CH_3$ | H | H | H | H | pic | |
| 4'-22X | Pt | 1 | 4' | Ph | H | $CF_3$ | H | $CH_3$ | $CH_3$ | H | H | H | H | acac | |
| 4'-22Y | Pt | 0 | 4' | Ph | H | $CF_3$ | H | $CH_3$ | $CH_3$ | H | H | H | H | — | — |
| 4'-23 | Pt | 1 | 4' | Ph | H | $CF_3$ | $CF_3$ | H | $CH_3$ | H | H | H | H | pic | |
| 4'-23X | Pt | 1 | 4' | Ph | H | $CF_3$ | $CF_3$ | H | $CH_3$ | H | H | H | H | acac | |
| 4'-23Y | Pt | 0 | 4' | Ph | H | $CF_3$ | $CF_3$ | H | $CH_3$ | H | H | H | H | — | — |
| 4'-24 | Pt | 1 | 4' | Ph | H | H | $NO_2$ | H | $CH_3$ | H | H | H | H | pic | |
| 4'-24X | Pt | 1 | 4' | Ph | H | H | $NO_2$ | H | $CH_3$ | H | H | H | H | acac | |
| 4'-24Y | Pt | 0 | 4' | Ph | H | H | $NO_2$ | H | $CH_3$ | H | H | H | H | — | — |
| 4'-25 | Pt | 1 | 4' | Ph | H | H | $NO_2$ | H | $^tC_4H_9$ | H | H | H | H | pic | |
| 4'-25X | Pt | 1 | 4' | Ph | H | H | $NO_2$ | H | $^tC_4H_9$ | H | H | H | H | acac | |
| 4'-25Y | Pt | 0 | 4' | Ph | H | H | $NO_2$ | H | $^tC_4H_9$ | H | H | H | H | — | — |
| 4'-26 | Pt | 1 | 4' | Ph | F | H | $NO_2$ | H | $CH_3$ | H | H | H | H | pic | |
| 4'-26X | Pt | 1 | 4' | Ph | F | H | $NO_2$ | H | $CH_3$ | H | H | H | H | acac | |
| 4'-26Y | Pt | 0 | 4' | Ph | F | H | $NO_2$ | H | $CH_3$ | H | H | H | H | — | — |
| 4'-27 | Pt | 1 | 4' | Ph | F | H | $NO_2$ | F | $CH_3$ | H | H | H | H | pic | |
| 4'-27X | Pt | 1 | 4' | Ph | F | H | $NO_2$ | F | $CH_3$ | H | H | H | H | acac | |
| 4'-27Y | Pt | 0 | 4' | Ph | F | H | $NO_2$ | F | $CH_3$ | H | H | H | H | — | — |
| 4'-28 | Pt | 1 | 4' | Ph | H | $NO_2$ | H | $NO_2$ | $CH_3$ | H | H | H | H | pic | |
| 4'-28X | Pt | 1 | 4' | Ph | H | $NO_2$ | H | $NO_2$ | $CH_3$ | H | H | H | H | acac | |
| 4'-28Y | Pt | 0 | 4' | Ph | H | $NO_2$ | H | $NO_2$ | $CH_3$ | H | H | H | H | — | — |
| 4'-29 | Pt | 1 | 4' | Ph | H | $NO_2$ | H | $NO_2$ | $^tC_4H_9$ | H | H | H | H | pic | |
| 4'-29X | Pt | 1 | 4' | Ph | H | $NO_2$ | H | $NO_2$ | $^tC_4H_9$ | H | H | H | H | acac | |
| 4'-29Y | Pt | 0 | 4' | Ph | H | $NO_2$ | H | $NO_2$ | $^tC_4H_9$ | H | H | H | H | — | — |
| 4'-30 | Pt | 1 | 4' | Ph | $NO_2$ | H | H | $NO_2$ | $CH_3$ | H | H | H | H | pic | |
| 4'-30X | Pt | 1 | 4' | Ph | $NO_2$ | H | H | $NO_2$ | $CH_3$ | H | H | H | H | acac | |
| 4'-30Y | Pt | 0 | 4' | Ph | $NO_2$ | H | H | $NO_2$ | $CH_3$ | H | H | H | H | — | — |
| 4'-31 | Pt | 1 | 4' | Ph | $NO_2$ | H | H | $NO_2$ | $^tC_4H_9$ | H | H | H | H | pic | |
| 4'-31X | Pt | 1 | 4' | Ph | $NO_2$ | H | H | $NO_2$ | $^tC_4H_9$ | H | H | H | H | acac | |
| 4'-31Y | Pt | 0 | 4' | Ph | $NO_2$ | H | H | $NO_2$ | $^tC_4H_9$ | H | H | H | H | — | — |
| 4'-32 | Pt | 1 | 4' | Ph | H | H | $CF_3$ | H | $CH_3$ | H | H | H | H | pic | |
| 4'-32X | Pt | 1 | 4' | Ph | H | H | $CF_3$ | H | $CH_3$ | H | H | H | H | acac | |
| 4'-32Y | Pt | 0 | 4' | Ph | H | H | $CF_3$ | H | $CH_3$ | H | H | H | H | — | — |
| 4'-33 | Pt | 1 | 4' | Ph | H | H | $CF_3$ | H | $^tC_4H_9$ | H | H | H | H | pic | |
| 4'-33X | Pt | 1 | 4' | Ph | H | H | $CF_3$ | H | $^tC_4H_9$ | H | H | H | H | acac | |
| 4'-33Y | Pt | 0 | 4' | Ph | H | H | $CF_3$ | H | $^tC_4H_9$ | H | H | H | H | — | — |
| 4'-34 | Pt | 1 | 4' | Ph | H | Cl | $CF_3$ | H | $CH_3$ | H | H | H | H | pic | |
| 4'-34X | Pt | 1 | 4' | Ph | H | Cl | $CF_3$ | H | $CH_3$ | H | H | H | H | acac | |
| 4'-34Y | Pt | 0 | 4' | Ph | H | Cl | $CF_3$ | H | $CH_3$ | H | H | H | H | — | — |
| 4'-35 | Pt | 1 | 4' | Ph | H | Cl | $CF_3$ | H | $^tC_4H_9$ | H | H | H | H | pic | |
| 4'-35X | Pt | 1 | 4' | Ph | H | Cl | $CF_3$ | H | $^tC_4H_9$ | H | H | H | H | acac | |
| 4'-35Y | Pt | 0 | 4' | Ph | H | Cl | $CF_3$ | H | $^tC_4H_9$ | H | H | H | H | — | — |
| 4'-36 | Pt | 1 | 4' | Ph | H | $NO_2$ | H | H | $CH_3$ | H | H | H | H | pic | |
| 4'-36X | Pt | 1 | 4' | Ph | H | $NO_2$ | H | H | $CH_3$ | H | H | H | H | acac | |
| 4'-36Y | Pt | 0 | 4' | Ph | H | $NO_2$ | H | H | $CH_3$ | H | H | H | H | — | — |
| 4'-37 | Pt | 1 | 4' | Ph | H | $CF_3$ | H | H | $CH_3$ | H | H | H | H | pic | |
| 4'-37X | Pt | 1 | 4' | Ph | H | $CF_3$ | H | H | $CH_3$ | H | H | H | H | acac | |
| 4'-37Y | Pt | 0 | 4' | Ph | H | $CF_3$ | H | H | $CH_3$ | H | H | H | H | — | — |
| 4'-38 | Pt | 1 | 4' | Ph | H | H | $NO_2$ | H | $CH_3$ | $CH_3$ | H | H | H | pic | |
| 4'-38X | Pt | 1 | 4' | Ph | H | H | $NO_2$ | H | $CH_3$ | $CH_3$ | H | H | H | acac | |
| 4'-38Y | Pt | 0 | 4' | Ph | H | H | $NO_2$ | H | $CH_3$ | $CH_3$ | H | H | H | — | — |
| 4'-39 | Pt | 1 | 4' | Ph | H | $NO_2$ | H | $CH_3$ | $^tC_4H_9$ | H | H | H | H | pic | |
| 4'-39X | Pt | 1 | 4' | Ph | H | $NO_2$ | H | $CH_3$ | $^tC_4H_9$ | H | H | H | H | acac | |

TABLE 32-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-39Y | Pt | 0 | 4' | Ph | H | NO₂ | H | CH₃ | ᵗC₄H₉ | H | H | H | H | — | — |
| 4'-40 | Pt | 1 | 4' | Ph | H | NO₂ | H | ᵗC₄H₉ | CH₃ | H | H | H | H | | pic |
| 4'-40X | Pt | 1 | 4' | Ph | H | NO₂ | H | ᵗC₄H₉ | CH₃ | H | H | H | H | | acac |
| 4'-40Y | Pt | 0 | 4' | Ph | H | NO₂ | H | ᵗC₄H₉ | CH₃ | H | H | H | H | — | — |
| 4'-41 | Pt | 1 | 4' | Ph | H | NO₂ | H | ᵗC₄H₉ | ᵗC₄H₉ | H | H | H | H | | pic |
| 4'-41X | Pt | 1 | 4' | Ph | H | NO₂ | H | ᵗC₄H₉ | ᵗC₄H₉ | H | H | H | H | | acac |
| 4'-41Y | Pt | 0 | 4' | Ph | H | NO₂ | H | ᵗC₄H₉ | ᵗC₄H₉ | H | H | H | H | — | — |
| 4'-42 | Pt | 1 | 4' | Ph | H | H | CH₃O | H | CH₃ | H | H | H | H | | pic |
| 4'-42X | Pt | 1 | 4' | Ph | H | H | CH₃O | H | CH₃ | H | H | H | H | | acac |
| 4'-42Y | Pt | 0 | 4' | Ph | H | H | CH₃O | H | CH₃ | H | H | H | H | — | — |
| 4'-43 | Pt | 1 | 4' | Ph | H | CH₃O | H | H | CH₃ | H | H | H | H | | pic |
| 4'-43X | Pt | 1 | 4' | Ph | H | CH₃O | H | H | CH₃ | H | H | H | H | | acac |
| 4'-43Y | Pt | 0 | 4' | Ph | H | CH₃O | H | H | CH₃ | H | H | H | H | — | — |
| 4'-44 | Pt | 1 | 4' | Ph | H | CH₃O | H | CH₃ | CH₃ | H | H | H | H | | pic |
| 4'-44X | Pt | 1 | 4' | Ph | H | CH₃O | H | CH₃ | CH₃ | H | H | H | H | | acac |
| 4'-44Y | Pt | 0 | 4' | Ph | H | CH₃O | H | CH₃ | CH₃ | H | H | H | H | — | — |
| 4'-45 | Pt | 1 | 4' | Ph | H | CH₃O | H | ᵗC₄H₉ | CH₃ | H | H | H | H | | pic |
| 4'-45X | Pt | 1 | 4' | Ph | H | CH₃O | H | ᵗC₄H₉ | CH₃ | H | H | H | H | | acac |
| 4'-45Y | Pt | 0 | 4' | Ph | H | CH₃O | H | ᵗC₄H₉ | CH₃ | H | H | H | H | — | — |
| 4'-46 | Pt | 1 | 4' | Ph | H | Si(CH₃)₃ | H | H | CH₃ | H | H | H | H | | pic |
| 4'-46X | Pt | 1 | 4' | Ph | H | Si(CH₃)₃ | H | H | CH₃ | H | H | H | H | | acac |
| 4'-46Y | Pt | 0 | 4' | Ph | H | Si(CH₃)₃ | H | H | CH₃ | H | H | H | H | — | — |
| 4'-47 | Pt | 1 | 4' | Ph | H | Si(CH₃)₃ | H | H | ᵗC₄H₉ | H | H | H | H | | pic |
| 4'-47X | Pt | 1 | 4' | Ph | H | Si(CH₃)₃ | H | H | ᵗC₄H₉ | H | H | H | H | | acac |
| 4'-47Y | Pt | 0 | 4' | Ph | H | Si(CH₃)₃ | H | H | ᵗC₄H₉ | H | H | H | H | — | — |
| 4'-48 | Pt | 1 | 4' | Ph | H | H | Si(CH₃)₃ | H | CH₃ | H | H | H | H | | pic |
| 4'-48X | Pt | 1 | 4' | Ph | H | H | Si(CH₃)₃ | H | CH₃ | H | H | H | H | | acac |
| 4'-48Y | Pt | 0 | 4' | Ph | H | H | Si(CH₃)₃ | H | CH₃ | H | H | H | H | — | — |
| 4'-49 | Pt | 1 | 4' | Ph | H | H | H | Si(CH₃)₃ | CH₃ | H | H | H | H | | pic |
| 4'-49X | Pt | 1 | 4' | Ph | H | H | H | Si(CH₃)₃ | CH₃ | H | H | H | H | | acac |
| 4'-49Y | Pt | 0 | 4' | Ph | H | H | H | Si(CH₃)₃ | CH₃ | H | H | H | H | — | — |
| 4'-50 | Pt | 1 | 4' | Ph | H | F | H | Si(CH₃)₃ | CH₃ | H | H | H | H | | pic |
| 4'-50X | Pt | 1 | 4' | Ph | H | F | H | Si(CH₃)₃ | CH₃ | H | H | H | H | | acac |
| 4'-50Y | Pt | 0 | 4' | Ph | H | F | H | Si(CH₃)₃ | CH₃ | H | H | H | H | — | — |
| 4'-51 | Pt | 1 | 4' | Ph | H | CF₃ | H | Si(CH₃)₃ | CH₃ | H | H | H | H | | pic |
| 4'-51X | Pt | 1 | 4' | Ph | H | CF₃ | H | Si(CH₃)₃ | CH₃ | H | H | H | H | | acac |
| 4'-51Y | Pt | 0 | 4' | Ph | H | CF₃ | H | Si(CH₃)₃ | CH₃ | H | H | H | H | — | — |
| 4'-52 | Pt | 1 | 4' | Ph | H | CF₃ | H | Si(CH₃)₃ | ᵗC₄H₉ | H | H | H | H | | pic |
| 4'-52X | Pt | 1 | 4' | Ph | H | CF₃ | H | Si(CH₃)₃ | ᵗC₄H₉ | H | H | H | H | | acac |
| 4'-52Y | Pt | 0 | 4' | Ph | H | CF₃ | H | Si(CH₃)₃ | ᵗC₄H₉ | H | H | H | H | — | — |
| 4'-53 | Pt | 1 | 4' | Ph | H | Si(CH₃)₃ | H | F | CH₃ | H | H | H | H | | pic |
| 4'-53X | Pt | 1 | 4' | Ph | H | Si(CH₃)₃ | H | F | CH₃ | H | H | H | H | | acac |
| 4'-53Y | Pt | 0 | 4' | Ph | H | Si(CH₃)₃ | H | F | CH₃ | H | H | H | H | — | — |
| 4'-54 | Pt | 1 | 4' | Ph | H | Si(CH₃)₃ | H | F | ᵗC₄H₉ | H | H | H | H | | pic |
| 4'-54X | Pt | 1 | 4' | Ph | H | Si(CH₃)₃ | H | F | ᵗC₄H₉ | H | H | H | H | | acac |
| 4'-54Y | Pt | 0 | 4' | Ph | H | Si(CH₃)₃ | H | F | ᵗC₄H₉ | H | H | H | H | — | — |
| 4'-55 | Pt | 1 | 4' | Ph | H | Si(CH₃)₃ | H | CF₃ | CH₃ | H | H | H | H | | pic |
| 4'-55X | Pt | 1 | 4' | Ph | H | Si(CH₃)₃ | H | CF₃ | CH₃ | H | H | H | H | | acac |
| 4'-55Y | Pt | 0 | 4' | Ph | H | Si(CH₃)₃ | H | CF₃ | CH₃ | H | H | H | H | — | — |
| 4'-56 | Pt | 1 | 4' | Ph | H | Si(CH₃)₃ | H | CF₃ | ᵗC₄H₉ | H | H | H | H | | pic |
| 4'-56X | Pt | 1 | 4' | Ph | H | Si(CH₃)₃ | H | CF₃ | ᵗC₄H₉ | H | H | H | H | | acac |
| 4'-56Y | Pt | 0 | 4' | Ph | H | Si(CH₃)₃ | H | CF₃ | ᵗC₄H₉ | H | H | H | H | — | — |
| 4'-57 | Pt | 1 | 4' | Ph | Si(CH₃)₃ | H | Si(CH₃)₃ | H | CH₃ | H | H | H | H | | pic |
| 4'-57X | Pt | 1 | 4' | Ph | Si(CH₃)₃ | H | Si(CH₃)₃ | H | CH₃ | H | H | H | H | | acac |
| 4'-57Y | Pt | 0 | 4' | Ph | Si(CH₃)₃ | H | Si(CH₃)₃ | H | CH₃ | H | H | H | H | — | — |
| 4'-58 | Pt | 1 | 4' | Ph | Si(CH₃)₃ | H | Si(CH₃)₃ | H | ᵗC₄H₉ | H | H | H | H | | pic |
| 4'-58X | Pt | 1 | 4' | Ph | Si(CH₃)₃ | H | Si(CH₃)₃ | H | ᵗC₄H₉ | H | H | H | H | | acac |
| 4'-58Y | Pt | 0 | 4' | Ph | Si(CH₃)₃ | H | Si(CH₃)₃ | H | ᵗC₄H₉ | H | H | H | H | — | — |
| 4'-59 | Pt | 1 | 4' | Ph | H | H | H | COCH₃ | CH₃ | H | H | H | H | | pic |
| 4'-59X | Pt | 1 | 4' | Ph | H | H | H | COCH₃ | CH₃ | H | H | H | H | | acac |
| 4'-59Y | Pt | 0 | 4' | Ph | H | H | H | COCH₃ | CH₃ | H | H | H | H | — | — |
| 4'-60 | Pt | 1 | 4' | Ph | H | H | COCH₃ | H | CH₃ | H | H | H | H | | pic |
| 4'-60X | Pt | 1 | 4' | Ph | H | H | COCH₃ | H | CH₃ | H | H | H | H | | acac |
| 4'-60Y | Pt | 0 | 4' | Ph | H | H | COCH₃ | H | CH₃ | H | H | H | H | — | — |
| 4'-61 | Pt | 1 | 4' | Ph | H | COCH₃ | H | H | CH₃ | H | H | H | H | | pic |
| 4'-61X | Pt | 1 | 4' | Ph | H | COCH₃ | H | H | CH₃ | H | H | H | H | | acac |
| 4'-61Y | Pt | 0 | 4' | Ph | H | COCH₃ | H | H | CH₃ | H | H | H | H | — | — |
| 4'-62 | Pt | 1 | 4' | Ph | H | H | BL | | CH₃ | H | H | H | H | | pic |
| 4'-62X | Pt | 1 | 4' | Ph | H | H | BL | | CH₃ | H | H | H | H | | acac |
| 4'-62Y | Pt | 0 | 4' | Ph | H | H | BL | | CH₃ | H | H | H | H | — | — |
| 4'-63 | Pt | 1 | 4' | Ph | H | H | BL | | ᵗC₄H₉ | H | H | H | H | | pic |
| 4'-63X | Pt | 1 | 4' | Ph | H | H | BL | | ᵗC₄H₉ | H | H | H | H | | acac |
| 4'-63Y | Pt | 0 | 4' | Ph | H | H | BL | | ᵗC₄H₉ | H | H | H | H | — | — |
| 4'-64 | Pt | 1 | 4' | Ph | H | BL | | H | CH₃ | H | H | H | H | | pic |
| 4'-64X | Pt | 1 | 4' | Ph | H | BL | | H | CH₃ | H | H | H | H | | acac |
| 4'-64Y | Pt | 0 | 4' | Ph | H | BL | | H | CH₃ | H | H | H | H | — | — |
| 4'-65 | Pt | 1 | 4' | Ph | H | BL | | H | ᵗC₄H₉ | H | H | H | H | | pic |

TABLE 32-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-65X | Pt | 1 | 4' | Ph | H | | BL | H | $^tC_4H_9$ | H | H | H | H | acac | |
| 4'-65Y | Pt | 0 | 4' | Ph | H | | BL | H | $^tC_4H_9$ | H | H | H | H | — | — |
| 4'-66 | Pt | 1 | 4' | Ph | H | H | | PL | $CH_3$ | H | H | H | H | pic | |
| 4'-66X | Pt | 1 | 4' | Ph | H | H | | PL | $CH_3$ | H | H | H | H | acac | |
| 4'-66Y | Pt | 0 | 4' | Ph | H | H | | PL | $CH_3$ | H | H | H | H | — | — |
| 4'-67 | Pt | 1 | 4' | Ph | H | H | | PL | $^tC_4H_9$ | H | H | H | H | pic | |
| 4'-67X | Pt | 1 | 4' | Ph | H | H | | PL | $^tC_4H_9$ | H | H | H | H | acac | |
| 4'-67Y | Pt | 0 | 4' | Ph | H | H | | PL | $^tC_4H_9$ | H | H | H | H | — | — |
| 4'-68 | Pt | 1 | 4' | Ph | H | | PL | H | $CH_3$ | H | H | H | H | pic | |
| 4'-68X | Pt | 1 | 4' | Ph | H | | PL | H | $CH_3$ | H | H | H | H | acac | |
| 4'-68Y | Pt | 0 | 4' | Ph | H | | PL | H | $CH_3$ | H | H | H | H | — | — |
| 4'-69 | Pt | 1 | 4' | Ph | H | | PL | H | $^tC_4H_9$ | H | H | H | H | pic | |
| 4'-69X | Pt | 1 | 4' | Ph | H | | PL | H | $^tC_4H_9$ | H | H | H | H | acac | |
| 4'-69Y | Pt | 0 | 4' | Ph | H | | PL | H | $^tC_4H_9$ | H | H | H | H | — | — |
| 4'-70 | Pt | 1 | 4' | Ph | H | H | | MEE1 | $CH_3$ | H | H | H | H | pic | |
| 4'-70X | Pt | 1 | 4' | Ph | H | H | | MEE1 | $CH_3$ | H | H | H | H | acac | |
| 4'-70Y | Pt | 0 | 4' | Ph | H | H | | MEE1 | $CH_3$ | H | H | H | H | — | — |
| 4'-71 | Pt | 1 | 4' | Ph | H | | MEE1 | H | $CH_3$ | H | H | H | H | pic | |
| 4'-71X | Pt | 1 | 4' | Ph | H | | MEE1 | H | $CH_3$ | H | H | H | H | acac | |
| 4'-71Y | Pt | 0 | 4' | Ph | H | | MEE1 | H | $CH_3$ | H | H | H | H | — | — |
| 4'-72 | Pt | 1 | 4' | Ph | H | H | | MEE2 | $CH_3$ | H | H | H | H | pic | |
| 4'-72X | Pt | 1 | 4' | Ph | H | H | | MEE2 | $CH_3$ | H | H | H | H | acac | |
| 4'-72Y | Pt | 0 | 4' | Ph | H | H | | MEE2 | $CH_3$ | H | H | H | H | — | — |
| 4'-73 | Pt | 1 | 4' | Ph | H | | MEE2 | H | $CH_3$ | H | H | H | H | pic | |
| 4'-73X | Pt | 1 | 4' | Ph | H | | MEE2 | H | $CH_3$ | H | H | H | H | acac | |
| 4'-73Y | Pt | 0 | 4' | Ph | H | | MEE2 | H | $CH_3$ | H | H | H | H | — | — |
| 4'-74 | Pt | 1 | 4' | Ph | H | H | | PA1 | $CH_3$ | H | H | H | H | pic | |
| 4'-74X | Pt | 1 | 4' | Ph | H | H | | PA1 | $CH_3$ | H | H | H | H | acac | |
| 4'-74Y | Pt | 0 | 4' | Ph | H | H | | PA1 | $CH_3$ | H | H | H | H | — | — |
| 4'-75 | Pt | 1 | 4' | Ph | H | | PA1 | H | $CH_3$ | H | H | H | H | pic | |
| 4'-75X | Pt | 1 | 4' | Ph | H | | PA1 | H | $CH_3$ | H | H | H | H | acac | |
| 4'-75Y | Pt | 0 | 4' | Ph | H | | PA1 | H | $CH_3$ | H | H | H | H | — | — |
| 4'-76 | Pt | 1 | 4' | Ph | H | H | | PA2 | $CH_3$ | H | H | H | H | pic | |
| 4'-76X | Pt | 1 | 4' | Ph | H | H | | PA2 | $CH_3$ | H | H | H | H | acac | |
| 4'-76Y | Pt | 0 | 4' | Ph | H | H | | PA2 | $CH_3$ | H | H | H | H | — | — |
| 4'-77 | Pt | 1 | 4' | Ph | H | | PA2 | H | $CH_3$ | H | H | H | H | pic | |
| 4'-77X | Pt | 1 | 4' | Ph | H | | PA2 | H | $CH_3$ | H | H | H | H | acac | |
| 4'-77Y | Pt | 0 | 4' | Ph | H | | PA2 | H | $CH_3$ | H | H | H | H | — | — |
| 4'-78 | Pt | 1 | 4' | Ph | H | H | | EA1 | $CH_3$ | H | H | H | H | pic | |
| 4'-78X | Pt | 1 | 4' | Ph | H | H | | EA1 | $CH_3$ | H | H | H | H | acac | |
| 4'-78Y | Pt | 0 | 4' | Ph | H | H | | EA1 | $CH_3$ | H | H | H | H | — | — |
| 4'-79 | Pt | 1 | 4' | Ph | H | | EA2 | H | $CH_3$ | H | H | H | H | pic | |
| 4'-79X | Pt | 1 | 4' | Ph | H | | EA2 | H | $CH_3$ | H | H | H | H | acac | |
| 4'-79Y | Pt | 0 | 4' | Ph | H | | EA2 | H | $CH_3$ | H | H | H | H | — | — |
| 4'-80 | Pt | 1 | 4' | Ph | H | H | | ME | $CH_3$ | H | H | H | H | pic | |
| 4'-80X | Pt | 1 | 4' | Ph | H | H | | ME | $CH_3$ | H | H | H | H | acac | |
| 4'-80Y | Pt | 0 | 4' | Ph | H | H | | ME | $CH_3$ | H | H | H | H | — | — |
| 4'-81 | Pt | 1 | 4' | Ph | H | | ME | H | $CH_3$ | H | H | H | H | pic | |
| 4'-81X | Pt | 1 | 4' | Ph | H | | ME | H | $CH_3$ | H | H | H | H | acac | |
| 4'-81Y | Pt | 0 | 4' | Ph | H | | ME | H | $CH_3$ | H | H | H | H | — | — |
| 4'-82 | Pt | 1 | 4' | Ph | H | H | | AT | $CH_3$ | H | H | H | H | pic | |
| 4'-82X | Pt | 1 | 4' | Ph | H | H | | AT | $CH_3$ | H | H | H | H | acac | |
| 4'-82Y | Pt | 0 | 4' | Ph | H | H | | AT | $CH_3$ | H | H | H | H | — | — |
| 4'-83 | Pt | 1 | 4' | Ph | H | | AT | H | $CH_3$ | H | H | H | H | pic | |
| 4'-83X | Pt | 1 | 4' | Ph | H | | AT | H | $CH_3$ | H | H | H | H | acac | |
| 4'-83Y | Pt | 0 | 4' | Ph | H | | AT | H | $CH_3$ | H | H | H | H | — | — |
| 4'-84 | Pt | 1 | 4' | Ph | H | H | | MES1 | $CH_3$ | H | H | H | H | pic | |
| 4'-84X | Pt | 1 | 4' | Ph | H | H | | MES1 | $CH_3$ | H | H | H | H | acac | |
| 4'-84Y | Pt | 0 | 4' | Ph | H | H | | MES1 | $CH_3$ | H | H | H | H | — | — |
| 4'-85 | Pt | 1 | 4' | Ph | H | | MES1 | H | $CH_3$ | H | H | H | H | pic | |
| 4'-85X | Pt | 1 | 4' | Ph | H | | MES1 | H | $CH_3$ | H | H | H | H | acac | |
| 4'-85Y | Pt | 0 | 4' | Ph | H | | MES1 | H | $CH_3$ | H | H | H | H | — | — |
| 4'-86 | Pt | 1 | 4' | Ph | H | H | | MES2 | $CH_3$ | H | H | H | H | pic | |
| 4'-86X | Pt | 1 | 4' | Ph | H | H | | MES2 | $CH_3$ | H | H | H | H | acac | |
| 4'-86Y | Pt | 0 | 4' | Ph | H | H | | MES2 | $CH_3$ | H | H | H | H | — | — |
| 4'-87 | Pt | 1 | 4' | Ph | H | | MES2 | H | $CH_3$ | H | H | H | H | pic | |
| 4'-87X | Pt | 1 | 4' | Ph | H | | MES2 | H | $CH_3$ | H | H | H | H | acac | |
| 4'-87Y | Pt | 0 | 4' | Ph | H | | MES2 | H | $CH_3$ | H | H | H | H | — | — |
| 4'-88 | Pt | 1 | 4' | Ph | H | H | | PS1 | $CH_3$ | H | H | H | H | pic | |
| 4'-88X | Pt | 1 | 4' | Ph | H | H | | PS1 | $CH_3$ | H | H | H | H | acac | |
| 4'-88Y | Pt | 0 | 4' | Ph | H | H | | PS1 | $CH_3$ | H | H | H | H | — | — |
| 4'-89 | Pt | 1 | 4' | Ph | H | | PS1 | H | $CH_3$ | H | H | H | H | pic | |
| 4'-89X | Pt | 1 | 4' | Ph | H | | PS1 | H | $CH_3$ | H | H | H | H | acac | |
| 4'-89Y | Pt | 0 | 4' | Ph | H | | PS1 | H | $CH_3$ | H | H | H | H | — | — |
| 4'-90 | Pt | 1 | 4' | Ph | H | H | | PS2 | $CH_3$ | H | H | H | H | pic | |
| 4'-90X | Pt | 1 | 4' | Ph | H | H | | PS2 | $CH_3$ | H | H | H | H | acac | |
| 4'-90Y | Pt | 0 | 4' | Ph | H | H | | PS2 | $CH_3$ | H | H | H | H | — | — |

TABLE 32-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-91 | Pt | 1 | 4' | Ph | H | | PS2 | H | CH₃ | H | H | H | H | pic | |
| 4'-91X | Pt | 1 | 4' | Ph | H | | PS2 | H | CH₃ | H | H | H | H | acac | |
| 4'-91Y | Pt | 0 | 4' | Ph | H | | PS2 | H | CH₃ | H | H | H | H | — | — |
| 4'-92 | Pt | 1 | 4' | Ph | H | H | | BAL1 | CH₃ | H | H | H | H | pic | |
| 4'-92X | Pt | 1 | 4' | Ph | H | H | | BAL1 | CH₃ | H | H | H | H | acac | |
| 4'-92Y | Pt | 0 | 4' | Ph | H | H | | BAL1 | CH₃ | H | H | H | H | — | — |
| 4'-93 | Pt | 1 | 4' | Ph | H | | BAL1 | H | CH₃ | H | H | H | H | pic | |
| 4'-93X | Pt | 1 | 4' | Ph | H | | BAL1 | H | CH₃ | H | H | H | H | acac | |
| 4'-93Y | Pt | 0 | 4' | Ph | H | | BAL1 | H | CH₃ | H | H | H | H | — | — |
| 4'-94 | Pt | 1 | 4' | Ph | H | H | | BAL2 | CH₃ | H | H | H | H | pic | |
| 4'-94X | Pt | 1 | 4' | Ph | H | H | | BAL2 | CH₃ | H | H | H | H | acac | |
| 4'-94Y | Pt | 0 | 4' | Ph | H | H | | BAL2 | CH₃ | H | H | H | H | — | — |
| 4'-95 | Pt | 1 | 4' | Ph | H | | BAL2 | H | CH₃ | H | H | H | H | pic | |
| 4'-95X | Pt | 1 | 4' | Ph | H | | BAL2 | H | CH₃ | H | H | H | H | acac | |
| 4'-95Y | Pt | 0 | 4' | Ph | H | | BAL2 | H | CH₃ | H | H | H | H | — | — |
| 4'-96 | Pt | 1 | 4' | Ph | H | H | | MEK1 | CH₃ | H | H | H | H | pic | |
| 4'-96X | Pt | 1 | 4' | Ph | H | H | | MEK1 | CH₃ | H | H | H | H | acac | |
| 4'-96Y | Pt | 0 | 4' | Ph | H | H | | MEK1 | CH₃ | H | H | H | H | — | — |
| 4'-97 | Pt | 1 | 4' | Ph | H | | MEK1 | H | CH₃ | H | H | H | H | pic | |
| 4'-97X | Pt | 1 | 4' | Ph | H | | MEK1 | H | CH₃ | H | H | H | H | acac | |
| 4'-97Y | Pt | 0 | 4' | Ph | H | | MEK1 | H | CH₃ | H | H | H | H | — | — |
| 4'-98 | Pt | 1 | 4' | Ph | H | H | | MEK2 | CH₃ | H | H | H | H | pic | |
| 4'-98X | Pt | 1 | 4' | Ph | H | H | | MEK2 | CH₃ | H | H | H | H | acac | |
| 4'-98Y | Pt | 0 | 4' | Ph | H | H | | MEK2 | CH₃ | H | H | H | H | — | — |
| 4'-99 | Pt | 1 | 4' | Ph | H | | MEK2 | H | CH₃ | H | H | H | H | pic | |
| 4'-99X | Pt | 1 | 4' | Ph | H | | MEK2 | H | CH₃ | H | H | H | H | acac | |
| 4'-99Y | Pt | 0 | 4' | Ph | H | | MEK2 | H | CH₃ | H | H | H | H | — | — |
| 4'-100 | Pt | 1 | 4' | Ph | H | H | | PAL1 | CH₃ | H | H | H | H | pic | |
| 4'-100X | Pt | 1 | 4' | Ph | H | H | | PAL1 | CH₃ | H | H | H | H | acac | |
| 4'-100Y | Pt | 0 | 4' | Ph | H | H | | PAL1 | CH₃ | H | H | H | H | — | — |
| 4'-101 | Pt | 1 | 4' | Ph | H | | PAL1 | H | CH₃ | H | H | H | H | pic | |
| 4'-101X | Pt | 1 | 4' | Ph | H | | PAL1 | H | CH₃ | H | H | H | H | acac | |
| 4'-101Y | Pt | 0 | 4' | Ph | H | | PAL1 | H | CH₃ | H | H | H | H | — | — |
| 4'-102 | Pt | 1 | 4' | Ph | H | H | | PAL2 | CH₃ | H | H | H | H | pic | |
| 4'-102X | Pt | 1 | 4' | Ph | H | H | | PAL2 | CH₃ | H | H | H | H | acac | |
| 4'-102Y | Pt | 0 | 4' | Ph | H | H | | PAL2 | CH₃ | H | H | H | H | — | — |
| 4'-103 | Pt | 1 | 4' | Ph | H | | PAL2 | H | CH₃ | H | H | H | H | pic | |
| 4'-103X | Pt | 1 | 4' | Ph | H | | PAL2 | H | CH₃ | H | H | H | H | acac | |
| 4'-103Y | Pt | 0 | 4' | Ph | H | | PAL2 | H | CH₃ | H | H | H | H | — | — |
| 4'-104 | Pt | 1 | 4' | Ph | H | H | | MMK | CH₃ | H | H | H | H | pic | |
| 4'-104X | Pt | 1 | 4' | Ph | H | H | | MMK | CH₃ | H | H | H | H | acac | |
| 4'-104Y | Pt | 0 | 4' | Ph | H | H | | MMK | CH₃ | H | H | H | H | — | — |
| 4'-105 | Pt | 1 | 4' | Ph | H | | MMK | H | CH₃ | H | H | H | H | pic | |
| 4'-105X | Pt | 1 | 4' | Ph | H | | MMK | H | CH₃ | H | H | H | H | acac | |
| 4'-105Y | Pt | 0 | 4' | Ph | H | | MMK | H | CH₃ | H | H | H | H | — | — |
| 4'-106 | Pt | 1 | 4' | Ph | H | H | | EES1 | CH₃ | H | H | H | H | pic | |
| 4'-106X | Pt | 1 | 4' | Ph | H | H | | EES1 | CH₃ | H | H | H | H | acac | |
| 4'-106Y | Pt | 0 | 4' | Ph | H | H | | EES1 | CH₃ | H | H | H | H | — | — |
| 4'-107 | Pt | 1 | 4' | Ph | H | | EES2 | H | CH₃ | H | H | H | H | pic | |
| 4'-107X | Pt | 1 | 4' | Ph | H | | EES2 | H | CH₃ | H | H | H | H | acac | |
| 4'-107Y | Pt | 0 | 4' | Ph | H | | EES2 | H | CH₃ | H | H | H | H | — | — |
| 4'-108 | Pt | 1 | 4' | Ph | H | H | | PAE1 | CH₃ | H | H | H | H | pic | |
| 4'-108X | Pt | 1 | 4' | Ph | H | H | | PAE1 | CH₃ | H | H | H | H | acac | |
| 4'-108Y | Pt | 0 | 4' | Ph | H | H | | PAE1 | CH₃ | H | H | H | H | — | — |
| 4'-109 | Pt | 1 | 4' | Ph | H | | PAE2 | H | CH₃ | H | H | H | H | pic | |
| 4'-109X | Pt | 1 | 4' | Ph | H | | PAE2 | H | CH₃ | H | H | H | H | acac | |
| 4'-109Y | Pt | 0 | 4' | Ph | H | | PAE2 | H | CH₃ | H | H | H | H | — | — |
| 4'-110 | Pt | 1 | 4' | Ph | H | H | | AME1 | CH₃ | H | H | H | H | pic | |
| 4'-110X | Pt | 1 | 4' | Ph | H | H | | AME1 | CH₃ | H | H | H | H | acac | |
| 4'-110Y | Pt | 0 | 4' | Ph | H | H | | AME1 | CH₃ | H | H | H | H | — | — |
| 4'-111 | Pt | 1 | 4' | Ph | H | | AME1 | H | CH₃ | H | H | H | H | pic | |
| 4'-111X | Pt | 1 | 4' | Ph | H | | AME1 | H | CH₃ | H | H | H | H | acac | |
| 4'-111Y | Pt | 0 | 4' | Ph | H | | AME1 | H | CH₃ | H | H | H | H | — | — |
| 4'-112 | Pt | 1 | 4' | Ph | H | H | | AME2 | CH₃ | H | H | H | H | pic | |
| 4'-112X | Pt | 1 | 4' | Ph | H | H | | AME2 | CH₃ | H | H | H | H | acac | |
| 4'-112Y | Pt | 0 | 4' | Ph | H | H | | AME2 | CH₃ | H | H | H | H | — | — |
| 4'-113 | Pt | 1 | 4' | Ph | H | | AME2 | H | CH₃ | H | H | H | H | pic | |
| 4'-113X | Pt | 1 | 4' | Ph | H | | AME2 | H | CH₃ | H | H | H | H | acac | |
| 4'-113Y | Pt | 0 | 4' | Ph | H | | AME2 | H | CH₃ | H | H | H | H | — | — |
| 4'-114 | Pt | 1 | 4' | Ph | H | H | | EAE1 | CH₃ | H | H | H | H | pic | |
| 4'-114X | Pt | 1 | 4' | Ph | H | H | | EAE1 | CH₃ | H | H | H | H | acac | |
| 4'-114Y | Pt | 0 | 4' | Ph | H | H | | EAE1 | CH₃ | H | H | H | H | — | — |
| 4'-115 | Pt | 1 | 4' | Ph | H | | EAE1 | H | CH₃ | H | H | H | H | pic | |
| 4'-115X | Pt | 1 | 4' | Ph | H | | EAE1 | H | CH₃ | H | H | H | H | acac | |
| 4'-115Y | Pt | 0 | 4' | Ph | H | | EAE1 | H | CH₃ | H | H | H | H | — | — |
| 4'-116 | Pt | 1 | 4' | Ph | H | H | | EAE2 | CH₃ | H | H | H | H | pic | |
| 4'-116X | Pt | 1 | 4' | Ph | H | H | | EAE2 | CH₃ | H | H | H | H | acac | |

TABLE 32-continued

| No. | M | m | BSS | SS | G | $T^1$ | $T^2$ | $T^3$ | $T^4$ | $T^5$ | $T^6$ | $T^7$ | $T^8$ | $T^9$ | $L^1$ | $L^2$ |
|---|---|---|---|---|---|---|---|---|---|---|---|---|---|---|---|---|
| 4'-116Y | Pt | 0 | 4' | Ph | | H | H | | EAE2 | | $CH_3$ | H | H | H | H | — | — |
| 4'-117 | Pt | 1 | 4' | Ph | | H | | EAE2 | | H | $CH_3$ | H | H | H | H | pic | |
| 4'-117X | Pt | 1 | 4' | Ph | | H | | EAE2 | | H | $CH_3$ | H | H | H | H | acac | |
| 4'-117Y | Pt | 0 | 4' | Ph | | H | | EAE2 | | H | $CH_3$ | H | H | H | H | — | — |
| 4'-118 | Pt | 1 | 4' | Ph | | H | H | | AAE1 | | $CH_3$ | H | H | H | H | pic | |
| 4'-118X | Pt | 1 | 4' | Ph | | H | H | | AAE1 | | $CH_3$ | H | H | H | H | acac | |
| 4'-118Y | Pt | 0 | 4' | Ph | | H | H | | AAE1 | | $CH_3$ | H | H | H | H | — | — |
| 4'-119 | Pt | 1 | 4' | Ph | | H | | AAE1 | | H | $CH_3$ | H | H | H | H | pic | |
| 4'-119X | Pt | 1 | 4' | Ph | | H | | AAE1 | | H | $CH_3$ | H | H | H | H | acac | |
| 4'-119Y | Pt | 0 | 4' | Ph | | H | | AAE1 | | H | $CH_3$ | H | H | H | H | — | — |
| 4'-120 | Pt | 1 | 4' | Ph | | H | H | | AAE2 | | $CH_3$ | H | H | H | H | pic | |
| 4'-120X | Pt | 1 | 4' | Ph | | H | H | | AAE2 | | $CH_3$ | H | H | H | H | acac | |
| 4'-120Y | Pt | 0 | 4' | Ph | | H | H | | AAE2 | | $CH_3$ | H | H | H | H | — | — |
| 4'-121 | Pt | 1 | 4' | Ph | | H | | AAE2 | | H | $CH_3$ | H | H | H | H | pic | |
| 4'-121X | Pt | 1 | 4' | Ph | | H | | AAE2 | | H | $CH_3$ | H | H | H | H | acac | |
| 4'-121Y | Pt | 0 | 4' | Ph | | H | | AAE2 | | H | $CH_3$ | H | H | H | H | — | — |
| 4'-122 | Pt | 1 | 4' | Ph | | H | H | | PME1 | | $CH_3$ | H | H | H | H | pic | |
| 4'-122X | Pt | 1 | 4' | Ph | | H | H | | PME1 | | $CH_3$ | H | H | H | H | acac | |
| 4'-122Y | Pt | 0 | 4' | Ph | | H | H | | PME1 | | $CH_3$ | H | H | H | H | — | — |
| 4'-123 | Pt | 1 | 4' | Ph | | H | | PME1 | | H | $CH_3$ | H | H | H | H | pic | |
| 4'-123X | Pt | 1 | 4' | Ph | | H | | PME1 | | H | $CH_3$ | H | H | H | H | acac | |
| 4'-123Y | Pt | 0 | 4' | Ph | | H | | PME1 | | H | $CH_3$ | H | H | H | H | — | — |
| 4'-124 | Pt | 1 | 4' | Ph | | H | H | | PME2 | | $CH_3$ | H | H | H | H | pic | |
| 4'-124X | Pt | 1 | 4' | Ph | | H | H | | PME2 | | $CH_3$ | H | H | H | H | acac | |
| 4'-124Y | Pt | 0 | 4' | Ph | | H | H | | PME2 | | $CH_3$ | H | H | H | H | — | — |
| 4'-125 | Pt | 1 | 4' | Ph | | H | | PME2 | | H | $CH_3$ | H | H | H | H | pic | |
| 4'-125X | Pt | 1 | 4' | Ph | | H | | PME2 | | H | $CH_3$ | H | H | H | H | acac | |
| 4'-125Y | Pt | 0 | 4' | Ph | | H | | PME2 | | H | $CH_3$ | H | H | H | H | — | — |
| 4'-126 | Pt | 1 | 4' | Ph | | H | H | | MET1 | | $CH_3$ | H | H | H | H | pic | |
| 4'-126X | Pt | 1 | 4' | Ph | | H | H | | MET1 | | $CH_3$ | H | H | H | H | acac | |
| 4'-126Y | Pt | 0 | 4' | Ph | | H | H | | MET1 | | $CH_3$ | H | H | H | H | — | — |
| 4'-127 | Pt | 1 | 4' | Ph | | H | | MET1 | | H | $CH_3$ | H | H | H | H | pic | |
| 4'-127X | Pt | 1 | 4' | Ph | | H | | MET1 | | H | $CH_3$ | H | H | H | H | acac | |
| 4'-127Y | Pt | 0 | 4' | Ph | | H | | MET1 | | H | $CH_3$ | H | H | H | H | — | — |
| 4'-128 | Pt | 1 | 4' | Ph | | H | H | | MET2 | | $CH_3$ | H | H | H | H | pic | |
| 4'-128X | Pt | 1 | 4' | Ph | | H | H | | MET2 | | $CH_3$ | H | H | H | H | acac | |
| 4'-128Y | Pt | 0 | 4' | Ph | | H | H | | MET2 | | $CH_3$ | H | H | H | H | — | — |
| 4'-129 | Pt | 1 | 4' | Ph | | H | | MET2 | | H | $CH_3$ | H | H | H | H | pic | |
| 4'-129X | Pt | 1 | 4' | Ph | | H | | MET2 | | H | $CH_3$ | H | H | H | H | acac | |
| 4'-129Y | Pt | 0 | 4' | Ph | | H | | MET2 | | H | $CH_3$ | H | H | H | H | — | — |
| 4'-130 | Pt | 1 | 4' | Ph | | H | H | | EE1 | | $CH_3$ | H | H | H | H | pic | |
| 4'-130X | Pt | 1 | 4' | Ph | | H | H | | EE1 | | $CH_3$ | H | H | H | H | acac | |
| 4'-130Y | Pt | 0 | 4' | Ph | | H | H | | EE1 | | $CH_3$ | H | H | H | H | — | — |
| 4'-131 | Pt | 1 | 4' | Ph | | H | | EE1 | | H | $CH_3$ | H | H | H | H | pic | |
| 4'-131X | Pt | 1 | 4' | Ph | | H | | EE1 | | H | $CH_3$ | H | H | H | H | acac | |
| 4'-131Y | Pt | 0 | 4' | Ph | | H | | EE1 | | H | $CH_3$ | H | H | H | H | — | — |
| 4'-132 | Pt | 1 | 4' | Ph | | H | H | | EE2 | | $CH_3$ | H | H | H | H | pic | |
| 4'-132X | Pt | 1 | 4' | Ph | | H | H | | EE2 | | $CH_3$ | H | H | H | H | acac | |
| 4'-132Y | Pt | 0 | 4' | Ph | | H | H | | EE2 | | $CH_3$ | H | H | H | H | — | — |
| 4'-133 | Pt | 1 | 4' | Ph | | H | | EE2 | | H | $CH_3$ | H | H | H | H | pic | |
| 4'-133X | Pt | 1 | 4' | Ph | | H | | EE2 | | H | $CH_3$ | H | H | H | H | acac | |
| 4'-133Y | Pt | 0 | 4' | Ph | | H | | EE2 | | H | $CH_3$ | H | H | H | H | — | — |
| 4'-134 | Pt | 1 | 4' | Ph | | H | H | | MS1 | | $CH_3$ | H | H | H | H | pic | |
| 4'-134X | Pt | 1 | 4' | Ph | | H | H | | MS1 | | $CH_3$ | H | H | H | H | acac | |
| 4'-134Y | Pt | 0 | 4' | Ph | | H | H | | MS1 | | $CH_3$ | H | H | H | H | — | — |
| 4'-135 | Pt | 1 | 4' | Ph | | H | | MS1 | | H | $CH_3$ | H | H | H | H | pic | |
| 4'-135X | Pt | 1 | 4' | Ph | | H | | MS1 | | H | $CH_3$ | H | H | H | H | acac | |
| 4'-135Y | Pt | 0 | 4' | Ph | | H | | MS1 | | H | $CH_3$ | H | H | H | H | — | — |
| 4'-136 | Pt | 1 | 4' | Ph | | H | H | | MS2 | | $CH_3$ | H | H | H | H | pic | |
| 4'-136X | Pt | 1 | 4' | Ph | | H | H | | MS2 | | $CH_3$ | H | H | H | H | acac | |
| 4'-136Y | Pt | 0 | 4' | Ph | | H | H | | MS2 | | $CH_3$ | H | H | H | H | — | — |
| 4'-137 | Pt | 1 | 4' | Ph | | H | | MS2 | | H | $CH_3$ | H | H | H | H | pic | |
| 4'-137X | Pt | 1 | 4' | Ph | | H | | MS2 | | H | $CH_3$ | H | H | H | H | acac | |
| 4'-137Y | Pt | 0 | 4' | Ph | | H | | MS2 | | H | $CH_3$ | H | H | H | H | — | — |

TABLE 33

| No. | M | m | BSS | SS | G | $T^1$ | $T^2$ | $T^3$ | $T^4$ | $T^5$ | $T^6$ | $T^7$ | $L^1$ | $L^2$ |
|---|---|---|---|---|---|---|---|---|---|---|---|---|---|---|
| 5'-1 | Pt | 1 | 5' | Ph | | H | H | H | H | H | $CH_3$ | H | pic | |
| 5'-1X | Pt | 1 | 5' | Ph | | H | H | H | H | H | $CH_3$ | H | acac | |
| 5'-1Y | Pt | 0 | 5' | Ph | | H | H | H | H | H | $CH_3$ | H | — | — |
| 5'-2 | Pt | 1 | 5' | Ph | | H | H | H | H | H | $^tC_4H_9$ | H | pic | |
| 5'-2X | Pt | 1 | 5' | Ph | | H | H | H | H | H | $^tC_4H_9$ | H | acac | |

TABLE 33-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-2Y | Pt | 0 | 5' | Ph | H | H | H | H | H | $^tC_4H_9$ | H | — | — |
| 5'-3 | Pt | 1 | 5' | Ph | H | F | H | F | H | $CH_3$ | H | pic | |
| 5'-3X | Pt | 1 | 5' | Ph | H | F | H | F | H | $CH_3$ | H | acac | |
| 5'-3Y | Pt | 0 | 5' | Ph | H | F | H | F | H | $CH_3$ | H | — | — |
| 5'-4 | Pt | 1 | 5' | Ph | H | F | H | F | H | $^tC_4H_9$ | H | pic | |
| 5'-4X | Pt | 1 | 5' | Ph | H | F | H | F | H | $^tC_4H_9$ | H | acac | |
| 5'-4Y | Pt | 0 | 5' | Ph | H | F | H | F | H | $^tC_4H_9$ | H | — | — |
| 5'-5 | Pt | 1 | 5' | Ph | $CF_3$ | H | $CF_3$ | H | H | $CH_3$ | H | pic | |
| 5'-5X | Pt | 1 | 5' | Ph | $CF_3$ | H | $CF_3$ | H | H | $CH_3$ | H | acac | |
| 5'-5Y | Pt | 0 | 5' | Ph | $CF_3$ | H | $CF_3$ | H | H | $CH_3$ | H | — | — |
| 5'-6 | Pt | 1 | 5' | Ph | $CF_3$ | H | $CF_3$ | H | H | $^tC_4H_9$ | H | pic | |
| 5'-6X | Pt | 1 | 5' | Ph | $CF_3$ | H | $CF_3$ | H | H | $^tC_4H_9$ | H | acac | |
| 5'-6Y | Pt | 0 | 5' | Ph | $CF_3$ | H | $CF_3$ | H | H | $^tC_4H_9$ | H | — | — |
| 5'-7 | Pt | 1 | 5' | Ph | H | F | $CF_3$ | H | H | $CH_3$ | H | pic | |
| 5'-7X | Pt | 1 | 5' | Ph | H | F | $CF_3$ | H | H | $CH_3$ | H | acac | |
| 5'-7Y | Pt | 0 | 5' | Ph | H | F | $CF_3$ | H | H | $CH_3$ | H | — | — |
| 5'-8 | Pt | 1 | 5' | Ph | F | H | $CF_3$ | H | H | $CH_3$ | H | pic | |
| 5'-8X | Pt | 1 | 5' | Ph | F | H | $CF_3$ | H | H | $CH_3$ | H | acac | |
| 5'-8Y | Pt | 0 | 5' | Ph | F | H | $CF_3$ | H | H | $CH_3$ | H | — | — |
| 5'-9 | Pt | 1 | 5' | Ph | F | F | F | F | H | $CH_3$ | H | pic | |
| 5'-9X | Pt | 1 | 5' | Ph | F | F | F | F | H | $CH_3$ | H | acac | |
| 5'-9Y | Pt | 0 | 5' | Ph | F | F | F | F | H | $CH_3$ | H | — | — |
| 5'-10 | Pt | 1 | 5' | Ph | H | F | H | $CH_3$ | H | $CH_3$ | H | pic | |
| 5'-10X | Pt | 1 | 5' | Ph | H | F | H | $CH_3$ | H | $CH_3$ | H | acac | |
| 5'-10Y | Pt | 0 | 5' | Ph | H | F | H | $CH_3$ | H | $CH_3$ | H | — | — |
| 5'-11 | Pt | 1 | 5' | Ph | H | F | H | $CH_3$ | H | $^tC_4H_9$ | H | pic | |
| 5'-11X | Pt | 1 | 5' | Ph | H | F | H | $CH_3$ | H | $^tC_4H_9$ | H | acac | |
| 5'-11Y | Pt | 0 | 5' | Ph | H | F | H | $CH_3$ | H | $^tC_4H_9$ | H | — | — |
| 5'-12 | Pt | 1 | 5' | Ph | H | F | H | $^tC_4H_9$ | H | $CH_3$ | H | pic | |
| 5'-12X | Pt | 1 | 5' | Ph | H | F | H | $^tC_4H_9$ | H | $CH_3$ | H | acac | |
| 5'-12Y | Pt | 0 | 5' | Ph | H | F | H | $^tC_4H_9$ | H | $CH_3$ | H | — | — |
| 5'-13 | Pt | 1 | 5' | Ph | H | F | H | $^tC_4H_9$ | H | $^tC_4H_9$ | H | pic | |
| 5'-13X | Pt | 1 | 5' | Ph | H | F | H | $^tC_4H_9$ | H | $^tC_4H_9$ | H | acac | |
| 5'-13Y | Pt | 0 | 5' | Ph | H | F | H | $^tC_4H_9$ | H | $^tC_4H_9$ | H | — | — |
| 5'-14 | Pt | 1 | 5' | Ph | H | $CF_3$ | H | $CF_3$ | H | $CH_3$ | H | pic | |
| 5'-14X | Pt | 1 | 5' | Ph | H | $CF_3$ | H | $CF_3$ | H | $CH_3$ | H | acac | |
| 5'-14Y | Pt | 0 | 5' | Ph | H | $CF_3$ | H | $CF_3$ | H | $CH_3$ | H | — | — |
| 5'-15 | Pt | 1 | 5' | Ph | H | $CF_3$ | H | $CF_3$ | H | $^tC_4H_9$ | H | pic | |
| 5'-15X | Pt | 1 | 5' | Ph | H | $CF_3$ | H | $CF_3$ | H | $^tC_4H_9$ | H | acac | |
| 5'-15Y | Pt | 0 | 5' | Ph | H | $CF_3$ | H | $CF_3$ | H | $^tC_4H_9$ | H | — | — |
| 5'-16 | Pt | 1 | 5' | Ph | $CF_3$ | H | H | $^tC_4H_9$ | H | $CH_3$ | H | pic | |
| 5'-16X | Pt | 1 | 5' | Ph | $CF_3$ | H | H | $^tC_4H_9$ | H | $CH_3$ | H | acac | |
| 5'-16Y | Pt | 0 | 5' | Ph | $CF_3$ | H | H | $^tC_4H_9$ | H | $CH_3$ | H | — | — |
| 5'-17 | Pt | 1 | 5' | Ph | $CF_3$ | H | H | $^tC_4H_9$ | H | $^tC_4H_9$ | H | pic | |
| 5'-17X | Pt | 1 | 5' | Ph | $CF_3$ | H | H | $^tC_4H_9$ | H | $^tC_4H_9$ | H | acac | |
| 5'-17Y | Pt | 0 | 5' | Ph | $CF_3$ | H | H | $^tC_4H_9$ | H | $^tC_4H_9$ | H | — | — |
| 5'-18 | Pt | 1 | 5' | Ph | H | $CF_3$ | H | $^tC_4H_9$ | H | $CH_3$ | H | pic | |
| 5'-18X | Pt | 1 | 5' | Ph | H | $CF_3$ | H | $^tC_4H_9$ | H | $CH_3$ | H | acac | |
| 5'-18Y | Pt | 0 | 5' | Ph | H | $CF_3$ | H | $^tC_4H_9$ | H | $CH_3$ | H | — | — |
| 5'-19 | Pt | 1 | 5' | Ph | H | $CF_3$ | H | $^tC_4H_9$ | H | $^tC_4H_9$ | H | pic | |
| 5'-19X | Pt | 1 | 5' | Ph | H | $CF_3$ | H | $^tC_4H_9$ | H | $^tC_4H_9$ | H | acac | |
| 5'-19Y | Pt | 0 | 5' | Ph | H | $CF_3$ | H | $^tC_4H_9$ | H | $^tC_4H_9$ | H | — | — |
| 5'-20 | Pt | 1 | 5' | Ph | H | $CF_3$ | H | $CH_3$ | H | $CH_3$ | H | pic | |
| 5'-20X | Pt | 1 | 5' | Ph | H | $CF_3$ | H | $CH_3$ | H | $CH_3$ | H | acac | |
| 5'-20Y | Pt | 0 | 5' | Ph | H | $CF_3$ | H | $CH_3$ | H | $CH_3$ | H | — | — |
| 5'-21 | Pt | 1 | 5' | Ph | H | $CF_3$ | $CF_3$ | H | H | $CH_3$ | H | pic | |
| 5'-21X | Pt | 1 | 5' | Ph | H | $CF_3$ | $CF_3$ | H | H | $CH_3$ | H | acac | |
| 5'-21Y | Pt | 0 | 5' | Ph | H | $CF_3$ | $CF_3$ | H | H | $CH_3$ | H | — | — |
| 5'-22 | Pt | 1 | 5' | Ph | H | H | $NO_2$ | H | H | $CH_3$ | H | pic | |
| 5'-22X | Pt | 1 | 5' | Ph | H | H | $NO_2$ | H | H | $CH_3$ | H | acac | |
| 5'-22Y | Pt | 0 | 5' | Ph | H | H | $NO_2$ | H | H | $CH_3$ | H | — | — |
| 5'-23 | Pt | 1 | 5' | Ph | H | H | $NO_2$ | H | H | $^tC_4H_9$ | H | pic | |
| 5'-23X | Pt | 1 | 5' | Ph | H | H | $NO_2$ | H | H | $^tC_4H_9$ | H | acac | |
| 5'-23Y | Pt | 0 | 5' | Ph | H | H | $NO_2$ | H | H | $^tC_4H_9$ | H | — | — |
| 5'-24 | Pt | 1 | 5' | Ph | F | H | $NO_2$ | H | H | $CH_3$ | H | pic | |
| 5'-24X | Pt | 1 | 5' | Ph | F | H | $NO_2$ | H | H | $CH_3$ | H | acac | |
| 5'-24Y | Pt | 0 | 5' | Ph | F | H | $NO_2$ | H | H | $CH_3$ | H | — | — |
| 5'-25 | Pt | 1 | 5' | Ph | F | H | $NO_2$ | H | H | $^tC_4H_9$ | H | pic | |
| 5'-25X | Pt | 1 | 5' | Ph | F | H | $NO_2$ | H | H | $^tC_4H_9$ | H | acac | |
| 5'-25Y | Pt | 0 | 5' | Ph | F | H | $NO_2$ | H | H | $^tC_4H_9$ | H | — | — |
| 5'-26 | Pt | 1 | 5' | Ph | F | H | $NO_2$ | F | H | $CH_3$ | H | pic | |
| 5'-26X | Pt | 1 | 5' | Ph | F | H | $NO_2$ | F | H | $CH_3$ | H | acac | |
| 5'-26Y | Pt | 0 | 5' | Ph | F | H | $NO_2$ | F | H | $CH_3$ | H | — | — |
| 5'-27 | Pt | 1 | 5' | Ph | F | H | $NO_2$ | F | H | $^tC_4H_9$ | H | pic | |
| 5'-27X | Pt | 1 | 5' | Ph | F | H | $NO_2$ | F | H | $^tC_4H_9$ | H | acac | |
| 5'-27Y | Pt | 0 | 5' | Ph | F | H | $NO_2$ | F | H | $^tC_4H_9$ | H | — | — |
| 5'-28 | Pt | 1 | 5' | Ph | H | $NO_2$ | H | $NO_2$ | H | $CH_3$ | H | pic | |

TABLE 33-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 5'-28X | Pt | 1 | 5' | Ph | H | NO$_2$ | H | NO$_2$ | H | CH$_3$ | H | acac |
| 5'-28Y | Pt | 0 | 5' | Ph | H | NO$_2$ | H | NO$_2$ | H | CH$_3$ | H | — — |
| 5'-29 | Pt | 1 | 5' | Ph | H | NO$_2$ | H | NO$_2$ | H | $^tC_4H_9$ | H | pic |
| 5'-29X | Pt | 1 | 5' | Ph | H | NO$_2$ | H | NO$_2$ | H | $^tC_4H_9$ | H | acac |
| 5'-29Y | Pt | 0 | 5' | Ph | H | NO$_2$ | H | NO$_2$ | H | $^tC_4H_9$ | H | — — |
| 5'-30 | Pt | 1 | 5' | Ph | NO$_2$ | H | H | NO$_2$ | H | CH$_3$ | H | pic |
| 5'-30X | Pt | 1 | 5' | Ph | NO$_2$ | H | H | NO$_2$ | H | CH$_3$ | H | acac |
| 5'-30Y | Pt | 0 | 5' | Ph | NO$_2$ | H | H | NO$_2$ | H | CH$_3$ | H | — — |
| 5'-31 | Pt | 1 | 5' | Ph | H | H | CF$_3$ | H | H | CH$_3$ | H | pic |
| 5'-31X | Pt | 1 | 5' | Ph | H | H | CF$_3$ | H | H | CH$_3$ | H | acac |
| 5'-31Y | Pt | 0 | 5' | Ph | H | H | CF$_3$ | H | H | CH$_3$ | H | — — |
| 5'-32 | Pt | 1 | 5' | Ph | H | Cl | CF$_3$ | H | H | CH$_3$ | H | pic |
| 5'-32X | Pt | 1 | 5' | Ph | H | Cl | CF$_3$ | H | H | CH$_3$ | H | acac |
| 5'-32Y | Pt | 0 | 5' | Ph | H | Cl | CF$_3$ | H | H | CH$_3$ | H | — — |
| 5'-33 | Pt | 1 | 5' | Ph | H | Cl | CF$_3$ | H | H | $^tC_4H_9$ | H | pic |
| 5'-33X | Pt | 1 | 5' | Ph | H | Cl | CF$_3$ | H | H | $^tC_4H_9$ | H | acac |
| 5'-33Y | Pt | 0 | 5' | Ph | H | Cl | CF$_3$ | H | H | $^tC_4H_9$ | H | — — |
| 5'-34 | Pt | 1 | 5' | Ph | H | NO$_2$ | H | H | H | CH$_3$ | H | pic |
| 5'-34X | Pt | 1 | 5' | Ph | H | NO$_2$ | H | H | H | CH$_3$ | H | acac |
| 5'-34Y | Pt | 0 | 5' | Ph | H | NO$_2$ | H | H | H | CH$_3$ | H | — — |
| 5'-35 | Pt | 1 | 5' | Ph | H | CF$_3$ | H | H | H | CH$_3$ | H | pic |
| 5'-35X | Pt | 1 | 5' | Ph | H | CF$_3$ | H | H | H | CH$_3$ | H | acac |
| 5'-35Y | Pt | 0 | 5' | Ph | H | CF$_3$ | H | H | H | CH$_3$ | H | — — |
| 5'-36 | Pt | 1 | 5' | Ph | H | NO$_2$ | H | CH$_3$ | H | CH$_3$ | H | pic |
| 5'-36X | Pt | 1 | 5' | Ph | H | NO$_2$ | H | CH$_3$ | H | CH$_3$ | H | acac |
| 5'-36Y | Pt | 0 | 5' | Ph | H | NO$_2$ | H | CH$_3$ | H | CH$_3$ | H | — — |
| 5'-37 | Pt | 1 | 5' | Ph | H | NO$_2$ | H | CH$_3$ | H | $^tC_4H_9$ | H | pic |
| 5'-37X | Pt | 1 | 5' | Ph | H | NO$_2$ | H | CH$_3$ | H | $^tC_4H_9$ | H | acac |
| 5'-37Y | Pt | 0 | 5' | Ph | H | NO$_2$ | H | CH$_3$ | H | $^tC_4H_9$ | H | — — |
| 5'-38 | Pt | 1 | 5' | Ph | H | NO$_2$ | H | $^tC_4H_9$ | H | CH$_3$ | H | pic |
| 5'-38X | Pt | 1 | 5' | Ph | H | NO$_2$ | H | $^tC_4H_9$ | H | CH$_3$ | H | acac |
| 5'-38Y | Pt | 0 | 5' | Ph | H | NO$_2$ | H | $^tC_4H_9$ | H | CH$_3$ | H | — — |
| 5'-39 | Pt | 1 | 5' | Ph | H | H | CH$_3$O | H | H | CH$_3$ | H | pic |
| 5'-39X | Pt | 1 | 5' | Ph | H | H | CH$_3$O | H | H | CH$_3$ | H | acac |
| 5'-39Y | Pt | 0 | 5' | Ph | H | H | CH$_3$O | H | H | CH$_3$ | H | — — |
| 5'-40 | Pt | 1 | 5' | Ph | H | CH$_3$O | H | H | H | CH$_3$ | H | pic |
| 5'-40X | Pt | 1 | 5' | Ph | H | CH$_3$O | H | H | H | CH$_3$ | H | acac |
| 5'-40Y | Pt | 0 | 5' | Ph | H | CH$_3$O | H | H | H | CH$_3$ | H | — — |
| 5'-41 | Pt | 1 | 5' | Ph | H | CH$_3$O | H | CH$_3$ | H | CH$_3$ | H | pic |
| 5'-41X | Pt | 1 | 5' | Ph | H | CH$_3$O | H | CH$_3$ | H | CH$_3$ | H | acac |
| 5'-41Y | Pt | 0 | 5' | Ph | H | CH$_3$O | H | CH$_3$ | H | CH$_3$ | H | — — |
| 5'-42 | Pt | 1 | 5' | Ph | H | CH$_3$O | H | $^tC_4H_9$ | H | CH$_3$ | H | pic |
| 5'-42X | Pt | 1 | 5' | Ph | H | CH$_3$O | H | $^tC_4H_9$ | H | CH$_3$ | H | acac |
| 5'-42Y | Pt | 0 | 5' | Ph | H | CH$_3$O | H | $^tC_4H_9$ | H | CH$_3$ | H | — — |
| 5'-43 | Pt | 1 | 5' | Ph | H | H | H | H | $^tC_4H_9$ | CH$_3$ | H | pic |
| 5'-43X | Pt | 1 | 5' | Ph | H | H | H | H | $^tC_4H_9$ | CH$_3$ | H | acac |
| 5'-43Y | Pt | 0 | 5' | Ph | H | H | H | H | $^tC_4H_9$ | CH$_3$ | H | — — |
| 5'-44 | Pt | 1 | 5' | Ph | H | F | H | F | $^tC_4H_9$ | CH$_3$ | H | pic |
| 5'-44X | Pt | 1 | 5' | Ph | H | F | H | F | $^tC_4H_9$ | CH$_3$ | H | acac |
| 5'-44Y | Pt | 0 | 5' | Ph | H | F | H | F | $^tC_4H_9$ | CH$_3$ | H | — — |
| 5'-45 | Pt | 1 | 5' | Ph | H | F | H | F | $^tC_4H_9$ | $^tC_4H_9$ | H | pic |
| 5'-45X | Pt | 1 | 5' | Ph | H | F | H | F | $^tC_4H_9$ | $^tC_4H_9$ | H | acac |
| 5'-45Y | Pt | 0 | 5' | Ph | H | F | H | F | $^tC_4H_9$ | $^tC_4H_9$ | H | — — |
| 5'-46 | Pt | 1 | 5' | Ph | CF$_3$ | H | CF$_3$ | H | $^tC_4H_9$ | CH$_3$ | H | pic |
| 5'-46X | Pt | 1 | 5' | Ph | CF$_3$ | H | CF$_3$ | H | $^tC_4H_9$ | CH$_3$ | H | acac |
| 5'-46Y | Pt | 0 | 5' | Ph | CF$_3$ | H | CF$_3$ | H | $^tC_4H_9$ | CH$_3$ | H | — — |
| 5'-47 | Pt | 1 | 5' | Ph | CF$_3$ | H | CF$_3$ | H | $^tC_4H_9$ | $^tC_4H_9$ | H | pic |
| 5'-47X | Pt | 1 | 5' | Ph | CF$_3$ | H | CF$_3$ | H | $^tC_4H_9$ | $^tC_4H_9$ | H | acac |
| 5'-47Y | Pt | 0 | 5' | Ph | CF$_3$ | H | CF$_3$ | H | $^tC_4H_9$ | $^tC_4H_9$ | H | — — |
| 5'-48 | Pt | 1 | 5' | Ph | H | CF$_3$ | H | CH$_3$ | $^tC_4H_9$ | CH$_3$ | H | pic |
| 5'-48X | Pt | 1 | 5' | Ph | H | CF$_3$ | H | CH$_3$ | $^tC_4H_9$ | CH$_3$ | H | acac |
| 5'-48Y | Pt | 0 | 5' | Ph | H | CF$_3$ | H | CH$_3$ | $^tC_4H_9$ | CH$_3$ | H | — — |
| 5'-49 | Pt | 1 | 5' | Ph | H | Si(CH$_3$)$_3$ | H | H | H | CH$_3$ | H | pic |
| 5'-49X | Pt | 1 | 5' | Ph | H | Si(CH$_3$)$_3$ | H | H | H | CH$_3$ | H | acac |
| 5'-49Y | Pt | 0 | 5' | Ph | H | Si(CH$_3$)$_3$ | H | H | H | CH$_3$ | H | — — |
| 5'-50 | Pt | 1 | 5' | Ph | H | Si(CH$_3$)$_3$ | H | H | H | $^tC_4H_9$ | H | pic |
| 5'-50X | Pt | 1 | 5' | Ph | H | Si(CH$_3$)$_3$ | H | H | H | $^tC_4H_9$ | H | acac |
| 5'-50Y | Pt | 0 | 5' | Ph | H | Si(CH$_3$)$_3$ | H | H | H | $^tC_4H_9$ | H | — — |
| 5'-51 | Pt | 1 | 5' | Ph | H | H | Si(CH$_3$)$_3$ | H | H | CH$_3$ | H | pic |
| 5'-51X | Pt | 1 | 5' | Ph | H | H | Si(CH$_3$)$_3$ | H | H | CH$_3$ | H | acac |
| 5'-51Y | Pt | 0 | 5' | Ph | H | H | Si(CH$_3$)$_3$ | H | H | CH$_3$ | H | — — |
| 5'-52 | Pt | 1 | 5' | Ph | H | H | H | Si(CH$_3$)$_3$ | H | CH$_3$ | H | pic |
| 5'-52X | Pt | 1 | 5' | Ph | H | H | H | Si(CH$_3$)$_3$ | H | CH$_3$ | H | acac |
| 5'-52Y | Pt | 0 | 5' | Ph | H | H | H | Si(CH$_3$)$_3$ | H | CH$_3$ | H | — — |
| 5'-53 | Pt | 1 | 5' | Ph | H | F | H | Si(CH$_3$)$_3$ | H | CH$_3$ | H | pic |
| 5'-53X | Pt | 1 | 5' | Ph | H | F | H | Si(CH$_3$)$_3$ | H | CH$_3$ | H | acac |
| 5'-53Y | Pt | 0 | 5' | Ph | H | F | H | Si(CH$_3$)$_3$ | H | CH$_3$ | H | — — |

TABLE 33-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 5'-54 | Pt | 1 | 5' | Ph | H | CF₃ | H | Si(CH₃)₃ | H | CH₃ | H | pic |
| 5'-54X | Pt | 1 | 5' | Ph | H | CF₃ | H | Si(CH₃)₃ | H | CH₃ | H | acac |
| 5'-54Y | Pt | 0 | 5' | Ph | H | CF₃ | H | Si(CH₃)₃ | H | CH₃ | H | — — |
| 5'-55 | Pt | 1 | 5' | Ph | H | Si(CH₃)₃ | H | F | H | CH₃ | H | pic |
| 5'-55X | Pt | 1 | 5' | Ph | H | Si(CH₃)₃ | H | F | H | CH₃ | H | acac |
| 5'-55Y | Pt | 0 | 5' | Ph | H | Si(CH₃)₃ | H | F | H | CH₃ | H | — — |
| 5'-56 | Pt | 1 | 5' | Ph | H | Si(CH₃)₃ | H | F | H | $^tC_4H_9$ | H | pic |
| 5'-56X | Pt | 1 | 5' | Ph | H | Si(CH₃)₃ | H | F | H | $^tC_4H_9$ | H | acac |
| 5'-56Y | Pt | 0 | 5' | Ph | H | Si(CH₃)₃ | H | F | H | $^tC_4H_9$ | H | — — |
| 5'-57 | Pt | 1 | 5' | Ph | H | Si(CH₃)₃ | H | CF₃ | H | CH₃ | H | pic |
| 5'-57X | Pt | 1 | 5' | Ph | H | Si(CH₃)₃ | H | CF₃ | H | CH₃ | H | acac |
| 5'-57Y | Pt | 0 | 5' | Ph | H | Si(CH₃)₃ | H | CF₃ | H | CH₃ | H | — — |
| 5'-58 | Pt | 1 | 5' | Ph | H | Si(CH₃)₃ | H | CF₃ | H | $^tC_4H_9$ | H | pic |
| 5'-58X | Pt | 1 | 5' | Ph | H | Si(CH₃)₃ | H | CF₃ | H | $^tC_4H_9$ | H | acac |
| 5'-58Y | Pt | 0 | 5' | Ph | H | Si(CH₃)₃ | H | CF₃ | H | $^tC_4H_9$ | H | — — |
| 5'-59 | Pt | 1 | 5' | Ph | Si(CH₃)₃ | H | Si(CH₃)₃ | H | H | CH₃ | H | pic |
| 5'-59X | Pt | 1 | 5' | Ph | Si(CH₃)₃ | H | Si(CH₃)₃ | H | H | CH₃ | H | acac |
| 5'-59Y | Pt | 0 | 5' | Ph | Si(CH₃)₃ | H | Si(CH₃)₃ | H | H | CH₃ | H | — — |
| 5'-60 | Pt | 1 | 5' | Ph | Si(CH₃)₃ | H | Si(CH₃)₃ | H | H | $^tC_4H_9$ | H | pic |
| 5'-60X | Pt | 1 | 5' | Ph | Si(CH₃)₃ | H | Si(CH₃)₃ | H | H | $^tC_4H_9$ | H | acac |
| 5'-60Y | Pt | 0 | 5' | Ph | Si(CH₃)₃ | H | Si(CH₃)₃ | H | H | $^tC_4H_9$ | H | — — |
| 5'-61 | Pt | 1 | 5' | Ph | H | H | H | COCH₃ | H | CH₃ | H | pic |
| 5'-61X | Pt | 1 | 5' | Ph | H | H | H | COCH₃ | H | CH₃ | H | acac |
| 5'-61Y | Pt | 0 | 5' | Ph | H | H | H | COCH₃ | H | CH₃ | H | — — |
| 5'-62 | Pt | 1 | 5' | Ph | H | H | COCH₃ | H | H | CH₃ | H | pic |
| 5'-62X | Pt | 1 | 5' | Ph | H | H | COCH₃ | H | H | CH₃ | H | acac |
| 5'-62Y | Pt | 0 | 5' | Ph | H | H | COCH₃ | H | H | CH₃ | H | — — |
| 5'-63 | Pt | 1 | 5' | Ph | H | COCH₃ | H | H | H | CH₃ | H | pic |
| 5'-63X | Pt | 1 | 5' | Ph | H | COCH₃ | H | H | H | CH₃ | H | acac |
| 5'-63Y | Pt | 0 | 5' | Ph | H | COCH₃ | H | H | H | CH₃ | H | — — |
| 5'-64 | Pt | 1 | 5' | Ph | H | H | | BL | H | CH₃ | H | pic |
| 5'-64X | Pt | 1 | 5' | Ph | H | H | | BL | H | CH₃ | H | acac |
| 5'-64Y | Pt | 0 | 5' | Ph | H | H | | BL | H | CH₃ | H | — — |
| 5'-65 | Pt | 1 | 5' | Ph | H | H | | BL | H | $^tC_4H_9$ | H | pic |
| 5'-65X | Pt | 1 | 5' | Ph | H | H | | BL | H | $^tC_4H_9$ | H | acac |
| 5'-65Y | Pt | 0 | 5' | Ph | H | H | | BL | H | $^tC_4H_9$ | H | — — |
| 5'-66 | Pt | 1 | 5' | Ph | H | | BL | | H | CH₃ | H | pic |
| 5'-66X | Pt | 1 | 5' | Ph | H | | BL | | H | CH₃ | H | acac |
| 5'-66Y | Pt | 0 | 5' | Ph | H | | BL | | H | CH₃ | H | — — |
| 5'-67 | Pt | 1 | 5' | Ph | H | | BL | | H | $^tC_4H_9$ | H | pic |
| 5'-67X | Pt | 1 | 5' | Ph | H | | BL | | H | $^tC_4H_9$ | H | acac |
| 5'-67Y | Pt | 0 | 5' | Ph | H | | BL | | H | $^tC_4H_9$ | H | — — |
| 5'-68 | Pt | 1 | 5' | Ph | H | H | | PL | | CH₃ | H | pic |
| 5'-68X | Pt | 1 | 5' | Ph | H | H | | PL | | CH₃ | H | acac |
| 5'-68Y | Pt | 0 | 5' | Ph | H | H | | PL | | CH₃ | H | — — |
| 5'-69 | Pt | 1 | 5' | Ph | H | H | | PL | | $^tC_4H_9$ | H | pic |
| 5'-69X | Pt | 1 | 5' | Ph | H | H | | PL | | $^tC_4H_9$ | H | acac |
| 5'-69Y | Pt | 0 | 5' | Ph | H | H | | PL | | $^tC_4H_9$ | H | — — |
| 5'-70 | Pt | 1 | 5' | Ph | H | | PL | | H | CH₃ | H | pic |
| 5'-70X | Pt | 1 | 5' | Ph | H | | PL | | H | CH₃ | H | acac |
| 5'-70Y | Pt | 0 | 5' | Ph | H | | PL | | H | CH₃ | H | — — |
| 5'-71 | Pt | 1 | 5' | Ph | H | | PL | | H | $^tC_4H_9$ | H | pic |
| 5'-71X | Pt | 1 | 5' | Ph | H | | PL | | H | $^tC_4H_9$ | H | acac |
| 5'-71Y | Pt | 0 | 5' | Ph | H | | PL | | H | $^tC_4H_9$ | H | — — |
| 5'-72 | Pt | 1 | 5' | Ph | H | H | | MEE1 | H | CH₃ | H | pic |
| 5'-72X | Pt | 1 | 5' | Ph | H | H | | MEE1 | H | CH₃ | H | acac |
| 5'-72Y | Pt | 0 | 5' | Ph | H | H | | MEE1 | H | CH₃ | H | — — |
| 5'-73 | Pt | 1 | 5' | Ph | H | | MEE1 | | H | CH₃ | H | pic |
| 5'-73X | Pt | 1 | 5' | Ph | H | | MEE1 | | H | CH₃ | H | acac |
| 5'-73Y | Pt | 0 | 5' | Ph | H | | MEE1 | | H | CH₃ | H | — — |
| 5'-74 | Pt | 1 | 5' | Ph | H | H | | MEE2 | H | CH₃ | H | pic |
| 5'-74X | Pt | 1 | 5' | Ph | H | H | | MEE2 | H | CH₃ | H | acac |
| 5'-74Y | Pt | 0 | 5' | Ph | H | H | | MEE2 | H | CH₃ | H | — — |
| 5'-75 | Pt | 1 | 5' | Ph | H | | MEE2 | | H | CH₃ | H | pic |
| 5'-75X | Pt | 1 | 5' | Ph | H | | MEE2 | | H | CH₃ | H | acac |
| 5'-75Y | Pt | 0 | 5' | Ph | H | | MEE2 | | H | CH₃ | H | — — |
| 5'-76 | Pt | 1 | 5' | Ph | H | H | | PA1 | H | CH₃ | H | pic |
| 5'-76X | Pt | 1 | 5' | Ph | H | H | | PA1 | H | CH₃ | H | acac |
| 5'-76Y | Pt | 0 | 5' | Ph | H | H | | PA1 | H | CH₃ | H | — — |
| 5'-77 | Pt | 1 | 5' | Ph | H | | PA1 | | H | CH₃ | H | pic |
| 5'-77X | Pt | 1 | 5' | Ph | H | | PA1 | | H | CH₃ | H | acac |
| 5'-77Y | Pt | 0 | 5' | Ph | H | | PA1 | | H | CH₃ | H | — — |
| 5'-78 | Pt | 1 | 5' | Ph | H | H | | PA2 | H | CH₃ | H | pic |
| 5'-78X | Pt | 1 | 5' | Ph | H | H | | PA2 | H | CH₃ | H | acac |
| 5'-78Y | Pt | 0 | 5' | Ph | H | H | | PA2 | H | CH₃ | H | — — |
| 5'-79 | Pt | 1 | 5' | Ph | H | | PA2 | | H | CH₃ | H | pic |
| 5'-79X | Pt | 1 | 5' | Ph | H | | PA2 | | H | CH₃ | H | acac |

TABLE 33-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-79Y | Pt | 0 | 5' | Ph | H | | PA2 | | H | H | $CH_3$ | H | — — |
| 5'-80 | Pt | 1 | 5' | Ph | H | H | | EA1 | H | H | $CH_3$ | H | pic |
| 5'-80X | Pt | 1 | 5' | Ph | H | H | | EA1 | H | H | $CH_3$ | H | acac |
| 5'-80Y | Pt | 0 | 5' | Ph | H | H | | EA1 | H | H | $CH_3$ | H | — — |
| 5'-81 | Pt | 1 | 5' | Ph | H | | EA2 | | H | H | $CH_3$ | H | pic |
| 5'-81X | Pt | 1 | 5' | Ph | H | | EA2 | | H | H | $CH_3$ | H | acac |
| 5'-81Y | Pt | 0 | 5' | Ph | H | | EA2 | | H | H | $CH_3$ | H | — — |
| 5'-82 | Pt | 1 | 5' | Ph | H | H | | ME | H | H | $CH_3$ | H | pic |
| 5'-82X | Pt | 1 | 5' | Ph | H | H | | ME | H | H | $CH_3$ | H | acac |
| 5'-82Y | Pt | 0 | 5' | Ph | H | H | | ME | H | H | $CH_3$ | H | — — |
| 5'-83 | Pt | 1 | 5' | Ph | H | | ME | | H | H | $CH_3$ | H | pic |
| 5'-83X | Pt | 1 | 5' | Ph | H | | ME | | H | H | $CH_3$ | H | acac |
| 5'-83Y | Pt | 0 | 5' | Ph | H | | ME | | H | H | $CH_3$ | H | — — |
| 5'-84 | Pt | 1 | 5' | Ph | H | H | | AT | H | H | $CH_3$ | H | pic |
| 5'-84X | Pt | 1 | 5' | Ph | H | H | | AT | H | H | $CH_3$ | H | acac |
| 5'-84Y | Pt | 0 | 5' | Ph | H | H | | AT | H | H | $CH_3$ | H | — — |
| 5'-85 | Pt | 1 | 5' | Ph | H | | AT | | H | H | $CH_3$ | H | pic |
| 5'-85X | Pt | 1 | 5' | Ph | H | | AT | | H | H | $CH_3$ | H | acac |
| 5'-85Y | Pt | 0 | 5' | Ph | H | | AT | | H | H | $CH_3$ | H | — — |
| 5'-86 | Pt | 1 | 5' | Ph | H | H | | MES1 | H | H | $CH_3$ | H | pic |
| 5'-86X | Pt | 1 | 5' | Ph | H | H | | MES1 | H | H | $CH_3$ | H | acac |
| 5'-86Y | Pt | 0 | 5' | Ph | H | H | | MES1 | H | H | $CH_3$ | H | — — |
| 5'-87 | Pt | 1 | 5' | Ph | H | | MES1 | | H | H | $CH_3$ | H | pic |
| 5'-87X | Pt | 1 | 5' | Ph | H | | MES1 | | H | H | $CH_3$ | H | acac |
| 5'-87Y | Pt | 0 | 5' | Ph | H | | MES1 | | H | H | $CH_3$ | H | — — |
| 5'-88 | Pt | 1 | 5' | Ph | H | H | | MES2 | H | H | $CH_3$ | H | pic |
| 5'-88X | Pt | 1 | 5' | Ph | H | H | | MES2 | H | H | $CH_3$ | H | acac |
| 5'-88Y | Pt | 0 | 5' | Ph | H | H | | MES2 | H | H | $CH_3$ | H | — — |
| 5'-89 | Pt | 1 | 5' | Ph | H | | MES2 | | H | H | $CH_3$ | H | pic |
| 5'-89X | Pt | 1 | 5' | Ph | H | | MES2 | | H | H | $CH_3$ | H | acac |
| 5'-89Y | Pt | 0 | 5' | Ph | H | | MES2 | | H | H | $CH_3$ | H | — — |
| 5'-90 | Pt | 1 | 5' | Ph | H | H | | PS1 | H | H | $CH_3$ | H | pic |
| 5'-90X | Pt | 1 | 5' | Ph | H | H | | PS1 | H | H | $CH_3$ | H | acac |
| 5'-90Y | Pt | 0 | 5' | Ph | H | H | | PS1 | H | H | $CH_3$ | H | — — |
| 5'-91 | Pt | 1 | 5' | Ph | H | | PS1 | | H | H | $CH_3$ | H | pic |
| 5'-91X | Pt | 1 | 5' | Ph | H | | PS1 | | H | H | $CH_3$ | H | acac |
| 5'-91Y | Pt | 0 | 5' | Ph | H | | PS1 | | H | H | $CH_3$ | H | — — |
| 5'-92 | Pt | 1 | 5' | Ph | H | H | | PS2 | H | H | $CH_3$ | H | pic |
| 5'-92X | Pt | 1 | 5' | Ph | H | H | | PS2 | H | H | $CH_3$ | H | acac |
| 5'-92Y | Pt | 0 | 5' | Ph | H | H | | PS2 | H | H | $CH_3$ | H | — — |
| 5'-93 | Pt | 1 | 5' | Ph | H | | PS2 | | H | H | $CH_3$ | H | pic |
| 5'-93X | Pt | 1 | 5' | Ph | H | | PS2 | | H | H | $CH_3$ | H | acac |
| 5'-93Y | Pt | 0 | 5' | Ph | H | | PS2 | | H | H | $CH_3$ | H | — — |
| 5'-94 | Pt | 1 | 5' | Ph | H | H | | BAL1 | H | H | $CH_3$ | H | pic |
| 5'-94X | Pt | 1 | 5' | Ph | H | H | | BAL1 | H | H | $CH_3$ | H | acac |
| 5'-94Y | Pt | 0 | 5' | Ph | H | H | | BAL1 | H | H | $CH_3$ | H | — — |
| 5'-95 | Pt | 1 | 5' | Ph | H | | BAL1 | | H | H | $CH_3$ | H | pic |
| 5'-95X | Pt | 1 | 5' | Ph | H | | BAL1 | | H | H | $CH_3$ | H | acac |
| 5'-95Y | Pt | 0 | 5' | Ph | H | | BAL1 | | H | H | $CH_3$ | H | — — |
| 5'-96 | Pt | 1 | 5' | Ph | H | H | | BAL2 | H | H | $CH_3$ | H | pic |
| 5'-96X | Pt | 1 | 5' | Ph | H | H | | BAL2 | H | H | $CH_3$ | H | acac |
| 5'-96Y | Pt | 0 | 5' | Ph | H | H | | BAL2 | H | H | $CH_3$ | H | — — |
| 5'-97 | Pt | 1 | 5' | Ph | H | | BAL2 | | H | H | $CH_3$ | H | pic |
| 5'-97X | Pt | 1 | 5' | Ph | H | | BAL2 | | H | H | $CH_3$ | H | acac |
| 5'-97Y | Pt | 0 | 5' | Ph | H | | BAL2 | | H | H | $CH_3$ | H | — — |
| 5'-98 | Pt | 1 | 5' | Ph | H | H | | MEK1 | H | H | $CH_3$ | H | pic |
| 5'-98X | Pt | 1 | 5' | Ph | H | H | | MEK1 | H | H | $CH_3$ | H | acac |
| 5'-98Y | Pt | 0 | 5' | Ph | H | H | | MEK1 | H | H | $CH_3$ | H | — — |
| 5'-99 | Pt | 1 | 5' | Ph | H | | MEK1 | | H | H | $CH_3$ | H | pic |
| 5'-99X | Pt | 1 | 5' | Ph | H | | MEK1 | | H | H | $CH_3$ | H | acac |
| 5'-99Y | Pt | 0 | 5' | Ph | H | | MEK1 | | H | H | $CH_3$ | H | — — |
| 5'-100 | Pt | 1 | 5' | Ph | H | H | | MEK2 | H | H | $CH_3$ | H | pic |
| 5'-100X | Pt | 1 | 5' | Ph | H | H | | MEK2 | H | H | $CH_3$ | H | acac |
| 5'-100Y | Pt | 0 | 5' | Ph | H | H | | MEK2 | H | H | $CH_3$ | H | — — |
| 5'-101 | Pt | 1 | 5' | Ph | H | | MEK2 | | H | H | $CH_3$ | H | pic |
| 5'-101X | Pt | 1 | 5' | Ph | H | | MEK2 | | H | H | $CH_3$ | H | acac |
| 5'-101Y | Pt | 0 | 5' | Ph | H | | MEK2 | | H | H | $CH_3$ | H | — — |
| 5'-102 | Pt | 1 | 5' | Ph | H | H | | PAL1 | H | H | $CH_3$ | H | pic |
| 5'-102X | Pt | 1 | 5' | Ph | H | H | | PAL1 | H | H | $CH_3$ | H | acac |
| 5'-102Y | Pt | 0 | 5' | Ph | H | H | | PAL1 | H | H | $CH_3$ | H | — — |
| 5'-103 | Pt | 1 | 5' | Ph | H | | PAL1 | | H | H | $CH_3$ | H | pic |
| 5'-103X | Pt | 1 | 5' | Ph | H | | PAL1 | | H | H | $CH_3$ | H | acac |
| 5'-103Y | Pt | 0 | 5' | Ph | H | | PAL1 | | H | H | $CH_3$ | H | — — |
| 5'-104 | Pt | 1 | 5' | Ph | H | H | | PAL2 | H | H | $CH_3$ | H | pic |
| 5'-104X | Pt | 1 | 5' | Ph | H | H | | PAL2 | H | H | $CH_3$ | H | acac |
| 5'-104Y | Pt | 0 | 5' | Ph | H | H | | PAL2 | H | H | $CH_3$ | H | — — |
| 5'-105 | Pt | 1 | 5' | Ph | H | | PAL2 | | H | H | $CH_3$ | H | pic |

TABLE 33-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 5'-105X | Pt | 1 | 5' | Ph | H | | PAL2 | | H | CH₃ | H | acac |
| 5'-105Y | Pt | 0 | 5' | Ph | H | | PAL2 | | H | CH₃ | H | — — |
| 5'-106 | Pt | 1 | 5' | Ph | H | H | | MMK | H | CH₃ | H | pic |
| 5'-106X | Pt | 1 | 5' | Ph | H | H | | MMK | H | CH₃ | H | acac |
| 5'-106Y | Pt | 0 | 5' | Ph | H | H | | MMK | H | CH₃ | H | — — |
| 5'-107 | Pt | 1 | 5' | Ph | H | | MMK | | H | CH₃ | H | pic |
| 5'-107X | Pt | 1 | 5' | Ph | H | | MMK | | H | CH₃ | H | acac |
| 5'-107Y | Pt | 0 | 5' | Ph | H | | MMK | | H | CH₃ | H | — — |
| 5'-108 | Pt | 1 | 5' | Ph | H | H | | EES1 | H | CH₃ | H | pic |
| 5'-108X | Pt | 1 | 5' | Ph | H | H | | EES1 | H | CH₃ | H | acac |
| 5'-108Y | Pt | 0 | 5' | Ph | H | H | | EES1 | H | CH₃ | H | — — |
| 5'-109 | Pt | 1 | 5' | Ph | H | | EES2 | | H | CH₃ | H | pic |
| 5'-109X | Pt | 1 | 5' | Ph | H | | EES2 | | H | CH₃ | H | acac |
| 5'-109Y | Pt | 0 | 5' | Ph | H | | EES2 | | H | CH₃ | H | — — |
| 5'-110 | Pt | 1 | 5' | Ph | H | H | | PAE1 | H | CH₃ | H | pic |
| 5'-110X | Pt | 1 | 5' | Ph | H | H | | PAE1 | H | CH₃ | H | acac |
| 5'-110Y | Pt | 0 | 5' | Ph | H | H | | PAE1 | H | CH₃ | H | — — |
| 5'-111 | Pt | 1 | 5' | Ph | H | | PAE2 | | H | CH₃ | H | pic |
| 5'-111X | Pt | 1 | 5' | Ph | H | | PAE2 | | H | CH₃ | H | acac |
| 5'-111Y | Pt | 0 | 5' | Ph | H | | PAE2 | | H | CH₃ | H | — — |
| 5'-112 | Pt | 1 | 5' | Ph | H | H | | AME1 | H | CH₃ | H | pic |
| 5'-112X | Pt | 1 | 5' | Ph | H | H | | AME1 | H | CH₃ | H | acac |
| 5'-112Y | Pt | 0 | 5' | Ph | H | H | | AME1 | H | CH₃ | H | — — |
| 5'-113 | Pt | 1 | 5' | Ph | H | | AME1 | | H | CH₃ | H | pic |
| 5'-113X | Pt | 1 | 5' | Ph | H | | AME1 | | H | CH₃ | H | acac |
| 5'-113Y | Pt | 0 | 5' | Ph | H | | AME1 | | H | CH₃ | H | — — |
| 5'-114 | Pt | 1 | 5' | Ph | H | H | | AME2 | H | CH₃ | H | pic |
| 5'-114X | Pt | 1 | 5' | Ph | H | H | | AME2 | H | CH₃ | H | acac |
| 5'-114Y | Pt | 0 | 5' | Ph | H | H | | AME2 | H | CH₃ | H | — — |
| 5'-115 | Pt | 1 | 5' | Ph | H | | AME2 | | H | CH₃ | H | pic |
| 5'-115X | Pt | 1 | 5' | Ph | H | | AME2 | | H | CH₃ | H | acac |
| 5'-115Y | Pt | 0 | 5' | Ph | H | | AME2 | | H | CH₃ | H | — — |
| 5'-116 | Pt | 1 | 5' | Ph | H | H | | EAE1 | H | CH₃ | H | pic |
| 5'-116X | Pt | 1 | 5' | Ph | H | H | | EAE1 | H | CH₃ | H | acac |
| 5'-116Y | Pt | 0 | 5' | Ph | H | H | | EAE1 | H | CH₃ | H | — — |
| 5'-117 | Pt | 1 | 5' | Ph | H | | EAE1 | | H | CH₃ | H | pic |
| 5'-117X | Pt | 1 | 5' | Ph | H | | EAE1 | | H | CH₃ | H | acac |
| 5'-117Y | Pt | 0 | 5' | Ph | H | | EAE1 | | H | CH₃ | H | — — |
| 5'-118 | Pt | 1 | 5' | Ph | H | H | | EAE2 | H | CH₃ | H | pic |
| 5'-118X | Pt | 1 | 5' | Ph | H | H | | EAE2 | H | CH₃ | H | acac |
| 5'-118Y | Pt | 0 | 5' | Ph | H | H | | EAE2 | H | CH₃ | H | — — |
| 5'-119 | Pt | 1 | 5' | Ph | H | | EAE2 | | H | CH₃ | H | pic |
| 5'-119X | Pt | 1 | 5' | Ph | H | | EAE2 | | H | CH₃ | H | acac |
| 5'-119Y | Pt | 0 | 5' | Ph | H | | EAE2 | | H | CH₃ | H | — — |
| 5'-120 | Pt | 1 | 5' | Ph | H | H | | AAE1 | H | CH₃ | H | pic |
| 5'-120X | Pt | 1 | 5' | Ph | H | H | | AAE1 | H | CH₃ | H | acac |
| 5'-120Y | Pt | 0 | 5' | Ph | H | H | | AAE1 | H | CH₃ | H | — — |
| 5'-121 | Pt | 1 | 5' | Ph | H | | AAE1 | | H | CH₃ | H | pic |
| 5'-121X | Pt | 1 | 5' | Ph | H | | AAE1 | | H | CH₃ | H | acac |
| 5'-121Y | Pt | 0 | 5' | Ph | H | | AAE1 | | H | CH₃ | H | — — |
| 5'-122 | Pt | 1 | 5' | Ph | H | H | | AAE2 | H | CH₃ | H | pic |
| 5'-122X | Pt | 1 | 5' | Ph | H | H | | AAE2 | H | CH₃ | H | acac |
| 5'-122Y | Pt | 0 | 5' | Ph | H | H | | AAE2 | H | CH₃ | H | — — |
| 5'-123 | Pt | 1 | 5' | Ph | H | | AAE2 | | H | CH₃ | H | pic |
| 5'-123X | Pt | 1 | 5' | Ph | H | | AAE2 | | H | CH₃ | H | acac |
| 5'-123Y | Pt | 0 | 5' | Ph | H | | AAE2 | | H | CH₃ | H | — — |
| 5'-124 | Pt | 1 | 5' | Ph | H | H | | PME1 | H | CH₃ | H | pic |
| 5'-124X | Pt | 1 | 5' | Ph | H | H | | PME1 | H | CH₃ | H | acac |
| 5'-124Y | Pt | 0 | 5' | Ph | H | H | | PME1 | H | CH₃ | H | — — |
| 5'-125 | Pt | 1 | 5' | Ph | H | | PME1 | | H | CH₃ | H | pic |
| 5'-125X | Pt | 1 | 5' | Ph | H | | PME1 | | H | CH₃ | H | acac |
| 5'-125Y | Pt | 0 | 5' | Ph | H | | PME1 | | H | CH₃ | H | — — |
| 5'-126 | Pt | 1 | 5' | Ph | H | H | | PME2 | H | CH₃ | H | pic |
| 5'-126X | Pt | 1 | 5' | Ph | H | H | | PME2 | H | CH₃ | H | acac |
| 5'-126Y | Pt | 0 | 5' | Ph | H | H | | PME2 | H | CH₃ | H | — — |
| 5'-127 | Pt | 1 | 5' | Ph | H | | PME2 | | H | CH₃ | H | pic |
| 5'-127X | Pt | 1 | 5' | Ph | H | | PME2 | | H | CH₃ | H | acac |
| 5'-127Y | Pt | 0 | 5' | Ph | H | | PME2 | | H | CH₃ | H | — — |
| 5'-128 | Pt | 1 | 5' | Ph | H | H | | MET1 | H | CH₃ | H | pic |
| 5'-128X | Pt | 1 | 5' | Ph | H | H | | MET1 | H | CH₃ | H | acac |
| 5'-128Y | Pt | 0 | 5' | Ph | H | H | | MET1 | H | CH₃ | H | — — |
| 5'-129 | Pt | 1 | 5' | Ph | H | | MET1 | | H | CH₃ | H | pic |
| 5'-129X | Pt | 1 | 5' | Ph | H | | MET1 | | H | CH₃ | H | acac |
| 5'-129Y | Pt | 0 | 5' | Ph | H | | MET1 | | H | CH₃ | H | — — |
| 5'-130 | Pt | 1 | 5' | Ph | H | H | | MET2 | H | CH₃ | H | pic |
| 5'-130X | Pt | 1 | 5' | Ph | H | H | | MET2 | H | CH₃ | H | acac |
| 5'-130Y | Pt | 0 | 5' | Ph | H | H | | MET2 | H | CH₃ | H | — — |

TABLE 33-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-131 | Pt | 1 | 5' | Ph | H | | MET2 | | H | H | $CH_3$ | H | pic |
| 5'-131X | Pt | 1 | 5' | Ph | H | | MET2 | | H | H | $CH_3$ | H | acac |
| 5'-131Y | Pt | 0 | 5' | Ph | H | | MET2 | | H | H | $CH_3$ | H | — — |
| 5'-132 | Pt | 1 | 5' | Ph | H | H | | EE1 | H | H | $CH_3$ | H | pic |
| 5'-132X | Pt | 1 | 5' | Ph | H | H | | EE1 | H | H | $CH_3$ | H | acac |
| 5'-132Y | Pt | 0 | 5' | Ph | H | H | | EE1 | H | H | $CH_3$ | H | — — |
| 5'-133 | Pt | 1 | 5' | Ph | H | | EE1 | | H | H | $CH_3$ | H | pic |
| 5'-133X | Pt | 1 | 5' | Ph | H | | EE1 | | H | H | $CH_3$ | H | acac |
| 5'-133Y | Pt | 0 | 5' | Ph | H | | EE1 | | H | H | $CH_3$ | H | — — |
| 5'-134 | Pt | 1 | 5' | Ph | H | H | | EE2 | H | H | $CH_3$ | H | pic |
| 5'-134X | Pt | 1 | 5' | Ph | H | H | | EE2 | H | H | $CH_3$ | H | acac |
| 5'-134Y | Pt | 0 | 5' | Ph | H | H | | EE2 | H | H | $CH_3$ | H | — — |
| 5'-135 | Pt | 1 | 5' | Ph | H | | EE2 | | H | H | $CH_3$ | H | pic |
| 5'-135X | Pt | 1 | 5' | Ph | H | | EE2 | | H | H | $CH_3$ | H | acac |
| 5'-135Y | Pt | 0 | 5' | Ph | H | | EE2 | | H | H | $CH_3$ | H | — — |
| 5'-136 | Pt | 1 | 5' | Ph | H | H | | MS1 | H | H | $CH_3$ | H | pic |
| 5'-136X | Pt | 1 | 5' | Ph | H | H | | MS1 | H | H | $CH_3$ | H | acac |
| 5'-136Y | Pt | 0 | 5' | Ph | H | H | | MS1 | H | H | $CH_3$ | H | — — |
| 5'-137 | Pt | 1 | 5' | Ph | H | | MS1 | | H | H | $CH_3$ | H | pic |
| 5'-137X | Pt | 1 | 5' | Ph | H | | MS1 | | H | H | $CH_3$ | H | acac |
| 5'-137Y | Pt | 0 | 5' | Ph | H | | MS1 | | H | H | $CH_3$ | H | — — |
| 5'-138 | Pt | 1 | 5' | Ph | H | H | | MS2 | H | H | $CH_3$ | H | pic |
| 5'-138X | Pt | 1 | 5' | Ph | H | H | | MS2 | H | H | $CH_3$ | H | acac |
| 5'-138Y | Pt | 0 | 5' | Ph | H | H | | MS2 | H | H | $CH_3$ | H | — — |
| 5'-139 | Pt | 1 | 5' | Ph | H | | MS2 | | H | H | $CH_3$ | H | pic |
| 5'-139X | Pt | 1 | 5' | Ph | H | | MS2 | | H | H | $CH_3$ | H | acac |
| 5'-139Y | Pt | 0 | 5' | Ph | H | | MS2 | | H | H | $CH_3$ | H | — — |

TABLE 34

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 6'-1 | Pt | 1 | 6' | Ph | H | H | H | H | $CH_3$ | H | H | pic | |
| 6'-1X | Pt | 1 | 6' | Ph | H | H | H | H | $CH_3$ | H | H | acac | |
| 6'-1Y | Pt | 0 | 6' | Ph | H | H | H | H | $CH_3$ | H | H | — | — |
| 6'-2 | Pt | 1 | 6' | Ph | H | H | H | H | $^tC_4H_9$ | H | H | pic | |
| 6'-2X | Pt | 1 | 6' | Ph | H | H | H | H | $^tC_4H_9$ | H | H | acac | |
| 6'-2Y | Pt | 0 | 6' | Ph | H | H | H | H | $^tC_4H_9$ | H | H | — | — |
| 6'-3 | Pt | 1 | 6' | Ph | H | F | H | F | $CH_3$ | H | H | pic | |
| 6'-3X | Pt | 1 | 6' | Ph | H | F | H | F | $CH_3$ | H | H | acac | |
| 6'-3Y | Pt | 0 | 6' | Ph | H | F | H | F | $CH_3$ | H | H | — | — |
| 6'-4 | Pt | 1 | 6' | Ph | H | F | H | F | $^tC_4H_9$ | H | H | pic | |
| 6'-4X | Pt | 1 | 6' | Ph | H | F | H | F | $^tC_4H_9$ | H | H | acac | |
| 6'-4Y | Pt | 0 | 6' | Ph | H | F | H | F | $^tC_4H_9$ | H | H | — | — |
| 6'-5 | Pt | 1 | 6' | Ph | F | H | H | F | $CH_3$ | H | H | pic | |
| 6'-5X | Pt | 1 | 6' | Ph | F | H | H | F | $CH_3$ | H | H | acac | |
| 6'-5Y | Pt | 0 | 6' | Ph | F | H | H | F | $CH_3$ | H | H | — | — |
| 6'-6 | Pt | 1 | 6' | Ph | F | H | H | F | $^tC_4H_9$ | H | H | pic | |
| 6'-6X | Pt | 1 | 6' | Ph | F | H | H | F | $^tC_4H_9$ | H | H | acac | |
| 6'-6Y | Pt | 0 | 6' | Ph | F | H | H | F | $^tC_4H_9$ | H | H | — | — |
| 6'-7 | Pt | 1 | 6' | Ph | $CF_3$ | H | $CF_3$ | H | $CH_3$ | H | H | pic | |
| 6'-7X | Pt | 1 | 6' | Ph | $CF_3$ | H | $CF_3$ | H | $CH_3$ | H | H | acac | |
| 6'-7Y | Pt | 0 | 6' | Ph | $CF_3$ | H | $CF_3$ | H | $CH_3$ | H | H | — | — |
| 6'-8 | Pt | 1 | 6' | Ph | $CF_3$ | H | $CF_3$ | H | $^tC_4H_9$ | H | H | pic | |
| 6'-8X | Pt | 1 | 6' | Ph | $CF_3$ | H | $CF_3$ | H | $^tC_4H_9$ | H | H | acac | |
| 6'-8Y | Pt | 0 | 6' | Ph | $CF_3$ | H | $CF_3$ | H | $^tC_4H_9$ | H | H | — | — |
| 6'-9 | Pt | 1 | 6' | Ph | H | F | $CF_3$ | H | $CH_3$ | H | H | pic | |
| 6'-9X | Pt | 1 | 6' | Ph | H | F | $CF_3$ | H | $CH_3$ | H | H | acac | |
| 6'-9Y | Pt | 0 | 6' | Ph | H | F | $CF_3$ | H | $CH_3$ | H | H | — | — |
| 6'-10 | Pt | 1 | 6' | Ph | F | H | $CF_3$ | H | $CH_3$ | H | H | pic | |
| 6'-10X | Pt | 1 | 6' | Ph | F | H | $CF_3$ | H | $CH_3$ | H | H | acac | |
| 6'-10Y | Pt | 0 | 6' | Ph | F | H | $CF_3$ | H | $CH_3$ | H | H | — | — |
| 6'-11 | Pt | 1 | 6' | Ph | F | F | F | F | $CH_3$ | H | H | pic | |
| 6'-11X | Pt | 1 | 6' | Ph | F | F | F | F | $CH_3$ | H | H | acac | |
| 6'-11Y | Pt | 0 | 6' | Ph | F | F | F | F | $CH_3$ | H | H | — | — |
| 6'-12 | Pt | 1 | 6' | Ph | H | F | H | $CH_3$ | $CH_3$ | H | H | pic | |
| 6'-12X | Pt | 1 | 6' | Ph | H | F | H | $CH_3$ | $CH_3$ | H | H | acac | |
| 6'-12Y | Pt | 0 | 6' | Ph | H | F | H | $CH_3$ | $CH_3$ | H | H | — | — |
| 6'-13 | Pt | 1 | 6' | Ph | H | F | H | $CH_3$ | $^tC_4H_9$ | H | H | pic | |
| 6'-13X | Pt | 1 | 6' | Ph | H | F | H | $CH_3$ | $^tC_4H_9$ | H | H | acac | |
| 6'-13Y | Pt | 0 | 6' | Ph | H | F | H | $CH_3$ | $^tC_4H_9$ | H | H | — | — |
| 6'-14 | Pt | 1 | 6' | Ph | H | F | H | $^tC_4H_9$ | $CH_3$ | H | H | pic | |
| 6'-14X | Pt | 1 | 6' | Ph | H | F | H | $^tC_4H_9$ | $CH_3$ | H | H | acac | |
| 6'-14Y | Pt | 0 | 6' | Ph | H | F | H | $^tC_4H_9$ | $CH_3$ | H | H | — | — |

TABLE 34-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 6'-15 | Pt | 1 | 6' | Ph | H | F | H | $^tC_4H_9$ | $^tC_4H_9$ | H | H | pic |
| 6'-15X | Pt | 1 | 6' | Ph | H | F | H | $^tC_4H_9$ | $^tC_4H_9$ | H | H | acac |
| 6'-15Y | Pt | 0 | 6' | Ph | H | F | H | $^tC_4H_9$ | $^tC_4H_9$ | H | H | — — |
| 6'-16 | Pt | 1 | 6' | Ph | H | $CF_3$ | H | $CF_3$ | $CH_3$ | H | H | pic |
| 6'-16X | Pt | 1 | 6' | Ph | H | $CF_3$ | H | $CF_3$ | $CH_3$ | H | H | acac |
| 6'-16Y | Pt | 0 | 6' | Ph | H | $CF_3$ | H | $CF_3$ | $CH_3$ | H | H | — — |
| 6'-17 | Pt | 1 | 6' | Ph | H | $CF_3$ | H | $CF_3$ | $^tC_4H_9$ | H | H | pic |
| 6'-17X | Pt | 1 | 6' | Ph | H | $CF_3$ | H | $CF_3$ | $^tC_4H_9$ | H | H | acac |
| 6'-17Y | Pt | 0 | 6' | Ph | H | $CF_3$ | H | $CF_3$ | $^tC_4H_9$ | H | H | — — |
| 6'-18 | Pt | 1 | 6' | Ph | $CF_3$ | H | H | $^tC_4H_9$ | $CH_3$ | H | H | pic |
| 6'-18X | Pt | 1 | 6' | Ph | $CF_3$ | H | H | $^tC_4H_9$ | $CH_3$ | H | H | acac |
| 6'-18Y | Pt | 0 | 6' | Ph | $CF_3$ | H | H | $^tC_4H_9$ | $CH_3$ | H | H | — — |
| 6'-19 | Pt | 1 | 6' | Ph | $CF_3$ | H | H | $^tC_4H_9$ | $^tC_4H_9$ | H | H | pic |
| 6'-19X | Pt | 1 | 6' | Ph | $CF_3$ | H | H | $^tC_4H_9$ | $^tC_4H_9$ | H | H | acac |
| 6'-19Y | Pt | 0 | 6' | Ph | $CF_3$ | H | H | $^tC_4H_9$ | $^tC_4H_9$ | H | H | — — |
| 6'-20 | Pt | 1 | 6' | Ph | H | $CF_3$ | H | $^tC_4H_9$ | $CH_3$ | H | H | pic |
| 6'-20X | Pt | 1 | 6' | Ph | H | $CF_3$ | H | $^tC_4H_9$ | $CH_3$ | H | H | acac |
| 6'-20Y | Pt | 0 | 6' | Ph | H | $CF_3$ | H | $^tC_4H_9$ | $CH_3$ | H | H | — — |
| 6'-21 | Pt | 1 | 6' | Ph | H | $CF_3$ | H | $^tC_4H_9$ | $^tC_4H_9$ | H | H | pic |
| 6'-21X | Pt | 1 | 6' | Ph | H | $CF_3$ | H | $^tC_4H_9$ | $^tC_4H_9$ | H | H | acac |
| 6'-21Y | Pt | 0 | 6' | Ph | H | $CF_3$ | H | $^tC_4H_9$ | $^tC_4H_9$ | H | H | — — |
| 6'-22 | Pt | 1 | 6' | Ph | H | $CF_3$ | H | $CH_3$ | $CH_3$ | H | H | pic |
| 6'-22X | Pt | 1 | 6' | Ph | H | $CF_3$ | H | $CH_3$ | $CH_3$ | H | H | acac |
| 6'-22Y | Pt | 0 | 6' | Ph | H | $CF_3$ | H | $CH_3$ | $CH_3$ | H | H | — — |
| 6'-23 | Pt | 1 | 6' | Ph | H | $CF_3$ | $CF_3$ | H | $CH_3$ | H | H | pic |
| 6'-23X | Pt | 1 | 6' | Ph | H | $CF_3$ | $CF_3$ | H | $CH_3$ | H | H | acac |
| 6'-23Y | Pt | 0 | 6' | Ph | H | $CF_3$ | $CF_3$ | H | $CH_3$ | H | H | — — |
| 6'-24 | Pt | 1 | 6' | Ph | H | H | $NO_2$ | H | $CH_3$ | H | H | pic |
| 6'-24X | Pt | 1 | 6' | Ph | H | H | $NO_2$ | H | $CH_3$ | H | H | acac |
| 6'-24Y | Pt | 0 | 6' | Ph | H | H | $NO_2$ | H | $CH_3$ | H | H | — — |
| 6'-25 | Pt | 1 | 6' | Ph | H | H | $NO_2$ | H | $^tC_4H_9$ | H | H | pic |
| 6'-25X | Pt | 1 | 6' | Ph | H | H | $NO_2$ | H | $^tC_4H_9$ | H | H | acac |
| 6'-25Y | Pt | 0 | 6' | Ph | H | H | $NO_2$ | H | $^tC_4H_9$ | H | H | — — |
| 6'-26 | Pt | 1 | 6' | Ph | F | H | $NO_2$ | H | $CH_3$ | H | H | pic |
| 6'-26X | Pt | 1 | 6' | Ph | F | H | $NO_2$ | H | $CH_3$ | H | H | acac |
| 6'-26Y | Pt | 0 | 6' | Ph | F | H | $NO_2$ | H | $CH_3$ | H | H | — — |
| 6'-27 | Pt | 1 | 6' | Ph | F | H | $NO_2$ | F | $CH_3$ | H | H | pic |
| 6'-27X | Pt | 1 | 6' | Ph | F | H | $NO_2$ | F | $CH_3$ | H | H | acac |
| 6'-27Y | Pt | 0 | 6' | Ph | F | H | $NO_2$ | F | $CH_3$ | H | H | — — |
| 6'-28 | Pt | 1 | 6' | Ph | H | $NO_2$ | H | $NO_2$ | $CH_3$ | H | H | pic |
| 6'-28X | Pt | 1 | 6' | Ph | H | $NO_2$ | H | $NO_2$ | $CH_3$ | H | H | acac |
| 6'-28Y | Pt | 0 | 6' | Ph | H | $NO_2$ | H | $NO_2$ | $CH_3$ | H | H | — — |
| 6'-29 | Pt | 1 | 6' | Ph | H | $NO_2$ | H | $NO_2$ | $^tC_4H_9$ | H | H | pic |
| 6'-29X | Pt | 1 | 6' | Ph | H | $NO_2$ | H | $NO_2$ | $^tC_4H_9$ | H | H | acac |
| 6'-29Y | Pt | 0 | 6' | Ph | H | $NO_2$ | H | $NO_2$ | $^tC_4H_9$ | H | H | — — |
| 6'-30 | Pt | 1 | 6' | Ph | $NO_2$ | H | H | $NO_2$ | $CH_3$ | H | H | pic |
| 6'-30X | Pt | 1 | 6' | Ph | $NO_2$ | H | H | $NO_2$ | $CH_3$ | H | H | acac |
| 6'-30Y | Pt | 0 | 6' | Ph | $NO_2$ | H | H | $NO_2$ | $CH_3$ | H | H | — — |
| 6'-31 | Pt | 1 | 6' | Ph | $NO_2$ | H | H | $NO_2$ | $^tC_4H_9$ | H | H | pic |
| 6'-31X | Pt | 1 | 6' | Ph | $NO_2$ | H | H | $NO_2$ | $^tC_4H_9$ | H | H | acac |
| 6'-31Y | Pt | 0 | 6' | Ph | $NO_2$ | H | H | $NO_2$ | $^tC_4H_9$ | H | H | — — |
| 6'-32 | Pt | 1 | 6' | Ph | H | H | $CF_3$ | H | $CH_3$ | H | H | pic |
| 6'-32X | Pt | 1 | 6' | Ph | H | H | $CF_3$ | H | $CH_3$ | H | H | acac |
| 6'-32Y | Pt | 0 | 6' | Ph | H | H | $CF_3$ | H | $CH_3$ | H | H | — — |
| 6'-33 | Pt | 1 | 6' | Ph | H | H | $CF_3$ | H | $^tC_4H_9$ | H | H | pic |
| 6'-33X | Pt | 1 | 6' | Ph | H | H | $CF_3$ | H | $^tC_4H_9$ | H | H | acac |
| 6'-33Y | Pt | 0 | 6' | Ph | H | H | $CF_3$ | H | $^tC_4H_9$ | H | H | — — |
| 6'-34 | Pt | 1 | 6' | Ph | H | Cl | $CF_3$ | H | $CH_3$ | H | H | pic |
| 6'-34X | Pt | 1 | 6' | Ph | H | Cl | $CF_3$ | H | $CH_3$ | H | H | acac |
| 6'-34Y | Pt | 0 | 6' | Ph | H | Cl | $CF_3$ | H | $CH_3$ | H | H | — — |
| 6'-35 | Pt | 1 | 6' | Ph | H | Cl | $CF_3$ | H | $^tC_4H_9$ | H | H | pic |
| 6'-35X | Pt | 1 | 6' | Ph | H | Cl | $CF_3$ | H | $^tC_4H_9$ | H | H | acac |
| 6'-35Y | Pt | 0 | 6' | Ph | H | Cl | $CF_3$ | H | $^tC_4H_9$ | H | H | — — |
| 6'-36 | Pt | 1 | 6' | Ph | H | $NO_2$ | H | H | $CH_3$ | H | H | pic |
| 6'-36X | Pt | 1 | 6' | Ph | H | $NO_2$ | H | H | $CH_3$ | H | H | acac |
| 6'-36Y | Pt | 0 | 6' | Ph | H | $NO_2$ | H | H | $CH_3$ | H | H | — — |
| 6'-37 | Pt | 1 | 6' | Ph | H | $CF_3$ | H | H | $CH_3$ | H | H | pic |
| 6'-37X | Pt | 1 | 6' | Ph | H | $CF_3$ | H | H | $CH_3$ | H | H | acac |
| 6'-37Y | Pt | 0 | 6' | Ph | H | $CF_3$ | H | H | $CH_3$ | H | H | — — |
| 6'-38 | Pt | 1 | 6' | Ph | H | $NO_2$ | H | $CH_3$ | $CH_3$ | H | H | pic |
| 6'-38X | Pt | 1 | 6' | Ph | H | $NO_2$ | H | $CH_3$ | $CH_3$ | H | H | acac |
| 6'-38Y | Pt | 0 | 6' | Ph | H | $NO_2$ | H | $CH_3$ | $CH_3$ | H | H | — — |
| 6'-39 | Pt | 1 | 6' | Ph | H | $NO_2$ | H | $CH_3$ | $^tC_4H_9$ | H | H | pic |
| 6'-39X | Pt | 1 | 6' | Ph | H | $NO_2$ | H | $CH_3$ | $^tC_4H_9$ | H | H | acac |
| 6'-39Y | Pt | 0 | 6' | Ph | H | $NO_2$ | H | $CH_3$ | $^tC_4H_9$ | H | H | — — |
| 6'-40 | Pt | 1 | 6' | Ph | H | $NO_2$ | H | $^tC_4H_9$ | $CH_3$ | H | H | pic |
| 6'-40X | Pt | 1 | 6' | Ph | H | $NO_2$ | H | $^tC_4H_9$ | $CH_3$ | H | H | acac |

TABLE 34-continued

| No. | M | m | BSS | SS G | T$^1$ | T$^2$ | T$^3$ | T$^4$ | T$^5$ | T$^6$ | T$^7$ | L$^1$ | L$^2$ |
|---|---|---|---|---|---|---|---|---|---|---|---|---|---|
| 6'-40Y | Pt | 0 | 6' | Ph | H | NO$_2$ | H | $^t$C$_4$H$_9$ | CH$_3$ | H | H | — | — |
| 6'-41 | Pt | 1 | 6' | Ph | H | NO$_2$ | H | $^t$C$_4$H$_9$ | $^t$C$_4$H$_9$ | H | H | pic | |
| 6'-41X | Pt | 1 | 6' | Ph | H | NO$_2$ | H | $^t$C$_4$H$_9$ | $^t$C$_4$H$_9$ | H | H | acac | |
| 6'-41Y | Pt | 0 | 6' | Ph | H | NO$_2$ | H | $^t$C$_4$H$_9$ | $^t$C$_4$H$_9$ | H | H | — | — |
| 6'-42 | Pt | 1 | 6' | Ph | H | H | CH$_3$O | H | CH$_3$ | H | H | pic | |
| 6'-42X | Pt | 1 | 6' | Ph | H | H | CH$_3$O | H | CH$_3$ | H | H | acac | |
| 6'-42Y | Pt | 0 | 6' | Ph | H | H | CH$_3$O | H | CH$_3$ | H | H | — | — |
| 6'-43 | Pt | 1 | 6' | Ph | H | CH$_3$O | H | H | CH$_3$ | H | H | pic | |
| 6'-43X | Pt | 1 | 6' | Ph | H | CH$_3$O | H | H | CH$_3$ | H | H | acac | |
| 6'-43Y | Pt | 0 | 6' | Ph | H | CH$_3$O | H | H | CH$_3$ | H | H | — | — |
| 6'-44 | Pt | 1 | 6' | Ph | H | CH$_3$O | H | CH$_3$ | CH$_3$ | H | H | pic | |
| 6'-44X | Pt | 1 | 6' | Ph | H | CH$_3$O | H | CH$_3$ | CH$_3$ | H | H | acac | |
| 6'-44Y | Pt | 0 | 6' | Ph | H | CH$_3$O | H | CH$_3$ | CH$_3$ | H | H | — | — |
| 6'-45 | Pt | 1 | 6' | Ph | H | CH$_3$O | H | $^t$C$_4$H$_9$ | CH$_3$ | H | H | pic | |
| 6'-45X | Pt | 1 | 6' | Ph | H | CH$_3$O | H | $^t$C$_4$H$_9$ | CH$_3$ | H | H | acac | |
| 6'-45Y | Pt | 0 | 6' | Ph | H | CH$_3$O | H | $^t$C$_4$H$_9$ | CH$_3$ | H | H | — | — |
| 6'-46 | Pt | 1 | 6' | Ph | H | Si(CH$_3$)$_3$ | H | H | CH$_3$ | H | H | pic | |
| 6'-46X | Pt | 1 | 6' | Ph | H | Si(CH$_3$)$_3$ | H | H | CH$_3$ | H | H | acac | |
| 6'-46Y | Pt | 0 | 6' | Ph | H | Si(CH$_3$)$_3$ | H | H | CH$_3$ | H | H | — | — |
| 6'-47 | Pt | 1 | 6' | Ph | H | Si(CH$_3$)$_3$ | H | H | $^t$C$_4$H$_9$ | H | H | pic | |
| 6'-47X | Pt | 1 | 6' | Ph | H | Si(CH$_3$)$_3$ | H | H | $^t$C$_4$H$_9$ | H | H | acac | |
| 6'-47Y | Pt | 0 | 6' | Ph | H | Si(CH$_3$)$_3$ | H | H | $^t$C$_4$H$_9$ | H | H | — | — |
| 6'-48 | Pt | 1 | 6' | Ph | H | H | Si(CH$_3$)$_3$ | H | CH$_3$ | H | H | pic | |
| 6'-48X | Pt | 1 | 6' | Ph | H | H | Si(CH$_3$)$_3$ | H | CH$_3$ | H | H | acac | |
| 6'-48Y | Pt | 0 | 6' | Ph | H | H | Si(CH$_3$)$_3$ | H | CH$_3$ | H | H | — | — |
| 6'-49 | Pt | 1 | 6' | Ph | H | H | H | Si(CH$_3$)$_3$ | CH$_3$ | H | H | pic | |
| 6'-49X | Pt | 1 | 6' | Ph | H | H | H | Si(CH$_3$)$_3$ | CH$_3$ | H | H | acac | |
| 6'-49Y | Pt | 0 | 6' | Ph | H | H | H | Si(CH$_3$)$_3$ | CH$_3$ | H | H | — | — |
| 6'-50 | Pt | 1 | 6' | Ph | H | F | H | Si(CH$_3$)$_3$ | CH$_3$ | H | H | pic | |
| 6'-50X | Pt | 1 | 6' | Ph | H | F | H | Si(CH$_3$)$_3$ | CH$_3$ | H | H | acac | |
| 6'-50Y | Pt | 0 | 6' | Ph | H | F | H | Si(CH$_3$)$_3$ | CH$_3$ | H | H | — | — |
| 6'-51 | Pt | 1 | 6' | Ph | H | CF$_3$ | H | Si(CH$_3$)$_3$ | CH$_3$ | H | H | pic | |
| 6'-51X | Pt | 1 | 6' | Ph | H | CF$_3$ | H | Si(CH$_3$)$_3$ | CH$_3$ | H | H | acac | |
| 6'-51Y | Pt | 0 | 6' | Ph | H | CF$_3$ | H | Si(CH$_3$)$_3$ | CH$_3$ | H | H | — | — |
| 6'-52 | Pt | 1 | 6' | Ph | H | CF$_3$ | H | Si(CH$_3$)$_3$ | $^t$C$_4$H$_9$ | H | H | pic | |
| 6'-52X | Pt | 1 | 6' | Ph | H | CF$_3$ | H | Si(CH$_3$)$_3$ | $^t$C$_4$H$_9$ | H | H | acac | |
| 6'-52Y | Pt | 0 | 6' | Ph | H | CF$_3$ | H | Si(CH$_3$)$_3$ | $^t$C$_4$H$_9$ | H | H | — | — |
| 6'-53 | Pt | 1 | 6' | Ph | H | Si(CH$_3$)$_3$ | H | F | CH$_3$ | H | H | pic | |
| 6'-53X | Pt | 1 | 6' | Ph | H | Si(CH$_3$)$_3$ | H | F | CH$_3$ | H | H | acac | |
| 6'-53Y | Pt | 0 | 6' | Ph | H | Si(CH$_3$)$_3$ | H | F | CH$_3$ | H | H | — | — |
| 6'-54 | Pt | 1 | 6' | Ph | H | Si(CH$_3$)$_3$ | H | F | $^t$C$_4$H$_9$ | H | H | pic | |
| 6'-54X | Pt | 1 | 6' | Ph | H | Si(CH$_3$)$_3$ | H | F | $^t$C$_4$H$_9$ | H | H | acac | |
| 6'-54Y | Pt | 0 | 6' | Ph | H | Si(CH$_3$)$_3$ | H | F | $^t$C$_4$H$_9$ | H | H | — | — |
| 6'-55 | Pt | 1 | 6' | Ph | H | Si(CH$_3$)$_3$ | H | CF$_3$ | CH$_3$ | H | H | pic | |
| 6'-55X | Pt | 1 | 6' | Ph | H | Si(CH$_3$)$_3$ | H | CF$_3$ | CH$_3$ | H | H | acac | |
| 6'-55Y | Pt | 0 | 6' | Ph | H | Si(CH$_3$)$_3$ | H | CF$_3$ | CH$_3$ | H | H | — | — |
| 6'-56 | Pt | 1 | 6' | Ph | H | Si(CH$_3$)$_3$ | H | CF$_3$ | $^t$C$_4$H$_9$ | H | H | pic | |
| 6'-56X | Pt | 1 | 6' | Ph | H | Si(CH$_3$)$_3$ | H | CF$_3$ | $^t$C$_4$H$_9$ | H | H | acac | |
| 6'-56Y | Pt | 0 | 6' | Ph | H | Si(CH$_3$)$_3$ | H | CF$_3$ | $^t$C$_4$H$_9$ | H | H | — | — |
| 6'-57 | Pt | 1 | 6' | Ph | Si(CH$_3$)$_3$ | H | Si(CH$_3$)$_3$ | H | CH$_3$ | H | H | pic | |
| 6'-57X | Pt | 1 | 6' | Ph | Si(CH$_3$)$_3$ | H | Si(CH$_3$)$_3$ | H | CH$_3$ | H | H | acac | |
| 6'-57Y | Pt | 0 | 6' | Ph | Si(CH$_3$)$_3$ | H | Si(CH$_3$)$_3$ | H | CH$_3$ | H | H | — | — |
| 6'-58 | Pt | 1 | 6' | Ph | Si(CH$_3$)$_3$ | H | Si(CH$_3$)$_3$ | H | $^t$C$_4$H$_9$ | H | H | pic | |
| 6'-58X | Pt | 1 | 6' | Ph | Si(CH$_3$)$_3$ | H | Si(CH$_3$)$_3$ | H | $^t$C$_4$H$_9$ | H | H | acac | |
| 6'-58Y | Pt | 0 | 6' | Ph | Si(CH$_3$)$_3$ | H | Si(CH$_3$)$_3$ | H | $^t$C$_4$H$_9$ | H | H | — | — |
| 6'-59 | Pt | 1 | 6' | Ph | H | H | H | COCH$_3$ | CH$_3$ | H | H | pic | |
| 6'-59X | Pt | 1 | 6' | Ph | H | H | H | COCH$_3$ | CH$_3$ | H | H | acac | |
| 6'-59Y | Pt | 0 | 6' | Ph | H | H | H | COCH$_3$ | CH$_3$ | H | H | — | — |
| 6'-60 | Pt | 1 | 6' | Ph | H | H | COCH$_3$ | H | CH$_3$ | H | H | pic | |
| 6'-60X | Pt | 1 | 6' | Ph | H | H | COCH$_3$ | H | CH$_3$ | H | H | acac | |
| 6'-60Y | Pt | 0 | 6' | Ph | H | H | COCH$_3$ | H | CH$_3$ | H | H | — | — |
| 6'-61 | Pt | 1 | 6' | Ph | H | COCH$_3$ | H | H | CH$_3$ | H | H | pic | |
| 6'-61X | Pt | 1 | 6' | Ph | H | COCH$_3$ | H | H | CH$_3$ | H | H | acac | |
| 6'-61Y | Pt | 0 | 6' | Ph | H | COCH$_3$ | H | H | CH$_3$ | H | H | — | — |
| 6'-62 | Pt | 1 | 6' | Ph | H | H | BL | | CH$_3$ | H | H | pic | |
| 6'-62X | Pt | 1 | 6' | Ph | H | H | BL | | CH$_3$ | H | H | acac | |
| 6'-62Y | Pt | 0 | 6' | Ph | H | H | BL | | CH$_3$ | H | H | — | — |
| 6'-63 | Pt | 1 | 6' | Ph | H | H | BL | | $^t$C$_4$H$_9$ | H | H | pic | |
| 6'-63X | Pt | 1 | 6' | Ph | H | H | BL | | $^t$C$_4$H$_9$ | H | H | acac | |
| 6'-63Y | Pt | 0 | 6' | Ph | H | H | BL | | $^t$C$_4$H$_9$ | H | H | — | — |
| 6'-64 | Pt | 1 | 6' | Ph | H | BL | | H | CH$_3$ | H | H | pic | |
| 6'-64X | Pt | 1 | 6' | Ph | H | BL | | H | CH$_3$ | H | H | acac | |
| 6'-64Y | Pt | 0 | 6' | Ph | H | BL | | H | CH$_3$ | H | H | — | — |
| 6'-65 | Pt | 1 | 6' | Ph | H | BL | | H | $^t$C$_4$H$_9$ | H | H | pic | |
| 6'-65X | Pt | 1 | 6' | Ph | H | BL | | H | $^t$C$_4$H$_9$ | H | H | acac | |
| 6'-65Y | Pt | 0 | 6' | Ph | H | BL | | H | $^t$C$_4$H$_9$ | H | H | — | — |
| 6'-66 | Pt | 1 | 6' | Ph | H | H | PL | | CH$_3$ | H | H | pic | |

TABLE 34-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 6'-66X | Pt | 1 | 6' | Ph | H | H |  | PL | CH₃ | H | H | acac |
| 6'-66Y | Pt | 0 | 6' | Ph | H | H |  | PL | CH₃ | H | H | — — |
| 6'-67 | Pt | 1 | 6' | Ph | H | H |  | PL | ᵗC₄H₉ | H | H | pic |
| 6'-67X | Pt | 1 | 6' | Ph | H | H |  | PL | ᵗC₄H₉ | H | H | acac |
| 6'-67Y | Pt | 0 | 6' | Ph | H | H |  | PL | ᵗC₄H₉ | H | H | — — |
| 6'-68 | Pt | 1 | 6' | Ph | H |  | PL |  | H CH₃ | H | H | pic |
| 6'-68X | Pt | 1 | 6' | Ph | H |  | PL |  | H CH₃ | H | H | acac |
| 6'-68Y | Pt | 0 | 6' | Ph | H |  | PL |  | H CH₃ | H | H | — — |
| 6'-69 | Pt | 1 | 6' | Ph | H |  | PL |  | H ᵗC₄H₉ | H | H | pic |
| 6'-69X | Pt | 1 | 6' | Ph | H |  | PL |  | H ᵗC₄H₉ | H | H | acac |
| 6'-69Y | Pt | 0 | 6' | Ph | H |  | PL |  | H ᵗC₄H₉ | H | H | — — |
| 6'-70 | Pt | 1 | 6' | Ph | H | H |  | MEE1 | CH₃ | H | H | pic |
| 6'-70X | Pt | 1 | 6' | Ph | H | H |  | MEE1 | CH₃ | H | H | acac |
| 6'-70Y | Pt | 0 | 6' | Ph | H | H |  | MEE1 | CH₃ | H | H | — — |
| 6'-71 | Pt | 1 | 6' | Ph | H |  | MEE1 |  | H CH₃ | H | H | pic |
| 6'-71X | Pt | 1 | 6' | Ph | H |  | MEE1 |  | H CH₃ | H | H | acac |
| 6'-71Y | Pt | 0 | 6' | Ph | H |  | MEE1 |  | H CH₃ | H | H | — — |
| 6'-72 | Pt | 1 | 6' | Ph | H | H |  | MEE2 | CH₃ | H | H | pic |
| 6'-72X | Pt | 1 | 6' | Ph | H | H |  | MEE2 | CH₃ | H | H | acac |
| 6'-72Y | Pt | 0 | 6' | Ph | H | H |  | MEE2 | CH₃ | H | H | — — |
| 6'-73 | Pt | 1 | 6' | Ph | H |  | MEE2 |  | H CH₃ | H | H | pic |
| 6'-73X | Pt | 1 | 6' | Ph | H |  | MEE2 |  | H CH₃ | H | H | acac |
| 6'-73Y | Pt | 0 | 6' | Ph | H |  | MEE2 |  | H CH₃ | H | H | — — |
| 6'-74 | Pt | 1 | 6' | Ph | H | H |  | PA1 | CH₃ | H | H | pic |
| 6'-74X | Pt | 1 | 6' | Ph | H | H |  | PA1 | CH₃ | H | H | acac |
| 6'-74Y | Pt | 0 | 6' | Ph | H | H |  | PA1 | CH₃ | H | H | — — |
| 6'-75 | Pt | 1 | 6' | Ph | H |  | PA1 |  | H CH₃ | H | H | pic |
| 6'-75X | Pt | 1 | 6' | Ph | H |  | PA1 |  | H CH₃ | H | H | acac |
| 6'-75Y | Pt | 0 | 6' | Ph | H |  | PA1 |  | H CH₃ | H | H | — — |
| 6'-76 | Pt | 1 | 6' | Ph | H | H |  | PA2 | CH₃ | H | H | pic |
| 6'-76X | Pt | 1 | 6' | Ph | H | H |  | PA2 | CH₃ | H | H | acac |
| 6'-76Y | Pt | 0 | 6' | Ph | H | H |  | PA2 | CH₃ | H | H | — — |
| 6'-77 | Pt | 1 | 6' | Ph | H |  | PA2 |  | H CH₃ | H | H | pic |
| 6'-77X | Pt | 1 | 6' | Ph | H |  | PA2 |  | H CH₃ | H | H | acac |
| 6'-77Y | Pt | 0 | 6' | Ph | H |  | PA2 |  | H CH₃ | H | H | — — |
| 6'-78 | Pt | 1 | 6' | Ph | H | H |  | EA1 | CH₃ | H | H | pic |
| 6'-78X | Pt | 1 | 6' | Ph | H | H |  | EA1 | CH₃ | H | H | acac |
| 6'-78Y | Pt | 0 | 6' | Ph | H | H |  | EA1 | CH₃ | H | H | — — |
| 6'-79 | Pt | 1 | 6' | Ph | H |  | EA2 |  | H CH₃ | H | H | pic |
| 6'-79X | Pt | 1 | 6' | Ph | H |  | EA2 |  | H CH₃ | H | H | acac |
| 6'-79Y | Pt | 0 | 6' | Ph | H |  | EA2 |  | H CH₃ | H | H | — — |
| 6'-80 | Pt | 1 | 6' | Ph | H | H |  | ME | CH₃ | H | H | pic |
| 6'-80X | Pt | 1 | 6' | Ph | H | H |  | ME | CH₃ | H | H | acac |
| 6'-80Y | Pt | 0 | 6' | Ph | H | H |  | ME | CH₃ | H | H | — — |
| 6'-81 | Pt | 1 | 6' | Ph | H |  | ME |  | H CH₃ | H | H | pic |
| 6'-81X | Pt | 1 | 6' | Ph | H |  | ME |  | H CH₃ | H | H | acac |
| 6'-81Y | Pt | 0 | 6' | Ph | H |  | ME |  | H CH₃ | H | H | — — |
| 6'-82 | Pt | 1 | 6' | Ph | H | H |  | AT | CH₃ | H | H | pic |
| 6'-82X | Pt | 1 | 6' | Ph | H | H |  | AT | CH₃ | H | H | acac |
| 6'-82Y | Pt | 0 | 6' | Ph | H | H |  | AT | CH₃ | H | H | — — |
| 6'-83 | Pt | 1 | 6' | Ph | H |  | AT |  | H CH₃ | H | H | pic |
| 6'-83X | Pt | 1 | 6' | Ph | H |  | AT |  | H CH₃ | H | H | acac |
| 6'-83Y | Pt | 0 | 6' | Ph | H |  | AT |  | H CH₃ | H | H | — — |
| 6'-84 | Pt | 1 | 6' | Ph | H | H |  | MES1 | CH₃ | H | H | pic |
| 6'-84X | Pt | 1 | 6' | Ph | H | H |  | MES1 | CH₃ | H | H | acac |
| 6'-84Y | Pt | 0 | 6' | Ph | H | H |  | MES1 | CH₃ | H | H | — — |
| 6'-85 | Pt | 1 | 6' | Ph | H |  | MES1 |  | H CH₃ | H | H | pic |
| 6'-85X | Pt | 1 | 6' | Ph | H |  | MES1 |  | H CH₃ | H | H | acac |
| 6'-85Y | Pt | 0 | 6' | Ph | H |  | MES1 |  | H CH₃ | H | H | — — |
| 6'-86 | Pt | 1 | 6' | Ph | H | H |  | MES2 | CH₃ | H | H | pic |
| 6'-86X | Pt | 1 | 6' | Ph | H | H |  | MES2 | CH₃ | H | H | acac |
| 6'-86Y | Pt | 0 | 6' | Ph | H | H |  | MES2 | CH₃ | H | H | — — |
| 6'-87 | Pt | 1 | 6' | Ph | H |  | MES2 |  | H CH₃ | H | H | pic |
| 6'-87X | Pt | 1 | 6' | Ph | H |  | MES2 |  | H CH₃ | H | H | acac |
| 6'-87Y | Pt | 0 | 6' | Ph | H |  | MES2 |  | H CH₃ | H | H | — — |
| 6'-88 | Pt | 1 | 6' | Ph | H | H |  | PS1 | CH₃ | H | H | pic |
| 6'-88X | Pt | 1 | 6' | Ph | H | H |  | PS1 | CH₃ | H | H | acac |
| 6'-88Y | Pt | 0 | 6' | Ph | H | H |  | PS1 | CH₃ | H | H | — — |
| 6'-89 | Pt | 1 | 6' | Ph | H |  | PS1 |  | H CH₃ | H | H | pic |
| 6'-89X | Pt | 1 | 6' | Ph | H |  | PS1 |  | H CH₃ | H | H | acac |
| 6'-89Y | Pt | 0 | 6' | Ph | H |  | PS1 |  | H CH₃ | H | H | — — |
| 6'-90 | Pt | 1 | 6' | Ph | H | H |  | PS2 | CH₃ | H | H | pic |
| 6'-90X | Pt | 1 | 6' | Ph | H | H |  | PS2 | CH₃ | H | H | acac |
| 6'-90Y | Pt | 0 | 6' | Ph | H | H |  | PS2 | CH₃ | H | H | — — |
| 6'-91 | Pt | 1 | 6' | Ph | H |  | PS2 |  | H CH₃ | H | H | pic |
| 6'-91X | Pt | 1 | 6' | Ph | H |  | PS2 |  | H CH₃ | H | H | acac |
| 6'-91Y | Pt | 0 | 6' | Ph | H |  | PS2 |  | H CH₃ | H | H | — — |

TABLE 34-continued

| No. | M | m | BSS | SS G | $T^1$ | $T^2$ | $T^3$ | $T^4$ | $T^5$ | $T^6$ | $T^7$ | $L^1$ $L^2$ |
|---|---|---|---|---|---|---|---|---|---|---|---|---|
| 6'-92 | Pt | 1 | 6' | Ph | H | H | | BAL1 | $CH_3$ | H | H | pic |
| 6'-92X | Pt | 1 | 6' | Ph | H | H | | BAL1 | $CH_3$ | H | H | acac |
| 6'-92Y | Pt | 0 | 6' | Ph | H | H | | BAL1 | $CH_3$ | H | H | — — |
| 6'-93 | Pt | 1 | 6' | Ph | H | | BAL1 | | H | $CH_3$ | H | H | pic |
| 6'-93X | Pt | 1 | 6' | Ph | H | | BAL1 | | H | $CH_3$ | H | H | acac |
| 6'-93Y | Pt | 0 | 6' | Ph | H | | BAL1 | | H | $CH_3$ | H | H | — — |
| 6'-94 | Pt | 1 | 6' | Ph | H | H | | BAL2 | $CH_3$ | H | H | pic |
| 6'-94X | Pt | 1 | 6' | Ph | H | H | | BAL2 | $CH_3$ | H | H | acac |
| 6'-94Y | Pt | 0 | 6' | Ph | H | H | | BAL2 | $CH_3$ | H | H | — — |
| 6'-95 | Pt | 1 | 6' | Ph | H | | BAL2 | | H | $CH_3$ | H | H | pic |
| 6'-95X | Pt | 1 | 6' | Ph | H | | BAL2 | | H | $CH_3$ | H | H | acac |
| 6'-95Y | Pt | 0 | 6' | Ph | H | | BAL2 | | H | $CH_3$ | H | H | — — |
| 6'-96 | Pt | 1 | 6' | Ph | H | H | | MEK1 | $CH_3$ | H | H | pic |
| 6'-96X | Pt | 1 | 6' | Ph | H | H | | MEK1 | $CH_3$ | H | H | acac |
| 6'-96Y | Pt | 0 | 6' | Ph | H | H | | MEK1 | $CH_3$ | H | H | — — |
| 6'-97 | Pt | 1 | 6' | Ph | H | | MEK1 | | H | $CH_3$ | H | H | pic |
| 6'-97X | Pt | 1 | 6' | Ph | H | | MEK1 | | H | $CH_3$ | H | H | acac |
| 6'-97Y | Pt | 0 | 6' | Ph | H | | MEK1 | | H | $CH_3$ | H | H | — — |
| 6'-98 | Pt | 1 | 6' | Ph | H | H | | MEK2 | $CH_3$ | H | H | pic |
| 6'-98X | Pt | 1 | 6' | Ph | H | H | | MEK2 | $CH_3$ | H | H | acac |
| 6'-98Y | Pt | 0 | 6' | Ph | H | H | | MEK2 | $CH_3$ | H | H | — — |
| 6'-99 | Pt | 1 | 6' | Ph | H | | MEK2 | | H | $CH_3$ | H | H | pic |
| 6'-99X | Pt | 1 | 6' | Ph | H | | MEK2 | | H | $CH_3$ | H | H | acac |
| 6'-99Y | Pt | 0 | 6' | Ph | H | | MEK2 | | H | $CH_3$ | H | H | — — |
| 6'-100 | Pt | 1 | 6' | Ph | H | H | | PAL1 | $CH_3$ | H | H | pic |
| 6'-100X | Pt | 1 | 6' | Ph | H | H | | PAL1 | $CH_3$ | H | H | acac |
| 6'-100Y | Pt | 0 | 6' | Ph | H | H | | PAL1 | $CH_3$ | H | H | — — |
| 6'-101 | Pt | 1 | 6' | Ph | H | | PAL1 | | H | $CH_3$ | H | H | pic |
| 6'-101X | Pt | 1 | 6' | Ph | H | | PAL1 | | H | $CH_3$ | H | H | acac |
| 6'-101Y | Pt | 0 | 6' | Ph | H | | PAL1 | | H | $CH_3$ | H | H | — — |
| 6'-102 | Pt | 1 | 6' | Ph | H | H | | PAL2 | $CH_3$ | H | H | pic |
| 6'-102X | Pt | 1 | 6' | Ph | H | H | | PAL2 | $CH_3$ | H | H | acac |
| 6'-102Y | Pt | 0 | 6' | Ph | H | H | | PAL2 | $CH_3$ | H | H | — — |
| 6'-103 | Pt | 1 | 6' | Ph | H | | PAL2 | | H | $CH_3$ | H | H | pic |
| 6'-103X | Pt | 1 | 6' | Ph | H | | PAL2 | | H | $CH_3$ | H | H | acac |
| 6'-103Y | Pt | 0 | 6' | Ph | H | | PAL2 | | H | $CH_3$ | H | H | — — |
| 6'-104 | Pt | 1 | 6' | Ph | H | H | | MMK | $CH_3$ | H | H | pic |
| 6'-104X | Pt | 1 | 6' | Ph | H | H | | MMK | $CH_3$ | H | H | acac |
| 6'-104Y | Pt | 0 | 6' | Ph | H | H | | MMK | $CH_3$ | H | H | — — |
| 6'-105 | Pt | 1 | 6' | Ph | H | | MMK | | H | $CH_3$ | H | H | pic |
| 6'-105X | Pt | 1 | 6' | Ph | H | | MMK | | H | $CH_3$ | H | H | acac |
| 6'-105Y | Pt | 0 | 6' | Ph | H | | MMK | | H | $CH_3$ | H | H | — — |
| 6'-106 | Pt | 1 | 6' | Ph | H | H | | EES1 | $CH_3$ | H | H | pic |
| 6'-106X | Pt | 1 | 6' | Ph | H | H | | EES1 | $CH_3$ | H | H | acac |
| 6'-106Y | Pt | 0 | 6' | Ph | H | H | | EES1 | $CH_3$ | H | H | — — |
| 6'-107 | Pt | 1 | 6' | Ph | H | | EES2 | | H | $CH_3$ | H | H | pic |
| 6'-107X | Pt | 1 | 6' | Ph | H | | EES2 | | H | $CH_3$ | H | H | acac |
| 6'-107Y | Pt | 0 | 6' | Ph | H | | EES2 | | H | $CH_3$ | H | H | — — |
| 6'-108 | Pt | 1 | 6' | Ph | H | H | | PAE1 | $CH_3$ | H | H | pic |
| 6'-108X | Pt | 1 | 6' | Ph | H | H | | PAE1 | $CH_3$ | H | H | acac |
| 6'-108Y | Pt | 0 | 6' | Ph | H | H | | PAE1 | $CH_3$ | H | H | — — |
| 6'-109 | Pt | 1 | 6' | Ph | H | | PAE2 | | H | $CH_3$ | H | H | pic |
| 6'-109X | Pt | 1 | 6' | Ph | H | | PAE2 | | H | $CH_3$ | H | H | acac |
| 6'-109Y | Pt | 0 | 6' | Ph | H | | PAE2 | | H | $CH_3$ | H | H | — — |
| 6'-110 | Pt | 1 | 6' | Ph | H | H | | AME1 | $CH_3$ | H | H | pic |
| 6'-110X | Pt | 1 | 6' | Ph | H | H | | AME1 | $CH_3$ | H | H | acac |
| 6'-110Y | Pt | 0 | 6' | Ph | H | H | | AME1 | $CH_3$ | H | H | — — |
| 6'-111 | Pt | 1 | 6' | Ph | H | | AME1 | | H | $CH_3$ | H | H | pic |
| 6'-111X | Pt | 1 | 6' | Ph | H | | AME1 | | H | $CH_3$ | H | H | acac |
| 6'-111Y | Pt | 0 | 6' | Ph | H | | AME1 | | H | $CH_3$ | H | H | — — |
| 6'-112 | Pt | 1 | 6' | Ph | H | H | | AME2 | $CH_3$ | H | H | pic |
| 6'-112X | Pt | 1 | 6' | Ph | H | H | | AME2 | $CH_3$ | H | H | acac |
| 6'-112Y | Pt | 0 | 6' | Ph | H | H | | AME2 | $CH_3$ | H | H | — — |
| 6'-113 | Pt | 1 | 6' | Ph | H | | AME2 | | H | $CH_3$ | H | H | pic |
| 6'-113X | Pt | 1 | 6' | Ph | H | | AME2 | | H | $CH_3$ | H | H | acac |
| 6'-113Y | Pt | 0 | 6' | Ph | H | | AME2 | | H | $CH_3$ | H | H | — — |
| 6'-114 | Pt | 1 | 6' | Ph | H | H | | EAE1 | $CH_3$ | H | H | pic |
| 6'-114X | Pt | 1 | 6' | Ph | H | H | | EAE1 | $CH_3$ | H | H | acac |
| 6'-114Y | Pt | 0 | 6' | Ph | H | H | | EAE1 | $CH_3$ | H | H | — — |
| 6'-115 | Pt | 1 | 6' | Ph | H | | EAE1 | | H | $CH_3$ | H | H | pic |
| 6'-115X | Pt | 1 | 6' | Ph | H | | EAE1 | | H | $CH_3$ | H | H | acac |
| 6'-115Y | Pt | 0 | 6' | Ph | H | | EAE1 | | H | $CH_3$ | H | H | — — |
| 6'-116 | Pt | 1 | 6' | Ph | H | H | | EAE2 | $CH_3$ | H | H | pic |
| 6'-116X | Pt | 1 | 6' | Ph | H | H | | EAE2 | $CH_3$ | H | H | acac |
| 6'-116Y | Pt | 0 | 6' | Ph | H | H | | EAE2 | $CH_3$ | H | H | — — |
| 6'-117 | Pt | 1 | 6' | Ph | H | | EAE2 | | H | $CH_3$ | H | H | pic |
| 6'-117X | Pt | 1 | 6' | Ph | H | | EAE2 | | H | $CH_3$ | H | H | acac |

TABLE 34-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 6'-117Y | Pt | 0 | 6' | Ph | H |  | EAE2 | H | CH₃ | H | H | — — |
| 6'-118 | Pt | 1 | 6' | Ph | H | H |  | AAE1 | CH₃ | H | H | pic |
| 6'-118X | Pt | 1 | 6' | Ph | H | H |  | AAE1 | CH₃ | H | H | acac |
| 6'-118Y | Pt | 0 | 6' | Ph | H | H |  | AAE1 | CH₃ | H | H | — — |
| 6'-119 | Pt | 1 | 6' | Ph | H |  | AAE1 | H | CH₃ | H | H | pic |
| 6'-119X | Pt | 1 | 6' | Ph | H |  | AAE1 | H | CH₃ | H | H | acac |
| 6'-119Y | Pt | 0 | 6' | Ph | H |  | AAE1 | H | CH₃ | H | H | — — |
| 6'-120 | Pt | 1 | 6' | Ph | H | H |  | AAE2 | CH₃ | H | H | pic |
| 6'-120X | Pt | 1 | 6' | Ph | H | H |  | AAE2 | CH₃ | H | H | acac |
| 6'-120Y | Pt | 0 | 6' | Ph | H | H |  | AAE2 | CH₃ | H | H | — — |
| 6'-121 | Pt | 1 | 6' | Ph | H |  | AAE2 | H | CH₃ | H | H | pic |
| 6'-121X | Pt | 1 | 6' | Ph | H |  | AAE2 | H | CH₃ | H | H | acac |
| 6'-121Y | Pt | 0 | 6' | Ph | H |  | AAE2 | H | CH₃ | H | H | — — |
| 6'-122 | Pt | 1 | 6' | Ph | H | H |  | PME1 | CH₃ | H | H | pic |
| 6'-122X | Pt | 1 | 6' | Ph | H | H |  | PME1 | CH₃ | H | H | acac |
| 6'-122Y | Pt | 0 | 6' | Ph | H | H |  | PME1 | CH₃ | H | H | — — |
| 6'-123 | Pt | 1 | 6' | Ph | H |  | PME1 | H | CH₃ | H | H | pic |
| 6'-123X | Pt | 1 | 6' | Ph | H |  | PME1 | H | CH₃ | H | H | acac |
| 6'-123Y | Pt | 0 | 6' | Ph | H |  | PME1 | H | CH₃ | H | H | — — |
| 6'-124 | Pt | 1 | 6' | Ph | H | H |  | PME2 | CH₃ | H | H | pic |
| 6'-124X | Pt | 1 | 6' | Ph | H | H |  | PME2 | CH₃ | H | H | acac |
| 6'-124Y | Pt | 0 | 6' | Ph | H | H |  | PME2 | CH₃ | H | H | — — |
| 6'-125 | Pt | 1 | 6' | Ph | H |  | PME2 | H | CH₃ | H | H | pic |
| 6'-125X | Pt | 1 | 6' | Ph | H |  | PME2 | H | CH₃ | H | H | acac |
| 6'-125Y | Pt | 0 | 6' | Ph | H |  | PME2 | H | CH₃ | H | H | — — |
| 6'-126 | Pt | 1 | 6' | Ph | H | H |  | MET1 | CH₃ | H | H | pic |
| 6'-126X | Pt | 1 | 6' | Ph | H | H |  | MET1 | CH₃ | H | H | acac |
| 6'-126Y | Pt | 0 | 6' | Ph | H | H |  | MET1 | CH₃ | H | H | — — |
| 6'-127 | Pt | 1 | 6' | Ph | H |  | MET1 | H | CH₃ | H | H | pic |
| 6'-127X | Pt | 1 | 6' | Ph | H |  | MET1 | H | CH₃ | H | H | acac |
| 6'-127Y | Pt | 0 | 6' | Ph | H |  | MET1 | H | CH₃ | H | H | — — |
| 6'-128 | Pt | 1 | 6' | Ph | H | H |  | MET2 | CH₃ | H | H | pic |
| 6'-128X | Pt | 1 | 6' | Ph | H | H |  | MET2 | CH₃ | H | H | acac |
| 6'-128Y | Pt | 0 | 6' | Ph | H | H |  | MET2 | CH₃ | H | H | — — |
| 6'-129 | Pt | 1 | 6' | Ph | H |  | MET2 | H | CH₃ | H | H | pic |
| 6'-129X | Pt | 1 | 6' | Ph | H |  | MET2 | H | CH₃ | H | H | acac |
| 6'-129Y | Pt | 0 | 6' | Ph | H |  | MET2 | H | CH₃ | H | H | — — |
| 6'-130 | Pt | 1 | 6' | Ph | H | H |  | EE1 | CH₃ | H | H | pic |
| 6'-130X | Pt | 1 | 6' | Ph | H | H |  | EE1 | CH₃ | H | H | acac |
| 6'-130Y | Pt | 0 | 6' | Ph | H | H |  | EE1 | CH₃ | H | H | — — |
| 6'-131 | Pt | 1 | 6' | Ph | H |  | EE1 | H | CH₃ | H | H | pic |
| 6'-131X | Pt | 1 | 6' | Ph | H |  | EE1 | H | CH₃ | H | H | acac |
| 6'-131Y | Pt | 0 | 6' | Ph | H |  | EE1 | H | CH₃ | H | H | — — |
| 6'-132 | Pt | 1 | 6' | Ph | H | H |  | EE2 | CH₃ | H | H | pic |
| 6'-132X | Pt | 1 | 6' | Ph | H | H |  | EE2 | CH₃ | H | H | acac |
| 6'-132Y | Pt | 0 | 6' | Ph | H | H |  | EE2 | CH₃ | H | H | — — |
| 6'-133 | Pt | 1 | 6' | Ph | H |  | EE2 | H | CH₃ | H | H | pic |
| 6'-133X | Pt | 1 | 6' | Ph | H |  | EE2 | H | CH₃ | H | H | acac |
| 6'-133Y | Pt | 0 | 6' | Ph | H |  | EE2 | H | CH₃ | H | H | — — |
| 6'-134 | Pt | 1 | 6' | Ph | H | H |  | MS1 | CH₃ | H | H | pic |
| 6'-134X | Pt | 1 | 6' | Ph | H | H |  | MS1 | CH₃ | H | H | acac |
| 6'-134Y | Pt | 0 | 6' | Ph | H | H |  | MS1 | CH₃ | H | H | — — |
| 6'-135 | Pt | 1 | 6' | Ph | H |  | MS1 | H | CH₃ | H | H | pic |
| 6'-135X | Pt | 1 | 6' | Ph | H |  | MS1 | H | CH₃ | H | H | acac |
| 6'-135Y | Pt | 0 | 6' | Ph | H |  | MS1 | H | CH₃ | H | H | — — |
| 6'-136 | Pt | 1 | 6' | Ph | H | H |  | MS2 | CH₃ | H | H | pic |
| 6'-136X | Pt | 1 | 6' | Ph | H | H |  | MS2 | CH₃ | H | H | acac |
| 6'-136Y | Pt | 0 | 6' | Ph | H | H |  | MS2 | CH₃ | H | H | — — |
| 6'-137 | Pt | 1 | 6' | Ph | H |  | MS2 | H | CH₃ | H | H | pic |
| 6'-137X | Pt | 1 | 6' | Ph | H |  | MS2 | H | CH₃ | H | H | acac |
| 6'-137Y | Pt | 0 | 6' | Ph | H |  | MS2 | H | CH₃ | H | H | — — |

TABLE 35

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 7'-1 | Pt | 1 | 7' | Ph | H | H | H | H | CH₃ | H | H | pic |
| 7'-1X | Pt | 1 | 7' | Ph | H | H | H | H | CH₃ | H | H | acac |
| 7'-1Y | Pt | 0 | 7' | Ph | H | H | H | H | CH₃ | H | H | — — |
| 7'-2 | Pt | 1 | 7' | Ph | H | H | H | H | $^tC_4H_9$ | H | H | pic |
| 7'-2X | Pt | 1 | 7' | Ph | H | H | H | H | $^tC_4H_9$ | H | H | acac |
| 7'-2Y | Pt | 0 | 7' | Ph | H | H | H | H | $^tC_4H_9$ | H | H | — — |
| 7'-3 | Pt | 1 | 7' | Ph | H | F | H | F | CH₃ | H | H | pic |
| 7'-3X | Pt | 1 | 7' | Ph | H | F | H | F | CH₃ | H | H | acac |

TABLE 35-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 7'-3Y | Pt | 0 | 7' | Ph | H | F | H | F | $CH_3$ | H | H | — | — |
| 7'-4 | Pt | 1 | 7' | Ph | H | F | H | F | $^tC_4H_9$ | H | H | pic | |
| 7'-4X | Pt | 1 | 7' | Ph | H | F | H | F | $^tC_4H_9$ | H | H | acac | |
| 7'-4Y | Pt | 0 | 7' | Ph | H | F | H | F | $^tC_4H_9$ | H | H | — | — |
| 7'-5 | Pt | 1 | 7' | Ph | F | H | H | F | $CH_3$ | H | H | pic | |
| 7'-5X | Pt | 1 | 7' | Ph | F | H | H | F | $CH_3$ | H | H | acac | |
| 7'-5Y | Pt | 0 | 7' | Ph | F | H | H | F | $CH_3$ | H | H | — | — |
| 7'-6 | Pt | 1 | 7' | Ph | F | H | H | F | $^tC_4H_9$ | H | H | pic | |
| 7'-6X | Pt | 1 | 7' | Ph | F | H | H | F | $^tC_4H_9$ | H | H | acac | |
| 7'-6Y | Pt | 0 | 7' | Ph | F | H | H | F | $^tC_4H_9$ | H | H | — | — |
| 7'-7 | Pt | 1 | 7' | Ph | $CF_3$ | H | $CF_3$ | H | $CH_3$ | H | H | pic | |
| 7'-7X | Pt | 1 | 7' | Ph | $CF_3$ | H | $CF_3$ | H | $CH_3$ | H | H | acac | |
| 7'-7Y | Pt | 0 | 7' | Ph | $CF_3$ | H | $CF_3$ | H | $CH_3$ | H | H | — | — |
| 7'-8 | Pt | 1 | 7' | Ph | $CF_3$ | H | $CF_3$ | H | $^tC_4H_9$ | H | H | pic | |
| 7'-8X | Pt | 1 | 7' | Ph | $CF_3$ | H | $CF_3$ | H | $^tC_4H_9$ | H | H | acac | |
| 7'-8Y | Pt | 0 | 7' | Ph | $CF_3$ | H | $CF_3$ | H | $^tC_4H_9$ | H | H | — | — |
| 7'-9 | Pt | 1 | 7' | Ph | H | F | $CF_3$ | H | $CH_3$ | H | H | pic | |
| 7'-9X | Pt | 1 | 7' | Ph | H | F | $CF_3$ | H | $CH_3$ | H | H | acac | |
| 7'-9Y | Pt | 0 | 7' | Ph | H | F | $CF_3$ | H | $CH_3$ | H | H | — | — |
| 7'-10 | Pt | 1 | 7' | Ph | F | H | $CF_3$ | H | $CH_3$ | H | H | pic | |
| 7'-10X | Pt | 1 | 7' | Ph | F | H | $CF_3$ | H | $CH_3$ | H | H | acac | |
| 7'-10Y | Pt | 0 | 7' | Ph | F | H | $CF_3$ | H | $CH_3$ | H | H | — | — |
| 7'-11 | Pt | 1 | 7' | Ph | F | F | F | F | $CH_3$ | H | H | pic | |
| 7'-11X | Pt | 1 | 7' | Ph | F | F | F | F | $CH_3$ | H | H | acac | |
| 7'-11Y | Pt | 0 | 7' | Ph | F | F | F | F | $CH_3$ | H | H | — | — |
| 7'-12 | Pt | 1 | 7' | Ph | H | F | H | $CH_3$ | $CH_3$ | H | H | pic | |
| 7'-12X | Pt | 1 | 7' | Ph | H | F | H | $CH_3$ | $CH_3$ | H | H | acac | |
| 7'-12Y | Pt | 0 | 7' | Ph | H | F | H | $CH_3$ | $CH_3$ | H | H | — | — |
| 7'-13 | Pt | 1 | 7' | Ph | H | F | H | $CH_3$ | $^tC_4H_9$ | H | H | pic | |
| 7'-13X | Pt | 1 | 7' | Ph | H | F | H | $CH_3$ | $^tC_4H_9$ | H | H | acac | |
| 7'-13Y | Pt | 0 | 7' | Ph | H | F | H | $CH_3$ | $^tC_4H_9$ | H | H | — | — |
| 7'-14 | Pt | 1 | 7' | Ph | H | F | H | $^tC_4H_9$ | $CH_3$ | H | H | pic | |
| 7'-14X | Pt | 1 | 7' | Ph | H | F | H | $^tC_4H_9$ | $CH_3$ | H | H | acac | |
| 7'-14Y | Pt | 0 | 7' | Ph | H | F | H | $^tC_4H_9$ | $CH_3$ | H | H | — | — |
| 7'-15 | Pt | 1 | 7' | Ph | H | F | H | $^tC_4H_9$ | $^tC_4H_9$ | H | H | pic | |
| 7'-15X | Pt | 1 | 7' | Ph | H | F | H | $^tC_4H_9$ | $^tC_4H_9$ | H | H | acac | |
| 7'-15Y | Pt | 0 | 7' | Ph | H | F | H | $^tC_4H_9$ | $^tC_4H_9$ | H | H | — | — |
| 7'-16 | Pt | 1 | 7' | Ph | H | $CF_3$ | H | $CF_3$ | $CH_3$ | H | H | pic | |
| 7'-16X | Pt | 1 | 7' | Ph | H | $CF_3$ | H | $CF_3$ | $CH_3$ | H | H | acac | |
| 7'-16Y | Pt | 0 | 7' | Ph | H | $CF_3$ | H | $CF_3$ | $CH_3$ | H | H | — | — |
| 7'-17 | Pt | 1 | 7' | Ph | H | $CF_3$ | H | $CF_3$ | $^tC_4H_9$ | H | H | pic | |
| 7'-17X | Pt | 1 | 7' | Ph | H | $CF_3$ | H | $CF_3$ | $^tC_4H_9$ | H | H | acac | |
| 7'-17Y | Pt | 0 | 7' | Ph | H | $CF_3$ | H | $CF_3$ | $^tC_4H_9$ | H | H | — | — |
| 7'-18 | Pt | 1 | 7' | Ph | $CF_3$ | H | H | $^tC_4H_9$ | $CH_3$ | H | H | pic | |
| 7'-18X | Pt | 1 | 7' | Ph | $CF_3$ | H | H | $^tC_4H_9$ | $CH_3$ | H | H | acac | |
| 7'-18Y | Pt | 0 | 7' | Ph | $CF_3$ | H | H | $^tC_4H_9$ | $CH_3$ | H | H | — | — |
| 7'-19 | Pt | 1 | 7' | Ph | $CF_3$ | H | H | $^tC_4H_9$ | $^tC_4H_9$ | H | H | pic | |
| 7'-19X | Pt | 1 | 7' | Ph | $CF_3$ | H | H | $^tC_4H_9$ | $^tC_4H_9$ | H | H | acac | |
| 7'-19Y | Pt | 0 | 7' | Ph | $CF_3$ | H | H | $^tC_4H_9$ | $^tC_4H_9$ | H | H | — | — |
| 7'-20 | Pt | 1 | 7' | Ph | H | $CF_3$ | H | $^tC_4H_9$ | $CH_3$ | H | H | pic | |
| 7'-20X | Pt | 1 | 7' | Ph | H | $CF_3$ | H | $^tC_4H_9$ | $CH_3$ | H | H | acac | |
| 7'-20Y | Pt | 0 | 7' | Ph | H | $CF_3$ | H | $^tC_4H_9$ | $CH_3$ | H | H | — | — |
| 7'-21 | Pt | 1 | 7' | Ph | H | $CF_3$ | H | $^tC_4H_9$ | $^tC_4H_9$ | H | H | pic | |
| 7'-21X | Pt | 1 | 7' | Ph | H | $CF_3$ | H | $^tC_4H_9$ | $^tC_4H_9$ | H | H | acac | |
| 7'-21Y | Pt | 0 | 7' | Ph | H | $CF_3$ | H | $^tC_4H_9$ | $^tC_4H_9$ | H | H | — | — |
| 7'-22 | Pt | 1 | 7' | Ph | H | $CF_3$ | H | $CH_3$ | $CH_3$ | H | H | pic | |
| 7'-22X | Pt | 1 | 7' | Ph | H | $CF_3$ | H | $CH_3$ | $CH_3$ | H | H | acac | |
| 7'-22Y | Pt | 0 | 7' | Ph | H | $CF_3$ | H | $CH_3$ | $CH_3$ | H | H | — | — |
| 7'-23 | Pt | 1 | 7' | Ph | H | $CF_3$ | $CF_3$ | H | $CH_3$ | H | H | pic | |
| 7'-23X | Pt | 1 | 7' | Ph | H | $CF_3$ | $CF_3$ | H | $CH_3$ | H | H | acac | |
| 7'-23Y | Pt | 0 | 7' | Ph | H | $CF_3$ | $CF_3$ | H | $CH_3$ | H | H | — | — |
| 7'-24 | Pt | 1 | 7' | Ph | H | H | $NO_2$ | H | $CH_3$ | H | H | pic | |
| 7'-24X | Pt | 1 | 7' | Ph | H | H | $NO_2$ | H | $CH_3$ | H | H | acac | |
| 7'-24Y | Pt | 0 | 7' | Ph | H | H | $NO_2$ | H | $CH_3$ | H | H | — | — |
| 7'-25 | Pt | 1 | 7' | Ph | H | H | $NO_2$ | H | $^tC_4H_9$ | H | H | pic | |
| 7'-25X | Pt | 1 | 7' | Ph | H | H | $NO_2$ | H | $^tC_4H_9$ | H | H | acac | |
| 7'-25Y | Pt | 0 | 7' | Ph | H | H | $NO_2$ | H | $^tC_4H_9$ | H | H | — | — |
| 7'-26 | Pt | 1 | 7' | Ph | F | H | $NO_2$ | H | $CH_3$ | H | H | pic | |
| 7'-26X | Pt | 1 | 7' | Ph | F | H | $NO_2$ | H | $CH_3$ | H | H | acac | |
| 7'-26Y | Pt | 0 | 7' | Ph | F | H | $NO_2$ | H | $CH_3$ | H | H | — | — |
| 7'-27 | Pt | 1 | 7' | Ph | F | H | $NO_2$ | F | $CH_3$ | H | H | pic | |
| 7'-27X | Pt | 1 | 7' | Ph | F | H | $NO_2$ | F | $CH_3$ | H | H | acac | |
| 7'-27Y | Pt | 0 | 7' | Ph | F | H | $NO_2$ | F | $CH_3$ | H | H | — | — |
| 7'-28 | Pt | 1 | 7' | Ph | H | $NO_2$ | H | $NO_2$ | $CH_3$ | H | H | pic | |
| 7'-28X | Pt | 1 | 7' | Ph | H | $NO_2$ | H | $NO_2$ | $CH_3$ | H | H | acac | |
| 7'-28Y | Pt | 0 | 7' | Ph | H | $NO_2$ | H | $NO_2$ | $CH_3$ | H | H | — | — |
| 7'-29 | Pt | 1 | 7' | Ph | H | $NO_2$ | H | $NO_2$ | $^tC_4H_9$ | H | H | pic | |

TABLE 35-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 7'-29X | Pt | 1 | 7' | Ph | H | $NO_2$ | H | $NO_2$ | $^tC_4H_9$ | H | H | acac |
| 7'-29Y | Pt | 0 | 7' | Ph | H | $NO_2$ | H | $NO_2$ | $^tC_4H_9$ | H | H | — — |
| 7'-30 | Pt | 1 | 7' | Ph | $NO_2$ | H | H | $NO_2$ | $CH_3$ | H | H | pic |
| 7'-30X | Pt | 1 | 7' | Ph | $NO_2$ | H | H | $NO_2$ | $CH_3$ | H | H | acac |
| 7'-30Y | Pt | 0 | 7' | Ph | $NO_2$ | H | H | $NO_2$ | $CH_3$ | H | H | — — |
| 7'-31 | Pt | 1 | 7' | Ph | $NO_2$ | H | H | $NO_2$ | $^tC_4H_9$ | H | H | pic |
| 7'-31X | Pt | 1 | 7' | Ph | $NO_2$ | H | H | $NO_2$ | $^tC_4H_9$ | H | H | acac |
| 7'-31Y | Pt | 0 | 7' | Ph | $NO_2$ | H | H | $NO_2$ | $^tC_4H_9$ | H | H | — — |
| 7'-32 | Pt | 1 | 7' | Ph | H | H | $CF_3$ | H | $CH_3$ | H | H | pic |
| 7'-32X | Pt | 1 | 7' | Ph | H | H | $CF_3$ | H | $CH_3$ | H | H | acac |
| 7'-32Y | Pt | 0 | 7' | Ph | H | H | $CF_3$ | H | $CH_3$ | H | H | — — |
| 7'-33 | Pt | 1 | 7' | Ph | H | H | $CF_3$ | H | $^tC_4H_9$ | H | H | pic |
| 7'-33X | Pt | 1 | 7' | Ph | H | H | $CF_3$ | H | $^tC_4H_9$ | H | H | acac |
| 7'-33Y | Pt | 0 | 7' | Ph | H | H | $CF_3$ | H | $^tC_4H_9$ | H | H | — — |
| 7'-34 | Pt | 1 | 7' | Ph | H | Cl | $CF_3$ | H | $CH_3$ | H | H | pic |
| 7'-34X | Pt | 1 | 7' | Ph | H | Cl | $CF_3$ | H | $CH_3$ | H | H | acac |
| 7'-34Y | Pt | 0 | 7' | Ph | H | Cl | $CF_3$ | H | $CH_3$ | H | H | — — |
| 7'-35 | Pt | 1 | 7' | Ph | H | Cl | $CF_3$ | H | $^tC_4H_9$ | H | H | pic |
| 7'-35X | Pt | 1 | 7' | Ph | H | Cl | $CF_3$ | H | $^tC_4H_9$ | H | H | acac |
| 7'-35Y | Pt | 0 | 7' | Ph | H | Cl | $CF_3$ | H | $^tC_4H_9$ | H | H | — — |
| 7'-36 | Pt | 1 | 7' | Ph | H | $NO_2$ | H | H | $CH_3$ | H | H | pic |
| 7'-36X | Pt | 1 | 7' | Ph | H | $NO_2$ | H | H | $CH_3$ | H | H | acac |
| 7'-36Y | Pt | 0 | 7' | Ph | H | $NO_2$ | H | H | $CH_3$ | H | H | — — |
| 7'-37 | Pt | 1 | 7' | Ph | H | $CF_3$ | H | H | $CH_3$ | H | H | pic |
| 7'-37X | Pt | 1 | 7' | Ph | H | $CF_3$ | H | H | $CH_3$ | H | H | acac |
| 7'-37Y | Pt | 0 | 7' | Ph | H | $CF_3$ | H | H | $CH_3$ | H | H | — — |
| 7'-38 | Pt | 1 | 7' | Ph | H | $NO_2$ | H | $CH_3$ | $CH_3$ | H | H | pic |
| 7'-38X | Pt | 1 | 7' | Ph | H | $NO_2$ | H | $CH_3$ | $CH_3$ | H | H | acac |
| 7'-38Y | Pt | 0 | 7' | Ph | H | $NO_2$ | H | $CH_3$ | $CH_3$ | H | H | — — |
| 7'-39 | Pt | 1 | 7' | Ph | H | $NO_2$ | H | $CH_3$ | $^tC_4H_9$ | H | H | pic |
| 7'-39X | Pt | 1 | 7' | Ph | H | $NO_2$ | H | $CH_3$ | $^tC_4H_9$ | H | H | acac |
| 7'-39Y | Pt | 0 | 7' | Ph | H | $NO_2$ | H | $CH_3$ | $^tC_4H_9$ | H | H | — — |
| 7'-40 | Pt | 1 | 7' | Ph | H | $NO_2$ | H | $^tC_4H_9$ | $CH_3$ | H | H | pic |
| 7'-40X | Pt | 1 | 7' | Ph | H | $NO_2$ | H | $^tC_4H_9$ | $CH_3$ | H | H | acac |
| 7'-40Y | Pt | 0 | 7' | Ph | H | $NO_2$ | H | $^tC_4H_9$ | $CH_3$ | H | H | — — |
| 7'-41 | Pt | 1 | 7' | Ph | H | $NO_2$ | H | $^tC_4H_9$ | $^tC_4H_9$ | H | H | pic |
| 7'-41X | Pt | 1 | 7' | Ph | H | $NO_2$ | H | $^tC_4H_9$ | $^tC_4H_9$ | H | H | acac |
| 7'-41Y | Pt | 0 | 7' | Ph | H | $NO_2$ | H | $^tC_4H_9$ | $^tC_4H_9$ | H | H | — — |
| 7'-42 | Pt | 1 | 7' | Ph | H | H | $CH_3O$ | H | $CH_3$ | H | H | pic |
| 7'-42X | Pt | 1 | 7' | Ph | H | H | $CH_3O$ | H | $CH_3$ | H | H | acac |
| 7'-42Y | Pt | 0 | 7' | Ph | H | H | $CH_3O$ | H | $CH_3$ | H | H | — — |
| 7'-43 | Pt | 1 | 7' | Ph | H | $CH_3O$ | H | H | $CH_3$ | H | H | pic |
| 7'-43X | Pt | 1 | 7' | Ph | H | $CH_3O$ | H | H | $CH_3$ | H | H | acac |
| 7'-43Y | Pt | 0 | 7' | Ph | H | $CH_3O$ | H | H | $CH_3$ | H | H | — — |
| 7'-44 | Pt | 1 | 7' | Ph | H | $CH_3O$ | H | $CH_3$ | $CH_3$ | H | H | pic |
| 7'-44X | Pt | 1 | 7' | Ph | H | $CH_3O$ | H | $CH_3$ | $CH_3$ | H | H | acac |
| 7'-44Y | Pt | 0 | 7' | Ph | H | $CH_3O$ | H | $CH_3$ | $CH_3$ | H | H | — — |
| 7'-45 | Pt | 1 | 7' | Ph | H | $CH_3O$ | H | $^tC_4H_9$ | $CH_3$ | H | H | pic |
| 7'-45X | Pt | 1 | 7' | Ph | H | $CH_3O$ | H | $^tC_4H_9$ | $CH_3$ | H | H | acac |
| 7'-45Y | Pt | 0 | 7' | Ph | H | $CH_3O$ | H | $^tC_4H_9$ | $CH_3$ | H | H | — — |
| 7'-46 | Pt | 1 | 7' | Ph | H | $Si(CH_3)_3$ | H | H | $CH_3$ | H | H | pic |
| 7'-46X | Pt | 1 | 7' | Ph | H | $Si(CH_3)_3$ | H | H | $CH_3$ | H | H | acac |
| 7'-46Y | Pt | 0 | 7' | Ph | H | $Si(CH_3)_3$ | H | H | $CH_3$ | H | H | — — |
| 7'-47 | Pt | 1 | 7' | Ph | H | $Si(CH_3)_3$ | H | H | $^tC_4H_9$ | H | H | pic |
| 7'-47X | Pt | 1 | 7' | Ph | H | $Si(CH_3)_3$ | H | H | $^tC_4H_9$ | H | H | acac |
| 7'-47Y | Pt | 0 | 7' | Ph | H | $Si(CH_3)_3$ | H | H | $^tC_4H_9$ | H | H | — — |
| 7'-48 | Pt | 1 | 7' | Ph | H | H | $Si(CH_3)_3$ | H | $CH_3$ | H | H | pic |
| 7'-48X | Pt | 1 | 7' | Ph | H | H | $Si(CH_3)_3$ | H | $CH_3$ | H | H | acac |
| 7'-48Y | Pt | 0 | 7' | Ph | H | H | $Si(CH_3)_3$ | H | $CH_3$ | H | H | — — |
| 7'-49 | Pt | 1 | 7' | Ph | H | H | H | $Si(CH_3)_3$ | $CH_3$ | H | H | pic |
| 7'-49X | Pt | 1 | 7' | Ph | H | H | H | $Si(CH_3)_3$ | $CH_3$ | H | H | acac |
| 7'-49Y | Pt | 0 | 7' | Ph | H | H | H | $Si(CH_3)_3$ | $CH_3$ | H | H | — — |
| 7'-50 | Pt | 1 | 7' | Ph | H | F | H | $Si(CH_3)_3$ | $CH_3$ | H | H | pic |
| 7'-50X | Pt | 1 | 7' | Ph | H | F | H | $Si(CH_3)_3$ | $CH_3$ | H | H | acac |
| 7'-50Y | Pt | 0 | 7' | Ph | H | F | H | $Si(CH_3)_3$ | $CH_3$ | H | H | — — |
| 7'-51 | Pt | 1 | 7' | Ph | H | $CF_3$ | H | $Si(CH_3)_3$ | $CH_3$ | H | H | pic |
| 7'-51X | Pt | 1 | 7' | Ph | H | $CF_3$ | H | $Si(CH_3)_3$ | $CH_3$ | H | H | acac |
| 7'-51Y | Pt | 0 | 7' | Ph | H | $CF_3$ | H | $Si(CH_3)_3$ | $CH_3$ | H | H | — — |
| 7'-52 | Pt | 1 | 7' | Ph | H | $CF_3$ | H | $Si(CH_3)_3$ | $^tC_4H_9$ | H | H | pic |
| 7'-52X | Pt | 1 | 7' | Ph | H | $CF_3$ | H | $Si(CH_3)_3$ | $^tC_4H_9$ | H | H | acac |
| 7'-52Y | Pt | 0 | 7' | Ph | H | $CF_3$ | H | $Si(CH_3)_3$ | $^tC_4H_9$ | H | H | — — |
| 7'-53 | Pt | 1 | 7' | Ph | H | $Si(CH_3)_3$ | H | F | $CH_3$ | H | H | pic |
| 7'-53X | Pt | 1 | 7' | Ph | H | $Si(CH_3)_3$ | H | F | $CH_3$ | H | H | acac |
| 7'-53Y | Pt | 0 | 7' | Ph | H | $Si(CH_3)_3$ | H | F | $CH_3$ | H | H | — — |
| 7'-54 | Pt | 1 | 7' | Ph | H | $Si(CH_3)_3$ | H | F | $^tC_4H_9$ | H | H | pic |
| 7'-54X | Pt | 1 | 7' | Ph | H | $Si(CH_3)_3$ | H | F | $^tC_4H_9$ | H | H | acac |
| 7'-54Y | Pt | 0 | 7' | Ph | H | $Si(CH_3)_3$ | H | F | $^tC_4H_9$ | H | H | — — |

TABLE 35-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 7'-55 | Pt | 1 | 7' | Ph | H | Si(CH₃)₃ | H | CF₃ | CH₃ | H | H | pic |
| 7'-55X | Pt | 1 | 7' | Ph | H | Si(CH₃)₃ | H | CF₃ | CH₃ | H | H | acac |
| 7'-55Y | Pt | 0 | 7' | Ph | H | Si(CH₃)₃ | H | CF₃ | CH₃ | H | H | — — |
| 7'-56 | Pt | 1 | 7' | Ph | H | Si(CH₃)₃ | H | CF₃ | ᵗC₄H₉ | H | H | pic |
| 7'-56X | Pt | 1 | 7' | Ph | H | Si(CH₃)₃ | H | CF₃ | ᵗC₄H₉ | H | H | acac |
| 7'-56Y | Pt | 0 | 7' | Ph | H | Si(CH₃)₃ | H | CF₃ | ᵗC₄H₉ | H | H | — — |
| 7'-57 | Pt | 1 | 7' | Ph | Si(CH₃)₃ | H | Si(CH₃)₃ | H | CH₃ | H | H | pic |
| 7'-57X | Pt | 1 | 7' | Ph | Si(CH₃)₃ | H | Si(CH₃)₃ | H | CH₃ | H | H | acac |
| 7'-57Y | Pt | 0 | 7' | Ph | Si(CH₃)₃ | H | Si(CH₃)₃ | H | CH₃ | H | H | — — |
| 7'-58 | Pt | 1 | 7' | Ph | Si(CH₃)₃ | H | Si(CH₃)₃ | H | ᵗC₄H₉ | H | H | pic |
| 7'-58X | Pt | 1 | 7' | Ph | Si(CH₃)₃ | H | Si(CH₃)₃ | H | ᵗC₄H₉ | H | H | acac |
| 7'-58Y | Pt | 0 | 7' | Ph | Si(CH₃)₃ | H | Si(CH₃)₃ | H | ᵗC₄H₉ | H | H | — — |
| 7'-59 | Pt | 1 | 7' | Ph | H | H | H | COCH₃ | CH₃ | H | H | pic |
| 7'-59X | Pt | 1 | 7' | Ph | H | H | H | COCH₃ | CH₃ | H | H | acac |
| 7'-59Y | Pt | 0 | 7' | Ph | H | H | H | COCH₃ | CH₃ | H | H | — — |
| 7'-60 | Pt | 1 | 7' | Ph | H | H | COCH₃ | H | CH₃ | H | H | pic |
| 7'-60X | Pt | 1 | 7' | Ph | H | H | COCH₃ | H | CH₃ | H | H | acac |
| 7'-60Y | Pt | 0 | 7' | Ph | H | H | COCH₃ | H | CH₃ | H | H | — — |
| 7'-61 | Pt | 1 | 7' | Ph | H | COCH₃ | H | H | CH₃ | H | H | pic |
| 7'-61X | Pt | 1 | 7' | Ph | H | COCH₃ | H | H | CH₃ | H | H | acac |
| 7'-61Y | Pt | 0 | 7' | Ph | H | COCH₃ | H | H | CH₃ | H | H | — — |
| 7'-62 | Pt | 1 | 7' | Ph | H | H | BL | | CH₃ | H | H | pic |
| 7'-62X | Pt | 1 | 7' | Ph | H | H | BL | | CH₃ | H | H | acac |
| 7'-62Y | Pt | 0 | 7' | Ph | H | H | BL | | CH₃ | H | H | — — |
| 7'-63 | Pt | 1 | 7' | Ph | H | H | BL | | ᵗC₄H₉ | H | H | pic |
| 7'-63X | Pt | 1 | 7' | Ph | H | H | BL | | ᵗC₄H₉ | H | H | acac |
| 7'-63Y | Pt | 0 | 7' | Ph | H | H | BL | | ᵗC₄H₉ | H | H | — — |
| 7'-64 | Pt | 1 | 7' | Ph | H | BL | | H | CH₃ | H | H | pic |
| 7'-64X | Pt | 1 | 7' | Ph | H | BL | | H | CH₃ | H | H | acac |
| 7'-64Y | Pt | 0 | 7' | Ph | H | BL | | H | CH₃ | H | H | — — |
| 7'-65 | Pt | 1 | 7' | Ph | H | BL | | H | ᵗC₄H₉ | H | H | pic |
| 7'-65X | Pt | 1 | 7' | Ph | H | BL | | H | ᵗC₄H₉ | H | H | acac |
| 7'-65Y | Pt | 0 | 7' | Ph | H | BL | | H | ᵗC₄H₉ | H | H | — — |
| 7'-66 | Pt | 1 | 7' | Ph | H | H | PL | | CH₃ | H | H | pic |
| 7'-66X | Pt | 1 | 7' | Ph | H | H | PL | | CH₃ | H | H | acac |
| 7'-66Y | Pt | 0 | 7' | Ph | H | H | PL | | CH₃ | H | H | — — |
| 7'-67 | Pt | 1 | 7' | Ph | H | H | PL | | ᵗC₄H₉ | H | H | pic |
| 7'-67X | Pt | 1 | 7' | Ph | H | H | PL | | ᵗC₄H₉ | H | H | acac |
| 7'-67Y | Pt | 0 | 7' | Ph | H | H | PL | | ᵗC₄H₉ | H | H | — — |
| 7'-68 | Pt | 1 | 7' | Ph | H | PL | | H | CH₃ | H | H | pic |
| 7'-68X | Pt | 1 | 7' | Ph | H | PL | | H | CH₃ | H | H | acac |
| 7'-68Y | Pt | 0 | 7' | Ph | H | PL | | H | CH₃ | H | H | — — |
| 7'-69 | Pt | 1 | 7' | Ph | H | PL | | H | ᵗC₄H₉ | H | H | pic |
| 7'-69X | Pt | 1 | 7' | Ph | H | PL | | H | ᵗC₄H₉ | H | H | acac |
| 7'-69Y | Pt | 0 | 7' | Ph | H | PL | | H | ᵗC₄H₉ | H | H | — — |
| 7'-70 | Pt | 1 | 7' | Ph | H | H | MEE1 | | CH₃ | H | H | pic |
| 7'-70X | Pt | 1 | 7' | Ph | H | H | MEE1 | | CH₃ | H | H | acac |
| 7'-70Y | Pt | 0 | 7' | Ph | H | H | MEE1 | | CH₃ | H | H | — — |
| 7'-71 | Pt | 1 | 7' | Ph | H | MEE1 | | H | CH₃ | H | H | pic |
| 7'-71X | Pt | 1 | 7' | Ph | H | MEE1 | | H | CH₃ | H | H | acac |
| 7'-71Y | Pt | 0 | 7' | Ph | H | MEE1 | | H | CH₃ | H | H | — — |
| 7'-72 | Pt | 1 | 7' | Ph | H | H | MEE2 | | CH₃ | H | H | pic |
| 7'-72X | Pt | 1 | 7' | Ph | H | H | MEE2 | | CH₃ | H | H | acac |
| 7'-72Y | Pt | 0 | 7' | Ph | H | H | MEE2 | | CH₃ | H | H | — — |
| 7'-73 | Pt | 1 | 7' | Ph | H | MEE2 | | H | CH₃ | H | H | pic |
| 7'-73X | Pt | 1 | 7' | Ph | H | MEE2 | | H | CH₃ | H | H | acac |
| 7'-73Y | Pt | 0 | 7' | Ph | H | MEE2 | | H | CH₃ | H | H | — — |
| 7'-74 | Pt | 1 | 7' | Ph | H | H | PA1 | | CH₃ | H | H | pic |
| 7'-74X | Pt | 1 | 7' | Ph | H | H | PA1 | | CH₃ | H | H | acac |
| 7'-74Y | Pt | 0 | 7' | Ph | H | H | PA1 | | CH₃ | H | H | — — |
| 7'-75 | Pt | 1 | 7' | Ph | H | PA1 | | H | CH₃ | H | H | pic |
| 7'-75X | Pt | 1 | 7' | Ph | H | PA1 | | H | CH₃ | H | H | acac |
| 7'-75Y | Pt | 0 | 7' | Ph | H | PA1 | | H | CH₃ | H | H | — — |
| 7'-76 | Pt | 1 | 7' | Ph | H | H | PA2 | | CH₃ | H | H | pic |
| 7'-76X | Pt | 1 | 7' | Ph | H | H | PA2 | | CH₃ | H | H | acac |
| 7'-76Y | Pt | 0 | 7' | Ph | H | H | PA2 | | CH₃ | H | H | — — |
| 7'-77 | Pt | 1 | 7' | Ph | H | PA2 | | H | CH₃ | H | H | pic |
| 7'-77X | Pt | 1 | 7' | Ph | H | PA2 | | H | CH₃ | H | H | acac |
| 7'-77Y | Pt | 0 | 7' | Ph | H | PA2 | | H | CH₃ | H | H | — — |
| 7'-78 | Pt | 1 | 7' | Ph | H | H | EA1 | | CH₃ | H | H | pic |
| 7'-78X | Pt | 1 | 7' | Ph | H | H | EA1 | | CH₃ | H | H | acac |
| 7'-78Y | Pt | 0 | 7' | Ph | H | H | EA1 | | CH₃ | H | H | — — |
| 7'-79 | Pt | 1 | 7' | Ph | H | EA2 | | H | CH₃ | H | H | pic |
| 7'-79X | Pt | 1 | 7' | Ph | H | EA2 | | H | CH₃ | H | H | acac |
| 7'-79Y | Pt | 0 | 7' | Ph | H | EA2 | | H | CH₃ | H | H | — — |
| 7'-80 | Pt | 1 | 7' | Ph | H | H | ME | | CH₃ | H | H | pic |
| 7'-80X | Pt | 1 | 7' | Ph | H | H | ME | | CH₃ | H | H | acac |

TABLE 35-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 7'-80Y | Pt | 0 | 7' | Ph | H | H | | ME | CH₃ | H | H | — | — |
| 7'-81 | Pt | 1 | 7' | Ph | H | | ME | | H | CH₃ | H | H | pic |
| 7'-81X | Pt | 1 | 7' | Ph | H | | ME | | H | CH₃ | H | H | acac |
| 7'-81Y | Pt | 0 | 7' | Ph | H | | ME | | H | CH₃ | H | H | — |
| 7'-82 | Pt | 1 | 7' | Ph | H | H | | AT | CH₃ | H | H | pic | |
| 7'-82X | Pt | 1 | 7' | Ph | H | H | | AT | CH₃ | H | H | acac | |
| 7'-82Y | Pt | 0 | 7' | Ph | H | H | | AT | CH₃ | H | H | — | — |
| 7'-83 | Pt | 1 | 7' | Ph | H | | AT | | H | CH₃ | H | H | pic |
| 7'-83X | Pt | 1 | 7' | Ph | H | | AT | | H | CH₃ | H | H | acac |
| 7'-83Y | Pt | 0 | 7' | Ph | H | | AT | | H | CH₃ | H | H | — |
| 7'-84 | Pt | 1 | 7' | Ph | H | H | | MES1 | CH₃ | H | H | pic | |
| 7'-84X | Pt | 1 | 7' | Ph | H | H | | MES1 | CH₃ | H | H | acac | |
| 7'-84Y | Pt | 0 | 7' | Ph | H | H | | MES1 | CH₃ | H | H | — | — |
| 7'-85 | Pt | 1 | 7' | Ph | H | | MES1 | | H | CH₃ | H | H | pic |
| 7'-85X | Pt | 1 | 7' | Ph | H | | MES1 | | H | CH₃ | H | H | acac |
| 7'-85Y | Pt | 0 | 7' | Ph | H | | MES1 | | H | CH₃ | H | H | — |
| 7'-86 | Pt | 1 | 7' | Ph | H | H | | MES2 | CH₃ | H | H | pic | |
| 7'-86X | Pt | 1 | 7' | Ph | H | H | | MES2 | CH₃ | H | H | acac | |
| 7'-86Y | Pt | 0 | 7' | Ph | H | H | | MES2 | CH₃ | H | H | — | — |
| 7'-87 | Pt | 1 | 7' | Ph | H | | MES2 | | H | CH₃ | H | H | pic |
| 7'-87X | Pt | 1 | 7' | Ph | H | | MES2 | | H | CH₃ | H | H | acac |
| 7'-87Y | Pt | 0 | 7' | Ph | H | | MES2 | | H | CH₃ | H | H | — |
| 7'-88 | Pt | 1 | 7' | Ph | H | H | | PS1 | CH₃ | H | H | pic | |
| 7'-88X | Pt | 1 | 7' | Ph | H | H | | PS1 | CH₃ | H | H | acac | |
| 7'-88Y | Pt | 0 | 7' | Ph | H | H | | PS1 | CH₃ | H | H | — | — |
| 7'-89 | Pt | 1 | 7' | Ph | H | | PS1 | | H | CH₃ | H | H | pic |
| 7'-89X | Pt | 1 | 7' | Ph | H | | PS1 | | H | CH₃ | H | H | acac |
| 7'-89Y | Pt | 0 | 7' | Ph | H | | PS1 | | H | CH₃ | H | H | — |
| 7'-90 | Pt | 1 | 7' | Ph | H | H | | PS2 | CH₃ | H | H | pic | |
| 7'-90X | Pt | 1 | 7' | Ph | H | H | | PS2 | CH₃ | H | H | acac | |
| 7'-90Y | Pt | 0 | 7' | Ph | H | H | | PS2 | CH₃ | H | H | — | — |
| 7'-91 | Pt | 1 | 7' | Ph | H | | PS2 | | H | CH₃ | H | H | pic |
| 7'-91X | Pt | 1 | 7' | Ph | H | | PS2 | | H | CH₃ | H | H | acac |
| 7'-91Y | Pt | 0 | 7' | Ph | H | | PS2 | | H | CH₃ | H | H | — |
| 7'-92 | Pt | 1 | 7' | Ph | H | H | | BAL1 | CH₃ | H | H | pic | |
| 7'-92X | Pt | 1 | 7' | Ph | H | H | | BAL1 | CH₃ | H | H | acac | |
| 7'-92Y | Pt | 0 | 7' | Ph | H | H | | BAL1 | CH₃ | H | H | — | — |
| 7'-93 | Pt | 1 | 7' | Ph | H | | BAL1 | | H | CH₃ | H | H | pic |
| 7'-93X | Pt | 1 | 7' | Ph | H | | BAL1 | | H | CH₃ | H | H | acac |
| 7'-93Y | Pt | 0 | 7' | Ph | H | | BAL1 | | H | CH₃ | H | H | — |
| 7'-94 | Pt | 1 | 7' | Ph | H | H | | BAL2 | CH₃ | H | H | pic | |
| 7'-94X | Pt | 1 | 7' | Ph | H | H | | BAL2 | CH₃ | H | H | acac | |
| 7'-94Y | Pt | 0 | 7' | Ph | H | H | | BAL2 | CH₃ | H | H | — | — |
| 7'-95 | Pt | 1 | 7' | Ph | H | | BAL2 | | H | CH₃ | H | H | pic |
| 7'-95X | Pt | 1 | 7' | Ph | H | | BAL2 | | H | CH₃ | H | H | acac |
| 7'-95Y | Pt | 0 | 7' | Ph | H | | BAL2 | | H | CH₃ | H | H | — |
| 7'-96 | Pt | 1 | 7' | Ph | H | H | | MEK1 | CH₃ | H | H | pic | |
| 7'-96X | Pt | 1 | 7' | Ph | H | H | | MEK1 | CH₃ | H | H | acac | |
| 7'-96Y | Pt | 0 | 7' | Ph | H | H | | MEK1 | CH₃ | H | H | — | — |
| 7'-97 | Pt | 1 | 7' | Ph | H | | MEK1 | | H | CH₃ | H | H | pic |
| 7'-97X | Pt | 1 | 7' | Ph | H | | MEK1 | | H | CH₃ | H | H | acac |
| 7'-97Y | Pt | 0 | 7' | Ph | H | | MEK1 | | H | CH₃ | H | H | — |
| 7'-98 | Pt | 1 | 7' | Ph | H | H | | MEK2 | CH₃ | H | H | pic | |
| 7'-98X | Pt | 1 | 7' | Ph | H | H | | MEK2 | CH₃ | H | H | acac | |
| 7'-98Y | Pt | 0 | 7' | Ph | H | H | | MEK2 | CH₃ | H | H | — | — |
| 7'-99 | Pt | 1 | 7' | Ph | H | | MEK2 | | H | CH₃ | H | H | pic |
| 7'-99X | Pt | 1 | 7' | Ph | H | | MEK2 | | H | CH₃ | H | H | acac |
| 7'-99Y | Pt | 0 | 7' | Ph | H | | MEK2 | | H | CH₃ | H | H | — |
| 7'-100 | Pt | 1 | 7' | Ph | H | H | | PAL1 | CH₃ | H | H | pic | |
| 7'-100X | Pt | 1 | 7' | Ph | H | H | | PAL1 | CH₃ | H | H | acac | |
| 7'-100Y | Pt | 0 | 7' | Ph | H | H | | PAL1 | CH₃ | H | H | — | — |
| 7'-101 | Pt | 1 | 7' | Ph | H | | PAL1 | | H | CH₃ | H | H | pic |
| 7'-101X | Pt | 1 | 7' | Ph | H | | PAL1 | | H | CH₃ | H | H | acac |
| 7'-101Y | Pt | 0 | 7' | Ph | H | | PAL1 | | H | CH₃ | H | H | — |
| 7'-102 | Pt | 1 | 7' | Ph | H | H | | PAL2 | CH₃ | H | H | pic | |
| 7'-102X | Pt | 1 | 7' | Ph | H | H | | PAL2 | CH₃ | H | H | acac | |
| 7'-102Y | Pt | 0 | 7' | Ph | H | H | | PAL2 | CH₃ | H | H | — | — |
| 7'-103 | Pt | 1 | 7' | Ph | H | | PAL2 | | H | CH₃ | H | H | pic |
| 7'-103X | Pt | 1 | 7' | Ph | H | | PAL2 | | H | CH₃ | H | H | acac |
| 7'-103Y | Pt | 0 | 7' | Ph | H | | PAL2 | | H | CH₃ | H | H | — |
| 7'-104 | Pt | 1 | 7' | Ph | H | H | | MMK | CH₃ | H | H | pic | |
| 7'-104X | Pt | 1 | 7' | Ph | H | H | | MMK | CH₃ | H | H | acac | |
| 7'-104Y | Pt | 0 | 7' | Ph | H | H | | MMK | CH₃ | H | H | — | — |
| 7'-105 | Pt | 1 | 7' | Ph | H | | MMK | | H | CH₃ | H | H | pic |
| 7'-105X | Pt | 1 | 7' | Ph | H | | MMK | | H | CH₃ | H | H | acac |
| 7'-105Y | Pt | 0 | 7' | Ph | H | | MMK | | H | CH₃ | H | H | — |
| 7'-106 | Pt | 1 | 7' | Ph | H | H | | EES1 | CH₃ | H | H | pic | |

TABLE 35-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 7'-106X | Pt | 1 | 7' | Ph | H | H | | EES1 | CH₃ | H | H | acac | |
| 7'-106Y | Pt | 0 | 7' | Ph | H | H | | EES1 | CH₃ | H | H | — | — |
| 7'-107 | Pt | 1 | 7' | Ph | H | | EES2 | H | CH₃ | H | H | pic | |
| 7'-107X | Pt | 1 | 7' | Ph | H | | EES2 | H | CH₃ | H | H | acac | |
| 7'-107Y | Pt | 0 | 7' | Ph | H | | EES2 | H | CH₃ | H | H | — | — |
| 7'-108 | Pt | 1 | 7' | Ph | H | H | | PAE1 | CH₃ | H | H | pic | |
| 7'-108X | Pt | 1 | 7' | Ph | H | H | | PAE1 | CH₃ | H | H | acac | |
| 7'-108Y | Pt | 0 | 7' | Ph | H | H | | PAE1 | CH₃ | H | H | — | — |
| 7'-109 | Pt | 1 | 7' | Ph | H | | PAE2 | H | CH₃ | H | H | pic | |
| 7'-109X | Pt | 1 | 7' | Ph | H | | PAE2 | H | CH₃ | H | H | acac | |
| 7'-109Y | Pt | 0 | 7' | Ph | H | | PAE2 | H | CH₃ | H | H | — | — |
| 7'-110 | Pt | 1 | 7' | Ph | H | H | | AME1 | CH₃ | H | H | pic | |
| 7'-110X | Pt | 1 | 7' | Ph | H | H | | AME1 | CH₃ | H | H | acac | |
| 7'-110Y | Pt | 0 | 7' | Ph | H | H | | AME1 | CH₃ | H | H | — | — |
| 7'-111 | Pt | 1 | 7' | Ph | H | | AME1 | H | CH₃ | H | H | pic | |
| 7'-111X | Pt | 1 | 7' | Ph | H | | AME1 | H | CH₃ | H | H | acac | |
| 7'-111Y | Pt | 0 | 7' | Ph | H | | AME1 | H | CH₃ | H | H | — | — |
| 7'-112 | Pt | 1 | 7' | Ph | H | H | | AME2 | CH₃ | H | H | pic | |
| 7'-112X | Pt | 1 | 7' | Ph | H | H | | AME2 | CH₃ | H | H | acac | |
| 7'-112Y | Pt | 0 | 7' | Ph | H | H | | AME2 | CH₃ | H | H | — | — |
| 7'-113 | Pt | 1 | 7' | Ph | H | | AME2 | H | CH₃ | H | H | pic | |
| 7'-113X | Pt | 1 | 7' | Ph | H | | AME2 | H | CH₃ | H | H | acac | |
| 7'-113Y | Pt | 0 | 7' | Ph | H | | AME2 | H | CH₃ | H | H | — | — |
| 7'-114 | Pt | 1 | 7' | Ph | H | H | | EAE1 | CH₃ | H | H | pic | |
| 7'-114X | Pt | 1 | 7' | Ph | H | H | | EAE1 | CH₃ | H | H | acac | |
| 7'-114Y | Pt | 0 | 7' | Ph | H | H | | EAE1 | CH₃ | H | H | — | — |
| 7'-115 | Pt | 1 | 7' | Ph | H | | EAE1 | H | CH₃ | H | H | pic | |
| 7'-115X | Pt | 1 | 7' | Ph | H | | EAE1 | H | CH₃ | H | H | acac | |
| 7'-115Y | Pt | 0 | 7' | Ph | H | | EAE1 | H | CH₃ | H | H | — | — |
| 7'-116 | Pt | 1 | 7' | Ph | H | H | | EAE2 | CH₃ | H | H | pic | |
| 7'-116X | Pt | 1 | 7' | Ph | H | H | | EAE2 | CH₃ | H | H | acac | |
| 7'-116Y | Pt | 0 | 7' | Ph | H | H | | EAE2 | CH₃ | H | H | — | — |
| 7'-117 | Pt | 1 | 7' | Ph | H | | EAE2 | H | CH₃ | H | H | pic | |
| 7'-117X | Pt | 1 | 7' | Ph | H | | EAE2 | H | CH₃ | H | H | acac | |
| 7'-117Y | Pt | 0 | 7' | Ph | H | | EAE2 | H | CH₃ | H | H | — | — |
| 7'-118 | Pt | 1 | 7' | Ph | H | H | | AAE1 | CH₃ | H | H | pic | |
| 7'-118X | Pt | 1 | 7' | Ph | H | H | | AAE1 | CH₃ | H | H | acac | |
| 7'-118Y | Pt | 0 | 7' | Ph | H | H | | AAE1 | CH₃ | H | H | — | — |
| 7'-119 | Pt | 1 | 7' | Ph | H | | AAE1 | H | CH₃ | H | H | pic | |
| 7'-119X | Pt | 1 | 7' | Ph | H | | AAE1 | H | CH₃ | H | H | acac | |
| 7'-119Y | Pt | 0 | 7' | Ph | H | | AAE1 | H | CH₃ | H | H | — | — |
| 7'-120 | Pt | 1 | 7' | Ph | H | H | | AAE2 | CH₃ | H | H | pic | |
| 7'-120X | Pt | 1 | 7' | Ph | H | H | | AAE2 | CH₃ | H | H | acac | |
| 7'-120Y | Pt | 0 | 7' | Ph | H | H | | AAE2 | CH₃ | H | H | — | — |
| 7'-121 | Pt | 1 | 7' | Ph | H | | AAE2 | H | CH₃ | H | H | pic | |
| 7'-121X | Pt | 1 | 7' | Ph | H | | AAE2 | H | CH₃ | H | H | acac | |
| 7'-121Y | Pt | 0 | 7' | Ph | H | | AAE2 | H | CH₃ | H | H | — | — |
| 7'-122 | Pt | 1 | 7' | Ph | H | H | | PME1 | CH₃ | H | H | pic | |
| 7'-122X | Pt | 1 | 7' | Ph | H | H | | PME1 | CH₃ | H | H | acac | |
| 7'-122Y | Pt | 0 | 7' | Ph | H | H | | PME1 | CH₃ | H | H | — | — |
| 7'-123 | Pt | 1 | 7' | Ph | H | | PME1 | H | CH₃ | H | H | pic | |
| 7'-123X | Pt | 1 | 7' | Ph | H | | PME1 | H | CH₃ | H | H | acac | |
| 7'-123Y | Pt | 0 | 7' | Ph | H | | PME1 | H | CH₃ | H | H | — | — |
| 7'-124 | Pt | 1 | 7' | Ph | H | H | | PME2 | CH₃ | H | H | pic | |
| 7'-124X | Pt | 1 | 7' | Ph | H | H | | PME2 | CH₃ | H | H | acac | |
| 7'-124Y | Pt | 0 | 7' | Ph | H | H | | PME2 | CH₃ | H | H | — | — |
| 7'-125 | Pt | 1 | 7' | Ph | H | | PME2 | H | CH₃ | H | H | pic | |
| 7'-125X | Pt | 1 | 7' | Ph | H | | PME2 | H | CH₃ | H | H | acac | |
| 7'-125Y | Pt | 0 | 7' | Ph | H | | PME2 | H | CH₃ | H | H | — | — |
| 7'-126 | Pt | 1 | 7' | Ph | H | H | | MET1 | CH₃ | H | H | pic | |
| 7'-126X | Pt | 1 | 7' | Ph | H | H | | MET1 | CH₃ | H | H | acac | |
| 7'-126Y | Pt | 0 | 7' | Ph | H | H | | MET1 | CH₃ | H | H | — | — |
| 7'-127 | Pt | 1 | 7' | Ph | H | | MET1 | H | CH₃ | H | H | pic | |
| 7'-127X | Pt | 1 | 7' | Ph | H | | MET1 | H | CH₃ | H | H | acac | |
| 7'-127Y | Pt | 0 | 7' | Ph | H | | MET1 | H | CH₃ | H | H | — | — |
| 7'-128 | Pt | 1 | 7' | Ph | H | H | | MET2 | CH₃ | H | H | pic | |
| 7'-128X | Pt | 1 | 7' | Ph | H | H | | MET2 | CH₃ | H | H | acac | |
| 7'-128Y | Pt | 0 | 7' | Ph | H | H | | MET2 | CH₃ | H | H | — | — |
| 7'-129 | Pt | 1 | 7' | Ph | H | | MET2 | H | CH₃ | H | H | pic | |
| 7'-129X | Pt | 1 | 7' | Ph | H | | MET2 | H | CH₃ | H | H | acac | |
| 7'-129Y | Pt | 0 | 7' | Ph | H | | MET2 | H | CH₃ | H | H | — | — |
| 7'-130 | Pt | 1 | 7' | Ph | H | H | | EE1 | CH₃ | H | H | pic | |
| 7'-130X | Pt | 1 | 7' | Ph | H | H | | EE1 | CH₃ | H | H | acac | |
| 7'-130Y | Pt | 0 | 7' | Ph | H | H | | EE1 | CH₃ | H | H | — | — |

TABLE 35-continued

| No. | M | m | BSS | SS | G | T¹ | T² | T³ | T⁴ | T⁵ | T⁶ | T⁷ | L¹ | L² |
|---|---|---|---|---|---|---|---|---|---|---|---|---|---|---|
| 7'-131 | Pt | 1 | 7' | | Ph | H | | EE1 | H | CH₃ | H | H | pic | |
| 7'-131X | Pt | 1 | 7' | | Ph | H | | EE1 | H | CH₃ | H | H | acac | |
| 7'-131Y | Pt | 0 | 7' | | Ph | H | | EE1 | H | CH₃ | H | H | — | — |
| 7'-132 | Pt | 1 | 7' | | Ph | H | H | | EE2 | CH₃ | H | H | pic | |
| 7'-132X | Pt | 1 | 7' | | Ph | H | H | | EE2 | CH₃ | H | H | acac | |
| 7'-132Y | Pt | 0 | 7' | | Ph | H | H | | EE2 | CH₃ | H | H | — | — |
| 7'-133 | Pt | 1 | 7' | | Ph | H | | EE2 | H | CH₃ | H | H | pic | |
| 7'-133X | Pt | 1 | 7' | | Ph | H | | EE2 | H | CH₃ | H | H | acac | |
| 7'-133Y | Pt | 0 | 7' | | Ph | H | | EE2 | H | CH₃ | H | H | — | — |
| 7'-134 | Pt | 1 | 7' | | Ph | H | H | | MS1 | CH₃ | H | H | pic | |
| 7'-134X | Pt | 1 | 7' | | Ph | H | H | | MS1 | CH₃ | H | H | acac | |
| 7'-134Y | Pt | 0 | 7' | | Ph | H | H | | MS1 | CH₃ | H | H | — | — |
| 7'-135 | Pt | 1 | 7' | | Ph | H | | MS1 | H | CH₃ | H | H | pic | |
| 7'-135X | Pt | 1 | 7' | | Ph | H | | MS1 | H | CH₃ | H | H | acac | |
| 7'-135Y | Pt | 0 | 7' | | Ph | H | | MS1 | H | CH₃ | H | H | — | — |
| 7'-136 | Pt | 1 | 7' | | Ph | H | H | | MS2 | CH₃ | H | H | pic | |
| 7'-136X | Pt | 1 | 7' | | Ph | H | H | | MS2 | CH₃ | H | H | acac | |
| 7'-136Y | Pt | 0 | 7' | | Ph | H | H | | MS2 | CH₃ | H | H | — | — |
| 7'-137 | Pt | 1 | 7' | | Ph | H | | MS2 | H | CH₃ | H | H | pic | |
| 7'-137X | Pt | 1 | 7' | | Ph | H | | MS2 | H | CH₃ | H | H | acac | |
| 7'-137Y | Pt | 0 | 7' | | Ph | H | | MS2 | H | CH₃ | H | H | — | — |

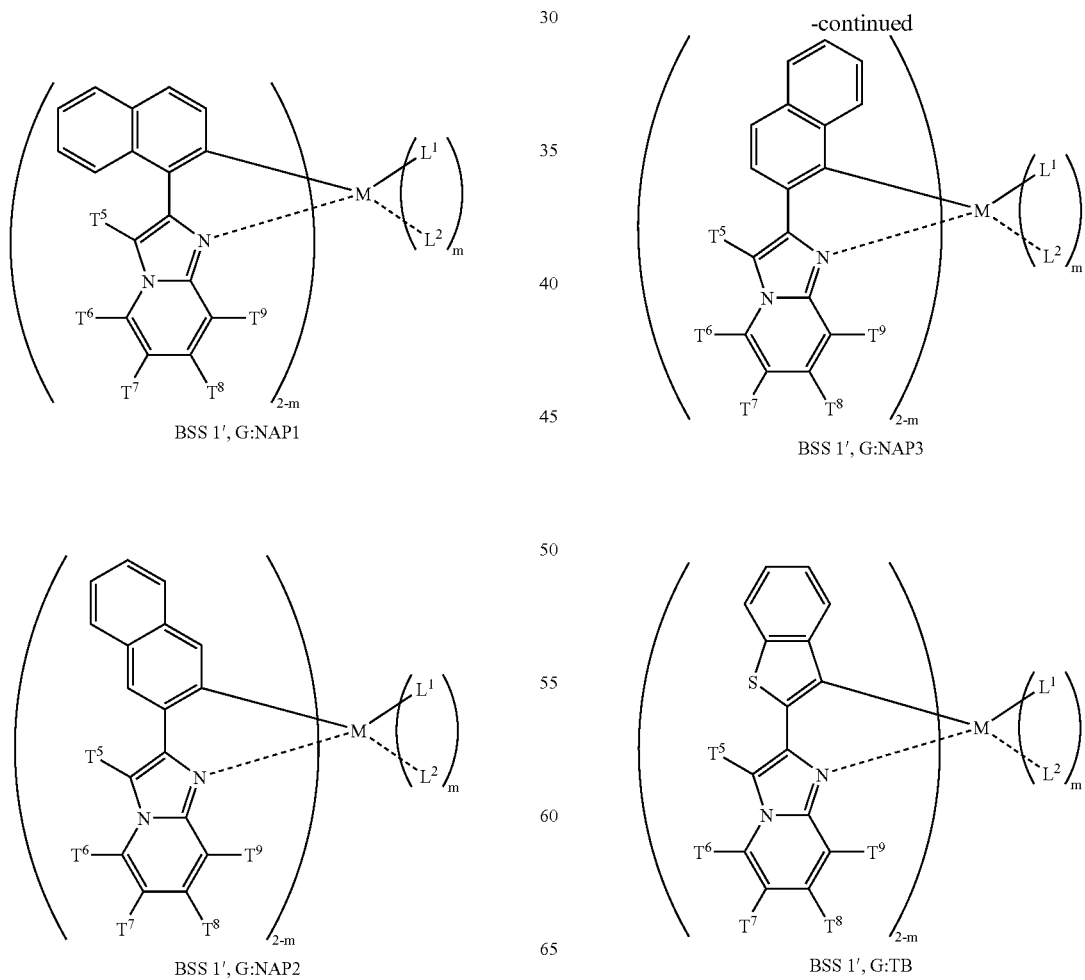

BSS 1', G:NAP1

BSS 1', G:NAP3

BSS 1', G:NAP2

BSS 1', G:TB

-continued
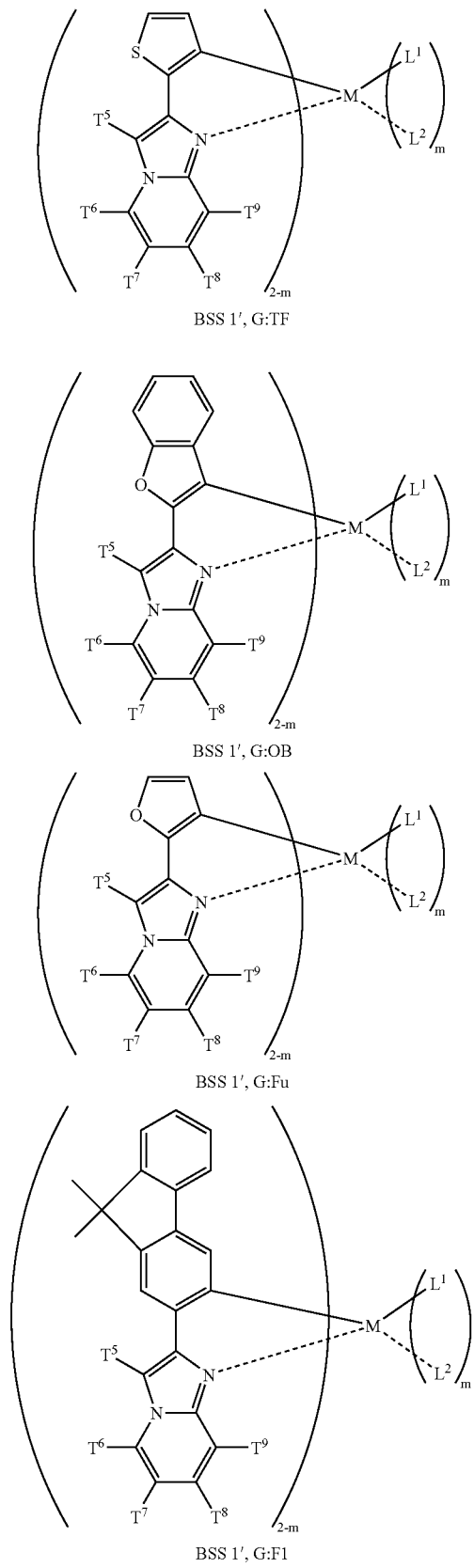
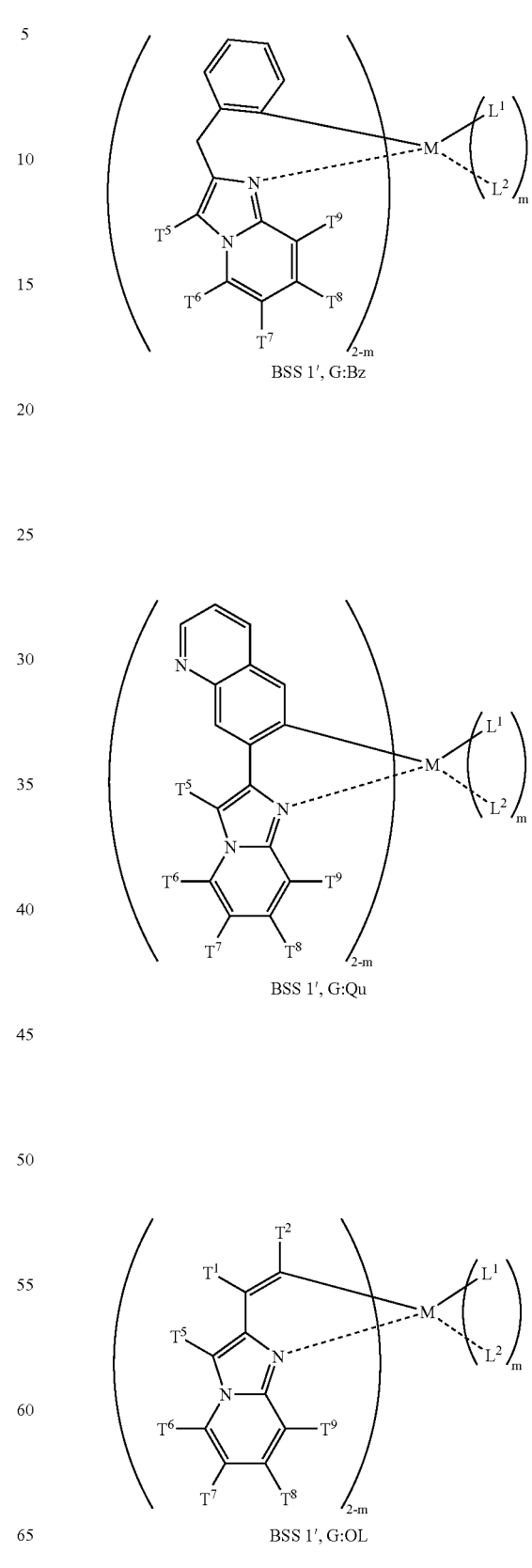

TABLE 36

| No. | M | m | BSS | SS G | T¹ | T² | T⁵ | T⁶ | T⁷ | T⁸ | T⁹ | L¹ L² |
|---|---|---|---|---|---|---|---|---|---|---|---|---|
| 1'-119 | Pt | 1 | 1' | Nap1 | — | — | H | H | H | H | H | pic |
| 1'-119X | Pt | 1 | 1' | Nap1 | — | — | H | H | H | H | H | acac |
| 1'-119Y | Pt | 0 | 1' | Nap1 | — | — | H | H | H | H | H | — |
| 1'-120 | Pt | 1 | 1' | Nap1 | — | — | $^tC_4H_9$ | H | H | H | H | pic |
| 1'-120X | Pt | 1 | 1' | Nap1 | — | — | $^tC_4H_9$ | H | H | H | H | acac |
| 1'-120Y | Pt | 0 | 1' | Nap1 | — | — | $^tC_4H_9$ | H | H | H | H | — |
| 1'-121 | Pt | 1 | 1' | Nap1 | — | — | $CH_3$ | H | H | H | H | pic |
| 1'-121X | Pt | 1 | 1' | Nap1 | — | — | $CH_3$ | H | H | H | H | acac |
| 1'-121Y | Pt | 0 | 1' | Nap1 | — | — | $CH_3$ | H | H | H | H | — |
| 1'-122 | Pt | 1 | 1' | Nap1 | — | — | $^tC_4H_9$ | $CH_3$ | H | H | H | pic |
| 1'-122X | Pt | 1 | 1' | Nap1 | — | — | $^tC_4H_9$ | $CH_3$ | H | H | H | acac |
| 1'-122Y | Pt | 0 | 1' | Nap1 | — | — | $^tC_4H_9$ | $CH_3$ | H | H | H | — |
| 1'-123 | Pt | 1 | 1' | Nap1 | — | — | $CH_3$ | $CH_3$ | H | H | H | pic |
| 1'-123X | Pt | 1 | 1' | Nap1 | — | — | $CH_3$ | $CH_3$ | H | H | H | acac |
| 1'-123Y | Pt | 0 | 1' | Nap1 | — | — | $CH_3$ | $CH_3$ | H | H | H | — |
| 1'-124 | Pt | 1 | 1' | Nap1 | — | — | H | $CH_3$ | H | H | H | pic |
| 1'-124X | Pt | 1 | 1' | Nap1 | — | — | H | $CH_3$ | H | H | H | acac |
| 1'-124Y | Pt | 0 | 1' | Nap1 | — | — | H | $CH_3$ | H | H | H | — |
| 1'-125 | Pt | 1 | 1' | Nap2 | — | — | H | H | H | H | H | pic |
| 1'-125X | Pt | 1 | 1' | Nap2 | — | — | H | H | H | H | H | acac |
| 1'-125Y | Pt | 0 | 1' | Nap2 | — | — | H | H | H | H | H | — |
| 1'-126 | Pt | 1 | 1' | Nap2 | — | — | $^tC_4H_9$ | H | H | H | H | pic |
| 1'-126X | Pt | 1 | 1' | Nap2 | — | — | $^tC_4H_9$ | H | H | H | H | acac |
| 1'-126Y | Pt | 0 | 1' | Nap2 | — | — | $^tC_4H_9$ | H | H | H | H | — |
| 1'-127 | Pt | 1 | 1' | Nap2 | — | — | $CH_3$ | H | H | H | H | pic |
| 1'-127X | Pt | 1 | 1' | Nap2 | — | — | $CH_3$ | H | H | H | H | acac |
| 1'-127Y | Pt | 0 | 1' | Nap2 | — | — | $CH_3$ | H | H | H | H | — |
| 1'-128 | Pt | 1 | 1' | Nap2 | — | — | $^tC_4H_9$ | $CH_3$ | H | H | H | pic |
| 1'-128X | Pt | 1 | 1' | Nap2 | — | — | $^tC_4H_9$ | $CH_3$ | H | H | H | acac |
| 1'-128Y | Pt | 0 | 1' | Nap2 | — | — | $^tC_4H_9$ | $CH_3$ | H | H | H | — |
| 1'-129 | Pt | 1 | 1' | Nap2 | — | — | $CH_3$ | $CH_3$ | H | H | H | pic |
| 1'-129X | Pt | 1 | 1' | Nap2 | — | — | $CH_3$ | $CH_3$ | H | H | H | acac |
| 1'-129Y | Pt | 0 | 1' | Nap2 | — | — | $CH_3$ | $CH_3$ | H | H | H | — |
| 1'-130 | Pt | 1 | 1' | Nap2 | — | — | H | $CH_3$ | H | H | H | pic |
| 1'-130X | Pt | 1 | 1' | Nap2 | — | — | H | $CH_3$ | H | H | H | acac |
| 1'-130Y | Pt | 0 | 1' | Nap2 | — | — | H | $CH_3$ | H | H | H | — |
| 1'-131 | Pt | 1 | 1' | Nap3 | — | — | H | H | H | H | H | pic |
| 1'-131X | Pt | 1 | 1' | Nap3 | — | — | H | H | H | H | H | acac |
| 1'-131Y | Pt | 0 | 1' | Nap3 | — | — | H | H | H | H | H | — |
| 1'-132 | Pt | 1 | 1' | Nap3 | — | — | $^tC_4H_9$ | H | H | H | H | pic |
| 1'-132X | Pt | 1 | 1' | Nap3 | — | — | $^tC_4H_9$ | H | H | H | H | acac |
| 1'-132Y | Pt | 0 | 1' | Nap3 | — | — | $^tC_4H_9$ | H | H | H | H | — |
| 1'-133 | Pt | 1 | 1' | Nap3 | — | — | $CH_3$ | H | H | H | H | pic |
| 1'-133X | Pt | 1 | 1' | Nap3 | — | — | $CH_3$ | H | H | H | H | acac |
| 1'-133Y | Pt | 0 | 1' | Nap3 | — | — | $CH_3$ | H | H | H | H | — |
| 1'-134 | Pt | 1 | 1' | Nap3 | — | — | $^tC_4H_9$ | $CH_3$ | H | H | H | pic |
| 1'-134X | Pt | 1 | 1' | Nap3 | — | — | $^tC_4H_9$ | $CH_3$ | H | H | H | acac |
| 1'-134Y | Pt | 0 | 1' | Nap3 | — | — | $^tC_4H_9$ | $CH_3$ | H | H | H | — |
| 1'-135 | Pt | 1 | 1' | Nap3 | — | — | $CH_3$ | $CH_3$ | H | H | H | pic |
| 1'-135X | Pt | 1 | 1' | Nap3 | — | — | $CH_3$ | $CH_3$ | H | H | H | acac |
| 1'-135Y | Pt | 0 | 1' | Nap3 | — | — | $CH_3$ | $CH_3$ | H | H | H | — |
| 1'-136 | Pt | 1 | 1' | Nap3 | — | — | H | $CH_3$ | H | H | H | pic |
| 1'-136X | Pt | 1 | 1' | Nap3 | — | — | H | $CH_3$ | H | H | H | acac |
| 1'-136Y | Pt | 0 | 1' | Nap3 | — | — | H | $CH_3$ | H | H | H | — |
| 1'-137 | Pt | 1 | 1' | TB | — | — | H | H | H | H | H | pic |
| 1'-137X | Pt | 1 | 1' | TB | — | — | H | H | H | H | H | acac |
| 1'-137Y | Pt | 0 | 1' | TB | — | — | H | H | H | H | H | — |
| 1'-138 | Pt | 1 | 1' | TB | — | — | $^tC_4H_9$ | H | H | H | H | pic |
| 1'-138X | Pt | 1 | 1' | TB | — | — | $^tC_4H_9$ | H | H | H | H | acac |
| 1'-138Y | Pt | 0 | 1' | TB | — | — | $^tC_4H_9$ | H | H | H | H | — |
| 1'-139 | Pt | 1 | 1' | TB | — | — | $CH_3$ | H | H | H | H | pic |
| 1'-139X | Pt | 1 | 1' | TB | — | — | $CH_3$ | H | H | H | H | acac |
| 1'-139Y | Pt | 0 | 1' | TB | — | — | $CH_3$ | H | H | H | H | — |
| 1'-140 | Pt | 1 | 1' | TB | — | — | $^tC_4H_9$ | $CH_3$ | H | H | H | pic |
| 1'-140X | Pt | 1 | 1' | TB | — | — | $^tC_4H_9$ | $CH_3$ | H | H | H | acac |
| 1'-140Y | Pt | 0 | 1' | TB | — | — | $^tC_4H_9$ | $CH_3$ | H | H | H | — |
| 1'-141 | Pt | 1 | 1' | TB | — | — | $CH_3$ | $CH_3$ | H | H | H | pic |
| 1'-141X | Pt | 1 | 1' | TB | — | — | $CH_3$ | $CH_3$ | H | H | H | acac |
| 1'-141Y | Pt | 0 | 1' | TB | — | — | $CH_3$ | $CH_3$ | H | H | H | — |
| 1'-142 | Pt | 1 | 1' | TB | — | — | H | $CH_3$ | H | H | H | pic |
| 1'-142X | Pt | 1 | 1' | TB | — | — | H | $CH_3$ | H | H | H | acac |
| 1'-142Y | Pt | 0 | 1' | TB | — | — | H | $CH_3$ | H | H | H | — |
| 1'-143 | Pt | 1 | 1' | TF | — | — | H | H | H | H | H | pic |
| 1'-143X | Pt | 1 | 1' | TF | — | — | H | H | H | H | H | acac |
| 1'-143Y | Pt | 0 | 1' | TF | — | — | H | H | H | H | H | — |
| 1'-144 | Pt | 1 | 1' | TF | — | — | $^tC_4H_9$ | H | H | H | H | pic |
| 1'-144X | Pt | 1 | 1' | TF | — | — | $^tC_4H_9$ | H | H | H | H | acac |

TABLE 36-continued

| No. | M | m | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 1'-144Y | Pt | 0 | 1' | TF | | — | — | $^tC_4H_9$ | H | H | H | H | — | — |
| 1'-145 | Pt | 1 | 1' | TF | | — | — | $CH_3$ | H | H | H | H | pic | |
| 1'-145X | Pt | 1 | 1' | TF | | — | — | $CH_3$ | H | H | H | H | acac | |
| 1'-145Y | Pt | 0 | 1' | TF | | — | — | $CH_3$ | H | H | H | H | — | — |
| 1'-146 | Pt | 1 | 1' | TF | | — | — | $^tC_4H_9$ | $CH_3$ | H | H | H | pic | |
| 1'-146X | Pt | 1 | 1' | TF | | — | — | $^tC_4H_9$ | $CH_3$ | H | H | H | acac | |
| 1'-146Y | Pt | 0 | 1' | TF | | — | — | $^tC_4H_9$ | $CH_3$ | H | H | H | — | — |
| 1'-147 | Pt | 1 | 1' | TF | | — | — | $CH_3$ | $CH_3$ | H | H | H | pic | |
| 1'-147X | Pt | 1 | 1' | TF | | — | — | $CH_3$ | $CH_3$ | H | H | H | acac | |
| 1'-147Y | Pt | 0 | 1' | TF | | — | — | $CH_3$ | $CH_3$ | H | H | H | — | — |
| 1'-148 | Pt | 1 | 1' | TF | | — | — | H | $CH_3$ | H | H | H | pic | |
| 1'-148X | Pt | 1 | 1' | TF | | — | — | H | $CH_3$ | H | H | H | acac | |
| 1'-148Y | Pt | 0 | 1' | TF | | — | — | H | $CH_3$ | H | H | H | — | — |
| 1'-149 | Pt | 1 | 1' | OB | | — | — | H | H | H | H | H | pic | |
| 1'-149X | Pt | 1 | 1' | OB | | — | — | H | H | H | H | H | acac | |
| 1'-149Y | Pt | 0 | 1' | OB | | — | — | H | H | H | H | H | — | — |
| 1'-150 | Pt | 1 | 1' | OB | | — | — | $^tC_4H_9$ | H | H | H | H | pic | |
| 1'-150X | Pt | 1 | 1' | OB | | — | — | $^tC_4H_9$ | H | H | H | H | acac | |
| 1'-150Y | Pt | 0 | 1' | OB | | — | — | $^tC_4H_9$ | H | H | H | H | — | — |
| 1'-151 | Pt | 1 | 1' | OB | | — | — | $CH_3$ | H | H | H | H | pic | |
| 1'-151X | Pt | 1 | 1' | OB | | — | — | $CH_3$ | H | H | H | H | acac | |
| 1'-151Y | Pt | 0 | 1' | OB | | — | — | $CH_3$ | H | H | H | H | — | — |
| 1'-152 | Pt | 1 | 1' | OB | | — | — | $^tC_4H_9$ | $CH_3$ | H | H | H | pic | |
| 1'-152X | Pt | 1 | 1' | OB | | — | — | $^tC_4H_9$ | $CH_3$ | H | H | H | acac | |
| 1'-152Y | Pt | 0 | 1' | OB | | — | — | $^tC_4H_9$ | $CH_3$ | H | H | H | — | — |
| 1'-153 | Pt | 1 | 1' | OB | | — | — | $CH_3$ | $CH_3$ | H | H | H | pic | |
| 1'-153X | Pt | 1 | 1' | OB | | — | — | $CH_3$ | $CH_3$ | H | H | H | acac | |
| 1'-153Y | Pt | 0 | 1' | OB | | — | — | $CH_3$ | $CH_3$ | H | H | H | — | — |
| 1'-154 | Pt | 1 | 1' | OB | | — | — | H | $CH_3$ | H | H | H | pic | |
| 1'-154X | Pt | 1 | 1' | OB | | — | — | H | $CH_3$ | H | H | H | acac | |
| 1'-154Y | Pt | 0 | 1' | OB | | — | — | H | $CH_3$ | H | H | H | — | — |
| 1'-155 | Pt | 1 | 1' | Fu | | — | — | H | H | H | H | H | pic | |
| 1'-155X | Pt | 1 | 1' | Fu | | — | — | H | H | H | H | H | acac | |
| 1'-155Y | Pt | 0 | 1' | Fu | | — | — | H | H | H | H | H | — | — |
| 1'-156 | Pt | 1 | 1' | Fu | | — | — | $^tC_4H_9$ | H | H | H | H | pic | |
| 1'-156X | Pt | 1 | 1' | Fu | | — | — | $^tC_4H_9$ | H | H | H | H | acac | |
| 1'-156Y | Pt | 0 | 1' | Fu | | — | — | $^tC_4H_9$ | H | H | H | H | — | — |
| 1'-157 | Pt | 1 | 1' | Fu | | — | — | $CH_3$ | H | H | H | H | pic | |
| 1'-157X | Pt | 1 | 1' | Fu | | — | — | $CH_3$ | H | H | H | H | acac | |
| 1'-157Y | Pt | 0 | 1' | Fu | | — | — | $CH_3$ | H | H | H | H | — | — |
| 1'-158 | Pt | 1 | 1' | Fu | | — | — | $^tC_4H_9$ | $CH_3$ | H | H | H | pic | |
| 1'-158X | Pt | 1 | 1' | Fu | | — | — | $^tC_4H_9$ | $CH_3$ | H | H | H | acac | |
| 1'-158Y | Pt | 0 | 1' | Fu | | — | — | $^tC_4H_9$ | $CH_3$ | H | H | H | — | — |
| 1'-159 | Pt | 1 | 1' | Fu | | — | — | $CH_3$ | $CH_3$ | H | H | H | pic | |
| 1'-159X | Pt | 1 | 1' | Fu | | — | — | $CH_3$ | $CH_3$ | H | H | H | acac | |
| 1'-159Y | Pt | 0 | 1' | Fu | | — | — | $CH_3$ | $CH_3$ | H | H | H | — | — |
| 1'-160 | Pt | 1 | 1' | Fu | | — | — | H | $CH_3$ | H | H | H | pic | |
| 1'-160X | Pt | 1 | 1' | Fu | | — | — | H | $CH_3$ | H | H | H | acac | |
| 1'-160Y | Pt | 0 | 1' | Fu | | — | — | H | $CH_3$ | H | H | H | — | — |
| 1'-161 | Pt | 1 | 1' | Fl | | — | — | H | H | H | H | H | pic | |
| 1'-161X | Pt | 1 | 1' | Fl | | — | — | H | H | H | H | H | acac | |
| 1'-161Y | Pt | 0 | 1' | Fl | | — | — | H | H | H | H | H | — | — |
| 1'-162 | Pt | 1 | 1' | Fl | | — | — | $^tC_4H_9$ | H | H | H | H | pic | |
| 1'-162X | Pt | 1 | 1' | Fl | | — | — | $^tC_4H_9$ | H | H | H | H | acac | |
| 1'-162Y | Pt | 0 | 1' | Fl | | — | — | $^tC_4H_9$ | H | H | H | H | — | — |
| 1'-163 | Pt | 1 | 1' | Fl | | — | — | $CH_3$ | H | H | H | H | pic | |
| 1'-163X | Pt | 1 | 1' | Fl | | — | — | $CH_3$ | H | H | H | H | acac | |
| 1'-163Y | Pt | 0 | 1' | Fl | | — | — | $CH_3$ | H | H | H | H | — | — |
| 1'-164 | Pt | 1 | 1' | Fl | | — | — | $^tC_4H_9$ | $CH_3$ | H | H | H | pic | |
| 1'-164X | Pt | 1 | 1' | Fl | | — | — | $^tC_4H_9$ | $CH_3$ | H | H | H | acac | |
| 1'-164Y | Pt | 0 | 1' | Fl | | — | — | $^tC_4H_9$ | $CH_3$ | H | H | H | — | — |
| 1'-165 | Pt | 1 | 1' | Fl | | — | — | $CH_3$ | $CH_3$ | H | H | H | pic | |
| 1'-165X | Pt | 1 | 1' | Fl | | — | — | $CH_3$ | $CH_3$ | H | H | H | acac | |
| 1'-165Y | Pt | 0 | 1' | Fl | | — | — | $CH_3$ | $CH_3$ | H | H | H | — | — |
| 1'-166 | Pt | 1 | 1' | Fl | | — | — | H | $CH_3$ | H | H | H | pic | |
| 1'-166X | Pt | 1 | 1' | Fl | | — | — | H | $CH_3$ | H | H | H | acac | |
| 1'-166Y | Pt | 0 | 1' | Fl | | — | — | H | $CH_3$ | H | H | H | — | — |
| 1'-167 | Pt | 1 | 1' | Bz | | — | — | H | H | H | H | H | pic | |
| 1'-167X | Pt | 1 | 1' | Bz | | — | — | H | H | H | H | H | acac | |
| 1'-167Y | Pt | 0 | 1' | Bz | | — | — | H | H | H | H | H | — | — |
| 1'-168 | Pt | 1 | 1' | Bz | | — | — | $^tC_4H_9$ | H | H | H | H | pic | |
| 1'-168X | Pt | 1 | 1' | Bz | | — | — | $^tC_4H_9$ | H | H | H | H | acac | |
| 1'-168Y | Pt | 0 | 1' | Bz | | — | — | $^tC_4H_9$ | H | H | H | H | — | — |
| 1'-169 | Pt | 1 | 1' | Bz | | — | — | $CH_3$ | H | H | H | H | pic | |
| 1'-169X | Pt | 1 | 1' | Bz | | — | — | $CH_3$ | H | H | H | H | acac | |
| 1'-169Y | Pt | 0 | 1' | Bz | | — | — | $CH_3$ | H | H | H | H | — | — |
| 1'-170 | Pt | 1 | 1' | Bz | | — | — | $^tC_4H_9$ | $CH_3$ | H | H | H | pic | |

TABLE 36-continued

| No. | M | m | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 1'-170X | Pt | 1 | 1' | | Bz | — | — | $^tC_4H_9$ | $CH_3$ | H | H | H | acac | |
| 1'-170Y | Pt | 0 | 1' | | Bz | — | — | $^tC_4H_9$ | $CH_3$ | H | H | H | — | — |
| 1'-171 | Pt | 1 | 1' | | Bz | — | — | $CH_3$ | $CH_3$ | H | H | H | pic | |
| 1'-171X | Pt | 1 | 1' | | Bz | — | — | $CH_3$ | $CH_3$ | H | H | H | acac | |
| 1'-171Y | Pt | 0 | 1' | | Bz | — | — | $CH_3$ | $CH_3$ | H | H | H | — | — |
| 1'-172 | Pt | 1 | 1' | | Bz | — | — | H | $CH_3$ | H | H | H | pic | |
| 1'-172X | Pt | 1 | 1' | | Bz | — | — | H | $CH_3$ | H | H | H | acac | |
| 1'-172Y | Pt | 0 | 1' | | Bz | — | — | H | $CH_3$ | H | H | H | — | — |
| 1'-173 | Pt | 1 | 1' | | Qu | — | — | H | H | H | H | H | pic | |
| 1'-173X | Pt | 1 | 1' | | Qu | — | — | H | H | H | H | H | acac | |
| 1'-173Y | Pt | 0 | 1' | | Qu | — | — | H | H | H | H | H | — | — |
| 1'-174 | Pt | 1 | 1' | | Qu | — | — | $^tC_4H_9$ | H | H | H | H | pic | |
| 1'-174X | Pt | 1 | 1' | | Qu | — | — | $^tC_4H_9$ | H | H | H | H | acac | |
| 1'-174Y | Pt | 0 | 1' | | Qu | — | — | $^tC_4H_9$ | H | H | H | H | — | — |
| 1'-175 | Pt | 1 | 1' | | Qu | — | — | $CH_3$ | H | H | H | H | pic | |
| 1'-175X | Pt | 1 | 1' | | Qu | — | — | $CH_3$ | H | H | H | H | acac | |
| 1'-175Y | Pt | 0 | 1' | | Qu | — | — | $CH_3$ | H | H | H | H | — | — |
| 1'-176 | Pt | 1 | 1' | | Qu | — | — | $^tC_4H_9$ | $CH_3$ | H | H | H | pic | |
| 1'-176X | Pt | 1 | 1' | | Qu | — | — | $^tC_4H_9$ | $CH_3$ | H | H | H | acac | |
| 1'-176Y | Pt | 0 | 1' | | Qu | — | — | $^tC_4H_9$ | $CH_3$ | H | H | H | — | — |
| 1'-177 | Pt | 1 | 1' | | Qu | — | — | $CH_3$ | $CH_3$ | H | H | H | pic | |
| 1'-177X | Pt | 1 | 1' | | Qu | — | — | $CH_3$ | $CH_3$ | H | H | H | acac | |
| 1'-177Y | Pt | 0 | 1' | | Qu | — | — | $CH_3$ | $CH_3$ | H | H | H | — | — |
| 1'-178 | Pt | 1 | 1' | | Qu | — | — | H | $CH_3$ | H | H | H | pic | |
| 1'-178X | Pt | 1 | 1' | | Qu | — | — | H | $CH_3$ | H | H | H | acac | |
| 1'-178Y | Pt | 0 | 1' | | Qu | — | — | H | $CH_3$ | H | H | H | — | — |
| 1'-179 | Pt | 1 | 1' | | OL | H | $^nC_4H_9$ | H | H | H | H | H | pic | |
| 1'-179X | Pt | 1 | 1' | | OL | H | $^nC_4H_9$ | H | H | H | H | H | acac | |
| 1'-179Y | Pt | 0 | 1' | | OL | H | $^nC_4H_9$ | H | H | H | H | H | — | — |
| 1'-180 | Pt | 1 | 1' | | OL | H | $^tC_4H_9$ | H | H | H | H | H | pic | |
| 1'-180X | Pt | 1 | 1' | | OL | H | $^tC_4H_9$ | H | H | H | H | H | acac | |
| 1'-180Y | Pt | 0 | 1' | | OL | H | $^tC_4H_9$ | H | H | H | H | H | — | — |
| 1'-181 | Pt | 1 | 1' | | OL | $CH_3$ | $^nC_4H_9$ | H | H | H | H | H | pic | |
| 1'-181X | Pt | 1 | 1' | | OL | $CH_3$ | $^nC_4H_9$ | H | H | H | H | H | acac | |
| 1'-181Y | Pt | 0 | 1' | | OL | $CH_3$ | $^nC_4H_9$ | H | H | H | H | H | — | — |
| 1'-182 | Pt | 1 | 1' | | OL | $CH_3$ | $^tC_4H_9$ | H | H | H | H | H | pic | |
| 1'-182X | Pt | 1 | 1' | | OL | $CH_3$ | $^tC_4H_9$ | H | H | H | H | H | acac | |
| 1'-182Y | Pt | 0 | 1' | | OL | $CH_3$ | $^tC_4H_9$ | H | H | H | H | H | — | — |
| 1'-183 | Pt | 1 | 1' | | OL | H | H | H | H | H | H | H | pic | |
| 1'-183X | Pt | 1 | 1' | | OL | H | H | H | H | H | H | H | acac | |
| 1'-183Y | Pt | 0 | 1' | | OL | H | H | H | H | H | H | H | — | — |
| 1'-184 | Pt | 1 | 1' | | OL | H | $^nC_4H_9$ | $CH_3$ | H | H | H | H | pic | |
| 1'-184X | Pt | 1 | 1' | | OL | H | $^nC_4H_9$ | $CH_3$ | H | H | H | H | acac | |
| 1'-184Y | Pt | 0 | 1' | | OL | H | $^nC_4H_9$ | $CH_3$ | H | H | H | H | — | — |
| 1'-185 | Pt | 1 | 1' | | OL | H | $^tC_4H_9$ | $CH_3$ | H | H | H | H | pic | |
| 1'-185X | Pt | 1 | 1' | | OL | H | $^tC_4H_9$ | $CH_3$ | H | H | H | H | acac | |
| 1'-185Y | Pt | 0 | 1' | | OL | H | $^tC_4H_9$ | $CH_3$ | H | H | H | H | — | — |
| 1'-186 | Pt | 1 | 1' | | OL | —$CH_2CH_2CH_2$— | | H | H | H | H | H | pic | |
| 1'-186X | Pt | 1 | 1' | | OL | —$CH_2CH_2CH_2$— | | H | H | H | H | H | acac | |
| 1'-186Y | Pt | 0 | 1' | | OL | —$CH_2CH_2CH_2$— | | H | H | H | H | H | — | — |

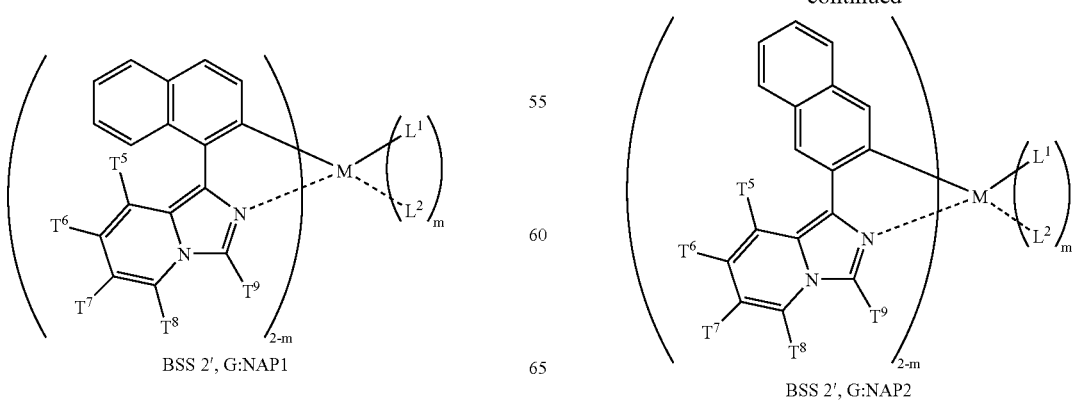

BSS 2', G:NAP1

BSS 2', G:NAP2

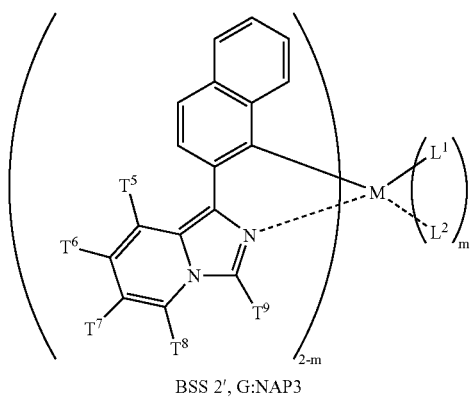
BSS 2′, G:NAP3
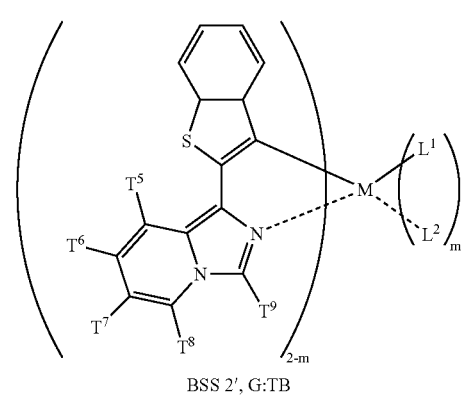
BSS 2′, G:TB
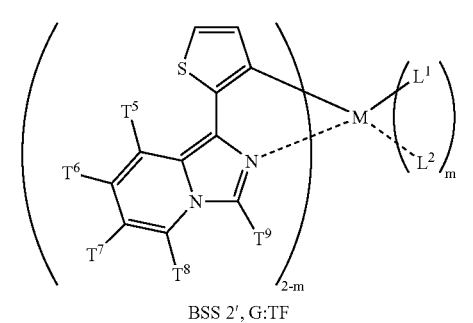
BSS 2′, G:TF
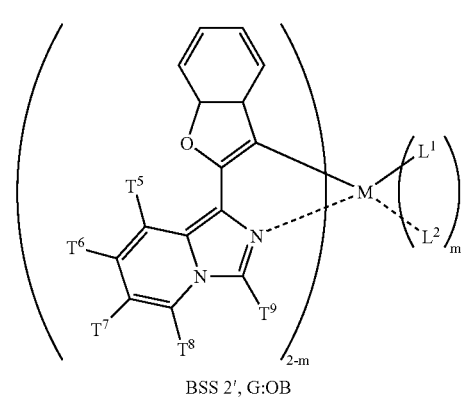
BSS 2′, G:OB
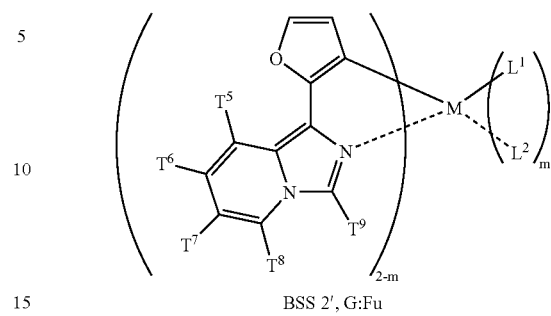
BSS 2′, G:Fu
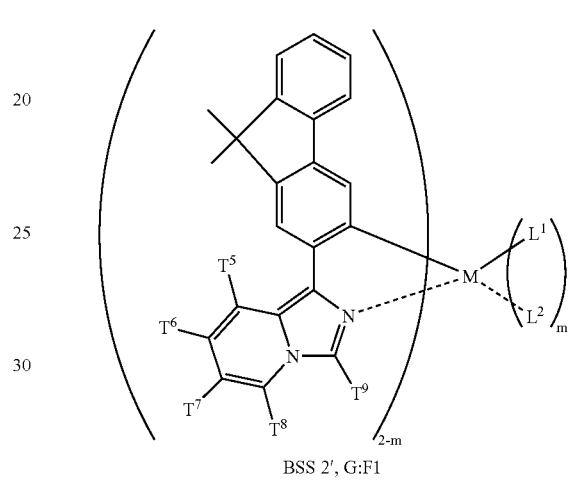
BSS 2′, G:Fl
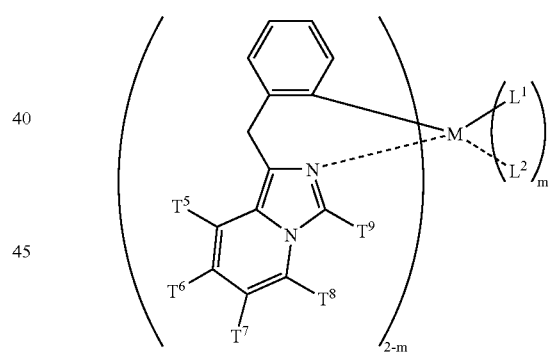
BSS 2′, G:Bz
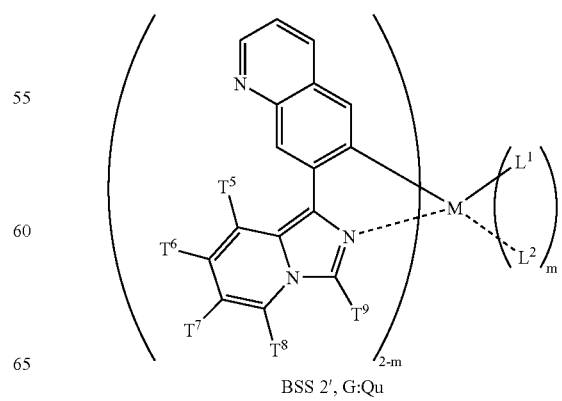
BSS 2′, G:Qu -continued

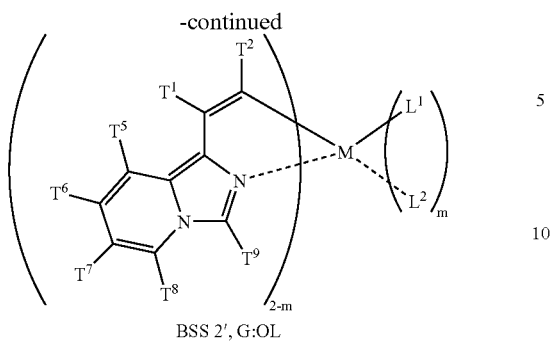

BSS 2', G:OL

TABLE 37

| No. | M | m | BSS | SS G | T¹ | T² | T⁵ | T⁶ | T⁷ | T⁸ | T⁹ | L¹ L² |
|---|---|---|---|---|---|---|---|---|---|---|---|---|
| 2'-119 | Pt | 1 | 2' | Nap1 | — | — | H | H | H | H | H | pic |
| 2'-119X | Pt | 1 | 2' | Nap1 | — | — | H | H | H | H | H | acac |
| 2'-119Y | Pt | 0 | 2' | Nap1 | — | — | H | H | H | H | H | — — |
| 2'-120 | Pt | 1 | 2' | Nap1 | — | — | $^tC_4H_9$ | H | H | H | H | pic |
| 2'-120X | Pt | 1 | 2' | Nap1 | — | — | $^tC_4H_9$ | H | H | H | H | acac |
| 2'-120Y | Pt | 0 | 2' | Nap1 | — | — | $^tC_4H_9$ | H | H | H | H | — — |
| 2'-121 | Pt | 1 | 2' | Nap1 | — | — | $CH_3$ | H | H | H | H | pic |
| 2'-121X | Pt | 1 | 2' | Nap1 | — | — | $CH_3$ | H | H | H | H | acac |
| 2'-121Y | Pt | 0 | 2' | Nap1 | — | — | $CH_3$ | H | H | H | H | — — |
| 2'-122 | Pt | 1 | 2' | Nap1 | — | — | $^tC_4H_9$ | H | H | $CH_3$ | H | pic |
| 2'-122X | Pt | 1 | 2' | Nap1 | — | — | $^tC_4H_9$ | H | H | $CH_3$ | H | acac |
| 2'-122Y | Pt | 0 | 2' | Nap1 | — | — | $^tC_4H_9$ | H | H | $CH_3$ | H | — — |
| 2'-123 | Pt | 1 | 2' | Nap1 | — | — | $CH_3$ | H | H | $CH_3$ | H | pic |
| 2'-123X | Pt | 1 | 2' | Nap1 | — | — | $CH_3$ | H | H | $CH_3$ | H | acac |
| 2'-123Y | Pt | 0 | 2' | Nap1 | — | — | $CH_3$ | H | H | $CH_3$ | H | — — |
| 2'-124 | Pt | 1 | 2' | Nap1 | — | — | H | H | H | $CH_3$ | H | pic |
| 2'-124X | Pt | 1 | 2' | Nap1 | — | — | H | H | H | $CH_3$ | H | acac |
| 2'-124Y | Pt | 0 | 2' | Nap1 | — | — | H | H | H | $CH_3$ | H | — — |
| 2'-125 | Pt | 1 | 2' | Nap2 | — | — | H | H | H | H | H | pic |
| 2'-125X | Pt | 1 | 2' | Nap2 | — | — | H | H | H | H | H | acac |
| 2'-125Y | Pt | 0 | 2' | Nap2 | — | — | H | H | H | H | H | — — |
| 2'-126 | Pt | 1 | 2' | Nap2 | — | — | $^tC_4H_9$ | H | H | H | H | pic |
| 2'-126X | Pt | 1 | 2' | Nap2 | — | — | $^tC_4H_9$ | H | H | H | H | acac |
| 2'-126Y | Pt | 0 | 2' | Nap2 | — | — | $^tC_4H_9$ | H | H | H | H | — — |
| 2'-127 | Pt | 1 | 2' | Nap2 | — | — | $CH_3$ | H | H | H | H | pic |
| 2'-127X | Pt | 1 | 2' | Nap2 | — | — | $CH_3$ | H | H | H | H | acac |
| 2'-127Y | Pt | 0 | 2' | Nap2 | — | — | $CH_3$ | H | H | H | H | — — |
| 2'-128 | Pt | 1 | 2' | Nap2 | — | — | $^tC_4H_9$ | H | H | $CH_3$ | H | pic |
| 2'-128X | Pt | 1 | 2' | Nap2 | — | — | $^tC_4H_9$ | H | H | $CH_3$ | H | acac |
| 2'-128Y | Pt | 0 | 2' | Nap2 | — | — | $^tC_4H_9$ | H | H | $CH_3$ | H | — — |
| 2'-129 | Pt | 1 | 2' | Nap2 | — | — | $CH_3$ | H | H | $CH_3$ | H | pic |
| 2'-129X | Pt | 1 | 2' | Nap2 | — | — | $CH_3$ | H | H | $CH_3$ | H | acac |
| 2'-129Y | Pt | 0 | 2' | Nap2 | — | — | $CH_3$ | H | H | $CH_3$ | H | — — |
| 2'-130 | Pt | 1 | 2' | Nap2 | — | — | H | H | H | $CH_3$ | H | pic |
| 2'-130X | Pt | 1 | 2' | Nap2 | — | — | H | H | H | $CH_3$ | H | acac |
| 2'-130Y | Pt | 0 | 2' | Nap2 | — | — | H | H | H | $CH_3$ | H | — — |
| 2'-131 | Pt | 1 | 2' | Nap3 | — | — | H | H | H | H | H | pic |
| 2'-131X | Pt | 1 | 2' | Nap3 | — | — | H | H | H | H | H | acac |
| 2'-131Y | Pt | 0 | 2' | Nap3 | — | — | H | H | H | H | H | — — |
| 2'-132 | Pt | 1 | 2' | Nap3 | — | — | $^tC_4H_9$ | H | H | H | H | pic |
| 2'-132X | Pt | 1 | 2' | Nap3 | — | — | $^tC_4H_9$ | H | H | H | H | acac |
| 2'-132Y | Pt | 0 | 2' | Nap3 | — | — | $^tC_4H_9$ | H | H | H | H | — — |
| 2'-133 | Pt | 1 | 2' | Nap3 | — | — | $CH_3$ | H | H | H | H | pic |
| 2'-133X | Pt | 1 | 2' | Nap3 | — | — | $CH_3$ | H | H | H | H | acac |
| 2'-133Y | Pt | 0 | 2' | Nap3 | — | — | $CH_3$ | H | H | H | H | — — |
| 2'-134 | Pt | 1 | 2' | Nap3 | — | — | $^tC_4H_9$ | H | H | $CH_3$ | H | pic |
| 2'-134X | Pt | 1 | 2' | Nap3 | — | — | $^tC_4H_9$ | H | H | $CH_3$ | H | acac |
| 2'-134Y | Pt | 0 | 2' | Nap3 | — | — | $^tC_4H_9$ | H | H | $CH_3$ | H | — — |
| 2'-135 | Pt | 1 | 2' | Nap3 | — | — | $CH_3$ | H | H | $CH_3$ | H | pic |
| 2'-135X | Pt | 1 | 2' | Nap3 | — | — | $CH_3$ | H | H | $CH_3$ | H | acac |
| 2'-135Y | Pt | 0 | 2' | Nap3 | — | — | $CH_3$ | H | H | $CH_3$ | H | — — |
| 2'-136 | Pt | 1 | 2' | Nap3 | — | — | H | H | H | $CH_3$ | H | pic |
| 2'-136X | Pt | 1 | 2' | Nap3 | — | — | H | H | H | $CH_3$ | H | acac |
| 2'-136Y | Pt | 0 | 2' | Nap3 | — | — | H | H | H | $CH_3$ | H | — — |
| 2'-137 | Pt | 1 | 2' | TB | — | — | H | H | H | H | H | pic |
| 2'-137X | Pt | 1 | 2' | TB | — | — | H | H | H | H | H | acac |

TABLE 37-continued

| No. | M | m | BSS | SS G | $T^1$ | $T^2$ | $T^5$ | $T^6$ | $T^7$ | $T^8$ | $T^9$ | $L^1$ | $L^2$ |
|---|---|---|---|---|---|---|---|---|---|---|---|---|---|
| 2'-137Y | Pt | 0 | 2' | TB | — | — | H | H | H | H | H | — | — |
| 2'-138 | Pt | 1 | 2' | TB | — | — | $^tC_4H_9$ | H | H | H | H | pic | |
| 2'-138X | Pt | 1 | 2' | TB | — | — | $^tC_4H_9$ | H | H | H | H | acac | |
| 2'-138Y | Pt | 0 | 2' | TB | — | — | $^tC_4H_9$ | H | H | H | H | — | — |
| 2'-139 | Pt | 1 | 2' | TB | — | — | $CH_3$ | H | H | H | H | pic | |
| 2'-139X | Pt | 1 | 2' | TB | — | — | $CH_3$ | H | H | H | H | acac | |
| 2'-139Y | Pt | 0 | 2' | TB | — | — | $CH_3$ | H | H | H | H | — | — |
| 2'-140 | Pt | 1 | 2' | TB | — | — | $^tC_4H_9$ | H | H | $CH_3$ | H | pic | |
| 2'-140X | Pt | 1 | 2' | TB | — | — | $^tC_4H_9$ | H | H | $CH_3$ | H | acac | |
| 2'-140Y | Pt | 0 | 2' | TB | — | — | $^tC_4H_9$ | H | H | $CH_3$ | H | — | — |
| 2'-141 | Pt | 1 | 2' | TB | — | — | $CH_3$ | H | H | $CH_3$ | H | pic | |
| 2'-141X | Pt | 1 | 2' | TB | — | — | $CH_3$ | H | H | $CH_3$ | H | acac | |
| 2'-141Y | Pt | 0 | 2' | TB | — | — | $CH_3$ | H | H | $CH_3$ | H | — | — |
| 2'-142 | Pt | 1 | 2' | TB | — | — | H | H | H | $CH_3$ | H | pic | |
| 2'-142X | Pt | 1 | 2' | TB | — | — | H | H | H | $CH_3$ | H | acac | |
| 2'-142Y | Pt | 0 | 2' | TB | — | — | H | H | H | $CH_3$ | H | — | — |
| 2'-143 | Pt | 1 | 2' | TF | — | — | H | H | H | H | H | pic | |
| 2'-143X | Pt | 1 | 2' | TF | — | — | H | H | H | H | H | acac | |
| 2'-143Y | Pt | 0 | 2' | TF | — | — | H | H | H | H | H | — | — |
| 2'-144 | Pt | 1 | 2' | TF | — | — | $^tC_4H_9$ | H | H | H | H | pic | |
| 2'-144X | Pt | 1 | 2' | TF | — | — | $^tC_4H_9$ | H | H | H | H | acac | |
| 2'-144Y | Pt | 0 | 2' | TF | — | — | $^tC_4H_9$ | H | H | H | H | — | — |
| 2'-145 | Pt | 1 | 2' | TF | — | — | $CH_3$ | H | H | H | H | pic | |
| 2'-145X | Pt | 1 | 2' | TF | — | — | $CH_3$ | H | H | H | H | acac | |
| 2'-145Y | Pt | 0 | 2' | TF | — | — | $CH_3$ | H | H | H | H | — | — |
| 2'-146 | Pt | 1 | 2' | TF | — | — | $^tC_4H_9$ | H | H | $CH_3$ | H | pic | |
| 2'-146X | Pt | 1 | 2' | TF | — | — | $^tC_4H_9$ | H | H | $CH_3$ | H | acac | |
| 2'-146Y | Pt | 0 | 2' | TF | — | — | $^tC_4H_9$ | H | H | $CH_3$ | H | — | — |
| 2'-147 | Pt | 1 | 2' | TF | — | — | $CH_3$ | H | H | $CH_3$ | H | pic | |
| 2'-147X | Pt | 1 | 2' | TF | — | — | $CH_3$ | H | H | $CH_3$ | H | acac | |
| 2'-147Y | Pt | 0 | 2' | TF | — | — | $CH_3$ | H | H | $CH_3$ | H | — | — |
| 2'-148 | Pt | 1 | 2' | TF | — | — | H | H | H | $CH_3$ | H | pic | |
| 2'-148X | Pt | 1 | 2' | TF | — | — | H | H | H | $CH_3$ | H | acac | |
| 2'-148Y | Pt | 0 | 2' | TF | — | — | H | H | H | $CH_3$ | H | — | — |
| 2'-149 | Pt | 1 | 2' | OB | — | — | H | H | H | H | H | pic | |
| 2'-149X | Pt | 1 | 2' | OB | — | — | H | H | H | H | H | acac | |
| 2'-149Y | Pt | 0 | 2' | OB | — | — | H | H | H | H | H | — | — |
| 2'-150 | Pt | 1 | 2' | OB | — | — | $^tC_4H_9$ | H | H | H | H | pic | |
| 2'-150X | Pt | 1 | 2' | OB | — | — | $^tC_4H_9$ | H | H | H | H | acac | |
| 2'-150Y | Pt | 0 | 2' | OB | — | — | $^tC_4H_9$ | H | H | H | H | — | — |
| 2'-151 | Pt | 1 | 2' | OB | — | — | $CH_3$ | H | H | H | H | pic | |
| 2'-151X | Pt | 1 | 2' | OB | — | — | $CH_3$ | H | H | H | H | acac | |
| 2'-151Y | Pt | 0 | 2' | OB | — | — | $CH_3$ | H | H | H | H | — | — |
| 2'-152 | Pt | 1 | 2' | OB | — | — | $^tC_4H_9$ | H | H | $CH_3$ | H | pic | |
| 2'-152X | Pt | 1 | 2' | OB | — | — | $^tC_4H_9$ | H | H | $CH_3$ | H | acac | |
| 2'-152Y | Pt | 0 | 2' | OB | — | — | $^tC_4H_9$ | H | H | $CH_3$ | H | — | — |
| 2'-153 | Pt | 1 | 2' | OB | — | — | $CH_3$ | H | H | $CH_3$ | H | pic | |
| 2'-153X | Pt | 1 | 2' | OB | — | — | $CH_3$ | H | H | $CH_3$ | H | acac | |
| 2'-153Y | Pt | 0 | 2' | OB | — | — | $CH_3$ | H | H | $CH_3$ | H | — | — |
| 2'-154 | Pt | 1 | 2' | OB | — | — | H | H | H | $CH_3$ | H | pic | |
| 2'-154X | Pt | 1 | 2' | OB | — | — | H | H | H | $CH_3$ | H | acac | |
| 2'-154Y | Pt | 0 | 2' | OB | — | — | H | H | H | $CH_3$ | H | — | — |
| 2'-155 | Pt | 1 | 2' | Fu | — | — | H | H | H | H | H | pic | |
| 2'-155X | Pt | 1 | 2' | Fu | — | — | H | H | H | H | H | acac | |
| 2'-155Y | Pt | 0 | 2' | Fu | — | — | H | H | H | H | H | — | — |
| 2'-156 | Pt | 1 | 2' | Fu | — | — | $^tC_4H_9$ | H | H | H | H | pic | |
| 2'-156X | Pt | 1 | 2' | Fu | — | — | $^tC_4H_9$ | H | H | H | H | acac | |
| 2'-156Y | Pt | 0 | 2' | Fu | — | — | $^tC_4H_9$ | H | H | H | H | — | — |
| 2'-157 | Pt | 1 | 2' | Fu | — | — | $CH_3$ | H | H | H | H | pic | |
| 2'-157X | Pt | 1 | 2' | Fu | — | — | $CH_3$ | H | H | H | H | acac | |
| 2'-157Y | Pt | 0 | 2' | Fu | — | — | $CH_3$ | H | H | H | H | — | — |
| 2'-158 | Pt | 1 | 2' | Fu | — | — | $^tC_4H_9$ | H | H | $CH_3$ | H | pic | |
| 2'-158X | Pt | 1 | 2' | Fu | — | — | $^tC_4H_9$ | H | H | $CH_3$ | H | acac | |
| 2'-158Y | Pt | 0 | 2' | Fu | — | — | $^tC_4H_9$ | H | H | $CH_3$ | H | — | — |
| 2'-159 | Pt | 1 | 2' | Fu | — | — | $CH_3$ | H | H | $CH_3$ | H | pic | |
| 2'-159X | Pt | 1 | 2' | Fu | — | — | $CH_3$ | H | H | $CH_3$ | H | acac | |
| 2'-159Y | Pt | 0 | 2' | Fu | — | — | $CH_3$ | H | H | $CH_3$ | H | — | — |
| 2'-160 | Pt | 1 | 2' | Fu | — | — | H | H | H | $CH_3$ | H | pic | |
| 2'-160X | Pt | 1 | 2' | Fu | — | — | H | H | H | $CH_3$ | H | acac | |
| 2'-160Y | Pt | 0 | 2' | Fu | — | — | H | H | H | $CH_3$ | H | — | — |
| 2'-161 | Pt | 1 | 2' | Fl | — | — | H | H | H | H | H | pic | |
| 2'-161X | Pt | 1 | 2' | Fl | — | — | H | H | H | H | H | acac | |
| 2'-161Y | Pt | 0 | 2' | Fl | — | — | H | H | H | H | H | — | — |
| 2'-162 | Pt | 1 | 2' | Fl | — | — | $^tC_4H_9$ | H | H | H | H | pic | |
| 2'-162X | Pt | 1 | 2' | Fl | — | — | $^tC_4H_9$ | H | H | H | H | acac | |
| 2'-162Y | Pt | 0 | 2' | Fl | — | — | $^tC_4H_9$ | H | H | H | H | — | — |
| 2'-163 | Pt | 1 | 2' | Fl | — | — | $CH_3$ | H | H | H | H | pic | |

TABLE 37-continued

| No. | M | m | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 2'-163X | Pt | 1 | 2' | Fl | | — | — | CH₃ | H | H | H | H | acac | |
| 2'-163Y | Pt | 0 | 2' | Fl | | — | — | CH₃ | H | H | H | H | — | — |
| 2'-164 | Pt | 1 | 2' | Fl | | — | — | ᵗC₄H₉ | H | H | CH₃ | H | pic | |
| 2'-164X | Pt | 1 | 2' | Fl | | — | — | ᵗC₄H₉ | H | H | CH₃ | H | acac | |
| 2'-164Y | Pt | 0 | 2' | Fl | | — | — | ᵗC₄H₉ | H | H | CH₃ | H | — | — |
| 2'-165 | Pt | 1 | 2' | Fl | | — | — | CH₃ | H | H | CH₃ | H | pic | |
| 2'-165X | Pt | 1 | 2' | Fl | | — | — | CH₃ | H | H | CH₃ | H | acac | |
| 2'-165Y | Pt | 0 | 2' | Fl | | — | — | CH₃ | H | H | CH₃ | H | — | — |
| 2'-166 | Pt | 1 | 2' | Fl | | — | — | H | H | H | CH₃ | H | pic | |
| 2'-166X | Pt | 1 | 2' | Fl | | — | — | H | H | H | CH₃ | H | acac | |
| 2'-166Y | Pt | 0 | 2' | Fl | | — | — | H | H | H | CH₃ | H | — | — |
| 2'-167 | Pt | 1 | 2' | Bz | | — | — | H | H | H | H | H | pic | |
| 2'-167X | Pt | 1 | 2' | Bz | | — | — | H | H | H | H | H | acac | |
| 2'-167Y | Pt | 0 | 2' | Bz | | — | — | H | H | H | H | H | — | — |
| 2'-168 | Pt | 1 | 2' | Bz | | — | — | ᵗC₄H₉ | H | H | H | H | pic | |
| 2'-168X | Pt | 1 | 2' | Bz | | — | — | ᵗC₄H₉ | H | H | H | H | acac | |
| 2'-168Y | Pt | 0 | 2' | Bz | | — | — | ᵗC₄H₉ | H | H | H | H | — | — |
| 2'-169 | Pt | 1 | 2' | Bz | | — | — | CH₃ | H | H | H | H | pic | |
| 2'-169X | Pt | 1 | 2' | Bz | | — | — | CH₃ | H | H | H | H | acac | |
| 2'-169Y | Pt | 0 | 2' | Bz | | — | — | CH₃ | H | H | H | H | — | — |
| 2'-170 | Pt | 1 | 2' | Bz | | — | — | ᵗC₄H₉ | H | H | CH₃ | H | pic | |
| 2'-170X | Pt | 1 | 2' | Bz | | — | — | ᵗC₄H₉ | H | H | CH₃ | H | acac | |
| 2'-170Y | Pt | 0 | 2' | Bz | | — | — | ᵗC₄H₉ | H | H | CH₃ | H | — | — |
| 2'-171 | Pt | 1 | 2' | Bz | | — | — | CH₃ | H | H | CH₃ | H | pic | |
| 2'-171X | Pt | 1 | 2' | Bz | | — | — | CH₃ | H | H | CH₃ | H | acac | |
| 2'-171Y | Pt | 0 | 2' | Bz | | — | — | CH₃ | H | H | CH₃ | H | — | — |
| 2'-172 | Pt | 1 | 2' | Bz | | — | — | H | H | H | CH₃ | H | pic | |
| 2'-172X | Pt | 1 | 2' | Bz | | — | — | H | H | H | CH₃ | H | acac | |
| 2'-172Y | Pt | 0 | 2' | Bz | | — | — | H | H | H | CH₃ | H | — | — |
| 2'-173 | Pt | 1 | 2' | Qu | | — | — | H | H | H | H | H | pic | |
| 2'-173X | Pt | 1 | 2' | Qu | | — | — | H | H | H | H | H | acac | |
| 2'-173Y | Pt | 0 | 2' | Qu | | — | — | H | H | H | H | H | — | — |
| 2'-174 | Pt | 1 | 2' | Qu | | — | — | ᵗC₄H₉ | H | H | H | H | pic | |
| 2'-174X | Pt | 1 | 2' | Qu | | — | — | ᵗC₄H₉ | H | H | H | H | acac | |
| 2'-174Y | Pt | 0 | 2' | Qu | | — | — | ᵗC₄H₉ | H | H | H | H | — | — |
| 2'-175 | Pt | 1 | 2' | Qu | | — | — | CH₃ | H | H | H | H | pic | |
| 2'-175X | Pt | 1 | 2' | Qu | | — | — | CH₃ | H | H | H | H | acac | |
| 2'-175Y | Pt | 0 | 2' | Qu | | — | — | CH₃ | H | H | H | H | — | — |
| 2'-176 | Pt | 1 | 2' | Qu | | — | — | ᵗC₄H₉ | H | H | CH₃ | H | pic | |
| 2'-176X | Pt | 1 | 2' | Qu | | — | — | ᵗC₄H₉ | H | H | CH₃ | H | acac | |
| 2'-176Y | Pt | 0 | 2' | Qu | | — | — | ᵗC₄H₉ | H | H | CH₃ | H | — | — |
| 2'-177 | Pt | 1 | 2' | Qu | | — | — | CH₃ | H | H | CH₃ | H | pic | |
| 2'-177X | Pt | 1 | 2' | Qu | | — | — | CH₃ | H | H | CH₃ | H | acac | |
| 2'-177Y | Pt | 0 | 2' | Qu | | — | — | CH₃ | H | H | CH₃ | H | — | — |
| 2'-178 | Pt | 1 | 2' | Qu | | — | — | H | H | H | CH₃ | H | pic | |
| 2'-178X | Pt | 1 | 2' | Qu | | — | — | H | H | H | CH₃ | H | acac | |
| 2'-178Y | Pt | 0 | 2' | Qu | | — | — | H | H | H | CH₃ | H | — | — |
| 2'-179 | Pt | 1 | 2' | OL | | H | ⁿC₄H₉ | H | H | H | H | H | pic | |
| 2'-179X | Pt | 1 | 2' | OL | | H | ⁿC₄H₉ | H | H | H | H | H | acac | |
| 2'-179Y | Pt | 0 | 2' | OL | | H | ⁿC₄H₉ | H | H | H | H | H | — | — |
| 2'-180 | Pt | 1 | 2' | OL | | H | ᵗC₄H₉ | H | H | H | H | H | pic | |
| 2'-180X | Pt | 1 | 2' | OL | | H | ᵗC₄H₉ | H | H | H | H | H | acac | |
| 2'-180Y | Pt | 0 | 2' | OL | | H | ᵗC₄H₉ | H | H | H | H | H | — | — |
| 2'-181 | Pt | 1 | 2' | OL | | CH₃ | ⁿC₄H₉ | H | H | H | H | H | pic | |
| 2'-181X | Pt | 1 | 2' | OL | | CH₃ | ⁿC₄H₉ | H | H | H | H | H | acac | |
| 2'-181Y | Pt | 0 | 2' | OL | | CH₃ | ⁿC₄H₉ | H | H | H | H | H | — | — |
| 2'-182 | Pt | 1 | 2' | OL | | CH₃ | ᵗC₄H₉ | H | H | H | H | H | pic | |
| 2'-182X | Pt | 1 | 2' | OL | | CH₃ | ᵗC₄H₉ | H | H | H | H | H | acac | |
| 2'-182Y | Pt | 0 | 2' | OL | | CH₃ | ᵗC₄H₉ | H | H | H | H | H | — | — |
| 2'-183 | Pt | 1 | 2' | OL | | H | H | H | H | H | H | H | pic | |
| 2'-183X | Pt | 1 | 2' | OL | | H | H | H | H | H | H | H | acac | |
| 2'-183Y | Pt | 0 | 2' | OL | | H | H | H | H | H | H | H | — | — |
| 2'-184 | Pt | 1 | 2' | OL | | H | ⁿC₄H₉ | CH₃ | H | H | H | H | pic | |
| 2'-184X | Pt | 1 | 2' | OL | | H | ⁿC₄H₉ | CH₃ | H | H | H | H | acac | |
| 2'-184Y | Pt | 0 | 2' | OL | | H | ⁿC₄H₉ | CH₃ | H | H | H | H | — | — |
| 2'-185 | Pt | 1 | 2' | OL | | H | ᵗC₄H₉ | CH₃ | H | H | H | H | pic | |
| 2'-185X | Pt | 1 | 2' | OL | | H | ᵗC₄H₉ | CH₃ | H | H | H | H | acac | |
| 2'-185Y | Pt | 0 | 2' | OL | | H | ᵗC₄H₉ | CH₃ | H | H | H | H | — | — |
| 2'-186 | Pt | 1 | 2' | OL | | —CH₂CH₂CH₂— | | H | H | H | H | H | pic | |
| 2'-186X | Pt | 1 | 2' | OL | | —CH₂CH₂CH₂— | | H | H | H | H | H | acac | |
| 2'-186Y | Pt | 0 | 2' | OL | | —CH₂CH₂CH₂— | | H | H | H | H | H | — | — |

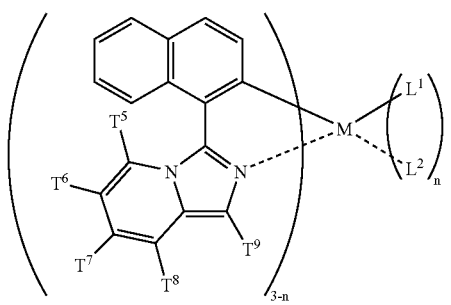
BSS 3, G:NAP1
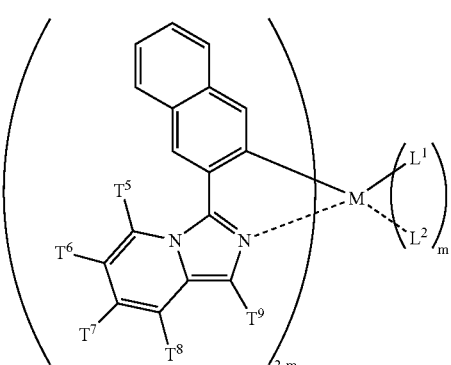
BSS 3, G:NAP2
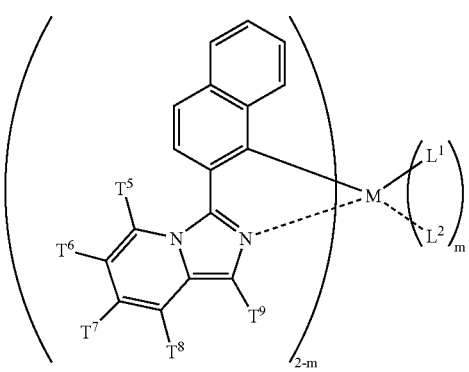
BSS 3, G:NAP3
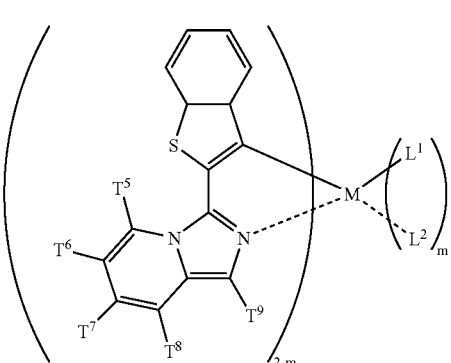
BSS 3′, G:TB
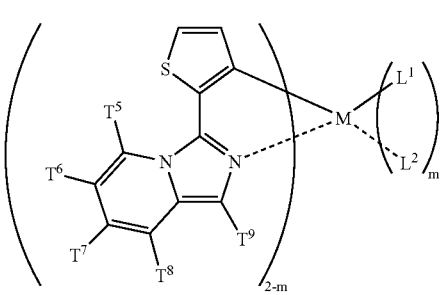
BSS 3′, G:TF
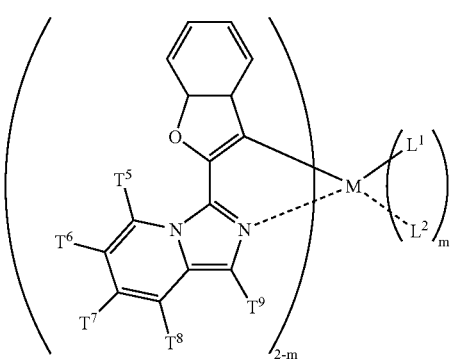
BSS 3′, G:OB
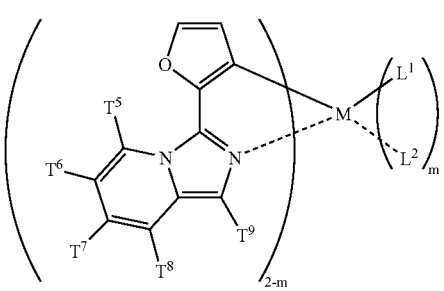
BSS 3′, G:Fu
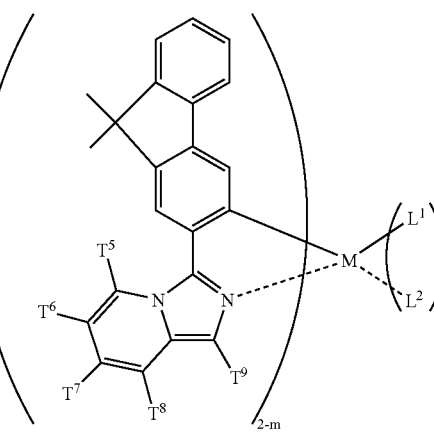
BSS 3′, G:Fl

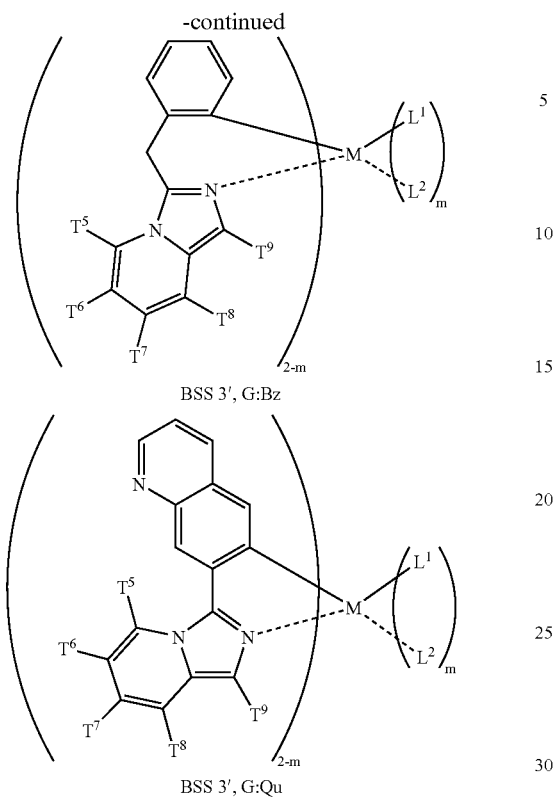

BSS 3', G:Bz

BSS 3', G:Qu

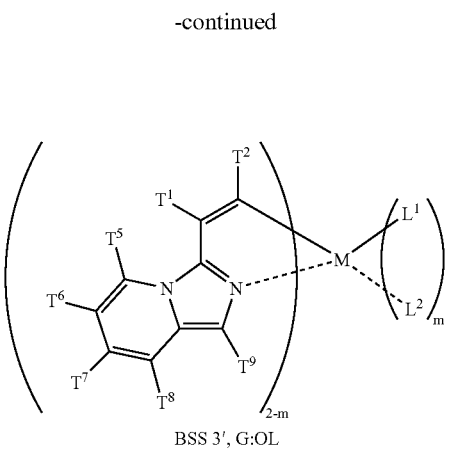

BSS 3', G:OL

TABLE 38

| No. | M | m | BSS | SS G | T¹ | T² | T⁵ | T⁶ | T⁷ | T⁸ | T⁹ | L¹ L² |
|---|---|---|---|---|---|---|---|---|---|---|---|---|
| 3'-117 | Pt | 1 | 3' | Nap1 | — | — | H | H | H | H | H | pic |
| 3'-117X | Pt | 1 | 3' | Nap1 | — | — | H | H | H | H | H | acac |
| 3'-117Y | Pt | 0 | 3' | Nap1 | — | — | H | H | H | H | H | — — |
| 3'-118 | Pt | 1 | 3' | Nap1 | — | — | $^tC_4H_9$ | H | H | H | H | pic |
| 3'-118X | Pt | 1 | 3' | Nap1 | — | — | $^tC_4H_9$ | H | H | H | H | acac |
| 3'-118Y | Pt | 0 | 3' | Nap1 | — | — | $^tC_4H_9$ | H | H | H | H | — — |
| 3'-119 | Pt | 1 | 3' | Nap1 | — | — | $CH_3$ | H | H | H | H | pic |
| 3'-119X | Pt | 1 | 3' | Nap1 | — | — | $CH_3$ | H | H | H | H | acac |
| 3'-119Y | Pt | 0 | 3' | Nap1 | — | — | $CH_3$ | H | H | H | H | — — |
| 3'-120 | Pt | 1 | 3' | Nap2 | — | — | H | H | H | H | H | pic |
| 3'-120X | Pt | 1 | 3' | Nap2 | — | — | H | H | H | H | H | acac |
| 3'-120Y | Pt | 0 | 3' | Nap2 | — | — | H | H | H | H | H | — — |
| 3'-121 | Pt | 1 | 3' | Nap2 | — | — | $^tC_4H_9$ | H | H | H | H | pic |
| 3'-121X | Pt | 1 | 3' | Nap2 | — | — | $^tC_4H_9$ | H | H | H | H | acac |
| 3'-121Y | Pt | 0 | 3' | Nap2 | — | — | $^tC_4H_9$ | H | H | H | H | — — |
| 3'-122 | Pt | 1 | 3' | Nap2 | — | — | $CH_3$ | H | H | H | H | pic |
| 3'-122X | Pt | 1 | 3' | Nap2 | — | — | $CH_3$ | H | H | H | H | acac |
| 3'-122Y | Pt | 0 | 3' | Nap2 | — | — | $CH_3$ | H | H | H | H | — — |
| 3'-123 | Pt | 1 | 3' | Nap3 | — | — | H | H | H | H | H | pic |
| 3'-123X | Pt | 1 | 3' | Nap3 | — | — | H | H | H | H | H | acac |
| 3'-123Y | Pt | 0 | 3' | Nap3 | — | — | H | H | H | H | H | — — |
| 3'-124 | Pt | 1 | 3' | Nap3 | — | — | $^tC_4H_9$ | H | H | H | H | pic |
| 3'-124X | Pt | 1 | 3' | Nap3 | — | — | $^tC_4H_9$ | H | H | H | H | acac |
| 3'-124Y | Pt | 0 | 3' | Nap3 | — | — | $^tC_4H_9$ | H | H | H | H | — — |
| 3'-125 | Pt | 1 | 3' | Nap3 | — | — | $CH_3$ | H | H | H | H | pic |
| 3'-125X | Pt | 1 | 3' | Nap3 | — | — | $CH_3$ | H | H | H | H | acac |
| 3'-125Y | Pt | 0 | 3' | Nap3 | — | — | $CH_3$ | H | H | H | H | — — |
| 3'-126 | Pt | 1 | 3' | TB | — | — | H | H | H | H | H | pic |
| 3'-126X | Pt | 1 | 3' | TB | — | — | H | H | H | H | H | acac |
| 3'-126Y | Pt | 0 | 3' | TB | — | — | H | H | H | H | H | — — |
| 3'-127 | Pt | 1 | 3' | TB | — | — | $^tC_4H_9$ | H | H | H | H | pic |
| 3'-127X | Pt | 1 | 3' | TB | — | — | $^tC_4H_9$ | H | H | H | H | acac |
| 3'-127Y | Pt | 0 | 3' | TB | — | — | $^tC_4H_9$ | H | H | H | H | — — |
| 3'-128 | Pt | 1 | 3' | TB | — | — | $CH_3$ | H | H | H | H | pic |
| 3'-128X | Pt | 1 | 3' | TB | — | — | $CH_3$ | H | H | H | H | acac |
| 3'-128Y | Pt | 0 | 3' | TB | — | — | $CH_3$ | H | H | H | H | — — |

TABLE 38-continued

| No. | M | m | BSS | SS | G | T$^1$ | T$^2$ | T$^5$ | T$^6$ | T$^7$ | T$^8$ | T$^9$ | L$^1$ | L$^2$ |
|---|---|---|---|---|---|---|---|---|---|---|---|---|---|---|
| 3'-129 | Pt | 1 | 3' | TF | | — | — | H | H | H | H | H | pic | |
| 3'-129X | Pt | 1 | 3' | TF | | — | — | H | H | H | H | H | acac | |
| 3'-129Y | Pt | 0 | 3' | TF | | — | — | H | H | H | H | H | — | — |
| 3'-130 | Pt | 1 | 3' | TF | | — | — | $^tC_4H_9$ | H | H | H | H | pic | |
| 3'-130X | Pt | 1 | 3' | TF | | — | — | $^tC_4H_9$ | H | H | H | H | acac | |
| 3'-130Y | Pt | 0 | 3' | TF | | — | — | $^tC_4H_9$ | H | H | H | H | — | — |
| 3'-131 | Pt | 1 | 3' | TF | | — | — | $CH_3$ | H | H | H | H | pic | |
| 3'-131X | Pt | 1 | 3' | TF | | — | — | $CH_3$ | H | H | H | H | acac | |
| 3'-131Y | Pt | 0 | 3' | TF | | — | — | $CH_3$ | H | H | H | H | — | — |
| 3'-132 | Pt | 1 | 3' | OB | | — | — | H | H | H | H | H | pic | |
| 3'-132X | Pt | 1 | 3' | OB | | — | — | H | H | H | H | H | acac | |
| 3'-132Y | Pt | 0 | 3' | OB | | — | — | H | H | H | H | H | — | — |
| 3'-133 | Pt | 1 | 3' | OB | | — | — | $^tC_4H_9$ | H | H | H | H | pic | |
| 3'-133X | Pt | 1 | 3' | OB | | — | — | $^tC_4H_9$ | H | H | H | H | acac | |
| 3'-133Y | Pt | 0 | 3' | OB | | — | — | $^tC_4H_9$ | H | H | H | H | — | — |
| 3'-134 | Pt | 1 | 3' | OB | | — | — | $CH_3$ | H | H | H | H | pic | |
| 3'-134X | Pt | 1 | 3' | OB | | — | — | $CH_3$ | H | H | H | H | acac | |
| 3'-134Y | Pt | 0 | 3' | OB | | — | — | $CH_3$ | H | H | H | H | — | — |
| 3'-135 | Pt | 1 | 3' | Fu | | — | — | H | H | H | H | H | pic | |
| 3'-135X | Pt | 1 | 3' | Fu | | — | — | H | H | H | H | H | acac | |
| 3'-135Y | Pt | 0 | 3' | Fu | | — | — | H | H | H | H | H | — | — |
| 3'-136 | Pt | 1 | 3' | Fu | | — | — | $^tC_4H_9$ | H | H | H | H | pic | |
| 3'-136X | Pt | 1 | 3' | Fu | | — | — | $^tC_4H_9$ | H | H | H | H | acac | |
| 3'-136Y | Pt | 0 | 3' | Fu | | — | — | $^tC_4H_9$ | H | H | H | H | — | — |
| 3'-137 | Pt | 1 | 3' | Fu | | — | — | $CH_3$ | H | H | H | H | pic | |
| 3'-137X | Pt | 1 | 3' | Fu | | — | — | $CH_3$ | H | H | H | H | acac | |
| 3'-137Y | Pt | 0 | 3' | Fu | | — | — | $CH_3$ | H | H | H | H | — | — |
| 3'-138 | Pt | 1 | 3' | Fl | | — | — | H | H | H | H | H | pic | |
| 3'-138X | Pt | 1 | 3' | Fl | | — | — | H | H | H | H | H | acac | |
| 3'-138Y | Pt | 0 | 3' | Fl | | — | — | H | H | H | H | H | — | — |
| 3'-139 | Pt | 1 | 3' | Fl | | — | — | $^tC_4H_9$ | H | H | H | H | pic | |
| 3'-139X | Pt | 1 | 3' | Fl | | — | — | $^tC_4H_9$ | H | H | H | H | acac | |
| 3'-139Y | Pt | 0 | 3' | Fl | | — | — | $^tC_4H_9$ | H | H | H | H | — | — |
| 3'-140 | Pt | 1 | 3' | Fl | | — | — | $CH_3$ | H | H | H | H | pic | |
| 3'-140X | Pt | 1 | 3' | Fl | | — | — | $CH_3$ | H | H | H | H | acac | |
| 3'-140Y | Pt | 0 | 3' | Fl | | — | — | $CH_3$ | H | H | H | H | — | — |
| 3'-141 | Pt | 1 | 3' | Bz | | — | — | H | H | H | H | H | pic | |
| 3'-141X | Pt | 1 | 3' | Bz | | — | — | H | H | H | H | H | acac | |
| 3'-141Y | Pt | 0 | 3' | Bz | | — | — | H | H | H | H | H | — | — |
| 3'-142 | Pt | 1 | 3' | Bz | | — | — | $^tC_4H_9$ | H | H | H | H | pic | |
| 3'-142X | Pt | 1 | 3' | Bz | | — | — | $^tC_4H_9$ | H | H | H | H | acac | |
| 3'-142Y | Pt | 0 | 3' | Bz | | — | — | $^tC_4H_9$ | H | H | H | H | — | — |
| 3'-143 | Pt | 1 | 3' | Bz | | — | — | $CH_3$ | H | H | H | H | pic | |
| 3'-143X | Pt | 1 | 3' | Bz | | — | — | $CH_3$ | H | H | H | H | acac | |
| 3'-143Y | Pt | 0 | 3' | Bz | | — | — | $CH_3$ | H | H | H | H | — | — |
| 3'-144 | Pt | 1 | 3' | Qu | | — | — | H | H | H | H | H | pic | |
| 3'-144X | Pt | 1 | 3' | Qu | | — | — | H | H | H | H | H | acac | |
| 3'-144Y | Pt | 0 | 3' | Qu | | — | — | H | H | H | H | H | — | — |
| 3'-145 | Pt | 1 | 3' | Qu | | — | — | $^tC_4H_9$ | H | H | H | H | pic | |
| 3'-145X | Pt | 1 | 3' | Qu | | — | — | $^tC_4H_9$ | H | H | H | H | acac | |
| 3'-145Y | Pt | 0 | 3' | Qu | | — | — | $^tC_4H_9$ | H | H | H | H | — | — |
| 3'-146 | Pt | 1 | 3' | Qu | | — | — | $CH_3$ | H | H | H | H | pic | |
| 3'-146X | Pt | 1 | 3' | Qu | | — | — | $CH_3$ | H | H | H | H | acac | |
| 3'-146Y | Pt | 0 | 3' | Qu | | — | — | $CH_3$ | H | H | H | H | — | — |
| 3'-147 | Pt | 1 | 3' | OL | | H | $^nC_4H_9$ | H | H | H | H | H | pic | |
| 3'-147X | Pt | 1 | 3' | OL | | H | $^nC_4H_9$ | H | H | H | H | H | acac | |
| 3'-147Y | Pt | 0 | 3' | OL | | H | $^nC_4H_9$ | H | H | H | H | H | — | — |
| 3'-148 | Pt | 1 | 3' | OL | | H | $^tC_4H_9$ | H | H | H | H | H | pic | |
| 3'-148X | Pt | 1 | 3' | OL | | H | $^tC_4H_9$ | H | H | H | H | H | acac | |
| 3'-148Y | Pt | 0 | 3' | OL | | H | $^tC_4H_9$ | H | H | H | H | H | — | — |
| 3'-149 | Pt | 1 | 3' | OL | | $CH_3$ | $^nC_4H_9$ | H | H | H | H | H | pic | |
| 3'-149X | Pt | 1 | 3' | OL | | $CH_3$ | $^nC_4H_9$ | H | H | H | H | H | acac | |
| 3'-149Y | Pt | 0 | 3' | OL | | $CH_3$ | $^nC_4H_9$ | H | H | H | H | H | — | — |
| 3'-150 | Pt | 1 | 3' | OL | | $CH_3$ | $^tC_4H_9$ | H | H | H | H | H | pic | |
| 3'-150X | Pt | 1 | 3' | OL | | $CH_3$ | $^tC_4H_9$ | H | H | H | H | H | acac | |
| 3'-150Y | Pt | 0 | 3' | OL | | $CH_3$ | $^tC_4H_9$ | H | H | H | H | H | — | — |
| 3'-151 | Pt | 1 | 3' | OL | | H | H | H | H | H | H | H | pic | |
| 3'-151X | Pt | 1 | 3' | OL | | H | H | H | H | H | H | H | acac | |
| 3'-151Y | Pt | 0 | 3' | OL | | H | H | H | H | H | H | H | — | — |
| 3'-152 | Pt | 1 | 3' | OL | | H | $^nC_4H_9$ | $CH_3$ | H | H | H | H | pic | |
| 3'-152X | Pt | 1 | 3' | OL | | H | $^nC_4H_9$ | $CH_3$ | H | H | H | H | acac | |
| 3'-152Y | Pt | 0 | 3' | OL | | H | $^nC_4H_9$ | $CH_3$ | H | H | H | H | — | — |
| 3'-153 | Pt | 1 | 3' | OL | | H | $^tC_4H_9$ | $CH_3$ | H | H | H | H | pic | |
| 3'-153X | Pt | 1 | 3' | OL | | H | $^tC_4H_9$ | $CH_3$ | H | H | H | H | acac | |
| 3'-153Y | Pt | 0 | 3' | OL | | H | $^tC_4H_9$ | $CH_3$ | H | H | H | H | — | — |

TABLE 38-continued
| No. | M | m | BSS | SS G | T¹ T² | T⁵ | T⁶ | T⁷ | T⁸ | T⁹ | L¹ | L² |
|---|---|---|---|---|---|---|---|---|---|---|---|---|
| 3'-154 | Pt | 1 | 3' | OL | —CH₂CH₂CH₂— | H | H | H | H | H | pic | |
| 3'-154X | Pt | 1 | 3' | OL | —CH₂CH₂CH₂— | H | H | H | H | H | acac | |
| 3'-154Y | Pt | C | 3' | OL | —CH₂CH₂CH₂— | H | H | H | H | H | — | — |
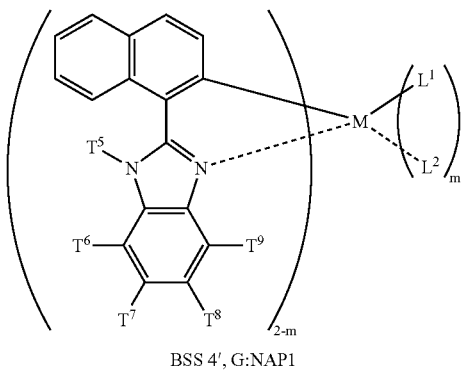
BSS 4', G:NAP1
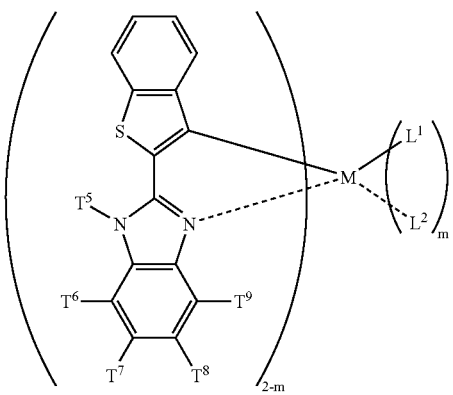
BSS 4', G:TB
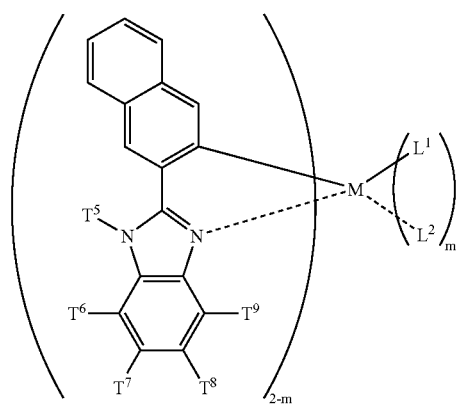
BSS 4', G:NAP2
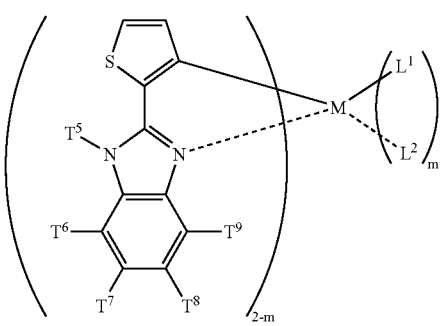
BSS 4', G:TF
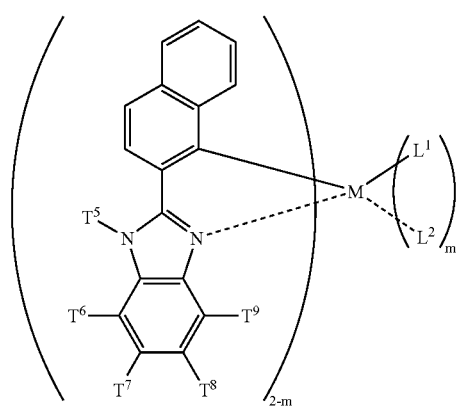
BSS 4', G:NAP3
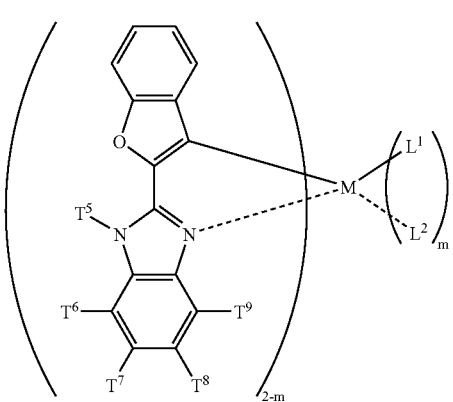
BSS 4', G:OB

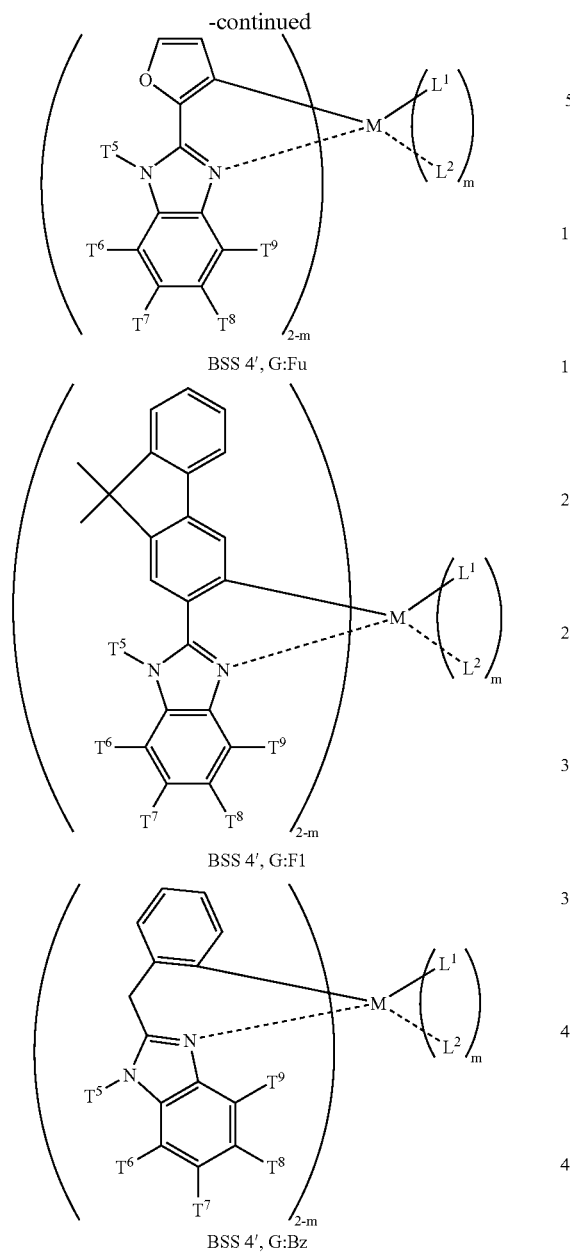
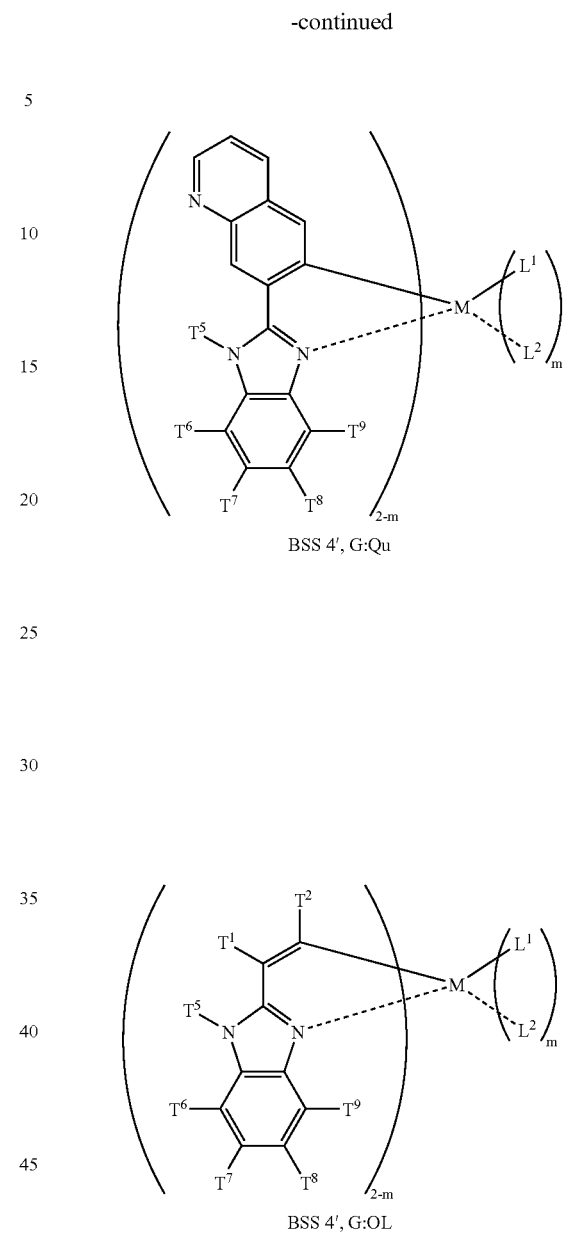

TABLE 39

| No. | M | m | BSS | SS G | T¹ | T² | T⁵ | T⁶ | T⁷ | T⁸ | T⁹ | L¹ | L² |
|---|---|---|---|---|---|---|---|---|---|---|---|---|---|
| 4'-138 | Pt | 1 | 4' | Nap1 | — | — | $CH_3$ | H | H | H | H | pic | |
| 4'-138X | Pt | 1 | 4' | Nap1 | — | — | $CH_3$ | H | H | H | H | acac | |
| 4'-138Y | Pt | 0 | 4' | Nap1 | — | — | $CH_3$ | H | H | H | H | — | — |
| 4'-139 | Pt | 1 | 4' | Nap1 | — | — | $^tC_4H_9$ | H | H | H | H | pic | |
| 4'-139X | Pt | 1 | 4' | Nap1 | — | — | $^tC_4H_9$ | H | H | H | H | acac | |
| 4'-139Y | Pt | 0 | 4' | Nap1 | — | — | $^tC_4H_9$ | H | H | H | H | — | — |
| 4'-140 | Pt | 1 | 4' | Nap2 | — | — | $CH_3$ | H | H | H | H | pic | |
| 4'-140X | Pt | 1 | 4' | Nap2 | — | — | $CH_3$ | H | H | H | H | acac | |
| 4'-140Y | Pt | 0 | 4' | Nap2 | — | — | $CH_3$ | H | H | H | H | — | — |
| 4'-141 | Pt | 1 | 4' | Nap2 | — | — | $^tC_4H_9$ | H | H | H | H | pic | |
| 4'-141X | Pt | 1 | 4' | Nap2 | — | — | $^tC_4H_9$ | H | H | H | H | acac | |
| 4'-141Y | Pt | 0 | 4' | Nap2 | — | — | $^tC_4H_9$ | H | H | H | H | — | — |
| 4'-142 | Pt | 1 | 4' | Nap3 | — | — | $CH_3$ | H | H | H | H | pic | |
| 4'-142X | Pt | 1 | 4' | Nap3 | — | — | $CH_3$ | H | H | H | H | acac | |
| 4'-142Y | Pt | 0 | 4' | Nap3 | — | — | $CH_3$ | H | H | H | H | — | — |

TABLE 39-continued

| No. | M | m | BSS | SS G | T¹ | T² | T⁵ | T⁶ | T⁷ | T⁸ | T⁹ | L¹ L² |
|---|---|---|---|---|---|---|---|---|---|---|---|---|
| 4'-143 | Pt | 1 | 4' | Nap3 | — | — | $^tC_4H_9$ | H | H | H | H | pic |
| 4'-143X | Pt | 1 | 4' | Nap3 | — | — | $^tC_4H_9$ | H | H | H | H | acac |
| 4'-143Y | Pt | 0 | 4' | Nap3 | — | — | $^tC_4H_9$ | H | H | H | H | — — |
| 4'-144 | Pt | 1 | 4' | TB | — | — | $CH_3$ | H | H | H | H | pic |
| 4'-144X | Pt | 1 | 4' | TB | — | — | $CH_3$ | H | H | H | H | acac |
| 4'-144Y | Pt | 0 | 4' | TB | — | — | $CH_3$ | H | H | H | H | — — |
| 4'-145 | Pt | 1 | 4' | TB | — | — | $^tC_4H_9$ | H | H | H | H | pic |
| 4'-145X | Pt | 1 | 4' | TB | — | — | $^tC_4H_9$ | H | H | H | H | acac |
| 4'-145Y | Pt | 0 | 4' | TB | — | — | $^tC_4H_9$ | H | H | H | H | — — |
| 4'-146 | Pt | 1 | 4' | TF | — | — | $CH_3$ | H | H | H | H | pic |
| 4'-146X | Pt | 1 | 4' | TF | — | — | $CH_3$ | H | H | H | H | acac |
| 4'-146Y | Pt | 0 | 4' | TF | — | — | $CH_3$ | H | H | H | H | — — |
| 4'-147 | Pt | 1 | 4' | TF | — | — | $^tC_4H_9$ | H | H | H | H | pic |
| 4'-147X | Pt | 1 | 4' | TF | — | — | $^tC_4H_9$ | H | H | H | H | acac |
| 4'-147Y | Pt | 0 | 4' | TF | — | — | $^tC_4H_9$ | H | H | H | H | — — |
| 4'-148 | Pt | 1 | 4' | OB | — | — | $CH_3$ | H | H | H | H | pic |
| 4'-148X | Pt | 1 | 4' | OB | — | — | $CH_3$ | H | H | H | H | acac |
| 4'-148Y | Pt | 0 | 4' | OB | — | — | $CH_3$ | H | H | H | H | — — |
| 4'-149 | Pt | 1 | 4' | OB | — | — | $^tC_4H_9$ | H | H | H | H | pic |
| 4'-149X | Pt | 1 | 4' | OB | — | — | $^tC_4H_9$ | H | H | H | H | acac |
| 4'-149Y | Pt | 0 | 4' | OB | — | — | $^tC_4H_9$ | H | H | H | H | — — |
| 4'-150 | Pt | 1 | 4' | Fu | — | — | $CH_3$ | H | H | H | H | pic |
| 4'-150X | Pt | 1 | 4' | Fu | — | — | $CH_3$ | H | H | H | H | acac |
| 4'-150Y | Pt | 0 | 4' | Fu | — | — | $CH_3$ | H | H | H | H | — — |
| 4'-151 | Pt | 1 | 4' | Fu | — | — | $^tC_4H_9$ | H | H | H | H | pic |
| 4'-151X | Pt | 1 | 4' | Fu | — | — | $^tC_4H_9$ | H | H | H | H | acac |
| 4'-151Y | Pt | 0 | 4' | Fu | — | — | $^tC_4H_9$ | H | H | H | H | — — |
| 4'-152 | Pt | 1 | 4' | Fl | — | — | $CH_3$ | H | H | H | H | pic |
| 4'-152X | Pt | 1 | 4' | Fl | — | — | $CH_3$ | H | H | H | H | acac |
| 4'-152Y | Pt | 0 | 4' | Fl | — | — | $CH_3$ | H | H | H | H | — — |
| 4'-153 | Pt | 1 | 4' | Fl | — | — | $^tC_4H_9$ | H | H | H | H | pic |
| 4'-153X | Pt | 1 | 4' | Fl | — | — | $^tC_4H_9$ | H | H | H | H | acac |
| 4'-153Y | Pt | 0 | 4' | Fl | — | — | $^tC_4H_9$ | H | H | H | H | — — |
| 4'-154 | Pt | 1 | 4' | Bz | — | — | $CH_3$ | H | H | H | H | pic |
| 4'-154X | Pt | 1 | 4' | Bz | — | — | $CH_3$ | H | H | H | H | acac |
| 4'-154Y | Pt | 0 | 4' | Bz | — | — | $CH_3$ | H | H | H | H | — — |
| 4'-155 | Pt | 1 | 4' | Bz | — | — | $^tC_4H_9$ | H | H | H | H | pic |
| 4'-155X | Pt | 1 | 4' | Bz | — | — | $^tC_4H_9$ | H | H | H | H | acac |
| 4'-155Y | Pt | 0 | 4' | Bz | — | — | $^tC_4H_9$ | H | H | H | H | — — |
| 4'-156 | Pt | 1 | 4' | Qu | — | — | $CH_3$ | H | H | H | H | pic |
| 4'-156X | Pt | 1 | 4' | Qu | — | — | $CH_3$ | H | H | H | H | acac |
| 4'-156Y | Pt | 0 | 4' | Qu | — | — | $CH_3$ | H | H | H | H | — — |
| 4'-157 | Pt | 1 | 4' | Qu | — | — | $^tC_4H_9$ | H | H | H | H | pic |
| 4'-157X | Pt | 1 | 4' | Qu | — | — | $^tC_4H_9$ | H | H | H | H | acac |
| 4'-157Y | Pt | 0 | 4' | Qu | — | — | $^tC_4H_9$ | H | H | H | H | — — |
| 4'-158 | Pt | 1 | 4' | OL | H | $^nC_4H_9$ | $CH_3$ | H | H | H | H | pic |
| 4'-158X | Pt | 1 | 4' | OL | H | $^nC_4H_9$ | $CH_3$ | H | H | H | H | acac |
| 4'-158Y | Pt | 0 | 4' | OL | H | $^nC_4H_9$ | $CH_3$ | H | H | H | H | — — |
| 4'-159 | Pt | 1 | 4' | OL | H | $^nC_4H_9$ | $^tC_4H_9$ | H | H | H | H | pic |
| 4'-159X | Pt | 1 | 4' | OL | H | $^nC_4H_9$ | $^tC_4H_9$ | H | H | H | H | acac |
| 4'-159Y | Pt | 0 | 4' | OL | H | $^nC_4H_9$ | $^tC_4H_9$ | H | H | H | H | — — |
| 4'-160 | Pt | 1 | 4' | OL | H | $^tC_4H_9$ | $CH_3$ | H | H | H | H | pic |
| 4'-160X | Pt | 1 | 4' | OL | H | $^tC_4H_9$ | $CH_3$ | H | H | H | H | acac |
| 4'-160Y | Pt | 0 | 4' | OL | H | $^tC_4H_9$ | $CH_3$ | H | H | H | H | — — |
| 4'-161 | Pt | 1 | 4' | OL | H | $^tC_4H_9$ | $^tC_4H_9$ | H | H | H | H | pic |
| 4'-161X | Pt | 1 | 4' | OL | H | $^tC_4H_9$ | $^tC_4H_9$ | H | H | H | H | acac |
| 4'-161Y | Pt | 0 | 4' | OL | H | $^tC_4H_9$ | $^tC_4H_9$ | H | H | H | H | — — |
| 4'-162 | Pt | 1 | 4' | OL | $CH_3$ | $^nC_4H_9$ | $CH_3$ | H | H | H | H | pic |
| 4'-162X | Pt | 1 | 4' | OL | $CH_3$ | $^nC_4H_9$ | $CH_3$ | H | H | H | H | acac |
| 4'-162Y | Pt | 0 | 4' | OL | $CH_3$ | $^nC_4H_9$ | $CH_3$ | H | H | H | H | — — |
| 4'-163 | Pt | 1 | 4' | OL | $CH_3$ | $^tC_4H_9$ | $CH_3$ | H | H | H | H | pic |
| 4'-163X | Pt | 1 | 4' | OL | $CH_3$ | $^tC_4H_9$ | $CH_3$ | H | H | H | H | acac |
| 4'-163Y | Pt | 0 | 4' | OL | $CH_3$ | $^tC_4H_9$ | $CH_3$ | H | H | H | H | — — |
| 4'-164 | Pt | 1 | 4' | OL | H | H | $CH_3$ | H | H | H | H | pic |
| 4'-164X | Pt | 1 | 4' | OL | H | H | $CH_3$ | H | H | H | H | acac |
| 4'-164Y | Pt | 0 | 4' | OL | H | H | $CH_3$ | H | H | H | H | — — |
| 4'-165 | Pt | 1 | 4' | OL | —$CH_2CH_2CH_2$— | | $CH_3$ | H | H | H | H | pic |
| 4'-165X | Pt | 1 | 4' | OL | —$CH_2CH_2CH_2$— | | $CH_3$ | H | H | H | H | acac |
| 4'-165Y | Pt | 0 | 4' | OL | —$CH_2CH_2CH_2$— | | $CH_3$ | H | H | H | H | — — |
| 4'-166 | Pt | 1 | 4' | OL | —$CH_2CH_2CH_2$— | | $^tC_4H_9$ | H | H | H | H | pic |
| 4'-166X | Pt | 1 | 4' | OL | —$CH_2CH_2CH_2$— | | $^tC_4H_9$ | H | H | H | H | acac |
| 4'-166Y | Pt | 0 | 4' | OL | —$CH_2CH_2CH_2$— | | $^tC_4H_9$ | H | H | H | H | — — |

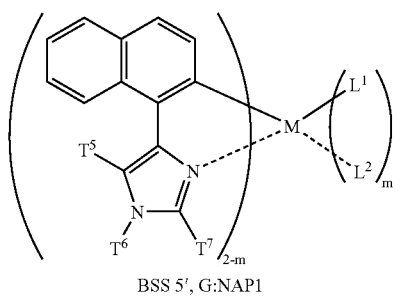
BSS 5', G:NAP1
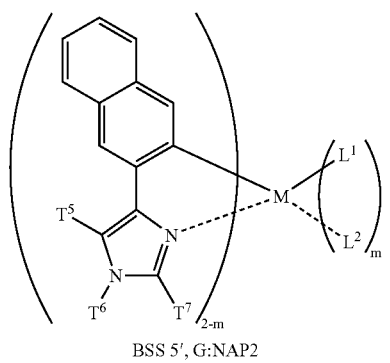
BSS 5', G:NAP2
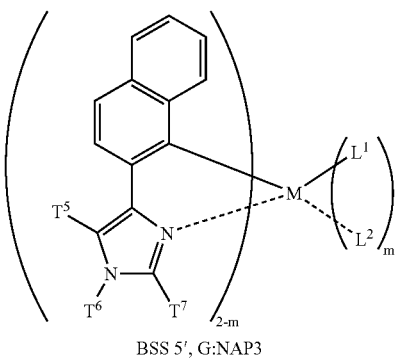
BSS 5', G:NAP3
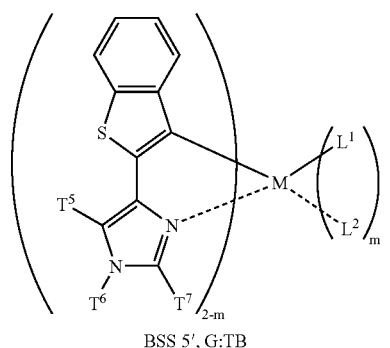
BSS 5', G:TB
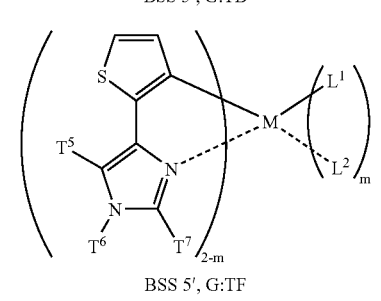
BSS 5', G:TF
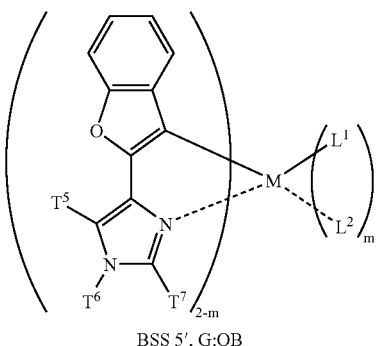
BSS 5', G:OB
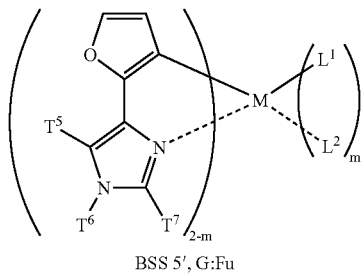
BSS 5', G:Fu
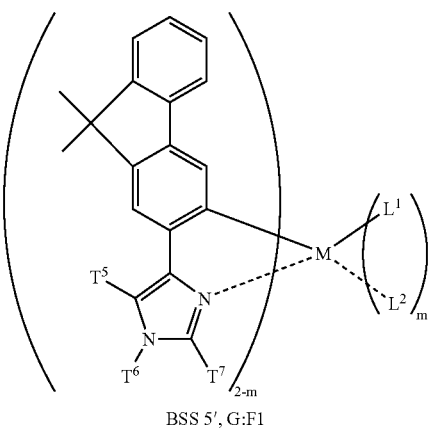
BSS 5', G:Fl
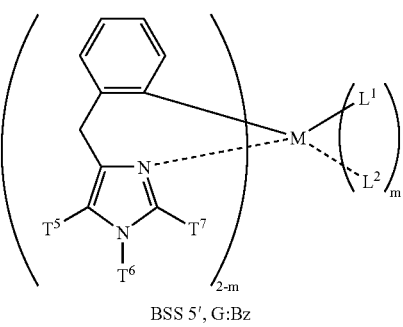
BSS 5', G:Bz

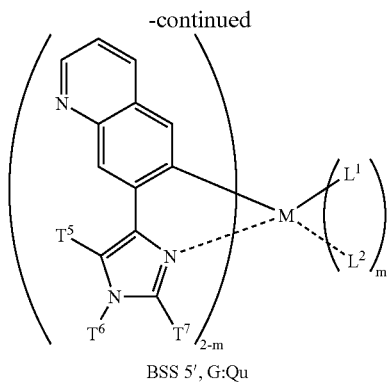

BSS 5', G:Qu

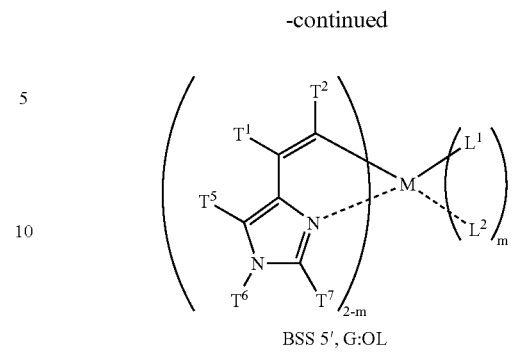

BSS 5', G:OL

TABLE 40

| No. | M | m | BSS | SS G | T$^1$ | T$^2$ | T$^5$ | T$^6$ | T$^7$ | L$^1$ | L$^2$ |
|---|---|---|---|---|---|---|---|---|---|---|---|
| 5'-140 | Pt | 1 | 5' | Nap1 | — | — | H | CH$_3$ | H | pic | |
| 5'-140X | Pt | 1 | 5' | Nap1 | — | — | H | CH$_3$ | H | acac | |
| 5'-140Y | Pt | 0 | 5' | Nap1 | — | — | H | CH$_3$ | H | — | — |
| 5'-141 | Pt | 1 | 5' | Nap1 | — | — | H | $^tC_4H_9$ | H | pic | |
| 5'-141X | Pt | 1 | 5' | Nap1 | — | — | H | $^tC_4H_9$ | H | acac | |
| 5'-141Y | Pt | 0 | 5' | Nap1 | — | — | H | $^tC_4H_9$ | H | — | — |
| 5'-142 | Pt | 1 | 5' | Nap1 | — | — | $^tC_4H_9$ | CH$_3$ | H | pic | |
| 5'-142X | Pt | 1 | 5' | Nap1 | — | — | $^tC_4H_9$ | CH$_3$ | H | acac | |
| 5'-142Y | Pt | 0 | 5' | Nap1 | — | — | $^tC_4H_9$ | CH$_3$ | H | — | — |
| 5'-143 | Pt | 1 | 5' | Nap1 | — | — | $^tC_4H_9$ | $^tC_4H_9$ | H | pic | |
| 5'-143X | Pt | 1 | 5' | Nap1 | — | — | $^tC_4H_9$ | $^tC_4H_9$ | H | acac | |
| 5'-143Y | Pt | 0 | 5' | Nap1 | — | — | $^tC_4H_9$ | $^tC_4H_9$ | H | — | — |
| 5'-144 | Pt | 1 | 5' | Nap1 | — | — | CH$_3$ | CH$_3$ | H | pic | |
| 5'-144X | Pt | 1 | 5' | Nap1 | — | — | CH$_3$ | CH$_3$ | H | acac | |
| 5'-144Y | Pt | 0 | 5' | Nap1 | — | — | CH$_3$ | CH$_3$ | H | — | — |
| 5'-145 | Pt | 1 | 5' | Nap1 | — | — | CH$_3$ | $^tC_4H_9$ | H | pic | |
| 5'-145X | Pt | 1 | 5' | Nap1 | — | — | CH$_3$ | $^tC_4H_9$ | H | acac | |
| 5'-145Y | Pt | 0 | 5' | Nap1 | — | — | CH$_3$ | $^tC_4H_9$ | H | — | — |
| 5'-146 | Pt | 1 | 5' | Nap2 | — | — | H | CH$_3$ | H | pic | |
| 5'-146X | Pt | 1 | 5' | Nap2 | — | — | H | CH$_3$ | H | acac | |
| 5'-146Y | Pt | 0 | 5' | Nap2 | — | — | H | CH$_3$ | H | — | — |
| 5'-147 | Pt | 1 | 5' | Nap2 | — | — | H | $^tC_4H_9$ | H | pic | |
| 5'-147X | Pt | 1 | 5' | Nap2 | — | — | H | $^tC_4H_9$ | H | acac | |
| 5'-147Y | Pt | 0 | 5' | Nap2 | — | — | H | $^tC_4H_9$ | H | — | — |
| 5'-148 | Pt | 1 | 5' | Nap2 | — | — | $^tC_4H_9$ | CH$_3$ | H | pic | |
| 5'-148X | Pt | 1 | 5' | Nap2 | — | — | $^tC_4H_9$ | CH$_3$ | H | acac | |
| 5'-148Y | Pt | 0 | 5' | Nap2 | — | — | $^tC_4H_9$ | CH$_3$ | H | — | — |
| 5'-149 | Pt | 1 | 5' | Nap2 | — | — | $^tC_4H_9$ | $^tC_4H_9$ | H | pic | |
| 5'-149X | Pt | 1 | 5' | Nap2 | — | — | $^tC_4H_9$ | $^tC_4H_9$ | H | acac | |
| 5'-149Y | Pt | 0 | 5' | Nap2 | — | — | $^tC_4H_9$ | $^tC_4H_9$ | H | — | — |
| 5'-150 | Pt | 1 | 5' | Nap2 | — | — | CH$_3$ | CH$_3$ | H | pic | |
| 5'-150X | Pt | 1 | 5' | Nap2 | — | — | CH$_3$ | CH$_3$ | H | acac | |
| 5'-150Y | Pt | 0 | 5' | Nap2 | — | — | CH$_3$ | CH$_3$ | H | — | — |
| 5'-151 | Pt | 1 | 5' | Nap2 | — | — | CH$_3$ | $^tC_4H_9$ | H | pic | |
| 5'-151X | Pt | 1 | 5' | Nap2 | — | — | CH$_3$ | $^tC_4H_9$ | H | acac | |
| 5'-151Y | Pt | 0 | 5' | Nap2 | — | — | CH$_3$ | $^tC_4H_9$ | H | — | — |
| 5'-152 | Pt | 1 | 5' | Nap3 | — | — | H | CH$_3$ | H | pic | |
| 5'-152X | Pt | 1 | 5' | Nap3 | — | — | H | CH$_3$ | H | acac | |
| 5'-152Y | Pt | 0 | 5' | Nap3 | — | — | H | CH$_3$ | H | — | — |
| 5'-153 | Pt | 1 | 5' | Nap3 | — | — | H | $^tC_4H_9$ | H | pic | |
| 5'-153X | Pt | 1 | 5' | Nap3 | — | — | H | $^tC_4H_9$ | H | acac | |
| 5'-153Y | Pt | 0 | 5' | Nap3 | — | — | H | $^tC_4H_9$ | H | — | — |
| 5'-154 | Pt | 1 | 5' | Nap3 | — | — | $^tC_4H_9$ | CH$_3$ | H | pic | |
| 5'-154X | Pt | 1 | 5' | Nap3 | — | — | $^tC_4H_9$ | CH$_3$ | H | acac | |
| 5'-154Y | Pt | 0 | 5' | Nap3 | — | — | $^tC_4H_9$ | CH$_3$ | H | — | — |
| 5'-155 | Pt | 1 | 5' | Nap3 | — | — | $^tC_4H_9$ | $^tC_4H_9$ | H | pic | |
| 5'-155X | Pt | 1 | 5' | Nap3 | — | — | $^tC_4H_9$ | $^tC_4H_9$ | H | acac | |
| 5'-155Y | Pt | 0 | 5' | Nap3 | — | — | $^tC_4H_9$ | $^tC_4H_9$ | H | — | — |
| 5'-156 | Pt | 1 | 5' | Nap3 | — | — | CH$_3$ | CH$_3$ | H | pic | |
| 5'-156X | Pt | 1 | 5' | Nap3 | — | — | CH$_3$ | CH$_3$ | H | acac | |
| 5'-156Y | Pt | 0 | 5' | Nap3 | — | — | CH$_3$ | CH$_3$ | H | — | — |
| 5'-157 | Pt | 1 | 5' | Nap3 | — | — | CH$_3$ | $^tC_4H_9$ | H | pic | |
| 5'-157X | Pt | 1 | 5' | Nap3 | — | — | CH$_3$ | $^tC_4H_9$ | H | acac | |
| 5'-157Y | Pt | 0 | 5' | Nap3 | — | — | CH$_3$ | $^tC_4H_9$ | H | — | — |
| 5'-158 | Pt | 1 | 5' | TB | — | — | H | CH$_3$ | H | pic | |

TABLE 40-continued

| No. | M | m | BSS | SS G | T¹ | T² | T⁵ | T⁶ | T⁷ | L¹ | L² |
|---|---|---|---|---|---|---|---|---|---|---|---|
| 5'-158X | Pt | 1 | 5' | TB | — | — | H | CH$_3$ | H | acac | |
| 5'-158Y | Pt | 0 | 5' | TB | — | — | H | CH$_3$ | H | — | |
| 5'-159 | Pt | 1 | 5' | TB | — | — | H | $^t$C$_4$H$_9$ | H | pic | |
| 5'-159X | Pt | 1 | 5' | TB | — | — | H | $^t$C$_4$H$_9$ | H | acac | |
| 5'-159Y | Pt | 0 | 5' | TB | — | — | H | $^t$C$_4$H$_9$ | H | — | |
| 5'-160 | Pt | 1 | 5' | TB | — | — | $^t$C$_4$H$_9$ | CH$_3$ | H | pic | |
| 5'-160X | Pt | 1 | 5' | TB | — | — | $^t$C$_4$H$_9$ | CH$_3$ | H | acac | |
| 5'-160Y | Pt | 0 | 5' | TB | — | — | $^t$C$_4$H$_9$ | CH$_3$ | H | — | |
| 5'-161 | Pt | 1 | 5' | TB | — | — | $^t$C$_4$H$_9$ | $^t$C$_4$H$_9$ | H | pic | |
| 5'-161X | Pt | 1 | 5' | TB | — | — | $^t$C$_4$H$_9$ | $^t$C$_4$H$_9$ | H | acac | |
| 5'-161Y | Pt | 0 | 5' | TB | — | — | $^t$C$_4$H$_9$ | $^t$C$_4$H$_9$ | H | — | |
| 5'-162 | Pt | 1 | 5' | TB | — | — | CH$_3$ | CH$_3$ | H | pic | |
| 5'-162X | Pt | 1 | 5' | TB | — | — | CH$_3$ | CH$_3$ | H | acac | |
| 5'-162Y | Pt | 0 | 5' | TB | — | — | CH$_3$ | CH$_3$ | H | — | |
| 5'-163 | Pt | 1 | 5' | TB | — | — | CH$_3$ | $^t$C$_4$H$_9$ | H | pic | |
| 5'-163X | Pt | 1 | 5' | TB | — | — | CH$_3$ | $^t$C$_4$H$_9$ | H | acac | |
| 5'-163Y | Pt | 0 | 5' | TB | — | — | CH$_3$ | $^t$C$_4$H$_9$ | H | — | |
| 5'-164 | Pt | 1 | 5' | TF | — | — | H | CH$_3$ | H | pic | |
| 5'-164X | Pt | 1 | 5' | TF | — | — | H | CH$_3$ | H | acac | |
| 5'-164Y | Pt | 0 | 5' | TF | — | — | H | CH$_3$ | H | — | |
| 5'-165 | Pt | 1 | 5' | TF | — | — | H | $^t$C$_4$H$_9$ | H | pic | |
| 5'-165X | Pt | 1 | 5' | TF | — | — | H | $^t$C$_4$H$_9$ | H | acac | |
| 5'-165Y | Pt | 0 | 5' | TF | — | — | H | $^t$C$_4$H$_9$ | H | — | |
| 5'-166 | Pt | 1 | 5' | TF | — | — | $^t$C$_4$H$_9$ | CH$_3$ | H | pic | |
| 5'-166X | Pt | 1 | 5' | TF | — | — | $^t$C$_4$H$_9$ | CH$_3$ | H | acac | |
| 5'-166Y | Pt | 0 | 5' | TF | — | — | $^t$C$_4$H$_9$ | CH$_3$ | H | — | |
| 5'-167 | Pt | 1 | 5' | TF | — | — | $^t$C$_4$H$_9$ | $^t$C$_4$H$_9$ | H | pic | |
| 5'-167X | Pt | 1 | 5' | TF | — | — | $^t$C$_4$H$_9$ | $^t$C$_4$H$_9$ | H | acac | |
| 5'-167Y | Pt | 0 | 5' | TF | — | — | $^t$C$_4$H$_9$ | $^t$C$_4$H$_9$ | H | — | |
| 5'-168 | Pt | 1 | 5' | TF | — | — | CH$_3$ | CH$_3$ | H | pic | |
| 5'-168X | Pt | 1 | 5' | TF | — | — | CH$_3$ | CH$_3$ | H | acac | |
| 5'-168Y | Pt | 0 | 5' | TF | — | — | CH$_3$ | CH$_3$ | H | — | |
| 5'-169 | Pt | 1 | 5' | TF | — | — | CH$_3$ | $^t$C$_4$H$_9$ | H | pic | |
| 5'-169X | Pt | 1 | 5' | TF | — | — | CH$_3$ | $^t$C$_4$H$_9$ | H | acac | |
| 5'-169Y | Pt | 0 | 5' | TF | — | — | CH$_3$ | $^t$C$_4$H$_9$ | H | — | |
| 5'-170 | Pt | 1 | 5' | OB | — | — | H | CH$_3$ | H | pic | |
| 5'-170X | Pt | 1 | 5' | OB | — | — | H | CH$_3$ | H | acac | |
| 5'-170Y | Pt | 0 | 5' | OB | — | — | H | CH$_3$ | H | — | |
| 5'-171 | Pt | 1 | 5' | OB | — | — | H | $^t$C$_4$H$_9$ | H | pic | |
| 5'-171X | Pt | 1 | 5' | OB | — | — | H | $^t$C$_4$H$_9$ | H | acac | |
| 5'-171Y | Pt | 0 | 5' | OB | — | — | H | $^t$C$_4$H$_9$ | H | — | |
| 5'-172 | Pt | 1 | 5' | OB | — | — | $^t$C$_4$H$_9$ | CH$_3$ | H | pic | |
| 5'-172X | Pt | 1 | 5' | OB | — | — | $^t$C$_4$H$_9$ | CH$_3$ | H | acac | |
| 5'-172Y | Pt | 0 | 5' | OB | — | — | $^t$C$_4$H$_9$ | CH$_3$ | H | — | |
| 5'-173 | Pt | 1 | 5' | OB | — | — | $^t$C$_4$H$_9$ | $^t$C$_4$H$_9$ | H | pic | |
| 5'-173X | Pt | 1 | 5' | OB | — | — | $^t$C$_4$H$_9$ | $^t$C$_4$H$_9$ | H | acac | |
| 5'-173Y | Pt | 0 | 5' | OB | — | — | $^t$C$_4$H$_9$ | $^t$C$_4$H$_9$ | H | — | |
| 5'-174 | Pt | 1 | 5' | OB | — | — | CH$_3$ | CH$_3$ | H | pic | |
| 5'-174X | Pt | 1 | 5' | OB | — | — | CH$_3$ | CH$_3$ | H | acac | |
| 5'-174Y | Pt | 0 | 5' | OB | — | — | CH$_3$ | CH$_3$ | H | — | |
| 5'-175 | Pt | 1 | 5' | OB | — | — | CH$_3$ | $^t$C$_4$H$_9$ | H | pic | |
| 5'-175X | Pt | 1 | 5' | OB | — | — | CH$_3$ | $^t$C$_4$H$_9$ | H | acac | |
| 5'-175Y | Pt | 0 | 5' | OB | — | — | CH$_3$ | $^t$C$_4$H$_9$ | H | — | |
| 5'-176 | Pt | 1 | 5' | Fu | — | — | H | CH$_3$ | H | pic | |
| 5'-176X | Pt | 1 | 5' | Fu | — | — | H | CH$_3$ | H | acac | |
| 5'-176Y | Pt | 0 | 5' | Fu | — | — | H | CH$_3$ | H | — | |
| 5'-177 | Pt | 1 | 5' | Fu | — | — | H | $^t$C$_4$H$_9$ | H | pic | |
| 5'-177X | Pt | 1 | 5' | Fu | — | — | H | $^t$C$_4$H$_9$ | H | acac | |
| 5'-177Y | Pt | 0 | 5' | Fu | — | — | H | $^t$C$_4$H$_9$ | H | — | |
| 5'-178 | Pt | 1 | 5' | Fu | — | — | $^t$C$_4$H$_9$ | CH$_3$ | H | pic | |
| 5'-178X | Pt | 1 | 5' | Fu | — | — | $^t$C$_4$H$_9$ | CH$_3$ | H | acac | |
| 5'-178Y | Pt | 0 | 5' | Fu | — | — | $^t$C$_4$H$_9$ | CH$_3$ | H | — | |
| 5'-179 | Pt | 1 | 5' | Fu | — | — | $^t$C$_4$H$_9$ | $^t$C$_4$H$_9$ | H | pic | |
| 5'-179X | Pt | 1 | 5' | Fu | — | — | $^t$C$_4$H$_9$ | $^t$C$_4$H$_9$ | H | acac | |
| 5'-179Y | Pt | 0 | 5' | Fu | — | — | $^t$C$_4$H$_9$ | $^t$C$_4$H$_9$ | H | — | |
| 5'-180 | Pt | 1 | 5' | Fu | — | — | CH$_3$ | CH$_3$ | H | pic | |
| 5'-180X | Pt | 1 | 5' | Fu | — | — | CH$_3$ | CH$_3$ | H | acac | |
| 5'-180Y | Pt | 0 | 5' | Fu | — | — | CH$_3$ | CH$_3$ | H | — | |
| 5'-181 | Pt | 1 | 5' | Fu | — | — | CH$_3$ | $^t$C$_4$H$_9$ | H | pic | |
| 5'-181X | Pt | 1 | 5' | Fu | — | — | CH$_3$ | $^t$C$_4$H$_9$ | H | acac | |
| 5'-181Y | Pt | 0 | 5' | Fu | — | — | CH$_3$ | $^t$C$_4$H$_9$ | H | — | |
| 5'-182 | Pt | 1 | 5' | Fl | — | — | H | CH$_3$ | H | pic | |
| 5'-182X | Pt | 1 | 5' | Fl | — | — | H | CH$_3$ | H | acac | |
| 5'-182Y | Pt | 0 | 5' | Fl | — | — | H | CH$_3$ | H | — | |
| 5'-183 | Pt | 1 | 5' | Fl | — | — | H | $^t$C$_4$H$_9$ | H | pic | |
| 5'-183X | Pt | 1 | 5' | Fl | — | — | H | $^t$C$_4$H$_9$ | H | acac | |
| 5'-183Y | Pt | 0 | 5' | Fl | — | — | H | $^t$C$_4$H$_9$ | H | — | |

TABLE 40-continued

| No. | M | m | BSS | SS | G | T¹ | T² | T⁵ | T⁶ | T⁷ | L¹ | L² |
|---|---|---|---|---|---|---|---|---|---|---|---|---|
| 5'-184 | Pt | 1 | 5' | Fl | | — | — | $^tC_4H_9$ | $CH_3$ | H | pic | |
| 5'-184X | Pt | 1 | 5' | Fl | | — | — | $^tC_4H_9$ | $CH_3$ | H | acac | |
| 5'-184Y | Pt | 0 | 5' | Fl | | — | — | $^tC_4H_9$ | $CH_3$ | H | — | |
| 5'-185 | Pt | 1 | 5' | Fl | | — | — | $^tC_4H_9$ | $^tC_4H_9$ | H | pic | |
| 5'-185X | Pt | 1 | 5' | Fl | | — | — | $^tC_4H_9$ | $^tC_4H_9$ | H | acac | |
| 5'-185Y | Pt | 0 | 5' | Fl | | — | — | $^tC_4H_9$ | $^tC_4H_9$ | H | — | |
| 5'-186 | Pt | 1 | 5' | Fl | | — | — | $CH_3$ | $CH_3$ | H | pic | |
| 5'-186X | Pt | 1 | 5' | Fl | | — | — | $CH_3$ | $CH_3$ | H | acac | |
| 5'-186Y | Pt | 0 | 5' | Fl | | — | — | $CH_3$ | $CH_3$ | H | — | |
| 5'-187 | Pt | 1 | 5' | Fl | | — | — | $CH_3$ | $^tC_4H_9$ | H | pic | |
| 5'-187X | Pt | 1 | 5' | Fl | | — | — | $CH_3$ | $^tC_4H_9$ | H | acac | |
| 5'-187Y | Pt | 0 | 5' | Fl | | — | — | $CH_3$ | $^tC_4H_9$ | H | — | |
| 5'-188 | Pt | 1 | 5' | Bz | | — | — | H | $CH_3$ | H | pic | |
| 5'-188X | Pt | 1 | 5' | Bz | | — | — | H | $CH_3$ | H | acac | |
| 5'-188Y | Pt | 0 | 5' | Bz | | — | — | H | $CH_3$ | H | — | |
| 5'-189 | Pt | 1 | 5' | Bz | | — | — | H | $^tC_4H_9$ | H | pic | |
| 5'-189X | Pt | 1 | 5' | Bz | | — | — | H | $^tC_4H_9$ | H | acac | |
| 5'-189Y | Pt | 0 | 5' | Bz | | — | — | H | $^tC_4H_9$ | H | — | |
| 5'-190 | Pt | 1 | 5' | Bz | | — | — | $^tC_4H_9$ | $CH_3$ | H | pic | |
| 5'-190X | Pt | 1 | 5' | Bz | | — | — | $^tC_4H_9$ | $CH_3$ | H | acac | |
| 5'-190Y | Pt | 0 | 5' | Bz | | — | — | $^tC_4H_9$ | $CH_3$ | H | — | |
| 5'-191 | Pt | 1 | 5' | Bz | | — | — | $^tC_4H_9$ | $^tC_4H_9$ | H | pic | |
| 5'-191X | Pt | 1 | 5' | Bz | | — | — | $^tC_4H_9$ | $^tC_4H_9$ | H | acac | |
| 5'-191Y | Pt | 0 | 5' | Bz | | — | — | $^tC_4H_9$ | $^tC_4H_9$ | H | — | |
| 5'-192 | Pt | 1 | 5' | Bz | | — | — | $CH_3$ | $CH_3$ | H | pic | |
| 5'-192X | Pt | 1 | 5' | Bz | | — | — | $CH_3$ | $CH_3$ | H | acac | |
| 5'-192Y | Pt | 0 | 5' | Bz | | — | — | $CH_3$ | $CH_3$ | H | — | |
| 5'-193 | Pt | 1 | 5' | Bz | | — | — | $CH_3$ | $^tC_4H_9$ | H | pic | |
| 5'-193X | Pt | 1 | 5' | Bz | | — | — | $CH_3$ | $^tC_4H_9$ | H | acac | |
| 5'-193Y | Pt | 0 | 5' | Bz | | — | — | $CH_3$ | $^tC_4H_9$ | H | — | |
| 5'-194 | Pt | 1 | 5' | Qu | | — | — | H | $CH_3$ | H | pic | |
| 5'-194X | Pt | 1 | 5' | Bz | | — | — | H | $CH_3$ | H | acac | |
| 5'-194Y | Pt | 0 | 5' | Bz | | — | — | H | $CH_3$ | H | — | |
| 5'-195 | Pt | 1 | 5' | Bz | | — | — | H | $^tC_4H_9$ | H | pic | |
| 5'-195X | Pt | 1 | 5' | Bz | | — | — | H | $^tC_4H_9$ | H | acac | |
| 5'-195Y | Pt | 0 | 5' | Bz | | — | — | H | $^tC_4H_9$ | H | — | |
| 5'-196 | Pt | 1 | 5' | Bz | | — | — | $^tC_4H_9$ | $CH_3$ | H | pic | |
| 5'-196X | Pt | 1 | 5' | Bz | | — | — | $^tC_4H_9$ | $CH_3$ | H | acac | |
| 5'-196Y | Pt | 0 | 5' | Bz | | — | — | $^tC_4H_9$ | $CH_3$ | H | — | |
| 5'-197 | Pt | 1 | 5' | Bz | | — | — | $^tC_4H_9$ | $^tC_4H_9$ | H | pic | |
| 5'-197X | Pt | 1 | 5' | Bz | | — | — | $^tC_4H_9$ | $^tC_4H_9$ | H | acac | |
| 5'-197Y | Pt | 0 | 5' | Bz | | — | — | $^tC_4H_9$ | $^tC_4H_9$ | H | — | |
| 5'-198 | Pt | 1 | 5' | Bz | | — | — | $CH_3$ | $CH_3$ | H | pic | |
| 5'-198X | Pt | 1 | 5' | Bz | | — | — | $CH_3$ | $CH_3$ | H | acac | |
| 5'-198Y | Pt | 0 | 5' | Bz | | — | — | $CH_3$ | $CH_3$ | H | — | |
| 5'-199 | Pt | 1 | 5' | Bz | | — | — | $CH_3$ | $^tC_4H_9$ | H | pic | |
| 5'-199X | Pt | 1 | 5' | Bz | | — | — | $CH_3$ | $^tC_4H_9$ | H | acac | |
| 5'-199Y | Pt | 0 | 5' | Bz | | — | — | $CH_3$ | $^tC_4H_9$ | H | — | |
| 5'-200 | Pt | 1 | 5' | OL | | H | $^nC_4H_9$ | H | $CH_3$ | H | pic | |
| 5'-200X | Pt | 1 | 5' | OL | | H | $^nC_4H_9$ | H | $CH_3$ | H | acac | |
| 5'-200Y | Pt | 0 | 5' | OL | | H | $^nC_4H_9$ | H | $CH_3$ | H | — | |
| 5'-201 | Pt | 1 | 5' | OL | | H | $^nC_4H_9$ | H | $^tC_4H_9$ | H | pic | |
| 5'-201X | Pt | 1 | 5' | OL | | H | $^nC_4H_9$ | H | $^tC_4H_9$ | H | acac | |
| 5'-201Y | Pt | 0 | 5' | OL | | H | $^nC_4H_9$ | H | $^tC_4H_9$ | H | — | |
| 5'-202 | Pt | 1 | 5' | OL | | H | $^tC_4H_9$ | H | $CH_3$ | H | pic | |
| 5'-202X | Pt | 1 | 5' | OL | | H | $^tC_4H_9$ | H | $CH_3$ | H | acac | |
| 5'-202Y | Pt | 0 | 5' | OL | | H | $^tC_4H_9$ | H | $CH_3$ | H | — | |
| 5'-203 | Pt | 1 | 5' | OL | | H | $^tC_4H_9$ | H | $^tC_4H_9$ | H | pic | |
| 5'-203X | Pt | 1 | 5' | OL | | H | $^tC_4H_9$ | H | $^tC_4H_9$ | H | acac | |
| 5'-203Y | Pt | 0 | 5' | OL | | H | $^tC_4H_9$ | H | $^tC_4H_9$ | H | — | |
| 5'-204 | Pt | 1 | 5' | OL | | $CH_3$ | $^nC_4H_9$ | H | $CH_3$ | H | pic | |
| 5'-204X | Pt | 1 | 5' | OL | | $CH_3$ | $^nC_4H_9$ | H | $CH_3$ | H | acac | |
| 5'-204Y | Pt | 0 | 5' | OL | | $CH_3$ | $^nC_4H_9$ | H | $CH_3$ | H | — | |
| 5'-205 | Pt | 1 | 5' | OL | | $CH_3$ | $^tC_4H_9$ | H | $CH_3$ | H | pic | |
| 5'-205X | Pt | 1 | 5' | OL | | $CH_3$ | $^tC_4H_9$ | H | $CH_3$ | H | acac | |
| 5'-205Y | Pt | 0 | 5' | OL | | $CH_3$ | $^tC_4H_9$ | H | $CH_3$ | H | — | |
| 5'-206 | Pt | 1 | 5' | OL | | H | H | H | $CH_3$ | H | pic | |
| 5'-206X | Pt | 1 | 5' | OL | | H | H | H | $CH_3$ | H | acac | |
| 5'-206Y | Pt | 0 | 5' | OL | | H | H | H | $CH_3$ | H | — | |
| 5'-207 | Pt | 1 | 5' | OL | | H | $^nC_4H_9$ | $CH_3$ | $^tC_4H_9$ | H | pic | |
| 5'-207X | Pt | 1 | 5' | OL | | H | $^nC_4H_9$ | $CH_3$ | $^tC_4H_9$ | H | acac | |
| 5'-207Y | Pt | 0 | 5' | OL | | H | $^nC_4H_9$ | $CH_3$ | $^tC_4H_9$ | H | — | |
| 5'-208 | Pt | 1 | 5' | OL | | H | $^tC_4H_9$ | $CH_3$ | $^tC_4H_9$ | H | pic | |
| 5'-208X | Pt | 1 | 5' | OL | | H | $^tC_4H_9$ | $CH_3$ | $^tC_4H_9$ | H | acac | |
| 5'-208Y | Pt | 0 | 5' | OL | | H | $^tC_4H_9$ | $CH_3$ | $^tC_4H_9$ | H | — | |
| 5'-209 | Pt | 1 | 5' | OL | | —$CH_2CH_2CH_2$— | | H | $CH_3$ | H | pic | |
| 5'-209X | Pt | 1 | 5' | OL | | —$CH_2CH_2CH_2$— | | H | $CH_3$ | H | acac | |

TABLE 40-continued
| No. | M | m | BSS | SS | G | T¹ | T² | T⁵ | T⁶ | T⁷ | L¹ | L² |
|---|---|---|---|---|---|---|---|---|---|---|---|---|
| 5'-209Y | Pt | 0 | 5' | | OL | —CH₂CH₂CH₂— | | H | CH₃ | H | — | — |
| 5'-210 | Pt | 1 | 5' | | OL | —CH₂CH₂CH₂— | | H | $^tC_4H_9$ | H | | pic |
| 5'210X | Pt | 1 | 5' | | OL | —CH₂CH₂CH₂— | | H | $^tC_4H_9$ | H | | acac |
| 5'-210Y | Pt | 0 | 5' | | OL | —CH₂CH₂CH₂— | | H | $^tC_4H_9$ | H | — | — |
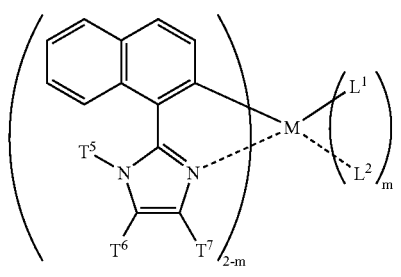
BSS 6', G:NAP1
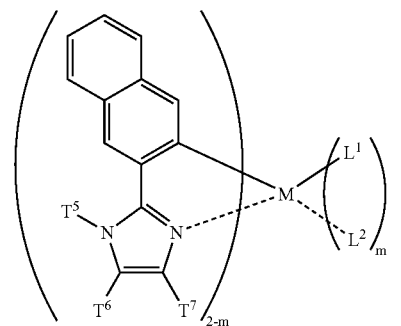
BSS 6', G:NAP2
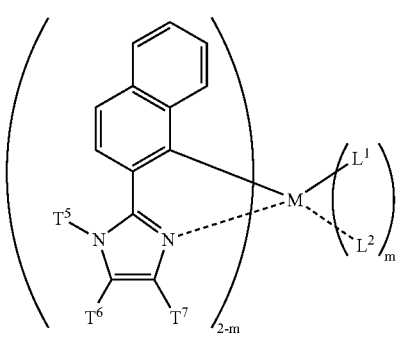
BSS 6', G:NAP3
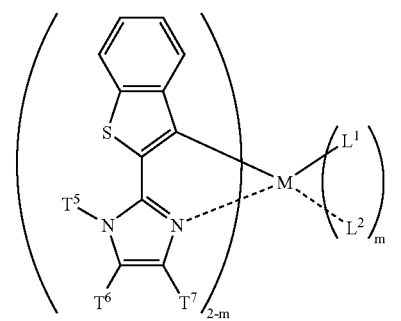
BSS 6', G:TB
-continued
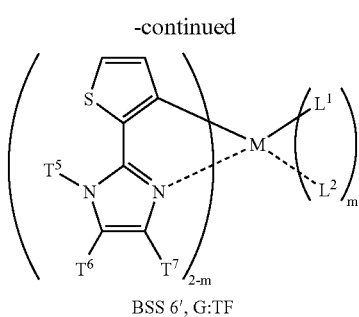
BSS 6', G:TF
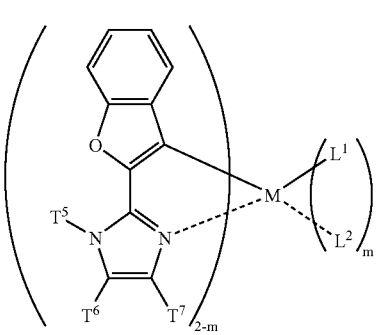
BSS 6', G:OB
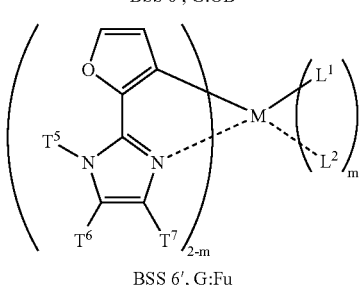
BSS 6', G:Fu
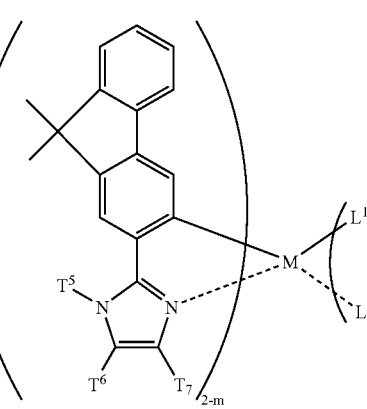
BSS 6', G:Fl

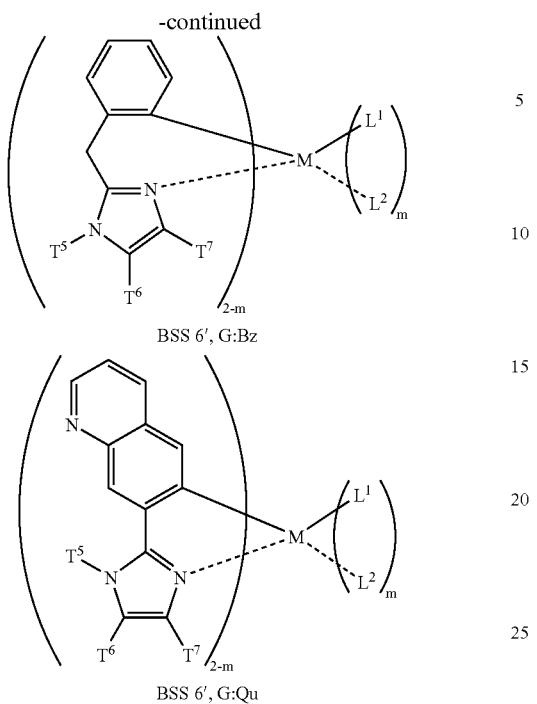

BSS 6', G:Bz

BSS 6', G:Qu

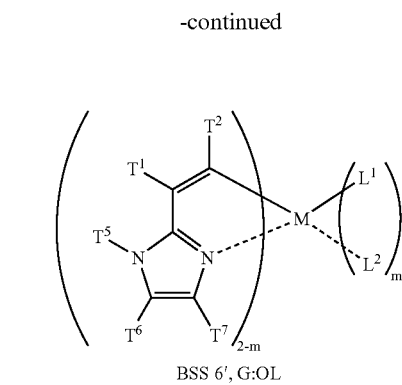

BSS 6', G:OL

TABLE 41

| No. | M | m | BSS | SS G | $T^1$ | $T^2$ | $T^5$ | $T^6$ | $T^7$ | $L^1$ | $L^2$ |
|---|---|---|---|---|---|---|---|---|---|---|---|
| 6'-138 | Pt | 1 | 6' | Nap1 | — | — | $CH_3$ | H | H | pic | |
| 6'-138X | Pt | 1 | 6' | Nap1 | — | — | $CH_3$ | H | H | acac | |
| 6'-138Y | Pt | 0 | 6' | Nap1 | — | — | $CH_3$ | H | H | — | — |
| 6'-139 | Pt | 1 | 6' | Nap1 | — | — | $^tC_4H_9$ | H | H | pic | |
| 6'-139X | Pt | 1 | 6' | Nap1 | — | — | $^tC_4H_9$ | H | H | acac | |
| 6'-139Y | Pt | 0 | 6' | Nap1 | — | — | $^tC_4H_9$ | H | H | — | — |
| 6'-140 | Pt | 1 | 6' | Nap2 | — | — | $CH_3$ | H | H | pic | |
| 6'-140X | Pt | 1 | 6' | Nap2 | — | — | $CH_3$ | H | H | acac | |
| 6'-140Y | Pt | 0 | 6' | Nap2 | — | — | $CH_3$ | H | H | — | — |
| 6'-141 | Pt | 1 | 6' | Nap2 | — | — | $^tC_4H_9$ | H | H | pic | |
| 6'-141X | Pt | 1 | 6' | Nap2 | — | — | $^tC_4H_9$ | H | H | acac | |
| 6'-141Y | Pt | 0 | 6' | Nap2 | — | — | $^tC_4H_9$ | H | H | — | — |
| 6'-142 | Pt | 1 | 6' | Nap3 | — | — | $CH_3$ | H | H | pic | |
| 6'-142X | Pt | 1 | 6' | Nap3 | — | — | $CH_3$ | H | H | acac | |
| 6'-142Y | Pt | 0 | 6' | Nap3 | — | — | $CH_3$ | H | H | — | — |
| 6'-143 | Pt | 1 | 6' | Nap3 | — | — | $^tC_4H_9$ | H | H | pic | |
| 6'-143X | Pt | 1 | 6' | Nap3 | — | — | $^tC_4H_9$ | H | H | acac | |
| 6'-143Y | Pt | 0 | 6' | Nap3 | — | — | $^tC_4H_9$ | H | H | — | — |
| 6'-144 | Pt | 1 | 6' | TB | — | — | $CH_3$ | H | H | pic | |
| 6'-144X | Pt | 1 | 6' | TB | — | — | $CH_3$ | H | H | acac | |
| 6'-144Y | Pt | 0 | 6' | TB | — | — | $CH_3$ | H | H | — | — |
| 6'-145 | Pt | 1 | 6' | TB | — | — | $^tC_4H_9$ | H | H | pic | |
| 6'-145X | Pt | 1 | 6' | TB | — | — | $^tC_4H_9$ | H | H | acac | |
| 6'-145Y | Pt | 0 | 6' | TB | — | — | $^tC_4H_9$ | H | H | — | — |
| 6'-146 | Pt | 1 | 6' | TF | — | — | $CH_3$ | H | H | pic | |
| 6'-146X | Pt | 1 | 6' | TF | — | — | $CH_3$ | H | H | acac | |
| 6'-146Y | Pt | 0 | 6' | TF | — | — | $CH_3$ | H | H | — | — |
| 6'-147 | Pt | 1 | 6' | TF | — | — | $^tC_4H_9$ | H | H | pic | |
| 6'-147X | Pt | 1 | 6' | TF | — | — | $^tC_4H_9$ | H | H | acac | |
| 6'-147Y | Pt | 0 | 6' | TF | — | — | $^tC_4H_9$ | H | H | — | — |
| 6'-148 | Pt | 1 | 6' | OB | — | — | $CH_3$ | H | H | pic | |
| 6'-148X | Pt | 1 | 6' | OB | — | — | $CH_3$ | H | H | acac | |
| 6'-148Y | Pt | 0 | 6' | OB | — | — | $CH_3$ | H | H | — | — |
| 6'-149 | Pt | 1 | 6' | OB | — | — | $^tC_4H_9$ | H | H | pic | |
| 6'-149X | Pt | 1 | 6' | OB | — | — | $^tC_4H_9$ | H | H | acac | |
| 6'-149Y | Pt | 0 | 6' | OB | — | — | $^tC_4H_9$ | H | H | — | — |
| 6'-150 | Pt | 1 | 6' | Fu | — | — | $CH_3$ | H | H | pic | |
| 6'-150X | Pt | 1 | 6' | Fu | — | — | $CH_3$ | H | H | acac | |
| 6'-150Y | Pt | 0 | 6' | Fu | — | — | $CH_3$ | H | H | — | — |
| 6'-151 | Pt | 1 | 6' | Fu | — | — | $^tC_4H_9$ | H | H | pic | |

TABLE 41-continued

| No. | M | m | BSS | SS G | T¹ | T² | T⁵ | T⁶ | T⁷ | L¹ | L² |
|---|---|---|---|---|---|---|---|---|---|---|---|
| 6'-151X | Pt | 1 | 6' | Fu | — | — | $^tC_4H_9$ | H | H | acac | |
| 6'-151Y | Pt | 0 | 6' | Fu | — | — | $^tC_4H_9$ | H | H | — | — |
| 6'-152 | Pt | 1 | 6' | Fl | — | — | $CH_3$ | H | H | pic | |
| 6'-152X | Pt | 1 | 6' | Fl | — | — | $CH_3$ | H | H | acac | |
| 6'-152Y | Pt | 0 | 6' | Fl | — | — | $CH_3$ | H | H | — | — |
| 6'-153 | Pt | 1 | 6' | Fl | — | — | $^tC_4H_9$ | H | H | pic | |
| 6'-153X | Pt | 1 | 6' | Fl | — | — | $^tC_4H_9$ | H | H | acac | |
| 6'-153Y | Pt | 0 | 6' | Fl | — | — | $^tC_4H_9$ | H | H | — | — |
| 6'-154 | Pt | 1 | 6' | Bz | — | — | $CH_3$ | H | H | pic | |
| 6'-154X | Pt | 1 | 6' | Bz | — | — | $CH_3$ | H | H | acac | |
| 6'-154Y | Pt | 0 | 6' | Bz | — | — | $CH_3$ | H | H | — | — |
| 6'-155 | Pt | 1 | 6' | Bz | — | — | $^tC_4H_9$ | H | H | pic | |
| 6'-155X | Pt | 1 | 6' | Bz | — | — | $^tC_4H_9$ | H | H | acac | |
| 6'-155Y | Pt | 0 | 6' | Bz | — | — | $^tC_4H_9$ | H | H | — | — |
| 6'-156 | Pt | 1 | 6' | Qu | — | — | $CH_3$ | H | H | pic | |
| 6'-156X | Pt | 1 | 6' | Qu | — | — | $CH_3$ | H | H | acac | |
| 6'-156Y | Pt | 0 | 6' | Qu | — | — | $CH_3$ | H | H | — | — |
| 6'-157 | Pt | 1 | 6' | Qu | — | — | $^tC_4H_9$ | H | H | pic | |
| 6'-157X | Pt | 1 | 6' | Qu | — | — | $^tC_4H_9$ | H | H | acac | |
| 6'-157Y | Pt | 0 | 6' | Qu | — | — | $^tC_4H_9$ | H | H | — | — |
| 6'-158 | Pt | 1 | 6' | OL | H | $^nC_4H_9$ | $CH_3$ | H | H | pic | |
| 6'-158X | Pt | 1 | 6' | OL | H | $^nC_4H_9$ | $CH_3$ | H | H | acac | |
| 6'-158Y | Pt | 0 | 6' | OL | H | $^nC_4H_9$ | $CH_3$ | H | H | — | — |
| 6'-159 | Pt | 1 | 6' | OL | H | $^nC_4H_9$ | $^tC_4H_9$ | H | H | pic | |
| 6'-159X | Pt | 1 | 6' | OL | H | $^nC_4H_9$ | $^tC_4H_9$ | H | H | acac | |
| 6'-159Y | Pt | 0 | 6' | OL | H | $^nC_4H_9$ | $^tC_4H_9$ | H | H | — | — |
| 6'-160 | Pt | 1 | 6' | OL | H | $^tC_4H_9$ | $CH_3$ | H | H | pic | |
| 6'-160X | Pt | 1 | 6' | OL | H | $^tC_4H_9$ | $CH_3$ | H | H | acac | |
| 6'-160Y | Pt | 0 | 6' | OL | H | $^tC_4H_9$ | $CH_3$ | H | H | — | — |
| 6'-161 | Pt | 1 | 6' | OL | H | $^tC_4H_9$ | $^tC_4H_9$ | H | H | pic | |
| 6'-161X | Pt | 1 | 6' | OL | H | $^tC_4H_9$ | $^tC_4H_9$ | H | H | acac | |
| 6'-161Y | Pt | 0 | 6' | OL | H | $^tC_4H_9$ | $^tC_4H_9$ | H | H | — | — |
| 6'-162 | Pt | 1 | 6' | OL | $CH_3$ | $^nC_4H_9$ | $CH_3$ | H | H | pic | |
| 6'-162X | Pt | 1 | 6' | OL | $CH_3$ | $^nC_4H_9$ | $CH_3$ | H | H | acac | |
| 6'-162Y | Pt | 0 | 6' | OL | $CH_3$ | $^nC_4H_9$ | $CH_3$ | H | H | — | — |
| 6'-163 | Pt | 1 | 6' | OL | $CH_3$ | $^tC_4H_9$ | $CH_3$ | H | H | pic | |
| 6'-163X | Pt | 1 | 6' | OL | $CH_3$ | $^tC_4H_9$ | $CH_3$ | H | H | acac | |
| 6'-163Y | Pt | 0 | 6' | OL | $CH_3$ | $^tC_4H_9$ | $CH_3$ | H | H | — | — |
| 6'-164 | Pt | 1 | 6' | OL | H | H | $CH_3$ | H | H | pic | |
| 6'-164X | Pt | 1 | 6' | OL | H | H | $CH_3$ | H | H | acac | |
| 6'-164Y | Pt | 0 | 6' | OL | H | H | $CH_3$ | H | H | — | — |
| 6'-165 | Pt | 1 | 6' | OL | —$CH_2CH_2CH_2$— | | $CH_3$ | H | H | pic | |
| 6'-165X | Pt | 1 | 6' | OL | —$CH_2CH_2CH_2$— | | $CH_3$ | H | H | acac | |
| 6'-165Y | Pt | 0 | 6' | OL | —$CH_2CH_2CH_2$— | | $CH_3$ | H | H | — | — |
| 6'-166 | Pt | 1 | 6' | OL | —$CH_2CH_2CH_2$— | | $^tC_4H_9$ | H | H | pic | |
| 6'-166X | Pt | 1 | 6' | OL | —$CH_2CH_2CH_2$— | | $^tC_4H_9$ | H | H | acac | |
| 6'-166Y | Pt | 0 | 6' | OL | —$CH_2CH_2CH_2$— | | $^tC_4H_9$ | H | H | — | — |

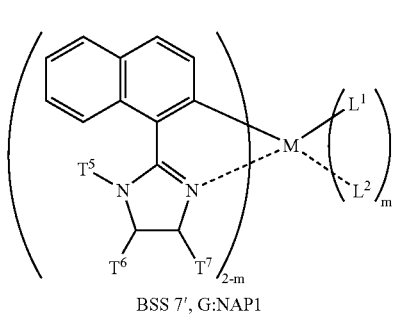

BSS 7', G:NAP1

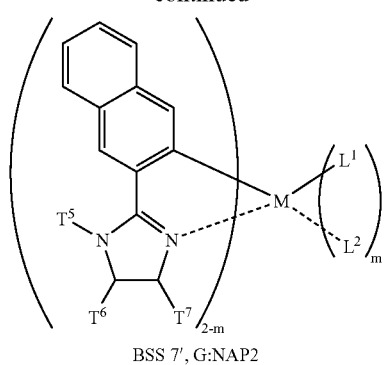

BSS 7', G:NAP2

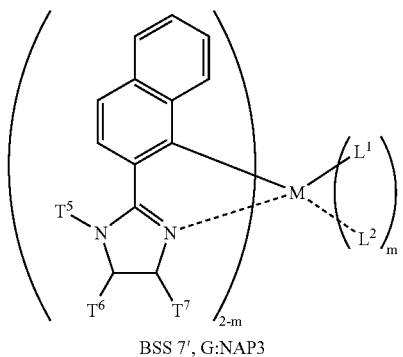
BSS 7', G:NAP3
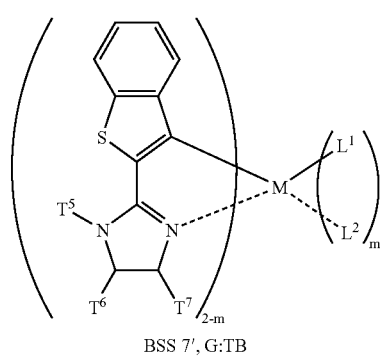
BSS 7', G:TB
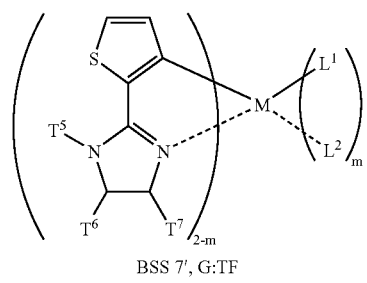
BSS 7', G:TF
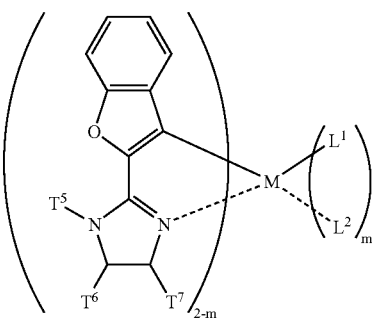
BSS 7', G:OB
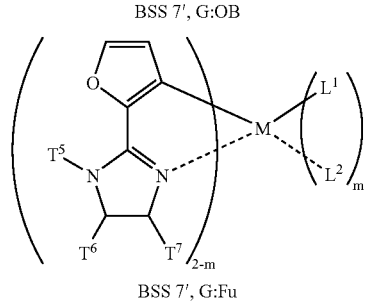
BSS 7', G:Fu
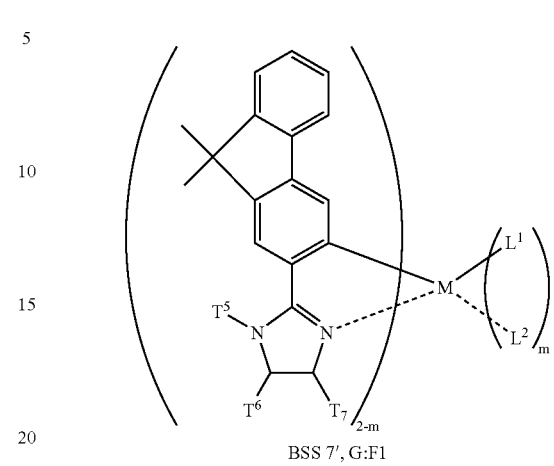
BSS 7', G:Fl
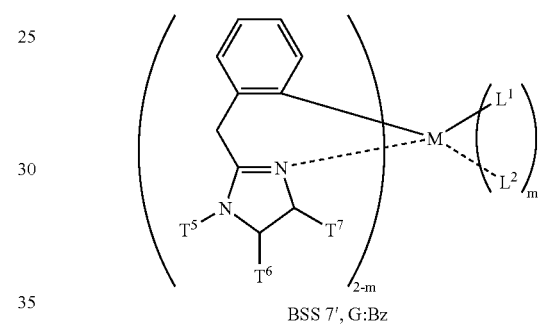
BSS 7', G:Bz
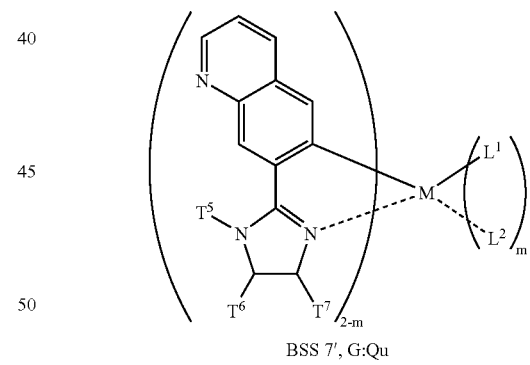
BSS 7', G:Qu
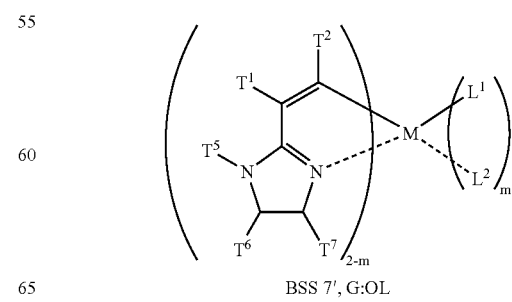
BSS 7', G:OL

TABLE 42

| No. | M | m | BSS | SS G | T¹ | T² | T⁵ | T⁶ | T⁷ | L¹ | L² |
|---|---|---|---|---|---|---|---|---|---|---|---|
| 7'-138 | Pt | 1 | 7' | Nap1 | — | — | $CH_3$ | H | H | pic | |
| 7'-138X | Pt | 1 | 7' | Nap1 | — | — | $CH_3$ | H | H | acac | |
| 7'-138Y | Pt | 0 | 7' | Nap1 | — | — | $CH_3$ | H | H | — | |
| 7'-139 | Pt | 1 | 7' | Nap1 | — | — | $^tC_4H_9$ | H | H | pic | |
| 7'-139X | Pt | 1 | 7' | Nap1 | — | — | $^tC_4H_9$ | H | H | acac | |
| 7'-139Y | Pt | 0 | 7' | Nap1 | — | — | $^tC_4H_9$ | H | H | — | |
| 7'-140 | Pt | 1 | 7' | Nap2 | — | — | $CH_3$ | H | H | pic | |
| 7'-140X | Pt | 1 | 7' | Nap2 | — | — | $CH_3$ | H | H | acac | |
| 7'-140Y | Pt | 0 | 7' | Nap2 | — | — | $CH_3$ | H | H | — | |
| 7'-141 | Pt | 1 | 7 | Nap2 | — | — | $^tC_4H_9$ | H | H | pic | |
| 7'-141X | Pt | 1 | 7' | Nap2 | — | — | $^tC_4H_9$ | H | H | acac | |
| 7'-141Y | Pt | 0 | 7' | Nap2 | — | — | $^tC_4H_9$ | H | H | — | |
| 7'-142 | Pt | 1 | 7' | Nap3 | — | — | $CH_3$ | H | H | pic | |
| 7'-142X | Pt | 1 | 7' | Nap3 | — | — | $CH_3$ | H | H | acac | |
| 7'-142Y | Pt | 0 | 7' | Nap3 | — | — | $CH_3$ | H | H | — | |
| 7'-143 | Pt | 1 | 7' | Nap3 | — | — | $^tC_4H_9$ | H | H | pic | |
| 7'-143X | Pt | 1 | 7' | Nap3 | — | — | $^tC_4H_9$ | H | H | acac | |
| 7'-143Y | Pt | 0 | 7' | Nap3 | — | — | $^tC_4H_9$ | H | H | — | |
| 7'-144 | Pt | 1 | 7' | TB | — | — | $CH_3$ | H | H | pic | |
| 7'-144X | Pt | 1 | 7' | TB | — | — | $CH_3$ | H | H | acac | |
| 7'-144Y | Pt | 0 | 7' | TB | — | — | $CH_3$ | H | H | — | |
| 7'-145 | Pt | 1 | 7' | TB | — | — | $^tC_4H_9$ | H | H | pic | |
| 7'-145X | Pt | 1 | 7' | TB | — | — | $^tC_4H_9$ | H | H | acac | |
| 7'-145Y | Pt | 0 | 7' | TB | — | — | $^tC_4H_9$ | H | H | — | |
| 7'-146 | Pt | 1 | 7' | TF | — | — | $CH_3$ | H | H | pic | |
| 7'-146X | Pt | 1 | 7 | TF | — | — | $CH_3$ | H | H | acac | |
| 7'-146Y | Pt | 0 | 7' | TF | — | — | $CH_3$ | H | H | — | |
| 7'-147 | Pt | 1 | 7' | TF | — | — | $^tC_4H_9$ | H | H | pic | |
| 7'-147X | Pt | 1 | 7' | TF | — | — | $^tC_4H_9$ | H | H | acac | |
| 7'-147Y | Pt | 0 | 7' | TF | — | — | $^tC_4H_9$ | H | H | — | |
| 7'-148 | Pt | 1 | 7' | OB | — | — | $CH_3$ | H | H | pic | |
| 7'-148X | Pt | 1 | 7' | OB | — | — | $CH_3$ | H | H | acac | |
| 7'-148Y | Pt | 0 | 7' | OB | — | — | $CH_3$ | H | H | — | |
| 7'-149 | Pt | 1 | 7' | OB | — | — | $^tC_4H_9$ | H | H | pic | |
| 7'-149X | Pt | 1 | 7' | OB | — | — | $^tC_4H_9$ | H | H | acac | |
| 7'-149Y | Pt | 0 | 7' | OB | — | — | $^tC_4H_9$ | H | H | — | |
| 7'-150 | Pt | 1 | 7' | Fu | — | — | $CH_3$ | H | H | pic | |
| 7'-150X | Pt | 1 | 7' | Fu | — | — | $CH_3$ | H | H | acac | |
| 7'-150Y | Pt | 0 | 7' | Fu | — | — | $CH_3$ | H | H | — | |
| 7'-151 | Pt | 1 | 7' | Fu | — | — | $^tC_4H_9$ | H | H | pic | |
| 7'-151X | Pt | 1 | 7' | Fu | — | — | $^tC_4H_9$ | H | H | acac | |
| 7'-151Y | Pt | 0 | 7' | Fu | — | — | $^tC_4H_9$ | H | H | — | |
| 7'-152 | Pt | 1 | 7' | Fl | — | — | $CH_3$ | H | H | pic | |
| 7'-152X | Pt | 1 | 7' | Fl | — | — | $CH_3$ | H | H | acac | |
| 7'-152Y | Pt | 0 | 7' | Fl | — | — | $CH_3$ | H | H | — | |
| 7'-153 | Pt | 1 | 7' | Fl | — | — | $^tC_4H_9$ | H | H | pic | |
| 7'-153X | Pt | 1 | 7' | Fl | — | — | $^tC_4H_9$ | H | H | acac | |
| 7'-153Y | Pt | 0 | 7' | Fl | — | — | $^tC_4H_9$ | H | H | — | |
| 7'-154 | Pt | 1 | 7' | Bz | — | — | $CH_3$ | H | H | pic | |
| 7'-154X | Pt | 1 | 7' | Bz | — | — | $CH_3$ | H | H | acac | |
| 7'-154Y | Pt | 0 | 7' | Bz | — | — | $CH_3$ | H | H | — | |
| 7'-155 | Pt | 1 | 7' | Bz | — | — | $^tC_4H_9$ | H | H | pic | |
| 7'-155X | Pt | 1 | 7' | Bz | — | — | $^tC_4H_9$ | H | H | acac | |
| 7'-155Y | Pt | 0 | 7' | Bz | — | — | $^tC_4H_9$ | H | H | — | |
| 7'-156 | Pt | 1 | 7' | Qu | — | — | $CH_3$ | H | H | pic | |
| 7'-156X | Pt | 1 | 7' | Qu | — | — | $CH_3$ | H | H | acac | |
| 7'-156Y | Pt | 0 | 7' | Qu | — | — | $CH_3$ | H | H | — | |
| 7'-157 | Pt | 1 | 7' | Qu | — | — | $^tC_4H_9$ | H | H | pic | |
| 7'-157X | Pt | 1 | 7' | Qu | — | — | $^tC_4H_9$ | H | H | acac | |
| 7'-157Y | Pt | 0 | 7' | Qu | — | — | $^tC_4H_9$ | H | H | — | |
| 7'-158 | Pt | 1 | 7' | OL | H | $^nC_4H_9$ | $CH_3$ | H | H | pic | |
| 7'-158X | Pt | 1 | 7' | OL | H | $^nC_4H_9$ | $CH_3$ | H | H | acac | |
| 7'-158Y | Pt | 0 | 7' | OL | H | $^nC_4H_9$ | $CH_3$ | H | H | — | |
| 7'-159 | Pt | 1 | 7' | OL | H | $^nC_4H_9$ | $^tC_4H_9$ | H | H | pic | |
| 7'-159X | Pt | 1 | 7' | OL | H | $^nC_4H_9$ | $^tC_4H_9$ | H | H | acac | |
| 7'-159Y | Pt | 0 | 7' | OL | H | $^nC_4H_9$ | $^tC_4H_9$ | H | H | — | |
| 7'-160 | Pt | 1 | 7' | OL | H | $^tC_4H_9$ | $CH_3$ | H | H | pic | |
| 7'-160X | Pt | 1 | 7' | OL | H | $^tC_4H_9$ | $CH_3$ | H | H | acac | |
| 7'-160Y | Pt | 0 | 7' | OL | H | $^tC_4H_9$ | $CH_3$ | H | H | — | |
| 7'-161 | Pt | 1 | 7' | OL | H | $^tC_4H_9$ | $^tC_4H_9$ | H | H | pic | |
| 7'-161X | Pt | 1 | 7' | OL | H | $^tC_4H_9$ | $^tC_4H_9$ | H | H | acac | |
| 7'-161Y | Pt | 0 | 7' | OL | H | $^tC_4H_9$ | $^tC_4H_9$ | H | H | — | |
| 7'-162 | Pt | 1 | 7' | OL | $CH_3$ | $^nC_4H_9$ | $CH_3$ | H | H | pic | |
| 7'-162X | Pt | 1 | 7' | OL | $CH_3$ | $^nC_4H_9$ | $CH_3$ | H | H | acac | |
| 7'-162Y | Pt | 0 | 7' | OL | $CH_3$ | $^nC_4H_9$ | $CH_3$ | H | H | — | |
| 7'-163 | Pt | 1 | 7' | OL | $CH_3$ | $^tC_4H_9$ | $CH_3$ | H | H | pic | |
| 7'-163X | Pt | 1 | 7' | OL | $CH_3$ | $^tC_4H_9$ | $CH_3$ | H | H | acac | |

TABLE 42-continued
| No. | M | m | BSS | SS | G | T¹ | T² | T⁵ | T⁶ | T⁷ | L¹ | L² |
|---|---|---|---|---|---|---|---|---|---|---|---|---|
| 7'-163Y | Pt | 0 | 7' | | OL | CH₃ | ᵗC₄H₉ | CH₃ | H | H | — | — |
| 7'-164 | Pt | 1 | 7' | | OL | H | H | CH₃ | H | H | pic | |
| 7'-164X | Pt | 1 | 7' | | OL | H | H | CH₃ | H | H | acac | |
| 7'-164Y | Pt | 0 | 7' | | OL | H | H | CH₃ | H | H | — | — |
| 7'-165 | Pt | 1 | 7' | | OL | —CH₂CH₂CH₂— | | CH₃ | H | H | pic | |
| 7'-165X | Pt | 1 | 7' | | OL | —CH₂CH₂CH₂— | | CH₃ | H | H | acac | |
| 7'-165Y | Pt | 0 | 7' | | OL | —CH₂CH₂CH₂— | | CH₃ | H | H | — | — |
| 7'-166 | Pt | 1 | 7' | | OL | —CH₂CH₂CH₂— | | ᵗC₄H₉ | H | H | pic | |
| 7'-166X | Pt | 1 | 7' | | OL | —CH₂CH₂CH₂— | | ᵗC₄H₉ | H | H | acac | |
| 7'-166Y | Pt | 0 | 7' | | OL | —CH₂CH₂CH₂— | | ᵗC₄H₉ | H | H | — | — |
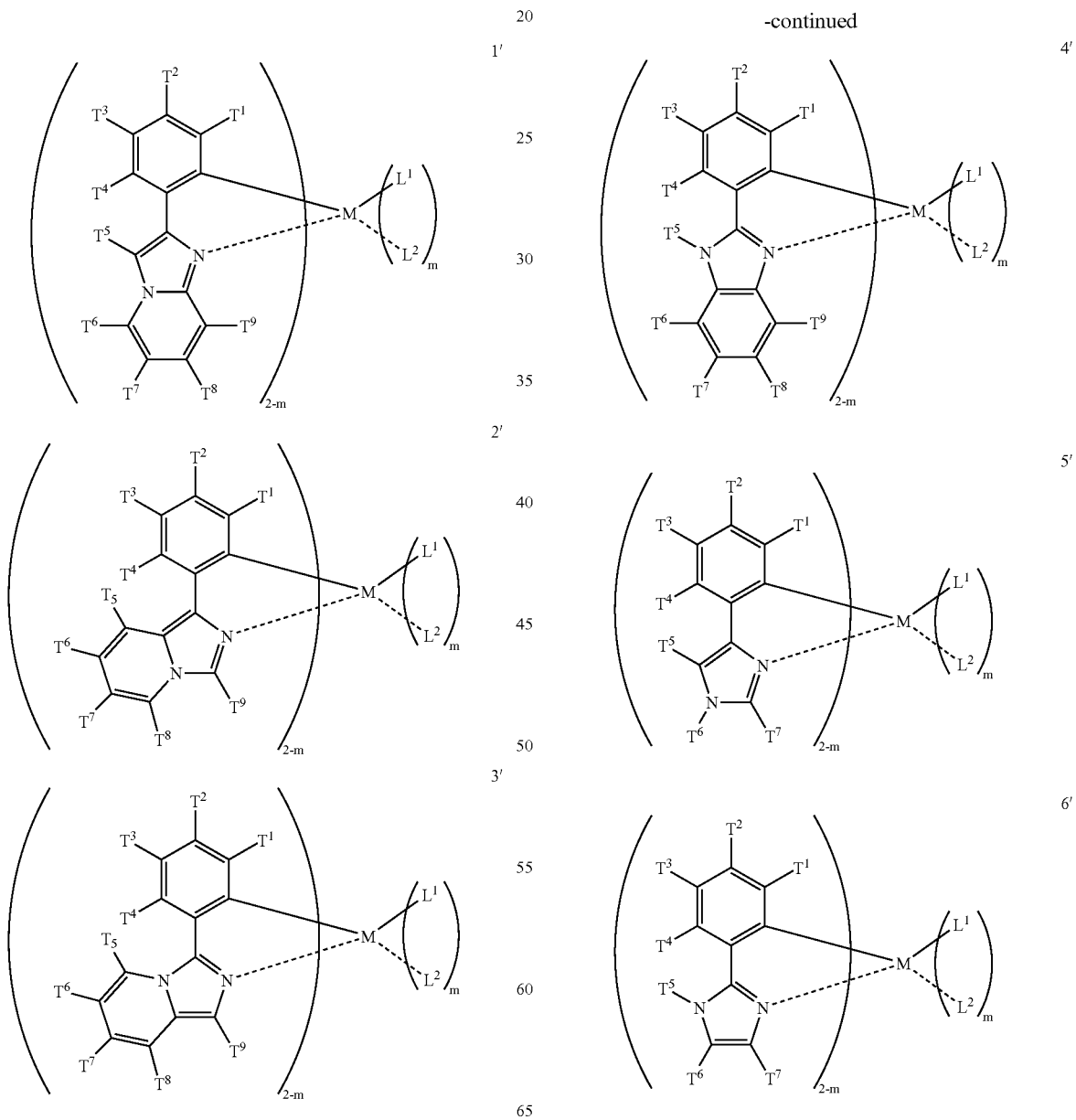

-continued

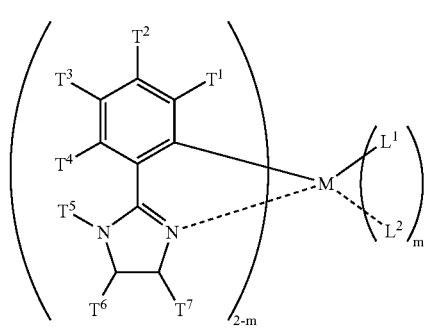

TABLE 43

| No. | M | m | BSS | SS G | T$^1$ | T$^2$ | T$^3$ | T$^4$ | T$^5$ | T$^6$ | T$^7$ | T$^8$ | T$^9$ | L$^1$ L$^2$ |
|---|---|---|---|---|---|---|---|---|---|---|---|---|---|---|
| 1'-187 | Pd | 1 | 1' | Ph | H | H | H | H | H | H | H | H | H | pic |
| 1'-187X | Pd | 1 | 1' | Ph | H | H | H | H | H | H | H | H | H | acac |
| 1'-187Y | Pd | 0 | 1' | Ph | H | H | H | H | H | H | H | H | H | — — |
| 1'-188 | Pd | 1 | 1' | Ph | H | F | H | F | H | H | H | H | H | pic |
| 1'-188X | Pd | 1 | 1' | Ph | H | F | H | F | H | H | H | H | H | acac |
| 1'-188Y | Pd | 0 | 1' | Ph | H | F | H | F | H | H | H | H | H | — — |
| 1'-189 | Pd | 1 | 1' | Ph | F | H | H | F | H | H | H | H | H | pic |
| 1'-189X | Pd | 1 | 1' | Ph | F | H | H | F | H | H | H | H | H | acac |
| 1'-189Y | Pd | 0 | 1' | Ph | F | H | H | F | H | H | H | H | H | — — |
| 1'-190 | Pd | 1 | 1' | Ph | CF$_3$ | H | CF$_3$ | H | H | H | H | H | H | pic |
| 1'-190X | Pd | 1 | 1' | Ph | CF$_3$ | H | CF$_3$ | H | H | H | H | H | H | acac |
| 1'-190Y | Pd | 0 | 1' | Ph | CF$_3$ | H | CF$_3$ | H | H | H | H | H | H | — — |
| 1'-191 | Pd | 1 | 1' | Ph | H | F | CF$_3$ | H | H | H | H | H | H | pic |
| 1'-191X | Pd | 1 | 1' | Ph | H | F | CF$_3$ | H | H | H | H | H | H | acac |
| 1'-191Y | Pd | 0 | 1' | Ph | H | F | CF$_3$ | H | H | H | H | H | H | — — |
| 1'-192 | Pd | 1 | 1' | Ph | F | H | CF$_3$ | H | H | H | H | H | H | pic |
| 1'-192X | Pd | 1 | 1' | Ph | F | H | CF$_3$ | H | H | H | H | H | H | acac |
| 1'-192Y | Pd | 0 | 1' | Ph | F | H | CF$_3$ | H | H | H | H | H | H | — — |
| 1'-193 | Pd | 1 | 1' | Ph | F | F | F | F | H | H | H | H | H | pic |
| 1'-193X | Pd | 1 | 1' | Ph | F | F | F | F | H | H | H | H | H | acac |
| 1'-193Y | Pd | 0 | 1' | Ph | F | F | F | F | H | H | H | H | H | — — |
| 1'-194 | Pd | 1 | 1' | Ph | H | F | H | CH$_3$ | H | H | H | H | H | pic |
| 1'-194X | Pd | 1 | 1' | Ph | H | F | H | CH$_3$ | H | H | H | H | H | acac |
| 1'-194Y | Pd | 0 | 1' | Ph | H | F | H | CH$_3$ | H | H | H | H | H | — — |
| 1'-195 | Pd | 1 | 1' | Ph | H | F | H | $^t$C$_4$H$_9$ | H | H | H | H | H | pic |
| 1'-195X | Pd | 1 | 1' | Ph | H | F | H | $^t$C$_4$H$_9$ | H | H | H | H | H | acac |
| 1'-195Y | Pd | 0 | 1' | Ph | H | F | H | $^t$C$_4$H$_9$ | H | H | H | H | H | — — |
| 1'-196 | Pd | 1 | 1' | Ph | H | CF$_3$ | H | CF$_3$ | H | H | H | H | H | pic |
| 1'-196X | Pd | 1 | 1' | Ph | H | CF$_3$ | H | CF$_3$ | H | H | H | H | H | acac |
| 1'-196Y | Pd | 0 | 1' | Ph | H | CF$_3$ | H | CF$_3$ | H | H | H | H | H | — — |
| 1'-197 | Pd | 1 | 1' | Ph | CF$_3$ | H | H | $^t$C$_4$H$_9$ | H | H | H | H | H | pic |
| 1'-197X | Pd | 1 | 1' | Ph | CF$_3$ | H | H | $^t$C$_4$H$_9$ | H | H | H | H | H | acac |
| 1'-197Y | Pd | 0 | 1' | Ph | CF$_3$ | H | H | $^t$C$_4$H$_9$ | H | H | H | H | H | — — |
| 1'-198 | Pd | 1 | 1' | Ph | H | CF$_3$ | H | $^t$C$_4$H$_9$ | H | H | H | H | H | pic |
| 1'-198X | Pd | 1 | 1' | Ph | H | CF$_3$ | H | $^t$C$_4$H$_9$ | H | H | H | H | H | acac |
| 1'-198Y | Pd | 0 | 1' | Ph | H | CF$_3$ | H | $^t$C$_4$H$_9$ | H | H | H | H | H | — — |
| 1'-199 | Pd | 1 | 1' | Ph | H | CF$_3$ | H | CH$_3$ | H | H | H | H | H | pic |
| 1'-199X | Pd | 1 | 1' | Ph | H | CF$_3$ | H | CH$_3$ | H | H | H | H | H | acac |
| 1'-199Y | Pd | 0 | 1' | Ph | H | CF$_3$ | H | CH$_3$ | H | H | H | H | H | — — |
| 1'-200 | Pd | 1 | 1' | Ph | H | CF$_3$ | CF$_3$ | H | H | H | H | H | H | pic |
| 1'-200X | Pd | 1 | 1' | Ph | H | CF$_3$ | CF$_3$ | H | H | H | H | H | H | acac |
| 1'-200Y | Pd | 0 | 1' | Ph | H | CF$_3$ | CF$_3$ | H | H | H | H | H | H | — — |
| 1'-201 | Pd | 1 | 1' | Ph | H | H | NO$_2$ | H | H | H | H | H | H | pic |
| 1'-201X | Pd | 1 | 1' | Ph | H | H | NO$_2$ | H | H | H | H | H | H | acac |
| 1'-201Y | Pd | 0 | 1' | Ph | H | H | NO$_2$ | H | H | H | H | H | H | — — |
| 1'-202 | Pd | 1 | 1' | Ph | F | H | NO$_2$ | H | H | H | H | H | H | pic |
| 1'-202X | Pd | 1 | 1' | Ph | F | H | NO$_2$ | H | H | H | H | H | H | acac |
| 1'-202Y | Pd | 0 | 1' | Ph | F | H | NO$_2$ | H | H | H | H | H | H | — — |
| 1'-203 | Pd | 1 | 1' | Ph | F | H | NO$_2$ | F | H | H | H | H | H | pic |
| 1'-203X | Pd | 1 | 1' | Ph | F | H | NO$_2$ | F | H | H | H | H | H | acac |
| 1'-203Y | Pd | 0 | 1' | Ph | F | H | NO$_2$ | F | H | H | H | H | H | — — |
| 1'-204 | Pd | 1 | 1' | Ph | H | NO$_2$ | H | NO$_2$ | H | H | H | H | H | pic |
| 1'-204X | Pd | 1 | 1' | Ph | H | NO$_2$ | H | NO$_2$ | H | H | H | H | H | acac |
| 1'-204Y | Pd | 0 | 1' | Ph | H | NO$_2$ | H | NO$_2$ | H | H | H | H | H | — — |
| 1'-205 | Pd | 1 | 1' | Ph | NO$_2$ | H | H | NO$_2$ | H | H | H | H | H | pic |
| 1'-205X | Pd | 1 | 1' | Ph | NO$_2$ | H | H | NO$_2$ | H | H | H | H | H | acac |

TABLE 43-continued

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1'-205Y | Pd | 0 | 1' | Ph | NO₂ | H | H | NO₂ | H | H | H | H | H | — — |
| 1'-206 | Pd | 1 | 1' | Ph | H | H | CF₃ | H | H | H | H | H | H | pic |
| 1'-206X | Pd | 1 | 1' | Ph | H | H | CF₃ | H | H | H | H | H | H | acac |
| 1'-206Y | Pd | 0 | 1' | Ph | H | H | CF₃ | H | H | H | H | H | H | — — |
| 1'-207 | Pd | 1 | 1' | Ph | H | Cl | CF₃ | H | H | H | H | H | H | pic |
| 1'-207X | Pd | 1 | 1' | Ph | H | Cl | CF₃ | H | H | H | H | H | H | acac |
| 1'-207Y | Pd | 0 | 1' | Ph | H | Cl | CF₃ | H | H | H | H | H | H | — — |
| 1'-208 | Pd | 1 | 1' | Ph | H | NO₂ | H | H | H | H | H | H | H | pic |
| 1'-208X | Pd | 1 | 1' | Ph | H | NO₂ | H | H | H | H | H | H | H | acac |
| 1'-208Y | Pd | 0 | 1' | Ph | H | NO₂ | H | H | H | H | H | H | H | — — |
| 1'-209 | Pd | 1 | 1' | Ph | H | CF₃ | H | H | H | H | H | H | H | pic |
| 1'-209X | Pd | 1 | 1' | Ph | H | CF₃ | H | H | H | H | H | H | H | acac |
| 1'-209Y | Pd | 0 | 1' | Ph | H | CF₃ | H | H | H | H | H | H | H | — — |
| 1'-210 | Pd | 1 | 1' | Ph | H | NO₂ | H | CH₃ | H | H | H | H | H | pic |
| 1'-210X | Pd | 1 | 1' | Ph | H | NO₂ | H | CH₃ | H | H | H | H | H | acac |
| 1'-210Y | Pd | 0 | 1' | Ph | H | NO₂ | H | CH₃ | H | H | H | H | H | — — |
| 1'-211 | Pd | 1 | 1' | Ph | H | NO₂ | H | $^tC_4H_9$ | H | H | H | H | H | pic |
| 1'-211X | Pd | 1 | 1' | Ph | H | NO₂ | H | $^tC_4H_9$ | H | H | H | H | H | acac |
| 1'-211Y | Pd | 0 | 1' | Ph | H | NO₂ | H | $^tC_4H_9$ | H | H | H | H | H | — — |
| 1'-212 | Pd | 1 | 1' | Ph | H | H | CH₃O | H | H | H | H | H | H | pic |
| 1'-212X | Pd | 1 | 1' | Ph | H | H | CH₃O | H | H | H | H | H | H | acac |
| 1'-212Y | Pd | 0 | 1' | Ph | H | H | CH₃O | H | H | H | H | H | H | — — |
| 1'-213 | Pd | 1 | 1' | Ph | H | CH₃O | H | H | H | H | H | H | H | pic |
| 1'-213X | Pd | 1 | 1' | Ph | H | CH₃O | H | H | H | H | H | H | H | acac |
| 1'-213Y | Pd | 0 | 1' | Ph | H | CH₃O | H | H | H | H | H | H | H | — — |
| 1'-214 | Pd | 1 | 1' | Ph | H | CH₃O | H | CH₃ | H | H | H | H | H | pic |
| 1'-214X | Pd | 1 | 1' | Ph | H | CH₃O | H | CH₃ | H | H | H | H | H | acac |
| 1'-214Y | Pd | 0 | 1' | Ph | H | CH₃O | H | CH₃ | H | H | H | H | H | — — |
| 1'-215 | Pd | 1 | 1' | Ph | H | CH₃O | H | $^tC_4H_9$ | H | H | H | H | H | pic |
| 1'-215X | Pd | 1 | 1' | Ph | H | CH₃O | H | $^tC_4H_9$ | H | H | H | H | H | acac |
| 1'-215Y | Pd | 0 | 1' | Ph | H | CH₃O | H | $^tC_4H_9$ | H | H | H | H | H | — — |
| 1'-216 | Pd | 1 | 1' | Ph | H | H | H | H | $^tC_4H_9$ | H | H | H | H | pic |
| 1'-216X | Pd | 1 | 1' | Ph | H | H | H | H | $^tC_4H_9$ | H | H | H | H | acac |
| 1'-216Y | Pd | 0 | 1' | Ph | H | H | H | H | $^tC_4H_9$ | H | H | H | H | — — |
| 1'-217 | Pd | 1 | 1' | Ph | H | F | H | F | $^tC_4H_9$ | H | H | H | H | pic |
| 1'-217X | Pd | 1 | 1' | Ph | H | F | H | F | $^tC_4H_9$ | H | H | H | H | acac |
| 1'-217Y | Pd | 0 | 1' | Ph | H | F | H | F | $^tC_4H_9$ | H | H | H | H | — — |
| 1'-218 | Pd | 1 | 1' | Ph | CF₃ | H | CF₃ | H | $^tC_4H_9$ | H | H | H | H | pic |
| 1'-218X | Pd | 1 | 1' | Ph | CF₃ | H | CF₃ | H | $^tC_4H_9$ | H | H | H | H | acac |
| 1'-218Y | Pd | 0 | 1' | Ph | CF₃ | H | CF₃ | H | $^tC_4H_9$ | H | H | H | H | — — |
| 1'-219 | Pd | 1 | 1' | Ph | H | CF₃ | H | CH₃ | $^tC_4H_9$ | H | H | H | H | pic |
| 1'-219X | Pd | 1 | 1' | Ph | H | CF₃ | H | CH₃ | $^tC_4H_9$ | H | H | H | H | acac |
| 1'-219Y | Pd | 0 | 1' | Ph | H | CF₃ | H | CH₃ | $^tC_4H_9$ | H | H | H | H | — — |
| 1'-220 | Pd | 1 | 1' | Ph | H | F | H | F | H | CH₃ | H | H | H | pic |
| 1'-220X | Pd | 1 | 1' | Ph | H | F | H | F | H | CH₃ | H | H | H | acac |
| 1'-220Y | Pd | 0 | 1' | Ph | H | F | H | F | H | CH₃ | H | H | H | — — |
| 1'-221 | Pd | 1 | 1' | Ph | CF₃ | H | CF₃ | H | H | CH₃ | H | H | H | pic |
| 1'-221X | Pd | 1 | 1' | Ph | CF₃ | H | CF₃ | H | H | CH₃ | H | H | H | acac |
| 1'-221Y | Pd | 0 | 1' | Ph | CF₃ | H | CF₃ | H | H | CH₃ | H | H | H | — — |
| 1'-222 | Pd | 1 | 1' | Ph | H | Si(CH₃)₃ | H | H | H | H | H | H | H | pic |
| 1'-222X | Pd | 1 | 1' | Ph | H | Si(CH₃)₃ | H | H | H | H | H | H | H | acac |
| 1'-222Y | Pd | 0 | 1' | Ph | H | Si(CH₃)₃ | H | H | H | H | H | H | H | — — |
| 1'-223 | Pd | 1 | 1' | Ph | H | H | Si(CH₃)₃ | H | H | H | H | H | H | pic |
| 1'-223X | Pd | 1 | 1' | Ph | H | H | Si(CH₃)₃ | H | H | H | H | H | H | acac |
| 1'-223Y | Pd | 0 | 1' | Ph | H | H | Si(CH₃)₃ | H | H | H | H | H | H | — — |
| 1'-224 | Pd | 1 | 1' | Ph | H | H | H | Si(CH₃)₃ | H | H | H | H | H | pic |
| 1'-224X | Pd | 1 | 1' | Ph | H | H | H | Si(CH₃)₃ | H | H | H | H | H | acac |
| 1'-224Y | Pd | 0 | 1' | Ph | H | H | H | Si(CH₃)₃ | H | H | H | H | H | — — |
| 1'-225 | Pd | 1 | 1' | Ph | H | F | H | Si(CH₃)₃ | H | H | H | H | H | pic |
| 1'-225X | Pd | 1 | 1' | Ph | H | F | H | Si(CH₃)₃ | H | H | H | H | H | acac |
| 1'-225Y | Pd | 0 | 1' | Ph | H | F | H | Si(CH₃)₃ | H | H | H | H | H | — — |
| 1'-226 | Pd | 1 | 1' | Ph | H | CF₃ | H | Si(CH₃)₃ | H | H | H | H | H | pic |
| 1'-226X | Pd | 1 | 1' | Ph | H | CF₃ | H | Si(CH₃)₃ | H | H | H | H | H | acac |
| 1'-226Y | Pd | 0 | 1' | Ph | H | CF₃ | H | Si(CH₃)₃ | H | H | H | H | H | — — |
| 1'-227 | Pd | 1 | 1' | Ph | H | Si(CH₃)₃ | H | F | H | H | H | H | H | pic |
| 1'-227X | Pd | 1 | 1' | Ph | H | Si(CH₃)₃ | H | F | H | H | H | H | H | acac |
| 1'-227Y | Pd | 0 | 1' | Ph | H | Si(CH₃)₃ | H | F | H | H | H | H | H | — — |
| 1'-228 | Pd | 1 | 1' | Ph | H | Si(CH₃)₃ | H | CF₃ | H | H | H | H | H | pic |
| 1'-228X | Pd | 1 | 1' | Ph | H | Si(CH₃)₃ | H | CF₃ | H | H | H | H | H | acac |
| 1'-228Y | Pd | 0 | 1' | Ph | H | Si(CH₃)₃ | H | CF₃ | H | H | H | H | H | — — |
| 1'-229 | Pd | 1 | 1' | Ph | Si(CH₃)₃ | H | Si(CH₃)₃ | H | H | H | H | H | H | pic |
| 1'-229X | Pd | 1 | 1' | Ph | Si(CH₃)₃ | H | Si(CH₃)₃ | H | H | H | H | H | H | acac |
| 1'-229Y | Pd | 0 | 1' | Ph | Si(CH₃)₃ | H | Si(CH₃)₃ | H | H | H | H | H | H | — — |
| 1'-230 | Pd | 1 | 1' | Ph | H | H | H | COCH₃ | H | H | H | H | H | pic |
| 1'-230X | Pd | 1 | 1' | Ph | H | H | H | COCH₃ | H | H | H | H | H | acac |
| 1'-230Y | Pd | 0 | 1' | Ph | H | H | H | COCH₃ | H | H | H | H | H | — — |
| 1'-231 | Pd | 1 | 1' | Ph | H | H | COCH₃ | H | H | H | H | H | H | pic |

TABLE 43-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 1'-231X | Pd | 1 | 1' | Ph | H | H | COCH₃ | H | H | H | H | H | H | acac | |
| 1'-231Y | Pd | 0 | 1' | Ph | H | H | COCH₃ | H | H | H | H | H | H | — | — |
| 1'-232 | Pd | 1 | 1' | Ph | H | COCH₃ | H | H | H | H | H | H | H | pic | |
| 1'-232X | Pd | 1 | 1' | Ph | H | COCH₃ | H | H | H | H | H | H | H | acac | |
| 1'-232Y | Pd | 0 | 1' | Ph | H | COCH₃ | H | H | H | H | H | H | H | — | — |
| 1'-233 | Pd | 1 | 1' | Ph | H | H | BL | H | H | H | H | H | H | pic | |
| 1'-233X | Pd | 1 | 1' | Ph | H | H | BL | H | H | H | H | H | H | acac | |
| 1'-233Y | Pd | 0 | 1' | Ph | H | H | BL | H | H | H | H | H | H | — | — |
| 1'-234 | Pd | 1 | 1' | Ph | H | BL | H | H | H | H | H | H | H | pic | |
| 1'-234X | Pd | 1 | 1' | Ph | H | BL | H | H | H | H | H | H | H | acac | |
| 1'-234Y | Pd | 0 | 1' | Ph | H | BL | H | H | H | H | H | H | H | — | — |
| 1'-235 | Pd | 1 | 1' | Ph | H | H | PL | H | H | H | H | H | H | pic | |
| 1'-235X | Pd | 1 | 1' | Ph | H | H | PL | H | H | H | H | H | H | acac | |
| 1'-235Y | Pd | 0 | 1' | Ph | H | H | PL | H | H | H | H | H | H | — | — |
| 1'-236 | Pd | 1 | 1' | Ph | H | PL | H | H | H | H | H | H | H | pic | |
| 1'-236X | Pd | 1 | 1' | Ph | H | PL | H | H | H | H | H | H | H | acac | |
| 1'-236Y | Pd | 0 | 1' | Ph | H | PL | H | H | H | H | H | H | H | — | — |
| 1'-237 | Pd | 1 | 1' | Ph | H | H | MEE1 | H | H | H | H | H | H | pic | |
| 1'-237X | Pd | 1 | 1' | Ph | H | H | MEE1 | H | H | H | H | H | H | acac | |
| 1'-237Y | Pd | 0 | 1' | Ph | H | H | MEE1 | H | H | H | H | H | H | — | — |
| 1'-238 | Pd | 1 | 1' | Ph | H | MEE1 | H | H | H | H | H | H | H | pic | |
| 1'-238X | Pd | 1 | 1' | Ph | H | MEE1 | H | H | H | H | H | H | H | acac | |
| 1'-238Y | Pd | 0 | 1' | Ph | H | MEE1 | H | H | H | H | H | H | H | — | — |
| 1'-239 | Pd | 1 | 1' | Ph | H | H | MEE2 | H | H | H | H | H | H | pic | |
| 1'-239X | Pd | 1 | 1' | Ph | H | H | MEE2 | H | H | H | H | H | H | acac | |
| 1'-239Y | Pd | 0 | 1' | Ph | H | H | MEE2 | H | H | H | H | H | H | — | — |
| 1'-240 | Pd | 1 | 1' | Ph | H | MEE2 | H | H | H | H | H | H | H | pic | |
| 1'-240X | Pd | 1 | 1' | Ph | H | MEE2 | H | H | H | H | H | H | H | acac | |
| 1'-240Y | Pd | 0 | 1' | Ph | H | MEE2 | H | H | H | H | H | H | H | — | — |
| 1'-241 | Pd | 1 | 1' | Ph | H | H | PA1 | H | H | H | H | H | H | pic | |
| 1'-241X | Pd | 1 | 1' | Ph | H | H | PA1 | H | H | H | H | H | H | acac | |
| 1'-241Y | Pd | 0 | 1' | Ph | H | H | PA1 | H | H | H | H | H | H | — | — |
| 1'-242 | Pd | 1 | 1' | Ph | H | PA1 | H | H | H | H | H | H | H | pic | |
| 1'-242X | Pd | 1 | 1' | Ph | H | PA1 | H | H | H | H | H | H | H | acac | |
| 1'-242Y | Pd | 0 | 1' | Ph | H | PA1 | H | H | H | H | H | H | H | — | — |
| 1'-243 | Pd | 1 | 1' | Ph | H | H | PA2 | H | H | H | H | H | H | pic | |
| 1'-243X | Pd | 1 | 1' | Ph | H | H | PA2 | H | H | H | H | H | H | acac | |
| 1'-243Y | Pd | 0 | 1' | Ph | H | H | PA2 | H | H | H | H | H | H | — | — |
| 1'-244 | Pd | 1 | 1' | Ph | H | PA2 | H | H | H | H | H | H | H | pic | |
| 1'-244X | Pd | 1 | 1' | Ph | H | PA2 | H | H | H | H | H | H | H | acac | |
| 1'-244Y | Pd | 0 | 1' | Ph | H | PA2 | H | H | H | H | H | H | H | — | — |
| 1'-245 | Pd | 1 | 1' | Ph | H | H | EA1 | H | H | H | H | H | H | pic | |
| 1'-245X | Pd | 1 | 1' | Ph | H | H | EA1 | H | H | H | H | H | H | acac | |
| 1'-245Y | Pd | 0 | 1' | Ph | H | H | EA1 | H | H | H | H | H | H | — | — |
| 1'-246 | Pd | 1 | 1' | Ph | H | EA2 | H | H | H | H | H | H | H | pic | |
| 1'-246X | Pd | 1 | 1' | Ph | H | EA2 | H | H | H | H | H | H | H | acac | |
| 1'-246Y | Pd | 0 | 1' | Ph | H | EA2 | H | H | H | H | H | H | H | — | — |
| 1'-247 | Pd | 1 | 1' | Ph | H | H | ME | H | H | H | H | H | H | pic | |
| 1'-247X | Pd | 1 | 1' | Ph | H | H | ME | H | H | H | H | H | H | acac | |
| 1'-247Y | Pd | 0 | 1' | Ph | H | H | ME | H | H | H | H | H | H | — | — |
| 1'-248 | Pd | 1 | 1' | Ph | H | ME | H | H | H | H | H | H | H | pic | |
| 1'-248X | Pd | 1 | 1' | Ph | H | ME | H | H | H | H | H | H | H | acac | |
| 1'-248Y | Pd | 0 | 1' | Ph | H | ME | H | H | H | H | H | H | H | — | — |
| 1'-249 | Pd | 1 | 1' | Ph | H | H | AT | H | H | H | H | H | H | pic | |
| 1'-249X | Pd | 1 | 1' | Ph | H | H | AT | H | H | H | H | H | H | acac | |
| 1'-249Y | Pd | 0 | 1' | Ph | H | H | AT | H | H | H | H | H | H | — | — |
| 1'-250 | Pd | 1 | 1' | Ph | H | AT | H | H | H | H | H | H | H | pic | |
| 1'-250X | Pd | 1 | 1' | Ph | H | AT | H | H | H | H | H | H | H | acac | |
| 1'-250Y | Pd | 0 | 1' | Ph | H | AT | H | H | H | H | H | H | H | — | — |
| 1'-251 | Pd | 1 | 1' | Ph | H | H | MES1 | H | H | H | H | H | H | pic | |
| 1'-251X | Pd | 1 | 1' | Ph | H | H | MES1 | H | H | H | H | H | H | acac | |
| 1'-251Y | Pd | 0 | 1' | Ph | H | H | MES1 | H | H | H | H | H | H | — | — |
| 1'-252 | Pd | 1 | 1' | Ph | H | MES1 | H | H | H | H | H | H | H | pic | |
| 1'-252X | Pd | 1 | 1' | Ph | H | MES1 | H | H | H | H | H | H | H | acac | |
| 1'-252Y | Pd | 0 | 1' | Ph | H | MES1 | H | H | H | H | H | H | H | — | — |
| 1'-253 | Pd | 1 | 1' | Ph | H | H | MES2 | H | H | H | H | H | H | pic | |
| 1'-253X | Pd | 1 | 1' | Ph | H | H | MES2 | H | H | H | H | H | H | acac | |
| 1'-253Y | Pd | 0 | 1' | Ph | H | H | MES2 | H | H | H | H | H | H | — | — |
| 1'-254 | Pd | 1 | 1' | Ph | H | MES2 | H | H | H | H | H | H | H | pic | |
| 1'-254X | Pd | 1 | 1' | Ph | H | MES2 | H | H | H | H | H | H | H | acac | |
| 1'-254Y | Pd | 0 | 1' | Ph | H | MES2 | H | H | H | H | H | H | H | — | — |
| 1'-255 | Pd | 1 | 1' | Ph | H | H | PS1 | H | H | H | H | H | H | pic | |
| 1'-255X | Pd | 1 | 1' | Ph | H | H | PS1 | H | H | H | H | H | H | acac | |
| 1'-255Y | Pd | 0 | 1' | Ph | H | H | PS1 | H | H | H | H | H | H | — | — |
| 1'-256 | Pd | 1 | 1' | Ph | H | PS1 | H | H | H | H | H | H | H | pic | |
| 1'-256X | Pd | 1 | 1' | Ph | H | PS1 | H | H | H | H | H | H | H | acac | |
| 1'-256Y | Pd | 0 | 1' | Ph | H | PS1 | H | H | H | H | H | H | H | — | — |

TABLE 43-continued

| No. | M | m | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 1'-257 | Pd | 1 | 1' | | Ph | H | H | | PS2 | | H | H | H | H | H | pic |
| 1'-257X | Pd | 1 | 1' | | Ph | H | H | | PS2 | | H | H | H | H | H | acac |
| 1'-257Y | Pd | 0 | 1' | | Ph | H | H | | PS2 | | H | H | H | H | H | — | — |
| 1'-258 | Pd | 1 | 1' | | Ph | H | | PS2 | | H | H | H | H | H | H | pic |
| 1'-258X | Pd | 1 | 1' | | Ph | H | | PS2 | | H | H | H | H | H | H | acac |
| 1'-258Y | Pd | 0 | 1' | | Ph | H | | PS2 | | H | H | H | H | H | H | — | — |
| 1'-259 | Pd | 1 | 1' | | Ph | H | H | | BAL1 | | H | H | H | H | H | pic |
| 1'-259X | Pd | 1 | 1' | | Ph | H | H | | BAL1 | | H | H | H | H | H | acac |
| 1'-259Y | Pd | 0 | 1' | | Ph | H | H | | BAL1 | | H | H | H | H | H | — | — |
| 1'-260 | Pd | 1 | 1' | | Ph | H | | BAL1 | | H | H | H | H | H | H | pic |
| 1'-260X | Pd | 1 | 1' | | Ph | H | | BAL1 | | H | H | H | H | H | H | acac |
| 1'-260Y | Pd | 0 | 1' | | Ph | H | | BAL1 | | H | H | H | H | H | H | — | — |
| 1'-261 | Pd | 1 | 1' | | Ph | H | H | | BAL2 | | H | H | H | H | H | pic |
| 1'-261X | Pd | 1 | 1' | | Ph | H | H | | BAL2 | | H | H | H | H | H | acac |
| 1'-261Y | Pd | 0 | 1' | | Ph | H | H | | BAL2 | | H | H | H | H | H | — | — |
| 1'-262 | Pd | 1 | 1' | | Ph | H | | BAL2 | | H | H | H | H | H | H | pic |
| 1'-262X | Pd | 1 | 1' | | Ph | H | | BAL2 | | H | H | H | H | H | H | acac |
| 1'-262Y | Pd | 0 | 1' | | Ph | H | | BAL2 | | H | H | H | H | H | H | — | — |
| 1'-263 | Pd | 1 | 1' | | Ph | H | H | | MEK1 | | H | H | H | H | H | pic |
| 1'-263X | Pd | 1 | 1' | | Ph | H | H | | MEK1 | | H | H | H | H | H | acac |
| 1'-263Y | Pd | 0 | 1' | | Ph | H | H | | MEK1 | | H | H | H | H | H | — | — |
| 1'-264 | Pd | 1 | 1' | | Ph | H | | MEK1 | | H | H | H | H | H | H | pic |
| 1'-264X | Pd | 1 | 1' | | Ph | H | | MEK1 | | H | H | H | H | H | H | acac |
| 1'-264Y | Pd | 0 | 1' | | Ph | H | | MEK1 | | H | H | H | H | H | H | — | — |
| 1'-265 | Pd | 1 | 1' | | Ph | H | H | | MEK2 | | H | H | H | H | H | pic |
| 1'-265X | Pd | 1 | 1' | | Ph | H | H | | MEK2 | | H | H | H | H | H | acac |
| 1'-265Y | Pd | 0 | 1' | | Ph | H | H | | MEK2 | | H | H | H | H | H | — | — |
| 1'-266 | Pd | 1 | 1' | | Ph | H | | MEK2 | | H | H | H | H | H | H | pic |
| 1'-266X | Pd | 1 | 1' | | Ph | H | | MEK2 | | H | H | H | H | H | H | acac |
| 1'-266Y | Pd | 0 | 1' | | Ph | H | | MEK2 | | H | H | H | H | H | H | — | — |
| 1'-267 | Pd | 1 | 1' | | Ph | H | H | | PAL1 | | H | H | H | H | H | pic |
| 1'-267X | Pd | 1 | 1' | | Ph | H | H | | PAL1 | | H | H | H | H | H | acac |
| 1'-267Y | Pd | 0 | 1' | | Ph | H | H | | PAL1 | | H | H | H | H | H | — | — |
| 1'-268 | Pd | 1 | 1' | | Ph | H | | PAL1 | | H | H | H | H | H | H | pic |
| 1'-268X | Pd | 1 | 1' | | Ph | H | | PAL1 | | H | H | H | H | H | H | acac |
| 1'-268Y | Pd | 0 | 1' | | Ph | H | | PAL1 | | H | H | H | H | H | H | — | — |
| 1'-269 | Pd | 1 | 1' | | Ph | H | H | | PAL2 | | H | H | H | H | H | pic |
| 1'-269X | Pd | 1 | 1' | | Ph | H | H | | PAL2 | | H | H | H | H | H | acac |
| 1'-269Y | Pd | 0 | 1' | | Ph | H | H | | PAL2 | | H | H | H | H | H | — | — |
| 1'-270 | Pd | 1 | 1' | | Ph | H | | PAL2 | | H | H | H | H | H | H | pic |
| 1'-270X | Pd | 1 | 1' | | Ph | H | | PAL2 | | H | H | H | H | H | H | acac |
| 1'-270Y | Pd | 0 | 1' | | Ph | H | | PAL2 | | H | H | H | H | H | H | — | — |
| 1'-271 | Pd | 1 | 1' | | Ph | H | H | | MMK | | H | H | H | H | H | pic |
| 1'-271X | Pd | 1 | 1' | | Ph | H | H | | MMK | | H | H | H | H | H | acac |
| 1'-271Y | Pd | 0 | 1' | | Ph | H | H | | MMK | | H | H | H | H | H | — | — |
| 1'-272 | Pd | 1 | 1' | | Ph | H | | MMK | | H | H | H | H | H | H | pic |
| 1'-272X | Pd | 1 | 1' | | Ph | H | | MMK | | H | H | H | H | H | H | acac |
| 1'-272Y | Pd | 0 | 1' | | Ph | H | | MMK | | H | H | H | H | H | H | — | — |
| 1'-273 | Pd | 1 | 1' | | Ph | H | H | | EES1 | | H | H | H | H | H | pic |
| 1'-273X | Pd | 1 | 1' | | Ph | H | H | | EES1 | | H | H | H | H | H | acac |
| 1'-273Y | Pd | 0 | 1' | | Ph | H | H | | EES1 | | H | H | H | H | H | — | — |
| 1'-274 | Pd | 1 | 1' | | Ph | H | | EES2 | | H | H | H | H | H | H | pic |
| 1'-274X | Pd | 1 | 1' | | Ph | H | | EES2 | | H | H | H | H | H | H | acac |
| 1'-274Y | Pd | 0 | 1' | | Ph | H | | EES2 | | H | H | H | H | H | H | — | — |
| 1'-275 | Pd | 1 | 1' | | Ph | H | H | | PAE1 | | H | H | H | H | H | pic |
| 1'-275X | Pd | 1 | 1' | | Ph | H | H | | PAE1 | | H | H | H | H | H | acac |
| 1'-275Y | Pd | 0 | 1' | | Ph | H | H | | PAE1 | | H | H | H | H | H | — | — |
| 1'-276 | Pd | 1 | 1' | | Ph | H | | PAE2 | | H | H | H | H | H | H | pic |
| 1'-276X | Pd | 1 | 1' | | Ph | H | | PAE2 | | H | H | H | H | H | H | acac |
| 1'-276Y | Pd | 0 | 1' | | Ph | H | | PAE2 | | H | H | H | H | H | H | — | — |
| 1'-277 | Pd | 1 | 1' | | Ph | H | H | | AME1 | | H | H | H | H | H | pic |
| 1'-277X | Pd | 1 | 1' | | Ph | H | H | | AME1 | | H | H | H | H | H | acac |
| 1'-277Y | Pd | 0 | 1' | | Ph | H | H | | AME1 | | H | H | H | H | H | — | — |
| 1'-278 | Pd | 1 | 1' | | Ph | H | | AME1 | | H | H | H | H | H | H | pic |
| 1'-278X | Pd | 1 | 1' | | Ph | H | | AME1 | | H | H | H | H | H | H | acac |
| 1'-278Y | Pd | 0 | 1' | | Ph | H | | AME1 | | H | H | H | H | H | H | — | — |
| 1'-279 | Pd | 1 | 1' | | Ph | H | H | | AME2 | | H | H | H | H | H | pic |
| 1'-279X | Pd | 1 | 1' | | Ph | H | H | | AME2 | | H | H | H | H | H | acac |
| 1'-279Y | Pd | 0 | 1' | | Ph | H | H | | AME2 | | H | H | H | H | H | — | — |
| 1'-280 | Pd | 1 | 1' | | Ph | H | | AME2 | | H | H | H | H | H | H | pic |
| 1'-280X | Pd | 1 | 1' | | Ph | H | | AME2 | | H | H | H | H | H | H | acac |
| 1'-280Y | Pd | 0 | 1' | | Ph | H | | AME2 | | H | H | H | H | H | H | — | — |
| 1'-281 | Pd | 1 | 1' | | Ph | H | H | | EAE1 | | H | H | H | H | H | pic |
| 1'-281X | Pd | 1 | 1' | | Ph | H | H | | EAE1 | | H | H | H | H | H | acac |
| 1'-281Y | Pd | 0 | 1' | | Ph | H | H | | EAE1 | | H | H | H | H | H | — | — |
| 1'-282 | Pd | 1 | 1' | | Ph | H | | EAE1 | | H | H | H | H | H | H | pic |
| 1'-282X | Pd | 1 | 1' | | Ph | H | | EAE1 | | H | H | H | H | H | H | acac |

TABLE 43-continued

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 1'-282Y | Pd | 0 | 1' | Ph | H | | EAE1 | H | H | H | H | H | H | — |
| 1'-283 | Pd | 1 | 1' | Ph | H | H | | EAE2 | H | H | H | H | H | pic |
| 1'-283X | Pd | 1 | 1' | Ph | H | H | | EAE2 | H | H | H | H | H | acac |
| 1'-283Y | Pd | 0 | 1' | Ph | H | H | | EAE2 | H | H | H | H | H | — |
| 1'-284 | Pd | 1 | 1' | Ph | H | | EAE2 | H | H | H | H | H | H | pic |
| 1'-284X | Pd | 1 | 1' | Ph | H | | EAE2 | H | H | H | H | H | H | acac |
| 1'-284Y | Pd | 0 | 1' | Ph | H | | EAE2 | H | H | H | H | H | H | — |
| 1'-285 | Pd | 1 | 1' | Ph | H | H | | AAE1 | H | H | H | H | H | pic |
| 1'-285X | Pd | 1 | 1' | Ph | H | H | | AAE1 | H | H | H | H | H | acac |
| 1'-285Y | Pd | 0 | 1' | Ph | H | H | | AAE1 | H | H | H | H | H | — |
| 1'-286 | Pd | 1 | 1' | Ph | H | | AAE1 | H | H | H | H | H | H | pic |
| 1'-286X | Pd | 1 | 1' | Ph | H | | AAE1 | H | H | H | H | H | H | acac |
| 1'-286Y | Pd | 0 | 1' | Ph | H | | AAE1 | H | H | H | H | H | H | — |
| 1'-287 | Pd | 1 | 1' | Ph | H | H | | AAE2 | H | H | H | H | H | pic |
| 1'-287X | Pd | 1 | 1' | Ph | H | H | | AAE2 | H | H | H | H | H | acac |
| 1'-287Y | Pd | 0 | 1' | Ph | H | H | | AAE2 | H | H | H | H | H | — |
| 1'-288 | Pd | 1 | 1' | Ph | H | | AAE2 | H | H | H | H | H | H | pic |
| 1'-288X | Pd | 1 | 1' | Ph | H | | AAE2 | H | H | H | H | H | H | acac |
| 1'-288Y | Pd | 0 | 1' | Ph | H | | AAE2 | H | H | H | H | H | H | — |
| 1'-289 | Pd | 1 | 1' | Ph | H | H | | PME1 | H | H | H | H | H | pic |
| 1'-289X | Pd | 1 | 1' | Ph | H | H | | PME1 | H | H | H | H | H | acac |
| 1'-289Y | Pd | 0 | 1' | Ph | H | H | | PME1 | H | H | H | H | H | — |
| 1'-290 | Pd | 1 | 1' | Ph | H | | PME1 | H | H | H | H | H | H | pic |
| 1'-290X | Pd | 1 | 1' | Ph | H | | PME1 | H | H | H | H | H | H | acac |
| 1'-290Y | Pd | 0 | 1' | Ph | H | | PME1 | H | H | H | H | H | H | — |
| 1'-291 | Pd | 1 | 1' | Ph | H | H | | PME2 | H | H | H | H | H | pic |
| 1'-291X | Pd | 1 | 1' | Ph | H | H | | PME2 | H | H | H | H | H | acac |
| 1'-291Y | Pd | 0 | 1' | Ph | H | H | | PME2 | H | H | H | H | H | — |
| 1'-292 | Pd | 1 | 1' | Ph | H | | PME2 | H | H | H | H | H | H | pic |
| 1'-292X | Pd | 1 | 1' | Ph | H | | PME2 | H | H | H | H | H | H | acac |
| 1'-292Y | Pd | 0 | 1' | Ph | H | | PME2 | H | H | H | H | H | H | — |
| 1'-293 | Pd | 1 | 1' | Ph | H | H | | MET1 | H | H | H | H | H | pic |
| 1'-293X | Pd | 1 | 1' | Ph | H | H | | MET1 | H | H | H | H | H | acac |
| 1'-293Y | Pd | 0 | 1' | Ph | H | H | | MET1 | H | H | H | H | H | — |
| 1'-294 | Pd | 1 | 1' | Ph | H | | MET1 | H | H | H | H | H | H | pic |
| 1'-294X | Pd | 1 | 1' | Ph | H | | MET1 | H | H | H | H | H | H | acac |
| 1'-294Y | Pd | 0 | 1' | Ph | H | | MET1 | H | H | H | H | H | H | — |
| 1'-295 | Pd | 1 | 1' | Ph | H | H | | MET2 | H | H | H | H | H | pic |
| 1'-295X | Pd | 1 | 1' | Ph | H | H | | MET2 | H | H | H | H | H | acac |
| 1'-295Y | Pd | 0 | 1' | Ph | H | H | | MET2 | H | H | H | H | H | — |
| 1'-296 | Pd | 1 | 1' | Ph | H | | MET2 | H | H | H | H | H | H | pic |
| 1'-296X | Pd | 1 | 1' | Ph | H | | MET2 | H | H | H | H | H | H | acac |
| 1'-296Y | Pd | 0 | 1' | Ph | H | | MET2 | H | H | H | H | H | H | — |
| 1'-297 | Pd | 1 | 1' | Ph | H | H | | EE1 | H | H | H | H | H | pic |
| 1'-297X | Pd | 1 | 1' | Ph | H | H | | EE1 | H | H | H | H | H | acac |
| 1'-297Y | Pd | 0 | 1' | Ph | H | H | | EE1 | H | H | H | H | H | — |
| 1'-298 | Pd | 1 | 1' | Ph | H | | EE1 | H | H | H | H | H | H | pic |
| 1'-298X | Pd | 1 | 1' | Ph | H | | EE1 | H | H | H | H | H | H | acac |
| 1'-298Y | Pd | 0 | 1' | Ph | H | | EE1 | H | H | H | H | H | H | — |
| 1'-299 | Pd | 1 | 1' | Ph | H | H | | EE2 | H | H | H | H | H | pic |
| 1'-299X | Pd | 1 | 1' | Ph | H | H | | EE2 | H | H | H | H | H | acac |
| 1'-299Y | Pd | 0 | 1' | Ph | H | H | | EE2 | H | H | H | H | H | — |
| 1'-300 | Pd | 1 | 1' | Ph | H | | EE2 | H | H | H | H | H | H | pic |
| 1'-300X | Pd | 1 | 1' | Ph | H | | EE2 | H | H | H | H | H | H | acac |
| 1'-300Y | Pd | 0 | 1' | Ph | H | | EE2 | H | H | H | H | H | H | — |
| 1'-301 | Pd | 1 | 1' | Ph | H | H | | MS1 | H | H | H | H | H | pic |
| 1'-301X | Pd | 1 | 1' | Ph | H | H | | MS1 | H | H | H | H | H | acac |
| 1'-301Y | Pd | 0 | 1' | Ph | H | H | | MS1 | H | H | H | H | H | — |
| 1'-302 | Pd | 1 | 1' | Ph | H | | MS1 | H | H | H | H | H | H | pic |
| 1'-302X | Pd | 1 | 1' | Ph | H | | MS1 | H | H | H | H | H | H | acac |
| 1'-302Y | Pd | 0 | 1' | Ph | H | | MS1 | H | H | H | H | H | H | — |
| 1'-303 | Pd | 1 | 1' | Ph | H | H | | MS2 | H | H | H | H | H | pic |
| 1'-303X | Pd | 1 | 1' | Ph | H | H | | MS2 | H | H | H | H | H | acac |
| 1'-303Y | Pd | 0 | 1' | Ph | H | H | | MS2 | H | H | H | H | H | — |
| 1'-304 | Pd | 1 | 1' | Ph | H | | MS2 | H | H | H | H | H | H | pic |
| 1'-304X | Pd | 1 | 1' | Ph | H | | MS2 | H | H | H | H | H | H | acac |
| 1'-304Y | Pd | 0 | 1' | Ph | H | | MS2 | H | H | H | H | H | H | — |

TABLE 44

| No. | M | m | BSS | SS G | T¹ | T² | T³ | T⁴ | T⁵ | T⁶ | T⁷ | T⁸ | T⁹ | L¹ L² |
|---|---|---|---|---|---|---|---|---|---|---|---|---|---|---|
| 2'-187 | Pd | 1 | 2' | Ph | H | H | H | H | H | H | H | H | H | pic |
| 2'-187X | Pd | 1 | 2' | Ph | H | H | H | H | H | H | H | H | H | acac |

TABLE 44-continued

| No. | M | m | BSS | SS G | $T^1$ | $T^2$ | $T^3$ | $T^4$ | $T^5$ | $T^6$ | $T^7$ | $T^8$ | $T^9$ | $L^1$ $L^2$ |
|---|---|---|---|---|---|---|---|---|---|---|---|---|---|---|
| 2'-187Y | Pd | 0 | 2' | Ph | H | H | H | H | H | H | H | H | H | — — |
| 2'-188 | Pd | 1 | 2' | Ph | H | F | H | F | H | H | H | H | H | pic |
| 2'-188X | Pd | 1 | 2' | Ph | H | F | H | F | H | H | H | H | H | acac |
| 2'-188Y | Pd | 0 | 2' | Ph | H | F | H | F | H | H | H | H | H | — — |
| 2'-189 | Pd | 1 | 2' | Ph | F | H | H | F | H | H | H | H | H | pic |
| 2'-189X | Pd | 1 | 2' | Ph | F | H | H | F | H | H | H | H | H | acac |
| 2'-189Y | Pd | 0 | 2' | Ph | F | H | H | F | H | H | H | H | H | — — |
| 2'-190 | Pd | 1 | 2' | Ph | $CF_3$ | H | $CF_3$ | H | H | H | H | H | H | pic |
| 2'-190X | Pd | 1 | 2' | Ph | $CF_3$ | H | $CF_3$ | H | H | H | H | H | H | acac |
| 2'-190Y | Pd | 0 | 2' | Ph | $CF_3$ | H | $CF_3$ | H | H | H | H | H | H | — — |
| 2'-191 | Pd | 1 | 2' | Ph | H | F | $CF_3$ | H | H | H | H | H | H | pic |
| 2'-191X | Pd | 1 | 2' | Ph | H | F | $CF_3$ | H | H | H | H | H | H | acac |
| 2'-191Y | Pd | 0 | 2' | Ph | H | F | $CF_3$ | H | H | H | H | H | H | — — |
| 2'-192 | Pd | 1 | 2' | Ph | F | H | $CF_3$ | H | H | H | H | H | H | pic |
| 2'-192X | Pd | 1 | 2' | Ph | F | H | $CF_3$ | H | H | H | H | H | H | acac |
| 2'-192Y | Pd | 0 | 2' | Ph | F | H | $CF_3$ | H | H | H | H | H | H | — — |
| 2'-193 | Pd | 1 | 2' | Ph | F | F | F | F | H | H | H | H | H | pic |
| 2'-193X | Pd | 1 | 2' | Ph | F | F | F | F | H | H | H | H | H | acac |
| 2'-193Y | Pd | 0 | 2' | Ph | F | F | F | F | H | H | H | H | H | — — |
| 2'-194 | Pd | 1 | 2' | Ph | H | F | H | $CH_3$ | H | H | H | H | H | pic |
| 2'-194X | Pd | 1 | 2' | Ph | H | F | H | $CH_3$ | H | H | H | H | H | acac |
| 2'-194Y | Pd | 0 | 2' | Ph | H | F | H | $CH_3$ | H | H | H | H | H | — — |
| 2'-195 | Pd | 1 | 2' | Ph | H | F | H | $^tC_4H_9$ | H | H | H | H | H | pic |
| 2'-195X | Pd | 1 | 2' | Ph | H | F | H | $^tC_4H_9$ | H | H | H | H | H | acac |
| 2'-195Y | Pd | 0 | 2' | Ph | H | F | H | $^tC_4H_9$ | H | H | H | H | H | — — |
| 2'-196 | Pd | 1 | 2' | Ph | H | $CF_3$ | H | $CF_3$ | H | H | H | H | H | pic |
| 2'-196X | Pd | 1 | 2' | Ph | H | $CF_3$ | H | $CF_3$ | H | H | H | H | H | acac |
| 2'-196Y | Pd | 0 | 2' | Ph | H | $CF_3$ | H | $CF_3$ | H | H | H | H | H | — — |
| 2'-197 | Pd | 1 | 2' | Ph | $CF_3$ | H | H | $^tC_4H_9$ | H | H | H | H | H | pic |
| 2'-197X | Pd | 1 | 2' | Ph | $CF_3$ | H | H | $^tC_4H_9$ | H | H | H | H | H | acac |
| 2'-197Y | Pd | 0 | 2' | Ph | $CF_3$ | H | H | $^tC_4H_9$ | H | H | H | H | H | — — |
| 2'-198 | Pd | 1 | 2' | Ph | H | $CF_3$ | H | $^tC_4H_9$ | H | H | H | H | H | pic |
| 2'-198X | Pd | 1 | 2' | Ph | H | $CF_3$ | H | $^tC_4H_9$ | H | H | H | H | H | acac |
| 2'-198Y | Pd | 0 | 2' | Ph | H | $CF_3$ | H | $^tC_4H_9$ | H | H | H | H | H | — — |
| 2'-199 | Pd | 1 | 2' | Ph | H | $CF_3$ | H | $CH_3$ | H | H | H | H | H | pic |
| 2'-199X | Pd | 1 | 2' | Ph | H | $CF_3$ | H | $CH_3$ | H | H | H | H | H | acac |
| 2'-199Y | Pd | 0 | 2' | Ph | H | $CF_3$ | H | $CH_3$ | H | H | H | H | H | — — |
| 2'-200 | Pd | 1 | 2' | Ph | H | $CF_3$ | $CF_3$ | H | H | H | H | H | H | pic |
| 2'-200X | Pd | 1 | 2' | Ph | H | $CF_3$ | $CF_3$ | H | H | H | H | H | H | acac |
| 2'-200Y | Pd | 0 | 2' | Ph | H | $CF_3$ | $CF_3$ | H | H | H | H | H | H | — — |
| 2'-201 | Pd | 1 | 2' | Ph | H | H | $NO_2$ | H | H | H | H | H | H | pic |
| 2'-201X | Pd | 1 | 2' | Ph | H | H | $NO_2$ | H | H | H | H | H | H | acac |
| 2'-201Y | Pd | 0 | 2' | Ph | H | H | $NO_2$ | H | H | H | H | H | H | — — |
| 2'-202 | Pd | 1 | 2' | Ph | F | H | $NO_2$ | H | H | H | H | H | H | pic |
| 2'-202X | Pd | 1 | 2' | Ph | F | H | $NO_2$ | H | H | H | H | H | H | acac |
| 2'-202Y | Pd | 0 | 2' | Ph | F | H | $NO_2$ | H | H | H | H | H | H | — — |
| 2'-203 | Pd | 1 | 2' | Ph | F | H | $NO_2$ | F | H | H | H | H | H | pic |
| 2'-203X | Pd | 1 | 2' | Ph | F | H | $NO_2$ | F | H | H | H | H | H | acac |
| 2'-203Y | Pd | 0 | 2' | Ph | F | H | $NO_2$ | F | H | H | H | H | H | — — |
| 2'-204 | Pd | 1 | 2' | Ph | H | $NO_2$ | H | $NO_2$ | H | H | H | H | H | pic |
| 2'-204X | Pd | 1 | 2' | Ph | H | $NO_2$ | H | $NO_2$ | H | H | H | H | H | acac |
| 2'-204Y | Pd | 0 | 2' | Ph | H | $NO_2$ | H | $NO_2$ | H | H | H | H | H | — — |
| 2'-205 | Pd | 1 | 2' | Ph | $NO_2$ | H | H | $NO_2$ | H | H | H | H | H | pic |
| 2'-205X | Pd | 1 | 2' | Ph | $NO_2$ | H | H | $NO_2$ | H | H | H | H | H | acac |
| 2'-205Y | Pd | 0 | 2' | Ph | $NO_2$ | H | H | $NO_2$ | H | H | H | H | H | — — |
| 2'-206 | Pd | 1 | 2' | Ph | H | H | $CF_3$ | H | H | H | H | H | H | pic |
| 2'-206X | Pd | 1 | 2' | Ph | H | H | $CF_3$ | H | H | H | H | H | H | acac |
| 2'-206Y | Pd | 0 | 2' | Ph | H | H | $CF_3$ | H | H | H | H | H | H | — — |
| 2'-207 | Pd | 1 | 2' | Ph | H | Cl | $CF_3$ | H | H | H | H | H | H | pic |
| 2'-207X | Pd | 1 | 2' | Ph | H | Cl | $CF_3$ | H | H | H | H | H | H | acac |
| 2'-207Y | Pd | 0 | 2' | Ph | H | Cl | $CF_3$ | H | H | H | H | H | H | — — |
| 2'-208 | Pd | 1 | 2' | Ph | H | $NO_2$ | H | H | H | H | H | H | H | pic |
| 2'-208X | Pd | 1 | 2' | Ph | H | $NO_2$ | H | H | H | H | H | H | H | acac |
| 2'-208Y | Pd | 0 | 2' | Ph | H | $NO_2$ | H | H | H | H | H | H | H | — — |
| 2'-209 | Pd | 1 | 2' | Ph | H | $CF_3$ | H | H | H | H | H | H | H | pic |
| 2'-209X | Pd | 1 | 2 | Ph | H | $CF_3$ | H | H | H | H | H | H | H | acac |
| 2'-209Y | Pd | 0 | 2' | Ph | H | $CF_3$ | H | H | H | H | H | H | H | — — |
| 2'-210 | Pd | 1 | 2' | Ph | H | $NO_2$ | H | $CH_3$ | H | H | H | H | H | pic |
| 2'-210X | Pd | 1 | 2' | Ph | H | $NO_2$ | H | $CH_3$ | H | H | H | H | H | acac |
| 2'-210Y | Pd | 0 | 2' | Ph | H | $NO_2$ | H | $CH_3$ | H | H | H | H | H | — — |
| 2'-211 | Pd | 1 | 2' | Ph | H | $NO_2$ | H | $^tC_4H_9$ | H | H | H | H | H | pic |
| 2'-211X | Pd | 1 | 2' | Ph | H | $NO_2$ | H | $^tC_4H_9$ | H | H | H | H | H | acac |
| 2'-211Y | Pd | 0 | 2' | Ph | H | $NO_2$ | H | $^tC_4H_9$ | H | H | H | H | H | — — |
| 2'-212 | Pd | 1 | 2' | Ph | H | H | $CH_3O$ | H | H | H | H | H | H | pic |
| 2'-212X | Pd | 1 | 2' | Ph | H | H | $CH_3O$ | H | H | H | H | H | H | acac |
| 2'-212Y | Pd | 0 | 2' | Ph | H | H | $CH_3O$ | H | H | H | H | H | H | — — |
| 2'-213 | Pd | 1 | 2' | Ph | H | $CH_3O$ | H | H | H | H | H | H | H | pic |

TABLE 44-continued

| No. | M | m | BSS | SS G | $T^1$ | $T^2$ | $T^3$ | $T^4$ | $T^5$ | $T^6$ | $T^7$ | $T^8$ | $T^9$ | $L^1$ $L^2$ |
|---|---|---|---|---|---|---|---|---|---|---|---|---|---|---|
| 2'-213X | Pd | 1 | 2' | Ph | H | CH$_3$O | H | H | H | H | H | H | H | acac |
| 2'-213Y | Pd | 0 | 2' | Ph | H | CH$_3$O | H | H | H | H | H | H | H | — — |
| 2'-214 | Pd | 1 | 2' | Ph | H | CH$_3$O | H | CH$_3$ | H | H | H | H | H | pic |
| 2'-214X | Pd | 1 | 2' | Ph | H | CH$_3$O | H | CH$_3$ | H | H | H | H | H | acac |
| 2'-214Y | Pd | 0 | 2' | Ph | H | CH$_3$O | H | CH$_3$ | H | H | H | H | H | — — |
| 2'-215 | Pd | 1 | 2' | Ph | H | CH$_3$O | H | $^tC_4H_9$ | H | H | H | H | H | pic |
| 2'-215X | Pd | 1 | 2' | Ph | H | CH$_3$O | H | $^tC_4H_9$ | H | H | H | H | H | acac |
| 2'-215Y | Pd | 0 | 2' | Ph | H | CH$_3$O | H | $^tC_4H_9$ | H | H | H | H | H | — — |
| 2'-216 | Pd | 1 | 2' | Ph | H | H | H | H | $^tC_4H_9$ | H | H | H | H | pic |
| 2'-216X | Pd | 1 | 2' | Ph | H | H | H | H | $^tC_4H_9$ | H | H | H | H | acac |
| 2'-216Y | Pd | 0 | 2' | Ph | H | H | H | H | $^tC_4H_9$ | H | H | H | H | — — |
| 2'-217 | Pd | 1 | 2' | Ph | H | F | H | F | $^tC_4H_9$ | H | H | H | H | pic |
| 2'-217X | Pd | 1 | 2' | Ph | H | F | H | F | $^tC_4H_9$ | H | H | H | H | acac |
| 2'-217Y | Pd | 0 | 2' | Ph | H | F | H | F | $^tC_4H_9$ | H | H | H | H | — — |
| 2'-218 | Pd | 1 | 2' | Ph | CF$_3$ | H | CF$_3$ | H | $^tC_4H_9$ | H | H | H | H | pic |
| 2'-218X | Pd | 1 | 2' | Ph | CF$_3$ | H | CF$_3$ | H | $^tC_4H_9$ | H | H | H | H | acac |
| 2'-218Y | Pd | 0 | 2' | Ph | CF$_3$ | H | CF$_3$ | H | $^tC_4H_9$ | H | H | H | H | — — |
| 2'-219 | Pd | 1 | 2' | Ph | H | CF$_3$ | H | CH$_3$ | $^tC_4H_9$ | H | H | H | H | pic |
| 2'-219X | Pd | 1 | 2' | Ph | H | CF$_3$ | H | CH$_3$ | $^tC_4H_9$ | H | H | H | H | acac |
| 2'-219Y | Pd | 0 | 2' | Ph | H | CF$_3$ | H | CH$_3$ | $^tC_4H_9$ | H | H | H | H | — — |
| 2'-220 | Pd | 1 | 2' | Ph | H | F | H | F | H | H | H | CH$_3$ | H | pic |
| 2'-220X | Pd | 1 | 2' | Ph | H | F | H | F | H | H | H | CH$_3$ | H | acac |
| 2'-220Y | Pd | 0 | 2' | Ph | H | F | H | F | H | H | H | CH$_3$ | H | — — |
| 2'-221 | Pd | 1 | 2' | Ph | CF$_3$ | H | CF$_3$ | H | H | H | H | CH$_3$ | H | pic |
| 2'-221X | Pd | 1 | 2' | Ph | CF$_3$ | H | CF$_3$ | H | H | H | H | CH$_3$ | H | acac |
| 2'-221Y | Pd | 0 | 2' | Ph | CF$_3$ | H | CF$_3$ | H | H | H | H | CH$_3$ | H | — — |
| 2'-222 | Pd | 1 | 2' | Ph | H | Si(CH$_3$)$_3$ | H | H | H | H | H | H | H | pic |
| 2'-222X | Pd | 1 | 2' | Ph | H | Si(CH$_3$)$_3$ | H | H | H | H | H | H | H | acac |
| 2'-222Y | Pd | 0 | 2' | Ph | H | Si(CH$_3$)$_3$ | H | H | H | H | H | H | H | — — |
| 2'-223 | Pd | 1 | 2' | Ph | H | H | Si(CH$_3$)$_3$ | H | H | H | H | H | H | pic |
| 2'-223X | Pd | 1 | 2' | Ph | H | H | Si(CH$_3$)$_3$ | H | H | H | H | H | H | acac |
| 2'-223Y | Pd | 0 | 2' | Ph | H | H | Si(CH$_3$)$_3$ | H | H | H | H | H | H | — — |
| 2'-224 | Pd | 1 | 2' | Ph | H | H | H | Si(CH$_3$)$_3$ | H | H | H | H | H | pic |
| 2'-224X | Pd | 1 | 2' | Ph | H | H | H | Si(CH$_3$)$_3$ | H | H | H | H | H | acac |
| 2'-224Y | Pd | 0 | 2' | Ph | H | H | H | Si(CH$_3$)$_3$ | H | H | H | H | H | — — |
| 2'-225 | Pd | 1 | 2' | Ph | H | F | H | Si(CH$_3$)$_3$ | H | H | H | H | H | pic |
| 2'-225X | Pd | 1 | 2' | Ph | H | F | H | Si(CH$_3$)$_3$ | H | H | H | H | H | acac |
| 2'-225Y | Pd | 0 | 2' | Ph | H | F | H | Si(CH$_3$)$_3$ | H | H | H | H | H | — — |
| 2'-226 | Pd | 1 | 2' | Ph | H | CF$_3$ | H | Si(CH$_3$)$_3$ | H | H | H | H | H | pic |
| 2'-226X | Pd | 1 | 2' | Ph | H | CF$_3$ | H | Si(CH$_3$)$_3$ | H | H | H | H | H | acac |
| 2'-226Y | Pd | 0 | 2' | Ph | H | CF$_3$ | H | Si(CH$_3$)$_3$ | H | H | H | H | H | — — |
| 2'-227 | Pd | 1 | 2' | Ph | H | Si(CH$_3$)$_3$ | H | F | H | H | H | H | H | pic |
| 2'-227X | Pd | 1 | 2' | Ph | H | Si(CH$_3$)$_3$ | H | F | H | H | H | H | H | acac |
| 2'-227Y | Pd | 0 | 2' | Ph | H | Si(CH$_3$)$_3$ | H | F | H | H | H | H | H | — — |
| 2'-228 | Pd | 1 | 2' | Ph | H | Si(CH$_3$)$_3$ | H | CF$_3$ | H | H | H | H | H | pic |
| 2'-228X | Pd | 1 | 2' | Ph | H | Si(CH$_3$)$_3$ | H | CF$_3$ | H | H | H | H | H | acac |
| 2'-228Y | Pd | 0 | 2' | Ph | H | Si(CH$_3$)$_3$ | H | CF$_3$ | H | H | H | H | H | — — |
| 2'-229 | Pd | 1 | 2' | Ph | Si(CH$_3$)$_3$ | H | Si(CH$_3$)$_3$ | H | H | H | H | H | H | pic |
| 2'-229X | Pd | 1 | 2' | Ph | Si(CH$_3$)$_4$ | H | Si(CH$_3$)$_4$ | H | H | H | H | H | H | acac |
| 2'-229Y | Pd | 0 | 2' | Ph | Si(CH$_3$)$_5$ | H | Si(CH$_3$)$_6$ | H | H | H | H | H | H | — — |
| 2'-230 | Pd | 1 | 2' | Ph | H | H | H | COCH$_3$ | H | H | H | H | H | pic |
| 2'-230X | Pd | 1 | 2' | Ph | H | H | H | COCH$_3$ | H | H | H | H | H | acac |
| 2'-230Y | Pd | 0 | 2' | Ph | H | H | H | COCH$_3$ | H | H | H | H | H | — — |
| 2'-231 | Pd | 1 | 2' | Ph | H | H | COCH$_3$ | H | H | H | H | H | H | pic |
| 2'-231X | Pd | 1 | 2' | Ph | H | H | COCH$_3$ | H | H | H | H | H | H | acac |
| 2'-231Y | Pd | 0 | 2' | Ph | H | H | COCH$_3$ | H | H | H | H | H | H | — — |
| 2'-232 | Pd | 1 | 2' | Ph | H | COCH$_3$ | H | H | H | H | H | H | H | pic |
| 2'-232X | Pd | 1 | 2' | Ph | H | COCH$_3$ | H | H | H | H | H | H | H | acac |
| 2'-232Y | Pd | 0 | 2' | Ph | H | COCH$_3$ | H | H | H | H | H | H | H | — — |
| 2'-233 | Pd | 1 | 2' | Ph | H | H | BL | | H | H | H | H | H | pic |
| 2'-233X | Pd | 1 | 2' | Ph | H | H | BL | | H | H | H | H | H | acac |
| 2'-233Y | Pd | 0 | 2' | Ph | H | H | BL | | H | H | H | H | H | — — |
| 2'-234 | Pd | 1 | 2' | Ph | H | BL | | H | H | H | H | H | H | pic |
| 2'-234X | Pd | 1 | 2' | Ph | H | BL | | H | H | H | H | H | H | acac |
| 2'-234Y | Pd | 0 | 2' | Ph | H | BL | | H | H | H | H | H | H | — — |
| 2'-235 | Pd | 1 | 2' | Ph | H | H | PL | | H | H | H | H | H | pic |
| 2'-235X | Pd | 1 | 2' | Ph | H | H | PL | | H | H | H | H | H | acac |
| 2'-235Y | Pd | 0 | 2' | Ph | H | H | PL | | H | H | H | H | H | — — |
| 2'-236 | Pd | 1 | 2' | Ph | H | PL | | H | H | H | H | H | H | pic |
| 2'-236X | Pd | 1 | 2' | Ph | H | PL | | H | H | H | H | H | H | acac |
| 2'-236Y | Pd | 0 | 2' | Ph | H | PL | | H | H | H | H | H | H | — — |
| 2'-237 | Pd | 1 | 2' | Ph | H | H | | MEE1 | H | H | H | H | H | pic |
| 2'-237X | Pd | 1 | 2' | Ph | H | H | | MEE1 | H | H | H | H | H | acac |
| 2'-237Y | Pd | 0 | 2' | Ph | H | H | | MEE1 | H | H | H | H | H | — — |
| 2'-238 | Pd | 1 | 2' | Ph | H | | MEE1 | H | H | H | H | H | H | pic |
| 2'-238X | Pd | 1 | 2' | Ph | H | | MEE1 | H | H | H | H | H | H | acac |
| 2'-238Y | Pd | 0 | 2' | Ph | H | | MEE1 | H | H | H | H | H | H | — — |

TABLE 44-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 2'-239 | Pd | 1 | 2' | Ph | H | H | | MEE2 | H | H | H | H | H | pic | |
| 2'-239X | Pd | 1 | 2' | Ph | H | H | | MEE2 | H | H | H | H | H | acac | |
| 2'-239Y | Pd | 0 | 2' | Ph | H | H | | MEE2 | H | H | H | H | H | — | — |
| 2'-240 | Pd | 1 | 2' | Ph | H | | MEE2 | H | H | H | H | H | H | pic | |
| 2'-240X | Pd | 1 | 2' | Ph | H | | MEE2 | H | H | H | H | H | H | acac | |
| 2'-240Y | Pd | 0 | 2' | Ph | H | | MEE2 | H | H | H | H | H | H | — | — |
| 2'-241 | Pd | 1 | 2' | Ph | H | H | | PA1 | H | H | H | H | H | pic | |
| 2'-241X | Pd | 1 | 2' | Ph | H | H | | PA1 | H | H | H | H | H | acac | |
| 2'-241Y | Pd | 0 | 2' | Ph | H | H | | PA1 | H | H | H | H | H | — | — |
| 2'-242 | Pd | 1 | 2' | Ph | H | | PA1 | H | H | H | H | H | H | pic | |
| 2'-242X | Pd | 1 | 2' | Ph | H | | PA1 | H | H | H | H | H | H | acac | |
| 2'-242Y | Pd | 0 | 2' | Ph | H | | PA1 | H | H | H | H | H | H | — | — |
| 2'-243 | Pd | 1 | 2' | Ph | H | H | | PA2 | H | H | H | H | H | pic | |
| 2'-243X | Pd | 1 | 2' | Ph | H | H | | PA2 | H | H | H | H | H | acac | |
| 2'-243Y | Pd | 0 | 2' | Ph | H | H | | PA2 | H | H | H | H | H | — | — |
| 2'-244 | Pd | 1 | 2' | Ph | H | | PA2 | H | H | H | H | H | H | pic | |
| 2'-244X | Pd | 1 | 2' | Ph | H | | PA2 | H | H | H | H | H | H | acac | |
| 2'-244Y | Pd | 0 | 2' | Ph | H | | PA2 | H | H | H | H | H | H | — | — |
| 2'-245 | Pd | 1 | 2' | Ph | H | H | | EA1 | H | H | H | H | H | pic | |
| 2'-245X | Pd | 1 | 2' | Ph | H | H | | EA1 | H | H | H | H | H | acac | |
| 2'-245Y | Pd | 0 | 2' | Ph | H | H | | EA1 | H | H | H | H | H | — | — |
| 2'-246 | Pd | 1 | 2' | Ph | H | | EA2 | H | H | H | H | H | H | pic | |
| 2'-246X | Pd | 1 | 2' | Ph | H | | EA2 | H | H | H | H | H | H | acac | |
| 2'-246Y | Pd | 0 | 2' | Ph | H | | EA2 | H | H | H | H | H | H | — | — |
| 2'-247 | Pd | 1 | 2' | Ph | H | H | | ME | H | H | H | H | H | pic | |
| 2'-247X | Pd | 1 | 2' | Ph | H | H | | ME | H | H | H | H | H | acac | |
| 2'-247Y | Pd | 0 | 2' | Ph | H | H | | ME | H | H | H | H | H | — | — |
| 2'-248 | Pd | 1 | 2' | Ph | H | | ME | H | H | H | H | H | H | pic | |
| 2'-248X | Pd | 1 | 2' | Ph | H | | ME | H | H | H | H | H | H | acac | |
| 2'-248Y | Pd | 0 | 2' | Ph | H | | ME | H | H | H | H | H | H | — | — |
| 2'-249 | Pd | 1 | 2' | Ph | H | H | | AT | H | H | H | H | H | pic | |
| 2'-249X | Pd | 1 | 2' | Ph | H | H | | AT | H | H | H | H | H | acac | |
| 2'-249Y | Pd | 0 | 2' | Ph | H | H | | AT | H | H | H | H | H | — | — |
| 2'-250 | Pd | 1 | 2' | Ph | H | | AT | H | H | H | H | H | H | pic | |
| 2'-250X | Pd | 1 | 2' | Ph | H | | AT | H | H | H | H | H | H | acac | |
| 2'-250Y | Pd | 0 | 2' | Ph | H | | AT | H | H | H | H | H | H | — | — |
| 2'-251 | Pd | 1 | 2' | Ph | H | H | | MES1 | H | H | H | H | H | pic | |
| 2'-251X | Pd | 1 | 2' | Ph | H | H | | MES1 | H | H | H | H | H | acac | |
| 2'-251Y | Pd | 0 | 2' | Ph | H | H | | MES1 | H | H | H | H | H | — | — |
| 2'-252 | Pd | 1 | 2' | Ph | H | | MES1 | H | H | H | H | H | H | pic | |
| 2'-252X | Pd | 1 | 2' | Ph | H | | MES1 | H | H | H | H | H | H | acac | |
| 2'-252Y | Pd | 0 | 2' | Ph | H | | MES1 | H | H | H | H | H | H | — | — |
| 2'-253 | Pd | 1 | 2' | Ph | H | H | | MES2 | H | H | H | H | H | pic | |
| 2'-253X | Pd | 1 | 2' | Ph | H | H | | MES2 | H | H | H | H | H | acac | |
| 2'-253Y | Pd | 0 | 2' | Ph | H | H | | MES2 | H | H | H | H | H | — | — |
| 2'-254 | Pd | 1 | 2' | Ph | H | | MES2 | H | H | H | H | H | H | pic | |
| 2'-254X | Pd | 1 | 2' | Ph | H | | MES2 | H | H | H | H | H | H | acac | |
| 2'-254Y | Pd | 0 | 2' | Ph | H | | MES2 | H | H | H | H | H | H | — | — |
| 2'-255 | Pd | 1 | 2' | Ph | H | H | | PS1 | H | H | H | H | H | pic | |
| 2'-255X | Pd | 1 | 2' | Ph | H | H | | PS1 | H | H | H | H | H | acac | |
| 2'-255Y | Pd | 0 | 2' | Ph | H | H | | PS1 | H | H | H | H | H | — | — |
| 2'-256 | Pd | 1 | 2' | Ph | H | | PS1 | H | H | H | H | H | H | pic | |
| 2'-256X | Pd | 1 | 2' | Ph | H | | PS1 | H | H | H | H | H | H | acac | |
| 2'-256Y | Pd | 0 | 2' | Ph | H | | PS1 | H | H | H | H | H | H | — | — |
| 2'-257 | Pd | 1 | 2' | Ph | H | H | | PS2 | H | H | H | H | H | pic | |
| 2'-257X | Pd | 1 | 2' | Ph | H | H | | PS2 | H | H | H | H | H | acac | |
| 2'-257Y | Pd | 0 | 2' | Ph | H | H | | PS2 | H | H | H | H | H | — | — |
| 2'-258 | Pd | 1 | 2' | Ph | H | | PS2 | H | H | H | H | H | H | pic | |
| 2'-258X | Pd | 1 | 2' | Ph | H | | PS2 | H | H | H | H | H | H | acac | |
| 2'-258Y | Pd | 0 | 2' | Ph | H | | PS2 | H | H | H | H | H | H | — | — |
| 2'-259 | Pd | 1 | 2' | Ph | H | H | | BAL1 | H | H | H | H | H | pic | |
| 2'-259X | Pd | 1 | 2' | Ph | H | H | | BAL1 | H | H | H | H | H | acac | |
| 2'-259Y | Pd | 0 | 2' | Ph | H | H | | BAL1 | H | H | H | H | H | — | — |
| 2'-260 | Pd | 1 | 2' | Ph | H | | BAL1 | H | H | H | H | H | H | pic | |
| 2'-260X | Pd | 1 | 2' | Ph | H | | BAL1 | H | H | H | H | H | H | acac | |
| 2'-260Y | Pd | 0 | 2' | Ph | H | | BAL1 | H | H | H | H | H | H | — | — |
| 2'-261 | Pd | 1 | 2' | Ph | H | H | | BAL2 | H | H | H | H | H | pic | |
| 2'-261X | Pd | 1 | 2' | Ph | H | H | | BAL2 | H | H | H | H | H | acac | |
| 2'-261Y | Pd | 0 | 2' | Ph | H | H | | BAL2 | H | H | H | H | H | — | — |
| 2'-262 | Pd | 1 | 2' | Ph | H | | BAL2 | H | H | H | H | H | H | pic | |
| 2'-262X | Pd | 1 | 2' | Ph | H | | BAL2 | H | H | H | H | H | H | acac | |
| 2'-262Y | Pd | 0 | 2' | Ph | H | | BAL2 | H | H | H | H | H | H | — | — |
| 2'-263 | Pd | 1 | 2' | Ph | H | H | | MEK1 | H | H | H | H | H | pic | |
| 2'-263X | Pd | 1 | 2' | Ph | H | H | | MEK1 | H | H | H | H | H | acac | |
| 2'-263Y | Pd | 0 | 2' | Ph | H | H | | MEK1 | H | H | H | H | H | — | — |
| 2'-264 | Pd | 1 | 2' | Ph | H | | MEK1 | H | H | H | H | H | H | pic | |
| 2'-264X | Pd | 1 | 2' | Ph | H | | MEK1 | H | H | H | H | H | H | acac | |

TABLE 44-continued

| No. | M | m | BSS | SS G | T$^1$ | T$^2$ | T$^3$ | T$^4$ | T$^5$ | T$^6$ | T$^7$ | T$^8$ | T$^9$ | L$^1$ | L$^2$ |
|---|---|---|---|---|---|---|---|---|---|---|---|---|---|---|---|
| 2'-264Y | Pd | 0 | 2' | Ph | H | | MEK1 | H | H | H | H | H | H | — | — |
| 2'-265 | Pd | 1 | 2' | Ph | H | H | | MEK2 | H | H | H | H | H | pic | |
| 2'-265X | Pd | 1 | 2' | Ph | H | H | | MEK2 | H | H | H | H | H | acac | |
| 2'-265Y | Pd | 0 | 2' | Ph | H | H | | MEK2 | H | H | H | H | H | — | — |
| 2'-266 | Pd | 1 | 2' | Ph | H | | MEK2 | H | H | H | H | H | H | pic | |
| 2'-266X | Pd | 1 | 2' | Ph | H | | MEK2 | H | H | H | H | H | H | acac | |
| 2'-266Y | Pd | 0 | 2' | Ph | H | | MEK2 | H | H | H | H | H | H | — | — |
| 2'-267 | Pd | 1 | 2' | Ph | H | H | | PAL1 | H | H | H | H | H | pic | |
| 2'-267X | Pd | 1 | 2' | Ph | H | H | | PAL1 | H | H | H | H | H | acac | |
| 2'-267Y | Pd | 0 | 2' | Ph | H | H | | PAL1 | H | H | H | H | H | — | — |
| 2'-268 | Pd | 1 | 2' | Ph | H | | PAL1 | H | H | H | H | H | H | pic | |
| 2'-268X | Pd | 1 | 2' | Ph | H | | PAL1 | H | H | H | H | H | H | acac | |
| 2'-268Y | Pd | 0 | 2' | Ph | H | | PAL1 | H | H | H | H | H | H | — | — |
| 2'-269 | Pd | 1 | 2' | Ph | H | H | | PAL2 | H | H | H | H | H | pic | |
| 2'-269X | Pd | 1 | 2' | Ph | H | H | | PAL2 | H | H | H | H | H | acac | |
| 2'-269Y | Pd | 0 | 2' | Ph | H | H | | PAL2 | H | H | H | H | H | — | — |
| 2'-270 | Pd | 1 | 2' | Ph | H | | PAL2 | H | H | H | H | H | H | pic | |
| 2'-270X | Pd | 1 | 2' | Ph | H | | PAL2 | H | H | H | H | H | H | acac | |
| 2'-270Y | Pd | 0 | 2' | Ph | H | | PAL2 | H | H | H | H | H | H | — | — |
| 2'-271 | Pd | 1 | 2' | Ph | H | H | | MMK | H | H | H | H | H | pic | |
| 2'-271X | Pd | 1 | 2' | Ph | H | H | | MMK | H | H | H | H | H | acac | |
| 2'-271Y | Pd | 0 | 2' | Ph | H | H | | MMK | H | H | H | H | H | — | — |
| 2'-272 | Pd | 1 | 2' | Ph | H | | MMK | H | H | H | H | H | H | pic | |
| 2'-272X | Pd | 1 | 2' | Ph | H | | MMK | H | H | H | H | H | H | acac | |
| 2'-272Y | Pd | 0 | 2' | Ph | H | | MMK | H | H | H | H | H | H | — | — |
| 2'-273 | Pd | 1 | 2' | Ph | H | H | | EES1 | H | H | H | H | H | pic | |
| 2'-273X | Pd | 1 | 2' | Ph | H | H | | EES1 | H | H | H | H | H | acac | |
| 2'-273Y | Pd | 0 | 2' | Ph | H | H | | EES1 | H | H | H | H | H | — | — |
| 2'-274 | Pd | 1 | 2' | Ph | H | | EES2 | H | H | H | H | H | H | pic | |
| 2'-274X | Pd | 1 | 2' | Ph | H | | EES2 | H | H | H | H | H | H | acac | |
| 2'-274Y | Pd | 0 | 2' | Ph | H | | EES2 | H | H | H | H | H | H | — | — |
| 2'-275 | Pd | 1 | 2' | Ph | H | H | | PAE1 | H | H | H | H | H | pic | |
| 2'-275X | Pd | 1 | 2' | Ph | H | H | | PAE1 | H | H | H | H | H | acac | |
| 2'-275Y | Pd | 0 | 2' | Ph | H | H | | PAE1 | H | H | H | H | H | — | — |
| 2'-276 | Pd | 1 | 2' | Ph | H | | PAE2 | H | H | H | H | H | H | pic | |
| 2'-276X | Pd | 1 | 2' | Ph | H | | PAE2 | H | H | H | H | H | H | acac | |
| 2'-276Y | Pd | 0 | 2' | Ph | H | | PAE2 | H | H | H | H | H | H | — | — |
| 2'-277 | Pd | 1 | 2' | Ph | H | H | | AME1 | H | H | H | H | H | pic | |
| 2'-277X | Pd | 1 | 2' | Ph | H | H | | AME1 | H | H | H | H | H | acac | |
| 2'-277Y | Pd | 0 | 2' | Ph | H | H | | AME1 | H | H | H | H | H | — | — |
| 2'-278 | Pd | 1 | 2' | Ph | H | | AME1 | H | H | H | H | H | H | pic | |
| 2'-278X | Pd | 1 | 2' | Ph | H | | AME1 | H | H | H | H | H | H | acac | |
| 2'-278Y | Pd | 0 | 2' | Ph | H | | AME1 | H | H | H | H | H | H | — | — |
| 2'-279 | Pd | 1 | 2' | Ph | H | H | | AME2 | H | H | H | H | H | pic | |
| 2'-279X | Pd | 1 | 2' | Ph | H | H | | AME2 | H | H | H | H | H | acac | |
| 2'-279Y | Pd | 0 | 2' | Ph | H | H | | AME2 | H | H | H | H | H | — | — |
| 2'-280 | Pd | 1 | 2' | Ph | H | | AME2 | H | H | H | H | H | H | pic | |
| 2'-280X | Pd | 1 | 2' | Ph | H | | AME2 | H | H | H | H | H | H | acac | |
| 2'-280Y | Pd | 0 | 2' | Ph | H | | AME2 | H | H | H | H | H | H | — | — |
| 2'-281 | Pd | 1 | 2' | Ph | H | H | | EAE1 | H | H | H | H | H | pic | |
| 2'-281X | Pd | 1 | 2' | Ph | H | H | | EAE1 | H | H | H | H | H | acac | |
| 2'-281Y | Pd | 0 | 2' | Ph | H | H | | EAE1 | H | H | H | H | H | — | — |
| 2'-282 | Pd | 1 | 2' | Ph | H | | EAE1 | H | H | H | H | H | H | pic | |
| 2'-282X | Pd | 1 | 2' | Ph | H | | EAE1 | H | H | H | H | H | H | acac | |
| 2'-282Y | Pd | 0 | 2' | Ph | H | | EAE1 | H | H | H | H | H | H | — | — |
| 2'-283 | Pd | 1 | 2' | Ph | H | H | | EAE2 | H | H | H | H | H | pic | |
| 2'-283X | Pd | 1 | 2' | Ph | H | H | | EAE2 | H | H | H | H | H | acac | |
| 2'-283Y | Pd | 0 | 2' | Ph | H | H | | EAE2 | H | H | H | H | H | — | — |
| 2'-284 | Pd | 1 | 2' | Ph | H | | EAE2 | H | H | H | H | H | H | pic | |
| 2'-284X | Pd | 1 | 2' | Ph | H | | EAE2 | H | H | H | H | H | H | acac | |
| 2'-284Y | Pd | 0 | 2' | Ph | H | | EAE2 | H | H | H | H | H | H | — | — |
| 2'-285 | Pd | 1 | 2' | Ph | H | H | | AAE1 | H | H | H | H | H | pic | |
| 2'-285X | Pd | 1 | 2' | Ph | H | H | | AAE1 | H | H | H | H | H | acac | |
| 2'-285Y | Pd | 0 | 2' | Ph | H | H | | AAE1 | H | H | H | H | H | — | — |
| 2'-286 | Pd | 1 | 2' | Ph | H | | AAE1 | H | H | H | H | H | H | pic | |
| 2'-286X | Pd | 1 | 2' | Ph | H | | AAE1 | H | H | H | H | H | H | acac | |
| 2'-286Y | Pd | 0 | 2' | Ph | H | | AAE1 | H | H | H | H | H | H | — | — |
| 2'-287 | Pd | 1 | 2' | Ph | H | H | | AAE2 | H | H | H | H | H | pic | |
| 2'-287X | Pd | 1 | 2' | Ph | H | H | | AAE2 | H | H | H | H | H | acac | |
| 2'-287Y | Pd | 0 | 2' | Ph | H | H | | AAE2 | H | H | H | H | H | — | — |
| 2'-288 | Pd | 1 | 2' | Ph | H | | AAE2 | H | H | H | H | H | H | pic | |
| 2'-288X | Pd | 1 | 2' | Ph | H | | AAE2 | H | H | H | H | H | H | acac | |
| 2'-288Y | Pd | 0 | 2' | Ph | H | | AAE2 | H | H | H | H | H | H | — | — |
| 2'-289 | Pd | 1 | 2' | Ph | H | H | | PME1 | H | H | H | H | H | pic | |
| 2'-289X | Pd | 1 | 2' | Ph | H | H | | PME1 | H | H | H | H | H | acac | |
| 2'-289Y | Pd | 0 | 2' | Ph | H | H | | PME1 | H | H | H | H | H | — | — |
| 2'-290 | Pd | 1 | 2' | Ph | H | | PME1 | H | H | H | H | H | H | pic | |

TABLE 44-continued

| No. | M | m | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 2'-290X | Pd | 1 | 2' | | Ph | H | | PME1 | H | H | H | H | H | H | acac | |
| 2'-290Y | Pd | 0 | 2' | | Ph | H | | PME1 | H | H | H | H | H | H | — | — |
| 2'-291 | Pd | 1 | 2' | | Ph | H | H | | PME2 | H | H | H | H | H | pic | |
| 2'-291X | Pd | 1 | 2' | | Ph | H | H | | PME2 | H | H | H | H | H | acac | |
| 2'-291Y | Pd | 0 | 2' | | Ph | H | H | | PME2 | H | H | H | H | H | — | — |
| 2'-292 | Pd | 1 | 2' | | Ph | H | | PME2 | H | H | H | H | H | H | pic | |
| 2'-292X | Pd | 1 | 2' | | Ph | H | | PME2 | H | H | H | H | H | H | acac | |
| 2'-292Y | Pd | 0 | 2' | | Ph | H | | PME2 | H | H | H | H | H | H | — | — |
| 2'-293 | Pd | 1 | 2' | | Ph | H | H | | MET1 | H | H | H | H | H | pic | |
| 2'-293X | Pd | 1 | 2' | | Ph | H | H | | MET1 | H | H | H | H | H | acac | |
| 2'-293Y | Pd | 0 | 2' | | Ph | H | H | | MET1 | H | H | H | H | H | — | — |
| 2'-294 | Pd | 1 | 2' | | Ph | H | | MET1 | H | H | H | H | H | H | pic | |
| 2'-294X | Pd | 1 | 2' | | Ph | H | | MET1 | H | H | H | H | H | H | acac | |
| 2'-294Y | Pd | 0 | 2' | | Ph | H | | MET1 | H | H | H | H | H | H | — | — |
| 2'-295 | Pd | 1 | 2' | | Ph | H | H | | MET2 | H | H | H | H | H | pic | |
| 2'-295X | Pd | 1 | 2' | | Ph | H | H | | MET2 | H | H | H | H | H | acac | |
| 2'-295Y | Pd | 0 | 2' | | Ph | H | H | | MET2 | H | H | H | H | H | — | — |
| 2'-296 | Pd | 1 | 2' | | Ph | H | | MET2 | H | H | H | H | H | H | pic | |
| 2'-296X | Pd | 1 | 2' | | Ph | H | | MET2 | H | H | H | H | H | H | acac | |
| 2'-296Y | Pd | 0 | 2' | | Ph | H | | MET2 | H | H | H | H | H | H | — | — |
| 2'-297 | Pd | 1 | 2' | | Ph | H | H | | EE1 | H | H | H | H | H | pic | |
| 2'-297X | Pd | 1 | 2' | | Ph | H | H | | EE1 | H | H | H | H | H | acac | |
| 2'-297Y | Pd | 0 | 2' | | Ph | H | H | | EE1 | H | H | H | H | H | — | — |
| 2'-298 | Pd | 1 | 2' | | Ph | H | | EE1 | H | H | H | H | H | H | pic | |
| 2'-298X | Pd | 1 | 2' | | Ph | H | | EE1 | H | H | H | H | H | H | acac | |
| 2'-298Y | Pd | 0 | 2' | | Ph | H | | EE1 | H | H | H | H | H | H | — | — |
| 2'-299 | Pd | 1 | 2' | | Ph | H | H | | EE2 | H | H | H | H | H | pic | |
| 2'-299X | Pd | 1 | 2' | | Ph | H | H | | EE2 | H | H | H | H | H | acac | |
| 2'-299Y | Pd | 0 | 2' | | Ph | H | H | | EE2 | H | H | H | H | H | — | — |
| 2'-300 | Pd | 1 | 2' | | Ph | H | | EE2 | H | H | H | H | H | H | pic | |
| 2'-300X | Pd | 1 | 2' | | Ph | H | | EE2 | H | H | H | H | H | H | acac | |
| 2'-300Y | Pd | 0 | 2' | | Ph | H | | EE2 | H | H | H | H | H | H | — | — |
| 2'-301 | Pd | 1 | 2' | | Ph | H | H | | MS1 | H | H | H | H | H | pic | |
| 2'-301X | Pd | 1 | 2' | | Ph | H | H | | MS1 | H | H | H | H | H | acac | |
| 2'-301Y | Pd | 0 | 2' | | Ph | H | H | | MS1 | H | H | H | H | H | — | — |
| 2'-302 | Pd | 1 | 2' | | Ph | H | | MS1 | H | H | H | H | H | H | pic | |
| 2'-302X | Pd | 1 | 2' | | Ph | H | | MS1 | H | H | H | H | H | H | acac | |
| 2'-302Y | Pd | 0 | 2' | | Ph | H | | MS1 | H | H | H | H | H | H | — | — |
| 2'-303 | Pd | 1 | 2' | | Ph | H | H | | MS2 | H | H | H | H | H | pic | |
| 2'-303X | Pd | 1 | 2' | | Ph | H | H | | MS2 | H | H | H | H | H | acac | |
| 2'-303Y | Pd | 0 | 2' | | Ph | H | H | | MS2 | H | H | H | H | H | — | — |
| 2'-304 | Pd | 1 | 2' | | Ph | H | | MS2 | H | H | H | H | H | H | pic | |
| 2'-304X | Pd | 1 | 2' | | Ph | H | | MS2 | H | H | H | H | H | H | acac | |
| 2'-304Y | Pd | 0 | 2' | | Ph | H | | MS2 | H | H | H | H | H | H | — | — |

TABLE 45

| No. | M | m | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 3'-155 | Pd | 1 | 3' | | Ph | H | H | H | H | H | H | H | H | H | pic | |
| 3'-155X | Pd | 1 | 3' | | Ph | H | H | H | H | H | H | H | H | H | acac | |
| 3'-155Y | Pd | 0 | 3' | | Ph | H | H | H | H | H | H | H | H | H | — | — |
| 3'-156 | Pd | 1 | 3' | | Ph | H | F | H | F | H | H | H | H | H | pic | |
| 3'-156X | Pd | 1 | 3' | | Ph | H | F | H | F | H | H | H | H | H | acac | |
| 3'-156Y | Pd | 0 | 3' | | Ph | H | F | H | F | H | H | H | H | H | — | — |
| 3'-157 | Pd | 1 | 3' | | Ph | F | H | H | F | H | H | H | H | H | pic | |
| 3'-157X | Pd | 1 | 3' | | Ph | F | H | H | F | H | H | H | H | H | acac | |
| 3'-157Y | Pd | 0 | 3' | | Ph | F | H | H | F | H | H | H | H | H | — | — |
| 3'-158 | Pd | 1 | 3' | | Ph | $CF_3$ | H | $CF_3$ | H | H | H | H | H | H | pic | |
| 3'-158X | Pd | 1 | 3' | | Ph | $CF_3$ | H | $CF_3$ | H | H | H | H | H | H | acac | |
| 3'-158Y | Pd | 0 | 3' | | Ph | $CF_3$ | H | $CF_3$ | H | H | H | H | H | H | — | — |
| 3'-159 | Pd | 1 | 3' | | Ph | H | F | $CF_3$ | H | H | H | H | H | H | pic | |
| 3'-159X | Pd | 1 | 3' | | Ph | H | F | $CF_3$ | H | H | H | H | H | H | acac | |
| 3'-159Y | Pd | 0 | 3' | | Ph | H | F | $CF_3$ | H | H | H | H | H | H | — | — |
| 3'-160 | Pd | 1 | 3' | | Ph | F | H | $CF_3$ | H | H | H | H | H | H | pic | |
| 3'-160X | Pd | 1 | 3' | | Ph | F | H | $CF_3$ | H | H | H | H | H | H | acac | |
| 3'-160Y | Pd | 0 | 3' | | Ph | F | H | $CF_3$ | H | H | H | H | H | H | — | — |
| 3'-161 | Pd | 1 | 3' | | Ph | F | F | F | F | H | H | H | H | H | pic | |
| 3'-161X | Pd | 1 | 3' | | Ph | F | F | F | F | H | H | H | H | H | acac | |
| 3'-161Y | Pd | 0 | 3' | | Ph | F | F | F | F | H | H | H | H | H | — | — |
| 3'-162 | Pd | 1 | 3' | | Ph | H | F | H | $CH_3$ | H | H | H | H | H | pic | |
| 3'-162X | Pd | 1 | 3' | | Ph | H | F | H | $CH_3$ | H | H | H | H | H | acac | |
| 3'-162Y | Pd | 0 | 3' | | Ph | H | F | H | $CH_3$ | H | H | H | H | H | — | — |
| 3'-163 | Pd | 1 | 3' | | Ph | H | F | H | $^tC_4H_9$ | H | H | H | H | H | pic | |

TABLE 45-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-163X | Pd | 1 | 3' | Ph | H | F | H | $^tC_4H_9$ | H | H | H | H | H | acac | |
| 3'-163Y | Pd | 0 | 3' | Ph | H | F | H | $^tC_4H_9$ | H | H | H | H | H | — | — |
| 3'-164 | Pd | 1 | 3' | Ph | H | $CF_3$ | H | $CF_3$ | H | H | H | H | H | pic | |
| 3'-164X | Pd | 1 | 3' | Ph | H | $CF_3$ | H | $CF_3$ | H | H | H | H | H | acac | |
| 3'-164Y | Pd | 0 | 3' | Ph | H | $CF_3$ | H | $CF_3$ | H | H | H | H | H | — | — |
| 3'-165 | Pd | 1 | 3' | Ph | $CF_3$ | H | H | $^tC_4H_9$ | H | H | H | H | H | pic | |
| 3'-165X | Pd | 1 | 3' | Ph | $CF_3$ | H | H | $^tC_4H_9$ | H | H | H | H | H | acac | |
| 3'-165Y | Pd | 0 | 3' | Ph | $CF_3$ | H | H | $^tC_4H_9$ | H | H | H | H | H | — | — |
| 3'-166 | Pd | 1 | 3' | Ph | H | $CF_3$ | H | $^tC_4H_9$ | H | H | H | H | H | pic | |
| 3'-166X | Pd | 1 | 3' | Ph | H | $CF_3$ | H | $^tC_4H_9$ | H | H | H | H | H | acac | |
| 3'-166Y | Pd | 0 | 3' | Ph | H | $CF_3$ | H | $^tC_4H_9$ | H | H | H | H | H | — | — |
| 3'-167 | Pd | 1 | 3' | Ph | H | $CF_3$ | H | $CH_3$ | H | H | H | H | H | pic | |
| 3'-167X | Pd | 1 | 3' | Ph | H | $CF_3$ | H | $CH_3$ | H | H | H | H | H | acac | |
| 3'-167Y | Pd | 0 | 3' | Ph | H | $CF_3$ | H | $CH_3$ | H | H | H | H | H | — | — |
| 3'-168 | Pd | 1 | 3' | Ph | H | $CF_3$ | $CF_3$ | H | H | H | H | H | H | pic | |
| 3'-168X | Pd | 1 | 3' | Ph | H | $CF_3$ | $CF_3$ | H | H | H | H | H | H | acac | |
| 3'-168Y | Pd | 0 | 3' | Ph | H | $CF_3$ | $CF_3$ | H | H | H | H | H | H | — | — |
| 3'-169 | Pd | 1 | 3' | Ph | H | H | $NO_2$ | H | H | H | H | H | H | pic | |
| 3'-169X | Pd | 1 | 3' | Ph | H | H | $NO_2$ | H | H | H | H | H | H | acac | |
| 3'-169Y | Pd | 0 | 3' | Ph | H | H | $NO_2$ | H | H | H | H | H | H | — | — |
| 3'-170 | Pd | 1 | 3' | Ph | F | H | $NO_2$ | H | H | H | H | H | H | pic | |
| 3'-170X | Pd | 1 | 3' | Ph | F | H | $NO_2$ | H | H | H | H | H | H | acac | |
| 3'-170Y | Pd | 0 | 3' | Ph | F | H | $NO_2$ | H | H | H | H | H | H | — | — |
| 3'-171 | Pd | 1 | 3' | Ph | F | H | $NO_2$ | F | H | H | H | H | H | pic | |
| 3'-171X | Pd | 1 | 3' | Ph | F | H | $NO_2$ | F | H | H | H | H | H | acac | |
| 3'-171Y | Pd | 0 | 3' | Ph | F | H | $NO_2$ | F | H | H | H | H | H | — | — |
| 3'-172 | Pd | 1 | 3' | Ph | H | $NO_2$ | H | $NO_2$ | H | H | H | H | H | pic | |
| 3'-172X | Pd | 1 | 3' | Ph | H | $NO_2$ | H | $NO_2$ | H | H | H | H | H | acac | |
| 3'-172Y | Pd | 0 | 3' | Ph | H | $NO_2$ | H | $NO_2$ | H | H | H | H | H | — | — |
| 3'-173 | Pd | 1 | 3' | Ph | $NO_2$ | H | H | $NO_2$ | H | H | H | H | H | pic | |
| 3'-173X | Pd | 1 | 3' | Ph | $NO_2$ | H | H | $NO_2$ | H | H | H | H | H | acac | |
| 3'-173Y | Pd | 0 | 3' | Ph | $NO_2$ | H | H | $NO_2$ | H | H | H | H | H | — | — |
| 3'-174 | Pd | 1 | 3' | Ph | H | H | $CF_3$ | H | H | H | H | H | H | pic | |
| 3'-174X | Pd | 1 | 3' | Ph | H | H | $CF_3$ | H | H | H | H | H | H | acac | |
| 3'-174Y | Pd | 0 | 3' | Ph | H | H | $CF_3$ | H | H | H | H | H | H | — | — |
| 3'-175 | Pd | 1 | 3' | Ph | H | Cl | $CF_3$ | H | H | H | H | H | H | pic | |
| 3'-175X | Pd | 1 | 3' | Ph | H | Cl | $CF_3$ | H | H | H | H | H | H | acac | |
| 3'-175Y | Pd | 0 | 3' | Ph | H | Cl | $CF_3$ | H | H | H | H | H | H | — | — |
| 3'-176 | Pd | 1 | 3' | Ph | H | $NO_2$ | H | H | H | H | H | H | H | pic | |
| 3'-176X | Pd | 1 | 3' | Ph | H | $NO_2$ | H | H | H | H | H | H | H | acac | |
| 3'-176Y | Pd | 0 | 3' | Ph | H | $NO_2$ | H | H | H | H | H | H | H | — | — |
| 3'-177 | Pd | 1 | 3' | Ph | H | $CF_3$ | H | H | H | H | H | H | H | pic | |
| 3'-177X | Pd | 1 | 3' | Ph | H | $CF_3$ | H | H | H | H | H | H | H | acac | |
| 3'-177Y | Pd | 0 | 3' | Ph | H | $CF_3$ | H | H | H | H | H | H | H | — | — |
| 3'-178 | Pd | 1 | 3' | Ph | H | $NO_2$ | H | $CH_3$ | H | H | H | H | H | pic | |
| 3'-178X | Pd | 1 | 3' | Ph | H | $NO_2$ | H | $CH_3$ | H | H | H | H | H | acac | |
| 3'-178Y | Pd | 0 | 3' | Ph | H | $NO_2$ | H | $CH_3$ | H | H | H | H | H | — | — |
| 3'-179 | Pd | 1 | 3' | Ph | H | $NO_2$ | H | $^tC_4H_9$ | H | H | H | H | H | pic | |
| 3'-179X | Pd | 1 | 3' | Ph | H | $NO_2$ | H | $^tC_4H_9$ | H | H | H | H | H | acac | |
| 3'-179Y | Pd | 0 | 3' | Ph | H | $NO_2$ | H | $^tC_4H_9$ | H | H | H | H | H | — | — |
| 3'-180 | Pd | 1 | 3' | Ph | H | H | $CH_3O$ | H | H | H | H | H | H | pic | |
| 3'-180X | Pd | 1 | 3' | Ph | H | H | $CH_3O$ | H | H | H | H | H | H | acac | |
| 3'-180Y | Pd | 0 | 3' | Ph | H | H | $CH_3O$ | H | H | H | H | H | H | — | — |
| 3'-181 | Pd | 1 | 3' | Ph | H | $CH_3O$ | H | H | H | H | H | H | H | pic | |
| 3'-181X | Pd | 1 | 3' | Ph | H | $CH_3O$ | H | H | H | H | H | H | H | acec | |
| 3'-181Y | Pd | 0 | 3' | Ph | H | $CH_3O$ | H | H | H | H | H | H | H | — | — |
| 3'-182 | Pd | 1 | 3' | Ph | H | $CH_3O$ | H | $CH_3$ | H | H | H | H | H | pic | |
| 3'-182X | Pd | 1 | 3' | Ph | H | $CH_3O$ | H | $CH_3$ | H | H | H | H | H | acac | |
| 3'-182Y | Pd | 0 | 3' | Ph | H | $CH_3O$ | H | $CH_3$ | H | H | H | H | H | — | — |
| 3'-183 | Pd | 1 | 3' | Ph | H | $CH_3O$ | H | $^tC_4H_9$ | H | H | H | H | H | pic | |
| 3'-183X | Pd | 1 | 3' | Ph | H | $CH_3O$ | H | $^tC_4H_9$ | H | H | H | H | H | acac | |
| 3'-183Y | Pd | 0 | 3' | Ph | H | $CH_3O$ | H | $^tC_4H_9$ | H | H | H | H | H | — | — |
| 3'-184 | Pd | 1 | 3' | Ph | H | H | H | H | $^tC_4H_9$ | H | H | H | H | pic | |
| 3'-184X | Pd | 1 | 3' | Ph | H | H | H | H | $^tC_4H_9$ | H | H | H | H | acac | |
| 3'-184Y | Pd | 0 | 3' | Ph | H | H | H | H | $^tC_4H_9$ | H | H | H | H | — | — |
| 3'-185 | Pd | 1 | 3' | Ph | H | F | H | F | $^tC_4H_9$ | H | H | H | H | pic | |
| 3'-185X | Pd | 1 | 3' | Ph | H | F | H | F | $^tC_4H_9$ | H | H | H | H | acac | |
| 3'-185Y | Pd | 0 | 3' | Ph | H | F | H | F | $^tC_4H_9$ | H | H | H | H | — | — |
| 3'-186 | Pd | 1 | 3' | Ph | $CF_3$ | H | $CF_3$ | H | $^tC_4H_9$ | H | H | H | H | pic | |
| 3'-186X | Pd | 1 | 3' | Ph | $CF_3$ | H | $CF_3$ | H | $^tC_4H_9$ | H | H | H | H | acac | |
| 3'-186Y | Pd | 0 | 3' | Ph | $CF_3$ | H | $CF_3$ | H | $^tC_4H_9$ | H | H | H | H | — | — |
| 3'-187 | Pd | 1 | 3' | Ph | H | $CF_3$ | H | $CH_3$ | $^tC_4H_9$ | H | H | H | H | pic | |
| 3'-187X | Pd | 1 | 3' | Ph | H | $CF_3$ | H | $CH_3$ | $^tC_4H_9$ | H | H | H | H | acac | |
| 3'-187Y | Pd | 0 | 3' | Ph | H | $CF_3$ | H | $CH_3$ | $^tC_4H_9$ | H | H | H | H | — | — |
| 3'-188 | Pd | 1 | 3' | Ph | H | $Si(CH_3)_3$ | H | H | H | H | H | H | H | pic | |
| 3'-188X | Pd | 1 | 3' | Ph | H | $Si(CH_3)_3$ | H | H | H | H | H | H | H | acac | |
| 3'-188Y | Pd | 0 | 3' | Ph | H | $Si(CH_3)_3$ | H | H | H | H | H | H | H | — | — |

TABLE 45-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-189 | Pd | 1 | 3' | Ph | H | H | Si(CH₃)₃ | H | H | H | H | H | H | pic | |
| 3'-189X | Pd | 1 | 3' | Ph | H | H | Si(CH₃)₃ | H | H | H | H | H | H | acac | |
| 3'-189Y | Pd | 0 | 3' | Ph | H | H | Si(CH₃)₃ | H | H | H | H | H | H | — | — |
| 3'-190 | Pd | 1 | 3' | Ph | H | H | H | Si(CH₃)₃ | H | H | H | H | H | pic | |
| 3'-190X | Pd | 1 | 3' | Ph | H | H | H | Si(CH₃)₃ | H | H | H | H | H | acac | |
| 3'-190Y | Pd | 0 | 3' | Ph | H | H | H | Si(CH₃)₃ | H | H | H | H | H | — | — |
| 3'-191 | Pd | 1 | 3' | Ph | H | H | F | H | Si(CH₃)₃ | H | H | H | H | H | pic |
| 3'-191X | Pd | 1 | 3' | Ph | H | H | F | H | Si(CH₃)₃ | H | H | H | H | H | acac |
| 3'-191Y | Pd | 0 | 3' | Ph | H | H | F | H | Si(CH₃)₃ | H | H | H | H | H | — — |
| 3'-192 | Pd | 1 | 3' | Ph | H | CF₃ | H | Si(CH₃)₃ | H | H | H | H | H | pic | |
| 3'-192X | Pd | 1 | 3' | Ph | H | CF₃ | H | Si(CH₃)₃ | H | H | H | H | H | acac | |
| 3'-192Y | Pd | 0 | 3' | Ph | H | CF₃ | H | Si(CH₃)₃ | H | H | H | H | H | — | — |
| 3'-193 | Pd | 1 | 3' | Ph | H | Si(CH₃)₃ | H | F | H | H | H | H | H | pic | |
| 3'-193X | Pd | 1 | 3' | Ph | H | Si(CH₃)₃ | H | F | H | H | H | H | H | acac | |
| 3'-193Y | Pd | 0 | 3' | Ph | H | Si(CH₃)₃ | H | F | H | H | H | H | H | — | — |
| 3'-194 | Pd | 1 | 3' | Ph | H | Si(CH₃)₃ | H | CF₃ | H | H | H | H | H | pic | |
| 3'-194X | Pd | 1 | 3' | Ph | H | Si(CH₃)₃ | H | CF₃ | H | H | H | H | H | acac | |
| 3'-194Y | Pd | 0 | 3' | Ph | H | Si(CH₃)₃ | H | CF₃ | H | H | H | H | H | — | — |
| 3'-195 | Pd | 1 | 3' | Ph | Si(CH₃)₃ | H | Si(CH₃)₃ | H | H | H | H | H | H | pic | |
| 3'-195X | Pd | 1 | 3' | Ph | Si(CH₃)₃ | H | Si(CH₃)₃ | H | H | H | H | H | H | acac | |
| 3'-195Y | Pd | 0 | 3' | Ph | Si(CH₃)₃ | H | Si(CH₃)₃ | H | H | H | H | H | H | — | — |
| 3'-196 | Pd | 1 | 3' | Ph | H | H | H | COCH₃ | H | H | H | H | H | pic | |
| 3'-196X | Pd | 1 | 3' | Ph | H | H | H | COCH₃ | H | H | H | H | H | acac | |
| 3'-196Y | Pd | 0 | 3' | Ph | H | H | H | COCH₃ | H | H | H | H | H | — | — |
| 3'-197 | Pd | 1 | 3' | Ph | H | H | COCH₃ | H | H | H | H | H | H | pic | |
| 3'-197X | Pd | 1 | 3' | Ph | H | H | COCH₃ | H | H | H | H | H | H | acac | |
| 3'-197Y | Pd | 0 | 3' | Ph | H | H | COCH₃ | H | H | H | H | H | H | — | — |
| 3'-198 | Pd | 1 | 3' | Ph | H | COCH₃ | H | H | H | H | H | H | H | pic | |
| 3'-198X | Pd | 1 | 3' | Ph | H | COCH₃ | H | H | H | H | H | H | H | acac | |
| 3'-198Y | Pd | 0 | 3' | Ph | H | COCH₃ | H | H | H | H | H | H | H | — | — |
| 3'-199 | Pd | 1 | 3' | Ph | H | H | BL | | H | H | H | H | H | pic | |
| 3'-199X | Pd | 1 | 3' | Ph | H | H | BL | H | H | H | H | H | H | acac | |
| 3'-199Y | Pd | 0 | 3' | Ph | H | H | BL | | H | H | H | H | H | — | — |
| 3'-200 | Pd | 1 | 3' | Ph | H | BL | | H | H | H | H | H | H | pic | |
| 3'-200X | Pd | 1 | 3' | Ph | H | BL | H | H | H | H | H | H | H | acac | |
| 3'-200Y | Pd | 0 | 3' | Ph | H | BL | | H | H | H | H | H | H | — | — |
| 3'-201 | Pd | 1 | 3' | Ph | H | H | PL | | H | H | H | H | H | pic | |
| 3'-201X | Pd | 1 | 3' | Ph | H | H | PL | H | H | H | H | H | H | acac | |
| 3'-201Y | Pd | 0 | 3' | Ph | H | H | PL | | H | H | H | H | H | — | — |
| 3'-202 | Pd | 1 | 3' | Ph | H | PL | | H | H | H | H | H | H | pic | |
| 3'-202X | Pd | 1 | 3' | Ph | H | PL | H | H | H | H | H | H | H | acac | |
| 3'-202Y | Pd | 0 | 3' | Ph | H | PL | | H | H | H | H | H | H | — | — |
| 3'-203 | Pd | 1 | 3' | Ph | H | H | MEE1 | | H | H | H | H | H | pic | |
| 3'-203X | Pd | 1 | 3' | Ph | H | H | MEE1 | H | H | H | H | H | H | acac | |
| 3'-203Y | Pd | 0 | 3' | Ph | H | H | MEE1 | | H | H | H | H | H | — | — |
| 3'-204 | Pd | 1 | 3' | Ph | H | MEE1 | | H | H | H | H | H | H | pic | |
| 3'-204X | Pd | 1 | 3' | Ph | H | MEE1 | H | H | H | H | H | H | H | acac | |
| 3'-204Y | Pd | 0 | 3' | Ph | H | MEE1 | | H | H | H | H | H | H | — | — |
| 3'-205 | Pd | 1 | 3' | Ph | H | H | MEE2 | | H | H | H | H | H | pic | |
| 3'-205X | Pd | 1 | 3' | Ph | H | H | MEE2 | H | H | H | H | H | H | acac | |
| 3'-205Y | Pd | 0 | 3' | Ph | H | H | MEE2 | | H | H | H | H | H | — | — |
| 3'-206 | Pd | 1 | 3' | Ph | H | MEE2 | | H | H | H | H | H | H | pic | |
| 3'-206X | Pd | 1 | 3' | Ph | H | MEE2 | H | H | H | H | H | H | H | acac | |
| 3'-206Y | Pd | 0 | 3' | Ph | H | MEE2 | | H | H | H | H | H | H | — | — |
| 3'-207 | Pd | 1 | 3' | Ph | H | H | PA1 | | H | H | H | H | H | pic | |
| 3'-207X | Pd | 1 | 3' | Ph | H | H | PA1 | H | H | H | H | H | H | acac | |
| 3'-207Y | Pd | 0 | 3' | Ph | H | H | PA1 | | H | H | H | H | H | — | — |
| 3'-208 | Pd | 1 | 3' | Ph | H | PA1 | | H | H | H | H | H | H | pic | |
| 3'-208X | Pd | 1 | 3' | Ph | H | PA1 | H | H | H | H | H | H | H | acac | |
| 3'-208Y | Pd | 0 | 3' | Ph | H | PA1 | | H | H | H | H | H | H | — | — |
| 3'-209 | Pd | 1 | 3' | Ph | H | H | PA2 | | H | H | H | H | H | pic | |
| 3'-209X | Pd | 1 | 3' | Ph | H | H | PA2 | H | H | H | H | H | H | acac | |
| 3'-209Y | Pd | 0 | 3' | Ph | H | H | PA2 | | H | H | H | H | H | — | — |
| 3'-210 | Pd | 1 | 3' | Ph | H | PA2 | | H | H | H | H | H | H | pic | |
| 3'-210X | Pd | 1 | 3' | Ph | H | PA2 | H | H | H | H | H | H | H | acac | |
| 3'-210Y | Pd | 0 | 3' | Ph | H | PA2 | | H | H | H | H | H | H | — | — |
| 3'-211 | Pd | 1 | 3' | Ph | H | H | EA1 | | H | H | H | H | H | pic | |
| 3'-211X | Pd | 1 | 3' | Ph | H | H | EA1 | H | H | H | H | H | H | acac | |
| 3'-211Y | Pd | 0 | 3' | Ph | H | H | EA1 | | H | H | H | H | H | — | — |
| 3'-212 | Pd | 1 | 3' | Ph | H | EA2 | | H | H | H | H | H | H | pic | |
| 3'-212X | Pd | 1 | 3' | Ph | H | EA2 | H | H | H | H | H | H | H | acac | |
| 3'-212Y | Pd | 0 | 3' | Ph | H | EA2 | | H | H | H | H | H | H | — | — |
| 3'-213 | Pd | 1 | 3' | Ph | H | H | ME | | H | H | H | H | H | pic | |
| 3'-213X | Pd | 1 | 3' | Ph | H | H | ME | H | H | H | H | H | H | acac | |
| 3'-213Y | Pd | 0 | 3' | Ph | H | H | ME | | H | H | H | H | H | — | — |
| 3'-214 | Pd | 1 | 3' | Ph | H | ME | | H | H | H | H | H | H | pic | |
| 3'-214X | Pd | 1 | 3' | Ph | H | ME | H | H | H | H | H | H | H | acac | |

TABLE 45-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 3'-214Y | Pd | 0 | 3' | Ph | H | ME | | H | H | H | H | H | H | — | — |
| 3'-215 | Pd | 1 | 3' | Ph | H | H | AT | | H | H | H | H | H | | pic |
| 3'-215X | Pd | 1 | 3' | Ph | H | H | AT | H | H | H | H | H | H | acac | |
| 3'-215Y | Pd | 0 | 3' | Ph | H | H | AT | | H | H | H | H | H | — | — |
| 3'-216 | Pd | 1 | 3' | Ph | H | AT | | H | H | H | H | H | H | | pic |
| 3'-216X | Pd | 1 | 3' | Ph | H | AT | H | H | H | H | H | H | H | acac | |
| 3'-216Y | Pd | 0 | 3' | Ph | H | AT | | H | H | H | H | H | H | — | — |
| 3'-217 | Pd | 1 | 3' | Ph | H | H | MES1 | | H | H | H | H | H | | pic |
| 3'-217X | Pd | 1 | 3' | Ph | H | H | MES1 | H | H | H | H | H | H | acac | |
| 3'-217Y | Pd | 0 | 3' | Ph | H | H | MES1 | | H | H | H | H | H | — | — |
| 3'-218 | Pd | 1 | 3' | Ph | H | MES1 | | H | H | H | H | H | H | | pic |
| 3'-218X | Pd | 1 | 3' | Ph | H | MES1 | H | H | H | H | H | H | H | acac | |
| 3'-218Y | Pd | 0 | 3' | Ph | H | MES1 | | H | H | H | H | H | H | — | — |
| 3'-219 | Pd | 1 | 3' | Ph | H | H | MES2 | | H | H | H | H | H | | pic |
| 3'-219X | Pd | 1 | 3' | Ph | H | H | MES2 | H | H | H | H | H | H | acac | |
| 3'-219Y | Pd | 0 | 3' | Ph | H | H | MES2 | | H | H | H | H | H | — | — |
| 3'-220 | Pd | 1 | 3' | Ph | H | MES2 | | H | H | H | H | H | H | | pic |
| 3'-220X | Pd | 1 | 3' | Ph | H | MES2 | H | H | H | H | H | H | H | acac | |
| 3'-220Y | Pd | 0 | 3' | Ph | H | MES2 | | H | H | H | H | H | H | — | — |
| 3'-221 | Pd | 1 | 3' | Ph | H | H | PS1 | | H | H | H | H | H | | pic |
| 3'-221X | Pd | 1 | 3' | Ph | H | H | PS1 | H | H | H | H | H | H | acac | |
| 3'-221Y | Pd | 0 | 3' | Ph | H | H | PS1 | | H | H | H | H | H | — | — |
| 3'-222 | Pd | 1 | 3' | Ph | H | PS1 | | H | H | H | H | H | H | | pic |
| 3'-222X | Pd | 1 | 3' | Ph | H | PS1 | H | H | H | H | H | H | H | acac | |
| 3'-222Y | Pd | 0 | 3' | Ph | H | PS1 | | H | H | H | H | H | H | — | — |
| 3'-223 | Pd | 1 | 3' | Ph | H | H | PS2 | | H | H | H | H | H | | pic |
| 3'-223X | Pd | 1 | 3' | Ph | H | H | PS2 | H | H | H | H | H | H | acac | |
| 3'-223Y | Pd | 0 | 3' | Ph | H | H | PS2 | | H | H | H | H | H | — | — |
| 3'-224 | Pd | 1 | 3' | Ph | H | PS2 | | H | H | H | H | H | H | | pic |
| 3'-224X | Pd | 1 | 3' | Ph | H | PS2 | H | H | H | H | H | H | H | acac | |
| 3'-224Y | Pd | 0 | 3' | Ph | H | PS2 | | H | H | H | H | H | H | — | — |
| 3'-225 | Pd | 1 | 3' | Ph | H | H | BAL1 | | H | H | H | H | H | | pic |
| 3'-225X | Pd | 1 | 3' | Ph | H | H | BAL1 | H | H | H | H | H | H | acac | |
| 3'-225Y | Pd | 0 | 3' | Ph | H | H | BAL1 | | H | H | H | H | H | — | — |
| 3'-226 | Pd | 1 | 3' | Ph | H | BAL1 | | H | H | H | H | H | H | | pic |
| 3'-226X | Pd | 1 | 3' | Ph | H | BAL1 | H | H | H | H | H | H | H | acac | |
| 3'-226Y | Pd | 0 | 3' | Ph | H | BAL1 | | H | H | H | H | H | H | — | — |
| 3'-227 | Pd | 1 | 3' | Ph | H | H | BAL2 | | H | H | H | H | H | | pic |
| 3'-227X | Pd | 1 | 3' | Ph | H | H | BAL2 | H | H | H | H | H | H | acac | |
| 3'-227Y | Pd | 0 | 3' | Ph | H | H | BAL2 | | H | H | H | H | H | — | — |
| 3'-228 | Pd | 1 | 3' | Ph | H | BAL2 | | H | H | H | H | H | H | | pic |
| 3'-228X | Pd | 1 | 3' | Ph | H | BAL2 | H | H | H | H | H | H | H | acac | |
| 3'-228Y | Pd | 0 | 3' | Ph | H | BAL2 | | H | H | H | H | H | H | — | — |
| 3'-229 | Pd | 1 | 3' | Ph | H | H | MEK1 | | H | H | H | H | H | | pic |
| 3'-229X | Pd | 1 | 3' | Ph | H | H | MEK1 | H | H | H | H | H | H | acac | |
| 3'-229Y | Pd | 0 | 3' | Ph | H | H | MEK1 | | H | H | H | H | H | — | — |
| 3'-230 | Pd | 1 | 3' | Ph | H | MEK1 | | H | H | H | H | H | H | | pic |
| 3'-230X | Pd | 1 | 3' | Ph | H | MEK1 | H | H | H | H | H | H | H | acac | |
| 3'-230Y | Pd | 0 | 3' | Ph | H | MEK1 | | H | H | H | H | H | H | — | — |
| 3'-231 | Pd | 1 | 3' | Ph | H | H | MEK2 | | H | H | H | H | H | | pic |
| 3'-231X | Pd | 1 | 3' | Ph | H | H | MEK2 | H | H | H | H | H | H | acac | |
| 3'-231Y | Pd | 0 | 3' | Ph | H | H | MEK2 | | H | H | H | H | H | — | — |
| 3'-232 | Pd | 1 | 3' | Ph | H | MEK2 | | H | H | H | H | H | H | | pic |
| 3'-232X | Pd | 1 | 3' | Ph | H | MEK2 | H | H | H | H | H | H | H | acac | |
| 3'-232Y | Pd | 0 | 3' | Ph | H | MEK2 | | H | H | H | H | H | H | — | — |
| 3'-233 | Pd | 1 | 3' | Ph | H | H | PAL1 | | H | H | H | H | H | | pic |
| 3'-233X | Pd | 1 | 3' | Ph | H | H | PAL1 | H | H | H | H | H | H | acac | |
| 3'-233Y | Pd | 0 | 3' | Ph | H | H | PAL1 | | H | H | H | H | H | — | — |
| 3'-234 | Pd | 1 | 3' | Ph | H | PAL1 | | H | H | H | H | H | H | | pic |
| 3'-234X | Pd | 1 | 3' | Ph | H | PAL1 | H | H | H | H | H | H | H | acac | |
| 3'-234Y | Pd | 0 | 3' | Ph | H | PAL1 | | H | H | H | H | H | H | — | — |
| 3'-235 | Pd | 1 | 3' | Ph | H | H | PAL2 | | H | H | H | H | H | | pic |
| 3'-235X | Pd | 1 | 3' | Ph | H | H | PAL2 | H | H | H | H | H | H | acac | |
| 3'-235Y | Pd | 0 | 3' | Ph | H | H | PAL2 | | H | H | H | H | H | — | — |
| 3'-236 | Pd | 1 | 3' | Ph | H | PAL2 | | H | H | H | H | H | H | | pic |
| 3'-236X | Pd | 1 | 3' | Ph | H | PAL2 | H | H | H | H | H | H | H | acac | |
| 3'-236Y | Pd | 0 | 3' | Ph | H | PAL2 | | H | H | H | H | H | H | — | — |
| 3'-237 | Pd | 1 | 3' | Ph | H | H | MMK | | H | H | H | H | H | | pic |
| 3'-237X | Pd | 1 | 3' | Ph | H | H | MMK | H | H | H | H | H | H | acac | |
| 3'-237Y | Pd | 0 | 3' | Ph | H | H | MMK | | H | H | H | H | H | — | — |
| 3'-238 | Pd | 1 | 3' | Ph | H | MMK | | H | H | H | H | H | H | | pic |
| 3'-238X | Pd | 1 | 3' | Ph | H | MMK | H | H | H | H | H | H | H | acac | |
| 3'-238Y | Pd | 0 | 3' | Ph | H | MMK | | H | H | H | H | H | H | — | — |
| 3'-239 | Pd | 1 | 3' | Ph | H | H | EES1 | | H | H | H | H | H | | pic |
| 3'-239X | Pd | 1 | 3' | Ph | H | H | EES1 | H | H | H | H | H | H | acac | |
| 3'-239Y | Pd | 0 | 3' | Ph | H | H | EES1 | | H | H | H | H | H | — | — |
| 3'-240 | Pd | 1 | 3' | Ph | H | EES2 | | H | H | H | H | H | H | | pic |

TABLE 45-continued

| No. | M | m | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 3'-240X | Pd | 1 | 3' | Ph | H | EES2 | H | H | H | H | H | H | H | acac | | |
| 3'-240Y | Pd | 0 | 3' | Ph | H | EES2 | | H | H | H | H | H | H | H | — | — |
| 3'-241 | Pd | 1 | 3' | Ph | H | H | PAE1 | | H | H | H | H | H | H | pic | |
| 3'-241X | Pd | 1 | 3' | Ph | H | H | PAE1 | H | H | H | H | H | H | acac | | |
| 3'-241Y | Pd | 0 | 3' | Ph | H | H | PAE1 | | H | H | H | H | H | H | — | — |
| 3'-242 | Pd | 1 | 3' | Ph | H | PAE2 | | H | H | H | H | H | H | H | pic | |
| 3'-242X | Pd | 1 | 3' | Ph | H | PAE2 | H | H | H | H | H | H | H | acac | | |
| 3'-242Y | Pd | 0 | 3' | Ph | H | PAE2 | | H | H | H | H | H | H | H | — | — |
| 3'-243 | Pd | 1 | 3' | Ph | H | H | AME1 | | H | H | H | H | H | H | pic | |
| 3'-243X | Pd | 1 | 3' | Ph | H | H | AME1 | H | H | H | H | H | H | acac | | |
| 3'-243Y | Pd | 0 | 3' | Ph | H | H | AME1 | | H | H | H | H | H | H | — | — |
| 3'-244 | Pd | 1 | 3' | Ph | H | AME1 | | H | H | H | H | H | H | H | pic | |
| 3'-244X | Pd | 1 | 3' | Ph | H | AME1 | H | H | H | H | H | H | H | acac | | |
| 3'-244Y | Pd | 0 | 3' | Ph | H | AME1 | | H | H | H | H | H | H | H | — | — |
| 3'-245 | Pd | 1 | 3' | Ph | H | H | AME2 | | H | H | H | H | H | H | pic | |
| 3'-245X | Pd | 1 | 3' | Ph | H | H | AME2 | H | H | H | H | H | H | acac | | |
| 3'-245Y | Pd | 0 | 3' | Ph | H | H | AME2 | | H | H | H | H | H | H | — | — |
| 3'-246 | Pd | 1 | 3' | Ph | H | AME2 | | H | H | H | H | H | H | H | pic | |
| 3'-246X | Pd | 1 | 3' | Ph | H | AME2 | H | H | H | H | H | H | H | acac | | |
| 3'-246Y | Pd | 0 | 3' | Ph | H | AME2 | | H | H | H | H | H | H | H | — | — |
| 3'-247 | Pd | 1 | 3' | Ph | H | H | EAE1 | | H | H | H | H | H | H | pic | |
| 3'-247X | Pd | 1 | 3' | Ph | H | H | EAE1 | H | H | H | H | H | H | acac | | |
| 3'-247Y | Pd | 0 | 3' | Ph | H | H | EAE1 | | H | H | H | H | H | H | — | — |
| 3'-248 | Pd | 1 | 3' | Ph | H | EAE1 | | H | H | H | H | H | H | H | pic | |
| 3'-248X | Pd | 1 | 3' | Ph | H | EAE1 | H | H | H | H | H | H | H | acac | | |
| 3'-248Y | Pd | 0 | 3' | Ph | H | EAE1 | | H | H | H | H | H | H | H | — | — |
| 3'-249 | Pd | 1 | 3' | Ph | H | H | EAE2 | | H | H | H | H | H | H | pic | |
| 3'-249X | Pd | 1 | 3' | Ph | H | H | EAE2 | H | H | H | H | H | H | acac | | |
| 3'-249Y | Pd | 0 | 3' | Ph | H | H | EAE2 | | H | H | H | H | H | H | — | — |
| 3'-250 | Pd | 1 | 3' | Ph | H | EAE2 | | H | H | H | H | H | H | H | pic | |
| 3'-250X | Pd | 1 | 3' | Ph | H | EAE2 | H | H | H | H | H | H | H | acac | | |
| 3'-250Y | Pd | 0 | 3' | Ph | H | EAE2 | | H | H | H | H | H | H | H | — | — |
| 3'-251 | Pd | 1 | 3' | Ph | H | H | AAE1 | | H | H | H | H | H | H | pic | |
| 3'-251X | Pd | 1 | 3' | Ph | H | H | AAE1 | H | H | H | H | H | H | acac | | |
| 3'-251Y | Pd | 0 | 3' | Ph | H | H | AAE1 | | H | H | H | H | H | H | — | — |
| 3'-252 | Pd | 1 | 3' | Ph | H | AAE1 | | H | H | H | H | H | H | H | pic | |
| 3'-252X | Pd | 1 | 3' | Ph | H | AAE1 | H | H | H | H | H | H | H | acac | | |
| 3'-252Y | Pd | 0 | 3' | Ph | H | AAE1 | | H | H | H | H | H | H | H | — | — |
| 3'-253 | Pd | 1 | 3' | Ph | H | H | AAE2 | | H | H | H | H | H | H | pic | |
| 3'-253X | Pd | 1 | 3' | Ph | H | H | AAE2 | H | H | H | H | H | H | acac | | |
| 3'-253Y | Pd | 0 | 3' | Ph | H | H | AAE2 | | H | H | H | H | H | H | — | — |
| 3'-254 | Pd | 1 | 3' | Ph | H | AAE2 | | H | H | H | H | H | H | H | pic | |
| 3'-254X | Pd | 1 | 3' | Ph | H | AAE2 | H | H | H | H | H | H | H | acac | | |
| 3'-254Y | Pd | 0 | 3' | Ph | H | AAE2 | | H | H | H | H | H | H | H | — | — |
| 3'-255 | Pd | 1 | 3' | Ph | H | H | PME1 | | H | H | H | H | H | H | pic | |
| 3'-255X | Pd | 1 | 3' | Ph | H | H | PME1 | H | H | H | H | H | H | acac | | |
| 3'-255Y | Pd | 0 | 3' | Ph | H | H | PME1 | | H | H | H | H | H | H | — | — |
| 3'-256 | Pd | 1 | 3' | Ph | H | PME1 | | H | H | H | H | H | H | H | pic | |
| 3'-256X | Pd | 1 | 3' | Ph | H | PME1 | H | H | H | H | H | H | H | acac | | |
| 3'-256Y | Pd | 0 | 3' | Ph | H | PME1 | | H | H | H | H | H | H | H | — | — |
| 3'-257 | Pd | 1 | 3' | Ph | H | H | PME2 | | H | H | H | H | H | H | pic | |
| 3'-257X | Pd | 1 | 3' | Ph | H | H | PME2 | H | H | H | H | H | H | acac | | |
| 3'-257Y | Pd | 0 | 3' | Ph | H | H | PME2 | | H | H | H | H | H | H | — | — |
| 3'-258 | Pd | 1 | 3' | Ph | H | PME2 | | H | H | H | H | H | H | H | pic | |
| 3'-258X | Pd | 1 | 3' | Ph | H | PME2 | H | H | H | H | H | H | H | acac | | |
| 3'-258Y | Pd | 0 | 3' | Ph | H | PME2 | | H | H | H | H | H | H | H | — | — |
| 3'-259 | Pd | 1 | 3' | Ph | H | H | MET1 | | H | H | H | H | H | H | pic | |
| 3'-259X | Pd | 1 | 3' | Ph | H | H | MET1 | H | H | H | H | H | H | acac | | |
| 3'-259Y | Pd | 0 | 3' | Ph | H | H | MET1 | | H | H | H | H | H | H | — | — |
| 3'-260 | Pd | 1 | 3' | Ph | H | MET1 | | H | H | H | H | H | H | H | pic | |
| 3'-260X | Pd | 1 | 3' | Ph | H | MET1 | H | H | H | H | H | H | H | acac | | |
| 3'-260Y | Pd | 0 | 3' | Ph | H | MET1 | | H | H | H | H | H | H | H | — | — |
| 3'-261 | Pd | 1 | 3' | Ph | H | H | MET2 | | H | H | H | H | H | H | pic | |
| 3'-261X | Pd | 1 | 3' | Ph | H | H | MET2 | H | H | H | H | H | H | acac | | |
| 3'-261Y | Pd | 0 | 3' | Ph | H | H | MET2 | | H | H | H | H | H | H | — | — |
| 3'-262 | Pd | 1 | 3' | Ph | H | MET2 | | H | H | H | H | H | H | H | pic | |
| 3'-262X | Pd | 1 | 3' | Ph | H | MET2 | H | H | H | H | H | H | H | acac | | |
| 3'-262Y | Pd | 0 | 3' | Ph | H | MET2 | | H | H | H | H | H | H | H | — | — |
| 3'-263 | Pd | 1 | 3' | Ph | H | H | EE1 | | H | H | H | H | H | H | pic | |
| 3'-263X | Pd | 1 | 3' | Ph | H | H | EE1 | H | H | H | H | H | H | acac | | |
| 3'-263Y | Pd | 0 | 3' | Ph | H | H | EE1 | | H | H | H | H | H | H | — | — |
| 3'-264 | Pd | 1 | 3' | Ph | H | EE1 | | H | H | H | H | H | H | H | pic | |
| 3'-264X | Pd | 1 | 3' | Ph | H | EE1 | H | H | H | H | H | H | H | acac | | |
| 3'-264Y | Pd | 0 | 3' | Ph | H | EE1 | | H | H | H | H | H | H | H | — | — |
| 3'-265 | Pd | 1 | 3' | Ph | H | H | EE2 | | H | H | H | H | H | H | pic | |
| 3'-265X | Pd | 1 | 3' | Ph | H | H | EE2 | H | H | H | H | H | H | acac | | |
| 3'-265Y | Pd | 0 | 3' | Ph | H | H | EE2 | | H | H | H | H | H | H | — | — |

TABLE 45-continued

| No. | M | m | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 3'-266 | Pd | 1 | 3' | | Ph | H | EE2 | | H | | H | H | H | H | H | pic |
| 3'-266X | Pd | 1 | 3' | | Ph | H | EE2 | | H | | H | H | H | H | acac | |
| 3'-266Y | Pd | 0 | 3' | | Ph | H | EE2 | | H | | H | H | H | H | — | — |
| 3'-267 | Pd | 1 | 3' | | Ph | H | H | MS1 | | | H | H | H | H | H | pic |
| 3'-267X | Pd | 1 | 3' | | Ph | H | H | MS1 | H | | H | H | H | H | acac | |
| 3'-267Y | Pd | 0 | 3' | | Ph | H | H | MS1 | | | H | H | H | H | — | — |
| 3'-268 | Pd | 1 | 3' | | Ph | H | MS1 | | H | | H | H | H | H | H | pic |
| 3'-268X | Pd | 1 | 3' | | Ph | H | MS1 | H | | | H | H | H | H | acac | |
| 3'-268Y | Pd | 0 | 3' | | Ph | H | MS1 | | H | | H | H | H | H | — | — |
| 3'-269 | Pd | 1 | 3' | | Ph | H | H | MS2 | | | H | H | H | H | H | pic |
| 3'-269X | Pd | 1 | 3' | | Ph | H | H | MS2 | H | | H | H | H | H | acac | |
| 3'-269Y | Pd | 0 | 3' | | Ph | H | H | MS2 | | | H | H | H | H | — | — |
| 3'-270 | Pd | 1 | 3' | | Ph | H | MS2 | | H | | H | H | H | H | H | pic |
| 3'-270X | Pd | 1 | 3' | | Ph | H | MS2 | H | | | H | H | H | H | acac | |
| 3'-270Y | Pd | 0 | 3' | | Ph | H | MS2 | | H | | H | H | H | H | — | — |

TABLE 46

| No. | M | m | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 4'-167 | Pd | 1 | 4' | | Ph | H | H | H | H | $CH_3$ | H | H | H | H | pic | |
| 4'-167X | Pd | 1 | 4' | | Ph | H | H | H | H | $CH_3$ | H | H | H | H | acac | |
| 4'-167Y | Pd | 0 | 4' | | Ph | H | H | H | H | $CH_3$ | H | H | H | H | — | — |
| 4'-168 | Pd | 1 | 4' | | Ph | H | H | H | H | $^tC_4H_9$ | H | H | H | H | pic | |
| 4'-168X | Pd | 1 | 4' | | Ph | H | H | H | H | $^tC_4H_9$ | H | H | H | H | acac | |
| 4'-168Y | Pd | 0 | 4' | | Ph | H | H | H | H | $^tC_4H_9$ | H | H | H | H | — | — |
| 4'-169 | Pd | 1 | 4' | | Ph | H | F | H | F | $CH_3$ | H | H | H | H | pic | |
| 4'-169X | Pd | 1 | 4' | | Ph | H | F | H | F | $CH_3$ | H | H | H | H | acac | |
| 4'-169Y | Pd | 0 | 4' | | Ph | H | F | H | F | $CH_3$ | H | H | H | H | — | — |
| 4'-170 | Pd | 1 | 4' | | Ph | H | F | H | F | $^tC_4H_9$ | H | H | H | H | pic | |
| 4'-170X | Pd | 1 | 4' | | Ph | H | F | H | F | $^tC_4H_9$ | H | H | H | H | acac | |
| 4'-170Y | Pd | 0 | 4' | | Ph | H | F | H | F | $^tC_4H_9$ | H | H | H | H | — | — |
| 4'-171 | Pd | 1 | 4' | | Ph | F | H | H | F | $CH_3$ | H | H | H | H | pic | |
| 4'-171X | Pd | 1 | 4' | | Ph | F | H | H | F | $CH_3$ | H | H | H | H | acac | |
| 4'-171Y | Pd | 0 | 4' | | Ph | F | H | H | F | $CH_3$ | H | H | H | H | — | — |
| 4'-172 | Pd | 1 | 4' | | Ph | F | H | H | F | $^tC_4H_9$ | H | H | H | H | pic | |
| 4'-172X | Pd | 1 | 4' | | Ph | F | H | H | F | $^tC_4H_9$ | H | H | H | H | acac | |
| 4'-172Y | Pd | 0 | 4' | | Ph | F | H | H | F | $^tC_4H_9$ | H | H | H | H | — | — |
| 4'-173 | Pd | 1 | 4' | | Ph | $CF_3$ | H | $CF_3$ | H | $CH_3$ | H | H | H | H | pic | |
| 4'-173X | Pd | 1 | 4' | | Ph | $CF_3$ | H | $CF_3$ | H | $CH_3$ | H | H | H | H | acac | |
| 4'-173Y | Pd | 0 | 4' | | Ph | $CF_3$ | H | $CF_3$ | H | $CH_3$ | H | H | H | H | — | — |
| 4'-174 | Pd | 1 | 4' | | Ph | $CF_3$ | H | $CF_3$ | H | $^tC_4H_9$ | H | H | H | H | pic | |
| 4'-174X | Pd | 1 | 4' | | Ph | $CF_3$ | H | $CF_3$ | H | $^tC_4H_9$ | H | H | H | H | acac | |
| 4'-174Y | Pd | 0 | 4' | | Ph | $CF_3$ | H | $CF_3$ | H | $^tC_4H_9$ | H | H | H | H | — | — |
| 4'-175 | Pd | 1 | 4' | | Ph | H | F | $CF_3$ | H | $CH_3$ | H | H | H | H | pic | |
| 4'-175X | Pd | 1 | 4' | | Ph | H | F | $CF_3$ | H | $CH_3$ | H | H | H | H | acac | |
| 4'-175Y | Pd | 0 | 4' | | Ph | H | F | $CF_3$ | H | $CH_3$ | H | H | H | H | — | — |
| 4'-176 | Pd | 1 | 4' | | Ph | F | H | $CF_3$ | H | $CH_3$ | H | H | H | H | pic | |
| 4'-176X | Pd | 1 | 4' | | Ph | F | H | $CF_3$ | H | $CH_3$ | H | H | H | H | acac | |
| 4'-176Y | Pd | 0 | 4' | | Ph | F | H | $CF_3$ | H | $CH_3$ | H | H | H | H | — | — |
| 4'-177 | Pd | 1 | 4' | | Ph | F | F | F | F | $CH_3$ | H | H | H | H | pic | |
| 4'-177X | Pd | 1 | 4' | | Ph | F | F | F | F | $CH_3$ | H | H | H | H | acac | |
| 4'-177Y | Pd | 0 | 4' | | Ph | F | F | F | F | $CH_3$ | H | H | H | H | — | — |
| 4'-178 | Pd | 1 | 4' | | Ph | H | F | H | $CH_3$ | $CH_3$ | H | H | H | H | pic | |
| 4'-178X | Pd | 1 | 4' | | Ph | H | F | H | $CH_3$ | $CH_3$ | H | H | H | H | acac | |
| 4'-178Y | Pd | 0 | 4' | | Ph | H | F | H | $CH_3$ | $CH_3$ | H | H | H | H | — | — |
| 4'-179 | Pd | 1 | 4' | | Ph | H | F | H | $CH_3$ | $^tC_4H_9$ | H | H | H | H | pic | |
| 4'-179X | Pd | 1 | 4' | | Ph | H | F | H | $CH_3$ | $^tC_4H_9$ | H | H | H | H | acac | |
| 4'-179Y | Pd | 0 | 4' | | Ph | H | F | H | $CH_3$ | $^tC_4H_9$ | H | H | H | H | — | — |
| 4'-180 | Pd | 1 | 4' | | Ph | H | F | H | $^tC_4H_9$ | $CH_3$ | H | H | H | H | pic | |
| 4'-180X | Pd | 1 | 4' | | Ph | H | F | H | $^tC_4H_9$ | $CH_3$ | H | H | H | H | acac | |
| 4'-180Y | Pd | 0 | 4' | | Ph | H | F | H | $^tC_4H_9$ | $CH_3$ | H | H | H | H | — | — |
| 4'-181 | Pd | 1 | 4' | | Ph | H | F | H | $^tC_4H_9$ | $^tC_4H_9$ | H | H | H | H | pic | |
| 4'-181X | Pd | 1 | 4' | | Ph | H | F | H | $^tC_4H_9$ | $^tC_4H_9$ | H | H | H | H | acac | |
| 4'-181Y | Pd | 0 | 4' | | Ph | H | F | H | $^tC_4H_9$ | $^tC_4H_9$ | H | H | H | H | — | — |
| 4'-182 | Pd | 1 | 4' | | Ph | H | $CF_3$ | H | $CF_3$ | $CH_3$ | H | H | H | H | pic | |
| 4'-182X | Pd | 1 | 4' | | Ph | H | $CF_3$ | H | $CF_3$ | $CH_3$ | H | H | H | H | acac | |
| 4'-182Y | Pd | 0 | 4' | | Ph | H | $CF_3$ | H | $CF_3$ | $CH_3$ | H | H | H | H | — | — |
| 4'-183 | Pd | 1 | 4' | | Ph | H | $CF_3$ | H | $CF_3$ | $^tC_4H_9$ | H | H | H | H | pic | |
| 4'-183X | Pd | 1 | 4' | | Ph | H | $CF_3$ | H | $CF_3$ | $^tC_4H_9$ | H | H | H | H | acac | |
| 4'-183Y | Pd | 0 | 4' | | Ph | H | $CF_3$ | H | $CF_3$ | $^tC_4H_9$ | H | H | H | H | — | — |
| 4'-184 | Pd | 1 | 4' | | Ph | $CF_3$ | H | H | $^tC_4H_9$ | $CH_3$ | H | H | H | H | pic | |
| 4'-184X | Pd | 1 | 4' | | Ph | $CF_3$ | H | H | $^tC_4H_9$ | $CH_3$ | H | H | H | H | acac | |
| 4'-184Y | Pd | 0 | 4' | | Ph | $CF_3$ | H | H | $^tC_4H_9$ | $CH_3$ | H | H | H | H | — | — |

TABLE 46-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-185 | Pd | 1 | 4' | Ph | CF$_3$ | H | H | $^tC_4H_9$ | $^tC_4H_9$ | H | H | H | H | pic | |
| 4'-185X | Pd | 1 | 4' | Ph | CF$_3$ | H | H | $^tC_4H_9$ | $^tC_4H_9$ | H | H | H | H | acac | |
| 4'-185Y | Pd | 0 | 4' | Ph | CF$_3$ | H | H | $^tC_4H_9$ | $^tC_4H_9$ | H | H | H | H | — | — |
| 4'-186 | Pd | 1 | 4' | Ph | H | CF$_3$ | H | $^tC_4H_9$ | CH$_3$ | H | H | H | H | pic | |
| 4'-186X | Pd | 1 | 4' | Ph | H | CF$_3$ | H | $^tC_4H_9$ | CH$_3$ | H | H | H | H | acac | |
| 4'-186Y | Pd | 0 | 4' | Ph | H | CF$_3$ | H | $^tC_4H_9$ | CH$_3$ | H | H | H | H | — | — |
| 4'-187 | Pd | 1 | 4' | Ph | H | CF$_3$ | H | $^tC_4H_9$ | $^tC_4H_9$ | H | H | H | H | pic | |
| 4'-187X | Pd | 1 | 4' | Ph | H | CF$_3$ | H | $^tC_4H_9$ | $^tC_4H_9$ | H | H | H | H | acac | |
| 4'-187Y | Pd | 0 | 4' | Ph | H | CF$_3$ | H | $^tC_4H_9$ | $^tC_4H_9$ | H | H | H | H | — | — |
| 4'-188 | Pd | 1 | 4' | Ph | H | CF$_3$ | H | CH$_3$ | CH$_3$ | H | H | H | H | pic | |
| 4'-188X | Pd | 1 | 4' | Ph | H | CF$_3$ | H | CH$_3$ | CH$_3$ | H | H | H | H | acac | |
| 4'-188Y | Pd | 0 | 4' | Ph | H | CF$_3$ | H | CH$_3$ | CH$_3$ | H | H | H | H | — | — |
| 4'-189 | Pd | 1 | 4' | Ph | H | CF$_3$ | CF$_3$ | H | CH$_3$ | H | H | H | H | pic | |
| 4'-189X | Pd | 1 | 4' | Ph | H | CF$_3$ | CF$_3$ | H | CH$_3$ | H | H | H | H | acac | |
| 4'-189Y | Pd | 0 | 4' | Ph | H | CF$_3$ | CF$_3$ | H | CH$_3$ | H | H | H | H | — | — |
| 4'-190 | Pd | 1 | 4' | Ph | H | H | NO$_2$ | H | CH$_3$ | H | H | H | H | pic | |
| 4'-190X | Pd | 1 | 4' | Ph | H | H | NO$_2$ | H | CH$_3$ | H | H | H | H | acac | |
| 4'-190Y | Pd | 0 | 4' | Ph | H | H | NO$_2$ | H | CH$_3$ | H | H | H | H | — | — |
| 4'-191 | Pd | 1 | 4' | Ph | H | H | NO$_2$ | H | $^tC_4H_9$ | H | H | H | H | pic | |
| 4'-191X | Pd | 1 | 4' | Ph | H | H | NO$_2$ | H | $^tC_4H_9$ | H | H | H | H | acac | |
| 4'-191Y | Pd | 0 | 4' | Ph | H | H | NO$_2$ | H | $^tC_4H_9$ | H | H | H | H | — | — |
| 4'-192 | Pd | 1 | 4' | Ph | F | H | NO$_2$ | H | CH$_3$ | H | H | H | H | pic | |
| 4'-192X | Pd | 1 | 4' | Ph | F | H | NO$_2$ | H | CH$_3$ | H | H | H | H | acac | |
| 4'-192Y | Pd | 0 | 4' | Ph | F | H | NO$_2$ | H | CH$_3$ | H | H | H | H | — | — |
| 4'-193 | Pd | 1 | 4' | Ph | F | H | NO$_2$ | F | CH$_3$ | H | H | H | H | pic | |
| 4'-193X | Pd | 1 | 4' | Ph | F | H | NO$_2$ | F | CH$_3$ | H | H | H | H | acac | |
| 4'-193Y | Pd | 0 | 4' | Ph | F | H | NO$_2$ | F | CH$_3$ | H | H | H | H | — | — |
| 4'-194 | Pd | 1 | 4' | Ph | H | NO$_2$ | H | NO$_2$ | CH$_3$ | H | H | H | H | pic | |
| 4'-194X | Pd | 1 | 4' | Ph | H | NO$_2$ | H | NO$_2$ | CH$_3$ | H | H | H | H | acac | |
| 4'-194Y | Pd | 0 | 4' | Ph | H | NO$_2$ | H | NO$_2$ | CH$_3$ | H | H | H | H | — | — |
| 4'-195 | Pd | 1 | 4' | Ph | H | NO$_2$ | H | NO$_2$ | $^tC_4H_9$ | H | H | H | H | pic | |
| 4'-195X | Pd | 1 | 4' | Ph | H | NO$_2$ | H | NO$_2$ | $^tC_4H_9$ | H | H | H | H | acac | |
| 4'-195Y | Pd | 0 | 4' | Ph | H | NO$_2$ | H | NO$_2$ | $^tC_4H_9$ | H | H | H | H | — | — |
| 4'-196 | Pd | 1 | 4' | Ph | NO$_2$ | H | H | NO$_2$ | CH$_3$ | H | H | H | H | pic | |
| 4'-196X | Pd | 1 | 4' | Ph | NO$_2$ | H | H | NO$_2$ | CH$_3$ | H | H | H | H | acac | |
| 4'-196Y | Pd | 0 | 4' | Ph | NO$_2$ | H | H | NO$_2$ | CH$_3$ | H | H | H | H | — | — |
| 4'-197 | Pd | 1 | 4' | Ph | NO$_2$ | H | H | NO$_2$ | $^tC_4H_9$ | H | H | H | H | pic | |
| 4'-197X | Pd | 1 | 4' | Ph | NO$_2$ | H | H | NO$_2$ | $^tC_4H_9$ | H | H | H | H | acac | |
| 4'-197Y | Pd | 0 | 4' | Ph | NO$_2$ | H | H | NO$_2$ | $^tC_4H_9$ | H | H | H | H | — | — |
| 4'-198 | Pd | 1 | 4' | Ph | H | H | CF$_3$ | H | CH$_3$ | H | H | H | H | pic | |
| 4'-198X | Pd | 1 | 4' | Ph | H | H | CF$_3$ | H | CH$_3$ | H | H | H | H | acac | |
| 4'-198Y | Pd | 0 | 4' | Ph | H | H | CF$_3$ | H | CH$_3$ | H | H | H | H | — | — |
| 4'-199 | Pd | 1 | 4' | Ph | H | H | CF$_3$ | H | $^tC_4H_9$ | H | H | H | H | pic | |
| 4'-199X | Pd | 1 | 4' | Ph | H | H | CF$_3$ | H | $^tC_4H_9$ | H | H | H | H | acac | |
| 4'-199Y | Pd | 0 | 4' | Ph | H | H | CF$_3$ | H | $^tC_4H_9$ | H | H | H | H | — | — |
| 4'-200 | Pd | 1 | 4' | Ph | H | Cl | CF$_3$ | H | CH$_3$ | H | H | H | H | pic | |
| 4'-200X | Pd | 1 | 4' | Ph | H | Cl | CF$_3$ | H | CH$_3$ | H | H | H | H | acac | |
| 4'-200Y | Pd | 0 | 4' | Ph | H | Cl | CF$_3$ | H | CH$_3$ | H | H | H | H | — | — |
| 4'-201 | Pd | 1 | 4' | Ph | H | Cl | CF$_3$ | H | $^tC_4H_9$ | H | H | H | H | pic | |
| 4'-201X | Pd | 1 | 4' | Ph | H | Cl | CF$_3$ | H | $^tC_4H_9$ | H | H | H | H | acac | |
| 4'-201Y | Pd | 0 | 4' | Ph | H | Cl | CF$_3$ | H | $^tC_4H_9$ | H | H | H | H | — | — |
| 4'-202 | Pd | 1 | 4' | Ph | H | NO$_2$ | H | H | CH$_3$ | H | H | H | H | pic | |
| 4'-202X | Pd | 1 | 4' | Ph | H | NO$_2$ | H | H | CH$_3$ | H | H | H | H | acac | |
| 4'-202Y | Pd | 0 | 4' | Ph | H | NO$_2$ | H | H | CH$_3$ | H | H | H | H | — | — |
| 4'-203 | Pd | 1 | 4' | Ph | H | CF$_3$ | H | H | CH$_3$ | H | H | H | H | pic | |
| 4'-203X | Pd | 1 | 4' | Ph | H | CF$_3$ | H | H | CH$_3$ | H | H | H | H | acac | |
| 4'-203Y | Pd | 0 | 4' | Ph | H | CF$_3$ | H | H | CH$_3$ | H | H | H | H | — | — |
| 4'-204 | Pd | 1 | 4' | Ph | H | NO$_2$ | H | CH$_3$ | CH$_3$ | H | H | H | H | pic | |
| 4'-204X | Pd | 1 | 4' | Ph | H | NO$_2$ | H | CH$_3$ | CH$_3$ | H | H | H | H | acac | |
| 4'-204Y | Pd | 0 | 4' | Ph | H | NO$_2$ | H | CH$_3$ | CH$_3$ | H | H | H | H | — | — |
| 4'-205 | Pd | 1 | 4' | Ph | H | NO$_2$ | H | CH$_3$ | $^tC_4H_9$ | H | H | H | H | pic | |
| 4'-205X | Pd | 1 | 4' | Ph | H | NO$_2$ | H | CH$_3$ | $^tC_4H_9$ | H | H | H | H | acac | |
| 4'-205Y | Pd | 0 | 4' | Ph | H | NO$_2$ | H | CH$_3$ | $^tC_4H_9$ | H | H | H | H | — | — |
| 4'-206 | Pd | 1 | 4' | Ph | H | NO$_2$ | H | $^tC_4H_9$ | CH$_3$ | H | H | H | H | pic | |
| 4'-206X | Pd | 1 | 4' | Ph | H | NO$_2$ | H | $^tC_4H_9$ | CH$_3$ | H | H | H | H | acac | |
| 4'-206Y | Pd | 0 | 4' | Ph | H | NO$_2$ | H | $^tC_4H_9$ | CH$_3$ | H | H | H | H | — | — |
| 4'-207 | Pd | 1 | 4' | Ph | H | NO$_2$ | H | $^tC_4H_9$ | $^tC_4H_9$ | H | H | H | H | pic | |
| 4'-207X | Pd | 1 | 4' | Ph | H | NO$_2$ | H | $^tC_4H_9$ | $^tC_4H_9$ | H | H | H | H | acac | |
| 4'-207Y | Pd | 0 | 4' | Ph | H | NO$_2$ | H | $^tC_4H_9$ | $^tC_4H_9$ | H | H | H | H | — | — |
| 4'-208 | Pd | 1 | 4' | Ph | H | H | CH$_3$O | H | CH$_3$ | H | H | H | H | pic | |
| 4'-208X | Pd | 1 | 4' | Ph | H | H | CH$_3$O | H | CH$_3$ | H | H | H | H | acac | |
| 4'-208Y | Pd | 0 | 4' | Ph | H | H | CH$_3$O | H | CH$_3$ | H | H | H | H | — | — |
| 4'-209 | Pd | 1 | 4' | Ph | H | CH$_3$O | H | H | CH$_3$ | H | H | H | H | pic | |
| 4'-209X | Pd | 1 | 4' | Ph | H | CH$_3$O | H | H | CH$_3$ | H | H | H | H | acac | |
| 4'-209Y | Pd | 0 | 4' | Ph | H | CH$_3$O | H | H | CH$_3$ | H | H | H | H | — | — |
| 4'-210 | Pd | 1 | 4' | Ph | H | CH$_3$O | H | CH$_3$ | CH$_3$ | H | H | H | H | pic | |
| 4'-210X | Pd | 1 | 4' | Ph | H | CH$_3$O | H | CH$_3$ | CH$_3$ | H | H | H | H | acac | |

TABLE 46-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-210Y | Pd | 0 | 4' | Ph | H | CH₃O | H | CH₃ | CH₃ | H | H | H | H | — | — |
| 4'-211 | Pd | 1 | 4' | Ph | H | CH₃O | H | ᵗC₄H₉ | CH₃ | H | H | H | H | | pic |
| 4'-211X | Pd | 1 | 4' | Ph | H | CH₃O | H | ᵗC₄H₉ | CH₃ | H | H | H | H | | acac |
| 4'-211Y | Pd | 0 | 4' | Ph | H | CH₃O | H | ᵗC₄H₉ | CH₃ | H | H | H | H | — | — |
| 4'-212 | Pd | 1 | 4' | Ph | H | Si(CH₃)₃ | H | H | CH₃ | H | H | H | H | | pic |
| 4'-212X | Pd | 1 | 4' | Ph | H | Si(CH₃)₃ | H | H | CH₃ | H | H | H | H | | acac |
| 4'-212Y | Pd | 0 | 4' | Ph | H | Si(CH₃)₃ | H | H | CH₃ | H | H | H | H | — | — |
| 4'-213 | Pd | 1 | 4' | Ph | H | Si(CH₃)₃ | H | H | ᵗC₄H₉ | H | H | H | H | | pic |
| 4'-213X | Pd | 1 | 4' | Ph | H | Si(CH₃)₃ | H | H | ᵗC₄H₉ | H | H | H | H | | acac |
| 4'-213Y | Pd | 0 | 4' | Ph | H | Si(CH₃)₃ | H | H | ᵗC₄H₉ | H | H | H | H | — | — |
| 4'-214 | Pd | 1 | 4' | Ph | H | H | Si(CH₃)₃ | H | CH₃ | H | H | H | H | | pic |
| 4'-214X | Pd | 1 | 4' | Ph | H | H | Si(CH₃)₃ | H | CH₃ | H | H | H | H | | acac |
| 4'-214Y | Pd | 0 | 4' | Ph | H | H | Si(CH₃)₃ | H | CH₃ | H | H | H | H | — | — |
| 4'-215 | Pd | 1 | 4' | Ph | H | H | H | Si(CH₃)₃ | CH₃ | H | H | H | H | | pic |
| 4'-215X | Pd | 1 | 4' | Ph | H | H | H | Si(CH₃)₃ | CH₃ | H | H | H | H | | acac |
| 4'-215Y | Pd | 0 | 4' | Ph | H | H | H | Si(CH₃)₃ | CH₃ | H | H | H | H | — | — |
| 4'-216 | Pd | 1 | 4' | Ph | H | F | H | Si(CH₃)₃ | CH₃ | H | H | H | H | | pic |
| 4'-216X | Pd | 1 | 4' | Ph | H | F | H | Si(CH₃)₃ | CH₃ | H | H | H | H | | acac |
| 4'-216Y | Pd | 0 | 4' | Ph | H | F | H | Si(CH₃)₃ | CH₃ | H | H | H | H | — | — |
| 4'-217 | Pd | 1 | 4' | Ph | H | CF₃ | H | Si(CH₃)₃ | CH₃ | H | H | H | H | | pic |
| 4'-217X | Pd | 1 | 4' | Ph | H | CF₃ | H | Si(CH₃)₃ | CH₃ | H | H | H | H | | acac |
| 4'-217Y | Pd | 0 | 4' | Ph | H | CF₃ | H | Si(CH₃)₃ | CH₃ | H | H | H | H | — | — |
| 4'-218 | Pd | 1 | 4' | Ph | H | CF₃ | H | Si(CH₃)₃ | ᵗC₄H₉ | H | H | H | H | | pic |
| 4'-218X | Pd | 1 | 4' | Ph | H | CF₃ | H | Si(CH₃)₃ | ᵗC₄H₉ | H | H | H | H | | acac |
| 4'-218Y | Pd | 0 | 4' | Ph | H | CF₃ | H | Si(CH₃)₃ | ᵗC₄H₉ | H | H | H | H | — | — |
| 4'-219 | Pd | 1 | 4' | Ph | H | Si(CH₃)₃ | H | F | CH₃ | H | H | H | H | | pic |
| 4'-219X | Pd | 1 | 4' | Ph | H | Si(CH₃)₃ | H | F | CH₃ | H | H | H | H | | acac |
| 4'-219Y | Pd | 0 | 4' | Ph | H | Si(CH₃)₃ | H | F | CH₃ | H | H | H | H | — | — |
| 4'-220 | Pd | 1 | 4' | Ph | H | Si(CH₃)₃ | H | F | ᵗC₄H₉ | H | H | H | H | | pic |
| 4'-220X | Pd | 1 | 4' | Ph | H | Si(CH₃)₃ | H | F | ᵗC₄H₉ | H | H | H | H | | acac |
| 4'-220Y | Pd | 0 | 4' | Ph | H | Si(CH₃)₃ | H | F | ᵗC₄H₉ | H | H | H | H | — | — |
| 4'-221 | Pd | 1 | 4' | Ph | H | Si(CH₃)₃ | H | CF₃ | CH₃ | H | H | H | H | | pic |
| 4'-221X | Pd | 1 | 4' | Ph | H | Si(CH₃)₃ | H | CF₃ | CH₃ | H | H | H | H | | acac |
| 4'-221Y | Pd | 0 | 4' | Ph | H | Si(CH₃)₃ | H | CF₃ | CH₃ | H | H | H | H | — | — |
| 4'-222 | Pd | 1 | 4' | Ph | H | Si(CH₃)₃ | H | CF₃ | ᵗC₄H₉ | H | H | H | H | | pic |
| 4'-222X | Pd | 1 | 4' | Ph | H | Si(CH₃)₃ | H | CF₃ | ᵗC₄H₉ | H | H | H | H | | acac |
| 4'-222Y | Pd | 0 | 4' | Ph | H | Si(CH₃)₃ | H | CF₃ | ᵗC₄H₉ | H | H | H | H | — | — |
| 4'-223 | Pd | 1 | 4' | Ph | Si(CH₃)₃ | H | Si(CH₃)₃ | H | CH₃ | H | H | H | H | | pic |
| 4'-223X | Pd | 1 | 4' | Ph | Si(CH₃)₃ | H | Si(CH₃)₃ | H | CH₃ | H | H | H | H | | acac |
| 4'-223Y | Pd | 0 | 4' | Ph | Si(CH₃)₃ | H | Si(CH₃)₃ | H | CH₃ | H | H | H | H | — | — |
| 4'-224 | Pd | 1 | 4' | Ph | Si(CH₃)₃ | H | Si(CH₃)₃ | H | ᵗC₄H₉ | H | H | H | H | | pic |
| 4'-224X | Pd | 1 | 4' | Ph | Si(CH₃)₃ | H | Si(CH₃)₃ | H | ᵗC₄H₉ | H | H | H | H | | acac |
| 4'-224Y | Pd | 0 | 4' | Ph | Si(CH₃)₃ | H | Si(CH₃)₃ | H | ᵗC₄H₉ | H | H | H | H | — | — |
| 4'-225 | Pd | 1 | 4' | Ph | H | H | H | COCH₃ | CH₃ | H | H | H | H | | pic |
| 4'-225X | Pd | 1 | 4' | Ph | H | H | H | COCH₃ | CH₃ | H | H | H | H | | acac |
| 4'-225Y | Pd | 0 | 4' | Ph | H | H | H | COCH₃ | CH₃ | H | H | H | H | — | — |
| 4'-226 | Pd | 1 | 4' | Ph | H | H | COCH₃ | H | CH₃ | H | H | H | H | | pic |
| 4'-226X | Pd | 1 | 4' | Ph | H | H | COCH₃ | H | CH₃ | H | H | H | H | | acac |
| 4'-226Y | Pd | 0 | 4' | Ph | H | H | COCH₃ | H | CH₃ | H | H | H | H | — | — |
| 4'-227 | Pd | 1 | 4' | Ph | H | COCH₃ | H | H | CH₃ | H | H | H | H | | pic |
| 4'-227X | Pd | 1 | 4' | Ph | H | COCH₃ | H | H | CH₃ | H | H | H | H | | acac |
| 4'-227Y | Pd | 0 | 4' | Ph | H | COCH₃ | H | H | CH₃ | H | H | H | H | — | — |
| 4'-228 | Pd | 1 | 4' | Ph | H | H | H | BL | CH₃ | H | H | H | H | | pic |
| 4'-228X | Pd | 1 | 4' | Ph | H | H | H | BL | CH₃ | H | H | H | H | | acac |
| 4'-228Y | Pd | 0 | 4' | Ph | H | H | H | BL | CH₃ | H | H | H | H | — | — |
| 4'-229 | Pd | 1 | 4' | Ph | H | H | H | BL | ᵗC₄H₉ | H | H | H | H | | pic |
| 4'-229X | Pd | 1 | 4' | Ph | H | H | H | BL | ᵗC₄H₉ | H | H | H | H | | acac |
| 4'-229Y | Pd | 0 | 4' | Ph | H | H | H | BL | ᵗC₄H₉ | H | H | H | H | — | — |
| 4'-230 | Pd | 1 | 4' | Ph | H | H | BL | H | CH₃ | H | H | H | H | | pic |
| 4'-230X | Pd | 1 | 4' | Ph | H | H | BL | H | CH₃ | H | H | H | H | | acac |
| 4'-230Y | Pd | 0 | 4' | Ph | H | H | BL | H | CH₃ | H | H | H | H | — | — |
| 4'-231 | Pd | 1 | 4' | Ph | H | H | BL | H | ᵗC₄H₉ | H | H | H | H | | pic |
| 4'-231X | Pd | 1 | 4' | Ph | H | H | BL | H | ᵗC₄H₉ | H | H | H | H | | acac |
| 4'-231Y | Pd | 0 | 4' | Ph | H | H | BL | H | ᵗC₄H₉ | H | H | H | H | — | — |
| 4'-232 | Pd | 1 | 4' | Ph | H | H | H | PL | CH₃ | H | H | H | H | | pic |
| 4'-232X | Pd | 1 | 4' | Ph | H | H | H | PL | CH₃ | H | H | H | H | | acac |
| 4'-232Y | Pd | 0 | 4' | Ph | H | H | H | PL | CH₃ | H | H | H | H | — | — |
| 4'-233 | Pd | 1 | 4' | Ph | H | H | H | PL | ᵗC₄H₉ | H | H | H | H | | pic |
| 4'-233X | Pd | 1 | 4' | Ph | H | H | H | PL | ᵗC₄H₉ | H | H | H | H | | acac |
| 4'-233Y | Pd | 0 | 4' | Ph | H | H | H | PL | ᵗC₄H₉ | H | H | H | H | — | — |
| 4'-234 | Pd | 1 | 4' | Ph | H | H | PL | H | CH₃ | H | H | H | H | | pic |
| 4'-234X | Pd | 1 | 4' | Ph | H | H | PL | H | CH₃ | H | H | H | H | | acac |
| 4'-234Y | Pd | 0 | 4' | Ph | H | H | PL | H | CH₃ | H | H | H | H | — | — |
| 4'-235 | Pd | 1 | 4' | Ph | H | H | PL | H | ᵗC₄H₉ | H | H | H | H | | pic |
| 4'-235X | Pd | 1 | 4' | Ph | H | H | PL | H | ᵗC₄H₉ | H | H | H | H | | acac |
| 4'-235Y | Pd | 0 | 4' | Ph | H | H | PL | H | ᵗC₄H₉ | H | H | H | H | — | — |
| 4'-236 | Pd | 1 | 4' | Ph | H | H | H | MEE1 | CH₃ | H | H | H | H | | pic |

TABLE 46-continued

| No. | M | m | BSS | SS G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|
| 4'-236X | Pd | 1 | 4' | Ph | H | H | | MEE1 | CH₃ | H | H | H | H | acac | |
| 4'-236Y | Pd | 0 | 4' | Ph | H | H | | MEE1 | CH₃ | H | H | H | H | — | — |
| 4'-237 | Pd | 1 | 4' | Ph | H | | MEE1 | | H | CH₃ | H | H | H | H | pic |
| 4'-237X | Pd | 1 | 4' | Ph | H | | MEE1 | | H | CH₃ | H | H | H | H | acac |
| 4'-237Y | Pd | 0 | 4' | Ph | H | | MEE1 | | H | CH₃ | H | H | H | H | — — |
| 4'-238 | Pd | 1 | 4' | Ph | H | H | | MEE2 | CH₃ | H | H | H | H | pic | |
| 4'-238X | Pd | 1 | 4' | Ph | H | H | | MEE2 | CH₃ | H | H | H | H | acac | |
| 4'-238Y | Pd | 0 | 4' | Ph | H | H | | MEE2 | CH₃ | H | H | H | H | — | — |
| 4'-239 | Pd | 1 | 4' | Ph | H | | MEE2 | | H | CH₃ | H | H | H | H | pic |
| 4'-239X | Pd | 1 | 4' | Ph | H | | MEE2 | | H | CH₃ | H | H | H | H | acac |
| 4'-239Y | Pd | 0 | 4' | Ph | H | | MEE2 | | H | CH₃ | H | H | H | H | — — |
| 4'-240 | Pd | 1 | 4' | Ph | H | H | | PA1 | CH₃ | H | H | H | H | pic | |
| 4'-240X | Pd | 1 | 4' | Ph | H | H | | PA1 | CH₃ | H | H | H | H | acac | |
| 4'-240Y | Pd | 0 | 4' | Ph | H | H | | PA1 | CH₃ | H | H | H | H | — | — |
| 4'-241 | Pd | 1 | 4' | Ph | H | | PA1 | | H | CH₃ | H | H | H | H | pic |
| 4'-241X | Pd | 1 | 4' | Ph | H | | PA1 | | H | CH₃ | H | H | H | H | acac |
| 4'-241Y | Pd | 0 | 4' | Ph | H | | PA1 | | H | CH₃ | H | H | H | H | — — |
| 4'-242 | Pd | 1 | 4' | Ph | H | H | | PA2 | CH₃ | H | H | H | H | pic | |
| 4'-242X | Pd | 1 | 4' | Ph | H | H | | PA2 | CH₃ | H | H | H | H | acac | |
| 4'-242Y | Pd | 0 | 4' | Ph | H | H | | PA2 | CH₃ | H | H | H | H | — | — |
| 4'-243 | Pd | 1 | 4' | Ph | H | | PA2 | | H | CH₃ | H | H | H | H | pic |
| 4'-243X | Pd | 1 | 4' | Ph | H | | PA2 | | H | CH₃ | H | H | H | H | acac |
| 4'-243Y | Pd | 0 | 4' | Ph | H | | PA2 | | H | CH₃ | H | H | H | H | — — |
| 4'-244 | Pd | 1 | 4' | Ph | H | H | | EA1 | CH₃ | H | H | H | H | pic | |
| 4'-244X | Pd | 1 | 4' | Ph | H | H | | EA1 | CH₃ | H | H | H | H | acac | |
| 4'-244Y | Pd | 0 | 4' | Ph | H | H | | EA1 | CH₃ | H | H | H | H | — | — |
| 4'-245 | Pd | 1 | 4' | Ph | H | | EA2 | | H | CH₃ | H | H | H | H | pic |
| 4'-245X | Pd | 1 | 4' | Ph | H | | EA2 | | H | CH₃ | H | H | H | H | acac |
| 4'-245Y | Pd | 0 | 4' | Ph | H | | EA2 | | H | CH₃ | H | H | H | H | — — |
| 4'-246 | Pd | 1 | 4' | Ph | H | H | | ME | CH₃ | H | H | H | H | pic | |
| 4'-246X | Pd | 1 | 4' | Ph | H | H | | ME | CH₃ | H | H | H | H | acac | |
| 4'-246Y | Pd | 0 | 4' | Ph | H | H | | ME | CH₃ | H | H | H | H | — | — |
| 4'-247 | Pd | 1 | 4' | Ph | H | | ME | | H | CH₃ | H | H | H | H | pic |
| 4'-247X | Pd | 1 | 4' | Ph | H | | ME | | H | CH₃ | H | H | H | H | acac |
| 4'-247Y | Pd | 0 | 4' | Ph | H | | ME | | H | CH₃ | H | H | H | H | — — |
| 4'-248 | Pd | 1 | 4' | Ph | H | H | | AT | CH₃ | H | H | H | H | pic | |
| 4'-248X | Pd | 1 | 4' | Ph | H | H | | AT | CH₃ | H | H | H | H | acac | |
| 4'-248Y | Pd | 0 | 4' | Ph | H | H | | AT | CH₃ | H | H | H | H | — | — |
| 4'-249 | Pd | 1 | 4' | Ph | H | | AT | | H | CH₃ | H | H | H | H | pic |
| 4'-249X | Pd | 1 | 4' | Ph | H | | AT | | H | CH₃ | H | H | H | H | acac |
| 4'-249Y | Pd | 0 | 4' | Ph | H | | AT | | H | CH₃ | H | H | H | H | — — |
| 4'-250 | Pd | 1 | 4' | Ph | H | H | | MES1 | CH₃ | H | H | H | H | pic | |
| 4'-250X | Pd | 1 | 4' | Ph | H | H | | MES1 | CH₃ | H | H | H | H | acac | |
| 4'-250Y | Pd | 0 | 4' | Ph | H | H | | MES1 | CH₃ | H | H | H | H | — | — |
| 4'-251 | Pd | 1 | 4' | Ph | H | | MES1 | | H | CH₃ | H | H | H | H | pic |
| 4'-251X | Pd | 1 | 4' | Ph | H | | MES1 | | H | CH₃ | H | H | H | H | acac |
| 4'-251Y | Pd | 0 | 4' | Ph | H | | MES1 | | H | CH₃ | H | H | H | H | — — |
| 4'-252 | Pd | 1 | 4' | Ph | H | H | | MES2 | CH₃ | H | H | H | H | pic | |
| 4'-252X | Pd | 1 | 4' | Ph | H | H | | MES2 | CH₃ | H | H | H | H | acac | |
| 4'-252Y | Pd | 0 | 4' | Ph | H | H | | MES2 | CH₃ | H | H | H | H | — | — |
| 4'-253 | Pd | 1 | 4' | Ph | H | | MES2 | | H | CH₃ | H | H | H | H | pic |
| 4'-253X | Pd | 1 | 4' | Ph | H | | MES2 | | H | CH₃ | H | H | H | H | acac |
| 4'-253Y | Pd | 0 | 4' | Ph | H | | MES2 | | H | CH₃ | H | H | H | H | — — |
| 4'-254 | Pd | 1 | 4' | Ph | H | H | | PS1 | CH₃ | H | H | H | H | pic | |
| 4'-254X | Pd | 1 | 4' | Ph | H | H | | PS1 | CH₃ | H | H | H | H | acac | |
| 4'-254Y | Pd | 0 | 4' | Ph | H | H | | PS1 | CH₃ | H | H | H | H | — | — |
| 4'-255 | Pd | 1 | 4' | Ph | H | | PS1 | | H | CH₃ | H | H | H | H | pic |
| 4'-255X | Pd | 1 | 4' | Ph | H | | PS1 | | H | CH₃ | H | H | H | H | acac |
| 4'-255Y | Pd | 0 | 4' | Ph | H | | PS1 | | H | CH₃ | H | H | H | H | — — |
| 4'-256 | Pd | 1 | 4' | Ph | H | H | | PS2 | CH₃ | H | H | H | H | pic | |
| 4'-256X | Pd | 1 | 4' | Ph | H | H | | PS2 | CH₃ | H | H | H | H | acac | |
| 4'-256Y | Pd | 0 | 4' | Ph | H | H | | PS2 | CH₃ | H | H | H | H | — | — |
| 4'-257 | Pd | 1 | 4' | Ph | H | | PS2 | | H | CH₃ | H | H | H | H | pic |
| 4'-257X | Pd | 1 | 4' | Ph | H | | PS2 | | H | CH₃ | H | H | H | H | acac |
| 4'-257Y | Pd | 0 | 4' | Ph | H | | PS2 | | H | CH₃ | H | H | H | H | — — |
| 4'-258 | Pd | 1 | 4' | Ph | H | H | | BAL1 | CH₃ | H | H | H | H | pic | |
| 4'-258X | Pd | 1 | 4' | Ph | H | H | | BAL1 | CH₃ | H | H | H | H | acac | |
| 4'-258Y | Pd | 0 | 4' | Ph | H | H | | BAL1 | CH₃ | H | H | H | H | — | — |
| 4'-259 | Pd | 1 | 4' | Ph | H | | BAL1 | | H | CH₃ | H | H | H | H | pic |
| 4'-259X | Pd | 1 | 4' | Ph | H | | BAL1 | | H | CH₃ | H | H | H | H | acac |
| 4'-259Y | Pd | 0 | 4' | Ph | H | | BAL1 | | H | CH₃ | H | H | H | H | — — |
| 4'-260 | Pd | 1 | 4' | Ph | H | H | | BAL2 | CH₃ | H | H | H | H | pic | |
| 4'-260X | Pd | 1 | 4' | Ph | H | H | | BAL2 | CH₃ | H | H | H | H | acac | |
| 4'-260Y | Pd | 0 | 4' | Ph | H | H | | BAL2 | CH₃ | H | H | H | H | — | — |
| 4'-261 | Pd | 1 | 4' | Ph | H | | BAL2 | | H | CH₃ | H | H | H | H | pic |
| 4'-261X | Pd | 1 | 4' | Ph | H | | BAL2 | | H | CH₃ | H | H | H | H | acac |
| 4'-261Y | Pd | 0 | 4' | Ph | H | | BAL2 | | H | CH₃ | H | H | H | H | — — |

TABLE 46-continued

| No. | M | m | BSS | SS G | T$^1$ | T$^2$ | T$^3$ | T$^4$ | T$^5$ | T$^6$ | T$^7$ | T$^8$ | T$^9$ | L$^1$ | L$^2$ |
|---|---|---|---|---|---|---|---|---|---|---|---|---|---|---|---|
| 4'-262 | Pd | 1 | 4' | Ph | H | H | | MEK1 | CH$_3$ | H | H | H | H | pic | |
| 4'-262X | Pd | 1 | 4' | Ph | H | H | | MEK1 | CH$_3$ | H | H | H | H | acac | |
| 4'-262Y | Pd | 0 | 4' | Ph | H | H | | MEK1 | CH$_3$ | H | H | H | H | — | — |
| 4'-263 | Pd | 1 | 4' | Ph | H | | MEK1 | H | CH$_3$ | H | H | H | H | pic | |
| 4'-263X | Pd | 1 | 4' | Ph | H | | MEK1 | H | CH$_3$ | H | H | H | H | acac | |
| 4'-263Y | Pd | 0 | 4' | Ph | H | | MEK1 | H | CH$_3$ | H | H | H | H | — | — |
| 4'-264 | Pd | 1 | 4' | Ph | H | H | | MEK2 | CH$_3$ | H | H | H | H | pic | |
| 4'-264X | Pd | 1 | 4' | Ph | H | H | | MEK2 | CH$_3$ | H | H | H | H | acac | |
| 4'-264Y | Pd | 0 | 4' | Ph | H | H | | MEK2 | CH$_3$ | H | H | H | H | — | — |
| 4'-265 | Pd | 1 | 4' | Ph | H | | MEK2 | H | CH$_3$ | H | H | H | H | pic | |
| 4'-265X | Pd | 1 | 4' | Ph | H | | MEK2 | H | CH$_3$ | H | H | H | H | acac | |
| 4'-265Y | Pd | 0 | 4' | Ph | H | | MEK2 | H | CH$_3$ | H | H | H | H | — | — |
| 4'-266 | Pd | 1 | 4' | Ph | H | H | | PAL1 | CH$_3$ | H | H | H | H | pic | |
| 4'-266X | Pd | 1 | 4' | Ph | H | H | | PAL1 | CH$_3$ | H | H | H | H | acac | |
| 4'-266Y | Pd | 0 | 4' | Ph | H | H | | PAL1 | CH$_3$ | H | H | H | H | — | — |
| 4'-267 | Pd | 1 | 4' | Ph | H | | PAL1 | H | CH$_3$ | H | H | H | H | pic | |
| 4'-267X | Pd | 1 | 4' | Ph | H | | PAL1 | H | CH$_3$ | H | H | H | H | acac | |
| 4'-267Y | Pd | 0 | 4' | Ph | H | | PAL1 | H | CH$_3$ | H | H | H | H | — | — |
| 4'-268 | Pd | 1 | 4' | Ph | H | H | | PAL2 | CH$_3$ | H | H | H | H | pic | |
| 4'-268X | Pd | 1 | 4' | Ph | H | H | | PAL2 | CH$_3$ | H | H | H | H | acac | |
| 4'-268Y | Pd | 0 | 4' | Ph | H | H | | PAL2 | CH$_3$ | H | H | H | H | — | — |
| 4'-269 | Pd | 1 | 4' | Ph | H | | PAL2 | H | CH$_3$ | H | H | H | H | pic | |
| 4'-269X | Pd | 1 | 4' | Ph | H | | PAL2 | H | CH$_3$ | H | H | H | H | acac | |
| 4'-269Y | Pd | 0 | 4' | Ph | H | | PAL2 | H | CH$_3$ | H | H | H | H | — | — |
| 4'-270 | Pd | 1 | 4' | Ph | H | H | | MMK | CH$_3$ | H | H | H | H | pic | |
| 4'-270X | Pd | 1 | 4' | Ph | H | H | | MMK | CH$_3$ | H | H | H | H | acac | |
| 4'-270Y | Pd | 0 | 4' | Ph | H | H | | MMK | CH$_3$ | H | H | H | H | — | — |
| 4'-271 | Pd | 1 | 4' | Ph | H | | MMK | H | CH$_3$ | H | H | H | H | pic | |
| 4'-271X | Pd | 1 | 4' | Ph | H | | MMK | H | CH$_3$ | H | H | H | H | acac | |
| 4'-271Y | Pd | 0 | 4' | Ph | H | | MMK | H | CH$_3$ | H | H | H | H | — | — |
| 4'-272 | Pd | 1 | 4' | Ph | H | H | | EES1 | CH$_3$ | H | H | H | H | pic | |
| 4'-272X | Pd | 1 | 4' | Ph | H | H | | EES1 | CH$_3$ | H | H | H | H | acac | |
| 4'-272Y | Pd | 0 | 4' | Ph | H | H | | EES1 | CH$_3$ | H | H | H | H | — | — |
| 4'-273 | Pd | 1 | 4' | Ph | H | | EES2 | H | CH$_3$ | H | H | H | H | pic | |
| 4'-273X | Pd | 1 | 4' | Ph | H | | EES2 | H | CH$_3$ | H | H | H | H | acac | |
| 4'-273Y | Pd | 0 | 4' | Ph | H | | EES2 | H | CH$_3$ | H | H | H | H | — | — |
| 4'-274 | Pd | 1 | 4' | Ph | H | H | | PAE1 | CH$_3$ | H | H | H | H | pic | |
| 4'-274X | Pd | 1 | 4' | Ph | H | H | | PAE1 | CH$_3$ | H | H | H | H | acac | |
| 4'-274Y | Pd | 0 | 4' | Ph | H | H | | PAE1 | CH$_3$ | H | H | H | H | — | — |
| 4'-275 | Pd | 0 | 4' | Ph | H | | PAE2 | H | CH$_3$ | H | H | H | H | pic | |
| 4'-275X | Pd | 1 | 4' | Ph | H | | PAE2 | H | CH$_3$ | H | H | H | H | acac | |
| 4'-275Y | Pd | 1 | 4' | Ph | H | | PAE2 | H | CH$_3$ | H | H | H | H | — | — |
| 4'-276 | Pd | 1 | 4' | Ph | H | H | | AME1 | CH$_3$ | H | H | H | H | pic | |
| 4'-276X | Pd | 1 | 4' | Ph | H | H | | AME1 | CH$_3$ | H | H | H | H | acac | |
| 4'-276Y | Pd | 0 | 4' | Ph | H | H | | AME1 | CH$_3$ | H | H | H | H | — | — |
| 4'-277 | Pd | 1 | 4' | Ph | H | | AME1 | H | CH$_3$ | H | H | H | H | pic | |
| 4'-277X | Pd | 1 | 4' | Ph | H | | AME1 | H | CH$_3$ | H | H | H | H | acac | |
| 4'-277Y | Pd | 0 | 4' | Ph | H | | AME1 | H | CH$_3$ | H | H | H | H | — | — |
| 4'-278 | Pd | 1 | 4' | Ph | H | H | | AME2 | CH$_3$ | H | H | H | H | pic | |
| 4'-278X | Pd | 1 | 4' | Ph | H | H | | AME2 | CH$_3$ | H | H | H | H | acac | |
| 4'-278Y | Pd | 0 | 4' | Ph | H | H | | AME2 | CH$_3$ | H | H | H | H | — | — |
| 4'-279 | Pd | 1 | 4' | Ph | H | | AME2 | H | CH$_3$ | H | H | H | H | pic | |
| 4'-279X | Pd | 1 | 4' | Ph | H | | AME2 | H | CH$_3$ | H | H | H | H | acac | |
| 4'-279Y | Pd | 0 | 4' | Ph | H | | AME2 | H | CH$_3$ | H | H | H | H | — | — |
| 4'-280 | Pd | 1 | 4' | Ph | H | H | | EAE1 | CH$_3$ | H | H | H | H | pic | |
| 4'-280X | Pd | 1 | 4' | Ph | H | H | | EAE1 | CH$_3$ | H | H | H | H | acac | |
| 4'-280Y | Pd | 0 | 4' | Ph | H | H | | EAE1 | CH$_3$ | H | H | H | H | — | — |
| 4'-281 | Pd | 1 | 4' | Ph | H | | EAE1 | H | CH$_3$ | H | H | H | H | pic | |
| 4'-281X | Pd | 1 | 4' | Ph | H | | EAE1 | H | CH$_3$ | H | H | H | H | acac | |
| 4'-281Y | Pd | 0 | 4' | Ph | H | | EAE1 | H | CH$_3$ | H | H | H | H | — | — |
| 4'-282 | Pd | 1 | 4' | Ph | H | H | | EAE2 | CH$_3$ | H | H | H | H | pic | |
| 4'-282X | Pd | 1 | 4' | Ph | H | H | | EAE2 | CH$_3$ | H | H | H | H | acac | |
| 4'-282Y | Pd | 0 | 4' | Ph | H | H | | EAE2 | CH$_3$ | H | H | H | H | — | — |
| 4'-283 | Pd | 1 | 4' | Ph | H | | EAE2 | H | CH$_3$ | H | H | H | H | pic | |
| 4'-283X | Pd | 1 | 4' | Ph | H | | EAE2 | H | CH$_3$ | H | H | H | H | acac | |
| 4'-283Y | Pd | 0 | 4' | Ph | H | | EAE2 | H | CH$_3$ | H | H | H | H | — | — |
| 4'-284 | Pd | 1 | 4' | Ph | H | H | | AAE1 | CH$_3$ | H | H | H | H | pic | |
| 4'-284X | Pd | 1 | 4' | Ph | H | H | | AAE1 | CH$_3$ | H | H | H | H | acac | |
| 4'-284Y | Pd | 0 | 4' | Ph | H | H | | AAE1 | CH$_3$ | H | H | H | H | — | — |
| 4'-285 | Pd | 1 | 4' | Ph | H | | AAE1 | H | CH$_3$ | H | H | H | H | pic | |
| 4'-285X | Pd | 1 | 4' | Ph | H | | AAE1 | H | CH$_3$ | H | H | H | H | acac | |
| 4'-285Y | Pd | 0 | 4' | Ph | H | | AAE1 | H | CH$_3$ | H | H | H | H | — | — |
| 4'-286 | Pd | 1 | 4' | Ph | H | H | | AAE2 | CH$_3$ | H | H | H | H | pic | |
| 4'-286X | Pd | 1 | 4' | Ph | H | H | | AAE2 | CH$_3$ | H | H | H | H | acac | |
| 4'-286Y | Pd | 0 | 4' | Ph | H | H | | AAE2 | CH$_3$ | H | H | H | H | — | — |
| 4'-287 | Pd | 1 | 4' | Ph | H | | AAE2 | H | CH$_3$ | H | H | H | H | pic | |
| 4'-287X | Pd | 1 | 4' | Ph | H | | AAE2 | H | CH$_3$ | H | H | H | H | acac | |

TABLE 46-continued

| No. | M | m | BSS | SS | G | T¹ | T² | T³ | T⁴ | T⁵ | T⁶ | T⁷ | T⁸ | T⁹ | L¹ | L² |
|---|---|---|---|---|---|---|---|---|---|---|---|---|---|---|---|---|
| 4'-287Y | Pd | 0 | 4' | Ph | | H | | AAE2 | H | $CH_3$ | H | H | H | H | — | — |
| 4'-288 | Pd | 1 | 4' | Ph | | H | H | | PME1 | $CH_3$ | H | H | H | H | | pic |
| 4'-288X | Pd | 1 | 4' | Ph | | H | H | | PME1 | $CH_3$ | H | H | H | H | | acac |
| 4'-288Y | Pd | 0 | 4' | Ph | | H | H | | PME1 | $CH_3$ | H | H | H | H | — | — |
| 4'-289 | Pd | 1 | 4' | Ph | | H | | PME1 | H | $CH_3$ | H | H | H | H | | pic |
| 4'-289X | Pd | 1 | 4' | Ph | | H | | PME1 | H | $CH_3$ | H | H | H | H | | acac |
| 4'-289Y | Pd | 0 | 4' | Ph | | H | | PME1 | H | $CH_3$ | H | H | H | H | — | — |
| 4'-290 | Pd | 1 | 4' | Ph | | H | H | | PME2 | $CH_3$ | H | H | H | H | | pic |
| 4'-290X | Pd | 1 | 4' | Ph | | H | H | | PME2 | $CH_3$ | H | H | H | H | | acac |
| 4'-290Y | Pd | 0 | 4' | Ph | | H | H | | PME2 | $CH_3$ | H | H | H | H | — | — |
| 4'-291 | Pd | 1 | 4' | Ph | | H | | PME2 | H | $CH_3$ | H | H | H | H | | pic |
| 4'-291X | Pd | 1 | 4' | Ph | | H | | PME2 | H | $CH_3$ | H | H | H | H | | acac |
| 4'-291Y | Pd | 0 | 4' | Ph | | H | | PME2 | H | $CH_3$ | H | H | H | H | — | — |
| 4'-292 | Pd | 1 | 4' | Ph | | H | H | | MET1 | $CH_3$ | H | H | H | H | | pic |
| 4'-292X | Pd | 1 | 4' | Ph | | H | H | | MET1 | $CH_3$ | H | H | H | H | | acac |
| 4'-292Y | Pd | 0 | 4' | Ph | | H | H | | MET1 | $CH_3$ | H | H | H | H | — | — |
| 4'-293 | Pd | 1 | 4' | Ph | | H | | MET1 | H | $CH_3$ | H | H | H | H | | pic |
| 4'-293X | Pd | 1 | 4' | Ph | | H | | MET1 | H | $CH_3$ | H | H | H | H | | acac |
| 4'-293Y | Pd | 0 | 4' | Ph | | H | | MET1 | H | $CH_3$ | H | H | H | H | — | — |
| 4'-294 | Pd | 1 | 4' | Ph | | H | H | | MET2 | $CH_3$ | H | H | H | H | | pic |
| 4'-294X | Pd | 1 | 4' | Ph | | H | H | | MET2 | $CH_3$ | H | H | H | H | | acac |
| 4'-294Y | Pd | 0 | 4' | Ph | | H | H | | MET2 | $CH_3$ | H | H | H | H | — | — |
| 4'-295 | Pd | 1 | 4' | Ph | | H | | MET2 | H | $CH_3$ | H | H | H | H | | pic |
| 4'-295X | Pd | 1 | 4' | Ph | | H | | MET2 | H | $CH_3$ | H | H | H | H | | acac |
| 4'-295Y | Pd | 0 | 4' | Ph | | H | | MET2 | H | $CH_3$ | H | H | H | H | — | — |
| 4'-296 | Pd | 1 | 4' | Ph | | H | H | | EE1 | $CH_3$ | H | H | H | H | | pic |
| 4'-296X | Pd | 1 | 4' | Ph | | H | H | | EE1 | $CH_3$ | H | H | H | H | | acac |
| 4'-296Y | Pd | 0 | 4' | Ph | | H | H | | EE1 | $CH_3$ | H | H | H | H | — | — |
| 4'-297 | Pd | 1 | 4' | Ph | | H | | EE1 | H | $CH_3$ | H | H | H | H | | pic |
| 4'-297X | Pd | 1 | 4' | Ph | | H | | EE1 | H | $CH_3$ | H | H | H | H | | acac |
| 4'-297Y | Pd | 0 | 4' | Ph | | H | | EE1 | H | $CH_3$ | H | H | H | H | — | — |
| 4'-298 | Pd | 1 | 4' | Ph | | H | H | | EE2 | $CH_3$ | H | H | H | H | | pic |
| 4'-298X | Pd | 1 | 4' | Ph | | H | H | | EE2 | $CH_3$ | H | H | H | H | | acac |
| 4'-298Y | Pd | 0 | 4' | Ph | | H | H | | EE2 | $CH_3$ | H | H | H | H | — | — |
| 4'-299 | Pd | 1 | 4' | Ph | | H | | EE2 | H | $CH_3$ | H | H | H | H | | pic |
| 4'-299X | Pd | 1 | 4' | Ph | | H | | EE2 | H | $CH_3$ | H | H | H | H | | acac |
| 4'-299Y | Pd | 0 | 4' | Ph | | H | | EE2 | H | $CH_3$ | H | H | H | H | — | — |
| 4'-300 | Pd | 1 | 4' | Ph | | H | H | | MS1 | $CH_3$ | H | H | H | H | | pic |
| 4'-300X | Pd | 1 | 4' | Ph | | H | H | | MS1 | $CH_3$ | H | H | H | H | | acac |
| 4'-300Y | Pd | 0 | 4' | Ph | | H | H | | MS1 | $CH_3$ | H | H | H | H | — | — |
| 4'-301 | Pd | 1 | 4' | Ph | | H | | MS1 | H | $CH_3$ | H | H | H | H | | pic |
| 4'-301X | Pd | 1 | 4' | Ph | | H | | MS1 | H | $CH_3$ | H | H | H | H | | acac |
| 4'-301Y | Pd | 0 | 4' | Ph | | H | | MS1 | H | $CH_3$ | H | H | H | H | — | — |
| 4'-302 | Pd | 1 | 4' | Ph | | H | H | | MS2 | $CH_3$ | H | H | H | H | | pic |
| 4'-302X | Pd | 1 | 4' | Ph | | H | H | | MS2 | $CH_3$ | H | H | H | H | | acac |
| 4'-302Y | Pd | 0 | 4' | Ph | | H | H | | MS2 | $CH_3$ | H | H | H | H | — | — |
| 4'-303 | Pd | 1 | 4' | Ph | | H | | MS2 | H | $CH_3$ | H | H | H | H | | pic |
| 4'-303X | Pd | 1 | 4' | Ph | | H | | MS2 | H | $CH_3$ | H | H | H | H | | acac |
| 4'-303Y | Pd | 0 | 4' | Ph | | H | | MS2 | H | $CH_3$ | H | H | H | H | — | — |

TABLE 47

| No. | M | m | BSS | SS | G | T¹ | T² | T³ | T⁴ | T⁵ | T⁶ | T⁷ | L¹ | L² |
|---|---|---|---|---|---|---|---|---|---|---|---|---|---|---|
| 5'-211 | Pd | 1 | 5' | Ph | | H | H | H | H | H | $CH_3$ | H | | pic |
| 5'-211X | Pd | 1 | 5' | Ph | | H | H | H | H | H | $CH_3$ | H | | acac |
| 5'-211Y | Pd | 0 | 5' | Ph | | H | H | H | H | H | $CH_3$ | H | — | — |
| 5'-212 | Pd | 1 | 5' | Ph | | H | H | H | H | H | $^tC_4H_9$ | H | | pic |
| 5'-212X | Pd | 1 | 5' | Ph | | H | H | H | H | H | $^tC_4H_9$ | H | | acac |
| 5'-212Y | Pd | 0 | 5' | Ph | | H | H | H | H | H | $^tC_4H_9$ | H | — | — |
| 5'-213 | Pd | 1 | 5' | Ph | | H | F | H | F | H | $CH_3$ | H | | pic |
| 5'-213X | Pd | 1 | 5' | Ph | | H | F | H | F | H | $CH_3$ | H | | acac |
| 5'-213Y | Pd | 0 | 5' | Ph | | H | F | H | F | H | $CH_3$ | H | — | — |
| 5'-214 | Pd | 1 | 5' | Ph | | H | F | H | F | H | $^tC_4H_9$ | H | | pic |
| 5'-214X | Pd | 1 | 5' | Ph | | H | F | H | F | H | $^tC_4H_9$ | H | | acac |
| 5'-214Y | Pd | 0 | 5' | Ph | | H | F | H | F | H | $^tC_4H_9$ | H | — | — |
| 5'-215 | Pd | 1 | 5' | Ph | | $CF_3$ | H | $CF_3$ | H | H | $CH_3$ | H | | pic |
| 5'-215X | Pd | 1 | 5' | Ph | | $CF_3$ | H | $CF_3$ | H | H | $CH_3$ | H | | acac |
| 5'-215Y | Pd | 0 | 5' | Ph | | $CF_3$ | H | $CF_3$ | H | H | $CH_3$ | H | — | — |
| 5'-216 | Pd | 1 | 5' | Ph | | $CF_3$ | H | $CF_3$ | H | H | $^tC_4H_9$ | H | | pic |
| 5'-216X | Pd | 1 | 5' | Ph | | $CF_3$ | H | $CF_3$ | H | H | $^tC_4H_9$ | H | | acac |
| 5'-216Y | Pd | 0 | 5' | Ph | | $CF_3$ | H | $CF_3$ | H | H | $^tC_4H_9$ | H | — | — |
| 5'-217 | Pd | 1 | 5' | Ph | | H | F | $CF_3$ | H | H | $CH_3$ | H | | pic |
| 5'-217X | Pd | 1 | 5' | Ph | | H | F | $CF_3$ | H | H | $CH_3$ | H | | acac |

TABLE 47-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-217Y | Pd | 0 | 5' | Ph | H | F | CF₃ | H | H | CH₃ | H | — | — |
| 5'-218 | Pd | 1 | 5' | Ph | F | H | CF₃ | H | H | CH₃ | H | pic | |
| 5'-218X | Pd | 1 | 5' | Ph | F | H | CF₃ | H | H | CH₃ | H | acac | |
| 5'-218Y | Pd | 0 | 5' | Ph | F | H | CF₃ | H | H | CH₃ | H | — | — |
| 5'-219 | Pd | 1 | 5' | Ph | F | F | F | F | H | CH₃ | H | pic | |
| 5'-219X | Pd | 1 | 5' | Ph | F | F | F | F | H | CH₃ | H | acac | |
| 5'-219Y | Pd | 0 | 5' | Ph | F | F | F | F | H | CH₃ | H | — | — |
| 5'-220 | Pd | 1 | 5' | Ph | H | F | H | CH₃ | H | CH₃ | H | pic | |
| 5'-220X | Pd | 1 | 5' | Ph | H | F | H | CH₃ | H | CH₃ | H | acac | |
| 5'-220Y | Pd | 0 | 5' | Ph | H | F | H | CH₃ | H | CH₃ | H | — | — |
| 5'-221 | Pd | 1 | 5' | Ph | H | F | H | CH₃ | H | ᵗC₄H₉ | H | pic | |
| 5'-221X | Pd | 1 | 5' | Ph | H | F | H | CH₃ | H | ᵗC₄H₉ | H | acac | |
| 5'-221Y | Pd | 0 | 5' | Ph | H | F | H | CH₃ | H | ᵗC₄H₉ | H | — | — |
| 5'-222 | Pd | 1 | 5' | Ph | H | F | H | ᵗC₄H₉ | H | CH₃ | H | pic | |
| 5'-222X | Pd | 1 | 5' | Ph | H | F | H | ᵗC₄H₉ | H | CH₃ | H | acac | |
| 5'-222Y | Pd | 0 | 5' | Ph | H | F | H | ᵗC₄H₉ | H | CH₃ | H | — | — |
| 5'-223 | Pd | 1 | 5' | Ph | H | F | H | ᵗC₄H₉ | H | ᵗC₄H₉ | H | pic | |
| 5'-223X | Pd | 1 | 5' | Ph | H | F | H | ᵗC₄H₉ | H | ᵗC₄H₉ | H | acac | |
| 5'-223Y | Pd | 0 | 5' | Ph | H | F | H | ᵗC₄H₉ | H | ᵗC₄H₉ | H | — | — |
| 5'-224 | Pd | 1 | 5' | Ph | H | CF₃ | H | CF₃ | H | CH₃ | H | pic | |
| 5'-224X | Pd | 1 | 5' | Ph | H | CF₃ | H | CF₃ | H | CH₃ | H | acac | |
| 5'-224Y | Pd | 0 | 5' | Ph | H | CF₃ | H | CF₃ | H | CH₃ | H | — | — |
| 5'-225 | Pd | 1 | 5' | Ph | H | CF₃ | H | CF₃ | H | ᵗC₄H₉ | H | pic | |
| 5'-225X | Pd | 1 | 5' | Ph | H | CF₃ | H | CF₃ | H | ᵗC₄H₉ | H | acac | |
| 5'-225Y | Pd | 0 | 5' | Ph | H | CF₃ | H | CF₃ | H | ᵗC₄H₉ | H | — | — |
| 5'-226 | Pd | 1 | 5' | Ph | CF₃ | H | H | ᵗC₄H₉ | H | CH₃ | H | pic | |
| 5'-226X | Pd | 1 | 5' | Ph | CF₃ | H | H | ᵗC₄H₉ | H | CH₃ | H | acac | |
| 5'-226Y | Pd | 0 | 5' | Ph | CF₃ | H | H | ᵗC₄H₉ | H | CH₃ | H | — | — |
| 5'-227 | Pd | 1 | 5' | Ph | CF₃ | H | H | ᵗC₄H₉ | H | ᵗC₄H₉ | H | pic | |
| 5'-227X | Pd | 1 | 5' | Ph | CF₃ | H | H | ᵗC₄H₉ | H | ᵗC₄H₉ | H | acac | |
| 5'-227Y | Pd | 0 | 5' | Ph | CF₃ | H | H | ᵗC₄H₉ | H | ᵗC₄H₉ | H | — | — |
| 5'-228 | Pd | 1 | 5' | Ph | H | CF₃ | H | ᵗC₄H₉ | H | CH₃ | H | pic | |
| 5'-228X | Pd | 1 | 5' | Ph | H | CF₃ | H | ᵗC₄H₉ | H | CH₃ | H | acac | |
| 5'-228Y | Pd | 0 | 5' | Ph | H | CF₃ | H | ᵗC₄H₉ | H | CH₃ | H | — | — |
| 5'-229 | Pd | 1 | 5' | Ph | H | CF₃ | H | ᵗC₄H₉ | H | ᵗC₄H₉ | H | pic | |
| 5'-229X | Pd | 1 | 5' | Ph | H | CF₃ | H | ᵗC₄H₉ | H | ᵗC₄H₉ | H | acac | |
| 5'-229Y | Pd | 0 | 5' | Ph | H | CF₃ | H | ᵗC₄H₉ | H | ᵗC₄H₉ | H | — | — |
| 5'-230 | Pd | 1 | 5' | Ph | H | CF₃ | H | CH₃ | H | CH₃ | H | pic | |
| 5'-230X | Pd | 1 | 5' | Ph | H | CF₃ | H | CH₃ | H | CH₃ | H | acac | |
| 5'-230Y | Pd | 0 | 5' | Ph | H | CF₃ | H | CH₃ | H | CH₃ | H | — | — |
| 5'-231 | Pd | 1 | 5' | Ph | H | CF₃ | CF₃ | H | H | CH₃ | H | pic | |
| 5'-231X | Pd | 1 | 5' | Ph | H | CF₃ | CF₃ | H | H | CH₃ | H | acac | |
| 5'-231Y | Pd | 0 | 5' | Ph | H | CF₃ | CF₃ | H | H | CH₃ | H | — | — |
| 5'-232 | Pd | 1 | 5' | Ph | H | H | NO₂ | H | H | CH₃ | H | pic | |
| 5'-232X | Pd | 1 | 5' | Ph | H | H | NO₂ | H | H | CH₃ | H | acac | |
| 5'-232Y | Pd | 0 | 5' | Ph | H | H | NO₂ | H | H | CH₃ | H | — | — |
| 5'-233 | Pd | 1 | 5' | Ph | H | H | NO₂ | H | H | ᵗC₄H₉ | H | pic | |
| 5'-233X | Pd | 1 | 5' | Ph | H | H | NO₂ | H | H | ᵗC₄H₉ | H | acac | |
| 5'-233Y | Pd | 0 | 5' | Ph | H | H | NO₂ | H | H | ᵗC₄H₉ | H | — | — |
| 5'-234 | Pd | 1 | 5' | Ph | F | H | NO₂ | H | H | CH₃ | H | pic | |
| 5'-234X | Pd | 1 | 5' | Ph | F | H | NO₂ | H | H | CH₃ | H | acac | |
| 5'-234Y | Pd | 0 | 5' | Ph | F | H | NO₂ | H | H | CH₃ | H | — | — |
| 5'-235 | Pd | 1 | 5' | Ph | F | H | NO₂ | H | H | ᵗC₄H₉ | H | pic | |
| 5'-235X | Pd | 1 | 5' | Ph | F | H | NO₂ | H | H | ᵗC₄H₉ | H | acac | |
| 5'-235Y | Pd | 0 | 5' | Ph | F | H | NO₂ | H | H | ᵗC₄H₉ | H | — | — |
| 5'-236 | Pd | 1 | 5' | Ph | F | H | NO₂ | F | H | CH₃ | H | pic | |
| 5'-236X | Pd | 1 | 5' | Ph | F | H | NO₂ | F | H | CH₃ | H | acac | |
| 5'-236Y | Pd | 0 | 5' | Ph | F | H | NO₂ | F | H | CH₃ | H | — | — |
| 5'-237 | Pd | 1 | 5' | Ph | F | H | NO₂ | F | H | ᵗC₄H₉ | H | pic | |
| 5'-237X | Pd | 1 | 5' | Ph | F | H | NO₂ | F | H | ᵗC₄H₉ | H | acac | |
| 5'-237Y | Pd | 0 | 5' | Ph | F | H | NO₂ | F | H | ᵗC₄H₉ | H | — | — |
| 5'-238 | Pd | 1 | 5' | Ph | H | NO₂ | H | NO₂ | H | CH₃ | H | pic | |
| 5'-238X | Pd | 1 | 5' | Ph | H | NO₂ | H | NO₂ | H | CH₃ | H | acac | |
| 5'-238Y | Pd | 0 | 5' | Ph | H | NO₂ | H | NO₂ | H | CH₃ | H | — | — |
| 5'-239 | Pd | 1 | 5' | Ph | H | NO₂ | H | NO₂ | H | ᵗC₄H₉ | H | pic | |
| 5'-239X | Pd | 1 | 5' | Ph | H | NO₂ | H | NO₂ | H | ᵗC₄H₉ | H | acac | |
| 5'-239Y | Pd | 0 | 5' | Ph | H | NO₂ | H | NO₂ | H | ᵗC₄H₉ | H | — | — |
| 5'-240 | Pd | 1 | 5' | Ph | NO₂ | H | H | NO₂ | H | CH₃ | H | pic | |
| 5'-240X | Pd | 1 | 5' | Ph | NO₂ | H | H | NO₂ | H | CH₃ | H | acac | |
| 5'-240Y | Pd | 0 | 5' | Ph | NO₂ | H | H | NO₂ | H | CH₃ | H | — | — |
| 5'-241 | Pd | 1 | 5' | Ph | H | H | CF₃ | H | H | CH₃ | H | pic | |
| 5'-241X | Pd | 1 | 5' | Ph | H | H | CF₃ | H | H | CH₃ | H | acac | |
| 5'-241Y | Pd | 0 | 5' | Ph | H | H | CF₃ | H | H | CH₃ | H | — | — |
| 5'-242 | Pd | 1 | 5' | Ph | H | Cl | CF₃ | H | H | CH₃ | H | pic | |
| 5'-242X | Pd | 1 | 5' | Ph | H | Cl | CF₃ | H | H | CH₃ | H | acac | |
| 5'-242Y | Pd | 0 | 5' | Ph | H | Cl | CF₃ | H | H | CH₃ | H | — | — |
| 5'-243 | Pd | 1 | 5' | Ph | H | Cl | CF₃ | H | H | ᵗC₄H₉ | H | pic | |

TABLE 47-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-243X | Pd | 1 | 5' | Ph | H | Cl | CF₃ | H | H | $^tC_4H_9$ | H | acac | |
| 5'-243Y | Pd | 0 | 5' | Ph | H | Cl | CF₃ | H | H | $^tC_4H_9$ | H | — | — |
| 5'-244 | Pd | 1 | 5' | Ph | H | NO₂ | H | H | H | CH₃ | H | pic | |
| 5'-244X | Pd | 1 | 5' | Ph | H | NO₂ | H | H | H | CH₃ | H | acac | |
| 5'-244Y | Pd | 0 | 5' | Ph | H | NO₂ | H | H | H | CH₃ | H | — | — |
| 5'-245 | Pd | 1 | 5' | Ph | H | CF₃ | H | H | H | CH₃ | H | pic | |
| 5'-245X | Pd | 1 | 5' | Ph | H | CF₃ | H | H | H | CH₃ | H | acac | |
| 5'-245Y | Pd | 0 | 5' | Ph | H | CF₃ | H | H | H | CH₃ | H | — | — |
| 5'-246 | Pd | 1 | 5' | Ph | H | NO₂ | H | CH₃ | H | CH₃ | H | pic | |
| 5'-246X | Pd | 1 | 5' | Ph | H | NO₂ | H | CH₃ | H | CH₃ | H | acac | |
| 5'-246Y | Pd | 0 | 5' | Ph | H | NO₂ | H | CH₃ | H | CH₃ | H | — | — |
| 5'-247 | Pd | 1 | 5' | Ph | H | NO₂ | H | CH₃ | H | $^tC_4H_9$ | H | pic | |
| 5'-247X | Pd | 1 | 5' | Ph | H | NO₂ | H | CH₃ | H | $^tC_4H_9$ | H | acac | |
| 5'-247Y | Pd | 0 | 5' | Ph | H | NO₂ | H | CH₃ | H | $^tC_4H_9$ | H | — | — |
| 5'-248 | Pd | 1 | 5' | Ph | H | NO₂ | H | $^tC_4H_9$ | H | CH₃ | H | pic | |
| 5'-248X | Pd | 1 | 5' | Ph | H | NO₂ | H | $^tC_4H_9$ | H | CH₃ | H | acac | |
| 5'-248Y | Pd | 0 | 5' | Ph | H | NO₂ | H | $^tC_4H_9$ | H | CH₃ | H | — | — |
| 5'-249 | Pd | 1 | 5' | Ph | H | H | CH₃O | H | H | CH₃ | H | pic | |
| 5'-249X | Pd | 1 | 5' | Ph | H | H | CH₃O | H | H | CH₃ | H | acac | |
| 5'-249Y | Pd | 0 | 5' | Ph | H | H | CH₃O | H | H | CH₃ | H | — | — |
| 5'-250 | Pd | 1 | 5' | Ph | H | CH₃O | H | H | H | CH₃ | H | pic | |
| 5'-250X | Pd | 1 | 5' | Ph | H | CH₃O | H | H | H | CH₃ | H | acac | |
| 5'-250Y | Pd | 0 | 5' | Ph | H | CH₃O | H | H | H | CH₃ | H | — | — |
| 5'-251 | Pd | 1 | 5' | Ph | H | CH₃O | H | CH₃ | H | CH₃ | H | pic | |
| 5'-251X | Pd | 1 | 5' | Ph | H | CH₃O | H | CH₃ | H | CH₃ | H | acac | |
| 5'-251Y | Pd | 0 | 5' | Ph | H | CH₃O | H | CH₃ | H | CH₃ | H | — | — |
| 5'-252 | Pd | 1 | 5' | Ph | H | CH₃O | H | $^tC_4H_9$ | H | CH₃ | H | pic | |
| 5'-252X | Pd | 1 | 5' | Ph | H | CH₃O | H | $^tC_4H_9$ | H | CH₃ | H | acac | |
| 5'-252Y | Pd | 0 | 5' | Ph | H | CH₃O | H | $^tC_4H_9$ | H | CH₃ | H | — | — |
| 5'-253 | Pd | 1 | 5' | Ph | H | H | H | H | $^tC_4H_9$ | CH₃ | H | pic | |
| 5'-253X | Pd | 1 | 5' | Ph | H | H | H | H | $^tC_4H_9$ | CH₃ | H | acac | |
| 5'-253Y | Pd | 0 | 5' | Ph | H | H | H | H | $^tC_4H_9$ | CH₃ | H | — | — |
| 5'-254 | Pd | 1 | 5' | Ph | H | F | H | F | $^tC_4H_9$ | CH₃ | H | pic | |
| 5'-254X | Pd | 1 | 5' | Ph | H | F | H | F | $^tC_4H_9$ | CH₃ | H | acac | |
| 5'-254Y | Pd | 0 | 5' | Ph | H | F | H | F | $^tC_4H_9$ | CH₃ | H | — | — |
| 5'-255 | Pd | 1 | 5' | Ph | H | F | H | F | $^tC_4H_9$ | $^tC_4H_9$ | H | pic | |
| 5'-255X | Pd | 1 | 5' | Ph | H | F | H | F | $^tC_4H_9$ | $^tC_4H_9$ | H | acac | |
| 5'-255Y | Pd | 0 | 5' | Ph | H | F | H | F | $^tC_4H_9$ | $^tC_4H_9$ | H | — | — |
| 5'-256 | Pd | 1 | 5' | Ph | CF₃ | H | CF₃ | H | $^tC_4H_9$ | CH₃ | H | pic | |
| 5'-256X | Pd | 1 | 5' | Ph | CF₃ | H | CF₃ | H | $^tC_4H_9$ | CH₃ | H | acac | |
| 5'-256Y | Pd | 0 | 5' | Ph | CF₃ | H | CF₃ | H | $^tC_4H_9$ | CH₃ | H | — | — |
| 5'-257 | Pd | 1 | 5' | Ph | CF₃ | H | CF₃ | H | $^tC_4H_9$ | $^tC_4H_9$ | H | pic | |
| 5'-257X | Pd | 1 | 5' | Ph | CF₃ | H | CF₃ | H | $^tC_4H_9$ | $^tC_4H_9$ | H | acac | |
| 5'-257Y | Pd | 0 | 5' | Ph | CF₃ | H | CF₃ | H | $^tC_4H_9$ | $^tC_4H_9$ | H | — | — |
| 5'-258 | Pd | 1 | 5' | Ph | H | CF₃ | H | CH₃ | $^tC_4H_9$ | CH₃ | H | pic | |
| 5'-258X | Pd | 1 | 5' | Ph | H | CF₃ | H | CH₃ | $^tC_4H_9$ | CH₃ | H | acac | |
| 5'-258Y | Pd | 0 | 5' | Ph | H | CF₃ | H | CH₃ | $^tC_4H_9$ | CH₃ | H | — | — |
| 5'-259 | Pd | 1 | 5' | Ph | H | Si(CH₃)₃ | H | H | H | CH₃ | H | pic | |
| 5'-259X | Pd | 1 | 5' | Ph | H | Si(CH₃)₃ | H | H | H | CH₃ | H | acac | |
| 5'-259Y | Pd | 0 | 5' | Ph | H | Si(CH₃)₃ | H | H | H | CH₃ | H | — | — |
| 5'-260 | Pd | 1 | 5' | Ph | H | Si(CH₃)₃ | H | H | H | $^tC_4H_9$ | H | pic | |
| 5'-260X | Pd | 1 | 5' | Ph | H | Si(CH₃)₃ | H | H | H | $^tC_4H_9$ | H | acac | |
| 5'-260Y | Pd | 0 | 5' | Ph | H | Si(CH₃)₃ | H | H | H | $^tC_4H_9$ | H | — | — |
| 5'-261 | Pd | 1 | 5' | Ph | H | H | Si(CH₃)₃ | H | H | CH₃ | H | pic | |
| 5'-261X | Pd | 1 | 5' | Ph | H | H | Si(CH₃)₃ | H | H | CH₃ | H | acac | |
| 5'-261Y | Pd | 0 | 5' | Ph | H | H | Si(CH₃)₃ | H | H | CH₃ | H | — | — |
| 5'-262 | Pd | 1 | 5' | Ph | H | H | H | Si(CH₃)₃ | H | CH₃ | H | pic | |
| 5'-262X | Pd | 1 | 5' | Ph | H | H | H | Si(CH₃)₃ | H | CH₃ | H | acac | |
| 5'-262Y | Pd | 0 | 5' | Ph | H | H | H | Si(CH₃)₃ | H | CH₃ | H | — | — |
| 5'-263 | Pd | 1 | 5' | Ph | H | F | H | Si(CH₃)₃ | H | CH₃ | H | pic | |
| 5'-263X | Pd | 1 | 5' | Ph | H | F | H | Si(CH₃)₃ | H | CH₃ | H | acac | |
| 5'-263Y | Pd | 0 | 5' | Ph | H | F | H | Si(CH₃)₃ | H | CH₃ | H | — | — |
| 5'-264 | Pd | 1 | 5' | Ph | H | CF₃ | H | Si(CH₃)₃ | H | CH₃ | H | pic | |
| 5'-264X | Pd | 1 | 5' | Ph | H | CF₃ | H | Si(CH₃)₃ | H | CH₃ | H | acac | |
| 5'-264Y | Pd | 0 | 5' | Ph | H | CF₃ | H | Si(CH₃)₃ | H | CH₃ | H | — | — |
| 5'-265 | Pd | 1 | 5' | Ph | H | Si(CH₃)₃ | H | F | H | CH₃ | H | pic | |
| 5'-265X | Pd | 1 | 5' | Ph | H | Si(CH₃)₃ | H | F | H | CH₃ | H | acac | |
| 5'-265Y | Pd | 0 | 5' | Ph | H | Si(CH₃)₃ | H | F | H | CH₃ | H | — | — |
| 5'-266 | Pd | 1 | 5' | Ph | H | Si(CH₃)₃ | H | F | H | $^tC_4H_9$ | H | pic | |
| 5'-266X | Pd | 1 | 5' | Ph | H | Si(CH₃)₃ | H | F | H | $^tC_4H_9$ | H | acac | |
| 5'-266Y | Pd | 0 | 5' | Ph | H | Si(CH₃)₃ | H | F | H | $^tC_4H_9$ | H | — | — |
| 5'-267 | Pd | 1 | 5' | Ph | H | Si(CH₃)₃ | H | CF₃ | H | CH₃ | H | pic | |
| 5'-267X | Pd | 1 | 5' | Ph | H | Si(CH₃)₃ | H | CF₃ | H | CH₃ | H | acac | |
| 5'-267Y | Pd | 0 | 5' | Ph | H | Si(CH₃)₃ | H | CF₃ | H | CH₃ | H | — | — |
| 5'-268 | Pd | 1 | 5' | Ph | H | Si(CH₃)₃ | H | CF₃ | H | $^tC_4H_9$ | H | pic | |
| 5'-268X | Pd | 1 | 5' | Ph | H | Si(CH₃)₃ | H | CF₃ | H | $^tC_4H_9$ | H | acac | |
| 5'-268Y | Pd | 0 | 5' | Ph | H | Si(CH₃)₃ | H | CF₃ | H | $^tC_4H_9$ | H | — | — |

TABLE 47-continued

| No. | M | m | BSS | SS | G | T¹ | T² | T³ | T⁴ | T⁵ | T⁶ | T⁷ | L¹ | L² |
|---|---|---|---|---|---|---|---|---|---|---|---|---|---|---|
| 5'-269 | Pd | 1 | 5' | | Ph | Si(CH₃)₃ | H | Si(CH₃)₃ | H | H | CH₃ | H | pic | |
| 5'-269X | Pd | 1 | 5' | | Ph | Si(CH₃)₃ | H | Si(CH₃)₃ | H | H | CH₃ | H | acac | |
| 5'-269Y | Pd | 0 | 5' | | Ph | Si(CH₃)₃ | H | Si(CH₃)₃ | H | H | CH₃ | H | — | — |
| 5'-270 | Pd | 1 | 5' | | Ph | Si(CH₃)₃ | H | Si(CH₃)₃ | H | H | ᵗC₄H₉ | H | pic | |
| 5'-270X | Pd | 1 | 5' | | Ph | Si(CH₃)₃ | H | Si(CH₃)₃ | H | H | ᵗC₄H₉ | H | acac | |
| 5'-270Y | Pd | 0 | 5' | | Ph | Si(CH₃)₃ | H | Si(CH₃)₃ | H | H | ᵗC₄H₉ | H | — | — |
| 5'-271 | Pd | 1 | 5' | | Ph | H | H | H | COCH₃ | H | CH₃ | H | pic | |
| 5'-271X | Pd | 1 | 5' | | Ph | H | H | H | COCH₃ | H | CH₃ | H | acac | |
| 5'-271Y | Pd | 0 | 5' | | Ph | H | H | H | COCH₃ | H | CH₃ | H | — | — |
| 5'-272 | Pd | 1 | 5' | | Ph | H | H | COCH₃ | H | H | CH₃ | H | pic | |
| 5'-272X | Pd | 1 | 5' | | Ph | H | H | COCH₃ | H | H | CH₃ | H | acac | |
| 5'-272Y | Pd | 0 | 5' | | Ph | H | H | COCH₃ | H | H | CH₃ | H | — | — |
| 5'-273 | Pd | 1 | 5' | | Ph | H | COCH₃ | H | H | H | CH₃ | H | pic | |
| 5'-273X | Pd | 1 | 5' | | Ph | H | COCH₃ | H | H | H | CH₃ | H | acac | |
| 5'-273Y | Pd | 0 | 5' | | Ph | H | COCH₃ | H | H | H | CH₃ | H | — | — |
| 5'-274 | Pd | 1 | 5' | | Ph | H | H | | BL | H | CH₃ | H | pic | |
| 5'-274X | Pd | 1 | 5' | | Ph | H | H | | BL | H | CH₃ | H | acac | |
| 5'-274Y | Pd | 0 | 5' | | Ph | H | H | | BL | H | CH₃ | H | — | — |
| 5'-275 | Pd | 1 | 5' | | Ph | H | H | | BL | H | ᵗC₄H₉ | H | pic | |
| 5'-275X | Pd | 1 | 5' | | Ph | H | H | | BL | H | ᵗC₄H₉ | H | acac | |
| 5'-275Y | Pd | 0 | 5' | | Ph | H | H | | BL | H | ᵗC₄H₉ | H | — | — |
| 5'-276 | Pd | 1 | 5' | | Ph | H | | BL | H | H | CH₃ | H | pic | |
| 5'-276X | Pd | 1 | 5' | | Ph | H | | BL | H | H | CH₃ | H | acac | |
| 5'-276Y | Pd | 0 | 5' | | Ph | H | | BL | H | H | CH₃ | H | — | — |
| 5'-277 | Pd | 1 | 5' | | Ph | H | | BL | H | H | ᵗC₄H₉ | H | pic | |
| 5'-277X | Pd | 1 | 5' | | Ph | H | | BL | H | H | ᵗC₄H₉ | H | acac | |
| 5'-277Y | Pd | 0 | 5' | | Ph | H | | BL | H | H | ᵗC₄H₉ | H | — | — |
| 5'-278 | Pd | 1 | 5' | | Ph | H | H | | PL | H | CH₃ | H | pic | |
| 5'-278X | Pd | 1 | 5' | | Ph | H | H | | PL | H | CH₃ | H | acac | |
| 5'-278Y | Pd | 0 | 5' | | Ph | H | H | | PL | H | CH₃ | H | — | — |
| 5'-279 | Pd | 1 | 5' | | Ph | H | H | | PL | H | ᵗC₄H₉ | H | pic | |
| 5'-279X | Pd | 1 | 5' | | Ph | H | H | | PL | H | ᵗC₄H₉ | H | acac | |
| 5'-279Y | Pd | 0 | 5' | | Ph | H | H | | PL | H | ᵗC₄H₉ | H | — | — |
| 5'-280 | Pd | 1 | 5' | | Ph | H | | PL | H | H | CH₃ | H | pic | |
| 5'-280X | Pd | 1 | 5' | | Ph | H | | PL | H | H | CH₃ | H | acac | |
| 5'-280Y | Pd | 0 | 5' | | Ph | H | | PL | H | H | CH₃ | H | — | — |
| 5'-281 | Pd | 1 | 5' | | Ph | H | | PL | H | H | ᵗC₄H₉ | H | pic | |
| 5'-281X | Pd | 1 | 5' | | Ph | H | | PL | H | H | ᵗC₄H₉ | H | acac | |
| 5'-281Y | Pd | 0 | 5' | | Ph | H | | PL | H | H | ᵗC₄H₉ | H | — | — |
| 5'-282 | Pd | 1 | 5' | | Ph | H | H | | MEE1 | H | CH₃ | H | pic | |
| 5'-282X | Pd | 1 | 5' | | Ph | H | H | | MEE1 | H | CH₃ | H | acac | |
| 5'-282Y | Pd | 0 | 5' | | Ph | H | H | | MEE1 | H | CH₃ | H | — | — |
| 5'-283 | Pd | 1 | 5' | | Ph | H | | MEE1 | H | H | CH₃ | H | pic | |
| 5'-283X | Pd | 1 | 5' | | Ph | H | | MEE1 | H | H | CH₃ | H | acac | |
| 5'-283Y | Pd | 0 | 5' | | Ph | H | | MEE1 | H | H | CH₃ | H | — | — |
| 5'-284 | Pd | 1 | 5' | | Ph | H | H | | MEE2 | H | CH₃ | H | pic | |
| 5'-284X | Pd | 1 | 5' | | Ph | H | H | | MEE2 | H | CH₃ | H | acac | |
| 5'-284Y | Pd | 0 | 5' | | Ph | H | H | | MEE2 | H | CH₃ | H | — | — |
| 5'-285 | Pd | 1 | 5' | | Ph | H | | MEE2 | H | H | CH₃ | H | pic | |
| 5'-285X | Pd | 1 | 5' | | Ph | H | | MEE2 | H | H | CH₃ | H | acac | |
| 5'-285Y | Pd | 0 | 5' | | Ph | H | | MEE2 | H | H | CH₃ | H | — | — |
| 5'-286 | Pd | 1 | 5' | | Ph | H | H | | PA1 | H | CH₃ | H | pic | |
| 5'-286X | Pd | 1 | 5' | | Ph | H | H | | PA1 | H | CH₃ | H | acac | |
| 5'-286Y | Pd | 0 | 5' | | Ph | H | H | | PA1 | H | CH₃ | H | — | — |
| 5'-287 | Pd | 1 | 5' | | Ph | H | | PA1 | H | H | CH₃ | H | pic | |
| 5'-287X | Pd | 1 | 5' | | Ph | H | | PA1 | H | H | CH₃ | H | acac | |
| 5'-287Y | Pd | 0 | 5' | | Ph | H | | PA1 | H | H | CH₃ | H | — | — |
| 5'-288 | Pd | 1 | 5' | | Ph | H | H | | PA2 | H | CH₃ | H | pic | |
| 5'-288X | Pd | 1 | 5' | | Ph | H | H | | PA2 | H | CH₃ | H | acac | |
| 5'-288Y | Pd | 0 | 5' | | Ph | H | H | | PA2 | H | CH₃ | H | — | — |
| 5'-289 | Pd | 1 | 5' | | Ph | H | | PA2 | H | H | CH₃ | H | pic | |
| 5'-289X | Pd | 1 | 5' | | Ph | H | | PA2 | H | H | CH₃ | H | acac | |
| 5'-289Y | Pd | 0 | 5' | | Ph | H | | PA2 | H | H | CH₃ | H | — | — |
| 5'-290 | Pd | 1 | 5' | | Ph | H | H | | EA1 | H | CH₃ | H | pic | |
| 5'-290X | Pd | 1 | 5' | | Ph | H | H | | EA1 | H | CH₃ | H | acac | |
| 5'-290Y | Pd | 0 | 5' | | Ph | H | H | | EA1 | H | CH₃ | H | — | — |
| 5'-291 | Pd | 1 | 5' | | Ph | H | | EA2 | H | H | CH₃ | H | pic | |
| 5'-291X | Pd | 1 | 5' | | Ph | H | | EA2 | H | H | CH₃ | H | acac | |
| 5'-291Y | Pd | 0 | 5' | | Ph | H | | EA2 | H | H | CH₃ | H | — | — |
| 5'-292 | Pd | 1 | 5' | | Ph | H | H | | ME | H | CH₃ | H | pic | |
| 5'-292X | Pd | 1 | 5' | | Ph | H | H | | ME | H | CH₃ | H | acac | |
| 5'-292Y | Pd | 0 | 5' | | Ph | H | H | | ME | H | CH₃ | H | — | — |
| 5'-293 | Pd | 1 | 5' | | Ph | H | | ME | H | H | CH₃ | H | pic | |
| 5'-293X | Pd | 1 | 5' | | Ph | H | | ME | H | H | CH₃ | H | acac | |
| 5'-293Y | Pd | 0 | 5' | | Ph | H | | ME | H | H | CH₃ | H | — | — |
| 5'-294 | Pd | 1 | 5' | | Ph | H | H | | AT | H | CH₃ | H | pic | |
| 5'-294X | Pd | 1 | 5' | | Ph | H | H | | AT | H | CH₃ | H | acac | |

TABLE 47-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-294Y | Pd | 0 | 5' | Ph | H | H | | AT | H | $CH_3$ | H | — | — |
| 5'-295 | Pd | 1 | 5' | Ph | H | | AT | | H | $CH_3$ | H | pic | |
| 5'-295X | Pd | 1 | 5' | Ph | H | | AT | | H | $CH_3$ | H | acac | |
| 5'-295Y | Pd | 0 | 5' | Ph | H | | AT | | H | $CH_3$ | H | — | — |
| 5'-296 | Pd | 1 | 5' | Ph | H | H | | MES1 | H | $CH_3$ | H | pic | |
| 5'-296X | Pd | 1 | 5' | Ph | H | H | | MES1 | H | $CH_3$ | H | acac | |
| 5'-296Y | Pd | 0 | 5' | Ph | H | H | | MES1 | H | $CH_3$ | H | — | — |
| 5'-297 | Pd | 1 | 5' | Ph | H | | MES1 | | H | $CH_3$ | H | pic | |
| 5'-297X | Pd | 1 | 5' | Ph | H | | MES1 | | H | $CH_3$ | H | acac | |
| 5'-297Y | Pd | 0 | 5' | Ph | H | | MES1 | | H | $CH_3$ | H | — | — |
| 5'-298 | Pd | 1 | 5' | Ph | H | H | | MES2 | H | $CH_3$ | H | pic | |
| 5'-298X | Pd | 1 | 5' | Ph | H | H | | MES2 | H | $CH_3$ | H | acac | |
| 5'-298Y | Pd | 0 | 5' | Ph | H | H | | MES2 | H | $CH_3$ | H | — | — |
| 5'-299 | Pd | 1 | 5' | Ph | H | | MES2 | | H | $CH_3$ | H | pic | |
| 5'-299X | Pd | 1 | 5' | Ph | H | | MES2 | | H | $CH_3$ | H | acac | |
| 5'-299Y | Pd | 0 | 5' | Ph | H | | MES2 | | H | $CH_3$ | H | — | — |
| 5'-300 | Pd | 1 | 5' | Ph | H | H | | PS1 | H | $CH_3$ | H | pic | |
| 5'-300X | Pd | 1 | 5' | Ph | H | H | | PS1 | H | $CH_3$ | H | acac | |
| 5'-300Y | Pd | 0 | 5' | Ph | H | H | | PS1 | H | $CH_3$ | H | — | — |
| 5'-301 | Pd | 1 | 5' | Ph | H | | PS1 | | H | $CH_3$ | H | pic | |
| 5'-301X | Pd | 1 | 5' | Ph | H | | PS1 | | H | $CH_3$ | H | acac | |
| 5'-301Y | Pd | 0 | 5' | Ph | H | | PS1 | | H | $CH_3$ | H | — | — |
| 5'-302 | Pd | 1 | 5' | Ph | H | H | | PS2 | H | $CH_3$ | H | pic | |
| 5'-302X | Pd | 1 | 5' | Ph | H | H | | PS2 | H | $CH_3$ | H | acac | |
| 5'-302Y | Pd | 0 | 5' | Ph | H | H | | PS2 | H | $CH_3$ | H | — | — |
| 5'-303 | Pd | 1 | 5' | Ph | H | | PS2 | | H | $CH_3$ | H | pic | |
| 5'-303X | Pd | 1 | 5' | Ph | H | | PS2 | | H | $CH_3$ | H | acac | |
| 5'-303Y | Pd | 0 | 5' | Ph | H | | PS2 | | H | $CH_3$ | H | — | — |
| 5'-304 | Pd | 1 | 5' | Ph | H | H | | BAL1 | H | $CH_3$ | H | pic | |
| 5'-304X | Pd | 1 | 5' | Ph | H | H | | BAL1 | H | $CH_3$ | H | acac | |
| 5'-304Y | Pd | 0 | 5' | Ph | H | H | | BAL1 | H | $CH_3$ | H | — | — |
| 5'-305 | Pd | 1 | 5' | Ph | H | | BAL1 | | H | $CH_3$ | H | pic | |
| 5'-305X | Pd | 1 | 5' | Ph | H | | BAL1 | | H | $CH_3$ | H | acac | |
| 5'-305Y | Pd | 0 | 5' | Ph | H | | BAL1 | | H | $CH_3$ | H | — | — |
| 5'-306 | Pd | 1 | 5' | Ph | H | H | | BAL2 | H | $CH_3$ | H | pic | |
| 5'-306X | Pd | 1 | 5' | Ph | H | H | | BAL2 | H | $CH_3$ | H | acac | |
| 5'-306Y | Pd | 0 | 5' | Ph | H | H | | BAL2 | H | $CH_3$ | H | — | — |
| 5'-307 | Pd | 1 | 5' | Ph | H | | BAL2 | | H | $CH_3$ | H | pic | |
| 5'-307X | Pd | 1 | 5' | Ph | H | | BAL2 | | H | $CH_3$ | H | acac | |
| 5'-307Y | Pd | 0 | 5' | Ph | H | | BAL2 | | H | $CH_3$ | H | — | — |
| 5'-308 | Pd | 1 | 5' | Ph | H | H | | MEK1 | H | $CH_3$ | H | pic | |
| 5'-308X | Pd | 1 | 5' | Ph | H | H | | MEK1 | H | $CH_3$ | H | acac | |
| 5'-308Y | Pd | 0 | 5' | Ph | H | H | | MEK1 | H | $CH_3$ | H | — | — |
| 5'-309 | Pd | 1 | 5' | Ph | H | | MEK1 | | H | $CH_3$ | H | pic | |
| 5'-309X | Pd | 1 | 5' | Ph | H | | MEK1 | | H | $CH_3$ | H | acac | |
| 5'-309Y | Pd | 0 | 5' | Ph | H | | MEK1 | | H | $CH_3$ | H | — | — |
| 5'-310 | Pd | 1 | 5' | Ph | H | H | | MEK2 | H | $CH_3$ | H | pic | |
| 5'-310X | Pd | 1 | 5' | Ph | H | H | | MEK2 | H | $CH_3$ | H | acac | |
| 5'-310Y | Pd | 0 | 5' | Ph | H | H | | MEK2 | H | $CH_3$ | H | — | — |
| 5'-311 | Pd | 1 | 5' | Ph | H | | MEK2 | | H | $CH_3$ | H | pic | |
| 5'-311X | Pd | 1 | 5' | Ph | H | | MEK2 | | H | $CH_3$ | H | acac | |
| 5'-311Y | Pd | 0 | 5' | Ph | H | | MEK2 | | H | $CH_3$ | H | — | — |
| 5'-312 | Pd | 1 | 5' | Ph | H | H | | PAL1 | H | $CH_3$ | H | pic | |
| 5'-312X | Pd | 1 | 5' | Ph | H | H | | PAL1 | H | $CH_3$ | H | acac | |
| 5'-312Y | Pd | 0 | 5' | Ph | H | H | | PAL1 | H | $CH_3$ | H | — | — |
| 5'-313 | Pd | 1 | 5' | Ph | H | | PAL1 | | H | $CH_3$ | H | pic | |
| 5'-313X | Pd | 1 | 5' | Ph | H | | PAL1 | | H | $CH_3$ | H | acac | |
| 5'-313Y | Pd | 0 | 5' | Ph | H | | PAL1 | | H | $CH_3$ | H | — | — |
| 5'-314 | Pd | 1 | 5' | Ph | H | H | | PAL2 | H | $CH_3$ | H | pic | |
| 5'-314X | Pd | 1 | 5' | Ph | H | H | | PAL2 | H | $CH_3$ | H | acac | |
| 5'-314Y | Pd | 0 | 5' | Ph | H | H | | PAL2 | H | $CH_3$ | H | — | — |
| 5'-315 | Pd | 1 | 5' | Ph | H | | PAL2 | | H | $CH_3$ | H | pic | |
| 5'-315X | Pd | 1 | 5' | Ph | H | | PAL2 | | H | $CH_3$ | H | acac | |
| 5'-315Y | Pd | 0 | 5' | Ph | H | | PAL2 | | H | $CH_3$ | H | — | — |
| 5'-316 | Pd | 1 | 5' | Ph | H | H | | MMK | H | $CH_3$ | H | pic | |
| 5'-316X | Pd | 1 | 5' | Ph | H | H | | MMK | H | $CH_3$ | H | acac | |
| 5'-316Y | Pd | 0 | 5' | Ph | H | H | | MMK | H | $CH_3$ | H | — | — |
| 5'-317 | Pd | 1 | 5' | Ph | H | | MMK | | H | $CH_3$ | H | pic | |
| 5'-317X | Pd | 1 | 5' | Ph | H | | MMK | | H | $CH_3$ | H | acac | |
| 5'-317Y | Pd | 0 | 5' | Ph | H | | MMK | | H | $CH_3$ | H | — | — |
| 5'-318 | Pd | 1 | 5' | Ph | H | H | | EES1 | H | $CH_3$ | H | pic | |
| 5'-318X | Pd | 1 | 5' | Ph | H | H | | EES1 | H | $CH_3$ | H | acac | |
| 5'-318Y | Pd | 0 | 5' | Ph | H | H | | EES1 | H | $CH_3$ | H | — | — |
| 5'-319 | Pd | 1 | 5' | Ph | H | | EES2 | | H | $CH_3$ | H | pic | |
| 5'-319X | Pd | 1 | 5' | Ph | H | | EES2 | | H | $CH_3$ | H | acac | |
| 5'-319Y | Pd | 0 | 5' | Ph | H | | EES2 | | H | $CH_3$ | H | — | — |
| 5'-320 | Pd | 1 | 5' | Ph | H | H | | PAE1 | H | $CH_3$ | H | pic | |

TABLE 47-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-320X | Pd | 1 | 5' | Ph | H | H | | PAE1 | H | CH₃ | H | acac | |
| 5'-320Y | Pd | 0 | 5' | Ph | H | H | | PAE1 | H | CH₃ | H | — | — |
| 5'-321 | Pd | 1 | 5' | Ph | H | | PAE2 | | H | CH₃ | H | pic | |
| 5'-321X | Pd | 1 | 5' | Ph | H | | PAE2 | | H | CH₃ | H | acac | |
| 5'-321Y | Pd | 0 | 5' | Ph | H | | PAE2 | | H | CH₃ | H | — | — |
| 5'-322 | Pd | 1 | 5' | Ph | H | H | | AME1 | H | CH₃ | H | pic | |
| 5'-322X | Pd | 1 | 5' | Ph | H | H | | AME1 | H | CH₃ | H | acac | |
| 5'-322Y | Pd | 0 | 5' | Ph | H | H | | AME1 | H | CH₃ | H | — | — |
| 5'-323 | Pd | 1 | 5' | Ph | H | | AME1 | | H | CH₃ | H | pic | |
| 5'-323X | Pd | 1 | 5' | Ph | H | | AME1 | | H | CH₃ | H | acac | |
| 5'-323Y | Pd | 0 | 5' | Ph | H | | AME1 | | H | CH₃ | H | — | — |
| 5'-324 | Pd | 1 | 5' | Ph | H | H | | AME2 | H | CH₃ | H | pic | |
| 5'-324X | Pd | 1 | 5' | Ph | H | H | | AME2 | H | CH₃ | H | acac | |
| 5'-324Y | Pd | 0 | 5' | Ph | H | H | | AME2 | H | CH₃ | H | — | — |
| 5'-325 | Pd | 1 | 5' | Ph | H | | AME2 | | H | CH₃ | H | pic | |
| 5'-325X | Pd | 1 | 5' | Ph | H | | AME2 | | H | CH₃ | H | acac | |
| 5'-325Y | Pd | 0 | 5' | Ph | H | | AME2 | | H | CH₃ | H | — | — |
| 5'-326 | Pd | 1 | 5' | Ph | H | H | | EAE1 | H | CH₃ | H | pic | |
| 5'-326X | Pd | 1 | 5' | Ph | H | H | | EAE1 | H | CH₃ | H | acac | |
| 5'-326Y | Pd | 0 | 5' | Ph | H | H | | EAE1 | H | CH₃ | H | — | — |
| 5'-327 | Pd | 1 | 5' | Ph | H | | EAE1 | | H | CH₃ | H | pic | |
| 5'-327X | Pd | 1 | 5' | Ph | H | | EAE1 | | H | CH₃ | H | acac | |
| 5'-327Y | Pd | 0 | 5' | Ph | H | | EAE1 | | H | CH₃ | H | — | — |
| 5'-328 | Pd | 1 | 5' | Ph | H | H | | EAE2 | H | CH₃ | H | pic | |
| 5'-328X | Pd | 1 | 5' | Ph | H | H | | EAE2 | H | CH₃ | H | acac | |
| 5'-328Y | Pd | 0 | 5' | Ph | H | H | | EAE2 | H | CH₃ | H | — | — |
| 5'-329 | Pd | 1 | 5' | Ph | H | | EAE2 | | H | CH₃ | H | pic | |
| 5'-329X | Pd | 1 | 5' | Ph | H | | EAE2 | | H | CH₃ | H | acac | |
| 5'-329Y | Pd | 0 | 5' | Ph | H | | EAE2 | | H | CH₃ | H | — | — |
| 5'-330 | Pd | 1 | 5' | Ph | H | H | | AAE1 | H | CH₃ | H | pic | |
| 5'-330X | Pd | 1 | 5' | Ph | H | H | | AAE1 | H | CH₃ | H | acac | |
| 5'-330Y | Pd | 0 | 5' | Ph | H | H | | AAE1 | H | CH₃ | H | — | — |
| 5'-331 | Pd | 1 | 5' | Ph | H | | AAE1 | | H | CH₃ | H | pic | |
| 5'-331X | Pd | 1 | 5' | Ph | H | | AAE1 | | H | CH₃ | H | acac | |
| 5'-331Y | Pd | 0 | 5' | Ph | H | | AAE1 | | H | CH₃ | H | — | — |
| 5'-332 | Pd | 1 | 5' | Ph | H | H | | AAE2 | H | CH₃ | H | pic | |
| 5'-332X | Pd | 1 | 5' | Ph | H | H | | AAE2 | H | CH₃ | H | acac | |
| 5'-332Y | Pd | 0 | 5' | Ph | H | H | | AAE2 | H | CH₃ | H | — | — |
| 5'-333 | Pd | 1 | 5' | Ph | H | | AAE2 | | H | CH₃ | H | pic | |
| 5'-333X | Pd | 1 | 5' | Ph | H | | AAE2 | | H | CH₃ | H | acac | |
| 5'-333Y | Pd | 0 | 5' | Ph | H | | AAE2 | | H | CH₃ | H | — | — |
| 5'-334 | Pd | 1 | 5' | Ph | H | H | | PME1 | H | CH₃ | H | pic | |
| 5'-334X | Pd | 1 | 5' | Ph | H | H | | PME1 | H | CH₃ | H | acac | |
| 5'-334Y | Pd | 0 | 5' | Ph | H | H | | PME1 | H | CH₃ | H | — | — |
| 5'-335 | Pd | 1 | 5' | Ph | H | | PME1 | | H | CH₃ | H | pic | |
| 5'-335X | Pd | 1 | 5' | Ph | H | | PME1 | | H | CH₃ | H | acac | |
| 5'-335Y | Pd | 0 | 5' | Ph | H | | PME1 | | H | CH₃ | H | — | — |
| 5'-336 | Pd | 1 | 5' | Ph | H | H | | PME2 | H | CH₃ | H | pic | |
| 5'-336X | Pd | 1 | 5' | Ph | H | H | | PME2 | H | CH₃ | H | acac | |
| 5'-336Y | Pd | 0 | 5' | Ph | H | H | | PME2 | H | CH₃ | H | — | — |
| 5'-337 | Pd | 1 | 5' | Ph | H | | PME2 | | H | CH₃ | H | pic | |
| 5'-337X | Pd | 1 | 5' | Ph | H | | PME2 | | H | CH₃ | H | acac | |
| 5'-337Y | Pd | 0 | 5' | Ph | H | | PME2 | | H | CH₃ | H | — | — |
| 5'-338 | Pd | 1 | 5' | Ph | H | H | | MET1 | H | CH₃ | H | pic | |
| 5'-338X | Pd | 1 | 5' | Ph | H | H | | MET1 | H | CH₃ | H | acac | |
| 5'-338Y | Pd | 0 | 5' | Ph | H | H | | MET1 | H | CH₃ | H | — | — |
| 5'-339 | Pd | 1 | 5' | Ph | H | | MET1 | | H | CH₃ | H | pic | |
| 5'-339X | Pd | 1 | 5' | Ph | H | | MET1 | | H | CH₃ | H | acac | |
| 5'-339Y | Pd | 0 | 5' | Ph | H | | MET1 | | H | CH₃ | H | — | — |
| 5'-340 | Pd | 1 | 5' | Ph | H | H | | MET2 | H | CH₃ | H | pic | |
| 5'-340X | Pd | 1 | 5' | Ph | H | H | | MET2 | H | CH₃ | H | acac | |
| 5'-340Y | Pd | 0 | 5' | Ph | H | H | | MET2 | H | CH₃ | H | — | — |
| 5'-341 | Pd | 1 | 5' | Ph | H | | MET2 | | H | CH₃ | H | pic | |
| 5'-341X | Pd | 1 | 5' | Ph | H | | MET2 | | H | CH₃ | H | acac | |
| 5'-341Y | Pd | 0 | 5' | Ph | H | | MET2 | | H | CH₃ | H | — | — |
| 5'-342 | Pd | 1 | 5' | Ph | H | H | | EE1 | H | CH₃ | H | pic | |
| 5'-342X | Pd | 1 | 5' | Ph | H | H | | EE1 | H | CH₃ | H | acac | |
| 5'-342Y | Pd | 0 | 5' | Ph | H | H | | EE1 | H | CH₃ | H | — | — |
| 5'-343 | Pd | 1 | 5' | Ph | H | | EE1 | | H | CH₃ | H | pic | |
| 5'-343X | Pd | 1 | 5' | Ph | H | | EE1 | | H | CH₃ | H | acac | |
| 5'-343Y | Pd | 0 | 5' | Ph | H | | EE1 | | H | CH₃ | H | — | — |
| 5'-344 | Pd | 1 | 5' | Ph | H | H | | EE2 | H | CH₃ | H | pic | |
| 5'-344X | Pd | 1 | 5' | Ph | H | H | | EE2 | H | CH₃ | H | acac | |
| 5'-344Y | Pd | 0 | 5' | Ph | H | H | | EE2 | H | CH₃ | H | — | — |
| 5'-345 | Pd | 1 | 5' | Ph | H | | EE2 | | H | CH₃ | H | pic | |
| 5'-345X | Pd | 1 | 5' | Ph | H | | EE2 | | H | CH₃ | H | acac | |
| 5'-345Y | Pd | 0 | 5' | Ph | H | | EE2 | | H | CH₃ | H | — | — |

TABLE 47-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 5'-346 | Pd | 1 | 5' | Ph | H | H | | MS1 | | H | CH₃ | H | pic |
| 5'-346X | Pd | 1 | 5' | Ph | H | H | | MS1 | | H | CH₃ | H | acac |
| 5'-346Y | Pd | 0 | 5' | Ph | H | H | | MS1 | | H | CH₃ | H | — — |
| 5'-347 | Pd | 1 | 5' | Ph | H | | MS1 | | H | H | CH₃ | H | pic |
| 5'-347X | Pd | 1 | 5' | Ph | H | | MS1 | | H | H | CH₃ | H | acac |
| 5'-347Y | Pd | 0 | 5' | Ph | H | | MS1 | | H | H | CH₃ | H | — — |
| 5'-348 | Pd | 1 | 5' | Ph | H | H | | MS2 | | H | CH₃ | H | pic |
| 5'-348X | Pd | 1 | 5' | Ph | H | H | | MS2 | | H | CH₃ | H | acac |
| 5'-348Y | Pd | 0 | 5' | Ph | H | H | | MS2 | | H | CH₃ | H | — — |
| 5'-349 | Pd | 1 | 5' | Ph | H | | MS2 | | H | H | CH₃ | H | pic |
| 5'-349X | Pd | 1 | 5' | Ph | H | | MS2 | | H | H | CH₃ | H | acac |
| 5'-349Y | Pd | 0 | 5' | Ph | H | | MS2 | | H | H | CH₃ | H | — — |

TABLE 48

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 6'-167 | Pd | 1 | 6' | Ph | H | H | H | H | CH₃ | H | H | pic | |
| 6'-167X | Pd | 1 | 6' | Ph | H | H | H | H | CH₃ | H | H | acac | |
| 6'-167Y | Pd | 0 | 6' | Ph | H | H | H | H | CH₃ | H | H | — | — |
| 6'-168 | Pd | 1 | 6' | Ph | H | H | H | H | ᵗC₄H₉ | H | H | pic | |
| 6'-168X | Pd | 1 | 6' | Ph | H | H | H | H | ᵗC₄H₉ | H | H | acac | |
| 6'-168Y | Pd | 0 | 6' | Ph | H | H | H | H | ᵗC₄H₉ | H | H | — | — |
| 6'-169 | Pd | 1 | 6' | Ph | H | F | H | F | CH₃ | H | H | pic | |
| 6'-169X | Pd | 1 | 6' | Ph | H | F | H | F | CH₃ | H | H | acac | |
| 6'-169Y | Pd | 0 | 6' | Ph | H | F | H | F | CH₃ | H | H | — | — |
| 6'-170 | Pd | 1 | 6' | Ph | H | F | H | F | ᵗC₄H₉ | H | H | pic | |
| 6'-170X | Pd | 1 | 6' | Ph | H | F | H | F | ᵗC₄H₉ | H | H | acac | |
| 6'-170Y | Pd | 0 | 6' | Ph | H | F | H | F | ᵗC₄H₉ | H | H | — | — |
| 6'-171 | Pd | 1 | 6' | Ph | F | H | H | F | CH₃ | H | H | pic | |
| 6'-171X | Pd | 1 | 6' | Ph | F | H | H | F | CH₃ | H | H | acac | |
| 6'-171Y | Pd | 0 | 6' | Ph | F | H | H | F | CH₃ | H | H | — | — |
| 6'-172 | Pd | 1 | 6' | Ph | F | H | H | F | ᵗC₄H₉ | H | H | pic | |
| 6'-172X | Pd | 1 | 6' | Ph | F | H | H | F | ᵗC₄H₉ | H | H | acac | |
| 6'-172Y | Pd | 0 | 6' | Ph | F | H | H | F | ᵗC₄H₉ | H | H | — | — |
| 6'-173 | Pd | 1 | 6' | Ph | CF₃ | H | CF₃ | H | CH₃ | H | H | pic | |
| 6'-173X | Pd | 1 | 6' | Ph | CF₃ | H | CF₃ | H | CH₃ | H | H | acac | |
| 6'-173Y | Pd | 0 | 6' | Ph | CF₃ | H | CF₃ | H | CH₃ | H | H | — | — |
| 6'-174 | Pd | 1 | 6' | Ph | CF₃ | H | CF₃ | H | ᵗC₄H₉ | H | H | pic | |
| 6'-174X | Pd | 1 | 6' | Ph | CF₃ | H | CF₃ | H | ᵗC₄H₉ | H | H | acac | |
| 6'-174Y | Pd | 0 | 6' | Ph | CF₃ | H | CF₃ | H | ᵗC₄H₉ | H | H | — | — |
| 6'-175 | Pd | 1 | 6' | Ph | H | F | CF₃ | H | CH₃ | H | H | pic | |
| 6'-175X | Pd | 1 | 6' | Ph | H | F | CF₃ | H | CH₃ | H | H | acac | |
| 6'-175Y | Pd | 0 | 6' | Ph | H | F | CF₃ | H | CH₃ | H | H | — | — |
| 6'-176 | Pd | 1 | 6' | Ph | F | H | CF₃ | H | CH₃ | H | H | pic | |
| 6'-176X | Pd | 1 | 6' | Ph | F | H | CF₃ | H | CH₃ | H | H | acac | |
| 6'-176Y | Pd | 0 | 6' | Ph | F | H | CF₃ | H | CH₃ | H | H | — | — |
| 6'-177 | Pd | 1 | 6' | Ph | F | F | F | F | CH₃ | H | H | pic | |
| 6'-177X | Pd | 1 | 6' | Ph | F | F | F | F | CH₃ | H | H | acac | |
| 6'-177Y | Pd | 0 | 6' | Ph | F | F | F | F | CH₃ | H | H | — | — |
| 6'-178 | Pd | 1 | 6' | Ph | H | F | H | CH₃ | CH₃ | H | H | pic | |
| 6'-178X | Pd | 1 | 6' | Ph | H | F | H | CH₃ | CH₃ | H | H | acac | |
| 6'-178Y | Pd | 0 | 6' | Ph | H | F | H | CH₃ | CH₃ | H | H | — | — |
| 6'-179 | Pd | 1 | 6' | Ph | H | F | H | CH₃ | ᵗC₄H₉ | H | H | pic | |
| 6'-179X | Pd | 1 | 6' | Ph | H | F | H | CH₃ | ᵗC₄H₉ | H | H | acac | |
| 6'-179Y | Pd | 0 | 6' | Ph | H | F | H | CH₃ | ᵗC₄H₉ | H | H | — | — |
| 6'-180 | Pd | 1 | 6' | Ph | H | F | H | ᵗC₄H₉ | CH₃ | H | H | pic | |
| 6'-180X | Pd | 1 | 6' | Ph | H | F | H | ᵗC₄H₉ | CH₃ | H | H | acac | |
| 6'-180Y | Pd | 0 | 6' | Ph | H | F | H | ᵗC₄H₉ | CH₃ | H | H | — | — |
| 6'-181 | Pd | 1 | 6' | Ph | H | F | H | ᵗC₄H₉ | ᵗC₄H₉ | H | H | pic | |
| 6'-181X | Pd | 1 | 6' | Ph | H | F | H | ᵗC₄H₉ | ᵗC₄H₉ | H | H | acac | |
| 6'-181Y | Pd | 0 | 6' | Ph | H | F | H | ᵗC₄H₉ | ᵗC₄H₉ | H | H | — | — |
| 6'-182 | Pd | 1 | 6' | Ph | H | CF₃ | H | CF₃ | CH₃ | H | H | pic | |
| 6'-182X | Pd | 1 | 6' | Ph | H | CF₃ | H | CF₃ | CH₃ | H | H | acac | |
| 6'-182Y | Pd | 0 | 6' | Ph | H | CF₃ | H | CF₃ | CH₃ | H | H | — | — |
| 6'-183 | Pd | 1 | 6' | Ph | H | CF₃ | H | CF₃ | ᵗC₄H₉ | H | H | pic | |
| 6'-183X | Pd | 1 | 6' | Ph | H | CF₃ | H | CF₃ | ᵗC₄H₉ | H | H | acac | |
| 6'-183Y | Pd | 0 | 6' | Ph | H | CF₃ | H | CF₃ | ᵗC₄H₉ | H | H | — | — |
| 6'-184 | Pd | 1 | 6' | Ph | CF₃ | H | H | ᵗC₄H₉ | CH₃ | H | H | pic | |
| 6'-184X | Pd | 1 | 6' | Ph | CF₃ | H | H | ᵗC₄H₉ | CH₃ | H | H | acac | |
| 6'-184Y | Pd | 0 | 6' | Ph | CF₃ | H | H | ᵗC₄H₉ | CH₃ | H | H | — | — |
| 6'-185 | Pd | 1 | 6' | Ph | CF₃ | H | H | ᵗC₄H₉ | ᵗC₄H₉ | H | H | pic | |
| 6'-185X | Pd | 1 | 6' | Ph | CF₃ | H | H | ᵗC₄H₉ | ᵗC₄H₉ | H | H | acac | |
| 6'-185Y | Pd | 0 | 6' | Ph | CF₃ | H | H | ᵗC₄H₉ | ᵗC₄H₉ | H | H | — | — |

TABLE 48-continued

| No. | M | m | BSS | SS | G | T$^1$ | T$^2$ | T$^3$ | T$^4$ | T$^5$ | T$^6$ | T$^7$ | L$^1$ | L$^2$ |
|---|---|---|---|---|---|---|---|---|---|---|---|---|---|---|
| 6'-186 | Pd | 1 | 6' | | Ph | H | CF$_3$ | H | $^t$C$_4$H$_9$ | CH$_3$ | H | H | pic | |
| 6'-186X | Pd | 1 | 6' | | Ph | H | CF$_3$ | H | $^t$C$_4$H$_9$ | CH$_3$ | H | H | acac | |
| 6'-186Y | Pd | 0 | 6' | | Ph | H | CF$_3$ | H | $^t$C$_4$H$_9$ | CH$_3$ | H | H | — | — |
| 6'-187 | Pd | 1 | 6' | | Ph | H | CF$_3$ | H | $^t$C$_4$H$_9$ | $^t$C$_4$H$_9$ | H | H | pic | |
| 6'-187X | Pd | 1 | 6' | | Ph | H | CF$_3$ | H | $^t$C$_4$H$_9$ | $^t$C$_4$H$_9$ | H | H | acac | |
| 6'-187Y | Pd | 0 | 6' | | Ph | H | CF$_3$ | H | $^t$C$_4$H$_9$ | $^t$C$_4$H$_9$ | H | H | — | — |
| 6'-188 | Pd | 1 | 6' | | Ph | H | CF$_3$ | H | CH$_3$ | CH$_3$ | H | H | pic | |
| 6'-188X | Pd | 1 | 6' | | Ph | H | CF$_3$ | H | CH$_3$ | CH$_3$ | H | H | acac | |
| 6'-188Y | Pd | 0 | 6' | | Ph | H | CF$_3$ | H | CH$_3$ | CH$_3$ | H | H | — | — |
| 6'-189 | Pd | 1 | 6' | | Ph | H | CF$_3$ | CF$_3$ | H | CH$_3$ | H | H | pic | |
| 6'-189X | Pd | 1 | 6' | | Ph | H | CF$_3$ | CF$_3$ | H | CH$_3$ | H | H | acac | |
| 6'-189Y | Pd | 0 | 6' | | Ph | H | CF$_3$ | CF$_3$ | H | CH$_3$ | H | H | — | — |
| 6'-190 | Pd | 1 | 6' | | Ph | H | H | NO$_2$ | H | CH$_3$ | H | H | pic | |
| 6'-190X | Pd | 1 | 6' | | Ph | H | H | NO$_2$ | H | CH$_3$ | H | H | acac | |
| 6'-190Y | Pd | 0 | 6' | | Ph | H | H | NO$_2$ | H | CH$_3$ | H | H | — | — |
| 6'-191 | Pd | 1 | 6' | | Ph | H | H | NO$_2$ | H | $^t$C$_4$H$_9$ | H | H | pic | |
| 6'-191X | Pd | 1 | 6' | | Ph | H | H | NO$_2$ | H | $^t$C$_4$H$_9$ | H | H | acac | |
| 6'-191Y | Pd | 0 | 6' | | Ph | H | H | NO$_2$ | H | $^t$C$_4$H$_9$ | H | H | — | — |
| 6'-192 | Pd | 1 | 6' | | Ph | F | H | NO$_2$ | H | CH$_3$ | H | H | pic | |
| 6'-192X | Pd | 1 | 6' | | Ph | F | H | NO$_2$ | H | CH$_3$ | H | H | acac | |
| 6'-192Y | Pd | 0 | 6' | | Ph | F | H | NO$_2$ | H | CH$_3$ | H | H | — | — |
| 6'-193 | Pd | 1 | 6' | | Ph | F | H | NO$_2$ | F | CH$_3$ | H | H | pic | |
| 6'-193X | Pd | 1 | 6' | | Ph | F | H | NO$_2$ | F | CH$_3$ | H | H | acac | |
| 6'-193Y | Pd | 0 | 6' | | Ph | F | H | NO$_2$ | F | CH$_3$ | H | H | — | — |
| 6'-194 | Pd | 1 | 6' | | Ph | H | NO$_2$ | H | NO$_2$ | CH$_3$ | H | H | pic | |
| 6'-194X | Pd | 1 | 6' | | Ph | H | NO$_2$ | H | NO$_2$ | CH$_3$ | H | H | acac | |
| 6'-194Y | Pd | 0 | 6' | | Ph | H | NO$_2$ | H | NO$_2$ | CH$_3$ | H | H | — | — |
| 6'-195 | Pd | 1 | 6' | | Ph | H | NO$_2$ | H | NO$_2$ | $^t$C$_4$H$_9$ | H | H | pic | |
| 6'-195X | Pd | 1 | 6' | | Ph | H | NO$_2$ | H | NO$_2$ | $^t$C$_4$H$_9$ | H | H | acac | |
| 6'-195Y | Pd | 0 | 6' | | Ph | H | NO$_2$ | H | NO$_2$ | $^t$C$_4$H$_9$ | H | H | — | — |
| 6'-196 | Pd | 1 | 6' | | Ph | NO$_2$ | H | H | NO$_2$ | CH$_3$ | H | H | pic | |
| 6'-196X | Pd | 1 | 6' | | Ph | NO$_2$ | H | H | NO$_2$ | CH$_3$ | H | H | acac | |
| 6'-196Y | Pd | 0 | 6' | | Ph | NO$_2$ | H | H | NO$_2$ | CH$_3$ | H | H | — | — |
| 6'-197 | Pd | 1 | 6' | | Ph | NO$_2$ | H | H | NO$_2$ | $^t$C$_4$H$_9$ | H | H | pic | |
| 6'-197X | Pd | 1 | 6' | | Ph | NO$_2$ | H | H | NO$_2$ | $^t$C$_4$H$_9$ | H | H | acac | |
| 6'-197Y | Pd | 0 | 6' | | Ph | NO$_2$ | H | H | NO$_2$ | $^t$C$_4$H$_9$ | H | H | — | — |
| 6'-198 | Pd | 1 | 6' | | Ph | H | H | CF$_3$ | H | CH$_3$ | H | H | pic | |
| 6'-198X | Pd | 1 | 6' | | Ph | H | H | CF$_3$ | H | CH$_3$ | H | H | acac | |
| 6'-198Y | Pd | 0 | 6' | | Ph | H | H | CF$_3$ | H | CH$_3$ | H | H | — | — |
| 6'-199 | Pd | 1 | 6' | | Ph | H | H | CF$_3$ | H | $^t$C$_4$H$_9$ | H | H | pic | |
| 6'-199X | Pd | 1 | 6' | | Ph | H | H | CF$_3$ | H | $^t$C$_4$H$_9$ | H | H | acac | |
| 6'-199Y | Pd | 0 | 6' | | Ph | H | H | CF$_3$ | H | $^t$C$_4$H$_9$ | H | H | — | — |
| 6'-200 | Pd | 1 | 6' | | Ph | H | Cl | CF$_3$ | H | CH$_3$ | H | H | pic | |
| 6'-200X | Pd | 1 | 6' | | Ph | H | Cl | CF$_3$ | H | CH$_3$ | H | H | acac | |
| 6'-200Y | Pd | 0 | 6' | | Ph | H | Cl | CF$_3$ | H | CH$_3$ | H | H | — | — |
| 6'-201 | Pd | 1 | 6' | | Ph | H | Cl | CF$_3$ | H | $^t$C$_4$H$_9$ | H | H | pic | |
| 6'-201X | Pd | 1 | 6' | | Ph | H | Cl | CF$_3$ | H | $^t$C$_4$H$_9$ | H | H | acac | |
| 6'-201Y | Pd | 0 | 6' | | Ph | H | Cl | CF$_3$ | H | $^t$C$_4$H$_9$ | H | H | — | — |
| 6'-202 | Pd | 1 | 6' | | Ph | H | NO$_2$ | H | H | CH$_3$ | H | H | pic | |
| 6'-202X | Pd | 1 | 6' | | Ph | H | NO$_2$ | H | H | CH$_3$ | H | H | acac | |
| 6'-202Y | Pd | 0 | 6' | | Ph | H | NO$_2$ | H | H | CH$_3$ | H | H | — | — |
| 6'-203 | Pd | 1 | 6' | | Ph | H | CF$_3$ | H | H | CH$_3$ | H | H | pic | |
| 6'-203X | Pd | 1 | 6' | | Ph | H | CF$_3$ | H | H | CH$_3$ | H | H | acac | |
| 6'-203Y | Pd | 0 | 6' | | Ph | H | CF$_3$ | H | H | CH$_3$ | H | H | — | — |
| 6'-204 | Pd | 1 | 6' | | Ph | H | NO$_2$ | H | CH$_3$ | CH$_3$ | H | H | pic | |
| 6'-204X | Pd | 1 | 6' | | Ph | H | NO$_2$ | H | CH$_3$ | CH$_3$ | H | H | acac | |
| 6'-204Y | Pd | 0 | 6' | | Ph | H | NO$_2$ | H | CH$_3$ | CH$_3$ | H | H | — | — |
| 6'-205 | Pd | 1 | 6' | | Ph | H | NO$_2$ | H | CH$_3$ | $^t$C$_4$H$_9$ | H | H | pic | |
| 6'-205X | Pd | 1 | 6' | | Ph | H | NO$_2$ | H | CH$_3$ | $^t$C$_4$H$_9$ | H | H | acac | |
| 6'-205Y | Pd | 0 | 6' | | Ph | H | NO$_2$ | H | CH$_3$ | $^t$C$_4$H$_9$ | H | H | — | — |
| 6'-206 | Pd | 1 | 6' | | Ph | H | NO$_2$ | H | $^t$C$_4$H$_9$ | CH$_3$ | H | H | pic | |
| 6'-206X | Pd | 1 | 6' | | Ph | H | NO$_2$ | H | $^t$C$_4$H$_9$ | CH$_3$ | H | H | acac | |
| 6'-206Y | Pd | 0 | 6' | | Ph | H | NO$_2$ | H | $^t$C$_4$H$_9$ | CH$_3$ | H | H | — | — |
| 6'-207 | Pd | 1 | 6' | | Ph | H | NO$_2$ | H | $^t$C$_4$H$_9$ | $^t$C$_4$H$_9$ | H | H | pic | |
| 6'-207X | Pd | 1 | 6' | | Ph | H | NO$_2$ | H | $^t$C$_4$H$_9$ | $^t$C$_4$H$_9$ | H | H | acac | |
| 6'-207Y | Pd | 0 | 6' | | Ph | H | NO$_2$ | H | $^t$C$_4$H$_9$ | $^t$C$_4$H$_9$ | H | H | — | — |
| 6'-208 | Pd | 1 | 6' | | Ph | H | H | CH$_3$O | H | CH$_3$ | H | H | pic | |
| 6'-208X | Pd | 1 | 6' | | Ph | H | H | CH$_3$O | H | CH$_3$ | H | H | acac | |
| 6'-208Y | Pd | 0 | 6' | | Ph | H | H | CH$_3$O | H | CH$_3$ | H | H | — | — |
| 6'-209 | Pd | 1 | 6' | | Ph | H | CH$_3$O | H | H | CH$_3$ | H | H | pic | |
| 6'-209X | Pd | 1 | 6' | | Ph | H | CH$_3$O | H | H | CH$_3$ | H | H | acac | |
| 6'-209Y | Pd | 0 | 6' | | Ph | H | CH$_3$O | H | H | CH$_3$ | H | H | — | — |
| 6'-210 | Pd | 1 | 6' | | Ph | H | CH$_3$O | H | CH$_3$ | CH$_3$ | H | H | pic | |
| 6'-210X | Pd | 1 | 6' | | Ph | H | CH$_3$O | H | CH$_3$ | CH$_3$ | H | H | acac | |
| 6'-210Y | Pd | 0 | 6' | | Ph | H | CH$_3$O | H | CH$_3$ | CH$_3$ | H | H | — | — |
| 6'-211 | Pd | 1 | 6' | | Ph | H | CH$_3$O | H | $^t$C$_4$H$_9$ | CH$_3$ | H | H | pic | |
| 6'-211X | Pd | 1 | 6' | | Ph | H | CH$_3$O | H | $^t$C$_4$H$_9$ | CH$_3$ | H | H | acac | |

TABLE 48-continued

| No. | M | m | BSS | SS G | T$^1$ | T$^2$ | T$^3$ | T$^4$ | T$^5$ | T$^6$ | T$^7$ | L$^1$ | L$^2$ |
|---|---|---|---|---|---|---|---|---|---|---|---|---|---|
| 6'-211Y | Pd | 0 | 6' | Ph | H | CH$_3$O | H | $^t$C$_4$H$_9$ | CH$_3$ | H | H | — | — |
| 6'-212 | Pd | 1 | 6' | Ph | H | Si(CH$_3$)$_3$ | H | H | CH$_3$ | H | H | pic | |
| 6'-212X | Pd | 1 | 6' | Ph | H | Si(CH$_3$)$_3$ | H | H | CH$_3$ | H | H | acac | |
| 6'-212Y | Pd | 0 | 6' | Ph | H | Si(CH$_3$)$_3$ | H | H | CH$_3$ | H | H | — | — |
| 6'-213 | Pd | 1 | 6' | Ph | H | Si(CH$_3$)$_3$ | H | H | $^t$C$_4$H$_9$ | H | H | pic | |
| 6'-213X | Pd | 1 | 6' | Ph | H | Si(CH$_3$)$_3$ | H | H | $^t$C$_4$H$_9$ | H | H | acac | |
| 6'-213Y | Pd | 0 | 6' | Ph | H | Si(CH$_3$)$_3$ | H | H | $^t$C$_4$H$_9$ | H | H | — | — |
| 6'-214 | Pd | 1 | 6' | Ph | H | H | Si(CH$_3$)$_3$ | H | CH$_3$ | H | H | pic | |
| 6'-214X | Pd | 1 | 6' | Ph | H | H | Si(CH$_3$)$_3$ | H | CH$_3$ | H | H | acac | |
| 6'-214Y | Pd | 0 | 6' | Ph | H | H | Si(CH$_3$)$_3$ | H | CH$_3$ | H | H | — | — |
| 6'-215 | Pd | 1 | 6' | Ph | H | H | H | Si(CH$_3$)$_3$ | CH$_3$ | H | H | pic | |
| 6'-215X | Pd | 1 | 6' | Ph | H | H | H | Si(CH$_3$)$_3$ | CH$_3$ | H | H | acac | |
| 6'-215Y | Pd | 0 | 6' | Ph | H | H | H | Si(CH$_3$)$_3$ | CH$_3$ | H | H | — | — |
| 6'-216 | Pd | 1 | 6' | Ph | H | F | H | Si(CH$_3$)$_3$ | CH$_3$ | H | H | pic | |
| 6'-216X | Pd | 1 | 6' | Ph | H | F | H | Si(CH$_3$)$_3$ | CH$_3$ | H | H | acac | |
| 6'-216Y | Pd | 0 | 6' | Ph | H | F | H | Si(CH$_3$)$_3$ | CH$_3$ | H | H | — | — |
| 6'-217 | Pd | 1 | 6' | Ph | H | CF$_3$ | H | Si(CH$_3$)$_3$ | CH$_3$ | H | H | pic | |
| 6'-217X | Pd | 1 | 6' | Ph | H | CF$_3$ | H | Si(CH$_3$)$_3$ | CH$_3$ | H | H | acac | |
| 6'-217Y | Pd | 0 | 6' | Ph | H | CF$_3$ | H | Si(CH$_3$)$_3$ | CH$_3$ | H | H | — | — |
| 6'-218 | Pd | 1 | 6' | Ph | H | CF$_3$ | H | Si(CH$_3$)$_3$ | $^t$C$_4$H$_9$ | H | H | pic | |
| 6'-218X | Pd | 1 | 6' | Ph | H | CF$_3$ | H | Si(CH$_3$)$_3$ | $^t$C$_4$H$_9$ | H | H | acac | |
| 6'-218Y | Pd | 0 | 6' | Ph | H | CF$_3$ | H | Si(CH$_3$)$_3$ | $^t$C$_4$H$_9$ | H | H | — | — |
| 6'-219 | Pd | 1 | 6' | Ph | H | Si(CH$_3$)$_3$ | H | F | CH$_3$ | H | H | pic | |
| 6'-219X | Pd | 1 | 6' | Ph | H | Si(CH$_3$)$_3$ | H | F | CH$_3$ | H | H | acac | |
| 6'-219Y | Pd | 0 | 6' | Ph | H | Si(CH$_3$)$_3$ | H | F | CH$_3$ | H | H | — | — |
| 6'-220 | Pd | 1 | 6' | Ph | H | Si(CH$_3$)$_3$ | H | F | $^t$C$_4$H$_9$ | H | H | pic | |
| 6'-220X | Pd | 1 | 6' | Ph | H | Si(CH$_3$)$_3$ | H | F | $^t$C$_4$H$_9$ | H | H | acac | |
| 6'-220Y | Pd | 0 | 6' | Ph | H | Si(CH$_3$)$_3$ | H | F | $^t$C$_4$H$_9$ | H | H | — | — |
| 6'-221 | Pd | 1 | 6' | Ph | H | Si(CH$_3$)$_3$ | H | CF$_3$ | CH$_3$ | H | H | pic | |
| 6'-221X | Pd | 1 | 6' | Ph | H | Si(CH$_3$)$_3$ | H | CF$_3$ | CH$_3$ | H | H | acac | |
| 6'-221Y | Pd | 0 | 6' | Ph | H | Si(CH$_3$)$_3$ | H | CF$_3$ | CH$_3$ | H | H | — | — |
| 6'-222 | Pd | 1 | 6' | Ph | H | Si(CH$_3$)$_3$ | H | CF$_3$ | $^t$C$_4$H$_9$ | H | H | pic | |
| 6'-222X | Pd | 1 | 6' | Ph | H | Si(CH$_3$)$_3$ | H | CF$_3$ | $^t$C$_4$H$_9$ | H | H | acac | |
| 6'-222Y | Pd | 0 | 6' | Ph | H | Si(CH$_3$)$_3$ | H | CF$_3$ | $^t$C$_4$H$_9$ | H | H | — | — |
| 6'-223 | Pd | 1 | 6' | Ph | Si(CH$_3$)$_3$ | H | Si(CH$_3$)$_3$ | H | CH$_3$ | H | H | pic | |
| 6'-223X | Pd | 1 | 6' | Ph | Si(CH$_3$)$_3$ | H | Si(CH$_3$)$_3$ | H | CH$_3$ | H | H | acac | |
| 6'-223Y | Pd | 0 | 6' | Ph | Si(CH$_3$)$_3$ | H | Si(CH$_3$)$_3$ | H | CH$_3$ | H | H | — | — |
| 6'-224 | Pd | 1 | 6' | Ph | Si(CH$_3$)$_3$ | H | Si(CH$_3$)$_3$ | H | $^t$C$_4$H$_9$ | H | H | pic | |
| 6'-224X | Pd | 1 | 6' | Ph | Si(CH$_3$)$_3$ | H | Si(CH$_3$)$_3$ | H | $^t$C$_4$H$_9$ | H | H | acac | |
| 6'-224Y | Pd | 0 | 6' | Ph | Si(CH$_3$)$_3$ | H | Si(CH$_3$)$_3$ | H | $^t$C$_4$H$_9$ | H | H | — | — |
| 6'-225 | Pd | 1 | 6' | Ph | H | H | H | COCH$_3$ | CH$_3$ | H | H | pic | |
| 6'-225X | Pd | 1 | 6' | Ph | H | H | H | COCH$_3$ | CH$_3$ | H | H | acac | |
| 6'-225Y | Pd | 0 | 6' | Ph | H | H | H | COCH$_3$ | CH$_3$ | H | H | — | — |
| 6'-226 | Pd | 1 | 6' | Ph | H | H | COCH$_3$ | H | CH$_3$ | H | H | pic | |
| 6'-226X | Pd | 1 | 6' | Ph | H | H | COCH$_3$ | H | CH$_3$ | H | H | acac | |
| 6'-226Y | Pd | 0 | 6' | Ph | H | H | COCH$_3$ | H | CH$_3$ | H | H | — | — |
| 6'-227 | Pd | 1 | 6' | Ph | H | COCH$_3$ | H | H | CH$_3$ | H | H | pic | |
| 6'-227X | Pd | 1 | 6' | Ph | H | COCH$_3$ | H | H | CH$_3$ | H | H | acac | |
| 6'-227Y | Pd | 0 | 6' | Ph | H | COCH$_3$ | H | H | CH$_3$ | H | H | — | — |
| 6'-228 | Pd | 1 | 6' | Ph | H | H | BL | | CH$_3$ | H | H | pic | |
| 6'-228X | Pd | 1 | 6' | Ph | H | H | BL | | CH$_3$ | H | H | acac | |
| 6'-228Y | Pd | 0 | 6' | Ph | H | H | BL | | CH$_3$ | H | H | — | — |
| 6'-229 | Pd | 1 | 6' | Ph | H | H | BL | | $^t$C$_4$H$_9$ | H | H | pic | |
| 6'-229X | Pd | 1 | 6' | Ph | H | H | BL | | $^t$C$_4$H$_9$ | H | H | acac | |
| 6'-229Y | Pd | 0 | 6' | Ph | H | H | BL | | $^t$C$_4$H$_9$ | H | H | — | — |
| 6'-230 | Pd | 1 | 6' | Ph | H | BL | | H | CH$_3$ | H | H | pic | |
| 6'-230X | Pd | 1 | 6' | Ph | H | BL | | H | CH$_3$ | H | H | acac | |
| 6'-230Y | Pd | 0 | 6' | Ph | H | BL | | H | CH$_3$ | H | H | — | — |
| 6'-231 | Pd | 1 | 6' | Ph | H | BL | | H | $^t$C$_4$H$_9$ | H | H | pic | |
| 6'-231X | Pd | 1 | 6' | Ph | H | BL | | H | $^t$C$_4$H$_9$ | H | H | acac | |
| 6'-231Y | Pd | 0 | 6' | Ph | H | BL | | H | $^t$C$_4$H$_9$ | H | H | — | — |
| 6'-232 | Pd | 1 | 6' | Ph | H | H | PL | | CH$_3$ | H | H | pic | |
| 6'-232X | Pd | 1 | 6' | Ph | H | H | PL | | CH$_3$ | H | H | acac | |
| 6'-232Y | Pd | 0 | 6' | Ph | H | H | PL | | CH$_3$ | H | H | — | — |
| 6'-233 | Pd | 1 | 6' | Ph | H | H | PL | | $^t$C$_4$H$_9$ | H | H | pic | |
| 6'-233X | Pd | 1 | 6' | Ph | H | H | PL | | $^t$C$_4$H$_9$ | H | H | acac | |
| 6'-233Y | Pd | 0 | 6' | Ph | H | H | PL | | $^t$C$_4$H$_9$ | H | H | — | — |
| 6'-234 | Pd | 1 | 6' | Ph | H | PL | | H | CH$_3$ | H | H | pic | |
| 6'-234X | Pd | 1 | 6' | Ph | H | PL | | H | CH$_3$ | H | H | acac | |
| 6'-234Y | Pd | 0 | 6' | Ph | H | PL | | H | CH$_3$ | H | H | — | — |
| 6'-235 | Pd | 1 | 6' | Ph | H | PL | | H | $^t$C$_4$H$_9$ | H | H | pic | |
| 6'-235X | Pd | 1 | 6' | Ph | H | PL | | H | $^t$C$_4$H$_9$ | H | H | acac | |
| 6'-235Y | Pd | 0 | 6' | Ph | H | PL | | H | $^t$C$_4$H$_9$ | H | H | — | — |
| 6'-236 | Pd | 1 | 6' | Ph | H | H | MEE1 | | CH$_3$ | H | H | pic | |
| 6'-236X | Pd | 1 | 6' | Ph | H | H | MEE1 | | CH$_3$ | H | H | acac | |
| 6'-236Y | Pd | 0 | 6' | Ph | H | H | MEE1 | | CH$_3$ | H | H | — | — |
| 6'-237 | Pd | 1 | 6' | Ph | H | MEE1 | | H | CH$_3$ | H | H | pic | |

TABLE 48-continued

| No. | M | m | BSS | SS G | $T^1$ | $T^2$ | $T^3$ | $T^4$ | $T^5$ | $T^6$ | $T^7$ | $L^1$ | $L^2$ |
|---|---|---|---|---|---|---|---|---|---|---|---|---|---|
| 6'-237X | Pd | 1 | 6' | Ph | H | | MEE1 | | CH$_3$ | H | H | acac | |
| 6'-237Y | Pd | 0 | 6' | Ph | H | | MEE1 | | CH$_3$ | H | H | — | — |
| 6'-238 | Pd | 1 | 6' | Ph | H | H | | MEE2 | CH$_3$ | H | H | pic | |
| 6'-238X | Pd | 1 | 6' | Ph | H | H | | MEE2 | CH$_3$ | H | H | acac | |
| 6'-238Y | Pd | 0 | 6' | Ph | H | H | | MEE2 | CH$_3$ | H | H | — | — |
| 6'-239 | Pd | 1 | 6' | Ph | H | | MEE2 | | CH$_3$ | H | H | pic | |
| 6'-239X | Pd | 1 | 6' | Ph | H | | MEE2 | | CH$_3$ | H | H | acac | |
| 6'-239Y | Pd | 0 | 6' | Ph | H | | MEE2 | | CH$_3$ | H | H | — | — |
| 6'-240 | Pd | 1 | 6' | Ph | H | H | | PA1 | CH$_3$ | H | H | pic | |
| 6'-240X | Pd | 1 | 6' | Ph | H | H | | PA1 | CH$_3$ | H | H | acac | |
| 6'-240Y | Pd | 0 | 6' | Ph | H | H | | PA1 | CH$_3$ | H | H | — | — |
| 6'-241 | Pd | 1 | 6' | Ph | H | | PA1 | | CH$_3$ | H | H | pic | |
| 6'-241X | Pd | 1 | 6' | Ph | H | | PA1 | | CH$_3$ | H | H | acac | |
| 6'-241Y | Pd | 0 | 6' | Ph | H | | PA1 | | CH$_3$ | H | H | — | — |
| 6'-242 | Pd | 1 | 6' | Ph | H | H | | PA2 | CH$_3$ | H | H | pic | |
| 6'-242X | Pd | 1 | 6' | Ph | H | H | | PA2 | CH$_3$ | H | H | acac | |
| 6'-242Y | Pd | 0 | 6' | Ph | H | H | | PA2 | CH$_3$ | H | H | — | — |
| 6'-243 | Pd | 1 | 6' | Ph | H | | PA2 | | CH$_3$ | H | H | pic | |
| 6'-243X | Pd | 1 | 6' | Ph | H | | PA2 | | CH$_3$ | H | H | acac | |
| 6'-243Y | Pd | 0 | 6' | Ph | H | | PA2 | | CH$_3$ | H | H | — | — |
| 6'-244 | Pd | 1 | 6' | Ph | H | H | | EA1 | CH$_3$ | H | H | pic | |
| 6'-244X | Pd | 1 | 6' | Ph | H | H | | EA1 | CH$_3$ | H | H | acac | |
| 6'-244Y | Pd | 0 | 6' | Ph | H | H | | EA1 | CH$_3$ | H | H | — | — |
| 6'-245 | Pd | 1 | 6' | Ph | H | | EA2 | | CH$_3$ | H | H | pic | |
| 6'-245X | Pd | 1 | 6' | Ph | H | | EA2 | | CH$_3$ | H | H | acac | |
| 6'-245Y | Pd | 0 | 6' | Ph | H | | EA2 | | CH$_3$ | H | H | — | — |
| 6'-246 | Pd | 1 | 6' | Ph | H | H | | ME | CH$_3$ | H | H | pic | |
| 6'-246X | Pd | 1 | 6' | Ph | H | H | | ME | CH$_3$ | H | H | acac | |
| 6'-246Y | Pd | 0 | 6' | Ph | H | H | | ME | CH$_3$ | H | H | — | — |
| 6'-247 | Pd | 1 | 6' | Ph | H | | ME | | CH$_3$ | H | H | pic | |
| 6'-247X | Pd | 1 | 6' | Ph | H | | ME | | CH$_3$ | H | H | acac | |
| 6'-247Y | Pd | 0 | 6' | Ph | H | | ME | | CH$_3$ | H | H | — | — |
| 6'-248 | Pd | 1 | 6' | Ph | H | H | | AT | CH$_3$ | H | H | pic | |
| 6'-248X | Pd | 1 | 6' | Ph | H | H | | AT | CH$_3$ | H | H | acac | |
| 6'-248Y | Pd | 0 | 6' | Ph | H | H | | AT | CH$_3$ | H | H | — | — |
| 6'-249 | Pd | 1 | 6' | Ph | H | | AT | | CH$_3$ | H | H | pic | |
| 6'-249X | Pd | 1 | 6' | Ph | H | | AT | | CH$_3$ | H | H | acac | |
| 6'-249Y | Pd | 0 | 6' | Ph | H | | AT | | CH$_3$ | H | H | — | — |
| 6'-250 | Pd | 1 | 6' | Ph | H | H | | MES1 | CH$_3$ | H | H | pic | |
| 6'-250X | Pd | 1 | 6' | Ph | H | H | | MES1 | CH$_3$ | H | H | acac | |
| 6'-250Y | Pd | 0 | 6' | Ph | H | H | | MES1 | CH$_3$ | H | H | — | — |
| 6'-251 | Pd | 1 | 6' | Ph | H | | MES1 | | CH$_3$ | H | H | pic | |
| 6'-251X | Pd | 1 | 6' | Ph | H | | MES1 | | CH$_3$ | H | H | acac | |
| 6'-251Y | Pd | 0 | 6' | Ph | H | | MES1 | | CH$_3$ | H | H | — | — |
| 6'-252 | Pd | 1 | 6' | Ph | H | H | | MES2 | CH$_3$ | H | H | pic | |
| 6'-252X | Pd | 1 | 6' | Ph | H | H | | MES2 | CH$_3$ | H | H | acac | |
| 6'-252Y | Pd | 0 | 6' | Ph | H | H | | MES2 | CH$_3$ | H | H | — | — |
| 6'-253 | Pd | 1 | 6' | Ph | H | | MES2 | | CH$_3$ | H | H | pic | |
| 6'-253X | Pd | 1 | 6' | Ph | H | | MES2 | | CH$_3$ | H | H | acac | |
| 6'-253Y | Pd | 0 | 6' | Ph | H | | MES2 | | CH$_3$ | H | H | — | — |
| 6'-254 | Pd | 1 | 6' | Ph | H | H | | PS1 | CH$_3$ | H | H | pic | |
| 6'-254X | Pd | 1 | 6' | Ph | H | H | | PS1 | CH$_3$ | H | H | acac | |
| 6'-254Y | Pd | 0 | 6' | Ph | H | H | | PS1 | CH$_3$ | H | H | — | — |
| 6'-255 | Pd | 1 | 6' | Ph | H | | PS1 | | CH$_3$ | H | H | pic | |
| 6'-255X | Pd | 1 | 6' | Ph | H | | PS1 | | CH$_3$ | H | H | acac | |
| 6'-255Y | Pd | 0 | 6' | Ph | H | | PS1 | | CH$_3$ | H | H | — | — |
| 6'-256 | Pd | 1 | 6' | Ph | H | H | | PS2 | CH$_3$ | H | H | pic | |
| 6'-256X | Pd | 1 | 6' | Ph | H | H | | PS2 | CH$_3$ | H | H | acac | |
| 6'-256Y | Pd | 0 | 6' | Ph | H | H | | PS2 | CH$_3$ | H | H | — | — |
| 6'-257 | Pd | 1 | 6' | Ph | H | | PS2 | | CH$_3$ | H | H | pic | |
| 6'-257X | Pd | 1 | 6' | Ph | H | | PS2 | | CH$_3$ | H | H | acac | |
| 6'-257Y | Pd | 0 | 6' | Ph | H | | PS2 | | CH$_3$ | H | H | — | — |
| 6'-258 | Pd | 1 | 6' | Ph | H | H | | BAL1 | CH$_3$ | H | H | pic | |
| 6'-258X | Pd | 1 | 6' | Ph | H | H | | BAL1 | CH$_3$ | H | H | acac | |
| 6'-258Y | Pd | 0 | 6' | Ph | H | H | | BAL1 | CH$_3$ | H | H | — | — |
| 6'-259 | Pd | 1 | 6' | Ph | H | | BAL1 | | CH$_3$ | H | H | pic | |
| 6'-259X | Pd | 1 | 6' | Ph | H | | BAL1 | | CH$_3$ | H | H | acac | |
| 6'-259Y | Pd | 0 | 6' | Ph | H | | BAL1 | | CH$_3$ | H | H | — | — |
| 6'-260 | Pd | 1 | 6' | Ph | H | H | | BAL2 | CH$_3$ | H | H | pic | |
| 6'-260X | Pd | 1 | 6' | Ph | H | H | | BAL2 | CH$_3$ | H | H | acac | |
| 6'-260Y | Pd | 0 | 6' | Ph | H | H | | BAL2 | CH$_3$ | H | H | — | — |
| 6'-261 | Pd | 1 | 6' | Ph | H | | BAL2 | | CH$_3$ | H | H | pic | |
| 6'-261X | Pd | 1 | 6' | Ph | H | | BAL2 | | CH$_3$ | H | H | acac | |
| 6'-261Y | Pd | 0 | 6' | Ph | H | | BAL2 | | CH$_3$ | H | H | — | — |
| 6'-262 | Pd | 1 | 6' | Ph | H | H | | MEK1 | CH$_3$ | H | H | pic | |
| 6'-262X | Pd | 1 | 6' | Ph | H | H | | MEK1 | CH$_3$ | H | H | acac | |
| 6'-262Y | Pd | 0 | 6' | Ph | H | H | | MEK1 | CH$_3$ | H | H | — | — |

TABLE 48-continued

| No. | M | m | BSS | SS G | T¹ | T² | T³ | T⁴ | T⁵ | T⁶ | T⁷ | L¹ | L² |
|---|---|---|---|---|---|---|---|---|---|---|---|---|---|
| 6'-263 | Pd | 1 | 6' | Ph | H | | MEK1 | | H | $CH_3$ | H | H | pic |
| 6'-263X | Pd | 1 | 6' | Ph | H | | MEK1 | | H | $CH_3$ | H | H | acac |
| 6'-263Y | Pd | 0 | 6' | Ph | H | | MEK1 | | H | $CH_3$ | H | H | — — |
| 6'-264 | Pd | 1 | 6' | Ph | H | H | | MEK2 | | $CH_3$ | H | H | pic |
| 6'-264X | Pd | 1 | 6' | Ph | H | H | | MEK2 | | $CH_3$ | H | H | acac |
| 6'-264Y | Pd | 0 | 6' | Ph | H | H | | MEK2 | | $CH_3$ | H | H | — — |
| 6'-265 | Pd | 1 | 6' | Ph | H | | MEK2 | | H | $CH_3$ | H | H | pic |
| 6'-265X | Pd | 1 | 6' | Ph | H | | MEK2 | | H | $CH_3$ | H | H | acac |
| 6'-265Y | Pd | 0 | 6' | Ph | H | | MEK2 | | H | $CH_3$ | H | H | — — |
| 6'-266 | Pd | 1 | 6' | Ph | H | H | | PAL1 | | $CH_3$ | H | H | pic |
| 6'-266X | Pd | 1 | 6' | Ph | H | H | | PAL1 | | $CH_3$ | H | H | acac |
| 6'-266Y | Pd | 0 | 6' | Ph | H | H | | PAL1 | | $CH_3$ | H | H | — — |
| 6'-267 | Pd | 1 | 6' | Ph | H | | PAL1 | | H | $CH_3$ | H | H | pic |
| 6'-267X | Pd | 1 | 6' | Ph | H | | PAL1 | | H | $CH_3$ | H | H | acac |
| 6'-267Y | Pd | 0 | 6' | Ph | H | | PAL1 | | H | $CH_3$ | H | H | — — |
| 6'-268 | Pd | 1 | 6' | Ph | H | H | | PAL2 | | $CH_3$ | H | H | pic |
| 6'-268X | Pd | 1 | 6' | Ph | H | H | | PAL2 | | $CH_3$ | H | H | acac |
| 6'-268Y | Pd | 0 | 6' | Ph | H | H | | PAL2 | | $CH_3$ | H | H | — — |
| 6'-269 | Pd | 1 | 6' | Ph | H | | PAL2 | | H | $CH_3$ | H | H | pic |
| 6'-269X | Pd | 1 | 6' | Ph | H | | PAL2 | | H | $CH_3$ | H | H | acac |
| 6'-269Y | Pd | 0 | 6' | Ph | H | | PAL2 | | H | $CH_3$ | H | H | — — |
| 6'-270 | Pd | 1 | 6' | Ph | H | H | | MMK | | $CH_3$ | H | H | pic |
| 6'-270X | Pd | 1 | 6' | Ph | H | H | | MMK | | $CH_3$ | H | H | acac |
| 6'-270Y | Pd | 0 | 6' | Ph | H | H | | MMK | | $CH_3$ | H | H | — — |
| 6'-271 | Pd | 1 | 6' | Ph | H | | MMK | | H | $CH_3$ | H | H | pic |
| 6'-271X | Pd | 1 | 6' | Ph | H | | MMK | | H | $CH_3$ | H | H | acac |
| 6'-271Y | Pd | 0 | 6' | Ph | H | | MMK | | H | $CH_3$ | H | H | — — |
| 6'-272 | Pd | 1 | 6' | Ph | H | H | | EES1 | | $CH_3$ | H | H | pic |
| 6'-272X | Pd | 1 | 6' | Ph | H | H | | EES1 | | $CH_3$ | H | H | acac |
| 6'-272Y | Pd | 0 | 6' | Ph | H | H | | EES1 | | $CH_3$ | H | H | — — |
| 6'-273 | Pd | 1 | 6' | Ph | H | | EES2 | | H | $CH_3$ | H | H | pic |
| 6'-273X | Pd | 1 | 6' | Ph | H | | EES2 | | H | $CH_3$ | H | H | acac |
| 6'-273Y | Pd | 0 | 6' | Ph | H | | EES2 | | H | $CH_3$ | H | H | — — |
| 6'-274 | Pd | 1 | 6' | Ph | H | H | | PAE1 | | $CH_3$ | H | H | pic |
| 6'-274X | Pd | 1 | 6' | Ph | H | H | | PAE1 | | $CH_3$ | H | H | acac |
| 6'-274Y | Pd | 0 | 6' | Ph | H | H | | PAE1 | | $CH_3$ | H | H | — — |
| 6'-275 | Pd | 1 | 6' | Ph | H | | PAE2 | | H | $CH_3$ | H | H | pic |
| 6'-275X | Pd | 1 | 6' | Ph | H | | PAE2 | | H | $CH_3$ | H | H | acac |
| 6'-275Y | Pd | 0 | 6' | Ph | H | | PAE2 | | H | $CH_3$ | H | H | — — |
| 6'-276 | Pd | 1 | 6' | Ph | H | H | | AME1 | | $CH_3$ | H | H | pic |
| 6'-276X | Pd | 1 | 6' | Ph | H | H | | AME1 | | $CH_3$ | H | H | acac |
| 6'-276Y | Pd | 0 | 6' | Ph | H | H | | AME1 | | $CH_3$ | H | H | — — |
| 6'-277 | Pd | 1 | 6' | Ph | H | | AME1 | | H | $CH_3$ | H | H | pic |
| 6'-277X | Pd | 1 | 6' | Ph | H | | AME1 | | H | $CH_3$ | H | H | acac |
| 6'-277Y | Pd | 0 | 6' | Ph | H | | AME1 | | H | $CH_3$ | H | H | — — |
| 6'-278 | Pd | 1 | 6' | Ph | H | H | | AME2 | | $CH_3$ | H | H | pic |
| 6'-278X | Pd | 1 | 6' | Ph | H | H | | AME2 | | $CH_3$ | H | H | acac |
| 6'-278Y | Pd | 0 | 6' | Ph | H | H | | AME2 | | $CH_3$ | H | H | — — |
| 6'-279 | Pd | 1 | 6' | Ph | H | | AME2 | | H | $CH_3$ | H | H | pic |
| 6'-279X | Pd | 1 | 6' | Ph | H | | AME2 | | H | $CH_3$ | H | H | acac |
| 6'-279Y | Pd | 0 | 6' | Ph | H | | AME2 | | H | $CH_3$ | H | H | — — |
| 6'-280 | Pd | 1 | 6' | Ph | H | H | | EAE1 | | $CH_3$ | H | H | pic |
| 6'-280X | Pd | 1 | 6' | Ph | H | H | | EAE1 | | $CH_3$ | H | H | acac |
| 6'-280Y | Pd | 0 | 6' | Ph | H | H | | EAE1 | | $CH_3$ | H | H | — — |
| 6'-281 | Pd | 1 | 6' | Ph | H | | EAE1 | | H | $CH_3$ | H | H | pic |
| 6'-281X | Pd | 1 | 6' | Ph | H | | EAE1 | | H | $CH_3$ | H | H | acac |
| 6'-281Y | Pd | 0 | 6' | Ph | H | | EAE1 | | H | $CH_3$ | H | H | — — |
| 6'-282 | Pd | 1 | 6' | Ph | H | H | | EAE2 | | $CH_3$ | H | H | pic |
| 6'-282X | Pd | 1 | 6' | Ph | H | H | | EAE2 | | $CH_3$ | H | H | acac |
| 6'-282Y | Pd | 0 | 6' | Ph | H | H | | EAE2 | | $CH_3$ | H | H | — — |
| 6'-283 | Pd | 1 | 6' | Ph | H | | EAE2 | | H | $CH_3$ | H | H | pic |
| 6'-283X | Pd | 1 | 6' | Ph | H | | EAE2 | | H | $CH_3$ | H | H | acac |
| 6'-283Y | Pd | 0 | 6' | Ph | H | | EAE2 | | H | $CH_3$ | H | H | — — |
| 6'-284 | Pd | 1 | 6' | Ph | H | H | | AAE1 | | $CH_3$ | H | H | pic |
| 6'-284X | Pd | 1 | 6' | Ph | H | H | | AAE1 | | $CH_3$ | H | H | acac |
| 6'-284Y | Pd | 0 | 6' | Ph | H | H | | AAE1 | | $CH_3$ | H | H | — — |
| 6'-285 | Pd | 1 | 6' | Ph | H | | AAE1 | | H | $CH_3$ | H | H | pic |
| 6'-285X | Pd | 1 | 6' | Ph | H | | AAE1 | | H | $CH_3$ | H | H | acac |
| 6'-285Y | Pd | 0 | 6' | Ph | H | | AAE1 | | H | $CH_3$ | H | H | — — |
| 6'-286 | Pd | 1 | 6' | Ph | H | H | | AAE2 | | $CH_3$ | H | H | pic |
| 6'-286X | Pd | 1 | 6' | Ph | H | H | | AAE2 | | $CH_3$ | H | H | acac |
| 6'-286Y | Pd | 0 | 6' | Ph | H | H | | AAE2 | | $CH_3$ | H | H | — — |
| 6'-287 | Pd | 1 | 6' | Ph | H | | AAE2 | | H | $CH_3$ | H | H | pic |
| 6'-287X | Pd | 1 | 6' | Ph | H | | AAE2 | | H | $CH_3$ | H | H | acac |
| 6'-287Y | Pd | 0 | 6' | Ph | H | | AAE2 | | H | $CH_3$ | H | H | — — |
| 6'-288 | Pd | 1 | 6' | Ph | H | H | | PME1 | | $CH_3$ | H | H | pic |
| 6'-288X | Pd | 1 | 6' | Ph | H | H | | PME1 | | $CH_3$ | H | H | acac |

TABLE 48-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 6'-288Y | Pd | 0 | 6' | Ph | H | H | PME1 | | CH₃ | H | H | — — |
| 6'-289 | Pd | 1 | 6' | Ph | H | PME1 | | H | CH₃ | H | H | pic |
| 6'-289X | Pd | 1 | 6' | Ph | H | PME1 | | H | CH₃ | H | H | acac |
| 6'-289Y | Pd | 0 | 6' | Ph | H | PME1 | | H | CH₃ | H | H | — — |
| 6'-290 | Pd | 1 | 6' | Ph | H | H | PME2 | | CH₃ | H | H | pic |
| 6'-290X | Pd | 1 | 6' | Ph | H | H | PME2 | | CH₃ | H | H | acac |
| 6'-290Y | Pd | 0 | 6' | Ph | H | H | PME2 | | CH₃ | H | H | — — |
| 6'-291 | Pd | 1 | 6' | Ph | H | PME2 | | H | CH₃ | H | H | pic |
| 6'-291X | Pd | 1 | 6' | Ph | H | PME2 | | H | CH₃ | H | H | acac |
| 6'-291Y | Pd | 0 | 6' | Ph | H | PME2 | | H | CH₃ | H | H | — — |
| 6'-292 | Pd | 1 | 6' | Ph | H | H | MET1 | | CH₃ | H | H | pic |
| 6'-292X | Pd | 1 | 6' | Ph | H | H | MET1 | | CH₃ | H | H | acac |
| 6'-292Y | Pd | 0 | 6' | Ph | H | H | MET1 | | CH₃ | H | H | — — |
| 6'-293 | Pd | 1 | 6' | Ph | H | MET1 | | H | CH₃ | H | H | pic |
| 6'-293X | Pd | 1 | 6' | Ph | H | MET1 | | H | CH₃ | H | H | acac |
| 6'-293Y | Pd | 0 | 6' | Ph | H | MET1 | | H | CH₃ | H | H | — — |
| 6'-294 | Pd | 1 | 6' | Ph | H | H | MET2 | | CH₃ | H | H | pic |
| 6'-294X | Pd | 1 | 6' | Ph | H | H | MET2 | | CH₃ | H | H | acac |
| 6'-294Y | Pd | 0 | 6' | Ph | H | H | MET2 | | CH₃ | H | H | — — |
| 6'-295 | Pd | 1 | 6' | Ph | H | MET2 | | H | CH₃ | H | H | pic |
| 6'-295X | Pd | 1 | 6' | Ph | H | MET2 | | H | CH₃ | H | H | acac |
| 6'-295Y | Pd | 0 | 6' | Ph | H | MET2 | | H | CH₃ | H | H | — — |
| 6'-296 | Pd | 1 | 6' | Ph | H | H | EE1 | | CH₃ | H | H | pic |
| 6'-296X | Pd | 1 | 6' | Ph | H | H | EE1 | | CH₃ | H | H | acac |
| 6'-296Y | Pd | 0 | 6' | Ph | H | H | EE1 | | CH₃ | H | H | — — |
| 6'-297 | Pd | 1 | 6' | Ph | H | EE1 | | H | CH₃ | H | H | pic |
| 6'-297X | Pd | 1 | 6' | Ph | H | EE1 | | H | CH₃ | H | H | acac |
| 6'-297Y | Pd | 0 | 6' | Ph | H | EE1 | | H | CH₃ | H | H | — — |
| 6'-298 | Pd | 1 | 6' | Ph | H | H | EE2 | | CH₃ | H | H | pic |
| 6'-298X | Pd | 1 | 6' | Ph | H | H | EE2 | | CH₃ | H | H | acac |
| 6'-298Y | Pd | 0 | 6' | Ph | H | H | EE2 | | CH₃ | H | H | — — |
| 6'-299 | Pd | 1 | 6' | Ph | H | EE2 | | H | CH₃ | H | H | pic |
| 6'-299X | Pd | 1 | 6' | Ph | H | EE2 | | H | CH₃ | H | H | acac |
| 6'-299Y | Pd | 0 | 6' | Ph | H | EE2 | | H | CH₃ | H | H | — — |
| 6'-300 | Pd | 1 | 6' | Ph | H | H | MS1 | | CH₃ | H | H | pic |
| 6'-300X | Pd | 1 | 6' | Ph | H | H | MS1 | | CH₃ | H | H | acac |
| 6'-300Y | Pd | 0 | 6' | Ph | H | H | MS1 | | CH₃ | H | H | — — |
| 6'-301 | Pd | 1 | 6' | Ph | H | MS1 | | H | CH₃ | H | H | pic |
| 6'-301X | Pd | 1 | 6' | Ph | H | MS1 | | H | CH₃ | H | H | acac |
| 6'-301Y | Pd | 0 | 6' | Ph | H | MS1 | | H | CH₃ | H | H | — — |
| 6'-302 | Pd | 1 | 6' | Ph | H | H | MS2 | | CH₃ | H | H | pic |
| 6'-302X | Pd | 1 | 6' | Ph | H | H | MS2 | | CH₃ | H | H | acac |
| 6'-302Y | Pd | 0 | 6' | Ph | H | H | MS2 | | CH₃ | H | H | — — |
| 6'-303 | Pd | 1 | 6' | Ph | H | MS2 | | H | CH₃ | H | H | pic |
| 6'-303X | Pd | 1 | 6' | Ph | H | MS2 | | H | CH₃ | H | H | acac |
| 6'-303Y | Pd | 0 | 6' | Ph | H | MS2 | | H | CH₃ | H | H | — — |

TABLE 49

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 7'-167 | Pd | 1 | 7' | Ph | H | H | H | H | CH₃ | H | H | pic |
| 7'-167X | Pd | 1 | 7' | Ph | H | H | H | H | CH₃ | H | H | acac |
| 7'-167Y | Pd | 0 | 7' | Ph | H | H | H | H | CH₃ | H | H | — — |
| 7'-168 | Pd | 1 | 7' | Ph | H | H | H | H | $^tC_4H_9$ | H | H | pic |
| 7'-168X | Pd | 1 | 7' | Ph | H | H | H | H | $^tC_4H_9$ | H | H | acac |
| 7'-168Y | Pd | 0 | 7' | Ph | H | H | H | H | $^tC_4H_9$ | H | H | — — |
| 7'-169 | Pd | 1 | 7' | Ph | H | F | H | F | CH₃ | H | H | pic |
| 7'-169X | Pd | 1 | 7' | Ph | H | F | H | F | CH₃ | H | H | acac |
| 7'-169Y | Pd | 0 | 7' | Ph | H | F | H | F | CH₃ | H | H | — — |
| 7'-170 | Pd | 1 | 7' | Ph | H | F | H | F | $^tC_4H_9$ | H | H | pic |
| 7'-170X | Pd | 1 | 7' | Ph | H | F | H | F | $^tC_4H_9$ | H | H | acac |
| 7'-170Y | Pd | 0 | 7' | Ph | H | F | H | F | $^tC_4H_9$ | H | H | — — |
| 7'-171 | Pd | 1 | 7' | Ph | F | H | H | F | CH₃ | H | H | pic |
| 7'-171X | Pd | 1 | 7' | Ph | F | H | H | F | CH₃ | H | H | acac |
| 7'-171Y | Pd | 0 | 7' | Ph | F | H | H | F | CH₃ | H | H | — — |
| 7'-172 | Pd | 1 | 7' | Ph | F | H | H | F | $^tC_4H_9$ | H | H | pic |
| 7'-172X | Pd | 1 | 7' | Ph | F | H | H | F | $^tC_4H_9$ | H | H | acac |
| 7'-172Y | Pd | 0 | 7' | Ph | F | H | H | F | $^tC_4H_9$ | H | H | — — |
| 7'-173 | Pd | 1 | 7' | Ph | CF₃ | H | CF₃ | H | CH₃ | H | H | pic |
| 7'-173X | Pd | 1 | 7' | Ph | CF₃ | H | CF₃ | H | CH₃ | H | H | acac |
| 7'-173Y | Pd | 0 | 7' | Ph | CF₃ | H | CF₃ | H | CH₃ | H | H | — — |
| 7'-174 | Pd | 1 | 7' | Ph | CF₃ | H | CF₃ | H | $^tC_4H_9$ | H | H | pic |
| 7'-174X | Pd | 1 | 7' | Ph | CF₃ | H | CF₃ | H | $^tC_4H_9$ | H | H | acac |

TABLE 49-continued

| No. | M | m | BSS | SS G | $T^1$ | $T^2$ | $T^3$ | $T^4$ | $T^5$ | $T^6$ | $T^7$ | $L^1$ | $L^2$ |
|---|---|---|---|---|---|---|---|---|---|---|---|---|---|
| 7'-174Y | Pd | 0 | 7' | Ph | $CF_3$ | H | $CF_3$ | H | $^tC_4H_9$ | H | H | — | — |
| 7'-175 | Pd | 1 | 7' | Ph | H | F | $CF_3$ | H | $CH_3$ | H | H | pic | |
| 7'-175X | Pd | 1 | 7' | Ph | H | F | $CF_3$ | H | $CH_3$ | H | H | acac | |
| 7'-175Y | Pd | 0 | 7' | Ph | H | F | $CF_3$ | H | $CH_3$ | H | H | — | — |
| 7'-176 | Pd | 1 | 7' | Ph | F | H | $CF_3$ | H | $CH_3$ | H | H | pic | |
| 7'-176X | Pd | 1 | 7' | Ph | F | H | $CF_3$ | H | $CH_3$ | H | H | acac | |
| 7'-176Y | Pd | 0 | 7' | Ph | F | H | $CF_3$ | H | $CH_3$ | H | H | — | — |
| 7'-177 | Pd | 1 | 7' | Ph | F | F | F | F | $CH_3$ | H | H | pic | |
| 7'-177X | Pd | 1 | 7' | Ph | F | F | F | F | $CH_3$ | H | H | acac | |
| 7'-177Y | Pd | 0 | 7' | Ph | F | F | F | F | $CH_3$ | H | H | — | — |
| 7'-178 | Pd | 1 | 7' | Ph | H | F | H | $CH_3$ | $CH_3$ | H | H | pic | |
| 7'-178X | Pd | 1 | 7' | Ph | H | F | H | $CH_3$ | $CH_3$ | H | H | acac | |
| 7'-178Y | Pd | 0 | 7' | Ph | H | F | H | $CH_3$ | $CH_3$ | H | H | — | — |
| 7'-179 | Pd | 1 | 7' | Ph | H | F | H | $CH_3$ | $^tC_4H_9$ | H | H | pic | |
| 7'-179X | Pd | 1 | 7' | Ph | H | F | H | $CH_3$ | $^tC_4H_9$ | H | H | acac | |
| 7'-179Y | Pd | 0 | 7' | Ph | H | F | H | $CH_3$ | $^tC_4H_9$ | H | H | — | — |
| 7'-180 | Pd | 1 | 7' | Ph | H | F | H | $^tC_4H_9$ | $CH_3$ | H | H | pic | |
| 7'-180X | Pd | 1 | 7' | Ph | H | F | H | $^tC_4H_9$ | $CH_3$ | H | H | acac | |
| 7'-180Y | Pd | 0 | 7' | Ph | H | F | H | $^tC_4H_9$ | $CH_3$ | H | H | — | — |
| 7'-181 | Pd | 1 | 7' | Ph | H | F | H | $^tC_4H_9$ | $^tC_4H_9$ | H | H | pic | |
| 7'-181X | Pd | 1 | 7' | Ph | H | F | H | $^tC_4H_9$ | $^tC_4H_9$ | H | H | acac | |
| 7'-181Y | Pd | 0 | 7' | Ph | H | F | H | $^tC_4H_9$ | $^tC_4H_9$ | H | H | — | — |
| 7'-182 | Pd | 1 | 7' | Ph | H | $CF_3$ | H | $CF_3$ | $CH_3$ | H | H | pic | |
| 7'-182X | Pd | 1 | 7' | Ph | H | $CF_3$ | H | $CF_3$ | $CH_3$ | H | H | acac | |
| 7'-182Y | Pd | 0 | 7' | Ph | H | $CF_3$ | H | $CF_3$ | $CH_3$ | H | H | — | — |
| 7'-183 | Pd | 1 | 7' | Ph | H | $CF_3$ | H | $CF_3$ | $^tC_4H_9$ | H | H | pic | |
| 7'-183X | Pd | 1 | 7' | Ph | H | $CF_3$ | H | $CF_3$ | $^tC_4H_9$ | H | H | acac | |
| 7'-183Y | Pd | 0 | 7' | Ph | H | $CF_3$ | H | $CF_3$ | $^tC_4H_9$ | H | H | — | — |
| 7'-184 | Pd | 1 | 7' | Ph | $CF_3$ | H | H | $^tC_4H_9$ | $CH_3$ | H | H | pic | |
| 7'-184X | Pd | 1 | 7' | Ph | $CF_3$ | H | H | $^tC_4H_9$ | $CH_3$ | H | H | acac | |
| 7'-184Y | Pd | 0 | 7' | Ph | $CF_3$ | H | H | $^tC_4H_9$ | $CH_3$ | H | H | — | — |
| 7'-185 | Pd | 1 | 7' | Ph | $CF_3$ | H | H | $^tC_4H_9$ | $^tC_4H_9$ | H | H | pic | |
| 7'-185X | Pd | 1 | 7' | Ph | $CF_3$ | H | H | $^tC_4H_9$ | $^tC_4H_9$ | H | H | acac | |
| 7'-185Y | Pd | 0 | 7' | Ph | $CF_3$ | H | H | $^tC_4H_9$ | $^tC_4H_9$ | H | H | — | — |
| 7'-186 | Pd | 1 | 7' | Ph | H | $CF_3$ | H | $^tC_4H_9$ | $CH_3$ | H | H | pic | |
| 7'-186X | Pd | 1 | 7' | Ph | H | $CF_3$ | H | $^tC_4H_9$ | $CH_3$ | H | H | acac | |
| 7'-186Y | Pd | 0 | 7' | Ph | H | $CF_3$ | H | $^tC_4H_9$ | $CH_3$ | H | H | — | — |
| 7'-187 | Pd | 1 | 7' | Ph | H | $CF_3$ | H | $^tC_4H_9$ | $^tC_4H_9$ | H | H | pic | |
| 7'-187X | Pd | 1 | 7' | Ph | H | $CF_3$ | H | $^tC_4H_9$ | $^tC_4H_9$ | H | H | acac | |
| 7'-187Y | Pd | 0 | 7' | Ph | H | $CF_3$ | H | $^tC_4H_9$ | $^tC_4H_9$ | H | H | — | — |
| 7'-188 | Pd | 1 | 7' | Ph | H | $CF_3$ | H | $CH_3$ | $CH_3$ | H | H | pic | |
| 7'-188X | Pd | 1 | 7' | Ph | H | $CF_3$ | H | $CH_3$ | $CH_3$ | H | H | acac | |
| 7'-188Y | Pd | 0 | 7' | Ph | H | $CF_3$ | H | $CH_3$ | $CH_3$ | H | H | — | — |
| 7'-189 | Pd | 1 | 7' | Ph | H | $CF_3$ | $CF_3$ | H | $CH_3$ | H | H | pic | |
| 7'-189X | Pd | 1 | 7' | Ph | H | $CF_3$ | $CF_3$ | H | $CH_3$ | H | H | acac | |
| 7'-189Y | Pd | 0 | 7' | Ph | H | $CF_3$ | $CF_3$ | H | $CH_3$ | H | H | — | — |
| 7'-190 | Pd | 1 | 7' | Ph | H | H | $NO_2$ | H | $CH_3$ | H | H | pic | |
| 7'-190X | Pd | 1 | 7' | Ph | H | H | $NO_2$ | H | $CH_3$ | H | H | acac | |
| 7'-190Y | Pd | 0 | 7' | Ph | H | H | $NO_2$ | H | $CH_3$ | H | H | — | — |
| 7'-191 | Pd | 1 | 7' | Ph | H | H | $NO_2$ | H | $^tC_4H_9$ | H | H | pic | |
| 7'-191X | Pd | 1 | 7' | Ph | H | H | $NO_2$ | H | $^tC_4H_9$ | H | H | acac | |
| 7'-191Y | Pd | 0 | 7' | Ph | H | H | $NO_2$ | H | $^tC_4H_9$ | H | H | — | — |
| 7'-192 | Pd | 1 | 7' | Ph | F | H | $NO_2$ | H | $CH_3$ | H | H | pic | |
| 7'-192X | Pd | 1 | 7' | Ph | F | H | $NO_2$ | H | $CH_3$ | H | H | acac | |
| 7'-192Y | Pd | 0 | 7' | Ph | F | H | $NO_2$ | H | $CH_3$ | H | H | — | — |
| 7'-193 | Pd | 1 | 7' | Ph | F | H | $NO_2$ | F | $CH_3$ | H | H | pic | |
| 7'-193X | Pd | 1 | 7' | Ph | F | H | $NO_2$ | F | $CH_3$ | H | H | acac | |
| 7'-193Y | Pd | 0 | 7' | Ph | F | H | $NO_2$ | F | $CH_3$ | H | H | — | — |
| 7'-194 | Pd | 1 | 7' | Ph | H | $NO_2$ | H | $NO_2$ | $CH_3$ | H | H | pic | |
| 7'-194X | Pd | 1 | 7' | Ph | H | $NO_2$ | H | $NO_2$ | $CH_3$ | H | H | acac | |
| 7'-194Y | Pd | 0 | 7' | Ph | H | $NO_2$ | H | $NO_2$ | $CH_3$ | H | H | — | — |
| 7'-195 | Pd | 1 | 7' | Ph | H | $NO_2$ | H | $NO_2$ | $^tC_4H_9$ | H | H | pic | |
| 7'-195X | Pd | 1 | 7' | Ph | H | $NO_2$ | H | $NO_2$ | $^tC_4H_9$ | H | H | acac | |
| 7'-195Y | Pd | 0 | 7' | Ph | H | $NO_2$ | H | $NO_2$ | $^tC_4H_9$ | H | H | — | — |
| 7'-196 | Pd | 1 | 7' | Ph | $NO_2$ | H | H | $NO_2$ | $CH_3$ | H | H | pic | |
| 7'-196X | Pd | 1 | 7' | Ph | $NO_2$ | H | H | $NO_2$ | $CH_3$ | H | H | acac | |
| 7'-196Y | Pd | 0 | 7' | Ph | $NO_2$ | H | H | $NO_2$ | $CH_3$ | H | H | — | — |
| 7'-197 | Pd | 1 | 7' | Ph | $NO_2$ | H | H | $NO_2$ | $^tC_4H_9$ | H | H | pic | |
| 7'-197X | Pd | 1 | 7' | Ph | $NO_2$ | H | H | $NO_2$ | $^tC_4H_9$ | H | H | acac | |
| 7'-197Y | Pd | 0 | 7' | Ph | $NO_2$ | H | H | $NO_2$ | $^tC_4H_9$ | H | H | — | — |
| 7'-198 | Pd | 1 | 7' | Ph | H | H | $CF_3$ | H | $CH_3$ | H | H | pic | |
| 7'-198X | Pd | 1 | 7' | Ph | H | H | $CF_3$ | H | $CH_3$ | H | H | acac | |
| 7'-198Y | Pd | 0 | 7' | Ph | H | H | $CF_3$ | H | $CH_3$ | H | H | — | — |
| 7'-199 | Pd | 1 | 7' | Ph | H | H | $CF_3$ | H | $^tC_4H_9$ | H | H | pic | |
| 7'-199X | Pd | 1 | 7' | Ph | H | H | $CF_3$ | H | $^tC_4H_9$ | H | H | acac | |
| 7'-199Y | Pd | 0 | 7' | Ph | H | H | $CF_3$ | H | $^tC_4H_9$ | H | H | — | — |
| 7'-200 | Pd | 1 | 7' | Ph | H | Cl | $CF_3$ | H | $CH_3$ | H | H | pic | |

TABLE 49-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 7'-200X | Pd | 1 | 7' | Ph | H | Cl | CF$_3$ | H | CH$_3$ | H | H | acac |
| 7'-200Y | Pd | 0 | 7' | Ph | H | Cl | CF$_3$ | H | CH$_3$ | H | H | — — |
| 7'-201 | Pd | 1 | 7' | Ph | H | Cl | CF$_3$ | H | $^t$C$_4$H$_9$ | H | H | pic |
| 7'-201X | Pd | 1 | 7' | Ph | H | Cl | CF$_3$ | H | $^t$C$_4$H$_9$ | H | H | acac |
| 7'-201Y | Pd | 0 | 7' | Ph | H | Cl | CF$_3$ | H | $^t$C$_4$H$_9$ | H | H | — — |
| 7'-202 | Pd | 1 | 7' | Ph | H | NO$_2$ | H | H | CH$_3$ | H | H | pic |
| 7'-202X | Pd | 1 | 7' | Ph | H | NO$_2$ | H | H | CH$_3$ | H | H | acac |
| 7'-202Y | Pd | 0 | 7' | Ph | H | NO$_2$ | H | H | CH$_3$ | H | H | — — |
| 7'-203 | Pd | 1 | 7' | Ph | H | CF$_3$ | H | H | CH$_3$ | H | H | pic |
| 7'-203X | Pd | 1 | 7' | Ph | H | CF$_3$ | H | H | CH$_3$ | H | H | acac |
| 7'-203Y | Pd | 0 | 7' | Ph | H | CF$_3$ | H | H | CH$_3$ | H | H | — — |
| 7'-204 | Pd | 1 | 7' | Ph | H | NO$_2$ | H | CH$_3$ | CH$_3$ | H | H | pic |
| 7'-204X | Pd | 1 | 7' | Ph | H | NO$_2$ | H | CH$_3$ | CH$_3$ | H | H | acac |
| 7'-204Y | Pd | 0 | 7' | Ph | H | NO$_2$ | H | CH$_3$ | CH$_3$ | H | H | — — |
| 7'-205 | Pd | 1 | 7' | Ph | H | NO$_2$ | H | CH$_3$ | $^t$C$_4$H$_9$ | H | H | pic |
| 7'-205X | Pd | 1 | 7' | Ph | H | NO$_2$ | H | CH$_3$ | $^t$C$_4$H$_9$ | H | H | acac |
| 7'-205Y | Pd | 0 | 7' | Ph | H | NO$_2$ | H | CH$_3$ | $^t$C$_4$H$_9$ | H | H | — — |
| 7'-206 | Pd | 1 | 7' | Ph | H | NO$_2$ | H | $^t$C$_4$H$_9$ | CH$_3$ | H | H | pic |
| 7'-206X | Pd | 1 | 7' | Ph | H | NO$_2$ | H | $^t$C$_4$H$_9$ | CH$_3$ | H | H | acac |
| 7'-206Y | Pd | 0 | 7' | Ph | H | NO$_2$ | H | $^t$C$_4$H$_9$ | CH$_3$ | H | H | — — |
| 7'-207 | Pd | 1 | 7' | Ph | H | NO$_2$ | H | $^t$C$_4$H$_9$ | $^t$C$_4$H$_9$ | H | H | pic |
| 7'-207X | Pd | 1 | 7' | Ph | H | NO$_2$ | H | $^t$C$_4$H$_9$ | $^t$C$_4$H$_9$ | H | H | acac |
| 7'-207Y | Pd | 0 | 7' | Ph | H | NO$_2$ | H | $^t$C$_4$H$_9$ | $^t$C$_4$H$_9$ | H | H | — — |
| 7'-208 | Pd | 1 | 7' | Ph | H | H | CH$_3$O | H | CH$_3$ | H | H | pic |
| 7'-208X | Pd | 1 | 7' | Ph | H | H | CH$_3$O | H | CH$_3$ | H | H | acac |
| 7'-208Y | Pd | 0 | 7' | Ph | H | H | CH$_3$O | H | CH$_3$ | H | H | — — |
| 7'-209 | Pd | 1 | 7' | Ph | H | CH$_3$O | H | H | CH$_3$ | H | H | pic |
| 7'-209X | Pd | 1 | 7' | Ph | H | CH$_3$O | H | H | CH$_3$ | H | H | acac |
| 7'-209Y | Pd | 0 | 7' | Ph | H | CH$_3$O | H | H | CH$_3$ | H | H | — — |
| 7'-210 | Pd | 1 | 7' | Ph | H | CH$_3$O | H | CH$_3$ | CH$_3$ | H | H | pic |
| 7'-210X | Pd | 1 | 7' | Ph | H | CH$_3$O | H | CH$_3$ | CH$_3$ | H | H | acac |
| 7'-210Y | Pd | 0 | 7' | Ph | H | CH$_3$O | H | CH$_3$ | CH$_3$ | H | H | — — |
| 7'-211 | Pd | 1 | 7' | Ph | H | CH$_3$O | H | $^t$C$_4$H$_9$ | CH$_3$ | H | H | pic |
| 7'-211X | Pd | 1 | 7' | Ph | H | CH$_3$O | H | $^t$C$_4$H$_9$ | CH$_3$ | H | H | acac |
| 7'-211Y | Pd | 0 | 7' | Ph | H | CH$_3$O | H | $^t$C$_4$H$_9$ | CH$_3$ | H | H | — — |
| 7'-212 | Pd | 1 | 7' | Ph | H | Si(CH$_3$)$_3$ | H | H | CH$_3$ | H | H | pic |
| 7'-212X | Pd | 1 | 7' | Ph | H | Si(CH$_3$)$_3$ | H | H | CH$_3$ | H | H | acac |
| 7'-212Y | Pd | 0 | 7' | Ph | H | Si(CH$_3$)$_3$ | H | H | CH$_3$ | H | H | — — |
| 7'-213 | Pd | 1 | 7' | Ph | H | Si(CH$_3$)$_3$ | H | H | $^t$C$_4$H$_9$ | H | H | pic |
| 7'-213X | Pd | 1 | 7' | Ph | H | Si(CH$_3$)$_3$ | H | H | $^t$C$_4$H$_9$ | H | H | acac |
| 7'-213Y | Pd | 0 | 7' | Ph | H | Si(CH$_3$)$_3$ | H | H | $^t$C$_4$H$_9$ | H | H | — — |
| 7'-214 | Pd | 1 | 7' | Ph | H | H | Si(CH$_3$)$_3$ | H | CH$_3$ | H | H | pic |
| 7'-214X | Pd | 1 | 7' | Ph | H | H | Si(CH$_3$)$_3$ | H | CH$_3$ | H | H | acac |
| 7'-214Y | Pd | 0 | 7' | Ph | H | H | Si(CH$_3$)$_3$ | H | CH$_3$ | H | H | — — |
| 7'-215 | Pd | 1 | 7' | Ph | H | H | H | Si(CH$_3$)$_3$ | CH$_3$ | H | H | pic |
| 7'-215X | Pd | 1 | 7' | Ph | H | H | H | Si(CH$_3$)$_3$ | CH$_3$ | H | H | acac |
| 7'-215Y | Pd | 0 | 7' | Ph | H | H | H | Si(CH$_3$)$_3$ | CH$_3$ | H | H | — — |
| 7'-216 | Pd | 1 | 7' | Ph | H | F | H | Si(CH$_3$)$_3$ | CH$_3$ | H | H | pic |
| 7'-216X | Pd | 1 | 7' | Ph | H | F | H | Si(CH$_3$)$_3$ | CH$_3$ | H | H | acac |
| 7'-216Y | Pd | 0 | 7' | Ph | H | F | H | Si(CH$_3$)$_3$ | CH$_3$ | H | H | — — |
| 7'-217 | Pd | 1 | 7' | Ph | H | CF$_3$ | H | Si(CH$_3$)$_3$ | CH$_3$ | H | H | pic |
| 7'-217X | Pd | 1 | 7' | Ph | H | CF$_3$ | H | Si(CH$_3$)$_3$ | CH$_3$ | H | H | acac |
| 7'-217Y | Pd | 0 | 7' | Ph | H | CF$_3$ | H | Si(CH$_3$)$_3$ | CH$_3$ | H | H | — — |
| 7'-218 | Pd | 1 | 7' | Ph | H | CF$_3$ | H | Si(CH$_3$)$_3$ | $^t$C$_4$H$_9$ | H | H | pic |
| 7'-218X | Pd | 1 | 7' | Ph | H | CF$_3$ | H | Si(CH$_3$)$_3$ | $^t$C$_4$H$_9$ | H | H | acac |
| 7'-218Y | Pd | 0 | 7' | Ph | H | CF$_3$ | H | Si(CH$_3$)$_3$ | $^t$C$_4$H$_9$ | H | H | — — |
| 7'-219 | Pd | 1 | 7' | Ph | H | Si(CH$_3$)$_3$ | H | F | CH$_3$ | H | H | pic |
| 7'-219X | Pd | 1 | 7' | Ph | H | Si(CH$_3$)$_3$ | H | F | CH$_3$ | H | H | acac |
| 7'-219Y | Pd | 0 | 7' | Ph | H | Si(CH$_3$)$_3$ | H | F | CH$_3$ | H | H | — — |
| 7'-220 | Pd | 1 | 7' | Ph | H | Si(CH$_3$)$_3$ | H | F | $^t$C$_4$H$_9$ | H | H | pic |
| 7'-220X | Pd | 1 | 7' | Ph | H | Si(CH$_3$)$_3$ | H | F | $^t$C$_4$H$_9$ | H | H | acac |
| 7'-220Y | Pd | 0 | 7' | Ph | H | Si(CH$_3$)$_3$ | H | F | $^t$C$_4$H$_9$ | H | H | — — |
| 7'-221 | Pd | 1 | 7' | Ph | H | Si(CH$_3$)$_3$ | H | CF$_3$ | CH$_3$ | H | H | pic |
| 7'-221X | Pd | 1 | 7' | Ph | H | Si(CH$_3$)$_3$ | H | CF$_3$ | CH$_3$ | H | H | acac |
| 7'-221Y | Pd | 0 | 7' | Ph | H | Si(CH$_3$)$_3$ | H | CF$_3$ | CH$_3$ | H | H | — — |
| 7'-222 | Pd | 1 | 7' | Ph | H | Si(CH$_3$)$_3$ | H | CF$_3$ | $^t$C$_4$H$_9$ | H | H | pic |
| 7'-222X | Pd | 1 | 7' | Ph | H | Si(CH$_3$)$_3$ | H | CF$_3$ | $^t$C$_4$H$_9$ | H | H | acac |
| 7'-222Y | Pd | 0 | 7' | Ph | H | Si(CH$_3$)$_3$ | H | CF$_3$ | $^t$C$_4$H$_9$ | H | H | — — |
| 7'-223 | Pd | 1 | 7' | Ph | Si(CH$_3$)$_3$ | H | Si(CH$_3$)$_3$ | H | CH$_3$ | H | H | pic |
| 7'-223X | Pd | 1 | 7' | Ph | Si(CH$_3$)$_3$ | H | Si(CH$_3$)$_3$ | H | CH$_3$ | H | H | acac |
| 7'-223Y | Pd | 0 | 7' | Ph | Si(CH$_3$)$_3$ | H | Si(CH$_3$)$_3$ | H | CH$_3$ | H | H | — — |
| 7'-224 | Pd | 1 | 7' | Ph | Si(CH$_3$)$_3$ | H | Si(CH$_3$)$_3$ | H | $^t$C$_4$H$_9$ | H | H | pic |
| 7'-224X | Pd | 1 | 7' | Ph | Si(CH$_3$)$_3$ | H | Si(CH$_3$)$_3$ | H | $^t$C$_4$H$_9$ | H | H | acac |
| 7'-224Y | Pd | 0 | 7' | Ph | Si(CH$_3$)$_3$ | H | Si(CH$_3$)$_3$ | H | $^t$C$_4$H$_9$ | H | H | — — |
| 7'-225 | Pd | 1 | 7' | Ph | H | H | H | COCH$_3$ | CH$_3$ | H | H | pic |
| 7'-225X | Pd | 1 | 7' | Ph | H | H | H | COCH$_3$ | CH$_3$ | H | H | acac |
| 7'-225Y | Pd | 0 | 7' | Ph | H | H | H | COCH$_3$ | CH$_3$ | H | H | — — |

TABLE 49-continued

| No. | M | m | BSS | SS G | $T^1$ | $T^2$ | $T^3$ | $T^4$ | $T^5$ | $T^6$ | $T^7$ | $L^1$ | $L^2$ |
|---|---|---|---|---|---|---|---|---|---|---|---|---|---|
| 7'-226 | Pd | 1 | 7' | Ph | H | H | COCH$_3$ | H | CH$_3$ | H | H | pic | |
| 7'-226X | Pd | 1 | 7' | Ph | H | H | COCH$_3$ | H | CH$_3$ | H | H | acac | |
| 7'-226Y | Pd | 0 | 7' | Ph | H | H | COCH$_3$ | H | CH$_3$ | H | H | — | — |
| 7'-227 | Pd | 1 | 7' | Ph | H | COCH$_3$ | H | H | CH$_3$ | H | H | pic | |
| 7'-227X | Pd | 1 | 7' | Ph | H | COCH$_3$ | H | H | CH$_3$ | H | H | acac | |
| 7'-227Y | Pd | 0 | 7' | Ph | H | COCH$_3$ | H | H | CH$_3$ | H | H | — | — |
| 7'-228 | Pd | 1 | 7' | Ph | H | H | BL | H | CH$_3$ | H | H | pic | |
| 7'-228X | Pd | 1 | 7' | Ph | H | H | BL | H | CH$_3$ | H | H | acac | |
| 7'-228Y | Pd | 0 | 7' | Ph | H | H | BL | H | CH$_3$ | H | H | — | — |
| 7'-229 | Pd | 1 | 7' | Ph | H | H | BL | H | $^tC_4H_9$ | H | H | pic | |
| 7'-229X | Pd | 1 | 7' | Ph | H | H | BL | H | $^tC_4H_9$ | H | H | acac | |
| 7'-229Y | Pd | 0 | 7' | Ph | H | H | BL | H | $^tC_4H_9$ | H | H | — | — |
| 7'-230 | Pd | 1 | 7' | Ph | H | BL | | H | CH$_3$ | H | H | pic | |
| 7'-230X | Pd | 1 | 7' | Ph | H | BL | | H | CH$_3$ | H | H | acac | |
| 7'-230Y | Pd | 0 | 7' | Ph | H | BL | | H | CH$_3$ | H | H | — | — |
| 7'-231 | Pd | 1 | 7' | Ph | H | BL | | H | $^tC_4H_9$ | H | H | pic | |
| 7'-231X | Pd | 1 | 7' | Ph | H | BL | | H | $^tC_4H_9$ | H | H | acac | |
| 7'-231Y | Pd | 0 | 7' | Ph | H | BL | | H | $^tC_4H_9$ | H | H | — | — |
| 7'-232 | Pd | 1 | 7' | Ph | H | H | PL | | CH$_3$ | H | H | pic | |
| 7'-232X | Pd | 1 | 7' | Ph | H | H | PL | | CH$_3$ | H | H | acac | |
| 7'-232Y | Pd | 0 | 7' | Ph | H | H | PL | | CH$_3$ | H | H | — | — |
| 7'-233 | Pd | 1 | 7' | Ph | H | H | PL | | $^tC_4H_9$ | H | H | pic | |
| 7'-233X | Pd | 1 | 7' | Ph | H | H | PL | | $^tC_4H_9$ | H | H | acac | |
| 7'-233Y | Pd | 0 | 7' | Ph | H | H | PL | | $^tC_4H_9$ | H | H | — | — |
| 7'-234 | Pd | 1 | 7' | Ph | H | PL | | H | CH$_3$ | H | H | pic | |
| 7'-234X | Pd | 1 | 7' | Ph | H | PL | | H | CH$_3$ | H | H | acac | |
| 7'-234Y | Pd | 0 | 7' | Ph | H | PL | | H | CH$_3$ | H | H | — | — |
| 7'-235 | Pd | 1 | 7' | Ph | H | PL | | H | $^tC_4H_9$ | H | H | pic | |
| 7'-235X | Pd | 1 | 7' | Ph | H | PL | | H | $^tC_4H_9$ | H | H | acac | |
| 7'-235Y | Pd | 0 | 7' | Ph | H | PL | | H | $^tC_4H_9$ | H | H | — | — |
| 7'-236 | Pd | 1 | 7' | Ph | H | H | MEE1 | | CH$_3$ | H | H | pic | |
| 7'-236X | Pd | 1 | 7' | Ph | H | H | MEE1 | | CH$_3$ | H | H | acac | |
| 7'-236Y | Pd | 0 | 7' | Ph | H | H | MEE1 | | CH$_3$ | H | H | — | — |
| 7'-237 | Pd | 1 | 7' | Ph | H | MEE1 | | H | CH$_3$ | H | H | pic | |
| 7'-237X | Pd | 1 | 7' | Ph | H | MEE1 | | H | CH$_3$ | H | H | acac | |
| 7'-237Y | Pd | 0 | 7' | Ph | H | MEE1 | | H | CH$_3$ | H | H | — | — |
| 7'-238 | Pd | 1 | 7' | Ph | H | H | MEE2 | | CH$_3$ | H | H | pic | |
| 7'-238X | Pd | 1 | 7' | Ph | H | H | MEE2 | | CH$_3$ | H | H | acac | |
| 7'-238Y | Pd | 0 | 7' | Ph | H | H | MEE2 | | CH$_3$ | H | H | — | — |
| 7'-239 | Pd | 1 | 7' | Ph | H | MEE2 | | H | CH$_3$ | H | H | pic | |
| 7'-239X | Pd | 1 | 7' | Ph | H | MEE2 | | H | CH$_3$ | H | H | acac | |
| 7'-239Y | Pd | 0 | 7' | Ph | H | MEE2 | | H | CH$_3$ | H | H | — | — |
| 7'-240 | Pd | 1 | 7' | Ph | H | H | PA1 | | CH$_3$ | H | H | pic | |
| 7'-240X | Pd | 1 | 7' | Ph | H | H | PA1 | | CH$_3$ | H | H | acac | |
| 7'-240Y | Pd | 0 | 7' | Ph | H | H | PA1 | | CH$_3$ | H | H | — | — |
| 7'-241 | Pd | 1 | 7' | Ph | H | PA1 | | H | CH$_3$ | H | H | pic | |
| 7'-241X | Pd | 1 | 7' | Ph | H | PA1 | | H | CH$_3$ | H | H | acac | |
| 7'-241Y | Pd | 0 | 7' | Ph | H | PA1 | | H | CH$_3$ | H | H | — | — |
| 7'-242 | Pd | 1 | 7' | Ph | H | H | PA2 | | CH$_3$ | H | H | pic | |
| 7'-242X | Pd | 1 | 7' | Ph | H | H | PA2 | | CH$_3$ | H | H | acac | |
| 7'-242Y | Pd | 0 | 7' | Ph | H | H | PA2 | | CH$_3$ | H | H | — | — |
| 7'-243 | Pd | 1 | 7' | Ph | H | PA2 | | H | CH$_3$ | H | H | pic | |
| 7'-243X | Pd | 1 | 7' | Ph | H | PA2 | | H | CH$_3$ | H | H | acac | |
| 7'-243Y | Pd | 0 | 7' | Ph | H | PA2 | | H | CH$_3$ | H | H | — | — |
| 7'-244 | Pd | 1 | 7' | Ph | H | H | EA1 | | CH$_3$ | H | H | pic | |
| 7'-244X | Pd | 1 | 7' | Ph | H | H | EA1 | | CH$_3$ | H | H | acac | |
| 7'-244Y | Pd | 0 | 7' | Ph | H | H | EA1 | | CH$_3$ | H | H | — | — |
| 7'-245 | Pd | 1 | 7' | Ph | H | EA2 | | H | CH$_3$ | H | H | pic | |
| 7'-245X | Pd | 1 | 7' | Ph | H | EA2 | | H | CH$_3$ | H | H | acac | |
| 7'-245Y | Pd | 0 | 7' | Ph | H | EA2 | | H | CH$_3$ | H | H | — | — |
| 7'-246 | Pd | 1 | 7' | Ph | H | H | ME | | CH$_3$ | H | H | pic | |
| 7'-246X | Pd | 1 | 7' | Ph | H | H | ME | | CH$_3$ | H | H | acac | |
| 7'-246Y | Pd | 0 | 7' | Ph | H | H | ME | | CH$_3$ | H | H | — | — |
| 7'-247 | Pd | 1 | 7' | Ph | H | ME | | H | CH$_3$ | H | H | pic | |
| 7'-247X | Pd | 1 | 7' | Ph | H | ME | | H | CH$_3$ | H | H | acac | |
| 7'-247Y | Pd | 0 | 7' | Ph | H | ME | | H | CH$_3$ | H | H | — | — |
| 7'-248 | Pd | 1 | 7' | Ph | H | H | AT | | CH$_3$ | H | H | pic | |
| 7'-248X | Pd | 1 | 7' | Ph | H | H | AT | | CH$_3$ | H | H | acac | |
| 7'-248Y | Pd | 0 | 7' | Ph | H | H | AT | | CH$_3$ | H | H | — | — |
| 7'-249 | Pd | 1 | 7' | Ph | H | AT | | H | CH$_3$ | H | H | pic | |
| 7'-249X | Pd | 1 | 7' | Ph | H | AT | | H | CH$_3$ | H | H | acac | |
| 7'-249Y | Pd | 0 | 7' | Ph | H | AT | | H | CH$_3$ | H | H | — | — |
| 7'-250 | Pd | 1 | 7' | Ph | H | H | MES1 | | CH$_3$ | H | H | pic | |
| 7'-250X | Pd | 1 | 7' | Ph | H | H | MES1 | | CH$_3$ | H | H | acac | |
| 7'-250Y | Pd | 0 | 7' | Ph | H | H | MES1 | | CH$_3$ | H | H | — | — |
| 7'-251 | Pd | 1 | 7' | Ph | H | MES1 | | H | CH$_3$ | H | H | pic | |
| 7'-251X | Pd | 1 | 7' | Ph | H | MES1 | | H | CH$_3$ | H | H | acac | |

TABLE 49-continued

| No. | M | m | BSS | SS G | $T^1$ | $T^2$ | $T^3$ | $T^4$ | $T^5$ | $T^6$ | $T^7$ | $L^1$ $L^2$ |
|---|---|---|---|---|---|---|---|---|---|---|---|---|
| 7'-251Y | Pd | 0 | 7' | Ph | H |   | MES1 | H | $CH_3$ | H | H | — |
| 7'-252 | Pd | 1 | 7' | Ph | H | H |   | MES2 | $CH_3$ | H | H | pic |
| 7'-252X | Pd | 1 | 7' | Ph | H | H |   | MES2 | $CH_3$ | H | H | acac |
| 7'-252Y | Pd | 0 | 7' | Ph | H | H |   | MES2 | $CH_3$ | H | H | — |
| 7'-253 | Pd | 1 | 7' | Ph | H |   | MES2 | H | $CH_3$ | H | H | pic |
| 7'-253X | Pd | 1 | 7' | Ph | H |   | MES2 | H | $CH_3$ | H | H | acac |
| 7'-253Y | Pd | 0 | 7' | Ph | H |   | MES2 | H | $CH_3$ | H | H | — |
| 7'-254 | Pd | 1 | 7' | Ph | H | H |   | PS1 | $CH_3$ | H | H | pic |
| 7'-254X | Pd | 1 | 7' | Ph | H | H |   | PS1 | $CH_3$ | H | H | acac |
| 7'-254Y | Pd | 0 | 7' | Ph | H | H |   | PS1 | $CH_3$ | H | H | — |
| 7'-255 | Pd | 1 | 7' | Ph | H |   | PS1 | H | $CH_3$ | H | H | pic |
| 7'-255X | Pd | 1 | 7' | Ph | H |   | PS1 | H | $CH_3$ | H | H | acac |
| 7'-255Y | Pd | 0 | 7' | Ph | H |   | PS1 | H | $CH_3$ | H | H | — |
| 7'-256 | Pd | 1 | 7' | Ph | H | H |   | PS2 | $CH_3$ | H | H | pic |
| 7'-256X | Pd | 1 | 7' | Ph | H | H |   | PS2 | $CH_3$ | H | H | acac |
| 7'-256Y | Pd | 0 | 7' | Ph | H | H |   | PS2 | $CH_3$ | H | H | — |
| 7'-257 | Pd | 1 | 7' | Ph | H |   | PS2 | H | $CH_3$ | H | H | pic |
| 7'-257X | Pd | 1 | 7' | Ph | H |   | PS2 | H | $CH_3$ | H | H | acac |
| 7'-257Y | Pd | 0 | 7' | Ph | H |   | P52 | H | $CH_3$ | H | H | — |
| 7'-258 | Pd | 1 | 7' | Ph | H | H |   | BAL1 | $CH_3$ | H | H | pic |
| 7'-258X | Pd | 1 | 7' | Ph | H | H |   | BAL1 | $CH_3$ | H | H | acac |
| 7'-258Y | Pd | 0 | 7' | Ph | H | H |   | BAL1 | $CH_3$ | H | H | — |
| 7'-259 | Pd | 1 | 7' | Ph | H |   | BAL1 | H | $CH_3$ | H | H | pic |
| 7'-259X | Pd | 1 | 7' | Ph | H |   | BAL1 | H | $CH_3$ | H | H | acac |
| 7'-259Y | Pd | 0 | 7' | Ph | H |   | BAL1 | H | $CH_3$ | H | H | — |
| 7'-260 | Pd | 1 | 7' | Ph | H | H |   | BAL2 | $CH_3$ | H | H | pic |
| 7'-260X | Pd | 1 | 7' | Ph | H | H |   | BAL2 | $CH_3$ | H | H | acac |
| 7'-260Y | Pd | 0 | 7' | Ph | H | H |   | BAL2 | $CH_3$ | H | H | — |
| 7'-261 | Pd | 1 | 7' | Ph | H |   | BAL2 | H | $CH_3$ | H | H | pic |
| 7'-261X | Pd | 1 | 7' | Ph | H |   | BAL2 | H | $CH_3$ | H | H | acac |
| 7'-261Y | Pd | 0 | 7' | Ph | H |   | BAL2 | H | $CH_3$ | H | H | — |
| 7'-262 | Pd | 1 | 7' | Ph | H | H |   | MEK1 | $CH_3$ | H | H | pic |
| 7'-262X | Pd | 1 | 7' | Ph | H | H |   | MEK1 | $CH_3$ | H | H | acac |
| 7'-262Y | Pd | 0 | 7' | Ph | H | H |   | MEK1 | $CH_3$ | H | H | — |
| 7'-263 | Pd | 1 | 7' | Ph | H |   | MEK1 | H | $CH_3$ | H | H | pic |
| 7'-263X | Pd | 1 | 7' | Ph | H |   | MEK1 | H | $CH_3$ | H | H | acac |
| 7'-263Y | Pd | 0 | 7' | Ph | H |   | MEK1 | H | $CH_3$ | H | H | — |
| 7'-264 | Pd | 1 | 7' | Ph | H | H |   | MEK2 | $CH_3$ | H | H | pic |
| 7'-264X | Pd | 1 | 7' | Ph | H | H |   | MEK2 | $CH_3$ | H | H | acac |
| 7'-264Y | Pd | 0 | 7' | Ph | H | H |   | MEK2 | $CH_3$ | H | H | — |
| 7'-265 | Pd | 1 | 7' | Ph | H |   | MEK2 | H | $CH_3$ | H | H | pic |
| 7'-265X | Pd | 1 | 7' | Ph | H |   | MEK2 | H | $CH_3$ | H | H | acac |
| 7'-265Y | Pd | 0 | 7' | Ph | H |   | MEK2 | H | $CH_3$ | H | H | — |
| 7'-266 | Pd | 1 | 7' | Ph | H | H |   | PAL1 | $CH_3$ | H | H | pic |
| 7'-266X | Pd | 1 | 7' | Ph | H | H |   | PAL1 | $CH_3$ | H | H | acac |
| 7'-266Y | Pd | 0 | 7' | Ph | H | H |   | PAL1 | $CH_3$ | H | H | — |
| 7'-267 | Pd | 1 | 7' | Ph | H |   | PAL1 | H | $CH_3$ | H | H | pic |
| 7'-267X | Pd | 1 | 7' | Ph | H |   | PAL1 | H | $CH_3$ | H | H | acac |
| 7'-267Y | Pd | 0 | 7' | Ph | H |   | PAL1 | H | $CH_3$ | H | H | — |
| 7'-268 | Pd | 1 | 7' | Ph | H | H |   | PAL2 | $CH_3$ | H | H | pic |
| 7'-268X | Pd | 1 | 7' | Ph | H | H |   | PAL2 | $CH_3$ | H | H | acac |
| 7'-268Y | Pd | 0 | 7' | Ph | H | H |   | PAL2 | $CH_3$ | H | H | — |
| 7'-269 | Pd | 1 | 7' | Ph | H |   | PAL2 | H | $CH_3$ | H | H | pic |
| 7'-269X | Pd | 1 | 7' | Ph | H |   | PAL2 | H | $CH_3$ | H | H | acac |
| 7'-269Y | Pd | 0 | 7' | Ph | H |   | PAL2 | H | $CH_3$ | H | H | — |
| 7'-270 | Pd | 1 | 7' | Ph | H | H |   | MMK | $CH_3$ | H | H | pic |
| 7'-270X | Pd | 1 | 7' | Ph | H | H |   | MMK | $CH_3$ | H | H | acac |
| 7'-270Y | Pd | 0 | 7' | Ph | H | H |   | MMK | $CH_3$ | H | H | — |
| 7'-271 | Pd | 1 | 7' | Ph | H |   | MMK | H | $CH_3$ | H | H | pic |
| 7'-271X | Pd | 1 | 7' | Ph | H |   | MMK | H | $CH_3$ | H | H | acac |
| 7'-271Y | Pd | 0 | 7' | Ph | H |   | MMK | H | $CH_3$ | H | H | — |
| 7'-272 | Pd | 1 | 7' | Ph | H | H |   | EES1 | $CH_3$ | H | H | pic |
| 7'-272X | Pd | 1 | 7' | Ph | H | H |   | EES1 | $CH_3$ | H | H | acac |
| 7'-272Y | Pd | 0 | 7' | Ph | H | H |   | EES1 | $CH_3$ | H | H | — |
| 7'-273 | Pd | 1 | 7' | Ph | H |   | EES2 | H | $CH_3$ | H | H | pic |
| 7'-273X | Pd | 1 | 7' | Ph | H |   | EES2 | H | $CH_3$ | H | H | acac |
| 7'-273Y | Pd | 0 | 7' | Ph | H |   | EES2 | H | $CH_3$ | H | H | — |
| 7'-274 | Pd | 1 | 7' | Ph | H | H |   | PAE1 | $CH_3$ | H | H | pic |
| 7'-274X | Pd | 1 | 7' | Ph | H | H |   | PAE1 | $CH_3$ | H | H | acac |
| 7'-274Y | Pd | 0 | 7' | Ph | H | H |   | PAE1 | $CH_3$ | H | H | — |
| 7'-275 | Pd | 1 | 7' | Ph | H |   | PAE2 | H | $CH_3$ | H | H | pic |
| 7'-275X | Pd | 1 | 7' | Ph | H |   | PAE2 | H | $CH_3$ | H | H | acac |
| 7'-275Y | Pd | 0 | 7' | Ph | H |   | PAE2 | H | $CH_3$ | H | H | — |
| 7'-276 | Pd | 1 | 7' | Ph | H | H |   | AME1 | $CH_3$ | H | H | pic |
| 7'-276X | Pd | 1 | 7' | Ph | H | H |   | AME1 | $CH_3$ | H | H | acac |
| 7'-276Y | Pd | 0 | 7' | Ph | H | H |   | AME1 | $CH_3$ | H | H | — |
| 7'-277 | Pd | 1 | 7' | Ph | H |   | AME1 | H | $CH_3$ | H | H | pic |

TABLE 49-continued

| No. | M | m | BSS | SS G | T¹ | T² | T³ | T⁴ | T⁵ | T⁶ | T⁷ | L¹ L² |
|---|---|---|---|---|---|---|---|---|---|---|---|---|
| 7'-277X | Pd | 1 | 7' | Ph | H | | AME1 | H | $CH_3$ | H | H | acac |
| 7'-277Y | Pd | 0 | 7' | Ph | H | | AME1 | H | $CH_3$ | H | H | — — |
| 7'-278 | Pd | 1 | 7' | Ph | H | H | | AME2 | $CH_3$ | H | H | pic |
| 7'-278X | Pd | 1 | 7' | Ph | H | H | | AME2 | $CH_3$ | H | H | acac |
| 7'-278Y | Pd | 0 | 7' | Ph | H | H | | AME2 | $CH_3$ | H | H | — — |
| 7'-279 | Pd | 1 | 7' | Ph | H | | AME2 | H | $CH_3$ | H | H | pic |
| 7'-279X | Pd | 1 | 7' | Ph | H | | AME2 | H | $CH_3$ | H | H | acac |
| 7'-279Y | Pd | 0 | 7' | Ph | H | | AME2 | H | $CH_3$ | H | H | — — |
| 7'-280 | Pd | 1 | 7' | Ph | H | H | | EAE1 | $CH_3$ | H | H | pic |
| 7'-280X | Pd | 1 | 7' | Ph | H | H | | EAE1 | $CH_3$ | H | H | acac |
| 7'-280Y | Pd | 0 | 7' | Ph | H | H | | EAE1 | $CH_3$ | H | H | — — |
| 7'-281 | Pd | 1 | 7' | Ph | H | | EAE1 | H | $CH_3$ | H | H | pic |
| 7'-281X | Pd | 1 | 7' | Ph | H | | EAE1 | H | $CH_3$ | H | H | acac |
| 7'-281Y | Pd | 0 | 7' | Ph | H | | EAE1 | H | $CH_3$ | H | H | — — |
| 7'-282 | Pd | 1 | 7' | Ph | H | H | | EAE2 | $CH_3$ | H | H | pic |
| 7'-282X | Pd | 1 | 7' | Ph | H | H | | EAE2 | $CH_3$ | H | H | acac |
| 7'-282Y | Pd | 0 | 7' | Ph | H | H | | EAE2 | $CH_3$ | H | H | — — |
| 7'-283 | Pd | 1 | 7' | Ph | H | | EAE2 | H | $CH_3$ | H | H | pic |
| 7'-283X | Pd | 1 | 7' | Ph | H | | EAE2 | H | $CH_3$ | H | H | acac |
| 7'-283Y | Pd | 0 | 7' | Ph | H | | EAE2 | H | $CH_3$ | H | H | — — |
| 7'-284 | Pd | 1 | 7' | Ph | H | H | | AAE1 | $CH_3$ | H | H | pic |
| 7'-284X | Pd | 1 | 7' | Ph | H | H | | AAE1 | $CH_3$ | H | H | acac |
| 7'-284Y | Pd | 0 | 7' | Ph | H | H | | AAE1 | $CH_3$ | H | H | — — |
| 7'-285 | Pd | 1 | 7' | Ph | H | | AAE1 | H | $CH_3$ | H | H | pic |
| 7'-285X | Pd | 1 | 7' | Ph | H | | AAE1 | H | $CH_3$ | H | H | acac |
| 7'-285Y | Pd | 0 | 7' | Ph | H | | AAE1 | H | $CH_3$ | H | H | — — |
| 7'-286 | Pd | 1 | 7' | Ph | H | H | | AAE2 | $CH_3$ | H | H | pic |
| 7'-286X | Pd | 1 | 7' | Ph | H | H | | AAE2 | $CH_3$ | H | H | acac |
| 7'-286Y | Pd | 0 | 7' | Ph | H | H | | AAE2 | $CH_3$ | H | H | — — |
| 7'-287 | Pd | 1 | 7' | Ph | H | | AAE2 | H | $CH_3$ | H | H | pic |
| 7'-287X | Pd | 1 | 7' | Ph | H | | AAE2 | H | $CH_3$ | H | H | acac |
| 7'-287Y | Pd | 0 | 7' | Ph | H | | AAE2 | H | $CH_3$ | H | H | — — |
| 7'-288 | Pd | 1 | 7' | Ph | H | H | | PME1 | $CH_3$ | H | H | pic |
| 7'-288X | Pd | 1 | 7' | Ph | H | H | | PME1 | $CH_3$ | H | H | acac |
| 7'-288Y | Pd | 0 | 7' | Ph | H | H | | PME1 | $CH_3$ | H | H | — — |
| 7'-289 | Pd | 1 | 7' | Ph | H | | PME1 | H | $CH_3$ | H | H | pic |
| 7'-289X | Pd | 1 | 7' | Ph | H | | PME1 | H | $CH_3$ | H | H | acac |
| 7'-289Y | Pd | 0 | 7' | Ph | H | | PME1 | H | $CH_3$ | H | H | — — |
| 7'-290 | Pd | 1 | 7' | Ph | H | H | | PME2 | $CH_3$ | H | H | pic |
| 7'-290X | Pd | 1 | 7' | Ph | H | H | | PME2 | $CH_3$ | H | H | acac |
| 7'-290Y | Pd | 0 | 7' | Ph | H | H | | PME2 | $CH_3$ | H | H | — — |
| 7'-291 | Pd | 1 | 7' | Ph | H | | PME2 | H | $CH_3$ | H | H | pic |
| 7'-291X | Pd | 1 | 7' | Ph | H | | PME2 | H | $CH_3$ | H | H | acac |
| 7'-291Y | Pd | 0 | 7' | Ph | H | | PME2 | H | $CH_3$ | H | H | — — |
| 7'-292 | Pd | 1 | 7' | Ph | H | H | | MET1 | $CH_3$ | H | H | pic |
| 7'-292X | Pd | 1 | 7' | Ph | H | H | | MET1 | $CH_3$ | H | H | acac |
| 7'-292Y | Pd | 0 | 7' | Ph | H | H | | MET1 | $CH_3$ | H | H | — — |
| 7'-293 | Pd | 1 | 7' | Ph | H | | MET1 | H | $CH_3$ | H | H | pic |
| 7'-293X | Pd | 1 | 7' | Ph | H | | MET1 | H | $CH_3$ | H | H | acac |
| 7'-293Y | Pd | 0 | 7' | Ph | H | | MET1 | H | $CH_3$ | H | H | — — |
| 7'-294 | Pd | 1 | 7' | Ph | H | H | | MET2 | $CH_3$ | H | H | pic |
| 7'-294X | Pd | 1 | 7' | Ph | H | H | | MET2 | $CH_3$ | H | H | acac |
| 7'-294Y | Pd | 0 | 7' | Ph | H | H | | MET2 | $CH_3$ | H | H | — — |
| 7'-295 | Pd | 1 | 7' | Ph | H | | MET2 | H | $CH_3$ | H | H | pic |
| 7'-295X | Pd | 1 | 7' | Ph | H | | MET2 | H | $CH_3$ | H | H | acac |
| 7'-295Y | Pd | 0 | 7' | Ph | H | | MET2 | H | $CH_3$ | H | H | — — |
| 7'-296 | Pd | 1 | 7' | Ph | H | H | | EE1 | $CH_3$ | H | H | pic |
| 7'-296X | Pd | 1 | 7' | Ph | H | H | | EE1 | $CH_3$ | H | H | acac |
| 7'-296Y | Pd | 0 | 7' | Ph | H | H | | EE1 | $CH_3$ | H | H | — — |
| 7'-297 | Pd | 1 | 7' | Ph | H | | EE1 | H | $CH_3$ | H | H | pic |
| 7'-297X | Pd | 1 | 7' | Ph | H | | EE1 | H | $CH_3$ | H | H | acac |
| 7'-297Y | Pd | 0 | 7' | Ph | H | | EE1 | H | $CH_3$ | H | H | — — |
| 7'-298 | Pd | 1 | 7' | Ph | H | H | | EE2 | $CH_3$ | H | H | pic |
| 7'-298X | Pd | 1 | 7' | Ph | H | H | | EE2 | $CH_3$ | H | H | acac |
| 7'-298Y | Pd | 0 | 7' | Ph | H | H | | EE2 | $CH_3$ | H | H | — — |
| 7'-299 | Pd | 1 | 7' | Ph | H | | EE2 | H | $CH_3$ | H | H | pic |
| 7'-299X | Pd | 1 | 7' | Ph | H | | EE2 | H | $CH_3$ | H | H | acac |
| 7'-299Y | Pd | 0 | 7' | Ph | H | | EE2 | H | $CH_3$ | H | H | — — |
| 7'-300 | Pd | 1 | 7' | Ph | H | H | | MS1 | $CH_3$ | H | H | pic |
| 7'-300X | Pd | 1 | 7' | Ph | H | H | | MS1 | $CH_3$ | H | H | acac |
| 7'-300Y | Pd | 0 | 7' | Ph | H | H | | MS1 | $CH_3$ | H | H | — — |
| 7'-301 | Pd | 1 | 7' | Ph | H | | MS1 | H | $CH_3$ | H | H | pic |
| 7'-301X | Pd | 1 | 7' | Ph | H | | MS1 | H | $CH_3$ | H | H | acac |
| 7'-301Y | Pd | 0 | 7' | Ph | H | | MS1 | H | $CH_3$ | H | H | — — |

TABLE 49-continued
| No. | M | m | BSS | SS | G | T¹ | T² | T³ | T⁴ | T⁵ | T⁶ | T⁷ | L¹ | L² |
|---|---|---|---|---|---|---|---|---|---|---|---|---|---|---|
| 7'-302 | Pd | 1 | 7' | | Ph | H | H | | MS2 | CH₃ | H | H | pic | |
| 7'-302X | Pd | 1 | 7' | | Ph | H | H | | MS2 | CH₃ | H | H | acac | |
| 7'-302Y | Pd | 0 | 7' | | Ph | H | H | | MS2 | CH₃ | H | H | — | — |
| 7'-303 | Pd | 1 | 7' | | Ph | H | | MS2 | H | CH₃ | H | H | pic | |
| 7'-303X | Pd | 1 | 7' | | Ph | H | | MS2 | H | CH₃ | H | H | acac | |
| 7'-303Y | Pd | 0 | 7' | | Ph | H | | MS2 | H | CH₃ | H | H | — | — |
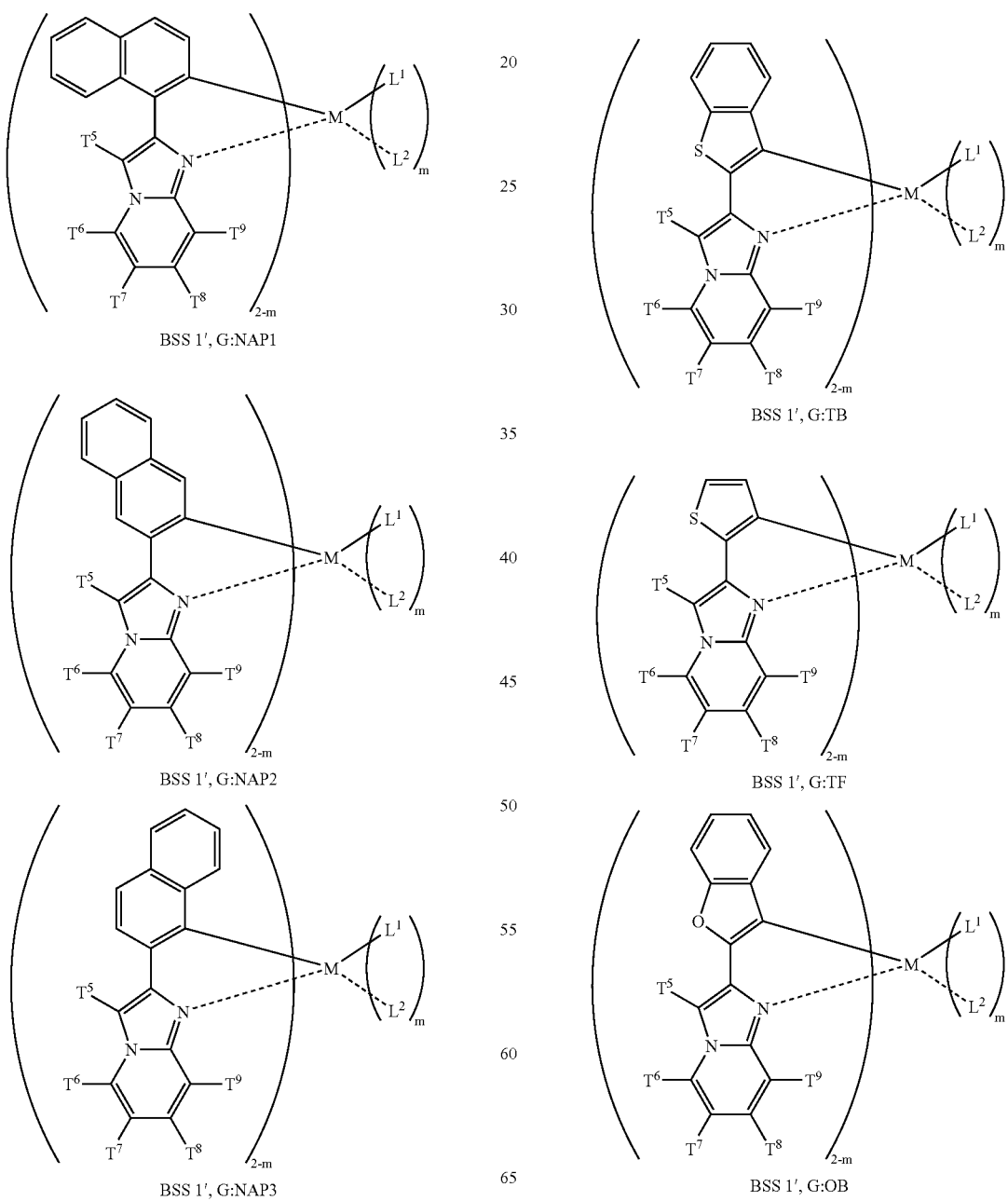

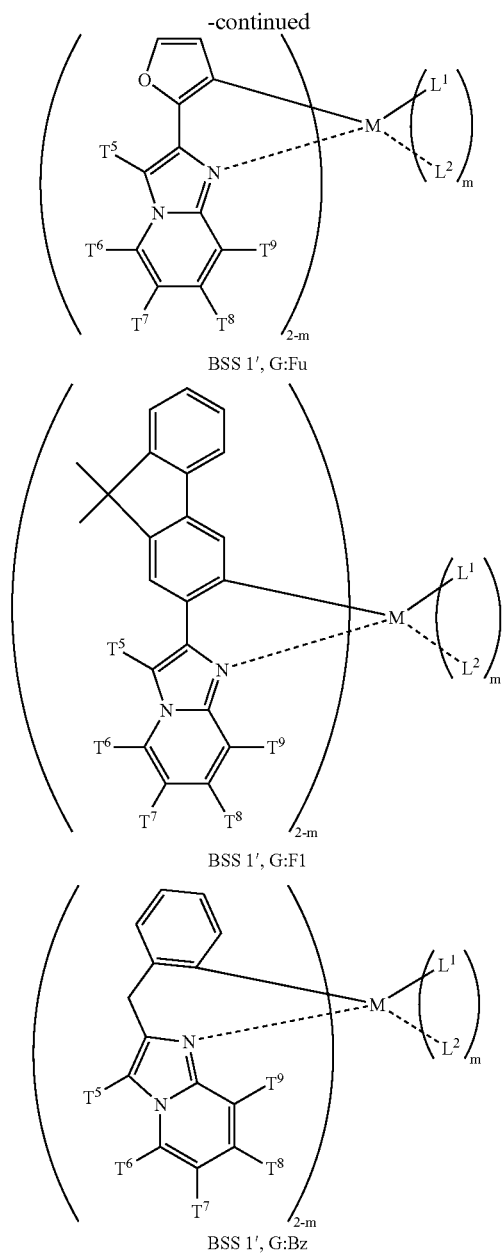
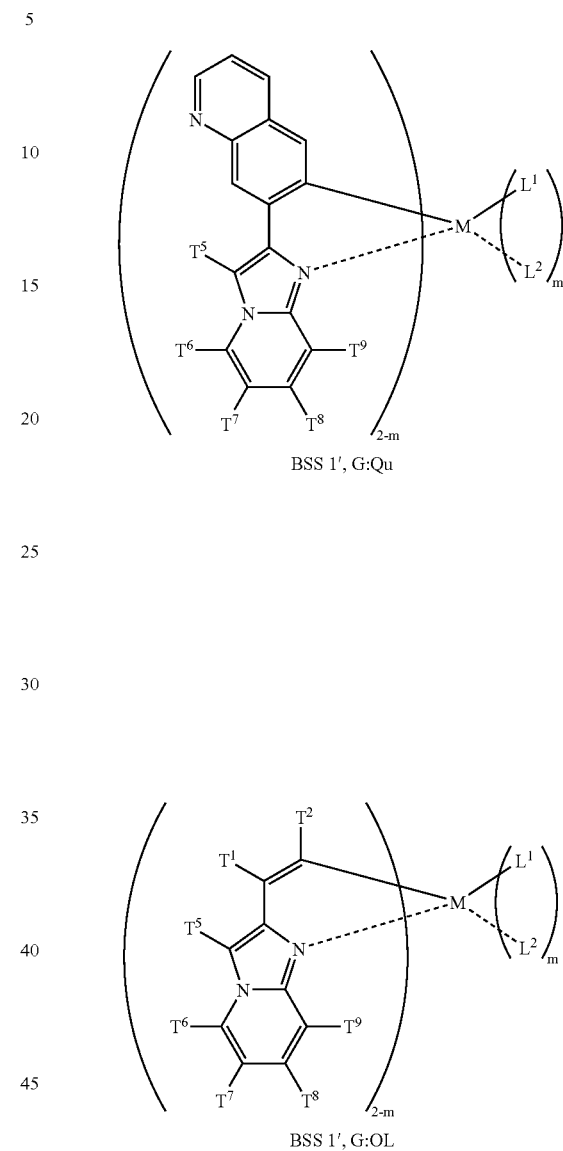

TABLE 50

| No. | M | m | BSS | SS | G | T¹ | T² | T⁵ | T⁶ | T⁷ | T⁸ | T⁹ | L¹ L² |
|---|---|---|---|---|---|---|---|---|---|---|---|---|---|
| 1'-305 | Pd | 1 | 1' | | Nap1 | — | — | H | H | H | H | H | pic |
| 1'-305X | Pd | 1 | 1' | | Nap1 | — | — | H | H | H | H | H | acac |
| 1'-305Y | Pd | 0 | 1' | | Nap1 | — | — | H | H | H | H | H | — — |
| 1'-306 | Pd | 1 | 1' | | Nap1 | — | — | $^tC_4H_9$ | H | H | H | H | pic |
| 1'-306X | Pd | 1 | 1' | | Nap1 | — | — | $^tC_4H_9$ | H | H | H | H | acac |
| 1'-306Y | Pd | 0 | 1' | | Nap1 | — | — | $^tC_4H_9$ | H | H | H | H | — — |
| 1'-307 | Pd | 1 | 1' | | Nap1 | — | — | $CH_3$ | H | H | H | H | pic |
| 1'-307X | Pd | 1 | 1' | | Nap1 | — | — | $CH_3$ | H | H | H | H | acac |
| 1'-307Y | Pd | 0 | 1' | | Nap1 | — | — | $CH_3$ | H | H | H | H | — — |
| 1'-308 | Pd | 1 | 1' | | Nap1 | — | — | $^tC_4H_9$ | $CH_3$ | H | H | H | pic |
| 1'-308X | Pd | 1 | 1' | | Nap1 | — | — | $^tC_4H_9$ | $CH_3$ | H | H | H | acac |
| 1'-308Y | Pd | 0 | 1' | | Nap1 | — | — | $^tC_4H_9$ | $CH_3$ | H | H | H | — — |
| 1'-309 | Pd | 1 | 1' | | Nap1 | — | — | $CH_3$ | $CH_3$ | H | H | H | pic |
| 1'-309X | Pd | 1 | 1' | | Nap1 | — | — | $CH_3$ | $CH_3$ | H | H | H | acac |
| 1'-309Y | Pd | 0 | 1' | | Nap1 | — | — | $CH_3$ | $CH_3$ | H | H | H | — — |

TABLE 50-continued

| No. | M | m | BSS | SS G | T¹ | T² | T⁵ | T⁶ | T⁷ | T⁸ | T⁹ | L¹ L² |
|---|---|---|---|---|---|---|---|---|---|---|---|---|
| 1'-310 | Pd | 1 | 1' | Nap1 | — | — | H | CH₃ | H | H | H | pic |
| 1'-310X | Pd | 1 | 1' | Nap1 | — | — | H | CH₃ | H | H | H | acac |
| 1'-310Y | Pd | 0 | 1' | Nap1 | — | — | H | CH₃ | H | H | H | — — |
| 1'-311 | Pd | 1 | 1' | Nap2 | — | — | H | H | H | H | H | pic |
| 1'-311X | Pd | 1 | 1' | Nap2 | — | — | H | H | H | H | H | acac |
| 1'-311Y | Pd | 0 | 1' | Nap2 | — | — | H | H | H | H | H | — — |
| 1'-312 | Pd | 1 | 1' | Nap2 | — | — | ᵗC₄H₉ | H | H | H | H | pic |
| 1'-312X | Pd | 1 | 1' | Nap2 | — | — | ᵗC₄H₉ | H | H | H | H | acac |
| 1'-312Y | Pd | 0 | 1' | Nap2 | — | — | ᵗC₄H₉ | H | H | H | H | — — |
| 1'-313 | Pd | 1 | 1' | Nap2 | — | — | CH₃ | H | H | H | H | pic |
| 1'-313X | Pd | 1 | 1' | Nap2 | — | — | CH₃ | H | H | H | H | acac |
| 1'-313Y | Pd | 0 | 1' | Nap2 | — | — | CH₃ | H | H | H | H | — — |
| 1'-314 | Pd | 1 | 1' | Nap2 | — | — | ᵗC₄H₉ | CH₃ | H | H | H | pic |
| 1'-314X | Pd | 1 | 1' | Nap2 | — | — | ᵗC₄H₉ | CH₃ | H | H | H | acac |
| 1'-314Y | Pd | 0 | 1' | Nap2 | — | — | ᵗC₄H₉ | CH₃ | H | H | H | — — |
| 1'-315 | Pd | 1 | 1' | Nap2 | — | — | CH₃ | CH₃ | H | H | H | pic |
| 1'-315X | Pd | 1 | 1' | Nap2 | — | — | CH₃ | CH₃ | H | H | H | acac |
| 1'-315Y | Pd | 0 | 1' | Nap2 | — | — | CH₃ | CH₃ | H | H | H | — — |
| 1'-316 | Pd | 1 | 1' | Nap2 | — | — | H | CH₃ | H | H | H | pic |
| 1'-316X | Pd | 1 | 1' | Nap2 | — | — | H | CH₃ | H | H | H | acac |
| 1'-316Y | Pd | 0 | 1' | Nap2 | — | — | H | CH₃ | H | H | H | — — |
| 1'-317 | Pd | 1 | 1' | Nap3 | — | — | H | H | H | H | H | pic |
| 1'-317X | Pd | 1 | 1' | Nap3 | — | — | H | H | H | H | H | acac |
| 1'-317Y | Pd | 0 | 1' | Nap3 | — | — | H | H | H | H | H | — — |
| 1'-318 | Pd | 1 | 1' | Nap3 | — | — | ᵗC₄H₉ | H | H | H | H | pic |
| 1'-318X | Pd | 1 | 1' | Nap3 | — | — | ᵗC₄H₉ | H | H | H | H | acac |
| 1'-318Y | Pd | 0 | 1' | Nap3 | — | — | ᵗC₄H₉ | H | H | H | H | — — |
| 1'-319 | Pd | 1 | 1' | Nap3 | — | — | CH₃ | H | H | H | H | pic |
| 1'-319X | Pd | 1 | 1' | Nap3 | — | — | CH₃ | H | H | H | H | acac |
| 1'-319Y | Pd | 0 | 1' | Nap3 | — | — | CH₃ | H | H | H | H | — — |
| 1'-320 | Pd | 1 | 1' | Nap3 | — | — | ᵗC₄H₉ | CH₃ | H | H | H | pic |
| 1'-320X | Pd | 1 | 1' | Nap3 | — | — | ᵗC₄H₉ | CH₃ | H | H | H | acac |
| 1'-320Y | Pd | 0 | 1' | Nap3 | — | — | ᵗC₄H₉ | CH₃ | H | H | H | — — |
| 1'-321 | Pd | 1 | 1' | Nap3 | — | — | CH₃ | CH₃ | H | H | H | pic |
| 1'-321X | Pd | 1 | 1' | Nap3 | — | — | CH₃ | CH₃ | H | H | H | acac |
| 1'-321Y | Pd | 0 | 1' | Nap3 | — | — | CH₃ | CH₃ | H | H | H | — — |
| 1'-322 | Pd | 1 | 1' | Nap3 | — | — | H | CH₃ | H | H | H | pic |
| 1'-322X | Pd | 1 | 1' | Nap3 | — | — | H | CH₃ | H | H | H | acac |
| 1'-322Y | Pd | 0 | 1' | Nap3 | — | — | H | CH₃ | H | H | H | — — |
| 1'-323 | Pd | 1 | 1' | TB | — | — | H | H | H | H | H | pic |
| 1'-323X | Pd | 1 | 1' | TB | — | — | H | H | H | H | H | acac |
| 1'-323Y | Pd | 0 | 1' | TB | — | — | H | H | H | H | H | — — |
| 1'-324 | Pd | 1 | 1' | TB | — | — | ᵗC₄H₉ | H | H | H | H | pic |
| 1'-324X | Pd | 1 | 1' | TB | — | — | ᵗC₄H₉ | H | H | H | H | acac |
| 1'-324Y | Pd | 0 | 1' | TB | — | — | ᵗC₄H₉ | H | H | H | H | — — |
| 1'-325 | Pd | 1 | 1' | TB | — | — | CH₃ | H | H | H | H | pic |
| 1'-325X | Pd | 1 | 1' | TB | — | — | CH₃ | H | H | H | H | acac |
| 1'-325Y | Pd | 0 | 1' | TB | — | — | CH₃ | H | H | H | H | — — |
| 1'-326 | Pd | 1 | 1' | TB | — | — | ᵗC₄H₉ | CH₃ | H | H | H | pic |
| 1'-326X | Pd | 1 | 1' | TB | — | — | ᵗC₄H₉ | CH₃ | H | H | H | acac |
| 1'-326Y | Pd | 0 | 1' | TB | — | — | ᵗC₄H₉ | CH₃ | H | H | H | — — |
| 1'-327 | Pd | 1 | 1' | TB | — | — | CH₃ | CH₃ | H | H | H | pic |
| 1'-327X | Pd | 1 | 1' | TB | — | — | CH₃ | CH₃ | H | H | H | acac |
| 1'-327Y | Pd | 0 | 1' | TB | — | — | CH₃ | CH₃ | H | H | H | — — |
| 1'-328 | Pd | 1 | 1' | TB | — | — | H | CH₃ | H | H | H | pic |
| 1'-328X | Pd | 1 | 1' | TB | — | — | H | CH₃ | H | H | H | acac |
| 1'-328Y | Pd | 0 | 1' | TB | — | — | H | CH₃ | H | H | H | — — |
| 1'-329 | Pd | 1 | 1' | TF | — | — | H | H | H | H | H | pic |
| 1'-329X | Pd | 1 | 1' | TF | — | — | H | H | H | H | H | acac |
| 1'-329Y | Pd | 0 | 1' | TF | — | — | H | H | H | H | H | — — |
| 1'-330 | Pd | 1 | 1' | TF | — | — | ᵗC₄H₉ | H | H | H | H | pic |
| 1'-330X | Pd | 1 | 1' | TF | — | — | ᵗC₄H₉ | H | H | H | H | acac |
| 1'-330Y | Pd | 0 | 1' | TF | — | — | ᵗC₄H₉ | H | H | H | H | — — |
| 1'-331 | Pd | 1 | 1' | TF | — | — | CH₃ | H | H | H | H | pic |
| 1'-331X | Pd | 1 | 1' | TF | — | — | CH₃ | H | H | H | H | acac |
| 1'-331Y | Pd | 0 | 1' | TF | — | — | CH₃ | H | H | H | H | — — |
| 1'-332 | Pd | 1 | 1' | TF | — | — | ᵗC₄H₉ | CH₃ | H | H | H | pic |
| 1'-332X | Pd | 1 | 1' | TF | — | — | ᵗC₄H₉ | CH₃ | H | H | H | acac |
| 1'-332Y | Pd | 0 | 1' | TF | — | — | ᵗC₄H₉ | CH₃ | H | H | H | — — |
| 1'-333 | Pd | 1 | 1' | TF | — | — | CH₃ | CH₃ | H | H | H | pic |
| 1'-333X | Pd | 1 | 1' | TF | — | — | CH₃ | CH₃ | H | H | H | acac |
| 1'-333Y | Pd | 0 | 1' | TF | — | — | CH₃ | CH₃ | H | H | H | — — |
| 1'-334 | Pd | 1 | 1' | TF | — | — | H | CH₃ | H | H | H | pic |
| 1'-334X | Pd | 1 | 1' | TF | — | — | H | CH₃ | H | H | H | acac |
| 1'-334Y | Pd | 0 | 1' | TF | — | — | H | CH₃ | H | H | H | — — |
| 1'-335 | Pd | 1 | 1' | OB | — | — | H | H | H | H | H | pic |
| 1'-335X | Pd | 1 | 1' | OB | — | — | H | H | H | H | H | acac |

TABLE 50-continued

| No. | M | m | BSS | SS G | T¹ | T² | T⁵ | T⁶ | T⁷ | T⁸ | T⁹ | L¹ | L² |
|---|---|---|---|---|---|---|---|---|---|---|---|---|---|
| 1'-335Y | Pd | 0 | 1' | OB | — | — | H | H | H | H | H | — | — |
| 1'-336 | Pd | 1 | 1' | OB | — | — | ᵗC₄H₉ | H | H | H | H | pic | |
| 1'-336X | Pd | 1 | 1' | OB | — | — | ᵗC₄H₉ | H | H | H | H | acac | |
| 1'-336Y | Pd | 0 | 1' | OB | — | — | ᵗC₄H₉ | H | H | H | H | — | — |
| 1'-337 | Pd | 1 | 1' | OB | — | — | CH₃ | H | H | H | H | pic | |
| 1'-337X | Pd | 1 | 1' | OB | — | — | CH₃ | H | H | H | H | acac | |
| 1'-337Y | Pd | 0 | 1' | OB | — | — | CH₃ | H | H | H | H | — | — |
| 1'-338 | Pd | 1 | 1' | OB | — | — | ᵗC₄H₉ | CH₃ | H | H | H | pic | |
| 1'-338X | Pd | 1 | 1' | OB | — | — | ᵗC₄H₉ | CH₃ | H | H | H | acac | |
| 1'-338Y | Pd | 0 | 1' | OB | — | — | ᵗC₄H₉ | CH₃ | H | H | H | — | — |
| 1'-339 | Pd | 1 | 1' | OB | — | — | CH₃ | CH₃ | H | H | H | pic | |
| 1'-339X | Pd | 1 | 1' | OB | — | — | CH₃ | CH₃ | H | H | H | acac | |
| 1'-339Y | Pd | 0 | 1' | OB | — | — | CH₃ | CH₃ | H | H | H | — | — |
| 1'-340 | Pd | 1 | 1' | OB | — | — | H | CH₃ | H | H | H | pic | |
| 1'-340X | Pd | 1 | 1' | OB | — | — | H | CH₃ | H | H | H | acac | |
| 1'-340Y | Pd | 0 | 1' | OB | — | — | H | CH₃ | H | H | H | — | — |
| 1'-341 | Pd | 1 | 1' | Fu | — | — | H | H | H | H | H | pic | |
| 1'-341X | Pd | 1 | 1' | Fu | — | — | H | H | H | H | H | acac | |
| 1'-341Y | Pd | 0 | 1' | Fu | — | — | H | H | H | H | H | — | — |
| 1'-342 | Pd | 1 | 1' | Fu | — | — | ᵗC₄H₉ | H | H | H | H | pic | |
| 1'-342X | Pd | 1 | 1' | Fu | — | — | ᵗC₄H₉ | H | H | H | H | acac | |
| 1'-342Y | Pd | 0 | 1' | Fu | — | — | ᵗC₄H₉ | H | H | H | H | — | — |
| 1'-343 | Pd | 1 | 1' | Fu | — | — | CH₃ | H | H | H | H | pic | |
| 1'-343X | Pd | 1 | 1' | Fu | — | — | CH₃ | H | H | H | H | acac | |
| 1'-343Y | Pd | 0 | 1' | Fu | — | — | CH₃ | H | H | H | H | — | — |
| 1'-344 | Pd | 1 | 1' | Fu | — | — | ᵗC₄H₉ | CH₃ | H | H | H | pic | |
| 1'-344X | Pd | 1 | 1' | Fu | — | — | ᵗC₄H₉ | CH₃ | H | H | H | acac | |
| 1'-344Y | Pd | 0 | 1' | Fu | — | — | ᵗC₄H₉ | CH₃ | H | H | H | — | — |
| 1'-345 | Pd | 1 | 1' | Fu | — | — | CH₃ | CH₃ | H | H | H | pic | |
| 1'-345X | Pd | 1 | 1' | Fu | — | — | CH₃ | CH₃ | H | H | H | acac | |
| 1'-345Y | Pd | 0 | 1' | Fu | — | — | CH₃ | CH₃ | H | H | H | — | — |
| 1'-346 | Pd | 1 | 1' | Fu | — | — | H | CH₃ | H | H | H | pic | |
| 1'-346X | Pd | 1 | 1' | Fu | — | — | H | CH₃ | H | H | H | acac | |
| 1'-346Y | Pd | 0 | 1' | Fu | — | — | H | CH₃ | H | H | H | — | — |
| 1'-347 | Pd | 1 | 1' | Fl | — | — | H | H | H | H | H | pic | |
| 1'-347X | Pd | 1 | 1' | Fl | — | — | H | H | H | H | H | acac | |
| 1'-347Y | Pd | 0 | 1' | Fl | — | — | H | H | H | H | H | — | — |
| 1'-348 | Pd | 1 | 1' | Fl | — | — | ᵗC₄H₉ | H | H | H | H | pic | |
| 1'-348X | Pd | 1 | 1' | Fl | — | — | ᵗC₄H₉ | H | H | H | H | acac | |
| 1'-348Y | Pd | 0 | 1' | Fl | — | — | ᵗC₄H₉ | H | H | H | H | — | — |
| 1'-349 | Pd | 1 | 1' | Fl | — | — | CH₃ | H | H | H | H | pic | |
| 1'-349X | Pd | 1 | 1' | Fl | — | — | CH₃ | H | H | H | H | acac | |
| 1'-349Y | Pd | 0 | 1' | Fl | — | — | CH₃ | H | H | H | H | — | — |
| 1'-350 | Pd | 1 | 1' | Fl | — | — | ᵗC₄H₉ | CH₃ | H | H | H | pic | |
| 1'-350X | Pd | 1 | 1' | Fl | — | — | ᵗC₄H₉ | CH₃ | H | H | H | acac | |
| 1'-350Y | Pd | 0 | 1' | Fl | — | — | ᵗC₄H₉ | CH₃ | H | H | H | — | — |
| 1'-351 | Pd | 1 | 1' | Fl | — | — | CH₃ | CH₃ | H | H | H | pic | |
| 1'-351X | Pd | 1 | 1' | Fl | — | — | CH₃ | CH₃ | H | H | H | acac | |
| 1'-351Y | Pd | 0 | 1' | Fl | — | — | CH₃ | CH₃ | H | H | H | — | — |
| 1'-352 | Pd | 1 | 1' | Fl | — | — | H | CH₃ | H | H | H | pic | |
| 1'-352X | Pd | 1 | 1' | Fl | — | — | H | CH₃ | H | H | H | acac | |
| 1'-352Y | Pd | 0 | 1' | Fl | — | — | H | CH₃ | H | H | H | — | — |
| 1'-353 | Pd | 1 | 1' | Bz | — | — | H | H | H | H | H | pic | |
| 1'-353X | Pd | 1 | 1' | Bz | — | — | H | H | H | H | H | acac | |
| 1'-353Y | Pd | 0 | 1' | Bz | — | — | H | H | H | H | H | — | — |
| 1'-354 | Pd | 1 | 1' | Bz | — | — | ᵗC₄H₉ | H | H | H | H | pic | |
| 1'-354X | Pd | 1 | 1' | Bz | — | — | ᵗC₄H₉ | H | H | H | H | acac | |
| 1'-354Y | Pd | 0 | 1' | Bz | — | — | ᵗC₄H₉ | H | H | H | H | — | — |
| 1'-355 | Pd | 1 | 1' | Bz | — | — | CH₃ | H | H | H | H | pic | |
| 1'-355X | Pd | 1 | 1' | Bz | — | — | CH₃ | H | H | H | H | acac | |
| 1'-355Y | Pd | 0 | 1' | Bz | — | — | CH₃ | H | H | H | H | — | — |
| 1'-356 | Pd | 1 | 1' | Bz | — | — | ᵗC₄H₉ | CH₃ | H | H | H | pic | |
| 1'-356X | Pd | 1 | 1' | Bz | — | — | ᵗC₄H₉ | CH₃ | H | H | H | acac | |
| 1'-356Y | Pd | 0 | 1' | Bz | — | — | ᵗC₄H₉ | CH₃ | H | H | H | — | — |
| 1'-357 | Pd | 1 | 1' | Bz | — | — | CH₃ | CH₃ | H | H | H | pic | |
| 1'-357X | Pd | 1 | 1' | Bz | — | — | CH₃ | CH₃ | H | H | H | acac | |
| 1'-357Y | Pd | 0 | 1' | Bz | — | — | CH₃ | CH₃ | H | H | H | — | — |
| 1'-358 | Pd | 1 | 1' | Bz | — | — | H | CH₃ | H | H | H | pic | |
| 1'-358X | Pd | 1 | 1' | Bz | — | — | H | CH₃ | H | H | H | acac | |
| 1'-358Y | Pd | 0 | 1' | Bz | — | — | H | CH₃ | H | H | H | — | — |
| 1'-359 | Pd | 1 | 1' | Qu | — | — | H | H | H | H | H | pic | |
| 1'-359X | Pd | 1 | 1' | Qu | — | — | H | H | H | H | H | acac | |
| 1'-359Y | Pd | 0 | 1' | Qu | — | — | H | H | H | H | H | — | — |
| 1'-360 | Pd | 1 | 1' | Qu | — | — | ᵗC₄H₉ | H | H | H | H | pic | |
| 1'-360X | Pd | 1 | 1' | Qu | — | — | ᵗC₄H₉ | H | H | H | H | acac | |
| 1'-360Y | Pd | 0 | 1' | Qu | — | — | ᵗC₄H₉ | H | H | H | H | — | — |
| 1'-361 | Pd | 1 | 1' | Qu | — | — | CH₃ | H | H | H | H | pic | |

TABLE 50-continued

| No. | M | m | BSS | SS | G | T¹ | T² | T⁵ | T⁶ | T⁷ | T⁸ | T⁹ | L¹ L² |
|---|---|---|---|---|---|---|---|---|---|---|---|---|---|
| 1'-361X | Pd | 1 | 1' | | Qu | — | — | CH₃ | H | H | H | H | acac |
| 1'-361Y | Pd | 0 | 1' | | Qu | — | — | CH₃ | H | H | H | H | — — |
| 1'-362 | Pd | 1 | 1' | | Qu | — | — | $^tC_4H_9$ | CH₃ | H | H | H | pic |
| 1'-362X | Pd | 1 | 1' | | Qu | — | — | $^tC_4H_9$ | CH₃ | H | H | H | acac |
| 1'-362Y | Pd | 0 | 1' | | Qu | — | — | $^tC_4H_9$ | CH₃ | H | H | H | — — |
| 1'-363 | Pd | 1 | 1' | | Qu | — | — | CH₃ | CH₃ | H | H | H | pic |
| 1'-363X | Pd | 1 | 1' | | Qu | — | — | CH₃ | CH₃ | H | H | H | acac |
| 1'-363Y | Pd | 0 | 1' | | Qu | — | — | CH₃ | CH₃ | H | H | H | — — |
| 1'-364 | Pd | 1 | 1' | | Qu | — | — | H | CH₃ | H | H | H | pic |
| 1'-364X | Pd | 1 | 1' | | Qu | — | — | H | CH₃ | H | H | H | acac |
| 1'-364Y | Pd | 0 | 1' | | Qu | — | — | H | CH₃ | H | H | H | — — |
| 1'-365 | Pd | 1 | 1' | | OL | H | $^nC_4H_9$ | H | H | H | H | H | pic |
| 1'-365X | Pd | 1 | 1' | | OL | H | $^nC_4H_9$ | H | H | H | H | H | acac |
| 1'-365Y | Pd | 0 | 1' | | OL | H | $^nC_4H_9$ | H | H | H | H | H | — — |
| 1'-366 | Pd | 1 | 1' | | OL | H | $^tC_4H_9$ | H | H | H | H | H | pic |
| 1'-366X | Pd | 1 | 1' | | OL | H | $^tC_4H_9$ | H | H | H | H | H | acac |
| 1'-366Y | Pd | 0 | 1' | | OL | H | $^tC_4H_9$ | H | H | H | H | H | — — |
| 1'-367 | Pd | 1 | 1' | | OL | CH₃ | $^nC_4H_9$ | H | H | H | H | H | pic |
| 1'-367X | Pd | 1 | 1' | | OL | CH₃ | $^nC_4H_9$ | H | H | H | H | H | acac |
| 1'-367Y | Pd | 0 | 1' | | OL | CH₃ | $^nC_4H_9$ | H | H | H | H | H | — — |
| 1'-368 | Pd | 1 | 1' | | OL | CH₃ | $^tC_4H_9$ | H | H | H | H | H | pic |
| 1'-368X | Pd | 1 | 1' | | OL | CH₃ | $^tC_4H_9$ | H | H | H | H | H | acac |
| 1'-368Y | Pd | 0 | 1' | | OL | CH₃ | $^tC_4H_9$ | H | H | H | H | H | — — |
| 1'-369 | Pd | 1 | 1' | | OL | H | H | H | H | H | H | H | pic |
| 1'-369X | Pd | 1 | 1' | | OL | H | H | H | H | H | H | H | acac |
| 1'-369Y | Pd | 0 | 1' | | OL | H | H | H | H | H | H | H | — — |
| 1'-370 | Pd | 1 | 1' | | OL | H | $^nC_4H_9$ | CH₃ | H | H | H | H | pic |
| 1'-370X | Pd | 1 | 1' | | OL | H | $^nC_4H_9$ | CH₃ | H | H | H | H | acac |
| 1'-370Y | Pd | 0 | 1' | | OL | H | $^nC_4H_9$ | CH₃ | H | H | H | H | — — |
| 1'-371 | Pd | 1 | 1' | | OL | H | $^tC_4H_9$ | CH₃ | H | H | H | H | pic |
| 1'-371X | Pd | 1 | 1' | | OL | H | $^tC_4H_9$ | CH₃ | H | H | H | H | acac |
| 1'-371Y | Pd | 0 | 1' | | OL | H | $^tC_4H_9$ | CH₃ | H | H | H | H | — — |
| 1'-372 | Pd | 1 | 1' | | OL | —CH₂CH₂CH₂— | | H | H | H | H | H | pic |
| 1'-372X | Pd | 1 | 1' | | OL | —CH₂CH₂CH₂— | | H | H | H | H | H | acac |
| 1'-372Y | Pd | 0 | 1' | | OL | —CH₂CH₂CH₂— | | H | H | H | H | H | — — |

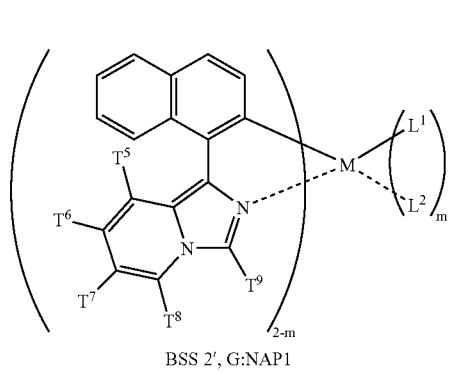

BSS 2', G:NAP1

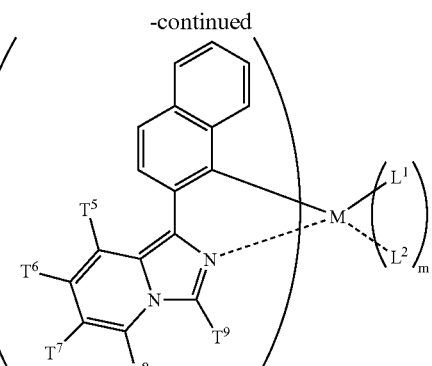

-continued

BSS 2', G:NAP3

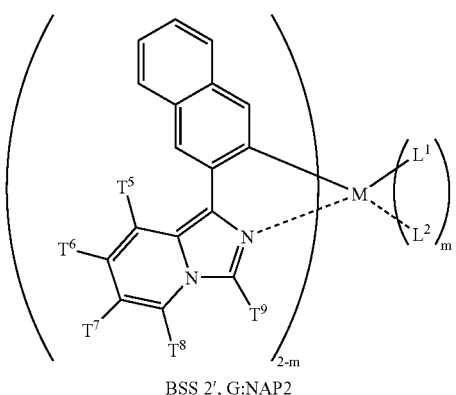

BSS 2', G:NAP2

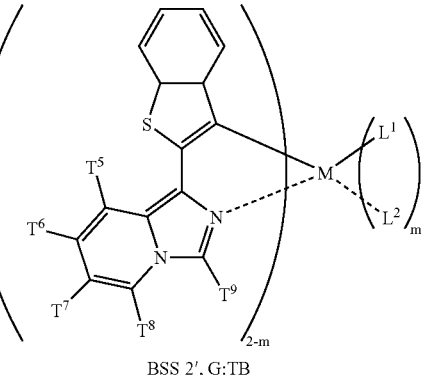

BSS 2', G:TB

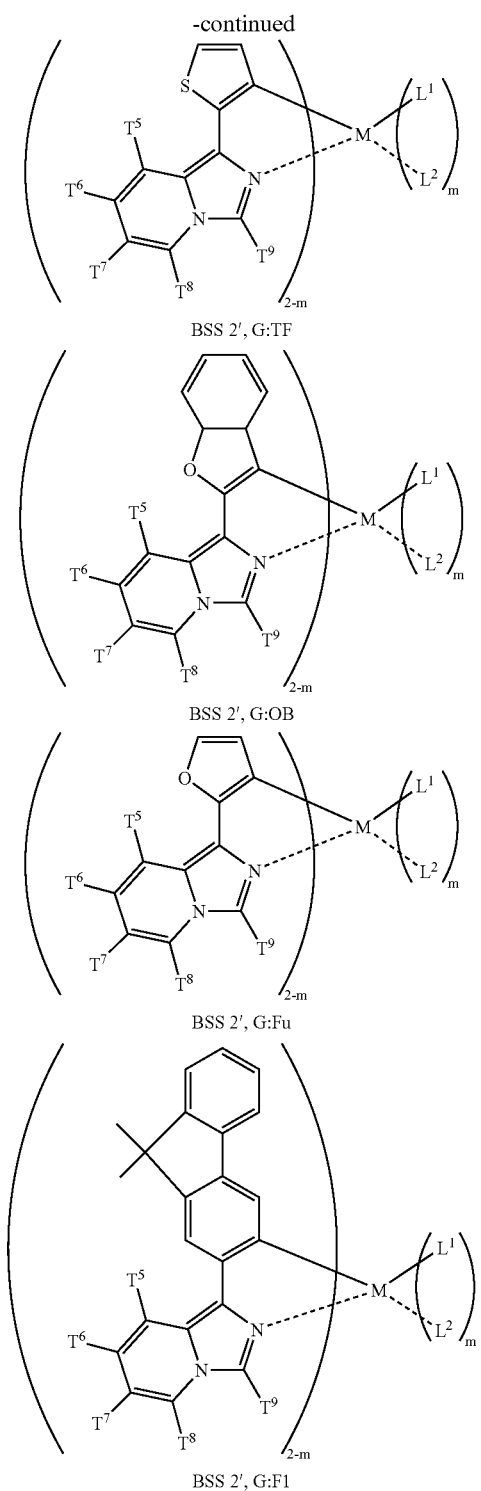
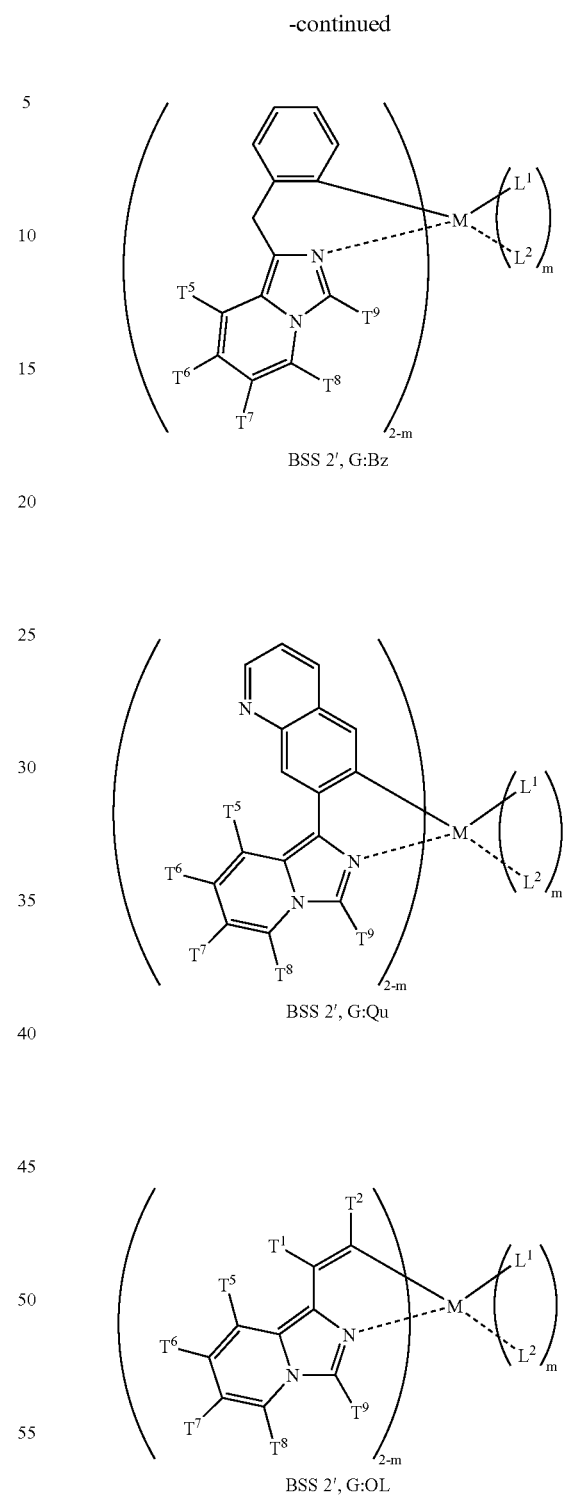
TABLE 51
| No. | M | m | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 2'-305 | Pd | 1 | 2' | | Nap1 | — | — | H | H | H | H | H | pic | |
| 2'-305X | Pd | 1 | 2' | | Nap1 | — | — | H | H | H | H | H | acac | |
| 2'-305Y | Pd | 0 | 2' | | Nap1 | — | — | H | H | H | H | H | — | — |

TABLE 51-continued

| No. | M | m | BSS | SS G | T$^1$ | T$^2$ | T$^5$ | T$^6$ | T$^7$ | T$^8$ | T$^9$ | L$^1$ L$^2$ |
|---|---|---|---|---|---|---|---|---|---|---|---|---|
| 2'-306 | Pd | 1 | 2' | Nap1 | — | — | $^tC_4H_9$ | H | H | H | H | pic |
| 2'-306X | Pd | 1 | 2' | Nap1 | — | — | $^tC_4H_9$ | H | H | H | H | acac |
| 2'-306Y | Pd | 0 | 2' | Nap1 | — | — | $^tC_4H_9$ | H | H | H | H | — — |
| 2'-307 | Pd | 1 | 2' | Nap1 | — | — | CH$_3$ | H | H | H | H | pic |
| 2'-307X | Pd | 1 | 2' | Nap1 | — | — | CH$_3$ | H | H | H | H | acac |
| 2'-307Y | Pd | 0 | 2' | Nap1 | — | — | CH$_3$ | H | H | H | H | — — |
| 2'-308 | Pd | 1 | 2' | Nap1 | — | — | $^tC_4H_9$ | H | H | CH$_3$ | H | pic |
| 2'-308X | Pd | 1 | 2' | Nap1 | — | — | $^tC_4H_9$ | H | H | CH$_3$ | H | acac |
| 2'-308Y | Pd | 0 | 2' | Nap1 | — | — | $^tC_4H_9$ | H | H | CH$_3$ | H | — — |
| 2'-309 | Pd | 1 | 2' | Nap1 | — | — | CH$_3$ | H | H | CH$_3$ | H | pic |
| 2'-309X | Pd | 1 | 2' | Nap1 | — | — | CH$_3$ | H | H | CH$_3$ | H | acac |
| 2'-309Y | Pd | 0 | 2' | Nap1 | — | — | CH$_3$ | H | H | CH$_3$ | H | — — |
| 2'-310 | Pd | 1 | 2' | Nap1 | — | — | H | H | H | CH$_3$ | H | pic |
| 2'-310X | Pd | 1 | 2' | Nap1 | — | — | H | H | H | CH$_3$ | H | acac |
| 2'-310Y | Pd | 0 | 2' | Nap1 | — | — | H | H | H | CH$_3$ | H | — — |
| 2'-311 | Pd | 1 | 2' | Nap2 | — | — | H | H | H | H | H | pic |
| 2'-311X | Pd | 1 | 2' | Nap2 | — | — | H | H | H | H | H | acac |
| 2'-311Y | Pd | 0 | 2' | Nap2 | — | — | H | H | H | H | H | — — |
| 2'-312 | Pd | 1 | 2' | Nap2 | — | — | $^tC_4H_9$ | H | H | H | H | pic |
| 2'-312X | Pd | 1 | 2' | Nap2 | — | — | $^tC_4H_9$ | H | H | H | H | acac |
| 2'-312Y | Pd | 0 | 2' | Nap2 | — | — | $^tC_4H_9$ | H | H | H | H | — — |
| 2'-313 | Pd | 1 | 2' | Nap2 | — | — | CH$_3$ | H | H | H | H | pic |
| 2'-313X | Pd | 1 | 2' | Nap2 | — | — | CH$_3$ | H | H | H | H | acac |
| 2'-313Y | Pd | 0 | 2' | Nap2 | — | — | CH$_3$ | H | H | H | H | — — |
| 2'-314 | Pd | 1 | 2' | Nap2 | — | — | $^tC_4H_9$ | H | H | CH$_3$ | H | pic |
| 2'-314X | Pd | 1 | 2' | Nap2 | — | — | $^tC_4H_9$ | H | H | CH$_3$ | H | acac |
| 2'-314Y | Pd | 0 | 2' | Nap2 | — | — | $^tC_4H_9$ | H | H | CH$_3$ | H | — — |
| 2'-315 | Pd | 1 | 2' | Nap2 | — | — | CH$_3$ | H | H | CH$_3$ | H | pic |
| 2'-315X | Pd | 1 | 2' | Nap2 | — | — | CH$_3$ | H | H | CH$_3$ | H | acac |
| 2'-315Y | Pd | 0 | 2' | Nap2 | — | — | CH$_3$ | H | H | CH$_3$ | H | — — |
| 2'-316 | Pd | 1 | 2' | Nap2 | — | — | H | H | H | CH$_3$ | H | pic |
| 2'-316X | Pd | 1 | 2' | Nap2 | — | — | H | H | H | CH$_3$ | H | acac |
| 2'-316Y | Pd | 0 | 2' | Nap2 | — | — | H | H | H | CH$_3$ | H | — — |
| 2'-317 | Pd | 1 | 2' | Nap3 | — | — | H | H | H | H | H | pic |
| 2'-317X | Pd | 1 | 2' | Nap3 | — | — | H | H | H | H | H | acac |
| 2'-317Y | Pd | 0 | 2' | Nap3 | — | — | H | H | H | H | H | — — |
| 2'-318 | Pd | 1 | 2' | Nap3 | — | — | $^tC_4H_9$ | H | H | H | H | pic |
| 2'-318X | Pd | 1 | 2' | Nap3 | — | — | $^tC_4H_9$ | H | H | H | H | acac |
| 2'-318Y | Pd | 0 | 2' | Nap3 | — | — | $^tC_4H_9$ | H | H | H | H | — — |
| 2'-319 | Pd | 1 | 2' | Nap3 | — | — | CH$_3$ | H | H | H | H | pic |
| 2'-319X | Pd | 1 | 2' | Nap3 | — | — | CH$_3$ | H | H | H | H | acac |
| 2'-319Y | Pd | 0 | 2' | Nap3 | — | — | CH$_3$ | H | H | H | H | — — |
| 2'-320 | Pd | 1 | 2' | Nap3 | — | — | $^tC_4H_9$ | H | H | CH$_3$ | H | pic |
| 2'-320X | Pd | 1 | 2' | Nap3 | — | — | $^tC_4H_9$ | H | H | CH$_3$ | H | acac |
| 2'-320Y | Pd | 0 | 2' | Nap3 | — | — | $^tC_4H_9$ | H | H | CH$_3$ | H | — — |
| 2'-321 | Pd | 1 | 2' | Nap3 | — | — | CH$_3$ | H | H | CH$_3$ | H | pic |
| 2'-321X | Pd | 1 | 2' | Nap3 | — | — | CH$_3$ | H | H | CH$_3$ | H | acac |
| 2'-321Y | Pd | 0 | 2' | Nap3 | — | — | CH$_3$ | H | H | CH$_3$ | H | — — |
| 2'-322 | Pd | 1 | 2' | Nap3 | — | — | H | H | H | CH$_3$ | H | pic |
| 2'-322X | Pd | 1 | 2' | Nap3 | — | — | H | H | H | CH$_3$ | H | acac |
| 2'-322Y | Pd | 0 | 2' | Nap3 | — | — | H | H | H | CH$_3$ | H | — — |
| 2'-323 | Pd | 1 | 2' | TB | — | — | H | H | H | H | H | pic |
| 2'-323X | Pd | 1 | 2' | TB | — | — | H | H | H | H | H | acac |
| 2'-323Y | Pd | 0 | 2' | TB | — | — | H | H | H | H | H | — — |
| 2'-324 | Pd | 1 | 2' | TB | — | — | $^tC_4H_9$ | H | H | H | H | pic |
| 2'-324X | Pd | 1 | 2' | TB | — | — | $^tC_4H_9$ | H | H | H | H | acac |
| 2'-324Y | Pd | 0 | 2' | TB | — | — | $^tC_4H_9$ | H | H | H | H | — — |
| 2'-325 | Pd | 1 | 2' | TB | — | — | CH$_3$ | H | H | H | H | pic |
| 2'-325X | Pd | 1 | 2' | TB | — | — | CH$_3$ | H | H | H | H | acac |
| 2'-325Y | Pd | 0 | 2' | TB | — | — | CH$_3$ | H | H | H | H | — — |
| 2'-326 | Pd | 1 | 2' | TB | — | — | $^tC_4H_9$ | H | H | CH$_3$ | H | pic |
| 2'-326X | Pd | 1 | 2' | TB | — | — | $^tC_4H_9$ | H | H | CH$_3$ | H | acac |
| 2'-326Y | Pd | 0 | 2' | TB | — | — | $^tC_4H_9$ | H | H | CH$_3$ | H | — — |
| 2'-327 | Pd | 1 | 2' | TB | — | — | CH$_3$ | H | H | CH$_3$ | H | pic |
| 2'-327X | Pd | 1 | 2' | TB | — | — | CH$_3$ | H | H | CH$_3$ | H | acac |
| 2'-327Y | Pd | 0 | 2' | TB | — | — | CH$_3$ | H | H | CH$_3$ | H | — — |
| 2'-328 | Pd | 1 | 2' | TB | — | — | H | H | H | CH$_3$ | H | pic |
| 2'-328X | Pd | 1 | 2' | TB | — | — | H | H | H | CH$_3$ | H | acac |
| 2'-328Y | Pd | 0 | 2' | TB | — | — | H | H | H | CH$_3$ | H | — — |
| 2'-329 | Pd | 1 | 2' | TF | — | — | H | H | H | H | H | pic |
| 2'-329X | Pd | 1 | 2' | TF | — | — | H | H | H | H | H | acac |
| 2'-329Y | Pd | 0 | 2' | TF | — | — | H | H | H | H | H | — — |
| 2'-330 | Pd | 1 | 2' | TF | — | — | $^tC_4H_9$ | H | H | H | H | pic |
| 2'-330X | Pd | 1 | 2' | TF | — | — | $^tC_4H_9$ | H | H | H | H | acac |
| 2'-330Y | Pd | 0 | 2' | TF | — | — | $^tC_4H_9$ | H | H | H | H | — — |
| 2'-331 | Pd | 1 | 2' | TF | — | — | CH$_3$ | H | H | H | H | pic |
| 2'-331X | Pd | 1 | 2' | TF | — | — | CH$_3$ | H | H | H | H | acac |

TABLE 51-continued

| No. | M | m | BSS | SS | G | T¹ | T² | T⁵ | T⁶ | T⁷ | T⁸ | T⁹ | L¹ | L² |
|---|---|---|---|---|---|---|---|---|---|---|---|---|---|---|
| 2'-331Y | Pd | 0 | 2' | TF | — | — | — | CH₃ | H | H | H | H | — | — |
| 2'-332 | Pd | 1 | 2' | TF | — | — | — | ᵗC₄H₉ | H | H | CH₃ | H | pic | |
| 2'-332X | Pd | 1 | 2' | TF | — | — | — | ᵗC₄H₉ | H | H | CH₃ | H | acac | |
| 2'-332Y | Pd | 0 | 2' | TF | — | — | — | ᵗC₄H₉ | H | H | CH₃ | H | — | — |
| 2'-333 | Pd | 1 | 2' | TF | — | — | — | CH₃ | H | H | CH₃ | H | pic | |
| 2'-333X | Pd | 1 | 2' | TF | — | — | — | CH₃ | H | H | CH₃ | H | acac | |
| 2'-333Y | Pd | 0 | 2' | TF | — | — | — | CH₃ | H | H | CH₃ | H | — | — |
| 2'-334 | Pd | 1 | 2' | TF | — | — | — | H | H | H | CH₃ | H | pic | |
| 2'-334X | Pd | 1 | 2' | TF | — | — | — | H | H | H | CH₃ | H | acac | |
| 2'-334Y | Pd | 0 | 2' | TF | — | — | — | H | H | H | CH₃ | H | — | — |
| 2'-335 | Pd | 1 | 2' | OB | — | — | — | H | H | H | H | H | pic | |
| 2'-335X | Pd | 1 | 2' | OB | — | — | — | H | H | H | H | H | acac | |
| 2'-335Y | Pd | 0 | 2' | OB | — | — | — | H | H | H | H | H | — | — |
| 2'-336 | Pd | 1 | 2' | OB | — | — | — | ᵗC₄H₉ | H | H | H | H | pic | |
| 2'-336X | Pd | 1 | 2' | OB | — | — | — | ᵗC₄H₉ | H | H | H | H | acac | |
| 2'-336Y | Pd | 0 | 2' | OB | — | — | — | ᵗC₄H₉ | H | H | H | H | — | — |
| 2'-337 | Pd | 1 | 2' | OB | — | — | — | CH₃ | H | H | H | H | pic | |
| 2'-337X | Pd | 1 | 2' | OB | — | — | — | CH₃ | H | H | H | H | acac | |
| 2'-337Y | Pd | 0 | 2' | OB | — | — | — | CH₃ | H | H | H | H | — | — |
| 2'-338 | Pd | 1 | 2' | OB | — | — | — | ᵗC₄H₉ | H | H | CH₃ | H | pic | |
| 2'-338X | Pd | 1 | 2' | OB | — | — | — | ᵗC₄H₉ | H | H | CH₃ | H | acac | |
| 2'-338Y | Pd | 0 | 2' | OB | — | — | — | ᵗC₄H₉ | H | H | CH₃ | H | — | — |
| 2'-339 | Pd | 1 | 2' | OB | — | — | — | CH₃ | H | H | CH₃ | H | pic | |
| 2'-339X | Pd | 1 | 2' | OB | — | — | — | CH₃ | H | H | CH₃ | H | acac | |
| 2'-339Y | Pd | 0 | 2' | OB | — | — | — | CH₃ | H | H | CH₃ | H | — | — |
| 2'-340 | Pd | 1 | 2' | OB | — | — | — | H | H | H | CH₃ | H | pic | |
| 2'-340X | Pd | 1 | 2' | OB | — | — | — | H | H | H | CH₃ | H | acac | |
| 2'-340Y | Pd | 0 | 2' | OB | — | — | — | H | H | H | CH₃ | H | — | — |
| 2'-341 | Pd | 1 | 2' | Fu | — | — | — | H | H | H | H | H | pic | |
| 2'-341X | Pd | 1 | 2' | Fu | — | — | — | H | H | H | H | H | acac | |
| 2'-341Y | Pd | 0 | 2' | Fu | — | — | — | H | H | H | H | H | — | — |
| 2'-342 | Pd | 1 | 2' | Fu | — | — | — | ᵗC₄H₉ | H | H | H | H | pic | |
| 2'-342X | Pd | 1 | 2' | Fu | — | — | — | ᵗC₄H₉ | H | H | H | H | acac | |
| 2'-342Y | Pd | 0 | 2' | Fu | — | — | — | ᵗC₄H₉ | H | H | H | H | — | — |
| 2'-343 | Pd | 1 | 2' | Fu | — | — | — | CH₃ | H | H | H | H | pic | |
| 2'-343X | Pd | 1 | 2' | Fu | — | — | — | CH₃ | H | H | H | H | acac | |
| 2'-343Y | Pd | 0 | 2' | Fu | — | — | — | CH₃ | H | H | H | H | — | — |
| 2'-344 | Pd | 1 | 2' | Fu | — | — | — | ᵗC₄H₉ | H | H | CH₃ | H | pic | |
| 2'-344X | Pd | 1 | 2' | Fu | — | — | — | ᵗC₄H₉ | H | H | CH₃ | H | acac | |
| 2'-344Y | Pd | 0 | 2' | Fu | — | — | — | ᵗC₄H₉ | H | H | CH₃ | H | — | — |
| 2'-345 | Pd | 1 | 2' | Fu | — | — | — | CH₃ | H | H | CH₃ | H | pic | |
| 2'-345X | Pd | 1 | 2' | Fu | — | — | — | CH₃ | H | H | CH₃ | H | acac | |
| 2'-345Y | Pd | 0 | 2' | Fu | — | — | — | CH₃ | H | H | CH₃ | H | — | — |
| 2'-346 | Pd | 1 | 2' | Fu | — | — | — | H | H | H | CH₃ | H | pic | |
| 2'-346X | Pd | 1 | 2' | Fu | — | — | — | H | H | H | CH₃ | H | acac | |
| 2'-346Y | Pd | 0 | 2' | Fu | — | — | — | H | H | H | CH₃ | H | — | — |
| 2'-347 | Pd | 1 | 2' | Fl | — | — | — | H | H | H | H | H | pic | |
| 2'-347X | Pd | 1 | 2' | Fl | — | — | — | H | H | H | H | H | acac | |
| 2'-347Y | Pd | 0 | 2' | Fl | — | — | — | H | H | H | H | H | — | — |
| 2'-348 | Pd | 1 | 2' | Fl | — | — | — | ᵗC₄H₉ | H | H | H | H | pic | |
| 2'-348X | Pd | 1 | 2' | Fl | — | — | — | ᵗC₄H₉ | H | H | H | H | acac | |
| 2'-348Y | Pd | 0 | 2' | Fl | — | — | — | ᵗC₄H₉ | H | H | H | H | — | — |
| 2'-349 | Pd | 1 | 2' | Fl | — | — | — | CH₃ | H | H | H | H | pic | |
| 2'-349X | Pd | 1 | 2' | Fl | — | — | — | CH₃ | H | H | H | H | acac | |
| 2'-349Y | Pd | 0 | 2' | Fl | — | — | — | CH₃ | H | H | H | H | — | — |
| 2'-350 | Pd | 1 | 2' | Fl | — | — | — | ᵗC₄H₉ | H | H | CH₃ | H | pic | |
| 2'-350X | Pd | 1 | 2' | Fl | — | — | — | ᵗC₄H₉ | H | H | CH₃ | H | acac | |
| 2'-350Y | Pd | 0 | 2' | Fl | — | — | — | ᵗC₄H₉ | H | H | CH₃ | H | — | — |
| 2'-351 | Pd | 1 | 2' | Fl | — | — | — | CH₃ | H | H | CH₃ | H | pic | |
| 2'-351X | Pd | 1 | 2' | Fl | — | — | — | CH₃ | H | H | CH₃ | H | acac | |
| 2'-351Y | Pd | 0 | 2' | Fl | — | — | — | CH₃ | H | H | CH₃ | H | — | — |
| 2'-352 | Pd | 1 | 2' | Fl | — | — | — | H | H | H | CH₃ | H | pic | |
| 2'-352X | Pd | 1 | 2' | Fl | — | — | — | H | H | H | CH₃ | H | acac | |
| 2'-352Y | Pd | 0 | 2' | Fl | — | — | — | H | H | H | CH₃ | H | — | — |
| 2'-353 | Pd | 1 | 2' | Bz | — | — | — | H | H | H | H | H | pic | |
| 2'-353X | Pd | 1 | 2' | Bz | — | — | — | H | H | H | H | H | acac | |
| 2'-353Y | Pd | 0 | 2' | Bz | — | — | — | H | H | H | H | H | — | — |
| 2'-354 | Pd | 1 | 2' | Bz | — | — | — | ᵗC₄H₉ | H | H | H | H | pic | |
| 2'-354X | Pd | 1 | 2' | Bz | — | — | — | ᵗC₄H₉ | H | H | H | H | acac | |
| 2'-354Y | Pd | 0 | 2' | Bz | — | — | — | ᵗC₄H₉ | H | H | H | H | — | — |
| 2'-355 | Pd | 1 | 2' | Bz | — | — | — | CH₃ | H | H | H | H | pic | |
| 2'-355X | Pd | 1 | 2' | Bz | — | — | — | CH₃ | H | H | H | H | acac | |
| 2'-355Y | Pd | 0 | 2' | Bz | — | — | — | CH₃ | H | H | H | H | — | — |
| 2'-356 | Pd | 1 | 2' | Bz | — | — | — | ᵗC₄H₉ | H | H | CH₃ | H | pic | |
| 2'-356X | Pd | 1 | 2' | Bz | — | — | — | ᵗC₄H₉ | H | H | CH₃ | H | acac | |
| 2'-356Y | Pd | 0 | 2' | Bz | — | — | — | ᵗC₄H₉ | H | H | CH₃ | H | — | — |
| 2'-357 | Pd | 1 | 2' | Bz | — | — | — | CH₃ | H | H | CH₃ | H | pic | |

TABLE 51-continued

| No. | M | m | BSS | SS G | T¹ | T² | T⁵ | T⁶ | T⁷ | T⁸ | T⁹ | L¹ | L² |
|---|---|---|---|---|---|---|---|---|---|---|---|---|---|
| 2'-357X | Pd | 1 | 2' | Bz | — | — | CH₃ | H | H | CH₃ | H | acac | |
| 2'-357Y | Pd | 0 | 2' | Bz | — | — | CH₃ | H | H | CH₃ | H | — | — |
| 2'-358 | Pd | 1 | 2' | Bz | — | — | H | H | H | CH₃ | H | pic | |
| 2'-358X | Pd | 1 | 2' | Bz | — | — | H | H | H | CH₃ | H | acac | |
| 2'-358Y | Pd | 0 | 2' | Bz | — | — | H | H | H | CH₃ | H | — | — |
| 2'-359 | Pd | 1 | 2' | Qu | — | — | H | H | H | H | H | pic | |
| 2'-359X | Pd | 1 | 2' | Qu | — | — | H | H | H | H | H | acac | |
| 2'-359Y | Pd | 0 | 2' | Qu | — | — | H | H | H | H | H | — | — |
| 2'-360 | Pd | 1 | 2' | Qu | — | — | ᵗC₄H₉ | H | H | H | H | pic | |
| 2'-360X | Pd | 1 | 2' | Qu | — | — | ᵗC₄H₉ | H | H | H | H | acac | |
| 2'-360Y | Pd | 0 | 2' | Qu | — | — | ᵗC₄H₉ | H | H | H | H | — | — |
| 2'-361 | Pd | 1 | 2' | Qu | — | — | CH₃ | H | H | H | H | pic | |
| 2'-361X | Pd | 1 | 2' | Qu | — | — | CH₃ | H | H | H | H | acac | |
| 2'-361Y | Pd | 0 | 2' | Qu | — | — | CH₃ | H | H | H | H | — | — |
| 2'-362 | Pd | 1 | 2' | Qu | — | — | ᵗC₄H₉ | H | H | CH₃ | H | pic | |
| 2'-362X | Pd | 1 | 2' | Qu | — | — | ᵗC₄H₉ | H | H | CH₃ | H | acac | |
| 2'-362Y | Pd | 0 | 2' | Qu | — | — | ᵗC₄H₉ | H | H | CH₃ | H | — | — |
| 2'-363 | Pd | 1 | 2' | Qu | — | — | CH₃ | H | H | CH₃ | H | pic | |
| 2'-363X | Pd | 1 | 2' | Qu | — | — | CH₃ | H | H | CH₃ | H | acac | |
| 2'-363Y | Pd | 0 | 2' | Qu | — | — | CH₃ | H | H | CH₃ | H | — | — |
| 2'-364 | Pd | 1 | 2' | Qu | — | — | H | H | H | CH₃ | H | pic | |
| 2'-364X | Pd | 1 | 2' | Qu | — | — | H | H | H | CH₃ | H | acac | |
| 2'-364Y | Pd | 0 | 2' | Qu | — | — | H | H | H | CH₃ | H | — | — |
| 2'-365 | Pd | 1 | 2' | OL | H | ⁿC₄H₉ | H | H | H | H | H | pic | |
| 2'-365X | Pd | 1 | 2' | OL | H | ⁿC₄H₉ | H | H | H | H | H | acac | |
| 2'-365Y | Pd | 0 | 2' | OL | H | ⁿC₄H₉ | H | H | H | H | H | — | — |
| 2'-366 | Pd | 1 | 2' | OL | H | ᵗC₄H₉ | H | H | H | H | H | pic | |
| 2'-366X | Pd | 1 | 2' | OL | H | ᵗC₄H₉ | H | H | H | H | H | acac | |
| 2'-366Y | Pd | 0 | 2' | OL | H | ᵗC₄H₉ | H | H | H | H | H | — | — |
| 2'-367 | Pd | 1 | 2' | OL | CH₃ | ⁿC₄H₉ | H | H | H | H | H | pic | |
| 2'-367X | Pd | 1 | 2' | OL | CH₃ | ⁿC₄H₉ | H | H | H | H | H | acac | |
| 2'-367Y | Pd | 0 | 2' | OL | CH₃ | ⁿC₄H₉ | H | H | H | H | H | — | — |
| 2'-368 | Pd | 1 | 2' | OL | CH₃ | ᵗC₄H₉ | H | H | H | H | H | pic | |
| 2'-368X | Pd | 1 | 2' | OL | CH₃ | ᵗC₄H₉ | H | H | H | H | H | acac | |
| 2'-368Y | Pd | 0 | 2' | OL | CH₃ | ᵗC₄H₉ | H | H | H | H | H | — | — |
| 2'-369 | Pd | 1 | 2' | OL | H | H | H | H | H | H | H | pic | |
| 2'-369X | Pd | 1 | 2' | OL | H | H | H | H | H | H | H | acac | |
| 2'-369Y | Pd | 0 | 2' | OL | H | H | H | H | H | H | H | — | — |
| 2'-370 | Pd | 1 | 2' | OL | H | ⁿC₄H₉ | CH₃ | H | H | H | H | pic | |
| 2'-370X | Pd | 1 | 2' | OL | H | ⁿC₄H₉ | CH₃ | H | H | H | H | acac | |
| 2'-370Y | Pd | 0 | 2' | OL | H | ⁿC₄H₉ | CH₃ | H | H | H | H | — | — |
| 2'-371 | Pd | 1 | 2' | OL | H | ᵗC₄H₉ | CH₃ | H | H | H | H | pic | |
| 2'-371X | Pd | 1 | 2' | OL | H | ᵗC₄H₉ | CH₃ | H | H | H | H | acac | |
| 2'-371Y | Pd | 0 | 2' | OL | H | ᵗC₄H₉ | CH₃ | H | H | H | H | — | — |
| 2'-372 | Pd | 1 | 2' | OL | —CH₂CH₂CH₂— | | H | H | H | H | H | pic | |
| 2'-372X | Pd | 1 | 2' | OL | —CH₂CH₂CH₂— | | H | H | H | H | H | acac | |
| 2'-372Y | Pd | 0 | 2' | OL | —CH₂CH₂CH₂— | | H | H | H | H | H | — | — |

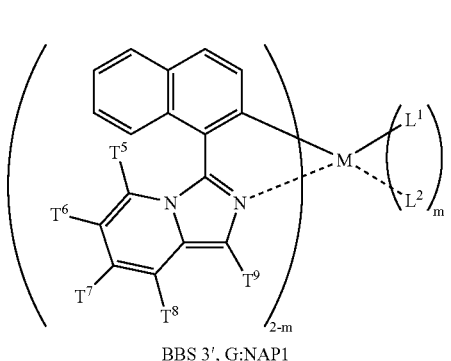

BBS 3', G:NAP1

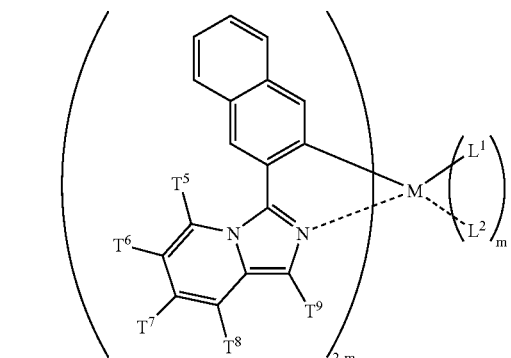

BBS 3', G:NAP2

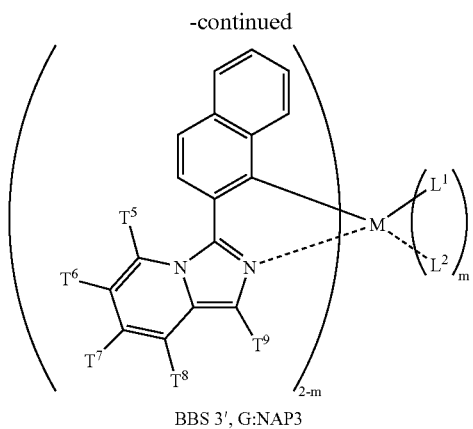
BBS 3′, G:NAP3
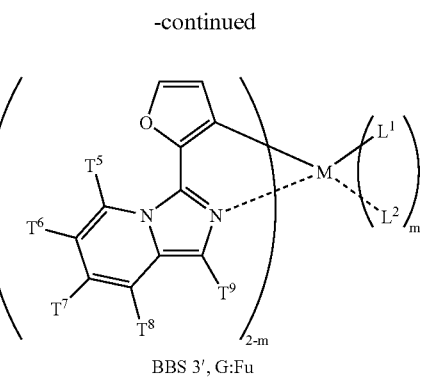
BBS 3′, G:Fu
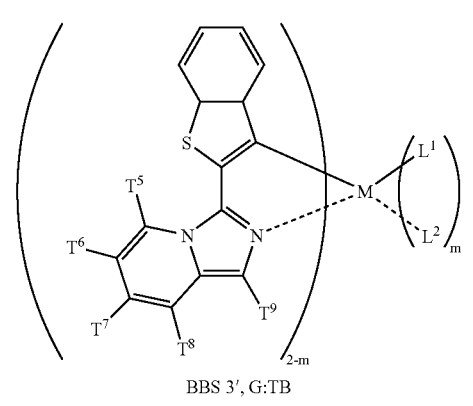
BBS 3′, G:TB
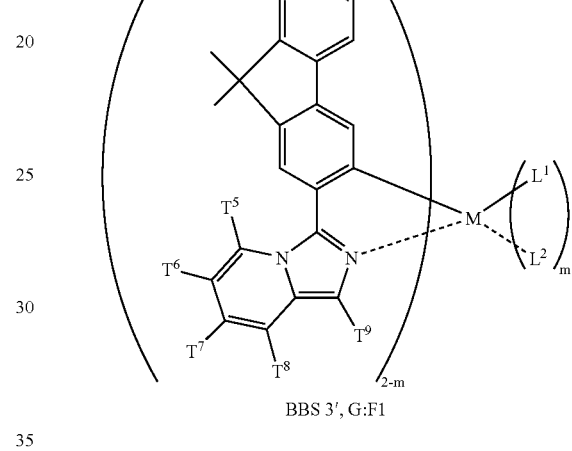
BBS 3′, G:Fl
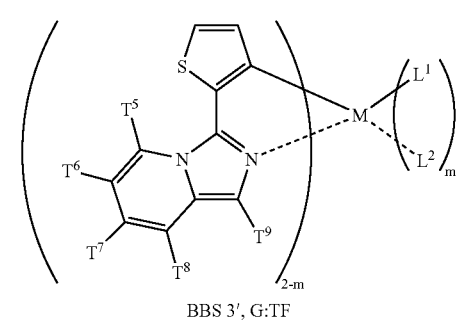
BBS 3′, G:TF
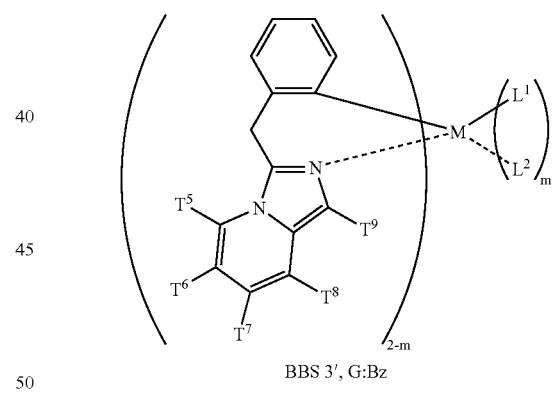
BBS 3′, G:Bz
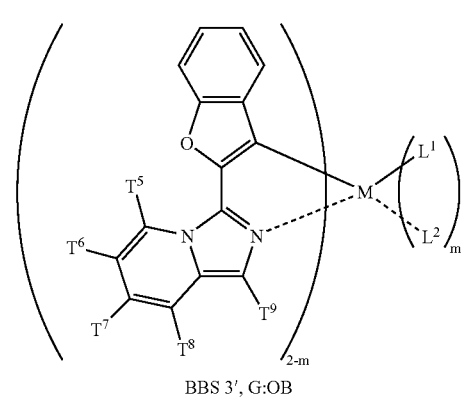
BBS 3′, G:OB
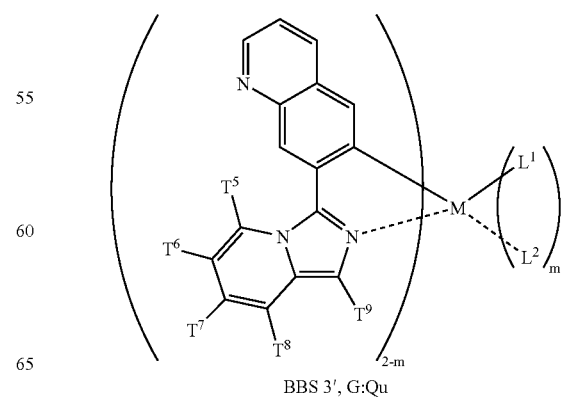
BBS 3′, G:Qu -continued

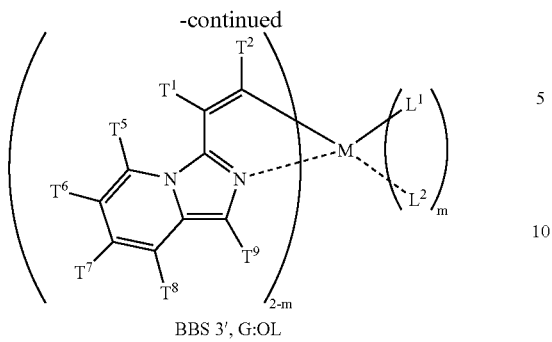

BBS 3', G:OL

TABLE 52

| No. | M | m | BSS | SS G | T¹ | T² | T⁵ | T⁶ | T⁷ | T⁸ | T⁹ | L¹ L² |
|---|---|---|---|---|---|---|---|---|---|---|---|---|
| 3'-271 | Pd | 1 | 3' | Nap1 | — | — | H | H | H | H | H | pic |
| 3'-271X | Pd | 1 | 3' | Nap1 | — | — | H | H | H | H | H | acac |
| 3'-271Y | Pd | 0 | 3' | Nap1 | — | — | H | H | H | H | H | — — |
| 3'-272 | Pd | 1 | 3' | Nap1 | — | — | $^tC_4H_9$ | H | H | H | H | pic |
| 3'-272X | Pd | 1 | 3' | Nap1 | — | — | $^tC_4H_9$ | H | H | H | H | acac |
| 3'-272Y | Pd | 0 | 3' | Nap1 | — | — | $^tC_4H_9$ | H | H | H | H | — — |
| 3'-273 | Pd | 1 | 3' | Nap1 | — | — | $CH_3$ | H | H | H | H | pic |
| 3'-273X | Pd | 1 | 3' | Nap1 | — | — | $CH_3$ | H | H | H | H | acac |
| 3'-273Y | Pd | 0 | 3' | Nap1 | — | — | $CH_3$ | H | H | H | H | — — |
| 3'-274 | Pd | 1 | 3' | Nap2 | — | — | H | H | H | H | H | pic |
| 3'-274X | Pd | 1 | 3' | Nap2 | — | — | H | H | H | H | H | acac |
| 3'-274Y | Pd | 0 | 3' | Nap2 | — | — | H | H | H | H | H | — — |
| 3'-275 | Pd | 1 | 3' | Nap2 | — | — | $^tC_4H_9$ | H | H | H | H | pic |
| 3'-275X | Pd | 1 | 3' | Nap2 | — | — | $^tC_4H_9$ | H | H | H | H | acac |
| 3'-275Y | Pd | 0 | 3' | Nap2 | — | — | $^tC_4H_9$ | H | H | H | H | — — |
| 3'-276 | Pd | 1 | 3' | Nap2 | — | — | $CH_3$ | H | H | H | H | pic |
| 3'-276X | Pd | 1 | 3' | Nap2 | — | — | $CH_3$ | H | H | H | H | acac |
| 3'-276Y | Pd | 0 | 3' | Nap2 | — | — | $CH_3$ | H | H | H | H | — — |
| 3'-277 | Pd | 1 | 3' | Nap3 | — | — | H | H | H | H | H | pic |
| 3'-277X | Pd | 1 | 3' | Nap3 | — | — | H | H | H | H | H | acac |
| 3'-277Y | Pd | 0 | 3' | Nap3 | — | — | H | H | H | H | H | — — |
| 3'-278 | Pd | 1 | 3' | Nap3 | — | — | $^tC_4H_9$ | H | H | H | H | pic |
| 3'-278X | Pd | 1 | 3' | Nap3 | — | — | $^tC_4H_9$ | H | H | H | H | acac |
| 3'-278Y | Pd | 0 | 3' | Nap3 | — | — | $^tC_4H_9$ | H | H | H | H | — — |
| 3'-279 | Pd | 1 | 3' | Nap3 | — | — | $CH_3$ | H | H | H | H | pic |
| 3'-279X | Pd | 1 | 3' | Nap3 | — | — | $CH_3$ | H | H | H | H | acac |
| 3'-279Y | Pd | 0 | 3' | Nap3 | — | — | $CH_3$ | H | H | H | H | — — |
| 3'-280 | Pd | 1 | 3' | TB | — | — | H | H | H | H | H | pic |
| 3'-280X | Pd | 1 | 3' | TB | — | — | H | H | H | H | H | acac |
| 3'-280Y | Pd | 0 | 3' | TB | — | — | H | H | H | H | H | — — |
| 3'-281 | Pd | 1 | 3' | TB | — | — | $^tC_4H_9$ | H | H | H | H | pic |
| 3'-281X | Pd | 1 | 3' | TB | — | — | $^tC_4H_9$ | H | H | H | H | acac |
| 3'-281Y | Pd | 0 | 3' | TB | — | — | $^tC_4H_9$ | H | H | H | H | — — |
| 3'-282 | Pd | 1 | 3' | TB | — | — | $CH_3$ | H | H | H | H | pic |
| 3'-282X | Pd | 1 | 3' | TB | — | — | $CH_3$ | H | H | H | H | acac |
| 3'-282Y | Pd | 0 | 3' | TB | — | — | $CH_3$ | H | H | H | H | — — |
| 3'-283 | Pd | 1 | 3' | TF | — | — | H | H | H | H | H | pic |
| 3'-283X | Pd | 1 | 3' | TF | — | — | H | H | H | H | H | acac |
| 3'-283Y | Pd | 0 | 3' | TF | — | — | H | H | H | H | H | — — |
| 3'-284 | Pd | 1 | 3' | TF | — | — | $^tC_4H_9$ | H | H | H | H | pic |
| 3'-284X | Pd | 1 | 3' | TF | — | — | $^tC_4H_9$ | H | H | H | H | acac |
| 3'-284Y | Pd | 0 | 3' | TF | — | — | $^tC_4H_9$ | H | H | H | H | — — |
| 3'-285 | Pd | 1 | 3' | TF | — | — | $CH_3$ | H | H | H | H | pic |
| 3'-285X | Pd | 1 | 3' | TF | — | — | $CH_3$ | H | H | H | H | acac |
| 3'-285Y | Pd | 0 | 3' | TF | — | — | $CH_3$ | H | H | H | H | — — |
| 3'-286 | Pd | 1 | 3' | OB | — | — | H | H | H | H | H | pic |
| 3'-286X | Pd | 1 | 3' | OB | — | — | H | H | H | H | H | acac |
| 3'-286Y | Pd | 0 | 3' | OB | — | — | H | H | H | H | H | — — |
| 3'-287 | Pd | 1 | 3' | OB | — | — | $^tC_4H_9$ | H | H | H | H | pic |
| 3'-287X | Pd | 1 | 3' | OB | — | — | $^tC_4H_9$ | H | H | H | H | acac |
| 3'-287Y | Pd | 0 | 3' | OB | — | — | $^tC_4H_9$ | H | H | H | H | — — |
| 3'-288 | Pd | 1 | 3' | OB | — | — | $CH_3$ | H | H | H | H | pic |
| 3'-288X | Pd | 1 | 3' | OB | — | — | $CH_3$ | H | H | H | H | acac |
| 3'-288Y | Pd | 0 | 3' | OB | — | — | $CH_3$ | H | H | H | H | — — |
| 3'-289 | Pd | 1 | 3' | Fu | — | — | H | H | H | H | H | pic |
| 3'-289X | Pd | 1 | 3' | Fu | — | — | H | H | H | H | H | acac |

TABLE 52-continued

| No. | M | m | BSS | SS | G | T$^1$ | T$^2$ | T$^5$ | T$^6$ | T$^7$ | T$^8$ | T$^9$ | L$^1$ L$^2$ |
|---|---|---|---|---|---|---|---|---|---|---|---|---|---|
| 3'-289Y | Pd | 0 | 3' | | Fu | — | — | H | H | H | H | H | — — |
| 3'-290 | Pd | 1 | 3' | | Fu | — | — | $^tC_4H_9$ | H | H | H | H | pic |
| 3'-290X | Pd | 1 | 3' | | Fu | — | — | $^tC_4H_9$ | H | H | H | H | acac |
| 3'-290Y | Pd | 0 | 3' | | Fu | — | — | $^tC_4H_9$ | H | H | H | H | — — |
| 3'-291 | Pd | 1 | 3' | | Fu | — | — | $CH_3$ | H | H | H | H | pic |
| 3'-291X | Pd | 1 | 3' | | Fu | — | — | $CH_3$ | H | H | H | H | acac |
| 3'-291Y | Pd | 0 | 3' | | Fu | — | — | $CH_3$ | H | H | H | H | — — |
| 3'-292 | Pd | 1 | 3' | | Fl | — | — | H | H | H | H | H | pic |
| 3'-292X | Pd | 1 | 3' | | Fl | — | — | H | H | H | H | H | acac |
| 3'-292Y | Pd | 0 | 3' | | Fl | — | — | H | H | H | H | H | — — |
| 3'-293 | Pd | 1 | 3' | | Fl | — | — | $^tC_4H_9$ | H | H | H | H | pic |
| 3'-293X | Pd | 1 | 3' | | Fl | — | — | $^tC_4H_9$ | H | H | H | H | acac |
| 3'-293Y | Pd | 0 | 3' | | Fl | — | — | $^tC_4H_9$ | H | H | H | H | — — |
| 3'-294 | Pd | 1 | 3' | | Fl | — | — | $CH_3$ | H | H | H | H | pic |
| 3'-294X | Pd | 1 | 3' | | Fl | — | — | $CH_3$ | H | H | H | H | acac |
| 3'-294Y | Pd | 0 | 3' | | Fl | — | — | $CH_3$ | H | H | H | H | — — |
| 3'-295 | Pd | 1 | 3' | | Bz | — | — | H | H | H | H | H | pic |
| 3'-295X | Pd | 1 | 3' | | Bz | — | — | H | H | H | H | H | acac |
| 3'-295Y | Pd | 0 | 3' | | Bz | — | — | H | H | H | H | H | — — |
| 3'-296 | Pd | 1 | 3' | | Bz | — | — | $^tC_4H_9$ | H | H | H | H | pic |
| 3'-296X | Pd | 1 | 3' | | Bz | — | — | $^tC_4H_9$ | H | H | H | H | acac |
| 3'-296Y | Pd | 0 | 3' | | Bz | — | — | $^tC_4H_9$ | H | H | H | H | — — |
| 3'-297 | Pd | 1 | 3' | | Bz | — | — | $CH_3$ | H | H | H | H | pic |
| 3'-297X | Pd | 1 | 3' | | Bz | — | — | $CH_3$ | H | H | H | H | acac |
| 3'-297Y | Pd | 0 | 3' | | Bz | — | — | $CH_3$ | H | H | H | H | — — |
| 3'-298 | Pd | 1 | 3' | | Qu | — | — | H | H | H | H | H | pic |
| 3'-298X | Pd | 1 | 3' | | Qu | — | — | H | H | H | H | H | acac |
| 3'-298Y | Pd | 0 | 3' | | Qu | — | — | H | H | H | H | H | — — |
| 3'-299 | Pd | 1 | 3' | | Qu | — | — | $^tC_4H_9$ | H | H | H | H | pic |
| 3'-299X | Pd | 1 | 3' | | Qu | — | — | $^tC_4H_9$ | H | H | H | H | acac |
| 3'-299Y | Pd | 0 | 3' | | Qu | — | — | $^tC_4H_9$ | H | H | H | H | — — |
| 3'-300 | Pd | 1 | 3' | | Qu | — | — | $CH_3$ | H | H | H | H | pic |
| 3'-300X | Pd | 1 | 3' | | Qu | — | — | $CH_3$ | H | H | H | H | acac |
| 3'-300Y | Pd | 0 | 3' | | Qu | — | — | $CH_3$ | H | H | H | H | — — |
| 3'-301 | Pd | 1 | 3' | | OL | H | $^nC_4H_9$ | H | H | H | H | H | pic |
| 3'-301X | Pd | 1 | 3' | | OL | H | $^nC_4H_9$ | H | H | H | H | H | acac |
| 3'-301Y | Pd | 0 | 3' | | OL | H | $^nC_4H_9$ | H | H | H | H | H | — — |
| 3'-302 | Pd | 1 | 3' | | OL | H | $^tC_4H_9$ | H | H | H | H | H | pic |
| 3'-302X | Pd | 1 | 3' | | OL | H | $^tC_4H_9$ | H | H | H | H | H | acac |
| 3'-302Y | Pd | 0 | 3' | | OL | H | $^tC_4H_9$ | H | H | H | H | H | — — |
| 3'-303 | Pd | 1 | 3' | | OL | $CH_3$ | $^nC_4H_9$ | H | H | H | H | H | pic |
| 3'-303X | Pd | 1 | 3' | | OL | $CH_3$ | $^nC_4H_9$ | H | H | H | H | H | acac |
| 3'-303Y | Pd | 0 | 3' | | OL | $CH_3$ | $^nC_4H_9$ | H | H | H | H | H | — — |
| 3'-304 | Pd | 1 | 3' | | OL | $CH_3$ | $^tC_4H_9$ | H | H | H | H | H | pic |
| 3'-304X | Pd | 1 | 3' | | OL | $CH_3$ | $^tC_4H_9$ | H | H | H | H | H | acac |
| 3'-304Y | Pd | 0 | 3' | | OL | $CH_3$ | $^tC_4H_9$ | H | H | H | H | H | — — |
| 3'-305 | Pd | 1 | 3' | | OL | H | H | H | H | H | H | H | pic |
| 3'-305X | Pd | 1 | 3' | | OL | H | H | H | H | H | H | H | acac |
| 3'-305Y | Pd | 0 | 3' | | OL | H | H | H | H | H | H | H | — — |
| 3'-306 | Pd | 1 | 3' | | OL | H | $^nC_4H_9$ | $CH_3$ | H | H | H | H | pic |
| 3'-306X | Pd | 1 | 3' | | OL | H | $^nC_4H_9$ | $CH_3$ | H | H | H | H | acac |
| 3'-306Y | Pd | 0 | 3' | | OL | H | $^nC_4H_9$ | $CH_3$ | H | H | H | H | — — |
| 3'-307 | Pd | 1 | 3' | | OL | H | $^tC_4H_9$ | $CH_3$ | H | H | H | H | pic |
| 3'-307X | Pd | 1 | 3' | | OL | H | $^tC_4H_9$ | $CH_3$ | H | H | H | H | acac |
| 3'-307Y | Pd | 0 | 3' | | OL | H | $^tC_4H_9$ | $CH_3$ | H | H | H | H | — — |
| 3'-308 | Pd | 1 | 3' | | OL | —$CH_2CH_2CH_2$— | | H | H | H | H | H | pic |
| 3'-308X | Pd | 1 | 3' | | OL | —$CH_2CH_2CH_2$— | | H | H | H | H | H | acac |
| 3'-308Y | Pd | 0 | 3' | | OL | —$CH_2CH_2CH_2$— | | H | H | H | H | H | — — |

-continued
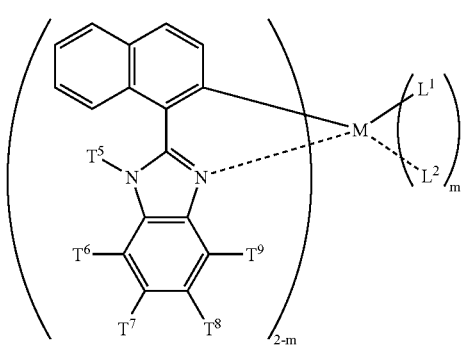
BSS 4', G:NAP1
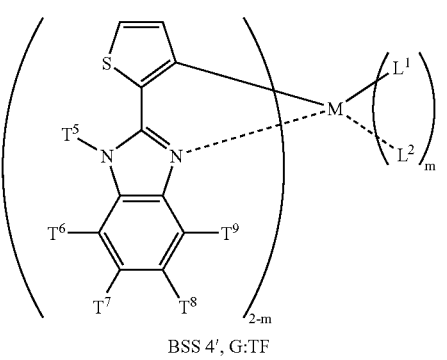
BSS 4', G:TF
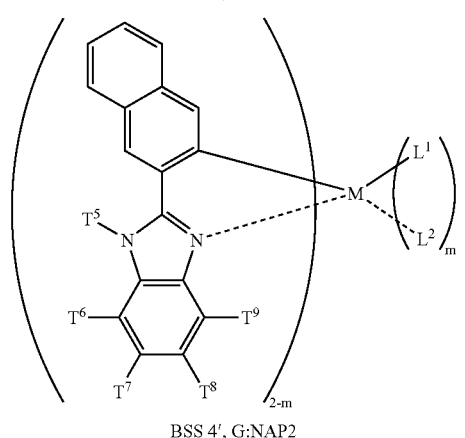
BSS 4', G:NAP2
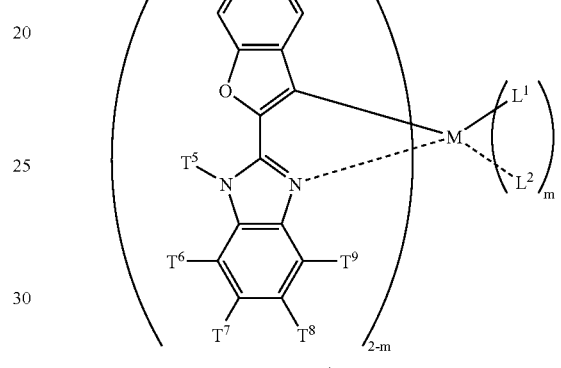
BSS 4', G:OB
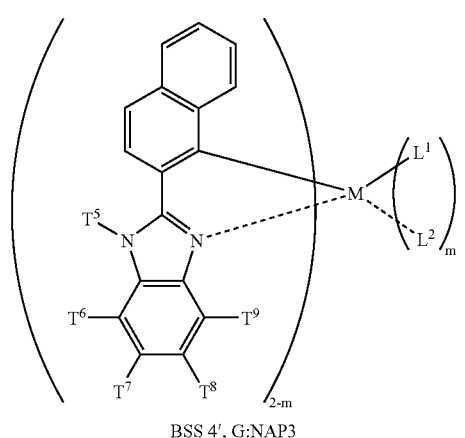
BSS 4', G:NAP3
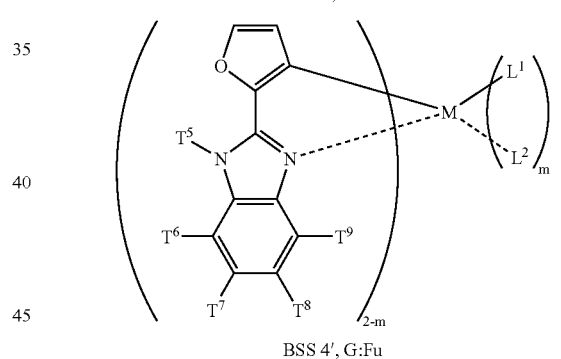
BSS 4', G:Fu
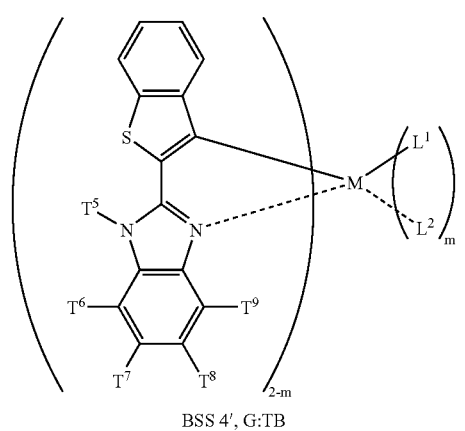
BSS 4', G:TB
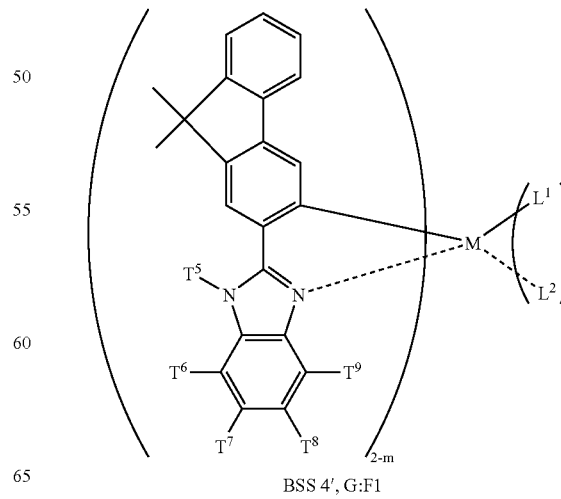
BSS 4', G:Fl

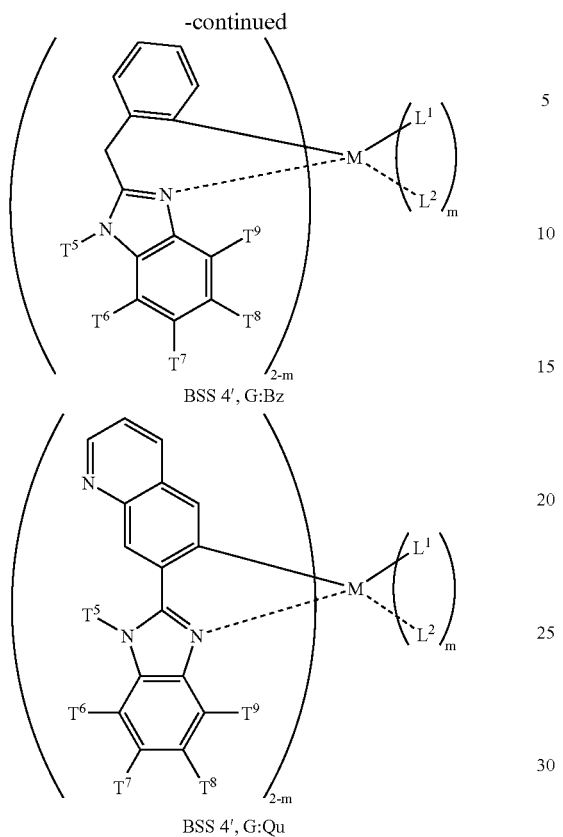
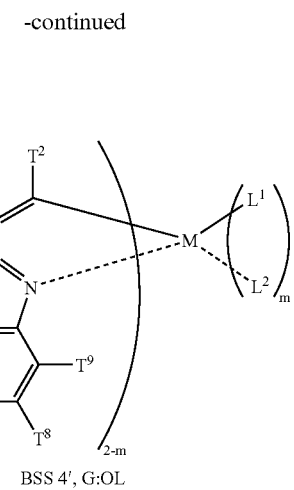

TABLE 53

| No. | M | m | BSS | SS | G | T$^1$ | T$^2$ | T$^5$ | T$^6$ | T$^7$ | T$^8$ | T$^9$ | L$^1$ | L$^2$ |
|---|---|---|---|---|---|---|---|---|---|---|---|---|---|---|
| 4'-304 | Pd | 1 | 4' | | Nap1 | — | — | CH$_3$ | H | H | H | H | pic | |
| 4'-304X | Pd | 1 | 4' | | Nap1 | — | — | CH$_3$ | H | H | H | H | acac | |
| 4'-304Y | Pd | 0 | 4' | | Nap1 | — | — | CH$_3$ | H | H | H | H | — | — |
| 4'-305 | Pd | 1 | 4' | | Nap1 | — | — | $^tC_4H_9$ | H | H | H | H | pic | |
| 4'-305X | Pd | 1 | 4' | | Nap1 | — | — | $^tC_4H_9$ | H | H | H | H | acac | |
| 4'-305Y | Pd | 0 | 4' | | Nap1 | — | — | $^tC_4H_9$ | H | H | H | H | — | — |
| 4'-306 | Pd | 1 | 4' | | Nap2 | — | — | CH$_3$ | H | H | H | H | pic | |
| 4'-306X | Pd | 1 | 4' | | Nap2 | — | — | CH$_3$ | H | H | H | H | acac | |
| 4'-306Y | Pd | 0 | 4' | | Nap2 | — | — | CH$_3$ | H | H | H | H | — | — |
| 4'-307 | Pd | 1 | 4' | | Nap2 | — | — | $^tC_4H_9$ | H | H | H | H | pic | |
| 4'-307X | Pd | 1 | 4' | | Nap2 | — | — | $^tC_4H_9$ | H | H | H | H | acac | |
| 4'-307Y | Pd | 0 | 4' | | Nap2 | — | — | $^tC_4H_9$ | H | H | H | H | — | — |
| 4'-308 | Pd | 1 | 4' | | Nap3 | — | — | CH$_3$ | H | H | H | H | pic | |
| 4'-308X | Pd | 1 | 4' | | Nap3 | — | — | CH$_3$ | H | H | H | H | acac | |
| 4'-308Y | Pd | 0 | 4' | | Nap3 | — | — | CH$_3$ | H | H | H | H | — | — |
| 4'-309 | Pd | 1 | 4' | | Nap3 | — | — | $^tC_4H_9$ | H | H | H | H | pic | |
| 4'-309X | Pd | 1 | 4' | | Nap3 | — | — | $^tC_4H_9$ | H | H | H | H | acac | |
| 4'-309Y | Pd | 0 | 4' | | Nap3 | — | — | $^tC_4H_9$ | H | H | H | H | — | — |
| 4'-310 | Pd | 1 | 4' | | TB | — | — | CH$_3$ | H | H | H | H | pic | |
| 4'-310X | Pd | 1 | 4' | | TB | — | — | CH$_3$ | H | H | H | H | acac | |
| 4'-310Y | Pd | 0 | 4' | | TB | — | — | CH$_3$ | H | H | H | H | — | — |
| 4'-311 | Pd | 1 | 4' | | TB | — | — | $^tC_4H_9$ | H | H | H | H | pic | |
| 4'-311X | Pd | 1 | 4' | | TB | — | — | $^tC_4H_9$ | H | H | H | H | acac | |
| 4'-311Y | Pd | 0 | 4' | | TB | — | — | $^tC_4H_9$ | H | H | H | H | — | — |
| 4'-312 | Pd | 1 | 4' | | TF | — | — | CH$_3$ | H | H | H | H | pic | |
| 4'-312X | Pd | 1 | 4' | | TF | — | — | CH$_3$ | H | H | H | H | acac | |
| 4'-312Y | Pd | 0 | 4' | | TF | — | — | CH$_3$ | H | H | H | H | — | — |
| 4'-313 | Pd | 1 | 4' | | TF | — | — | $^tC_4H_9$ | H | H | H | H | pic | |
| 4'-313X | Pd | 1 | 4' | | TF | — | — | $^tC_4H_9$ | H | H | H | H | acac | |
| 4'-313Y | Pd | 0 | 4' | | TF | — | — | $^tC_4H_9$ | H | H | H | H | — | — |
| 4'-314 | Pd | 1 | 4' | | OB | — | — | CH$_3$ | H | H | H | H | pic | |
| 4'-314X | Pd | 1 | 4' | | OB | — | — | CH$_3$ | H | H | H | H | acac | |
| 4'-314Y | Pd | 0 | 4' | | OB | — | — | CH$_3$ | H | H | H | H | — | — |
| 4'-315 | Pd | 1 | 4' | | OB | — | — | $^tC_4H_9$ | H | H | H | H | pic | |

TABLE 53-continued

| No. | M | m | BSS | SS G | T¹ | T² | T⁵ | T⁶ | T⁷ | T⁸ | T⁹ | L¹ L² |
|---|---|---|---|---|---|---|---|---|---|---|---|---|
| 4'-315X | Pd | 1 | 4' | OB | — | — | $^tC_4H_9$ | H | H | H | H | acac |
| 4'-315Y | Pd | 0 | 4' | OB | — | — | $^tC_4H_9$ | H | H | H | H | — — |
| 4'-316 | Pd | 1 | 4' | Fu | — | — | $CH_3$ | H | H | H | H | pic |
| 4'-316X | Pd | 1 | 4' | Fu | — | — | $CH_3$ | H | H | H | H | acac |
| 4'-316Y | Pd | 0 | 4' | Fu | — | — | $CH_3$ | H | H | H | H | — — |
| 4'-317 | Pd | 1 | 4' | Fu | — | — | $^tC_4H_9$ | H | H | H | H | pic |
| 4'-317X | Pd | 1 | 4' | Fu | — | — | $^tC_4H_9$ | H | H | H | H | acac |
| 4'-317Y | Pd | 0 | 4' | Fu | — | — | $^tC_4H_9$ | H | H | H | H | — — |
| 4'-318 | Pd | 1 | 4' | Fl | — | — | $CH_3$ | H | H | H | H | pic |
| 4'-318X | Pd | 1 | 4' | Fl | — | — | $CH_3$ | H | H | H | H | acac |
| 4'-318Y | Pd | 0 | 4' | Fl | — | — | $CH_3$ | H | H | H | H | — — |
| 4'-319 | Pd | 1 | 4' | Fl | — | — | $^tC_4H_9$ | H | H | H | H | pic |
| 4'-319X | Pd | 1 | 4' | Fl | — | — | $^tC_4H_9$ | H | H | H | H | acac |
| 4'-319Y | Pd | 0 | 4' | Fl | — | — | $^tC_4H_9$ | H | H | H | H | — — |
| 4'-320 | Pd | 1 | 4' | Bz | — | — | $CH_3$ | H | H | H | H | pic |
| 4'-320X | Pd | 1 | 4' | Bz | — | — | $CH_3$ | H | H | H | H | acac |
| 4'-320Y | Pd | 0 | 4' | Bz | — | — | $CH_3$ | H | H | H | H | — — |
| 4'-321 | Pd | 1 | 4' | Bz | — | — | $^tC_4H_9$ | H | H | H | H | pic |
| 4'-321X | Pd | 1 | 4' | Bz | — | — | $^tC_4H_9$ | H | H | H | H | acac |
| 4'-321Y | Pd | 0 | 4' | Bz | — | — | $^tC_4H_9$ | H | H | H | H | — — |
| 4'-322 | Pd | 1 | 4' | Qu | — | — | $CH_3$ | H | H | H | H | pic |
| 4'-322X | Pd | 1 | 4' | Qu | — | — | $CH_3$ | H | H | H | H | acac |
| 4'-322Y | Pd | 0 | 4' | Qu | — | — | $CH_3$ | H | H | H | H | — — |
| 4'-323 | Pd | 1 | 4' | Qu | — | — | $^tC_4H_9$ | H | H | H | H | pic |
| 4'-323X | Pd | 1 | 4' | Qu | — | — | $^tC_4H_9$ | H | H | H | H | acac |
| 4'-323Y | Pd | 0 | 4' | Qu | — | — | $^tC_4H_9$ | H | H | H | H | — — |
| 4'-324 | Pd | 1 | 4' | OL | H | $^nC_4H_9$ | $CH_3$ | H | H | H | H | pic |
| 4'-324X | Pd | 1 | 4' | OL | H | $^nC_4H_9$ | $CH_3$ | H | H | H | H | acac |
| 4'-324Y | Pd | 0 | 4' | OL | H | $^nC_4H_9$ | $CH_3$ | H | H | H | H | — — |
| 4'-325 | Pd | 1 | 4' | OL | H | $^nC_4H_9$ | $^tC_4H_9$ | H | H | H | H | pic |
| 4'-325X | Pd | 1 | 4' | OL | H | $^nC_4H_9$ | $^tC_4H_9$ | H | H | H | H | acac |
| 4'-325Y | Pd | 0 | 4' | OL | H | $^nC_4H_9$ | $^tC_4H_9$ | H | H | H | H | — — |
| 4'-326 | Pd | 1 | 4' | OL | H | $^tC_4H_9$ | $CH_3$ | H | H | H | H | pic |
| 4'-326X | Pd | 1 | 4' | OL | H | $^tC_4H_9$ | $CH_3$ | H | H | H | H | acac |
| 4'-326Y | Pd | 0 | 4' | OL | H | $^tC_4H_9$ | $CH_3$ | H | H | H | H | — — |
| 4'-327 | Pd | 1 | 4' | OL | H | $^tC_4H_9$ | $^tC_4H_9$ | H | H | H | H | pic |
| 4'-327X | Pd | 1 | 4' | OL | H | $^tC_4H_9$ | $^tC_4H_9$ | H | H | H | H | acac |
| 4'-327Y | Pd | 0 | 4' | OL | H | $^tC_4H_9$ | $^tC_4H_9$ | H | H | H | H | — — |
| 4'-328 | Pd | 1 | 4' | OL | $CH_3$ | $^nC_4H_9$ | $CH_3$ | H | H | H | H | pic |
| 4'-328X | Pd | 1 | 4' | OL | $CH_3$ | $^nC_4H_9$ | $CH_3$ | H | H | H | H | acac |
| 4'-328Y | Pd | 0 | 4' | OL | $CH_3$ | $^nC_4H_9$ | $CH_3$ | H | H | H | H | — — |
| 4'-329 | Pd | 1 | 4' | OL | $CH_3$ | $^tC_4H_9$ | $CH_3$ | H | H | H | H | pic |
| 4'-329X | Pd | 1 | 4' | OL | $CH_3$ | $^tC_4H_9$ | $CH_3$ | H | H | H | H | acac |
| 4'-329Y | Pd | 0 | 4' | OL | $CH_3$ | $^tC_4H_9$ | $CH_3$ | H | H | H | H | — — |
| 4'-330 | Pd | 1 | 4' | OL | H | H | $CH_3$ | H | H | H | H | pic |
| 4'-330X | Pd | 1 | 4' | OL | H | H | $CH_3$ | H | H | H | H | acac |
| 4'-330Y | Pd | 0 | 4' | OL | H | H | $CH_3$ | H | H | H | H | — — |
| 4'-331 | Pd | 1 | 4' | OL | —$CH_2CH_2CH_2$— | | $CH_3$ | H | H | H | H | pic |
| 4'-331X | Pd | 1 | 4' | OL | —$CH_2CH_2CH_2$— | | $CH_3$ | H | H | H | H | acac |
| 4'-331Y | Pd | 0 | 4' | OL | —$CH_2CH_2CH_2$— | | $CH_3$ | H | H | H | H | — — |
| 4'-332 | Pd | 1 | 4' | OL | —$CH_2CH_2CH_2$— | | $^tC_4H_9$ | H | H | H | H | pic |
| 4'-332X | Pd | 1 | 4' | OL | —$CH_2CH_2CH_2$— | | $^tC_4H_9$ | H | H | H | H | acac |
| 4'-332Y | Pd | 0 | 4' | OL | —$CH_2CH_2CH_2$— | | $^tC_4H_9$ | H | H | H | H | — — |

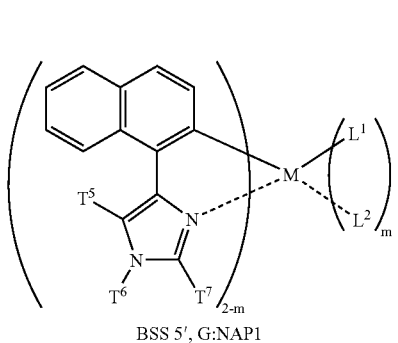

BSS 5', G:NAP1

-continued

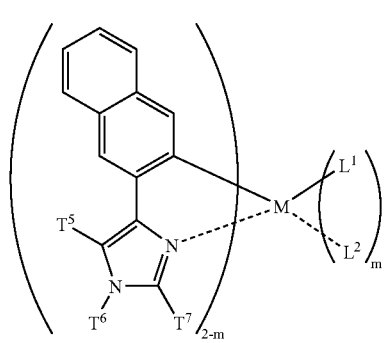

BSS 5', G:NAP2

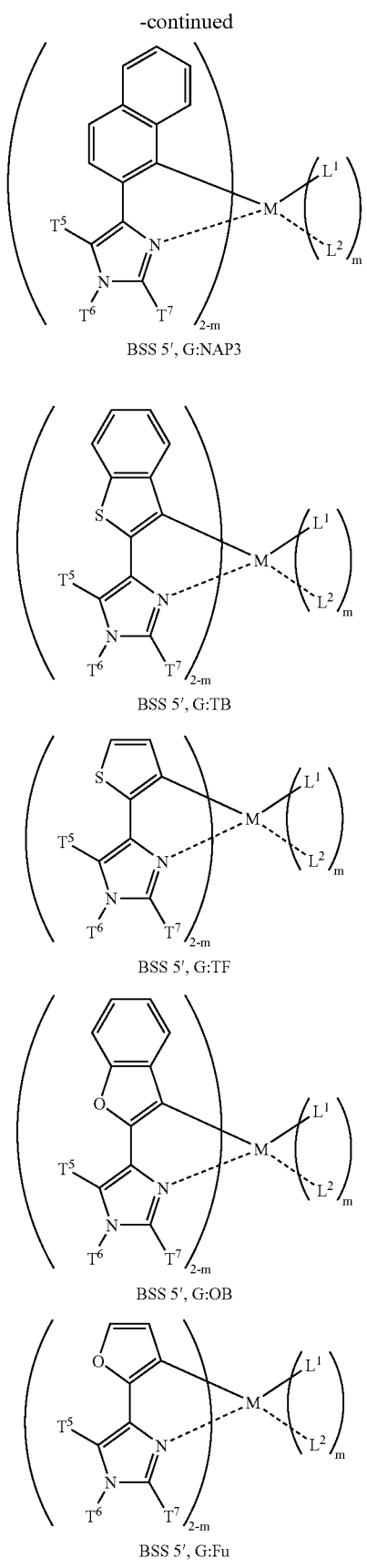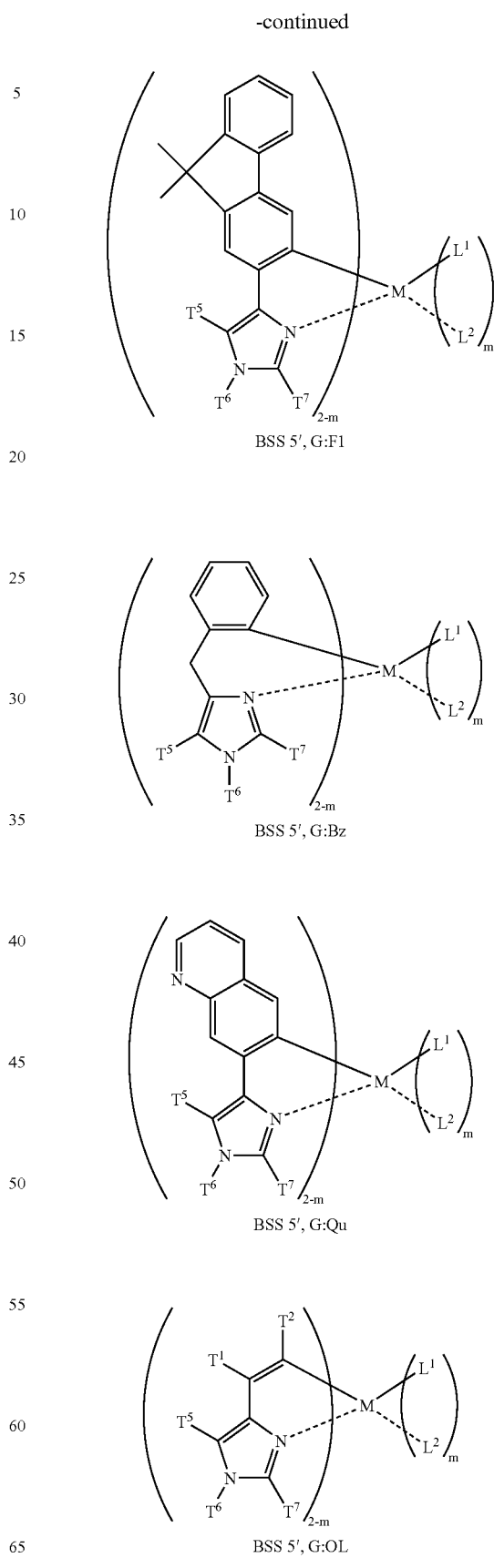

TABLE 54

| No. | M | m | BSS | SS G | T¹ | T² | T⁵ | T⁶ | T⁷ | L¹ L² |
|---|---|---|---|---|---|---|---|---|---|---|
| 5'-350 | Pd | 1 | 5' | Nap1 | — | — | H | $CH_3$ | H | pic |
| 5'-350X | Pd | 1 | 5' | Nap1 | — | — | H | $CH_3$ | H | acac |
| 5'-350Y | Pd | 0 | 5' | Nap1 | — | — | H | $CH_3$ | H | — |
| 5'-351 | Pd | 1 | 5' | Nap1 | — | — | H | $^tC_4H_9$ | H | pic |
| 5'-351X | Pd | 1 | 5' | Nap1 | — | — | H | $^tC_4H_9$ | H | acac |
| 5'-351Y | Pd | 0 | 5' | Nap1 | — | — | H | $^tC_4H_9$ | H | — |
| 5'-352 | Pd | 1 | 5' | Nap1 | — | — | $^tC_4H_9$ | $CH_3$ | H | pic |
| 5'-352X | Pd | 1 | 5' | Nap1 | — | — | $^tC_4H_9$ | $CH_3$ | H | acac |
| 5'-352Y | Pd | 0 | 5' | Nap1 | — | — | $^tC_4H_9$ | $CH_3$ | H | — |
| 5'-353 | Pd | 1 | 5' | Nap1 | — | — | $^tC_4H_9$ | $^tC_4H_9$ | H | pic |
| 5'-353X | Pd | 1 | 5' | Nap1 | — | — | $^tC_4H_9$ | $^tC_4H_9$ | H | acac |
| 5'-353Y | Pd | 0 | 5' | Nap1 | — | — | $^tC_4H_9$ | $^tC_4H_9$ | H | — |
| 5'-354 | Pd | 1 | 5' | Nap1 | — | — | $CH_3$ | $CH_3$ | H | pic |
| 5'-354X | Pd | 1 | 5' | Nap1 | — | — | $CH_3$ | $CH_3$ | H | acac |
| 5'-354Y | Pd | 0 | 5' | Nap1 | — | — | $CH_3$ | $CH_3$ | H | — |
| 5'-355 | Pd | 1 | 5' | Nap1 | — | — | $CH_3$ | $^tC_4H_9$ | H | pic |
| 5'-355X | Pd | 1 | 5' | Nap1 | — | — | $CH_3$ | $^tC_4H_9$ | H | acac |
| 5'-355Y | Pd | 0 | 5' | Nap1 | — | — | $CH_3$ | $^tC_4H_9$ | H | — |
| 5'-356 | Pd | 1 | 5' | Nap2 | — | — | H | $CH_3$ | H | pic |
| 5'-356X | Pd | 1 | 5' | Nap2 | — | — | H | $CH_3$ | H | acac |
| 5'-356Y | Pd | 0 | 5' | Nap2 | — | — | H | $CH_3$ | H | — |
| 5'-357 | Pd | 1 | 5' | Nap2 | — | — | H | $^tC_4H_9$ | H | pic |
| 5'-357X | Pd | 1 | 5' | Nap2 | — | — | H | $^tC_4H_9$ | H | acac |
| 5'-357Y | Pd | 0 | 5' | Nap2 | — | — | H | $^tC_4H_9$ | H | — |
| 5'-358 | Pd | 1 | 5' | Nap2 | — | — | $^tC_4H_9$ | $CH_3$ | H | pic |
| 5'-358X | Pd | 1 | 5' | Nap2 | — | — | $^tC_4H_9$ | $CH_3$ | H | acac |
| 5'-358Y | Pd | 0 | 5' | Nap2 | — | — | $^tC_4H_9$ | $CH_3$ | H | — |
| 5'-359 | Pd | 1 | 5' | Nap2 | — | — | $^tC_4H_9$ | $^tC_4H_9$ | H | pic |
| 5'-359X | Pd | 1 | 5' | Nap2 | — | — | $^tC_4H_9$ | $^tC_4H_9$ | H | acac |
| 5'-359Y | Pd | 0 | 5' | Nap2 | — | — | $^tC_4H_9$ | $^tC_4H_9$ | H | — |
| 5'-360 | Pd | 1 | 5' | Nap2 | — | — | $CH_3$ | $CH_3$ | H | pic |
| 5'-360X | Pd | 1 | 5' | Nap2 | — | — | $CH_3$ | $CH_3$ | H | acac |
| 5'-360Y | Pd | 0 | 5' | Nap2 | — | — | $CH_3$ | $CH_3$ | H | — |
| 5'-361 | Pd | 1 | 5' | Nap2 | — | — | $CH_3$ | $^tC_4H_9$ | H | pic |
| 5'-361X | Pd | 1 | 5' | Nap2 | — | — | $CH_3$ | $^tC_4H_9$ | H | acac |
| 5'-361Y | Pd | 0 | 5' | Nap2 | — | — | $CH_3$ | $^tC_4H_9$ | H | — |
| 5'-362 | Pd | 1 | 5' | Nap3 | — | — | H | $CH_3$ | H | pic |
| 5'-362X | Pd | 1 | 5' | Nap3 | — | — | H | $CH_3$ | H | acac |
| 5'-362Y | Pd | 0 | 5' | Nap3 | — | — | H | $CH_3$ | H | — |
| 5'-363 | Pd | 1 | 5' | Nap3 | — | — | H | $^tC_4H_9$ | H | pic |
| 5'-363X | Pd | 1 | 5' | Nap3 | — | — | H | $^tC_4H_9$ | H | acac |
| 5'-363Y | Pd | 0 | 5' | Nap3 | — | — | H | $^tC_4H_9$ | H | — |
| 5'-364 | Pd | 1 | 5' | Nap3 | — | — | $^tC_4H_9$ | $CH_3$ | H | pic |
| 5'-364X | Pd | 1 | 5' | Nap3 | — | — | $^tC_4H_9$ | $CH_3$ | H | acac |
| 5'-364Y | Pd | 0 | 5' | Nap3 | — | — | $^tC_4H_9$ | $CH_3$ | H | — |
| 5'-365 | Pd | 1 | 5' | Nap3 | — | — | $^tC_4H_9$ | $^tC_4H_9$ | H | pic |
| 5'-365X | Pd | 1 | 5' | Nap3 | — | — | $^tC_4H_9$ | $^tC_4H_9$ | H | acac |
| 5'-365Y | Pd | 0 | 5' | Nap3 | — | — | $^tC_4H_9$ | $^tC_4H_9$ | H | — |
| 5'-366 | Pd | 1 | 5' | Nap3 | — | — | $CH_3$ | $CH_3$ | H | pic |
| 5'-366X | Pd | 1 | 5' | Nap3 | — | — | $CH_3$ | $CH_3$ | H | acac |
| 5'-366Y | Pd | 0 | 5' | Nap3 | — | — | $CH_3$ | $CH_3$ | H | — |
| 5'-367 | Pd | 1 | 5' | Nap3 | — | — | $CH_3$ | $^tC_4H_9$ | H | pic |
| 5'-367X | Pd | 1 | 5' | Nap3 | — | — | $CH_3$ | $^tC_4H_9$ | H | acac |
| 5'-367Y | Pd | 0 | 5' | Nap3 | — | — | $CH_3$ | $^tC_4H_9$ | H | — |
| 5'-368 | Pd | 1 | 5' | TB | — | — | H | $CH_3$ | H | pic |
| 5'-368X | Pd | 1 | 5' | TB | — | — | H | $CH_3$ | H | acac |
| 5'-368Y | Pd | 0 | 5' | TB | — | — | H | $CH_3$ | H | — |
| 5'-369 | Pd | 1 | 5' | TB | — | — | H | $^tC_4H_9$ | H | pic |
| 5'-369X | Pd | 1 | 5' | TB | — | — | H | $^tC_4H_9$ | H | acac |
| 5'-369Y | Pd | 0 | 5' | TB | — | — | H | $^tC_4H_9$ | H | — |
| 5'-370 | Pd | 1 | 5' | TB | — | — | $^tC_4H_9$ | $CH_3$ | H | pic |
| 5'-370X | Pd | 1 | 5' | TB | — | — | $^tC_4H_9$ | $CH_3$ | H | acac |
| 5'-370Y | Pd | 0 | 5' | TB | — | — | $^tC_4H_9$ | $CH_3$ | H | — |
| 5'-371 | Pd | 1 | 5' | TB | — | — | $^tC_4H_9$ | $^tC_4H_9$ | H | pic |
| 5'-371X | Pd | 1 | 5' | TB | — | — | $^tC_4H_9$ | $^tC_4H_9$ | H | acac |
| 5'-371Y | Pd | 0 | 5' | TB | — | — | $^tC_4H_9$ | $^tC_4H_9$ | H | — |
| 5'-372 | Pd | 1 | 5' | TB | — | — | $CH_3$ | $CH_3$ | H | pic |
| 5'-372X | Pd | 1 | 5' | TB | — | — | $CH_3$ | $CH_3$ | H | acac |
| 5'-372Y | Pd | 0 | 5' | TB | — | — | $CH_3$ | $CH_3$ | H | — |
| 5'-373 | Pd | 1 | 5' | TB | — | — | $CH_3$ | $^tC_4H_9$ | H | pic |
| 5'-373X | Pd | 1 | 5' | TB | — | — | $CH_3$ | $^tC_4H_9$ | H | acac |
| 5'-373Y | Pd | 0 | 5' | TB | — | — | $CH_3$ | $^tC_4H_9$ | H | — |
| 5'-374 | Pd | 1 | 5' | TF | — | — | H | $CH_3$ | H | pic |
| 5'-374X | Pd | 1 | 5' | TF | — | — | H | $CH_3$ | H | acac |
| 5'-374Y | Pd | 0 | 5' | TF | — | — | H | $CH_3$ | H | — |
| 5'-375 | Pd | 1 | 5' | TF | — | — | H | $^tC_4H_9$ | H | pic |
| 5'-375X | Pd | 1 | 5' | TF | — | — | H | $^tC_4H_9$ | H | acac |

TABLE 54-continued

| No. | M | m | BSS | SS G | T$^1$ | T$^2$ | T$^5$ | T$^6$ | T$^7$ | L$^1$ L$^2$ |
|---|---|---|---|---|---|---|---|---|---|---|
| 5'-375Y | Pd | 0 | 5' | TF | — | — | H | $^t$C$_4$H$_9$ | H | — |
| 5'-376 | Pd | 1 | 5' | TF | — | — | $^t$C$_4$H$_9$ | CH$_3$ | H | pic |
| 5'-376X | Pd | 1 | 5' | TF | — | — | $^t$C$_4$H$_9$ | CH$_3$ | H | acac |
| 5'-376Y | Pd | 0 | 5' | TF | — | — | $^t$C$_4$H$_9$ | CH$_3$ | H | — |
| 5'-377 | Pd | 1 | 5' | TF | — | — | $^t$C$_4$H$_9$ | $^t$C$_4$H$_9$ | H | pic |
| 5'-377X | Pd | 1 | 5' | TF | — | — | $^t$C$_4$H$_9$ | $^t$C$_4$H$_9$ | H | acac |
| 5'-377Y | Pd | 0 | 5' | TF | — | — | $^t$C$_4$H$_9$ | $^t$C$_4$H$_9$ | H | — |
| 5'-378 | Pd | 1 | 5' | TF | — | — | CH$_3$ | CH$_3$ | H | pic |
| 5'-378X | Pd | 1 | 5' | TF | — | — | CH$_3$ | CH$_3$ | H | acac |
| 5'-378Y | Pd | 0 | 5' | TF | — | — | CH$_3$ | CH$_3$ | H | — |
| 5'-379 | Pd | 1 | 5' | TF | — | — | CH$_3$ | $^t$C$_4$H$_9$ | H | pic |
| 5'-379X | Pd | 1 | 5' | TF | — | — | CH$_3$ | $^t$C$_4$H$_9$ | H | acac |
| 5'-379Y | Pd | 0 | 5' | TF | — | — | CH$_3$ | $^t$C$_4$H$_9$ | H | — |
| 5'-380 | Pd | 1 | 5' | OB | — | — | H | CH$_3$ | H | pic |
| 5'-380X | Pd | 1 | 5' | OB | — | — | H | CH$_3$ | H | acac |
| 5'-380Y | Pd | 0 | 5' | OB | — | — | H | CH$_3$ | H | — |
| 5'-381 | Pd | 1 | 5' | OB | — | — | H | $^t$C$_4$H$_9$ | H | pic |
| 5'-381X | Pd | 1 | 5' | OB | — | — | H | $^t$C$_4$H$_9$ | H | acac |
| 5'-381Y | Pd | 0 | 5' | OB | — | — | H | $^t$C$_4$H$_9$ | H | — |
| 5'-382 | Pd | 1 | 5' | OB | — | — | $^t$C$_4$H$_9$ | CH$_3$ | H | pic |
| 5'-382X | Pd | 1 | 5' | OB | — | — | $^t$C$_4$H$_9$ | CH$_3$ | H | acac |
| 5'-382Y | Pd | 0 | 5' | OB | — | — | $^t$C$_4$H$_9$ | CH$_3$ | H | — |
| 5'-383 | Pd | 1 | 5' | OB | — | — | $^t$C$_4$H$_9$ | $^t$C$_4$H$_9$ | H | pic |
| 5'-383X | Pd | 1 | 5' | OB | — | — | $^t$C$_4$H$_9$ | $^t$C$_4$H$_9$ | H | acac |
| 5'-383Y | Pd | 0 | 5' | OB | — | — | $^t$C$_4$H$_9$ | $^t$C$_4$H$_9$ | H | — |
| 5'-384 | Pd | 1 | 5' | OB | — | — | CH$_3$ | CH$_3$ | H | pic |
| 5'-384X | Pd | 1 | 5' | OB | — | — | CH$_3$ | CH$_3$ | H | acac |
| 5'-384Y | Pd | 0 | 5' | OB | — | — | CH$_3$ | CH$_3$ | H | — |
| 5'-385 | Pd | 1 | 5' | OB | — | — | CH$_3$ | $^t$C$_4$H$_9$ | H | pic |
| 5'-385X | Pd | 1 | 5' | OB | — | — | CH$_3$ | $^t$C$_4$H$_9$ | H | acac |
| 5'-385Y | Pd | 0 | 5' | OB | — | — | CH$_3$ | $^t$C$_4$H$_9$ | H | — |
| 5'-386 | Pd | 1 | 5' | Fu | — | — | H | CH$_3$ | H | pic |
| 5'-386X | Pd | 1 | 5' | Fu | — | — | H | CH$_3$ | H | acac |
| 5'-386Y | Pd | 0 | 5' | Fu | — | — | H | CH$_3$ | H | — |
| 5'-387 | Pd | 1 | 5' | Fu | — | — | H | $^t$C$_4$H$_9$ | H | pic |
| 5'-387X | Pd | 1 | 5' | Fu | — | — | H | $^t$C$_4$H$_9$ | H | acac |
| 5'-387Y | Pd | 0 | 5' | Fu | — | — | H | $^t$C$_4$H$_9$ | H | — |
| 5'-388 | Pd | 1 | 5' | Fu | — | — | $^t$C$_4$H$_9$ | CH$_3$ | H | pic |
| 5'-388X | Pd | 1 | 5' | Fu | — | — | $^t$C$_4$H$_9$ | CH$_3$ | H | acac |
| 5'-388Y | Pd | 0 | 5' | Fu | — | — | $^t$C$_4$H$_9$ | CH$_3$ | H | — |
| 5'-389 | Pd | 1 | 5' | Fu | — | — | $^t$C$_4$H$_9$ | $^t$C$_4$H$_9$ | H | pic |
| 5'-389X | Pd | 1 | 5' | Fu | — | — | $^t$C$_4$H$_9$ | $^t$C$_4$H$_9$ | H | acac |
| 5'-389Y | Pd | 0 | 5' | Fu | — | — | $^t$C$_4$H$_9$ | $^t$C$_4$H$_9$ | H | — |
| 5'-390 | Pd | 1 | 5' | Fu | — | — | CH$_3$ | CH$_3$ | H | pic |
| 5'-390X | Pd | 1 | 5' | Fu | — | — | CH$_3$ | CH$_3$ | H | acac |
| 5'-390Y | Pd | 0 | 5' | Fu | — | — | CH$_3$ | CH$_3$ | H | — |
| 5'-391 | Pd | 1 | 5' | Fu | — | — | CH$_3$ | $^t$C$_4$H$_9$ | H | pic |
| 5'-391X | Pd | 1 | 5' | Fu | — | — | CH$_3$ | $^t$C$_4$H$_9$ | H | acac |
| 5'-391Y | Pd | 0 | 5' | Fu | — | — | CH$_3$ | $^t$C$_4$H$_9$ | H | — |
| 5'-392 | Pd | 1 | 5' | Fl | — | — | H | CH$_3$ | H | pic |
| 5'-392X | Pd | 1 | 5' | Fl | — | — | H | CH$_3$ | H | acac |
| 5'-392Y | Pd | 0 | 5' | Fl | — | — | H | CH$_3$ | H | — |
| 5'-393 | Pd | 1 | 5' | Fl | — | — | H | $^t$C$_4$H$_9$ | H | pic |
| 5'-393X | Pd | 1 | 5' | Fl | — | — | H | $^t$C$_4$H$_9$ | H | acac |
| 5'-393Y | Pd | 0 | 5' | Fl | — | — | H | $^t$C$_4$H$_9$ | H | — |
| 5'-394 | Pd | 1 | 5' | Fl | — | — | $^t$C$_4$H$_9$ | CH$_3$ | H | pic |
| 5'-394X | Pd | 1 | 5' | Fl | — | — | $^t$C$_4$H$_9$ | CH$_3$ | H | acac |
| 5'-394Y | Pd | 0 | 5' | Fl | — | — | $^t$C$_4$H$_9$ | CH$_3$ | H | — |
| 5'-395 | Pd | 1 | 5' | Fl | — | — | $^t$C$_4$H$_9$ | $^t$C$_4$H$_9$ | H | pic |
| 5'-395X | Pd | 1 | 5' | Fl | — | — | $^t$C$_4$H$_9$ | $^t$C$_4$H$_9$ | H | acac |
| 5'-395Y | Pd | 0 | 5' | Fl | — | — | $^t$C$_4$H$_9$ | $^t$C$_4$H$_9$ | H | — |
| 5'-396 | Pd | 1 | 5' | Fl | — | — | CH$_3$ | CH$_3$ | H | pic |
| 5'-396X | Pd | 1 | 5' | Fl | — | — | CH$_3$ | CH$_3$ | H | acac |
| 5'-396Y | Pd | 0 | 5' | Fl | — | — | CH$_3$ | CH$_3$ | H | — |
| 5'-397 | Pd | 1 | 5' | Fl | — | — | CH$_3$ | $^t$C$_4$H$_9$ | H | pic |
| 5'-397X | Pd | 1 | 5' | Fl | — | — | CH$_3$ | $^t$C$_4$H$_9$ | H | acac |
| 5'-397Y | Pd | 0 | 5' | Fl | — | — | CH$_3$ | $^t$C$_4$H$_9$ | H | — |
| 5'-398 | Pd | 1 | 5' | Bz | — | — | H | CH$_3$ | H | pic |
| 5'-398X | Pd | 1 | 5' | Bz | — | — | H | CH$_3$ | H | acac |
| 5'-398Y | Pd | 0 | 5' | Bz | — | — | H | CH$_3$ | H | — |
| 5'-399 | Pd | 1 | 5' | Bz | — | — | H | $^t$C$_4$H$_9$ | H | pic |
| 5'-399X | Pd | 1 | 5' | Bz | — | — | H | $^t$C$_4$H$_9$ | H | acac |
| 5'-399Y | Pd | 0 | 5' | Bz | — | — | H | $^t$C$_4$H$_9$ | H | — |
| 5'-400 | Pd | 1 | 5' | Bz | — | — | $^t$C$_4$H$_9$ | CH$_3$ | H | pic |
| 5'-400X | Pd | 1 | 5' | Bz | — | — | $^t$C$_4$H$_9$ | CH$_3$ | H | acac |
| 5'-400Y | Pd | 0 | 5' | Bz | — | — | $^t$C$_4$H$_9$ | CH$_3$ | H | — |
| 5'-401 | Pd | 1 | 5' | Bz | — | — | $^t$C$_4$H$_9$ | $^t$C$_4$H$_9$ | H | pic |

TABLE 54-continued

| No. | M | m | BSS | SS | G | T¹ | T² | T⁵ | T⁶ | T⁷ | L¹ | L² |
|---|---|---|---|---|---|---|---|---|---|---|---|---|
| 5'-401X | Pd | 1 | 5' | Bz | — | — | — | $^tC_4H_9$ | $^tC_4H_9$ | H | acac | |
| 5'-401Y | Pd | 0 | 5' | Bz | — | — | — | $^tC_4H_9$ | $^tC_4H_9$ | H | — | — |
| 5'-402 | Pd | 1 | 5' | Bz | — | — | — | $CH_3$ | $CH_3$ | H | pic | |
| 5'-402X | Pd | 1 | 5' | Bz | — | — | — | $CH_3$ | $CH_3$ | H | acac | |
| 5'-402Y | Pd | 0 | 5' | Bz | — | — | — | $CH_3$ | $CH_3$ | H | — | — |
| 5'-403 | Pd | 1 | 5' | Bz | — | — | — | $CH_3$ | $^tC_4H_9$ | H | pic | |
| 5'-403X | Pd | 1 | 5' | Bz | — | — | — | $CH_3$ | $^tC_4H_9$ | H | acac | |
| 5'-403Y | Pd | 0 | 5' | Bz | — | — | — | $CH_3$ | $^tC_4H_9$ | H | — | — |
| 5'-404 | Pd | 1 | 5' | Qu | — | — | — | H | $CH_3$ | H | pic | |
| 5'-404X | Pd | 1 | 5' | Bz | — | — | — | H | $CH_3$ | H | acac | |
| 5'-404Y | Pd | 0 | 5' | Bz | — | — | — | H | $CH_3$ | H | — | — |
| 5'-405 | Pd | 1 | 5' | Bz | — | — | — | H | $^tC_4H_9$ | H | pic | |
| 5'-405X | Pd | 1 | 5' | Bz | — | — | — | H | $^tC_4H_9$ | H | acac | |
| 5'-405Y | Pd | 0 | 5' | Bz | — | — | — | H | $^tC_4H_9$ | H | — | — |
| 5'-406 | Pd | 1 | 5' | Bz | — | — | — | $^tC_4H_9$ | $CH_3$ | H | pic | |
| 5'-406X | Pd | 1 | 5' | Bz | — | — | — | $^tC_4H_9$ | $CH_3$ | H | acac | |
| 5'-406Y | Pd | 0 | 5' | Bz | — | — | — | $^tC_4H_9$ | $CH_3$ | H | — | — |
| 5'-407 | Pd | 1 | 5' | Bz | — | — | — | $^tC_4H_9$ | $^tC_4H_9$ | H | pic | |
| 5'-407X | Pd | 1 | 5' | Bz | — | — | — | $^tC_4H_9$ | $^tC_4H_9$ | H | acac | |
| 5'-407Y | Pd | 0 | 5' | Bz | — | — | — | $^tC_4H_9$ | $^tC_4H_9$ | H | — | — |
| 5'-408 | Pd | 1 | 5' | Bz | — | — | — | $CH_3$ | $CH_3$ | H | pic | |
| 5'-408X | Pd | 1 | 5' | Bz | — | — | — | $CH_3$ | $CH_3$ | H | acac | |
| 5'-408Y | Pd | 0 | 5' | Bz | — | — | — | $CH_3$ | $CH_3$ | H | — | — |
| 5'-409 | Pd | 1 | 5' | Bz | — | — | — | $CH_3$ | $^tC_4H_9$ | H | pic | |
| 5'-409X | Pd | 1 | 5' | Bz | — | — | — | $CH_3$ | $^tC_4H_9$ | H | acac | |
| 5'-409Y | Pd | 0 | 5' | Bz | — | — | — | $CH_3$ | $^tC_4H_9$ | H | — | — |
| 5'-410 | Pd | 1 | 5' | OL | H | $^nC_4H_9$ | H | $CH_3$ | H | pic | | |
| 5'-410X | Pd | 1 | 5' | OL | H | $^nC_4H_9$ | H | $CH_3$ | H | acac | | |
| 5'-410Y | Pd | 0 | 5' | OL | H | $^nC_4H_9$ | H | $CH_3$ | H | — | — | |
| 5'-411 | Pd | 1 | 5' | OL | H | $^nC_4H_9$ | H | $^tC_4H_9$ | H | pic | | |
| 5'-411X | Pd | 1 | 5' | OL | H | $^nC_4H_9$ | H | $^tC_4H_9$ | H | acac | | |
| 5'-411Y | Pd | 0 | 5' | OL | H | $^nC_4H_9$ | H | $^tC_4H_9$ | H | — | — | |
| 5'-412 | Pd | 1 | 5' | OL | H | $^tC_4H_9$ | H | $CH_3$ | H | pic | | |
| 5'-412X | Pd | 1 | 5' | OL | H | $^tC_4H_9$ | H | $CH_3$ | H | acac | | |
| 5'-412Y | Pd | 0 | 5' | OL | H | $^tC_4H_9$ | H | $CH_3$ | H | — | — | |
| 5'-413 | Pd | 1 | 5' | OL | H | $^tC_4H_9$ | H | $^tC_4H_9$ | H | pic | | |
| 5'-413X | Pd | 1 | 5' | OL | H | $^tC_4H_9$ | H | $^tC_4H_9$ | H | acac | | |
| 5'-413Y | Pd | 0 | 5' | OL | H | $^tC_4H_9$ | H | $^tC_4H_9$ | H | — | — | |
| 5'-414 | Pd | 1 | 5' | OL | $CH_3$ | $^nC_4H_9$ | H | $CH_3$ | H | pic | | |
| 5'-414X | Pd | 1 | 5' | OL | $CH_3$ | $^nC_4H_9$ | H | $CH_3$ | H | acac | | |
| 5'-414Y | Pd | 0 | 5' | OL | $CH_3$ | $^nC_4H_9$ | H | $CH_3$ | H | — | — | |
| 5'-415 | Pd | 1 | 5' | OL | $CH_3$ | $^tC_4H_9$ | H | $CH_3$ | H | pic | | |
| 5'-415X | Pd | 1 | 5' | OL | $CH_3$ | $^tC_4H_9$ | H | $CH_3$ | H | acac | | |
| 5'-415Y | Pd | 0 | 5' | OL | $CH_3$ | $^tC_4H_9$ | H | $CH_3$ | H | — | — | |
| 5'-416 | Pd | 1 | 5' | OL | H | H | H | $CH_3$ | H | pic | | |
| 5'-416X | Pd | 1 | 5' | OL | H | H | H | $CH_3$ | H | acac | | |
| 5'-416Y | Pd | 0 | 5' | OL | H | H | H | $CH_3$ | H | — | — | |
| 5'-417 | Pd | 1 | 5' | OL | H | $^nC_4H_9$ | $CH_3$ | $^tC_4H_9$ | H | pic | | |
| 5'-417X | Pd | 1 | 5' | OL | H | $^nC_4H_9$ | $CH_3$ | $^tC_4H_9$ | H | acac | | |
| 5'-417Y | Pd | 0 | 5' | OL | H | $^nC_4H_9$ | $CH_3$ | $^tC_4H_9$ | H | — | — | |
| 5'-418 | Pd | 1 | 5' | OL | H | $^tC_4H_9$ | $CH_3$ | $^tC_4H_9$ | H | pic | | |
| 5'-418X | Pd | 1 | 5' | OL | H | $^tC_4H_9$ | $CH_3$ | $^tC_4H_9$ | H | acac | | |
| 5'-418Y | Pd | 0 | 5' | OL | H | $^tC_4H_9$ | $CH_3$ | $^tC_4H_9$ | H | — | — | |
| 5'-419 | Pd | 1 | 5' | OL | —$CH_2CH_2CH_2$— | | H | $CH_3$ | H | pic | | |
| 5'-419X | Pd | 1 | 5' | OL | —$CH_2CH_2CH_2$— | | H | $CH_3$ | H | acac | | |
| 5'-419Y | Pd | 0 | 5' | OL | —$CH_2CH_2CH_2$— | | H | $CH_3$ | H | — | — | |
| 5'-420 | Pd | 1 | 5' | OL | —$CH_2CH_2CH_2$— | | H | $^tC_4H_9$ | H | pic | | |
| 5'-420X | Pd | 1 | 5' | OL | —$CH_2CH_2CH_2$— | | H | $^tC_4H_9$ | H | acac | | |
| 5'-420Y | Pd | 0 | 5' | OL | —$CH_2CH_2CH_2$— | | H | $^tC_4H_9$ | H | — | — | |

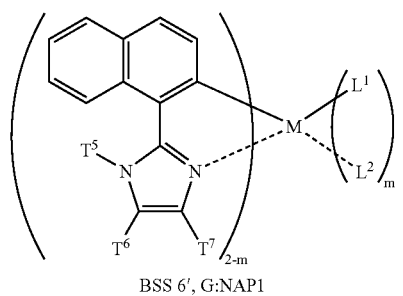
BSS 6', G:NAP1
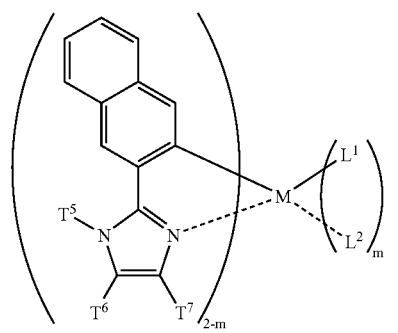
BSS 6', G:NAP2
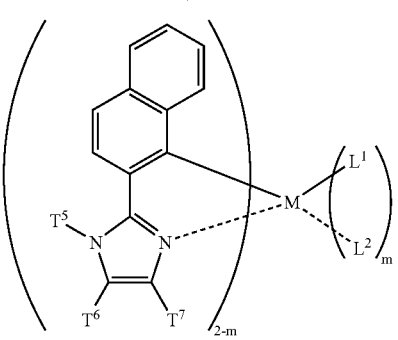
BSS 6', G:NAP3
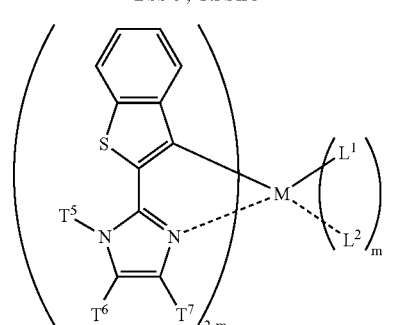
BSS 6', G:TB
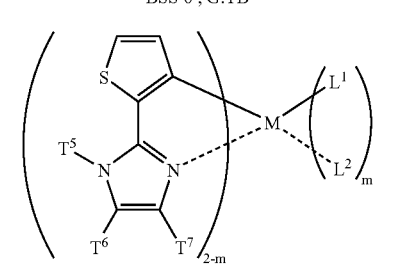
BSS 6', G:TF
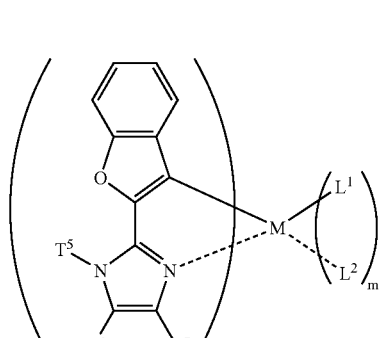
BSS 6', G:OB
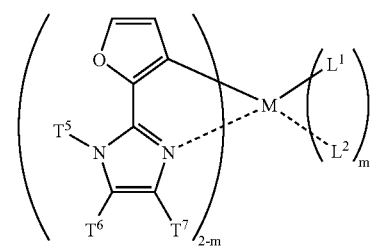
BSS 6', G:Fu
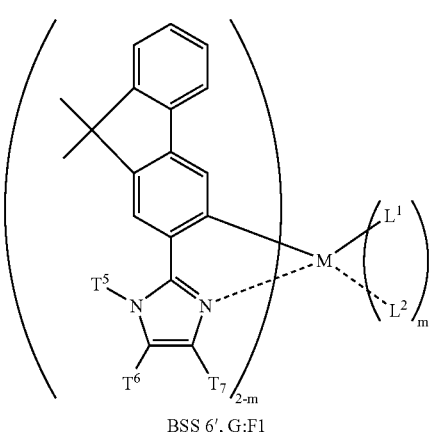
BSS 6', G:Fl
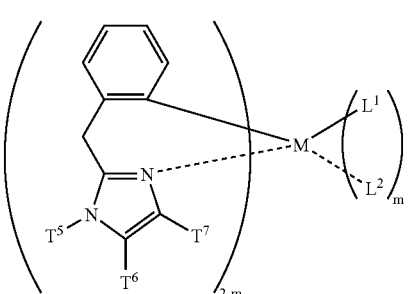
BSS 6', G:Bz -continued

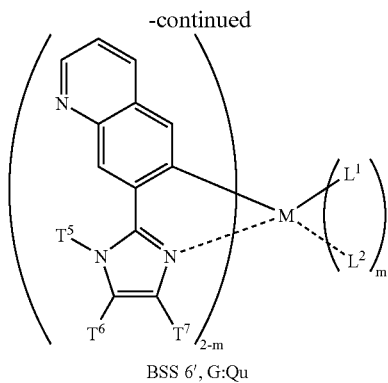

BSS 6', G:Qu

-continued

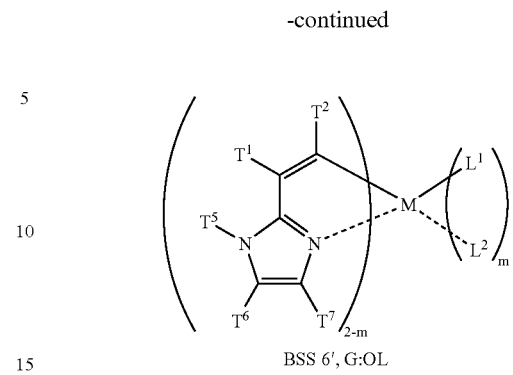

BSS 6', G:OL

TABLE 55

| No. | M | m | BSS | SS G | $T^1$ | $T^2$ | $T^5$ | $T^6$ | $T^7$ | $L^1$ $L^2$ |
|---|---|---|---|---|---|---|---|---|---|---|
| 6'-304 | Pd | 1 | 6' | Nap1 | — | — | $CH_3$ | H | H | pic |
| 6'-304X | Pd | 1 | 6' | Nap1 | — | — | $CH_3$ | H | H | acac |
| 6'-304Y | Pd | 0 | 6' | Nap1 | — | — | $CH_3$ | H | H | — — |
| 6'-305 | Pd | 1 | 6' | Nap1 | — | — | $^tC_4H_9$ | H | H | pic |
| 6'-305X | Pd | 1 | 6' | Nap1 | — | — | $^tC_4H_9$ | H | H | acac |
| 6'-305Y | Pd | 0 | 6' | Nap1 | — | — | $^tC_4H_9$ | H | H | — — |
| 6'-306 | Pd | 1 | 6' | Nap2 | — | — | $CH_3$ | H | H | pic |
| 6'-306X | Pd | 1 | 6' | Nap2 | — | — | $CH_3$ | H | H | acac |
| 6'-306Y | Pd | 0 | 6' | Nap2 | — | — | $CH_3$ | H | H | — — |
| 6'-307 | Pd | 1 | 6' | Nap2 | — | — | $^tC_4H_9$ | H | H | pic |
| 6'-307X | Pd | 1 | 6' | Nap2 | — | — | $^tC_4H_9$ | H | H | acac |
| 6'-307Y | Pd | 0 | 6' | Nap2 | — | — | $^tC_4H_9$ | H | H | — — |
| 6'-308 | Pd | 1 | 6' | Nap3 | — | — | $CH_3$ | H | H | pic |
| 6'-308X | Pd | 1 | 6' | Nap3 | — | — | $CH_3$ | H | H | acac |
| 6'-308Y | Pd | 0 | 6' | Nap3 | — | — | $CH_3$ | H | H | — — |
| 6'-309 | Pd | 1 | 6' | Nap3 | — | — | $^tC_4H_9$ | H | H | pic |
| 6'-309X | Pd | 1 | 6' | Nap3 | — | — | $^tC_4H_9$ | H | H | acac |
| 6'-309Y | Pd | 0 | 6' | Nap3 | — | — | $^tC_4H_9$ | H | H | — — |
| 6'-310 | Pd | 1 | 6' | TB | — | — | $CH_3$ | H | H | pic |
| 6'-310X | Pd | 1 | 6' | TB | — | — | $CH_3$ | H | H | acac |
| 6'-310Y | Pd | 0 | 6' | TB | — | — | $CH_3$ | H | H | — — |
| 6'-311 | Pd | 1 | 6' | TB | — | — | $^tC_4H_9$ | H | H | pic |
| 6'-311X | Pd | 1 | 6' | TB | — | — | $^tC_4H_9$ | H | H | acac |
| 6'-311Y | Pd | 0 | 6' | TB | — | — | $^tC_4H_9$ | H | H | — — |
| 6'-312 | Pd | 1 | 6' | TF | — | — | $CH_3$ | H | H | pic |
| 6'-312X | Pd | 1 | 6' | TF | — | — | $CH_3$ | H | H | acac |
| 6'-312Y | Pd | 0 | 6' | TF | — | — | $CH_3$ | H | H | — — |
| 6'-313 | Pd | 1 | 6' | TF | — | — | $^tC_4H_9$ | H | H | pic |
| 6'-313X | Pd | 1 | 6' | TF | — | — | $^tC_4H_9$ | H | H | acac |
| 6'-313Y | Pd | 0 | 6' | TF | — | — | $^tC_4H_9$ | H | H | — — |
| 6'-314 | Pd | 1 | 6' | OB | — | — | $CH_3$ | H | H | pic |
| 6'-314X | Pd | 1 | 6' | OB | — | — | $CH_3$ | H | H | acac |
| 6'-314Y | Pd | 0 | 6' | OB | — | — | $CH_3$ | H | H | — — |
| 6'-315 | Pd | 1 | 6' | OB | — | — | $^tC_4H_9$ | H | H | pic |
| 6'-315X | Pd | 1 | 6' | OB | — | — | $^tC_4H_9$ | H | H | acac |
| 6'-315Y | Pd | 0 | 6' | OB | — | — | $^tC_4H_9$ | H | H | — — |
| 6'-316 | Pd | 1 | 6' | Fu | — | — | $CH_3$ | H | H | pic |
| 6'-316X | Pd | 1 | 6' | Fu | — | — | $CH_3$ | H | H | acac |
| 6'-316Y | Pd | 0 | 6' | Fu | — | — | $CH_3$ | H | H | — — |
| 6'-317 | Pd | 1 | 6' | Fu | — | — | $^tC_4H_9$ | H | H | pic |
| 6'-317X | Pd | 1 | 6' | Fu | — | — | $^tC_4H_9$ | H | H | acac |
| 6'-317Y | Pd | 0 | 6' | Fu | — | — | $^tC_4H_9$ | H | H | — — |
| 6'-318 | Pd | 1 | 6' | Fl | — | — | $CH_3$ | H | H | pic |
| 6'-318X | Pd | 1 | 6' | Fl | — | — | $CH_3$ | H | H | acac |
| 6'-318Y | Pd | 0 | 6' | Fl | — | — | $CH_3$ | H | H | — — |
| 6'-319 | Pd | 1 | 6' | Fl | — | — | $^tC_4H_9$ | H | H | pic |
| 6'-319X | Pd | 1 | 6' | Fl | — | — | $^tC_4H_9$ | H | H | acac |
| 6'-319Y | Pd | 0 | 6' | Fl | — | — | $^tC_4H_9$ | H | H | — — |
| 6'-320 | Pd | 1 | 6' | Bz | — | — | $CH_3$ | H | H | pic |
| 6'-320X | Pd | 1 | 6' | Bz | — | — | $CH_3$ | H | H | acac |
| 6'-320Y | Pd | 0 | 6' | Bz | — | — | $CH_3$ | H | H | — — |
| 6'-321 | Pd | 1 | 6' | Bz | — | — | $^tC_4H_9$ | H | H | pic |
| 6'-321X | Pd | 1 | 6' | Bz | — | — | $^tC_4H_9$ | H | H | acac |
| 6'-321Y | Pd | 0 | 6' | Bz | — | — | $^tC_4H_9$ | H | H | — — |
| 6'-322 | Pd | 1 | 6' | Qu | — | — | $CH_3$ | H | H | pic |

TABLE 55-continued

| No. | M | m | BSS | SS G | $T^1$ | $T^2$ | $T^5$ | $T^6$ | $T^7$ | $L^1$ | $L^2$ |
|---|---|---|---|---|---|---|---|---|---|---|---|
| 6'-322X | Pd | 1 | 6' | Qu | — | — | $CH_3$ | H | H | acac | |
| 6'-322Y | Pd | 0 | 6' | Qu | — | — | $CH_3$ | H | H | — | — |
| 6'-323 | Pd | 1 | 6' | Qu | — | — | $^tC_4H_9$ | H | H | pic | |
| 6'-323X | Pd | 1 | 6' | Qu | — | — | $^tC_4H_9$ | H | H | acac | |
| 6'-323Y | Pd | 0 | 6' | Qu | — | — | $^tC_4H_9$ | H | H | — | — |
| 6'-324 | Pd | 1 | 6' | OL | H | $^nC_4H_9$ | $CH_3$ | H | H | pic | |
| 6'-324X | Pd | 1 | 6' | OL | H | $^nC_4H_9$ | $CH_3$ | H | H | acac | |
| 6'-324Y | Pd | 0 | 6' | OL | H | $^nC_4H_9$ | $CH_3$ | H | H | — | — |
| 6'-325 | Pd | 1 | 6' | OL | H | $^nC_4H_9$ | $^tC_4H_9$ | H | H | pic | |
| 6'-325X | Pd | 1 | 6' | OL | H | $^nC_4H_9$ | $^tC_4H_9$ | H | H | acac | |
| 6'-325Y | Pd | 0 | 6' | OL | H | $^nC_4H_9$ | $^tC_4H_9$ | H | H | — | — |
| 6'-326 | Pd | 1 | 6' | OL | H | $^tC_4H_9$ | $CH_3$ | H | H | pic | |
| 6'-326X | Pd | 1 | 6' | OL | H | $^tC_4H_9$ | $CH_3$ | H | H | acac | |
| 6'-326Y | Pd | 0 | 6' | OL | H | $^tC_4H_9$ | $CH_3$ | H | H | — | — |
| 6'-327 | Pd | 1 | 6' | OL | H | $^tC_4H_9$ | $^tC_4H_9$ | H | H | pic | |
| 6'-327X | Pd | 1 | 6' | OL | H | $^tC_4H_9$ | $^tC_4H_9$ | H | H | acac | |
| 6'-327Y | Pd | 0 | 6' | OL | H | $^tC_4H_9$ | $^tC_4H_9$ | H | H | — | — |
| 6'-328 | Pd | 1 | 6' | OL | $CH_3$ | $^nC_4H_9$ | $CH_3$ | H | H | pic | |
| 6'-328X | Pd | 1 | 6' | OL | $CH_3$ | $^nC_4H_9$ | $CH_3$ | H | H | acac | |
| 6'-328Y | Pd | 0 | 6' | OL | $CH_3$ | $^nC_4H_9$ | $CH_3$ | H | H | — | — |
| 6'-329 | Pd | 1 | 6' | OL | $CH_3$ | $^tC_4H_9$ | $CH_3$ | H | H | pic | |
| 6'-329X | Pd | 1 | 6' | OL | $CH_3$ | $^tC_4H_9$ | $CH_3$ | H | H | acac | |
| 6'-329Y | Pd | 0 | 6' | OL | $CH_3$ | $^tC_4H_9$ | $CH_3$ | H | H | — | — |
| 6'-330 | Pd | 1 | 6' | OL | H | H | $CH_3$ | H | H | pic | |
| 6'-330X | Pd | 1 | 6' | OL | H | H | $CH_3$ | H | H | acac | |
| 6'-330Y | Pd | 0 | 6' | OL | H | H | $CH_3$ | H | H | — | — |
| 6'-331 | Pd | 1 | 6' | OL | —$CH_2CH_2CH_2$— | | $CH_3$ | H | H | pic | |
| 6'-331X | Pd | 1 | 6' | OL | —$CH_2CH_2CH_2$— | | $CH_3$ | H | H | acac | |
| 6'-331Y | Pd | 0 | 6' | OL | —$CH_2CH_2CH_2$— | | $CH_3$ | H | H | — | — |
| 6'-332 | Pd | 1 | 6' | OL | —$CH_2CH_2CH_2$— | | $^tC_4H_9$ | H | H | pic | |
| 6'-332X | Pd | 1 | 6' | OL | —$CH_2CH_2CH_2$— | | $^tC_4H_9$ | H | H | acac | |
| 6'-332Y | Pd | 0 | 6' | OL | —$CH_2CH_2CH_2$— | | $^tC_4H_9$ | H | H | — | — |

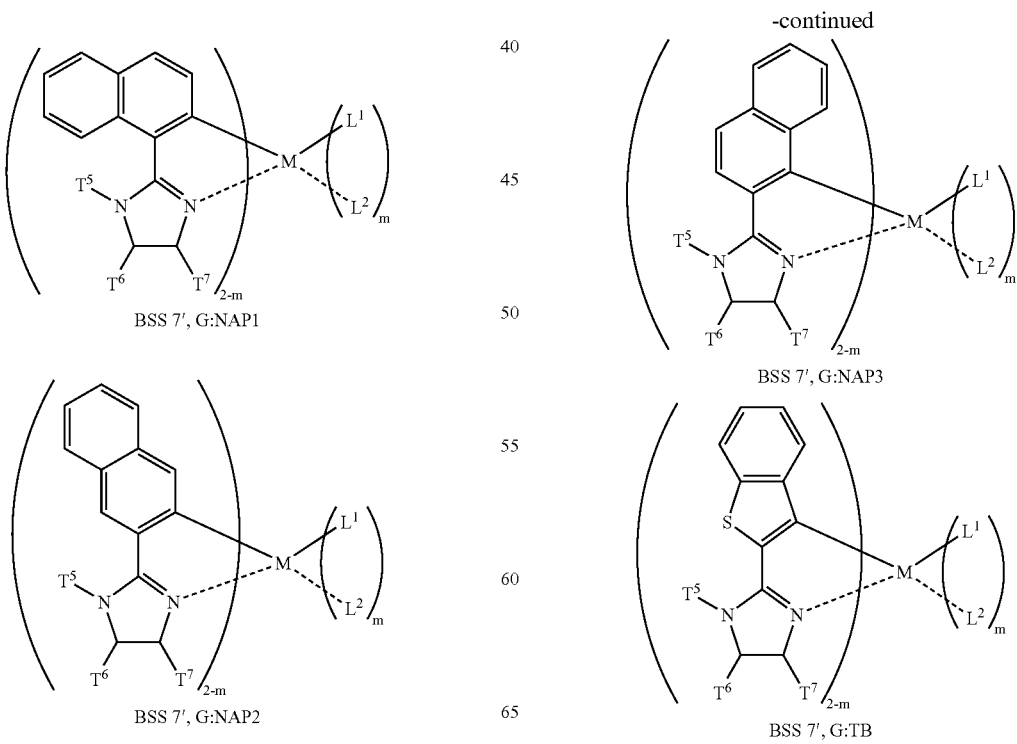

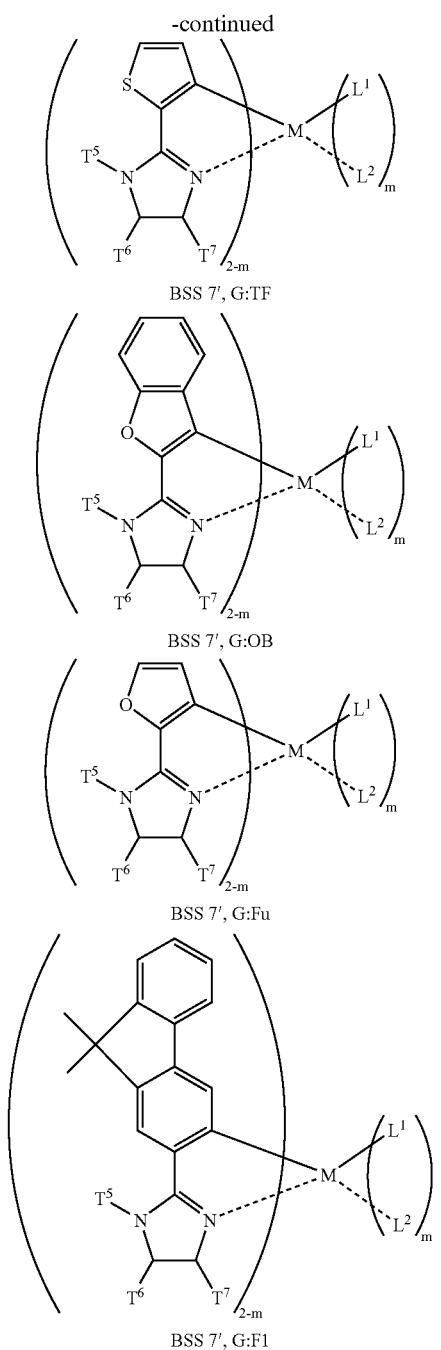
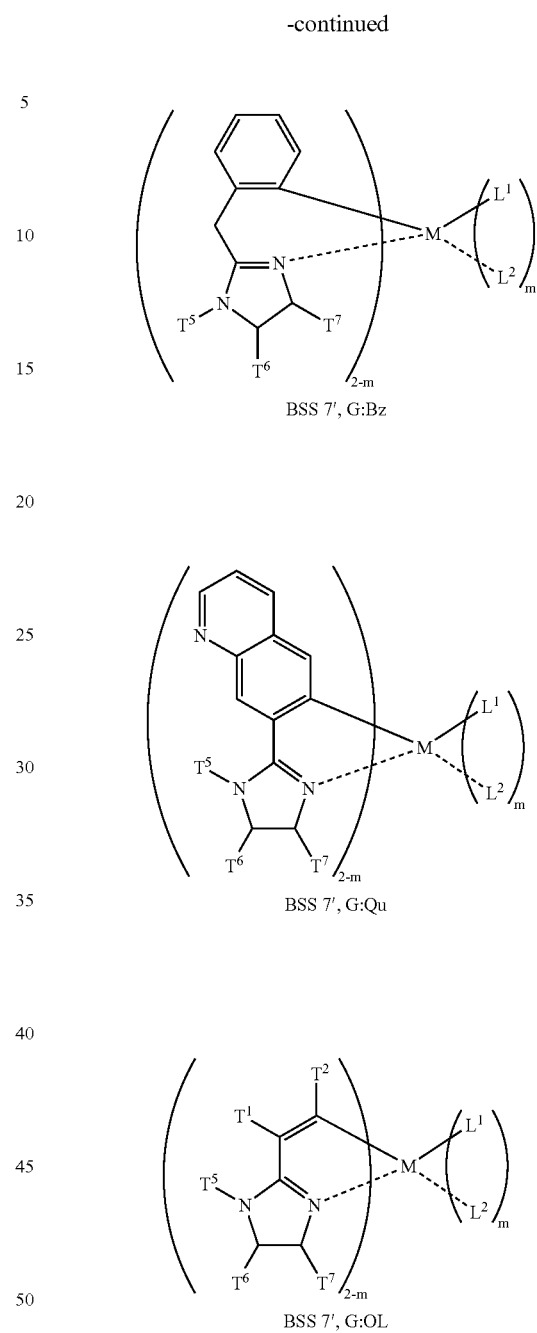
TABLE 56
| No. | M | m | BSS | SS | G | T¹ | T² | T⁵ | T⁶ | T⁷ | L¹ | L² |
|---|---|---|---|---|---|---|---|---|---|---|---|---|
| 7'-304 | Pd | 1 | 7' | | Nap1 | — | — | CH$_3$ | H | H | pic | |
| 7'-304X | Pd | 1 | 7' | | Nap1 | — | — | CH$_3$ | H | H | acac | |
| 7'-304Y | Pd | 0 | 7' | | Nap1 | — | — | CH$_3$ | H | H | — | — |
| 7'-305 | Pd | 1 | 7' | | Nap1 | — | — | $^tC_4H_9$ | H | H | pic | |
| 7'-305X | Pd | 1 | 7' | | Nap1 | — | — | $^tC_4H_9$ | H | H | acac | |
| 7'-305Y | Pd | 0 | 7' | | Nap1 | — | — | $^tC_4H_9$ | H | H | — | — |
| 7'-306 | Pd | 1 | 7' | | Nap2 | — | — | CH$_3$ | H | H | pic | |
| 7'-306X | Pd | 1 | 7' | | Nap2 | — | — | CH$_3$ | H | H | acac | |
| 7'-306Y | Pd | 0 | 7' | | Nap2 | — | — | CH$_3$ | H | H | — | — |
| 7'-307 | Pd | 1 | 7' | | Nap2 | — | — | $^tC_4H_9$ | H | H | pic | |

TABLE 56-continued

| No. | M | m | BSS | SS G | T¹ | T² | T⁵ | T⁶ | T⁷ | L¹ | L² |
|---|---|---|---|---|---|---|---|---|---|---|---|
| 7'-307X | Pd | 1 | 7' | Nap2 | — | — | $^tC_4H_9$ | H | H | acac | |
| 7'-307Y | Pd | 0 | 7' | Nap2 | — | — | $^tC_4H_9$ | H | H | — | — |
| 7'-308 | Pd | 1 | 7' | Nap3 | — | — | $CH_3$ | H | H | pic | |
| 7'-308X | Pd | 1 | 7' | Nap3 | — | — | $CH_3$ | H | H | acac | |
| 7'-308Y | Pd | 0 | 7' | Nap3 | — | — | $CH_3$ | H | H | — | — |
| 7'-309 | Pd | 1 | 7' | Nap3 | — | — | $^tC_4H_9$ | H | H | pic | |
| 7'-309X | Pd | 1 | 7' | Nap3 | — | — | $^tC_4H_9$ | H | H | acac | |
| 7'-309Y | Pd | 0 | 7' | Nap3 | — | — | $^tC_4H_9$ | H | H | — | — |
| 7'-310 | Pd | 1 | 7' | TB | — | — | $CH_3$ | H | H | pic | |
| 7'-310X | Pd | 1 | 7' | TB | — | — | $CH_3$ | H | H | acac | |
| 7'-310Y | Pd | 0 | 7' | TB | — | — | $CH_3$ | H | H | — | — |
| 7'-311 | Pd | 1 | 7' | TB | — | — | $^tC_4H_9$ | H | H | pic | |
| 7'-311X | Pd | 1 | 7' | TB | — | — | $^tC_4H_9$ | H | H | acac | |
| 7'-311Y | Pd | 0 | 7' | TB | — | — | $^tC_4H_9$ | H | H | — | — |
| 7'-312 | Pd | 1 | 7' | TF | — | — | $CH_3$ | H | H | pic | |
| 7'-312X | Pd | 1 | 7' | TF | — | — | $CH_3$ | H | H | acac | |
| 7'-312Y | Pd | 0 | 7' | TF | — | — | $CH_3$ | H | H | — | — |
| 7'-313 | Pd | 1 | 7' | TF | — | — | $^tC_4H_9$ | H | H | pic | |
| 7'-313X | Pd | 1 | 7' | TF | — | — | $^tC_4H_9$ | H | H | acac | |
| 7'-313Y | Pd | 0 | 7' | TF | — | — | $^tC_4H_9$ | H | H | — | — |
| 7'-314 | Pd | 1 | 7' | OB | — | — | $CH_3$ | H | H | pic | |
| 7'-314X | Pd | 1 | 7' | OB | — | — | $CH_3$ | H | H | acac | |
| 7'-314Y | Pd | 0 | 7' | OB | — | — | $CH_3$ | H | H | — | — |
| 7'-315 | Pd | 1 | 7' | OB | — | — | $^tC_4H_9$ | H | H | pic | |
| 7'-315X | Pd | 1 | 7' | OB | — | — | $^tC_4H_9$ | H | H | acac | |
| 7'-315Y | Pd | 0 | 7' | OB | — | — | $^tC_4H_9$ | H | H | — | — |
| 7'-316 | Pd | 1 | 7' | Fu | — | — | $CH_3$ | H | H | pic | |
| 7'-316X | Pd | 1 | 7' | Fu | — | — | $CH_3$ | H | H | acac | |
| 7'-316Y | Pd | 0 | 7' | Fu | — | — | $CH_3$ | H | H | — | — |
| 7'-317 | Pd | 1 | 7' | Fu | — | — | $^tC_4H_9$ | H | H | pic | |
| 7'-317X | Pd | 1 | 7' | Fu | — | — | $^tC_4H_9$ | H | H | acac | |
| 7'-317Y | Pd | 0 | 7' | Fu | — | — | $^tC_4H_9$ | H | H | — | — |
| 7'-318 | Pd | 1 | 7' | Fl | — | — | $CH_3$ | H | H | pic | |
| 7'-318X | Pd | 1 | 7' | Fl | — | — | $CH_3$ | H | H | acac | |
| 7'-318Y | Pd | 0 | 7' | Fl | — | — | $CH_3$ | H | H | — | — |
| 7'-319 | Pd | 1 | 7' | Fl | — | — | $^tC_4H_9$ | H | H | pic | |
| 7'-319X | Pd | 1 | 7' | Fl | — | — | $^tC_4H_9$ | H | H | acac | |
| 7'-319Y | Pd | 0 | 7' | Fl | — | — | $^tC_4H_9$ | H | H | — | — |
| 7'-320 | Pd | 1 | 7' | Bz | — | — | $CH_3$ | H | H | pic | |
| 7'-320X | Pd | 1 | 7' | Bz | — | — | $CH_3$ | H | H | acac | |
| 7'-320Y | Pd | 0 | 7' | Bz | — | — | $CH_3$ | H | H | — | — |
| 7'-321 | Pd | 1 | 7' | Bz | — | — | $^tC_4H_9$ | H | H | pic | |
| 7'-321X | Pd | 1 | 7' | Bz | — | — | $^tC_4H_9$ | H | H | acac | |
| 7'-321Y | Pd | 0 | 7' | Bz | — | — | $^tC_4H_9$ | H | H | — | — |
| 7'-322 | Pd | 1 | 7' | Qu | — | — | $CH_3$ | H | H | pic | |
| 7'-322X | Pd | 1 | 7' | Qu | — | — | $CH_3$ | H | H | acac | |
| 7'-322Y | Pd | 0 | 7' | Qu | — | — | $CH_3$ | H | H | — | — |
| 7'-323 | Pd | 1 | 7' | Qu | — | — | $^tC_4H_9$ | H | H | pic | |
| 7'-323X | Pd | 1 | 7' | Qu | — | — | $^tC_4H_9$ | H | H | acac | |
| 7'-323Y | Pd | 0 | 7' | Qu | — | — | $^tC_4H_9$ | H | H | — | — |
| 7'-324 | Pd | 1 | 7' | OL | H | $^nC_4H_9$ | $CH_3$ | H | H | pic | |
| 7'-324X | Pd | 1 | 7' | OL | H | $^nC_4H_9$ | $CH_3$ | H | H | acac | |
| 7'-324Y | Pd | 0 | 7' | OL | H | $^nC_4H_9$ | $CH_3$ | H | H | — | — |
| 7'-325 | Pd | 1 | 7' | OL | H | $^nC_4H_9$ | $^tC_4H_9$ | H | H | pic | |
| 7'-325X | Pd | 1 | 7' | OL | H | $^nC_4H_9$ | $^tC_4H_9$ | H | H | acac | |
| 7'-325Y | Pd | 0 | 7' | OL | H | $^nC_4H_9$ | $^tC_4H_9$ | H | H | — | — |
| 7'-326 | Pd | 1 | 7' | OL | H | $^tC_4H_9$ | $CH_3$ | H | H | pic | |
| 7'-326X | Pd | 1 | 7' | OL | H | $^tC_4H_9$ | $CH_3$ | H | H | acac | |
| 7'-326Y | Pd | 0 | 7' | OL | H | $^tC_4H_9$ | $CH_3$ | H | H | — | — |
| 7'-327 | Pd | 1 | 7' | OL | H | $^tC_4H_9$ | $^tC_4H_9$ | H | H | pic | |
| 7'-327X | Pd | 1 | 7' | OL | H | $^tC_4H_9$ | $^tC_4H_9$ | H | H | acac | |
| 7'-327Y | Pd | 0 | 7' | OL | H | $^tC_4H_9$ | $^tC_4H_9$ | H | H | — | — |
| 7'-328 | Pd | 1 | 7' | OL | CH3 | $^nC_4H_9$ | $CH_3$ | H | H | pic | |
| 7'-328X | Pd | 1 | 7' | OL | $CH_3$ | $^nC_4H_9$ | $CH_3$ | H | H | acac | |
| 7'-328Y | Pd | 0 | 7' | OL | CH3 | $^nC_4H_9$ | $CH_3$ | H | H | — | — |
| 7'-329 | Pd | 1 | 7' | OL | $CH_3$ | $^tC_4H_9$ | $CH_3$ | H | H | pic | |
| 7'-329X | Pd | 1 | 7' | OL | $CH_3$ | $^tC_4H_9$ | $CH_3$ | H | H | acac | |
| 7'-329Y | Pd | 0 | 7' | OL | $CH_3$ | $^tC_4H_9$ | $CH_3$ | H | H | — | — |
| 7'-330 | Pd | 1 | 7' | OL | H | H | $CH_3$ | H | H | pic | |
| 7'-330X | Pd | 1 | 7' | OL | H | H | $CH_3$ | H | H | acac | |
| 7'-330Y | Pd | 0 | 7' | OL | H | H | $CH_3$ | H | H | — | — |
| 7'-331 | Pd | 1 | 7' | OL | —$CH_2CH_2CH_2$— | | $CH_3$ | H | H | pic | |
| 7'-331X | Pd | 1 | 7' | OL | —$CH_2CH_2CH_2$— | | $CH_3$ | H | H | acac | |
| 7'-331Y | Pd | 0 | 7' | OL | —$CH_2CH_2CH_2$— | | $CH_3$ | H | H | — | — |

TABLE 56-continued

| No. | M | m | BSS | SS G | T¹ | T² | T⁵ | T⁶ | T⁷ | L¹ | L² |
|---|---|---|---|---|---|---|---|---|---|---|---|
| 7'-332 | Pd | 1 | 7' | OL | —CH$_2$CH$_2$CH$_2$— | $^t$C$_4$H$_9$ | H | H | | pic | |
| 7'-332X | Pd | 1 | 7' | OL | —CH$_2$CH$_2$CH$_2$— | $^t$C$_4$H$_9$ | H | H | | acac | |
| 7'-332Y | Pd | 0 | 7' | OL | —CH$_2$CH$_2$CH$_2$— | $^t$C$_4$H$_9$ | H | H | | — | — |

The metal complex compound of the present invention is preferably a material for a light emitting element and in particular, more preferably a material for the organic EL device.

The present invention also provides an organic EL device which comprises at least one organic thin film layer sandwiched between a pair of electrode consisting of an anode and a cathode, wherein the organic thin film layer comprises the above metal complex compound of the present invention, which emits light by applying an electric voltage between the pair of electrode.

With regard to the amount of the metal complex compound of the present invention contained in the organic thin film layer, it is usually 0.1 to 100% by weight, preferably 1 to 30% by weight of total mass of the light emitting layer.

It is preferable for the organic EL device of the present invention that the light emitting layer comprises the metal complex compound of the present invention. Further, the light emitting layer is usually formed to a thin film by means of vapor deposition process or coating process, however, it is preferable that the layer comprising the metal complex compound of the present invention is formed into film by coating process because it simplifies the production process.

In the organic EL device of the present invention, a monolayer-type organic thin layer consists of a light emitting layer, which comprises the metal complex compound of the present invention. Typical examples of the construction of the organic EL device include (an anode/a hole injecting layer (a hole transporting layer)/a light emitting layer/a cathode); (an anode/a light emitting layer/an electron injecting layer (an electron transporting layer)/a cathode); and (an anode/a hole injecting layer (a hole transporting layer)/a light emitting layer/an electron injecting layer (an electron transporting layer)/(a cathode).

The anode in the organic EL device covers a role of injecting holes into a hole injecting layer, a hole transporting layer or into a light emitting layer, and as the material for the anode, metals, alloys, metal oxides, electroconductive compounds, or these mixtures may be employable. Specific examples of the material for the anode include electroconductive metal oxides such as tin oxide, zinc oxide, indium oxide, indium tin oxide (ITO), etc.; metals such as gold, silver, chromium, nickel, etc.; mixtures or laminated materials of these electroconductive metal oxide and metals; inorganic electroconductive substance such as copper iodide, copper sulfide, etc.; organic electroconductive materials such as polyaniline, polythiophene, polypyrrole, etc.; and laminated materials of the above materials with ITO; preferably are the electroconductive metal oxides. Particularly, it is preferable to employ ITO from viewpoints such as productivity, enhanced electroconductivity, transparency, etc. Regarding with a film thickness of the anode, it is possible to be appropriately selected depending on the material.

With regard to the cathode, it covers a role of injecting electrons into an electron injecting layer, an electron transporting layer or into a light emitting layer. Specific examples of the material for the cathode include alkali metals (for example, Li, Na, K, etc.) and their fluoride or oxidate, alkaline earth metals (for example, Mg, Ca, etc.) and their fluoride or oxidate, gold, silver, lead, aluminum, sodium-potassium alloy or sodium-potassium mixed metals, lithium-aluminum alloy or lithium-aluminum mixed metals, magnesium-silver alloy or the magnesium-silver mixed metals, or rare earth metals such as indium, ytterbium, etc. Among those, preferable examples are aluminum, lithium-aluminum alloy or lithium-aluminum mixed metals, magnesium-silver alloy or magnesium-silver mixed metals, etc. The cathode may be a monolayer structure of the above material, and may be a laminated structure of the layer containing the above material. For example, the laminated structure such as aluminum/lithium fluoride, aluminum/lithium oxide or the like is preferable. Regarding with a film thickness of the cathode, it is possible to be appropriately selected depending on the material.

It may be appropriate that the hole injecting layer and the hole transporting layer of the organic EL device of the present invention have any function of injecting holes from the anode, transporting holes, or barriering the electrons injected from the cathode. Specific examples include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino substituted chalcone derivatives, styryl anthracene derivatives, fluorenone derivatives, hydrazone derivatives, stilbene derivatives, silazane derivatives, aromatic tertiary amine compounds, styryl amine compound, aromaticdimethylidene-based compounds, porphyrin-based compounds, polysilane-based compounds, poly(N-vinyl carbazole) derivatives, aniline-based copolymer; electroconductive polymer oligomer such as thiophene oligomer, polythiophene, etc.; organosilane derivatives, metal complex compound of the present invention, etc. The hole injecting layer and the hole transporting layer may be composed of single layer comprising one or more kind of these hole injecting materials and those hole transporting materials or may be laminated with themselves or a layer comprising another kind of compound.

It may be appropriate that the electron injecting layer and the electron transporting layer of the organic EL device of the present invention have any function of injecting electrons from the cathode, transporting electrons, or barriering the holes injected from the anode. Specific examples include triazole derivatives, oxazole derivatives, oxadiazole derivatives, imidazole derivatives, fluorenone derivatives, anthraquinodimethane derivatives, anthrone derivatives, diphenylchinone derivatives, thiopyrandioxide derivatives, carbodiimide derivatives, fluorenylidene methane derivatives, distyrylpyrazine derivatives; aromatic ring tetracarboxylic acid anhydride such as naphthalene, perylene, etc.; phthalocyanine derivatives, various metal complexes represented by metal complexes of 8-quinolinol derivatives or metal complexes having benzoxazole or benzothiazole as ligand; organosilane derivatives, metal complex compound of the present invention, etc. The electron injecting layer may be composed of single layer comprising one or more kind of these electron injecting materials or may be laminated with an electron injecting layer comprising another kind of compound.

It is preferable that the light emitting layer in the organic EL device of the present invention has functions capable of injecting holes from the anode or the hole injecting layer when an electric field is applied, of injecting electrons from the cathode or the electron injecting layer, of mobilizing the injected electric charges (electrons and holes) by means of the electric field, and of providing a space for recombination of the electrons and holes thereby urging the light emission. It is preferable for the organic EL device of the present invention that the light emitting layer at least comprises the metal complex compound of the present invention, and it may comprise a host material which employs the metal complex compound as a guest material. Examples of the above host material include such as those having a carbazole skeleton, those having a diarylamine skeleton, those having a pyridine skeleton, those having a pyrazine skeleton, those having a triazine skeleton, those having an arylsilane skeleton, etc. It is preferable that T1 (energy level in the minimum triplet excitation state) of the host material is larger than T1 level of the guest material. The host material may be either a low molecular weight compound or a high molecular weight compound. Further, the light emitting layer in which the above light emitting materials are doped into the above host materials can be formed by co-deposition of the host materials and the light emitting materials such as the above metal complex compound, etc.

In the organic EL device of the present invention, although a process for forming each layers are not particularly specified, various kinds of process such as a vacuum deposition process, a LB process, a resistance heating deposition process, an electron beam process, a sputtering process, a molecular lamination process, a coating process (a spin coating process, a casting process, a dip coating process), an ink-jet process, a printing process are employable and the coating process of applying the materials over a substrate is preferable in the present invention.

In the above coating process, preparing a coating solution by dissolving the metal complex compound of the present invention into a solvent, and by applying the coating solution over the surface of a predetermined layer (or, electrode), followed by drying may form the organic thin film layer. In the coating solution, a resin may be contained either by dissolved in a solvent or by dispersing into the solvent. Regarding with the resin, both non-conjugate high polymer (for example, polyvinylcarbazole) and conjugate high polymer (for example, polyolefin-based high polymer) are employable. Specific examples include polyvinylchloride, polycarbonate, polystyrene, polymethyl methacrylate, poly butylmethacrylate, polyester, polysulfone, polyphenylene oxide, polybutadiene, poly (N-vinyl carbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, etc.

EXAMPLES

The present invention will be described in more detail by reference to the following examples. However, it should be noted that these examples are only illustrative and not intended to limit the invention thereto.

Example 1

Synthesis of Metal complex Compound 1-1

The route for synthesis of Metal complex Compound 1-1 is illustrated as the following.

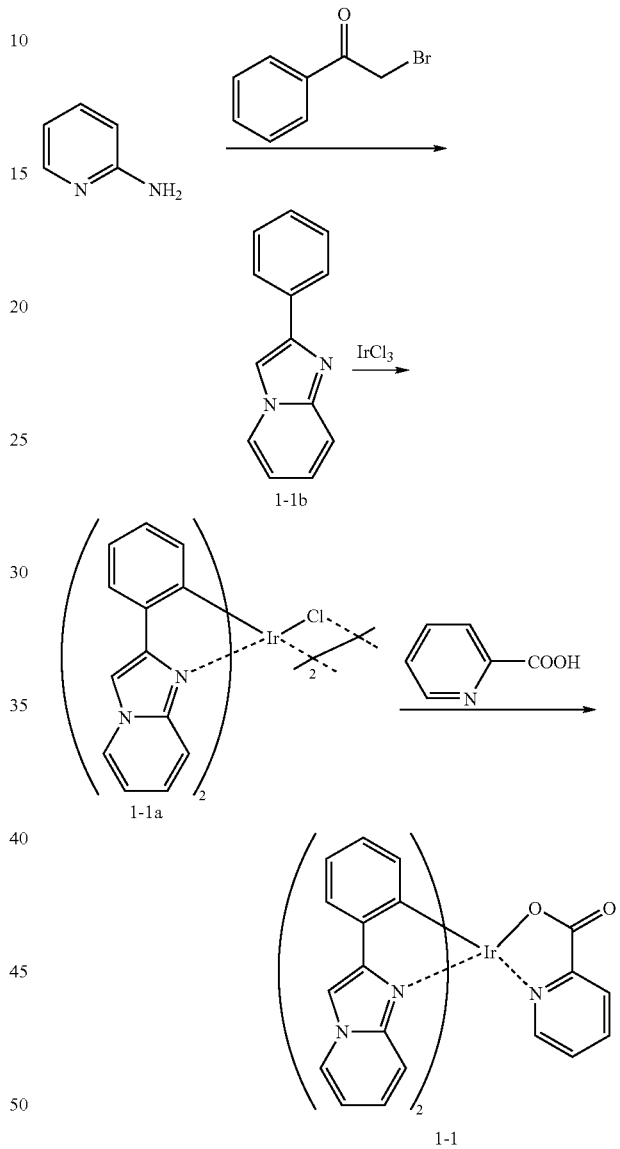

In the above route, the structural formula of Intermediate 1-1a expresses a dimer configuration.

(1) Synthesis of Intermediate 1-1b

Placing 2-aminopyridine in an amount of 3.5 g (36 mmol), α-bromoacetophenone in an amount of 7.2 g (36 mmol) and sodium hydrogen carbonate in an amount of 3.6 g (43 mmol) into a flask, the resultant mixture reacted among 120 milliliter of ethanol for 4 hours at the room temperature and subsequently for 2 hours under refluxing. Separating insoluble by filtration, the resultant filtrate was concentrated. Extracting with the use of methylene chloride in an amount of 150 milliliter, the resultant extract was washed three times using 200 milliliter of water. After drying an organic layer with the use of magnesium sulfide and removing the solvent, brown crystals were obtained. Refining the crystals by means of silicagel column (hexane/methylene chloride), 6.3 g of 2-phenylimidazo[1,2-a]pyridine Intermediate 1-1b as white crystals was obtained (yield: 90%). The white crystals were confirmed as the aimed compound from $^1$H-NMR spectrum. The measurement result is shown as follows:

$^1$H-NMR (CDCl$_3$): δ 7.8-8.3 (m, 4H), δ 7.0-8.3 (m, 5H), δ 0.6-6.9 (m, 1H)

(2) Synthesis of Intermediate 1-1a

Placing Intermediate 1-1b in an amount of 5.0 g (25.7 mmol) and IrCl$_3$ hydrate (available from Strem Chemicals, Inc.) in an amount of 1.9 g (6.4 mmol) into a flask, replacing the atmosphere with argon gas, and after pouring 2-ethoxy-ethanol in an amount of 40 milliliter, the resultant mixture was reacted for 15 hours under refluxing. A resultant yellow precipitation was separated by filtration, followed by washing twice with the use of ethanol in an amount of 5 milliliter. Further, it was dissolved in 150 milliliter of methylene chloride, and the resultant solution was washed with the use of HCl aqueous solution, followed by washing three times with the use of water. After drying the resultant solution with the use of magnesium sulfate, the solvent was distilled away and as a result, 1.39 g of Intermediate 1-1a as yellow crystals was obtained (yield: 35%).

(3) Synthesis of Metal Complex Compound 1-1

Placing Intermediate 1-1a in an amount of 1.39 g (1.13 mmol) and 2-pyridinecarboxylic acid in an amount of 0.55 g (4.52 mmol) into a flask, replacing the atmosphere with argon gas, and after pouring 1,2-dichloroethane in an amount of 20 milliliter, the resultant mixture was reacted for 17 hours under refluxing. Separating the resultant yellow precipitation, dissolving the precipitation into 400 milliliter of methylene chloride, it was washed three times using 150 milliliter of water. After drying the resultant solution with the use of magnesium sulfate, the solvent was distilled away and then, washing the resultant mixture with using a small amount of methylene chloride, 0.85 g of Metal complex Compound 1-1 as yellow crystals was obtained (yield: 54%). The yellow crystals were confirmed as the aimed compound from $^1$H-NMR spectrum and from the result in accordance with Field Desorption Mass Spectrum (FD-MS) analysis. The measurement result is shown as follows:

FD-MS: m/z=701

Further, by measuring phosphorus light (methylene chloride solution) of the resultant Metal complex Compound 1-1, it was found that λ max (wave length of peak light emission intensity) of phosphorus light was 580 nm.

Example 2

Synthesis of Metal Complex Compound 1-2

The route of synthesis of Metal complex Compound 1-2 is illustrated in the following.

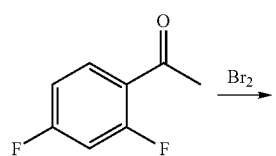

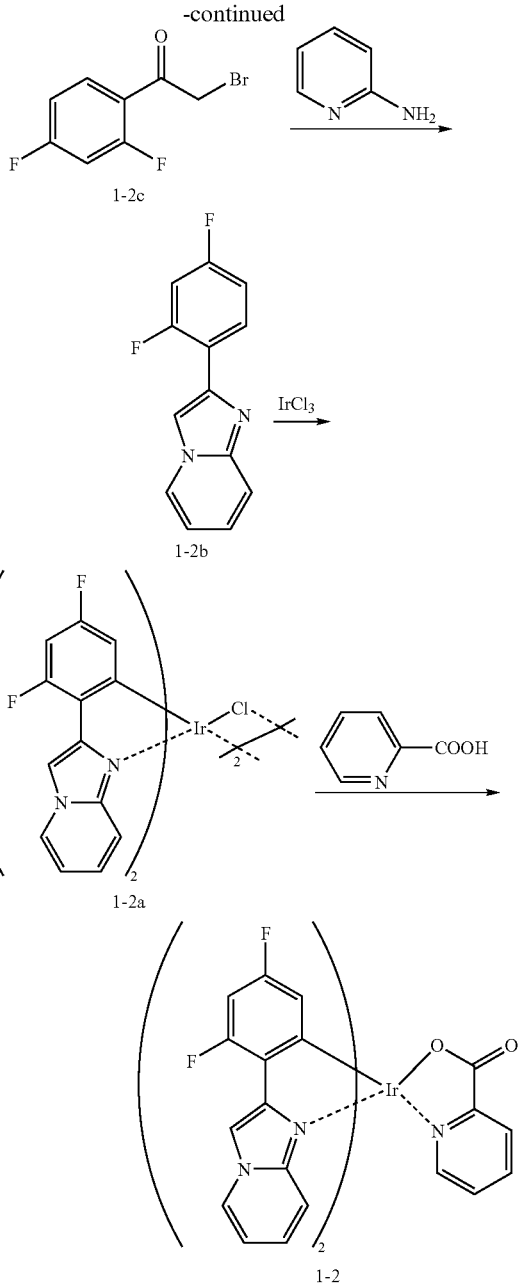

In the above route, the structural formula of Intermediate 1-1a expresses a dimer configuration.

(1) Synthesis of Intermediate 1-2c

While cooling acetic acid solution prepared by dissolving 25 g (160.1 mmol) of 2,4-difluorophenyl acetophenone in an amount of 50 milliliter down to 10° C. or cooler, 25.5 g (160.1 mmol) of bromine was dripped and the resultant solution reacted for 7 hours. Throwing the resultant solution into 300 milliliter of water, the solution was extracted with the use of methylene chloride. After drying an organic layer with the use of magnesium sulfide, the solvent was removed. Refining the resultant residues by means of silica column (hexane), 23.4 g of α-bromo-2,4-difluorophenyl acetophenone Intermediate 1-2c as brown oil was obtained (yield: 62%). The brown oil was confirmed as the aimed compound from $^1$H-NMR spectrum. The measurement result is shown as follows:

$^1$H-NMR (CDCl$_3$): δ 7.87-8.14 (m, 1H), δ 6.8-7.13 (m, 2H), δ 4.49 (d, 2H)

(2) Synthesis of Intermediate Product 1-2b

Placing 2-aminopyridine in an amount of 3.3 g (35.5 mmol), Intermediate 1-2c in an amount of 8.4 g (35.5 mmol) and sodium hydrogen carbonate in an amount of 3.6 g (43 mmol) into a flask, the resultant mixture reacted among 120 milliliter of ethanol for 4 hours at the room temperature and subsequently for 2 hours under refluxing. Separating insolubles by filtration, the resultant filtrate was concentrated. Extracting with the use of dichloromethane in an amount of 150 milliliter, the resultant extract was washed three times using 200 milliliter of water. After drying an organic layer with the use of magnesium sulfide and removing the solvent, brown crystals were obtained. Refining the crystals by means of silicagel column (hexane/methylene chloride), 7.3 g of 2-(2',4'-difluorophenyl)imidazo[1,2-a]pyridine Intermediate 1-2b was obtained (yield: 89%). The brown crystals were confirmed as the aimed compound from $^1$H-NMR spectrum. The measurement result is shown as follows:

$^1$H-NMR (CDCl$_3$): δ 7.9-8.45 (m, 3H), δ 7.5-7.7 (m, 1H), δ 6.7-7.28 (m, 4H)

(3) Synthesis of Intermediate 1-2a

Placing Intermediate 1-2b in an amount of 4.7 g (20.6 mmol) and IrCl$_3$ hydrate (available from Strem Chemicals, Inc.) in an amount of 1.53 g (5.1 mmol) into a flask, replacing the atmosphere with argon gas, and after pouring 2-ethoxyethanol in an amount of 25 milliliter, the resultant mixture was reacted for 15 hours under refluxing. A resultant pale yellow precipitation was separated by filtration, followed by washing twice with the use of ethanol in an amount of 5 milliliter. Further, it was dissolved in 150 milliliter of methylene chloride, and the resultant solution was washed three times with the use of HCl aqueous solution, followed by washing twice with the use of water. After drying the resultant solution with the use of magnesium sulfate, the solvent was distilled away and as a result, 1.39 g of Intermediate 1-2a as yellow crystals was obtained (yield: 35%).

(4) Synthesis of Metal Complex Compound 1-2

Placing Intermediate 1-2a in an amount of 1.39 g (1.13 mmol) and 2-picolinic acid in an amount of 0.55 g (4.52 mmol) into a flask, the atmosphere was replaced with argon gas. Pouring 20 milliliter of 1,2-dichloroethane into the resultant solution, it was reacted for 17 hours under refluxing. Separating the resultant yellow precipitation, dissolving the precipitation into 400 milliliter of methylene chloride, it was washed three times using 150 milliliter of water. After drying the resultant solution with the use of magnesium sulfate, the solvent was distilled away and then, washing the resultant mixture using a small amount of methylene chloride, 0.85 g of Metal complex Compound 1-2 as yellow crystals was obtained (yield: 54%). The yellow crystals were confirmed as the aimed compound from $^1$H-NMR spectrum and from the result in accordance with FD-MS analysis. The measurement result is shown as follows:

$^1$H-NMR (CDCl$_3$): δ 7.84-8.30 (m, 7H), δ 7.2-7.47 (m, 2H), δ 6.7-7.0.(m, 3H), δ 6.2-6.6 (m, 2H), δ 5.44-5.88 (m, 4H)

FD-MS: m/z=773

Further, by measuring phosphorus light (methylene chloride solution) of the resultant Metal complex Compound 1-2, it was found that λ max of phosphorus light was 529 nm.

Example 3

Synthesis of Metal Complex Compound 6-1

The route for synthesis of Metal complex Compound 6-1 is illustrated in the following.

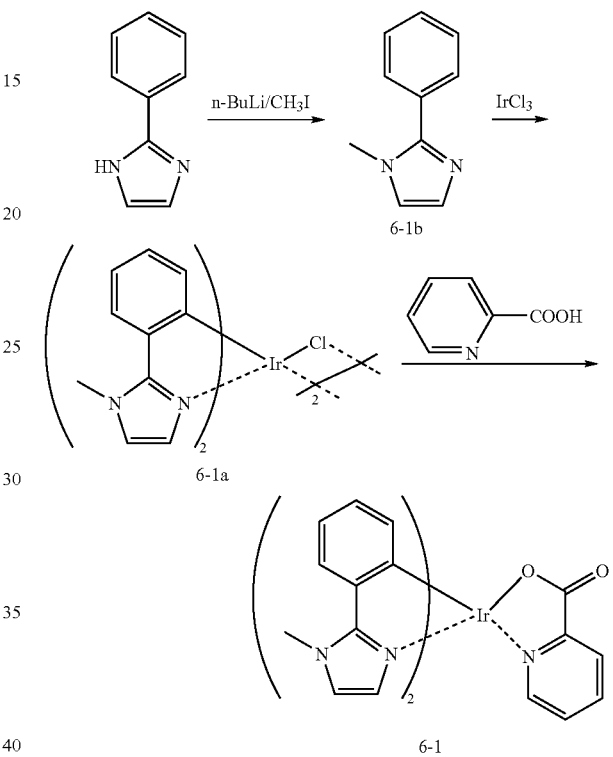

In the above route, the structural formula of Intermediate 6-1a expresses a dimer configuration.

(1) Synthesis of Intermediate 6-1b

Placing 2-phenylimidazole in an amount of 8.6 g (60 mmol) into a flask having a dropping funnel, and after replacing the atmosphere with argon gas, 180 milliliter of tetrahydrofuran was added. Under cooling with ice, n-butyllithium of 1.56 mol/liter in an amount of 39.1 milliliter (61 mmol) was dripped down into the solution spending 30 minutes and subsequently, 8.6 g (61 mmol) of methyl iodide dissolved into 10 milliliter of tetrahydrofuran was dripped down. After termination of dripping down, the resultant solution was reacted at the room temperature for 3 hours. Concentrating the reacted solution and extracting the resultant solid using 150 milliliter of methylene chloride, it was washed three times using 150 milliliter of water. After drying an organic layer with the use of magnesium sulfate, the solvent was removed. Refining the crystals by means of silicagel column (hexane/methylene chloride), 6.1 g of 1-methyl-2-phenylimidazo Intermediate 6-1b as white crystals was obtained (yield: 69%). The white crystals were confirmed as the aimed compound from $^1$H-NMR spectrum. The measurement result is shown as follows:

$^1$H-NMR (CDCl$_3$): δ 7.29-7.67 (m, 5H), δ 6.93-7.10 (m, 2H), δ 3.69 (s, 3H)

(2) Synthesis of Intermediate 6-1a

Placing Intermediate 6-1b in an amount of 4.1 g (26.2 mmol) and IrCl₃ hydrate (available from Strem Chemicals, Inc.) in an amount of 1.95 g (6.5 mmol) into a flask, replacing the atmosphere with argon gas, and after pouring 2-ethoxyethanol in an amount of 30 milliliter, the resultant mixture was reacted for 11 hours under refluxing. A resultant yellow precipitation was separated by filtration, followed by washing twice with the use of ethanol in an amount of 5 milliliter. Further, it was dissolved in 600 milliliter of methylene chloride, and the resultant solution was washed three times using 200 milliliter of water. After drying the resultant solution with the use of magnesium sulfate, the solvent was distillated away and as a result, 1.35 g of Intermediate 6-1a as pale yellow crystals was obtained (yield: 38%). The pale yellow crystals were confirmed as the aimed compound from ¹H-NMR spectrum. The measurement result is shown as follows:

¹H-NMR (CD₂Cl₂): δ 7.26-7.42 (m, 2H), δ 6.47-6.94 (m, 3H), δ 6.0-6.09 (m, 1H), δ 4.13 (s, 3H)

(3) Synthesis of Metal Complex Compound 6-1

Placing Intermediate 6-1a in an amount of 1.32 g (1.21 mmol) and 2-picolinic acid in an amount of 0.59 g (4.87 mmol) into a flask, the atmosphere was replaced with argon gas. Pouring 15 milliliter of 1,2-dichloroethane into the resultant solution, it was reacted for 8 hours under refluxing. Separating the resultant yellow precipitation, dissolving the precipitation into 200 milliliter of methylene chloride, it was washed 4 times using 150 milliliter of water. After drying the resultant solution with the use of magnesium sulfate, the solvent was distillated away and further, re-crystallized from methylene chloride/hexane. As a result 1.17 g of Metal complex Compound 6-1 as yellow crystals was obtained (yield: 78%). The yellow crystals were confirmed as the aimed compound from ¹H-NMR spectrum. The measurement result is shown as follows:

¹H-NMR (CDCl₃): δ 8.1-8.2 (m, 1H), δ 7.75-7.90 (m, 2H), δ 7.2-7.51 (m, 3H), δ 6.3-7.0 (m, 9H), δ 6.13 (d, 1H), δ 4.06 (s, 3H)

Further, by measuring phosphorus light (methylene chloride solution) of the resultant Metal complex Compound 6-1, it was found that λ max of phosphorus light was 562 nm.

Comparative Example 1

Placing 4-phenylimidazole in an amount of 3.8 g (26.3 mmol) and IrCl₃ hydrate (available from Strem Chemicals, Inc.) in an amount of 1.96 g (6.6 mmol) into a flask, the atmosphere was replaced with argon gas. Adding 30 milliliter of 2-ethoxyethanol, the resultant solution reacted for 18 hours under refluxing and as a result, a homogeneous blackish brown solution was prepared without any precipitate. Distillating the solvent away, the resultant solution was processed and a black solid was obtained, however, it was not identified as an aimed Ir metal complex compound (Q below). Comparing with Example 3, when a hydrogen atom exists at N position of imidazole as illustrated below, it was understood that any substituent such as a methyl group is necessary because synthesizing Ir complex is difficult.

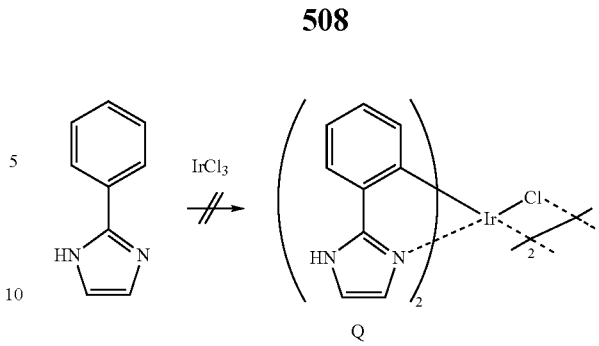

Example 4

Synthesis of Metal Complex Compound 7-1

The route for synthesis of Metal complex Compound 7-1 is illustrated in the following.

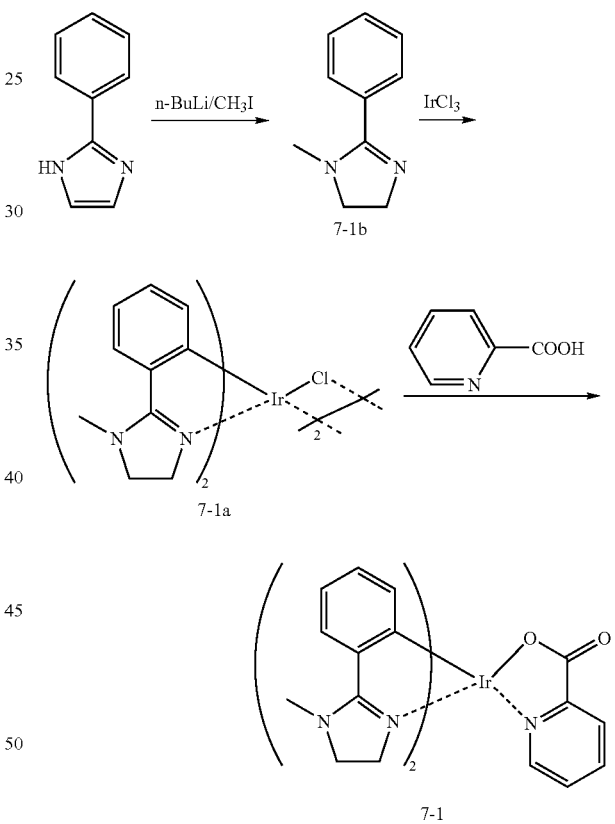

In the above route, the structural formula of Intermediate 7-1a expresses a dimer configuration.

(1) Synthesis of Intermediate 7-1b

Placing 2-phenylimidazole in an amount of 8.9 g (60.8 mmol) into a flask having a dropping funnel, and after replacing the atmosphere with argon gas, 210 milliliter of tetrahydrofuran was added. Under cooling with ice, n-butyllithium of 1.56 mol/liter in an amount of 39.3 milliliter (61.2 mmol) was dripped down into the solution spending 30 minutes and subsequently, 8.7 g (61.3 mmol) of methyl iodide dissolved into 10 milliliter of tetrahydrofuran was dripped down. After termination of dripping down, the resultant solution was reacted at the room temperature for 3 hours. Concentrating the reacted solution and extracting the resultant solid using 150 milliliter of methylene chloride, it was washed three times using 150 milliliter of water. After drying an organic layer with the use of magnesium sulfate, the solvent was removed. Refining the crystals by means of silicagel column (hexane/methylene chloride), 8.0 g of 1-methyl-2-phenylimidazo Intermediate 7-1b as white crystals was obtained (yield: 83%). The white crystals were confirmed as the aimed compound from $^1$H-NMR spectrum. The measurement result is shown as follows:

$^1$H-NMR (CDCl$_3$): δ 7.33-7.60 (m, 5H), δ 3.27-3.98 (m, 4H), δ 2.76 (s, 3H)

(2) Synthesis of Intermediate 7-1a

Placing Intermediate 7-1b in an amount of 4.4 g (27.5 mmol) and IrCl$_3$ hydrate (available from Strem Chemicals, Inc.) in an amount of 2.1 g (6.9 mmol) into a flask, the atmosphere was replaced with argon gas. Pouring 30 milliliter of 2-ethoxyethanol into the resultant solution, it was reacted for 16 hours under refluxing. A resultant yellow precipitation was separated by filtration, followed by washing twice with the use of ethanol in an amount of 5 milliliter. Further, it was dissolved in 200 milliliter of methylene chloride, and the resultant solution was washed 4 times using 200 milliliter of water. After drying the resultant solution with the use of magnesium sulfate, the solvent was distillated away and as a result, 2.1 g of Intermediate 7-1a as orange crystals was obtained (yield: 57%). The orange crystals were confirmed as the aimed compound from $^1$H-NMR spectrum. The measurement result is shown as follows:

$^1$H-NMR (DMSO-d$_6$): δ 7.51-7.61 (m, 1H), δ 6.69-6.97 (m, 3H), δ 3.60-4.1 (m, 4H), δ 3.33 (s, 3H)

(3) Synthesis of Metal Complex Compound 7-1

Placing Intermediate 7-1a in an amount of 1.95 g (1.78 mmol) and 2-picolinic acid in an amount of 0.88 g (7.14 mmol) into a flask, the atmosphere was replaced with argon gas. Pouring 20 milliliter of 1,2-dichloroethane into the resultant solution, it was reacted for 17 hours under refluxing. Removing the solvent from the reacted solution and dissolving the resultant brown solid using 150 milliliter of methylene chloride, it was washed 5 times using 200 milliliter of water. After drying the resultant solution with the use of magnesium sulfate, the solvent was distillated away and further, refined by means of silica column (methylene chloride/hexane). Intermediate 7-1 as brown crystals in an amount of 1.2 g was obtained (yield: 53%). It was confirmed in accordance with FD-MS that the brown crystals were the aimed compound. The measurement result is shown as follows:

FD-MS: m/z=632

Further, by measuring phosphorus light (methylene chloride solution) of the resultant Metal complex Compound 7-1, it was found that λ max of phosphorus light was 562 nm.

Example 5

Synthesis of Metal Complex Compound 5-1

The route for synthesis of Metal complex Compound 5-1 is illustrated in the following.

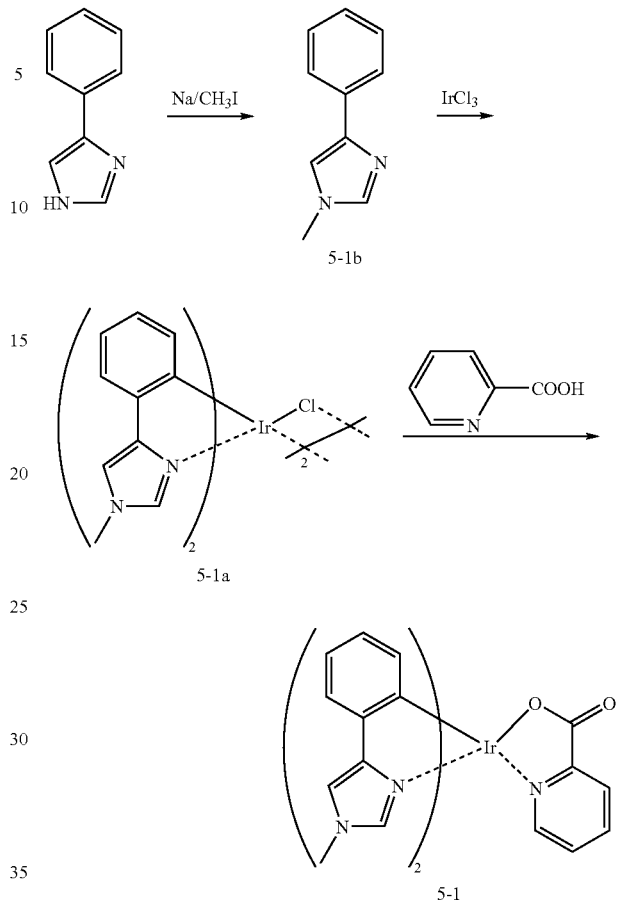

(1) Synthesis of Intermediate 5-1b

Placing 4-phenylimidazole in an amount of 9.6 g (67 mmol) into a flask having a dropping funnel, and after replacing the atmosphere with argon gas, 50 milliliter of dimethylsulfoxide was added. Adding 2.8 g (60% in oil, 70 mmol equivalent) of NaH little by little into the solution and after achieving the addition of entire amount, the resultant solution was heated for 2 hours at a temperature of 80° C. Subsequently, 9.6 g (68 mmol) of methyl iodide dissolved into 15 milliliter of methylsulfoxide was dripped down and the resultant solution was heated again for further 15 hours at the temperature of 80° C.

Throwing the resultant solution into 200 milliliter of water, the solution was extracted using 200 milliliter of ethylene chloride. After separating an organic layer, it was washed 5 times using 200 milliliter of water, and it was dried with the use of magnesium sulfate. After concentrating the solution, refining the resultant pale brown solids by means of silicagel column (methylene chloride), 5.5 g of 1-methyl-4-phenylimidazo Intermediate 5-1b as white crystals was obtained (yield: 52%).

(2) Synthesis of Intermediate 5-1a

Placing Intermediate 5-1b in an amount of 3.0 g (18.9 mmol) and IrCl$_3$ hydrate (available from Strem Chemicals, Inc.) in an amount of 1.41 g (4.7 mmol) into a flask, the atmosphere was replaced with argon gas. Pouring 15 milliliter of 2-ethoxyethanol into the resultant solution, it was reacted for 13 hours under refluxing. A resultant white precipitation was separated by filtration, followed by washing twice with the use of ethanol in an amount of 5 milliliter. Further, it was dissolved in 500 milliliter of methylene chloride, and the resultant solution was washed 3 times using 150 milliliter of water. After drying the resultant solution with the use of magnesium sulfate, the solvent was distillated away and as a result, 1.77 g of Intermediate 5-1a as white crystals was obtained (yield: 69%).

(3) Synthesis of Metal Complex Compound 5-1

Placing Intermediate 5-1a in an amount of 1.38 g (1.27 mmol) and 2-picolinic acid in an amount of 0.62 g (5.1 mmol) into a flask, the atmosphere was replaced with argon gas. Pouring 20 milliliter of 1,2-dichloroethane into the resultant solution, it was reacted for 12 hours under refluxing. Separating the resultant yellow precipitation, dissolving the precipitation into 300 milliliter of methylene chloride, it was washed 4 times using 200 milliliter of water. After drying the solution with the use of magnesium sulfate, the solvent was distillated away. Resultant yellow crystals were refined with silicagel column (methylene chloride/methanol). Intermediate 5-1 as pale yellow crystals in an amount of 0.4 g was obtained (yield: 26%).

Further, by measuring phosphorus light (methylene chloride solution) of the resultant Metal complex Compound 5-1, it was found that λ max of phosphorus light was 453 nm.

Example 6

Fabrication of Organic EL Device

A glass substrate of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The cleaned substrate having the transparent electrode lines was attached to a substrate holder, and on the surface of the cleaned substrate at the side having the transparent electrode, a film of 4,4'-bis[N-(4-biphenyl)-N-(4-biphenyl)amino]biphenyl below having a thickness of 40 nm was formed so that the formed film covered the transparent electrode. The formed film worked as the hole transporting layer. Further, a host material (CBP) below together with adding a photo luminescent Ir-Metal Complex Compound 1-1 as a dopant were vapor deposited obtaining a film thickness of 30 nm on the formed film. The formed film worked as a light emitting layer. A concentration of Compound 1-1 in the light emitting layer was 5% by weight. On the light emitting layer, a film of (1,1-bisphenyl)-4-olate)bis(2-methyl-8-quinolinolato)aluminum (BAlq) below having a thickness of 10 nm was formed. The formed film of BAlq worked as the hole barrier layer. On the film formed above, a film of aluminum complex of 8-hydroxyquinoline (Alq) having a thickness of 30 nm was formed. The film of Alq worked as the electron injecting layer. Subsequently, lithium fluoride (LiF) being alkali metal halide was vapor deposited up to 0.15 nm in thickness and then, aluminum was vapor deposited up to 150 nm in thickness. The Al/LiF worked as a cathode.

An organic EL device was fabricated in the manner described above. The device fabricated above was examined by feeding electric current. Yellowish green light was emitted at a luminance of 103 cd/m² under a voltage of 6.7 V and a current density of 2.79 mA/cm². The CIE chromaticity coordinates were (0.347, 0.494), and the current efficiency was 3.7 cd/A. Additionally, λ max of light emission was 533 nm.

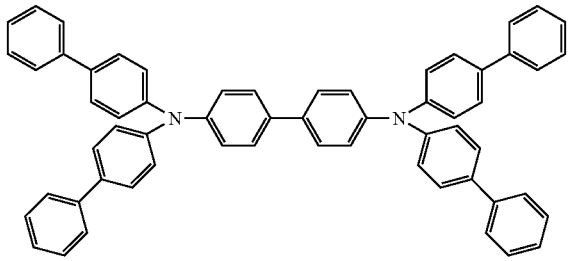

4,4'-bis[N-(4-biphenyl)-N-(4-biphenyl)amino]biphenyl

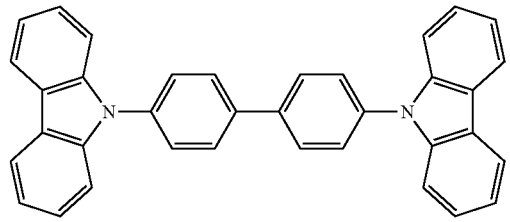

CBP

INDUSTRIAL APPLICABILITY

As described above in detail, the organic EL device employing the novel metal complex compound of the present invention emits various phosphorous light including blue light having an enhanced current efficiency and prolonged lifetime. Accordingly, the present invention is applicable for a field such as various display devices, display panels, backlights, illuminating light sources, beacon lights, signboards, and interior designs, particularly suitable as display device for color displays.

What is claimed is:

1. A metal complex compound having a partial structure represented by the following general formula (I):

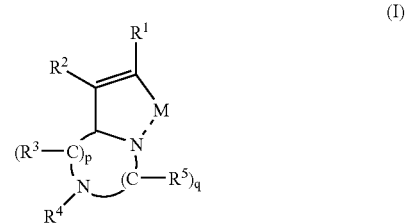

(I)

wherein $R^1$ to $R^3$ and $R^5$ each independently represents a hydrogen atom, a cyano group, a nitro group, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, a substituted or unsubstituted acyl group having 1 to 20 carbon atoms or a substituted or unsubstituted aromatic group having 1 to 30 carbon atoms; $R^4$ represents a cyano group, a nitro group, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, a substituted or unsubstituted acyl group having 1 to 20 carbon atoms or a substituted or unsubstituted aromatic group having 1 to 30 carbon atoms;

$R^1$ and $R^2$ bond to each other to form a ring structure selected from the group consisting of benzene, pyridine, naphthalene, benzothiazole, quinoline, thiazole, furan, benzofuran and 9.9-dimethylfluorene; a pair of one $R^3$ and $R^4$ and a pair of $R^4$ and one $R^5$ may bond to each other to form a ring structure;

p and q each independently represents an integer of 0 to 3; p+q being 2 or 3; when p is an integer of 2 or greater, the plurality of $R^3$ may bond to each other to form a ring structure;

when q is an integer of 2 or greater, the plurality of $R^5$ may bond to each other to form a ring structure, with the provisos that when p is 0 and q is 2, the plurality of $R^5$ do not bond to each other to form a ring structures and when p is 0, q is 2, and $R^1$ and $R^2$ bond to each other to form a ring structure, the ring structure is not substituted with phenyl; and M represents a metal atom selected from the group consisting of iridium (Ir) atom, rhodium (Rh) atom, and platinum (Pt) atom.

2. The metal complex compound according to claim 1, which is a material for an light emitting element.

3. The metal complex compound according to claim 1, wherein said partial structure is represented by any one of the following general formulae (i) to (iii) and (v) to (vii):

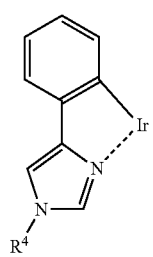
(i)

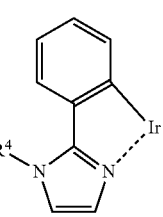
(ii)

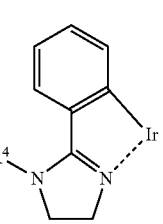
(iii)

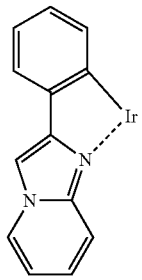
(v)

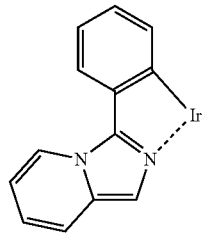
(vi)

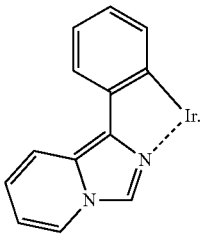
(vii)

4. The metal complex compound according to claim 1, wherein said partial structure is represented by any one of following general formulae (i') to (iii') and (v') to (vii'):

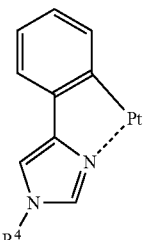
(i')

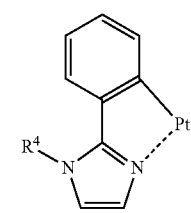
(ii')

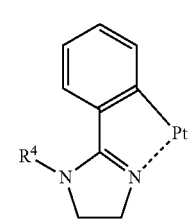
(iii')

(v')
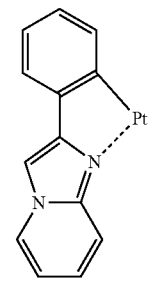
(vi')
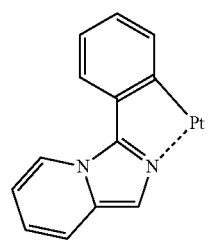
(vii')
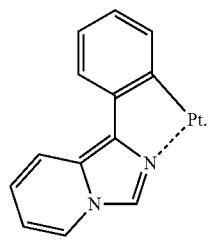
5. The metal complex compound according to claim 1, which is represented by any one of the following general formulae 1 to 3, 5 to 7, 1' to 3' and 5' to 7':
1
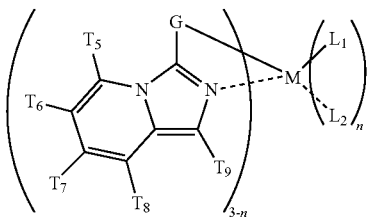
2
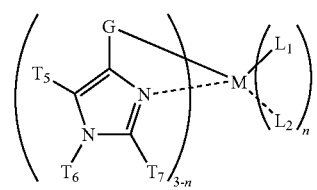
3
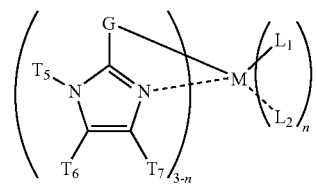
5
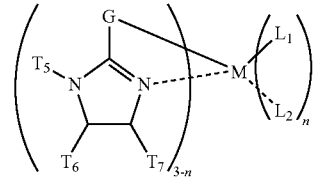
6
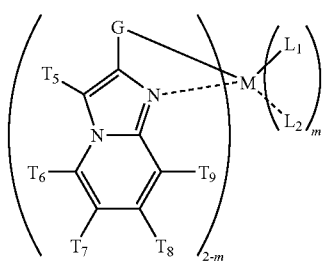
7
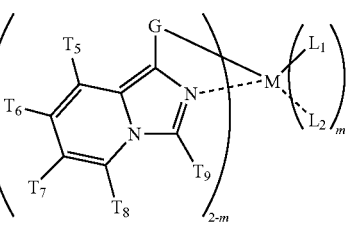
1'
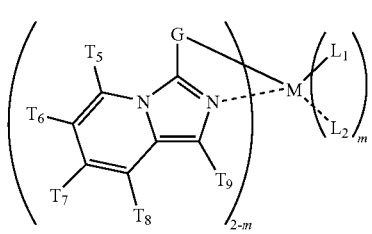
2'
3'

-continued

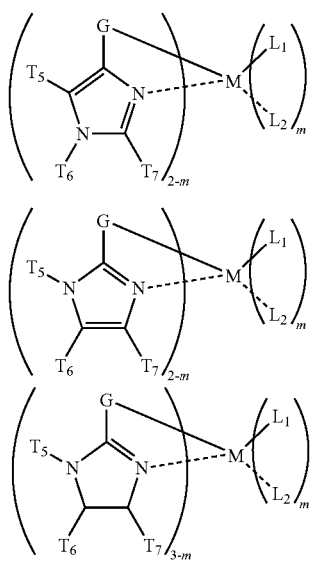

wherein T⁵ to T⁹ each independently represents a hydrogen atom, a cyano group, a nitro group, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, a substituted or unsubstituted acyl group having 1 to 20 carbon atoms or a substituted or unsubstituted aromatic group having 1 to 30 carbon atoms with the proviso that T⁵ and T⁶ are not hydrogen atoms when they bond to a nitrogen atom; and among substituents T⁵ through T⁶ which are on the same ring or condensed ring structure, a pair of T⁵ and T⁶, a pair of T⁶ T⁷, a pair of T⁷ and T⁸ and a pair of T⁸ and T⁹ may bond to each other to form a ring structure;

M represents a metal atom selected from the group consisting of iridium (Ir) atom, rhodium (Rh) atom, and platinum (Pt) atom; and L¹ and L² each independently represents any one structure represented by the following structures:

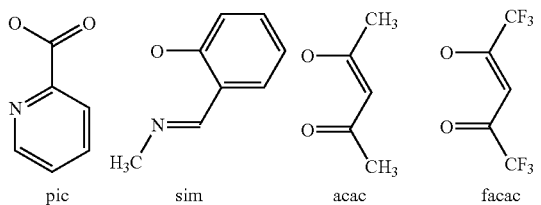

n represents an integer of 0 to 2, and m represents an integer of 0 or 1

G represents any one structure represented by the following structures:

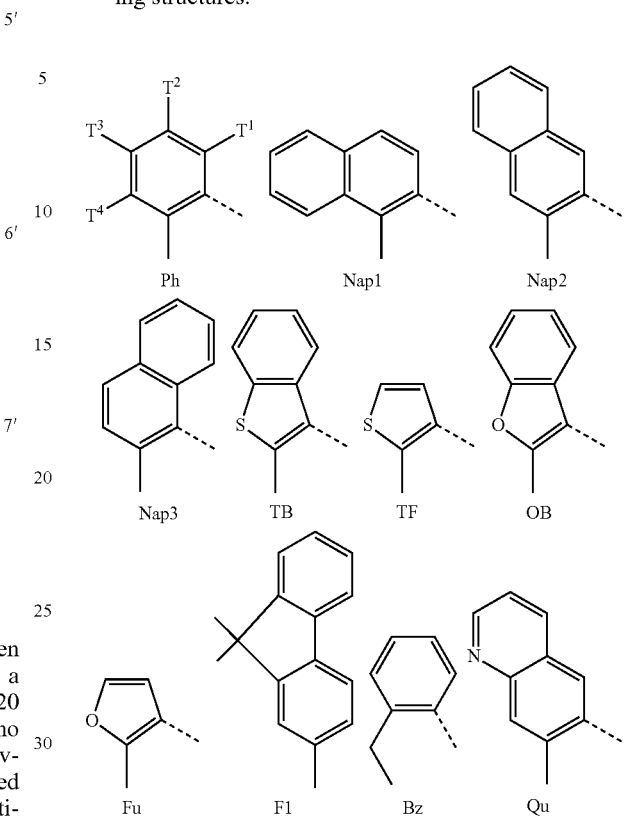

wherein a dotted line "..." represents a covalent bond with the above M; and

T¹ to T⁴ in Ph each independently represents a hydrogen atom, a cyano group, a nitro group, a halogen atom, a substituted or unsubstituted alkyl group having 1 to 20 carbon atoms, a substituted or unsubstituted amino group, a substituted or unsubstituted alkoxyl group having 1 to 20 carbon atoms, a substituted or unsubstituted alkylsilyl group having 1 to 20 carbon atoms, or a substituted or unsubstituted acyl group having 1 to 20 carbon atoms.

6. An organic electroluminescence device which comprises at least one organic thin film layer sandwiched between a pair of electrode consisting of an anode and a cathode, wherein the organic thin film layer comprises the metal complex compound according to claim 1, which emits light by applying an electric voltage between the pair of electrode.

7. The organic electroluminescence device according to claim 6, wherein said light emitting layer comprises said metal complex compound.

8. The organic electroluminescence device according to claim 6, wherein said organic thin film layer comprising the metal complex compound is formed by coating process.

* * * * *